(12) United States Patent
Mita et al.

(10) Patent No.: US 8,987,464 B2
(45) Date of Patent: Mar. 24, 2015

(54) ISOXAZOLINE-SUBSTITUTED BENZAMIDE COMPOUND AND PESTICIDE

(71) Applicant: Nissan Chemical Industries, Ltd., Tokyo (JP)

(72) Inventors: Takeshi Mita, Funabashi (JP); Yuki Furukawa, Funabashi (JP); Ken-ichi Toyama, Funabashi (JP); Manabu Yaosaka, Funabashi (JP); Eitatsu Ikeda, Funabashi (JP); Yoshihide Masuzawa, Funabashi (JP); Mitsuaki Komoda, Minamisaitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 14/157,048

(22) Filed: Jan. 16, 2014

(65) Prior Publication Data

US 2014/0135496 A1 May 15, 2014

Related U.S. Application Data

(60) Division of application No. 13/010,479, filed on Jan. 20, 2011, now Pat. No. 8,673,951, which is a division of application No. 12/073,159, filed on Feb. 29, 2008, now Pat. No. 7,951,828, which is a continuation-in-part of application No. PCT/JP2006/317797, filed on Sep. 1, 2006.

(30) Foreign Application Priority Data

| Sep. 2, 2005 | (JP) | 2005-254446 |
| Sep. 2, 2005 | (JP) | 2005-254449 |
| Sep. 2, 2005 | (JP) | 2005-254451 |
| Sep. 6, 2005 | (JP) | 2005-257344 |
| Feb. 22, 2006 | (JP) | 2006-045804 |
| Mar. 27, 2006 | (JP) | 2006-085597 |
| Apr. 17, 2006 | (JP) | 2006-113060 |
| May 19, 2006 | (JP) | 2006-139953 |

(51) Int. Cl.
*C07C 237/32* (2006.01)
*C07D 213/36* (2006.01)
(Continued)

(52) U.S. Cl.
CPC .............. *C07C 237/32* (2013.01); *A01N 43/80* (2013.01); *C07D 413/04* (2013.01);
(Continued)

(58) Field of Classification Search
USPC .......................... 546/323; 564/164
See application file for complete search history.

(56) References Cited

U.S. PATENT DOCUMENTS

2007/0066617 A1 3/2007 Mita et al.

FOREIGN PATENT DOCUMENTS

| JP | A-2001-064268 | 3/2001 |
| JP | A-2003-212834 | 7/2003 |

(Continued)

OTHER PUBLICATIONS

Mita, et al. Document No. 143:306321, retrieved from CAPLUS, Sep. 15, 2005.*

(Continued)

*Primary Examiner* — Shawquia Jackson
(74) *Attorney, Agent, or Firm* — Oliff PLC

(57) ABSTRACT

An isoxazoline-substituted benzamide compound of formula (1) or a salt thereof:

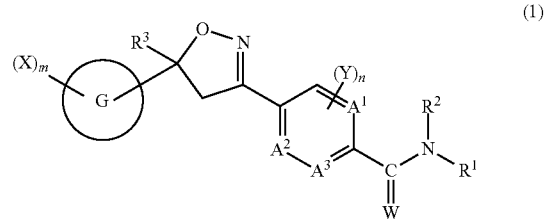

wherein $A^1$, $A^2$ and $A^3$ independently of one another are carbon atom or nitrogen atom, G is benzene ring, etc., W is oxygen atom or sulfur atom, etc., X is halogen atom, $C_1$-$C_6$haloalkyl, etc., Y is halogen atom, $C_1$-$C_6$alkyl, etc., $R^1$ is —CH=$NOR^{1a}$, —C(O)$OR^{1c}$, —C(O)$NHR^{1d}$, phenyl substituted with $(Z)_{p1}$, D-14, D-52, D-53, D-55 to D-59, etc., $R^{1a}$ is $C_1$-$C_6$alkyl, etc., $R^{1c}$ is $C_1$-$C_6$alkyl, etc., $R^{1d}$ is hydrogen atom, —C(O)$R^{15}$, —C(O)$OR^{15}$, etc., $R^2$ is $C_1$-$C_6$alkyl, —CH$_2$$R^{14a}$, $C_1$-$C_6$alkynyl, —C(O)$R^{15}$, —C(O)$OR^{15}$, etc., further when $R^1$ is —CH=$NOR^{1a}$, —C(O)$OR^{1c}$ or —C(O)$N(R^{1e})R^{1d}$, $R^2$ may be hydrogen atom, $R^3$ is $C_1$-$C_6$haloalkyl, etc., $R^{14a}$ is cyano, —$OR^{25}$, etc., $R^{15}$ is $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, $C_3$-$C_6$cycloalkyl, $C_2$-$C_6$alkenyl, etc., $R^{25}$ is $C_1$-$C_4$alkyl, $C_1$-$C_4$haloalkyl, —C(O)$R^{32}$ or —C(O)$OR^{32}$, etc., $R^{32}$ is $C_1$-$C_6$alkyl or $C_3$-$C_6$cycloalkyl, etc., Z is halogen atom, cyano, nitro, $C_1$-$C_6$alkyl, $C_1$-$C_6$alkoxy, etc., m is an integer of 0 to 5, n is an integer of 0 to 4, p1 is an integer of 1 to 5. The pesticide containing these compounds.

5 Claims, No Drawings

(51) Int. Cl.
*A01N 43/80* (2006.01)
*C07D 413/04* (2006.01)
*C07C 237/36* (2006.01)
*C07D 213/75* (2006.01)
*C07D 213/81* (2006.01)
*C07D 237/20* (2006.01)
*C07D 239/42* (2006.01)
*C07D 241/20* (2006.01)
*C07D 401/12* (2006.01)

(52) U.S. Cl.
CPC ........... *C07C 237/36* (2013.01); *C07D 213/75* (2013.01); *C07D 213/81* (2013.01); *C07D 237/20* (2013.01); *C07D 239/42* (2013.01); *C07D 241/20* (2013.01); *C07D 401/12* (2013.01)
USPC .......................................... 546/323; 564/164

(56) References Cited

FOREIGN PATENT DOCUMENTS

| | | |
|---|---|---|
| WO | WO 95/14683 | 6/1995 |
| WO | WO 96/38426 | 12/1996 |
| WO | WO 97/23212 | 7/1997 |
| WO | WO 97/48395 | 12/1997 |
| WO | WO 99/14210 | 3/1999 |
| WO | WO 2005/085216 | 9/2005 |

OTHER PUBLICATIONS

Machine Translation of JP-A-2005-035964 published Feb. 10, 2005.
Machine Translation of JP-A-2004-051614 published Feb. 19, 2004.
Machine Translation of JP-A-2005-272452 published Oct. 6, 2005.
S.H. Hwang et al.; "Solid-Phase Synthesis of an Isoxazolinopyrrole Library;" Journal of Combination Chemistry; vol. 6; 2004; pp. 142-148.
European Search Report for corresponding European application No. 06 79 7653 dated Oct. 7, 2009.

* cited by examiner

ISOXAZOLINE-SUBSTITUTED BENZAMIDE COMPOUND AND PESTICIDE

This is a Division of application Ser. No. 13/010,479 filed Jan. 20, 2011, which in turn is a Division of application Ser. No. 12/073,159 filed Feb. 29, 2008, which in turn is a Continuation in Part of Application No. PCT/JP2006/317797 filed Sep. 1, 2006, which claims the priority to Japanese Patent Application Nos. 2006-139953 (filed May 19, 2006), 2006-113060 (filed Apr. 17, 2006), 2006-085597 (filed Mar. 27, 2006), 2006-045804 (filed Feb. 22, 2006), 2005-257344 (filed Sep. 6, 2005), 2005-254451 (filed Sep. 2, 2005), 2005-254446 (filed Sep. 2, 2005), and 2005-254449 (filed Sep. 2, 2005). The disclosures of the prior applications are hereby incorporated by reference herein in their entireties.

TECHNICAL FIELD

The present invention relates to a novel isoxazoline-substituted benzamide compound and the salt thereof, and a pesticide characterized by containing the compound as an active ingredient. The pesticide in the present invention means a pest controlling agent applied for harmful arthropods in agricultural and horticultural field or livestock farming and hygienic field (endo-parasiticides and ecto-parasiticides for mammals or birds as domestic animals or pets, or hygienic pest- or unpleasant pest-controlling agents for domestic or business use). In addition, agricultural chemicals in the present invention mean insecticides, acaricides, nematicides, herbicides and fungicides, and the like.

BACKGROUND ART

Conventionally, as to isoxazoline-substituted benzamide compounds, it is known that N-(2-alkoxyiminoalkyl)-4-(5-substituted-5-substituted aryl-4,5-dihydroisooxazole-3-yl) benzamide compounds, N-(2,2,2-trifluoroethoxycarbonyl)-4-(5-substituted-5-substituted aryl-4,5-dihydroisooxazole-3-yl)benzamide compounds and N-(2-pyrimidyl)-4-(5-substituted-5-substituted aryl-4,5-dihydroisooxazole-3-yl) benzamide compounds, and the like show pesticidal activity, particularly insecticidal and acaricidal activity (see, Patent Document 1). However, there is no disclosure on N-substituted-4-(5-substituted-5-substituted aryl-4,5-dihydroisooxazole-3-yl)benzamide compounds and N,N-disubstituted-4-(5-substituted-5-substituted aryl-4,5-dihydroisoxazole-3-yl)benzamide compounds having a specific amide substituent according to the present invention.

In addition, as to other isoxazoline-substituted benzamide compounds, it is known that 4-(5-substituted carbamoylmethyl-4,5-dihydroisoxazole-3-yl)benzamide derivatives, 3-(5-substituted carbamoylmethyl-5-substituted alkyl-4,5-dihydroisoxazole-3-yl)benzamide derivatives and 4-(5-substituted carbamoylmethyl-4,5-dihydroisoxazole-3-yl)benzamidine derivatives have platelet glycoprotein IIb/IIIa fibrinogen receptor complex competitive activity or factor Xa inhibition activity or the like, and can be used as a thrombolysis agent or a therapeutic agent of thronbo-embolic disorder (see, for example Patent Documents 2-5), etc. Further, it is known that other specific substituted isoxazoline compound can be used as a production intermediate of HIV protease inhibitors (see, for example Patent Document 6). However, there is no disclosure on N-substituted-4-(5-substituted-5-substituted aryl-4,5-dihydroisooxazole-3-yl)benzamide compounds and N,N-disubstituted-4-(5-substituted-5-substituted aryl-4,5-dihydroisoxazole-3-yl)benzamide compounds having a specific amide substituent according to the present invention, and further the usefulness thereof as a pesticide is not known at all.

On the other hand, as to 4-hydroxyiminomethyl benzamide derivatives, N-(arylmethyl)-4-hydroxyiminomethyl)benzamide (see, Patent Document 1) and the like are known. However, N-substituted-4-hydroxyiminomethyl benzamide derivatives and N,N-disubstituted-4-hydroxyiminomethyl benzamide derivatives having a specific amide substituent that can be used as a production intermediate of the pesticides according to the present invention are not described in any documents and thus novel compounds.

Patent Document 1: WO 2005/085216 Pamphlet
Patent Document 2: WO 96/038426 Pamphlet
Patent Document 3: WO 97/023212 Pamphlet
Patent Document 4: WO 95/014683 Pamphlet
Patent Document 5: WO 97/048395 Pamphlet
Patent Document 6: WO 99/014210 Pamphlet

DISCLOSURE OF INVENTION

Problems to be Solved by the Invention

The development of pesticides for controlling several pests such as agricultural and horticultural pests, forestall pests, or hygienic pests, etc. expands, and a number of different agents have been practically utilized to the present.

However, recently, pests acquire resistance by the use of pesticides such as insecticides or fungicides over long term, and thus control by the insecticides or fungicides that have been conventionally used becomes difficult. In addition, a part of known pesticides has a high toxicity, or some of them start to disturb native ecosystems due to long-term persistency. Under the circumstances, it is expected all the time to develop a novel pesticide having a low toxicity and a low persistency.

Means for Solving the Problems

The inventors have eagerly investigated in order to solve the above-mentioned problems, and as a result of it, they found that novel isoxazoline-substituted benzamide compounds of formula (1) are extremely useful compounds having excellent pest controlling activity, particularly insecticidal activity and acaricidal activity, and having little adverse affect on non-targeted beings such as mammals, fishes and useful insects, etc. Thus, the present invention has been accomplished.

That is, the present invention relates to the following aspects (1) to (17):
(1) An isoxazoline-substituted benzamide compound of formula (1) or a salt thereof:

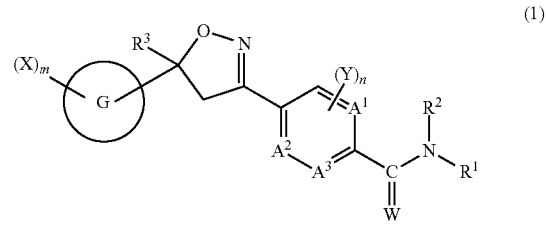

wherein $A^1$, $A^2$ and $A^3$ independently of one another are carbon atom or nitrogen atom, G is benzene ring, nitrogen-containing 6-membered aromatic heterocyclic ring, furan ring, thiophene ring, or 5-membered aromatic heterocyclic ring containing two or more hetero atoms selected from oxygen atom, sulfur atom and nitrogen atom, W is oxygen atom or sulfur atom, X is halogen atom, cyano, nitro, azido, —SCN, —SF$_5$, $C_1$-$C_6$alkyl, $C_1$-$C_6$alkyl arbitrarily substituted with $R^4$, $C_3$-$C_8$cycloalkyl, $C_3$-$C_8$cycloalkyl arbitrarily substituted with $R^4$, E-1 to E-50, $C_2$-$C_6$alkenyl, $C_2$-$C_6$alkenyl arbitrarily substituted with $R^4$, $C_3$-$C_8$cycloalkenyl, $C_3$-$C_8$halocycloalkenyl, $C_2$-$C_6$alkynyl, $C_2$-$C_6$alkynyl arbitrarily substituted with $R^4$, —OH, —OR$^5$, —OSO$_2$R$^5$, —SH, —S(O)$_r$R$^5$, —NH$_2$, —N(R$^7$)R$^6$, —N=CHOR$^8$, —N=C(R$^9$)OR$^8$, —CHO, —C(O)R$^9$, —C(O)OR$^9$, —C(O)SR$^9$, —C(O)NH$_2$, —C(O)N(R$^{10}$)R$^9$, —C(S)OR$^9$, —C(S)SR$^9$, —C(S)NH$_2$, —C(S)N(R$^{10}$)R$^9$, —CH=NOR$^{11}$, —C(R$^9$)=NOR$^{11}$, M-5, M-20, M-40 to M-43, M-46 to M-48, —S(O)$_2$OR$^9$, —S(O)$_2$NH$_2$, —S(O)$_2$N(R$^{10}$)R$^9$, —Si(R$^{12a}$)(R$^{12b}$)R$^{12}$, phenyl, phenyl substituted with $(Z)_{p1}$, or D-1 to D-65, when m is an integer of 2 or more, each X may be identical with or different from each other, further, when two Xs are adjacent, the adjacent two Xs may form 5-membered or 6-membered ring together with carbon atoms to which the two Xs are bonded by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$N(R$^{13}$)—, —CH$_2$N(R$^{13}$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N(R$^{13}$)CH=CH—, —OCH=N—, —SCH=N—, —N(R$^{13}$)CH=N—, —N(R$^{13}$)N=CH—, —CH=CHCH=CH—, —OCH$_2$CH=CH—, —N=CHCH=CH—, —N=CHCH=N— or —N=CHN=CH—, in this case, hydrogen atoms bonded to each carbon atom forming the ring may be arbitrarily substituted with Z, further when the hydrogen atoms are substituted with two or more Zs at the same time, each Z may be identical with or different from each other, Y is halogen atom, cyano, nitro, azido, —SCN, —SF$_5$, $C_1$-$C_6$alkyl, $C_1$-$C_6$alkyl arbitrarily substituted with $R^4$, $C_3$-$C_8$cycloalkyl, $C_3$-$C_8$cycloalkyl arbitrarily substituted with $R^4$, E-1 to E-50, $C_2$-$C_6$alkynyl, $C_2$-$C_6$alkynyl arbitrarily substituted with $R^4$, —OH, —OR$^5$, —OSO$_2$R$^5$, —SH, —S(O)$_r$R$^5$, —NH$_2$, —N(R$^7$)R$^6$, —N(R$^7$)C(O)R$^{9a}$, —N(R$^7$)C(O)OR$^{9a}$, —N(R$^7$)C(O)SR$^{9a}$, —N(R$^7$)C(S)OR$^{9a}$, —N(R$^7$)C(S)SR$^{9a}$, —N(R$^7$)S(O)$_2$R$^{9a}$, —N=CHOR$^8$, —N=C(R$^9$)OR$^8$, —C(O)NH$_2$, —C(O)N(R$^{10}$)R$^9$, —C(S)NH$_2$, —C(S)N(R$^{10}$)R$^9$, —Si(R$^{12a}$)(R$^{12b}$)R$^2$, phenyl, phenyl substituted with $(Z)_{p1}$, D-1 to D-65, when n is an integer of 2 or more, each Y may be identical with or different from each other, further, when two Ys are adjacent, the adjacent two Ys may form 5-membered or 6-membered ring together with carbon atoms to which the two Ys are bonded by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —SCH$_2$S—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —SCH$_2$CH$_2$S—, —OCH=N— or —SCH=N—, in this case, hydrogen atoms bonded to each carbon atom forming the ring may be arbitrarily substituted with Z, further when the hydrogen atoms are substituted with two or more Zs at the same time, each Z may be identical with or different from each other, $R^1$ is —C(R$^{1b}$)=NOR$^{1a}$, M-5, M-20, M-48, —C(O)OR$^{1c}$, —C(O)SR$^{1c}$, —C(S)OR$^{1c}$, —C(S)SR$^{1c}$, —C(O)N(R$^{1e}$)R$^{1d}$, —C(S)N(R$^{1e}$)R$^{1d}$, —C(R$^{1b}$)=NN(R$^{1e}$)R$^{1f}$, phenyl, phenyl substituted with $(Z)_{p1}$ or D-1 to D-65, $R^{1a}$ is hydrogen atom, $C_1$-$C_{12}$alkyl, $C_1$-$C_{12}$haloalkyl, $C_1$-$C_6$alkyl arbitrarily substituted with $R^{14}$, $C_3$-$C_{12}$cycloalkyl, $C_3$-$C_{12}$halocycloalkyl, $C_3$-$C_8$cyloalkyl arbitrarily substituted with $R^{14}$, E-4 to E-10, E-24 to E-29, E-31, E-32, E-35, E-46, $C_3$-$C_{12}$alkenyl, $C_3$-$C_{12}$haloalkenyl, $C_3$-$C_6$alkenyl arbitrarily substituted with $R^{14}$, $C_3$-$C_{12}$cycloalkenyl, $C_3$-$C_{12}$halocycloalkenyl, $C_3$-$C_{12}$alkynyl, $C_3$-$C_{12}$haloalkynyl, $C_3$-$C_6$alkynyl arbitrarily substituted with $R^{14}$, phenyl, phenyl substituted with $(Z)_{p1}$, D-52, D-55 to D-58 or D-59, $R^{1b}$ is hydrogen atom, $C_1$-$C_{12}$alkyl, $C_1$-$C_{12}$haloalkyl, $C_1$-$C_6$alkoxyC$_1$-$C_6$alkyl, $C_1$-$C_6$alkylthioC$_1$-$C_6$alkyl, $C_3$-$C_{12}$cycloalkyl, phenyl or phenyl substituted with $(Z)_{p1}$, $R^{1c}$ is $C_1$-$C_{12}$alkyl, $C_1$-$C_6$alkyl arbitrarily substituted with $R^{14}$, $C_3$-$C_{12}$cycloalkyl, $C_3$-$C_{12}$halocycloalkyl, $C_3$-$C_8$cyloalkyl arbitrarily substituted with $R^{14}$, E-3, E-5 to E-10, E-24 to E-29, E-31, E-32, E-35, E-46, $C_3$-$C_{12}$alkenyl, $C_3$-$C_{12}$haloalkenyl, $C_3$-$C_6$alkenyl arbitrarily substituted with $R^{14}$, $C_3$-$C_{12}$cycloalkenyl, $C_3$-$C_{12}$halocycloalkenyl, $C_3$-$C_{12}$alkynyl, $C_3$-$C_{12}$haloalkynyl, $C_3$-$C_6$alkynyl arbitrarily substituted with $R^{14}$ —N=C(R$^{17b}$)R$^{17a}$, phenyl, phenyl substituted with $(Z)_{p1}$, D-1 to D-4, D-6 to D-13, D-15 to D-23, D-25 to D-37, D-39, D-40, D-42, D-43, D-45, D-47, D-50 to D-64 or D-65, $R^{1d}$ is hydrogen atom, —C(O)R$^{15}$, —C(O)OR$^{15}$, —C(O)SR$^{15}$, —C(S)R$^{15}$, —C(S)OR$^{15}$, —C(S)SR$^{15}$ or —SO$_2$R$^{15}$ $R^{1e}$ is hydrogen atom, $C_1$-$C_{12}$alkyl, $C_1$-$C_{12}$haloalkyl, cyanoC$_1$-$C_6$alkyl, $C_1$-$C_6$alkoxyC$_1$-$C_6$alkyl, $C_1$-$C_6$alkylthioC$_1$-$C_6$alkyl, $C_1$-$C_6$alkylsulfonyl C$_1$-$C_6$alkyl, $C_3$-$C_{12}$alkenyl, $C_3$-$C_{12}$alkynyl or benzyl, $R^{1f}$ is —CHO, —C(O)R$^{15}$, —C(O)OR$^{15}$, —C(O)SR$^{15}$, —C(S)OR$^{15}$, —C(S)SR$^{15}$, —C(S)NH$_2$ or —C(S)N(R$^{16}$)R$^{15}$, $R^2$ is cyano, $C_1$-$C_{12}$alkyl, —CH$_2$R$^{14a}$, E-5, E-7, E-9, E-24, E-27, E-30, $C_3$-$C_{12}$cycloalkyl, $C_3$-$C_{12}$halocycloalkyl, $C_3$-$C_{12}$alkynyl, $C_3$-$C_{12}$haloalkynyl, $C_3$-$C_6$alkynyl arbitrarily substituted with $R^{14a}$, —CHO, —C(O)R$^{15}$, —C(O)OR$^{15}$, —C(O)SR$^{15}$, —C(S)OR$^{15}$, —C(S)SR$^{15}$, —C(O)C(O)OR$^{15}$, —SR$^{15}$, —S(O)$_2$R$^{15}$, —S(O)$_2$N(R$^{16}$)R$^{15}$, —SN(R$^{20}$)R$^{19}$, phenyl or phenyl substituted with $(Z)_{p1}$, further when $R^1$ is —C(R$^{1b}$)=NOR$^{1a}$, M-5, M-20, M-48, or —C(Rb)=NN(R$^{1e}$)R$^{1f}$, $R^2$ may be hydrogen atom, $C_1$-$C_{12}$haloalkyl, $C_3$-$C_8$cycloalkylC$_1$-$C_6$alkyl, $C_1$-$C_6$alkyl arbitrarily substituted with $R^{14a}$, $C_3$-$C_{12}$alkenyl, $C_3$-$C_{12}$haloalkenyl or $C_3$-$C_6$alkenyl arbitrarily substituted with $R^{14a}$, when $R^1$ is —C(O)OR$^{1c}$, —C(O)SR$^{1c}$, —C(S)OR$^{1c}$ or —C(S)SR$^{1c}$, $R^2$ may be hydrogen atom, halomethyl or —CH(R$^{14b}$)R$^{14a}$, when $R^1$ is —C(O)N(R$^{1e}$)R$^{1d}$ or —C(S)N(R$^{1e}$)R$^{1d}$, $R^2$ may be hydrogen atom, $C_1$-$C_{12}$haloalkyl, $C_3$-$C_8$cycloalkylC$_1$-$C_6$alkyl, $C_1$-$C_6$alkyl arbitrarily substituted with $R^{14a}$, $C_3$-$C_{12}$cycloalkyl, $C_3$-$C_{12}$halocycloalkyl, $C_3$-$C_{12}$alkenyl, $C_3$-$C_{12}$haloalkenyl or $C_3$-$C_6$alkenyl arbitrarily substituted with $R^{14a}$, when $R^1$ is phenyl, phenyl substituted with $(Z)_{p1}$ or D-1 to D-65, $R^2$ may be $C_1$-$C_{12}$haloalkyl, $C_3$-$C_8$cycloalkylC$_1$-$C_6$alkyl, $C_1$-$C_6$alkyl arbitrarily substituted with $R^{14a}$, $C_3$-$C_{12}$cycloalkyl, $C_3$-$C_{12}$halocycloalkyl, $C_3$-$C_{12}$alkenyl, $C_3$-$C_{12}$haloalkenyl, $C_3$-$C_6$alkenyl arbitrarily substituted with $R^{14a}$, —C(O)NH$_2$, —C(O)N(R$^{16}$)R$^{15}$, —OH, —OR$^{17}$, —N(R$^{18}$)R$^{17}$ or —N=C(R$^{17b}$)R$^{17a}$, or $R^2$ together with $R^1$ may form =C(R$^{2b}$)R$^{2a}$, or further when substituent Y is present on an adjacent position, $R^2$ together with Y may form 5- or 6-membered ring together with the atoms to which the $R^2$ and Y are bonded by forming —CH$_2$—, —CH$_2$CH$_2$—, —CH$_2$O—, —CH$_2$S—, —CH$_2$N(R$^6$)—, —CH=CH— or —CH=N—, in this case, the hydrogen atom bonded to each carbon atom forming the ring may be arbitrarily substituted with halogen atom, C$_1$-C$_6$alkyl, C$_1$-C$_6$haloalkyl, C$_1$-C$_6$alkylidene, C$_1$-C$_6$haloalkylidene, oxo or thioxo, R$^{2a}$ is hydrogen atom, —OR$^{1c}$, —SR$^{1c}$, C$_1$-C$_6$alkylsulfonyl, —NH$_2$, C$_1$-C$_6$alkylamino or di(C$_1$-C$_6$alkyl)amino, R$^{2b}$ is R$^{1b}$, C$_1$-C$_6$alkoxy, C$_1$-C$_6$haloalkoxy, phenoxy, phenoxy substituted with (Z)$_{p1}$, C$_1$-C$_6$alkylthio, C$_1$-C$_6$haloalkylthio, —SCH$_2$R$^{14a}$, C$_3$-C$_6$alkenylthio, C$_3$-C$_6$haloalkenylthio, C$_3$-C$_6$alkynylthio, C$_3$-C$_6$haloalkynylthio, —SC(O)R$^{15}$, —SC(O)OR$^{15}$, phenylthio, phenylthio substituted with (Z)$_{p1}$ or di(C$_1$-C$_6$alkyl)amino, R$^3$ is halogen atom, cyano, C$_1$-C$_6$alkyl, C$_1$-C$_6$alkyl arbitrarily substituted with R$^4$, C$_3$-C$_8$cycloalkyl, C$_3$-C$_8$cycloalkyl arbitrarily substituted with R$^4$, E-1 to E-50, C$_3$-C$_6$alkenyl, C$_2$-C$_6$alkenyl arbitrarily substituted with R$^4$, C$_3$-C$_6$alkynyl, C$_2$-C$_6$alkynyl arbitrarily substituted with R$^4$, —OR$^5$, —S(O)$_r$R$^5$, —N(R$^{10}$)R$^9$, —N(RO)R$^{9a}$, —CHO, —C(O)R$^9$, —C(O)OR$^9$, —C(O)SR$^9$, —C(O)NH$_2$, —C(O)N(R$^{10}$)R$^9$, —C(S)OR$^9$, —C(S)SR$^9$, —C(S)NH$_2$, —C(S)N(Ro)R$^9$, —CH=NOR$^{11}$, —C(R$^9$)=NOR$^{11}$, M-5, M-20, M-48, —Si(R$^{12a}$)(R$^{12b}$)R$^{12}$, —P(O)(OR$^{21}$)$_2$, phenyl, phenyl substituted with (Z)$_{p1}$ or D-1 to D-65, D-1 to D-65 are aromatic heterocyclic rings of the following formulae, respectively

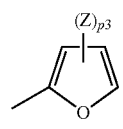
D-1

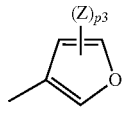
D-2

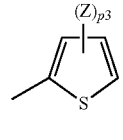
D-3

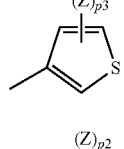
D-4

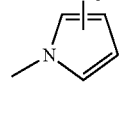
D-5

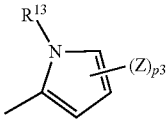
D-6

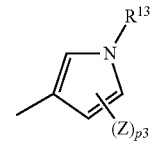
D-7

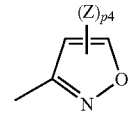
D-8

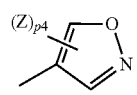
D-9

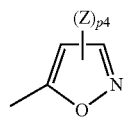
D-10

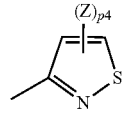
D-11

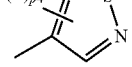
D-12

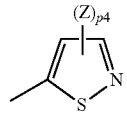
D-13

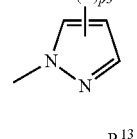
D-14

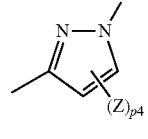
D-15

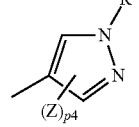
D-16

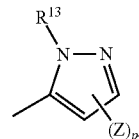
D-17

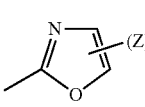
D-18

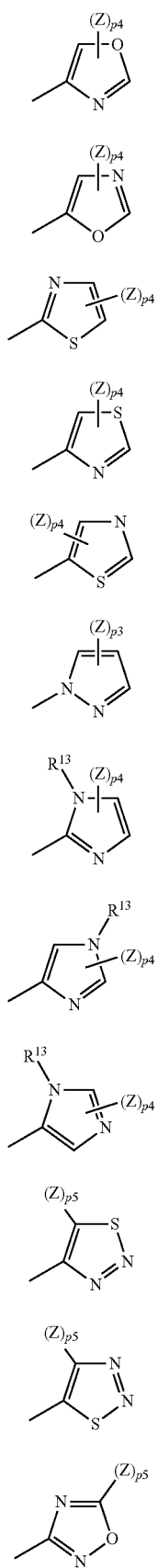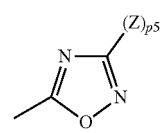

-continued
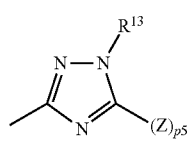 D-42
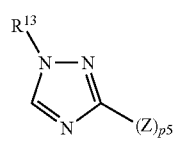 D-43
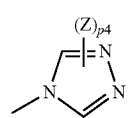 D-44
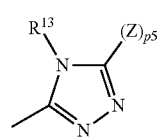 D-45
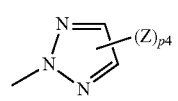 D-46
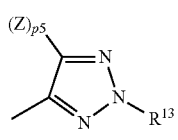 D-47
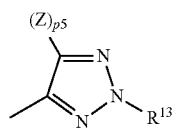 D-47
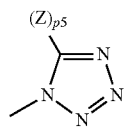 D-48
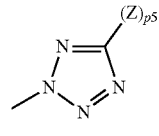 D-49
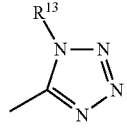 D-50
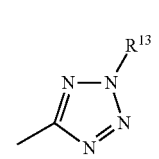 D-51
-continued
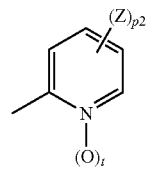 D-52
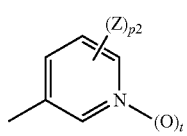 D-53
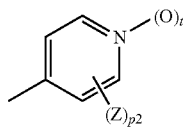 D-54
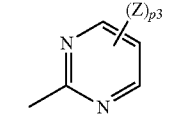 D-55
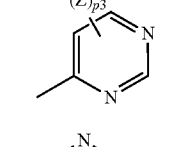 D-56
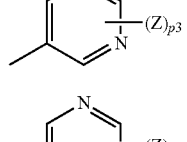 D-57
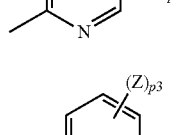 D-58
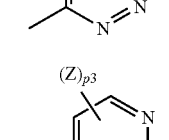 D-59
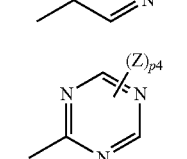 D-60
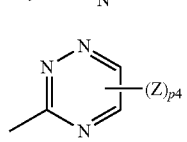 D-61
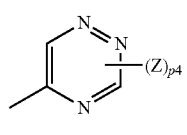 D-62
D-63

-continued

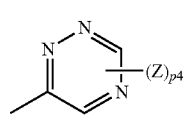
D-64

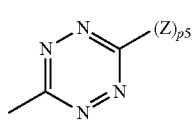
D-65

Z is halogen atom, cyano, nitro, $C_1$-$C_6$alkyl, $C_1$-$C_6$haloalkyl, $C_1$-$C_4$alkoxy $C_1$-$C_4$alkyl, $C_1$-$C_4$haloalkoxy $C_1$-$C_4$alkyl, $C_1$-$C_4$alkylthio $C_1$-$C_4$alkyl, $C_1$-$C_4$haloalkylthio $C_1$-$C_4$alkyl, $C_1$-$C_4$alkylsulfinyl $C_1$-$C_4$alkyl, $C_1$-$C_4$haloalkylsulfinyl $C_1$-$C_4$alkyl, $C_1$-$C_4$alkylsulfonyl $C_1$-$C_4$alkyl, $C_1$-$C_4$haloalkylsulfonyl $C_1$-$C_4$alkyl, $C_3$-$C_6$cycloalkyl, $C_3$-$C_6$halocycloalkyl, —OH, $C_1$-$C_6$alkoxy, $C_1$-$C_6$haloalkoxy, $C_1$-$C_6$alkylsulfonyloxy, $C_1$-$C_6$haloalkylsulfonyloxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, —$NH_2$, $C_1$-$C_6$alkylamino, di($C_1$-$C_6$alkyl)amino, $C_1$-$C_6$alkoxycarbonyl, $C_1$-$C_6$haloalkoxycarbonyl, —$C(O)NH_2$, $C_1$-$C_6$alkylaminocarbonyl, $C_1$-$C_6$haloalkylaminocarbonyl, di($C_1$-$C_6$alkyl)aminocarbonyl, —$C(S)NH_2$, —$S(O)_2NH_2$, $C_1$-$C_6$alkylaminosulfonyl, di($C_1$-$C_6$alkyl)aminosulfonyl, phenyl or phenyl arbitrarily substituted with halogen atom, when p1, p2, p3 or p4 is an integer of 2 or more, each Z may be identical with or different from each other, further, when two Zs are adjacent, the adjacent two Zs may form 5-membered or 6-membered ring together with carbon atoms to which the two Zs are bonded by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH═CH—CH═CH—, in this case, hydrogen atoms bonded to each carbon atom forming the ring may be arbitrarily substituted with halogen atom, cyano, nitro, $C_1$-$C_4$alkyl, $C_1$-$C_4$haloalkyl, $C_1$-$C_4$alkoxy or $C_1$-$C_4$alkylthio, when $R^1$ is phenyl substituted with $(Z)_{p1}$ or D-1 to D-65 and Z is present on an adjacent position of $R^1$ bonding position, Z together with $R^2$ may form 5- to 7-membered ring together with the carbon atom to which Z and $R^2$ are bonded by forming —$CH_2CH_2$—, —$CH_2O$—, —$CH_2S$—, —$CH_2N(R^{13})$—, —$CH_2CH_2CH_2$—, —$CH_2CH_2O$—, —$CH_2OCH_2$—, —$CH_2CH_2S$—, —$CH_2SCH_2$—, —$CH_2CH_2N(R^{13})$—, —$CH_2N(R^{13})CH_2$—, —$CH_2CH_2CH_2CH_2$—, —$CH_2CH_2CH_2O$—, —$CH_2CH_2CH_2S$— or —$CH_2CH_2CH_2N(R^{13})$—, in this case, the hydrogen atom bonded to each carbon atom forming the ring may be arbitrarily substituted with halogen atom, cyano, nitro, $C_1$-$C_4$alkyl, $C_1$-$C_4$haloalkyl, $C_1$-$C_4$alkoxy or $C_1$-$C_6$alkylthio, E-1 to E-50 are saturated heterocyclic rings of the following formulae, repectively

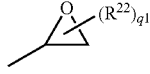
E-1

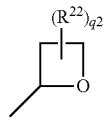
E-2

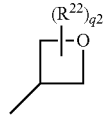
E-3

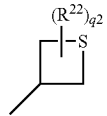
E-4

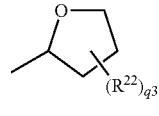
E-5

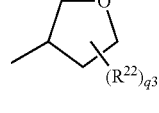
E-6

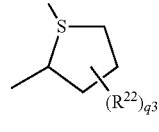
E-7

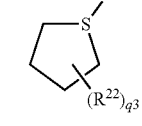
E-8

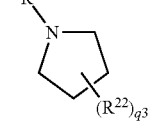
E-9

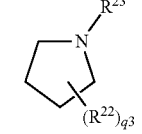
E-10

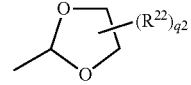
E-11

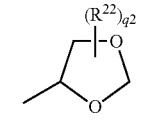
E-12

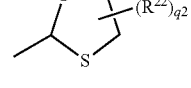
E-13

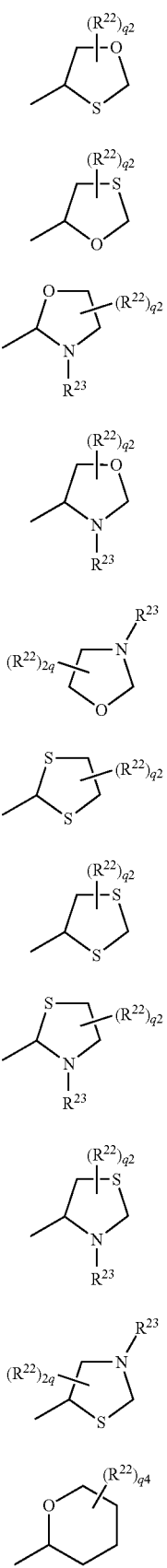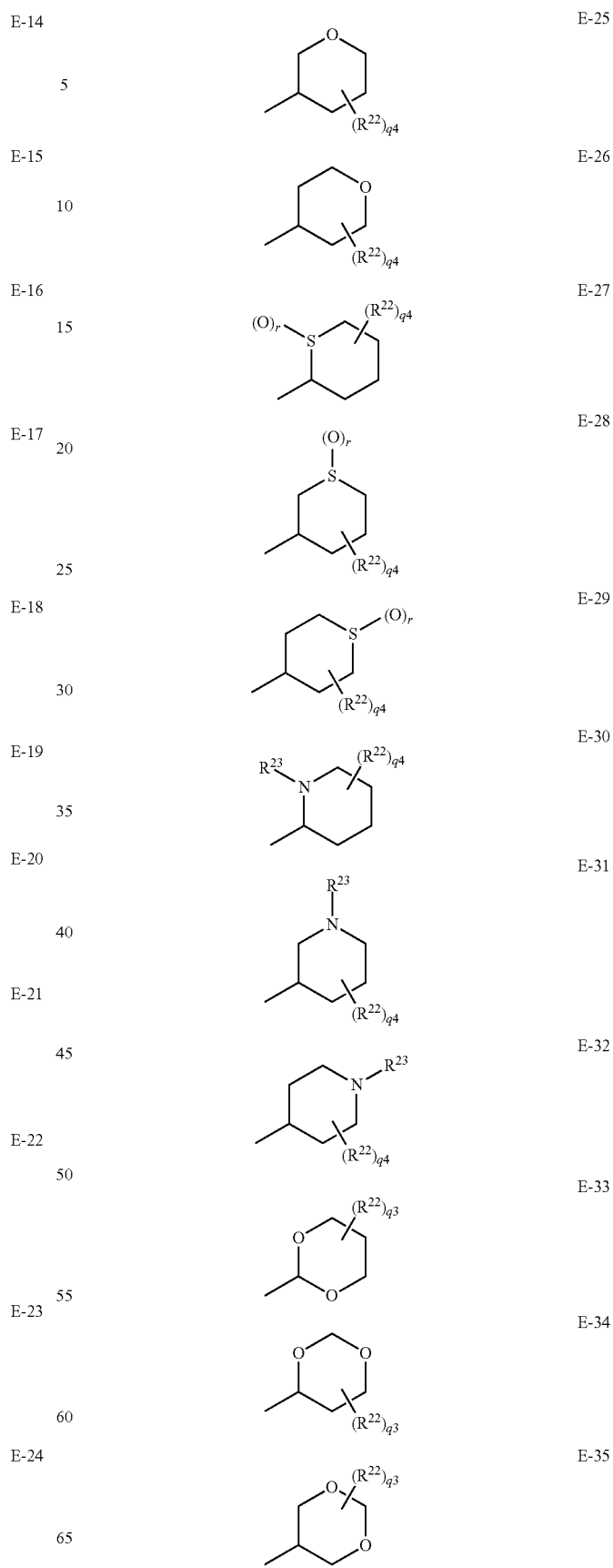

-continued

E-36 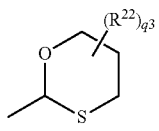

E-37 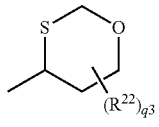

E-38 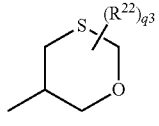

E-39 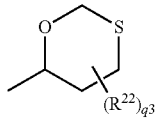

E-40 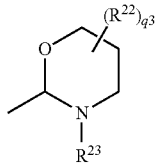

E-41 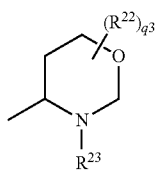

E-42 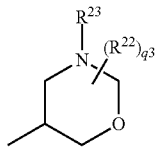

E-43 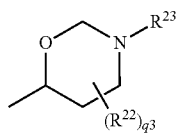

E-44 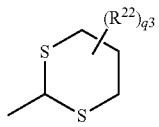

E-45 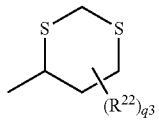

E-46 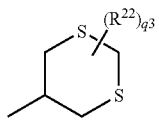

-continued

E-47 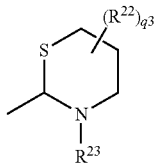

E-48 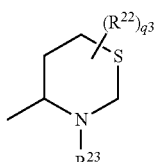

E-49 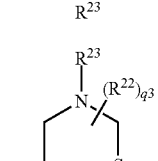

E-50 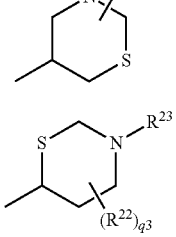

$R^4$ is halogen atom, cyano, $C_3$-$C_8$cycloalkyl, $C_3$-$C_8$halocycloalkyl, E-5 to E-50, —OH, —OR$^5$, —SH, —S(O)$_r$R$^5$, —N(R$^7$)R$^6$, —N(R$^7$)C(O)R$^{9a}$, —N(R$^7$)C(O)OR$^{9a}$, —N(R$^7$)C(O)SR$^{9a}$, —N(R$^7$)C(S)OR$^{9a}$, —N(R$^7$)C(S)SR$^{9a}$, —N(R$^7$)S(O)$_2$R$^{9a}$, —C(O)OR$^9$, —C(O)N(R$^{10}$)R$^9$, —Si(R$^{12a}$)(R$^{12b}$)R$^{12}$, phenyl, phenyl substituted with (Z)$_{p1}$ or D-1 to D-65, $R^5$ is $C_1$-$C_6$alkyl, $C_1$-$C_6$alkyl arbitrarily substituted with R$^{24}$, $C_3$-$C_8$cycloalkyl, $C_3$-$C_8$cycloalkyl arbitrarily substituted with R$^{24}$, E-3 to E-10, E-24 to E-32, E-35, E-46, $C_2$-$C_6$alkenyl, $C_2$-$C_6$alkenyl arbitrarily substituted with R$^{24}$, $C_3$-$C_8$cycloalkenyl, $C_3$-$C_8$halocycloalkenyl, $C_3$-$C_6$alkynyl, $C_3$-$C_6$alkynyl arbitrarily substituted with R$^{24}$, $C_1$-$C_6$alkylcarbonyl, $C_1$-$C_6$alkoxycarbonyl, phenyl, phenyl substituted with (Z)$_{p1}$, D-1 to D-4, D-6 to D-13, D-15 to D-23, D-25 to D-37, D-39, D-40, D-42, D-43, D-45, D-47, D-50 to D-64 or D-65, $R^6$ is $C_1$-$C_6$alkyl, $C_1$-$C_6$alkyl arbitrarily substituted with R$^{24}$, $C_3$-$C_8$cycloalkyl, $C_3$-$C_8$halocycloalkyl, $C_3$-$C_6$alkenyl, $C_3$-$C_6$haloalkenyl, $C_3$-$C_6$alkynyl, $C_3$-$C_6$haloalkynyl, —CHO, —C(O)R$^9$, —C(O)OR$^9$, —C(O)SR$^9$, —C(O)NH$_2$, —C(O)N(R$^{10}$)R$^9$, —C(S)OR$^9$, —C(S)SR$^9$, —C(S)NH$_2$, —C(S)N(R$^{10}$)R$^9$, —C(O)C(O)R$^9$, —C(O)C(O)OR$^9$, —OH, —S(O)$_2$R$^9$, —S(O)$_2$N(R$^{10}$)R$^9$, —P(O)(OR$^{21}$)$_2$ or —P(S)(OR$^{21}$)$_2$, $R^7$ is hydrogen atom, $C_1$-$C_6$alkyl, $C_1$-$C_6$alkyl arbitrarily substituted with R$^{24}$, $C_3$-$C_8$cycloalkyl, $C_3$-$C_6$alkenyl, $C_3$-$C_6$haloalkenyl, $C_3$-$C_6$alkynyl, $C_3$-$C_6$haloalkynyl, —CHO, $C_1$-$C_6$alkylcarbonyl, $C_1$-$C_6$haloalkylcarbonyl or $C_1$-$C_6$alkoxycarbonyl, or R$^7$ together with R$^6$ may form 3- to 7-membered ring together with the nitrogen atom bonding them by forming $C_2$-$C_6$alkylene chain, in this case, the alkylene chain may contain one oxygen atom, sulfur atom or nitrogen atom, and may be arbitrarily substituted with halogen atom, $C_1$-$C_6$alkyl, $C_1$-$C_6$haloalkyl, oxo or thioxo, $R^8$ is $C_1$-$C_6$alkyl, $C_1$-$C_6$haloalkyl, $C_3$-$C_6$alkenyl, phenyl or phenyl substituted with (Z)$_{p1}$, R⁹ is C₁-C₆alkyl, C₁-C₆alkyl arbitrarily substituted with R²⁴, C₃-C₈cycloalkyl, C₃-C₈halocycloalkyl, E-1 to E-50, C₃-C₆alkenyl, C₃-C₆haloalkenyl, C₃-C₆alkynyl or C₃-C₆haloalkynyl, R⁹ᵃ is phenyl, phenyl substituted with (Z)$_{p1}$ or D-1 to D-65, R¹⁰ is hydrogen atom, C₁-C₆alkyl, C₁-C₆haloalkyl, C₃-C₆cycloalkyl C₁-C₄alkyl, C₁-C₆alkoxy C₁-C₄alkyl, C₁-C₆alkylthio C₁-C₄alkyl, cyano C₁-C₆alkyl, C₃-C₆alkenyl or C₃-C₆alkynyl, or R¹⁰ together with R⁹ may form 3- to 7-membered ring with the nitrogen atom bonding them by forming C₂-C₆alkylene chain, in this case, the alkylene chain may contain one oxygen atom, sulfur atom or nitrogen atom, and may be arbitrarily substituted with halogen atom, C₁-C₆alkyl, C₁-C₆alkoxy, —CHO, C₁-C₆alkylcarbonyl or C₁-C₆alkoxycarbonyl, R¹¹ is hydrogen atom, C₁-C₆alkyl, C₁-C₆haloalkyl, phenyl C₁-C₄alkyl, phenyl C₁-C₄alkyl substituted with (Z)$_{p1}$, C₃-C₆alkenyl, C₃-C₆haloalkenyl, C₃-C₆alkynyl or C₃-C₆haloalkynyl, R¹² is C₁-C₆alkyl, C₁-C₆haloalkyl, C₁-C₆alkoxy, phenyl or phenyl substituted with (Z)$_{p1}$, R¹²ᵃ and R¹²ᵇ independently of each other are C₁-C₆alkyl, C₁-C₆haloalkyl or C₁-C₆alkoxy, R¹³ is hydrogen atom, C₁-C₆alkyl, C₁-C₆haloalkyl, C₁-C₆alkoxycarbonyl C₁-C₄alkyl, C₁-C₆haloalkoxycarbonyl C₁-C₄alkyl, phenyl C₁-C₄alkyl, phenyl C₁-C₄alkyl substituted with (Z)$_{p1}$, C₂-C₆alkenyl, C₂-C₆haloalkenyl, C₃-C₆alkynyl, C₃-C₆haloalkynyl, C₁-C₆alkoxy, C₁-C₆alkoxycarbonyl, C₁-C₆haloalkoxycarbonyl, phenyl or phenyl substituted with (Z)$_{p1}$, further, in case where Z is present in an adjacent position of R¹³, the adjacent R¹³ and Z may form 6-membered ring together with the atom bonding them by forming —CH₂CH₂CH₂CH₂—, —CH=CH—CH=CH—, —N=CH—CH=CH—, —CH=N—CH=CH—, —CH=CH—N=CH— or —CH=CH—CH=N—, in this case, hydrogen atoms bonded to each carbon atom forming the ring may be arbitrarily substituted with halogen atom, C₁-C₄alkyl or C₁-C₄haloalkyl, R¹⁴ is cyano, nitro, C₃-C₈cycloalkyl, C₃-C₈halocycloalkyl, hydroxy C₃-C₆cycloalkyl, C₁-C₄alkoxy C₃-C₆cycloalkyl, E-10 to E-12, E-19, E-24 to E-29, E-31 to E-33, E-44, —OR²⁵, —N(R²⁶)R²⁵, —SH, —S(O)$_r$R²⁷, C₅-C₈cycloalkenyl, C₅-C₈halocycloalkenyl, —CHO, —C(O)R²⁸, —C(O)OH, —C(O)OR²⁸, —C(O)SR²⁸, —C(O)NH₂, —C(O)N(R²⁹)R²⁸, —C(S)OR²⁸, —C(S)SR²⁸, —C(S)NH₂, —C(S)N(R²⁹)R²⁸, —CH=NOR³⁰, —C(R²⁸)=NOR³⁰, —C(=NR²⁹)OR²⁸, —C(=NR²⁹)SR²⁸, —C(=NR²⁹)N(R²⁹ᵃ)R²⁸ᵃ, —C(=NOR³⁰)N(R²⁹ᵃ)R²⁸ᵃ, —C(O)C(O)OR²⁸, —SO₂OH, —SO₂NH₂, —SO₂N(R²⁹)R²⁸, —Si(R¹²ᵃ)(R¹²ᵇ)R¹², —P(O)(OR²¹)₂, —P(S)(OR²¹)₂, —P(phenyl)₂, —P(O)(phenyl)₂, M-1 to M-48, phenyl, phenyl substituted with (Z)$_{p1}$, naphthyl, D-1 to D-4, D-15 to D-17, D-21 to D-23, D-52 to D-58 or D-59, M-1 to M-48 are partially saturated heterocyclic rings of the following formulae, respectively

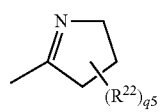
M-1

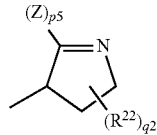
M-2

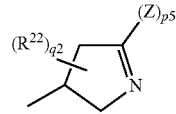
M-3

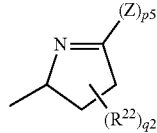
M-4

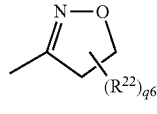
M-5

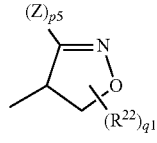
M-6

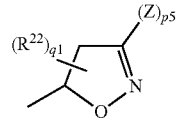
M-7

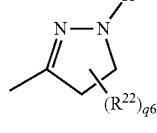
M-8

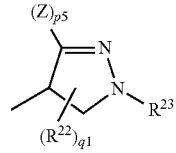
M-9

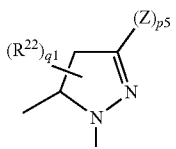
M-10

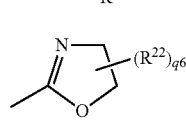
M-11

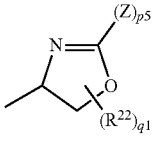
M-12

| | |
|---|---|
| 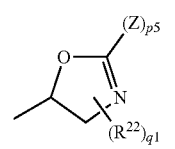 | M-13 |
| 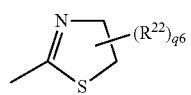 | M-14 |
| 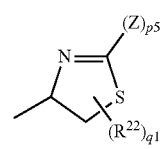 | M-15 |
| 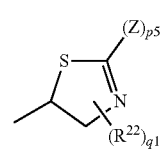 | M-16 |
| 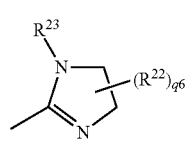 | M-17 |
| 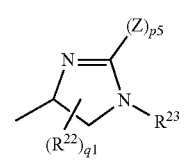 | M-18 |
| 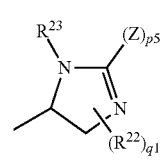 | M-19 |
| 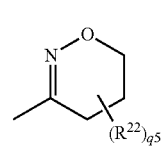 | M-20 |
| 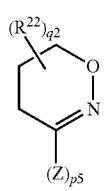 | M-21 |
| 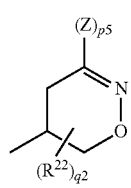 | M-22 |
| | |
|---|---|
| 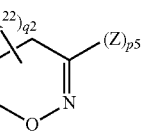 | M-23 |
| 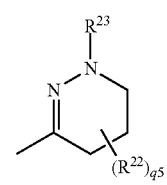 | M-24 |
| 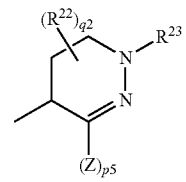 | M-25 |
| 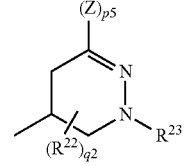 | M-26 |
| 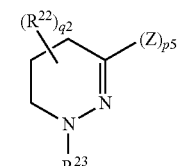 | M-27 |
| 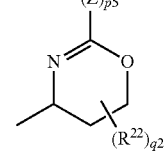 | M-28 |
| 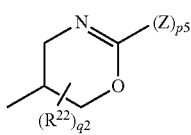 | M-29 |
| 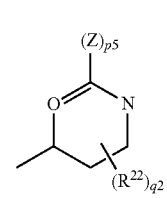 | M-30 |
| | M-31 |

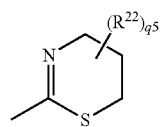 M-32

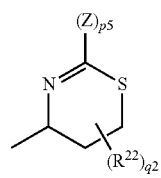 M-33

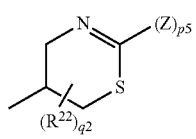 M-34

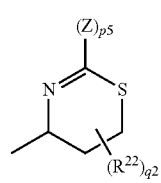 M-35

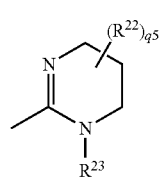 M-36

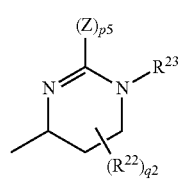 M-37

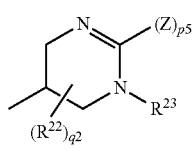 M-38

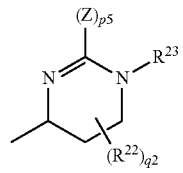 M-39

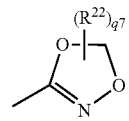 M-40

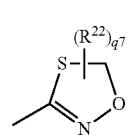 M-41

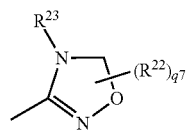 M-42

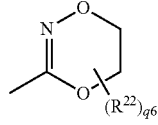 M-43

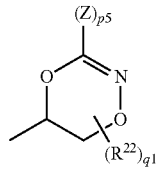 M-44

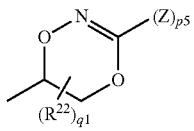 M-45

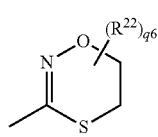 M-46

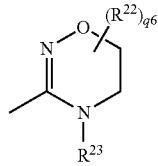 M-47

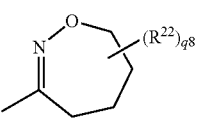 M-48

$R^{14a}$ is cyano, nitro, —$OR^{25}$, —$N(R^{26})R^{25}$, —$S(O)_rR^{27}$, —CHO, —$C(O)R^{28}$, —$C(O)OR^{28}$, —$C(O)SR^{28}$, —$C(O)NH_2$, —$C(S)OR^{28}$, —$C(S)SR^{28}$, —$C(S)NH_2$, —$C(O)C(O)OR^{28}$, —$Si(R^{12a})(R^{12b})R^{12}$, —$P(O)(OR^{21})_2$, —$P(S)(OR^{21})_2$ or phenyl, $R^{14b}$ is $C_1$-$C_6$alkyl or $C_3$-$C_6$cycloalkyl, $R^{15}$ is $C_1$-$C_6$alkyl, $C_1$-$C_6$alkyl arbitrarily substituted with $R^{31}$, $C_3$-$C_8$cycloalkyl, $C_3$-$C_8$halocycloalkyl, E-1 to E-50, $C_2$-$C_6$alkenyl, $C_2$-$C_6$haloalkenyl, $C_3$-$C_8$cycloalkenyl, $C_3$-$C_8$halocycloalkenyl, $C_2$-$C_6$alkynyl, $C_2$-$C_6$haloalkynyl, phenyl, phenyl substituted with $(Z)_{p1}$, naphthyl or D-1 to D-65, $R^{16}$ is hydrogen atom, $C_1$-$C_6$alkyl, $C_1$-$C_6$haloalkyl, $C_3$-$C_6$cycloalkyl $C_1$-$C_4$alkyl, $C_1$-$C_6$alkoxy $C_1$-$C_4$alkyl, $C_1$-$C_6$alkylthio $C_1$-$C_4$alkyl, cyano$C_1$-$C_6$alkyl, $C_3$-$C_6$alkenyl or $C_3$-$C_6$alkynyl, or $R^{16}$ together with $R^{15}$ may form 3- to 7-membered ring with the nitrogen atom bonding them by forming $C_2$-$C_6$alkylene chain, in this case, the alkylene chain may contain one oxygen atom, sulfur atom or nitrogen atom, and may be arbitrarily substituted with halogen atom, $C_1$-$C_6$alkyl, $C_1$-$C_6$alkoxy, —CHO, $C_1$-$C_6$alkylcarbonyl or $C_1$-$C_6$alkoxycarbonyl, $R^{17}$ is hydrogen atom, $C_1$-$C_6$alkyl, $C_1$-$C_6$alkyl arbitrarily substituted with $R^{14}$, $C_3$-$C_6$cycloalkyl, $C_3$-$C_8$halocycloalkyl, E-6, E-8, E-10, E-25, E-26, E-28, E-29, E-31, E-32, $C_3$-$C_6$alkenyl, $C_3$-$C_6$haloalkenyl, $C_3$-$C_6$alkynyl, $C_3$-$C_6$haloalkynyl, —CHO, —C(O)$R^{28}$, —C(O)O$R^{28}$, —C(O)S$R^{28}$, —C(O)NH$_2$, —C(O)N($R^{29}$)$R^{28}$, —C(S)O$R^{28}$, —C(S)S$R^{28}$, —C(S)NH$_2$, —C(S)N($R^{29}$)$R^{28}$, —S(O)$_2$$R^{28}$, —S(O)$_2$NH$_2$, —S(O)$_2$N($R^{29}$)$R^{28}$, —P(O)(O$R^{21}$)$_2$, —P(S)(O$R^{21}$)$_2$, phenyl, phenyl substituted with (Z)$_{p1}$, D-1 to D-13, D-15 ro D-25, D-30 to D-37, D-42, D-43, D-45, D-50 to D-64 or D-65, $R^{17a}$ is hydrogen atom, $C_1$-$C_6$alkyl, $C_1$-$C_6$haloalkyl, $C_1$-$C_6$alkoxy $C_1$-$C_4$alkyl, $C_1$-$C_6$alkylthio $C_1$-$C_4$alkyl, $C_1$-$C_4$alkylsulfonyl $C_1$-$C_4$alkyl, $C_1$-$C_4$alkoxycarbonyl $C_1$-$C_4$alkyl, phenyl $C_1$-$C_4$alkyl, phenyl $C_1$-$C_4$alkyl substituted with (Z)$_{p1}$, $C_3$-$C_6$cycloalkyl, E-1 to E-50, phenyl $C_2$-$C_4$alkenyl, di($C_1$-$C_6$alkyl)amino, phenyl, phenyl substituted with (Z)$_{p1}$ or D-1 to D-65, $R^{17b}$ is hydrogen atom, $C_1$-$C_6$alkyl, $C_1$-$C_6$alkoxy, $C_1$-$C_6$alkylthio or di($C_1$-$C_6$alkyl)amino, or $R^{17b}$ together with $R^{17a}$ may form 4- to 6-membered ring with the carbon atom bonding them by forming $C_3$-$C_5$alkylene chain or $C_4$-$C_5$alkenylene chain, in this case, the alkylene chain or the alkenylene chain may contain one oxygen atom, sulfur atom or nitrogen atom, and may be arbitrarily substituted with halogen atom, $C_1$-$C_6$alkyl, $C_1$-$C_6$haloalkyl, —CHO, $C_1$-$C_6$alkylcarbonyl or $C_1$-$C_6$alkoxycarbonyl, $R^{18}$ is hydrogen atom, $C_1$-$C_6$alkyl, $C_1$-$C_6$haloalkyl, $C_1$-$C_6$alkoxy $C_1$-$C_4$alkyl, $C_1$-$C_4$haloalkoxy $C_1$-$C_4$alkyl, $C_1$-$C_4$alkylthio $C_1$-$C_4$alkyl, $C_1$-$C_4$haloalkylthio $C_1$-$C_4$alkyl, $C_1$-$C_4$alkylsulfonyl $C_1$-$C_4$alkyl, $C_1$-$C_6$haloalkylsulfonyl $C_1$-$C_4$alkyl, cyano$C_1$-$C_4$alkyl, $C_1$-$C_4$alkoxycarbonyl $C_1$-$C_4$alkyl, phenyl $C_1$-$C_4$alkyl, $C_2$-$C_6$alkenyl, $C_2$-$C_6$haloalkenyl, $C_3$-$C_6$alkynyl, $C_3$-$C_6$haloalkynyl, —CHO, —C(O)$R^{15}$, —C(O)O$R^{15}$, —C(O)S$R^{15}$, —C(S)O$R^{15}$—C(S)S$R^{15}$, $C_1$-$C_6$alkylsulfonyl or $C_1$-$C_6$haloalkylsulfonyl, or $R^{18}$ together with $R^{17}$ may form 5- to 6-membered ring with the nitrogen atom bonding them by forming $C_4$-$C_5$alkylene chain, in this case, the alkylene chain may contain one oxygen atom, sulfur atom or nitrogen atom, and may be arbitrarily substituted with $C_1$-$C_6$alkyl, $C_1$-$C_6$alkoxy $C_1$-$C_6$alkyl, —CHO, $C_1$-$C_6$alkylcarbonyl or $C_1$-$C_6$alkoxycarbonyl, $R^{19}$ is $C_1$-$C_{12}$alkyl, $C_1$-$C_{12}$haloalkyl, $C_1$-$C_{12}$alkoxy $C_1$-$C_{12}$alkyl, cyano$C_1$-$C_{12}$alkyl, $C_1$-$C_{12}$alkoxycarbonyl $C_1$-$C_{12}$alkyl, phenyl $C_1$-$C_6$alkyl, phenyl $C_1$-$C_6$alkyl substituted with (Z)$_{p1}$, $C_3$-$C_{12}$alkenyl, $C_3$-$C_{12}$haloalkenyl, $C_3$-$C_{12}$alkynyl, $C_3$-$C_{12}$haloalkynyl, $C_1$-$C_{12}$alkylcarbonyl, $C_1$-$C_{12}$alkoxycarbonyl, —C(O)ON=C(CH$_3$)SCH$_3$, —C(O)ON=C(SCH$_3$)C(O)N(CH$_3$)$_2$, phenyl or phenyl substituted with (Z)$_{p1}$ $R^{20}$ is $C_1$-$C_{12}$alkyl, $C_1$-$C_{12}$haloalkyl, $C_1$-$C_{12}$alkoxy $C_1$-$C_{12}$alkyl, cyano$C_1$-$C_{12}$alkyl, $C_1$-$C_{12}$alkoxycarbonyl $C_1$-$C_{12}$alkyl, phenyl $C_1$-$C_6$alkyl, phenyl $C_1$-$C_6$alkyl substituted with (Z)$_{p1}$, $C_3$-$C_{12}$alkenyl, $C_3$-$C_{12}$haloalkenyl, $C_3$-$C_{12}$alkynyl, $C_3$-$C_{12}$haloalkynyl, phenyl or phenyl substituted with (Z)$_{p1}$, or $R^{20}$ together with $R^{19}$ may form 5- to 8-membered ring with the nitrogen atom bonding them by forming $C_4$-$C_7$alkylene chain, in this case, the alkylene chain may contain one oxygen atom or sulfur atom, and may be arbitrarily substituted with $C_1$-$C_4$alkyl or $C_1$-$C_4$alkoxy, $R^{21}$ is $C_1$-$C_6$alkyl or $C_1$-$C_6$haloalkyl, $R^{22}$ is halogen atom, cyano, $C_1$-$C_6$alkyl, $C_1$-$C_6$haloalkyl, hydroxy$C_1$-$C_6$alkyl, $C_1$-$C_4$alkoxy$C_1$-$C_4$alkyl, $C_1$-$C_4$alkoxycarbonyl $C_1$-$C_4$alkyl, $C_1$-$C_4$alkoxy, $C_1$-$C_6$alkylthio, $C_1$-$C_6$alkylamino, di($C_1$-$C_4$alkyl)amino, $C_1$-$C_6$alkoxycarbonyl, phenyl or phenyl substituted with (Z)$_{p1}$, when q1 to q8 are integers of 2 or more, each $R^{22}$ may be identical with or different from each other, further, when two $R^{22}$S are present on the same carbon atom, the two $R^{22}$S together may form oxo, thioxo, imino, $C_1$-$C_6$alkylimino, $C_1$-$C_6$alkoxyimino or $C_1$-$C_6$alkylidene, $R^{23}$ is hydrogen atom, $C_1$-$C_6$alkyl, $C_1$-$C_6$alkyl arbitrarily substituted with $R^{31}$, $C_3$-$C_6$cycloalkyl, $C_3$-$C_6$alkenyl, $C_3$-$C_6$haloalkenyl, $C_3$-$C_6$alkynyl, —OH, benzyloxy, —CHO, —C(O)$R^{32}$, —C(O)O$R^{32}$, —C(O)S$R^{32}$, —C(O)NHR$^{33}$, —C(O)N($R^{33}$)$R^{32}$, —C(S)NHR$^{33}$, —C(S)N($R^{33}$)$R^{32}$, —S(O)$_2$$R^{32}$, —P(O)(O$R^{21}$)$_2$, —P(S)(O$R^{21}$)$_2$, phenyl, phenyl substituted with (Z)$_{p1}$ or D-5, $R^{24}$ is halogen atom, cyano, $C_3$-$C_8$cycloalkyl, $C_3$-$C_8$halocycloalkyl, E-1 to E-50, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfonyl, $C_1$-$C_6$haloalkylsulfonyl, $C_1$-$C_6$alkylamino, di($C_1$-$C_6$alkyl)amino, —CHO, $C_1$-$C_6$alkylcarbonyl, $C_1$-$C_6$haloalkylcarbonyl, $C_1$-$C_6$alkoxycarbonyl, $C_1$-$C_6$haloalkoxycarbonyl, $C_1$-$C_6$alkylaminocarbonyl, di($C_1$-$C_6$alkyl)aminocarbonyl, phenyl, phenyl substituted with (Z)$_{p1}$, or D-1 to D-65, $R^{25}$ is hydrogen atom, $C_1$-$C_8$alkyl, $C_1$-$C_8$alkyl arbitrarily substituted with $R^{31}$, $C_3$-$C_8$cycloalkyl, $C_3$-$C_8$cycloalkyl arbitrarily substituted with $R^{31}$, E-3 to E-10, E-24 to E-32, E-35, E-46, $C_3$-$C_8$alkenyl, $C_3$-$C_8$alkenyl arbitrarily substituted with $R^{31}$, $C_3$-$C_8$alkynyl, $C_3$-$C_8$alkynyl arbitrarily substituted with $R^{31}$, —CHO, —C(O)$R^{32}$, —C(O)O$R^{32}$, —C(O)S$R^{32}$, —C(O)NHR$^{33}$, —C(O)N($R^{33}$)$R^{32}$, —C(S)$R^{32}$, —C(S)OR$^{32}$, —C(S)SR$^{32}$, —C(S)NHR$^{33}$, —C(S)N($R^{33}$)$R^{32}$, —C(O)C(O)$R^{32}$, —C(O)C(O)O$R^{32}$, —SO$_2$$R^{32}$, —S(O)$_2$N($R^{33}$)$R^{32}$, —Si($R^{12a}$)($R^{12b}$)$R^{12}$, —P(O)(O$R^{21}$)$_2$, —P(S)(O$R^{21}$)$_2$, phenyl, phenyl substituted with (Z)$_{p1}$, D-1 to D-4, D-6 to D-13, D-15 to D-23, D-25 to D-37, D-39, D-40, D-42, D-43, D-45, D-47, D-50 to D-64 or D-65, $R^{26}$ is hydrogen atom, $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, $C_3$-$C_6$cyclloalkyl, $C_3$-$C_6$alkenyl, $C_3$-$C_6$alkynyl, $C_1$-$C_6$alkoxy, phenyl or phenyl substituted with (Z)$_{p1}$, or $R^{26}$ together with $R^{25}$ may form 3- to 7-membered ring with the nitrogen atom bonding them by forming $C_2$-$C_6$alkylene chain, in this case, the alkylene chain may contain one oxygen atom, sulfur atom or nitrogen atom, and may be arbitrarily substituted with halogen atom, $C_1$-$C_6$alkyl, $C_1$-$C_6$haloalkyl, $C_1$-$C_6$alkoxy, —CHO, $C_1$-$C_6$alkylcarbonyl, $C_1$-$C_6$alkoxycarbonyl, phenyl, phenyl substituted with (Z)$_{p1}$, oxo or thioxo, $R^{27}$ is $C_1$-$C_8$alkyl, $C_1$-$C_8$alkyl arbitrarily substituted with $R^{31}$, $C_3$-$C_8$cycloalkyl, $C_3$-$C_8$cycloalkyl arbitrarily substituted with $R^{31}$, E-3, E-5 to E-10, E-24 to E-32, E-35, E-46, $C_3$-$C_8$alkenyl, $C_3$-$C_8$alkenyl arbitrarily substituted with $R^{31}$, $C_3$-$C_8$alkynyl, $C_3$-$C_8$alkynyl arbitrarily substituted with $R^{31}$, —CHO, —C(O)$R^{32}$, —C(O)O$R^{32}$, —C(O)S$R^{32}$, —C(O)NHR$^{33}$, —C(O)N($R^{33}$)$R^{32}$, —C(S)$R^{32}$, —C(S)OR$^{32}$, —C(S)SR$^{32}$, —C(S)NHR$^{33}$—C(S)N($R^{33}$)$R^{32}$, —C(O)C(O)$R^{32}$, —C(O)C(O)O$R^{32}$, —SH, $C_1$-$C_6$alkylthio, $C_1$-$C_8$haloalkylthio, phenylthio, phenylthio substituted with (Z)$_{p1}$, —P(O)(O$R^{21}$)$_2$, —P(S)(O$R^{21}$)$_2$, phenyl or phenyl substituted with (Z)$_{p1}$, D-18, D-21, D-25, D-30 to D-35, D-50, D-52, D-55 or D-56, $R^{28}$ and $R^{28a}$ independently of each other are $C_1$-$C_6$alkyl, $C_1$-$C_6$alkyl arbitrarily substituted with $R^{31}$, $C_3$-$C_8$cycloalkyl, $C_3$-$C_8$cycloalkyl arbitrarily substituted with $R^{31}$, $C_2$-$C_8$alkenyl $C_3$-$C_8$cycloalkyl, $C_2$-$C_6$haloalkenyl $C_3$-$C_8$cycloalkyl, E-1 to E-50, $C_2$-$C_8$alkenyl, $C_2$-$C_8$alkenyl arbitrarily substituted with $R^{31}$, $C_2$-$C_8$alkynyl, $C_2$-$C_8$alkynyl arbitrarily substituted with $R^{31}$, phenyl, phenyl substituted with (Z)$_{p1}$ or D-1 to D-65, $R^{29}$ and $R^{29a}$ independently of each other are hydrogen atom, $C_1$-$C_6$alkyl, $C_1$-$C_6$alkyl arbitrarily substituted with $R^{31}$, $C_3$-$C_6$alkenyl, $C_3$-$C_6$haloalkenyl, $C_3$-$C_6$alkynyl, $C_3$-$C_6$haloalkynyl, phenyl or phenyl substituted with $(Z)_{p1}$, or $R^{29}$ together with $R^{28}$ may form 3- to 6-membered ring with the nitrogen atom bonding them by forming $C_2$-$C_5$alkylene chain, in this case, the alkylene chain may contain one oxygen atom, sulfur atom or nitrogen atom, and may be arbitrarily substituted with halogen atom, $C_1$-$C_6$alkyl, $C_1$-$C_6$alkoxy, —CHO, $C_1$-$C_6$alkylcarbonyl, $C_1$-$C_6$alkoxycarbonyl, phenyl or phenyl substituted with $(Z)_{p1}$, $R^{30}$ is $C_1$-$C_8$alkyl, $C_1$-$C_8$alkyl arbitrarily substituted with $R^{31}$, $C_3$-$C_8$cycloalkyl, $C_3$-$C_8$alkenyl, $C_3$-$C_8$alkenyl arbitrarily substituted with $R^{31}$, $C_3$-$C_8$alkynyl or $C_3$-$C_8$alkynyl arbitrarily substituted with $R^{31}$, $R^{31}$ is halogen atom, cyano, nitro, $C_3$-$C_8$cycloalkyl, $C_3$-$C_8$halocycloalkyl, E-5 to E-8, E-11 to E-15, E-19, E-20, E-24 to E-29, E-33 to E-39, E-44 to E-46, —OH, —$OR^{32}$, —$OC(O)R^{32}$, —$OC(O)OR^{32}$, —$OC(O)NHR^{33}$, —$OC(O)N(R^{33})R^{32}$, —$OC(S)NHR^{33}$—$OC(S)N(R^{33})R^{32}$, —SH, —$S(O)_rR^{32}$, —$SC(O)R^{32}$, —$SC(O)OR^{32}$, —$SC(O)NHR^{33}$, —$SC(O)N(R^{33})R^{32}$, —$SC(S)NHR^{33}$, —$SC(S)N(R^{33})R^{32}$, —$NHR^{33}$, —$N(R^{33})R^{32}$, —$N(R^{33})CHO$, —$N(R^{33})C(O)R^{32}$, —$N(R^{33})C(O)OR^{32}$, —$N(R^{33})C(O)NHR^{33a}$, —$N(R^{33})C(O)N(R^{33a})R^{32}$, —$N(R^{33})C(S)NHR^{33a}$, —$N(R^{33})C(S)N(R^{33a})R^{32}$, —CHO, —$C(O)R^{32}$, —$C(O)OH$, —$C(O)OR^{32}$, —$C(O)SR^{32}$, —$C(O)NHR^{33}$, —$C(O)N(R^{33})R^{32}$, —$C(O)C(O)OR^{32}$, —$Si(R^{12a})(R^{12b})R^{12}$—$P(O)(OR^{21})_2$, —$P(S)(OR^{21})_2$, —$P(phenyl)_2$, —$P(O)(phenyl)_2$, phenyl, phenyl substituted with $(Z)_{p1}$, or D-1 to D-65, $R^{32}$ is $C_1$-$C_6$alkyl, $C_1$-$C_6$haloalkyl, $C_1$-$C_6$alkyl arbitrarily substituted with $R^{34}$, $C_3$-$C_6$cycloalkyl, $C_3$-$C_6$halocycloalkyl, $C_2$-$C_6$alkenyl $C_3$-$C_8$cycloalkyl, $C_2$-$C_6$haloalkenyl $C_3$-$C_8$cycloalkyl, E-5 to E-8, E-24 to E-29, $C_2$-$C_8$alkenyl, $C_2$-$C_8$haloalkenyl, $C_3$-$C_8$cycloalkenyl, $C_3$-$C_8$halocycloalkenyl, $C_2$-$C_8$alkynyl, $C_2$-$C_6$haloalkynyl, phenyl, phenyl substituted with $(Z)_{p1}$ or D-1 to D-65, $R^{33}$ and $R^{33a}$ independently of each other are hydrogen atom, $C_1$-$C_6$alkyl, $C_1$-$C_6$haloalkyl, $C_3$-$C_8$cycloalkyl, $C_3$-$C_6$alkenyl, $C_3$-$C_6$alkynyl, $C_1$-$C_6$alkylcarbonyl, $C_1$-$C_6$haloalkylcarbonyl, $C_1$-$C_6$alkoxycarbonyl, $C_1$-$C_6$haloalkoxycarbonyl, phenoxycarbonyl, phenoxycarbonyl substituted with $(Z)_{p1}$, phenylcarbonyl, phenylcarbonyl substituted with $(Z)_{p1}$, $C_1$-$C_6$alkylsulfonyl, $C_1$-$C_6$haloalkylsulfonyl, phenyl, phenyl substituted with $(Z)_{p1}$, D1 to D-4, D-6 to D-13, D-15 to D-23, D-25 to D-37, D-39, D-40, D-42, D-43, D-45, D-47, D-50 to D-64 or D-65, or $R^{33}$ together with $R^{32}$ may form 3- to 6-membered ring with the nitrogen atom bonding them by forming $C_2$-$C_5$alkylene chain, in this case, the alkylene chain may contain one oxygen atom, sulfur atom or nitrogen atom, and may be arbitrarily substituted with halogen atom, $C_1$-$C_6$alkyl, $C_1$-$C_6$alkoxy, —CHO, $C_1$-$C_6$alkylcarbonyl, $C_1$-$C_6$alkoxycarbonyl, phenyl or phenyl substituted with $(Z)_{p1}$, $R^{34}$ is cyano, $C_3$-$C_6$cycloalkyl, $C_3$-$C_6$halocycloalkyl, E-5 to E-8, E-24 to E-29, $C_1$-$C_4$alkoxy, $C_1$-$C_4$haloalkoxy, phenoxy, phenoxy substituted with $(Z)_{p1}$, $C_1$-$C_4$alkylthio, $C_1$-$C_4$haloalkylthio, $C_1$-$C_4$alkylsulfonyl, $C_1$-$C_4$haloalkylsulfonyl, phenylthio, phenylthio substituted with $(Z)_{p1}$, —$N(R^{36})R^{35}$, $C_1$-$C_6$alkylcarbonyl, $C_1$-$C_6$haloalkylcarbonyl, $C_1$-$C_6$alkoxycarbonyl, di($C_1$-$C_6$alkyl)aminocarbonyl, tri($C_1$-$C_4$alkyl)silyl, phenyl, phenyl substituted with $(Z)_{p1}$, naphthyl or D-1 to D-65, $R^{35}$ is hydrogen atom, $C_1$-$C_6$alkyl, $C_1$-$C_6$alkylcarbonyl, $C_1$-$C_6$haloalkylcarbonyl, $C_1$-$C_6$alkoxycarbonyl, phenylcarbonyl or phenylcarbonyl substituted with $(Z)_{p1}$, $R^{36}$ is hydrogen atom or $C_1$-$C_6$alkyl, m is an integer of 0 to 5, n is an integer of 0 to 4, p1 is an integer of 1 to 5, p2 is an integer of 0 to 4, p3 is an integer of 0 to 3, p4 is an integer of 0 to 2, p5 is an integer of 0 or 1, q1 is an integer of 0 to 3, q2 is an integer of 0 to 5, q3 is an integer of 0 to 7, q4 is an integer of 0 to 9, q5 is an integer of 0 to 6, q6 is an integer of 0 to 4, q7 is an integer of 0 to 2, q8 is an integer of 0 to 8, r is an integer of 0 to 2, and t is an integer of 0 or 1.

(2) The isoxazoline-substituted benzamide compound or the salt thereof as set forth in (1), wherein G is an aromatic 6-membered ring shown in any one of G-1, G-3 or G-4 or an aromatic 5-membered ring shown in any one of G-13, G-14, G-17, G-18, G-20, G-21 or G-22

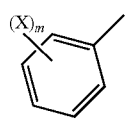
G-1

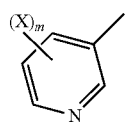
G-3

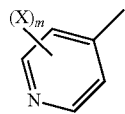
G-4

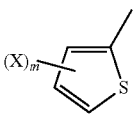
G-13

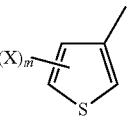
G-14

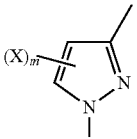
G-17

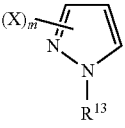
G-18

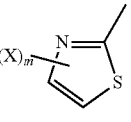
G-20

G-21

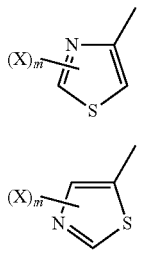

G-22

X is halogen atom, cyano, nitro, —SF$_5$, C$_1$-C$_6$alkyl, C$_1$-C$_6$alkyl arbitrarily substituted with R$^4$, C$_3$-C$_8$cycloalkyl, C$_3$-C$_8$haloycloalkyl, C$_2$-C$_6$alkenyl, C$_2$-C$_6$halolkenyl, C$_2$-C$_6$alkynyl, C$_2$-C$_6$halolkynyl, —OH, —OR$^5$, —OSO$_2$R$^5$, —S(O)$_r$R$^5$ or tri(C$_1$-C$_6$alkyl)silyl, when m is an integer of 2 or 3, each X may be identical with or different from each other, further, when two Xs are adjacent, the adjacent two Xs may form 5-membered or 6-membered ring together with carbon atoms to which the two Xs are bonded by forming —CF$_2$OCF$_2$—, —OCF$_2$O—, —CF$_2$OCF$_2$O— or —OCF$_2$CF$_2$O—, Y is halogen atom, cyano, nitro, C$_1$-C$_6$alkyl, C$_1$-C$_6$alkyl arbitrarily substituted with R$^4$, C$_2$-C$_6$alkynyl, tri(C$_1$-C$_6$alkyl)silylethynyl, —OR$^5$, —OSO$_2$R$^5$, —S(O)$_r$R$^5$, —NH$_2$, —N(R$^7$)R$^6$, —N=C(R$^9$)OR$^8$, —C(O)NH$_2$ or —C(S)NH$_2$, when n is 2, each Y may be identical with or different from each other, R$^1$ is —C(R$^{1b}$)=NOR$^{1a}$, M-5, M-20, —C(O)OR$^{1c}$, —C(O)SR$^{1c}$, —C(S)OR$^{1c}$, —C(S)SR$^{1c}$, —C(O)N(R$^{1e}$)R$^{1d}$, —C(S)N(R$^{1e}$)R$^{1d}$, —C(R$^{1b}$)=NN(R$^{1e}$)R$^{1f}$, phenyl, phenyl substituted with (Z)$_{p1}$, D-1 to D-5, D-7 to D-17, D-21 to D-45, D-47 to D-63 or D-65, R$^{1a}$ is hydrogen atom, C$_1$-C$_6$alkyl, C$_1$-C$_6$haloalkyl, C$_1$-C$_4$alkyl arbitrarily substituted with R$^{14}$, C$_3$-C$_6$cycloalkyl, E-4, E-6, E-8, E-10, E-25, E-26, E-28, E-29, E-31, E-32, E-35, C$_3$-C$_6$alkenyl, C$_3$-C$_6$haloalkenyl, C$_3$-C$_6$alkynyl, C$_3$-C$_6$haloalkynyl, phenylC$_3$-C$_6$alkynyl, phenyl or phenyl substituted with (Z)$_{p1}$, R$^{1b}$ is hydrogen atom, C$_1$-C$_6$alkyl, C$_1$-C$_6$haloalkyl, C$_1$-C$_4$alkoxyC$_1$-C$_4$alkyl, C$_1$-C$_4$alkylthioC$_1$-C$_4$alkyl or C$_3$-C$_6$cycloalkyl, R$^{1c}$ is C$_1$-C$_6$alkyl, C$_1$-C$_4$alkyl arbitrarily substituted with R$^{14}$, C$_3$-C$_6$cycloalkyl, E-5, E-6, E-8, E-10, E-25, E-26, E-28, E-29, E-31, E-32, E-35, C$_2$-C$_6$alkenyl, C$_3$-C$_6$haloalkenyl, C$_3$-C$_6$alkynyl, C$_3$-C$_6$haloalkynyl, phenyl or phenyl substituted with (Z)$_{p1}$, R$^{1d}$ is hydrogen atom, —C(O)R$^{15}$, —C(O)OR$^{15}$, —C(O)SR$^{15}$, —C(S)OR$^{15}$, —C(S)SR$^{15}$ or —S(O)$_2$R$^{15}$, R$^{1e}$ is hydrogen atom or C$_1$-C$_6$alkyl, R$^{1f}$ is C$_1$-C$_6$alkylcarbonyl or C$_1$-C$_6$alkoxycarbonyl, R$^2$ is C$_1$-C$_6$alkyl, —CH$_2$R$^{14a}$, E-5, E-24, C$_3$-C$_6$alkynyl, —C(O)R$^{15}$, —C(O)OR$^{15}$, —C(O)SR$^{15}$, —C(S)OR$^{15}$, —C(S)SR$^{15}$, —C(O)C(O)OR$^{15}$, C$_1$-C$_6$alkylthio, C$_1$-C$_6$haloalkylthio, phenylthio, C$_1$-C$_6$alkylsulfonyl, —SN(R$^{20}$)R$^{19}$, phenyl or phenyl substituted with (Z)$_{p1}$, further when R$^1$ is —C(R$^{1b}$)=NOR$^{1a}$, M-5, M-20 or —C(R$^{1b}$)=NN(R$^{1e}$)R$^{1f}$, R$^2$ may be hydrogen atom or C$_3$-C$_6$alkenyl, when R$^1$ is —C(O)OR$^{1c}$, —C(O)SR$^{1c}$, —C(S)OR$^{1c}$ or —C(S)SR$^{1c}$, R$^2$ may be hydrogen atom, when R$^1$ is —C(O)N(R$^{1e}$)R$^{1d}$ or —C(S)N(R$^{1e}$)R$^{1d}$, R$^2$ may be hydrogen atom, C$_1$-C$_6$haloalkyl, C$_3$-C$_6$cycloalkylC$_1$-C$_4$alkyl, C$_3$-C$_6$cycloalkyl or C$_3$-C$_6$alkenyl, when R$^1$ is phenyl, phenyl substituted with (Z)$_{p1}$ or D-1 to D-5, D7 to D-17, D21 to D-45, D-47 to D-63 or D-65, R$^2$ may be C$_1$-C$_6$haloalkyl, C$_3$-C$_6$cycloalkyl, C$_3$-C$_6$alkenyl, —C(O)NH$_2$, di(C$_1$-C$_6$alkyl)aminocarbonyl, —N(R$^{18}$)R$^{17}$ or —N=C(R$^{17b}$)R$^{17a}$, or R$^2$ together with R$^1$ may form =C(R$^{2b}$)R$^{2a}$, R$^{2a}$ is —OR$^{1c}$, —SR$^{1c}$ or di(C$_1$-C$_6$alkyl)amino, R$^{2b}$ is R$^{1b}$, C$_1$-C$_6$alkylthio, C$_1$-C$_6$haloalkylthio, —SCH$_2$R$^{14a}$, C$_3$-C$_6$alkenylthio, C$_3$-C$_6$haloalkenylthio, C$_3$-C$_6$alkynylthio, C$_3$-C$_6$haloalkynylthio or —SC(O)R$^{15}$, R$^3$ is C$_1$-C$_6$alkyl, C$_1$-C$_6$haloalkyl, C$_1$-C$_4$alkoxy C$_1$-C$_4$haloalkyl, C$_1$-C$_4$haloalkoxy C$_1$-C$_4$haloalkyl, C$_1$-C$_4$alkylthio C$_1$-C$_4$haloalkyl, C$_1$-C$_4$haloalkylthio C$_1$-C$_6$haloalkyl, cyano C$_1$-C$_6$haloalkyl, C$_3$-C$_6$cycloalkyl or C$_3$-C$_8$halocycloalkyl, Z is halogen atom, cyano, nitro, C$_1$-C$_6$alkyl, C$_1$-C$_6$haloalkyl, C$_1$-C$_6$alkoxy, C$_1$-C$_6$haloalkoxy, C$_1$-C$_6$alkylsulfonyloxy, C$_1$-C$_6$haloalkylsulfonyloxy, C$_1$-C$_6$alkylthio, C$_1$-C$_6$haloalkylthio, C$_1$-C$_6$alkylsulfinyl, C$_1$-C$_6$haloalkylsulfinyl, C$_1$-C$_6$alkylsulfonyl, C$_1$-C$_6$haloalkylsulfonyl, C$_1$-C$_6$alkoxycarbonyl, —C(O)NH$_2$, —C(S)NH$_2$ or phenyl, when p1, p2, p3 or p4 is an integer of 2 or more, each Z may be identical with or different from each other, further, when two Zs are adjacent, the adjacent two Zs may form 5-membered or 6-membered ring together with carbon atoms to which the two Zs are bonded by forming —OCH$_2$O— or —OCH$_2$CH$_2$O—, in this case, hydrogen atoms bonded to each carbon atom forming the ring may be arbitrarily substituted with halogen atom, R$^4$ is halogen atom, —OH, C$_1$-C$_6$alkoxy, C$_1$-C$_6$haloalkoxy, C$_1$-C$_6$alkylthio, C$_1$-C$_6$haloalkylthio, C$_1$-C$_6$alkylsulfinyl, C$_1$-C$_6$haloalkylsulfinyl, C$_1$-C$_6$alkylsulfonyl or C$_1$-C$_6$haloalkylsulfonyl, R$^5$ is C$_1$-C$_6$alkyl, C$_1$-C$_6$haloalkyl, C$_1$-C$_3$haloalkoxy C$_1$-C$_3$haloalkyl, C$_2$-C$_6$alkenyl, C$_2$-C$_6$haloalkenyl, C$_3$-C$_6$alkynyl, C$_3$-C$_6$haloalkynyl or C$_1$-C$_6$alkoxycarbonyl, R$^6$ is C$_1$-C$_6$alkyl, C$_1$-C$_6$haloalkyl, —CHO, —C(O)R$^9$, —C(O)OR$^9$, —C(O)SR$^9$, —C(S)OR$^9$, —C(S)SR$^9$ or —S(O)$_2$R$^9$, R$^7$ is hydrogen atom, C$_1$-C$_6$alkyl or C$_1$-C$_6$haloalkyl, R$^8$ is C$_1$-C$_6$alkyl, R$^9$ is C$_1$-C$_6$alkyl, C$_1$-C$_6$haloalkyl, C$_3$-C$_8$cycloalkyl or C$_3$-C$_8$halocycloalkyl, R$^{13}$ is C$_1$-C$_6$alkyl, C$_1$-C$_6$haloalkyl or phenyl, R$^{14}$ is cyano, nitro, C$_3$-C$_6$cycloalkyl, C$_3$-C$_6$halocycloalkyl, E-5 to E-8, E-10 to E-12, E-19, E-24 to E-29, E-31 to E-33, E-44, —OR$^{25}$, —N(R$^{26}$)R$^{25}$, —S(O)$_r$R$^{27}$, C$_5$-C$_6$cycloalkenyl, C$_5$-C$_8$halocycloalkenyl, M-1, —CHO, C$_1$-C$_6$alkylcarbonyl, —C(O)R$^{28}$, —C(O)SR$^{28}$, —C(O)NH$_2$, —C(O)N(R$^{29}$)R$^{28}$, M-11, M-28, —C(S)OR$^{28}$, —C(S)SR$^{28}$, —C(S)NH$_2$, —C(S)N(R$^{29}$)R$^{28}$, M-14, M-32, —CH=NOR$^{30}$, —C(R$^{28}$)=NOR$^{30}$, M-5, —SO$_2$N(R$^{29}$)R$^{28}$, tri(C$_1$-C$_6$alkyl)silyl, phenyl, phenyl substituted with (Z)$_{p1}$, D-1, D-2, D-52, D-53 or D-54, R$^{14a}$ is cyano, —OR$^{25}$, —N(R$^{26}$)R$^{25}$, —S(O)$_r$R$^{27}$, —CHO, C$_1$-C$_6$alkylcarbonyl, phenylcarbonyl, C$_1$-C$_6$alkoxycarbonyl, tri(C$_1$-C$_6$alkyl)silyl or phenyl, R$^{15}$ is C$_1$-C$_6$alkyl, C$_1$-C$_6$haloalkyl, C$_1$-C$_4$alkyl arbitrarily substituted with R$^{31}$, C$_3$-C$_6$cycloalkyl, C$_2$-C$_6$alkenyl, C$_2$-C$_6$haloalkenyl, C$_3$-C$_8$halocycloalkenyl, C$_2$-C$_6$alkynyl, phenyl, phenyl substituted with (Z)$_{p1}$, naphthyl, D-1 to D-4, D-28, D-52, D-53 or D-54, R$^{17}$ is hydrogen atom, C$_1$-C$_6$alkyl, —CHO, —C(O)R$^{28}$, —C(O)OR$^{28}$, —C(O)NH$_2$, —C(O)N(R$^{29}$)R$^{28}$, —S(O)$_2$R$^{28}$, —S(O)$_2$NH$_2$, —S(O)$_2$N(R$^{29}$)R$^{28}$ or phenyl, R$^{17a}$ is C$_1$-C$_6$alkyl, di(C$_1$-C$_6$alkyl)amino, phenyl, phenyl substituted with (Z)$_{p1}$, D-52, D-53 or D-54, R$^{17b}$ is hydrogen atom or C$_1$-C$_6$alkyl, R$^{18}$ is hydrogen atom, C$_1$-C$_6$alkyl or C$_1$-C$_6$alkylcarbonyl, $R^{19}$ is $C_1$-$C_6$alkyl, $C_1$-$C_4$alkoxy $C_1$-$C_4$alkyl, $C_1$-$C_6$alkoxycarbonyl $C_1$-$C_4$alkyl, phenyl $C_1$-$C_4$alkyl, phenyl $C_1$-$C_4$alkyl substituted with $(Z)_{p1}$ or $C_1$-$C_6$alkoxycarbonyl, $R^{20}$ is $C_1$-$C_6$alkyl, phenyl $C_1$-$C_4$alkyl or phenyl $C_1$-$C_4$alkyl substituted with $(Z)_{p1}$, or $R^{20}$ together with $R^{19}$ may form 5- or 6-membered ring with the nitrogen atom bonding them by forming $C_4$-$C_5$alkylene chain, in this case, the alkylene chain may contain one oxygen atom or sulfur atom, and may be arbitrarily substituted with methyl or methoxy, $R^{21}$ is $C_1$-$C_6$alkyl, $R^{22}$ is $C_1$-$C_6$alkyl, $C_1$-$C_6$haloalkyl, phenyl or phenyl substituted with $(Z)_{p1}$, when q2 is 2, each $R^{22}$ may be identical with or different from each other, $R^{23}$ is —CHO, $C_1$-$C_6$alkylcarbonyl, $C_1$-$C_6$haloalkylcarbonyl or $C_1$-$C_6$alkoxycarbonyl, $R^{25}$ is $C_1$-$C_6$alkyl, $C_1$-$C_6$haloalkyl, $C_1$-$C_4$alkyl arbitrarily substituted with $R^{31}$, $C_3$-$C_6$cycloalkyl, E-6, E-8, E-25, E-26, E-28, E-29, $C_3$-$C_6$alkenyl, $C_3$-$C_6$alkynyl, —C(O)$R^{32}$, —C(O)O$R^{32}$, —C(O)NH$_2$, —C(O)N($R^{33}$)$R^{32}$, —C(S)N($R^{33}$)$R^{32}$, —SO$_2R^{32}$, —S(O)$_2$N($R^{33}$)$R^{32}$, —P(O)(O$R^{21}$)$_2$, —P(S)(O$R^{21}$)$_2$ or phenyl, $R^{26}$ is hydrogen atom, $C_1$-$C_6$alkyl, $C_1$-$C_6$alkoxy or phenyl, or $R^{26}$ together with $R^{25}$ may form 5- to 7-membered ring with the nitrogen atom bonding them by forming $C_4$-$C_6$alkylene chain, in this case, the alkylene chain may contain one oxygen atom or sulfur atom, $R^{27}$ is $C_1$-$C_8$alkyl, $C_1$-$C_8$haloalkyl, $C_1$-$C_4$alkyl arbitrarily substituted with $R^{31}$ $C_3$-$C_6$alkenyl, $C_3$-$C_6$alkynyl, $C_1$-$C_6$alkylthio, —C(O)$R^{32}$, —C(O)N($R^{33}$)$R^{32}$, —C(S)$R^{32}$, —C(S)O$R^{32}$, —C(S)N($R^{33}$)$R^{32}$, phenyl, D-21, D-34, D-35, D-50, D-52 or D-55, $R^{28}$ is $C_1$-$C_6$alkyl, $C_1$-$C_6$haloalkyl or phenyl, $R^{29}$ is hydrogen atom or $C_1$-$C_6$alkyl, or $R^{29}$ together with $R^{28}$ may form 5- to 6-membered ring with the nitrogen atom bonding them by forming $C_4$-$C_5$alkylene chain, in this case, the alkylene chain may contain one oxygen atom or sulfur atom, $R^{30}$ is $C_1$-$C_6$alkyl, $R^{31}$ is cyano, $C_3$-$C_6$cycloalkyl, $C_3$-$C_6$halocycloalkyl, E-5 to E-8, E-11, E-19, —O$R^{32}$, —OC(O)$R^{32}$, —OC(O)O$R^{32}$, $C_1$-$C_4$alkylthio, phenylthio, $C_1$-$C_4$alkylsulfinyl, $C_1$-$C_4$alkylsulfonyl, $C_1$-$C_4$alkoxycarbonyl, phenyl or phenyl substituted with $(Z)_{p1}$, $R^{32}$ is $C_1$-$C_6$alkyl, $C_1$-$C_6$haloalkyl, $C_1$-$C_4$alkyl arbitrarily substituted with $R^{34}$, $C_3$-$C_6$cycloalkyl, $C_2$-$C_6$alkenyl, phenyl, D-1 to D-4, D-14, D-52, D-53 or D-54, $R^{33}$ is hydrogen atom or $C_1$-$C_6$alkyl, or $R^{33}$ together with $R^{32}$ may form 5- to 6-membered ring with the nitrogen atom bonding them by forming $C_4$-$C_5$alkylene chain, in this case, the alkylene chain may contain one oxygen atom or sulfur atom, $R^{34}$ is E-5, $C_1$-$C_4$alkoxy, phenoxy, $C_1$-$C_4$alkylthio, phenylthio, —N($R^{36}$)$R^{35}$, phenyl, D-1, D-3, D-52, D-53 or D-54, $R^{35}$ is hydrogen atom, $C_1$-$C_6$alkyl, $C_1$-$C_6$alkoxycarbonyl or phenylcarbonyl, $R^{36}$ is hydrogen atom or $C_1$-$C_6$alkyl, m is an integer of 1 to 3, n is an integer of 0 to 2, q2 is an integer of 0 to 2, q3, q4 and q5 are 0, and q6 is an integer of 0 or 1.

(3) The isoxazoline-substituted benzamide compound or the salt thereof as set forth in (2), wherein $A^1$ is carbon atom or nitrogen atom, $A^2$ and $A^3$ are carbon atoms, G is G-1, X is halogen atom, cyano, nitro, —SF$_5$, $C_1$-$C_6$alkyl, $C_1$-$C_6$haloalkyl, hydroxy$C_1$-$C_6$haloalkyl, $C_1$-$C_6$alkoxy$C_1$-$C_6$haloalkyl, $C_3$-$C_8$halocycloalkyl, —O$R^5$, —OSO$_2R^5$ or —S(O)$_rR^5$, when m is 2 or 3, each X may be identical with or different from each other, Y is halogen atom, cyano, nitro, $C_1$-$C_6$alkyl, $C_1$-$C_6$haloalkyl, $C_1$-$C_4$alkyl arbitrarily substituted with $R^4$, —O$R^5$, —S$R^5$, —NH$_2$, —N($R^7$)$R^6$ or —C(S)NH$_2$, when n is 2, each Y may be identical with or different from each other, $R^1$ is —C($R^{1b}$)=NO$R^{1a}$, —C(O)O$R^{1c}$, —C(O)S$R^{1c}$, —C(S)O$R^{1c}$, —C(O)N($R^{1e}$)$R^{1d}$—C(S)N($R^{1e}$)$R^{1d}$, phenyl, phenyl substituted with $(Z)_{p1}$, D-3, D-8, D-10, D-11, D-13 to D-15, D-17, D-22, D-35, D-52 to D-58 or D-59, $R^{1a}$ is hydrogen atom, $C_1$-$C_6$alkyl, $C_1$-$C_6$haloalkyl, $C_3$-$C_6$cycloalkyl $C_1$-$C_4$alkyl, $C_3$-$C_6$alkenyl or $C_3$-$C_6$alkynyl, $R^{1b}$ is hydrogen atom or $C_1$-$C_6$alkyl, $R^{1c}$ is $C_1$-$C_6$alkyl, $C_1$-$C_4$alkyl arbitrarily substituted with $R^{14}$ or $C_3$-$C_6$cycloalkyl, $R^{1d}$ is hydrogen atom, —C(O)$R^{15}$, —C(O)O$R^{15}$ or —C(O)S$R^{15}$, $R^2$ is $C_1$-$C_6$alkyl, —CH$_2R^{14a}$, E-5, E-24, $C_3$-$C_6$alkynyl, —C(O)$R^{15}$, —C(O)O$R^{15}$, —C(O)S$R^{15}$, —C(S)O$R^{15}$, —C(S)S$R^{15}$, —C(O)C(O)O$R^{15}$, $C_1$-$C_6$haloalkylthio, —SN($R^{20}$)$R^{19}$, phenyl or phenyl substituted with $(Z)_{p1}$, further when $R^1$ is —C($R^{1b}$)=NO$R^{1a}$, —C(O)O$R^{1c}$, —C(O)S$R^{1c}$, —C(S)O$R^{1c}$, —C(O)N($R^{1e}$)$R^{1d}$ or —C(S)N($R^{1e}$)$R^{1d}$, $R^2$ may be hydrogen atom, when $R^1$ is phenyl, phenyl substituted with $(Z)_{p1}$, D-3, D-8, D-10, D-11, D-13 to D-15, D-17, D-22, D-35, D-52 to D-58 or D-59, $R^2$ may be $C_1$-$C_6$haloalkyl or $C_3$-$C_6$alkenyl, or $R^2$ together with $R^1$ may form =C($R^{2b}$)$R^{2a}$, $R^{2a}$ is $C_1$-$C_6$alkoxy or di($C_1$-$C_6$alkyl)amino, $R^{2b}$ is $R^{1b}$, $C_1$-$C_6$alkylthio, —SCH$_2R^{14a}$, $C_3$-$C_6$alkenylthio, $C_3$-$C_6$alkynylthio or $C_1$-$C_6$alkylcarbonylthio, $R^3$ is $C_1$-$C_6$haloalkyl or $C_3$-$C_8$halocycloalkyl, $R^4$ is —OH, $C_1$-$C_6$alkoxy, $C_1$-$C_6$haloalkoxy, $C_1$-$C_6$alkylthio or $C_1$-$C_6$haloalkylthio, $R^5$ is $C_1$-$C_6$alkyl, $C_1$-$C_6$haloalkyl or $C_1$-$C_3$haloalkoxy $C_1$-$C_3$haloalkyl, $R^6$ is $C_1$-$C_6$alkyl, —CHO, $C_1$-$C_6$alkylcarbonyl, $C_1$-$C_6$haloalkylcarbonyl, $C_1$-$C_6$alkoxycarbonyl, $C_1$-$C_6$alkylthiocarbonyl, $C_1$-$C_6$alkoxythiocarbonyl, $C_1$-$C_6$alkyldithiocarbonyl, $C_1$-$C_6$alkylsulfonyl or $C_1$-$C_6$haloalkylsulfonyl, $R^7$ is hydrogen atom or $C_1$-$C_6$alkyl $R^{14}$ is cyano, $C_3$-$C_6$cycloalkyl, $C_1$-$C_6$alkoxy, $C_1$-$C_4$alkoxy $C_1$-$C_4$alkoxy, $C_1$-$C_6$alkylthio, —S(D-52), —S(D-55), $C_1$-$C_6$alkylsulfonyl, —NHC(O)$R^{32}$, —NHC(O)O$R^{32}$, $C_1$-$C_6$alkylcarbonyl or $C_1$-$C_6$alkoxycarbonyl, $R^{14a}$ is cyano, —O$R^{25}$, —NHC(O)O$R^{32}$, —S(O)$_rR^{27}$, $C_1$-$C_6$alkylcarbonyl, $C_1$-$C_6$alkoxycarbonyl or phenyl, $R^{15}$ is $C_1$-$C_6$alkyl, $C_1$-$C_6$haloalkyl, $C_1$-$C_4$alkyl arbitrarily substituted with $R^{31}$, $C_3$-$C_6$cycloalkyl, $C_2$-$C_6$alkenyl, $C_2$-$C_6$alkynyl, phenyl, phenyl substituted with $(Z)_{p1}$, D-52, D-53 or D-54, $R^{19}$ is $C_1$-$C_6$alkyl, $C_1$-$C_6$alkoxycarbonyl $C_1$-$C_4$alkyl or $C_1$-$C_6$alkoxycarbonyl, $R^{20}$ is $C_1$-$C_6$alkyl or benzyl, $R^{25}$ is $C_1$-$C_6$alkyl, $C_1$-$C_6$haloalkyl, $C_1$-$C_4$alkoxy $C_1$-$C_4$alkyl, benzyl, $C_3$-$C_6$alkenyl, $C_3$-$C_6$alkynyl, —C(O)$R^{32}$ or —C(O)O$R^{32}$, $R^{27}$ is $C_1$-$C_6$alkyl, $C_1$-$C_6$haloalkyl, —C(O)$R^{32}$ or —C(S)O$R^{32}$, $R^{31}$ is $C_3$-$C_6$cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl or phenyl, $R^{32}$ is $C_1$-$C_6$alkyl, $C_1$-$C_6$haloalkyl, $C_3$-$C_6$cycloalkyl or phenyl, p1 is an integer of 1 to 3, p2 and p3 are an integer of 0 to 2, and p4 is an integer of 0 or 1.

(4) The isoxazoline-substituted benzamide compound or the salt thereof as set forth in (3), wherein $A^1$ is carbon atom, W is oxygen atom, X is halogen atom, cyano, nitro, $C_1$-$C_6$alkyl, $C_1$-$C_6$haloalkyl, —$OR^5$ or —$S(O)_rR^5$, when m is 2 or 3, each X may be identical with or different from each other, Y is halogen atom, cyano, nitro, $C_1$-$C_6$alkyl, $C_1$-$C_6$haloalkyl, —$OR^5$, —$SR^5$, —$NH_2$ or —$N(R^7)R^6$, $R^1$ is —CH=$NOR^{1a}$, —$C(O)OR^{1c}$, —$C(O)N(R^{1e})R^{1d}$, phenyl substituted with $(Z)_{p1}$, D-52, D-55, D-56, D-57 or D-58, $R^{1a}$ is $C_1$-$C_6$alkyl, $R^{1c}$ is $C_1$-$C_6$alkyl or $C_3$-$C_6$cycloalkyl, $R^{1d}$ is hydrogen atom, —$C(O)R^{15}$ or —$C(O)OR^{15}$, $R^2$ is $C_1$-$C_6$alkyl, —$CH_2R^{14a}$, E-5, $C_3$-$C_6$alkynyl, —$C(O)R^{15}$, —$C(O)OR^{15}$, —$C(O)C(O)OR^{15}$ or $C_1$-$C_6$haloalkylthio, further when $R^1$ is —CH=$NOR^{1a}$, —C(O)ORO or —$C(O)N(R^{1e})R^{1d}$, $R^2$ may be hydrogen atom, $R^3$ is $C_1$-$C_6$haloalkyl, Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl or $C_1$-$C_6$alkylsulfonyl, when p1, p2 or p3 is an integer of 2 or more, each Z may be identical with or different from each other, $R^5$ is $C_1$-$C_6$alkyl or $C_1$-$C_6$haloalkyl, $R^6$ is $C_1$-$C_6$alkyl, —CHO, $C_1$-$C_6$alkylcarbonyl or $C_1$-$C_6$alkoxycarbonyl, $R^{14a}$ is cyano, —$OR^{25}$ or —$NHC(O)OR^{32}$, $R^{15}$ is $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, $C_1$-$C_4$alkylsulfinyl $C_1$-$C_4$alkyl, $C_1$-$C_4$alkylsulfonyl $C_1$-$C_4$alkyl, $C_3$-$C_6$cycloalkyl, $C_2$-$C_6$alkenyl, $C_2$-$C_6$alkynyl, phenyl, phenyl substituted with $(Z)_{p1}$ or D-52, $R^{25}$ is $C_1$-$C_4$alkyl, $C_1$-$C_4$haloalkyl, —$C(O)R^{32}$ or —$C(O)OR^{32}$, $R^{32}$ is $C_1$-$C_6$alkyl or $C_3$-$C_6$cycloalkyl, n is an integer of 0 or 1, q3 is 0, and t is 0.

(5) The isoxazoline-substituted benzamide compound or the salt thereof as set forth in (4), wherein $R^1$ is —CH=$NOR^{1a}$, $R^{1a}$ is $C_1$-$C_6$alkyl, $R^2$ is hydrogen atom, —$CH_2R^{14a}$, $C_3$-$C_6$alkynyl or $C_1$-$C_6$alkoxycarbonyl, $R^{14a}$ is cyano or —$OR^{25}$, $R^{25}$ is $C_1$-$C_4$alkyl, $C_1$-$C_4$haloalkyl or —$C(O)R^{32}$, and $R^{32}$ is $C_1$-$C_6$alkyl.

(6) The isoxazoline-substituted benzamide compound or the salt thereof as set forth in (4), wherein $R^1$ is —$C(O)OR^{1c}$, $R^{1c}$ is $C_1$-$C_6$alkyl or $C_3$-$C_6$cycloalkyl, $R^2$ is hydrogen atom, $C_1$-$C_6$alkyl, —$CH_2R^{14a}$, E-5, —$C(O)R^{15}$, $C_1$-$C_6$alkoxycarbonyl, $C_1$-$C_6$haloalkoxycarbonyl or $C_1$-$C_6$haloalkylthio, $R^{14a}$ is cyano, —$OR^{25}$ or —$NHC(O)OR^{32}$, $R^{15}$ is $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl or $C_3$-$C_6$cycloalkyl, $R^{25}$ is $C_1$-$C_4$alkyl, $C_1$-$C_4$haloalkyl or —$C(O)OR^{32}$, and $R^{32}$ is $C_1$-$C_6$alkyl.

(7) The isoxazoline-substituted benzamide compound or the salt thereof as set forth in (4), wherein $R^1$ is —$C(O)N(R^{1e})R^{1d}$ $R^{1d}$ is hydrogen atom, —$C(O)R^{15}$ or —$C(O)OR^{15}$, $R^2$ is hydrogen atom or $C_1$-$C_6$alkyl, and $R^{15}$ is $C_1$-$C_6$alkyl or $C_1$-$C_6$haloalkyl.

(8) The isoxazoline-substituted benzamide compound or the salt thereof as set forth in (4), wherein $R^1$ is phenyl substituted with $(Z)_{p1}$, D-52, D-55, D-56, D-57 or D-58, $R^2$ is $C_1$-$C_6$alkyl, —$CH_2R^{14a}$, $C_3$-$C_6$alkynyl, —$C(O)R^{15}$, —$C(O)OR^{15}$ or —$C(O)C(O)OR^5$, Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl or $C_1$-$C_6$alkylsulfonyl, when p1, p2 or p3 is an integer of 2 or more, each Z may be identical with or different from each other, $R^{14a}$ is cyano or —$OR^{25}$, $R^{15}$ is $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, $C_1$-$C_4$alkylsulfinyl $C_1$-$C_4$alkyl, $C_1$-$C_4$alkylsulfonyl $C_1$-$C_4$alkyl, $C_3$-$C_6$cycloalkyl, $C_2$-$C_6$alkenyl, $C_2$-$C_6$alkynyl, phenyl, phenyl substituted with $(Z)_p$, or D-52, $R^{25}$ is $C_1$-$C_4$alkyl, $C_1$-$C_4$haloalkyl, —$C(O)R^{32}$ or —$C(O)OR^{32}$, and $R^{32}$ is $C_1$-$C_6$alkyl or $C_3$-$C_6$cycloalkyl.

(9) 4-Hydroxyiminomethyl substituted benzamide compound of formula (2) or a salt thereof:

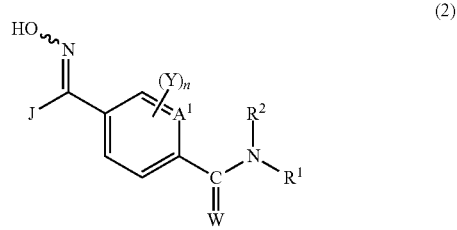

(2)

wherein $A^1$ is carbon atom or nitrogen atom,

J is hydrogen atom or halogen atom,

W is oxygen atom or sulfur atom,

Y is halogen atom, cyano, nitro, $C_1$-$C_6$alkyl, $C_1$-$C_6$haloalkyl, $C_1$-$C_4$alkyl arbitrarily substituted with $R^4$, —$OR^5$, —$N(R^7)R^6$ or —$C(S)NH_2$, when n is 2, each Y may be identical with or different from each other, $R^1$ is —$C(R^{1b})$=$NOR^{1a}$, —$C(O)OR^{1c}$, —$C(O)SR^{1c}$, —$C(S)OR^{1c}$, —$C(O)N(R^{1e})R^{1d}$, —$C(S)N(R^{1e})R^{1d}$, phenyl, phenyl substituted with $(Z)_{p1}$, D-3, D-8, D-10, D-11, D-13 to D-15, D-17, D-22, D-35, D-52 to D-58 or D-59, $R^{1a}$ is $C_1$-$C_6$alkyl, $C_1$-$C_6$haloalkyl, $C_3$-$C_8$cyloalkyl $C_1$-$C_4$alkyl, $C_3$-$C_6$alkenyl or $C_3$-$C_6$alkynyl, $R^{1b}$ is hydrogen atom or $C_1$-$C_6$alkyl, $R^{1c}$ is $C_1$-$C_6$alkyl, $C_1$-$C_4$alkyl arbitrarily substituted with $R^{14}$ or $C_3$-$C_6$cycloalkyl, $R^{1d}$ is hydrogen atom, —$C(O)R^{15}$, —$C(O)OR^{15}$ or —$C(O)SR^{15}$ $R^{1e}$ is hydrogen atom or $C_1$-$C_6$alkyl, $R^2$ is $C_1$-$C_6$alkyl, —$CH_2R^{14a}$, E-5, E-24, $C_3$-$C_6$alkynyl, —$C(O)R^{15}$, —$C(O)OR^{15}$, —$C(O)SR^{15}$, —$C(S)OR^{15}$, —$C(S)SR^{15}$, —$C(O)C(O)OR^{15}$, phenyl or phenyl substituted with $(Z)_{p1}$, further when $R^1$ is —$C(R^{1b})$=$NOR^{1a}$, —$C(O)OR^{1c}$, —$C(O)SR^{1c}$, —$C(S)OR^{1c}$, —$C(O)N(R^{1e})R^{1d}$ or —$C(S)N(R^{1e})R^{1d}$, $R^2$ may be hydrogen atom, when $R^1$ is phenyl, phenyl substituted with (Z), 1, D-3, D-8, D-10, D-11, D-13 to D-15, D-17, D-22, D-35, D-52 to D-58 or D-59,
$R^2$ may be $C_1$-$C_6$haloalkyl or $C_3$-$C_6$alkenyl,
or $R^2$ together with $R^1$ may form =$C(R^{2b})R^{2a}$,
$R^{2a}$ is $C_1$-$C_6$alkoxy or di($C_1$-$C_6$alkyl)amino,
$R^{2b}$ is $C_1$-$C_6$alkyl or $C_1$-$C_6$alkylcarbonylthio,
D-3, D-8, D-10, D-11, D-13 to D-15, D-17, D-22, D-35, D-52 to D-58 and D-59 are aromatic heterocyclic rings of the following formulae, respectively D-3
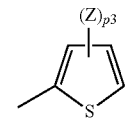

D-8
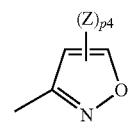

D-10
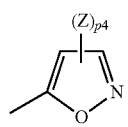

D-11
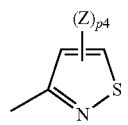

D-13
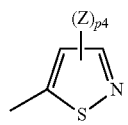

D-14
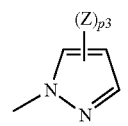

D-15
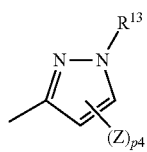

D-17
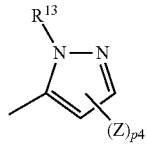

D-22
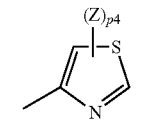

D-35
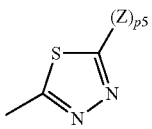

-continued

D-52
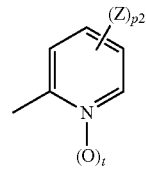

D-53
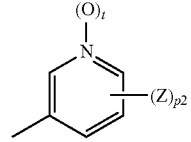

D-54
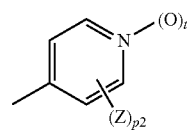

D-55
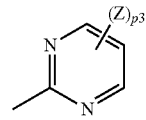

D-56
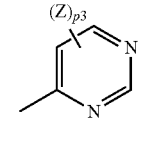

D-57
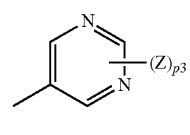

D-58
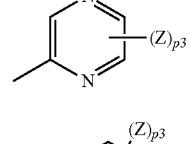

D-59
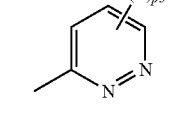

Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylsulfonyloxy, $C_1$-$C_6$haloalkylsulfonyloxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, $C_1$-$C_6$alkoxycarbonyl, —C(O)NH$_2$ or —C(S)NH$_2$, when p1, p2 or p3 is an integer of 2 or more, each Z may be identical with or different from each other, further, when two Zs are adjacent, the adjacent two Zs may form 5-membered or 6-membered ring together with carbon atoms to which the two Zs are bonded by forming —OCH$_2$O— or —OCH$_2$CH$_2$O—, in this case, hydrogen atoms bonded to each carbon atom forming the ring may be arbitrarily substituted with halogen atom, E-5 and E-24 are saturated heterocyclic rings of the following formulae, respectively,

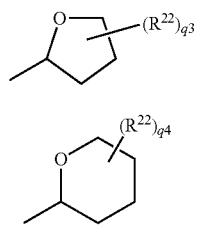

E-5

E-24

$R^4$ is $C_1$-$C_6$alkoxy or $C_1$-$C_6$haloalkoxy,
$R^5$ is $C_1$-$C_6$alkyl or $C_1$-$C_6$haloalkyl,
$R^6$ is —CHO, $C_1$-$C_6$alkylcarbonyl, $C_1$-$C_6$haloalkylcarbonyl, $C_1$-$C_6$alkoxycarbonyl, $C_1$-$C_6$alkylthiocarbonyl, $C_1$-$C_6$alkoxythiocarbonyl, $C_1$-$C_6$alkyldithiocarbonyl, $C_1$-$C_6$alkylsulfonyl or $C_1$-$C_6$haloalkylsulfonyl,
$R^7$ is hydrogen atom or $C_1$-$C_6$alkyl
$R^{13}$ is $C_1$-$C_6$alkyl or $C_1$-$C_6$haloalkyl,
$R^{14}$ is cyano, $C_3$-$C_6$cycloalkyl, $C_1$-$C_6$alkoxy, $C_1$-$C_4$alkoxy $C_1$-$C_4$alkoxy, $C_1$-$C_6$alkylsulfonyl, —NHC(O)$R^{32}$, —NHC(O)O$R^{32}$, $C_1$-$C_6$alkylcarbonyl or $C_1$-$C_6$alkoxycarbonyl,
$R^{14a}$ is cyano, —O$R^{25}$, —NHC(O)O$R^{32}$, —S(O)$_r R^{27}$, $C_1$-$C_6$alkylcarbonyl, $C_1$-$C_6$alkoxycarbonyl or phenyl,
$R^{15}$ is $C_1$-$C_6$alkyl, $C_1$-$C_6$haloalkyl, $C_1$-$C_4$alkyl arbitrarily substituted with $R^{31}$, $C_3$-$C_6$cycloalkyl, $C_2$-$C_6$alkenyl, $C_2$-$C_6$alkynyl, phenyl, phenyl substituted with $(Z)_{p1}$, D-52, D-53 or D-54,
$R^{25}$ is $C_1$-$C_6$alkyl, $C_1$-$C_6$haloalkyl, $C_1$-$C_4$alkoxy $C_1$-$C_4$alkyl, benzyl, $C_3$-$C_6$alkenyl, $C_3$-$C_6$alkynyl, —C(O)$R^{32}$ or —C(O)O$R^{32}$,
$R^{27}$ is $C_1$-$C_6$alkyl, $C_1$-$C_6$haloalkyl, —C(O)$R^{32}$ or —C(S)O$R^{32}$,
$R^{31}$ is $C_3$-$C_6$cycloalkyl, $C_1$-$C_4$alkoxy, $C_1$-$C_4$haloalkoxy, $C_1$-$C_4$alkylsulfonyl or phenyl,
$R^{32}$ is $C_1$-$C_6$alkyl, $C_1$-$C_6$haloalkyl, $C_3$-$C_6$cycloalkyl or phenyl,
n is an integer of 0 to 2,
p1 is an integer of 1 to 3,
p2 and p3 are an integer of 0 to 2,
p4 and p5 are an integer of 0 or 1,
q3 and q4 are 0,
r is an integer of 0 or 2, and
t is an integer of 0 or 1.

(10) 4-Hydroxyiminomethyl substituted benzamide compound or the salt thereof as set forth in (9), wherein
$A^1$ is carbon atom,
W is oxygen atom,
Y is halogen atom, cyano, nitro, $C_1$-$C_6$alkyl, $C_1$-$C_6$haloalkyl, —O$R^5$ or —N($R^7$)$R^6$
$R^1$ is —CH=NO$R^{1a}$,
$R^{1a}$ is $C_1$-$C_6$alkyl,
$R^2$ is hydrogen atom, —CH$_2R^{14a}$, $C_3$-$C_6$alkynyl or $C_1$-$C_6$alkoxycarbonyl,
$R^5$ is $C_1$-$C_6$alkyl or $C_1$-$C_6$haloalkyl,
$R^6$ is —CHO, $C_1$-$C_6$alkylcarbonyl or $C_1$-$C_6$alkoxycarbonyl,
$R^{14a}$ is cyano or —O$R^{25}$,
$R^{25}$ is $C_1$-$C_4$alkyl, $C_1$-$C_4$haloalkyl or —C(O)O$R^{32}$, and
$R^{32}$ is $C_1$-$C_6$alkyl.

(11) 4-Hydroxyiminomethyl substituted benzamide compound or the salt thereof as set forth in (9), wherein
$A^1$ is carbon atom,
W is oxygen atom,
Y is halogen atom, cyano, nitro, $C_1$-$C_6$alkyl, $C_1$-$C_6$haloalkyl, —O$R^5$ or —N($R^7$)$R^6$,
$R^1$ is —C(O)O$R^{1c}$, $R^{1c}$ is $C_1$-$C_6$alkyl or $C_3$-$C_6$cycloalkyl,
$R^2$ is hydrogen atom, $C_1$-$C_6$alkyl, —CH$_2R^{14a}$, E-5, —C(O)$R^{15}$, $C_1$-$C_6$alkoxycarbonyl, $C_1$-$C_6$haloalkoxycarbonyl or $C_1$-$C_6$haloalkylthio,
$R^5$ is $C_1$-$C_6$alkyl or $C_1$-$C_6$haloalkyl,
$R^6$ is —CHO, $C_1$-$C_6$alkylcarbonyl or $C_1$-$C_6$alkoxycarbonyl,
$R^{14a}$ is cyano, —O$R^{25}$, or —NHC(O)O$R^{32}$,
$R^{15}$ is $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl or $C_3$-$C_6$cycloalkyl,
$R^{25}$ is $C_1$-$C_4$alkyl, $C_1$-$C_4$haloalkyl or —C(O)O$R^{32}$,
$R^{32}$ is $C_1$-$C_6$alkyl,
n is an integer of 0 or 1, and
q3 is 0.

(12) 4-Hydroxyiminomethyl substituted benzamide compound or the salt thereof as set forth in (9), wherein
$A^1$ is carbon atom,
W is oxygen atom,
Y is halogen atom, cyano, nitro, $C_1$-$C_6$alkyl, $C_1$-$C_6$haloalkyl, —O$R^5$ or —N($R^7$)$R^6$,
$R^1$ is —C(O)N($R^{1e}$)$R^{1d}$,
$R^{1d}$ is hydrogen atom, —C(O)$R^{15}$ or —C(O)O$R^{15}$,
$R^{1e}$ is hydrogen atom or $C_1$-$C_6$alkyl,
$R^2$ is hydrogen atom or $C_1$-$C_6$alkyl,
$R^5$ is $C_1$-$C_6$alkyl or $C_1$-$C_6$haloalkyl,
$R^6$ is —CHO, $C_1$-$C_6$alkylcarbonyl or $C_1$-$C_6$alkoxycarbonyl,
$R^{15}$ is $C_1$-$C_6$alkyl or $C_1$-$C_6$haloalkyl, and
n is an integer of 0 or 1.

(13) 4-Hydroxyiminomethyl substituted benzamide compound or the salt thereof as set forth in (9), wherein
$A^1$ is carbon atom,
W is oxygen atom,
Y is halogen atom, cyano, nitro, $C_1$-$C_6$alkyl, $C_1$-$C_6$haloalkyl, —O$R^5$ or —N($R^7$)$R^6$,
$R^1$ is phenyl substituted with $(Z)_{p1}$, D-52, D-55, D-56, D-57 or D-58,
$R^2$ is $C_1$-$C_6$alkyl, —CH$_2R^{14a}$, $C_3$-$C_6$alkynyl, —C(O)$R^{15}$, —C(O)O$R^{15}$ or —C(O)C(O)O$R^{15}$,
Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl or $C_1$-$C_6$alkylsulfonyl, when p1, p2 or p3 is an integer of 2 or more, each Z may be identical with or different from each other,
$R^5$ is $C_1$-$C_6$alkyl or $C_1$-$C_6$haloalkyl,
$R^6$ is —CHO, $C_1$-$C_6$alkylcarbonyl or $C_1$-$C_6$alkoxycarbonyl,
$R^{14a}$ is cyano or —O$R^{25}$,
$R^{15}$ is $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, $C_1$-$C_4$alkylsulfinyl $C_1$-$C_4$alkyl, $C_1$-$C_4$alkylsulfonyl $C_1$-$C_4$alkyl, $C_3$-$C_6$cycloalkyl, $C_2$-$C_6$alkenyl, $C_2$-$C_6$alkynyl, phenyl, phenyl substituted with $(Z)_{p1}$ or D-52,
$R^{25}$ is $C_1$-$C_4$alkyl, $C_1$-$C_4$haloalkyl, —C(O)$R^{32}$ or —C(O)O$R^{32}$,
$R^{32}$ is $C_1$-$C_6$alkyl or $C_3$-$C_6$cycloalkyl,
n is an integer of 0 or 1, and
t is 0.

(14) A pesticide containing as an active ingredient one or more selected from isoxazoline-substituted benzamide compound and the salt thereof as set forth in (1) to (8).

(15) An agrochemical containing as an active ingredient one or more selected from isoxazoline-substituted benzamide compound and the salt thereof as set forth in (1) to (8).

(16) An endo- or ecto-parasiticide for mammals or birds containing as an active ingredient one or more selected from isoxazoline-substituted benzamide compound and the salt thereof as set forth in (1) to (8).

(17) An insecticide or acaricide containing as an active ingredient one or more selected from isoxazoline-substituted benzamide compound and the salt thereof as set forth in (1) to (8).

Effect of the Invention

The compound according to the present invention has an excellent insecticidal and acaricidal activity for many agricultural insect pests, spider mites, endo- or ecto-parasiticide for mammals or birds, and exerts a control effect sufficient for pest insects that acquire resistance against exiting insecticides. Further, the compound has little adverse affect on mammals, fishes and beneficial insects, and has a low persistency and a low impact on the environment. Therefore, the present invention can provide a useful and novel pesticide.

BEST MODE FOR CARRYING OUT THE INVENTION

Active compounds used as the pesticide in the present invention are the compounds of formulae (1) to (8) mentioned above, and the compounds of formulae (9) to (13) mentioned above are generally novel production intermediates used for the production of these active compounds.

In the compounds included in the present invention, some compounds have geometrical isomers of E-form and Z-form depending on the kind of substituents. The present invention includes these E-forms, Z-forms and mixtures containing E-form and Z-form in an arbitrary proportion. In addition, the compounds included in the present invention have optically active forms resulting from the presence of 1 or more asymmetric carbon atoms, and the present invention includes all optically active forms or racemates. Further, in the compounds of formula (1) according to the present invention, some compounds wherein $R^2$ is hydrogen atom are present in tautomer, and the present invention also includes these structures.

The compounds included in the present invention can be converted to acid addition salts for example salts of hydrohalide acid such as hydrofluoric acid, hydrochloric acid, hydrobromic acid, hydriodic acid or the like, salts of inorganic acids such as nitric acid, sulfuric acid, phosphoric acid, chloric acid, perchloric acid or the like, salts of sulfonic acid such as methansulfonic acid, ethansulfonic acid, trufluoromethansulfonic acid, benzene sulfonic acid, p-toluene sulfonic acid or the like, salts of carboxylic acid such as formic acid, acetic acid, propionic acid, trifluoroacetic acid, fumaric acid, tar- taric acid, oxalic acid, maleic acid, malic acid, succinic acid, benzoic acid, mandelic acid, ascorbic acid, lactic acid, gluconic acid, citric acid or the like, or salts of amino acid such as glutamic acid, aspartic acid or the like, according to a conventional method.

The compounds included in the present invention can be converted to metal salts for example salts of alkali metal such as lithium, sodium, potassium, salts of alkaline earth metal such as calcium, barium, magnesium, or salts of aluminum, according to a conventional method.

Hereinafter, concrete examples of each substituent shown in the specification are described. In the specification, "n-" means normal, "i-" means iso, "s-" means secondary, and "t-" means tertiary, and "Ph" means phenyl.

Halogen atom in the compounds of the present invention includes fluorine atom, chlorine atom, bromine atom and iodine atom. In the interim, the indication of "halo" in the specification also means these halogen atoms.

In the specification, the indication of "$C_a$-$C_b$alkyl" means straight-chain or branched-chain hydrocarbon groups having carbon atom number of a to b, and includes for example methyl, ethyl, n-propyl, i-propyl, n-butyl, i-butyl, s-butyl, t-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, 1-methylpentyl, 2-methylpentyl, 1,1-dimethylbutyl, 1,3-dimethylbutyl, heptyl, octyl, nonyl, decyl, undecyl, dodecyl and the like. It is selected from the scope of the indicated carbon atom number.

In the specification, the indication of "$C_a$-$C_b$haloalkyl" means straight-chain or branched-chain hydrocarbon groups having carbon atom number of a to b that a hydrogen atom (hydrogen atoms) bonded to carbon atom is (are) arbitrarily substituted with a halogen atom (halogen atoms). In this case, if it is substituted with two or more halogen atoms, these halogen atoms may be identical with or different from each other. Concrete examples thereof are for example fluorom-

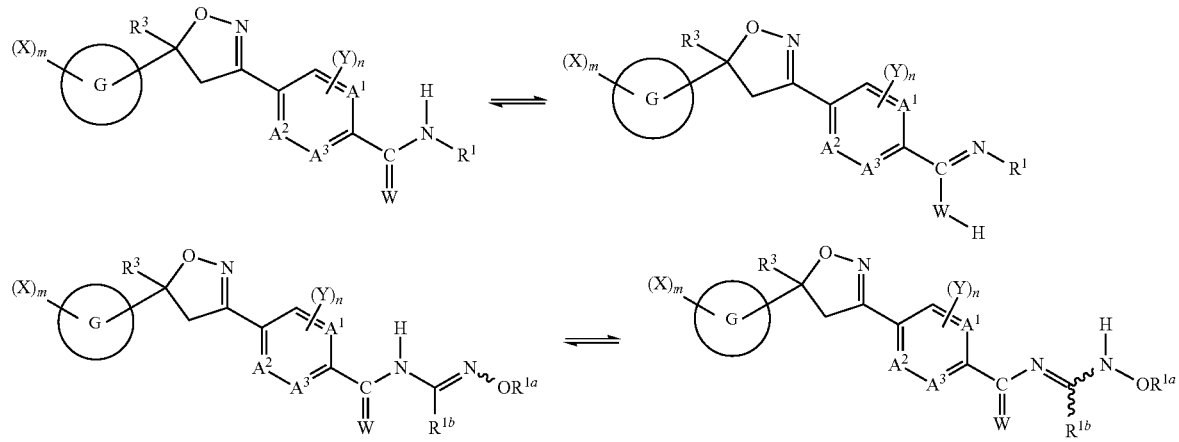

ethyl, chloromethyl, bromomethyl, iodomethyl, difluoromethyl, chlorofluoromethyl, dichloromethyl, bromofluoromethyl, trifluoromethyl, chlorodifluoromethyl, dichlorofluoromethyl, trichloromethyl, bromodifluoromethyl, bromochlorofluoromethyl, dibromofluoromethyl, 2-fluoroethyl, 2-chloroethyl, 2-bromoethyl, 2,2-difluoroethyl, 2-chloro-2-fluoroethyl, 2,2-dichloroethyl, 2-bromo-2-fluoroethyl, 2,2,2-trifluoroethyl, 2-chloro-2,2-difluoroethyl, 2,2-dichloro-2-fluoroethyl, 2,2,2-trichloroethyl, 2-bromo-2,2-difluoroethyl, 2-bromo-2-chloro-2-fluoroethyl, 2-bromo- 2,2-dichloroethyl, 1,1,2,2-tetrafluoroethyl, pentafluoroethyl, 1-chloro-1,2,2,2-tetrafluoroethyl, 2-chloro-1,2,2,2-tetrafluoroethyl, 1,2-dichloro-1,2,2-trifluoroethyl, 2-bromo-1,1,2,2-tetrafluoroethyl, 2-fluoropropyl, 2-chloropropyl, 2-bromopropyl, 2-chloro-2-fluoropropyl, 2,3-dichloropropyl, 2-bromo-3-fluoropropyl, 3-bromo-2-chloropropyl, 2,3-dibromopropyl, 3,3,3-trifluoropropyl, 3-bromo-3,3-difluoropropyl, 2,2,3,3-tetrafluoropropyl, 2-chloro-3,3,3-trifluoropropyl, 2,2,3,3,3-pentafluoropropyl, 1,1,2,3,3,3-hexafluoropropyl, heptafluoropropyl, 2,3-dichloro-1,1,2,3,3-pentafluoropropyl, 2-fluoro-1-methylethyl, 2-chloro-1-methylethyl, 2-bromo-1-methylethyl, 2,2,2-trifluoro-1-(trifluoromethyl)ethyl, 1,2,2,2-tetrafluoro-1-(trifluoromethyl)ethyl, 2,2,3,3,4,4-hexafluorobutyl, 2,2,3,4,4,4-hexafluorobutyl, 2,2,3,3,4,4,4-heptafluorobutyl, 1,1,2,2,3,3,4,4-octafluorobutyl, nonafluorobutyl, 4-chloro-1,1,2,2,3,3,4,4-octafluorobutyl, 2-fluoro-2-methylpropyl, 2-chloro-1,1-dimethylethyl, 2-bromo-1,1-dimethylethyl, 5-chloro-2,2,3,4,4,5,5-heptafluoropentyl, tridecafluorohexyl, and the like. It is selected from the scope of the indicated carbon atom number.

In the specification, the indication of "$C_a$-$C_b$cycloalkyl" means cyclic hydrocarbon groups having carbon atom number of a to b, and can form 3-membered to 6-membered single ring or conjugated ring structure. In addition, each ring may be arbitrarily substituted alkyl group in the scope of the indicated carbon atom number. Concrete examples thereof are for example cyclopropyl, 1-methylcyclopropyl, 2-methylcyclopropyl, 2,2-dimethylcyclopropyl, 2,2,3,3-tetramethylcyclopropyl, cyclobutyl, cyclopentyl, 2-methylcyclopentyl, 3-methylcyclopentyl, cyclohexyl, 2-methylcyclohexyl, 3-methylcyclohexyl, 4-methylcyclohexyl, bicyclo[2.2.1]heptan-2-yl and the like. It is selected from the scope of the indicated carbon atom number.

In the specification, the indication of "$C_a$-$C_b$halocycloalkyl" means cyclic hydrocarbon groups having carbon atom number of a to b that a hydrogen atom (hydrogen atoms) bonded to carbon atom is (are) arbitrarily substituted with a halogen atom (halogen atoms), and can form 3-membered to 6-membered single ring or conjugated ring structure. In addition, each ring may be arbitrarily substituted alkyl group in the scope of the indicated carbon atom number. The substitution for halogen atom may be in the ring structure moiety, the side chain moiety or both of them. Further, if it is substituted with two or more halogen atoms, these halogen atoms may be identical with or different from each other. Concrete examples thereof are for example 2,2-difluorocyclopropyl, 2,2-dichlorocyclopropyl, 2,2-dibromocyclopropyl, 2,2-difluoro-1-methylcyclopropyl, 2,2-dichloro-1-methylcyclopropyl, 2,2-dibromo-1-methylcyclopropyl, 2,2,3,3-tetrafluorocyclobutyl, 2-(trifluoromethyl)cyclohexyl, 3-(trifluoromethyl)cyclohexyl, 4-(trifluoromethyl)cyclohexyl and the like. It is selected from the scope of the indicated carbon atom number.

In the specification, the indication of "$C_a$-$C_b$alkenyl" means straight-chain or branched-chain unsaturated hydrocarbon groups having carbon atom number of a to b and having 1 or more double bonds. Concrete examples thereof are for example vinyl, 1-propenyl, 2-propenyl, 1-methylethenyl, 2-butenyl, 1-methyl-2-propenyl, 2-methyl-2-propenyl, 2-pentenyl, 2-methyl-2-butenyl, 3-methyl-2-butenyl, 2-ethyl-2-propenyl, 1,1-dimethyl-2-propenyl, 2-hexenyl, 2-methyl-2-pentenyl, 2,4-dimethyl-2,6-heptadienyl, 3,7-dimethyl-2,6-octadienyl, and the like. It is selected from the scope of the indicated carbon atom number.

In the specification, the indication of "$C_a$-$C_b$haloalkenyl" means straight-chain or branched-chain unsaturated hydrocarbon groups having carbon atom number of a to b and having 1 or more double bonds, which a hydrogen atom (hydrogen atoms) bonded to carbon atom is (are) arbitrarily substituted with a halogen atom (halogen atoms). In this case, if it is substituted with two or more halogen atoms, these halogen atoms may be identical with or different from each other. Concrete examples thereof are for example 2,2-dichlorovinyl, 2-fluoro-2-propenyl, 2-chloro-2-propenyl, 3-chloro-2-propenyl, 2-bromo-2-propenyl, 3-bromo-2-propenyl, 3,3-difluoro-2-propenyl, 2,3-dichloro-2-propenyl, 3,3-dichloro-2-propenyl, 2,3-dibromo-2-propenyl, 2,3,3-trifluoro-2-propenyl, 2,3,3-trichloro-2-propenyl, 1-(trifluoromethyl)ethenyl, 3-chloro-2-butenyl, 3-bromo-2-butenyl, 4,4-difluoro-3-butenyl, 3,4,4-trifluoro-3-butenyl, 3-chloro-4,4,4-trifluoro-2-butenyl, 3-bromo-2-methyl-2-propenyl, and the like. It is selected from the scope of the indicated carbon atom number.

In the specification, the indication of "$C_a$-$C_b$cycloalkenyl" means cyclic unsaturated hydrocarbon groups having carbon atom number of a to b and having 1 or more double bonds, and can form 3-membered to 6-membered single ring or conjugated ring structure. In addition, each ring may be arbitrarily substituted alkyl group in the scope of the indicated carbon atom number, and further the double bond may be either endo- or exo-form. Concrete examples thereof are for example 2-cyclopenten-1-yl, 3-cyclopenten-1-yl, 2-cyclohexen-1-yl, 3-cyclohexen-1-yl, bicyclo[2.2.1]-5-hepten-2-yl and the like. It is selected from the scope of the indicated carbon atom number.

In the specification, the indication of "$C_a$-$C_b$halocycloalkenyl" means cyclic unsaturated hydrocarbon groups having carbon atom number of a to b and having 1 or more double bonds, which a hydrogen atom (hydrogen atoms) bonded to carbon atom is (are) arbitrarily substituted with a halogen atom (halogen atoms), and can form 3-membered to 6-membered single ring or conjugated ring structure. In addition, each ring may be arbitrarily substituted alkyl group in the scope of the indicated carbon atom number, and further the double bond may be either endo- or exo-form. The substitution for halogen atom may be in the ring structure moiety, the side chain moiety or both of them. Further, if it is substituted with two or more halogen atoms, these halogen atoms may be identical with or different from each other. Concrete examples thereof are for example 2-chlorobicyclo[2.2.1]-5-hepten-2-yl and the like. It is selected from the scope of the indicated carbon atom number.

In the specification, the indication of "$C_a$-$C_b$alkylidene" means straight-chain or branched-chain unsaturated hydrocarbon groups having carbon atom number of a to b that are bonded by double bond. Concrete examples thereof are for example methylidene, ethylidene, propylidene, 1-methylethylidene, butylidene, 1-methylpropylidene, pentylidene, 1-methylbutylidene, 1-ethylethylidene, hexylidene, and the like. It is selected from the scope of the indicated carbon atom number.

In the specification, the indication of "$C_a$-$C_b$haloalkylidene" means straight-chain or branched-chain unsaturated hydrocarbon groups having carbon atom number of a to b that have 1 or more double bonds and are bonded by double bond, which a hydrogen atom (hydrogen atoms) bonded to carbon atom is (are) arbitrarily substituted with a halogen atom (halogen atoms). Further, if it is substituted with two or more halogen atoms, these halogen atoms may be identical with or different from each other. Concrete examples thereof are for example difluoromethylidene, dichloromethylidene, 2,2,2-trifluoroethylidene, and the like. It is selected from the scope of the indicated carbon atom number.

In the specification, the indication of "$C_a$-$C_b$alkynyl" means straight-chain or branched-chain unsaturated hydrocarbon groups having carbon atom number of a to b and having 1 or more triple bonds. Concrete examples thereof are for example ethynyl, 1-propynyl, 2-propynyl, 2-butynyl, 1-methyl-2-propynyl, 2-pentynyl, 1-methyl-2-butynyl, 1,1-dimethyl-2-propynyl, 2-hexynyl, and the like. It is selected from the scope of the indicated carbon atom number.

In the specification, the indication of "$C_a$-$C_b$halolkynyl" means straight-chain or branched-chain unsaturated hydrocarbon groups having carbon atom number of a to b and having 1 or more triple bonds, which a hydrogen atom (hydrogen atoms) bonded to carbon atom is (are) arbitrarily substituted with a halogen atom (halogen atoms). In this case, if it is substituted with two or more halogen atoms, these halogen atoms may be identical with or different from each other. Concrete examples thereof are for example 2-chloroethynyl, 2-bromoethynyl, 2-iodoethynyl, 3-chloro-2-propynyl, 3-bromo-2-propynyl, 3-iodo-2-propynyl, and the like. It is selected from the scope of the indicated carbon atom number.

In the specification, the indication of "$C_a$-$C_b$alkoxy" means alkyl-O— groups wherein the alkyl has carbon atom number of a to b, and includes for example methoxy, ethoxy, n-propyloxy, i-propyloxy, n-butyloxy, i-butyloxy, s-butyloxy, t-butyloxy, n-pentyloxy, n-hexyloxy and the like. It is selected from the scope of the indicated carbon atom number.

In the specification, the indication of "$C_a$-$C_b$haloalkoxy" means haloalkyl-O— groups wherein the haloalkyl has carbon atom number of a to b, and includes for example difluoromethoxy, trifluoromethoxy, chlorodifluoromethoxy, bromodifluoromethoxy, 2-fluoroethoxy, 2-chloroethoxy, 2,2,2-trifluoroethoxy, 1,1,2,2-tetrafluoroethoxy, 2-chloro-1,1,2-trifluoroethoxy, 2-bromo-1,1,2-trifluoroethoxy, pentafluoroethoxy, 2,2-dichloro-1,1,2-trifluoroethoxy, 2,2,2-trichloro-1,1-difluoroethoxy, 2-bromo-1,1,2,2-tetrafluoroethoxy, 2,2,3,3-tetrafluoropropyloxy, 1,1,2,3,3,3-hexafluoropropyloxy, 2,2,2-trifluoro-1-(trifluoromethyl)ethoxy, heptafluoropropyloxy, 2-bromo-1 μl, 2,3,3,3-hexafluoropropyloxy, and the like. It is selected from the scope of the indicated carbon atom number.

In the specification, the indication of "$C_a$-$C_b$alkylthio" means alkyl-S— groups wherein the alkyl has carbon atom number of a to b, and includes for example methylthio, ethylthio, n-propylthio, i-propylthio, n-butylthio, i-butylthio, s-butylthio, t-butylthio, n-pentylthio, n-hexylthio and the like. It is selected from the scope of the indicated carbon atom number.

In the specification, the indication of "$C_a$-$C_b$haloalkylthio" means haloalkyl-S— groups wherein the haloalkyl has carbon atom number of a to b, and includes for example difluoromethylthio, trifluoromethylthio, chlorodifluoromethylthio, bromodifluoromethylthio, 2,2,2-trifluoroethylthio, 1,1,2,2-tetrafluoroethylthio, 2-chloro-1,1,2-trifluoroethylthio, pentafluoroethylthio, 2-bromo-1,1,2,2-tetrafluoroethylthio, 1,1,2,3,3,3-hexafluoropropylthio, heptafluoropropylthio, 1,2,2,2-tetrafluoro-1-(trifluoromethyl)ethylthio, nonafluorobutylthio, and the like. It is selected from the scope of the indicated carbon atom number.

In the specification, the indication of "$C_a$-$C_b$alkenylthio" means alkenyl-S— groups wherein the alkenyl has carbon atom number of a to b, and includes for example 2-propenylthio, 2-butenylthio, 2-methyl-2-propenylthio, 3-methyl-2-butenylthio, and the like. It is selected from the scope of the indicated carbon atom number.

In the specification, the indication of "$C_a$-$C_b$alkynylthio" means alkynyl-S— groups wherein the alkynyl has carbon atom number of a to b, and includes for example 2-propynylthio, 2-butynylthio, and the like. It is selected from the scope of the indicated carbon atom number.

In the specification, the indication of "$C_a$-$C_b$alkylsulfinyl" means alkyl-S(O)— groups wherein the alkyl has carbon atom number of a to b, and includes for example methylsulfinyl, ethylsulfinyl, n-propylsulfinyl, i-propylsulfinyl, n-butylsulfinyl, i-butylsulfinyl, s-butylsulfinyl, t-butylsulfinyl, and the like. It is selected from the scope of the indicated carbon atom number.

In the specification, the indication of "$C_a$-$C_b$haloalkylsulfinyl" means haloalkyl-S(O)— groups wherein the haloalkyl has carbon atom number of a to b, and includes for example difluoromethylsulfinyl, trifluoromethylsulfinyl, chlorodifluoromethylsulfinyl, bromodifluoromethylsulfinyl, 2,2,2-trifluoroethylsulfinyl, 2-bromo-1,1,2,2-tetrafluoroethylsulfinyl, 1,2,2,2-tetrafluoro-1-(trifluoromethyl)ethylsulfinyl, nonafluorobutylsulfinyl, and the like. It is selected from the scope of the indicated carbon atom number.

In the specification, the indication of "$C_a$-$C_b$alkylsulfonyl" means alkyl-$SO_2$— groups wherein the alkyl has carbon atom number of a to b, and includes for example methylsulfonyl, ethylsulfonyl, n-propylsulfonyl, i-propylsulfonyl, n-butylsulfonyl, i-butylsulfonyl, s-butylsulfonyl, t-butylsulfonyl, n-pentylsulfonyl, n-hexylsulfonyl, and the like. It is selected from the scope of the indicated carbon atom number.

In the specification, the indication of "$C_a$-$C_b$haloalkylsulfonyl" means haloalkyl-$SO_2$— groups wherein the haloalkyl has carbon atom number of a to b, and includes for example difluoromethylsulfonyl, trifluoromethylsulfonyl, chlorodifluoromethylsulfonyl, bromodifluoromethylsulfonyl, 2,2,2-trifluoroethylsulfonyl, 1,1,2,2-tetrafluoroethylsulfonyl, 2-chloro-1,1,2-trifluoroethylsulfonyl, 2-bromo-1,1,2,2-tetrafluoroethylsulfonyl, and the like. It is selected from the scope of the indicated carbon atom number.

In the specification, the indication of "$C_a$-$C_b$alkylamino" means amino groups, which either hydrogen atom is substituted with the above-mentioned alkyl group having carbon atom number of a to b, and includes for example methylamino, ethylamino, n-propylamino, i-propylamino, n-butylamino, i-butylamino, t-butylamino, and the like. It is selected from the scope of the indicated carbon atom number.

In the specification, the indication of "di($C_a$-$C_b$alkyl)amino" means amino groups, which both hydrogen atoms are substituted with the above-mentioned alkyl groups having carbon atom number of a to b that may be identical with or different from each other, and includes for example dimethylamino, ethyl(methyl)amino, diethylamino, n-propyl(methyl)amino, i-propyl(methyl)amino, di(n-propyl)amino, n-butyl(methyl)amino, i-butyl(methyl)amino, t-butyl(methyl)amino, and the like. It is selected from the scope of the indicated carbon atom number.

In the specification, the indication of "$C_a$-$C_b$alkylimino" means alkyl-N=groups wherein the alkyl has carbon atom number of a to b, and includes for example methylimino, ethylimino, n-propylimino, i-propylimino, n-butylimino, i-butylimino, s-butylimino, n-pentylimino, n-hexylimino, and the like. It is selected from the scope of the indicated carbon atom number.

In the specification, the indication of "$C_a$-$C_b$alkoxyimino" means alkoxy-N=groups wherein the alkoxy has carbon atom number of a to b, and includes for example methoxyimino, ethoxyimino, n-propyloxyimino, i-propyloxyimino, n-butyloxyimino, n-pentyloxyimino, n-hexyloxyimino, and the like. It is selected from the scope of the indicated carbon atom number.

In the specification, the indication of "$C_a$-$C_b$alkylcarbonyl" means alkyl-C(O)— groups wherein the alkyl has carbon atom number of a to b, and includes for example acetyl, propionyl, butyryl, isobutyryl, valeryl, isovaleryl, 2-methylbutanoyl, pivaloyl, hexanoyl, heptanoyl, and the like. It is selected from the scope of the indicated carbon atom number.

In the specification, the indication of "$C_a$-$C_b$haloalkylcarbonyl" means haloalkyl-C(O)— groups wherein the haloalkyl has carbon atom number of a to b, and includes for example fluoroacetyl, chloroacetyl, difluoroacetyl, dichloroacetyl, trifluoroacetyl, chlorodifluoroacetyl, bromodifluoroacetyl, trichloroacetyl, pentafluoropropionyl, heptafluorobutanoyl, 3-chloro-2,2-dimethylpropanoyl, and the like. It is selected from the scope of the indicated carbon atom number.

In the specification, the indication of "$C_a$-$C_b$alkoxycarbonyl" means alkyl-O—C(O)— groups wherein the alkyl has carbon atom number of a to b, and includes for example methoxycarbonyl, ethoxycarbonyl, n-propyloxycarbonyl, 1-propyloxycarbonyl, n-butoxycarbonyl, i-butoxycarbonyl, t-butoxycarbonyl, and the like. It is selected from the scope of the indicated carbon atom number.

In the specification, the indication of "$C_a$-$C_b$haloalkoxycarbonyl" means haloalkyl-O—C(O)— groups wherein the haloalkyl has carbon atom number of a to b, and includes for example 2-chloroethoxycarbonyl, 2,2-difluoroethoxycarbonyl, 2,2,2-trifluoroethoxycarbonyl, 2,2,2-trichloroethoxycarbonyl, and the like. It is selected from the scope of the indicated carbon atom number.

In the specification, the indication of "$C_a$-$C_b$alkylthiocarbonyl" means alkyl-S—C(O)— groups wherein the alkyl has carbon atom number of a to b, and includes for example methylthio-C(O)—, ethylthio-C(O)—, n-propylthio-C(O)—, i-propylthio-C(O)—, n-butylthio-C(O)—, i-butylthio-C(O)—, t-butylthio-C(O)—, and the like. It is selected from the scope of the indicated carbon atom number.

In the specification, the indication of "$C_a$-$C_b$alkoxythiocarbonyl" means alkyl-O—C(S)— groups wherein the alkyl has carbon atom number of a to b, and includes for example methoxy-C(S)—, ethoxy-C(S)—, n-propyloxy-C(S)—, i-propyloxy-C(S)—, and the like. It is selected from the scope of the indicated carbon atom number.

In the specification, the indication of "$C_a$-$C_b$alkyldithiocarbonyl" means alkyl-S—C(S)— groups wherein the alkyl has carbon atom number of a to b, and includes for example methylthio-C(S)—, ethylthio-C(S)—, n-propylthio-C(S)—, i-propylthio-C(S)—, and the like. It is selected from the scope of the indicated carbon atom number.

In the specification, the indication of "$C_a$-$C_b$alkylaminocarbonyl" means carbamoyl groups, which either hydrogen atom is substituted with the above-mentioned alkyl group having carbon atom number of a to b, and includes for example methylcarbamoyl, ethylcarbamoyl, n-propylcarbamoyl, i-propylcarbamoyl, n-butylcarbamoyl, i-butylcarbamoyl, s-butylcarbamoyl, t-butylcarbamoyl, and the like. It is selected from the scope of the indicated carbon atom number.

In the specification, the indication of "$C_a$-$C_b$haloalkylaminocarbonyl" means carbamoyl groups, which either hydrogen atom is substituted with the above-mentioned haloalkyl group having carbon atom number of a to b, and includes for example 2-fluoroethylcarbamoyl, 2-chloroethylcarbamoyl, 2,2-difluoroethylcarbamoyl, 2,2,2-trifluoroethylcarbamoyl, and the like. It is selected from the scope of the indicated carbon atom number.

In the specification, the indication of "di($C_a$-$C_b$alkyl)aminocarbonyl" means carbamoyl groups, which both hydrogen atoms are substituted with the above-mentioned alkyl group having carbon atom number of a to b that may be identical with or different from each other, and includes for example N,N-dimethylcarbamoyl, N-ethyl-N-methylcarbamoyl, N,N-diethylcarbamoyl, N,N-di-n-propylcarbamoyl, N,N-di-n-butylcarbamoyl, and the like. It is selected from the scope of the indicated carbon atom number.

In the specification, the indication of "$C_a$-$C_b$alkylaminosulfonyl" means sulfamoyl groups, which either hydrogen atom is substituted with the above-mentioned alkyl group having carbon atom number of a to b, and includes for example methylsulfamoyl, ethylsulfamoyl, n-propylsulfamoyl, i-propylsulfamoyl, n-butylsulfamoyl, i-butylsulfamoyl, s-butylsulfamoyl, t-butylsulfamoyl, and the like. It is selected from the scope of the indicated carbon atom number.

In the specification, the indication of "di($C_a$-$C_b$alkyl)aminosulfonyl" means sulfamoyl groups, which both hydrogen atoms are substituted with the above-mentioned alkyl group having carbon atom number of a to b that may be identical with or different from each other, and includes for example N,N-dimethylsulfamoyl, N-ethyl-N-methylsulfamoyl, N,N-diethylsulfamoyl, N,N-di-n-propylsulfamoyl, N,N-di-n-butylsulfamoyl, and the like. It is selected from the scope of the indicated carbon atom number.

In the specification, the indication of "tri($C_a$-$C_b$alkyl)silyl" means silyl groups substituted with the above-mentioned alkyl group having carbon atom number of a to b that may be identical with or different from each other, and includes for example trimethylsilyl, triethylsilyl, tri(n-propyl)silyl, ethyldimethylsilyl, n-propyldimethylsilyl, n-butyldimethylsilyl, i-butyldimethylsilyl, t-butyldimethylsilyl, and the like. It is selected from the scope of the indicated carbon atom number.

In the specification, the indication of "$C_a$-$C_b$alkylcarbonyloxy" means alkylcarbonyl-O— groups wherein the alkyl has carbon atom number of a to b, and includes for example acetoxy, propionyloxy, butyryloxy, isobutyryloxy, valeryloxy, isovaleryloxy, 2-methylbutanoyloxy, pivaloyloxy, and the like. It is selected from the scope of the indicated carbon atom number.

In the specification, the indication of "$C_a$-$C_b$alkoxycarbonyloxy" means alkoxycarbonyl-O— groups wherein the alkyl has carbon atom number of a to b, and includes for example methoxycarbonyloxy, ethoxycarbonyloxy, n-propylcarbonyloxy, i-propylcarbonyloxy, n-butylcarbonyloxy, and the like. It is selected from the scope of the indicated carbon atom number.

In the specification, the indication of "$C_a$-$C_b$alkylsulfonyloxy" means alkylsulfonyl-O— groups wherein the alkyl has carbon atom number of a to b, and includes for example methylsulfonyloxy, ethylsulfonyloxy, n-propylsulfonyloxy, i-propylsulfonyloxy, and the like. It is selected from the scope of the indicated carbon atom number.

In the specification, the indication of "$C_a$-$C_b$haloalkylsulfonyloxy" means haloalkylsulfonyl-O— groups wherein the haloalkyl has carbon atom number of a to b, and includes for example difluoromethylsulfonyloxy, trifluoromethylsulfonyloxy, chlorodifluoromethylsulfonyloxy, bromodifluoromethanesulfonyloxy, and the like. It is selected from the scope of the indicated carbon atom number.

In the specification, the indication of "$C_a$-$C_b$alkylcarbonylthio" means alkylcarbonyl-S— groups wherein the alkyl has carbon atom number of a to b, and includes for example acetylthio, propionylthio, butyrylthio, isobutyrylthio, pivaloylthio, and the like. It is selected from the scope of the indicated carbon atom number.

In the specification, the indication of "$C_a$-$C_b$cycloalkyl $C_d$-$C_e$alkyl", "hydroxy $C_d$-$C_e$alkyl", "$C_a$-$C_b$alkoxy $C_d$-$C_e$alkyl", "$C_a$-$C_b$haloalkoxy $C_d$-$C_e$alkyl", "phenoxy $C_d$-$C_e$alky", "$C_a$-$C_b$alkylthio $C_d$-$C_e$alkyl", "$C_a$-$C_b$haloalkylthio $C_d$-$C_e$alkyl", "phenylthio $C_d$-$C_e$alkyl", "$C_a$-$C_b$alkylsulfinyl $C_d$-$C_e$alkyl", "$C_a$-$C_b$haloalkylsulfinyl $C_d$-$C_e$alkyl", "$C_a$-$C_b$alkylsulfonyl $C_d$-$C_e$alkyl", "$C_a$-$C_b$haloalkylsulfonyl $C_d$-$C_e$alkyl", "$C_a$-$C_b$alkoxycarbonyl $C_d$-$C_e$alkyl", "$C_a$-$C_b$haloalkoxycarbonyl $C_d$-$C_e$alkyl", "cyano $C_d$-$C_e$alkyl", "phenyl $C_d$-$C_e$alkyl", or "phenyl $C_d$-$C_e$alkyl substituted with $(Z)_{p1}$" means alkyl groups having carbon atom number of d to e, which a hydrogen atom (hydrogen atoms) bonded to carbon atom is (are) arbitrarily substituted with the $C_a$-$C_b$cycloalkyl, $C_a$-$C_b$alkoxy, $C_a$-$C_b$haloalkoxy, $C_a$-$C_b$alkylthio, $C_a$-$C_b$haloalkylthio, $C_a$-$C_b$alkylsulfinyl, $C_a$-$C_b$haloalkylsulfinyl, $C_a$-$C_b$alkylsulfonyl, $C_a$-$C_b$haloalkylsulfonyl, $C_a$-$C_b$alkoxycarbonyl, $C_a$-$C_b$haloalkoxycarbonyl, hydroxy, cyano, phenoxy, phenylthio, phenyl, or phenyl substituted with $(Z)_{p1}$ that has the meaning mentioned above, respectively. It is selected from the scope of the indicated carbon atom number.

In the specification, the indication of "$C_a$-$C_b$alkyl arbitrarily substituted with $R^4$", "$C_a$-$C_b$alkyl arbitrarily substituted with $R^{14}$", "$C_a$-$C_b$alkyl arbitrarily substituted with $R^{14a}$", "$C_a$-$C_b$alkyl arbitrarily substituted with $R^{24}$", "$C_a$-$C_b$alkyl arbitrarily substituted with $R^{31}$" or "$C_a$-$C_b$alkyl arbitrarily substituted with $R^{34}$" means straight-chain or branched-chain hydrocarbon groups having carbon atom number of a to b, which a hydrogen atom (hydrogen atoms) bonded to carbon atom is (are) arbitrarily substituted with $R^4$, $R^{14}$, $R^{14a}$, $R^{24}$, $R^{31}$ or $R^{34}$. It is selected from the scope of the indicated carbon atom number.

In this case, when two or more substituents $R^4$, $R^{14}$, $R^{14a}$, $R^{24}$, $R^{31}$ or $R^{34}$ are present on the $C_a$-$C_b$alkyl, respective $R^4$, $R^{14}$, $R^{14a}$, $R^{24}$, $R^{31}$ or $R^{34}$ may be identical with or different from each other.

In the specification, the indication of "hydroxy $C_d$-$C_e$haloalkyl", "$C_a$-$C_b$alkoxy $C_d$-$C_e$haloalkyl", "$C_a$-$C_b$haloalkoxy $C_d$-$C_e$haloalkyl", "$C_a$-$C_b$alkylthio $C_d$-$C_e$haloalkyl", "$C_a$-$C_b$haloalkylthio $C_d$-$C_e$haloalkyl" or "cyano $C_d$-$C_e$haloalkyl" means the haloalkyl having carbon atom number of d to e, which a hydrogen atom (hydrogen atoms) or a halogen atom (halogen atoms) bonded to carbon atom is (are) arbitrarily substituted with the $C_a$-$C_b$alkoxy, $C_a$-$C_b$haloalkoxy, $C_a$-$C_b$alkylthio, $C_a$-$C_b$haloalkylthio, hydroxy or cyano. It is selected from the scope of the indicated carbon atom number.

In the specification, the indication of "hydroxy $C_d$-$C_e$cycloalkyl", "$C_a$-$C_b$alkoxy $C_d$-$C_e$cycloalkyl", "$C_a$-$C_b$alkenyl $C_d$-$C_e$cycloalkyl" or "$C_a$-$C_b$haloalkenyl $C_d$-$C_e$cycloalkyl" means the cycloalkyl having carbon atom number of d to e, which a hydrogen atom (hydrogen atoms) bonded to carbon atom is (are) arbitrarily substituted with $C_a$-$C_b$alkoxy, $C_a$-$C_b$alkenyl, $C_a$-$C_b$haloalkenyl or hydroxy. It is selected from the scope of the indicated carbon atom number.

In the specification, the indication of "$C_a$-$C_b$cycloalkyl arbitrarily substituted with $R^4$", "$C_a$-$C_b$cycloalkyl arbitrarily substituted with $R^{14}$", "$C_a$-$C_b$cycloalkyl arbitrarily substituted with $R^{14a}$", "$C_a$-$C_b$cycloalkyl arbitrarily substituted with $R^{24}$" or "$C_a$-$C_b$cycloalkyl arbitrarily substituted with $R^{31}$" means the cycloalkyl groups having carbon atom number of a to b, which a hydrogen atom (hydrogen atoms) bonded to carbon atom is (are) arbitrarily substituted with $R^4$, $R^{14}$, $R^{14a}$, $R^{24}$ or $R^{31}$. The substitution for $R^4$, $R^{14}$, $R^{14a}$, $R^{24}$ or $R^{31}$ may be in the ring structure moiety, the side chain moiety or both of them. In this case, when two or more substituents $R^4$, $R^{14}$, $R^{14a}$, $R^{24}$ or $R^{31}$ are present on the $C_a$-$C_b$cycloalkyl, respective $R^4$, $R^{14}$, $R^{14a}$, $R^{24}$ or $R^{31}$ may be identical with or different from each other.

In the specification, the indication of "$C_a$-$C_b$alkoxy $C_d$-$C_e$alkenyl" or "phenyl $C_d$-$C_e$alkenyl" means the alkenyl having carbon atom number of a to b, which a hydrogen atom (hydrogen atoms) bonded to carbon atom is (are) arbitrarily substituted with $C_a$-$C_b$alkoxy or phenyl. It is selected from the scope of the indicated carbon atom number.

In the specification, the indication of "$C_a$-$C_b$alkenyl arbitrarily substituted with $R^4$", "$C_a$-$C_b$alkenyl arbitrarily substituted with $R^{14}$", "$C_a$-$C_b$alkenyl arbitrarily substituted with $R^{14a}$", "$C_a$-$C_b$alkenyl arbitrarily substituted with $R^{24}$" or "$C_a$-$C_b$alkenyl arbitrarily substituted with $R^{31}$" means the alkenyl groups having carbon atom number of a to b, which a hydrogen atom (hydrogen atoms) bonded to carbon atom is (are) arbitrarily substituted with $R^4$, $R^{14}$, $R^{14a}$, $R^{24}$ or $R^{31}$. It is selected from the scope of the indicated carbon atom number. In this case, when two or more substituents $R^4$, $R^{14}$, $R^{14a}$, $R^{24}$ or $R^{31}$ are present on the $C_a$-$C_b$alkenyl, respective $R^4$, $R^{14}$, $R^{14a}$, $R^{24}$ or $R^{31}$ may be identical with or different from each other.

In the specification, the indication of "$C_a$-$C_b$alkynyl arbitrarily substituted with $R^4$", "$C_a$-$C_b$alkynyl arbitrarily substituted with $R^{14}$", "$C_a$-$C_b$alkynyl arbitrarily substituted with $R^{14a}$", "$C_a$-$C_b$alkynyl arbitrarily substituted with $R^{24}$" or "$C_a$-$C_b$alkynyl arbitrarily substituted with $R^{31}$" means the alkynyl groups having carbon atom number of a to b, which a hydrogen atom (hydrogen atoms) bonded to carbon atom is (are) arbitrarily substituted with $R^4$, $R^{14}$, $R^{14a}$, $R^{24}$ or $R^{31}$. It is selected from the scope of the indicated carbon atom number. In this case, when two or more substituents $R^4$, $R^{14}$, $R^{14a}$, $R^{24}$ or $R^{31}$ are present on the $C_a$-$C_b$alkenyl, respective $R^4$, $R^{14}$, $R^{14a}$, $R^{24}$ or $R^{31}$ may be identical with or different from each other.

In the specification, the indication of "$C_a$-$C_b$alkoxy $C_d$-$C_e$alkoxy" means the $C_d$-$C_e$alkoxy, which a hydrogen atom (hydrogen atoms) bonded to carbon atom is (are) arbitrarily substituted with $C_a$-$C_b$alkoxy. It is selected from the scope of the indicated carbon atom number.

In the specification, the indication of "$C_a$-$C_b$alkoxy $C_d$-$C_e$alkylthio", "$C_a$-$C_b$haloalkoxy $C_d$-$C_e$alkylthio", "$C_a$-$C_b$alkylthio $C_d$-$C_e$alkylthio" or "cyano $C_d$-$C_e$alkylthio" or the like means the $C_d$-$C_e$alkylthio, which a hydrogen atom (hydrogen atoms) bonded to carbon atom is (are) arbitrarily substituted with $C_a$-$C_b$alkoxy, $C_a$-$C_b$haloalkoxy, $C_a$-$C_b$alkylthio or cyano. It is selected from the scope of the indicated carbon atom number.

In the specification, concrete examples of the indication of "$R^7$ together with $R^6$ may form 3- to 7-membered ring together with the nitrogen atom bonding them by forming $C_2$-$C_6$ alkylene chain, in this case, the alkylene chain may contain one oxygen atom, sulfur atom or nitrogen atom", "$R^{10}$ together with $R^9$ may form 3- to 7-membered ring with the nitrogen atom bonding them by forming $C_2$-$C_6$alkylene chain, in this case, the alkylene chain may contain one oxygen atom, sulfur atom or nitrogen atom", "$R^{16}$ together with $R^{15}$ may form 3- to 7-membered ring with the nitrogen atom bonding them by forming $C_2$-$C_6$alkylene chain, in this case, the alkylene chain may contain one oxygen atom, sulfur atom or nitrogen atom", and "$R^{26}$ together with $R^{25}$ may form 3- to 6-membered ring with the nitrogen atom bonding them by forming $C_2$-$C_5$alkylene chain, in this case, the alkylene chain may contain one oxygen atom or sulfur atom", are for example aziridine, azetidine, azetidine-2-one, pyrrolidine, pyrrolidine-2-one, oxazolidine, oxazolidine-2-one, oxazolidine-2-thione, thiazoridine, thiazoridine-2-one, thiazoridine-2-thione, imidazolidine, imidazolidine-2-one, imidazolidine-2-thione, piperidine, piperidine-2-one, piperidine-2-thione,
2H-3,4,5,6-tetrahydro-1,3-oxadine-2-one, 2H-3,4,5,6-tetrahydro-1,3-oxadine-2-thione, morpholine, 2H-3,4,5,6-tetrahydro-1,3-thiadine-2-one, 2H-3,4,5,6-tetrahydro-1,3-thiadine-2-thione, thiomorpholine, perhydropyrimidine-2-one, piperazine, homopiperidine, homopiperidine-2-one, heptamethyleneimine, and the like. It is selected from the scope of the indicated carbon atom number.

In the specification, concrete examples of the indication of "$R^{18}$ together with $R^{17}$ may form 5- to 6-membered ring with the nitrogen atom bonding them by forming $C_4$-$C_5$alkylene chain, in this case, the alkylene chain may contain one oxygen atom, sulfur atom or nitrogen atom", "$R^{20}$ together with $R^{19}$ may form 5- to 8-membered ring with the nitrogen atom bonding them by forming $C_4$-$C_7$alkylene chain, in this case, the alkylene chain may contain one oxygen atom or sulfur atom", "$R^{29}$ together with $R^{28}$ may form 3- to 6-membered ring with the nitrogen atom bonding them by forming $C_2$-$C_5$alkylene chain, in this case, the alkylene chain may contain one oxygen atom or sulfur atom", and "$R^{33}$ together with $R^{32}$ may form 3- to 6-membered ring with the nitrogen atom bonding them by forming $C_2$-$C_5$alkylene chain, in this case, the alkylene chain may contain one oxygen atom or sulfur atom", are for example aziridine, azetidine, pyrrolidine, oxazolidine, thiazoridine, imidazolidine, piperidine, morpholine, thiomorpholine, piperazine, homopiperidine, heptamethyleneimine, and the like. It is selected from the scope of the indicated carbon atom number.

In the specification, concrete examples of the indication of "$R^{17b}$ together with $R^{17a}$ may form 4- to 6-membered ring with the carbon atom bonding them by forming $C_3$-$C_5$alkylene chain, in this case, the alkylene chain may contain one oxygen atom, sulfur atom or nitrogen atom" are for example cyclopentylidene, tetrahydrofuran-3-ylidene, tetrahydrothiphen-3-ylidene, cyclohexylidene, tetrahydropyran-3-ylidene, tetrahydropyran-4-ylidene, tetrahydrothiopyran-3-ylidene, tetrahydrothiopyran-4-ylidene, and the like. It is selected from the scope of the indicated carbon atom number.

In the compounds included in the present invention, the combination of the atoms of $A^1$, $A^2$ and $A^3$ includes for example the following groups.

That is, A-I: $A^1$, $A^2$ and $A^3$ are carbon atoms.
A-II: $A^1$ is nitrogen atom, $A^2$ and $A^3$ are carbon atoms.
A-III: $A^2$ is nitrogen atom, $A^1$ and $A^3$ are carbon atoms.
A-IV: $A^1$ and $A^3$ are nitrogen atoms, $A^2$ is carbon atom.
A-V: $A^1$ and $A^2$ are nitrogen atoms, $A^3$ is carbon atom.
A-V: $A^2$ and $A^3$ are nitrogen atoms, $A^1$ is carbon atom.

In the compounds included in the present invention, the substituent shown in G includes aromatic 6-membered and 5-membered rings. Among them, aromatic 6-membered rings shown in G-1, G-3 and G-4 and aromatic 5-membered rings shown in any one of G-13, G-14, G-17, G-18, G-20, G-21 and G-22 are preferable, and aromatic 6-membered ring shown in G-1 is particularly preferable.

In the compounds included in the present invention, the substituent W includes for example oxygen atom or sulfur atom.

In the compounds included in the present invention, the substituent X includes for example the following groups. In each case mentioned below, when m is an integer of 2 or more, Xs may be identical with or different from each other.

That is, X-I: halogen atom and $C_1$-$C_6$haloalkyl.
X-II: halogen atom, cyano, nitro, $C_1$-$C_6$alkyl, $C_1$-$C_6$haloalkyl, —$OR^5$, and —$S(O)_rR^5$ (wherein $R^5$ is $C_1$-$C_6$alkyl or $C_1$-$C_6$haloalkyl, and r is an integer of 0 to 2).
X-III: halogen atom, cyano, nitro, —$SF_5$, $C_1$-$C_6$alkyl, $C_1$-$C_6$haloalkyl, hydroxy $C_1$-$C_6$haloalkyl, $C_1$-$C_6$alkoxy $C_1$-$C_6$haloalkyl, $C_3$-$C_8$halocycloalkyl, —$OR^5$, —$OSO_2R^5$, and —$S(O)_rR^5$ (wherein $R^5$ is $C_1$-$C_6$alkyl, $C_1$-$C_6$haloalkyl or $C_1$-$C_3$haloalkoxy $C_1$-$C_3$haloalkyl, and r is an integer of 0 to 2).
X-IV: halogen atom, $C_1$-$C_6$haloalkyl, $C_1$-$C_6$haloalkyl arbitrarily substituted with $R^4$ (wherein $R^4$ is —OH, $C_1$-$C_6$alkoxy or $C_1$-$C_6$haloalkoxy), $C_3$-$C_8$halocycloalkyl, $C_2$-$C_6$haloalkenyl, $C_2$-$C_6$haloalkynyl, —$OR^5$, —$OSO_2R^5$, and —$S(O)_rR^5$ (wherein $R^5$ is $C_1$-$C_6$haloalkyl, $C_1$-$C_3$haloalkoxy $C_1$-$C_3$haloalkyl, $C_2$-$C_6$haloalkenyl or $C_3$-$C_6$haloalkynyl, and r is an integer of 0 to 2).
X-V: halogen atom, $C_1$-$C_6$alkyl, $C_1$-$C_6$haloalkyl, $C_1$-$C_6$alkyl arbitrarily substituted with $R^4$ (wherein $R^4$ is $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl or $C_1$-$C_6$haloalkylsulfonyl), $C_3$-$C_8$cycloalkyl, $C_2$-$C_6$alkenyl, $C_2$-$C_6$alkynyl, —OH, —$OR^5$, —$OSO_2R^5$ and —$S(O)_rR^5$ (wherein $R^5$ is $C_1$-$C_6$alkyl, $C_2$-$C_6$alkenyl, $C_3$-$C_6$alkynyl, or $C_1$-$C_6$alkoxycarbonyl, and r is an integer of 0 to 2).
X-VI: halogen atom, $C_1$-$C_6$haloalkyl, cyano, nitro, —$SF_5$ and tri($C_1$-$C_6$alkyl)silyl.
X-VII: m is 2, two adjacent Xs form 5- or 6-membered ring with the carbon atoms to which the two Xs are bonded by forming —$CF_2OCF_2$—, —$OCF_2O$—, —$CF_2OCF_2O$— or —$OCF_2CF_2O$—.

In the compounds included in the present invention, m indicating the number of substituent X is an integer of 0 to 5. Among them, m is preferably 1, 2 and 3.

In the compounds included in the present invention, the substituent Y includes for example the following groups. In each case mentioned below, when n is an integer of 2 or more, Ys may be identical with or different from each other.

That is, Y-I: halogen atom, $C_1$-$C_6$alkyl and $C_1$-$C_6$haloalkyl.
Y-II: halogen atom, cyano, nitro, $C_1$-$C_6$alkyl, $C_1$-$C_6$haloalkyl, —$OR^5$, —$SR^5$ (wherein $R^5$ is $C_1$-$C_6$alkyl or $C_1$-$C_6$haloalkyl), —$NH_2$ and —$N(R^7)R^6$ (wherein $R^6$ is $C_1$-$C_6$alkyl, —CHO, $C_1$-$C_6$alkylcarbonyl or $C_1$-$C_6$alkoxycarbonyl, and $R^7$ is hydrogen atom or $C_1$-$C_6$alkyl).
Y-III: halogen atom, cyano, nitro, $C_1$-$C_6$alkyl, $C_1$-$C_6$haloalkyl, $C_1$-$C_4$alkyl arbitrarily substituted with $R^4$ (wherein $R^4$ is —OH, $C_1$-$C_6$alkoxy, $C_1$-$C_6$haloalkoxy, $C_1$-$C_6$alkylthio or $C_1$-$C_6$haloalkylthio), —$OR^5$, —$SR^5$ (wherein $R^5$ is $C_1$-$C_6$alkyl or $C_1$-$C_6$haloalkyl), —$NH_2$, —$N(R^7)R^6$ (wherein $R^6$ is $C_1$-$C_6$alkyl, —CHO, $C_1$-$C_6$alkylcarbonyl, $C_1$-$C_6$haloalkylcarbonyl, $C_1$-$C_6$alkoxycarbonyl, $C_1$-$C_6$alkylthiocarbonyl, $C_1$-$C_6$alkoxythiocarbonyl, $C_1$-$C_6$alkyldithiocarbonyl, $C_1$-$C_6$alkylsulfonyl or $C_1$-$C_6$haloalkylsulfonyl, $R^7$ is hydrogen atom or $C_1$-$C_6$alkyl) and —$C(S)NH_2$.
Y-IV: halogen atom, cyano, $C_1$-$C_6$alkyl and $C_1$-$C_6$alkyl arbitrarily substituted with $R^4$ (wherein $R^4$ is halogen atom, —OH, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl or $C_1$-$C_6$haloalkylsulfonyl), $C_2$-$C_6$alkynyl, tri($C_1$-$C_6$alkyl)silylethynyl, —$C(O)NH_2$ and —$C(S)NH_2$.
Y-V: halogen atom, $C_1$-$C_6$alkyl, —$OR^5$, —$OSO_2R^5$ and —$S(O)_rR^5$ (wherein $R^5$ is $C_1$-$C_6$alkyl, $C_1$-$C_6$haloalkyl, $C_2$-$C_6$alkenyl, $C_2$-$C_6$haloalkenyl, $C_3$-$C_6$alkynyl or $C_3$-$C_6$haloalkynyl and r is an integer of 0 to 2).
Y-VI: halogen atom, nitro, $C_1$-$C_6$alkyl, —$NH_2$, —$N(R^7)R^6$ (wherein $R^6$ is $C_1$-$C_6$alkyl, $C_1$-$C_6$haloalkyl, —CHO, —$C(O)R^9$, —$C(O)OR^9$, —$C(O)SR^9$, —$C(S)OR^9$, —$C(S)SR^9$ or —$S(O)_2R^9$ (wherein $R^7$ is hydrogen atom, $C_1$-$C_6$alkyl or $C_1$-$C_6$haloalkyl, and $R^9$ is $C_1$-$C_6$alkyl, $C_1$-$C_6$haloalkyl, $C_3$-$C_6$cycloalkyl or $C_3$-$C_6$halocycloalkyl), and —N=C($R^9$) $OR^8$ (wherein $R^8$ is $C_1$-$C_6$alkyl, and $R^9$ is $C_1$-$C_6$alkyl or $C_1$-$C_6$haloalkyl).

In the compounds included in the present invention, n indicating the number of substituent Y is an integer of 0 to 4. Among them, n is preferably 0 and 1.

In the compounds included in the present invention, the substituent $R^1$ includes for example the following groups.

That is, $R^1$-I: —CH=$NOR^{1a}$ (wherein $R^{1a}$ is $C_1$-$C_6$alkyl).
$R^1$-II: —C(O)$OR^{1c}$ (wherein $R^{1c}$ is $C_1$-$C_6$alkyl or $C_3$-$C_6$cycloalkyl).
$R^1$-III: —C(O)N($R^{1e}$)$R^{1d}$ (wherein $R^{1d}$ is hydrogen atom, —C(O)$R^{15}$ or —C(O)$OR^{15}$, $R^{1e}$ is hydrogen atom or $C_1$-$C_6$alkyl, and $R^{15}$ is $C_1$-$C_6$alkyl or $C_1$-$C_6$haloalkyl).
$R^1$—IV: phenyl substituted with $(Z)_{p1}$, D-52, D-55, D-56, D-57 and D-58 (wherein Z is halogen atom or cyano, when p1, p2 or p3 is an integer of 2 or more, each Z may be identical with or different from each other, p1 is an integer of 1 to 3, p2 and p3 are an integer of 0 to 2 and t is 0).
$R^1$-V: —C($R^{1b}$)=$NOR^{1a}$ (wherein $R^{1a}$ is hydrogen atom, $C_1$-$C_6$alkyl, $C_1$-$C_6$haloalkyl, $C_3$-$C_6$cycloalkyl $C_1$-$C_4$alkyl, $C_3$-$C_6$alkenyl or $C_3$-$C_6$alkynyl, and $R^{1b}$ is hydrogen atom or $C_1$-$C_6$alkyl).
$R^1$-VI: —C(O)$OR^{1c}$, —C(O)$SR^{1c}$ and —C(S)$OR^{1c}$ (wherein $R^{1c}$ is $C_1$-$C_6$alkyl, $C_1$-$C_4$alkyl arbitrarily substituted with $R^{14}$ or $C_3$-$C_6$cycloalkyl, $R^{14}$ is cyano, $C_3$-$C_6$cycloalkyl, $C_1$-$C_6$alkoxy, $C_1$-$C_4$alkoxy $C_1$-$C_4$alkoxy, $C_1$-$C_6$alkylthio, —S(D-52), —S(D-55), $C_1$-$C_6$alkylsulfonyl, —NHC(O)$R^{32}$, —NHC(O)$OR^{32}$, $C_1$-$C_6$alkylcarbonyl or $C_1$-$C_6$alkoxycarbonyl, $R^{32}$ is $C_1$-$C_6$alkyl or $C_3$-$C_6$cycloalkyl, Z is halogen atom or $C_1$-$C_6$alkyl, p2 and p3 are an integer of 0 or 1, and t is 0).
$R^1$-VII: —C(O)N($R^{1e}$)$R^{1d}$ or —C(S)N($R^{1e}$)$R^{1d}$ (wherein $R^{1d}$ is hydrogen atom, —C(O)$R^{15}$, —C(O)$OR^{15}$ or —C(O)$SR^{15}$, $R^{1e}$ is hydrogen atom or $C_1$-$C_6$alkyl, $R^{15}$ is $C_1$-$C_6$alkyl, $C_1$-$C_6$haloalkyl, phenyl or phenyl substituted with $(Z)_{p1}$, Z is halogen atom, cyano, nitro or $C_1$-$C_6$alkoxy, when p1 is 2, each Z may be identical with or different from each other, p1 is an integer of 1 or 2).
$R^1$-VIII: phenyl, phenyl substituted with $(Z)_{p1}$, D-3, D-8, D-10, D-11, D-13 to D-15, D-17, D-22, D-35, D-52 to D-58 or D-59 (wherein $R^{13}$ is $C_1$-$C_6$alkyl or $C_1$-$C_6$haloalkyl, Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylsulfonyloxy, $C_1$-$C_6$haloalkylsulfonyloxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, $C_1$-$C_6$alkoxycarbonyl, —C(O)$NH_2$ or —C(S)$NH_2$, when p1, p2 or p3 is an integer of 2 or more, each Z may be identical with or different from each other, further, when two Zs are adjacent, the adjacent two Zs may form 5-membered or 6-membered ring together with carbon atoms to which the two Zs are bonded by forming —OCH$_2$O— or —OCH$_2$CH$_2$O—, in this case, hydrogen atoms bonded to each carbon atom forming the ring may be arbitrarily substituted with halogen atom, p1 is an integer of 1 to 3, p2 and p3 are an integer of 0 to 2, p4 and p5 are an integer of 0 or 1 and t is an integer of 0 or 1).
$R^1$-IX: —C($R^{1b}$)=$NOR^{1a}$ (wherein $R^{1a}$ is hydrogen atom, $C_1$-$C_6$alkyl, $C_1$-$C_6$haloalkyl, $C_1$-$C_4$alkyl arbitrarily substituted with $R^{14}$, $C_3$-$C_6$cycloalkyl, E-4, E-6, E-8, E-10, E-25, E-26, E-28, E-29, E-31, E-32, E-35, $C_3$-$C_6$alkenyl, $C_3$-$C_6$haloalkenyl, $C_3$-$C_6$alkynyl, $C_3$-$C_6$haloalkynyl, phenylC$_3$-C$_6$alkynyl, phenyl or phenyl substituted with $(Z)_{p1}$, $R^{1b}$ is hydrogen atom, $C_1$-$C_6$alkyl, $C_1$-$C_6$haloalkyl, $C_1$-$C_4$alkoxy$C_1$-$C_4$alkyl, $C_1$-$C_4$alkylthio$C_1$-$C_4$alkyl or $C_3$-$C_6$cycloalkyl, $R^{14}$ is cyano, $C_3$-$C_6$cycloalkyl, $C_3$-$C_6$halocycloalkyl, E-5 to E-8, E-10 to E-12, E-19, E-24 to E-29, E-31 to E-33, E-44, —$OR^{25}$, —N($R^{26}$)$R^{25}$, —S(O)$_r$$R^{27}$, $C_5$-$C_6$cycloalkenyl, $C_5$-$C_8$halocycloalkenyl, M-1, —C(O)$R^{28}$, —C(O)$OR^{28}$, —C(O)$NH_2$, —C(O)N($R^{29}$)$R^{28}$, M-11, M-28, —C(S)$OR^{28}$, —C(S)$SR^{28}$, —C(S)$NH_2$, —C(S)N($R^{29}$)$R^{28}$, M-14, M-32, —CH=$NOR^{30}$, —C($R^{28}$)=$NOR^{30}$, M-5, —SO$_2$N($R^{29}$)$R^{28}$, phenyl, phenyl substituted with $(Z)_{p1}$, D-1, D-2, D-52, D-53 or D-54, $R^{22}$ is $C_1$-$C_6$alkyl or $C_1$-$C_6$haloalkyl, when q2 is 2, each $R^{22}$ may be identical with or different from each other, $R^{23}$ is —CHO, $C_1$-$C_6$alkylcarbonyl or $C_1$-$C_6$alkoxycarbonyl, $R^{25}$ is $C_1$-$C_6$alkyl, $C_1$-$C_6$haloalkyl, $C_1$-$C_4$alkyl arbitrarily substituted with $R^{31}$, —C(O)$R^{32}$, —C(O)$OR^{32}$, —C(O)N($R^{33}$)$R^{32}$, —C(S)N($R^{33}$)$R^{32}$, —SO$_2$$R^{32}$, —S(O)$_2$N($R^{33}$)$R^{32}$, —P(O)(OR$^{21}$)$_2$, —P(S)(OR$^{21}$)$_2$ or phenyl, $R^{21}$ is $C_1$-$C_6$alkyl, $R^{26}$ is hydrogen atom, $C_1$-$C_6$alkyl or $C_1$-$C_6$alkoxy, or $R^{26}$ together with $R^{25}$ may form 5- to 7-membered ring with the nitrogen atom bonding them by forming $C_4$-$C_6$alkylene chain, in this case, the alkylene chain may contain one oxygen atom or sulfur atom, $R^{27}$ is $C_1$-$C_8$alkyl, $C_1$-$C_4$alkyl arbitrarily substituted with $R^{31}$, $C_3$-$C_6$alkenyl, $C_3$-$C_6$alkynyl, —C(O)$R^{32}$, —C(O)N($R^{33}$)$R^{32}$, —C(S)N($R^{33}$)$R^{32}$, phenyl or D-55, $R^{28}$ is $C_1$-$C_6$alkyl, $R^{29}$ is hydrogen atom or $C_1$-$C_6$alkyl, or $R^{29}$ together with $R^{28}$ may form 5- to 6-membered ring with the nitrogen atom bonding them by forming $C_4$-$C_5$alkylene chain, in this case, the alkylene chain may contain one oxygen atom or sulfur atom, $R^{30}$ is $C_1$-$C_6$alkyl, $R^{31}$ is $C_1$-$C_4$alkoxy, $C_1$-$C_4$alkoxy $C_1$-$C_4$alkoxy, $C_1$-$C_4$alkylthio or phenyl, $R^{32}$ is $C_1$-$C_6$alkyl, $C_1$-$C_6$haloalkyl, $C_1$-$C_4$alkyl arbitrarily substituted with $R^{34}$, $C_2$-$C_6$alkenyl or phenyl, $R^{33}$ is hydrogen atom or $C_1$-$C_6$alkyl, or $R^{33}$ together with $R^{32}$ may form 5- to 6-membered ring with the nitrogen atom bonding them by forming $C_4$-$C_5$alkylene chain, in this case, the alkylene chain may contain one oxygen atom or sulfur atom, $R^{34}$ is $C_1$-$C_4$alkoxy, $C_1$-$C_4$alkylthio, phenyl, D-52, D-53 or D-54, Z is halogen atom, when p1 is 2, each Z may be identical with or different from each other, p1 is an integer of 1 or 2, p2 and p3 are an integer of 0 or 1, q2 is an integer of 0 to 2, q3, q4 and q5 are 0, q6 is an integer of 0 or 1, r is an integer of 0 to 2, and t is 0), M-5 and M-20 (wherein $R^{22}$ is $C_1$-$C_6$alkyl, phenyl or phenyl substituted with $(Z)_{p1}$, Z is halogen atom, when p1 is 2, each Z may be identical with or different from each other, p1 is an integer of 1 or 2, q5 is 0, and q6 is an integer of 0 to 1), and —C($R^{1b}$)=NN($R^{1e}$)$R^{1f}$ (wherein $R^{1b}$ is hydrogen atom, $C_1$-$C_6$alkyl, $C_1$-$C_6$haloalkyl, $C_1$-$C_4$alkoxy$C_1$-$C_4$alkyl, $C_1$-$C_4$alkylthio$C_1$-$C_4$alkyl or $C_3$-$C_6$cycloalkyl, $R^{1e}$ is hydrogen atom or $C_1$-$C_6$alkyl, and $R^{1f}$ is $C_1$-$C_6$alkylcarbonyl or $C_1$-$C_6$alkoxycarbonyl).
$R^1$-X: —C(O)$OR^{1c}$, —C(O)$SR^{1c}$, —C(S)$OR^{1c}$ and —C(S)$SR^{1c}$ (wherein $R^{1c}$ is $C_1$-$C_6$alkyl, $C_1$-$C_4$alkyl arbitrarily substituted with $R^{14}$, $C_3$-$C_6$cycloalkyl, E-5, E-6, E-8, E-10, E-25, E-26, E-28, E-29, E-31, E-32, E-35, $C_2$-$C_6$alkenyl, $C_3$-$C_6$haloalkenyl, $C_3$-$C_6$alkynyl, $C_3$-$C_6$haloalkynyl, phenyl or phenyl substituted with $(Z)_{p1}$, $R^{14}$ is cyano, nitro, $C_3$-$C_6$cycloalkyl, $C_3$-$C_6$halocycloalkyl, E-5 to E-8, E-10 to E-12, E-19, E-24 to E-29, E-31 to E-33, E-44, —$OR^{25}$, —N($R^{26}$)$R^{25}$, —S(O)$_r$$R^{27}$, $C_5$-$C_6$cycloalkenyl, M-1, —CHO, $C_1$-$C_6$alkylcarbonyl, —C(O)$OR^{28}$, —C(O)$SR^{28}$, —C(O)$NH_2$, —C(O)N($R^{29}$)$R^{28}$, M-11, M-28, —C(S)$OR^{28}$, —C(S)$SR^{28}$, —C(S)$NH_2$, —C(S)N($R^{29}$)$R^{28}$, M-14, M-32, —CH=$NOR^{30}$, —C($R^{28}$)=$NOR^{30}$, M-5, —SO$_2$N($R^{29}$)$R^{28}$, tri($C_1$-$C_6$alkyl)silyl, phenyl, phenyl substituted with $(Z)_{p1}$, D-1, D-52, D-53 or D-54, $R^{22}$ is $C_1$-$C_6$alkyl or $C_1$-$C_6$haloalkyl, when q2 is 2, each $R^{22}$ may be identical with or different from each other, $R^{23}$ is —CHO, $C_1$-$C_6$alkylcarbonyl, $C_1$-$C_6$haloalkylcarbonyl or $C_1$-$C_6$alkoxycarbonyl, $R^{25}$ is $C_1$-$C_6$alkyl, $C_1$-$C_6$haloalkyl, $C_1$-$C_4$alkyl arbitrarily substituted with $R^{31}$, —C(O)$R^{32}$, —C(O)O$R^{32}$, —C(O)N($R^{33}$)$R^{32}$, —C(S)N($R^{33}$)$R^{32}$, —SO$_2$$R^{32}$, —S(O)$_2$N($R^{33}$)$R^{32}$, —P(O)(O$R^{21}$)$_2$, —P(S)(O$R^{21}$)$_2$ or phenyl, $R^{21}$ is $C_1$-$C_6$alkyl,
$R^{26}$ is hydrogen atom, $C_1$-$C_6$alkyl or $C_1$-$C_6$alkoxy, or $R^{26}$ together with $R^{25}$ may form 5- to 7-membered ring with the nitrogen atom bonding them by forming $C_4$-$C_6$alkylene chain, in this case, the alkylene chain may contain one oxygen atom or sulfur atom, $R^{27}$ is $C_1$-$C_4$alkyl, $C_1$-$C_4$alkyl arbitrarily substituted with $R^{31}$, $C_3$-$C_6$alkenyl, $C_3$-$C_6$alkynyl, $C_1$-$C_6$alkylthio, $C_1$-$C_8$alkylcarbonyl, —C(O)N($R^{33}$)$R^{32}$, —C(S)N($R^{33}$)$R^{32}$, phenyl, D-21, D-52 or D-55, $R^{28}$ is $C_1$-$C_6$alkyl or $C_1$-$C_6$haloalkyl, $R^{29}$ is hydrogen atom or $C_1$-$C_6$alkyl, or $R^{29}$ together with $R^{28}$ may form 5- to 6-membered ring with the nitrogen atom bonding them by forming $C_4$-$C_5$alkylene chain, in this case, the alkylene chain may contain one oxygen atom or sulfur atom, $R^{30}$ is $C_1$-$C_6$alkyl, $R^{31}$ is $C_1$-$C_4$alkoxy, $C_1$-$C_4$haloalkoxy, $C_1$-$C_4$alkoxy $C_1$-$C_4$alkoxy, $C_1$-$C_4$alkylthio or phenyl, $R^{32}$ is $C_1$-$C_6$alkyl, $C_1$-$C_6$haloalkyl, $C_1$-$C_4$alkyl arbitrarily substituted with $R^{34}$, $C_3$-$C_6$cycloalkyl, $C_3$-$C_6$alkenyl or phenyl, $R^{33}$ is hydrogen atom or $C_1$-$C_6$alkyl, or $R^{33}$ together with $R^{32}$ may form 5- to 7-membered ring with the nitrogen atom bonding them by forming $C_4$-$C_6$alkylene chain, in this case, the alkylene chain may contain one oxygen atom or sulfur atom, $R^{34}$ is $C_1$-$C_4$alkoxy, $C_1$-$C_4$alkylthio, phenyl, D-52, D-53 or D-54, Z is halogen atom, cyano, nitro, $C_1$-$C_6$alkyl or $C_1$-$C_6$alkoxy, when p1 is 2, each Z may be identical with or different from each other, p1 is an integer of 1 or 2, p2, p3 and p4 are an integer of 0 or 1, q2 is an integer of 0 to 2, q3, q4 and q5 are 0, q6 is an integer of 0 or 1, r is an integer of 0 to 2, and t is 0).
$R^1$-XI: —C(O)N($R^{1e}$)$R^{1d}$ and —C(S)N($R^{1e}$)$R^{1d}$ (wherein $R^{1d}$ is hydrogen atom, —C(O)$R^{15}$, —C(O)O$R^{15}$, —C(O)S$R^{15}$, —C(S)O$R^{15}$, —C(S)S$R^{15}$ or —S(O)$_2$$R^{15}$, $R^{1e}$ is hydrogen atom or $C_1$-$C_6$alkyl, $R^{15}$ is $C_1$-$C_6$alkyl, $C_1$-$C_6$haloalkyl, $C_1$-$C_4$alkyl arbitrarily substituted with $R^{31}$, $C_3$-$C_6$cycloalkyl, $C_2$-$C_6$alkenyl, $C_2$-$C_6$haloalkenyl, $C_3$-$C_8$halocycloalkenyl, $C_2$-$C_6$alkynyl, phenyl, phenyl substituted with $(Z)_{p1}$, D-1 to D-4, D-28, D-52, D-53 or D-54, $R^{31}$ is $C_1$-$C_4$alkoxy, phenoxy, $C_1$-$C_4$alkylthio, phenylthio, $C_1$-$C_4$alkoxycarbonyl or phenyl, Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylthio or $C_1$-$C_6$alkylsulfonyl, when p1 is 2, each Z may be identical with or different from each other, p1 is an integer of 1 or 2, p2, p3 and p5 are an integer of 0 or 1, and t is 0).
$R^1$-XII: phenyl, phenyl substituted with $(Z)_{p1}$, D-1 to D-5, D-7 to D-17, D-21 to D-45, D-47 to D-63 or D-65 (wherein $R^{13}$ is $C_1$-$C_6$alkyl or $C_1$-$C_6$haloalkyl, Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylsulfonyloxy, $C_1$-$C_6$haloalkylsulfonyloxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, $C_1$-$C_6$alkoxycarbonyl, —C(O)NH$_2$ or —C(S)NH$_2$, when p1, p2, p3 or p4 is an integer of 2 or more, each Z may be identical with or different from each other, when two Zs are adjacent, the adjacent two Zs may form 5-membered or 6-membered ring together with carbon atoms to which the two Zs are bonded by forming —OCH$_2$O— or —OCH$_2$CH$_2$O—, in this case, hydrogen atoms bonded to each carbon atom forming the ring may be arbitrarily substituted with halogen atom, p1 is an integer of 1 to 5, p2 is an integer of 0 to 4, p3 is an integer of 0 to 3, p4 is an integer of 0 to 2, p5 is an integer of 0 or 1, and t is an integer of 0 or 1).

In the compounds included in the present invention, the substituent $R^2$ includes for example the following groups.
That is, $R^2$-I: hydrogen atom. —CH$_2$$R^{14a}$ (wherein $R^{14a}$ is cyano or —O$R^{25}$, $R^{25}$ is $C_1$-$C_4$alkyl, $C_1$-$C_4$haloalkyl or —C(O)O$R^{32}$, and $R^{32}$ is $C_1$-$C_6$alkyl), $C_3$-$C_6$alkynyl and $C_1$-$C_6$alkoxycarbonyl.
$R^2$-II: hydrogen atom, $C_1$-$C_6$alkyl, —CH$_2$$R^{14a}$ (wherein $R^{14a}$ is cyano, —O$R^{25}$ or —NHC(O)$R^{32}$, $R^{25}$ is $C_1$-$C_4$alkyl, $C_1$-$C_4$haloalkyl or —C(O)O$R^{32}$, and $R^{32}$ is $C_1$-$C_6$alkyl), E-5 (wherein q3 is 0), —C(O)$R^{15}$ (wherein $R^{15}$ is $C_1$-$C_6$alkyl, $C_1$-$C_6$haloalkyl, $C_1$-$C_4$alkoxy$C_1$-$C_4$alkyl, $C_1$-$C_4$alkylthio $C_1$-$C_4$alkyl or $C_3$-$C_6$cycloalkyl), $C_1$-$C_6$alkoxycarbonyl, $C_1$-$C_6$haloalkoxycarbonyl or $C_1$-$C_6$haloalkylthio.
$R^2$-III: hydrogen atom and $C_1$-$C_6$alkyl.
$R^2$-IV: $C_1$-$C_6$alkyl, —CH$_2$$R^{14a}$ (wherein $R^{14a}$ is cyano or —O$R^{25}$, $R^{25}$ is $C_1$-$C_4$alkyl, $C_1$-$C_4$haloalkyl, —C(O)$R^{32}$ or —C(O)O$R^{32}$, and $R^{32}$ is $C_1$-$C_6$alkyl or $C_3$-$C_6$cycloalkyl), $C_3$-$C_6$alkynyl, —C(O)$R^{15}$, —C(O)O$R^{15}$ and —C(O)C(O)O$R^{15}$ (wherein $R^{15}$ is $C_1$-$C_6$alkyl, $C_1$-$C_6$haloalkyl, $C_1$-$C_4$alkoxy$C_1$-$C_4$alkyl, $C_1$-$C_4$alkylthio $C_1$-$C_4$alkyl, $C_1$-$C_4$alkylsulfinyl $C_1$-$C_4$alkyl, $C_1$-$C_4$alkylsulfonyl $C_1$-$C_4$alkyl, $C_3$-$C_6$cycloalkyl, $C_2$-$C_6$alkenyl, $C_2$-$C_6$alkynyl, phenyl, phenyl substituted with $(Z)_{p1}$, or D-52, Z is halogen atom, cyano, nitro, $C_1$-$C_6$alkyl, $C_1$-$C_6$alkoxy, $C_1$-$C_6$alkylthio, $C_1$-$C_6$alkylsulfinyl or $C_1$-$C_6$alkylsulfonyl, when p1 is 2, each Z may be identical with or different from each other, p1 is an integer of 1 or 2, p2 is an integer of 0 or 1, and t is 0).
$R^2$-V: hydrogen atom. $C_1$-$C_6$alkyl, —CH$_2$$R^{14a}$ (wherein $R^{14a}$ is cyano, —O$R^{25}$ or —S(O)$_r$$R^{27}$, $R^{25}$ is $C_1$-$C_6$alkyl, $C_1$-$C_6$haloalkyl, —C(O)$R^{32}$ or —C(O)O$R^{32}$, $R^{27}$ is $C_1$-$C_6$alkyl or $C_1$-$C_6$haloalkyl, $R^{32}$ is $C_1$-$C_6$alkyl or $C_3$-$C_6$cycloalkyl, and r is an integer of 0 to 2), $C_3$-$C_6$alkynyl, —C(O)O$R^{15}$, —C(O)S$R^{15}$, —C(S)O$R^{15}$, —C(S)S$R^{15}$ (wherein $R^{15}$ is $C_1$-$C_6$alkyl, $C_1$-$C_6$haloalkyl, $C_1$-$C_4$alkoxy$C_1$-$C_4$alkyl, $C_3$-$C_6$cycloalkyl, $C_2$-$C_6$alkenyl, $C_2$-$C_6$alkynyl or phenyl), $C_1$-$C_6$haloalkylthio and —SN($R^{20}$)$R^{19}$ (wherein $R^{19}$ is $C_1$-$C_6$alkyl, $C_1$-$C_6$alkoxycarbonyl $C_1$-$C_4$alky or $C_1$-$C_6$alkoxycarbonyl, and $R^{20}$ is $C_1$-$C_6$alkyl or benzyl).
$R^2$-VI: hydrogen atom. $C_1$-$C_6$alkyl, —CH$_2$$R^{14a}$ (wherein $R^{14a}$ is cyano, —O$R^{25}$, —NHC(O)O$R^{32}$, —S(O)$_r$$R^{27}$, $C_1$-$C_6$alkylcarbonyl, $C_1$-$C_6$alkoxycarbonyl or phenyl, $R^{25}$ is $C_1$-$C_6$alkyl, $C_1$-$C_6$haloalkyl, $C_1$-$C_4$alkoxy $C_1$-$C_4$alkyl, benzyl, $C_3$-$C_6$alkenyl, $C_3$-$C_6$alkynyl, —C(O)$R^{32}$ or —C(O)O$R^{32}$, $R^{27}$ is $C_1$-$C_6$alkyl, $C_1$-$C_6$haloalkyl, —C(O)$R^{32}$ or —C(S)O$R^{32}$, $R^{32}$ is $C_1$-$C_6$alkyl, $C_1$-$C_6$haloalkyl, $C_3$-$C_6$cycloalkyl or phenyl, and r is an integer of 0 to 2), E-5, E-24 (wherein q3 and q4 are 0), $C_3$-$C_6$alkynyl, —C(O)$R^{15}$, —C(O)C(O)O$R^{15}$ (wherein $R^{15}$ is $C_1$-$C_6$alkyl, $C_1$-$C_6$haloalkyl, $C_1$-$C_4$alkyl arbitrarily substituted with $R^{31}$, $C_3$-$C_6$cycloalkyl, phenyl, phenyl substituted with $(Z)_{p1}$, D-52, D-53 or D-54, $R^{31}$ is $C_1$-$C_4$alkoxy, $C_1$-$C_4$alkylthio, $C_1$-$C_4$alkylsulfinyl or $C_1$-$C_4$alkylsulfonyl, Z is halogen atom, cyano, nitro, $C_1$-$C_6$alkyl, $C_1$-$C_6$alkoxy, $C_1$-$C_6$alkylthio, $C_1$-$C_6$alkylsulfinyl or $C_1$-$C_6$alkylsulfonyl, when p1 is 2, each Z may be identical with or different from each other, p1 is an integer of 1 or 2, p2 is an integer of 0 or 1, and t is 0), $C_1$-$C_6$alkoxycarbonyl, $C_1$-$C_6$haloalkoxycarbonyl, $C_1$-$C_6$haloalkylthio and —SN($R^{20}$)$R^{19}$ (wherein $R^{19}$ is $C_1$-$C_6$alkyl, $C_1$-$C_6$alkoxycarbonyl $C_1$-$C_4$alkyl or $C_1$-$C_6$alkoxycarbonyl, and $R^{20}$ is $C_1$-$C_6$alkyl or benzyl).
$R^2$-VII: hydrogen atom. $C_1$-$C_6$alkyl, —CH$_2$$R^{14a}$ (wherein $R^{14a}$ is cyano or —O$R^{25}$, $R^{25}$ is $C_1$-$C_6$alkyl, $C_1$-$C_6$haloalkyl or —C(O)O$R^{32}$, $R^{32}$ is $C_1$-$C_6$alkyl or $C_1$-$C_6$cycloalkyl), $C_3$-$C_6$alkynyl, phenyl and phenyl substituted with $(Z)_{p1}$ (wherein Z is halogen atom, and p1 is 1).

R²-VIII: $C_1$-$C_6$alkyl, $C_1$-$C_6$haloalkyl, —$CH_2R^{14a}$ (wherein $R^{14a}$ is cyano, —$OR^{25}$, —$S(O)_rR^{27}$, $C_1$-$C_6$alkylcarbonyl or $C_1$-$C_6$alkoxycarbonyl, $R^{25}$ is $C_1$-$C_6$alkyl, $C_1$-$C_6$haloalkyl, $C_1$-$C_4$alkoxy $C_1$-$C_4$alkyl, benzyl, $C_3$-$C_6$alkenyl, $C_3$-$C_6$alkynyl, —$C(O)R^{32}$ or —$C(O)OR^{32}$, $R^{27}$ is $C_1$-$C_6$alkyl, $C_1$-$C_6$haloalkyl, —$C(O)R^{32}$ or —$C(S)OR^{32}$, $R^{32}$ is $C_1$-$C_6$alkyl, $C_1$-$C_6$haloalkyl, $C_3$-$C_6$cycloalkyl or phenyl, and r is an integer of 0 to 2), $C_3$-$C_6$alkenyl, $C_3$-$C_6$alkynyl, —$C(O)R^{15}$, —$C(O)OR^{15}$, —$C(O)SR^{15}$, —$C(S)OR^{15}$, —$C(S)SR^{15}$, —$C(O)C(O)OR^{15}$ (wherein $R^{15}$ is $C_1$-$C_6$alkyl, $C_1$-$C_6$haloalkyl, $C_1$-$C_4$alkyl arbitrarily substituted with $R^{31}$, $C_3$-$C_6$cycloalkyl, $C_2$-$C_6$alkenyl, $C_2$-$C_6$alkynyl, phenyl, phenyl substituted with $(Z)_{p1}$, D-52, D-53 or D-54, $R^{31}$ is $C_3$-$C_6$cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl or phenyl, Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl or $C_1$-$C_6$alkylsulfonyl, when p1 is 2, each Z may be identical with or different from each other, p1 is an integer of 1 or 2, and p2 is an integer of 0 or 1, and t is 0), $C_1$-$C_6$haloalkylthio and —$SN(R^{20})R^{19}$ (wherein $R^{19}$ is $C_1$-$C_6$alkyl, $C_1$-$C_6$alkoxycarbonyl $C_1$-$C_4$alky or $C_1$-$C_6$alkoxycarbonyl, and $R^{20}$ is $C_1$-$C_6$alkyl or benzyl).

R²-IX: hydrogen atom.

R²-X: $C_1$-$C_6$alkyl, $C_3$-$C_6$alkynyl, $C_1$-$C_6$alkylthio, $C_1$-$C_6$haloalkylthio, phenylthio and —$SN(R^{20})R^{19}$ (wherein $R^{19}$ is $C_1$-$C_6$alkyl, $C_1$-$C_4$alkoxy $C_1$-$C_4$alkyl, $C_1$-$C_6$alkoxycarbonyl $C_1$-$C_4$alkyl, phenyl $C_1$-$C_4$alkyl, phenyl $C_1$-$C_4$alkyl substituted with $(Z)_{p1}$ or $C_1$-$C_6$alkoxycarbonyl, and $R^{20}$ is $C_1$-$C_6$alkyl, phenyl $C_1$-$C_4$alkyl or phenyl $C_1$-$C_4$alkyl substituted with $(Z)_{p1}$, or $R^{20}$ together with $R^{19}$ may form 5- or 6-membered ring with the nitrogen atom bonding them by forming $C_4$-$C_5$alkylene chain, in this case, the alkylene chain may contain one oxygen atom or sulfur atom, and may be arbitrarily substituted with methyl or methoxy).

R²-XI: $C_1$-$C_6$haloalkyl, —$CH_2R^{14a}$ (wherein $R^{14a}$ is cyano, —$OR^{25}$, —$N(R^{26})R^{25}$, —$S(O)_rR^{27}$, $C_1$-$C_6$alkoxycarbonyl or phenyl, $R^{25}$ is $C_1$-$C_6$alkyl, $C_1$-$C_6$haloalkyl, $C_1$-$C_4$alkyl arbitrarily substituted with $R^{31}$, —$C(O)R^{32}$, —$C(O)OR^{32}$, —$C(O)N(R^{33})R^{32}$, —$SO_2R^{32}$ or phenyl, $R^{26}$ is hydrogen atom or $C_1$-$C_6$alkyl, $R^{27}$ is $C_1$-$C_8$alkyl, $C_1$-$C_8$haloalkyl, —$C(O)R^{32}$, —$C(S)OR^{32}$ or —$C(S)N(R^{33})R^{32}$, $R^{31}$ is $C_1$-$C_4$alkoxy or phenyl, $R^{32}$ is $C_1$-$C_6$alkyl, phenyl $C_1$-$C_4$alkyl, $C_3$-$C_6$cycloalkyl or phenyl, $R^{33}$ is hydrogen atom or $C_1$-$C_6$alkyl, or $R^{33}$ together with $R^{32}$ may form 5- to 6-membered ring with the nitrogen atom bonding them by forming $C_4$-$C_5$alkylene chain, in this case, the alkylene chain may contain one oxygen atom or sulfur atom, and r is an integer of 0 to 2) and $C_3$-$C_6$alkenyl.

R²-XII: E-5, E-24 (wherein q3 and q4 are 0), $C_1$-$C_6$alkoxycarbonyl and $C_1$-$C_6$haloalkoxycarbonyl.

R²-XIII: $C_1$-$C_6$alkyl, $C_1$-$C_6$haloalkyl, $C_3$-$C_6$cycloalkyl $C_1$-$C_4$alkyl, —$CH_2R^{14a}$ (wherein $R^{14a}$ is cyano, —$OR^{25}$ or phenyl, $R^{25}$ is $C_1$-$C_6$alkyl, $C_1$-$C_6$haloalkyl or —$C(O)OR^{32}$, $R^{32}$ is $C_1$-$C_6$alkyl or $C_3$-$C_6$cycloalkyl), $C_3$-$C_6$cycloalkyl, $C_3$-$C_6$alkenyl, $C_3$-$C_6$alkynyl, phenyl and phenyl substituted with $(Z)_{p1}$ (wherein Z is halogen atom, cyano, nitro or $C_1$-$C_6$alkoxy, and p1 is 1).

R²-XIV: $C_3$-$C_6$cycloalkyl, —$C(O)NH_2$, di($C_1$-$C_6$alkyl)aminocarbonyl, —$N(R^{18})R^{17}$ (wherein $R^{17}$ is hydrogen atom, $C_1$-$C_6$alkyl, —CHO, —$C(O)R^{28}$, —$C(O)OR^{28}$, —$C(O)NH_2$, —$C(O)N(R^{29})R^{28}$, —$S(O)_2R^{28}$, —$S(O)_2NH_2$, —$S(O)_2N(R^{29})R^{28}$ or phenyl, $R^{18}$ is hydrogen atom, $C_1$-$C_6$alkyl or $C_1$-$C_6$alkylcarbonyl, $R^{28}$ is $C_1$-$C_6$alkyl, $C_1$-$C_6$haloalkyl or phenyl, $R^{29}$ is hydrogen atom or $C_1$-$C_6$alkyl), —N=$C(R^{17b})R^{17a}$ (wherein $R^{17a}$ is $C_1$-$C_6$alkyl or phenyl, $R^{17b}$ is hydrogen atom or $C_1$-$C_6$alkyl), phenyl and phenyl substituted with $(Z)_{p1}$ (wherein Z is halogen atom, cyano, nitro or $C_1$-$C_6$alkoxy, and p1 is 1).

R²-XV: —$CH_2R^{14a}$ (wherein $R^{14a}$ is cyano, —$OR^{25}$, —$N(R^{26})R^{25}$, —$S(O)_rR^{27}$, tri($C_1$-$C_6$alkyl)silyl, —CHO, $C_1$-$C_6$alkylcarbonyl, phenylcarbonyl, $C_1$-$C_6$alkoxycarbonyl or phenyl, $R^{25}$ is $C_1$-$C_6$alkyl, $C_1$-$C_6$haloalkyl, $C_1$-$C_4$alkyl arbitrarily substituted with $R^{31}$, $C_3$-$C_6$cycloalkyl, E-6, E-8, E-25, E-26, E-28, E-29, $C_3$-$C_6$alkenyl, $C_3$-$C_6$alkynyl, —$C(O)R^{32}$, —$C(O)OR^{32}$, —$C(O)NH_2$, —$C(O)N(R^{33})R^{32}$, $C_1$-$C_6$alkylsulfonyl or phenyl, $R^{26}$ is hydrogen atom, $C_1$-$C_6$alkyl or phenyl, or $R^{26}$ together with $R^{25}$ may form 5- to 6-membered ring with the nitrogen atom bonding them by forming $C_4$-$C_5$alkylene chain, in this case, the alkylene chain may contain one oxygen atom or sulfur atom, $R^{27}$ is $C_1$-$C_6$alkyl, $C_1$-$C_6$haloalkyl, $C_1$-$C_4$alkyl arbitrarily substituted with $R^{31}$, —$C(O)R^{32}$, —$C(S)R^{32}$, —$C(S)OR^{32}$, —$C(S)N(R^{33})R^{32}$, phenyl, D-34, D-35 or D-50, $R^{13}$ is $C_1$-$C_6$alkyl or phenyl, $R^{31}$ is cyano, $C_3$-$C_6$cycloalkyl, $C_3$-$C_6$halocycloalkyl, E-5 to E-8, E-11, E-19, —$OR^{32}$, —$OC(O)R^{32}$, —$OC(O)OR^{32}$, $C_1$-$C_4$alkylthio, $C_1$-$C_4$alkylsulfinyl, $C_1$-$C_4$alkylsulfonyl, $C_1$-$C_4$alkoxycarbonyl or phenyl, $R^{32}$ is $C_1$-$C_6$alkyl, $C_1$-$C_6$haloalkyl, $C_1$-$C_4$alkyl arbitrarily substituted with $R^{34}$, $C_3$-$C_6$cycloalkyl, phenyl, D-1 to D-4, D-14, D-52, D-53 or D-54, $R^{33}$ is hydrogen atom or $C_1$-$C_6$alkyl, or $R^{33}$ together with $R^{32}$ may form 5- to 6-membered ring with the nitrogen atom bonding them by forming $C_4$-$C_5$alkylene chain, in this case, the alkylene chain may contain one oxygen atom or sulfur atom, $R^{34}$ is E-5, $C_1$-$C_4$alkoxy, phenoxy, phenylthio, —$N(R^{36})R^{35}$, phenyl, D-1, D-3 or D-53, $R^{35}$ is hydrogen atom, $C_1$-$C_6$alkyl, $C_1$-$C_6$alkoxycarbonyl or phenylcarbonyl, $R^{36}$ is hydrogen atom or $C_1$-$C_6$alkyl, Z is halogen atom, cyano, nitro, $C_1$-$C_6$alkyl, $C_1$-$C_6$haloalkyl, $C_1$-$C_6$alkoxy, $C_1$-$C_6$alkylthio or phenyl, when p1, p2 or p3 is an integer of 2 or more, each Z may be identical with or different from each other, p1 is an integer of 1 to 3, p2 and p3 are an integer of 0 to 2, p5 is an integer of 0 or 1, q2, q3 and q4 are 0, r is an integer of 0 to 2, and t is 0), and $C_1$-$C_6$alkylsulfonyl.

R²-XVI: —$C(O)R^{15}$ and —$C(O)C(O)OR^{15}$ (wherein $R^{15}$ is $C_1$-$C_6$alkyl, $C_1$-$C_6$haloalkyl, $C_1$-$C_4$alkyl arbitrarily substituted with $R^{31}$, $C_3$-$C_6$cycloalkyl, $C_2$-$C_6$alkenyl, $C_2$-$C_6$alkynyl, phenyl, phenyl substituted with $(Z)_{p1}$, naphthyl, D-1 to D-4, D-52, D-53 or D-54, $R^{31}$ is $C_3$-$C_6$cycloalkyl, $C_1$-$C_4$alkoxy, $C_1$-$C_4$alkylsulfinyl or $C_1$-$C_4$alkylsulfonyl, Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl or $C_1$-$C_6$alkylsulfonyl, when p1, p2 or p3 is an integer of 2 or more, each Z may be identical with or different from each other, p1 is an integer of 1 to 3, p2 is an integer of 0 to 2, and t is 0).

R²-XVII: —$C(O)OR^{15}$, —$C(O)SR^{15}$, —$C(S)OR^{15}$ and —$C(S)SR^{15}$ (wherein $R^{15}$ is $C_1$-$C_6$alkyl, $C_1$-$C_6$haloalkyl, $C_1$-$C_4$alkyl arbitrarily substituted with $R^{31}$, $C_3$-$C_6$cycloalkyl, $C_2$-$C_6$alkenyl, $C_2$-$C_6$alkynyl, phenyl, phenyl substituted with $(Z)_{p1}$, naphthyl, D-1 to D-4, D-52, D-53 or D-54, $R^{31}$ is $C_3$-$C_6$cycloalkyl, —$OR^{32}$, $C_1$-$C_4$alkylthio, $C_1$-$C_4$alkylsulfinyl, $C_1$-$C_4$alkylsulfonyl, phenyl or phenyl substituted with $(Z)_{p1}$, $R^{32}$ is $C_1$-$C_6$alkyl, $C_1$-$C_4$alkoxy $C_1$-$C_4$alkyl, benzyl or phenyl, Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl or $C_1$-$C_6$alkylsulfonyl, when p1, p2 or p3 is an integer of 2 or more, each Z may be identical with or different from each other, p1 is an integer of 1 to 3, p2 and p3 are an integer of 0 to 2, and t is 0).

R²-XVIII: R² together with R¹ forms =$C(R^{2b})R^{2a}$ (wherein $R^{2a}$ is —$OR^{1c}$, —$SR^{1c}$ or di($C_1$-$C_6$alkyl)amino, $R^{1c}$ is $C_1$-$C_6$alkyl or $C_3$-$C_6$cycloalkyl, $R^{2b}$ is $R^{1b}$, $C_1$-$C_6$alkylthio, $C_1$-$C_6$haloalkylthio, —$SCH_2R^{14a}$, $C_3$-$C_6$alkenylthio, $C_3$-$C_6$haloalkenylthio, $C_3$-$C_6$alkynylthio, $C_3$-$C_6$haloalkynylthio or —$SC(O)R^{15}$, $R^{1b}$ is hydrogen atom, $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl or $C_3$-$C_6$cycloalkyl, $R^{14a}$ is cyano, $C_1$-$C_6$alkoxy, $C_1$-$C_6$haloalkoxy, $C_1$-$C_6$alkylthio, $C_1$-$C_6$haloalkylthio, $C_1$-$C_6$alkoxycarbonyl or phenyl, $R^{15}$ is $C_1$-$C_6$alkyl, $C_1$-$C_6$haloalkyl, $C_3$-$C_6$cycloalkyl or phenyl).

In the compounds included in the present invention, the substituent $R^3$ includes for example the following groups.

That is, $R^3$-I: —$CF_3$ and —$CF_2Cl$.

$R^3$-II: —$CHF_2$, —$CF_3$, —$CF_2Cl$, —$CF_2Br$, —$CF_2CHF_2$ and —$CF_2CF_3$.

$R^3$-III: $C_1$-$C_6$alkyl substituted with 2 or more of arbitrary halogen atoms.

$R^3$-IV: $C_1$-$C_6$haloalkyl.

$R^3$-V: $C_1$-$C_6$haloalkyl and $C_3$-$C_8$halocycloalkyl.

$R^3$-VI: $C_1$-$C_6$alkyl, $C_1$-$C_6$haloalkyl, $C_1$-$C_4$alkoxy $C_1$-$C_4$haloalkyl, $C_1$-$C_4$haloalkoxy $C_1$-$C_4$haloalkyl, $C_1$-$C_4$alkylthio $C_1$-$C_4$haloalkyl, $C_1$-$C_4$haloalkylthio $C_1$-$C_4$haloalkyl, cyano $C_1$-$C_6$haloalkyl, $C_3$-$C_6$cycloalkyl and $C_3$-$C_8$halocycloalkyl.

Each group showing the scope of each substituent in the compounds included in the present invention can be arbitrarily combined one another, and all combination thereof falls within the scope of the present invention. Examples of the combination of the scope of X, Y, $R^1$ and $R^2$ include for example the combination showing in Table 1. In the meantime, the combination of Table 1 is for illustrative purposes, and the present invention is not limited thereto.

TABLE 1

| X | Y | $R^1$ | $R^2$ |
|---|---|---|---|
| X-I | Y-I | $R^1$-I | $R^2$-I |
| X-I | Y-I | $R^1$-I | $R^2$-V |
| X-I | Y-I | $R^1$-I | $R^2$-IX |
| X-I | Y-I | $R^1$-I | $R^2$-X |
| X-I | Y-I | $R^1$-I | $R^2$-XI |
| X-I | Y-I | $R^1$-I | $R^2$-XVII |
| X-I | Y-I | $R^1$-II | $R^2$-II |
| X-I | Y-I | $R^1$-II | $R^2$-VI |
| X-I | Y-I | $R^1$-II | $R^2$-IX |
| X-I | Y-I | $R^1$-II | $R^2$-X |
| X-I | Y-I | $R^1$-II | $R^2$-XII |
| X-I | Y-I | $R^1$-II | $R^2$-XV |
| X-I | Y-I | $R^1$-II | $R^2$-XVI |
| X-I | Y-I | $R^1$-III | $R^2$-III |
| X-I | Y-I | $R^1$-III | $R^2$-VII |
| X-I | Y-I | $R^1$-III | $R^2$-IX |
| X-I | Y-I | $R^1$-III | $R^2$-XIII |
| X-I | Y-I | $R^1$-IV | $R^2$-IV |
| X-I | Y-I | $R^1$-IV | $R^2$-VIII |
| X-I | Y-I | $R^1$-IV | $R^2$-X |
| X-I | Y-I | $R^1$-IV | $R^2$-XIV |
| X-I | Y-I | $R^1$-IV | $R^2$-XV |
| X-I | Y-I | $R^1$-IV | $R^2$-XVI |
| X-I | Y-I | $R^1$-IV | $R^2$-XVII |
| X-I | Y-I | $R^1$-V | $R^2$-I |
| X-I | Y-I | $R^1$-V | $R^2$-V |
| X-I | Y-I | $R^1$-V | $R^2$-IX |
| X-I | Y-I | $R^1$-V | $R^2$-X |
| X-I | Y-I | $R^1$-V | $R^2$-XI |
| X-I | Y-I | $R^1$-V | $R^2$-XVII |
| X-I | Y-I | $R^1$-VI | $R^2$-II |
| X-I | Y-I | $R^1$-VI | $R^2$-VI |
| X-I | Y-I | $R^1$-VI | $R^2$-IX |
| X-I | Y-I | $R^1$-VI | $R^2$-X |
| X-I | Y-I | $R^1$-VI | $R^2$-XII |
| X-I | Y-I | $R^1$-VI | $R^2$-XV |
| X-I | Y-I | $R^1$-VI | $R^2$-XVI |
| X-I | Y-I | $R^1$-VII | $R^2$-III |
| X-I | Y-I | $R^1$-VII | $R^2$-VII |
| X-I | Y-I | $R^1$-VII | $R^2$-IX |
| X-I | Y-I | $R^1$-VII | $R^2$-XIII |
| X-I | Y-I | $R^1$-VIII | $R^2$-IV |
| X-I | Y-I | $R^1$-VIII | $R^2$-VIII |
| X-I | Y-I | $R^1$-VIII | $R^2$-X |
| X-I | Y-I | $R^1$-VIII | $R^2$-IX |
| X-I | Y-I | $R^1$-VIII | $R^2$-XV |
| X-I | Y-I | $R^1$-VIII | $R^2$-XVI |
| X-I | Y-I | $R^1$-VIII | $R^2$-XVII |
| X-I | Y-I | $R^1$-IX | $R^2$-I |
| X-I | Y-I | $R^1$-IX | $R^2$-V |
| X-I | Y-I | $R^1$-IX | $R^2$-IX |
| X-I | Y-I | $R^1$-X | $R^2$-II |
| X-I | Y-I | $R^1$-X | $R^2$-VI |
| X-I | Y-I | $R^1$-X | $R^2$-IX |
| X-I | Y-I | $R^1$-XI | $R^2$-III |
| X-I | Y-I | $R^1$-XI | $R^2$-VII |
| X-I | Y-I | $R^1$-XI | $R^2$-IX |
| X-I | Y-I | $R^1$-XII | $R^2$-IV |
| X-I | Y-I | $R^1$-XII | $R^2$-VIII |
| X-I | Y-I | $R^1$-XII | $R^2$-X |
| X-I | Y-I | $R^1$-XII | $R^2$-XV |
| X-I | Y-I | — | $R^2$-XVIII |
| X-I | Y-II | $R^1$-I | $R^2$-I |
| X-I | Y-II | $R^1$-I | $R^2$-V |
| X-I | Y-II | $R^1$-I | $R^2$-IX |
| X-I | Y-II | $R^1$-I | $R^2$-X |
| X-I | Y-II | $R^1$-I | $R^2$-XI |
| X-I | Y-II | $R^1$-I | $R^2$-XVII |
| X-I | Y-II | $R^1$-II | $R^2$-II |
| X-I | Y-II | $R^1$-II | $R^2$-VI |
| X-I | Y-II | $R^1$-II | $R^2$-IX |
| X-I | Y-II | $R^1$-II | $R^2$-X |
| X-I | Y-II | $R^1$-II | $R^2$-XII |
| X-I | Y-II | $R^1$-II | $R^2$-XV |
| X-I | Y-II | $R^1$-II | $R^2$-XVI |
| X-I | Y-II | $R^1$-III | $R^2$-III |
| X-I | Y-II | $R^1$-III | $R^2$-VII |
| X-I | Y-II | $R^1$-III | $R^2$-IX |
| X-I | Y-II | $R^1$-III | $R^2$-XIII |
| X-I | Y-II | $R^1$-IV | $R^2$-IV |
| X-I | Y-II | $R^1$-IV | $R^2$-VIII |
| X-I | Y-II | $R^1$-IV | $R^2$-X |
| X-I | Y-II | $R^1$-IV | $R^2$-XIV |
| X-I | Y-II | $R^1$-IV | $R^2$-XV |
| X-I | Y-II | $R^1$-IV | $R^2$-XVI |
| X-I | Y-II | $R^1$-IV | $R^2$-XVII |
| X-I | Y-II | $R^1$-V | $R^2$-I |
| X-I | Y-II | $R^1$-V | $R^2$-V |
| X-I | Y-II | $R^1$-V | $R^2$-IX |
| X-I | Y-II | $R^1$-VI | $R^2$-II |
| X-I | Y-II | $R^1$-VI | $R^2$-VI |
| X-I | Y-II | $R^1$-VI | $R^2$-IX |
| X-I | Y-II | $R^1$-VII | $R^2$-III |
| X-I | Y-II | $R^1$-VII | $R^2$-VII |
| X-I | Y-II | $R^1$-VII | $R^2$-IX |
| X-I | Y-II | $R^1$-VIII | $R^2$-IV |
| X-I | Y-II | $R^1$-VIII | $R^2$-VIII |
| X-I | Y-II | $R^1$-IX | $R^2$-I |
| X-I | Y-II | $R^1$-IX | $R^2$-IX |
| X-I | Y-II | $R^1$-X | $R^2$-II |
| X-I | Y-II | $R^1$-X | $R^2$-IX |
| X-I | Y-II | $R^1$-XI | $R^2$-III |
| X-I | Y-II | $R^1$-XI | $R^2$-IX |
| X-I | Y-II | $R^1$-XII | $R^2$-IV |
| X-I | Y-II | — | $R^2$-XVIII |
| X-I | Y-III | $R^1$-I | $R^2$-I |
| X-I | Y-III | $R^1$-I | $R^2$-V |
| X-I | Y-III | $R^1$-I | $R^2$-IX |
| X-I | Y-III | $R^1$-II | $R^2$-II |
| X-I | Y-III | $R^1$-II | $R^2$-VI |
| X-I | Y-III | $R^1$-II | $R^2$-IX |
| X-I | Y-III | $R^1$-III | $R^2$-III |
| X-I | Y-III | $R^1$-III | $R^2$-VII |
| X-I | Y-III | $R^1$-III | $R^2$-IX |
| X-I | Y-III | $R^1$-IV | $R^2$-IV |
| X-I | Y-III | $R^1$-IV | $R^2$-VIII |

TABLE 1-continued

| X | Y | R¹ | R² |
|---|---|---|---|
| X-I | Y-III | R¹-V | R²-I |
| X-I | Y-III | R¹-V | R²-IX |
| X-I | Y-III | R¹-VI | R²-II |
| X-I | Y-III | R¹-VI | R²-IX |
| X-I | Y-III | R¹-VII | R²-III |
| X-I | Y-III | R¹-VII | R²-IX |
| X-I | Y-III | R¹-VIII | R²-IV |
| X-I | Y-III | — | R²-XVIII |
| X-I | Y-IV | R¹-I | R²-I |
| X-I | Y-IV | R¹-I | R²-IX |
| X-I | Y-IV | R¹-II | R²-II |
| X-I | Y-IV | R¹-II | R²-IX |
| X-I | Y-IV | R¹-III | R²-III |
| X-I | Y-IV | R¹-III | R²-IX |
| X-I | Y-IV | R¹-IV | R²-IV |
| X-I | Y-V | R¹-I | R²-I |
| X-I | Y-V | R¹-I | R²-IX |
| X-I | Y-V | R¹-II | R²-II |
| X-I | Y-V | R¹-II | R²-IX |
| X-I | Y-V | R¹-III | R²-III |
| X-I | Y-V | R¹-III | R²-IX |
| X-I | Y-V | R¹-IV | R²-IV |
| X-I | Y-VI | R¹-I | R²-I |
| X-I | Y-VI | R¹-I | R²-IX |
| X-I | Y-VI | R¹-II | R²-II |
| X-I | Y-VI | R¹-II | R²-IX |
| X-I | Y-VI | R¹-III | R²-III |
| X-I | Y-VI | R¹-III | R²-IX |
| X-I | Y-VI | R¹-IV | R²-IV |
| X-II | Y-I | R¹-I | R²-I |
| X-II | Y-I | R¹-I | R²-V |
| X-II | Y-I | R¹-I | R²-IX |
| X-II | Y-I | R¹-I | R²-X |
| X-II | Y-I | R¹-I | R²-XI |
| X-II | Y-I | R¹-I | R²-XVII |
| X-II | Y-I | R¹-II | R²-II |
| X-II | Y-I | R¹-II | R²-VI |
| X-II | Y-I | R¹-II | R²-IX |
| X-II | Y-I | R¹-II | R²-X |
| X-II | Y-I | R¹-II | R²-XII |
| X-II | Y-I | R¹-II | R²-XV |
| X-II | Y-I | R¹-II | R²-XVI |
| X-II | Y-I | R¹-III | R²-III |
| X-II | Y-I | R¹-III | R²-VII |
| X-II | Y-I | R¹-III | R²-IX |
| X-II | Y-I | R¹-III | R²-XIII |
| X-II | Y-I | R¹-IV | R²-IV |
| X-II | Y-I | R¹-IV | R²-VIII |
| X-II | Y-I | R¹-IV | R²-X |
| X-II | Y-I | R¹-IV | R²-XIV |
| X-II | Y-I | R¹-IV | R²-XV |
| X-II | Y-I | R¹-IV | R²-XVI |
| X-II | Y-I | R¹-IV | R²-XVII |
| X-II | Y-I | R¹-V | R²-I |
| X-II | Y-I | R¹-V | R²-V |
| X-II | Y-I | R¹-V | R²-IX |
| X-II | Y-I | R¹-VI | R²-II |
| X-II | Y-I | R¹-VI | R²-VI |
| X-II | Y-I | R¹-VI | R²-IX |
| X-II | Y-I | R¹-VII | R²-III |
| X-II | Y-I | R¹-VII | R²-VII |
| X-II | Y-I | R¹-VII | R²-IX |
| X-II | Y-I | R¹-VIII | R²-IV |
| X-II | Y-I | R¹-VIII | R²-VIII |
| X-II | Y-I | R¹-IX | R²-I |
| X-II | Y-I | R¹-IX | R²-IX |
| X-II | Y-I | R¹-X | R²-II |
| X-II | Y-I | R¹-X | R²-IX |
| X-II | Y-I | R¹-XI | R²-III |
| X-II | Y-I | R¹-XI | R²-IX |
| X-II | Y-I | R¹-XII | R²-IV |
| X-II | Y-I | — | R²-XVIII |
| X-II | Y-II | R¹-I | R²-I |
| X-II | Y-II | R¹-I | R²-V |
| X-II | Y-II | R¹-I | R²-IX |
| X-II | Y-II | R¹-I | R²-X |
| X-II | Y-II | R¹-I | R²-XI |
| X-II | Y-II | R¹-I | R²-XVII |
| X-II | Y-II | R¹-II | R²-II |
| X-II | Y-II | R¹-II | R²-VI |
| X-II | Y-II | R¹-II | R²-IX |
| X-II | Y-II | R¹-II | R²-X |
| X-II | Y-II | R¹-II | R²-XII |
| X-II | Y-II | R¹-II | R²-XV |
| X-II | Y-II | R¹-II | R²-XVI |
| X-II | Y-II | R¹-III | R²-III |
| X-II | Y-II | R¹-III | R²-VII |
| X-II | Y-II | R¹-III | R²-IX |
| X-II | Y-II | R¹-III | R²-XIII |
| X-II | Y-II | R¹-IV | R²-IV |
| X-II | Y-II | R¹-IV | R²-VIII |
| X-II | Y-II | R¹-IV | R²-X |
| X-II | Y-II | R¹-IV | R²-XIV |
| X-II | Y-II | R¹-IV | R²-XV |
| X-II | Y-II | R¹-IV | R²-XVI |
| X-II | Y-II | R¹-IV | R²-XVII |
| X-II | Y-II | R¹-V | R²-I |
| X-II | Y-II | R¹-V | R²-V |
| X-II | Y-II | R¹-V | R²-IX |
| X-II | Y-II | R¹-VI | R²-II |
| X-II | Y-II | R¹-VI | R²-VI |
| X-II | Y-II | R¹-VI | R²-IX |
| X-II | Y-II | R¹-VII | R²-III |
| X-II | Y-II | R¹-VII | R²-VII |
| X-II | Y-II | R¹-VII | R²-IX |
| X-II | Y-II | R¹-VIII | R²-IV |
| X-II | Y-II | R¹-VIII | R²-VIII |
| X-II | Y-II | R¹-IX | R²-I |
| X-II | Y-II | R¹-IX | R²-IX |
| X-II | Y-II | R¹-X | R²-II |
| X-II | Y-II | R¹-X | R²-IX |
| X-II | Y-II | R¹-XI | R²-III |
| X-II | Y-II | R¹-XI | R²-IX |
| X-II | Y-II | R¹-XII | R²-IV |
| X-II | Y-II | — | R²-XVIII |
| X-II | Y-III | R¹-I | R²-I |
| X-II | Y-III | R¹-I | R²-V |
| X-II | Y-III | R¹-I | R²-IX |
| X-II | Y-III | R¹-II | R²-II |
| X-II | Y-III | R¹-II | R²-VI |
| X-II | Y-III | R¹-II | R²-IX |
| X-II | Y-III | R¹-III | R²-III |
| X-II | Y-III | R¹-III | R²-VII |
| X-II | Y-III | R¹-III | R²-IX |
| X-II | Y-III | R¹-IV | R²-IV |
| X-II | Y-III | R¹-IV | R²-VIII |
| X-II | Y-III | R¹-VIII | R²-IV |
| X-II | Y-IV | R¹-I | R²-I |
| X-II | Y-IV | R¹-I | R²-IX |
| X-II | Y-IV | R¹-II | R²-II |
| X-II | Y-IV | R¹-II | R²-IX |
| X-II | Y-IV | R¹-III | R²-III |
| X-II | Y-IV | R¹-III | R²-IX |
| X-II | Y-IV | R¹-IV | R²-IV |
| X-II | Y-V | R¹-I | R²-I |
| X-II | Y-V | R¹-I | R²-IX |
| X-II | Y-V | R¹-II | R²-II |
| X-II | Y-V | R¹-II | R²-IX |
| X-II | Y-V | R¹-III | R²-III |
| X-II | Y-V | R¹-III | R²-IX |
| X-II | Y-V | R¹-IV | R²-IV |
| X-II | Y-VI | R¹-I | R²-I |
| X-II | Y-VI | R¹-I | R²-IX |
| X-II | Y-VI | R¹-II | R²-II |
| X-II | Y-VI | R¹-II | R²-IX |
| X-II | Y-VI | R¹-III | R²-III |
| X-II | Y-VI | R¹-III | R²-IX |
| X-II | Y-VI | R¹-IV | R²-IV |
| X-III | Y-I | R¹-I | R²-I |
| X-III | Y-I | R¹-I | R²-V |
| X-III | Y-I | R¹-I | R²-IX |
| X-III | Y-I | R¹-II | R²-II |
| X-III | Y-I | R¹-II | R²-VI |
| X-III | Y-I | R¹-II | R²-IX |
| X-III | Y-I | R¹-III | R²-III |
| X-III | Y-I | R¹-III | R²-VII |

TABLE 1-continued

| X | Y | R¹ | R² |
|---|---|---|---|
| X-III | Y-I | R¹-III | R²-IX |
| X-III | Y-I | R¹-IV | R²-IV |
| X-III | Y-I | R¹-IV | R²-VIII |
| X-III | Y-I | R¹-V | R²-I |
| X-III | Y-I | R¹-V | R²-IX |
| X-III | Y-I | R¹-VI | R²-II |
| X-III | Y-I | R¹-VI | R²-IX |
| X-III | Y-I | R¹-VII | R²-III |
| X-III | Y-I | R¹-VII | R²-IX |
| X-III | Y-I | R¹-VIII | R²-IV |
| X-III | Y-I | — | R²-XVIII |
| X-III | Y-II | R¹-I | R²-I |
| X-III | Y-II | R¹-I | R²-V |
| X-III | Y-II | R¹-I | R²-IX |
| X-III | Y-II | R¹-II | R²-II |
| X-III | Y-II | R¹-II | R²-VI |
| X-III | Y-II | R¹-II | R²-IX |
| X-III | Y-II | R¹-III | R²-III |
| X-III | Y-II | R¹-III | R²-VII |
| X-III | Y-II | R¹-III | R²-IX |
| X-III | Y-II | R¹-IV | R²-IV |
| X-III | Y-II | R¹-IV | R²-VIII |
| X-III | Y-II | R¹-VIII | R²-IV |
| X-III | Y-III | R¹-I | R²-I |
| X-III | Y-III | R¹-I | R²-V |
| X-III | Y-III | R¹-I | R²-IX |
| X-III | Y-III | R¹-II | R²-II |
| X-III | Y-III | R¹-II | R²-VI |
| X-III | Y-III | R¹-II | R²-IX |
| X-III | Y-III | R¹-III | R²-III |
| X-III | Y-III | R¹-III | R²-VII |
| X-III | Y-III | R¹-III | R²-IX |
| X-III | Y-III | R¹-IV | R²-IV |
| X-III | Y-III | R¹-IV | R²-VIII |
| X-III | Y-III | R¹-VIII | R²-IV |
| X-III | Y-IV | R¹-I | R²-I |
| X-III | Y-IV | R¹-I | R²-IX |
| X-III | Y-IV | R¹-II | R²-II |
| X-III | Y-IV | R¹-II | R²-IX |
| X-III | Y-IV | R¹-III | R²-III |
| X-III | Y-IV | R¹-III | R²-IX |
| X-III | Y-IV | R¹-IV | R²-IV |
| X-III | Y-V | R¹-I | R²-I |
| X-III | Y-V | R¹-I | R²-IX |
| X-III | Y-V | R¹-II | R²-II |
| X-III | Y-V | R¹-II | R²-IX |
| X-III | Y-V | R¹-III | R²-III |
| X-III | Y-V | R¹-III | R²-IX |
| X-III | Y-V | R¹-IV | R²-IV |
| X-III | Y-VI | R¹-I | R²-I |
| X-III | Y-VI | R¹-I | R²-IX |
| X-III | Y-VI | R¹-II | R²-II |
| X-III | Y-VI | R¹-II | R²-IX |
| X-III | Y-VI | R¹-III | R²-III |
| X-III | Y-VI | R¹-III | R²-IX |
| X-III | Y-VI | R¹-IV | R²-IV |
| X-IV | Y-I | R¹-I | R²-I |
| X-IV | Y-I | R¹-I | R²-IX |
| X-IV | Y-I | R¹-II | R²-II |
| X-IV | Y-I | R¹-II | R²-IX |
| X-IV | Y-I | R¹-III | R²-III |
| X-IV | Y-I | R¹-III | R²-IX |
| X-IV | Y-I | R¹-IV | R²-IV |
| X-IV | Y-II | R¹-I | R²-I |
| X-IV | Y-II | R¹-I | R²-IX |
| X-IV | Y-II | R¹-II | R²-II |
| X-IV | Y-II | R¹-II | R²-IX |
| X-IV | Y-II | R¹-III | R²-III |
| X-IV | Y-II | R¹-III | R²-IX |
| X-IV | Y-II | R¹-IV | R²-IV |
| X-IV | Y-III | R¹-I | R²-I |
| X-IV | Y-III | R¹-I | R²-IX |
| X-IV | Y-III | R¹-II | R²-II |
| X-IV | Y-III | R¹-II | R²-IX |
| X-IV | Y-III | R¹-III | R²-III |
| X-IV | Y-III | R¹-III | R²-IX |
| X-IV | Y-III | R¹-IV | R²-IV |
| X-IV | Y-IV | R¹-I | R²-I |
| X-IV | Y-IV | R¹-I | R²-IX |
| X-IV | Y-IV | R¹-II | R²-II |
| X-IV | Y-IV | R¹-II | R²-IX |
| X-IV | Y-IV | R¹-III | R²-III |
| X-IV | Y-IV | R¹-III | R²-IX |
| X-IV | Y-IV | R¹-IV | R²-IV |
| X-IV | Y-V | R¹-I | R²-I |
| X-IV | Y-V | R¹-I | R²-IX |
| X-IV | Y-V | R¹-II | R²-II |
| X-IV | Y-V | R¹-II | R²-IX |
| X-IV | Y-V | R¹-III | R²-III |
| X-IV | Y-V | R¹-III | R²-IX |
| X-IV | Y-V | R¹-IV | R²-IV |
| X-IV | Y-VI | R¹-I | R²-I |
| X-IV | Y-VI | R¹-I | R²-IX |
| X-IV | Y-VI | R¹-II | R²-II |
| X-IV | Y-VI | R¹-II | R²-IX |
| X-IV | Y-VI | R¹-III | R²-III |
| X-IV | Y-VI | R¹-III | R²-IX |
| X-IV | Y-VI | R¹-IV | R²-IV |
| X-V | Y-I | R¹-I | R²-I |
| X-V | Y-I | R¹-I | R²-IX |
| X-V | Y-I | R¹-II | R²-II |
| X-V | Y-I | R¹-II | R²-IX |
| X-V | Y-I | R¹-III | R²-III |
| X-V | Y-I | R¹-III | R²-IX |
| X-V | Y-I | R¹-IV | R²-IV |
| X-V | Y-II | R¹-I | R²-I |
| X-V | Y-II | R¹-I | R²-IX |
| X-V | Y-II | R¹-II | R²-II |
| X-V | Y-II | R¹-II | R²-IX |
| X-V | Y-II | R¹-III | R²-III |
| X-V | Y-II | R¹-III | R²-IX |
| X-V | Y-II | R¹-IV | R²-IV |
| X-V | Y-III | R¹-I | R²-I |
| X-V | Y-III | R¹-I | R²-IX |
| X-V | Y-III | R¹-II | R²-II |
| X-V | Y-III | R¹-II | R²-IX |
| X-V | Y-III | R¹-III | R²-III |
| X-V | Y-III | R¹-III | R²-IX |
| X-V | Y-III | R¹-IV | R²-IV |
| X-V | Y-IV | R¹-I | R²-I |
| X-V | Y-IV | R¹-I | R²-IX |
| X-V | Y-IV | R¹-II | R²-II |
| X-V | Y-IV | R¹-II | R²-IX |
| X-V | Y-IV | R¹-III | R²-III |
| X-V | Y-IV | R¹-III | R²-IX |
| X-V | Y-IV | R¹-IV | R²-IV |
| X-V | Y-V | R¹-I | R²-I |
| X-V | Y-V | R¹-I | R²-IX |
| X-V | Y-V | R¹-II | R²-II |
| X-V | Y-V | R¹-III | R²-IX |
| X-V | Y-V | R¹-III | R²-III |
| X-V | Y-V | R¹-III | R²-IX |
| X-V | Y-V | R¹-IV | R²-IV |
| X-V | Y-VI | R¹-I | R²-I |
| X-V | Y-VI | R¹-I | R²-IX |
| X-V | Y-VI | R¹-II | R²-II |
| X-V | Y-VI | R¹-II | R²-IX |
| X-V | Y-VI | R¹-III | R²-III |
| X-V | Y-VI | R¹-III | R²-IX |
| X-V | Y-VI | R¹-IV | R²-IV |
| X-VI | Y-I | R¹-I | R²-I |
| X-VI | Y-I | R¹-I | R²-IX |
| X-VI | Y-I | R¹-II | R²-II |
| X-VI | Y-I | R¹-II | R²-IX |
| X-VI | Y-I | R¹-III | R²-III |
| X-VI | Y-I | R¹-III | R²-IX |
| X-VI | Y-I | R¹-IV | R²-IV |
| X-VI | Y-II | R¹-I | R²-I |
| X-VI | Y-II | R¹-I | R²-IX |
| X-VI | Y-II | R¹-II | R²-II |
| X-VI | Y-II | R¹-II | R²-IX |
| X-VI | Y-II | R¹-III | R²-III |
| X-VI | Y-II | R¹-III | R²-IX |
| X-VI | Y-II | R¹-IV | R²-IV |
| X-VI | Y-III | R¹-I | R²-I |
| X-VI | Y-III | R¹-I | R²-IX |

TABLE 1-continued

| X | Y | R¹ | R² |
|---|---|---|---|
| X-VI | Y-III | R¹-II | R²-II |
| X-VI | Y-III | R¹-II | R²-IX |
| X-VI | Y-III | R¹-III | R²-III |
| X-VI | Y-III | R¹-III | R²-IX |
| X-VI | Y-III | R¹-IV | R²-IV |
| X-VI | Y-IV | R¹-I | R²-I |
| X-VI | Y-IV | R¹-I | R²-IX |
| X-VI | Y-IV | R¹-II | R²-II |
| X-VI | Y-IV | R¹-II | R²-IX |
| X-VI | Y-IV | R¹-III | R²-III |
| X-VI | Y-IV | R¹-III | R²-IX |
| X-VI | Y-IV | R¹-IV | R²-IV |
| X-VI | Y-V | R¹-I | R²-I |
| X-VI | Y-V | R¹-I | R²-IX |
| X-VI | Y-V | R¹-II | R²-II |
| X-VI | Y-V | R¹-II | R²-IX |
| X-VI | Y-V | R¹-III | R²-III |
| X-VI | Y-V | R¹-III | R²-IX |
| X-VI | Y-V | R¹-IV | R²-IV |
| X-VI | Y-VI | R¹-I | R²-I |
| X-VI | Y-VI | R¹-I | R²-IX |
| X-VI | Y-VI | R¹-II | R²-II |
| X-VI | Y-VI | R¹-II | R²-IX |
| X-VI | Y-VI | R¹-III | R²-III |
| X-VI | Y-VI | R¹-III | R²-IX |
| X-VI | Y-VI | R¹-IV | R²-IV |
| X-VII | Y-I | R¹-I | R²-I |
| X-VII | Y-I | R¹-I | R²-IX |
| X-VII | Y-I | R¹-II | R²-II |
| X-VII | Y-I | R¹-II | R²-IX |
| X-VII | Y-I | R¹-III | R²-III |
| X-VII | Y-I | R¹-III | R²-IX |
| X-VII | Y-I | R¹-IV | R²-IV |
| X-VII | Y-II | R¹-I | R²-I |
| X-VII | Y-II | R¹-I | R²-IX |
| X-VII | Y-II | R¹-II | R²-II |
| X-VII | Y-II | R¹-II | R²-IX |
| X-VII | Y-II | R¹-III | R²-III |
| X-VII | Y-II | R¹-III | R²-IX |
| X-VII | Y-II | R¹-IV | R²-IV |
| X-VII | Y-III | R¹-I | R²-I |
| X-VII | Y-III | R¹-I | R²-IX |
| X-VII | Y-III | R¹-II | R²-II |
| X-VII | Y-III | R¹-II | R²-IX |
| X-VII | Y-III | R¹-III | R²-III |
| X-VII | Y-III | R¹-III | R²-IX |
| X-VII | Y-III | R¹-IV | R²-IV |
| X-VII | Y-IV | R¹-I | R²-I |
| X-VII | Y-IV | R¹-I | R²-IX |
| X-VII | Y-IV | R¹-II | R²-II |
| X-VII | Y-IV | R¹-II | R²-IX |
| X-VII | Y-IV | R¹-III | R²-III |
| X-VII | Y-IV | R¹-III | R²-IX |
| X-VII | Y-IV | R¹-IV | R²-IV |
| X-VII | Y-V | R¹-I | R²-I |
| X-VII | Y-V | R¹-I | R²-IX |
| X-VII | Y-V | R¹-II | R²-II |
| X-VII | Y-V | R¹-II | R²-IX |
| X-VII | Y-V | R¹-III | R²-III |
| X-VII | Y-V | R¹-III | R²-IX |
| X-VII | Y-V | R¹-IV | R²-IV |
| X-VII | Y-VI | R¹-I | R²-I |
| X-VII | Y-VI | R¹-I | R²-IX |
| X-VII | Y-VI | R¹-II | R²-II |
| X-VII | Y-VI | R¹-II | R²-IX |
| X-VII | Y-VI | R¹-III | R²-III |
| X-VII | Y-VI | R¹-III | R²-IX |
| X-VII | Y-VI | R¹-IV | R²-IV |

The compounds of the present invention can be produced for example according to the methods mentioned below.

Production Method A

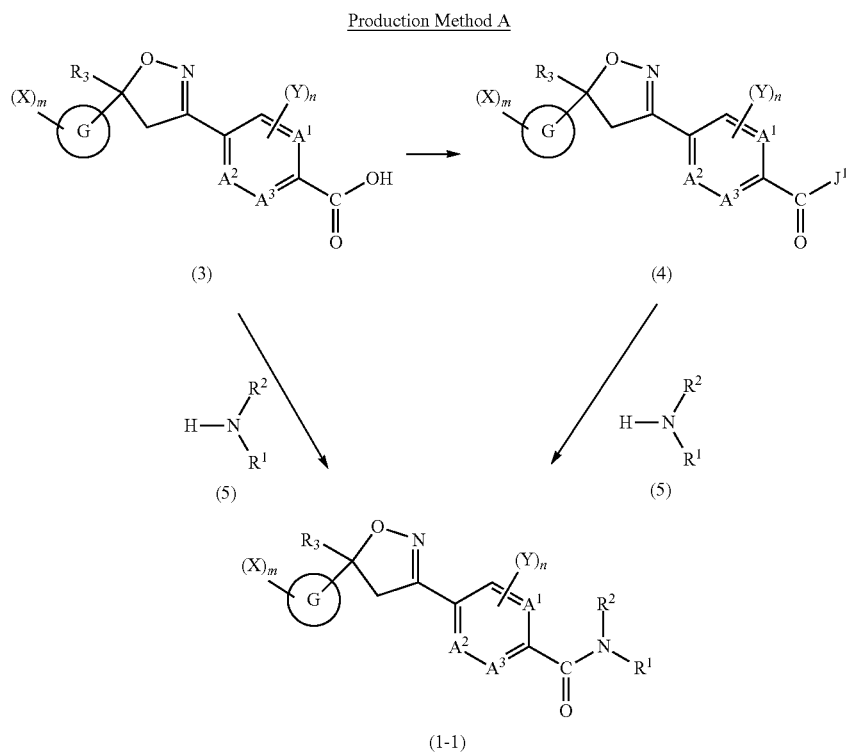

The compound of formula (1-1) (wherein $A^1, A^2, A^3$, G, X, Y, $R^1, R^2, R^3$, m and n are as defined above) that W in the formula (1) is oxygen atom according to the present invention can be obtained by reacting the compound of formula (3) (wherein $A^1, A^2, A^3$, G, X, Y, $R^3$, m and n are as defined above) with a halogenating agent such as thionyl chloride, phosphorus pentaoxide or oxalyl chloride or the like according to any methods known from documents such as a method stated in J. Med. Chem., 1991, vol. 34, p. 1630, or the like, with an organic acid halide such as pivaloyl chloride or isobutyl chloroformate or the like optionally in the presence of a base aqccording to a method stated in Tetrahedron Lett., 2003, vol. 44, p. 4819, or J. Med. Chem., 1991, vol. 34, p. 222, or the like, or with carbonyldiimidazole or sulfonyldiimidazole, etc. according to a method stated in J. Org. Chem., 1989, vol. 54, p. 5620 or the like, to synthesize the compound of formula (4) (wherein $A^1, A^2, A^3$, G, X, Y, $R^3$, m and n are as defined above, $J^1$ is chlorine atom, bromine atom, $C_1$-$C_4$alkylcarbonyloxy (for example pivaloyloxy), $C_1$-$C_4$alkoxycarbonyloxy (for example isobutyloxycarbonyloxy) or azolyl (for example imidazole-1-yl)), and reacting the compound of formula (4) with the compound of formula (5) (wherein $R^1$ and $R^2$ are as defined above) optionally by use of a solvent inactive for the reaction, optionally in the presence of a base.

The reaction substrates can be used in an amount of 1 to 50 equivalents of the compound of formula (5) based on 1 equivalent of the compound of formula (4).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, t-butyl methyl ether, 1,2-dimethoxyethane, tetrahydrofuran, 1,4-dioxane or the like, esters such as ethyl acetate, ethyl propionate or the like, amides such as N,N-dimethylformamide, N,N-dimethylacetamide, N-methyl-2-pyrolidone or the like, amines such as triethyl amine, tributyl amine, N,N-dimethyl aniline or the like, pyridines such as pyridine, picoline or the like, acetonitrile and water, and the like. These solvents may be used alone or in a mixture of two or more.

The addition of a base is not necessarily required. However, when the base is used, alkali metal hydroxides such as sodium hydroxide, potassium hydroxide or the like, alkali metal carbonates such as sodium carbonate, potassium carbonate or the like, alkali metal bicarbonates such as sodium hydrogen carbonate, potassium hydrogen carbonate or the like, organic bases such as triethyamine, tributylamine, N,N-dimethylaniline, pyridine, 4-(dimethylamino)pyridine, imidazole, 1,8-diazabicyclo[5.4.0]-7-undecene, and the like can be used in an amount of 1 to 4 equivalents based on the compound of formula (4).

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 10 equivalents of the compound of formula (5) based on 1 equivalent of the compound of formula (4), optionally in the presence of 1 to 2 equivalents of a base such as potassium carbonate, triethylamine, pyridine, 4-(dimethylamino)pyridine or the like, without solvent or in a solvent such as dichloromethane, chloroform, diethyl ether, tetrahydrofurane, 1,4-dioxane, ethyl acetate, acetonitrile or the like, at a temperature ranging from 0° C. to the reflux temperature of these solvents for 10 minutes to 24 hours.

In addition, the compound of formula (1-1) according to the present invention can be also obtained by directly reacting the compound of formula (3) with the compound of formula (5) (wherein $R^1$ and $R^2$ are as defined above) by use of a condensation agent optionally by use of a solvent inactive for the reaction, optionally in the presence of a base.

The reaction substrates can be used in an amount of 1 to 100 equivalents of the compound of formula (5) based on 1 equivalent of the compound of formula (3).

The condensation agent is not specifically limited if it is a compound used for ordinary amide synthesis, but it is for example Mukaiyama agent (2-chloro-N-methylpyridinium iodide), DCC (1,3-dicyclohexyl carbodiimide), WSC (1-ethyl-3-(3-dimethylaminopropyl)-carbodiimide hydrochloride), CDI (carbonyl diimidazole), dimethylpropynyl sulfonium bromide, propargyl triphenyl phosphonium bromide, DEPC (diethyl phosphorocyanidate) or the like, and can be used in an amount of 1 to 4 equivalents based on the compound of formula (3).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, t-butyl methyl ether, 1,2-dimethoxyethane, tetrahydrofuran, 1,4-dioxane or the like, esters such as ethyl acetate, ethyl propionate or the like, amides such as N,N-dimethylformamide, N,N-dimethylacetamide, N-methyl-2-pyrolidone or the like, amines such as triethyl amine, tributyl amine, N,N-dimethyl aniline or the like, pyridines such as pyridine, picoline or the like, acetonitrile and dimethylsulfoxide, and the like. These solvents may be used alone or in a mixture of two or more.

The addition of a base is not necessarily required. However, when the base is used, alkali metal hydroxides such as sodium hydroxide, potassium hydroxide or the like, alkali metal carbonates such as sodium carbonate, potassium carbonate or the like, alkali metal bicarbonates such as sodium hydrogen carbonate, potassium hydrogen carbonate or the like, organic bases such as triethyamine, tributylamine, N,N-dimethylaniline, pyridine, 4-(dimethylamino)pyridine, imidazole, 1,8-diazabicyclo[5.4.0]-7-undecene, and the like can be used in an amount of 1 to 4 equivalents based on the compound of formula (3).

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 20 equivalents of the compound of formula (5) and 1 to 4 equivalents of a condensation agent such as WSC (1-ethyl-3-(3-dimethylaminopropyl)-carbodiimide hydrochloride), CDI (carbonyl diimidazole) or the like based on 1 equivalent of the compound of formula (3), optionally in the presence of 1 to 4 equivalents of a base such as potassium carbonate, triethylamine, pyridine, 4-(dimethylamino)pyridine or the like, without solvent or in a solvent such as dichloromethane, chloroform, diethyl ether, tetrahydrofurane, 1,4-dioxane or the like, at a temperature ranging from 0° C. to the reflux temperature of these solvents for 10 minutes to 24 hours.

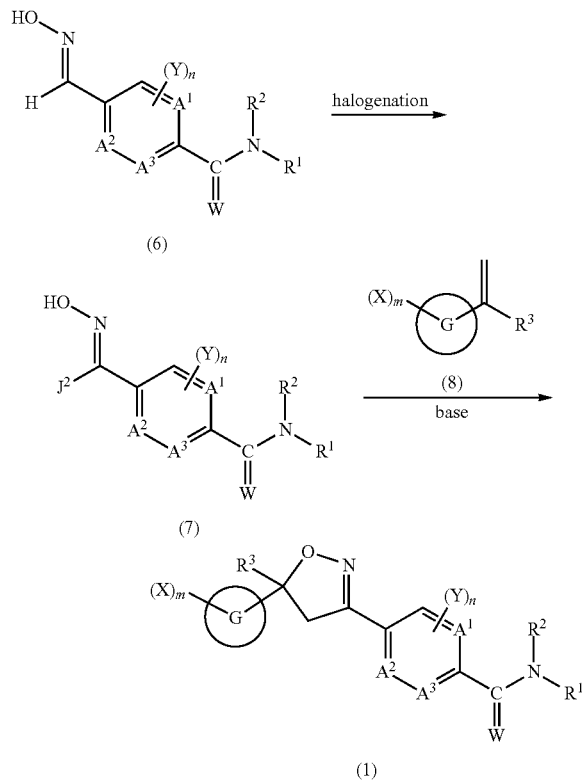

Production Method B (6)

(7)

(1)

Hydroxamic chloride of formula (7) (wherein $A^1$, $A^2$, $A^3$, W, Y, $R^1$, $R^2$ and n are as defined above, $J^2$ means halogen atom such as chlorine atom and bromine atom or the like) can be obtained by halogenating the compound of formula (6) (wherein $A^1$, $A^2$, $A^3$, W, Y, $R^1$, $R^2$ and n are as defined above) using a halogenating reagent optionally by using a solvent inactive for the reaction, optionally in the presence of a base.

Halogenating agents include for example N-halosuccinimides such as N-chlorosuccinimide, N-bromosuccinimide or the like, hypohalogenous acid alkali metal salts such as sodium hypochlorite or the like, hypohalogenous acid esters such as hypochlorous acid-t-butyl ester or the like, simple substance halogens such as chlorine gas or the like, and it can be used in an amount of 1 to 10 equivalents based on the compound of formula (6).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, t-butyl methyl ether, 1,2-dimethoxyethane, tetrahydrofuran, 1,4-dioxane or the like, esters such as ethyl acetate, ethyl propionate or the like, amides such as N,N-dimethylformamide, N,N-dimethylacetamide, N-methyl-2-pyrolidone or the like, alcohols such as methanol, ethanol, ethylene glycol or the like, carboxylic acids such as acetic acid, propionic acid or the like, acetonitrile and water, and the like. These solvents may be used alone or in a mixture of two or more.

The reaction temperature may be an arbitrary temperature ranging from −60° C. to the reflux temperature of a reaction mixture, and the reaction time may be an arbitrary time ranging from 5 minutes to 24 hours although it varies depending on the concentration of the reaction substrates or the reaction temperature.

The compounds of formula (1) (wherein $A^1$, $A^2$, $A^3$, G, W, X, Y, $R^1$, $R^2$, $R^3$, m and n are as defined above) according to the present invention can be obtained by reacting the compound of formula (7) obtained as above with the compound of formula (8) (wherein G, X, $R^3$ and m are as defined above) in the presence of a base optionally by use of a solvent inactive for the reaction.

The reaction substrates can be used in an amount of 1 to 5 equivalents of the compound of formula (8) based on 1 equivalent of the compound of formula (7).

The used base includes for example alkali metal hydroxides such as sodium hydroxide, potassium hydroxide or the like, alkali metal carbonates such as sodium carbonate, potassium carbonate or the like, alkali metal bicarbonates such as sodium hydrogen carbonate, potassium hydrogen carbonate or the like, organic bases such as triethyamine, tributylamine, N,N-dimethylaniline, pyridine, 4-(dimethylamino)pyridine, imidazole, 1,8-diazabicyclo[5.4.0]-7-undecene, and the like can be used in an amount of 1 to 5 equivalents based on the compound of formula (7).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, 1,2-dimethoxyethane, tetrahydrofuran, 1,4-dioxane or the like, esters such as ethyl acetate, ethyl propionate or the like, amides such as N,N-dimethylformamide, N,N-dimethylacetamide, N-methyl-2-pyrolidone or the like, and acetonitrile, and the like. These solvents may be used alone or in a mixture of two or more.

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, the compound of formula (7) can be obtained for example by carrying out the reaction by using 1 to 2 equivalents of a halogenating agent such as N-chlorosuccinimide, sodium hypochlorite aqueous solution, hypochlorous acid-t-butyl ester, chlorine gas or the like based on 1 equivalent of the compound of formula (6) in a solvent such as dichloromethane, chloroform, 1,2-dimethoxyethane, tetrahydrofurane, 1,4-dioxane, N,N-dimethylformamide or the like, at a temperature ranging from 00° C. to the reflux temperature of these solvents for 10 minutes to 2 hours. Then, preferably without the isolation of the compound of formula (7), 1 to 2 equivalents of the compound of formula (8) and 1 to 2 equivalents of a base such as sodium carbonate, sodium hydrogen carbonate, triethyl amine or the like are added, and the reaction is carried out at a temperature ranging from 0° C. to the reflux temperature of these solvents for 10 minutes to 24 hours.

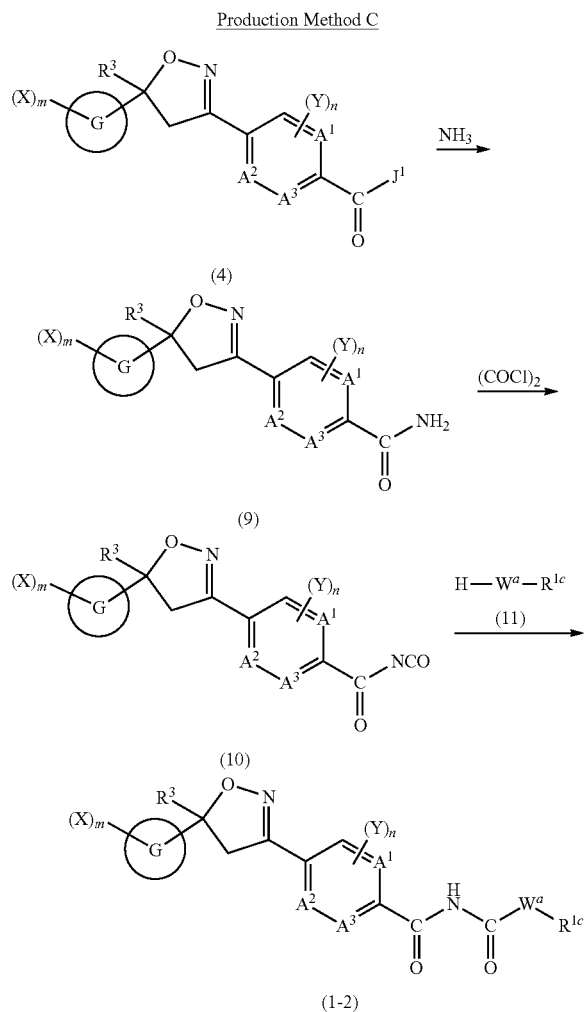

The substituted acylisocyanate of formula (10) (wherein $A^1, A^2, A^3, G, X, Y, R^3$, m and n are as defined above) can be obtained by reacting the compound of formula (4) (wherein $A^1, A^2, A^3, G, X, Y, R^3$, m, n and $J^1$ are as defined above) used in Production Method A with ammonia water or the like according to any methods known from documents such as a method stated in J. Med. Chem., 1991, vol. 34, p. 1630, or the like to synthesize the compound of formula (9) (wherein $A^1$, $A^2$, $A^3$, G, X, Y, $R^3$, m and n are as defined above), and reacting the compound of formula (9) with oxalyl chloride under an inert gas atmosphere such as nitrogen or argon, etc., optionally by use of a solvent inactive for the reaction.

The reaction substrates can be used in an amount of 1 to 2 equivalents of oxaly chloride based on 1 equivalent of the compound of formula (9).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, and the like. These solvents may be used alone or in a mixture of two or more.

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by adding 1 to 1.5 equivalent of oxalyl chloride based on 1 equivalent of the compound of formula (9), for example under nitrogen atmosphere, by use of a solvent such as toluene, dichloromethane, 1,2-dichloroethane or the like, at a temperature ranging from 0° C. to room temperature, and then reacting at a temperature ranging from room temperature to the reflux temperature of these solvents for 10 minutes to 24 hours.

The compound of formula (1-2) (wherein $A^1, A^2, A^3$, G, X, Y, $R^{1c}$, $R^3$, m and n are as defined above, $W^a$ is oxygen atom or sulfur atom) that in the formula (1) W is oxygen atom, $R^1$ is —C(O)—$W^a$—$R^{1c}$ and $R^2$ is hydrogen atom according to the present invention can be obtained by reacting the substituted acylisocyanate of formula (10) obtained as above with the alcohol or thiol of formula (11) (wherein $W^a$ is oxygen atom or sulfur atom, $R^{1c}$ is as defined above), optionally in the presence of a base, optionally by use of a solvent inactive for the reaction.

The reaction substrates can be used in an amount of 1 to 100 equivalents of the compound of formula (11) based on 1 equivalent of the compound of formula (10).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, t-butyl methyl ether, 1,2-dimethoxyethane, tetrahydrofuran, 1,4-dioxane or the like, ketones such as acetone, methyl ethyl ketone or the like, esters such as ethyl acetate, ethyl propionate or the like, amides such as N,N-dimethylformamide, N,N-dimethylacetamide, N-methyl-2-pyrolidone or the like, amines such as triethyl amine, tributyl amine, N,N-dimethyl aniline or the like, pyridines such as pyridine, picoline or the like, acetonitrile and dimethylsulfoxide, and the like. These solvents may be used alone or in a mixture of two or more.

The addition of a base is not necessarily required. However, when the base is used, alkali metal carbonates such as sodium carbonate, potassium carbonate or the like, alkali metal bicarbonates such as sodium hydrogen carbonate, potassium hydrogen carbonate or the like, organic bases such as triethyamine, tributylamine, N,N-dimethylaniline, pyridine, 4-(dimethylamino)pyridine, imidazole, 1,8-diazabicyclo[5.4.0]-7-undecene, and the like can be used in an amount of 1 to 4 equivalents based on the compound of formula (10).

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 20 equivalents of the compound of formula (11) based on 1 equivalent of the compound of formula (10), optionally in the presence of 1 to 4 equivalents of a base such as potassium carbonate, triethylamine, pyridine, 4-(dimethylamino)pyridine or the like, without solvent or in a solvent such as benzene, toluene, dichloromethane, chloroform, diethyl ether, tetrahydrofurane, 1,4-dioxane or the like, at a temperature ranging from 0° C. to the reflux temperature of these solvents for 10 minutes to 24 hours.

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 20 equivalents of ammonia water or ammonia gas based on 1 equivalent of the compound of formula (10), by use of a solvent such as benzene, toluene, dichloromethane, chloroform, diethyl ether, tetrahydrofurane, 1,4-dioxane or the like, at a temperature ranging from 0° C. to to the reflux temperature of these solvents for 10 minutes to 24 hours.

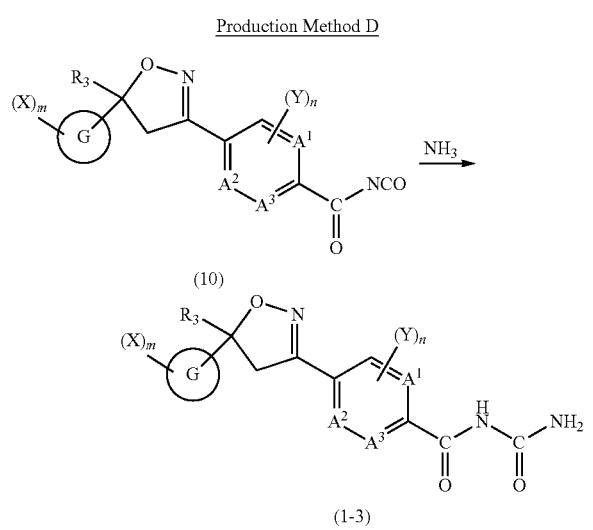

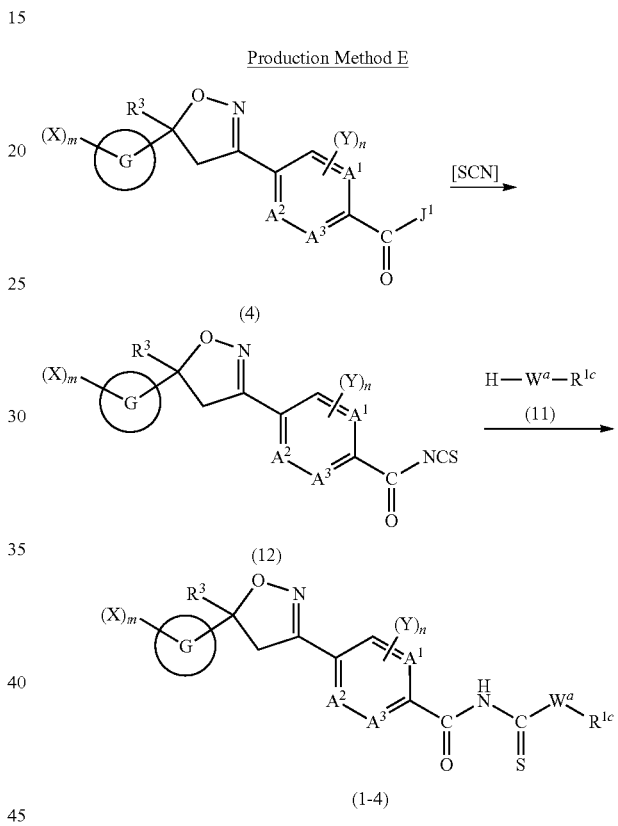

The compound of formula (1-3) (wherein $A^1$, $A^2$, $A^3$, G, X, Y, $R^3$, m and n are as defined) that in formula (1) W is oxygen atom, $R^1$ is —C(O)NH$_2$, and $R^2$ is hydrogen atom, according to the present invention can be obtained by reacting the substituted acylisocyanate of formula (10) (wherein $A^1$, $A^2$, $A^3$, G, X, Y, $R^3$, m and n are as defined above) used in Production Method C with ammonia, optionally by using a solvent inactive for the reaction.

The reaction substrates can be used in an amount of 1 to 100 equivalents of ammonia based on 1 equivalent of the compound of formula (10).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, t-butyl methyl ether, 1,2-dimethoxyethane, tetrahydrofuran, 1,4-dioxane or the like, ketones such as acetone, methyl ethyl ketone or the like, esters such as ethyl acetate, ethyl propionate or the like, amides such as N,N-dimethylformamide, N,N-dimethylacetamide, N-methyl-2-pyrolidone or the like, amines such as triethyl amine, tributyl amine, N,N-dimethyl aniline or the like, pyridines such as pyridine, picoline or the like, acetonitrile and dimethylsulfoxide, and the like. These solvents may be used alone or in a mixture of two or more.

The substituted acylisothiocyanate of formula (12) (wherein $A^1$, $A^2$, $A^3$, G, X, Y, $R^3$, m and n are as defined above) can be obtained by reacting the compound of formula (4) (wherein $A^1$, $A^2$, $A^3$, G, X, Y, $R^3$, m, n and $J^1$ are as defined above) used in Production Method A with a thiocyanate such as potassium thiocyanate, sodium thiocyanate, ammonium thiocyanate or lead thiocyanate or the like, under an inert gas atmosphere such as nitrogen or argon, etc., optionally by use of a solvent inactive for the reaction.

The reaction substrates can be used in an amount of 1 to 10 equivalents of thiocyanate based on 1 equivalent of the compound of formula (4).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, t-butyl methyl ether, 1,2-dimethoxyethane, tetrahydrofuran, 1,4-dioxane or the like, ketones such as acetone, methyl ethyl ketone or the like, esters such as ethyl acetate, ethyl propionate or the like, amides such as N,N-dimethylformamide, N,N-dimethylacetamide, N-methyl-2-pyrolidone or the like, and acetonitrile, and the like. These solvents may be used alone or in a mixture of two or more.

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by adding 1 to 1.5 equivalent of potassium thiocyanate, sodium thiocyanate or ammonium thiocyanate based on 1 equivalent of the compound of formula (4), for example under nitrogen atmosphere, by use of a solvent such as benzene, toluene, dichloromethane, acetone, acetonitrile or the like, at a temperature ranging from 0° C. to room temperature, and then reacting at a temperature ranging from room temperature to the reflux temperature of these solvents for 10 minutes to 24 hours.

The compound of formula (1-4) (wherein $A^1$, $A^2$, $A^3$, G, X, Y, $R^{1c}$, $R^3$, m and n are as defined above, $W^a$ is oxygen atom or sulfur atom) that in the formula (1) W is oxygen atom, $R^1$ is —C(S)—$W^a$—$R^{1c}$ and $R^2$ is hydrogen atom according to the present invention can be obtained by reacting the substituted acylisothiocyanate of formula (12) obtained as above with the alcohol or thiol of formula (11) (wherein $W^a$ and $R^{1c}$ are as defined above) under a condition similar to that of Production Method C.

Production Method F

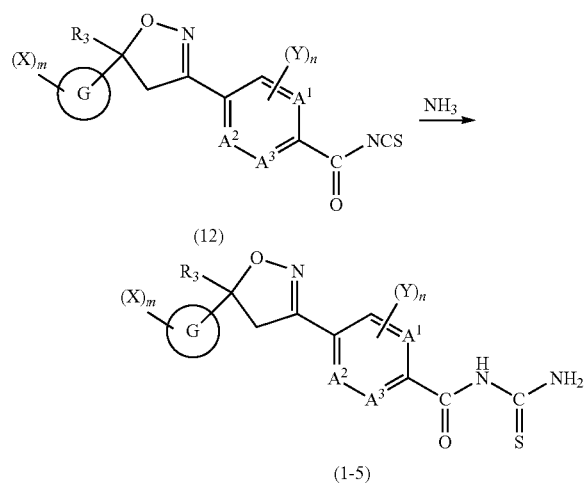

(12)

(1-5)

The substituted acylisothiocyanate of formula (1-5) (wherein $A^1$, $A^2$, $A^3$, G, X, Y, $R^3$, m and n are as defined above) that in the formula (1) W is oxygen atom, $R^1$ is —C(S)NH$_2$ and $R^2$ is hydrogen atom according to the present invention can be obtained by reacting the compound of formula (12) (wherein $A^1$, $A^2$, $A^3$, G, X, Y, $R^3$, m and n are as defined above) used in Production Method E with ammonia under a condition similar to that of Production Method D.

Production Method G

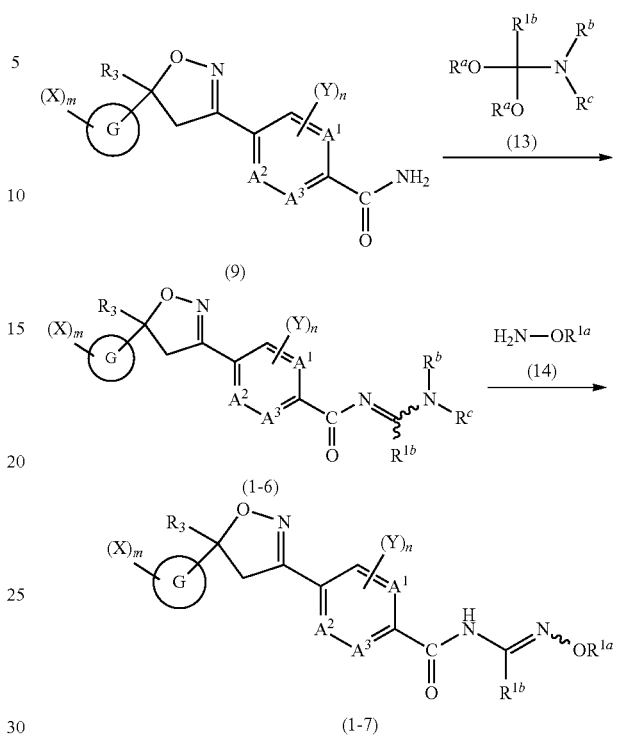

(9)

(1-6)

(1-7)

The substituted acylisothiocyanate of formula (1-6) (wherein $A^1$, $A^2$, $A^3$, G, X, Y, $R^{1b}$, $R^3$, m and n are as defined above, $R^b$ and $R^c$ independently of each other are $C_1$-$C_6$alkyl) that in the formula (1) W is oxygen atom, $R^2$ together with $R^1$ forms =C($R^{1b}$)N(R)$R^b$ according to the present invention can be obtained by reacting the compound of formula (9) (wherein $A^1$, $A^2$, $A^3$, G, X, Y, $R^3$, m and n are as defined above) used in Production Method C with the compound of formula (13) (wherein $R^{1b}$ is as defined above, $R^a$, $R^b$ and $R^c$ independently of one another are $C_1$-$C_6$alkyl), optionally under an inert gas atmosphere such as nitrogen or argon, etc., optionally in the presence of an acid catalyst, optionally by use of a solvent inactive for the reaction.

The reaction substrates can be used in an amount of 1 to 100 equivalents of the compound of formula (13) based on 1 equivalent of the compound of formula (9).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, alcohols such as methanol, ethanol, 2-propanol, 2-methoxyethanol or the like, ethers such as diethyl ether, t-butyl methyl ether, 1,2-dimethoxyethane, tetrahydrofuran, 1,4-dioxane or the like, amides such as N,N-dimethylformamide, N,N-dimethylacetamide, N-methyl-2-pyrolidone or the like, and the like. These solvents may be used alone or in a mixture of two or more.

The addition of a catalyst is not necessarily required. However, when the catalyst is used, mineral acids such as hydrochloric acid, sulfuric acid, nitric acid or the like, organic acids such as formic acid, acetic acid, propionic acid, trifluoroacetic acid, methane sulfonic acid, benzene sulfonic acid, p-toluene sulfonic acid or the like, Lewis acid such as zinc chloride, zinc iodide, titanium tetrachloride, cerium chloride, ytterbium trifluoride, boron trifluoride-ether complex or the like, and the like can be used in an amount of 0.001 to 1 equivalent based on the compound of formula (4).

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 2 to 10 equivalents of the compound of formula (13) based on 1 equivalent of the compound of formula (9), for example under nitrogen atmosphere, without solvent or in a solvent such as benzene, toluene or the like, at a temperature ranging from room temperature to the reflux temperature of these solvents for 1 to 24 hours.

The compound of formula (1-7) (wherein $A^1, A^2, A^3$, G, X, Y, $R^{1a}$, $R^{1b}$, $R^3$, m and n are as defined above) that in the formula (1) W is oxygen atom, $R^1$ is —C($R^{1b}$)=NOR$^{1a}$ and $R^2$ is hydrogen atom according to the present invention can be obtained by reacting the compound of formula (1-6) obtained as above according to the present invention with the alkoxyamines or the salts thereof of formula (14) (wherein $R^{1a}$ is as defined above), optionally in the presence of a base, optionally by use of a solvent inactive for the reaction.

The reaction substrates can be used in an amount of 1 to 20 equivalents of the compound of formula (14) based on 1 equivalent of the compound of formula (1-6).

In case where a solvent is used, the solvent is not specifically limited if it dose not inhibit the progress of the reaction, but it includes for example alcohols such as methanol, ethanol, 2-propanol, 2-methoxyethanol or the like, ethers such as diethyl ether, t-butyl methyl ether, 1,2-dimethoxyethane, tetrahydrofuran, 1,4-dioxane or the like, amides such as N,N-dimethylformamide, N,N-dimethylacetoamide, N-methyl-2-pyrolidone or the like, amines such as triethyl amine, tributyl amine, N,N-dimethyl aniline or the like, pyridines such as pyridine, picoline or the like, and the like. These solvents may be used alone or in a mixture of two or more.

The addition of a base is not necessarily required. However, when the compound of formula (14) is a salt with hydrochloric acid, sulfonic acid or the like, for example alkali metal carbonates such as sodium carbonate, potassium carbonate or the like, alkali metal bicarbonates such as sodium hydrogen carbonate, potassium hydrogen carbonate or the like, organic bases such as triethyamine, tributylamine, N,N-dimethylaniline, pyridine, 4-(dimethylamino)pyridine, imidazole, 1,8-diazabicyclo[5.4.0]-7-undecene, and the like can be used in an amount of 1 to 4 equivalents based on the compound of formula (14).

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 5 equivalents of the compound of formula (14) based on 1 equivalent of the compound of formula (1-6), in case where the compound of formula (14) is a salt, by adding 1 to 4 equivalents of a base such as triethylamine, 1,8-diazabicyclo [5.4.0]-7-undecene or the like, without solvent or in a solvent such as methanol, ethanol, diethyl ether, tetrahydrofurane, 1,4-dioxane or the like, at a temperature ranging from room temperature to the reflux temperature of these solvents for 10 minutes to 24 hours.

Production Method H

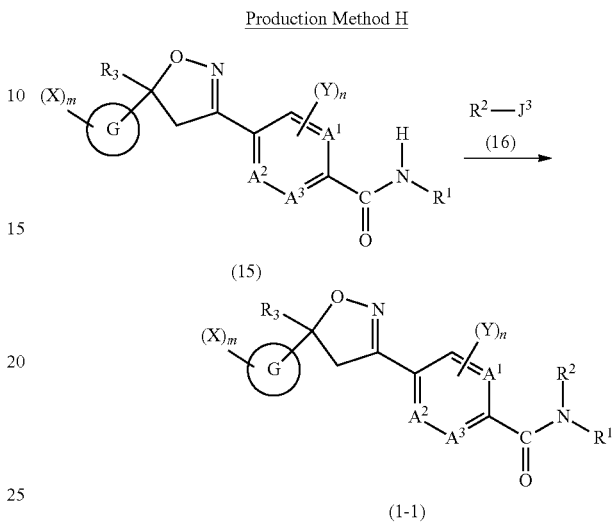

The substituted acylisothiocyanate of formula (1-1) (wherein $A^1, A^2, A^3$, G, X, Y, $R^3$, m and n are as defined above, $R^1$ is —C($R^{1b}$)=NOR$^{1a}$, M-5, M-20, M-48, —C(O)OR$^{1c}$, —C(O)SR$^{1c}$, phenyl, phenyl substituted with $(Z)_{p1}$ or D-1 to D-65, $R^2$ has the meaning mentioned above other than hydrogen atom) that W in the formula (1) is oxygen atom according to the present invention can be obtained by reacting the compound of formula (15) (wherein $A^1, A^2, A^3$, G, X, Y, $R^3$, m and n are as defined above, $R^1$ is —C($R^{1b}$)=NOR$^{1a}$, M-5, M-20, M-48, —C(O)OR$^{1c}$, —C(O)SR$^{1c}$, phenyl, phenyl substituted with $(Z)_{p1}$ or D-1 to D-65 or the like) with the compound of formula (16) (wherein $R^2$ has the meaning mentioned above other than hydrogen atom, $J^3$ is a good leaving group such as chlorine atom, bromine atom, iodine atom, $C_1$-$C_4$alkylcarbonyloxy (for example pivaloyloxy), $C_1$-$C_4$alkylsulfonate (for example methane sulfonyloxy), $C_1$-$C_4$haloalkylsulfonate (for example trifluoromethane sulfonyloxy), arylsulfonate (for example benzene sulfonyloxy or p-toluenesulfonyloxy) or azolyl (for example imidazole-1-yl)), optionally in the presence of a base, optionally by use of a solvent inactive for the reaction.

The reaction substrates can be used in an amount of 1 to 50 equivalents of the compound of formula (16) based on 1 equivalent of the compound of formula (15).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, t-butyl methyl ether, 1,2-dimethoxyethane, tetrahydrofuran, 1,4-dioxane or the like, esters such as ethyl acetate, ethyl propionate or the like, amides such as dimethylformamide, dimethylacetamide, N-methyl-2-pyrolidone or the like, amines such as triethyl amine, tributyl amine, N,N-dimethyl aniline or the like, pyridines such as pyridine, picoline or the like, alcohols such as methanol, ethanol, ethylene glycol or the like, acetonitrile, dimethylsulfoxide, sulfolane, 1,3-dimethyl-2-imidazolidinone and water, and the like. These solvents may be used alone or in a mixture of two or more.

In case where a base is used, for example alkali metal hydrides such as sodium hydride, potassium hydride or the like, alkali metal hydroxides such as sodium hydroxide, potassium hydroxide or the like, alkali metal alkoxides such as sodium ethoxide, potassium t-butoxide or the like, alkali metal amides such as lithium diisopropylamide, lithium hexamethyldisilazane, sodium amide or the like, organic metal compounds such as t-butyl lithium or the like, alkali metal carbonates such as sodium carbonate, potassium carbonate, sodium hydrogen carbonate or the like, organic bases such as triethyamine, tributylamine, N,N-dimethylaniline, pyridine, 4-(dimethylamino)pyridine, imidazole, 1,8-diazabicyclo[5.4.0]-7-undecene, and the like can be used in an amount of 1 to 4 equivalents based on the compound of formula (15).

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 10 equivalents of the compound of formula (16) based on 1 equivalent of the compound of formula (15), in a polar solvent such as tetrahydrofurane, 1,4-dioxane, acetonitrile, N,N-dimethylformamide or the like, optionally by use of a base such as sodium hydride, potassium t-butoxide, potassium hydroxide, potassium carbonate, triethylamine, pyridine or the like in an amount of 1 to 3 equivalents based on 1 equivalent of the compound of formula (15), at a temperature ranging from 000° C. to 90° C. for 10 minutes to 24 hours.

Production Method I

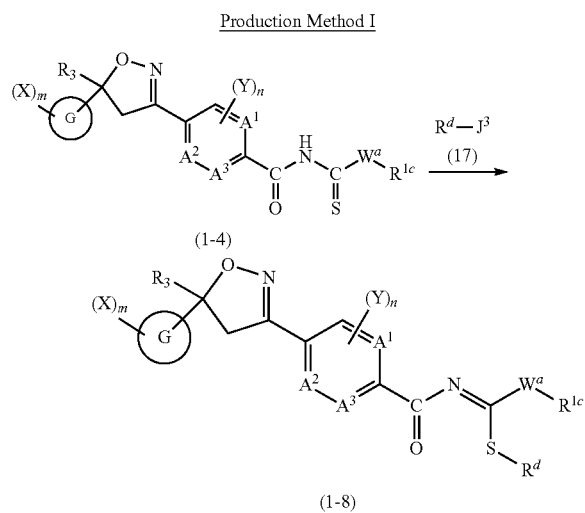

The substituted acylisothiocyanate of formula (1-8) (wherein $A^1$, $A^2$, $A^3$, G, Wa, X, Y, $R^{1c}$, $R^3$, m and n are as defined above, $R^d$ is $C_1$-$C_6$alkyl, $C_1$-$C_6$haloalkyl, —$CH_2R^{14a}$, $C_3$-$C_6$alkenyl, $C_3$-$C_6$haloalkenyl, $C_3$-$C_6$alkynyl, $C_3$-$C_6$haloalkynyl, —C(O)$R^{15}$, —C(O)O$R^{15}$ or the like, $R^{14a}$, $R^{15}$ and $J^3$ have the meaning mentioned above) that in the formula (1) W is oxygen atom and $R^2$ together with $R^1$ forms =C(S$R^d$)—$W^a$—$R^{1c}$ according to the present invention can be obtained by reacting the compound of formula (1-4) (wherein $A^1$, $A^2$, $A^3$, G, Wa, X, Y, $R^{1c}$, $R^3$, m and n are as defined above) that can be synthesized by use of Production Method E according to the present invention with the compound of formula (17) (wherein $R^d$ is $C_1$-$C_6$alkyl, $C_1$-$C_6$haloalkyl, —$CH_2R^{14a}$, $C_3$-$C_6$alkenyl, $C_3$-$C_6$haloalkenyl, $C_3$-$C_6$alkynyl, $C_3$-$C_6$haloalkynyl, —C(O)$R^{15}$—C(O)O$R^{15}$ or the like, $R^{14a}$, $R^{15}$ and $J^3$ have the meaning mentioned above), by use of a condition similar to that of Produciton Method H.

Production Method J

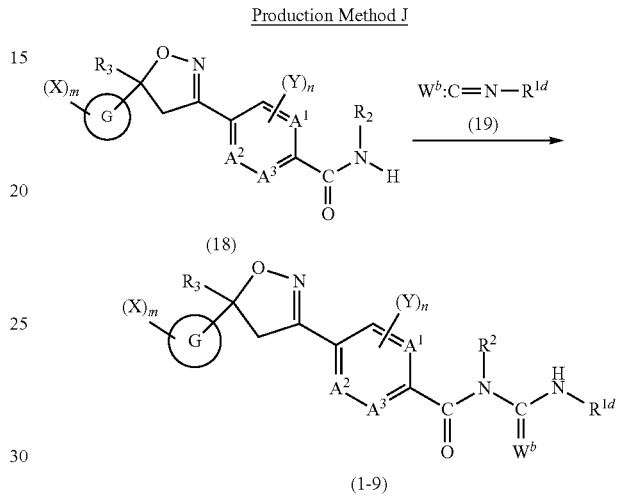

The compound of formula (1-9) (wherein $A^1$, $A^2$, $A^3$, G, X, Y, $R^{1d}$, $R^2$, $R^3$, m and n are as defined above, $W^b$ is oxygen atom or sulfur atom) that in the formula (1) W is oxygen atom and $R^1$ is —C($W^b$)NH$R^d$ according to the present invention can be obtained by reacting the compound of formula (18) (wherein $A^1$, $A^2$, $A^3$, G, X, Y, $R^2$, $R^3$, m and n are as defined above) with the compound of formula (19) (wherein $W^b$ is oxygen atom or sulfur atom, $R^{1d}$ has the meaning mentioned above), optionally in the presence of a base, optionally by use of a solvent inactive for the reaction.

The reaction substrates can be used in an amount of 1 to 10 equivalents of the compound of formula (19) based on 1 equivalent of the compound of formula (18).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, t-butyl methyl ether, 1,2-dimethoxyethane, tetrahydrofuran, 1,4-dioxane or the like, ketones such as acetone, methyl ethyl ketone or the like, alcohols such as methanol, ethanol, ethylene glycol or the like, and acetonitrile, and the like. These solvents may be used alone or in a mixture of two or more.

In case where a base is used, for example alkali metal hydrides such as sodium hydride, potassium hydride or the like, alkali metal carbonates such as sodium carbonate, potassium carbonate, sodium hydrogen carbonate or the like, organic bases such as triethyamine, tributylamine, N,N-dimethylaniline, pyridine, 4-(dimethylamino)pyridine, imidazole, 1,8-diazabicyclo[5.4.0]-7-undecene, and the like can be used in an amount of 1 to 5 equivalents based on the compound of formula (18).

The reaction temperature may be an arbitrary temperature ranging from −20° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 2 equivalents of the compound of formula (19) based on 1 equivalent of the compound of formula (18), in a solvent such as benzene, toluene, 1,2-dichloroethane, tetrahydrofuran, ethanol, acetonitrile or the like, optionally by use of a base such as sodium hydride, pyridine or the like in an amount of 1 to 2 equivalents based on 1 equivalent of the compound of formula (18), at a temperature ranging from room temperature to the reflux temperature of a reaction mixture for 1 to 24 hours.

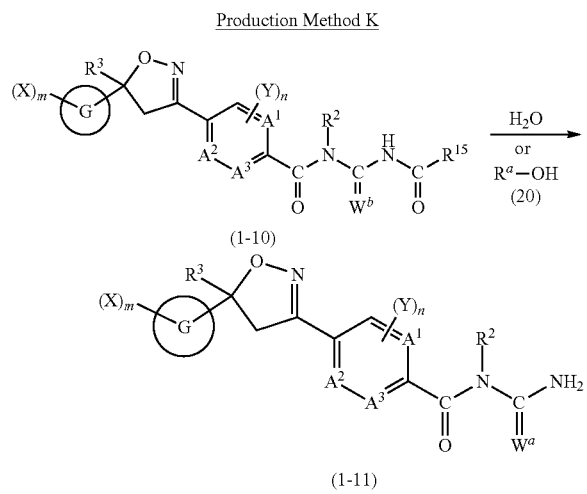

The compound of formula (1-11) (wherein $A^1$, $A^2$, $A^3$, G, X, Y, $R^2$, $R^3$, m and n are as defined above, $W^b$ is oxygen atom or sulfur atom) that in the formula (1) W is oxygen atom and $R^1$ is —C($W^b$)NH$_2$ according to the present invention can be obtained by reacting the compound of formula (1-10) (wherein $A^1$, $A^2$, $A^3$, G, X, Y, $R^2$, $R^3$, m and n are as defined above, $W^b$ is oxygen atom or sulfur atom, $R^{15}$ is $C_1$-$C_4$haloalkyl (for example trichloromethyl or the like)) that is the compound of formula (1-9) of the present invention wherein $R^{1d}$ is —C(O)$R^{15}$ and can be synthesized according to Production method I with water or the alcohol of formula (20) (wherein $R^a$ is $C_1$-$C_4$alkyl), optionally in the presence of an acid or base catalyst, optionally by use of a solvent inactive for the reaction.

The reaction substrates can be used in an amount of 1 to 100 equivalents of water or the alcohol of formula (20) based on 1 equivalent of the compound of formula (1-10) according to the present invention.

In case where a solvent is used, the solvent is not specifically limited if it dose not inhibit the progress of the reaction, but it includes for example aromatic hydrocarbons such as benzene, toluene, xylene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, t-butyl methyl ether, 1,2-dimethoxyethane, tetrahydrofuran, 1,4-dioxane or the like, esters such as ethyl acetate, ethyl propionate or the like, amides such as dimethylformamide, dimethylacetamide, N-methyl-2-pyrolidone or the like, alcohols such as methanol, ethanol, ethylene glycol or the like, acetonitrile, dimethylsulfoxide, sulfolane, 1,3-dimethyl-2-imidazolidinone and water, and the like. These solvents may be used alone or in a mixture of two or more.

In case where an acid catalyst is used, as the catalyst for reaction, for example mineral acids such as hydrochloric acid, sulfuric acid, nitric acid or the like, organic acids such as formic acid, acetic acid, propionic acid, trifluoroacetic acid, methane sulfonic acid, benzene sulfonic acid, p-toluene sulfonic acid or the like, or silica gel, and the like can be used in an amount of 0.001 to 1 equivalent based on the compound of formula (1-10) according to the present invention or in an amount of 10 to 1000 g/mol.

In case where a base catalyst is used, for example alkali metal hydroxides such as sodium hydroxide, potassium hydroxide or the like, alkali metal carbonates such as sodium carbonate, potassium carbonate, sodium hydrogen carbonate or the like, organic bases such as triethyamine, tributylamine, N,N-dimethylaniline, pyridine, 4-(dimethylamino)pyridine, imidazole, 1,8-diazabicyclo[5.4.0]-7-undecene, and the like can be used in an amount of 0.001 to 1 equivalent based on the compound of formula (1-10) according to the present invention.

The reaction temperature may be an arbitrary temperature ranging from 0° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 0.01 to 0.1 equivalent of an acid catalyst such as hydrochloric acid or sulfuric acid, etc. based on 1 equivalent of the compound of formula (1-10) according to the present invention, in a solvent such as methanol or the like, at a temperature ranging from room temperature to the reflux temperature of a reaction mixture for 10 minutes to 24 hours.

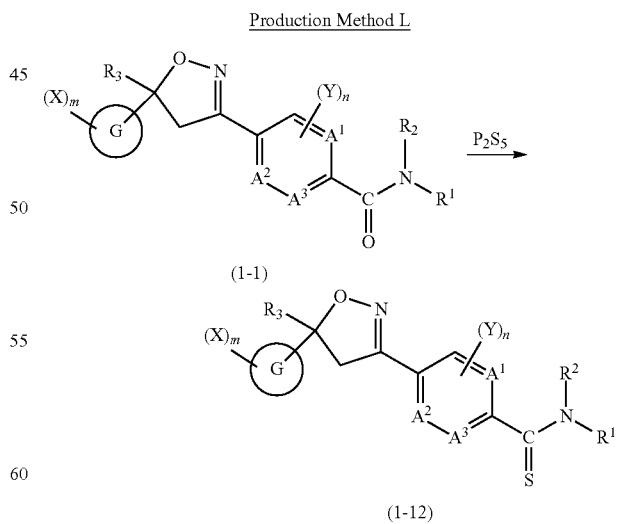

The compound of formula (1-12) (wherein $A^1$, $A^2$, $A^3$, G, X, Y, $R^1$, $R^2$, $R^3$, m and n are as defined above) according to the present invention that is the compound of formula (1) wherein W is sulfur atom can be obtained by reacting the compound of formula (1-1) (wherein $A^1, A^2, A^3, G, X, Y, R^1, R^2, R^3$, m and n are as defined above) according to the present invention that is the compound of formula (1) wherein W is oxygen atom with a sulfurizing agent such as diphosphorus pentasulfide, diphosphorus pentasulfide-HMDO (hexamethyldisiloxane), Lawesson's Reagent (2,4-bis(4-methoxyphenyl)-1,3,2,4-dithiadiphosphetane-2,4-disulfide), optionally by using a solvent inactive for the reaction, optionally in the presence of a base.

The reaction substrates can be used in an amount of 1 to 50 equivalents of the sulfurizing agent based on 1 equivalent of the compound of formula (1-1).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, t-butyl methyl ether, 1,2-dimethoxyethane, tetrahydrofuran, 1,4-dioxane or the like, amines such as triethyl amine, tributyl amine, N,N-dimethyl aniline or the like, pyridines such as pyridine, picoline or the like, and HMPA (hexamethylphosphoric triamide), and the like. These solvents may be used alone or in a mixture of two or more.

The addition of a base is not necessarily required. However, when the base is used, alkali metal carbonates such as sodium carbonate, potassium carbonate, sodium hydrogen carbonate or the like, organic bases such as triethyamine, tributylamine, N,N-dimethylaniline, pyridine, 4-(dimethylamino)pyridine, imidazole, 1,8-diazabicyclo[5.4.0]-7-undecene, and the like can be used in an amount of 1 to 10 equivalents based on the compound of formula (1-1).

The reaction temperature may be an arbitrary temperature ranging from 0° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 10 equivalents of a sulfurizing agent such as diphosphorus pentasulfide, diphosphorus pentasulfide-HMDO, Lawesson's Reagent or the like, based on 1 equivalent of the compound of formula (1-1), optionally in the presence of 1 to 4 equivalents of a base such as sodium hydrogen carbonate, triethyamine, pyridine or the like, in a solvent such as benzene, toluene, chlorobenzene, dichloromethane, chloroform, 1,2-dimethoxyethane, tetrahydrofurane, 1,4-dioxane, HMPA or the like, at a temperature ranging from room temperature to the reflux temperature of the reaction mixture for 10 minutes to 50 hours, or in a solvent amount of pyridine at a temperature of 80° C. to the reflux temperature of the reaction mixture for 1 to 3 hours.

In Production Method A to Production Method L, the aimed compound of the present invention can be obtained by subjecting the reaction mixture after the completion of the reaction to ordinary post-treatment such as a direct concentration, or a concentration after dissolving in an organic solvent and washing with water or a concentration after placing in ice water and extracting with an organic solvent. In addition, when a purification is required, it can be separated and purified by an arbitrary purification process such as recrystallization, column chromatograph, thin layer chromatograph, liquid chromatograph collection or the like.

The compound of formula (3) used in Production Method A can be synthesized as follows, for example.

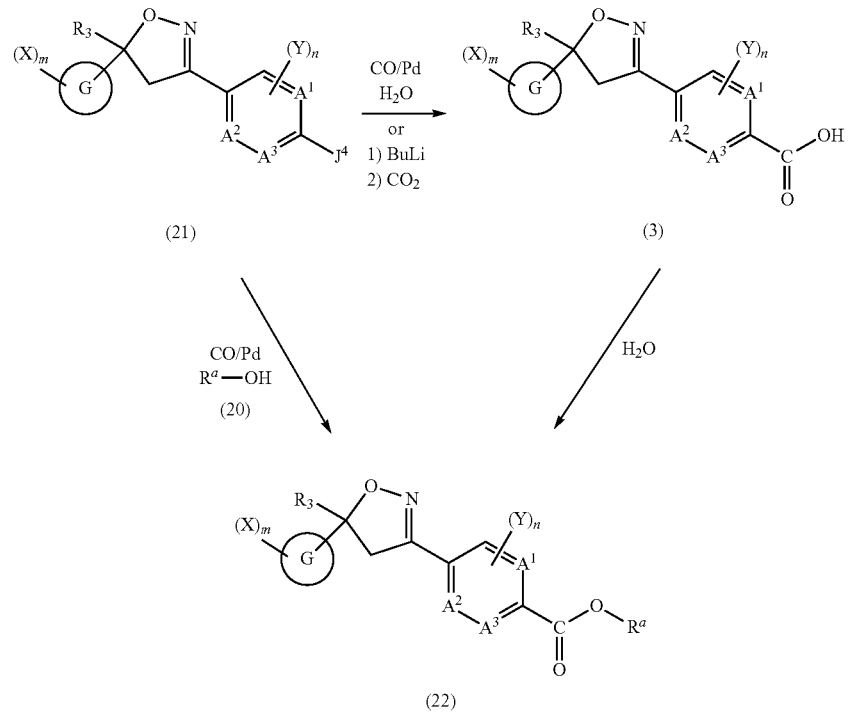

Reaction Scheme 1

That is, the compound of formula (3) (wherein $A^1$, $A^2$, $A^3$, G, X, Y, $R^3$, m and n are as defined above) can be obtained by reacting the compound of formula (21) wherein $A^1$, $A^2$, $A^3$, G, X, Y, $R^3$, m and n are as defined above, $J^4$ is bromine atom, iodine atom, halosulfonyloxy (for example fluorosulfonyloxy), $C_1$-$C_4$haloalkylsulfonyloxy (for example trifluoromethane sulfonyloxy) or arylsulfonyloxy (for example benzenesulfonyloxy) according to a known method disclosed in documents, for example by CO insertion reaction by use of a transition metal catalyst such as palladium or the like stated in J. Org. Chem., 1999, vol. 64, p. 6921 or the like, or by a process by lithiation and then reaction with carbonic acid gas stated in Chem. Rev., 1990, vol. 90, p. 879.

In addition, the compound of formula (3) can be obtained by subjecting the compound of formula (21) to a reaction according to a reaction condition for CO insertion reaction by use of a transition metal catalyst such as palladium or the like stated in J. Org. Chem., 1974, vol. 39, p. 3318 or the like to convert the compound of formula (22) (wherein $A^1$, $A^2$, $A^3$, G, X, Y, $R^3$, m and n are as defined above, $R^a$ is $C_1$-$C_6$alkyl), and then hydrolizing according to an ordinary ester hydrolysis disclosed in documents, for example a reaction condition stated in Angew. Chem., 1951, vol. 63, p. 329, J. Am. Chem. Soc., 1929, vol. 51, p. 1865 or the like.

Some of the compounds of formula (5) used in Production Method A are known compounds, and a part thereof is commercially available. Also, the compounds other than the above-mentioned compounds can be synthesized according to methods stated in for example Can. J. Chem., 1979, vol. 57, p. 1253, J. Chem. Soc., Chem. Commun., 1987, p. 114, J. Org. Chem., 1985, vol. 50, p. 3243 and 1995, vol. 60, p. 8124, Synlett, 2005, p. 2214, WO 2002/062805, JP 10-130221 or the like.

The compounds of formula (6) used in Production Method B can be synthesized as follows, for example.

Reaction Scheme 2

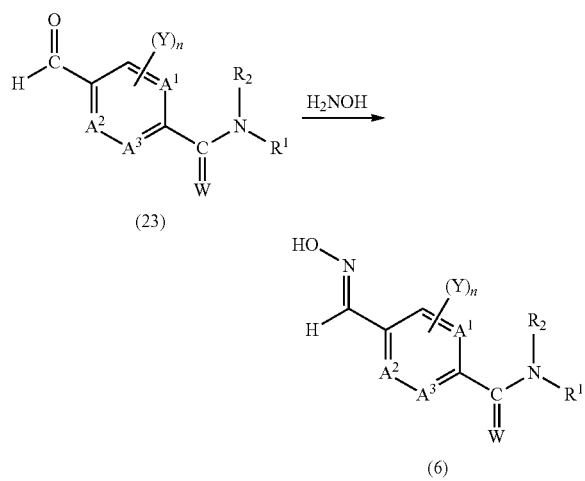

(6)

That is, the compound of formula (6) (wherein $A^1$, $A^2$, $A^3$, W, Y, $R^1$, $R^2$ and n are as defined above) can be easily synthesized by reacting the compound of formula (23) (wherein $A^1$, $A^2$, $A^3$, W, Y, $R^1$, $R^2$ and n are as defined above) with hydroxyamine or the salt thereof according to known methods disclosed in documents, for example the method stated in J. Med. Chem., 2001, vol. 44, p. 2308 or the like.

The compounds of formula (8) used in Production Method B can be

Reaction Scheme 3

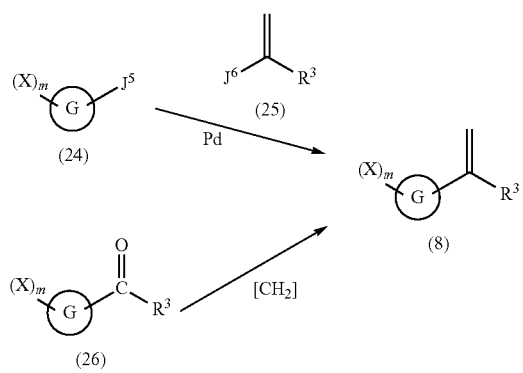

That is, the compound of formula (8) (wherein G, X, $R^3$ and m are as defined above) can be obtained by reacting the known compound of formula (24) (wherein G, X and m are as defined above, $J^5$ is bromine atom, iodine atom, $C_1$-$C_4$haloalkylsulfonyloxy (for example trifluoromethanesulfonyloxy), —B(OH)$_2$, 4,4,5,5-tetramethyl-1,3,2-dioxaborolan-2-yl, —Si(OEt)$_3$, —ZnCl, —ZnBr or —ZnI, etc.) with the compound of formula (25) (wherein $R^3$ is as defined above, $J^6$ is halogen atom such as bromine atom, iodine atom or the like, or —B(OH)$_2$) according to an ordinary crosscoupling reaction by use of a transition metal catalyst such as palladium or the like disclosed in documents, for example a reaction condtioin stated in J. Org. Chem., 1991, vol. 56, p. 7336, Tetrahedron Lett., 2001, vol. 42, p. 4083 or the like.

Some of the compounds of formula (25) used in the above-mentioned process are known compounds, and a part thereof is commercially available. Also, the compounds other than the above-mentioned compounds can be synthesized according to methods disclosed in documents, for example a method stated in J. Am. Chem. Soc., 1971, vol. 93, p. 1925, Tetrahedron Lett., 1990, vol. 31, p. 1919 and 2001, vol. 42, p. 4083 or the like.

In addition, the compounds of formula (8) can be obtained by reacting the compound of formula (26) (wherein G, X, $R^3$ and m are as defined above) according to a reaction of converting carbonyl to olefine disclosed in documents, for example a reaction condition stated in J. Org. Chem., 1986, vol. 51, p. 5252 and 1994, vol. 59, p. 2898, Synthesis, 1991, p. 29, Tetrahedron Lett., 1985, vol. 26, p. 5579 or the like.

The compounds of formula (11) used in Production method C and Production method E are known compounds, and a part thereof is commercially available. Also, the compounds other than the above-mentioned compounds can be easily synthesized according to general synthesis methods of alcohols and thiols that are disclosed in documents.

The compounds of formula (13) used in Production Method G are known compounds and a part thereof is commercially available. Also, the compounds other than the above-mentioned compounds can be easily synthesized according to any methods disclosed in documents, for example a method stated in J. Org. Chem., 1984, vol. 49, p. 3659 or the like The compounds of formula (14) used in Production Method G are known compounds and a part thereof is commercially available. Also, the compounds other than the above-mentioned compounds can be easily synthesized according to any methods disclosed in documents, for example a method stated in J. Org. Chem., 2005, vol. 70, p. 6991 or the like The compounds of formula (15) used in Production Method H can be synthesized as follows, for example.
Reaction Scheme 4
The compounds of formula (15) used in Production Method H can be synthesized as follows, for example.

Reaction Scheme 4

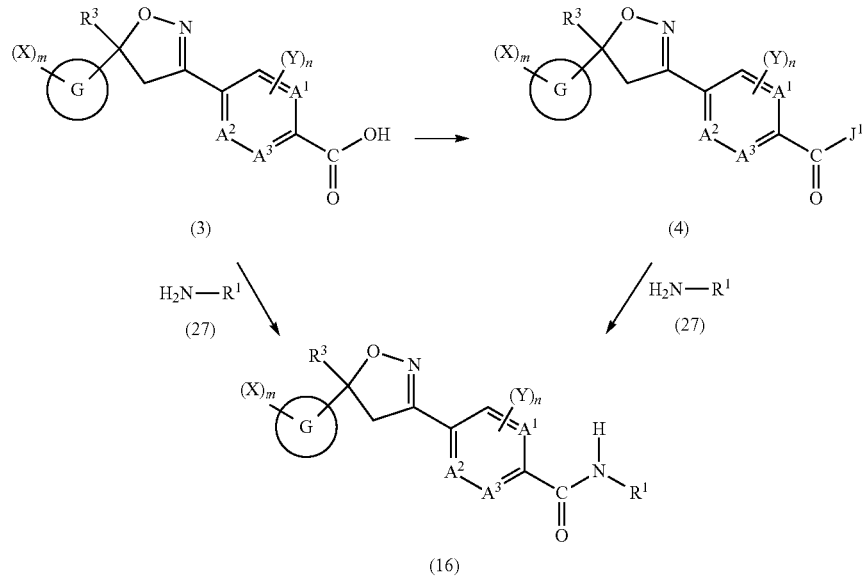

That is, the compound of formula (16) (wherein $A^1$, $A^2$, $A^3$, G, X, Y, $R^1$, $R^3$, m and n are as defined above) can be obtained by reacting the compound of formula (3) (wherein $A^1$, $A^2$, $A^3$, G, X, Y, $R^3$, m and n are as defined above) with the known compound of formula (27) (wherein $R^1$ is as defined above) under a condition similar to that of Production Method A.

Some of the compounds of formula (16) used in Production Method H and of the compounds of formula (17) used in Production Method I are known compounds, and a part thereof is commercially available. Also, the compounds other than the above-mentioned compounds can be synthesized according to methods disclosed in documents, for example a method stated in Chem. Pharm, Bull., 1986, vol. 34, p. 540 and 2001, vol. 49, p. 1102, J. Am. Chem. Soc., 1964, vol. 86, p. 4383, J. Org. Chem., 1983, vol. 48, p. 5280, Org. Synth., 1988, Collective Volume 6, p. 101, Synlett, 2005, p. 2847, Synthesis, 1990, p. 1159, JP 05-125017, EP 0,051,273, GB 2,161,802 or the like.

The compounds of formula (18) used in Production Method J can be synthesized as follows, for example.

Reaction Scheme 5

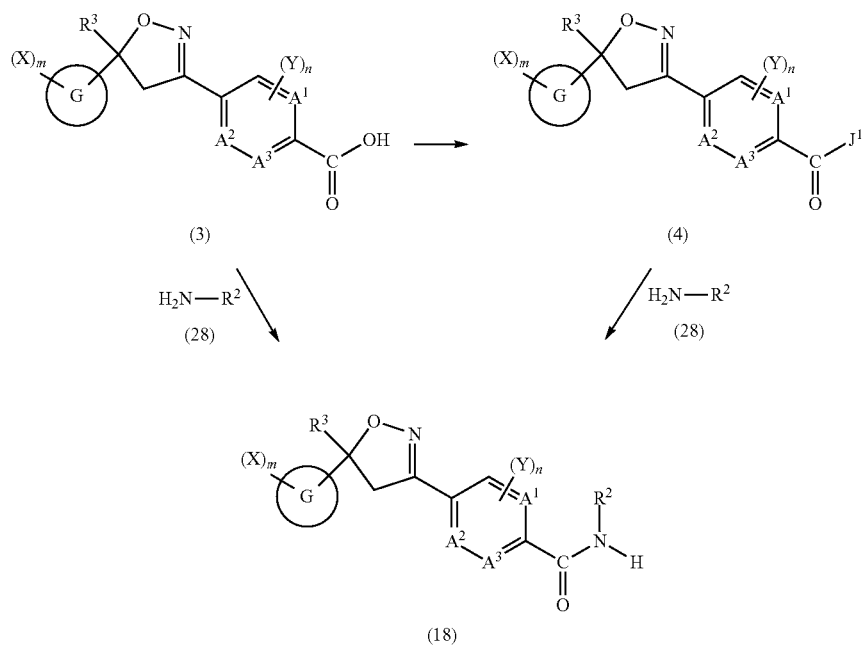

That is, the compound of formula (18) (wherein $A^1, A^2, A^3$, G, X, Y, $R^2$, $R^3$, m and n are as defined above) can be obtained by reacting the compound of formula (3) (wherein $A^1, A^2, A^3$, G, X, Y, $R^3$, m and n are as defined above) with the known compound of formula (28) (wherein $R^2$ is as defined above) under a condition similar to that of Production Method A.

The compounds of formula (19) used in Production Method J are known compounds, and a part thereof is commercially available. Also, the compounds other than the above-mentioned compounds can be synthesized according to for example a general synthesis method of acylisocyanates stated in Angew. Chem., 1977, vol. 89, p. 789, Chem. Ber, 1982, vol. 115, p. 1252, J. Med. Chem., 1991, vol. 34, p. 1630, EP 0,585,165 or the like, a general synthesis method of sulfonylisocyanates stated in J. Org. Chem., 1985, vol. 50, p. 169 or the like, a general synthesis method of acylisothiocyanates stated in Chem. Ber, 1982, vol. 115, p. 1252 and 1983, vol. 116, p. 1297, J. Org. Chem., 1990, vol. 55, p. 5230.

The compounds of formula (21) can be synthesized as follows, for example.

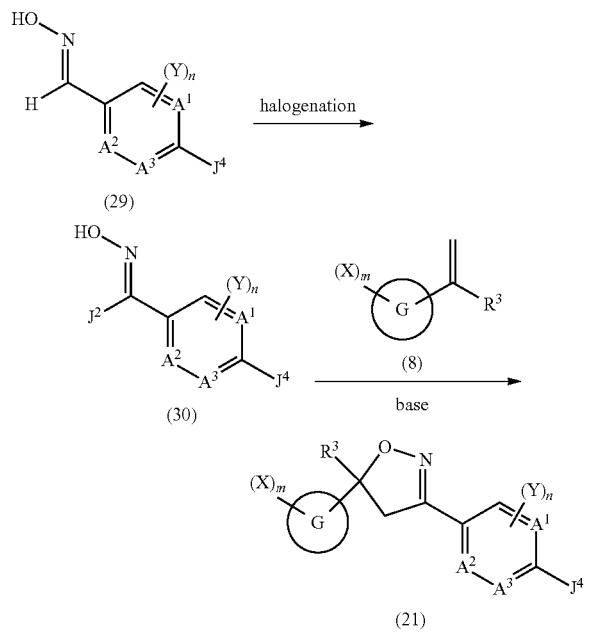

That is, the compounds of formula (21) (wherein $A^1$, $A^2$, $A^3$, G, X, Y, $R^3$, m, n and $J^4$ are as defined above) can be obtained by halogenating the compound of formula (29) (wherein $A^1, A^2, A^3$, Y, n and $J^4$ are as defined above) under a condition similar to that of Production Method B to obtain the compound of formula (30) (wherein $A^1, A^2, A^3$, Y, n, $J^3$ and $J^4$ are as defied above), and then reacting it with the compound of formula (8) (wherein G, X, $R^3$ and m are as defined above).

The compound of formula (29) used above can be easily synthesized by use of the corresponding known substituted aromatic aldehyde similarly to the process described in Reaction Scheme 2.

The compound of formula (23) can be synthesized for example according to Reaction Scheme 7 or Reaction Scheme 8.

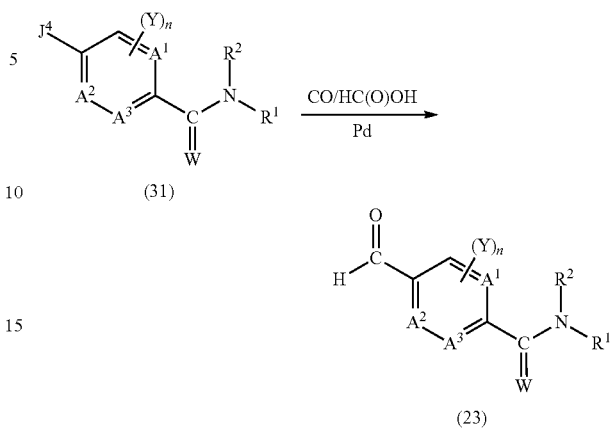

The compounds of formula (23) (wherein $A^1, A^2, A^3$, W, Y, $R^1$, $R^2$ and n are as defined above) can be obtained by subjecting the compound of formula (31) (wherein $A^1, A^2, A^3$, W, Y, $R^1$, $R^2$, n and $J^4$ are as defined above) to CO insertion reaction according to known methods disclosed in documents, for example the reaction by use of a transition metal catalyst such as palladium or the like in the presence of hydride source such as formic acid or the like stated in Bull. Chem. Soc. Jpn., 1994, vol. 67, p. 2329, J. Am. Chem. Soc., 1986, vol. 108, p. 452, or the like.

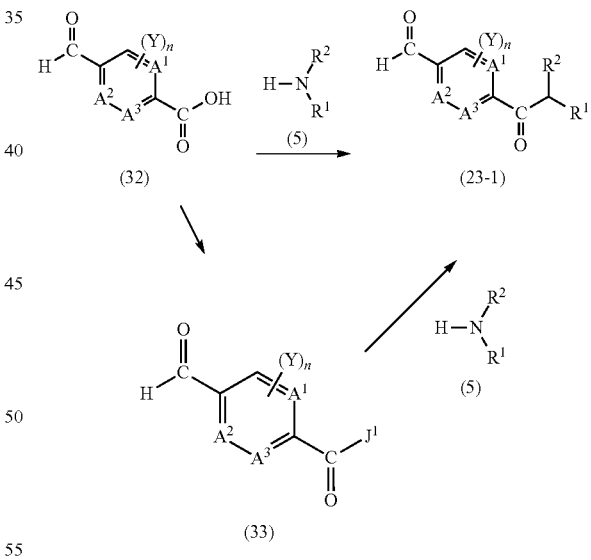

The compounds of formula (23-1) (wherein $A^1, A^2, A^3$, Y, $R^1$, $R^2$ and n are as defined above) that are the compounds of formula (23) wherein W is oxygen atom can be synthesized by reacting the compound of formula (32) (wherein $A^1$, $A^2$, $A^3$, Y and n are as defined above) with the compound of formula (5) (wherein $R^1$ and $R^2$ are as defined above) by use of the method similar to that of Production Method A.

The compound of formula (32) used above can be easily synthesized by use of the corresponding known benzoate under a reaction condition of a general hydrolysis of esters that are stated in documents.

The compounds of formula (26) can be synthesized as follows, for example.

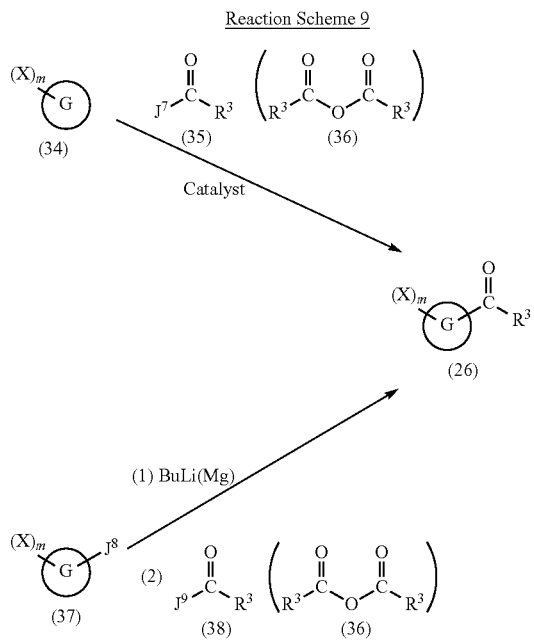

Reaction Scheme 9

That is, the compounds of formula (26) (wherein X, $R^3$ and m are as defined above, G is benzene ring) can be obtained by reacting the known compound of formula (34) (wherein X and m are as defined above, G is benzene ring) with the known compound of formula (35) (wherein $R^3$ is as defined above, $J^7$ is a leaving group such as halogen atom, trifluoromethanesulfonyloxy, 2-pyridyloxy or the like), or the known compound of formula (36) (wherein $R^3$ is as defined above) according to a genaral acylating reaction of aromatic ring disclosed in documents, for example a method stated in Chem. Lett., 1990, p. 783, J. Org. Chem., 1991, vol. 56, p. 1963 or the like.

In addition, the compound of formula (26) (wherein G, X, $R^3$ and m are as defined above) can be obtained according to general methods disclosed in documents for example by a method stated in J. Am. Chem. Soc., 1955, vol. 77, p. 3657, Tetrahedron Lett., 1980, vol. 21, p. 2129 and 1991, vol. 32, p. 2003, U.S. Pat. No. 5,514,816 in which the compound of formula (37) (wherein G, X and m are as defined above, $J^8$ is bromine atom or iodine atom) is lithiated and the resulting compound is reacted with the known compound of formula (38) (wherein $R^3$ is as defined above, $J^9$ is halogen atom, hydroxy, metal salt (for example, —OLi, —ONa), $C_1$-$C_4$alkoxy (for example, methoxy, ethoxy), di($C_1$-$C_4$alkyl) amino (for example, diethylamino), $C_1$-$C_4$alkoxy $C_1$-$C_4$alkyl amino (for example O,N-dimethylhydroxyamino) or cyclic amino (for example, piperidin-1-yl, morpholin-4-yl, 4-methylpiperadin-1-yl)), or the known compound of formula (36), or by a method stated in Heterocycles, 1987, vol. 25, p. 221, Synth. Commun., 1985, vol. 15, p. 1291 and 1990, vol. 20, p. 1469, DE 19727042, or the like in which a Grignard reagent is formed and then it is reacted with the compound of formula (38) or the compound of formula (36).

The compounds of formula (31) can be synthesized according to for example Reaction Scheme 10 to Reaction Scheme 18.

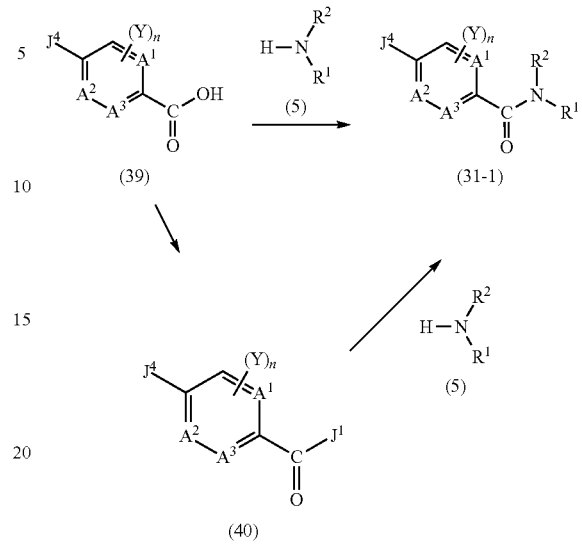

Reaction Scheme 10

The compounds of formula (31-1) (wherein $A^1$, $A^2$, $A^3$, Y, $R^1$, $R^2$, n and $J^4$ are as defined above) that are the compounds of formula (31) wherein W is oxygen atom can be obtained by reacting the known compound of formula (39) (wherein $A^1$, $A^2$, $A^3$, Y, n and $J^4$ are as defined above) with the compound of formula (5) (wherein $R^1$ and $R^2$ are as defined above) by use of the method similar to Production Method A.

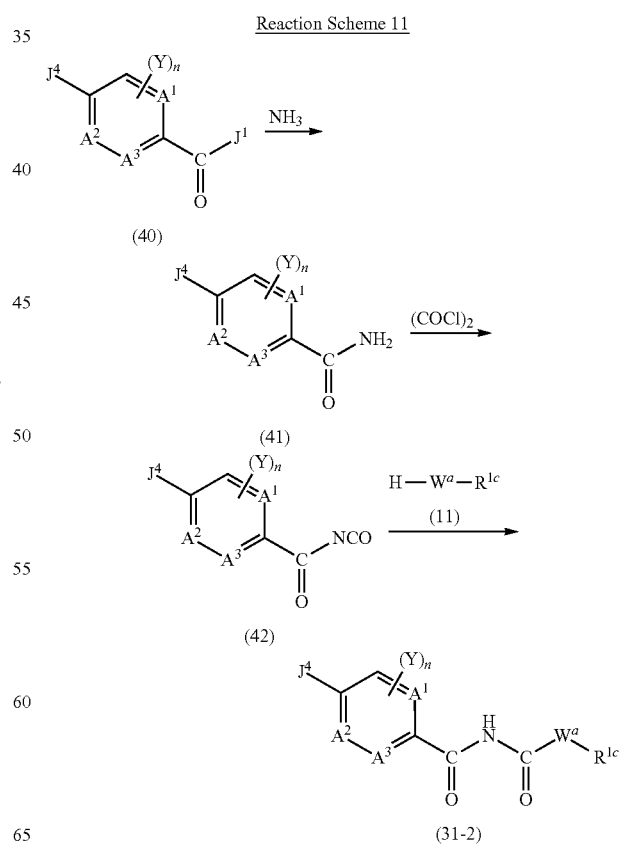

Reaction Scheme 11

The compounds of formula (31-2) (wherein $A^1$, $A^2$, $A^3$, Y, $R^{1c}$, n and $J^4$ are as defined above, $W^a$ is oxygen atom or sulfur atom) that are the compounds of formula (31) wherein W is oxygen atom, $R^1$ is —C(O)—$W^a$—$R^{1c}$ and $R^2$ is hydrogen atom can be obtained by reacting the compound of formula (40) (wherein $A^1$, $A^2$, $A^3$, Y, n, $J^1$ and $J^4$ are as defined above) as a starting material according to a method similar to that of Production Method C.

Reaction Scheme 12

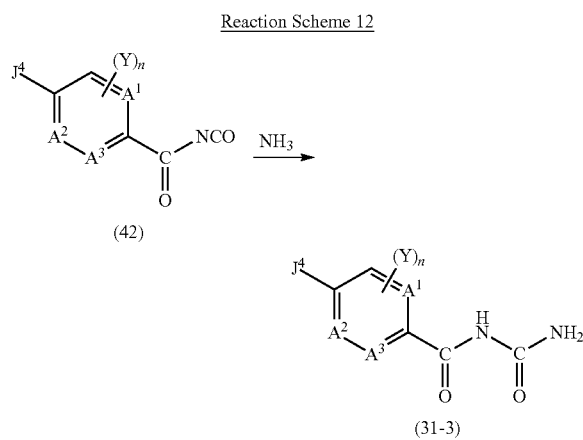

The compounds of formula (31-3) (wherein $A^1$, $A^2$, $A^3$, Y, n and $J^4$ are as defined above) that are the compounds of formula (31) wherein W is oxygen atom, $R^1$ is —C(O)$NH_2$ and $R^2$ is hydrogen atom can be obtained by reacting the substituted acylisocyanate of formula (42) (wherein $A^1$, $A^2$, $A^3$, Y, n and $J^4$ are as defined above) with ammonia according to a method similar to that of Production Method D.

Reaction Scheme 13

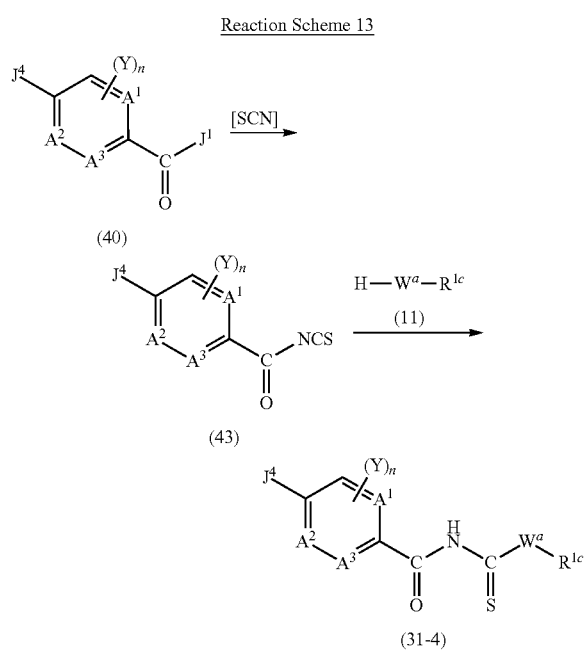

The compounds of formula (31-4) (wherein $A^1$, $A^2$, $A^3$, Y, $R^{1c}$, n and $J^4$ are as defined above, $W^a$ is oxygen atom or sulfur atom) that are the compounds of formula (31) wherein W is oxygen atom, $R^1$ is —C(S)—$W^a$—$R^{1c}$ and $R^2$ is hydrogen atom can be obtained by reacting the compound of formula (40) (wherein $A^1$, $A^2$, $A^3$, Y, n, $J^1$ and $J^4$ are as defined above) as a starting material according to a method similar to that of Production Method E.

Reaction Scheme 14

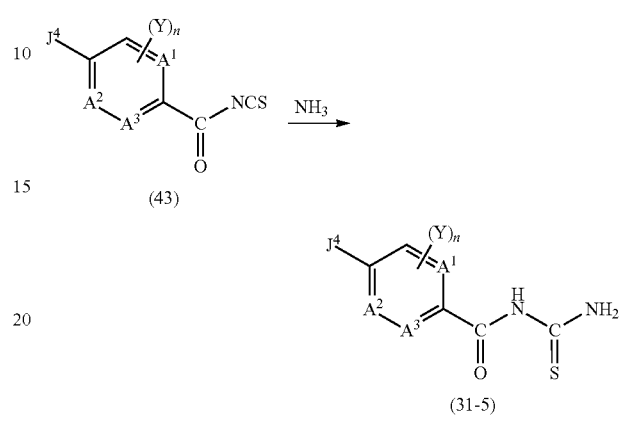

The compounds of formula (31-5) (wherein $A^1$, $A^2$, $A^3$, Y, n and $J^4$ are as defined above) that are the compounds of formula (31) wherein W is oxygen atom, $R^1$ is —C(S)$NH_2$ and $R^2$ is hydrogen atom can be obtained by reacting the substituted acylisothiocyanate of formula (43) (wherein $A^1$, $A^2$, $A^3$, Y, n and $J^4$ are as defined above) with ammonia according to a method similar to that of Production Method D.

Reaction Scheme 15

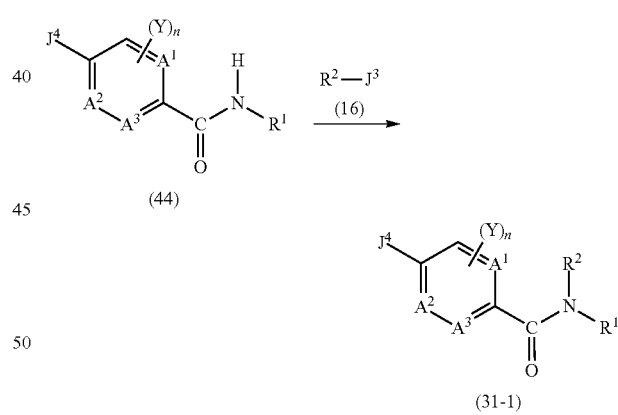

The compounds of formula (31-1) (wherein $A^1$, $A^2$, $A^3$, Y, $R^1$, n and $J^4$ are as defined above, and $R^2$ has the meaning other than hydrogen atom) that are the compounds of formula (31) wherein W is oxygen atom can be obtained by reacting the compound of formula (44) (wherein $A^1$, $A^2$, $A^3$, Y, $R^1$, n and $J^4$ are as defined above) with the compound of formula (16) (wherein $R^2$ and $J^3$ are as defined above) under a condition similar to that of Production Method H.

The compounds of formula (44) used above can be produced from the above-mentioned known compound of formula (39) according to a method similar to that of Production Methods A, C and E.

Reaction Scheme 16

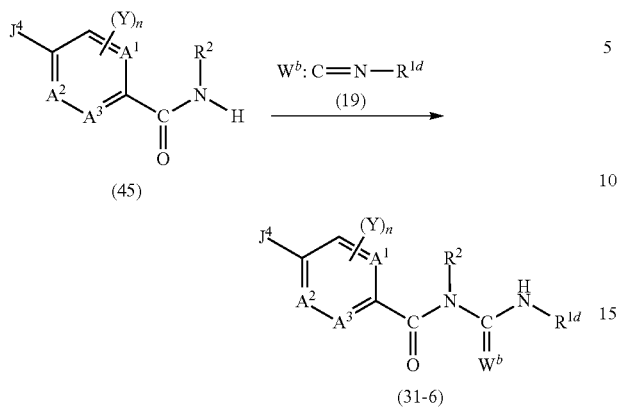

(45) → (31-6)

Reaction Scheme 18

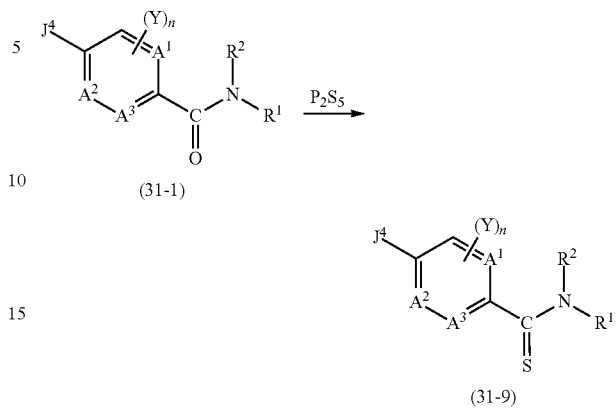

(31-1) → (31-9)

The compounds of formula (31-6) (wherein $A^1$, $A^2$, $A^3$, Y, $R^{1d}$, $R^2$, n and $J^4$ are as defined above, and $W^b$ is oxygen atom or sulfur atom) that are the compounds of formula (31) wherein W is oxygen atom and $R^1$ is —C($W^b$)NHR$^{1d}$ can be obtained by reacting the compound of formula (45) (wherein $A^1$, $A^2$, $A^3$, Y, $R^2$, n and $J^4$ are as defined above) with the compound of formula (19) (wherein $W^b$ and $R^{1d}$ are as defined above) under a condition similar to that of Production Method J.

The compounds of formula (45) used above can be produced from the above-mentioned known compound of formula (39) according to a method similar to that of Production Method A.

Reaction Scheme 17

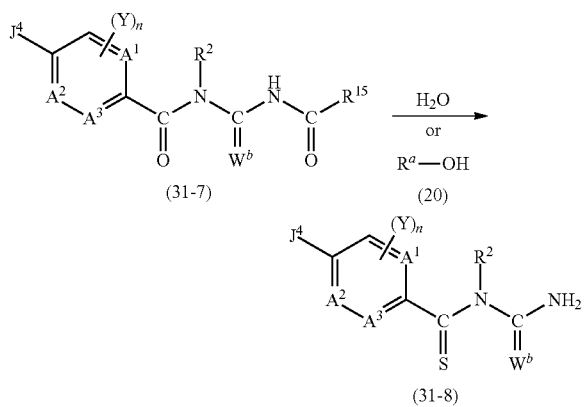

(31-7) + (20) → (31-8)

The compound of formula (31-8) (wherein $A^1$, $A^2$, $A^3$, Y, $R^2$, n and $J^4$ are as defined above, $W^b$ is oxygen atom or sulfur atom) that in the formula (31) W is oxygen atom and $R^1$ is —C($W^b$)NH$_2$ can be obtained by reacting the compound of formula (31-7) (wherein $A^1$, $A^2$, $A^3$, Y, $R^2$, n and $J^4$ are as defined above, $W^b$ is oxygen atom or sulfur atom, $R^{15}$ is $C_1$-$C_4$ haloalkyl (for example trichloromethyl or the like)) that is the compound of formula (31-6) wherein $R^{1d}$ is —C(O)R$^{15}$ and can be synthesized by use of Reaction Scheme 16 with water or the alcohol of formula (20) (wherein $R^a$ is as defined above), under a condition similar to that of Production Method K.

The compounds of formula (31-9) (wherein $A^1$, $A^2$, $A^3$, Y, $R^1$, $R^2$, n and $J^4$ are as defined above) that are the compounds of formula (31) wherein W is sulfur atom can be obtained by reacting the compound of formula (31-1) (wherein $A^1$, $A^2$, $A^3$, Y, $R^1$, $R^2$, n and $J^4$ are as defined above) that are the compounds of formula (31) wherein W is oxygen atom with a sulfurizing agent under a condition similar to that of Production Method L.

In each reaction, after the completion of the reaction, each production intermediate that is a starting compound in Production Method A to Production Method L can be obtained by carrying out normal post-treatments.

In addition, each production intermediate produced by the above-mentioned methods can be used for the following reaction step as such without isolation or purification.

The active compounds included in the present invention concretely include for example the compounds shown in Tables 2 and 3. The compounds that can be used as novel production intermediates for producing the active compounds included in the present invention concretely include for example the compounds shown in Table 4. In the interim, the compounds shown in Tables 2 to 4 are for purposes of illustration and the present invention is not limited thereto.

In the meantime, in Tables, the indication "Et" means ethyl, hereinafter similarly thereto, "n-Pr" and "Pr-n" mean normal propyl, "i-Pr" and "Pr-i" mean isopropyl, "c-Pr" and "Pr-c" mean cyclopropyl, "n-Bu" and "Bu-n" mean normal butyl, "i-Bu" and "Bu-i" mean isobutyl, "s-Bu" and "Bu-s" mean secondary butyl, "c-Bu" and "Bu-c" mean cyclobutyl, "t-Bu" and "Bu-t" mean tertiary butyl, "n-Pen" and "Pen-n" mean normal pentyl, "c-Pen" and "Pen-c" mean cyclopentyl, "n-Hex" and "Hex-n" mean normal hexyl, "c-Hex" and "Hex-c" mean cyclohexyl, "Hept" means heptyl, "Oct" means octyl, "Ph" means phenyl, "1-Naph" means 1-naphthyl, "2-Naph" means 2-naphthyl, TMS means trimethylsilyl, and in Tables, aromatic heterocyclic rings of D-1a to D-65b are the following structures, respectively

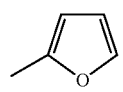

D-1a

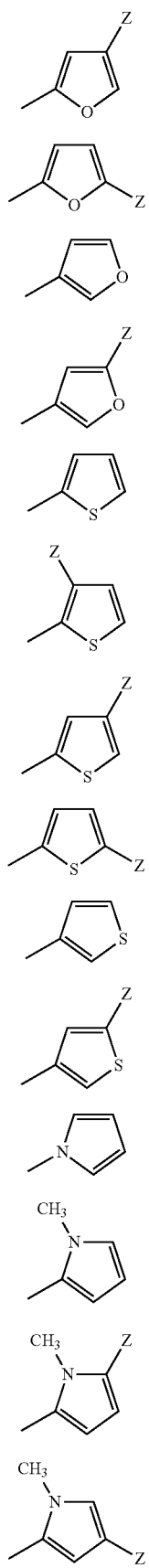
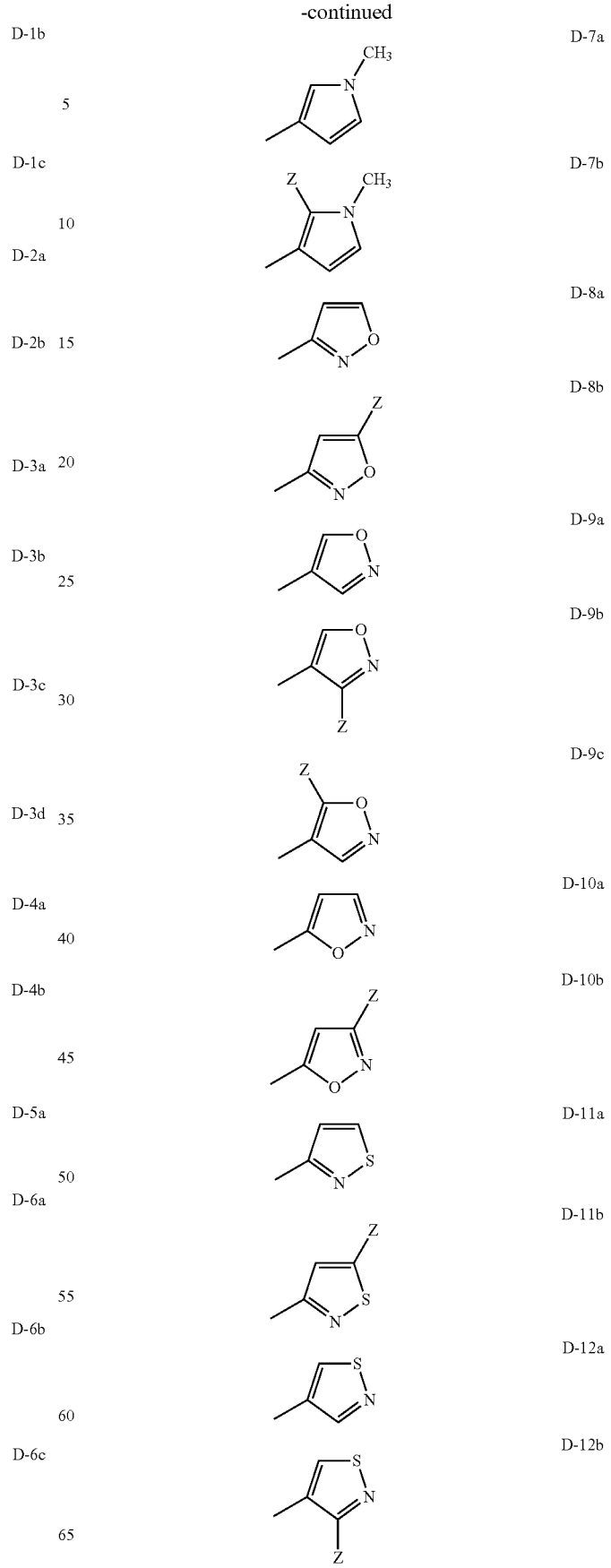

| | | |
|---|---|---|
| 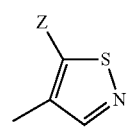 | D-12c | 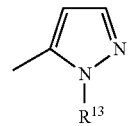 D-17a |
| 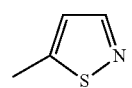 | D-13a | 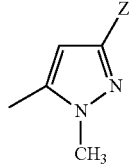 D-17b |
| 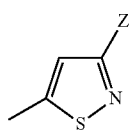 | D-13b | 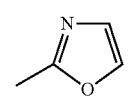 D-18a |
| 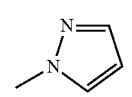 | D-14a | 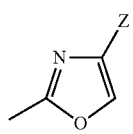 D-18b |
| 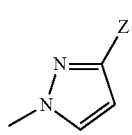 | D-14b | 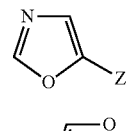 D-18c |
| 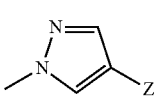 | D-14c | 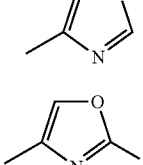 D-19a |
| 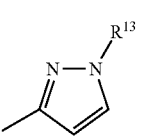 | D-15a | 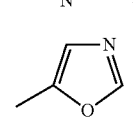 D-19b |
| 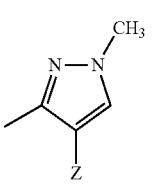 | D-15b | 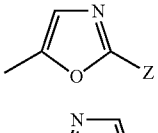 D-20a |
| 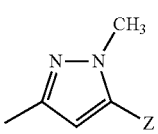 | D-15c | 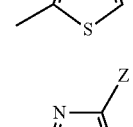 D-20b |
| 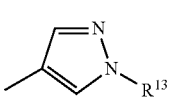 | D-16a | 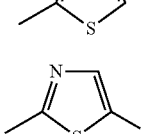 D-21a |
| 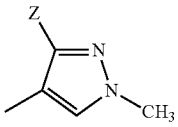 | D-16b | 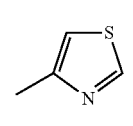 D-21b |
| 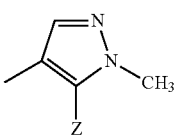 | D-16c | 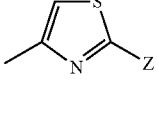 D-21c |
| | | D-22a |
| | | D-22b |

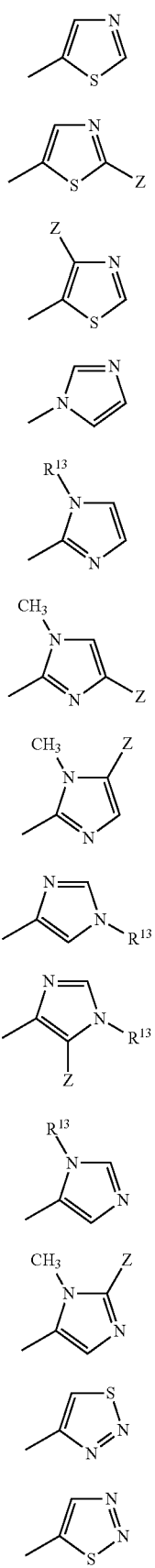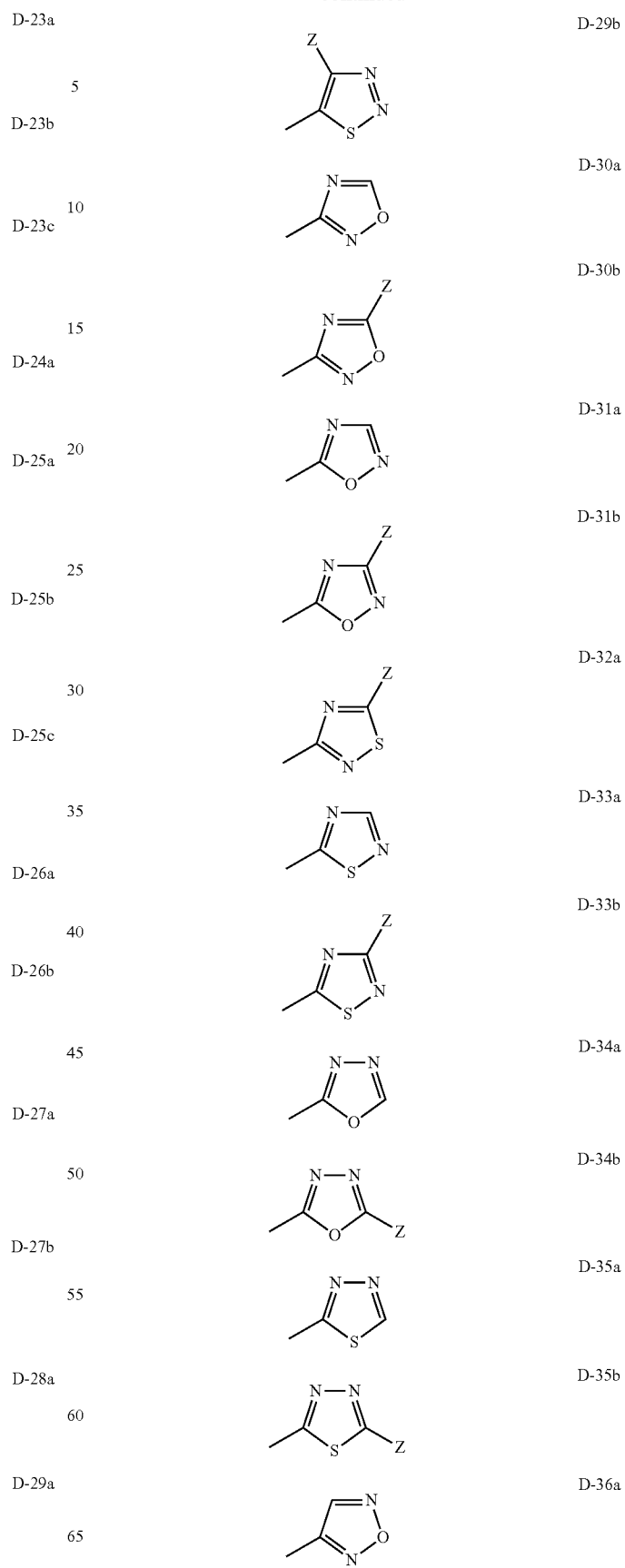

| 99 -continued | | 100 -continued | |
|---|---|---|---|
| 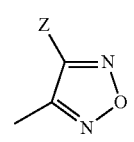 | D-36b | 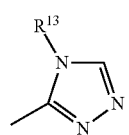 | D-45a |
| 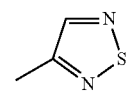 | D-37a | 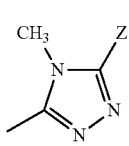 | D-45b |
|  | D-37b | 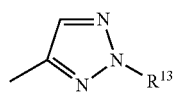 | D-47a |
| 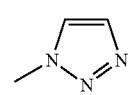 | D-38a | 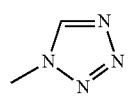 | D-48a |
| 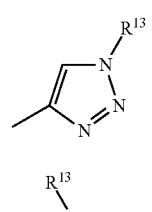 | D-39a | 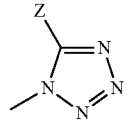 | D-48b |
| 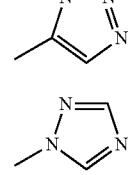 | D-40a | 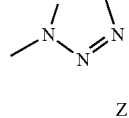 | D-49a |
| 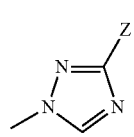 | D-41a | 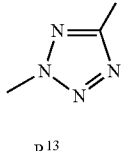 | D-49b |
| 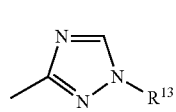 | D-41b | 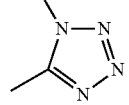 | D-50a |
| 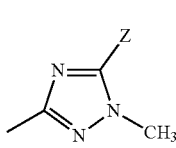 | D-42a | 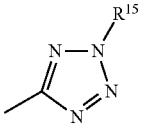 | D-51a |
| 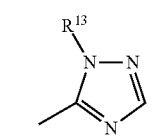 | D-42b | 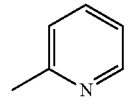 | D-52a |
| 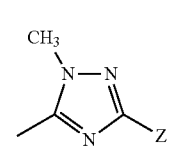 | D-43a | 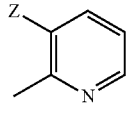 | D-52b |
| 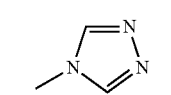 | D-43b | 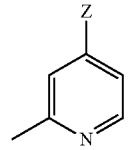 | D-52c |
| | D-44a | | |

-continued
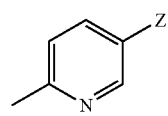
D-52d
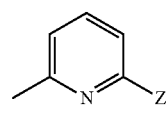
D-52e
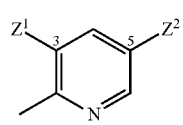
D-52f
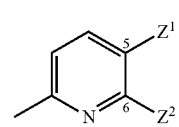
D-52g
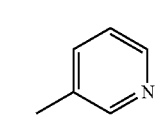
D-53a
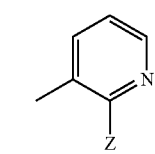
D-53b
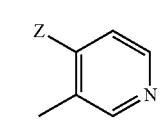
D-53c
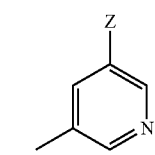
D-53d
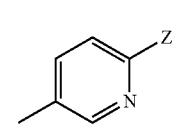
D-53e
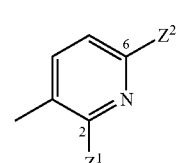
D-53f
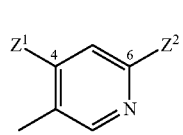
D-53g
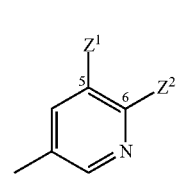
D-53h
-continued
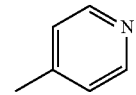
D-54a
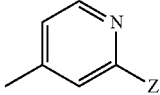
D-54b
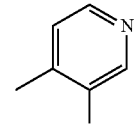
D-54c
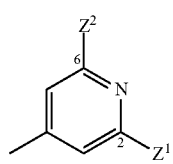
D-54d
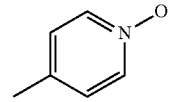
D-54e
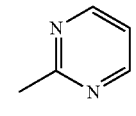
D-55a
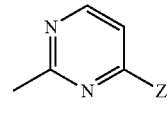
D-55b
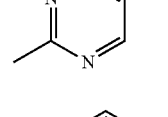
D-55c
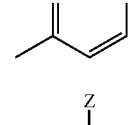
D-56a
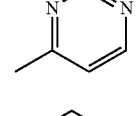
D-56b
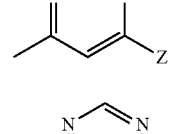
D-56c
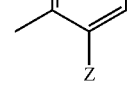
D-56d

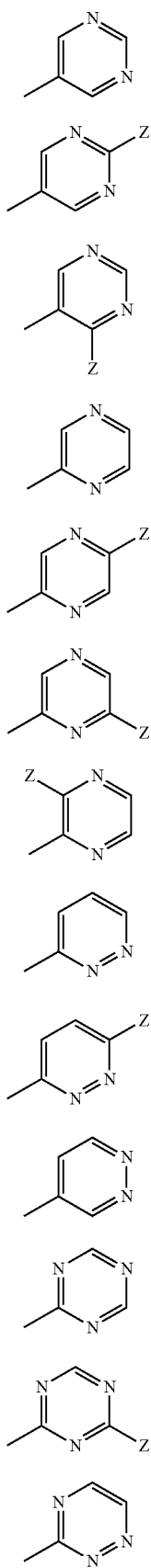
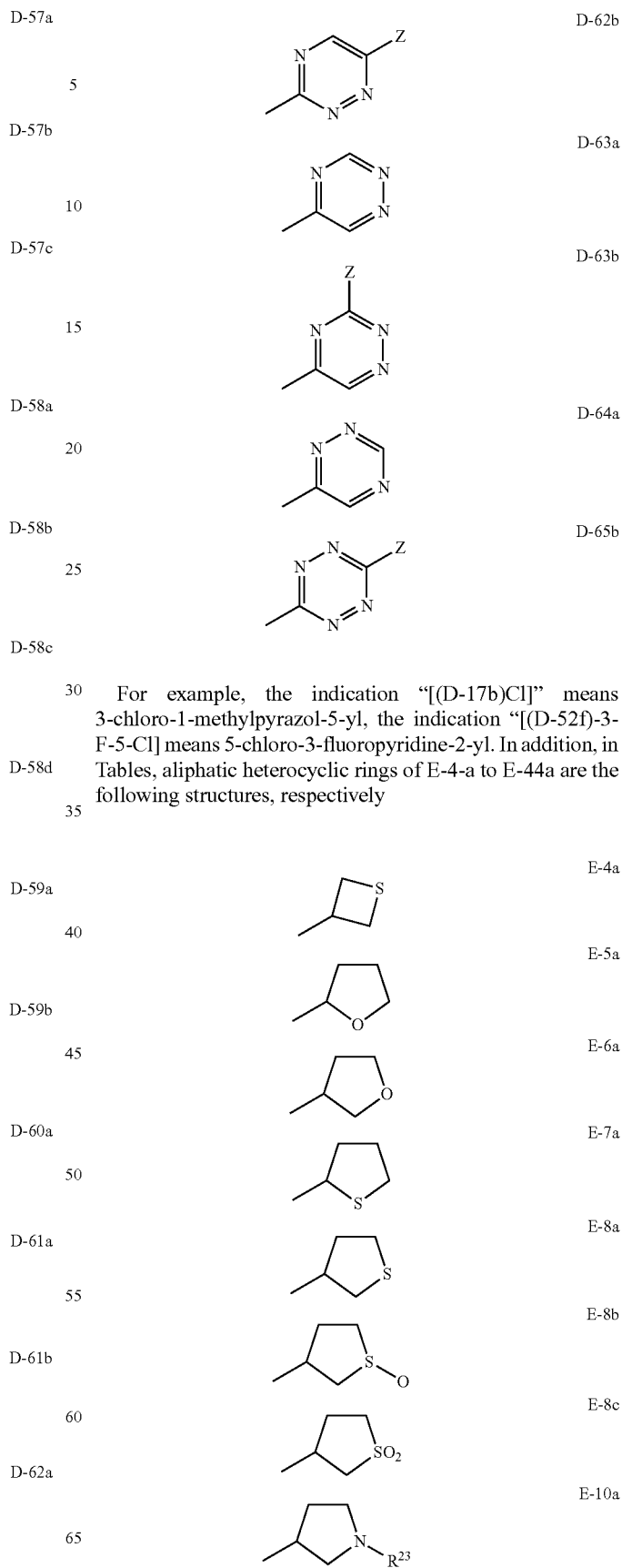
For example, the indication "[(D-17b)Cl]" means 3-chloro-1-methylpyrazol-5-yl, the indication "[(D-52f)-3-F-5-Cl] means 5-chloro-3-fluoropyridine-2-yl. In addition, in Tables, aliphatic heterocyclic rings of E-4-a to E-44a are the following structures, respectively -continued E-11a 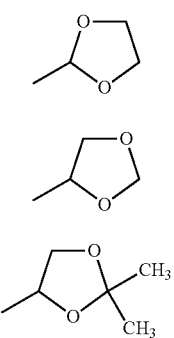

E-12a

E-12c

E-19a 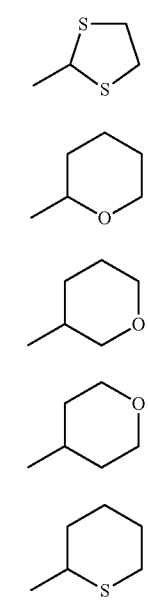

E-24a

E-25a

E-26a

E-27a

E-28a

E-29a

E-31a 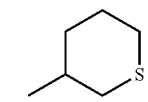

E-32a 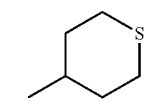

E-33a 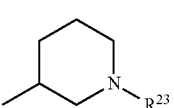

E-35a 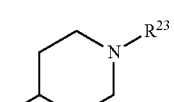

-continued

E-44a 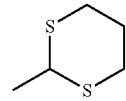

For example, the indication "[C(O)OCH$_2$(E-9a)C(O)CH$_3$]" means N-acetylpyrrolidine-3-ylmethoxycarbonyl, the indication "[C(O)O(E-9a)C(O)OCH$_3$]" means N-methoxycarbonylpyrrolidine-3-yloxycarbonyl.

Further, in Tables, partially saturated heterocyclic rings of M-1a to M-32a are the following structures, respectively M-1a 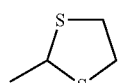

M-5a 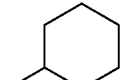

M-5b 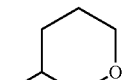

M-5c 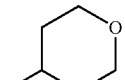

M-11a 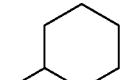

M-11b 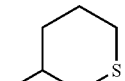

M-11c 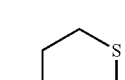

M-14a 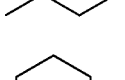

M-14b 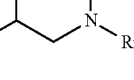

M-14c 

M-20a 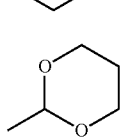

-continued
M-28a 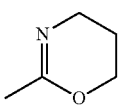
M-32a 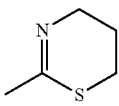
For example, the indication "[(M-5c)CH₃]" means 5-methyl-4,5-dihydroisoxazole-3-yl, the indication "[(M-5c)Ph-4-F]" means 5-(4-fluorophenyl)-4,5-dihydroisoxazole-3-yl. Further, in Tables, T-1 to T-21 are the following structures, respectively
T-1: 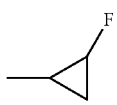
T-2: 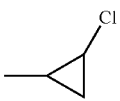
T-3: 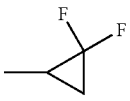
T-4: 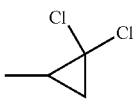
T-5: 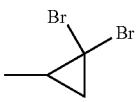
T-6: 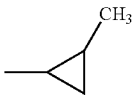
T-7: 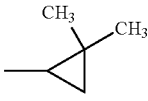
T-8: 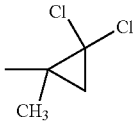
-continued
T-9: 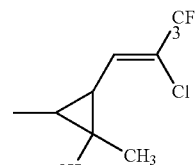
T-10: 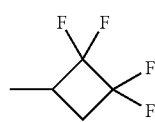
T-11: 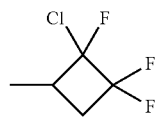
T-12: 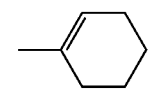
T-13: 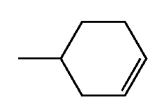
T-14: 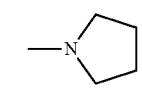
T-15: 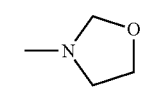
T-16: 
T-17: 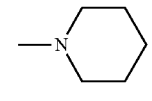
T-18: 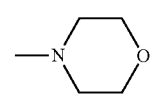
T-19: 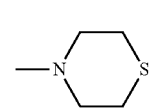

T-20:
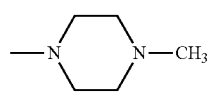
T-21:
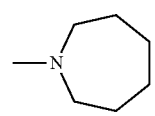
TABLE 2
In the table, the number showing the substitution position of substituent $(X)_m$ corresponds to the position number indicated in the following structural formulae. The indication "—" means no-substitution.
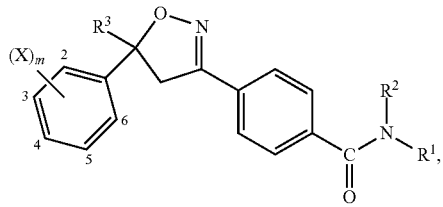
[1]-1
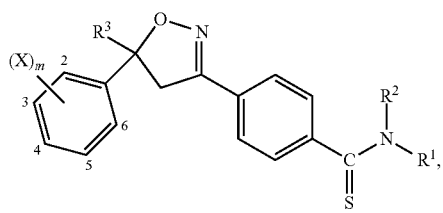
[1]-2
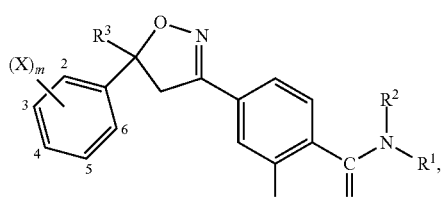
[1]-3
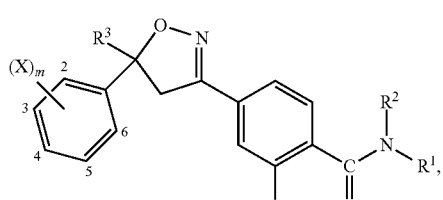
[1]-4
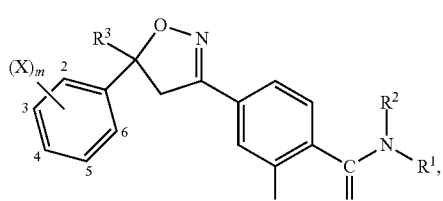
[1]-5
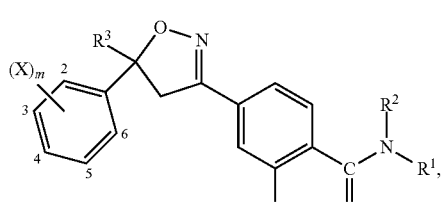
[1]-6

TABLE 2-continued
In the table, the number showing the substitution position of substituent $(X)_m$ corresponds to the position number indicated in the following structural formulae. The indication "—" means no-substitution.
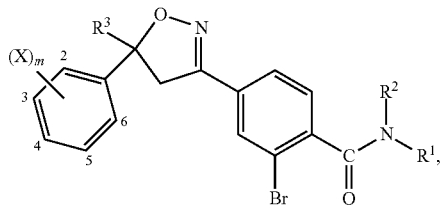 [1]-7
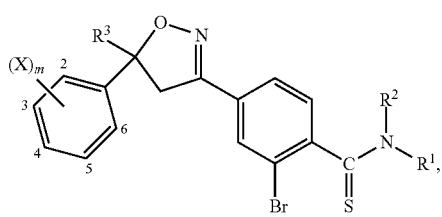 [1]-8
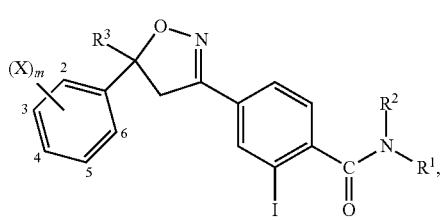 [1]-9
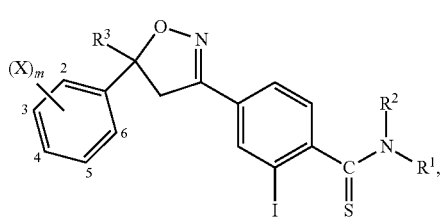 [1]-10
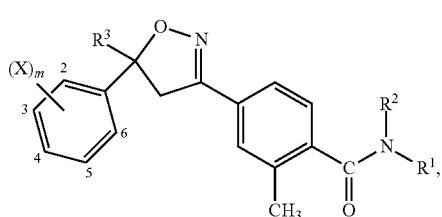 [1]-11
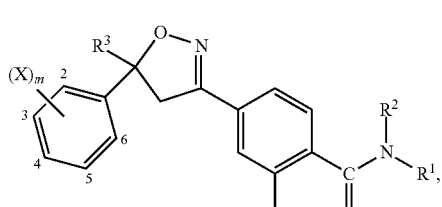 [1]-12
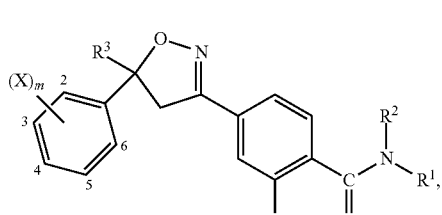 [1]-13

TABLE 2-continued
In the table, the number showing the substitution position of substituent $(X)_m$ corresponds to the position number indicated in the following structural formulae. The indication "—" means no-substitution.
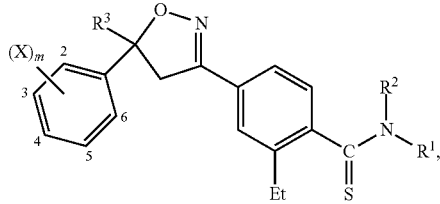 [1]-14
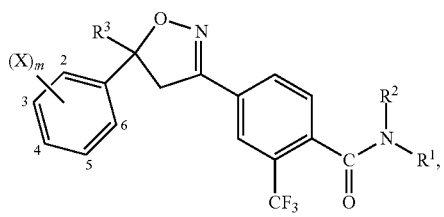 [1]-15
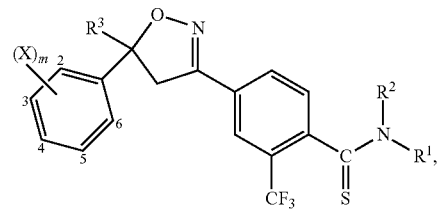 [1]-16
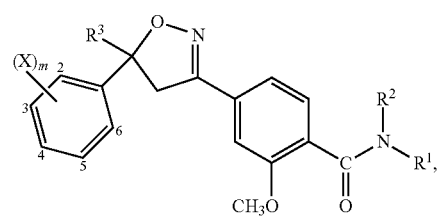 [1]-17
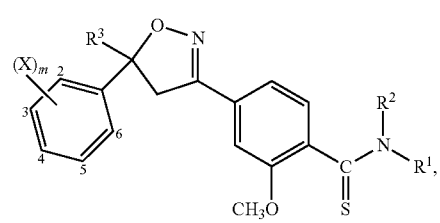 [1]-18
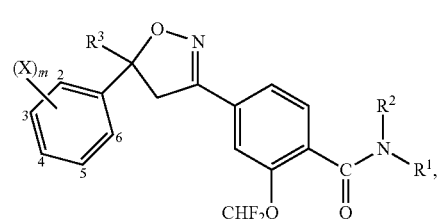 [1]-19
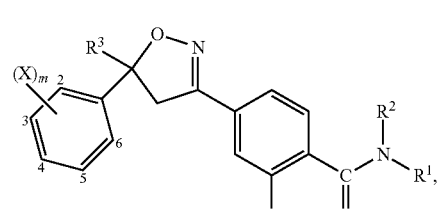 [1]-20

TABLE 2-continued
In the table, the number showing the substitution position of substituent (X)$_m$ corresponds to the position number indicated in the following structural formulae. The indication "—" means no-substitution.
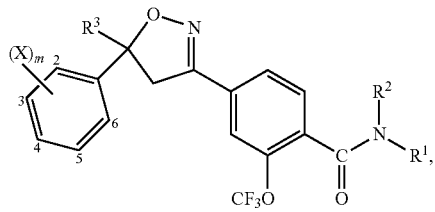 [1]-21
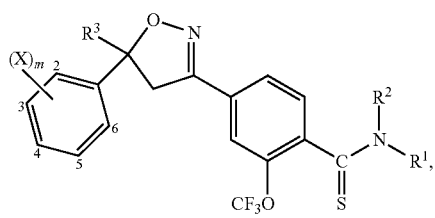 [1]-22
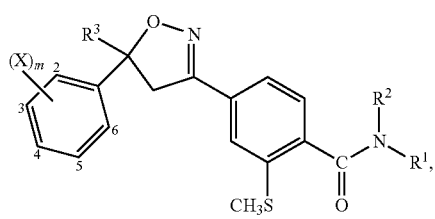 [1]-23
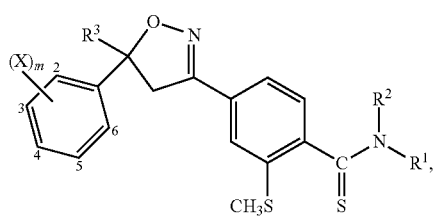 [1]-24
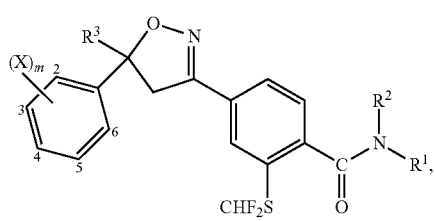 [1]-25
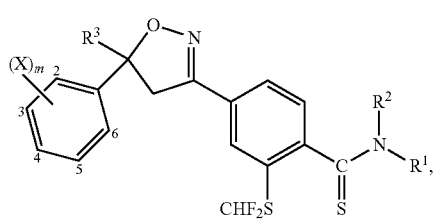 [1]-26
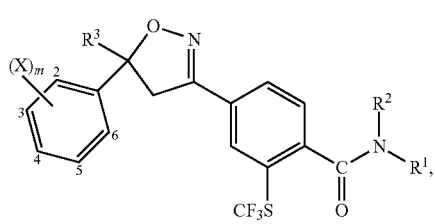 [1]-27

TABLE 2-continued
In the table, the number showing the substitution position of substituent $(X)_m$ corresponds to the position number indicated in the following structural formulae. The indication "—" means no-substitution.
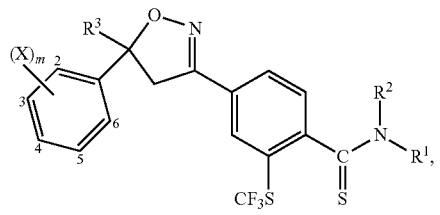  [1]-28
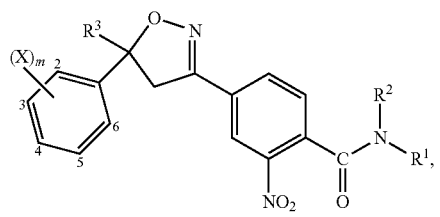  [1]-29
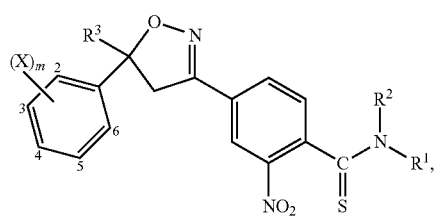  [1]-30
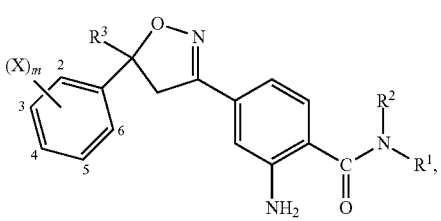  [1]-31
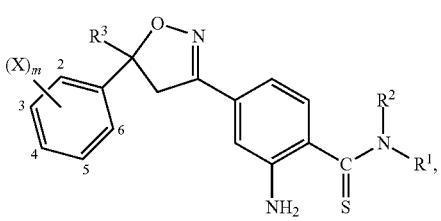  [1]-32
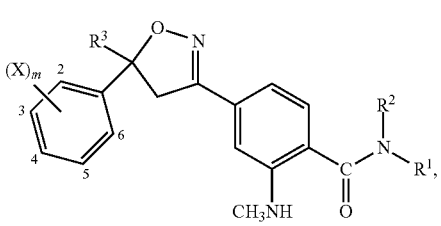  [1]-33
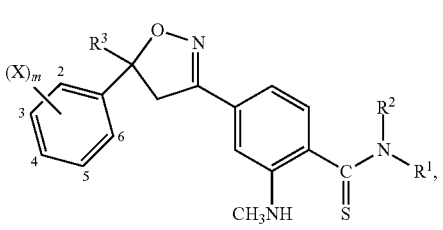  [1]-34

TABLE 2-continued
In the table, the number showing the substitution position of substituent $(X)_m$ corresponds to the position number indicated in the following structural formulae. The indication "—" means no-substitution.
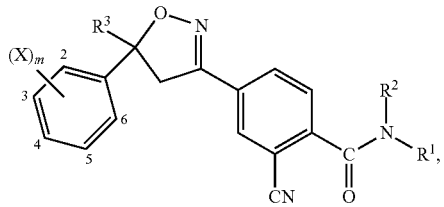 [1]-35
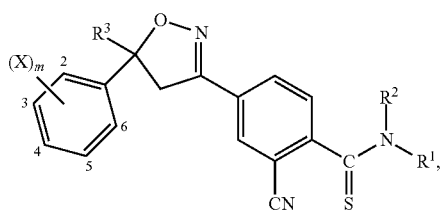 [1]-36
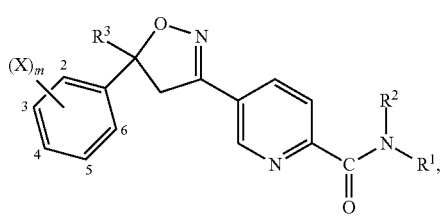 [1]-37
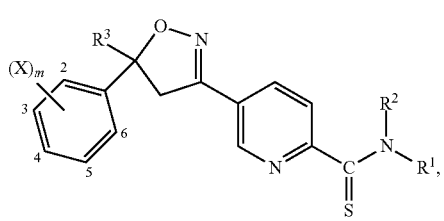 [1]-38
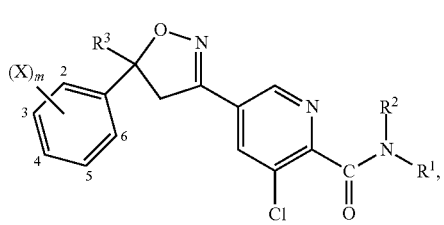 [1]-39
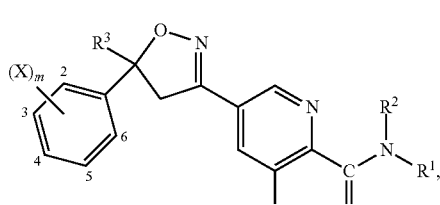 [1]-40
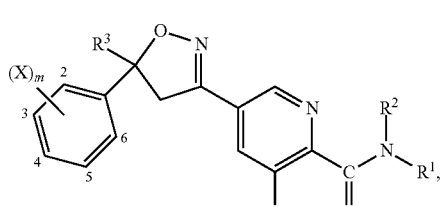 [1]-41

TABLE 2-continued
In the table, the number showing the substitution position of substituent (X)$_m$ corresponds to the position number indicated in the following structural formulae. The indication "—" means no-substitution.
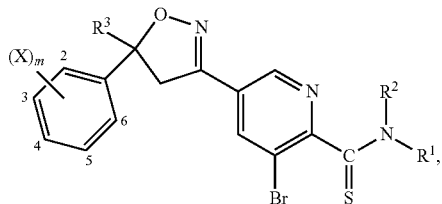 [1]-42
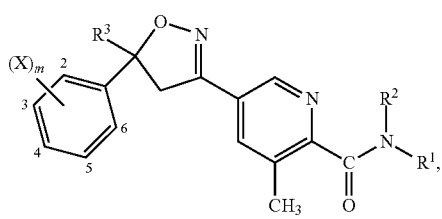 [1]-43
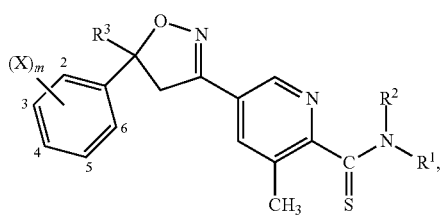 [1]-44
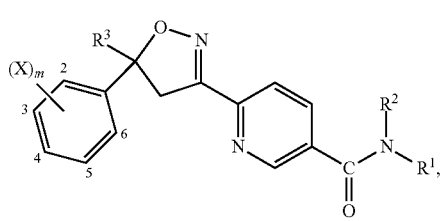 [1]-45
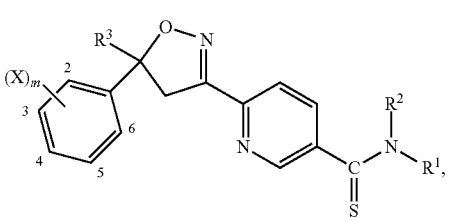 [1]-46
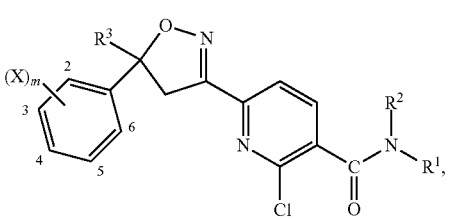 [1]-47
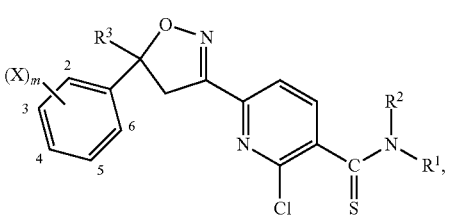 [1]-48

TABLE 2-continued
In the table, the number showing the substitution position of substituent (X)$_m$ corresponds to the position number indicated in the following structural formulae. The indication "—" means no-substitution.
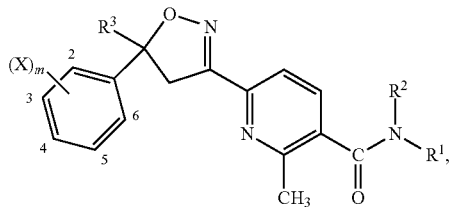
[1]-49
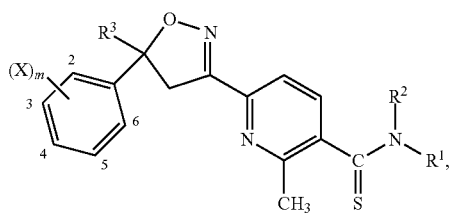
[1]-50
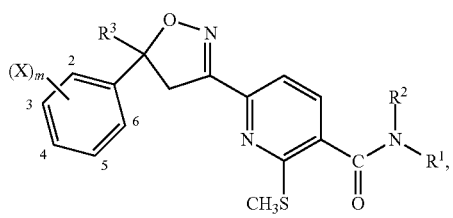
[1]-51
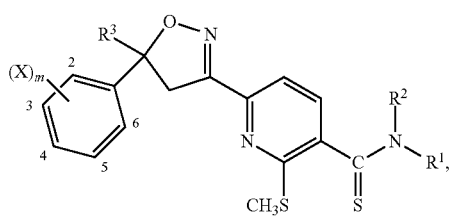
[1]-52
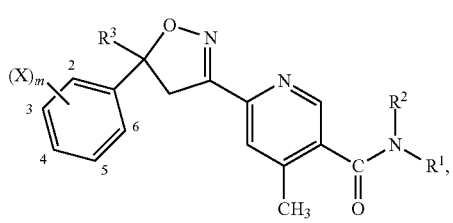
[1]-53
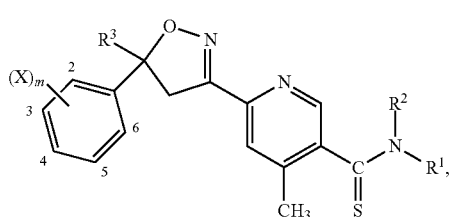
[1]-54
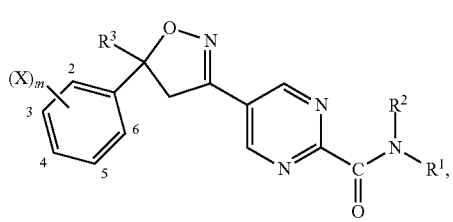
[1]-55

TABLE 2-continued

In the table, the number showing the substitution position of substituent (X)$_m$ corresponds to the position number indicated in the following structural formulae. The indication "—" means no-substitution.

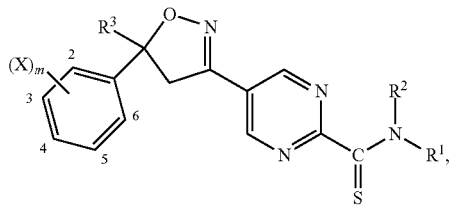  [1]-56

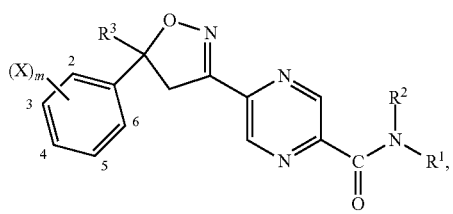  [1]-57

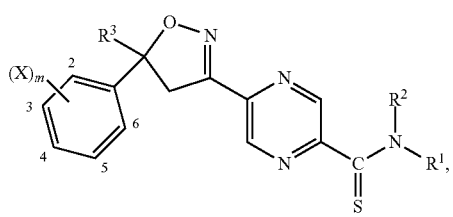  [1]-58

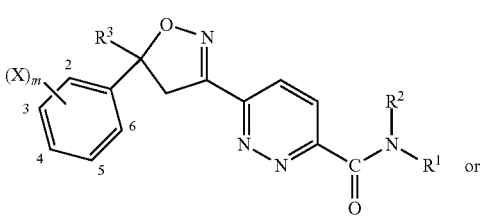  [1]-59 or

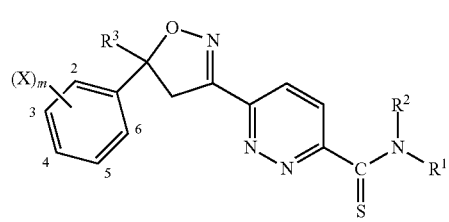  [1]-60

| (X)$_m$ | R$^3$ | R$^2$ | R$^1$ |
|---|---|---|---|
| 3-F | CF$_3$ | H | CH=NOCH$_3$ |
| 3-F | CF$_3$ | H | CH=NOEt |
| 3-F | CF$_3$ | CH$_2$OEt | C(O)OCH$_3$ |
| 3-F | CF$_3$ | CH$_2$OCH$_2$CF$_3$ | C(O)OCH$_3$ |
| 3-F | CF$_3$ | C(O)Et | C(O)OCH$_3$ |
| 3-F | CF$_3$ | C(O)CH$_3$ | (D-55c)Cl |
| 3-F | CF$_3$ | C(O)Pr-i | (D-55c)Cl |
| 3-F | CF$_3$ | C(O)OCH$_3$ | (D-55c)Cl |
| 3-F | CF$_3$ | C(O)OCH$_3$ | (D-55c)Br |
| 3-F | CF$_3$ | H | CH=NOCH$_3$ |
| 3-Cl | CF$_3$ | H | CH=NOCH$_3$ |
| 3-Cl | CF$_3$ | H | CH=NOEt |
| 3-Cl | CF$_3$ | H | C(O)OCH$_3$ |
| 3-Cl | CF$_3$ | Et | C(O)OCH$_3$ |
| 3-Cl | CF$_3$ | CH$_2$OCH$_3$ | C(O)OCH$_3$ |
| 3-Cl | CF$_3$ | CH$_2$OEt | C(O)OCH$_3$ |
| 3-Cl | CF$_3$ | CH$_2$OCH$_2$CF$_3$ | C(O)OCH$_3$ |
| 3-Cl | CF$_3$ | C(O)Et | C(O)OCH$_3$ |
| 3-Cl | CF$_3$ | C(O)OCH$_3$ | C(O)OEt |
| 3-Cl | CF$_3$ | H | C(O)NH$_2$ |
| 3-Cl | CF$_3$ | CH$_3$ | (D-55c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl | $CF_3$ | $CH_2OCH_3$ | (D-55c)Cl |
| 3-Cl | $CF_3$ | $C(O)CH_3$ | (D-55c)Cl |
| 3-Cl | $CF_3$ | C(O)Et | (D-55c)Cl |
| 3-Cl | $CF_3$ | C(O)Pr-i | (D-55c)Cl |
| 3-Cl | $CF_3$ | $C(O)CH_2OCH_3$ | (D-55c)Cl |
| 3-Cl | $CF_3$ | $C(O)OCH_3$ | (D-55c)Cl |
| 3-Cl | $CF_3$ | $C(O)CH_3$ | (D-55c)Br |
| 3-Cl | $CF_3$ | C(O)Et | (D-55c)Br |
| 3-Cl | $CF_3$ | C(O)Pr-i | (D-55c)Br |
| 3-Cl | $CF_2Cl$ | H | $CH=NOCH_3$ |
| 3-Cl | $CF_2Cl$ | $CH_2OEt$ | $C(O)OCH_3$ |
| 3-Cl | $CF_2Cl$ | C(O)Et | $C(O)OCH_3$ |
| 3-Cl | $CF_2Cl$ | $C(O)CH_3$ | (D-55c)Cl |
| 3-Cl | $CF_2Cl$ | $C(O)OCH_3$ | (D-55c)Cl |
| 4-Cl | $CF_3$ | H | CH=NOEt |
| 3-Br | $CF_3$ | H | $CH=NOCH_3$ |
| 3-Br | $CF_3$ | $CH_2OCH_3$ | $CH=NOCH_3$ |
| 3-Br | $CF_3$ | H | CH=NOEt |
| 3-Br | $CF_3$ | H | $C(O)OCH_3$ |
| 3-Br | $CF_3$ | Et | $C(O)OCH_3$ |
| 3-Br | $CF_3$ | $CH_2OCH_3$ | $C(O)OCH_3$ |
| 3-Br | $CF_3$ | $CH_2OEt$ | $C(O)OCH_3$ |
| 3-Br | $CF_3$ | $CH_2OCH_2CF_3$ | $C(O)OCH_3$ |
| 3-Br | $CF_3$ | $CH_2OC(O)CH_3$ | $C(O)OCH_3$ |
| 3-Br | $CF_3$ | $CH_2OC(O)Et$ | $C(O)OCH_3$ |
| 3-Br | $CF_3$ | $CH_2OC(O)OCH_3$ | $C(O)OCH_3$ |
| 3-Br | $CF_3$ | E-5a | $C(O)OCH_3$ |
| 3-Br | $CF_3$ | C(O)Et | $C(O)OCH_3$ |
| 3-Br | $CF_3$ | C(O)Pr-n | $C(O)OCH_3$ |
| 3-Br | $CF_3$ | C(O)Bu-t | $C(O)OCH_3$ |
| 3-Br | $CF_3$ | $C(O)CH_2SCH_3$ | $C(O)OCH_3$ |
| 3-Br | $CF_3$ | $C(O)OCH_3$ | C(O)Et |
| 3-Br | $CF_3$ | H | C(O)OPr-i |
| 3-Br | $CF_3$ | H | $C(O)NH_2$ |
| 3-Br | $CF_3$ | $C(O)OCH_3$ | (D-52d)Cl |
| 3-Br | $CF_3$ | $CH_3$ | (D-55c)Cl |
| 3-Br | $CF_3$ | $CH_2OCH_3$ | (D-55c)Cl |
| 3-Br | $CF_3$ | $C(O)CH_3$ | (D-55c)Cl |
| 3-Br | $CF_3$ | C(O)Et | (D-55c)Cl |
| 3-Br | $CF_3$ | C(O)Pr-i | (D-55c)Cl |
| 3-Br | $CF_3$ | $C(O)CH_2OCH_3$ | (D-55c)Cl |
| 3-Br | $CF_3$ | $C(O)CH_2OEt$ | (D-55c)Cl |
| 3-Br | $CF_3$ | $C(O)CH_2SCH_3$ | (D-55c)Cl |
| 3-Br | $CF_3$ | $C(O)OCH_3$ | (D-55c)Cl |
| 3-Br | $CF_3$ | C(O)Pr-n | (D-55c)Cl |
| 3-Br | $CF_3$ | $C(O)OCH_2CH_2Cl$ | (D-55c)Cl |
| 3-Br | $CF_3$ | $C(O)OCH_2CH_2OCH_3$ | (D-55c)Cl |
| 3-Br | $CF_3$ | $C(O)OCH_2CH=CH_2$ | (D-55c)Cl |
| 3-Br | $CF_3$ | $CH_2OC(O)CH_3$ | (D-55c)Br |
| 3-Br | $CF_3$ | $C(O)CH_3$ | (D-55c)Br |
| 3-Br | $CF_3$ | C(O)Et | (D-55c)Br |
| 3-Br | $CF_3$ | C(O)Pr-n | (D-55c)Br |
| 3-Br | $CF_3$ | C(O)Pr-i | (D-55c)Br |
| 3-Br | $CF_3$ | $C(O)OCH_3$ | (D-55c)Br |
| 3-Br | $CF_3$ | C(O)Et | (D-55c)Br |
| 3-Br | $CF_2Cl$ | H | $CH=NOCH_3$ |
| 3-Br | $CF_2Cl$ | H | CH=NOEt |
| 3-Br | $CF_2Cl$ | $CH_2OEt$ | $C(O)OCH_3$ |
| 3-Br | $CF_2Cl$ | $CH_2OCH_2CF_3$ | $C(O)OCH_3$ |
| 3-Br | $CF_2Cl$ | C(O)Et | $C(O)OCH_3$ |
| 3-Br | $CF_2Cl$ | $C(O)CH_3$ | (D-55c)Cl |
| 3-Br | $CF_2Cl$ | C(O)Pr-i | (D-55c)Cl |
| 3-Br | $CF_2Cl$ | $C(O)OCH_3$ | (D-55c)Cl |
| 3-Br | $CF_2Cl$ | $C(O)CH_3$ | (D-55c)Br |
| 4-Br | $CF_3$ | $CH_2OEt$ | $C(O)OCH_3$ |
| 3-I | $CHF_2$ | $CH_2OCH_2CF_3$ | $C(O)OCH_3$ |
| 3-I | $CF_3$ | H | $CH=NOCH_3$ |
| 3-I | $CF_3$ | $CH_2OCH_3$ | $CH=NOCH_3$ |
| 3-I | $CF_3$ | H | CH=NOEt |
| 3-I | $CF_3$ | H | $C(O)OCH_3$ |
| 3-I | $CF_3$ | Et | $C(O)OCH_3$ |
| 3-I | $CF_3$ | $CH_2OCH_3$ | $C(O)OCH_3$ |
| 3-I | $CF_3$ | $CH_2OEt$ | $C(O)OCH_3$ |
| 3-I | $CF_3$ | $CH_2OCH_2CF_3$ | $C(O)OCH_3$ |
| 3-I | $CF_3$ | $CH_2OC(O)CH_3$ | $C(O)OCH_3$ |
| 3-I | $CF_3$ | $CH_2OC(O)Et$ | $C(O)OCH_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-I | CF$_3$ | CH$_2$OC(O)OCH$_3$ | C(O)OCH$_3$ |
| 3-I | CF$_3$ | E-5a | C(O)OCH$_3$ |
| 3-I | CF$_3$ | C(O)CH$_3$ | C(O)OCH$_3$ |
| 3-I | CF$_3$ | C(O)Et | C(O)OCH$_3$ |
| 3-I | CF$_3$ | C(O)Pr-n | C(O)OCH$_3$ |
| 3-I | CF$_3$ | C(O)Pr-i | C(O)OCH$_3$ |
| 3-I | CF$_3$ | C(O)Bu-t | C(O)OCH$_3$ |
| 3-I | CF$_3$ | C(O)CH$_2$OCH$_3$ | C(O)OCH$_3$ |
| 3-I | CF$_3$ | C(O)CH$_2$SCH$_3$ | C(O)OCH$_3$ |
| 3-I | CF$_3$ | C(O)OCH$_3$ | C(O)OEt |
| 3-I | CF$_3$ | H | C(O)OPr-i |
| 3-I | CF$_3$ | C(O)OCH$_3$ | C(O)OPr-i |
| 3-I | CF$_3$ | H | C(O)NH$_2$ |
| 3-I | CF$_3$ | CH$_3$ | (D-52d)Cl |
| 3-I | CF$_3$ | CH$_2$OCH$_3$ | (D-52d)Cl |
| 3-I | CF$_3$ | C(O)OCH$_3$ | (D-52d)Cl |
| 3-I | CF$_3$ | CH$_3$ | (D-55c)Cl |
| 3-I | CF$_3$ | CH$_2$OCH$_3$ | (D-55c)Cl |
| 3-I | CF$_3$ | CH$_2$OC(O)CH$_3$ | (D-55c)Cl |
| 3-I | CF$_3$ | CH$_2$OC(O)Bu-t | (D-55c)Cl |
| 3-I | CF$_3$ | CH$_2$OC(O)OCH$_3$ | (D-55c)Cl |
| 3-I | CF$_3$ | CH$_2$CN | (D-55c)Cl |
| 3-I | CF$_3$ | C(O)CH$_3$ | (D-55c)Cl |
| 3-I | CF$_3$ | C(O)Et | (D-55c)Cl |
| 3-I | CF$_3$ | C(O)Pr-n | (D-55c)Cl |
| 3-I | CF$_3$ | C(O)Pr-i | (D-55c)Cl |
| 3-I | CF$_3$ | C(O)Pr-c | (D-55c)Cl |
| 3-I | CF$_3$ | C(O)Bu-t | (D-55c)Cl |
| 3-I | CF$_3$ | C(O)CH$_2$Cl | (D-55c)Cl |
| 3-I | CF$_3$ | C(O)CH$_2$OCH$_3$ | (D-55c)Cl |
| 3-I | CF$_3$ | C(O)CH$_2$OEt | (D-55c)Cl |
| 3-I | CF$_3$ | C(O)CH$_2$SCH$_3$ | (D-55c)Cl |
| 3-I | CF$_3$ | C(O)CH$_2$S(O)CH$_3$ | (D-55c)Cl |
| 3-I | CF$_3$ | C(O)C(O)OEt | (D-55c)Cl |
| 3-I | CF$_3$ | C(O)OCH$_3$ | (D-55c)Cl |
| 3-I | CF$_3$ | C(O)OPr-n | (D-55c)Cl |
| 3-I | CF$_3$ | C(O)OCH$_2$Cl | (D-55c)Cl |
| 3-I | CF$_3$ | C(O)OCH$_2$CH$_2$Cl | (D-55c)Cl |
| 3-I | CF$_3$ | C(O)OCH$_2$CH$_2$OCH$_3$ | (D-55c)Cl |
| 3-I | CF$_3$ | C(O)OCH$_2$CH=CH$_2$ | (D-55c)Cl |
| 3-I | CF$_3$ | CH$_3$ | (D-55c)Br |
| 3-I | CF$_3$ | CH$_2$OC(O)CH$_3$ | (D-55c)Br |
| 3-I | CF$_3$ | C(O)CH$_3$ | (D-55c)Br |
| 3-I | CF$_3$ | C(O)Et | (D-55c)Br |
| 3-I | CF$_3$ | C(O)Pr-n | (D-55c)Br |
| 3-I | CF$_3$ | C(O)Pr-i | (D-55c)Br |
| 3-I | CF$_3$ | C(O)OCH$_3$ | (D-55c)Br |
| 3-I | CF$_3$ | C(O)Et | (D-55c)Br |
| 3-I | CF$_3$ | C(O)OCH$_2$CH$_2$OCH$_3$ | (D-55c)Br |
| 3-I | CF$_3$ | C(O)Pr-i | D-57a |
| 3-I | CF$_2$Cl | H | CH=NOCH$_3$ |
| 3-I | CF$_2$Cl | H | CH=NOEt |
| 3-I | CF$_2$Cl | H | C(O)OCH$_3$ |
| 3-I | CF$_2$Cl | Et | C(O)OCH$_3$ |
| 3-I | CF$_2$Cl | CH$_2$OCH$_3$ | C(O)OCH$_3$ |
| 3-I | CF$_2$Cl | CH$_2$OEt | C(O)OCH$_3$ |
| 3-I | CF$_2$Cl | CH$_2$OCH$_2$CF$_3$ | C(O)OCH$_3$ |
| 3-I | CF$_2$Cl | C(O)Et | C(O)OCH$_3$ |
| 3-I | CF$_2$Cl | C(O)OCH$_3$ | C(O)OEt |
| 3-I | CF$_2$Cl | H | C(O)NH$_2$ |
| 3-I | CF$_2$Cl | CH$_3$ | (D-55c)Cl |
| 3-I | CF$_2$Cl | CH$_2$OCH$_3$ | (D-55c)Cl |
| 3-I | CF$_2$Cl | C(O)CH$_3$ | (D-55c)Cl |
| 3-I | CF$_2$Cl | C(O)Et | (D-55c)Cl |
| 3-I | CF$_2$Cl | C(O)Pr-i | (D-55c)Cl |
| 3-I | CF$_2$Cl | C(O)CH$_2$OCH$_3$ | (D-55c)Cl |
| 3-I | CF$_2$Cl | C(O)OCH$_3$ | (D-55c)Cl |
| 3-I | CF$_2$Cl | C(O)CH$_3$ | (D-55c)Br |
| 3-I | CF$_2$Cl | C(O)Et | (D-55c)Br |
| 3-I | CF$_2$Cl | C(O)Pr-i | (D-55c)Br |
| 3-I | CF$_2$Br | C(O)Et | C(O)OCH$_3$ |
| 3-I | CF$_2$CHF$_2$ | C(O)CH$_3$ | (D-55c)Cl |
| 4-I | CF$_3$ | C(O)Pr-i | (D-55c)Cl |
| 3-CH$_3$ | CF$_3$ | C(O)OCH$_3$ | (D-55c)Cl |
| 3-Et | CF$_3$ | C(O)CH$_3$ | (D-55c)Br |
| 3-i-Pr | CF$_3$ | H | CH=NOCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-t-Bu | CF$_3$ | H | CH=NOEt |
| 3-CF$_3$ | CHF$_2$ | CH$_2$OEt | C(O)OCH$_3$ |
| 3-CF$_3$ | CF$_3$ | H | CH=NOCH$_3$ |
| 3-CF$_3$ | CF$_3$ | CH$_2$OCH$_3$ | CH=NOCH$_3$ |
| 3-CF$_3$ | CF$_3$ | H | CH=NOEt |
| 3-CF$_3$ | CF$_3$ | H | C(O)OCH$_3$ |
| 3-CF$_3$ | CF$_3$ | Et | C(O)OCH$_3$ |
| 3-CF$_3$ | CF$_3$ | CH$_2$OCH$_3$ | C(O)OCH$_3$ |
| 3-CF$_3$ | CF$_3$ | CH$_2$OEt | C(O)OCH$_3$ |
| 3-CF$_3$ | CF$_3$ | CH$_2$OCH$_2$CF$_3$ | C(O)OCH$_3$ |
| 3-CF$_3$ | CF$_3$ | CH$_2$OC(O)CH$_3$ | C(O)OCH$_3$ |
| 3-CF$_3$ | CF$_3$ | CH$_2$OC(O)Et | C(O)OCH$_3$ |
| 3-CF$_3$ | CF$_3$ | CH$_2$OC(O)OCH$_3$ | C(O)OCH$_3$ |
| 3-CF$_3$ | CF$_3$ | E-5a | C(O)OCH$_3$ |
| 3-CF$_3$ | CF$_3$ | C(O)CH$_3$ | C(O)OCH$_3$ |
| 3-CF$_3$ | CF$_3$ | C(O)Et | C(O)OCH$_3$ |
| 3-CF$_3$ | CF$_3$ | C(O)Pr-n | C(O)OCH$_3$ |
| 3-CF$_3$ | CF$_3$ | C(O)Pr-i | C(O)OCH$_3$ |
| 3-CF$_3$ | CF$_3$ | C(O)Bu-t | C(O)OCH$_3$ |
| 3-CF$_3$ | CF$_3$ | C(O)CH$_2$OCH$_3$ | C(O)OCH$_3$ |
| 3-CF$_3$ | CF$_3$ | C(O)CH$_2$SCH$_3$ | C(O)OCH$_3$ |
| 3-CF$_3$ | CF$_3$ | C(O)OCH$_3$ | C(O)OEt |
| 3-CF$_3$ | CF$_3$ | H | C(O)OPr-i |
| 3-CF$_3$ | CF$_3$ | C(O)OCH$_3$ | C(O)OPr-i |
| 3-CF$_3$ | CF$_3$ | H | C(O)NH$_2$ |
| 3-CF$_3$ | CF$_3$ | CH$_3$ | (D-52d)Cl |
| 3-CF$_3$ | CF$_3$ | CH$_2$OCH$_3$ | (D-52d)Cl |
| 3-CF$_3$ | CF$_3$ | C(O)OCH$_3$ | (D-52d)Cl |
| 3-CF$_3$ | CF$_3$ | CH$_3$ | (D-55c)Cl |
| 3-CF$_3$ | CF$_3$ | CH$_2$OCH$_3$ | (D-55c)Cl |
| 3-CF$_3$ | CF$_3$ | CH$_2$OC(O)CH$_3$ | (D-55c)Cl |
| 3-CF$_3$ | CF$_3$ | CH$_2$OC(O)Bu-t | (D-55c)Cl |
| 3-CF$_3$ | CF$_3$ | CH$_2$OC(O)OCH$_3$ | (D-55c)Cl |
| 3-CF$_3$ | CF$_3$ | CH$_2$CN | (D-55c)Cl |
| 3-CF$_3$ | CF$_3$ | C(O)CH$_3$ | (D-55c)Cl |
| 3-CF$_3$ | CF$_3$ | C(O)Et | (D-55c)Cl |
| 3-CF$_3$ | CF$_3$ | C(O)Pr-n | (D-55c)Cl |
| 3-CF$_3$ | CF$_3$ | C(O)Pr-i | (D-55c)Cl |
| 3-CF$_3$ | CF$_3$ | C(O)Pr-c | (D-55c)Cl |
| 3-CF$_3$ | CF$_3$ | C(O)Bu-t | (D-55c)Cl |
| 3-CF$_3$ | CF$_3$ | C(O)CH$_2$Cl | (D-55c)Cl |
| 3-CF$_3$ | CF$_3$ | C(O)CH$_2$OCH$_3$ | (D-55c)Cl |
| 3-CF$_3$ | CF$_3$ | C(O)CH$_2$OEt | (D-55c)Cl |
| 3-CF$_3$ | CF$_3$ | C(O)CH$_2$SCH$_3$ | (D-55c)Cl |
| 3-CF$_3$ | CF$_3$ | C(O)CH$_2$S(O)CH$_3$ | (D-55c)Cl |
| 3-CF$_3$ | CF$_3$ | C(O)C(O)OEt | (D-55c)Cl |
| 3-CF$_3$ | CF$_3$ | C(O)OCH$_3$ | (D-55c)Cl |
| 3-CF$_3$ | CF$_3$ | C(O)Pr-n | (D-55c)Cl |
| 3-CF$_3$ | CF$_3$ | C(O)OCH$_2$Cl | (D-55c)Cl |
| 3-CF$_3$ | CF$_3$ | C(O)OCH$_2$CH$_2$Cl | (D-55c)Cl |
| 3-CF$_3$ | CF$_3$ | C(O)OCH$_2$CH$_2$OCH$_3$ | (D-55c)Cl |
| 3-CF$_3$ | CF$_3$ | C(O)OCH$_2$CH=CH$_2$ | (D-55c)Cl |
| 3-CF$_3$ | CF$_3$ | CH$_3$ | (D-55c)Br |
| 3-CF$_3$ | CF$_3$ | CH$_2$OC(O)CH$_3$ | (D-55c)Br |
| 3-CF$_3$ | CF$_3$ | C(O)CH$_3$ | (D-55c)Br |
| 3-CF$_3$ | CF$_3$ | C(O)Et | (D-55c)Br |
| 3-CF$_3$ | CF$_3$ | C(O)Pr-n | (D-55c)Br |
| 3-CF$_3$ | CF$_3$ | C(O)Pr-i | (D-55c)Br |
| 3-CF$_3$ | CF$_3$ | C(O)OCH$_3$ | (D-55c)Br |
| 3-CF$_3$ | CF$_3$ | C(O)OEt | (D-55c)Br |
| 3-CF$_3$ | CF$_3$ | C(O)OCH$_2$CH$_2$OCH$_3$ | (D-55c)Br |
| 3-CF$_3$ | CF$_3$ | C(O)Pr-i | D-57a |
| 3-CF$_3$ | CF$_2$Cl | H | CH=NOCH$_3$ |
| 3-CF$_3$ | CF$_2$Cl | H | CH=NOEt |
| 3-CF$_3$ | CF$_2$Cl | H | C(O)OCH$_3$ |
| 3-CF$_3$ | CF$_2$Cl | Et | C(O)OCH$_3$ |
| 3-CF$_3$ | CF$_2$Cl | CH$_2$OCH$_3$ | C(O)OCH$_3$ |
| 3-CF$_3$ | CF$_2$Cl | CH$_2$OEt | C(O)OCH$_3$ |
| 3-CF$_3$ | CF$_2$Cl | CH$_2$OCH$_2$CF$_3$ | C(O)OCH$_3$ |
| 3-CF$_3$ | CF$_2$Cl | C(O)Et | C(O)OCH$_3$ |
| 3-CF$_3$ | CF$_2$Cl | C(O)OCH$_3$ | C(O)OEt |
| 3-CF$_3$ | CF$_2$Cl | H | C(O)NH$_2$ |
| 3-CF$_3$ | CF$_2$Cl | CH$_3$ | (D-55c)Cl |
| 3-CF$_3$ | CF$_2$Cl | CH$_2$OCH$_3$ | (D-55c)Cl |
| 3-CF$_3$ | CF$_2$Cl | C(O)CH$_3$ | (D-55c)Cl |
| 3-CF$_3$ | CF$_2$Cl | C(O)Et | (D-55c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-CF$_3$ | CF$_2$Cl | C(O)Pr-i | (D-55c)Cl |
| 3-CF$_3$ | CF$_2$Cl | C(O)CH$_2$OCH$_3$ | (D-55c)Cl |
| 3-CF$_3$ | CF$_2$Cl | C(O)OCH$_3$ | (D-55c)Cl |
| 3-CF$_3$ | CF$_2$Cl | C(O)CH$_3$ | (D-55c)Br |
| 3-CF$_3$ | CF$_2$Cl | C(O)Et | (D-55c)Br |
| 3-CF$_3$ | CF$_2$Cl | C(O)Pr-i | (D-55c)Br |
| 3-CF$_3$ | CF$_2$Br | CH$_2$OCH$_2$CF$_3$ | C(O)OCH$_3$ |
| 3-CF$_3$ | CF$_2$CHF$_2$ | C(O)Et | C(O)OCH$_3$ |
| 4-CF$_3$ | CF$_3$ | C(O)CH$_3$ | (D-55c)Cl |
| 3-CF$_2$CF$_3$ | CHF$_2$ | C(O)Pr-i | (D-55c)Cl |
| 3-CF$_2$CF$_3$ | CF$_3$ | H | CH=NOCH$_3$ |
| 3-CF$_2$CF$_3$ | CF$_3$ | CH$_2$OCH$_3$ | CH=NOCH$_3$ |
| 3-CF$_2$CF$_3$ | CF$_3$ | H | CH=NOEt |
| 3-CF$_2$CF$_3$ | CF$_3$ | H | C(O)OCH$_3$ |
| 3-CF$_2$CF$_3$ | CF$_3$ | Et | C(O)OCH$_3$ |
| 3-CF$_2$CF$_3$ | CF$_3$ | CH$_2$OCH$_3$ | C(O)OCH$_3$ |
| 3-CF$_2$CF$_3$ | CF$_3$ | CH$_2$OEt | C(O)OCH$_3$ |
| 3-CF$_2$CF$_3$ | CF$_3$ | CH$_2$OCH$_2$CF$_3$ | C(O)OCH$_3$ |
| 3-CF$_2$CF$_3$ | CF$_3$ | CH$_2$OC(O)CH$_3$ | C(O)OCH$_3$ |
| 3-CF$_2$CF$_3$ | CF$_3$ | CH$_2$OC(O)Et | C(O)OCH$_3$ |
| 3-CF$_2$CF$_3$ | CF$_3$ | CH$_2$OC(O)OCH$_3$ | C(O)OCH$_3$ |
| 3-CF$_2$CF$_3$ | CF$_3$ | E-5a | C(O)OCH$_3$ |
| 3-CF$_2$CF$_3$ | CF$_3$ | C(O)CH$_3$ | C(O)OCH$_3$ |
| 3-CF$_2$CF$_3$ | CF$_3$ | C(O)Et | C(O)OCH$_3$ |
| 3-CF$_2$CF$_3$ | CF$_3$ | C(O)Pr-n | C(O)OCH$_3$ |
| 3-CF$_2$CF$_3$ | CF$_3$ | C(O)Pr-i | C(O)OCH$_3$ |
| 3-CF$_2$CF$_3$ | CF$_3$ | C(O)Bu-t | C(O)OCH$_3$ |
| 3-CF$_2$CF$_3$ | CF$_3$ | C(O)CH$_2$OCH$_3$ | C(O)OCH$_3$ |
| 3-CF$_2$CF$_3$ | CF$_3$ | C(O)CH$_2$SCH$_3$ | C(O)OCH$_3$ |
| 3-CF$_2$CF$_3$ | CF$_3$ | C(O)OCH$_3$ | C(O)OEt |
| 3-CF$_2$CF$_3$ | CF$_3$ | H | C(O)OPr-i |
| 3-CF$_2$CF$_3$ | CF$_3$ | C(O)OCH$_3$ | C(O)OPr-i |
| 3-CF$_2$CF$_3$ | CF$_3$ | H | C(O)NH$_2$ |
| 3-CF$_2$CF$_3$ | CF$_3$ | CH$_3$ | (D-52d)Cl |
| 3-CF$_2$CF$_3$ | CF$_3$ | CH$_2$OCH$_3$ | (D-52d)Cl |
| 3-CF$_2$CF$_3$ | CF$_3$ | C(O)OCH$_3$ | (D-52d)Cl |
| 3-CF$_2$CF$_3$ | CF$_3$ | CH$_3$ | (D-55c)Cl |
| 3-CF$_2$CF$_3$ | CF$_3$ | CH$_2$OCH$_3$ | (D-55c)Cl |
| 3-CF$_2$CF$_3$ | CF$_3$ | CH$_2$OC(O)CH$_3$ | (D-55c)Cl |
| 3-CF$_2$CF$_3$ | CF$_3$ | CH$_2$OC(O)Bu-t | (D-55c)Cl |
| 3-CF$_2$CF$_3$ | CF$_3$ | CH$_2$OC(O)OCH$_3$ | (D-55c)Cl |
| 3-CF$_2$CF$_3$ | CF$_3$ | CH$_2$CN | (D-55c)Cl |
| 3-CF$_2$CF$_3$ | CF$_3$ | C(O)CH$_3$ | (D-55c)Cl |
| 3-CF$_2$CF$_3$ | CF$_3$ | C(O)Et | (D-55c)Cl |
| 3-CF$_2$CF$_3$ | CF$_3$ | C(O)Pr-n | (D-55c)Cl |
| 3-CF$_2$CF$_3$ | CF$_3$ | C(O)Pr-i | (D-55c)Cl |
| 3-CF$_2$CF$_3$ | CF$_3$ | C(O)Pr-c | (D-55c)Cl |
| 3-CF$_2$CF$_3$ | CF$_3$ | C(O)Bu-t | (D-55c)Cl |
| 3-CF$_2$CF$_3$ | CF$_3$ | C(O)CH$_2$Cl | (D-55c)Cl |
| 3-CF$_2$CF$_3$ | CF$_3$ | C(O)CH$_2$OCH$_3$ | (D-55c)Cl |
| 3-CF$_2$CF$_3$ | CF$_3$ | C(O)CH$_2$OEt | (D-55c)Cl |
| 3-CF$_2$CF$_3$ | CF$_3$ | C(O)CH$_2$SCH$_3$ | (D-55c)Cl |
| 3-CF$_2$CF$_3$ | CF$_3$ | C(O)CH$_2$S(O)CH$_3$ | (D-55c)Cl |
| 3-CF$_2$CF$_3$ | CF$_3$ | C(O)C(O)OEt | (D-55c)Cl |
| 3-CF$_2$CF$_3$ | CF$_3$ | C(O)OCH$_3$ | (D-55c)Cl |
| 3-CF$_2$CF$_3$ | CF$_3$ | C(O)OPr-n | (D-55c)Cl |
| 3-CF$_2$CF$_3$ | CF$_3$ | C(O)OCH$_2$Cl | (D-55c)Cl |
| 3-CF$_2$CF$_3$ | CF$_3$ | C(O)OCH$_2$CH$_2$Cl | (D-55c)Cl |
| 3-CF$_2$CF$_3$ | CF$_3$ | C(O)OCH$_2$CH$_2$OCH$_3$ | (D-55c)Cl |
| 3-CF$_2$CF$_3$ | CF$_3$ | C(O)OCH$_2$CH=CH$_2$ | (D-55c)Cl |
| 3-CF$_2$CF$_3$ | CF$_3$ | CH$_3$ | (D-55c)Br |
| 3-CF$_2$CF$_3$ | CF$_3$ | CH$_2$OC(O)CH$_3$ | (D-55c)Br |
| 3-CF$_2$CF$_3$ | CF$_3$ | C(O)CH$_3$ | (D-55c)Br |
| 3-CF$_2$CF$_3$ | CF$_3$ | C(O)Et | (D-55c)Br |
| 3-CF$_2$CF$_3$ | CF$_3$ | C(O)Pr-n | (D-55c)Br |
| 3-CF$_2$CF$_3$ | CF$_3$ | C(O)Pr-i | (D-55c)Br |
| 3-CF$_2$CF$_3$ | CF$_3$ | C(O)OCH$_3$ | (D-55c)Br |
| 3-CF$_2$CF$_3$ | CF$_3$ | C(O)OEt | (D-55c)Br |
| 3-CF$_2$CF$_3$ | CF$_3$ | C(O)OCH$_2$CH$_2$OCH$_3$ | (D-55c)Br |
| 3-CF$_2$CF$_3$ | CF$_3$ | C(O)Pr-i | D-57a |
| 3-CF$_2$CF$_3$ | CF$_2$Cl | H | CH=NOCH$_3$ |
| 3-CF$_2$CF$_3$ | CF$_2$Cl | H | CH=NOEt |
| 3-CF$_2$CF$_3$ | CF$_2$Cl | H | C(O)OCH$_3$ |
| 3-CF$_2$CF$_3$ | CF$_2$Cl | Et | C(O)OCH$_3$ |
| 3-CF$_2$CF$_3$ | CF$_2$Cl | CH$_2$OCH$_3$ | C(O)OCH$_3$ |
| 3-CF$_2$CF$_3$ | CF$_2$Cl | CH$_2$OEt | C(O)OCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-CF$_2$CF$_3$ | CF$_2$Cl | CH$_2$OCH$_2$CF$_3$ | C(O)OCH$_3$ |
| 3-CF$_2$CF$_3$ | CF$_2$Cl | C(O)Et | C(O)OCH$_3$ |
| 3-CF$_2$CF$_3$ | CF$_2$Cl | C(O)OCH$_3$ | C(O)OEt |
| 3-CF$_2$CF$_3$ | CF$_2$Cl | H | C(O)NH$_2$ |
| 3-CF$_2$CF$_3$ | CF$_2$Cl | CH$_3$ | (D-55c)Cl |
| 3-CF$_2$CF$_3$ | CF$_2$Cl | CH$_2$OCH$_3$ | (D-55c)Cl |
| 3-CF$_2$CF$_3$ | CF$_2$Cl | C(O)CH$_3$ | (D-55c)Cl |
| 3-CF$_2$CF$_3$ | CF$_2$Cl | C(O)Et | (D-55c)Cl |
| 3-CF$_2$CF$_3$ | CF$_2$Cl | C(O)Pr-i | (D-55c)Cl |
| 3-CF$_2$CF$_3$ | CF$_2$Cl | C(O)CH$_2$OCH$_3$ | (D-55c)Cl |
| 3-CF$_2$CF$_3$ | CF$_2$Cl | C(O)OCH$_3$ | (D-55c)Cl |
| 3-CF$_2$CF$_3$ | CF$_2$Cl | C(O)CH$_3$ | (D-55c)Br |
| 3-CF$_2$CF$_3$ | CF$_2$Cl | C(O)Et | (D-55c)Br |
| 3-CF$_2$CF$_3$ | CF$_2$Cl | C(O)Pr-i | (D-55c)Br |
| 3-CF$_2$CF$_3$ | CF$_2$Br | C(O)OCH$_3$ | (D-55c)Br |
| 3-CF$_2$CF$_3$ | CF$_2$CHF$_2$ | C(O)CH$_3$ | (D-55c)Br |
| 3-CF$_2$CF$_2$CF$_3$ | CF$_3$ | H | CH=NOCH$_3$ |
| 3-CF$_2$CF$_2$CF$_3$ | CF$_3$ | CH$_2$OCH$_3$ | CH=NOCH$_3$ |
| 3-CF$_2$CF$_2$CF$_3$ | CF$_3$ | H | CH=NOEt |
| 3-CF$_2$CF$_2$CF$_3$ | CF$_3$ | H | C(O)OCH$_3$ |
| 3-CF$_2$CF$_2$CF$_3$ | CF$_3$ | Et | C(O)OCH$_3$ |
| 3-CF$_2$CF$_2$CF$_3$ | CF$_3$ | CH$_2$OCH$_3$ | C(O)OCH$_3$ |
| 3-CF$_2$CF$_2$CF$_3$ | CF$_3$ | CH$_2$OEt | C(O)OCH$_3$ |
| 3-CF$_2$CF$_2$CF$_3$ | CF$_3$ | CH$_2$OCH$_2$CF$_3$ | C(O)OCH$_3$ |
| 3-CF$_2$CF$_2$CF$_3$ | CF$_3$ | CH$_2$OC(O)CH$_3$ | C(O)OCH$_3$ |
| 3-CF$_2$CF$_2$CF$_3$ | CF$_3$ | CH$_2$OC(O)Et | C(O)OCH$_3$ |
| 3-CF$_2$CF$_2$CF$_3$ | CF$_3$ | CH$_2$OC(O)OCH$_3$ | C(O)OCH$_3$ |
| 3-CF$_2$CF$_2$CF$_3$ | CF$_3$ | E-5a | C(O)OCH$_3$ |
| 3-CF$_2$CF$_2$CF$_3$ | CF$_3$ | C(O)Et | C(O)OCH$_3$ |
| 3-CF$_2$CF$_2$CF$_3$ | CF$_3$ | C(O)Pr-n | C(O)OCH$_3$ |
| 3-CF$_2$CF$_2$CF$_3$ | CF$_3$ | C(O)Bu-t | C(O)OCH$_3$ |
| 3-CF$_2$CF$_2$CF$_3$ | CF$_3$ | C(O)CH$_2$SCH$_3$ | C(O)OCH$_3$ |
| 3-CF$_2$CF$_2$CF$_3$ | CF$_3$ | C(O)OCH$_3$ | C(O)OEt |
| 3-CF$_2$CF$_2$CF$_3$ | CF$_3$ | H | C(O)OPr-i |
| 3-CF$_2$CF$_2$CF$_3$ | CF$_3$ | H | C(O)NH$_2$ |
| 3-CF$_2$CF$_2$CF$_3$ | CF$_3$ | C(O)OCH$_3$ | (D-52d)Cl |
| 3-CF$_2$CF$_2$CF$_3$ | CF$_3$ | CH$_3$ | (D-55c)Cl |
| 3-CF$_2$CF$_2$CF$_3$ | CF$_3$ | CH$_2$OCH$_3$ | (D-55c)Cl |
| 3-CF$_2$CF$_2$CF$_3$ | CF$_3$ | C(O)CH$_3$ | (D-55c)Cl |
| 3-CF$_2$CF$_2$CF$_3$ | CF$_3$ | C(O)Et | (D-55c)Cl |
| 3-CF$_2$CF$_2$CF$_3$ | CF$_3$ | C(O)Pr-i | (D-55c)Cl |
| 3-CF$_2$CF$_2$CF$_3$ | CF$_3$ | C(O)CH$_2$OCH$_3$ | (D-55c)Cl |
| 3-CF$_2$CF$_2$CF$_3$ | CF$_3$ | C(O)CH$_2$OEt | (D-55c)Cl |
| 3-CF$_2$CF$_2$CF$_3$ | CF$_3$ | C(O)CH$_2$SCH$_3$ | (D-55c)Cl |
| 3-CF$_2$CF$_2$CF$_3$ | CF$_3$ | C(O)OCH$_3$ | (D-55c)Cl |
| 3-CF$_2$CF$_2$CF$_3$ | CF$_3$ | C(O)OPr-n | (D-55c)Cl |
| 3-CF$_2$CF$_2$CF$_3$ | CF$_3$ | C(O)OCH$_2$CH$_2$Cl | (D-55c)Cl |
| 3-CF$_2$CF$_2$CF$_3$ | CF$_3$ | C(O)OCH$_2$CH$_2$OCH$_3$ | (D-55c)Cl |
| 3-CF$_2$CF$_2$CF$_3$ | CF$_3$ | C(O)OCH$_2$CH=CH$_2$ | (D-55c)Cl |
| 3-CF$_2$CF$_2$CF$_3$ | CF$_3$ | CH$_2$OC(O)CH$_3$ | (D-55c)Br |
| 3-CF$_2$CF$_2$CF$_3$ | CF$_3$ | C(O)CH$_3$ | (D-55c)Br |
| 3-CF$_2$CF$_2$CF$_3$ | CF$_3$ | C(O)Et | (D-55c)Br |
| 3-CF$_2$CF$_2$CF$_3$ | CF$_3$ | C(O)Pr-n | (D-55c)Br |
| 3-CF$_2$CF$_2$CF$_3$ | CF$_3$ | C(O)Pr-i | (D-55c)Br |
| 3-CF$_2$CF$_2$CF$_3$ | CF$_3$ | C(O)OCH$_3$ | (D-55c)Br |
| 3-CF$_2$CF$_2$CF$_3$ | CF$_3$ | C(O)OEt | (D-55c)Br |
| 3-CF$_2$CF$_2$CF$_3$ | CF$_2$Cl | H | CH=NOCH$_3$ |
| 3-CF$_2$CF$_2$CF$_3$ | CF$_2$Cl | H | CH=NOEt |
| 3-CF$_2$CF$_2$CF$_3$ | CF$_2$Cl | CH$_2$OEt | C(O)OCH$_3$ |
| 3-CF$_2$CF$_2$CF$_3$ | CF$_2$Cl | CH$_2$OCH$_2$CF$_3$ | C(O)OCH$_3$ |
| 3-CF$_2$CF$_2$CF$_3$ | CF$_2$Cl | C(O)Et | C(O)OCH$_3$ |
| 3-CF$_2$CF$_2$CF$_3$ | CF$_2$Cl | C(O)CH$_3$ | (D-55c)Cl |
| 3-CF$_2$CF$_2$CF$_3$ | CF$_2$Cl | C(O)Pr-i | (D-55c)Cl |
| 3-CF$_2$CF$_2$CF$_3$ | CF$_2$Cl | C(O)OCH$_3$ | (D-55c)Cl |
| 3-CF$_2$CF$_2$CF$_3$ | CF$_2$Cl | C(O)CH$_3$ | (D-55c)Br |
| 3-CF(CF$_3$)$_2$ | CF$_3$ | H | CH=NOCH$_3$ |
| 3-CF(CF$_3$)$_2$ | CF$_3$ | CH$_2$OCH$_3$ | CH=NOCH$_3$ |
| 3-CF(CF$_3$)$_2$ | CF$_3$ | H | CH=NOEt |
| 3-CF(CF$_3$)$_2$ | CF$_3$ | H | C(O)OCH$_3$ |
| 3-CF(CF$_3$)$_2$ | CF$_3$ | Et | C(O)OCH$_3$ |
| 3-CF(CF$_3$)$_2$ | CF$_3$ | CH$_2$OCH$_3$ | C(O)OCH$_3$ |
| 3-CF(CF$_3$)$_2$ | CF$_3$ | CH$_2$OEt | C(O)OCH$_3$ |
| 3-CF(CF$_3$)$_2$ | CF$_3$ | CH$_2$OCH$_2$CF$_3$ | C(O)OCH$_3$ |
| 3-CF(CF$_3$)$_2$ | CF$_3$ | CH$_2$OC(O)CH$_3$ | C(O)OCH$_3$ |
| 3-CF(CF$_3$)$_2$ | CF$_3$ | CH$_2$OC(O)Et | C(O)OCH$_3$ |
| 3-CF(CF$_3$)$_2$ | CF$_3$ | CH$_2$OC(O)OCH$_3$ | C(O)OCH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-CF(CF$_3$)$_2$ | CF$_3$ | E-5a | C(O)OCH$_3$ |
| 3-CF(CF$_3$)$_2$ | CF$_3$ | C(O)Et | C(O)OCH$_3$ |
| 3-CF(CF$_3$)$_2$ | CF$_3$ | C(O)Pr-n | C(O)OCH$_3$ |
| 3-CF(CF$_3$)$_2$ | CF$_3$ | C(O)Bu-t | C(O)OCH$_3$ |
| 3-CF(CF$_3$)$_2$ | CF$_3$ | C(O)CH$_2$SCH$_3$ | C(O)OCH$_3$ |
| 3-CF(CF$_3$)$_2$ | CF$_3$ | C(O)OCH$_3$ | C(O)OEt |
| 3-CF(CF$_3$)$_2$ | CF$_3$ | H | C(O)OPr-i |
| 3-CF(CF$_3$)$_2$ | CF$_3$ | H | C(O)NH$_2$ |
| 3-CF(CF$_3$)$_2$ | CF$_3$ | C(O)OCH$_3$ | (D-52d)Cl |
| 3-CF(CF$_3$)$_2$ | CF$_3$ | CH$_3$ | (D-55c)Cl |
| 3-CF(CF$_3$)$_2$ | CF$_3$ | CH$_2$OCH$_3$ | (D-55c)Cl |
| 3-CF(CF$_3$)$_2$ | CF$_3$ | C(O)CH$_3$ | (D-55c)Cl |
| 3-CF(CF$_3$)$_2$ | CF$_3$ | C(O)Et | (D-55c)Cl |
| 3-CF(CF$_3$)$_2$ | CF$_3$ | C(O)Pr-i | (D-55c)Cl |
| 3-CF(CF$_3$)$_2$ | CF$_3$ | C(O)CH$_2$OCH$_3$ | (D-55c)Cl |
| 3-CF(CF$_3$)$_2$ | CF$_3$ | C(O)CH$_2$OEt | (D-55c)Cl |
| 3-CF(CF$_3$)$_2$ | CF$_3$ | C(O)CH$_2$SCH$_3$ | (D-55c)Cl |
| 3-CF(CF$_3$)$_2$ | CF$_3$ | C(O)OCH$_3$ | (D-55c)Cl |
| 3-CF(CF$_3$)$_2$ | CF$_3$ | C(O)OPr-n | (D-55c)Cl |
| 3-CF(CF$_3$)$_2$ | CF$_3$ | C(O)OCH$_2$CH$_2$Cl | (D-55c)Cl |
| 3-CF(CF$_3$)$_2$ | CF$_3$ | C(O)OCH$_2$CH$_2$OCH$_3$ | (D-55c)Cl |
| 3-CF(CF$_3$)$_2$ | CF$_3$ | C(O)OCH$_2$CH=CH$_2$ | (D-55c)Cl |
| 3-CF(CF$_3$)$_2$ | CF$_3$ | CH$_2$OC(O)CH$_3$ | (D-55c)Br |
| 3-CF(CF$_3$)$_2$ | CF$_3$ | C(O)CH$_3$ | (D-55c)Br |
| 3-CF(CF$_3$)$_2$ | CF$_3$ | C(O)Et | (D-55c)Br |
| 3-CF(CF$_3$)$_2$ | CF$_3$ | C(O)Pr-n | (D-55c)Br |
| 3-CF(CF$_3$)$_2$ | CF$_3$ | C(O)Pr-i | (D-55c)Br |
| 3-CF(CF$_3$)$_2$ | CF$_3$ | C(O)OCH$_3$ | (D-55c)Br |
| 3-CF(CF$_3$)$_2$ | CF$_3$ | C(O)OEt | (D-55c)Br |
| 3-CF(CF$_3$)$_2$ | CF$_2$Cl | H | CH=NOCH$_3$ |
| 3-CF(CF$_3$)$_2$ | CF$_2$Cl | H | CH=NOEt |
| 3-CF(CF$_3$)$_2$ | CF$_2$Cl | CH$_2$OEt | C(O)OCH$_3$ |
| 3-CF(CF$_3$)$_2$ | CF$_2$Cl | CH$_2$OCH$_2$CF$_3$ | C(O)OCH$_3$ |
| 3-CF(CF$_3$)$_2$ | CF$_2$Cl | C(O)Et | C(O)OCH$_3$ |
| 3-CF(CF$_3$)$_2$ | CF$_2$Cl | C(O)CH$_3$ | (D-55c)Cl |
| 3-CF(CF$_3$)$_2$ | CF$_2$Cl | C(O)Pr-i | (D-55c)Cl |
| 3-CF(CF$_3$)$_2$ | CF$_2$Cl | C(O)OCH$_3$ | (D-55c)Cl |
| 3-CF(CF$_3$)$_2$ | CF$_2$Cl | C(O)CH$_3$ | (D-55c)Br |
| 3-CF$_2$CF$_2$CF$_2$CF$_3$ | CF$_3$ | H | CH=NOCH$_3$ |
| 3-CF$_2$CF$_2$CF$_2$CF$_3$ | CF$_3$ | H | CH=NOEt |
| 3-CF$_2$CF$_2$CF$_2$CF$_3$ | CF$_3$ | H | C(O)OCH$_3$ |
| 3-CF$_2$CF$_2$CF$_2$CF$_3$ | CF$_3$ | Et | C(O)OCH$_3$ |
| 3-CF$_2$CF$_2$CF$_2$CF$_3$ | CF$_3$ | CH$_2$OCH$_3$ | C(O)OCH$_3$ |
| 3-CF$_2$CF$_2$CF$_2$CF$_3$ | CF$_3$ | CH$_2$OEt | C(O)OCH$_3$ |
| 3-CF$_2$CF$_2$CF$_2$CF$_3$ | CF$_3$ | CH$_2$OCH$_2$CF$_3$ | C(O)OCH$_3$ |
| 3-CF$_2$CF$_2$CF$_2$CF$_3$ | CF$_3$ | C(O)Et | C(O)OCH$_3$ |
| 3-CF$_2$CF$_2$CF$_2$CF$_3$ | CF$_3$ | C(O)OCH$_3$ | C(O)OEt |
| 3-CF$_2$CF$_2$CF$_2$CF$_3$ | CF$_3$ | H | C(O)NH$_2$ |
| 3-CF$_2$CF$_2$CF$_2$CF$_3$ | CF$_3$ | CH$_3$ | (D-55c)Cl |
| 3-CF$_2$CF$_2$CF$_2$CF$_3$ | CF$_3$ | CH$_2$OCH$_3$ | (D-55c)Cl |
| 3-CF$_2$CF$_2$CF$_2$CF$_3$ | CF$_3$ | C(O)CH$_3$ | (D-55c)Cl |
| 3-CF$_2$CF$_2$CF$_2$CF$_3$ | CF$_3$ | C(O)Et | (D-55c)Cl |
| 3-CF$_2$CF$_2$CF$_2$CF$_3$ | CF$_3$ | C(O)Pr-i | (D-55c)Cl |
| 3-CF$_2$CF$_2$CF$_2$CF$_3$ | CF$_3$ | C(O)CH$_2$OCH$_3$ | (D-55c)Cl |
| 3-CF$_2$CF$_2$CF$_2$CF$_3$ | CF$_3$ | C(O)OCH$_3$ | (D-55c)Cl |
| 3-CF$_2$CF$_2$CF$_2$CF$_3$ | CF$_3$ | C(O)OCH3 | (D-55c)Br |
| 3-CF$_2$CF$_2$CF$_2$CF$_3$ | CF$_3$ | C(O)Et | (D-55c)Br |
| 3-CF$_2$CF$_2$CF$_2$CF$_3$ | CF$_3$ | C(O)Pr-i | (D-55c)Br |
| 3-CF$_2$CF$_2$CF$_2$CF$_3$ | CF$_2$Cl | H | CH=NOCH$_3$ |
| 3-CH$_2$OCH$_2$CF$_3$ | CF$_3$ | H | CH=NOEt |
| 3-C(CF$_3$)$_2$OH | CF$_3$ | H | CH=NOCH$_3$ |
| 3-C(CF$_3$)$_2$OH | CF$_3$ | H | CH=NOEt |
| 3-C(CF$_3$)$_2$OH | CF$_3$ | H | C(O)OCH$_3$ |
| 3-C(CF$_3$)$_2$OH | CF$_3$ | Et | C(O)OCH$_3$ |
| 3-C(CF$_3$)$_2$OH | CF$_3$ | CH$_2$OCH$_3$ | C(O)OCH$_3$ |
| 3-C(CF$_3$)$_2$OH | CF$_3$ | CH$_2$OEt | C(O)OCH$_3$ |
| 3-C(CF$_3$)$_2$OH | CF$_3$ | CH$_2$OCH$_2$CF$_3$ | C(O)OCH$_3$ |
| 3-C(CF$_3$)$_2$OH | CF$_3$ | C(O)Et | C(O)OCH$_3$ |
| 3-C(CF$_3$)$_2$OH | CF$_3$ | C(O)OCH$_3$ | C(O)OEt |
| 3-C(CF$_3$)$_2$OH | CF$_3$ | H | C(O)NH$_2$ |
| 3-C(CF$_3$)$_2$OH | CF$_3$ | CH$_3$ | (D-55c)Cl |
| 3-C(CF$_3$)$_2$OH | CF$_3$ | CH$_2$OCH$_3$ | (D-55c)Cl |
| 3-C(CF$_3$)$_2$OH | CF$_3$ | C(O)CH$_3$ | (D-55c)Cl |
| 3-C(CF$_3$)$_2$OH | CF$_3$ | C(O)Et | (D-55c)Cl |
| 3-C(CF$_3$)$_2$OH | CF$_3$ | C(O)Pr-i | (D-55c)Cl |
| 3-C(CF$_3$)$_2$OH | CF$_3$ | C(O)CH$_2$OCH$_3$ | (D-55c)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-C(CF$_3$)$_2$OH | CF$_3$ | C(O)OCH$_3$ | (D-55c)Cl |
| 3-C(CF$_3$)$_2$OH | CF$_3$ | C(O)CH$_3$ | (D-55c)Br |
| 3-C(CF$_3$)$_2$OH | CF$_3$ | C(O)Et | (D-55c)Br |
| 3-C(CF$_3$)$_2$OH | CF$_3$ | C(O)Pr-i | (D-55c)Br |
| 3-C(CF$_3$)$_2$OH | CF$_2$Cl | CH$_2$OEt | C(O)OCH$_3$ |
| 3-C(CF$_3$)$_2$OCH$_3$ | CF$_3$ | H | CH=NOCH$_3$ |
| 3-C(CF$_3$)$_2$OCH$_3$ | CF$_3$ | H | CH=NOEt |
| 3-C(CF$_3$)$_2$OCH$_3$ | CF$_3$ | H | C(O)OCH$_3$ |
| 3-C(CF$_3$)$_2$OCH$_3$ | CF$_3$ | Et | C(O)OCH$_3$ |
| 3-C(CF$_3$)$_2$OCH$_3$ | CF$_3$ | CH$_2$OCH$_3$ | C(O)OCH$_3$ |
| 3-C(CF$_3$)$_2$OCH$_3$ | CF$_3$ | CH$_2$OEt | C(O)OCH$_3$ |
| 3-C(CF$_3$)$_2$OCH$_3$ | CF$_3$ | CH$_2$OCH$_2$CF$_3$ | C(O)OCH$_3$ |
| 3-C(CF$_3$)$_2$OCH$_3$ | CF$_3$ | C(O)Et | C(O)OCH$_3$ |
| 3-C(CF$_3$)$_2$OCH$_3$ | CF$_3$ | C(O)OCH$_3$ | C(O)OEt |
| 3-C(CF$_3$)$_2$OCH$_3$ | CF$_3$ | H | C(O)NH$_2$ |
| 3-C(CF$_3$)$_2$OCH$_3$ | CF$_3$ | CH$_3$ | (D-55c)Cl |
| 3-C(CF$_3$)$_2$OCH$_3$ | CF$_3$ | CH$_2$OCH$_2$ | (D-55c)Cl |
| 3-C(CF$_3$)$_2$OCH$_3$ | CF$_3$ | C(O)CH$_3$ | (D-55c)Cl |
| 3-C(CF$_3$)$_2$OCH$_3$ | CF$_3$ | C(O)Et | (D-55c)Cl |
| 3-C(CF$_3$)$_2$OCH$_3$ | CF$_3$ | C(O)Pr-i | (D-55c)Cl |
| 3-C(CF$_3$)$_2$OCH$_3$ | CF$_3$ | C(O)CH$_2$OCH$_3$ | (D-55c)Cl |
| 3-C(CF$_3$)$_2$OCH$_3$ | CF$_3$ | C(O)OCH$_3$ | (D-55c)Cl |
| 3-C(CF$_3$)$_2$OCH$_3$ | CF$_3$ | C(O)CH$_3$ | (D-55c)Br |
| 3-C(CF$_3$)$_2$OCH$_3$ | CF$_3$ | C(O)Et | (D-55c)Br |
| 3-C(CF$_3$)$_2$OCH$_3$ | CF$_3$ | C(O)Pr-i | (D-55c)Br |
| 3-C(CF$_3$)$_2$OCH$_3$ | CF$_2$Cl | CH$_2$OCH$_2$CF$_3$ | C(O)OCH$_3$ |
| 3-CH$_2$SCH$_3$ | CF$_3$ | C(O)Et | C(O)OCH$_3$ |
| 3-CH$_2$SEt | CF$_3$ | C(O)CH$_3$ | (D-55c)Cl |
| 3-CH$_2$SPr-i | CF$_3$ | C(O)Pr-i | (D-55c)Cl |
| 3-CH$_2$SPr-c | CF$_3$ | C(O)OCH$_3$ | (D-55c)Cl |
| 3-CH$_2$SCF$_3$ | CF$_3$ | C(O)CH$_3$ | (D-55c)Br |
| 3-CH$_2$S(O)CF$_3$ | CF$_3$ | H | CH=NOCH$_3$ |
| 3-CH$_2$SO$_2$CF$_3$ | CF$_3$ | H | CH=NOEt |
| 3-CH$_2$SCH$_2$CF$_3$ | CF$_3$ | CH$_2$OEt | C(O)OCH$_3$ |
| 3-(T-3) | CF$_3$ | H | CH=NOCH$_3$ |
| 3-(T-3) | CF$_3$ | CH$_2$OEt | C(O)OCH$_3$ |
| 3-(T-3) | CF$_3$ | C(O)Et | C(O)OCH$_3$ |
| 3-(T-3) | CF$_3$ | C(O)CH$_3$ | (D-55c)Cl |
| 3-(T-3) | CF$_3$ | C(O)OCH$_3$ | (D-55c)Cl |
| 3-(T-4) | CF$_3$ | H | CH=NOCH$_3$ |
| 3-(T-4) | CF$_3$ | CH$_2$OEt | C(O)OCH$_3$ |
| 3-(T-4) | CF$_3$ | C(O)Et | C(O)OCH$_3$ |
| 3-(T-4) | CF$_3$ | C(O)CH$_3$ | (D-55c)Cl |
| 3-(T-4) | CF$_3$ | C(O)OCH$_3$ | (D-55c)Cl |
| 3-(T-5) | CF$_3$ | H | CH=NOCH$_3$ |
| 3-(T-5) | CF$_3$ | CH$_2$OEt | C(O)OCH$_3$ |
| 3-(T-5) | CF$_3$ | C(O)Et | C(O)OCH$_3$ |
| 3-(T-5) | CF$_3$ | C(O)CH$_3$ | (D-55c)Cl |
| 3-(T-5) | CF$_3$ | C(O)OCH$_3$ | (D-55c)Cl |
| 3-OCHF$_2$ | CF$_3$ | CH$_2$OCH$_2$CF$_3$ | C(O)OCH$_3$ |
| 4-OCHF$_2$ | CF$_3$ | C(O)Et | C(O)OCH$_3$ |
| 3-OCF$_3$ | CF$_3$ | H | CH=NOCH$_3$ |
| 3-OCF$_3$ | CF$_3$ | H | CH=NOEt |
| 3-OCF$_3$ | CF$_3$ | H | C(O)OCH$_3$ |
| 3-OCF$_3$ | CF$_3$ | Et | C(O)OCH$_3$ |
| 3-OCF$_3$ | CF$_3$ | CH$_2$OCH$_3$ | C(O)OCH$_3$ |
| 3-OCF$_3$ | CF$_3$ | CH$_2$OEt | C(O)OCH$_3$ |
| 3-OCF$_3$ | CF$_3$ | CH$_2$OCH$_2$CF$_3$ | C(O)OCH$_3$ |
| 3-OCF$_3$ | CF$_3$ | C(O)Et | C(O)OCH$_3$ |
| 3-OCF$_3$ | CF$_3$ | C(O)OCH$_3$ | C(O)OEt |
| 3-OCF$_3$ | CF$_3$ | H | C(O)NH$_2$ |
| 3-OCF$_3$ | CF$_3$ | CH$_3$ | (D-55c)Cl |
| 3-OCF$_3$ | CF$_3$ | CH$_2$OCH$_3$ | (D-55c)Cl |
| 3-OCF$_3$ | CF$_3$ | C(O)CH$_3$ | (D-55c)Cl |
| 3-OCF$_3$ | CF$_3$ | C(O)Et | (D-55c)Cl |
| 3-OCF$_3$ | CF$_3$ | C(O)Pr-i | (D-55c)Cl |
| 3-OCF$_3$ | CF$_3$ | C(O)CH$_2$OCH$_3$ | (D-55c)Cl |
| 3-OCF$_3$ | CF$_3$ | C(O)OCH$_3$ | (D-55c)Cl |
| 3-OCF$_3$ | CF$_3$ | C(O)CH$_3$ | (D-55c)Br |
| 3-OCF$_3$ | CF$_3$ | C(O)Et | (D-55c)Br |
| 3-OCF$_3$ | CF$_3$ | C(O)Pr-i | (D-55c)Br |
| 3-OCF$_3$ | CF$_2$Cl | H | CH=NOCH$_3$ |
| 3-OCF$_3$ | CF$_2$Cl | CH$_2$OEt | C(O)OCH$_3$ |
| 3-OCF$_3$ | CF$_2$Cl | C(O)Et | C(O)OCH$_3$ |
| 3-OCF$_3$ | CF$_2$Cl | C(O)CH$_3$ | (D-55c)Cl |
| 3-OCF$_3$ | CF$_2$Cl | C(O)OCH$_3$ | (D-55c)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 4-OCF$_3$ | CF$_3$ | C(O)CH$_3$ | (D-55c)Cl |
| 3-OCF$_2$Br | CF$_3$ | H | CH=NOCH$_3$ |
| 3-OCF$_2$Br | CF$_3$ | H | CH=NOEt |
| 3-OCF$_2$Br | CF$_3$ | H | C(O)OCH$_3$ |
| 3-OCF$_2$Br | CF$_3$ | Et | C(O)OCH$_3$ |
| 3-OCF$_2$Br | CF$_3$ | CH$_2$OCH$_3$ | C(O)OCH$_3$ |
| 3-OCF$_2$Br | CF$_3$ | CH$_2$OEt | C(O)OCH$_3$ |
| 3-OCF$_2$Br | CF$_3$ | CH$_2$OCH$_2$CF$_3$ | C(O)OCH$_3$ |
| 3-OCF$_2$Br | CF$_3$ | C(O)Et | C(O)OCH$_3$ |
| 3-OCF$_2$Br | CF$_3$ | C(O)OCH$_3$ | C(O)OEt |
| 3-OCF$_2$Br | CF$_3$ | H | C(O)NH$_2$ |
| 3-OCF$_2$Br | CF$_3$ | CH$_3$ | (D-55c)Cl |
| 3-OCF$_2$Br | CF$_3$ | CH$_2$OCH$_3$ | (D-55c)Cl |
| 3-OCF$_2$Br | CF$_3$ | C(O)CH$_3$ | (D-55c)Cl |
| 3-OCF$_2$Br | CF$_3$ | C(O)Et | (D-55c)Cl |
| 3-OCF$_2$Br | CF$_3$ | C(O)Pr-i | (D-55c)Cl |
| 3-OCF$_2$Br | CF$_3$ | C(O)CH$_2$OCH$_3$ | (D-55c)Cl |
| 3-OCF$_2$Br | CF$_3$ | C(O)OCH$_3$ | (D-55c)Cl |
| 3-OCF$_2$Br | CF$_3$ | C(O)CH$_3$ | (D-55c)Br |
| 3-OCF$_2$Br | CF$_3$ | C(O)Et | (D-55c)Br |
| 3-OCF$_2$Br | CF$_3$ | C(O)Pr-i | (D-55c)Br |
| 3-OCF$_2$Br | CF$_2$Cl | H | CH=NOCH$_3$ |
| 3-OCF$_2$Br | CF$_2$Cl | CH$_2$OEt | C(O)OCH$_3$ |
| 3-OCF$_2$Br | CF$_2$Cl | C(O)Et | C(O)OCH$_3$ |
| 3-OCF$_2$Br | CF$_2$Cl | C(O)CH$_3$ | (D-55c)Cl |
| 3-OCF$_2$Br | CF$_2$Cl | C(O)OCH$_3$ | (D-55c)Cl |
| 3-OCH$_2$CH$_2$Cl | CF$_3$ | C(O)Pr-i | (D-55c)Cl |
| 3-OCH$_2$CF$_3$ | CF$_3$ | C(O)OCH$_3$ | (D-55c)Cl |
| 3-OCF$_2$CHF$_2$ | CF$_3$ | H | CH=NOCH$_3$ |
| 3-OCF$_2$CHF$_2$ | CF$_3$ | H | CH=NOEt |
| 3-OCF$_2$CHF$_2$ | CF$_3$ | H | C(O)OCH$_3$ |
| 3-OCF$_2$CHF$_2$ | CF$_3$ | Et | C(O)OCH$_3$ |
| 3-OCF$_2$CHF$_2$ | CF$_3$ | CH$_2$OCH$_3$ | C(O)OCH$_3$ |
| 3-OCF$_2$CHF$_2$ | CF$_3$ | CH$_2$OEt | C(O)OCH$_3$ |
| 3-OCF$_2$CHF$_2$ | CF$_3$ | CH$_2$OCH$_2$CF$_3$ | C(O)OCH$_3$ |
| 3-OCF$_2$CHF$_2$ | CF$_3$ | C(O)Et | C(O)OCH$_3$ |
| 3-OCF$_2$CHF$_2$ | CF$_3$ | C(O)OCH$_3$ | C(O)OEt |
| 3-OCF$_2$CHF$_2$ | CF$_3$ | H | C(O)NH$_2$ |
| 3-OCF$_2$CHF$_2$ | CF$_3$ | CH$_3$ | (D-55c)Cl |
| 3-OCF$_2$CHF$_2$ | CF$_3$ | CH$_2$OCH$_3$ | (D-55c)Cl |
| 3-OCF$_2$CHF$_2$ | CF$_3$ | C(O)CH$_3$ | (D-55c)Cl |
| 3-OCF$_2$CHF$_2$ | CF$_3$ | C(O)Et | (D-55c)Cl |
| 3-OCF$_2$CHF$_2$ | CF$_3$ | C(O)Pr-i | (D-55c)Cl |
| 3-OCF$_2$CHF$_2$ | CF$_3$ | C(O)CH$_2$OCH$_3$ | (D-55c)Cl |
| 3-OCF$_2$CHF$_2$ | CF$_3$ | C(O)OCH$_3$ | (D-55c)Cl |
| 3-OCF$_2$CHF$_2$ | CF$_3$ | C(O)CH$_3$ | (D-55c)Br |
| 3-OCF$_2$CHF$_2$ | CF$_3$ | C(O)Et | (D-55c)Br |
| 3-OCF$_2$CHF$_2$ | CF$_3$ | C(O)Pr-i | (D-55c)Br |
| 3-OCF$_2$CHF$_2$ | CF$_2$Cl | C(O)CH$_3$ | (D-55c)Br |
| 3-OCF$_2$CHFCl | CF$_3$ | H | CH=NOCH$_3$ |
| 3-OCF$_2$CHFCl | CF$_3$ | H | CH=NOEt |
| 3-OCF$_2$CHFCl | CF$_3$ | H | C(O)OCH$_3$ |
| 3-OCF$_2$CHFCl | CF$_3$ | Et | C(O)OCH$_3$ |
| 3-OCF$_2$CHFCl | CF$_3$ | CH$_2$OCH$_3$ | C(O)OCH$_3$ |
| 3-OCF$_2$CHFCl | CF$_3$ | CH$_2$OEt | C(O)OCH$_3$ |
| 3-OCF$_2$CHFCl | CF$_3$ | CH$_2$OCH$_2$CF$_3$ | C(O)OCH$_3$ |
| 3-OCF$_2$CHFCl | CF$_3$ | C(O)Et | C(O)OCH$_3$ |
| 3-OCF$_2$CHFCl | CF$_3$ | C(O)OCH$_3$ | C(O)OEt |
| 3-OCF$_2$CHFCl | CF$_3$ | H | C(O)NH$_2$ |
| 3-OCF$_2$CHFCl | CF$_3$ | CH$_3$ | (D-55c)Cl |
| 3-OCF$_2$CHFCl | CF$_3$ | CH$_2$OCH$_3$ | (D-55c)Cl |
| 3-OCF$_2$CHFCl | CF$_3$ | C(O)CH$_3$ | (D-55c)Cl |
| 3-OCF$_2$CHFCl | CF$_3$ | C(O)Et | (D-55c)Cl |
| 3-OCF$_2$CHFCl | CF$_3$ | C(O)Pr-i | (D-55c)Cl |
| 3-OCF$_2$CHFCl | CF$_3$ | C(O)CH$_2$OCH$_3$ | (D-55c)Cl |
| 3-OCF$_2$CHFCl | CF$_3$ | C(O)OCH$_3$ | (D-55c)Cl |
| 3-OCF$_2$CHFCl | CF$_3$ | C(O)CH$_3$ | (D-55c)Br |
| 3-OCF$_2$CHFCl | CF$_3$ | C(O)Et | (D-55c)Br |
| 3-OCF$_2$CHFCl | CF$_3$ | C(O)Pr-i | (D-55c)Br |
| 3-OCF$_2$CHFBr | CF$_2$Cl | H | CH=NOCH$_3$ |
| 3-OCF$_2$CF$_2$Br | CF$_3$ | H | CH=NOEt |
| 3-OCF$_2$CF$_2$Br | CF$_3$ | CH$_2$OEt | C(O)OCH$_3$ |
| 3-OCF$_2$CFCl$_2$ | CF$_3$ | CH$_2$OCH$_2$CF$_3$ | C(O)OCH$_3$ |
| 3-OCF$_2$CCl$_3$ | CF$_3$ | C(O)Et | C(O)OCH$_3$ |
| 3-OCH$_2$CF$_2$CHF$_2$ | CF$_3$ | C(O)CH$_3$ | (D-55c)Cl |
| 3-OCF$_2$CHFCF$_3$ | CF$_3$ | H | CH=NOCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-OCF$_2$CHFCF$_3$ | CF$_3$ | H | CH=NOEt |
| 3-OCF$_2$CHFCF$_3$ | CF$_3$ | H | C(O)OCH$_3$ |
| 3-OCF$_2$CHFCF$_3$ | CF$_3$ | Et | C(O)OCH$_3$ |
| 3-OCF$_2$CHFCF$_3$ | CF$_3$ | CH$_2$OCH$_3$ | C(O)OCH$_3$ |
| 3-OCF$_2$CHFCF$_3$ | CF$_3$ | CH$_2$OEt | C(O)OCH$_3$ |
| 3-OCF$_2$CHFCF$_3$ | CF$_3$ | CH$_2$OCH$_2$CF$_3$ | C(O)OCH$_3$ |
| 3-OCF$_2$CHFCF$_3$ | CF$_3$ | C(O)Et | C(O)OCH$_3$ |
| 3-OCF$_2$CHFCF$_3$ | CF$_3$ | C(O)OCH$_3$ | C(O)OEt |
| 3-OCF$_2$CHFCF$_3$ | CF$_3$ | H | C(O)NH$_2$ |
| 3-OCF$_2$CHFCF$_3$ | CF$_3$ | CH$_3$ | (D-55c)Cl |
| 3-OCF$_2$CHFCF$_3$ | CF$_3$ | CH$_2$OCH$_3$ | (D-55c)Cl |
| 3-OCF$_2$CHFCF$_3$ | CF$_3$ | C(O)CH$_3$ | (D-55c)Cl |
| 3-OCF$_2$CHFCF$_3$ | CF$_3$ | C(O)Et | (D-55c)Cl |
| 3-OCF$_2$CHFCF$_3$ | CF$_3$ | C(O)Pr-i | (D-55c)Cl |
| 3-OCF$_2$CHFCF$_3$ | CF$_3$ | C(O)CH$_2$OCH$_3$ | (D-55c)Cl |
| 3-OCF$_2$CHFCF$_3$ | CF$_3$ | C(O)OCH$_3$ | (D-55c)Cl |
| 3-OCF$_2$CHFCF$_3$ | CF$_3$ | C(O)CH$_3$ | (D-55c)Br |
| 3-OCF$_2$CHFCF$_3$ | CF$_3$ | C(O)Et | (D-55c)Br |
| 3-OCF$_2$CHFCF$_3$ | CF$_3$ | C(O)Pr-i | (D-55c)Br |
| 3-OCF$_2$CHFCF$_3$ | CF$_2$Cl | (O)Pr-i | (D-55c)Cl |
| 3-OCH(CF$_3$)$_2$ | F$_3$ | C(O)OCH$_3$ | (D-55c)Cl |
| 3-OCF$_2$CFBrCF$_3$ | F$_3$ | C(O)CH$_3$ | (D-55c)Br |
| 3-OCF$_2$CHFOCF$_3$ | CF$_3$ | H | CH=NOCH$_3$ |
| 3-OCF$_2$CHFOCF$_3$ | CF$_3$ | H | CH=NOEt |
| 3-OCF$_2$CHFOCF$_3$ | CF$_3$ | H | C(O)OCH$_3$ |
| 3-OCF$_2$CHFOCF$_3$ | CF$_3$ | Et | C(O)OCH$_3$ |
| 3-OCF$_2$CHFOCF$_3$ | CF$_3$ | CH$_2$OCH$_3$ | C(O)OCH$_3$ |
| 3-OCF$_2$CHFOCF$_3$ | CF$_3$ | CH$_2$OEt | C(O)OCH$_3$ |
| 3-OCF$_2$CHFOCF$_3$ | CF$_3$ | CH$_2$OCH$_2$CF$_3$ | C(O)OCH$_3$ |
| 3-OCF$_2$CHFOCF$_3$ | CF$_3$ | C(O)Et | C(O)OCH$_3$ |
| 3-OCF$_2$CHFOCF$_3$ | CF$_3$ | C(O)OCH$_3$ | C(O)OEt |
| 3-OCF$_2$CHFOCF$_3$ | CF$_3$ | H | C(O)NH$_2$ |
| 3-OCF$_2$CHFOCF$_3$ | CF$_3$ | CH$_3$ | (D-55c)Cl |
| 3-OCF$_2$CHFOCF$_3$ | CF$_3$ | CH$_2$OCH$_3$ | (D-55c)Cl |
| 3-OCF$_2$CHFOCF$_3$ | CF$_3$ | C(O)CH$_3$ | (D-55c)Cl |
| 3-OCF$_2$CHFOCF$_3$ | CF$_3$ | C(O)Et | (D-55c)Cl |
| 3-OCF$_2$CHFOCF$_3$ | CF$_3$ | C(O)Pr-i | (D-55c)Cl |
| 3-OCF$_2$CHFOCF$_3$ | CF$_3$ | C(O)CH$_2$OCH$_3$ | (D-55c)Cl |
| 3-OCF$_2$CHFOCF$_3$ | CF$_3$ | C(O)OCH$_3$ | (D-55c)Cl |
| 3-OCF$_2$CHFOCF$_3$ | CF$_3$ | C(O)CH$_3$ | (D-55c)Br |
| 3-OCF$_2$CHFOCF$_3$ | CF$_3$ | C(O)Et | (D-55c)Br |
| 3-OCF$_2$CHFOCF$_3$ | CF$_3$ | C(O)Pr-i | (D-55c)Br |
| 3-OCF$_2$CHFOCF$_3$ | CF$_2$Cl | H | CH=NOCH$_3$ |
| 3-OCF$_2$CHFOCF$_2$CF$_2$CF$_3$ | CF$_3$ | H | CH=NOCH$_3$ |
| 3-OCF$_2$CHFOCF$_2$CF$_2$CF$_3$ | CF$_3$ | CH$_2$OEt | C(O)OCH$_3$ |
| 3-OCF$_2$CHFOCF$_2$CF$_2$CF$_3$ | CF$_3$ | C(O)Et | C(O)OCH$_3$ |
| 3-OCF$_2$CHFOCF$_2$CF$_2$CF$_3$ | CF$_3$ | C(O)CH$_3$ | (D-55c)Cl |
| 3-OCF$_2$CHFOCF$_2$CF$_2$CF$_3$ | CF$_3$ | C(O)OCH$_3$ | (D-55c)Cl |
| 3-OCH$_2$CH=CF$_2$ | CF$_3$ | H | CH=NOEt |
| 3-OCH$_2$CF=CF$_2$ | CF$_3$ | CH$_2$OEt | C(O)OCH$_3$ |
| 3-OCH$_2$CH=CCl$_2$ | CF$_3$ | CH$_2$OCH$_2$CF$_3$ | C(O)OCH$_3$ |
| 3-OCH$_2$CCl=CCl$_2$ | CF$_3$ | C(O)Et | C(O)OCH$_3$ |
| 3-OSO$_2$CHCl$_2$ | CF$_3$ | C(O)CH$_3$ | (D-55c)Cl |
| 3-OSO$_2$CF$_3$ | CF$_3$ | C(O)Pr-i | (D-55c)Cl |
| 3-OSO$_2$CH$_2$CF$_3$ | CF$_3$ | C(O)OCH$_3$ | (D-55c)Cl |
| 3-OPh | CF$_3$ | C(O)CH$_3$ | (D-55c)Br |
| 3-O(Ph-2-Cl) | CF$_3$ | H | CH=NOCH$_3$ |
| 3-O(Ph-3-Cl) | CF$_3$ | H | CH=NOEt |
| 3-O(Ph-4-Cl) | CF$_3$ | CH$_2$OEt | C(O)OCH$_3$ |
| 3-O(Ph-4-Br) | CF$_3$ | CH$_2$OCH$_2$CF$_3$ | C(O)OCH$_3$ |
| 3-O(Ph-2-CF$_3$) | CF$_3$ | C(O)Et | C(O)OCH$_3$ |
| 3-O(Ph-3-CF$_3$) | CF$_3$ | C(O)CH$_3$ | (D-55c)Cl |
| 3-O(Ph-4-CF$_3$) | CF$_3$ | C(O)Pr-i | (D-55c)Cl |
| 3-O(Ph-2-Cl-4-CF$_3$) | CF$_3$ | C(O)OCH$_3$ | (D-55c)Cl |
| 3-O(D-21c)Br | CF$_3$ | C(O)CH$_3$ | (D-55c)Br |
| 3-O(D-21c)CF$_3$ | CF$_3$ | H | CH=NOCH$_3$ |
| 3-O(D-52d)Br | CF$_3$ | H | CH=NOEt |
| 3-O(D-52d)CF$_3$ | CF$_3$ | CH$_2$OEt | C(O)OCH$_3$ |
| 2-O[(D-52f)-3-Cl-5-CF$_3$] | CF$_3$ | CH$_2$OCH$_2$CF$_3$ | C(O)OCH$_3$ |
| 3-O[(D-52f)-3-Cl-5-C F$_3$] | CF$_3$ | C(O)Et | C(O)OCH$_3$ |
| 3-O(D-55c)Br | CF$_3$ | C(O)CH$_3$ | (D-55c)Cl |
| 3-SCH$_3$ | CF$_3$ | C(O)Pr-i | (D-55c)Cl |
| 3-S(O)CH$_3$ | CF$_3$ | C(O)OCH$_3$ | (D-55c)Cl |
| 3-SO$_2$CH$_3$ | CF$_3$ | C(O)CH$_3$ | (D-55c)Br |
| 3-SEt | CF$_3$ | H | CH=NOCH$_3$ |
| 3-S(O)Et | CF$_3$ | H | CH=NOEt |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-SO$_2$Et | CF$_3$ | CH$_2$OEt | C(O)OCH$_3$ |
| 3-SPr-n | CF$_3$ | CH$_2$OCH$_2$CF$_3$ | C(O)OCH$_3$ |
| 3-S(O)Pr-n | CF$_3$ | C(O)Et | C(O)OCH$_3$ |
| 3-SO$_2$Pr-n | CF$_3$ | C(O)CH$_3$ | (D-55c)Cl |
| 3-SPr-i | CF$_3$ | C(O)Pr-i | (D-55c)Cl |
| 3-S(O)Pr-i | CF$_3$ | C(O)OCH$_3$ | (D-55c)Cl |
| 3-SO$_2$Pr-i | CF$_3$ | C(O)CH$_3$ | (D-55c)Br |
| 3-SBu-n | CF$_3$ | H | CH=NOCH$_3$ |
| 3-S(O)Bu-n | CF$_3$ | H | CH=NOEt |
| 3-SO$_2$Bu-n | CF$_3$ | CH$_2$OEt | C(O)OCH$_3$ |
| 3-SBu-t | CF$_3$ | CH$_2$OCH$_2$CF$_3$ | C(O)OCH$_3$ |
| 3-S(O)Bu-t | CF$_3$ | C(O)Et | C(O)OCH$_3$ |
| 3-SO$_2$Bu-t | CF$_3$ | C(O)CH$_3$ | (D-55c)Cl |
| 3-SCH$_2$F | CF$_3$ | C(O)Pr-i | (D-55c)Cl |
| 3-S(O)CH$_2$F | CF$_3$ | C(O)OCH$_3$ | (D-55c)Cl |
| 3-SO$_2$CH$_2$F | CF$_3$ | C(O)CH$_3$ | (D-55c)Br |
| 3-SCHF$_2$ | CF$_3$ | H | CH=NOCH$_3$ |
| 3-S(O)CHF$_2$ | CF$_3$ | H | CH=NOEt |
| 3-SO$_2$CHF$_2$ | CF$_3$ | CH$_2$OE | C(O)OCH$_3$ |
| 3-SCF$_3$ | CF$_3$ | H | CH=NOCH$_3$ |
| 3-SCF$_3$ | CF$_3$ | CH$_2$OCH$_3$ | CH=NOCH$_3$ |
| 3-SCF$_3$ | CF$_3$ | H | CH=NOEt |
| 3-SCF$_3$ | CF$_3$ | H | C(O)OCH$_3$ |
| 3-SCF$_3$ | CF$_3$ | Et | C(O)OCH$_3$ |
| 3-SCF$_3$ | CF$_3$ | CH$_2$OCH$_3$ | C(O)OCH$_3$ |
| 3-SCF$_3$ | CF$_3$ | CH$_2$OEt | C(O)OCH$_3$ |
| 3-SCF$_3$ | CF$_3$ | CH$_2$OCH$_2$CF$_3$ | C(O)OCH$_3$ |
| 3-SCF$_3$ | CF$_3$ | CH$_2$OC(O)CH$_3$ | C(O)OCH$_3$ |
| 3-SCF$_3$ | CF$_3$ | CH$_2$OC(O)Et | C(O)OCH$_3$ |
| 3-SCF$_3$ | CF$_3$ | CH$_2$OC(O)OCH$_3$ | C(O)OCH$_3$ |
| 3-SCF$_3$ | CF$_3$ | E-5a | C(O)OCH$_3$ |
| 3-SCF$_3$ | CF$_3$ | C(O)Et | C(O)OCH$_3$ |
| 3-SCF$_3$ | CF$_3$ | C(O)Pr-n | C(O)OCH$_3$ |
| 3-SCF$_3$ | CF$_3$ | C(O)Bu-t | C(O)OCH$_3$ |
| 3-SCF$_3$ | CF$_3$ | C(O)CH$_2$SCH$_3$ | C(O)OCH$_3$ |
| 3-SCF$_3$ | CF$_3$ | C(O)OCH$_3$ | C(O)OEt |
| 3-SCF$_3$ | CF$_3$ | H | C(O)OPr-i |
| 3-SCF$_3$ | CF$_3$ | H | C(O)NH$_2$ |
| 3-SCF$_3$ | CF$_3$ | C(O)OCH$_3$ | (D-52d)Cl |
| 3-SCF$_3$ | CF$_3$ | CH$_3$ | (D-55c)Cl |
| 3-SCF$_3$ | CF$_3$ | CH$_2$OCH$_3$ | (D-55c)Cl |
| 3-SCF$_3$ | CF$_3$ | C(O)CH$_3$ | (D-55c)Cl |
| 3-SCF$_3$ | CF$_3$ | C(O)Et | (D-55c)Cl |
| 3-SCF$_3$ | CF$_3$ | C(O)Pr-i | (D-55c)Cl |
| 3-SCF$_3$ | CF$_3$ | C(O)CH$_2$OCH$_3$ | (D-55c)Cl |
| 3-SCF$_3$ | CF$_3$ | C(O)CH$_2$OEt | (D-55c)Cl |
| 3-SCF$_3$ | CF$_3$ | C(O)CH$_2$SCH$_3$ | (D-55c)Cl |
| 3-SCF$_3$ | CF$_3$ | C(O)OCH$_3$ | (D-55c)Cl |
| 3-SCF$_3$ | CF$_3$ | C(O)OPr-n | (D-55c)Cl |
| 3-SCF$_3$ | CF$_3$ | C(O)OCH$_2$CH$_2$Cl | (D-55c)Cl |
| 3-SCF$_3$ | CF$_3$ | C(O)OCH$_2$CH$_2$OCH$_3$ | (D-55c)Cl |
| 3-SCF$_3$ | CF$_3$ | C(O)OCH$_2$CH=CH$_2$ | (D-55c)Cl |
| 3-SCF$_3$ | CF$_3$ | CH$_2$OC(O)CH$_3$ | (D-55c)Br |
| 3-SCF$_3$ | CF$_3$ | C(O)CH$_3$ | (D-55c)Br |
| 3-SCF$_3$ | CF$_3$ | C(O)Et | (D-55c)Br |
| 3-SCF$_3$ | CF$_3$ | C(O)Pr-n | (D-55c)Br |
| 3-SCF$_3$ | CF$_3$ | C(O)Pr-i | (D-55c)Br |
| 3-SCF$_3$ | CF$_3$ | C(O)OCH$_3$ | (D-55c)Br |
| 3-SCF$_3$ | CF$_3$ | C(O)OEt | (D-55c)Br |
| 3-SCF$_3$ | CF$_2$Cl | H | CH=NOCH$_3$ |
| 3-SCF$_3$ | CF$_2$Cl | H | CH=NOEt |
| 3-SCF$_3$ | CF$_2$Cl | CH$_2$OEt | C(O)OCH$_3$ |
| 3-SCF$_3$ | CF$_2$Cl | CH$_2$OCH$_2$CF$_3$ | C(O)OCH$_3$ |
| 3-SCF$_3$ | CF$_2$Cl | C(O)Et | C(O)OCH$_3$ |
| 3-SCF$_3$ | CF$_2$Cl | C(O)CH$_3$ | (D-55c)Cl |
| 3-SCF$_3$ | CF$_2$Cl | C(O)Pr-i | (D-55c)Cl |
| 3-SCF$_3$ | CF$_2$Cl | C(O)OCH$_3$ | (D-55c)Cl |
| 3-SCF$_3$ | CF$_2$Cl | C(O)CH$_3$ | (D-55c)Br |
| 3-S(O)CF$_3$ | CF$_3$ | H | CH=NOCH$_3$ |
| 3-S(O)CF$_3$ | CF$_3$ | CH$_2$OEt | C(O)OCH$_3$ |
| 3-S(O)CF$_3$ | CF$_3$ | C(O)Et | C(O)OCH$_3$ |
| 3-S(O)CF$_3$ | CF$_3$ | C(O)CH$_3$ | (D-55c)Cl |
| 3-S(O)CF$_3$ | CF$_3$ | C(O)OCH$_3$ | (D-55c)Cl |
| 3-SO$_2$CF$_3$ | CF$_3$ | H | CH=NOCH$_3$ |
| 3-SO$_2$CF$_3$ | CF$_3$ | CH$_2$OEt | C(O)OCH$_3$ |
| 3-SO$_2$CF$_3$ | CF$_3$ | C(O)Et | C(O)OCH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-SO$_2$CF$_3$ | CF$_3$ | C(O)CH$_3$ | (D-55c)Cl |
| 3-SO$_2$CF$_3$ | CF$_3$ | C(O)OCH$_3$ | (D-55c)Cl |
| 3-SCF$_2$Cl | CF$_3$ | H | CH=NOCH$_3$ |
| 3-SCF$_2$Cl | CF$_3$ | CH$_2$OCH$_3$ | CH=NOCH$_3$ |
| 3-SCF$_2$Cl | CF$_3$ | H | CH=NOEt |
| 3-SCF$_2$Cl | CF$_3$ | H | C(O)OCH$_3$ |
| 3-SCF$_2$Cl | CF$_3$ | Et | C(O)OCH$_3$ |
| 3-SCF$_2$Cl | CF$_3$ | CH$_2$OCH$_3$ | C(O)OCH$_3$ |
| 3-SCF$_2$Cl | CF$_3$ | CH$_2$OEt | C(O)OCH$_3$ |
| 3-SCF$_2$Cl | CF$_3$ | CH$_2$OCH$_2$CF$_3$ | C(O)OCH$_3$ |
| 3-SCF$_2$Cl | CF$_3$ | CH$_2$OC(O)CH$_3$ | C(O)OCH$_3$ |
| 3-SCF$_2$Cl | CF$_3$ | CH$_2$OC(O)Et | C(O)OCH$_3$ |
| 3-SCF$_2$Cl | CF$_3$ | CH$_2$OC(O)OCH$_3$ | C(O)OCH$_3$ |
| 3-SCF$_2$Cl | CF$_3$ | E-5a | C(O)OCH$_3$ |
| 3-SCF$_2$Cl | CF$_3$ | C(O)Et | C(O)OCH$_3$ |
| 3-SCF$_2$Cl | CF$_3$ | C(O)Pr-n | C(O)OCH$_3$ |
| 3-SCF$_2$Cl | CF$_3$ | C(O)Bu-t | C(O)OCH$_3$ |
| 3-SCF$_2$Cl | CF$_3$ | C(O)CH$_2$SCH$_3$ | C(O)OCH$_3$ |
| 3-SCF$_2$Cl | CF$_3$ | C(O)OCH$_3$ | C(O)OEt |
| 3-SCF$_2$Cl | CF$_3$ | H | C(O)OPr-i |
| 3-SCF$_2$Cl | CF$_3$ | H | C(O)NH$_2$ |
| 3-SCF$_2$Cl | CF$_3$ | C(O)OCH$_3$ | (D-52d)Cl |
| 3-SCF$_2$Cl | CF$_3$ | CH$_3$ | (D-55c)Cl |
| 3-SCF$_2$Cl | CF$_3$ | CH$_2$OCH$_3$ | (D-55c)Cl |
| 3-SCF$_2$Cl | CF$_3$ | C(O)CH$_3$ | (D-55c)Cl |
| 3-SCF$_2$Cl | CF$_3$ | C(O)Et | (D-55c)Cl |
| 3-SCF$_2$Cl | CF$_3$ | C(O)Pr-i | (D-55c)Cl |
| 3-SCF$_2$Cl | CF$_3$ | C(O)CH$_2$OCH$_3$ | (D-55c)Cl |
| 3-SCF$_2$Cl | CF$_3$ | C(O)CH$_2$OEt | (D-55c)Cl |
| 3-SCF$_2$Cl | CF$_3$ | C(O)CH$_2$SCH$_3$ | (D-55c)Cl |
| 3-SCF$_2$Cl | CF$_3$ | C(O)OCH$_3$ | (D-55c)Cl |
| 3-SCF$_2$Cl | CF$_3$ | C(O)OPr-n | (D-55c)Cl |
| 3-SCF$_2$Cl | CF$_3$ | C(O)OCH$_2$CH$_2$Cl | (D-55c)Cl |
| 3-SCF$_2$Cl | CF$_3$ | C(O)OCH$_2$CH$_2$OCH$_3$ | (D-55c)Cl |
| 3-SCF$_2$Cl | CF$_3$ | C(O)OCH$_2$CH=CH$_2$ | (D-55c)Cl |
| 3-SCF$_2$Cl | CF$_3$ | CH$_2$OC(O)CH$_3$ | (D-55c)Br |
| 3-SCF$_2$Cl | CF$_3$ | C(O)CH$_3$ | (D-55c)Br |
| 3-SCF$_2$Cl | CF$_3$ | C(O)Et | (D-55c)Br |
| 3-SCF$_2$Cl | CF$_3$ | C(O)Pr-n | (D-55c)Br |
| 3-SCF$_2$Cl | CF$_3$ | C(O)Pr-i | (D-55c)Br |
| 3-SCF$_2$Cl | CF$_3$ | C(O)OCH$_3$ | (D-55c)Br |
| 3-SCF$_2$Cl | CF$_3$ | C(O)OEt | (D-55c)Br |
| 3-SCF$_2$Cl | CF$_2$Cl | H | CH=NOCH$_3$ |
| 3-SCF$_2$Cl | CF$_2$Cl | H | CH=NOEt |
| 3-SCF$_2$Cl | CF$_2$Cl | CH$_2$OEt | C(O)OCH$_3$ |
| 3-SCF$_2$Cl | CF$_2$Cl | CH$_2$OCH$_2$CF$_3$ | C(O)OCH$_3$ |
| 3-SCF$_2$Cl | CF$_2$Cl | C(O)Et | C(O)OCH$_3$ |
| 3-SCF$_2$Cl | CF$_2$Cl | C(O)CH$_3$ | (D-55c)Cl |
| 3-SCF$_2$Cl | CF$_2$Cl | C(O)Pr-i | (D-55c)Cl |
| 3-SCF$_2$Cl | CF$_2$Cl | C(O)OCH$_3$ | (D-55c)Cl |
| 3-SCF$_2$Cl | CF$_2$Cl | C(O)CH$_3$ | (D-55c)Br |
| 3-S(O)CF$_2$Cl | CF$_3$ | CH$_2$OCH$_2$CF$_3$ | C(O)OCH$_3$ |
| 3-SO$_2$CF$_2$Cl | CF$_3$ | C(O)Et | C(O)OCH$_3$ |
| 3-SCF$_2$Br | CF$_3$ | H | CH=NOCH$_3$ |
| 3-SCF$_2$Br | CF$_3$ | CH$_2$OCH$_3$ | CH=NOCH$_3$ |
| 3-SCF$_2$Br | CF$_3$ | H | CH=NOEt |
| 3-SCF$_2$Br | CF$_3$ | H | C(O)OCH$_3$ |
| 3-SCF$_2$Br | CF$_3$ | Et | C(O)OCH$_3$ |
| 3-SCF$_2$Br | CF$_3$ | CH$_2$OCH$_3$ | C(O)OCH$_3$ |
| 3-SCF$_2$Br | CF$_3$ | CH$_2$OEt | C(O)OCH$_3$ |
| 3-SCF$_2$Br | CF$_3$ | CH$_2$OCH$_2$CF$_3$ | C(O)OCH$_3$ |
| 3-SCF$_2$Br | CF$_3$ | CH$_2$OC(O)CH$_3$ | C(O)OCH$_3$ |
| 3-SCF$_2$Br | CF$_3$ | CH$_2$OC(O)Et | C(O)OCH$_3$ |
| 3-SCF$_2$Br | CF$_3$ | CH$_2$OC(O)OCH$_3$ | C(O)OCH$_3$ |
| 3-SCF$_2$Br | CF$_3$ | E-5a | C(O)OCH$_3$ |
| 3-SCF$_2$Br | CF$_3$ | C(O)Et | C(O)OCH$_3$ |
| 3-SCF$_2$Br | CF$_3$ | C(O)Pr-n | C(O)OCH$_3$ |
| 3-SCF$_2$Br | CF$_3$ | C(O)Bu-t | C(O)OCH$_3$ |
| 3-SCF$_2$Br | CF$_3$ | C(O)CH$_2$SCH$_3$ | C(O)OCH$_3$ |
| 3-SCF$_2$Br | CF$_3$ | C(O)OCH$_3$ | C(O)OEt |
| 3-SCF$_2$Br | CF$_3$ | H | C(O)OPr-i |
| 3-SCF$_2$Br | CF$_3$ | H | C(O)NH$_2$ |
| 3-SCF$_2$Br | CF$_3$ | C(O)OCH$_3$ | (D-52d)Cl |
| 3-SCF$_2$Br | CF$_3$ | CH$_3$ | (D-55c)Cl |
| 3-SCF$_2$Br | CF$_3$ | CH$_2$OCH$_3$ | (D-55c)Cl |
| 3-SCF$_2$Br | CF$_3$ | C(O)CH$_3$ | (D-55c)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-SCF$_2$Br | CF$_3$ | C(O)Et | (D-55c)Cl |
| 3-SCF$_2$Br | CF$_3$ | C(O)Pr-i | (D-55c)Cl |
| 3-SCF$_2$Br | CF$_3$ | C(O)CH$_2$OCH$_3$ | (D-55c)Cl |
| 3-SCF$_2$Br | CF$_3$ | C(O)CH$_2$OEt | (D-55c)Cl |
| 3-SCF$_2$Br | CF$_3$ | C(O)CH$_2$SCH$_3$ | (D-55c)Cl |
| 3-SCF$_2$Br | CF$_3$ | C(O)OCH$_3$ | (D-55c)Cl |
| 3-SCF$_2$Br | CF$_3$ | C(O)OPr-n | (D-55c)Cl |
| 3-SCF$_2$Br | CF$_3$ | C(O)OCH$_2$CH$_2$Cl | (D-55c)Cl |
| 3-SCF$_2$Br | CF$_3$ | C(O)OCH$_2$CH$_2$OCH$_3$ | (D-55c)Cl |
| 3-SCF$_2$Br | CF$_3$ | C(O)OCH$_2$CH=CH$_2$ | (D-55c)Cl |
| 3-SCF$_2$Br | CF$_3$ | CH$_2$OC(O)CH$_3$ | (D-55c)Br |
| 3-SCF$_2$Br | CF$_3$ | C(O)CH$_3$ | (D-55c)Br |
| 3-SCF$_2$Br | CF$_3$ | C(O)Et | (D-55c)Br |
| 3-SCF$_2$Br | CF$_3$ | C(O)Pr-n | (D-55c)Br |
| 3-SCF$_2$Br | CF$_3$ | C(O)Pr-i | (D-55c)Br |
| 3-SCF$_2$Br | CF$_3$ | C(O)OCH$_3$ | (D-55c)Br |
| 3-SCF$_2$Br | CF$_3$ | C(O)OEt | (D-55c)Br |
| 3-SCF$_2$Br | CF$_3$ | H | CH=NOCH$_3$ |
| 3-SCF$_2$Br | CF$_3$ | H | CH=NOEt |
| 3-SCF$_2$Br | CF$_3$ | CH2OEt | C(O)OCH$_3$ |
| 3-SCF$_2$Br | CF$_2$Cl | CH$_2$OCH$_2$CF$_3$ | C(O)OCH$_3$ |
| 3-SCF$_2$Br | CF$_2$Cl | C(O)Et | C(O)OCH$_3$ |
| 3-SCF$_2$Br | CF$_2$Cl | C(O)CH$_3$ | (D-55c)Cl |
| 3-SCF$_2$Br | CF$_2$Cl | C(O)Pr-i | (D-55c)Cl |
| 3-SCF$_2$Br | CF$_2$Cl | C(O)OCH$_3$ | (D-55c)Cl |
| 3-SCF$_2$Br | CF$_2$Cl | C(O)CH$_3$ | (D-55c)Br |
| 3-S(O)CF$_2$Br | CF$_3$ | C(O)CH$_3$ | (D-55c)Cl |
| 3-SO$_2$CF$_2$Br | CF$_3$ | C(O)Pr-i | (D-55c)Cl |
| 3-SCH$_2$CF$_3$ | CF$_3$ | C(O)OCH$_3$ | (D-55c)Cl |
| 3-SCF$_2$CHF$_2$ | CF$_3$ | C(O)CH$_3$ | (D-55c)Br |
| 3-SCF$_2$CHFCl | CF$_3$ | H | CH=NOCH$_3$ |
| 3-SCF$_2$CF$_3$ | CF$_3$ | H | CH=NOEt |
| 3-SCF$_2$CF$_2$Br | CF$_3$ | CH$_2$OEt | C(O)OCH$_3$ |
| 3-SCF$_2$CHFCF$_3$ | CF$_3$ | CH$_2$OCH$_2$CF$_3$ | C(O)OCH$_3$ |
| 3-SCF$_2$CF$_2$CF$_3$ | CF$_3$ | C(O)Et | C(O)OCH$_3$ |
| 3-S(Ph-4-Cl) | CF$_3$ | C(O)CH$_3$ | (D-55c)Cl |
| 3-S(Ph-4-Br) | CF$_3$ | C(O)Pr-i | (D-55c)Cl |
| 3-S(Ph-4-CF$_3$) | CF$_3$ | C(O)OCH$_3$ | (D-55c)Cl |
| 3-S(D-21c)Br | CF$_3$ | C(O)CH$_3$ | (D-55c)Br |
| 3-S(D-21c)CF$_3$ | CF$_3$ | H | CH=NOCH$_3$ |
| 3-S(D-52d)Br | CF$_3$ | H | CH=NOEt |
| 3-S(D-52d)CF$_3$ | CF$_3$ | CH$_2$OEt | C(O)OCH$_3$ |
| 3-S[(D-52f)-3-Cl-5-CF$_3$] | CF$_3$ | CH$_2$OCH$_2$CF$_3$ | C(O)OCH$_3$ |
| 3-S(D-55c)Br | CF$_3$ | C(O)Et | C(O)OCH$_3$ |
| 3-SF$_5$ | CHF$_2$ | C(O)CH$_3$ | (D-55c)Cl |
| 3-SF$_5$ | CF$_3$ | H | CH=NOCH$_3$ |
| 3-SF$_5$ | CF$_3$ | CH$_2$OCH$_3$ | CH=NOCH$_3$ |
| 3-SF$_5$ | CF$_3$ | H | CH=NOEt |
| 3-SF$_5$ | CF$_3$ | H | C(O)OCH$_3$ |
| 3-SF$_5$ | CF$_3$ | Et | C(O)OCH$_3$ |
| 3-SF$_5$ | CF$_3$ | CH$_2$OCH$_3$ | C(O)OCH$_3$ |
| 3-SF$_5$ | CF$_3$ | CH$_2$OEt | C(O)OCH$_3$ |
| 3-SF$_5$ | CF$_3$ | CH$_2$OCH$_2$CF$_3$ | C(O)OCH$_3$ |
| 3-SF$_5$ | CF$_3$ | CH$_2$OC(O)CH$_3$ | C(O)OCH$_3$ |
| 3-SF$_5$ | CF$_3$ | CH$_2$OC(O)Et | C(O)OCH$_3$ |
| 3-SF$_5$ | CF$_3$ | CH$_2$OC(O)OCH$_3$ | C(O)OCH$_3$ |
| 3-SF$_5$ | CF$_3$ | E-5a | C(O)OCH$_3$ |
| 3-SF$_5$ | CF$_3$ | C(O)CH$_3$ | C(O)OCH$_3$ |
| 3-SF$_5$ | CF$_3$ | C(O)Et | C(O)OCH$_3$ |
| 3-SF$_5$ | CF$_3$ | C(O)Pr-n | C(O)OCH$_3$ |
| 3-SF$_5$ | CF$_3$ | C(O)Pr-i | C(O)OCH$_3$ |
| 3-SF$_5$ | CF$_3$ | C(O)Bu-t | C(O)OCH$_3$ |
| 3-SF$_5$ | CF$_3$ | C(O)CH$_2$OCH$_3$ | C(O)OCH$_3$ |
| 3-SF$_5$ | CF$_3$ | C(O)CH$_2$SCH$_3$ | C(O)OCH$_3$ |
| 3-SF$_5$ | CF$_3$ | C(O)OCH$_3$ | C(O)OEt |
| 3-SF$_5$ | CF$_3$ | H | C(O)OPr-i |
| 3-SF$_5$ | CF$_3$ | C(O)OCH$_3$ | C(O)OPr-i |
| 3-SF$_5$ | CF$_3$ | H | C(O)NH$_2$ |
| 3-SF$_5$ | CF$_3$ | CH$_3$ | (D-52d)Cl |
| 3-SF$_5$ | CF$_3$ | CH$_2$OCH$_3$ | (D-52d)Cl |
| 3-SF$_5$ | CF$_3$ | C(O)OCH$_3$ | (D-52d)Cl |
| 3-SF$_5$ | CF$_3$ | CH$_3$ | (D-55c)Cl |
| 3-SF$_5$ | CF$_3$ | CH$_2$OCH$_3$ | (D-55c)Cl |
| 3-SF$_5$ | CF$_3$ | CH$_2$OC(O)CH$_3$ | (D-55c)Cl |
| 3-SF$_5$ | CF$_3$ | CH$_2$OC(O)Bu-t | (D-55c)Cl |
| 3-SF$_5$ | CF$_3$ | CH$_2$OC(O)OCH$_3$ | (D-55c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-SF$_5$ | CF$_3$ | CH$_2$CN | (D-55c)Cl |
| 3-SF$_5$ | CF$_3$ | C(O)CH$_3$ | (D-55c)Cl |
| 3-SF$_5$ | CF$_3$ | C(O)Et | (D-55c)Cl |
| 3-SF$_5$ | CF$_3$ | C(O)Pr-n | (D-55c)Cl |
| 3-SF$_5$ | CF$_3$ | C(O)Pr-i | (D-55c)Cl |
| 3-SF$_5$ | CF$_3$ | C(O)Pr-c | (D-55c)Cl |
| 3-SF$_5$ | CF$_3$ | C(O)Bu-t | (D-55c)Cl |
| 3-SF$_5$ | CF$_3$ | C(O)CH$_2$Cl | (D-55c)Cl |
| 3-SF$_5$ | CF$_3$ | C(O)CH$_2$OCH$_3$ | (D-55c)Cl |
| 3-SF$_5$ | CF$_3$ | C(O)CH$_2$OEt | (D-55c)Cl |
| 3-SF$_5$ | CF$_3$ | C(O)CH$_2$SCH$_3$ | (D-55c)Cl |
| 3-SF$_5$ | CF$_3$ | C(O)CH$_2$S(O)CH$_3$ | (D-55c)Cl |
| 3-SF$_5$ | CF$_3$ | C(O)C(O)OEt | (D-55c)Cl |
| 3-SF$_5$ | CF$_3$ | C(O)OCH$_3$ | (D-55c)Cl |
| 3-SF$_5$ | CF$_3$ | C(O)OPr-n | (D-55c)Cl |
| 3-SF$_5$ | CF$_3$ | C(O)OCH$_2$Cl | (D-55c)Cl |
| 3-SF$_5$ | CF$_3$ | C(O)OCH$_2$CH$_2$Cl | (D-55c)Cl |
| 3-SF$_5$ | CF$_3$ | C(O)OCH$_2$CH$_2$OCH$_3$ | (D-55c)Cl |
| 3-SF$_5$ | CF$_3$ | C(O)OCH$_2$CH=CH$_2$ | (D-55c)Cl |
| 3-SF$_5$ | CF$_3$ | CH$_3$ | (D-55c)Br |
| 3-SF$_5$ | CF$_3$ | CH$_2$OC(O)CH$_3$ | (D-55c)Br |
| 3-SF$_5$ | CF$_3$ | C(O)CH$_3$ | (D-55c)Br |
| 3-SF$_5$ | CF$_3$ | C(O)Et | (D-55c)Br |
| 3-SF$_5$ | CF$_3$ | C(O)Pr-n | (D-55c)Br |
| 3-SF$_5$ | CF$_3$ | C(O)Pr-i | (D-55c)Br |
| 3-SF$_5$ | CF$_3$ | C(O)OCH$_3$ | (D-55c)Br |
| 3-SF$_5$ | CF$_3$ | C(O)OEt | (D-55c)Br |
| 3-SF$_5$ | CF$_3$ | C(O)OCH$_2$CH$_2$OCH$_3$ | (D-55c)Br |
| 3-SF$_5$ | CF$_3$ | C(O)Pr-i | D-57a |
| 3-SF$_5$ | CF$_3$ | H | CH=NOCH$_3$ |
| 3-SF$_5$ | CF$_2$Cl | H | CH=NOEt |
| 3-SF$_5$ | CF$_2$Cl | H | C(O)OCH$_3$ |
| 3-SF$_5$ | CF$_2$Cl | Et | C(O)OCH$_3$ |
| 3-SF$_5$ | CF$_2$Cl | CH$_2$OCH$_3$ | C(O)OCH$_3$ |
| 3-SF$_5$ | CF$_2$Cl | CH$_2$OEt | C(O)OCH$_3$ |
| 3-SF$_5$ | CF$_2$Cl | CH$_2$OCH$_2$CF$_3$ | C(O)OCH$_3$ |
| 3-SF$_5$ | CF$_2$Cl | C(O)Et | C(O)OCH$_3$ |
| 3-SF$_5$ | CF$_2$Cl | C(O)OCH$_3$ | C(O)OEt |
| 3-SF$_5$ | CF$_2$Cl | H | C(O)NH$_2$ |
| 3-SF$_5$ | CF$_2$Cl | CH$_3$ | (D-55c)Cl |
| 3-SF$_5$ | CF$_2$Cl | CH$_2$OCH$_3$ | (D-55c)Cl |
| 3-SF$_5$ | CF$_2$Cl | C(O)CH$_3$ | (D-55c)Cl |
| 3-SF$_5$ | CF$_2$Cl | C(O)Et | (D-55c)Cl |
| 3-SF$_5$ | CF$_2$Cl | C(O)Pr-i | (D-55c)Cl |
| 3-SF$_5$ | CF$_2$Cl | C(O)CH$_2$OCH$_3$ | (D-55c)Cl |
| 3-SF$_5$ | CF$_2$Cl | C(O)OCH$_3$ | (D-55c)Cl |
| 3-SF$_5$ | CF$_2$Cl | C(O)CH$_3$ | (D-55c)Br |
| 3-SF$_5$ | CF$_2$Cl | C(O)Et | (D-55c)Br |
| 3-SF$_5$ | CF$_2$Cl | C(O)Pr-i | (D-55c)Br |
| 3-SF$_5$ | CF$_2$Br | C(O)Pr-i | (D-55c)Br |
| 3-SF$_5$ | CF$_2$CHF$_2$ | C(O)OCH$_3$ | (D-55c)Cl |
| 3-NO$_2$ | CF$_3$ | C(O)CH$_3$ | (D-55c)Br |
| 3-CN | CF$_3$ | H | CH=NOCH$_3$ |
| 3-C(O)NH$_2$ | CF$_3$ | H | CH=NOEt |
| 3-C(S)NH$_2$ | CF$_3$ | CH$_2$OEt | C(O)OCH$_3$ |
| 3-SO$_2$NHCH$_3$ | CF$_3$ | CH$_2$OCH$_2$CF$_3$ | C(O)OCH$_3$ |
| 3-SO$_2$N(CH$_3$)$_2$ | CF$_3$ | C(O)Et | C(O)OCH$_3$ |
| 3-Si(CH$_3$)$_3$ | CF$_3$ | C(O)CH$_3$ | (D-55c)Cl |
| 2,3-F$_2$ | CF$_3$ | C(O)Pr-i | (D-55c)Cl |
| 2,4-F$_2$ | CF$_3$ | C(O)OCH$_3$ | (D-55c)Cl |
| 2,5-F$_2$ | CF$_3$ | C(O)CH$_3$ | (D-55c)Br |
| 3,4-F$_2$ | CF$_3$ | H | CH=NOCH$_3$ |
| 3,4-F$_2$ | CF$_3$ | H | CH=NOEt |
| 3,4-F$_2$ | CF$_3$ | CH$_2$OEt | C(O)OCH$_3$ |
| 3,4-F$_2$ | CF$_3$ | CH$_2$OCH$_2$CF$_3$ | C(O)OCH$_3$ |
| 3,4-F$_2$ | CF$_3$ | C(O)Et | C(O)OCH$_3$ |
| 3,4-F$_2$ | CF$_3$ | C(O)CH$_3$ | (D-55c)Cl |
| 3,4-F$_2$ | CF$_3$ | C(O)Pr-i | (D-55c)Cl |
| 3,4-F$_2$ | CF$_3$ | C(O)OCH$_3$ | (D-55c)Cl |
| 3,4-F$_2$ | CF$_3$ | C(O)CH$_3$ | (D-55c)Br |
| 3,5-F$_2$ | CF$_3$ | H | CH=NOCH$_3$ |
| 3,5-F$_2$ | CF$_3$ | H | CH=NOEt |
| 3,5-F$_2$ | CF$_3$ | CH$_2$OEt | C(O)OCH$_3$ |
| 3,5-F$_2$ | CF$_3$ | CH$_2$OCH$_2$CF$_3$ | C(O)OCH$_3$ |
| 3,5-F$_2$ | CF$_3$ | C(O)Et | C(O)OCH$_3$ |
| 3,5-F$_2$ | CF$_3$ | C(O)CH$_3$ | (D-55c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-F$_2$ | CF$_3$ | C(O)Pr-i | (D-55c)Cl |
| 3,5-F$_2$ | CF$_3$ | C(O)OCH$_3$ | (D-55c)Cl |
| 3,5-F$_2$ | CF$_3$ | C(O)CH$_3$ | (D-55c)Br |
| 2-Cl-4-F | CF$_3$ | H | CH=NOCH$_3$ |
| 2-F-3-Cl | CF$_3$ | H | CH=NOEt |
| 3-Cl-4-F | CHF$_2$ | CH$_2$OEt | C(O)OCH$_3$ |
| 3-Cl-4-F | CF$_3$ | H | CH=NOCH$_3$ |
| 3-Cl-4-F | CF$_3$ | CH$_2$OCH$_3$ | CH=NOCH$_3$ |
| 3-Cl-4-F | CF$_3$ | H | CH=NOEt |
| 3-Cl-4-F | CF$_3$ | H | C(O)OCH$_3$ |
| 3-Cl-4-F | CF$_3$ | Et | C(O)OCH$_3$ |
| 3-Cl-4-F | CF$_3$ | CH$_2$OCH$_3$ | C(O)OCH$_3$ |
| 3-Cl-4-F | CF$_3$ | CH$_2$OEt | C(O)OCH$_3$ |
| 3-Cl-4-F | CF$_3$ | CH$_2$OCH$_2$CF$_3$ | C(O)OCH$_3$ |
| 3-Cl-4-F | CF$_3$ | CH$_2$OC(O)CH$_3$ | C(O)OCH$_3$ |
| 3-Cl-4-F | CF$_3$ | CH2OC(O)Et | C(O)OCH$_3$ |
| 3-Cl-4-F | CF$_3$ | CH$_2$OC(O)OCH$_3$ | C(O)OCH$_3$ |
| 3-Cl-4-F | CF$_3$ | E-5a | C(O)OCH$_3$ |
| 3-Cl-4-F | CF$_3$ | C(O)OCH$_3$ | C(O)OCH$_3$ |
| 3-Cl-4-F | CF$_3$ | C(O)Et | C(O)OCH$_3$ |
| 3-Cl-4-F | CF$_3$ | C(O)Pr-n | C(O)OCH$_3$ |
| 3-Cl-4-F | CF$_3$ | C(O)Pr-i | C(O)OCH$_3$ |
| 3-Cl-4-F | CF$_3$ | C(O)Bu-t | C(O)OCH$_3$ |
| 3-Cl-4-F | CF$_3$ | C(O)CH$_2$OCH$_3$ | C(O)OCH$_3$ |
| 3-Cl-4-F | CF$_3$ | C(O)CH$_2$SCH$_3$ | C(O)OCH$_3$ |
| 3-Cl-4-F | CF$_3$ | C(O)OCH$_3$ | C(O)OEt |
| 3-Cl-4-F | CF$_3$ | H | C(O)OPr-i |
| 3-Cl-4-F | CF$_3$ | C(O)OCH$_3$ | C(O)OPr-i |
| 3-Cl-4-F | CF$_3$ | H | C(O)NH$_2$ |
| 3-Cl-4-F | CF$_3$ | CH$_3$ | (D-52d)Cl |
| 3-Cl-4-F | CF$_3$ | CH$_2$OCH$_3$ | (D-52d)Cl |
| 3-Cl-4-F | CF$_3$ | C(O)OCH$_3$ | (D-52d)Cl |
| 3-Cl-4-F | CF$_3$ | CH$_3$ | (D-55c)Cl |
| 3-Cl-4-F | CF$_3$ | CH$_2$OCH$_3$ | (D-55c)Cl |
| 3-Cl-4-F | CF$_3$ | CH$_2$OC(O)CH$_3$ | (D-55c)Cl |
| 3-Cl-4-F | CF$_3$ | CH$_2$OC(O)Bu-t | (D-55c)Cl |
| 3-Cl-4-F | CF$_3$ | CH$_2$OC(O)OCH$_3$ | (D-55c)Cl |
| 3-Cl-4-F | CF$_3$ | CH$_2$CN | (D-55c)Cl |
| 3-Cl-4-F | CF$_3$ | C(O)CH$_3$ | (D-55c)Cl |
| 3-Cl-4-F | CF$_3$ | C(O)Et | (D-55c)Cl |
| 3-Cl-4-F | CF$_3$ | C(O)Pr-n | (D-55c)Cl |
| 3-Cl-4-F | CF$_3$ | C(O)Pr-i | (D-55c)Cl |
| 3-Cl-4-F | CF$_3$ | C(O)Pr-c | (D-55c)Cl |
| 3-Cl-4-F | CF$_3$ | C(O)Bu-t | (D-55c)Cl |
| 3-Cl-4-F | CF$_3$ | C(O)CH$_2$Cl | (D-55c)Cl |
| 3-Cl-4-F | CF$_3$ | C(O)CH$_2$OCH$_3$ | (D-55c)Cl |
| 3-Cl-4-F | CF$_3$ | C(O)CH$_2$OEt | (D-55c)Cl |
| 3-Cl-4-F | CF$_3$ | C(O)CH$_2$SCH$_3$ | (D-55c)Cl |
| 3-Cl-4-F | CF$_3$ | C(O)CH$_2$S(O)CH$_3$ | (D-55c)Cl |
| 3-Cl-4-F | CF$_3$ | C(O)C(O)OEt | (D-55c)Cl |
| 3-Cl-4-F | CF$_3$ | C(O)OCH$_3$ | (D-55c)Cl |
| 3-Cl-4-F | CF$_3$ | C(O)OPr-n | (D-55c)Cl |
| 3-Cl-4-F | CF$_3$ | C(O)OCH$_2$Cl | (D-55c)Cl |
| 3-Cl-4-F | CF$_3$ | C(O)OCH$_2$CH$_2$Cl | (D-55c)Cl |
| 3-Cl-4-F | CF$_3$ | C(O)OCH$_2$CH$_2$OCH$_3$ | (D-55c)Cl |
| 3-Cl-4-F | CF$_3$ | C(O)OCH$_2$CH=CH$_2$ | (D-55c)Cl |
| 3-Cl-4-F | CF$_3$ | CH$_3$ | (D-55c)Br |
| 3-Cl-4-F | CF$_3$ | CH$_2$OC(O)CH$_3$ | (D-55c)Br |
| 3-Cl-4-F | CF$_3$ | C(O)CH$_3$ | (D-55c)Br |
| 3-Cl-4-F | CF$_3$ | C(O)Et | (D-55c)Br |
| 3-Cl-4-F | CF$_3$ | C(O)Pr-n | (D-55c)Br |
| 3-Cl-4-F | CF$_3$ | C(O)Pr-i | (D-55c)Br |
| 3-Cl-4-F | CF$_3$ | C(O)OCH$_3$ | (D-55c)Br |
| 3-Cl-4-F | CF$_3$ | C(O)OEt | (D-55c)Br |
| 3-Cl-4-F | CF$_3$ | C(O)OCH$_2$CH$_2$OCH$_3$ | (D-55c)Br |
| 3-Cl-4-F | CF$_3$ | C(O)Pr-i | D-57a |
| 3-Cl-4-F | CF$_2$Cl | H | CH=NOCH$_3$ |
| 3-Cl-4-F | CF$_2$Cl | H | CH=NOEt |
| 3-Cl-4-F | CF$_2$Cl | H | C(O)OCH$_3$ |
| 3-Cl-4-F | CF$_2$Cl | Et | C(O)OCH$_3$ |
| 3-Cl-4-F | CF$_2$Cl | CH$_2$OCH$_3$ | C(O)OCH$_3$ |
| 3-Cl-4-F | CF$_2$Cl | CH$_2$OEt | C(O)OCH$_3$ |
| 3-Cl-4-F | CF$_2$Cl | CH$_2$OCH$_2$CF$_3$ | C(O)OCH$_3$ |
| 3-Cl-4-F | CF$_2$Cl | C(O)Et | C(O)OCH$_3$ |
| 3-Cl-4-F | CF$_2$Cl | C(O)OCH$_3$ | C(O)OEt |
| 3-Cl-4-F | CF$_2$Cl | H | C(O)NH$_2$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-4-F | CF$_2$Cl | CH$_3$ | (D-55c)Cl |
| 3-Cl-4-F | CF$_2$Cl | CH$_2$OCH$_3$ | (D-55c)Cl |
| 3-Cl-4-F | CF$_2$Cl | C(O)CH$_3$ | (D-55c)Cl |
| 3-Cl-4-F | CF$_2$Cl | C(O)Et | (D-55c)Cl |
| 3-Cl-4-F | CF$_2$Cl | C(O)Pr-i | (D-55c)Cl |
| 3-Cl-4-F | CF$_2$Cl | C(O)CH$_2$OCH$_3$ | (D-55c)Cl |
| 3-Cl-4-F | CF$_2$Cl | C(O)OCH$_3$ | (D-55c)Cl |
| 3-Cl-4-F | CF$_2$Cl | C(O)CH$_3$ | (D-55c)Br |
| 3-Cl-4-F | CF$_2$Cl | C(O)Et | (D-55c)Br |
| 3-Cl-4-F | CF$_2$Cl | C(O)Pr-i | (D-55c)Br |
| 3-Cl-4-F | CF$_2$Br | CH$_2$OCH$_2$CF$_3$ | C(O)OCH$_3$ |
| 3-Cl-4-F | CF$_2$CHF$_2$ | C(O)Et | C(O)OCH$_3$ |
| 2-F-4-Cl | CF$_3$ | C(O)CH$_3$ | (D-55c)Cl |
| 2-F-4-Cl | CF$_3$ | C(O)Pr-i | (D-55c)Cl |
| 3-F-5-Cl | CHF$_2$ | C(O)OCH$_3$ | (D-55c)Cl |
| 3-F-5-Cl | CF$_3$ | H | CH=NOCH$_3$ |
| 3-F-5-Cl | CF$_3$ | CH$_2$OCH$_3$ | CH=NOCH$_3$ |
| 3-F-5-Cl | CF$_3$ | H | CH=NOEt |
| 3-F-5-Cl | CF$_3$ | H | C(O)OCH$_3$ |
| 3-F-5-Cl | CF$_3$ | Et | C(O)OCH$_3$ |
| 3-F-5-Cl | CF$_3$ | CH$_2$OCH$_3$ | C(O)OCH$_3$ |
| 3-F-5-Cl | CF$_3$ | CH$_2$OEt | C(O)OCH$_3$ |
| 3-F-5-Cl | CF$_3$ | CH$_2$OCH$_2$CF$_3$ | C(O)OCH$_3$ |
| 3-F-5-Cl | CF$_3$ | CH$_2$OC(O)CH$_3$ | C(O)OCH$_3$ |
| 3-F-5-Cl | CF$_3$ | CH$_2$OC(O)Et | C(O)OCH$_3$ |
| 3-F-5-Cl | CF$_3$ | CH$_2$OC(O)OCH$_3$ | C(O)OCH$_3$ |
| 3-F-5-Cl | CF$_3$ | E-5a | C(O)OCH$_3$ |
| 3-F-5-Cl | CF$_3$ | C(O)CH$_3$ | C(O)OCH$_3$ |
| 3-F-5-Cl | CF$_3$ | C(O)Et | C(O)OCH$_3$ |
| 3-F-5-Cl | CF$_3$ | C(O)Pr-n | C(O)OCH$_3$ |
| 3-F-5-Cl | CF$_3$ | C(O)Pr-i | C(O)OCH$_3$ |
| 3-F-5-Cl | CF$_3$ | C(O)Bu-t | C(O)OCH$_3$ |
| 3-F-5-Cl | CF$_3$ | C(O)CH$_2$OCH$_3$ | C(O)OCH$_3$ |
| 3-F-5-Cl | CF$_3$ | C(O)CH$_2$SCH$_3$ | C(O)OCH$_3$ |
| 3-F-5-Cl | CF$_3$ | C(O)OCH$_3$ | C(O)OEt |
| 3-F-5-Cl | CF$_3$ | H | C(O)OPr-i |
| 3-F-5-Cl | CF$_3$ | C(O)OCH$_3$ | C(O)OPr-i |
| 3-F-5-Cl | CF$_3$ | H | C(O)NH$_2$ |
| 3-F-5-Cl | CF$_3$ | CH$_3$ | (D-52d)Cl |
| 3-F-5-Cl | CF$_3$ | CH$_2$OCH$_3$ | (D-52d)Cl |
| 3-F-5-Cl | CF$_3$ | C(O)OCH$_3$ | (D-52d)Cl |
| 3-F-5-Cl | CF$_3$ | CH$_3$ | (D-55c)Cl |
| 3-F-5-Cl | CF$_3$ | CH$_2$OCH$_3$ | (D-55c)Cl |
| 3-F-5-Cl | CF$_3$ | CH$_2$OC(O)CH$_3$ | (D-55c)Cl |
| 3-F-5-Cl | CF$_3$ | CH$_2$OC(O)Bu-t | (D-55c)Cl |
| 3-F-5-Cl | CF$_3$ | CH$_2$OC(O)OCH$_3$ | (D-55c)Cl |
| 3-F-5-Cl | CF$_3$ | CH$_2$CN | (D-55c)Cl |
| 3-F-5-Cl | CF$_3$ | C(O)CH$_3$ | (D-55c)Cl |
| 3-F-5-Cl | CF$_3$ | C(O)Et | (D-55c)Cl |
| 3-F-5-Cl | CF$_3$ | C(O)Pr-n | (D-55c)Cl |
| 3-F-5-Cl | CF$_3$ | C(O)Pr-i | (D-55c)Cl |
| 3-F-5-Cl | CF$_3$ | C(O)Pr-c | (D-55c)Cl |
| 3-F-5-Cl | CF$_3$ | C(O)Bu-t | (D-55c)Cl |
| 3-F-5-Cl | CF$_3$ | C(O)CH$_2$Cl | (D-55c)Cl |
| 3-F-5-Cl | CF$_3$ | C(O)CH$_2$OCH$_3$ | (D-55c)Cl |
| 3-F-5-Cl | CF$_3$ | C(O)CH$_2$OEt | (D-55c)Cl |
| 3-F-5-Cl | CF$_3$ | C(O)CH$_2$SCH$_3$ | (D-55c)Cl |
| 3-F-5-Cl | CF$_3$ | C(O)CH$_2$S(O)CH$_3$ | (D-55c)Cl |
| 3-F-5-Cl | CF$_3$ | C(O)C(O)OEt | (D-55c)Cl |
| 3-F-5-Cl | CF$_3$ | C(O)OCH$_3$ | (D-55c)Cl |
| 3-F-5-Cl | CF$_3$ | C(O)OPr-n | (D-55c)Cl |
| 3-F-5-Cl | CF$_3$ | C(O)OCH$_2$Cl | (D-55c)Cl |
| 3-F-5-Cl | CF$_3$ | C(O)OCH$_2$CH$_2$Cl | (D-55c)Cl |
| 3-F-5-Cl | CF$_3$ | C(O)OCH$_2$CH$_2$OCH$_3$ | (D-55c)Cl |
| 3-F-5-Cl | CF$_3$ | C(O)OCH$_2$CH=CH$_2$ | (D-55c)Cl |
| 3-F-5-Cl | CF$_3$ | CH$_3$ | (D-55c)Br |
| 3-F-5-Cl | CF$_3$ | CH$_2$OC(O)CH$_3$ | (D-55c)Br |
| 3-F-5-Cl | CF$_3$ | C(O)CH$_3$ | (D-55c)Br |
| 3-F-5-Cl | CF$_3$ | C(O)Et | (D-55c)Br |
| 3-F-5-Cl | CF$_3$ | C(O)Pr-n | (D-55c)Br |
| 3-F-5-Cl | CF$_3$ | C(O)Pr-i | (D-55c)Br |
| 3-F-5-Cl | CF$_3$ | C(O)OCH$_3$ | (D-55c)Br |
| 3-F-5-Cl | CF$_3$ | C(O)OEt | (D-55c)Br |
| 3-F-5-Cl | CF$_3$ | C(O)OCH$_2$CH$_2$OCH$_3$ | (D-55c)Br |
| 3-F-5-Cl | CF$_3$ | C(O)Pr-i | D-57a |
| 3-F-5-Cl | CF$_2$Cl | H | CH=NOCH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-F-5-Cl | CF$_2$Cl | H | CH=NOEt |
| 3-F-5-Cl | CF$_2$Cl | H | C(O)OCH$_3$ |
| 3-F-5-Cl | CF$_2$Cl | Et | C(O)OCH$_3$ |
| 3-F-5-Cl | CF$_2$Cl | CH$_2$OCH$_3$ | C(O)OCH$_3$ |
| 3-F-5-Cl | CF$_2$Cl | CH$_2$OEt | C(O)OCH$_3$ |
| 3-F-5-Cl | CF$_2$Cl | CH$_2$OCH$_2$CF$_3$ | C(O)OCH$_3$ |
| 3-F-5-Cl | CF$_2$Cl | C(O)Et | C(O)OCH$_3$ |
| 3-F-5-Cl | CF$_2$Cl | C(O)OCH$_3$ | C(O)OEt |
| 3-F-5-Cl | CF$_2$Cl | H | C(O)NH$_2$ |
| 3-F-5-Cl | CF$_2$Cl | CH$_3$ | (D-55c)Cl |
| 3-F-5-Cl | CF$_2$Cl | CH$_2$OCH$_3$ | (D-55c)Cl |
| 3-F-5-Cl | CF$_2$Cl | C(O)CH$_3$ | (D-55c)Cl |
| 3-F-5-Cl | CF$_2$Cl | C(O)Et | (D-55c)Cl |
| 3-F-5-Cl | CF$_2$Cl | C(O)Pr-i | (D-55c)Cl |
| 3-F-5-Cl | CF$_2$Cl | C(O)CH$_2$OCH$_3$ | (D-55c)Cl |
| 3-F-5-Cl | CF$_2$Cl | C(O)OCH$_3$ | (D-55c)Cl |
| 3-F-5-Cl | CF$_2$Cl | C(O)CH$_3$ | (D-55c)Br |
| 3-F-5-Cl | CF$_2$Cl | C(O)Et | (D-55c)Br |
| 3-F-5-Cl | CF$_2$Cl | C(O)Pr-i | (D-55c)Br |
| 3-F-5-Cl | CF$_2$Br | C(O)CH$_3$ | (D-55c)Br |
| 3-F-5-Cl | CF$_2$CHF$_2$ | H | CH=NOCH$_3$ |
| 2,3-Cl$_2$ | CF$_3$ | H | CH=NOEt |
| 2,4-Cl$_2$ | CF$_3$ | CH$_2$OEt | C(O)OCH$_3$ |
| 2,4-Cl$_2$ | CF$_3$ | CH$_2$OCH$_2$CF$_3$ | C(O)OCH$_3$ |
| 3,4-Cl$_2$ | CHF$_2$ | C(O)Et | C(O)OCH$_3$ |
| 3,4-Cl$_2$ | CF$_3$ | H | CH=NOCH$_3$ |
| 3,4-Cl$_2$ | CF$_3$ | CH$_2$OCH$_3$ | CH=NOCH$_3$ |
| 3,4-Cl$_2$ | CF$_3$ | H | CH=NOEt |
| 3,4-Cl$_2$ | CF$_3$ | H | C(O)OCH$_3$ |
| 3,4-Cl$_2$ | CF$_3$ | Et | C(O)OCH$_3$ |
| 3,4-Cl$_2$ | CF$_3$ | CH$_2$OCH$_3$ | C(O)OCH$_3$ |
| 3,4-Cl$_2$ | CF$_3$ | CH$_2$OEt | C(O)OCH$_3$ |
| 3,4-Cl$_2$ | CF$_3$ | CH$_2$OCH$_2$CF$_3$ | C(O)OCH$_3$ |
| 3,4-Cl$_2$ | CF$_3$ | CH$_2$OC(O)CH$_3$ | C(O)OCH$_3$ |
| 3,4-Cl$_2$ | CF$_3$ | CH$_2$OC(O)Et | C(O)OCH$_3$ |
| 3,4-Cl$_2$ | CF$_3$ | CH$_2$OC(O)OCH$_3$ | C(O)OCH$_3$ |
| 3,4-Cl$_2$ | CF$_3$ | E-5a | C(O)OCH$_3$ |
| 3,4-Cl$_2$ | CF$_3$ | C(O)CH$_3$ | C(O)OCH$_3$ |
| 3,4-Cl$_2$ | CF$_3$ | C(O)Et | C(O)OCH$_3$ |
| 3,4-Cl$_2$ | CF$_3$ | C(O)Pr-n | C(O)OCH$_3$ |
| 3,4-Cl$_2$ | CF$_3$ | C(O)Pr-i | C(O)OCH$_3$ |
| 3,4-Cl$_2$ | CF$_3$ | C(O)Bu-t | C(O)OCH$_3$ |
| 3,4-Cl$_2$ | CF$_3$ | C(O)CH$_2$OCH$_3$ | C(O)OCH$_3$ |
| 3,4-Cl$_2$ | CF$_3$ | C(O)CH$_2$SCH$_3$ | C(O)OCH$_3$ |
| 3,4-Cl$_2$ | CF$_3$ | C(O)OCH$_3$ | C(O)OEt |
| 3,4-Cl$_2$ | CF$_3$ | H | C(O)OPr-i |
| 3,4-Cl$_2$ | CF$_3$ | C(O)OCH$_3$ | C(O)OPr-i |
| 3,4-Cl$_2$ | CF$_3$ | H | C(O)NH$_2$ |
| 3,4-Cl$_2$ | CF$_3$ | CH$_3$ | (D-52d)Cl |
| 3,4-Cl$_2$ | CF$_3$ | CH$_2$OCH$_3$ | (D-52d)Cl |
| 3,4-Cl$_2$ | CF$_3$ | C(O)OCH$_3$ | (D-52d)Cl |
| 3,4-Cl$_2$ | CF$_3$ | CH$_3$ | (D-55c)Cl |
| 3,4-Cl$_2$ | CF$_3$ | CH$_2$OCH$_3$ | (D-55c)Cl |
| 3,4-Cl$_2$ | CF$_3$ | CH$_2$OC(O)CH$_3$ | (D-55c)Cl |
| 3,4-Cl$_2$ | CF$_3$ | CH$_2$OC(O)Bu-t | (D-55c)Cl |
| 3,4-Cl$_2$ | CF$_3$ | CH$_2$OC(O)OCH$_3$ | (D-55c)Cl |
| 3,4-Cl$_2$ | CF$_3$ | CH$_2$CN | (D-55c)Cl |
| 3,4-Cl$_2$ | CF$_3$ | C(O)CH$_3$ | (D-55c)Cl |
| 3,4-Cl$_2$ | CF$_3$ | C(O)Et | (D-55c)Cl |
| 3,4-Cl$_2$ | CF$_3$ | C(O)Pr-n | (D-55c)Cl |
| 3,4-Cl$_2$ | CF$_3$ | C(O)Pr-i | (D-55c)Cl |
| 3,4-Cl$_2$ | CF$_3$ | C(O)Pr-c | (D-55c)Cl |
| 3,4-Cl$_2$ | CF$_3$ | C(O)Bu-t | (D-55c)Cl |
| 3,4-Cl$_2$ | CF$_3$ | C(O)CH$_2$Cl | (D-55c)Cl |
| 3,4-Cl$_2$ | CF$_3$ | C(O)CH$_2$OCH$_3$ | (D-55c)Cl |
| 3,4-Cl$_2$ | CF$_3$ | C(O)CH$_2$OEt | (D-55c)Cl |
| 3,4-Cl$_2$ | CF$_3$ | C(O)CH$_2$SCH$_3$ | (D-55c)Cl |
| 3,4-Cl$_2$ | CF$_3$ | C(O)CH$_2$S(O)CH$_3$ | (D-55c)Cl |
| 3,4-Cl$_2$ | CF$_3$ | C(O)C(O)OEt | (D-55c)Cl |
| 3,4-Cl$_2$ | CF$_3$ | C(O)OCH$_3$ | (D-55c)Cl |
| 3,4-Cl$_2$ | CF$_3$ | C(O)OPr-n | (D-55c)Cl |
| 3,4-Cl$_2$ | CF$_3$ | C(O)OCH$_2$Cl | (D-55c)Cl |
| 3,4-Cl$_2$ | CF$_3$ | C(O)OCF$_2$CH$_2$Cl | (D-55c)Cl |
| 3,4-Cl$_2$ | CF$_3$ | C(O)OCH$_2$CH$_2$OCH$_3$ | (D-55c)Cl |
| 3,4-Cl$_2$ | CF$_3$ | C(O)OCH$_2$CH=CH$_2$ | (D-55c)Cl |
| 3,4-Cl$_2$ | CF$_3$ | CH$_3$ | (D-55c)Br |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4-Cl$_2$ | CF$_3$ | CH$_2$OC(O)CH$_3$ | (D-55c)Br |
| 3,4-Cl$_2$ | CF$_3$ | C(O)CH$_3$ | (D-55c)Br |
| 3,4-Cl$_2$ | CF$_3$ | C(O)Et | (D-55c)Br |
| 3,4-Cl$_2$ | CF$_3$ | C(O)Pr-n | (D-55c)Br |
| 3,4-Cl$_2$ | CF$_3$ | C(O)Pr-i | (D-55c)Br |
| 3,4-Cl$_2$ | CF$_3$ | C(O)OCH$_3$ | (D-55c)Br |
| 3,4-Cl$_2$ | CF$_3$ | C(O)OEt | (D-55c)Br |
| 3,4-Cl$_2$ | CF$_3$ | C(O)OCH$_2$CH$_2$OCH$_3$ | (D-55c)Br |
| 3,4-Cl$_2$ | CF$_3$ | C(O)Pr-i | D-57a |
| 3,4-Cl$_2$ | CF$_2$Cl | H | CH=NOCH$_3$ |
| 3,4-Cl$_2$ | CF$_2$Cl | H | CH=NOEt |
| 3,4-Cl$_2$ | CF$_2$Cl | H | C(O)OCH$_3$ |
| 3,4-Cl$_2$ | CF$_2$Cl | Et | C(O)OCH$_3$ |
| 3,4-Cl$_2$ | CF$_2$Cl | CH$_2$OCH$_3$ | C(O)OCH$_3$ |
| 3,4-Cl$_2$ | CF$_2$Cl | CH$_2$OEt | C(O)OCH$_3$ |
| 3,4-Cl$_2$ | CF$_2$Cl | CH$_2$OCH$_2$CF$_3$ | C(O)OCH$_3$ |
| 3,4-Cl$_2$ | CF$_2$Cl | C(O)Et | C(O)OCH$_3$ |
| 3,4-Cl$_2$ | CF$_2$Cl | C(O)OCH$_3$ | C(O)OEt |
| 3,4-Cl$_2$ | CF$_2$Cl | H | C(O)NH$_2$ |
| 3,4-Cl$_2$ | CF$_2$Cl | CH$_3$ | (D-55c)Cl |
| 3,4-Cl$_2$ | CF$_2$Cl | CH$_2$OCH$_3$ | (D-55c)Cl |
| 3,4-Cl$_2$ | CF$_2$Cl | C(O)CH$_3$ | (D-55c)Cl |
| 3,4-Cl$_2$ | CF$_2$Cl | C(O)Et | (D-55c)Cl |
| 3,4-Cl$_2$ | CF$_2$Cl | C(O)Pr-i | (D-55c)Cl |
| 3,4-Cl$_2$ | CF$_2$Cl | C(O)CH$_2$OCH$_3$ | (D-55c)Cl |
| 3,4-Cl$_2$ | CF$_2$Cl | C(O)OCH$_3$ | (D-55c)Cl |
| 3,4-Cl$_2$ | CF$_2$Cl | C(O)CH$_3$ | (D-55c)Br |
| 3,4-Cl$_2$ | CF$_2$Cl | C(O)Et | (D-55c)Br |
| 3,4-Cl$_2$ | CF$_2$Cl | C(O)Pr-i | (D-55c)Br |
| 3,4-Cl$_2$ | CF$_2$Br | C(O)CH$_3$ | (D-55c)Cl |
| 3,4-Cl$_2$ | CF$_2$CHF$_2$ | C(O)Pr-i | (D-55c)Cl |
| 3,5-Cl$_2$ | CH$_3$ | C(O)OCH$_3$ | (D-55c)Cl |
| 3,5-Cl$_2$ | Et | C(O)CH$_3$ | (D-55c)Br |
| 3,5-Cl$_2$ | n-Pr | H | CH=NOCH$_3$ |
| 3,5-Cl$_2$ | i-Pr | H | CH=NOEt |
| 3,5-Cl$_2$ | c-Pr | CH$_2$OEt | C(O)OCH$_3$ |
| 3,5-Cl$_2$ | CH$_2$F | CH$_2$OCH$_2$CF$_3$ | C(O)OCH$_3$ |
| 3,5-Cl$_2$ | CH$_2$Cl | C(O)Et | C(O)OCH$_3$ |
| 3,5-Cl$_2$ | CH$_2$Br | C(O)CH$_3$ | (D-55c)Cl |
| 3,5-Cl$_2$ | CH$_2$I | C(O)Pr-i | (D-55c)Cl |
| 3,5-Cl$_2$ | CHF$_2$ | H | CH=NOCH$_3$ |
| 3,5-Cl$_2$ | CHF$_2$ | H | CH=NOEt |
| 3,5-Cl$_2$ | CHF$_2$ | H | C(O)OCH$_3$ |
| 3,5-Cl$_2$ | CHF$_2$ | Et | C(O)OCH$_3$ |
| 3,5-Cl$_2$ | CHF$_2$ | CH$_2$OCH$_3$ | C(O)OCH$_3$ |
| 3,5-Cl$_2$ | CHF$_2$ | CH$_2$OEt | C(O)OCH$_3$ |
| 3,5-Cl$_2$ | CHF$_2$ | CH$_2$OCH$_2$CF$_3$ | C(O)OCH$_3$ |
| 3,5-Cl$_2$ | CHF$_2$ | C(O)Et | C(O)OCH$_3$ |
| 3,5-Cl$_2$ | CHF$_2$ | C(O)OCH$_3$ | C(O)OEt |
| 3,5-Cl$_2$ | CHF$_2$ | H | C(O)NH$_2$ |
| 3,5-Cl$_2$ | CHF$_2$ | CH$_3$ | (D-55c)Cl |
| 3,5-Cl$_2$ | CHF$_2$ | CH$_2$OCH$_3$ | (D-55c)Cl |
| 3,5-Cl$_2$ | CHF$_2$ | C(O)OCH$_3$ | (D-55c)Cl |
| 3,5-Cl$_2$ | CHF$_2$ | C(O)Et | (D-55c)Cl |
| 3,5-Cl$_2$ | CHF$_2$ | C(O)Pr-i | (D-55c)Cl |
| 3,5-Cl$_2$ | CHF$_2$ | C(O)CH$_2$OCH$_3$ | (D-55c)Cl |
| 3,5-Cl$_2$ | CHF$_2$ | C(O)OCH$_3$ | (D-55c)Cl |
| 3,5-Cl$_2$ | CHF$_2$ | C(O)CH$_3$ | (D-55c)Br |
| 3,5-Cl$_2$ | CHF$_2$ | C(O)Et | (D-55c)Br |
| 3,5-Cl$_2$ | CHF$_2$ | C(O)Pr-i | (D-55c)Br |
| 3,5-Cl$_2$ | CHFCl | H | CH=NOCH$_3$ |
| 3,5-Cl$_2$ | CHFCl | H | CH=NOEt |
| 3,5-Cl$_2$ | CHFCl | CH$_2$OEt | C(O)OCH$_3$ |
| 3,5-Cl$_2$ | CHFCl | CH$_2$OCH$_2$CF$_3$ | C(O)OCH$_3$ |
| 3,5-Cl$_2$ | CHFCl | C(O)Et | C(O)OCH$_3$ |
| 3,5-Cl$_2$ | CHFCl | C(O)CH$_3$ | (D-55c)Cl |
| 3,5-Cl$_2$ | CHFCl | C(O)Pr-i | (D-55c)Cl |
| 3,5-Cl$_2$ | CHFCl | C(O)OCH$_3$ | (D-55c)Cl |
| 3,5-Cl$_2$ | CHFCl | C(O)CH$_3$ | (D-55c)Br |
| 3,5-Cl$_2$ | CHCl$_2$ | H | CH=NOCH$_3$ |
| 3,5-Cl$_2$ | CHCl$_2$ | H | CH=NOEt |
| 3,5-Cl$_2$ | CHCl$_2$ | CH$_2$OEt | C(O)OCH$_3$ |
| 3,5-Cl$_2$ | CHCl$_2$ | CH$_2$OCH$_2$CF$_3$ | C(O)OCH$_3$ |
| 3,5-Cl$_2$ | CHCl$_2$ | C(O)Et | C(O)OCH$_3$ |
| 3,5-Cl$_2$ | CHCl$_2$ | C(O)CH$_3$ | (D-55c)Cl |
| 3,5-Cl$_2$ | CHCl$_2$ | C(O)Pr-i | (D-55c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CHCl$_2$ | C(O)OCH$_3$ | (D-55c)Cl |
| 3,5-Cl$_2$ | CHCl$_2$ | C(O)CH$_3$ | (D-55c)Br |
| 3,5-Cl$_2$ | CHFBr | H | CH=NOCH$_3$ |
| 3,5-Cl$_2$ | CHFBr | H | CH=NOEt |
| 3,5-Cl$_2$ | CHFBr | CH$_2$OEt | C(O)OCH$_3$ |
| 3,5-Cl$_2$ | CHFBr | CH$_2$OCH$_2$CF$_3$ | C(O)OCH$_3$ |
| 3,5-Cl$_2$ | CHFBr | C(O)Et | C(O)OCH$_3$ |
| 3,5-Cl$_2$ | CHFBr | C(O)CH$_3$ | (D-55c)Cl |
| 3,5-Cl$_2$ | CHFBr | C(O)Pr-i | (D-55c)Cl |
| 3,5-Cl$_2$ | CHFBr | C(O)OCH$_3$ | (D-55c)Cl |
| 3,5-Cl$_2$ | CHFBr | C(O)CH$_3$ | (D-55c)Br |
| 3,5-Cl$_2$ | CF$_3$ | H | CH=NOH |
| 3,5-Cl$_2$ | CF$_3$ | H | CH=NOCH$_3$ |
| 3,5-Cl$_2$ | CF$_3$ | H | CH=NOCH$_3$(E) |
| 3,5-Cl$_2$ | CF$_3$ | H | CH=NOCH$_3$(Z) |
| 3,5-Cl$_2$ | CF$_3$ | CH$_3$ | CH=NOCH$_3$ |
| 3,5-Cl$_2$ | CF$_3$ | CH$_3$ | CH=NOCH$_3$(E) |
| 3,5-Cl$_2$ | CF$_3$ | CH$_3$ | CH=NOCH$_3$(Z) |
| 3,5-Cl$_2$ | CF$_3$ | Et | CH=NOCH$_3$ |
| 3,5-Cl$_2$ | CF$_3$ | n-Pr | CH=NOCH$_3$ |
| 3,5-Cl$_2$ | CF$_3$ | i-Pr | CH=NOCH$_3$ |
| 3,5-Cl$_2$ | CF$_3$ | CH$_2$OCH$_3$ | CH=NOCH$_3$ |
| 3,5-Cl$_2$ | CF$_3$ | CH$_2$OEt | CH=NOCH$_3$ |
| 3,5-Cl$_2$ | CF$_3$ | CH$_2$OPr-n | CH=NOCH$_3$ |
| 3,5-Cl$_2$ | CF$_3$ | CH$_2$OPr-i | CH=NOCH$_3$ |
| 3,5-Cl$_2$ | CF$_3$ | CH$_2$OPr-c | CH=NOCH$_3$ |
| 3,5-Cl$_2$ | CF$_3$ | CH$_2$OCH$_2$Pr-c | CH=NOCH$_3$ |
| 3,5-Cl$_2$ | CF$_3$ | CH$_2$OCH$_2$CH$_2$F | CH=NOCH$_3$ |
| 3,5-Cl$_2$ | CF$_3$ | CH$_2$OCH$_2$CH$_2$Cl | CH=NOCH$_3$ |
| 3,5-Cl$_2$ | CF$_3$ | CH$_2$OCH$_2$CHF$_2$ | CH=NOCH$_3$ |
| 3,5-Cl$_2$ | CF$_3$ | CH$_2$OCH$_2$CHCl$_2$ | CH=NOCH$_3$ |
| 3,5-Cl$_2$ | CF$_3$ | CH$_2$OCH$_2$CF$_3$ | CH=NOCH$_3$ |
| 3,5-Cl$_2$ | CF$_3$ | CH$_2$OCH$_2$CF$_2$Cl | CH=NOCH$_3$ |
| 3,5-Cl$_2$ | CF$_3$ | CH$_2$OCH$_2$CCl$_3$ | CH=NOCH$_3$ |
| 3,5-Cl$_2$ | CF$_3$ | CH$_2$OCH$_2$CH$_2$CH$_2$F | CH=NOCH$_3$ |
| 3,5-Cl$_2$ | CF$_3$ | CH$_2$OCH$_2$CH$_2$CF$_3$ | CH=NOCH$_3$ |
| 3,5-Cl$_2$ | CF$_3$ | CH$_2$OCH$_2$CF$_2$CHF$_2$ | CH=NOCH$_3$ |
| 3,5-Cl$_2$ | CF$_3$ | CH$_2$OCH$_2$CF$_2$CF$_3$ | CH=NOCH$_3$ |
| 3,5-Cl$_2$ | CF$_3$ | CH$_2$OCH(CH$_3$)CH$_2$F | CH=NOCH$_3$ |
| 3,5-Cl$_2$ | CF$_3$ | CH$_2$OCH(CH$_2$F)$_2$ | CH=NOCH$_3$ |
| 3,5-Cl$_2$ | CF$_3$ | CH$_2$OCH(CH$_3$)CF$_3$ | CH=NOCH$_3$ |
| 3,5-Cl$_2$ | CF$_3$ | CH$_2$OCH$_2$CH$_2$OCH$_3$ | CH=NOCH$_3$ |
| 3,5-Cl$_2$ | CF$_3$ | CH$_2$OCH$_2$CH$_2$OCH$_2$CF$_3$ | CH=NOCH$_3$ |
| 3,5-Cl$_2$ | CF$_3$ | CH$_2$OCH$_2$CH$_2$OCH$_2$CH$_2$OCH$_3$ | CH=NOCH$_3$ |
| 3,5-Cl$_2$ | CF$_3$ | CH$_2$OCH$_2$CH$_2$OPh | CH=NOCH$_3$ |
| 3,5-Cl$_2$ | CF$_3$ | CH$_2$OCH$_2$(E-5a) | CH=NOCH$_3$ |
| 3,5-Cl$_2$ | CF$_3$ | CH$_2$OCH$_2$(E-6a) | CH=NOCH$_3$ |
| 3,5-Cl$_2$ | CF$_3$ | CH$_2$OCH$_2$(E-11a) | CH=NOCH$_3$ |
| 3,5-Cl$_2$ | CF$_3$ | CH$_2$O(E-6a) | CH=NOCH$_3$ |
| 3,5-Cl$_2$ | CF$_3$ | CH$_2$O(E-25a) | CH=NOCH$_3$ |
| 3,5-Cl$_2$ | CF$_3$ | CH$_2$O(E-26a) | CH=NOCH$_3$ |
| 3,5-Cl$_2$ | CF$_3$ | CH$_2$OCH$_2$CH$_2$SCH$_3$ | CH=NOCH$_3$ |
| 3,5-Cl$_2$ | CF$_3$ | CH$_2$OCH$_2$CH$_2$S(O)CH$_3$ | CH=NOCH$_3$ |
| 3,5-Cl$_2$ | CF$_3$ | CH$_2$OCH$_2$CH$_2$SO$_2$CH$_3$ | CH=NOCH$_3$ |
| 3,5-Cl$_2$ | CF$_3$ | CH$_2$OCH$_2$CH$_2$SCH$_2$CH$_2$OCH$_3$ | CH=NOCH$_3$ |
| 3,5-Cl$_2$ | CF$_3$ | CH$_2$OCH$_2$CH$_2$SO$_2$CH$_2$CH$_2$OCH$_3$ | CH=NOCH$_3$ |
| 3,5-Cl$_2$ | CF$_3$ | CH$_2$OCH$_2$CH$_2$SCH$_2$CH$_2$SCH$_3$ | CH=NOCH$_3$ |
| 3,5-Cl$_2$ | CF$_3$ | CH$_2$OCH$_2$CH$_2$SCH$_2$CH=CH$_2$ | CH=NOCH$_3$ |
| 3,5-Cl$_2$ | CF$_3$ | CH$_2$OCH$_2$CH$_2$SCH$_2$C≡CH | CH=NOCH$_3$ |
| 3,5-Cl$_2$ | CF$_3$ | CH$_2$OCH$_2$CH$_2$SCH$_2$Ph | CH=NOCH$_3$ |
| 3,5-Cl$_2$ | CF$_3$ | CH$_2$OCH$_2$CH$_2$SO$_2$CH$_2$Ph | CH=NOCH$_3$ |
| 3,5-Cl$_2$ | CF$_3$ | CH$_2$OCH$_2$CH$_2$SPh | CH=NOCH$_3$ |
| 3,5-Cl$_2$ | CF$_3$ | CH$_2$OCH$_2$CH$_2$S(O)Ph | CH=NOCH$_3$ |
| 3,5-Cl$_2$ | CF$_3$ | CH$_2$OCH$_2$CH$_2$SO$_2$Ph | CH=NOCH$_3$ |
| 3,5-Cl$_2$ | CF$_3$ | CH$_2$OCH$_2$(E-7a) | CH=NOCH$_3$ |
| 3,5-Cl$_2$ | CF$_3$ | CH$_2$OCH$_2$(E-8a) | CH=NOCH$_3$ |
| 3,5-Cl$_2$ | CF$_3$ | CH$_2$OCH$_2$(E-8b) | CH=NOCH$_3$ |
| 3,5-Cl$_2$ | CF$_3$ | CH$_2$OCH$_2$(E-8c) | CH=NOCH$_3$ |
| 3,5-Cl$_2$ | CF$_3$ | CH$_2$OCH$_2$(E-19a) | CH=NOCH$_3$ |
| 3,5-Cl$_2$ | CF$_3$ | CH$_2$O(E-8a) | CH=NOCH$_3$ |
| 3,5-Cl$_2$ | CF$_3$ | CH$_2$O(E-8b) | CH=NOCH$_3$ |
| 3,5-Cl$_2$ | CF$_3$ | CH$_2$O(E-8c) | CH=NOCH$_3$ |
| 3,5-Cl$_2$ | CF$_3$ | CH$_2$O(E-28a) | CH=NOCH$_3$ |
| 3,5-Cl$_2$ | CF$_3$ | CH$_2$O(E-29a) | CH=NOCH$_3$ |
| 3,5-Cl$_2$ | CF$_3$ | CH$_2$OCH$_2$CN | CH=NOCH$_3$ |
| 3,5-Cl$_2$ | CF$_3$ | CH$_2$OCH(CH$_3$)CN | CH=NOCH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | CH$_2$OC(CH$_3$)$_2$CN | CH=NOCH$_3$ |
| 3,5-Cl$_2$ | CF$_3$ | CH$_2$OCH$_2$CH$_2$CN | CH=NOCH$_3$ |
| 3,5-Cl$_2$ | CF$_3$ | CH$_2$OCH$_2$C(O)OCH$_3$ | CH=NOCH$_3$ |
| 3,5-Cl$_2$ | CF$_3$ | CH$_2$OCH$_2$CH=CH$_2$ | CH=NOCH$_3$ |
| 3,5-Cl$_2$ | CF$_3$ | CH$_2$OCH$_2$C≡CH | CH=NOCH$_3$ |
| 3,5-Cl$_2$ | CF$_3$ | CH$_2$OCH$_2$Ph | CH=NOCH$_3$ |
| 3,5-Cl$_2$ | CF$_3$ | CH$_2$OC(O)CH$_3$ | CH=NOCH$_3$ |
| 3,5-Cl$_2$ | CF$_3$ | CH$_2$OC(O)Et | CH=NOCH$_3$ |
| 3,5-Cl$_2$ | CF$_3$ | CH$_2$OC(O)Pr-n | CH=NOCH$_3$ |
| 3,5-Cl$_2$ | CF$_3$ | CH$_2$OC(O)Pr-i | CH=NOCH$_3$ |
| 3,5-Cl$_2$ | CF$_3$ | CH$_2$OC(O)Pr-c | CH=NOCH$_3$ |
| 3,5-Cl$_2$ | CF$_3$ | CH$_2$OC(O)Bu-n | CH=NOCH$_3$ |
| 3,5-Cl$_2$ | CF$_3$ | CH$_2$OC(O)Bu-i | CH=NOCH$_3$ |
| 3,5-Cl$_2$ | CF$_3$ | CH$_2$OC(O)Bu-s | CH=NOCH$_3$ |
| 3,5-Cl$_2$ | CF$_3$ | CH$_2$OC(O)Bu-t | CH=NOCH$_3$ |
| 3,5-Cl$_2$ | CF$_3$ | CH$_2$OC(O)CH$_2$Ph | CH=NOCH$_3$ |
| 3,5-Cl$_2$ | CF$_3$ | CH$_2$OC(O)Ph | CH=NOCH$_3$ |
| 3,5-Cl$_2$ | CF$_3$ | CH$_2$OC(O)OCH$_3$ | CH=NOCH$_3$ |
| 3,5-Cl$_2$ | CF$_3$ | CH$_2$OC(O)OEt | CH=NOCH$_3$ |
| 3,5-Cl$_2$ | CF$_3$ | CH$_2$OC(O)OBu-n | CH=NOCH$_3$ |
| 3,5-Cl$_2$ | CF$_3$ | CH$_2$OC(O)OBu-i | CH=NOCH$_3$ |
| 3,5-Cl$_2$ | CF$_3$ | CH$_2$OC(O)OCH$_2$Ph | CH=NOCH$_3$ |
| 3,5-Cl$_2$ | CF$_3$ | CH$_2$OC(O)OPh | CH=NOCH$_3$ |
| 3,5-Cl$_2$ | CF$_3$ | CH$_2$OC(O)NHPh | CH=NOCH$_3$ |
| 3,5-Cl$_2$ | CF$_3$ | CH$_2$OPh | CH=NOCH$_3$ |
| 3,5-Cl$_2$ | CF$_3$ | CH$_2$SCH$_3$ | CH=NOCH$_3$ |
| 3,5-Cl$_2$ | CF$_3$ | CH$_2$SO$_2$CH$_3$ | CH=NOCH$_3$ |
| 3,5-Cl$_2$ | CF$_3$ | CH$_2$SC(O)CH$_3$ | CH=NOCH$_3$ |
| 3,5-Cl$_2$ | CF$_3$ | CH$_2$SC(O)Et | CH=NOCH$_3$ |
| 3,5-Cl$_2$ | CF$_3$ | CH$_2$SC(O)Ph | CH=NOCH$_3$ |
| 3,5-Cl$_2$ | CF$_3$ | CH$_2$SC(S)OCH$_3$ | CH=NOCH$_3$ |
| 3,5-Cl$_2$ | CF$_3$ | CH$_2$SC(S)OEt | CH=NOCH$_3$ |
| 3,5-Cl$_2$ | CF$_3$ | CH$_2$SC(S)OPr-n | CH=NOCH$_3$ |
| 3,5-Cl$_2$ | CF$_3$ | CH$_2$SC(S)OPr-i | CH=NOCH$_3$ |
| 3,5-Cl$_2$ | CF$_3$ | CH$_2$SC(S)N(CH$_3$)$_2$ | CH=NOCH$_3$ |
| 3,5-Cl$_2$ | CF$_3$ | CH$_2$SC(S)(T-14) | CH=NOCH$_3$ |
| 3,5-Cl$_2$ | CF$_3$ | CH$_2$N(CH$_3$)$_2$ | CH=NOCH$_3$ |
| 3,5-Cl$_2$ | CF$_3$ | CH$_2$N(CH$_3$)C(O)CH$_3$ | CH=NOCH$_3$ |
| 3,5-Cl$_2$ | CF$_3$ | CH$_2$NHC(O)OCH$_3$ | CH=NOCH$_3$ |
| 3,5-Cl$_2$ | CF$_3$ | CH$_2$N(CH$_3$)C(O)OCH$_3$ | CH=NOCH$_3$ |
| 3,5-Cl$_2$ | CF$_3$ | CH$_2$N(CH$_3$)SO$_2$CH$_3$ | CH=NOCH$_3$ |
| 3,5-Cl$_2$ | CF$_3$ | CH$_2$CN | CH=NOCH$_3$ |
| 3,5-Cl$_2$ | CF$_3$ | CH$_2$C(O)OCH$_3$ | CH=NOCH$_3$ |
| 3,5-Cl$_2$ | CF$_3$ | CH$_2$CH=CH$_2$ | CH=NOCH$_3$ |
| 3,5-Cl$_2$ | CF$_3$ | CH$_2$C≡CH | CH=NOCH$_3$ |
| 3,5-Cl$_2$ | CF$_3$ | CH$_2$Ph | CH=NOCH$_3$ |
| 3,5-Cl$_2$ | CF$_3$ | C(O)CH$_3$ | CH=NOCH$_3$ |
| 3,5-Cl$_2$ | CF$_3$ | C(O)OCH$_3$ | CH=NOCH$_3$ |
| 3,5-Cl$_2$ | CF$_3$ | C(O)OCH$_3$ | CH=NOCH$_3$(E) |
| 3,5-Cl$_2$ | CF$_3$ | C(O)OCH$_3$ | CH=NOCH$_3$(Z) |
| 3,5-Cl$_2$ | CF$_3$ | C(O)OEt | CH=NOCH$_3$ |
| 3,5-Cl$_2$ | CF$_3$ | C(O)OPr-n | CH=NOCH$_3$ |
| 3,5-Cl$_2$ | CF$_3$ | C(O)OPr-i | CH=NOCH$_3$ |
| 3,5-Cl$_2$ | CF$_3$ | C(O)OPr-c | CH=NOCH$_3$ |
| 3,5-Cl$_2$ | CF$_3$ | C(O)OBu-i | CH=NOCH$_3$ |
| 3,5-Cl$_2$ | CF$_3$ | C(O)OCH$_2$Cl | CH=NOCH$_3$ |
| 3,5-Cl$_2$ | CF$_3$ | C(O)OCH$_2$CH$_2$Cl | CH=NOCH$_3$ |
| 3,5-Cl$_2$ | CF$_3$ | C(O)OCH$_2$CH$_2$OCH$_3$ | CH=NOCH$_3$ |
| 3,5-Cl$_2$ | CF$_3$ | C(O)OCH$_2$CH$_2$SO$_2$CH$_3$ | CH=NOCH$_3$ |
| 3,5-Cl$_2$ | CF$_3$ | C(O)OCH$_2$CH=CH$_2$ | CH=NOCH$_3$ |
| 3,5-Cl$_2$ | CF$_3$ | C(O)OCH$_2$C≡CH | CH=NOCH$_3$ |
| 3,5-Cl$_2$ | CF$_3$ | C(O)SCH$_3$ | CH=NOCH$_3$ |
| 3,5-Cl$_2$ | CF$_3$ | C(S)OCH$_3$ | CH=NOCH$_3$ |
| 3,5-Cl$_2$ | CF$_3$ | C(S)SCH$_3$ | CH=NOCH$_3$ |
| 3,5-Cl$_2$ | CF$_3$ | SCCl$_3$ | CH=NOCH$_3$ |
| 3,5-Cl$_2$ | CF$_3$ | SN(Bu-n)$_2$ | CH=NOCH$_3$ |
| 3,5-Cl$_2$ | CF$_3$ | S(T-18) | CH=NOCH$_3$ |
| 3,5-Cl$_2$ | CF$_3$ | SN(Pr-i)CH$_2$CH$_2$C(O)OEt | CH=NOCH$_3$ |
| 3,5-Cl$_2$ | CF$_3$ | SN(CH$_2$Ph)CH$_2$CH$_2$C(O)OEt | CH=NOCH$_3$ |
| 3,5-Cl$_2$ | CF$_3$ | SN(CH$_3$)C(O)OBu-n | CH=NOCH$_3$ |
| 3,5-Cl$_2$ | CF$_3$ | H | CH=NOEt |
| 3,5-Cl$_2$ | CF$_3$ | H | CH=NOEt(E) |
| 3,5-Cl$_2$ | CF$_3$ | H | CH=NOEt(Z) |
| 3,5-Cl$_2$ | CF$_3$ | CH$_3$ | CH=NOEt |
| 3,5-Cl$_2$ | CF$_3$ | Et | CH=NOEt |
| 3,5-Cl$_2$ | CF$_3$ | CH$_2$OCH$_3$ | CH=NOEt |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | CH$_2$OEt | CH=NOEt |
| 3,5-Cl$_2$ | CF$_3$ | CH$_2$OCH$_2$CH$_2$Cl | CH=NOEt |
| 3,5-Cl$_2$ | CF$_3$ | CH$_2$OCH$_2$CF$_3$ | CH=NOEt |
| 3,5-Cl$_2$ | CF$_3$ | CH$_2$OCH$_2$CH$_2$OCH$_3$ | CH=NOEt |
| 3,5-Cl$_2$ | CF$_3$ | CH$_2$OCH$_2$Ph | CH=NOEt |
| 3,5-Cl$_2$ | CF$_3$ | CH$_2$OC(O)CH$_3$ | CH=NOEt |
| 3,5-Cl$_2$ | CF$_3$ | CH$_2$OC(O)Et | CH=NOEt |
| 3,5-Cl$_2$ | CF$_3$ | CH$_2$OC(O)Pr-n | CH=NOEt |
| 3,5-Cl$_2$ | CF$_3$ | CH$_2$OC(O)Pr-i | CH=NOEt |
| 3,5-Cl$_2$ | CF$_3$ | CH$_2$OC(O)Pr-c | CH=NOEt |
| 3,5-Cl$_2$ | CF$_3$ | CH$_2$OC(O)Bu-n | CH=NOEt |
| 3,5-Cl$_2$ | CF$_3$ | CH$_2$OC(O)Bu-i | CH=NOEt |
| 3,5-Cl$_2$ | CF$_3$ | CH$_2$OC(O)Bu-s | CH=NOEt |
| 3,5-Cl$_2$ | CF$_3$ | CH$_2$OC(O)Bu-t | CH=NOEt |
| 3,5-Cl$_2$ | CF$_3$ | CH$_2$OC(O)CH$_2$Ph | CH=NOEt |
| 3,5-Cl$_2$ | CF$_3$ | CH$_2$OC(O)Ph | CH=NOEt |
| 3,5-Cl$_2$ | CF$_3$ | CH$_2$OC(O)OCH$_3$ | CH=NOEt |
| 3,5-Cl$_2$ | CF$_3$ | CH$_2$OC(O)OEt | CH=NOEt |
| 3,5-Cl$_2$ | CF$_3$ | CH$_2$OC(O)OBu-n | CH=NOEt |
| 3,5-Cl$_2$ | CF$_3$ | CH$_2$OC(O)OBu-i | CH=NOEt |
| 3,5-Cl$_2$ | CF$_3$ | CH$_2$OC(O)OCH$_2$Ph | CH=NOEt |
| 3,5-Cl$_2$ | CF$_3$ | CH$_2$OC(O)OPh | CH=NOEt |
| 3,5-Cl$_2$ | CF$_3$ | CH$_2$OC(O)NHPh | CH=NOEt |
| 3,5-Cl$_2$ | CF$_3$ | CH$_2$OPh | CH=NOEt |
| 3,5-Cl$_2$ | CF$_3$ | CH$_2$SCH$_3$ | CH=NOEt |
| 3,5-Cl$_2$ | CF$_3$ | CH$_2$SO2CH$_3$ | CH=NOEt |
| 3,5-Cl$_2$ | CF$_3$ | CH$_2$SC(O)CH$_3$ | CH=NOEt |
| 3,5-Cl$_2$ | CF$_3$ | CH$_2$SC(O)Et | CH=NOEt |
| 3,5-Cl$_2$ | CF$_3$ | CH$_2$SC(O)Ph | CH=NOEt |
| 3,5-Cl$_2$ | CF$_3$ | CH$_2$SC(S)OCH$_3$ | CH=NOEt |
| 3,5-Cl$_2$ | CF$_3$ | CH$_2$SC(S)OEt | CH=NOEt |
| 3,5-Cl$_2$ | CF$_3$ | CH$_2$SC(S)OPr-n | CH=NOEt |
| 3,5-Cl$_2$ | CF$_3$ | CH$_2$SC(S)OPr-i | CH=NOEt |
| 3,5-Cl$_2$ | CF$_3$ | CH$_2$SC(S)N(CH$_3$)$_2$ | CH=NOEt |
| 3,5-Cl$_2$ | CF$_3$ | CH$_2$SC(S)(T-14) | CH=NOEt |
| 3,5-Cl$_2$ | CF$_3$ | CH$_2$N(CH$_3$)$_2$ | CH=NOEt |
| 3,5-Cl$_2$ | CF$_3$ | CH$_2$N(CH$_3$)C(O)CH$_3$ | CH=NOEt |
| 3,5-Cl$_2$ | CF$_3$ | CH$_2$NHC(O)OCH$_3$ | CH=NOEt |
| 3,5-Cl$_2$ | CF$_3$ | CH$_2$N(CH$_3$)C(O)OCH$_3$ | CH=NOEt |
| 3,5-Cl$_2$ | CF$_3$ | CH$_2$N(CH$_3$)SO$_2$CH$_3$ | CH=NOEt |
| 3,5-Cl$_2$ | CF$_3$ | CH$_2$CN | CH=NOEt |
| 3,5-Cl$_2$ | CF$_3$ | CH$_2$C(O)OCH$_3$ | CH=NOEt |
| 3,5-Cl$_2$ | CF$_3$ | CH$_2$CH=CH$_2$ | CH=NOEt |
| 3,5-Cl$_2$ | CF$_3$ | CH$_2$C≡CH | CH=NOEt |
| 3,5-Cl$_2$ | CF$_3$ | CH$_2$Ph | CH=NOEt |
| 3,5-Cl$_2$ | CF$_3$ | C(O)CH$_3$ | CH=NOEt |
| 3,5-Cl$_2$ | CF$_3$ | C(O)OCH$_3$ | CH=NOEt |
| 3,5-Cl$_2$ | CF$_3$ | C(O)OEt | CH=NOEt |
| 3,5-Cl$_2$ | CF$_3$ | C(O)OPr-n | CH=NOEt |
| 3,5-Cl$_2$ | CF$_3$ | C(O)OPr-i | CH=NOEt |
| 3,5-Cl$_2$ | CF$_3$ | C(O)OPr-c | CH=NOEt |
| 3,5-Cl$_2$ | CF$_3$ | C(O)OBu-n | CH=NOEt |
| 3,5-Cl$_2$ | CF$_3$ | C(O)OBu-i | CH=NOEt |
| 3,5-Cl$_2$ | CF$_3$ | C(O)OCH$_2$Cl | CH=NOEt |
| 3,5-Cl$_2$ | CF$_3$ | C(O)OCH$_2$CH$_2$Cl | CH=NOEt |
| 3,5-Cl$_2$ | CF$_3$ | C(O)OCH2CH$_2$OCH$_3$ | CH=NOEt |
| 3,5-Cl$_2$ | CF$_3$ | C(O)OCH$_2$CH$_2$SO$_2$CH$_3$ | CH=NOEt |
| 3,5-Cl$_2$ | CF$_3$ | C(O)OCH=CH$_2$ | CH=NOEt |
| 3,5-Cl$_2$ | CF$_3$ | C(O)OCH$_2$CH=CH$_2$ | CH=NOEt |
| 3,5-Cl$_2$ | CF$_3$ | C(O)OCH$_2$C≡CH | CH=NOEt |
| 3,5-Cl$_2$ | CF$_3$ | C(O)SCH$_3$ | CH=NOEt |
| 3,5-Cl$_2$ | CF$_3$ | C(S)OCH$_3$ | CH=NOEt |
| 3,5-Cl$_2$ | CF$_3$ | C(S)SCH$_3$ | CH=NOEt |
| 3,5-Cl$_2$ | CF$_3$ | SCCl$_3$ | CH=NOEt |
| 3,5-Cl$_2$ | CF$_3$ | SN(Bu-n)$_2$ | CH=NOEt |
| 3,5-Cl$_2$ | CF$_3$ | S(T-18) | CH=NOEt |
| 3,5-Cl$_2$ | CF$_3$ | SN(Pr-i)CH$_2$CH$_2$C(O)OEt | CH=NOEt |
| 3,5-Cl$_2$ | CF$_3$ | SN(CH$_2$Ph)CH$_2$CH$_2$C(O)OEt | CH=NOEt |
| 3,5-Cl$_2$ | CF$_3$ | SN(CH$_3$)C(O)OBu-n | CH=NOEt |
| 3,5-Cl$_2$ | CF$_3$ | H | CH=NOPr-n |
| 3,5-Cl$_2$ | CF$_3$ | CH$_2$OCH$_3$ | CH=NOPr-n |
| 3,5-Cl$_2$ | CF$_3$ | CH$_2$OEt | CH=NOPr-n |
| 3,5-Cl$_2$ | CF$_3$ | CH$_2$OCH$_2$CHF$_2$ | CH=NOPr-n |
| 3,5-Cl$_2$ | CF$_3$ | CH$_2$OCH$_2$CF$_3$ | CH=NOPr-n |
| 3,5-Cl$_2$ | CF$_3$ | CH$_2$OCH$_2$CH$_2$OCH$_3$ | CH=NOPr-n |
| 3,5-Cl$_2$ | CF$_3$ | CH$_2$OC(O)CH3 | CH=NOPr-n |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | CH$_2$OC(O)Et | CH=NOPr-n |
| 3,5-Cl$_2$ | CF$_3$ | CH$_2$OC(O)Pr-n | CH=NOPr-n |
| 3,5-Cl$_2$ | CF$_3$ | CH$_2$OC(O)Pr-i | CH=NOPr-n |
| 3,5-Cl$_2$ | CF$_3$ | CH$_2$OC(O)Pr-c | CH=NOPr-n |
| 3,5-Cl$_2$ | CF$_3$ | CH$_2$OC(O)Bu-n | CH=NOPr-n |
| 3,5-Cl$_2$ | CF$_3$ | CH$_2$OC(O)Bu-i | CH=NOPr-n |
| 3,5-Cl$_2$ | CF$_3$ | CH$_2$OC(O)Bu-s | CH=NOPr-n |
| 3,5-Cl$_2$ | CF$_3$ | CH$_2$OC(O)Bu-t | CH=NOPr-n |
| 3,5-Cl$_2$ | CF$_3$ | CH$_2$OC(O)Ph | CH=NOPr-n |
| 3,5-Cl$_2$ | CF$_3$ | CH$_2$OC(O)OCH$_3$ | CH=NOPr-n |
| 3,5-Cl$_2$ | CF$_3$ | CH$_2$OC(O)OEt | CH=NOPr-n |
| 3,5-Cl$_2$ | CF$_3$ | CH$_2$OC(O)OPh | CH=NOPr-n |
| 3,5-Cl$_2$ | CF$_3$ | CH$_2$CN | CH=NOPr-n |
| 3,5-Cl$_2$ | CF$_3$ | CH$_2$C≡CH | CH=NOPr-n |
| 3,5-Cl$_2$ | CF$_3$ | C(O)OCH$_3$ | CH=NOPr-n |
| 3,5-Cl$_2$ | CF$_3$ | SCCl$_3$ | CH=NOPr-n |
| 3,5-Cl$_2$ | CF$_3$ | H | CH=NOPr-i |
| 3,5-Cl$_2$ | CF$_3$ | CH$_2$OCH$_3$ | CH=NOPr-i |
| 3,5-Cl$_2$ | CF$_3$ | CH$_2$OC(O)CH$_3$ | CH=NOPr-i |
| 3,5-Cl$_2$ | CF$_3$ | CH$_2$CN | CH=NOPr-i |
| 3,5-Cl$_2$ | CF$_3$ | C(O)OCH$_3$ | CH=NOPr-i |
| 3,5-Cl$_2$ | CF$_3$ | SCCl$_3$ | CH=NOPr-i |
| 3,5-Cl$_2$ | CF$_3$ | H | CH=NOPr-c |
| 3,5-Cl$_2$ | CF$_3$ | H | CH=NOBu-n |
| 3,5-Cl$_2$ | CF$_3$ | H | CH=NOBu-i |
| 3,5-Cl$_2$ | CF$_3$ | H | CH=NOCH$_2$Pr-c |
| 3,5-Cl$_2$ | CF$_3$ | H | CH=NOBu-s(R) |
| 3,5-Cl$_2$ | CF$_3$ | H | CH=NOBu-s(S) |
| 3,5-Cl$_2$ | CF$_3$ | H | CH=NOBu-c |
| 3,5-Cl$_2$ | CF$_3$ | H | CH=NOBu-t |
| 3,5-Cl$_2$ | CF$_3$ | H | CH=NOPen-n |
| 3,5-Cl$_2$ | CF$_3$ | H | CH=NOCH$_2$Bu-i |
| 3,5-Cl$_2$ | CF$_3$ | H | CH=NOCH$_2$Bu-s |
| 3,5-Cl$_2$ | CF$_3$ | H | CH=NOCH$_2$Bu-c |
| 3,5-Cl$_2$ | CF$_3$ | H | CH=NOCH$_2$Bu-t |
| 3,5-Cl$_2$ | CF$_3$ | H | CH=NOPen-c |
| 3,5-Cl$_2$ | CF$_3$ | H | CH=NOHex-n |
| 3,5-Cl$_2$ | CF$_3$ | H | CH=NOHex-c |
| 3,5-Cl$_2$ | CF$_3$ | H | CH=NOCH$_2$F |
| 3,5-Cl$_2$ | CF$_3$ | H | CH=NOCHF$_2$ |
| 3,5-Cl$_2$ | CF$_3$ | H | CH=NOCH$_2$CH$_2$F |
| 3,5-Cl$_2$ | CF$_3$ | H | CH=NOCHFCH$_3$ |
| 3,5-Cl$_2$ | CF$_3$ | H | CH=NOCH$_2$CH$_2$Cl |
| 3,5-Cl$_2$ | CF$_3$ | CH$_2$OCH$_3$ | CH=NOCH$_2$CH$_2$Cl |
| 3,5-Cl$_2$ | CF$_3$ | CH$_2$OC(O)CH$_3$ | CH=NOCH$_2$CH$_2$Cl |
| 3,5-Cl$_2$ | CF$_3$ | CH$_2$CN | CH=NOCH$_2$CH$_2$Cl |
| 3,5-Cl$_2$ | CF$_3$ | C(O)OCH3 | CH=NOCH$_2$CH$_2$Cl |
| 3,5-Cl$_2$ | CF$_3$ | SCCl$_3$ | CH=NOCH$_2$CH$_2$Cl |
| 3,5-Cl$_2$ | CF$_3$ | H | CH=NOCH$_2$CHF$_2$ |
| 3,5-Cl$_2$ | CF$_3$ | CH$_2$OCH$_3$ | CH=NOCH$_2$CHF$_2$ |
| 3,5-Cl$_2$ | CF$_3$ | CH$_2$OC(O)CH$_3$ | CH=NOCH$_2$CHF$_2$ |
| 3,5-Cl$_2$ | CF$_3$ | CH$_2$CN | CH=NOCH$_2$CHF$_2$ |
| 3,5-Cl$_2$ | CF$_3$ | C(O)OCH$_3$ | CH=NOCH$_2$CHF$_2$ |
| 3,5-Cl$_2$ | CF$_3$ | SCCl$_3$ | CH=NOCH$_2$CHF$_2$ |
| 3,5-Cl$_2$ | CF$_3$ | H | CH=NOCH$_2$CHCl$_2$ |
| 3,5-Cl$_2$ | CF$_3$ | H | CH=NOCH$_2$CF$_3$ |
| 3,5-Cl$_2$ | CF$_3$ | CH$_2$OCH$_3$ | CH=NOCH$_2$CF$_3$ |
| 3,5-Cl$_2$ | CF$_3$ | CH$_2$OEt | CH=NOCH$_2$CF$_3$ |
| 3,5-Cl$_2$ | CF$_3$ | CH$_2$OCH$_2$CHF$_2$ | CH=NOCH$_2$CF$_3$ |
| 3,5-Cl$_2$ | CF$_3$ | CH$_2$OCH$_2$CF$_3$ | CH=NOCH$_2$CF$_3$ |
| 3,5-Cl$_2$ | CF$_3$ | CH$_2$OCH$_2$CH$_2$OCH$_3$ | CH=NOCH$_2$CF$_3$ |
| 3,5-Cl$_2$ | CF$_3$ | CH$_2$OC(O)CH$_3$ | CH=NOCH$_2$CF$_3$ |
| 3,5-Cl$_2$ | CF$_3$ | CH$_2$OC(O)Et | CH=NOCH$_2$CF$_3$ |
| 3,5-Cl$_2$ | CF$_3$ | CH$_2$OC(O)Pr-n | CH=NOCH$_2$CF$_3$ |
| 3,5-Cl$_2$ | CF$_3$ | CH$_2$OC(O)Pr-i | CH=NOCH$_2$CF$_3$ |
| 3,5-Cl$_2$ | CF$_3$ | CH$_2$OC(O)Pr-c | CH=NOCH$_2$CF$_3$ |
| 3,5-Cl$_2$ | CF$_3$ | CH$_2$OC(O)Bu-n | CH=NOCH$_2$CF$_3$ |
| 3,5-Cl$_2$ | CF$_3$ | CH$_2$OC(O)Bu-i | CH=NOCH$_2$CF$_3$ |
| 3,5-Cl$_2$ | CF$_3$ | CH$_2$OC(O)Bu-s | CH=NOCH$_2$CF$_3$ |
| 3,5-Cl$_2$ | CF$_3$ | CH$_2$OC(O)Bu-t | CH=NOCH$_2$CF$_3$ |
| 3,5-Cl$_2$ | CF$_3$ | CH$_2$OC(O)Ph | CH=NOCH$_2$CF$_3$ |
| 3,5-Cl$_2$ | CF$_3$ | CH$_2$OC(O)OCH$_3$ | CH=NOCH$_2$CF$_3$ |
| 3,5-Cl$_2$ | CF$_3$ | CH$_2$OC(O)OEt | CH=NOCH$_2$CF$_3$ |
| 3,5-Cl$_2$ | CF$_3$ | CH$_2$OC(O)OPh | CH=NOCH$_2$CF$_3$ |
| 3,5-Cl$_2$ | CF$_3$ | CH$_2$CN | CH=NOCH$_2$CF$_3$ |
| 3,5-Cl$_2$ | CF$_3$ | CH$_2$C≡CH | CH=NOCH$_2$CF$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | C(O)OCH$_3$ | CH=NOCH$_2$CF$_3$ |
| 3,5-Cl$_2$ | CF$_3$ | SCCl$_3$ | CH=NOCH$_2$CF$_3$ |
| 3,5-Cl$_2$ | CF$_3$ | H | CH=NOCH$_2$CF$_2$Cl |
| 3,5-Cl$_2$ | CF$_3$ | H | CH=NOCH$_2$CH$_2$F |
| 3,5-Cl$_2$ | CF$_3$ | H | CH=NOCH$_2$CH$_2$Cl |
| 3,5-Cl$_2$ | CF$_3$ | H | CH=NOCH$_2$CHClCH$_3$(R) |
| 3,5-Cl$_2$ | CF$_3$ | H | CH=NOCH$_2$CHClCH$_3$(S) |
| 3,5-Cl$_2$ | CF$_3$ | H | CH=NOCH$_2$CH$_2$CF$_3$ |
| 3,5-Cl$_2$ | CF$_3$ | H | CH=NOCH$_2$CF$_2$CHF$_2$ |
| 3,5-Cl$_2$ | CF$_3$ | H | CH=NOCH$_2$CF$_2$CF$_3$ |
| 3,5-Cl$_2$ | CF$_3$ | H | CH=NOCF$_2$CHFCF$_3$ |
| 3,5-Cl$_2$ | CF$_3$ | H | CH=NOCH(CH$_3$)CH$_2$F |
| 3,5-Cl$_2$ | CF$_3$ | H | CH=NOCH(CH$_3$)CH$_2$Cl(R) |
| 3,5-Cl$_2$ | CF$_3$ | H | CH=NOCH(CH$_3$)CH$_2$Cl(S) |
| 3,5-Cl$_2$ | CF$_3$ | H | CH=NOCH(CH$_2$F)$_2$ |
| 3,5-Cl$_2$ | CF$_3$ | H | CH=NOCH(CH$_2$F)CH$_2$Cl |
| 3,5-Cl$_2$ | CF$_3$ | H | CH=NOCH(CH$_3$)CF$_3$ |
| 3,5-Cl$_2$ | CF$_3$ | H | CH=NOCH(CF$_3$)$_2$ |
| 3,5-Cl$_2$ | CF$_3$ | H | CH=NOCH$_2$(T-1) |
| 3,5-Cl$_2$ | CF$_3$ | H | CH=NOCH$_2$(T-2) |
| 3,5-Cl$_2$ | CF$_3$ | H | CH=NOCH$_2$(T-3) |
| 3,5-Cl$_2$ | CF$_3$ | H | CH=NOCH$_2$(T-4) |
| 3,5-Cl$_2$ | CF$_3$ | H | CH=NOCH$_2$(T-5) |
| 3,5-Cl$_2$ | CF$_3$ | H | CH=NOCH$_2$(T-8) |
| 3,5-Cl$_2$ | CF$_3$ | H | CH=NOCH$_2$(T-9) |
| 3,5-Cl$_2$ | CF$_3$ | H | CH=NOCH$_2$(T-10) |
| 3,5-Cl$_2$ | CF$_3$ | H | CH=NOCH$_2$(T-11) |
| 3,5-Cl$_2$ | CF$_3$ | H | CH=NOCH$_2$CH$_2$OCH$_3$ |
| 3,5-Cl$_2$ | CF$_3$ | H | CH=NOCH$_2$CH$_2$OCH$_2$CH$_2$Cl |
| 3,5-Cl$_2$ | CF$_3$ | H | CH=NOCH$_2$CH$_2$OCH$_2$CF$_3$ |
| 3,5-Cl$_2$ | CF$_3$ | H | CH=NOCH$_2$CH$_2$OCH$_2$CH$_2$OCH$_3$ |
| 3,5-Cl$_2$ | CF$_3$ | H | CH=NOCH$_2$CH$_2$OCH$_2$CH$_2$OCH$_2$CH$_2$OCH$_3$ |
| 3,5-Cl$_2$ | CF$_3$ | H | CH=NOCH$_2$CH$_2$OCH$_2$CH$_2$SCH$_3$ |
| 3,5-Cl$_2$ | CF$_3$ | H | CH=NOCH$_2$CH$_2$OCH$_2$Ph |
| 3,5-Cl$_2$ | CF$_3$ | H | CH=NOCH$_2$CH$_2$OC(O)CH$_3$ |
| 3,5-Cl$_2$ | CF$_3$ | H | CH=NOCH$_2$CH$_2$OC(O)NHCH$_3$ |
| 3,5-Cl$_2$ | CF$_3$ | H | CH=NOCH$_2$CH$_2$OC(O)N(CH$_3$)$_2$ |
| 3,5-Cl$_2$ | CF$_3$ | H | CH=NOCH$_2$CH$_2$OC(O)NHCH$_2$CH$_2$OCH$_3$ |
| 3,5-Cl$_2$ | CF$_3$ | H | CH=NOCH$_2$CH$_2$OC(O)NHCH$_2$CH$_2$SCH$_3$ |
| 3,5-Cl$_2$ | CF$_3$ | H | CH=NOCH$_2$CH$_2$OC(O)NHCH$_2$CH=CH$_2$ |
| 3,5-Cl$_2$ | CF$_3$ | H | CH=NOCH$_2$CH$_2$OC(O)NHCH$_2$Ph |
| 3,5-Cl$_2$ | CF$_3$ | H | CH=NOCH$_2$CH$_2$OC(O)NHCH$_2$(D-52a) |
| 3,5-Cl$_2$ | CF$_3$ | H | CH=NOCH$_2$CH$_2$OC(O)NHCH$_2$(D-53a) |
| 3,5-Cl$_2$ | CF$_3$ | H | CH=NOCH$_2$CH$_2$OC(O)NHCH$_2$(D-54a) |
| 3,5-Cl$_2$ | CF$_3$ | H | CH=NOCH$_2$CH$_2$OC(O)NHPh |
| 3,5-Cl$_2$ | CF$_3$ | H | CH=NOCH$_2$CH$_2$OC(O)(T-14) |
| 3,5-Cl$_2$ | CF$_3$ | H | CH=NOCH$_2$CH$_2$OC(O)(T-18) |
| 3,5-Cl$_2$ | CF$_3$ | H | CH=NOCH$_2$CH$_2$OC(O)(T-19) |
| 3,5-Cl$_2$ | CF$_3$ | H | CH=NOCH$_2$CH$_2$OC(S)NHCH$_3$ |
| 3,5-Cl$_2$ | CF$_3$ | H | CH=NOCH$_2$CH$_2$OC(S)N(CH$_3$)$_2$ |
| 3,5-Cl$_2$ | CF$_3$ | H | CH=NOCH$_2$CH$_2$OPh |
| 3,5-Cl$_2$ | CF$_3$ | H | CH=NOCH$_2$CH$_2$OP(O)(OEt)$_2$ |
| 3,5-Cl$_2$ | CF$_3$ | H | CH=NOCH$_2$CH$_2$OP(S)(OCH$_3$)$_2$ |
| 3,5-Cl$_2$ | CF$_3$ | H | CH=NOCH$_2$(E-5a) |
| 3,5-Cl$_2$ | CF$_3$ | H | CH=NOCH$_2$(E-6a) |
| 3,5-Cl$_2$ | CF$_3$ | H | CH=NOCH$_2$(E-11a) |
| 3,5-Cl$_2$ | CF$_3$ | H | CH=NOCH$_2$(E-12a) |
| 3,5-Cl$_2$ | CF$_3$ | H | CH=NOCH$_2$(E-12c) |
| 3,5-Cl$_2$ | CF$_3$ | H | CH=NOCH$_2$(E-24a) |
| 3,5-Cl$_2$ | CF$_3$ | H | CH=NOCH$_2$(E-25a) |
| 3,5-Cl$_2$ | CF$_3$ | H | CH=NOCH$_2$(E-26a) |
| 3,5-Cl$_2$ | CF$_3$ | H | CH=NOCH$_2$(E-33a) |
| 3,5-Cl$_2$ | CF$_3$ | H | CH=NO(E-6a) |
| 3,5-Cl$_2$ | CF$_3$ | H | CH=NO(E-25a) |
| 3,5-Cl$_2$ | CF$_3$ | H | CH=NO(E-26a) |
| 3,5-Cl$_2$ | CF$_3$ | H | CH=NO(E-35a) |
| 3,5-Cl$_2$ | CF$_3$ | H | CH=NOCH$_2$CH$_2$SCH$_3$ |
| 3,5-Cl$_2$ | CF$_3$ | H | CH=NOCH$_2$CH$_2$S(O)CH$_3$ |
| 3,5-Cl$_2$ | CF$_3$ | H | CH=NOCH$_2$CH$_2$SO$_2$CH$_3$ |
| 3,5-Cl$_2$ | CF$_3$ | H | CH=NOCH$_2$CH$_2$SCH$_2$CH$_2$OCH$_3$ |
| 3,5-Cl$_2$ | CF$_3$ | H | CH=NOCH$_2$CH$_2$SO$_2$CH$_2$CH$_2$OCH$_3$ |
| 3,5-Cl$_2$ | CF$_3$ | H | CH=NOCH$_2$CH$_2$SCH$_2$CH$_2$SCH$_3$ |
| 3,5-Cl$_2$ | CF$_3$ | H | CH=NOCH$_2$CH$_2$SCH$_2$CH=CH$_2$ |
| 3,5-Cl$_2$ | CF$_3$ | H | CH=NOCH$_2$CH$_2$SCH$_2$C≡CH |
| 3,5-Cl$_2$ | CF$_3$ | H | CH=NOCH$_2$CH$_2$SCH$_2$Ph |
| 3,5-Cl$_2$ | CF$_3$ | H | CH=NOCH$_2$CH$_2$SO$_2$CH$_2$Ph |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | CH=NOCH$_2$CH$_2$SC(O)CH3 |
| 3,5-Cl$_2$ | CF$_3$ | H | CH=NOCH$_2$CH$_2$SC(O)N(CH$_3$)$_2$ |
| 3,5-Cl$_2$ | CF$_3$ | H | CH=NOCH$_2$CH$_2$SC(S)NHCH$_3$ |
| 3,5-Cl$_2$ | CF$_3$ | H | CH=NOCH$_2$CH$_2$SC(S)N(CH$_3$)$_2$ |
| 3,5-Cl$_2$ | CF$_3$ | H | CH=NOCH$_2$CH$_2$SPh |
| 3,5-Cl$_2$ | CF$_3$ | H | CH=NOCH$_2$CH$_2$S(O)Ph |
| 3,5-Cl$_2$ | CF$_3$ | H | CH=NOCH$_2$CH$_2$SO$_2$Ph |
| 3,5-Cl$_2$ | CF$_3$ | H | CH=NOCH$_2$CH$_2$S(D-55a) |
| 3,5-Cl$_2$ | CF$_3$ | H | CH=NOCH$_2$CH$_2$S(O)(D-55a) |
| 3,5-Cl$_2$ | CF$_3$ | H | CH=NOCH$_2$CH$_2$SO$_2$(D-55a) |
| 3,5-Cl$_2$ | CF$_3$ | H | CH=NOCH$_2$CH$_2$SO$_2$NHCH$_3$ |
| 3,5-Cl$_2$ | CF$_3$ | H | CH=NOCH$_2$CH$_2$SO$_2$N(CH$_3$)$_2$ |
| 3,5-Cl$_2$ | CF$_3$ | H | CH=NOCH$_2$CH$_2$SO$_2$(T-14) |
| 3,5-Cl$_2$ | CF$_3$ | H | CH=NOCH$_2$CH$_2$SO$_2$(T-18) |
| 3,5-Cl$_2$ | CF$_3$ | H | CH=NOCH$_2$CH$_2$SO$_2$(T-19) |
| 3,5-Cl$_2$ | CF$_3$ | H | CH=NOCH$_2$(E-7a) |
| 3,5-Cl$_2$ | CF$_3$ | H | CH=NOCH$_2$(E-8a) |
| 3,5-Cl$_2$ | CF$_3$ | H | CH=NOCH$_2$(E-8b) |
| 3,5-Cl$_2$ | CF$_3$ | H | CH=NOCH$_2$(E-8c) |
| 3,5-Cl$_2$ | CF$_3$ | H | CH=NOCH$_2$(E-19a) |
| 3,5-Cl$_2$ | CF$_3$ | H | CH=NOCH$_2$(E-27a) |
| 3,5-Cl$_2$ | CF$_3$ | H | CH=NOCH$_2$(E-28a) |
| 3,5-Cl$_2$ | CF$_3$ | H | CH=NOCH$_2$(E-29a) |
| 3,5-Cl$_2$ | CF$_3$ | H | CH=NOCH$_2$(E-44a) |
| 3,5-Cl$_2$ | CF$_3$ | H | CH=NO(E-4a) |
| 3,5-Cl$_2$ | CF$_3$ | H | CH=NO(E-8a) |
| 3,5-Cl$_2$ | CF$_3$ | H | CH=NO(E-8b) |
| 3,5-Cl$_2$ | CF$_3$ | H | CH=NO(E-8c) |
| 3,5-Cl$_2$ | CF$_3$ | H | CH=NO(E-28a) |
| 3,5-Cl$_2$ | CF$_3$ | H | CH=NO(E-29a) |
| 3,5-Cl$_2$ | CF$_3$ | H | CH=NOCH$_2$CH$_2$N(CH$_3$)$_2$ |
| 3,5-Cl$_2$ | CF$_3$ | H | CH=NOCH$_2$CH$_2$(T-14) |
| 3,5-Cl$_2$ | CF$_3$ | H | CH=NOCH$_2$CH$_2$(T-17) |
| 3,5-Cl$_2$ | CF$_3$ | H | CH=NOCH$_2$CH$_2$(T-18) |
| 3,5-Cl$_2$ | CF$_3$ | H | CH=NOCH$_2$CH$_2$(T-19) |
| 3,5-Cl$_2$ | CF$_3$ | H | CH=NOCH$_2$CH$_2$(T-21) |
| 3,5-Cl$_2$ | CF$_3$ | H | CH=NOCH$_2$CH$_2$NHC(O)CH$_3$ |
| 3,5-Cl$_2$ | CF$_3$ | H | CH=NOCH$_2$CH$_2$N(CH$_3$)C(O)CH$_3$ |
| 3,5-Cl$_2$ | CF$_3$ | H | CH=NOCH$_2$CH$_2$NHC(O)OCH$_3$ |
| 3,5-Cl$_2$ | CF$_3$ | H | CH=NOCH$_2$CH$_2$NHC(O)NHCH$_3$ |
| 3,5-Cl$_2$ | CF$_3$ | H | CH=NOCH$_2$CH$_2$NHC(O)N(CH$_3$)$_2$ |
| 3,5-Cl$_2$ | CF$_3$ | H | CH=NOCH$_2$CH$_2$NHC(O)Ph |
| 3,5-Cl$_2$ | CF$_3$ | H | CH=NOCH$_2$CH$_2$NHC(S)NHEt |
| 3,5-Cl$_2$ | CF$_3$ | H | CH=NOCH$_2$CH$_2$N(CH$_3$)OCH$_3$ |
| 3,5-Cl$_2$ | CF$_3$ | H | CH=NOCH$_2$CH$_2$NHSO$_2$CH$_3$ |
| 3,5-Cl$_2$ | CF$_3$ | H | CH=NOCH$_2$CH$_2$N(CH3)SO$_2$CH$_3$ |
| 3,5-Cl$_2$ | CF$_3$ | H | CH=NOCH$_2$CH$_2$NHSO$_2$CF$_3$ |
| 3,5-Cl$_2$ | CF$_3$ | H | CH=NOCH$_2$CH$_2$N(CH$_3$)SO$_2$CF$_3$ |
| 3,5-Cl$_2$ | CF$_3$ | H | CH=NOCH$_2$CH$_2$NHSO$_2$Ph |
| 3,5-Cl$_2$ | CF$_3$ | H | CH=NOCH$_2$CH$_2$NHSO$_2$N(CH$_3$)$_2$ |
| 3,5-Cl$_2$ | CF$_3$ | H | CH=NOCH$_2$CH$_2$NHP(S)(OCH$_3$)$_2$ |
| 3,5-Cl$_2$ | CF$_3$ | H | CH=NOCH$_2$(E-10a)C(O)CH$_3$ |
| 3,5-Cl$_2$ | CF$_3$ | H | CH=NOCH$_2$(E-10a)C(O)OCH$_3$ |
| 3,5-Cl$_2$ | CF$_3$ | H | CH=NOCH$_2$(E-31a)C(O)CH$_3$ |
| 3,5-Cl$_2$ | CF$_3$ | H | CH=NOCH$_2$(E-32a)C(O)CH$_3$ |
| 3,5-Cl$_2$ | CF$_3$ | H | CH=NOCH$_2$(E-32a)C(O)OCH$_3$ |
| 3,5-Cl$_2$ | CF$_3$ | H | CH=NO(E-10a)CHO |
| 3,5-Cl$_2$ | CF$_3$ | H | CH=NO(E-10a)C(O)CH$_3$ |
| 3,5-Cl$_2$ | CF$_3$ | H | CH=NO(E-10a)C(O)OCH$_3$ |
| 3,5-Cl$_2$ | CF$_3$ | H | CH=NO(E-31 a)C(O)CH$_3$ |
| 3,5-Cl$_2$ | CF$_3$ | H | CH=NO(E-31 a)C(O)OCH$_3$ |
| 3,5-Cl$_2$ | CF$_3$ | H | CH=NO(E-32a)C(O)CH$_3$ |
| 3,5-Cl$_2$ | CF$_3$ | H | CH=NO(E-32a)C(O)OCH$_3$ |
| 3,5-Cl$_2$ | CF$_3$ | H | CH=NOCH$_2$CH(CH$_3$)NO$_2$ |
| 3,5-Cl$_2$ | CF$_3$ | H | CH=NOCH$_2$(M-1a) |
| 3,5-Cl$_2$ | CF$_3$ | H | CH=NOCH$_2$CH=NOCH$_3$ |
| 3,5-Cl$_2$ | CF$_3$ | H | CH=NOCH$_2$C(CH$_3$)=NOCH$_3$ |
| 3,5-Cl$_2$ | CF$_3$ | H | CH=NOCH(CH$_3$)CH=NOCH$_3$ |
| 3,5-Cl$_2$ | CF$_3$ | H | CH=NOCH$_2$CH$_2$CH=NOCH$_3$ |
| 3,5-Cl$_2$ | CF$_3$ | H | CH=NOCH$_2$(M-5a) |
| 3,5-Cl$_2$ | CF$_3$ | H | CH=NOCH$_2$(M-5c)CF$_3$ |
| 3,5-Cl$_2$ | CF$_3$ | H | CH=NOCH$_2$CN |
| 3,5-Cl$_2$ | CF$_3$ | H | CH=NOCH$_2$CH$_2$CN |
| 3,5-Cl$_2$ | CF$_3$ | H | CH=NOCH$_2$C(O)OCH$_3$ |
| 3,5-Cl$_2$ | CF$_3$ | H | CH=NOCH$_2$C(O)SCH$_3$ |
| 3,5-Cl$_2$ | CF$_3$ | H | CH=NOCH$_2$C(O)NH$_2$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | H | CH=NOCH$_2$C(O)NHCH$_3$ |
| 3,5-Cl$_2$ | CF$_3$ | H | CH=NOCH$_2$C(O)N(CH$_3$)$_2$ |
| 3,5-Cl$_2$ | CF$_3$ | H | CH=NOCH$_2$C(O)(T-14) |
| 3,5-Cl$_2$ | CF$_3$ | H | CH=NOCH$_2$C(O)(T-15) |
| 3,5-Cl$_2$ | CF$_3$ | H | CH=NOCH$_2$C(O)(T-16) |
| 3,5-Cl$_2$ | CF$_3$ | H | CH=NOCH$_2$C(O)(T-18) |
| 3,5-Cl$_2$ | CF$_3$ | H | CH=NOCH$_2$C(O)(T-19) |
| 3,5-Cl$_2$ | CF$_3$ | H | CH=NOCH$_2$C(O)(T-20) |
| 3,5-Cl$_2$ | CF$_3$ | H | CH=NOCH$_2$(M-11a) |
| 3,5-Cl$_2$ | CF$_3$ | H | CH=NOCH$_2$(M-11b)CF$_3$ |
| 3,5-Cl$_2$ | CF$_3$ | H | CH=NOCH$_2$(M-11c)CF$_3$ |
| 3,5-Cl$_2$ | CF$_3$ | H | CH=NOCH$_2$(M-28a) |
| 3,5-Cl$_2$ | CF$_3$ | H | CH=NOCH$_2$C(S)OCH$_3$ |
| 3,5-Cl$_2$ | CF$_3$ | H | CH=NOCH$_2$C(S)SCH$_3$ |
| 3,5-Cl$_2$ | CF$_3$ | H | CH=NOCH$_2$C(S)NH$_2$ |
| 3,5-Cl$_2$ | CF$_3$ | H | CH=NOCH$_2$C(S)NHCH$_3$ |
| 3,5-Cl$_2$ | CF$_3$ | H | CH=NOCH$_2$(M-14a) |
| 3,5-Cl$_2$ | CF$_3$ | H | CH=NOCH$_2$(M-14b)CF$_3$ |
| 3,5-Cl$_2$ | CF$_3$ | H | CH=NOCH$_2$(M-14c)CF$_3$ |
| 3,5-Cl$_2$ | CF$_3$ | H | CH=NOCH$_2$(M-32a) |
| 3,5-Cl$_2$ | CF$_3$ | H | CH=NOCH=CH$_2$ |
| 3,5-Cl$_2$ | CF$_3$ | H | CH=NOCH$_2$CH=CH$_2$ |
| 3,5-Cl$_2$ | CF$_3$ | CH$_2$OCH$_3$ | CH=NOCH$_2$CH=CH$_2$ |
| 3,5-Cl$_2$ | CF$_3$ | CH$_2$OEt | CH=NOCH$_2$CH=CH$_2$ |
| 3,5-Cl$_2$ | CF$_3$ | CH$_2$OCH$_2$CHF$_2$ | CH=NOCH$_2$CH=CH$_2$ |
| 3,5-Cl$_2$ | CF$_3$ | CH$_2$OCH$_2$CF$_3$ | CH=NOCH$_2$CH=CH$_2$ |
| 3,5-Cl$_2$ | CF$_3$ | CH$_2$OCH$_2$CH$_2$OCH$_3$ | CH=NOCH$_2$CH=CH$_2$ |
| 3,5-Cl$_2$ | CF$_3$ | CH$_2$OC(O)CH$_3$ | CH=NOCH$_2$CH=CH$_2$ |
| 3,5-Cl$_2$ | CF$_3$ | CH$_2$OC(O)Et | CH=NOCH$_2$CH=CH$_2$ |
| 3,5-Cl$_2$ | CF$_3$ | CH$_2$OC(O)Pr-n | CH=NOCH$_2$CH=CH$_2$ |
| 3,5-Cl$_2$ | CF$_3$ | CH$_2$OC(O)Pr-i | CH=NOCH$_2$CH=CH$_2$ |
| 3,5-Cl$_2$ | CF$_3$ | CH$_2$OC(O)Pr-c | CH=NOCH$_2$CH=CH$_2$ |
| 3,5-Cl$_2$ | CF$_3$ | CH$_2$OC(O)Bu-n | CH=NOCH$_2$CH=CH$_2$ |
| 3,5-Cl$_2$ | CF$_3$ | CH$_2$OC(O)Bu-i | CH=NOCH$_2$CH=CH$_2$ |
| 3,5-Cl$_2$ | CF$_3$ | CH$_2$OC(O)Bu-s | CH=NOCH$_2$CH=CH$_2$ |
| 3,5-Cl$_2$ | CF$_3$ | CH$_2$OC(O)Bu-t | CH=NOCH$_2$CH=CH$_2$ |
| 3,5-Cl$_2$ | CF$_3$ | CH$_2$OC(O)Ph | CH=NOCH$_2$CH=CH$_2$ |
| 3,5-Cl$_2$ | CF$_3$ | CH$_2$OC(O)OCH$_3$ | CH=NOCH$_2$CH=CH$_2$ |
| 3,5-Cl$_2$ | CF$_3$ | CH$_2$OC(O)OEt | CH=NOCH$_2$CH=CH$_2$ |
| 3,5-Cl$_2$ | CF$_3$ | CH$_2$OC(O)OPh | CH=NOCH$_2$CH=CH$_2$ |
| 3,5-Cl$_2$ | CF$_3$ | CH$_2$CN | CH=NOCH$_2$CH=CH$_2$ |
| 3,5-Cl$_2$ | CF$_3$ | CH$_2$C≡CH | CH=NOCH$_2$CH=CH$_2$ |
| 3,5-Cl$_2$ | CF$_3$ | C(O)OCH$_3$ | CH=NOCH$_2$CH=CH$_2$ |
| 3,5-Cl$_2$ | CF$_3$ | SCCl$_3$ | CH=NOCH$_2$CH=CH$_2$ |
| 3,5-Cl$_2$ | CF$_3$ | H | CH=NOCH$_2$CH=CHCH$_3$ |
| 3,5-Cl$_2$ | CF$_3$ | H | CH=NOCH$_2$C(CH$_3$)=CH$_2$ |
| 3,5-Cl$_2$ | CF$_3$ | H | CH=NOCH$_2$(T-12) |
| 3,5-Cl$_2$ | CF$_3$ | H | CH=NOCH$_2$CF=CH$_2$ |
| 3,5-Cl$_2$ | CF$_3$ | H | CH=NOCH$_2$CH=CHCl |
| 3,5-Cl$_2$ | CF$_3$ | H | CH=NOCH$_2$CCl=CH$_2$ |
| 3,5-Cl$_2$ | CF$_3$ | H | CH=NOCH$_2$CH=CCl$_2$ |
| 3,5-Cl$_2$ | CF$_3$ | H | CH=NOCH$_2$CCl=CHCl |
| 3,5-Cl$_2$ | CF$_3$ | H | CH=NOCH$_2$C≡CH |
| 3,5-Cl$_2$ | CF$_3$ | CH$_2$OCH$_3$ | CH=NOCH$_2$C≡CH |
| 3,5-Cl$_2$ | CF$_3$ | CH$_2$OEt | CH=NOCH$_2$C≡CH |
| 3,5-Cl$_2$ | CF$_3$ | CH$_2$OCH$_2$CHF$_2$ | CH=NOCH$_2$C≡CH |
| 3,5-Cl$_2$ | CF$_3$ | CH$_2$OCH$_2$CF$_3$ | CH=NOCH$_2$C≡CH |
| 3,5-Cl$_2$ | CF$_3$ | CH$_2$OCH$_2$CH$_2$OCH$_3$ | CH=NOCH$_2$C≡CH |
| 3,5-Cl$_2$ | CF$_3$ | CH$_2$OC(O)CH$_3$ | CH=NOCH$_2$C≡CH |
| 3,5-Cl$_2$ | CF$_3$ | CH$_2$OC(O)Et | CH=NOCH$_2$C≡CH |
| 3,5-Cl$_2$ | CF$_3$ | CH$_2$OC(O)Pr-n | CH=NOCH$_2$C≡CH |
| 3,5-Cl$_2$ | CF$_3$ | CH$_2$OC(O)Pr-i | CH=NOCH$_2$C≡CH |
| 3,5-Cl$_2$ | CF$_3$ | CH$_2$OC(O)Pr-c | CH=NOCH$_2$C≡CH |
| 3,5-Cl$_2$ | CF$_3$ | CH$_2$OC(O)Bu-n | CH=NOCH$_2$C≡CH |
| 3,5-Cl$_2$ | CF$_3$ | CH$_2$OC(O)Bu-i | CH=NOCH$_2$C≡CH |
| 3,5-Cl$_2$ | CF$_3$ | CH$_2$OC(O)Bu-s | CH=NOCH$_2$C≡CH |
| 3,5-Cl$_2$ | CF$_3$ | CH$_2$OC(O)Bu-t | CH=NOCH$_2$C≡CH |
| 3,5-Cl$_2$ | CF$_3$ | CH$_2$OC(O)Ph | CH=NOCH$_2$C≡CH |
| 3,5-Cl$_2$ | CF$_3$ | CH$_2$OC(O)OCH$_3$ | CH=NOCH$_2$C≡CH |
| 3,5-Cl$_2$ | CF$_3$ | CH$_2$OC(O)OEt | CH=NOCH$_2$C≡CH |
| 3,5-Cl$_2$ | CF$_3$ | CH$_2$OC(O)OPh | CH=NOCH$_2$C≡CH |
| 3,5-Cl$_2$ | CF$_3$ | CH$_2$CN | CH=NOCH$_2$C≡CH |
| 3,5-Cl$_2$ | CF$_3$ | CH$_2$C≡CH | CH=NOCH$_2$C≡CH |
| 3,5-Cl$_2$ | CF$_3$ | C(O)OCH$_3$ | CH=NOCH$_2$C≡CH |
| 3,5-Cl$_2$ | CF$_3$ | SCCl$_3$ | CH=NOCH$_2$C≡CH |
| 3,5-Cl$_2$ | CF$_3$ | H | CH=NOCH$_2$C≡CCl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | H | CH=NOCH$_2$C≡CBr |
| 3,5-Cl$_2$ | CF$_3$ | H | CH=NOCH$_2$C≡Cl |
| 3,5-Cl$_2$ | CF$_3$ | H | CH=NOCH$_2$C≡CPh |
| 3,5-Cl$_2$ | CF$_3$ | H | CH=NOCH$_2$Ph |
| 3,5-Cl$_2$ | CF$_3$ | H | CH=NOCH$_2$(Ph-2-F) |
| 3,5-Cl$_2$ | CF$_3$ | H | CH=NOCH$_2$(Ph-3-F) |
| 3,5-Cl$_2$ | CF$_3$ | H | CH=NOCH$_2$(Ph-4-F) |
| 3,5-Cl$_2$ | CF$_3$ | H | CH=NOCH$_2$(D-1a) |
| 3,5-Cl$_2$ | CF$_3$ | H | CH=NOCH$_2$(D-2a) |
| 3,5-Cl$_2$ | CF$_3$ | H | CH=NOCH$_2$(D-52a) |
| 3,5-Cl$_2$ | CF$_3$ | H | CH=NOCH$_2$(D-53a) |
| 3,5-Cl$_2$ | CF$_3$ | H | CH=NOCH$_2$(D-54a) |
| 3,5-Cl$_2$ | CF$_3$ | H | CH=NOPh |
| 3,5-Cl$_2$ | CF$_3$ | H | CH=NO(Ph-2-F) |
| 3,5-Cl$_2$ | CF$_3$ | H | CH=NO(Ph-3-F) |
| 3,5-Cl$_2$ | CF$_3$ | H | CH=NO(Ph-4-F) |
| 3,5-Cl$_2$ | CF$_3$ | H | CH=NO(Ph-2-Cl) |
| 3,5-Cl$_2$ | CF$_3$ | H | CH=NO(Ph-3-Cl) |
| 3,5-Cl$_2$ | CF$_3$ | H | CH=NO(Ph-4-Cl) |
| 3,5-Cl$_2$ | CF$_3$ | H | C(CH$_3$)=NOCH$_3$ |
| 3,5-Cl$_2$ | CF$_3$ | H | C(CH$_3$)=NOEt |
| 3,5-Cl$_2$ | CF$_3$ | H | C(CH$_3$)=NOPr-n |
| 3,5-Cl$_2$ | CF$_3$ | H | C(CH$_3$)=NOCH$_2$CF$_3$ |
| 3,5-Cl$_2$ | CF$_3$ | H | C(CH$_3$)=NOCH$_2$CH=CH$_2$ |
| 3,5-Cl$_2$ | CF$_3$ | H | C(CH$_3$)=NOCH$_2$C≡CH |
| 3,5-Cl$_2$ | CF$_3$ | H | C(Et)=NOCH$_3$ |
| 3,5-Cl$_2$ | CF$_3$ | H | C(Et)=NOEt |
| 3,5-Cl$_2$ | CF$_3$ | H | C(Pr-n)=NOCH$_3$ |
| 3,5-Cl$_2$ | CF$_3$ | H | C(Pr-n)=NOEt |
| 3,5-Cl$_2$ | CF$_3$ | H | C(Pr-i)=NOCH$_3$ |
| 3,5-Cl$_2$ | CF$_3$ | H | C(Pr-i)=NOEt |
| 3,5-Cl$_2$ | CF$_3$ | H | C(Pr-c)=NOCH$_3$ |
| 3,5-Cl$_2$ | CF$_3$ | H | C(Pr-c)=NOEt |
| 3,5-Cl$_2$ | CF$_3$ | H | C(CH$_2$F)=NOCH$_3$ |
| 3,5-Cl$_2$ | CF$_3$ | H | C(CH$_2$F)=NOEt |
| 3,5-Cl$_2$ | CF$_3$ | H | C(CH$_2$OCH$_3$)=NOCH$_3$ |
| 3,5-Cl$_2$ | CF$_3$ | H | C(CH$_2$OCH$_3$)=NOEt |
| 3,5-Cl$_2$ | CF$_3$ | H | C(CH$_2$SCH$_3$)=NOCH$_3$ |
| 3,5-Cl$_2$ | CF$_3$ | H | C(CH$_2$SCH$_3$)=NOEt |
| 3,5-Cl$_2$ | CF$_3$ | H | M-5a |
| 3,5-Cl$_2$ | CF$_3$ | H | (M-5b)CH$_3$ |
| 3,5-Cl$_2$ | CF$_3$ | H | (M-5c)CH$_3$ |
| 3,5-Cl$_2$ | CF$_3$ | H | (M-5c)Ph |
| 3,5-Cl$_2$ | CF$_3$ | H | (M-5c)Ph-2-F |
| 3,5-Cl$_2$ | CF$_3$ | H | (M-5c)Ph-3-F |
| 3,5-Cl$_2$ | CF$_3$ | H | (M-5c)Ph-4-F |
| 3,5-Cl$_2$ | CF$_3$ | H | (M-5c)Ph-2-Cl |
| 3,5-Cl$_2$ | CF$_3$ | H | (M-5c)Ph-3-Cl |
| 3,5-Cl$_2$ | CF$_3$ | H | (M-5c)Ph-4-Cl |
| 3,5-Cl$_2$ | CF$_3$ | CH$_3$ | M-20a |
| 3,5-Cl$_2$ | CF$_3$ | H | CH=NN(CH3)CHO |
| 3,5-Cl$_2$ | CF$_3$ | H | CH=NNHC(O)CH$_3$ |
| 3,5-Cl$_2$ | CF$_3$ | H | CH=NN(CH$_3$)C(O)CH$_3$ |
| 3,5-Cl$_2$ | CF$_3$ | H | CH=NNHC(O)OCH$_3$ |
| 3,5-Cl$_2$ | CF$_3$ | H | CH=NN(CH$_3$)C(O)OHC$_3$ |
| 3,5-Cl$_2$ | CF$_3$ | H | CH=NNHC(O)OCH$_2$CF$_3$ |
| 3,5-Cl$_2$ | CF$_3$ | H | CH=NN(CH$_3$)C(O)NHEt |
| 3,5-Cl$_2$ | CF$_3$ | H | CH=NN(CH$_3$)C(S)SCH$_3$ |
| 3,5-Cl$_2$ | CF$_3$ | H | CH=NN(CH$_3$)C(S)NH$_2$ |
| 3,5-Cl$_2$ | CF$_3$ | H | CH=NN(CH$_3$)C(S)NHCH$_3$ |
| 3,5-Cl$_2$ | CF$_3$ | H | CH=NNHC(S)N(CH$_3$)$_2$ |
| 3,5-Cl$_2$ | CF$_3$ | H | C(O)OCH$_3$ |
| 3,5-Cl$_2$ | CF$_3$ | CH$_3$ | C(O)OCH$_3$ |
| 3,5-Cl$_2$ | CF$_3$ | Et | C(O)OCH$_3$ |
| 3,5-Cl$_2$ | CF$_3$ | n-Pr | C(O)OCH$_3$ |
| 3,5-Cl$_2$ | CF$_3$ | i-Pr | C(O)OCH$_3$ |
| 3,5-Cl$_2$ | CF$_3$ | n-Bu | C(O)OCH$_3$ |
| 3,5-Cl$_2$ | CF$_3$ | i-Bu | C(O)OCH$_3$ |
| 3,5-Cl$_2$ | CF$_3$ | s-Bu | C(O)OCH$_3$ |
| 3,5-Cl$_2$ | CF$_3$ | n-Pen | C(O)OCH$_3$ |
| 3,5-Cl$_2$ | CF$_3$ | CH$_2$Bu-i | C(O)OCH$_3$ |
| 3,5-Cl$_2$ | CF$_3$ | CH$_2$Bu-s | C(O)OCH$_3$ |
| 3,5-Cl$_2$ | CF$_3$ | CH(CH3)Pr-n | C(O)OCH$_3$ |
| 3,5-Cl$_2$ | CF$_3$ | CH(Et)$_2$ | C(O)OCH$_3$ |
| 3,5-Cl$_2$ | CF$_3$ | n-Hex | C(O)OCH$_3$ |
| 3,5-Cl$_2$ | CF$_3$ | CH(CH$_3$)Bu-i | C(O)OCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | Hept | C(O)OCH$_3$ |
| 3,5-Cl$_2$ | CF$_3$ | Oct | C(O)OCH$_3$ |
| 3,5-Cl$_2$ | CF$_3$ | CH$_2$OCH$_3$ | C(O)OCH$_3$ |
| 3,5-Cl$_2$ | CF$_3$ | CH$_2$OEt | C(O)OCH$_3$ |
| 3,5-Cl$_2$ | CF$_3$ | CH$_2$OPr-n | C(O)OCH$_3$ |
| 3,5-Cl$_2$ | CF$_3$ | CH$_2$OPr-i | C(O)OCH$_3$ |
| 3,5-Cl$_2$ | CF$_3$ | CH$_2$OPr-c | C(O)OCH$_3$ |
| 3,5-Cl$_2$ | CF$_3$ | CH$_2$OBu-n | C(O)OCH$_3$ |
| 3,5-Cl$_2$ | CF$_3$ | CH$_2$OBu-i | C(O)OCH$_3$ |
| 3,5-Cl$_2$ | CF$_3$ | CH$_2$OCH$_2$Pr-c | C(O)OCH$_3$ |
| 3,5-Cl$_2$ | CF$_3$ | CH$_2$OBu-s(R) | C(O)OCH$_3$ |
| 3,5-Cl$_2$ | CF$_3$ | CH$_2$OBu-s(S) | C(O)OCH$_3$ |
| 3,5-Cl$_2$ | CF$_3$ | CH$_2$OBu-c | C(O)OCH$_3$ |
| 3,5-Cl$_2$ | CF$_3$ | CH$_2$OBu-t | C(O)OCH$_3$ |
| 3,5-Cl$_2$ | CF$_3$ | CH$_2$OPen-n | C(O)OCH$_3$ |
| 3,5-Cl$_2$ | CF$_3$ | CH$_2$OCH$_2$Bu-i | C(O)OCH$_3$ |
| 3,5-Cl$_2$ | CF$_3$ | CH$_2$OCH$_2$Bu-s | C(O)OCH$_3$ |
| 3,5-Cl$_2$ | CF$_3$ | CH$_2$OCH$_2$Bu-c | C(O)OCH$_3$ |
| 3,5-Cl$_2$ | CF$_3$ | CH$_2$OCH$_2$(T-6) | C(O)OCH$_3$ |
| 3,5-Cl$_2$ | CF$_3$ | CH$_2$OCH$_2$Bu-t | C(O)OCH$_3$ |
| 3,5-Cl$_2$ | CF$_3$ | CH$_2$OCH(CH$_3$)Pr-n | C(O)OCH$_3$ |
| 3,5-Cl$_2$ | CF$_3$ | CH$_2$OCH(Et)$_2$ | C(O)OCH$_3$ |
| 3,5-Cl$_2$ | CF$_3$ | CH$_2$OC(CH$_3$)$_2$Et | C(O)OCH$_3$ |
| 3,5-Cl$_2$ | CF$_3$ | CH$_2$OPen-c | C(O)OCH$_3$ |
| 3,5-Cl$_2$ | CF$_3$ | CH$_2$OHex-n | C(O)OCH$_3$ |
| 3,5-Cl$_2$ | CF$_3$ | CH$_2$OCH$_2$(T-7) | C(O)OCH$_3$ |
| 3,5-Cl$_2$ | CF$_3$ | CH$_2$OCH$_2$Pen-c | C(O)OCH$_3$ |
| 3,5-Cl$_2$ | CF$_3$ | CH$_2$OHex-c | C(O)OCH$_3$ |
| 3,5-Cl$_2$ | CF$_3$ | CH$_2$OCH$_2$Hex-c | C(O)OCH$_3$ |
| 3,5-Cl$_2$ | CF$_3$ | CH$_2$OCH$_2$CH$_2$F | C(O)OCH$_3$ |
| 3,5-Cl$_2$ | CF$_3$ | CH$_2$OCH$_2$CH$_2$Cl | C(O)OCH$_3$ |
| 3,5-Cl$_2$ | CF$_3$ | CH$_2$OCH$_2$CHF$_2$ | C(O)OCH$_3$ |
| 3,5-Cl$_2$ | CF$_3$ | CH$_2$OCH$_2$CHCl$_2$ | C(O)OCH$_3$ |
| 3,5-Cl$_2$ | CF$_3$ | CH$_2$OCH$_2$CF$_3$ | C(O)OCH$_3$ |
| 3,5-Cl$_2$ | CF$_3$ | CH$_2$OCH$_2$CF$_2$Cl | C(O)OCH$_3$ |
| 3,5-Cl$_2$ | CF$_3$ | CH$_2$OCH$_2$CCl$_3$ | C(O)OCH$_3$ |
| 3,5-Cl$_2$ | CF$_3$ | CH$_2$OCH$_2$CH$_2$CH$_2$F | C(O)OCH$_3$ |
| 3,5-Cl$_2$ | CF$_3$ | CH$_2$OCH$_2$CH$_2$CH$_2$Cl | C(O)OCH$_3$ |
| 3,5-Cl$_2$ | CF$_3$ | CH$_2$OCH$_2$CHClCH$_3$(R) | C(O)OCH$_3$ |
| 3,5-Cl$_2$ | CF$_3$ | CH$_2$OCH$_2$CHClCH$_3$(S) | C(O)OCH$_3$ |
| 3,5-Cl$_2$ | CF$_3$ | CH$_2$OCH$_2$CHFCH$_2$Cl | C(O)OCH$_3$ |
| 3,5-Cl$_2$ | CF$_3$ | CH$_2$OCH$_2$CHClCH$_2$Cl | C(O)OCH$_3$ |
| 3,5-Cl$_2$ | CF$_3$ | CH$_2$OCH$_2$CH$_2$CF$_3$ | C(O)OCH$_3$ |
| 3,5-Cl$_2$ | CF$_3$ | CH$_2$OCH$_2$CF$_2$CHF$_2$ | C(O)OCH$_3$ |
| 3,5-Cl$_2$ | CF$_3$ | CH$_2$OCH$_2$CF$_2$CF$_3$ | C(O)OCH$_3$ |
| 3,5-Cl$_2$ | CF$_3$ | CH$_2$OCH(CH$_3$)CH$_2$F | C(O)OCH$_3$ |
| 3,5-Cl$_2$ | CF$_3$ | CH$_2$OCH(CH$_3$)CH2Cl(R) | C(O)OCH$_3$ |
| 3,5-Cl$_2$ | CF$_3$ | CH$_2$OCH(CH$_3$)CH$_2$Cl(S) | C(O)OCH$_3$ |
| 3,5-Cl$_2$ | CF$_3$ | CH$_2$OCH(CH$_2$F)$_2$ | C(O)OCH$_3$ |
| 3,5-Cl$_2$ | CF$_3$ | CH$_2$OCH(CH$_3$)CF$_3$ | C(O)OCH$_3$ |
| 3,5-Cl$_2$ | CF$_3$ | CH$_2$OCH(CF$_3$)$_2$ | C(O)OCH$_3$ |
| 3,5-Cl$_2$ | CF$_3$ | CH$_2$OCH$_2$(T-1) | C(O)OCH$_3$ |
| 3,5-Cl$_2$ | CF$_3$ | CH$_2$OCH$_2$(T-2) | C(O)OCH$_3$ |
| 3,5-Cl$_2$ | CF$_3$ | CH$_2$OCH$_2$(T-3) | C(O)OCH$_3$ |
| 3,5-Cl$_2$ | CF$_3$ | CH$_2$OCH$_2$(T-4) | C(O)OCH$_3$ |
| 3,5-Cl$_2$ | CF$_3$ | CH$_2$OCH$_2$(T-5) | C(O)OCH$_3$ |
| 3,5-Cl$_2$ | CF$_3$ | CH$_2$OCH$_2$CH$_2$OCH$_3$ | C(O)OCH$_3$ |
| 3,5-Cl$_2$ | CF$_3$ | CH$_2$OCH$_2$CH$_2$OEt | C(O)OCH$_3$ |
| 3,5-Cl$_2$ | CF$_3$ | CH$_2$OCH$_2$CH$_2$OCH$_2$CF$_3$ | C(O)OCH$_3$ |
| 3,5-Cl$_2$ | CF$_3$ | CH$_2$OCH$_2$CH$_2$OCH$_2$CH$_2$OCH$_3$ | C(O)OCH$_3$ |
| 3,5-Cl$_2$ | CF$_3$ | CH$_2$OCH$_2$CH$_2$OC(O)NHCH$_3$ | C(O)OCH$_3$ |
| 3,5-Cl$_2$ | CF$_3$ | CH$_2$OCH$_2$CH$_2$OC(O)N(CH$_3$)$_2$ | C(O)OCH$_3$ |
| 3,5-Cl$_2$ | CF$_3$ | CH$_2$OCH$_2$CH2OC(S)NHCH$_3$ | C(O)OCH$_3$ |
| 3,5-Cl$_2$ | CF$_3$ | CH$_2$OCH$_2$CH$_2$OC(S)N(CH$_3$)$_2$ | C(O)OCH$_3$ |
| 3,5-Cl$_2$ | CF$_3$ | CH$_2$OCH$_2$CH2OPh | C(O)OCH$_3$ |
| 3,5-Cl$_2$ | CF$_3$ | CH$_2$OCH$_2$(E-5a) | C(O)OCH$_3$ |
| 3,5-Cl$_2$ | CF$_3$ | CH$_2$OCH$_2$(E-6a) | C(O)OCH$_3$ |
| 3,5-Cl$_2$ | CF$_3$ | CH$_2$OCH$_2$(E-11a) | C(O)OCH$_3$ |
| 3,5-Cl$_2$ | CF$_3$ | CH$_2$O(E-6a) | C(O)OCH$_3$ |
| 3,5-Cl$_2$ | CF$_3$ | CH$_2$O(E-25a) | C(O)OCH$_3$ |
| 3,5-Cl$_2$ | CF$_3$ | CH$_2$O(E-26a) | C(O)OCH$_3$ |
| 3,5-Cl$_2$ | CF$_3$ | CH$_2$OCH$_2$CH$_2$SCH$_3$ | C(O)OCH$_3$ |
| 3,5-Cl$_2$ | CF$_3$ | CH$_2$OCH$_2$CH$_2$S(O)CH$_3$ | C(O)OCH$_3$ |
| 3,5-Cl$_2$ | CF$_3$ | CH$_2$OCH$_2$CH$_2$SO$_2$CH$_3$ | C(O)OCH$_3$ |
| 3,5-Cl$_2$ | CF$_3$ | CH$_2$OCH$_2$CH$_2$SEt | C(O)OCH$_3$ |
| 3,5-Cl$_2$ | CF$_3$ | CH$_2$OCH$_2$CH$_2$S(O)Et | C(O)OCH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | CH$_2$OCH$_2$CH$_2$SO$_2$Et | C(O)OCH$_3$ |
| 3,5-Cl$_2$ | CF$_3$ | CH$_2$OCH$_2$CH$_2$SCH$_2$CH$_2$OCH$_3$ | C(O)OCH$_3$ |
| 3,5-Cl$_2$ | CF$_3$ | CH$_2$OCH$_2$CH$_2$SO$_2$CH$_2$CH$_2$OCH$_3$ | C(O)OCH$_3$ |
| 3,5-Cl$_2$ | CF$_3$ | CH$_2$OCH$_2$CH$_2$SCH$_2$CH$_2$SCH$_3$ | C(O)OCH$_3$ |
| 3,5-Cl$_2$ | CF$_3$ | CH$_2$OCH$_2$CH$_2$SCH$_2$CH=CH$_2$ | C(O)OCH$_3$ |
| 3,5-Cl$_2$ | CF$_3$ | CH$_2$OCH$_2$CH$_2$SCH$_2$C≡CH | C(O)OCH$_3$ |
| 3,5-Cl$_2$ | CF$_3$ | CH$_2$OCH$_2$CH$_2$SCH$_2$Ph | C(O)OCH$_3$ |
| 3,5-Cl$_2$ | CF$_3$ | CH$_2$OCH$_2$CH$_2$SO$_2$CH$_2$Ph | C(O)OCH$_3$ |
| 3,5-Cl$_2$ | CF$_3$ | CH$_2$OCH$_2$CH$_2$SC(O)N(CH$_3$)$_2$ | C(O)OCH$_3$ |
| 3,5-Cl$_2$ | CF$_3$ | CH$_2$OCH$_2$CH$_2$SC(S)NHCH$_3$ | C(O)OCH$_3$ |
| 3,5-Cl$_2$ | CF$_3$ | CH$_2$OCH$_2$CH$_2$SC(S)N(CH$_3$)$_2$ | C(O)OCH$_3$ |
| 3,5-Cl$_2$ | CF$_3$ | CH$_2$OCH$_2$CH$_2$SPh | C(O)OCH$_3$ |
| 3,5-Cl$_2$ | CF$_3$ | CH$_2$OCH$_2$CH$_2$S(O)Ph | C(O)OCH$_3$ |
| 3,5-Cl$_2$ | CF$_3$ | CH$_2$OCH$_2$CH$_2$SO$_2$Ph | C(O)OCH$_3$ |
| 3,5-Cl$_2$ | CF$_3$ | CH$_2$OCH$_2$CH$_2$SO$_2$NHCH$_3$ | C(O)OCH$_3$ |
| 3,5-Cl$_2$ | CF$_3$ | CH$_2$OCH$_2$CH$_2$SO$_2$N(CH$_3$)$_2$ | C(O)OCH$_3$ |
| 3,5-Cl$_2$ | CF$_3$ | CH$_2$OCH$_2$(E-7a) | C(O)OCH$_3$ |
| 3,5-Cl$_2$ | CF$_3$ | CH$_2$OCH$_2$(E-8a) | C(O)OCH$_3$ |
| 3,5-Cl$_2$ | CF$_3$ | CH$_2$OCH$_2$(E-8b) | C(O)OCH$_3$ |
| 3,5-Cl$_2$ | CF$_3$ | CH$_2$OCH$_2$(E-8c) | C(O)OCH$_3$ |
| 3,5-Cl$_2$ | CF$_3$ | CH$_2$OCH$_2$(E-19a) | C(O)OCH$_3$ |
| 3,5-Cl$_2$ | CF$_3$ | CH$_2$O(E-8a) | C(O)OCH$_3$ |
| 3,5-Cl$_2$ | CF$_3$ | CH$_2$O(E-8b) | C(O)OCH$_3$ |
| 3,5-Cl$_2$ | CF$_3$ | CH$_2$O(E-8c) | C(O)OCH$_3$ |
| 3,5-Cl$_2$ | CF$_3$ | CH$_2$O(E-28a) | C(O)OCH$_3$ |
| 3,5-Cl$_2$ | CF$_3$ | CH$_2$O(E-29a) | C(O)OCH$_3$ |
| 3,5-Cl$_2$ | CF$_3$ | CH$_2$OCH$_2$CN | C(O)OCH$_3$ |
| 3,5-Cl$_2$ | CF$_3$ | CH$_2$OCH(CH$_3$)CN | C(O)OCH$_3$ |
| 3,5-Cl$_2$ | CF$_3$ | CH$_2$OC(CH$_3$)$_2$CN | C(O)OCH$_3$ |
| 3,5-Cl$_2$ | CF$_3$ | CH$_2$OCH$_2$CH$_2$CN | C(O)OCH$_3$ |
| 3,5-Cl$_2$ | CF$_3$ | CH$_2$OCH$_2$C(O)OCH$_3$ | C(O)OCH$_3$ |
| 3,5-Cl$_2$ | CF$_3$ | CH$_2$OCH$_2$CH=CH$_2$ | C(O)OCH$_3$ |
| 3,5-Cl$_2$ | CF$_3$ | CH$_2$OCH$_2$CF=CH$_2$ | C(O)OCH$_3$ |
| 3,5-Cl$_2$ | CF$_3$ | CH$_2$OCH$_2$CH=CHCl | C(O)OCH$_3$ |
| 3,5-Cl$_2$ | CF$_3$ | CH$_2$OCH$_2$CCl=CH$_2$ | C(O)OCH$_3$ |
| 3,5-Cl$_2$ | CF$_3$ | CH$_2$OCH$_2$CH=CCl$_2$ | C(O)OCH$_3$ |
| 3,5-Cl$_2$ | CF$_3$ | CH$_2$OCH$_2$CCl=CHCl | C(O)OCH$_3$ |
| 3,5-Cl$_2$ | CF$_3$ | CH$_2$OCH$_2$C≡CH | C(O)OCH$_3$ |
| 3,5-Cl$_2$ | CF$_3$ | CH$_2$OCH(CH$_3$)C≡CH | C(O)OCH$_3$ |
| 3,5-Cl$_2$ | CF$_3$ | CH$_2$OC(CH$_3$)$_2$C≡CH | C(O)OCH$_3$ |
| 3,5-Cl$_2$ | CF$_3$ | CH$_2$OCH$_2$C≡CCl | C(O)OCH$_3$ |
| 3,5-Cl$_2$ | CF$_3$ | CH$_2$OCH$_2$C≡CBr | C(O)OCH$_3$ |
| 3,5-Cl$_2$ | CF$_3$ | CH$_2$OCH$_2$C≡Cl | C(O)OCH$_3$ |
| 3,5-Cl$_2$ | CF$_3$ | CH$_2$OCH$_2$Ph | C(O)OCH$_3$ |
| 3,5-Cl$_2$ | CF$_3$ | CH$_2$OC(O)CH$_3$ | C(O)OCH$_3$ |
| 3,5-Cl$_2$ | CF$_3$ | CH$_2$OC(O)Et | C(O)OCH$_3$ |
| 3,5-Cl$_2$ | CF$_3$ | CH$_2$OC(O)Pr-n | C(O)OCH$_3$ |
| 3,5-Cl$_2$ | CF$_3$ | CH$_2$OC(O)Pr-i | C(O)OCH$_3$ |
| 3,5-Cl$_2$ | CF$_3$ | CH$_2$OC(O)Pr-c | C(O)OCH$_3$ |
| 3,5-Cl$_2$ | CF$_3$ | CH$_2$OC(O)Bu-n | C(O)OCH$_3$ |
| 3,5-Cl$_2$ | CF$_3$ | CH$_2$OC(O)Bu-i | C(O)OCH$_3$ |
| 3,5-Cl$_2$ | CF$_3$ | CH$_2$OC(O)Bu-s | C(O)OCH$_3$ |
| 3,5-Cl$_2$ | CF$_3$ | CH$_2$OC(O)Bu-t | C(O)OCH$_3$ |
| 3,5-Cl$_2$ | CF$_3$ | CH$_2$OC(O)CH$_2$Ph | C(O)OCH$_3$ |
| 3,5-Cl$_2$ | CF$_3$ | CH$_2$OC(O)OCH$_3$ | C(O)OCH$_3$ |
| 3,5-Cl$_2$ | CF$_3$ | CH$_2$OC(O)OEt | C(O)OCH$_3$ |
| 3,5-Cl$_2$ | CF$_3$ | CH$_2$OC(O)OPr-i | C(O)OCH$_3$ |
| 3,5-Cl$_2$ | CF$_3$ | CH$_2$OC(O)OBu-n | C(O)OCH$_3$ |
| 3,5-Cl$_2$ | CF$_3$ | CH$_2$OC(O)OBu-i | C(O)OCH$_3$ |
| 3,5-Cl$_2$ | CF$_3$ | CH$_2$OC(O)OCH$_2$Ph | C(O)OCH$_3$ |
| 3,5-Cl$_2$ | CF$_3$ | CH$_2$OC(O)OPh | C(O)OCH$_3$ |
| 3,5-Cl$_2$ | CF$_3$ | CH$_2$OC(O)NHPh | C(O)OCH$_3$ |
| 3,5-Cl$_2$ | CF$_3$ | CH$_2$OC(O)Ph | C(O)OCH$_3$ |
| 3,5-Cl$_2$ | CF$_3$ | CH$_2$OPh | C(O)OCH$_3$ |
| 3,5-Cl$_2$ | CF$_3$ | CH(CH$_3$)OC(O)CH$_3$ | C(O)OCH$_3$ |
| 3,5-Cl$_2$ | CF$_3$ | CH(CH$_3$)OC(O)Et | C(O)OCH$_3$ |
| 3,5-Cl$_2$ | CF$_3$ | CH(CH$_3$)OC(O)Pr-n | C(O)OCH$_3$ |
| 3,5-Cl$_2$ | CF$_3$ | CH(CH$_3$)OC(O)Pr-i | C(O)OCH$_3$ |
| 3,5-Cl$_2$ | CF$_3$ | CH(CH$_3$)OC(O)Bu-n | C(O)OCH$_3$ |
| 3,5-Cl$_2$ | CF$_3$ | CH(CH$_3$)OC(O)Bu-t | C(O)OCH$_3$ |
| 3,5-Cl$_2$ | CF$_3$ | CH(CH$_3$)OC(O)OCH$_3$ | C(O)OCH$_3$ |
| 3,5-Cl$_2$ | CF$_3$ | CH(CH$_3$)OC(O)OEt | C(O)OCH$_3$ |
| 3,5-Cl$_2$ | CF$_3$ | CH(CH$_3$)OC(O)OPr-n | C(O)OCH$_3$ |
| 3,5-Cl$_2$ | CF$_3$ | CH(CH$_3$)OC(O)OPr-i | C(O)OCH$_3$ |
| 3,5-Cl$_2$ | CF$_3$ | CH(CH$_3$)OC(O)OBu-n | C(O)OCH$_3$ |
| 3,5-Cl$_2$ | CF$_3$ | CH(CH$_3$)OC(O)OBu-i | C(O)OCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | CH(CH$_3$)OC(O)OPen-n | C(O)OCH$_3$ |
| 3,5-Cl$_2$ | CF$_3$ | CH(CH$_3$)OC(O)OCH$_2$CH$_2$Pr-i | C(O)OCH$_3$ |
| 3,5-Cl$_2$ | CF$_3$ | CH(CH$_3$)OC(O)OHex-n | C(O)OCH$_3$ |
| 3,5-Cl$_2$ | CF$_3$ | CH(CH$_3$)OC(O)OCH$_2$CH$_2$Cl | C(O)OCH$_3$ |
| 3,5-Cl$_2$ | CF$_3$ | CH(CH$_3$)OC(O)OCH$_2$CH$_2$OCH$_3$ | C(O)OCH$_3$ |
| 3,5-Cl$_2$ | CF$_3$ | CH(CH$_3$)OC(O)OCH$_2$CH$_2$SCH$_3$ | C(O)OCH$_3$ |
| 3,5-Cl$_2$ | CF$_3$ | CH(CH$_3$)OC(O)OCH$_2$CH=CH$_2$ | C(O)OCH$_3$ |
| 3,5-Cl$_2$ | CF$_3$ | CH(CH$_3$)OC(O)OCH$_2$C≡CH | C(O)OCH$_3$ |
| 3,5-Cl$_2$ | CF$_3$ | CH(CH$_3$)OC(O)OCH$_2$Ph | C(O)OCH$_3$ |
| 3,5-Cl$_2$ | CF$_3$ | CH(CH$_3$)OC(O)OPh | C(O)OCH$_3$ |
| 3,5-Cl$_2$ | CF$_3$ | CH(CH$_3$)OC(O)SCH$_3$ | C(O)OCH$_3$ |
| 3,5-Cl$_2$ | CF$_3$ | CH(CH$_3$)OC(O)SEt | C(O)OCH$_3$ |
| 3,5-Cl$_2$ | CF$_3$ | CH(CH$_3$)OC(O)N(Et)$_2$ | C(O)OCH$_3$ |
| 3,5-Cl$_2$ | CF$_3$ | CH(Et)OC(O)CH$_3$ | C(O)OCH$_3$ |
| 3,5-Cl$_2$ | CF$_3$ | CH(Et)OC(O)Bu-n | C(O)OCH$_3$ |
| 3,5-Cl$_2$ | CF$_3$ | CH(Et)OC(O)Bu-t | C(O)OCH$_3$ |
| 3,5-Cl$_2$ | CF$_3$ | CH(Et)OC(O)OEt | C(O)OCH$_3$ |
| 3,5-Cl$_2$ | CF$_3$ | CH(Pr-n)OC(O)CH$_3$ | C(O)OCH$_3$ |
| 3,5-Cl$_2$ | CF$_3$ | CH(Pr-n)OC(O)Bu-n | C(O)OCH$_3$ |
| 3,5-Cl$_2$ | CF$_3$ | CH(Pr-n)OC(O)Bu-t | C(O)OCH$_3$ |
| 3,5-Cl$_2$ | CF$_3$ | CH(Pr-i)OC(O)CH$_3$ | C(O)OCH$_3$ |
| 3,5-Cl$_2$ | CF$_3$ | CH(Pr-i)OC(O)Bu-t | C(O)OCH$_3$ |
| 3,5-Cl$_2$ | CF$_3$ | CH(Pr-i)OC(O)OCH$_3$ | C(O)OCH$_3$ |
| 3,5-Cl$_2$ | CF$_3$ | CH(Hex-c)OC(O)CH$_3$ | C(O)OCH$_3$ |
| 3,5-Cl$_2$ | CF$_3$ | CH(Ph)OC(O)OCH$_3$ | C(O)OCH$_3$ |
| 3,5-Cl$_2$ | CF$_3$ | E-5a | C(O)OCH$_3$ |
| 3,5-Cl$_2$ | CF$_3$ | E-24a | C(O)OCH$_3$ |
| 3,5-Cl$_2$ | CF$_3$ | CH$_2$SCH$_3$ | C(O)OCH$_3$ |
| 3,5-Cl$_2$ | CF$_3$ | CH$_2$SO$_2$CH$_3$ | C(O)OCH$_3$ |
| 3,5-Cl$_2$ | CF$_3$ | CH$_2$SC(O)CH$_3$ | C(O)OCH$_3$ |
| 3,5-Cl$_2$ | CF$_3$ | CH$_2$SC(O)Et | C(O)OCH$_3$ |
| 3,5-Cl$_2$ | CF$_3$ | CH$_2$SC(O)Ph | C(O)OCH$_3$ |
| 3,5-Cl$_2$ | CF$_3$ | CH$_2$SC(S)OCH$_3$ | C(O)OCH$_3$ |
| 3,5-Cl$_2$ | CF$_3$ | CH$_2$SC(S)OEt | C(O)OCH$_3$ |
| 3,5-Cl$_2$ | CF$_3$ | CH$_2$SC(S)OPr-n | C(O)OCH$_3$ |
| 3,5-Cl$_2$ | CF$_3$ | CH$_2$SC(S)OPr-i | C(O)OCH$_3$ |
| 3,5-Cl$_2$ | CF$_3$ | CH$_2$SC(S)N(CH$_3$)$_2$ | C(O)OCH$_3$ |
| 3,5-Cl$_2$ | CF$_3$ | CH$_2$SC(S)(T-14) | C(O)OCH$_3$ |
| 3,5-Cl$_2$ | CF$_3$ | CH$_2$N(CH$_3$)$_2$ | C(O)OCH$_3$ |
| 3,5-Cl$_2$ | CF$_3$ | CH$_2$N(CH$_3$)C(O)CH$_3$ | C(O)OCH$_3$ |
| 3,5-Cl$_2$ | CF$_3$ | CH$_2$NHC(O)OCH$_3$ | C(O)OCH$_3$ |
| 3,5-Cl$_2$ | CF$_3$ | CH$_2$N(CH$_3$)C(O)OCH$_3$ | C(O)OCH$_3$ |
| 3,5-Cl$_2$ | CF$_3$ | CH$_2$N(CH$_3$)SO$_2$CH$_3$ | C(O)OCH$_3$ |
| 3,5-Cl$_2$ | CF$_3$ | CH$_2$C(O)Ph | C(O)OCH$_3$ |
| 3,5-Cl$_2$ | CF$_3$ | CH$_2$CN | C(O)OCH$_3$ |
| 3,5-Cl$_2$ | CF$_3$ | CH$_2$C(O)OCH$_3$ | C(O)OCH$_3$ |
| 3,5-Cl$_2$ | CF$_3$ | CH$_2$C≡CH | C(O)OCH$_3$ |
| 3,5-Cl$_2$ | CF$_3$ | CH$_2$Ph | C(O)OCH$_3$ |
| 3,5-Cl$_2$ | CF$_3$ | CH(CH$_3$)Ph | C(O)OCH$_3$ |
| 3,5-Cl$_2$ | CF$_3$ | CH(CH$_3$)Ph(R) | C(O)OCH$_3$ |
| 3,5-Cl$_2$ | CF$_3$ | CH(CH$_3$)Ph(S) | C(O)OCH$_3$ |
| 3,5-Cl$_2$ | CF$_3$ | C(O)CH$_3$ | C(O)OCH$_3$ |
| 3,5-Cl$_2$ | CF$_3$ | C(O)Et | C(O)OCH$_3$ |
| 3,5-Cl$_2$ | CF$_3$ | C(O)Pr-n | C(O)OCH$_3$ |
| 3,5-Cl$_2$ | CF$_3$ | C(O)Pr-i | C(O)OCH$_3$ |
| 3,5-Cl$_2$ | CF$_3$ | C(O)Pr-c | C(O)OCH$_3$ |
| 3,5-Cl$_2$ | CF$_3$ | C(O)Bu-n | C(O)OCH$_3$ |
| 3,5-Cl$_2$ | CF$_3$ | C(O)Bu-i | C(O)OCH$_3$ |
| 3,5-Cl$_2$ | CF$_3$ | C(O)Bu-s | C(O)OCH$_3$ |
| 3,5-Cl$_2$ | CF$_3$ | C(O)Bu-t | C(O)OCH$_3$ |
| 3,5-Cl$_2$ | CF$_3$ | C(O)CH$_2$Cl | C(O)OCH$_3$ |
| 3,5-Cl$_2$ | CF$_3$ | C(O)CH$_2$OCH$_3$ | C(O)OCH$_3$ |
| 3,5-Cl$_2$ | CF$_3$ | C(O)CH$_2$OEt | C(O)OCH$_3$ |
| 3,5-Cl$_2$ | CF$_3$ | C(O)CH$_2$SCH$_3$ | C(O)OCH$_3$ |
| 3,5-Cl$_2$ | CF$_3$ | C(O)CH$_2$SO$_2$CH$_3$ | C(O)OCH$_3$ |
| 3,5-Cl$_2$ | CF$_3$ | C(O)CH=CH$_2$ | C(O)OCH$_3$ |
| 3,5-Cl$_2$ | CF$_3$ | C(O)Ph | C(O)OCH$_3$ |
| 3,5-Cl$_2$ | CF$_3$ | C(O)(Ph-4-Cl) | C(O)OCH$_3$ |
| 3,5-Cl$_2$ | CF$_3$ | C(O)(Ph-4-CH$_3$) | C(O)OCH$_3$ |
| 3,5-Cl$_2$ | CF$_3$ | C(O)(Ph-4-OCH$_3$) | C(O)OCH$_3$ |
| 3,5-Cl$_2$ | CF$_3$ | C(O)(Ph-4-NO$_2$) | C(O)OCH$_3$ |
| 3,5-Cl$_2$ | CF$_3$ | C(O)(Ph-4-CN) | C(O)OCH$_3$ |
| 3,5-Cl$_2$ | CF$_3$ | C(O)(D-52a) | C(O)OCH$_3$ |
| 3,5-Cl$_2$ | CF$_3$ | C(O)OCH$_3$ | C(O)OCH$_3$ |
| 3,5-Cl$_2$ | CF$_3$ | C(O)OCH$_2$Cl | C(O)OCH$_3$ |
| 3,5-Cl$_2$ | CF$_3$ | C(O)OCH$_2$CH$_2$Cl | C(O)OCH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | SCCl$_3$ | C(O)OCH$_3$ |
| 3,5-Cl$_2$ | CF$_3$ | SN(Bu-n)$_2$ | C(O)OCH$_3$ |
| 3,5-Cl$_2$ | CF$_3$ | S(T-18) | C(O)OCH$_3$ |
| 3,5-Cl$_2$ | CF$_3$ | SN(Pr-i)CH$_2$CH$_2$C(O)OEt | C(O)OCH$_3$ |
| 3,5-Cl$_2$ | CF$_3$ | SN(CH$_2$Ph)CH$_2$CH$_2$C(O)OEt | C(O)OCH$_3$ |
| 3,5-Cl$_2$ | CF$_3$ | SN(CH$_3$)C(O)OBu-n | C(O)OCH$_3$ |
| 3,5-Cl$_2$ | CF$_3$ | H | C(O)OEt |
| 3,5-Cl$_2$ | CF$_3$ | CH$_3$ | C(O)OEt |
| 3,5-Cl$_2$ | CF$_3$ | Et | C(O)OEt |
| 3,5-Cl$_2$ | CF$_3$ | CH$_2$OCH$_3$ | C(O)OEt |
| 3,5-Cl$_2$ | CF$_3$ | CH$_2$OEt | C(O)OEt |
| 3,5-Cl$_2$ | CF$_3$ | CH$_2$OCH$_2$CH$_2$Cl | C(O)OEt |
| 3,5-Cl$_2$ | CF$_3$ | CH$_2$OCH$_2$CHF$_2$ | C(O)OEt |
| 3,5-Cl$_2$ | CF$_3$ | CH$_2$OCH$_2$CF$_3$ | C(O)OEt |
| 3,5-Cl$_2$ | CF$_3$ | CH$_2$OCH$_2$CH$_2$OCH$_3$ | C(O)OEt |
| 3,5-Cl$_2$ | CF$_3$ | CH$_2$OCH2Ph | C(O)OEt |
| 3,5-Cl$_2$ | CF$_3$ | CH$_2$OC(O)CH$_3$ | C(O)OEt |
| 3,5-Cl$_2$ | CF$_3$ | CH$_2$OC(O)Et | C(O)OEt |
| 3,5-Cl$_2$ | CF$_3$ | CH$_2$OC(O)Pr-n | C(O)OEt |
| 3,5-Cl$_2$ | CF$_3$ | CH$_2$OC(O)Pr-i | C(O)OEt |
| 3,5-Cl$_2$ | CF$_3$ | CH$_2$OC(O)Pr-c | C(O)OEt |
| 3,5-Cl$_2$ | CF$_3$ | CH$_2$OC(O)Bu-n | C(O)OEt |
| 3,5-Cl$_2$ | CF$_3$ | CH$_2$OC(O)Bu-i | C(O)OEt |
| 3,5-Cl$_2$ | CF$_3$ | CH$_2$OC(O)Bu-s | C(O)OEt |
| 3,5-Cl$_2$ | CF$_3$ | CH$_2$OC(O)Bu-t | C(O)OEt |
| 3,5-Cl$_2$ | CF$_3$ | CH$_2$OC(O)OCH$_3$ | C(O)OEt |
| 3,5-Cl$_2$ | CF$_3$ | CH$_2$OC(O)OEt | C(O)OEt |
| 3,5-Cl$_2$ | CF$_3$ | CH$_2$OC(O)OPh | C(O)OEt |
| 3,5-Cl$_2$ | CF$_3$ | CH$_2$OC(O)Ph | C(O)OEt |
| 3,5-Cl$_2$ | CF$_3$ | CH$_2$SC(O)CH$_3$ | C(O)OEt |
| 3,5-Cl$_2$ | CF$_3$ | CH$_2$SC(S)OCH$_3$ | C(O)OEt |
| 3,5-Cl$_2$ | CF$_3$ | CH$_2$SC(S)N(CH$_3$)$_2$ | C(O)OEt |
| 3,5-Cl$_2$ | CF$_3$ | CH$_2$NHC(O)OEt | C(O)OEt |
| 3,5-Cl$_2$ | CF$_3$ | CH$_2$CN | C(O)OEt |
| 3,5-Cl$_2$ | CF$_3$ | CH$_2$C≡CH | C(O)OEt |
| 3,5-Cl$_2$ | CF$_3$ | C(O)CH$_3$ | C(O)OEt |
| 3,5-Cl$_2$ | CF$_3$ | C(O)Et | C(O)OEt |
| 3,5-Cl$_2$ | CF$_3$ | C(O)Pr-n | C(O)OEt |
| 3,5-Cl$_2$ | CF$_3$ | C(O)Pr-i | C(O)OEt |
| 3,5-Cl$_2$ | CF$_3$ | C(O)Pr-c | C(O)OEt |
| 3,5-Cl$_2$ | CF$_3$ | C(O)Bu-n | C(O)OEt |
| 3,5-Cl$_2$ | CF$_3$ | C(O)Bu-i | C(O)OEt |
| 3,5-Cl$_2$ | CF$_3$ | C(O)Bu-s | C(O)OEt |
| 3,5-Cl$_2$ | CF$_3$ | C(O)Bu-t | C(O)OEt |
| 3,5-Cl$_2$ | CF$_3$ | C(O)CH$_2$OCH$_3$ | C(O)OEt |
| 3,5-Cl$_2$ | CF$_3$ | C(O)CH$_2$SCH$_3$ | C(O)OEt |
| 3,5-Cl$_2$ | CF$_3$ | C(O)OCH$_3$ | C(O)OEt |
| 3,5-Cl$_2$ | CF$_3$ | C(O)OEt | C(O)OEt |
| 3,5-Cl$_2$ | CF$_3$ | C(O)OCH$_2$Cl | C(O)OEt |
| 3,5-Cl$_2$ | CF$_3$ | C(O)OCH$_2$CH$_2$Cl | C(O)OEt |
| 3,5-Cl$_2$ | CF$_3$ | SCCl$_3$ | C(O)OEt |
| 3,5-Cl$_2$ | CF$_3$ | SN(Bu-n)$_2$ | C(O)OEt |
| 3,5-Cl$_2$ | CF$_3$ | SN(Pr-i)CH$_2$CH$_2$C(O)OEt | C(O)OEt |
| 3,5-Cl$_2$ | CF$_3$ | SN(CH$_2$Ph)CH$_2$CH$_2$C(O)OEt | C(O)OEt |
| 3,5-Cl$_2$ | CF$_3$ | SN(CH$_3$)C(O)OBu-n | C(O)OEt |
| 3,5-Cl$_2$ | CF$_3$ | H | C(O)OPr-n |
| 3,5-Cl$_2$ | CF$_3$ | CH$_3$ | C(O)OPr-n |
| 3,5-Cl$_2$ | CF$_3$ | CH$_2$OCH$_3$ | C(O)OPr-n |
| 3,5-Cl$_2$ | CF$_3$ | C(O)CH$_3$ | C(O)OPr-n |
| 3,5-Cl$_2$ | CF$_3$ | C(O)OCH$_3$ | C(O)OPr-n |
| 3,5-Cl$_2$ | CF$_3$ | C(O)OEt | C(O)OPr-n |
| 3,5-Cl$_2$ | CF$_3$ | H | C(O)OPr-i |
| 3,5-Cl$_2$ | CF$_3$ | CH$_3$ | C(O)OPr-i |
| 3,5-Cl$_2$ | CF$_3$ | Et | C(O)OPr-i |
| 3,5-Cl$_2$ | CF$_3$ | CH$_2$OCH$_3$ | C(O)OPr-i |
| 3,5-Cl$_2$ | CF$_3$ | C(O)OEt | C(O)OPr-i |
| 3,5-Cl$_2$ | CF$_3$ | CH$_2$OCH$_2$CH$_2$Cl | C(O)OPr-i |
| 3,5-Cl$_2$ | CF$_3$ | CH$_2$OCH$_2$CHF$_2$ | C(O)OPr-i |
| 3,5-Cl$_2$ | CF$_3$ | CH$_2$OCH$_2$CF$_3$ | C(O)OPr-i |
| 3,5-Cl$_2$ | CF$_3$ | CH$_2$OCH$_2$CH$_2$OCH$_3$ | C(O)OPr-i |
| 3,5-Cl$_2$ | CF$_3$ | CH$_2$OCH$_2$Ph | C(O)OPr-i |
| 3,5-Cl$_2$ | CF$_3$ | CH$_2$OC(O)CH$_3$ | C(O)OPr-i |
| 3,5-Cl$_2$ | CF$_3$ | CH$_2$OC(O)Et | C(O)OPr-i |
| 3,5-Cl$_2$ | CF$_3$ | CH$_2$OC(O)Pr-n | C(O)OPr-i |
| 3,5-Cl$_2$ | CF$_3$ | CH$_2$OC(O)Pr-i | C(O)OPr-i |
| 3,5-Cl$_2$ | CF$_3$ | CH$_2$OC(O)Pr-c | C(O)OPr-i |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | CH$_2$OC(O)Bu-n | C(O)OPr-i |
| 3,5-Cl$_2$ | CF$_3$ | CH$_2$OC(O)Bu-i | C(O)OPr-i |
| 3,5-Cl$_2$ | CF$_3$ | CH$_2$OC(O)Bu-s | C(O)OPr-i |
| 3,5-Cl$_2$ | CF$_3$ | CH$_2$OC(O)Bu-t | C(O)OPr-i |
| 3,5-Cl$_2$ | CF$_3$ | CH$_2$OC(O)OCH$_3$ | C(O)OPr-i |
| 3,5-Cl$_2$ | CF$_3$ | CH$_2$OC(O)OEt | C(O)OPr-i |
| 3,5-Cl$_2$ | CF$_3$ | CH$_2$OC(O)OPh | C(O)OPr-i |
| 3,5-Cl$_2$ | CF$_3$ | CH$_2$OC(O)Ph | C(O)OPr-i |
| 3,5-Cl$_2$ | CF$_3$ | CH$_2$SC(O)CH$_3$ | C(O)OPr-i |
| 3,5-Cl$_2$ | CF$_3$ | CH$_2$SC(S)OCH$_3$ | C(O)OPr-i |
| 3,5-Cl$_2$ | CF$_3$ | CH$_2$SC(S)N(CH$_3$)$_2$ | C(O)OPr-i |
| 3,5-Cl$_2$ | CF$_3$ | CH$_2$NHC(O)OEt | C(O)OPr-i |
| 3,5-Cl$_2$ | CF$_3$ | CH$_2$CN | C(O)OPr-i |
| 3,5-Cl$_2$ | CF$_3$ | CH$_2$C≡CH | C(O)OPr-i |
| 3,5-Cl$_2$ | CF$_3$ | C(O)CH$_3$ | C(O)OPr-i |
| 3,5-Cl$_2$ | CF$_3$ | C(O)Et | C(O)OPr-i |
| 3,5-Cl$_2$ | CF$_3$ | C(O)Pr-n | C(O)OPr-i |
| 3,5-Cl$_2$ | CF$_3$ | C(O)Pr-i | C(O)OPr-i |
| 3,5-Cl$_2$ | CF$_3$ | C(O)Pr-c | C(O)OPr-i |
| 3,5-Cl$_2$ | CF$_3$ | C(O)Bu-n | C(O)OPr-i |
| 3,5-Cl$_2$ | CF$_3$ | C(O)Bu-i | C(O)OPr-i |
| 3,5-Cl$_2$ | CF$_3$ | C(O)Bu-s | C(O)OPr-i |
| 3,5-Cl$_2$ | CF$_3$ | C(O)Bu-t | C(O)OPr-i |
| 3,5-Cl$_2$ | CF$_3$ | C(O)CH$_2$OCH$_3$ | C(O)OPr-i |
| 3,5-Cl$_2$ | CF$_3$ | C(O)CH$_2$SCH$_3$ | C(O)OPr-i |
| 3,5-Cl$_2$ | CF$_3$ | C(O)OCH$_3$ | C(O)OPr-i |
| 3,5-Cl$_2$ | CF$_3$ | C(O)OEt | C(O)OPr-i |
| 3,5-Cl$_2$ | CF$_3$ | C(O)OCH$_2$Cl | C(O)OPr-i |
| 3,5-Cl$_2$ | CF$_3$ | C(O)OCH$_2$CH$_2$Cl | C(O)OPr-i |
| 3,5-Cl$_2$ | CF$_3$ | SCCl$_3$ | C(O)OPr-i |
| 3,5-Cl$_2$ | CF$_3$ | SN(Bu-n)$_2$ | C(O)OPr-i |
| 3,5-Cl$_2$ | CF$_3$ | SN(Pr-i)CH$_2$CH$_2$C(O)OEt | C(O)OPr-i |
| 3,5-Cl$_2$ | CF$_3$ | SN(CH$_2$Ph)CH$_2$CH$_2$C(O)OEt | C(O)OPr-i |
| 3,5-Cl$_2$ | CF$_3$ | SN(CH$_3$)C(O)OBu-n | C(O)OPr-i |
| 3,5-Cl$_2$ | CF$_3$ | H | C(O)OPr-c |
| 3,5-Cl$_2$ | CF$_3$ | CH$_3$ | C(O)OPr-c |
| 3,5-Cl$_2$ | CF$_3$ | CH$_2$OCH$_3$ | C(O)OPr-c |
| 3,5-Cl$_2$ | CF$_3$ | C(O)CH$_3$ | C(O)OPr-c |
| 3,5-Cl$_2$ | CF$_3$ | C(O)OCH$_3$ | C(O)OPr-c |
| 3,5-Cl$_2$ | CF$_3$ | C(O)OEt | C(O)OPr-c |
| 3,5-Cl$_2$ | CF$_3$ | H | C(O)OBu-n |
| 3,5-Cl$_2$ | CF$_3$ | CH$_3$ | C(O)OBu-n |
| 3,5-Cl$_2$ | CF$_3$ | H | C(O)OBu-i |
| 3,5-Cl$_2$ | CF$_3$ | CH$_3$ | C(O)OBu-i |
| 3,5-Cl$_2$ | CF$_3$ | H | C(O)OCH$_2$Pr-c |
| 3,5-Cl$_2$ | CF$_3$ | CH$_3$ | C(O)OCH$_2$Pr-c |
| 3,5-Cl$_2$ | CF$_3$ | CH$_2$OCH$_3$ | C(O)OCH$_2$Pr-c |
| 3,5-Cl$_2$ | CF$_3$ | C(O)CH$_3$ | C(O)OCH$_2$Pr-c |
| 3,5-Cl$_2$ | CF$_3$ | C(O)OCH$_3$ | C(O)OCH$_2$Pr-c |
| 3,5-Cl$_2$ | CF$_3$ | C(O)OEt | C(O)OCH$_2$Pr-c |
| 3,5-Cl$_2$ | CF$_3$ | H | C(O)OBu-s(R) |
| 3,5-Cl$_2$ | CF$_3$ | CH$_3$ | C(O)OBu-s(R) |
| 3,5-Cl$_2$ | CF$_3$ | H | C(O)OBu-s(S) |
| 3,5-Cl$_2$ | CF$_3$ | CH$_3$ | C(O)OBu-s(S) |
| 3,5-Cl$_2$ | CF$_3$ | H | C(O)OBu-c |
| 3,5-Cl$_2$ | CF$_3$ | H | C(O)OBu-t |
| 3,5-Cl$_2$ | CF$_3$ | CH$_3$ | C(O)OBu-t |
| 3,5-Cl$_2$ | CF$_3$ | Et | C(O)OBu-t |
| 3,5-Cl$_2$ | CF$_3$ | CH$_2$OCH$_3$ | C(O)OBu-t |
| 3,5-Cl$_2$ | CF$_3$ | C(O)CH$_3$ | C(O)OBu-t |
| 3,5-Cl$_2$ | CF$_3$ | C(O)Et | C(O)OBu-t |
| 3,5-Cl$_2$ | CF$_3$ | C(O)CH$_2$CF$_3$ | C(O)OBu-t |
| 3,5-Cl$_2$ | CF$_3$ | C(O)OCH$_3$ | C(O)OBu-t |
| 3,5-Cl$_2$ | CF$_3$ | H | C(O)OPen-n |
| 3,5-Cl$_2$ | CF$_3$ | H | C(O)OCH$_2$Bu-i |
| 3,5-Cl$_2$ | CF$_3$ | H | C(O)OCH$_2$Bu-s |
| 3,5-Cl$_2$ | CF$_3$ | H | C(O)OCH$_2$Bu-c |
| 3,5-Cl$_2$ | CF$_3$ | H | C(O)OCH$_2$(T-6) |
| 3,5-Cl$_2$ | CF$_3$ | H | C(O)OCH$_2$Bu-t |
| 3,5-Cl$_2$ | CF$_3$ | H | C(O)OCH(CH$_3$)Pr-n |
| 3,5-Cl$_2$ | CF$_3$ | H | C(O)OCH(Et)$_2$ |
| 3,5-Cl$_2$ | CF$_3$ | H | C(O)OC(CH$_3$)$_2$Et |
| 3,5-Cl$_2$ | CF$_3$ | H | C(O)OPen-c |
| 3,5-Cl$_2$ | CF$_3$ | CH$_3$ | C(O)OPen-c |
| 3,5-Cl$_2$ | CF$_3$ | H | C(O)OHex-n |
| 3,5-Cl$_2$ | CF$_3$ | H | C(O)OCH$_2$(T-7) |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | H | C(O)OCH$_2$Pen-c |
| 3,5-Cl$_2$ | CF$_3$ | H | C(O)OHex-c |
| 3,5-Cl$_2$ | CF$_3$ | H | C(O)OCH$_2$Hex-c |
| 3,5-Cl$_2$ | CF$_3$ | H | C(O)OCH$_2$(T-1) |
| 3,5-Cl$_2$ | CF$_3$ | H | C(O)OCH$_2$(T-2) |
| 3,5-Cl$_2$ | CF$_3$ | H | C(O)OCH$_2$(T-3) |
| 3,5-Cl$_2$ | CF$_3$ | H | C(O)OCH$_2$(T-4) |
| 3,5-Cl$_2$ | CF$_3$ | H | C(O)OCH$_2$(T-5) |
| 3,5-Cl$_2$ | CF$_3$ | H | C(O)OCH$_2$(T-10) |
| 3,5-Cl$_2$ | CF$_3$ | H | C(O)OCH2(T-11) |
| 3,5-Cl$_2$ | CF$_3$ | H | C(O)OCH$_2$CH$_2$OCH$_3$ |
| 3,5-Cl$_2$ | CF$_3$ | CH$_3$ | C(O)OCH$_2$CH$_2$OCH$_3$ |
| 3,5-Cl$_2$ | CF$_3$ | CH$_2$OCH$_3$ | C(O)OCH$_2$CH$_2$OCH$_3$ |
| 3,5-Cl$_2$ | CF$_3$ | C(O)CH$_3$ | C(O)OCH$_2$CH$_2$OCH$_3$ |
| 3,5-Cl$_2$ | CF$_3$ | C(O)OCH$_3$ | C(O)OCH$_2$CH$_2$OCH$_3$ |
| 3,5-Cl$_2$ | CF$_3$ | C(O)OEt | C(O)OCH$_2$CH$_2$OCH$_3$ |
| 3,5-Cl$_2$ | CF$_3$ | H | C(O)OCH$_2$CH$_2$OEt |
| 3,5-Cl$_2$ | CF$_3$ | H | C(O)OCH$_2$CH$_2$OPr-i |
| 3,5-Cl$_2$ | CF$_3$ | H | C(O)OCH$_2$CH$_2$OCH$_2$CH$_2$Cl |
| 3,5-Cl$_2$ | CF$_3$ | H | C(O)OCH$_2$CH$_2$OCH$_2$CF$_3$ |
| 3,5-Cl$_2$ | CF$_3$ | H | C(O)OCH$_2$CH$_2$OCH$_2$CH$_2$OCH$_3$ |
| 3,5-Cl$_2$ | CF$_3$ | H | C(O)OCH$_2$CH$_2$OCH$_2$CH$_2$OCH$_2$CF$_3$ |
| 3,5-Cl$_2$ | CF$_3$ | H | C(O)OCH$_2$CH$_2$OCH$_2$CH$_2$OCH$_2$CH$_2$OCH$_3$ |
| 3,5-Cl$_2$ | CF$_3$ | H | C(O)OCH$_2$CH$_2$OCH$_2$CH$_2$SCH$_3$ |
| 3,5-Cl$_2$ | CF$_3$ | H | C(O)OCH$_2$CH$_2$OCH$_2$Ph |
| 3,5-Cl$_2$ | CF$_3$ | H | C(O)OCH$_2$CH$_2$OC(O)CH$_3$ |
| 3,5-Cl$_2$ | CF$_3$ | H | C(O)OCH$_2$CH$_2$OC(O)NHCH$_3$ |
| 3,5-Cl$_2$ | CF$_3$ | H | C(O)OCH$_2$CH$_2$OC(O)NHEt |
| 3,5-Cl$_2$ | CF$_3$ | H | C(O)OCH$_2$CH$_2$OC(O)NHPr-i |
| 3,5-Cl$_2$ | CF$_3$ | H | C(O)OCH$_2$CH$_2$OC(O)NHCH$_2$CF$_3$ |
| 3,5-Cl$_2$ | CF$_3$ | H | C(O)OCH$_2$CH$_2$OC(O)NHCH$_2$CH$_2$OCH$_3$ |
| 3,5-Cl$_2$ | CF$_3$ | H | C(O)OCH$_2$CH$_2$OC(O)NHCH$_2$CH$_2$SCH$_3$ |
| 3,5-Cl$_2$ | CF$_3$ | H | C(O)OCH$_2$CH$_2$OC(O)NHCH$_2$CH=CH$_2$ |
| 3,5-Cl$_2$ | CF$_3$ | H | C(O)OCH$_2$CH$_2$OC(O)NHCH$_2$Ph |
| 3,5-Cl$_2$ | CF$_3$ | H | C(O)OCH$_2$CH$_2$OC(O)NHCH$_2$(D-52a) |
| 3,5-Cl$_2$ | CF$_3$ | H | C(O)OCH$_2$CH$_2$OC(O)NHCH$_2$(D-53a) |
| 3,5-Cl$_2$ | CF$_3$ | H | C(O)OCH$_2$CH$_2$OC(O)NHCH$_2$(D-54a) |
| 3,5-Cl$_2$ | CF$_3$ | H | C(O)OCH$_2$CH$_2$OC(O)NHPh |
| 3,5-Cl$_2$ | CF$_3$ | H | C(O)OCH$_2$CH$_2$OC(O)N(CH$_3$)$_2$ |
| 3,5-Cl$_2$ | CF$_3$ | H | C(O)OCH$_2$CH$_2$OC(O)N(Et)$_2$ |
| 3,5-Cl$_2$ | CF$_3$ | H | C(O)OCH$_2$CH$_2$OC(O)(T-14) |
| 3,5-Cl$_2$ | CF$_3$ | H | C(O)OCH$_2$CH$_2$OC(O)(T-17) |
| 3,5-Cl$_2$ | CF$_3$ | H | C(O)OCH$_2$CH$_2$OC(O)(T-18) |
| 3,5-Cl$_2$ | CF$_3$ | H | C(O)OCH$_2$CH$_2$OC(O)(T-19) |
| 3,5-Cl$_2$ | CF$_3$ | H | C(O)OCH$_2$CH$_2$OC(O)(T-21) |
| 3,5-Cl$_2$ | CF$_3$ | H | C(O)OCH$_2$CH$_2$OC(S)NHCH$_3$ |
| 3,5-Cl$_2$ | CF$_3$ | H | C(O)OCH$_2$CH$_2$OC(S)NHEt |
| 3,5-Cl$_2$ | CF$_3$ | H | C(O)OCH$_2$CH$_2$OC(S)NHCH$_2$CF$_3$ |
| 3,5-Cl$_2$ | CF$_3$ | H | C(O)OCH$_2$CH$_2$OC(S)N(CH$_3$)$_2$ |
| 3,5-Cl$_2$ | CF$_3$ | H | C(O)OCH$_2$CH$_2$OPh |
| 3,5-Cl$_2$ | CF$_3$ | H | C(O)OCH$_2$CH$_2$OP(O)(OEt)$_2$ |
| 3,5-Cl$_2$ | CF$_3$ | H | C(O)OCH$_2$CH$_2$OP(S)(OCH$_3$)$_2$ |
| 3,5-Cl$_2$ | CF$_3$ | H | C(O)OCH$_2$CH$_2$OP(S)(OEt)$_2$ |
| 3,5-Cl$_2$ | CF$_3$ | H | C(O)OCH$_2$CH(CH$_3$)OCH$_3$ |
| 3,5-Cl$_2$ | CF$_3$ | H | C(O)OCH$_2$CH(CH$_3$)OCH$_3$(R) |
| 3,5-Cl$_2$ | CF$_3$ | H | C(O)OCH$_2$CH(CH$_3$)OCH$_3$(S) |
| 3,5-Cl$_2$ | CF$_3$ | H | C(O)OCH(CH$_3$)CH$_2$OCH$_3$ |
| 3,5-Cl$_2$ | CF$_3$ | H | C(O)OCH(CH$_3$)CH$_2$OCH$_3$(R) |
| 3,5-Cl$_2$ | CF$_3$ | H | C(O)OCH(CH$_3$)CH$_2$OCH$_3$(S) |
| 3,5-Cl$_2$ | CF$_3$ | H | C(O)OCH$_2$(E-5a) |
| 3,5-Cl$_2$ | CF$_3$ | H | C(O)OCH$_2$(E-6a) |
| 3,5-Cl$_2$ | CF$_3$ | H | C(O)OCH2(E-11a) |
| 3,5-Cl$_2$ | CF$_3$ | H | C(O)OCH$_2$(E-12a) |
| 3,5-Cl$_2$ | CF$_3$ | H | C(O)OCH$_2$(E-12c) |
| 3,5-Cl$_2$ | CF$_3$ | H | C(O)OCH$_2$(E-24a) |
| 3,5-Cl$_2$ | CF$_3$ | H | C(O)OCH$_2$(E-25a) |
| 3,5-Cl$_2$ | CF$_3$ | H | C(O)OCH$_2$(E-26a) |
| 3,5-Cl$_2$ | CF$_3$ | H | C(O)OCH$_2$(E-33a) |
| 3,5-Cl$_2$ | CF$_3$ | H | C(O)O(E-5a) |
| 3,5-Cl$_2$ | CF$_3$ | H | C(O)O(E-6a) |
| 3,5-Cl$_2$ | CF$_3$ | H | C(O)O(E-25a) |
| 3,5-Cl$_2$ | CF$_3$ | H | C(O)O(E-26a) |
| 3,5-Cl$_2$ | CF$_3$ | H | C(O)O(E-35a) |
| 3,5-Cl$_2$ | CF$_3$ | H | C(O)OCH$_2$CH$_2$SCH$_3$ |
| 3,5-Cl$_2$ | CF$_3$ | H | C(O)OCH$_2$CH$_2$S(O)CH$_3$ |
| 3,5-Cl$_2$ | CF$_3$ | H | C(O)OCH$_2$CH$_2$SO$_2$CH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | H | C(O)OCH$_2$CH$_2$SEt |
| 3,5-Cl$_2$ | CF$_3$ | H | C(O)OCH$_2$CH$_2$S(O)Et |
| 3,5-Cl$_2$ | CF$_3$ | H | C(O)OCH$_2$CH$_2$SO$_2$Et |
| 3,5-Cl$_2$ | CF$_3$ | H | C(O)OCH$_2$CH$_2$SCH$_2$CH$_2$OCH$_3$ |
| 3,5-Cl$_2$ | CF$_3$ | H | C(O)OCH$_2$CH$_2$SO$_2$CH$_2$CH$_2$OCH$_3$ |
| 3,5-Cl$_2$ | CF$_3$ | H | C(O)OCH$_2$CH$_2$SCH$_2$CH$_2$SCH$_3$ |
| 3,5-Cl$_2$ | CF$_3$ | H | C(O)OCH$_2$CH$_2$SCH$_2$CH=CH$_2$ |
| 3,5-Cl$_2$ | CF$_3$ | H | C(O)OCH$_2$CH$_2$SCH$_2$C≡CH |
| 3,5-Cl$_2$ | CF$_3$ | H | C(O)OCH$_2$CH$_2$SCH$_2$Ph |
| 3,5-Cl$_2$ | CF$_3$ | H | C(O)OCH$_2$CH$_2$SO$_2$CH$_2$Ph |
| 3,5-Cl$_2$ | CF$_3$ | H | C(O)OCH$_2$CH$_2$SC(O)CH$_3$ |
| 3,5-Cl$_2$ | CF$_3$ | H | C(O)OCH$_2$CH$_2$SC(O)N(CH$_3$)$_2$ |
| 3,5-Cl$_2$ | CF$_3$ | H | C(O)OCH$_2$CH$_2$SC(S)NHCH$_3$ |
| 3,5-Cl$_2$ | CF$_3$ | H | C(O)OCH$_2$CH$_2$SC(S)N(CH$_3$)$_2$ |
| 3,5-Cl$_2$ | CF$_3$ | H | C(O)OCH$_2$CH$_2$SPh |
| 3,5-Cl$_2$ | CF$_3$ | H | C(O)OCH$_2$CH$_2$S(O)Ph |
| 3,5-Cl$_2$ | CF$_3$ | H | C(O)OCH$_2$CH$_2$SO$_2$Ph |
| 3,5-Cl$_2$ | CF$_3$ | H | C(O)OCH$_2$CH$_2$S(D-21a) |
| 3,5-Cl$_2$ | CF$_3$ | H | C(O)OCH$_2$CH$_2$SO$_2$(D-21a) |
| 3,5-Cl$_2$ | CF$_3$ | H | C(O)OCH$_2$CH$_2$S(D-52a) |
| 3,5-Cl$_2$ | CF$_3$ | H | C(O)OCH$_2$CH$_2$S(O)(D-52a) |
| 3,5-Cl$_2$ | CF$_3$ | H | C(O)OCH$_2$CH$_2$SO$_2$(D-52a) |
| 3,5-Cl$_2$ | CF$_3$ | H | C(O)OCH$_2$CH$_2$S(D-55a) |
| 3,5-Cl$_2$ | CF$_3$ | H | C(O)OCH$_2$CH$_2$S(O)(D-55a) |
| 3,5-Cl$_2$ | CF$_3$ | H | C(O)OCH$_2$CH$_2$SO$_2$(D-55a) |
| 3,5-Cl$_2$ | CF$_3$ | H | C(O)OCH$_2$CH$_2$SSCH$_3$ |
| 3,5-Cl$_2$ | CF$_3$ | H | C(O)OCH$_2$CH$_2$SO$_2$NHCH$_3$ |
| 3,5-Cl$_2$ | CF$_3$ | H | C(O)OCH$_2$CH$_2$SO$_2$N(CH$_3$)$_2$ |
| 3,5-Cl$_2$ | CF$_3$ | H | C(O)OCH$_2$CH$_2$SO$_2$(T-14) |
| 3,5-Cl$_2$ | CF$_3$ | H | C(O)OCH$_2$CH$_2$SO$_2$(T-17) |
| 3,5-Cl$_2$ | CF$_3$ | H | C(O)OCH$_2$CH$_2$SO$_2$(T-18) |
| 3,5-Cl$_2$ | CF$_3$ | H | C(O)OCH$_2$CH$_2$SO$_2$(T-19) |
| 3,5-Cl$_2$ | CF$_3$ | H | C(O)OCH$_2$CH(CH$_3$)SCH$_3$ |
| 3,5-Cl$_2$ | CF$_3$ | H | C(O)OCH$_2$CH(CH$_3$)SCH$_3$(R) |
| 3,5-Cl$_2$ | CF$_3$ | H | C(O)OCH$_2$CH(CH$_3$)SCH$_3$(S) |
| 3,5-Cl$_2$ | CF$_3$ | H | C(O)OCH$_2$CH(CH$_3$)S(O)CH$_3$ |
| 3,5-Cl$_2$ | CF$_3$ | H | C(O)OCH$_2$CH(CH$_3$)SO$_2$CH$_3$ |
| 3,5-Cl$_2$ | CF$_3$ | H | C(O)OCH(CH$_3$)CH$_2$SCH$_3$ |
| 3,5-Cl$_2$ | CF$_3$ | H | C(O)OCH(CH$_3$)CH$_2$SCH$_3$(R) |
| 3,5-Cl$_2$ | CF$_3$ | H | C(O)OCH(CH$_3$)CH$_2$SCH$_3$(S) |
| 3,5-Cl$_2$ | CF$_3$ | H | C(O)OCH(CH$_3$)CH$_2$S(O)CH$_3$ |
| 3,5-Cl$_2$ | CF$_3$ | H | C(O)OCH(CH$_3$)CH$_2$SO$_2$CH$_3$ |
| 3,5-Cl$_2$ | CF$_3$ | H | C(O)OCH$_2$CH$_2$CH$_2$SCH$_3$ |
| 3,5-Cl$_2$ | CF$_3$ | H | C(O)OCH$_2$(E-7a) |
| 3,5-Cl$_2$ | CF$_3$ | H | C(O)OCH$_2$(E-8a) |
| 3,5-Cl$_2$ | CF$_3$ | H | C(O)OCH$_2$(E-8b) |
| 3,5-Cl$_2$ | CF$_3$ | H | C(O)OCH$_2$(E-8c) |
| 3,5-Cl$_2$ | CF$_3$ | H | C(O)OCH$_2$(E-19a) |
| 3,5-Cl$_2$ | CF$_3$ | H | C(O)OCH$_2$(E-27a) |
| 3,5-Cl$_2$ | CF$_3$ | H | C(O)OCH$_2$(E-28a) |
| 3,5-Cl$_2$ | CF$_3$ | H | C(O)OCH$_2$(E-29a) |
| 3,5-Cl$_2$ | CF$_3$ | H | C(O)OCH$_2$(E-44a) |
| 3,5-Cl$_2$ | CF$_3$ | H | C(O)O(E-8a) |
| 3,5-Cl$_2$ | CF$_3$ | H | C(O)O(E-8b) |
| 3,5-Cl$_2$ | CF$_3$ | H | C(O)O(E-8c) |
| 3,5-Cl$_2$ | CF$_3$ | H | C(O)O(E-28a) |
| 3,5-Cl$_2$ | CF$_3$ | H | C(O)O(E-29a) |
| 3,5-Cl$_2$ | CF$_3$ | H | C(O)OCH$_2$CH$_2$N(CH$_3$)$_2$ |
| 3,5-Cl$_2$ | CF$_3$ | H | C(O)OCH$_2$CH$_2$(T-14) |
| 3,5-Cl$_2$ | CF$_3$ | H | C(O)OCH$_2$CH$_2$(T-17) |
| 3,5-Cl$_2$ | CF$_3$ | H | C(O)OCH$_2$CH$_2$(T-18) |
| 3,5-Cl$_2$ | CF$_3$ | H | C(O)OCH$_2$CH$_2$(T-19) |
| 3,5-Cl$_2$ | CF$_3$ | H | C(O)OCH$_2$CH$_2$(T-21) |
| 3,5-Cl$_2$ | CF$_3$ | H | C(O)OCH$_2$CH$_2$NHC(O)CH$_3$ |
| 3,5-Cl$_2$ | CF$_3$ | H | C(O)OCH$_2$CH$_2$N(CH$_3$)C(O)CH$_3$ |
| 3,5-Cl$_2$ | CF$_3$ | H | C(O)OCH$_2$CH$_2$NHC(O)Et |
| 3,5-Cl$_2$ | CF$_3$ | H | C(O)OCH$_2$CH$_2$NHC(O)Pr-n |
| 3,5-Cl$_2$ | CF$_3$ | H | C(O)OCH$_2$CH$_2$NHC(O)Pr-i |
| 3,5-Cl$_2$ | CF$_3$ | H | C(O)OCH$_2$CH$_2$NHC(O)Pr-c |
| 3,5-Cl$_2$ | CF$_3$ | H | C(O)OCH$_2$CH$_2$NHC(O)Bu-n |
| 3,5-Cl$_2$ | CF$_3$ | H | C(O)OCH$_2$CH$_2$NHC(O)Bu-i |
| 3,5-Cl$_2$ | CF$_3$ | H | C(O)OCH$_2$CH$_2$NHC(O)Bu-s |
| 3,5-Cl$_2$ | CF$_3$ | H | C(O)OCH$_2$CH$_2$NHC(O)Bu-t |
| 3,5-Cl$_2$ | CF$_3$ | H | C(O)OCH$_2$CH$_2$NHC(O)CF$_3$ |
| 3,5-Cl$_2$ | CF$_3$ | H | C(O)OCH$_2$CH$_2$NHC(O)CF$_2$Cl |
| 3,5-Cl$_2$ | CF$_3$ | H | C(O)OCH$_2$CH$_2$NHC(O)Ph |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | C(O)OCH$_2$CH$_2$NHC(O)OCH$_3$ |
| 3,5-Cl$_2$ | CF$_3$ | H | C(O)OCH$_2$CH$_2$NHC(O)OEt |
| 3,5-Cl$_2$ | CF$_3$ | H | C(O)OCH$_2$CH$_2$NHC(O)OPr-n |
| 3,5-Cl$_2$ | CF$_3$ | H | C(O)OCH$_2$CH$_2$NHC(O)OBu-t |
| 3,5-Cl$_2$ | CF$_3$ | H | C(O)OCH$_2$CH$_2$NHC(O)OCH$_2$CF$_3$ |
| 3,5-Cl$_2$ | CF$_3$ | H | C(O)OCH$_2$CH$_2$NHC(O)NHCH$_3$ |
| 3,5-Cl$_2$ | CF$_3$ | H | C(O)OCH$_2$CH$_2$NHC(O)N(CH$_3$)$_2$ |
| 3,5-Cl$_2$ | CF$_3$ | H | C(O)OCH$_2$CH$_2$NHC(S)NHEt |
| 3,5-Cl$_2$ | CF$_3$ | H | C(O)OCH$_2$CH$_2$NHC(S)NHCH$_2$CF$_3$ |
| 3,5-Cl$_2$ | CF$_3$ | H | C(O)OCH$_2$CH$_2$N(CH$_3$)OCH$_3$ |
| 3,5-Cl$_2$ | CF$_3$ | H | C(O)OCH$_2$CH$_2$NHSO$_2$CH$_3$ |
| 3,5-Cl$_2$ | CF$_3$ | H | C(O)OCH$_2$CH$_2$N(CH$_3$)SO$_2$CH$_3$ |
| 3,5-Cl$_2$ | CF$_3$ | H | C(O)OCH$_2$CH$_2$NHSO$_2$Et |
| 3,5-Cl$_2$ | CF$_3$ | H | C(O)OCH$_2$CH$_2$NHSO$_2$CF$_3$ |
| 3,5-Cl$_2$ | CF$_3$ | H | C(O)OCH$_2$CH$_2$N(CH$_3$)SO$_2$CF$_3$ |
| 3,5-Cl$_2$ | CF$_3$ | H | C(O)OCH$_2$CH$_2$NHSO$_2$Ph |
| 3,5-Cl$_2$ | CF$_3$ | H | C(O)OCH$_2$CH$_2$NHSO$_2$N(CH$_3$)$_2$ |
| 3,5-Cl$_2$ | CF$_3$ | H | C(O)OCH$_2$CH$_2$NHP(S)(OCH$_3$)$_2$ |
| 3,5-Cl$_2$ | CF$_3$ | H | C(O)OCH$_2$CH(CH$_3$)NHC(O)CH$_3$ |
| 3,5-Cl$_2$ | CF$_3$ | H | C(O)OCH$_2$CH(CH$_3$)NHC(O)OCH$_3$ |
| 3,5-Cl$_2$ | CF$_3$ | H | C(O)OCH(CH$_3$)CH$_2$NHC(O)CH$_3$ |
| 3,5-Cl$_2$ | CF$_3$ | H | C(O)OCH(CH$_3$)CH$_2$NHC(O)OCH$_3$ |
| 3,5-Cl$_2$ | CF$_3$ | H | C(O)OCH$_2$(E-10a)C(O)CH$_3$ |
| 3,5-Cl$_2$ | CF$_3$ | H | C(O)OCH$_2$(E-10a)C(O)OCH$_3$ |
| 3,5-Cl$_2$ | CF$_3$ | H | C(O)OCH$_2$(E-31a)C(O)CH$_3$ |
| 3,5-Cl$_2$ | CF$_3$ | H | C(O)OCH$_2$(E-32a)C(O)CH$_3$ |
| 3,5-Cl$_2$ | CF$_3$ | H | C(O)OCH$_2$(E-32a)C(O)OCH$_3$ |
| 3,5-Cl$_2$ | CF$_3$ | H | C(O)O(E-10a)CHO |
| 3,5-Cl$_2$ | CF$_3$ | H | C(O)O(E-10a)C(O)CH$_3$ |
| 3,5-Cl$_2$ | CF$_3$ | H | C(O)O(E-10a)C(O)CF$_3$ |
| 3,5-Cl$_2$ | CF$_3$ | H | C(O)O(E-10a)C(O)Bu-t |
| 3,5-Cl$_2$ | CF$_3$ | H | C(O)O(E-10a)C(O)OCH$_3$ |
| 3,5-Cl$_2$ | CF$_3$ | H | C(O)O(E-31a)C(O)CH$_3$ |
| 3,5-Cl$_2$ | CF$_3$ | H | C(O)O(E-31a)C(O)OCH$_3$ |
| 3,5-Cl$_2$ | CF$_3$ | H | C(O)O(E-32a)C(O)CH$_3$ |
| 3,5-Cl$_2$ | CF$_3$ | H | C(O)O(E-32a)C(O)OCH$_3$ |
| 3,5-Cl$_2$ | CF$_3$ | H | C(O)OCH$_2$CH(CH$_3$)NO$_2$ |
| 3,5-Cl$_2$ | CF$_3$ | H | C(O)OC(CH$_3$)$_2$CHO |
| 3,5-Cl$_2$ | CF$_3$ | H | C(O)OCH$_2$C(O)CH$_3$ |
| 3,5-Cl$_2$ | CF$_3$ | H | C(O)OCH(CH$_3$)C(O)CH$_3$ |
| 3,5-Cl$_2$ | CF$_3$ | H | C(O)OCH$_2$(M-1a) |
| 3,5-Cl$_2$ | CF$_3$ | H | C(O)OCH$_2$CH=NOH |
| 3,5-Cl$_2$ | CF$_3$ | H | C(O)OCH$_2$CH=NOCH$_3$ |
| 3,5-Cl$_2$ | CF$_3$ | H | C(O)OCH$_2$C(CH$_3$)=NOH |
| 3,5-Cl$_2$ | CF$_3$ | H | C(O)OCH$_2$C(CH$_3$)=NOCH$_3$ |
| 3,5-Cl$_2$ | CF$_3$ | H | C(O)OCH(CH$_3$)CH=NOCH$_3$ |
| 3,5-Cl$_2$ | CF$_3$ | H | C(O)OCH$_2$CH$_2$CH=NOCH$_3$ |
| 3,5-Cl$_2$ | CF$_3$ | H | C(O)OCH$_2$(M-5a) |
| 3,5-Cl$_2$ | CF$_3$ | H | C(O)OCH$_2$(M-5c)CF$_3$ |
| 3,5-Cl$_2$ | CF$_3$ | H | C(O)OCH$_2$CN |
| 3,5-Cl$_2$ | CF$_3$ | H | C(O)OCH(CH$_3$)CN |
| 3,5-Cl$_2$ | CF$_3$ | H | C(O)OC(CH$_3$)$_2$CN |
| 3,5-Cl$_2$ | CF$_3$ | H | C(O)OCH$_2$CH$_2$CN |
| 3,5-Cl$_2$ | CF$_3$ | CH$_3$ | C(O)OCH$_2$CH$_2$CN |
| 3,5-Cl$_2$ | CF$_3$ | H | C(O)OCH$_2$C(O)OCH$_3$ |
| 3,5-Cl$_2$ | CF$_3$ | CH$_3$ | C(O)OCH$_2$C(O)OCH$_3$ |
| 3,5-Cl$_2$ | CF$_3$ | CH$_2$OCH | C(O)OCH$_2$C(O)OCH$_3$ |
| 3,5-Cl$_2$ | CF$_3$ | C(O)CH$_3$ | C(O)OCH$_2$C(O)OCH$_3$ |
| 3,5-Cl$_2$ | CF$_3$ | C(O)OCH$_3$ | C(O)OCH$_2$C(O)OCH$_3$ |
| 3,5-Cl$_2$ | CF$_3$ | C(O)OEt | C(O)OCH$_2$C(O)OCH$_3$ |
| 3,5-Cl$_2$ | CF$_3$ | H | C(O)OCH$_2$C(O)OEt |
| 3,5-Cl$_2$ | CF$_3$ | H | C(O)OCH$_2$C(O)OPr-i |
| 3,5-Cl$_2$ | CF$_3$ | H | C(O)OCH$_2$C(O)OBu-t |
| 3,5-Cl$_2$ | CF$_3$ | H | C(O)OCH$_2$C(O)OCH$_2$CF$_3$ |
| 3,5-Cl$_2$ | CF$_3$ | H | C(O)OCH(CH$_3$)C(O)OCH$_3$ |
| 3,5-Cl$_2$ | CF$_3$ | H | C(O)OCH(CH$_3$)C(O)OCH$_3$ |
| 3,5-Cl$_2$ | CF$_3$ | H | C(O)OCH(CH$_3$)C(O)OEt |
| 3,5-Cl$_2$ | CF$_3$ | H | C(O)OCH(CH$_3$)C(O)OCH$_2$CF$_3$ |
| 3,5-Cl$_2$ | CF$_3$ | H | C(O)OCH$_2$C(O)SCH$_3$ |
| 3,5-Cl$_2$ | CF$_3$ | H | C(O)OCH$_2$C(O)NH$_2$ |
| 3,5-Cl$_2$ | CF$_3$ | H | C(O)OCH$_2$C(O)NHCH$_3$ |
| 3,5-Cl$_2$ | CF$_3$ | H | C(O)OCH$_2$C(O)N(CH$_3$)$_2$ |
| 3,5-Cl$_2$ | CF$_3$ | H | C(O)OCH$_2$C(O)(T-14) |
| 3,5-Cl$_2$ | CF$_3$ | H | C(O)OCH$_2$C(O)(T-15) |
| 3,5-Cl$_2$ | CF$_3$ | H | C(O)OCH$_2$C(O)(T-16) |
| 3,5-Cl$_2$ | CF$_3$ | H | C(O)OCH$_2$C(O)(T-17) |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | H | C(O)OCH$_2$C(O)(T-18) |
| 3,5-Cl$_2$ | CF$_3$ | H | C(O)OCH$_2$C(O)(T-19) |
| 3,5-Cl$_2$ | CF$_3$ | H | C(O)OCH(CH$_3$)C(O)NH$_2$ |
| 3,5-Cl$_2$ | CF$_3$ | H | C(O)OCH(CH$_3$)C(O)NHCH$_3$ |
| 3,5-Cl$_2$ | CF$_3$ | H | C(O)OCH(Et)C(O)NHCH$_3$ |
| 3,5-Cl$_2$ | CF$_3$ | H | C(O)OCH$_2$(M-11a) |
| 3,5-Cl$_2$ | CF$_3$ | H | C(O)OCH$_2$(M-11b)CF$_3$ |
| 3,5-Cl$_2$ | CF$_3$ | H | C(O)OCH$_2$(M-11c)CF$_3$ |
| 3,5-Cl$_2$ | CF$_3$ | H | C(O)OCH$_2$(M-28a) |
| 3,5-Cl$_2$ | CF$_3$ | H | C(O)OCH$_2$C(S)OCH$_3$ |
| 3,5-Cl$_2$ | CF$_3$ | H | C(O)OCH$_2$C(S)SCH$_3$ |
| 3,5-Cl$_2$ | CF$_3$ | H | C(O)OCH$_2$C(S)NH$_2$ |
| 3,5-Cl$_2$ | CF$_3$ | H | C(O)OCH$_2$C(S)NHCH$_3$ |
| 3,5-Cl$_2$ | CF$_3$ | H | C(O)OCH(CH$_3$)C(S)NH$_2$ |
| 3,5-Cl$_2$ | CF$_3$ | H | C(O)OCH(CH$_3$)C(S)NHCH$_3$ |
| 3,5-Cl$_2$ | CF$_3$ | H | C(O)OCH$_2$(M-14a) |
| 3,5-Cl$_2$ | CF$_3$ | H | C(O)OCH$_2$(M-14b)CF$_3$ |
| 3,5-Cl$_2$ | CF$_3$ | H | C(O)OCH$_2$(M-14c)CF$_3$ |
| 3,5-Cl$_2$ | CF$_3$ | H | C(O)OCH$_2$(M-32a) |
| 3,5-Cl$_2$ | CF$_3$ | H | C(O)OCH$_2$CH$_2$-TMS |
| 3,5-Cl$_2$ | CF$_3$ | H | C(O)OCH$_2$CH$_2$CH$_2$-TMS |
| 3,5-Cl$_2$ | CF$_3$ | H | C(O)OCH$_2$CH=CH$_2$ |
| 3,5-Cl$_2$ | CF$_3$ | CH$_3$ | C(O)OCH$_2$CH=CH$_2$ |
| 3,5-Cl$_2$ | CF$_3$ | CH$_2$OCH$_3$ | C(O)OCH$_2$CH=CH$_2$ |
| 3,5-Cl$_2$ | CF$_3$ | C(O)CH$_3$ | C(O)OCH$_2$CH=CH$_2$ |
| 3,5-Cl$_2$ | CF$_3$ | C(O)OCH$_3$ | C(O)OCH$_2$CH=CH$_2$ |
| 3,5-Cl$_2$ | CF$_3$ | C(O)OEt | C(O)OCH$_2$CH=CH$_2$ |
| 3,5-Cl$_2$ | CF$_3$ | H | C(O)OCH$_2$CH=CHCH$_3$ |
| 3,5-Cl$_2$ | CF$_3$ | H | C(O)OCH$_2$C(CH$_3$)=CH$_2$ |
| 3,5-Cl$_2$ | CF$_3$ | CH$_3$ | C(O)OCH$_2$C(CH$_3$)=CH$_2$ |
| 3,5-Cl$_2$ | CF$_3$ | H | C(O)OCH(Et)CH=CH$_2$ |
| 3,5-Cl$_2$ | CF$_3$ | H | C(O)OC(CH$_3$)$_2$CH=CH$_2$ |
| 3,5-Cl$_2$ | CF$_3$ | H | C(O)OCH$_2$C(CH$_3$)=CHCH$_3$ |
| 3,5-Cl$_2$ | CF$_3$ | H | C(O)OCH$_2$CH=C(CH$_3$)$_2$ |
| 3,5-Cl$_2$ | CF$_3$ | H | C(O)OCH$_2$(T-12) |
| 3,5-Cl$_2$ | CF$_3$ | H | C(O)OCH$_2$(T-13) |
| 3,5-Cl$_2$ | CF$_3$ | H | C(O)OCH$_2$CF=CH$_2$ |
| 3,5-Cl$_2$ | CF$_3$ | H | C(O)OCH$_2$CH=CHCl |
| 3,5-Cl$_2$ | CF$_3$ | H | C(O)OCH$_2$CCl=CH$_2$ |
| 3,5-Cl$_2$ | CF$_3$ | H | C(O)OCH$_2$CH=CHBr |
| 3,5-Cl$_2$ | CF$_3$ | H | C(O)OCH$_2$CBr=CH$_2$ |
| 3,5-Cl$_2$ | CF$_3$ | H | C(O)OCH$_2$CH=CCl$_2$ |
| 3,5-Cl$_2$ | CF$_3$ | H | C(O)OCH$_2$CCl=CHCl |
| 3,5-Cl$_2$ | CF$_3$ | H | C(O)OCH$_2$CBr=CHBr |
| 3,5-Cl$_2$ | CF$_3$ | H | C(O)OCH$_2$CH=CClCH$_3$ |
| 3,5-Cl$_2$ | CF$_3$ | H | C(O)OCH$_2$CCl=CCl$_2$ |
| 3,5-Cl$_2$ | CF$_3$ | H | C(O)OCH$_2$C(CH$_3$)=CHBr |
| 3,5-Cl$_2$ | CF$_3$ | H | C(O)OCH$_2$CH=CClCH$_3$ |
| 3,5-Cl$_2$ | CF$_3$ | H | C(O)OCH$_2$CH=CBrCH$_3$ |
| 3,5-Cl$_2$ | CF$_3$ | H | C(O)OCH$_2$CH=CClCF$_3$ |
| 3,5-Cl$_2$ | CF$_3$ | H | C(O)OCH$_2$C(OCH$_3$)=CH$_2$ |
| 3,5-Cl$_2$ | CF$_3$ | H | C(O)OCH$_2$CBr=CHOCH$_3$ |
| 3,5-Cl$_2$ | CF$_3$ | H | C(O)OCH$_2$C(CH$_3$)=CHOEt |
| 3,5-Cl$_2$ | CF$_3$ | CH$_3$ | C(O)OCH$_2$C≡CH |
| 3,5-Cl$_2$ | CF$_3$ | CH$_2$OCH$_3$ | C(O)OCH$_2$C≡CH |
| 3,5-Cl$_2$ | CF$_3$ | C(O)CH$_3$ | C(O)OCH$_2$C≡CH |
| 3,5-Cl$_2$ | CF$_3$ | C(O)OCH$_3$ | C(O)OCH$_2$C≡CH |
| 3,5-Cl$_2$ | CF$_3$ | C(O)OEt | C(O)OCH$_2$C≡CH |
| 3,5-Cl$_2$ | CF$_3$ | H | C(O)OCH$_2$C≡CCH$_3$ |
| 3,5-Cl$_2$ | CF$_3$ | H | C(O)OCH(CH$_3$)C≡CH |
| 3,5-Cl$_2$ | CF$_3$ | H | C(O)OC(CH$_3$)$_2$C≡CH |
| 3,5-Cl$_2$ | CF$_3$ | H | C(O)OCH$_2$C≡CCl |
| 3,5-Cl$_2$ | CF$_3$ | H | C(O)OCH$_2$C≡CBr |
| 3,5-Cl$_2$ | CF$_3$ | H | C(O)OCH$_2$C≡Cl |
| 3,5-Cl$_2$ | CF$_3$ | H | C(O)OCH$_2$C≡CCF$_3$ |
| 3,5-Cl$_2$ | CF$_3$ | H | C(O)OCH$_2$C≡CCF$_2$Br |
| 3,5-Cl$_2$ | CF$_3$ | H | C(O)OCH$_2$C≡C-TMS |
| 3,5-Cl$_2$ | CF$_3$ | H | C(O)OCH$_2$C≡CPh |
| 3,5-Cl$_2$ | CF$_3$ | H | C(O)OCH$_2$(Ph-2-F) |
| 3,5-Cl$_2$ | CF$_3$ | H | C(O)OCH$_2$(Ph-3-F) |
| 3,5-Cl$_2$ | CF$_3$ | H | C(O)OCH$_2$(Ph-4-F) |
| 3,5-Cl$_2$ | CF$_3$ | CH$_3$ | C(O)OCH$_2$(Ph-4-F) |
| 3,5-Cl$_2$ | CF$_3$ | H | C(O)OCH$_2$(Ph-3-OCH$_3$) |
| 3,5-Cl$_2$ | CF$_3$ | H | C(O)OCH$_2$(Ph-4-OCH$_3$) |
| 3,5-Cl$_2$ | CF$_3$ | H | C(O)OCH$_2$(Ph-3-NO$_2$) |
| 3,5-Cl$_2$ | CF$_3$ | H | C(O)OCH$_2$(Ph-4-NO$_2$) |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | H | C(O)OCH$_2$(Ph-4-CN) |
| 3,5-Cl$_2$ | CF$_3$ | H | C(O)OCH$_2$(Ph-2,5-F$_2$) |
| 3,5-Cl$_2$ | CF$_3$ | H | C(O)OCH$_2$(Ph-3,4-F$_2$) |
| 3,5-Cl$_2$ | CF$_3$ | H | C(O)OCH$_2$(Ph-3,5-F$_2$) |
| 3,5-Cl$_2$ | CF$_3$ | H | C(O)OCH(CH$_3$)Ph |
| 3,5-Cl$_2$ | CF$_3$ | H | C(O)OCH(CH$_3$)Ph(R) |
| 3,5-Cl$_2$ | CF$_3$ | H | C(O)OCH(CH$_3$)Ph(S) |
| 3,5-Cl$_2$ | CF$_3$ | H | C(O)OCH(CF$_3$)Ph |
| 3,5-Cl$_2$ | CF$_3$ | H | C(O)OCH(CF$_3$)Ph(R) |
| 3,5-Cl$_2$ | CF$_3$ | H | C(O)OCH(CF$_3$)Ph(S) |
| 3,5-Cl$_2$ | CF$_3$ | H | C(O)OCH(CN)Ph |
| 3,5-Cl$_2$ | CF$_3$ | H | C(O)OCH(CN)Ph(R) |
| 3,5-Cl$_2$ | CF$_3$ | H | C(O)OCH(CN)Ph(S) |
| 3,5-Cl$_2$ | CF$_3$ | H | C(O)OC(CH$_3$)$_2$Ph |
| 3,5-Cl$_2$ | CF$_3$ | H | C(O)OCH$_2$(D-1a) |
| 3,5-Cl$_2$ | CF$_3$ | H | C(O)OCH$_2$(D-52a) |
| 3,5-Cl$_2$ | CF$_3$ | H | C(O)OCH$_2$(D-52a) |
| 3,5-Cl$_2$ | CF$_3$ | H | C(O)OCH$_2$(D-53a) |
| 3,5-Cl$_2$ | CF$_3$ | H | C(O)OCH$_2$(D-54a) |
| 3,5-Cl$_2$ | CF$_3$ | H | C(O)ON=C(CH$_3$)$_2$ |
| 3,5-Cl$_2$ | CF$_3$ | H | C(O)ON=CHPh |
| 3,5-Cl$_2$ | CF$_3$ | H | C(O)ON=C(CH$_3$)Ph |
| 3,5-Cl$_2$ | CF$_3$ | H | C(O)OPh |
| 3,5-Cl$_2$ | CF$_3$ | H | C(O)O(Ph-2-F) |
| 3,5-Cl$_2$ | CF$_3$ | H | C(O)O(Ph-3-F) |
| 3,5-Cl$_2$ | CF$_3$ | H | C(O)O(Ph-4-F) |
| 3,5-Cl$_2$ | CF$_3$ | H | C(O)O(Ph-2-Cl) |
| 3,5-Cl$_2$ | CF$_3$ | H | C(O)O(Ph-3-Cl) |
| 3,5-Cl$_2$ | CF$_3$ | H | C(O)O(Ph-4-Cl) |
| 3,5-Cl$_2$ | CF$_3$ | H | C(O)SCH$_3$ |
| 3,5-Cl$_2$ | CF$_3$ | CH$_3$ | C(O)SCH$_3$ |
| 3,5-Cl$_2$ | CF$_3$ | CH$_2$OCH$_3$ | C(O)SCH$_3$ |
| 3,5-Cl$_2$ | CF$_3$ | C(O)CH$_3$ | C(O)SCH$_3$ |
| 3,5-Cl$_2$ | CF$_3$ | C(O)OCH$_3$ | C(O)SCH$_3$ |
| 3,5-Cl$_2$ | CF$_3$ | H | C(O)SEt |
| 3,5-Cl$_2$ | CF$_3$ | H | C(O)SPr-n |
| 3,5-Cl$_2$ | CF$_3$ | CH$_3$ | C(O)SPr-n |
| 3,5-Cl$_2$ | CF$_3$ | H | C(O)SPr-i |
| 3,5-Cl$_2$ | CF$_3$ | H | C(O)SPh |
| 3,5-Cl$_2$ | CF$_3$ | H | C(O)NH$_2$ |
| 3,5-Cl$_2$ | CF$_3$ | CH$_3$ | C(O)NH$_2$ |
| 3,5-Cl$_2$ | CF$_3$ | Et | C(O)NH$_2$ |
| 3,5-Cl$_2$ | CF$_3$ | n-Pr | C(O)NH$_2$ |
| 3,5-Cl$_2$ | CF$_3$ | i-Pr | C(O)NH$_2$ |
| 3,5-Cl$_2$ | CF$_3$ | c-Pr | C(O)NH$_2$ |
| 3,5-Cl$_2$ | CF$_3$ | CH$_2$Pr-c | C(O)NH$_2$ |
| 3,5-Cl$_2$ | CF$_3$ | c-Bu | C(O)NH$_2$ |
| 3,5-Cl$_2$ | CF$_3$ | CH$_2$CF$_3$ | C(O)NH$_2$ |
| 3,5-Cl$_2$ | CF$_3$ | CH$_2$OCH$_3$ | C(O)NH$_2$ |
| 3,5-Cl$_2$ | CF$_3$ | CH$_2$OEt | C(O)NH$_2$ |
| 3,5-Cl$_2$ | CF$_3$ | CH$_2$OCH$_2$CF$_3$ | C(O)NH$_2$ |
| 3,5-Cl$_2$ | CF$_3$ | CH$_2$CH$_2$OCH$_3$ | C(O)NH$_2$ |
| 3,5-Cl$_2$ | CF$_3$ | CH$_2$CN | C(O)NH$_2$ |
| 3,5-Cl$_2$ | CF$_3$ | CH$_2$CH=CH$_2$ | C(O)NH$_2$ |
| 3,5-Cl$_2$ | CF$_3$ | CH$_2$C≡CH | C(O)NH$_2$ |
| 3,5-Cl$_2$ | CF$_3$ | CH$_2$Ph | C(O)NH$_2$ |
| 3,5-Cl$_2$ | CF$_3$ | Ph | C(O)NH$_2$ |
| 3,5-Cl$_2$ | CF$_3$ | Ph-4-F | C(O)NH$_2$ |
| 3,5-Cl$_2$ | CF$_3$ | Ph-4-OCH$_3$ | C(O)NH$_2$ |
| 3,5-Cl$_2$ | CF$_3$ | Ph-4-NO$_2$ | C(O)NH$_2$ |
| 3,5-Cl$_2$ | CF$_3$ | Ph-4-CN | C(O)NH$_2$ |
| 3,5-Cl$_2$ | CF$_3$ | H | C(O)NHC(O)CH$_3$ |
| 3,5-Cl$_2$ | CF$_3$ | CH$_3$ | C(O)NHC(O)CH$_3$ |
| 3,5-Cl$_2$ | CF$_3$ | Et | C(O)NHC(O)CH$_3$ |
| 3,5-Cl$_2$ | CF$_3$ | n-Pr | C(O)NHC(O)CH$_3$ |
| 3,5-Cl$_2$ | CF$_3$ | i-Pr | C(O)NHC(O)CH$_3$ |
| 3,5-Cl$_2$ | CF$_3$ | CH$_2$OCH$_3$ | C(O)NHC(O)CH$_3$ |
| 3,5-Cl$_2$ | CF$_3$ | CH$_2$OEt | C(O)NHC(O)CH$_3$ |
| 3,5-Cl$_2$ | CF$_3$ | CH$_2$OCH$_2$CF$_3$ | C(O)NHC(O)CH$_3$ |
| 3,5-Cl$_2$ | CF$_3$ | CH$_2$CN | C(O)NHC(O)CH$_3$ |
| 3,5-Cl$_2$ | CF$_3$ | CH$_2$C≡CH | C(O)NHC(O)CH$_3$ |
| 3,5-Cl$_2$ | CF$_3$ | CH$_2$Ph | C(O)NHC(O)CH$_3$ |
| 3,5-Cl$_2$ | CF$_3$ | H | C(O)NHC(O)Et |
| 3,5-Cl$_2$ | CF$_3$ | H | C(O)NHC(O)Pr-n |
| 3,5-Cl$_2$ | CF$_3$ | H | C(O)NHC(O)Pr-i |
| 3,5-Cl$_2$ | CF$_3$ | H | C(O)NHC(O)Pr-c |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | H | C(O)NHC(O)CH$_2$Cl |
| 3,5-Cl$_2$ | CF$_3$ | CH$_3$ | C(O)NHC(O)CH$_2$Cl |
| 3,5-Cl$_2$ | CF$_3$ | Ph | C(O)NHC(O)CH$_2$Cl |
| 3,5-Cl$_2$ | CF$_3$ | Ph-4-F | C(O)NHC(O)CH$_2$Cl |
| 3,5-Cl$_2$ | CF$_3$ | Ph-4-OCH$_3$ | C(O)NHC(O)CH$_2$Cl |
| 3,5-Cl$_2$ | CF$_3$ | Ph-4-NO$_2$ | C(O)NHC(O)CH$_2$Cl |
| 3,5-Cl$_2$ | CF$_3$ | Ph-4-CN | C(O)NHC(O)CH$_2$Cl |
| 3,5-Cl$_2$ | CF$_3$ | H | C(O)NHC(O)CHF$_2$ |
| 3,5-Cl$_2$ | CF$_3$ | H | C(O)NHC(O)CHFCl |
| 3,5-Cl$_2$ | CF$_3$ | H | C(O)NHC(O)CF$_3$ |
| 3,5-Cl$_2$ | CF$_3$ | H | C(O)NHC(O)CF$_2$Cl |
| 3,5-Cl$_2$ | CF$_3$ | H | C(O)NHC(O)CCl$_3$ |
| 3,5-Cl$_2$ | CF$_3$ | CH$_3$ | C(O)NHC(O)CCl$_3$ |
| 3,5-Cl$_2$ | CF$_3$ | H | C(O)NHC(O)CH$_2$CH$_2$Br |
| 3,5-Cl$_2$ | CF$_3$ | H | C(O)NHC(O)CH(CH$_3$)CH$_2$Cl |
| 3,5-Cl$_2$ | CF$_3$ | H | C(O)NHC(O)CH$_2$OCH$_3$ |
| 3,5-Cl$_2$ | CF$_3$ | H | C(O)NHC(O)CH$_2$OPh |
| 3,5-Cl$_2$ | CF$_3$ | H | C(O)NHC(O)CH$_2$SCH$_3$ |
| 3,5-Cl$_2$ | CF$_3$ | H | C(O)NHC(O)CH$_2$Ph |
| 3,5-Cl$_2$ | CF$_3$ | H | C(O)NHC(O)C(O)OEt |
| 3,5-Cl$_2$ | CF$_3$ | H | C(O)NHC(O)CH=CH$_2$ |
| 3,5-Cl$_2$ | CF$_3$ | H | C(O)NHC(O)Ph |
| 3,5-Cl$_2$ | CF$_3$ | CH$_3$ | C(O)NHC(O)Ph |
| 3,5-Cl$_2$ | CF$_3$ | H | C(O)NHC(O)(D-1a) |
| 3,5-Cl$_2$ | CF$_3$ | H | C(O)NHC(O)(D-28a) |
| 3,5-Cl$_2$ | CF$_3$ | H | C(O)NHC(O)(D-52a) |
| 3,5-Cl$_2$ | CF$_3$ | H | C(O)NHC(O)(D-53a) |
| 3,5-Cl$_2$ | CF$_3$ | H | C(O)NHC(O)OCH$_3$ |
| 3,5-Cl$_2$ | CF$_3$ | CH$_3$ | C(O)NHC(O)OCH$_3$ |
| 3,5-Cl$_2$ | CF$_3$ | Et | C(O)NHC(O)OCH$_3$ |
| 3,5-Cl$_2$ | CF$_3$ | n-Pr | C(O)NHC(O)OCH$_3$ |
| 3,5-Cl$_2$ | CF$_3$ | i-Pr | C(O)NHC(O)OCH$_3$ |
| 3,5-Cl$_2$ | CF$_3$ | CH$_2$OCH$_3$ | C(O)NHC(O)OCH$_3$ |
| 3,5-Cl$_2$ | CF$_3$ | CH$_2$OEt | C(O)NHC(O)OCH$_3$ |
| 3,5-Cl$_2$ | CF$_3$ | CH$_2$OCH$_2$CF$_3$ | C(O)NHC(O)OCH$_3$ |
| 3,5-Cl$_2$ | CF$_3$ | CH$_2$CN | C(O)NHC(O)OCH$_3$ |
| 3,5-Cl$_2$ | CF$_3$ | CH$_2$C≡CH | C(O)NHC(O)OCH$_3$ |
| 3,5-Cl$_2$ | CF$_3$ | CH$_2$Ph | C(O)NHC(O)OCH$_3$ |
| 3,5-Cl$_2$ | CF$_3$ | Ph | C(O)NHC(O)OCH$_3$ |
| 3,5-Cl$_2$ | CF$_3$ | Ph-4-F | C(O)NHC(O)OCH$_3$ |
| 3,5-Cl$_2$ | CF$_3$ | Ph-4-OCH$_3$ | C(O)NHC(O)OCH$_3$ |
| 3,5-Cl$_2$ | CF$_3$ | Ph-4-NO$_2$ | C(O)NHC(O)OCH$_3$ |
| 3,5-Cl$_2$ | CF$_3$ | Ph-4-CN | C(O)NHC(O)OCH$_3$ |
| 3,5-Cl$_2$ | CF$_3$ | H | C(O)N(Et)C(O)OCH$_3$ |
| 3,5-Cl$_2$ | CF$_3$ | CH$_3$ | C(O)N(Et)C(O)OCH$_3$ |
| 3,5-Cl$_2$ | CF$_3$ | H | C(O)NHC(O)OEt |
| 3,5-Cl$_2$ | CF$_3$ | H | C(O)NHC(O)OPr-n |
| 3,5-Cl$_2$ | CF$_3$ | H | C(O)NHC(O)OPr-i |
| 3,5-Cl$_2$ | CF$_3$ | H | C(O)NHC(O)OPr-c |
| 3,5-Cl$_2$ | CF$_3$ | H | C(O)NHC(O)OBu-n |
| 3,5-Cl$_2$ | CF$_3$ | H | C(O)NHC(O)OBu-t |
| 3,5-Cl$_2$ | CF$_3$ | H | C(O)NHC(O)OCH$_2$CH$_2$Cl |
| 3,5-Cl$_2$ | CF$_3$ | H | C(O)NHC(O)OCH$_2$CCl$_3$ |
| 3,5-Cl$_2$ | CF$_3$ | H | C(O)NHC(O)OCH(CH$_3$)CH$_2$Cl |
| 3,5-Cl$_2$ | CF$_3$ | H | C(O)NHC(O)OC(CH$_3$)$_2$CCl$_3$ |
| 3,5-Cl$_2$ | CF$_3$ | H | C(O)NHC(O)OCH$_2$Ph |
| 3,5-Cl$_2$ | CF$_3$ | H | C(O)NHC(O)OPh |
| 3,5-Cl$_2$ | CF$_3$ | H | C(O)NHC(O)SCH$_3$ |
| 3,5-Cl$_2$ | CF$_3$ | CH$_3$ | C(O)NHC(O)SCH$_3$ |
| 3,5-Cl$_2$ | CF$_3$ | H | C(O)NHC(O)SEt |
| 3,5-Cl$_2$ | CF$_3$ | H | C(O)NHC(O)SPr-n |
| 3,5-Cl$_2$ | CF$_3$ | H | C(O)NHC(O)SBu-n |
| 3,5-Cl$_2$ | CF$_3$ | H | C(O)NHC(O)SBu-i |
| 3,5-Cl$_2$ | CF$_3$ | H | C(O)NHC(O)SCH$_2$C(O)OEt |
| 3,5-Cl$_2$ | CF$_3$ | H | C(O)NHC(O)SCH$_2$Ph |
| 3,5-Cl$_2$ | CF$_3$ | H | C(O)NHC(O)SPh |
| 3,5-Cl$_2$ | CF$_3$ | H | C(O)NHC(S)Bu-t |
| 3,5-Cl$_2$ | CF$_3$ | H | C(O)NHC(S)CCl$_3$ |
| 3,5-Cl$_2$ | CF$_3$ | H | C(O)NHC(S)CH$_2$Ph |
| 3,5-Cl$_2$ | CF$_3$ | H | C(O)NHC(S)Ph |
| 3,5-Cl$_2$ | CF$_3$ | H | C(O)NHC(S)OEt |
| 3,5-Cl$_2$ | CF$_3$ | CH$_3$ | C(O)NHC(S)OEt |
| 3,5-Cl$_2$ | CF$_3$ | H | C(O)NHSO$_2$CH$_3$ |
| 3,5-Cl$_2$ | CF$_3$ | CH$_3$ | C(O)NHSO$_2$CH$_3$ |
| 3,5-Cl$_2$ | CF$_3$ | H | C(O)NHSO$_2$CH$_2$CH$_2$Cl |
| 3,5-Cl$_2$ | CF$_3$ | H | C(O)NHSO$_2$CHClCH$_2$Cl |

TABLE 2-continued

In the table, the number showing the substitution position of substituent (X)$_m$
corresponds to the position number indicated in the following
structural formulae. The indication "—" means no-substitution.

| | | | |
|---|---|---|---|
| 3,5-Cl$_2$ | CF$_3$ | H | C(O)NHSO$_2$CHBrCH$_2$Br |
| 3,5-Cl$_2$ | CF$_3$ | H | C(O)NHSO$_2$CH$_2$CCl$_3$ |
| 3,5-Cl$_2$ | CF$_3$ | H | C(O)NHSO$_2$CHClCHCl$_2$ |
| 3,5-Cl$_2$ | CF$_3$ | H | C(O)NHSO$_2$CHClCHClCH$_3$ |
| 3,5-Cl$_2$ | CF$_3$ | H | C(O)NHSO$_2$CH$_2$Ph |
| 3,5-Cl$_2$ | CF$_3$ | H | C(O)NHSO$_2$CH=CH$_2$ |
| 3,5-Cl$_2$ | CF$_3$ | H | C(O)NHSO$_2$CH=CHCH$_3$ |
| 3,5-Cl$_2$ | CF$_3$ | H | C(O)NHSO$_2$CH=CHCl |
| 3,5-Cl$_2$ | CF$_3$ | H | C(O)NHSO$_2$Ph |
| 3,5-Cl$_2$ | CF$_3$ | H | C(S)OCH$_3$ |
| 3,5-Cl$_2$ | CF$_3$ | CH$_3$ | C(S)OCH$_3$ |
| 3,5-Cl$_2$ | CF$_3$ | CH$_2$OCH$_3$ | C(S)OCH$_3$ |
| 3,5-Cl$_2$ | CF$_3$ | C(O)CH$_3$ | C(S)OCH$_3$ |
| 3,5-Cl$_2$ | CF$_3$ | C(O)OCH$_3$ | C(S)OCH$_3$ |
| 3,5-Cl$_2$ | CF$_3$ | H | C(S)OEt |
| 3,5-Cl$_2$ | CF$_3$ | H | C(S)OPr-n |
| 3,5-Cl$_2$ | CF$_3$ | H | C(S)OPr-i |
| 3,5-Cl$_2$ | CF$_3$ | H | C(S)OBu-t |
| 3,5-Cl$_2$ | CF$_3$ | H | C(S)OCCl$_3$ |
| 3,5-Cl$_2$ | CF$_3$ | H | C(S)SCH$_3$ |
| 3,5-Cl$_2$ | CF$_3$ | H | C(S)SEt |
| 3,5-Cl$_2$ | CF$_3$ | H | C(S)SPr-i |
| 3,5-Cl$_2$ | CF$_3$ | H | C(S)SBu-t |
| 3,5-Cl$_2$ | CF$_3$ | H | C(S)NH$_2$ |
| 3,5-Cl$_2$ | CF$_3$ | CH$_3$ | C(S)NH$_2$ |
| 3,5-Cl$_2$ | CF$_3$ | Et | C(S)NH$_2$ |
| 3,5-Cl$_2$ | CF$_3$ | n-Pr | C(S)NH$_2$ |
| 3,5-Cl$_2$ | CF$_3$ | i-Pr | C(S)NH$_2$ |
| 3,5-Cl$_2$ | CF$_3$ | c-Pr | C(S)NH$_2$ |
| 3,5-Cl$_2$ | CF$_3$ | CH$_2$Pr-c | C(S)NH$_2$ |
| 3,5-Cl$_2$ | CF$_3$ | c-Bu | C(S)NH$_2$ |
| 3,5-Cl$_2$ | CF$_3$ | CH$_2$CF$_3$ | C(S)NH$_2$ |
| 3,5-Cl$_2$ | CF$_3$ | CH$_2$OCH$_3$ | C(S)NH$_2$ |
| 3,5-Cl$_2$ | CF$_3$ | CH$_2$OEt | C(S)NH$_2$ |
| 3,5-Cl$_2$ | CF$_3$ | CH$_2$OCH$_2$CF$_3$ | C(S)NH$_2$ |
| 3,5-Cl$_2$ | CF$_3$ | CH$_2$CH$_2$OCH$_3$ | C(S)NH$_2$ |
| 3,5-Cl$_2$ | CF$_3$ | CH$_2$CN | C(S)NH$_2$ |
| 3,5-Cl$_2$ | CF$_3$ | CH$_2$CH=CH$_2$ | C(S)NH$_2$ |
| 3,5-Cl$_2$ | CF$_3$ | CH$_2$C≡CH | C(S)NH$_2$ |
| 3,5-Cl$_2$ | CF$_3$ | CH$_2$Ph | C(S)NH$_2$ |
| 3,5-Cl$_2$ | CF$_3$ | H | C(S)NHC(O)CH$_3$ |
| 3,5-Cl$_2$ | CF$_3$ | CH$_3$ | C(S)NHC(O)CH$_3$ |
| 3,5-Cl$_2$ | CF$_3$ | H | C(S)NHC(O)Et |
| 3,5-Cl$_2$ | CF$_3$ | H | C(S)NHC(O)Pr-i |
| 3,5-Cl$_2$ | CF$_3$ | H | C(S)NHC(O)Bu-n |
| 3,5-Cl$_2$ | CF$_3$ | H | C(S)NHC(O)Pen-n |
| 3,5-Cl$_2$ | CF$_3$ | H | C(S)NHC(O)CH$_2$Cl |
| 3,5-Cl$_2$ | CF$_3$ | H | C(S)NHC(O)CCl$_3$ |
| 3,5-Cl$_2$ | CF$_3$ | H | C(S)NHC(O)CH$_2$OPh |
| 3,5-Cl$_2$ | CF$_3$ | H | C(S)NHC(O)CH$_2$SCH$_3$ |
| 3,5-Cl$_2$ | CF$_3$ | H | C(S)NHC(O)CH$_2$SPh |
| 3,5-Cl$_2$ | CF$_3$ | H | C(S)NHC(O)CH$_2$Ph |
| 3,5-Cl$_2$ | CF$_3$ | H | C(S)NHC(O)(T-9) |
| 3,5-Cl$_2$ | CF$_3$ | H | C(S)NHC(O)C(O)OEt |
| 3,5-Cl$_2$ | CF$_3$ | H | C(S)NHC(O)CCl=CCl$_2$ |
| 3,5-Cl$_2$ | CF$_3$ | H | C(S)NHC(O)CH=CClCH$_3$ |
| 3,5-Cl$_2$ | CF$_3$ | H | C(S)NHC(O)CH$_2$CH$_2$C≡CH |
| 3,5-Cl$_2$ | CF$_3$ | H | C(S)NHC(O)Ph |
| 3,5-Cl$_2$ | CF$_3$ | H | C(S)NHC(O)(D-1 a) |
| 3,5-Cl$_2$ | CF$_3$ | H | C(S)NHC(O)(D-2b)NO$_2$ |
| 3,5-Cl$_2$ | CF$_3$ | H | C(S)NHC(O)(D-3a) |
| 3,5-Cl$_2$ | CF$_3$ | H | C(S)NHC(O)(D-52a) |
| 3,5-Cl$_2$ | CF$_3$ | H | C(S)NHC(O)(D-53a) |
| 3,5-Cl$_2$ | CF$_3$ | H | C(S)NHC(O)(D-53b)Cl |
| 3,5-Cl$_2$ | CF$_3$ | H | C(S)NHC(O)(D-54a) |
| 3,5-Cl$_2$ | CF$_3$ | H | C(S)NHC(O)OCH$_3$ |
| 3,5-Cl$_2$ | CF$_3$ | CH$_3$ | C(S)NHC(O)OCH$_3$ |
| 3,5-Cl$_2$ | CF$_3$ | H | C(S)NHC(O)OEt |
| 3,5-Cl$_2$ | CF$_3$ | H | C(S)NHC(O)OBu-t |
| 3,5-Cl$_2$ | CF$_3$ | H | C(S)NHC(O)OCH$_2$CCl$_3$ |
| 3,5-Cl$_2$ | CF$_3$ | H | C(S)NHC(O)OC(CH$_3$)$_2$CCl$_3$ |
| 3,5-Cl$_2$ | CF$_3$ | H | C(S)NHC(O)OCH$_2$CH=CH$_2$ |
| 3,5-Cl$_2$ | CF$_3$ | H | C(S)NHC(O)OPh |
| 3,5-Cl$_2$ | CF$_3$ | H | C(S)NHC(O)SEt |
| 3,5-Cl$_2$ | CF$_3$ | CH$_3$ | C(S)NHC(O)SEt |
| 3,5-Cl$_2$ | CF$_3$ | H | C(S)NHC(O)SPr-n |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | H | C(S)NHC(O)SPh |
| 3,5-Cl$_2$ | CF$_3$ | H | C(S)NHC(S)Ph |
| 3,5-Cl$_2$ | CF$_3$ | H | C(S)NHC(S)OEt |
| 3,5-Cl$_2$ | CF$_3$ | CH$_3$ | C(S)NHC(S)OEt |
| 3,5-Cl$_2$ | CF$_3$ | H | C(S)NHC(S)OPr-n |
| 3,5-Cl$_2$ | CF$_3$ | H | C(S)NHC(S)SEt |
| 3,5-Cl$_2$ | CF$_3$ | CH$_3$ | C(S)NHC(S)SEt |
| 3,5-Cl$_2$ | CF$_3$ | H | C(S)NHC(S)SPr-n |
| 3,5-Cl$_2$ | CF$_3$ | H | C(S)NHC(S)SCN |
| 3,5-Cl$_2$ | CF$_3$ | H | C(S)NHSO$_2$CH$_3$ |
| 3,5-Cl$_2$ | CF$_3$ | CH$_3$ | C(S)NHSO$_2$CH$_3$ |
| 3,5-Cl$_2$ | CF$_3$ | CH$_3$ | Ph |
| 3,5-Cl$_2$ | CF$_3$ | Et | Ph |
| 3,5-Cl$_2$ | CF$_3$ | i-Pr | Ph |
| 3,5-Cl$_2$ | CF$_3$ | CH$_2$OCH$_3$ | Ph |
| 3,5-Cl$_2$ | CF$_3$ | C(O)CH$_3$ | Ph |
| 3,5-Cl$_2$ | CF$_3$ | C(O)OCH$_3$ | Ph |
| 3,5-Cl$_2$ | CF$_3$ | CH$_3$ | Ph-2-F |
| 3,5-Cl$_2$ | CF$_3$ | CH$_2$OCH$_3$ | Ph-2-F |
| 3,5-Cl$_2$ | CF$_3$ | C(O)CH$_3$ | Ph-2-F |
| 3,5-Cl$_2$ | CF$_3$ | C(O)OCH$_3$ | Ph-2-F |
| 3,5-Cl$_2$ | CF$_3$ | CH$_3$ | Ph-3-F |
| 3,5-Cl$_2$ | CF$_3$ | CH$_2$OCH$_3$ | Ph-3-F |
| 3,5-Cl$_2$ | CF$_3$ | C(O)CH$_3$ | Ph-3-F |
| 3,5-Cl$_2$ | CF$_3$ | C(O)OCH$_3$ | Ph-3-F |
| 3,5-Cl$_2$ | CF$_3$ | CH$_3$ | Ph-4-F |
| 3,5-Cl$_2$ | CF$_3$ | Et | Ph-4-F |
| 3,5-Cl$_2$ | CF$_3$ | CH$_2$CF$_3$ | Ph-4-F |
| 3,5-Cl$_2$ | CF$_3$ | CH$_2$OCH$_3$ | Ph-4-F |
| 3,5-Cl$_2$ | CF$_3$ | CH$_2$CN | Ph-4-F |
| 3,5-Cl$_2$ | CF$_3$ | CH$_2$CH=CH$_2$ | Ph-4-F |
| 3,5-Cl$_2$ | CF$_3$ | C(O)CH$_3$ | Ph-4-F |
| 3,5-Cl$_2$ | CF$_3$ | C(O)Et | Ph-4-F |
| 3,5-Cl$_2$ | CF$_3$ | C(O)Pr-c | Ph-4-F |
| 3,5-Cl$_2$ | CF$_3$ | C(O)Bu-i | Ph-4-F |
| 3,5-Cl$_2$ | CF$_3$ | C(O)CH$_2$OCH$_3$ | Ph-4-F |
| 3,5-Cl$_2$ | CF$_3$ | C(O)(D-52a) | Ph-4-F |
| 3,5-Cl$_2$ | CF$_3$ | C(O)OCH$_3$ | Ph-4-F |
| 3,5-Cl$_2$ | CF$_3$ | NH$_2$ | Ph-4-F |
| 3,5-Cl$_2$ | CF$_3$ | NHCH$_3$ | Ph-4-F |
| 3,5-Cl$_2$ | CF$_3$ | N(CH$_3$)$_2$ | Ph-4-F |
| 3,5-Cl$_2$ | CF$_3$ | NHEt | Ph-4-F |
| 3,5-Cl$_2$ | CF$_3$ | NHPr-i | Ph-4-F |
| 3,5-Cl$_2$ | CF$_3$ | NHCH$_2$C≡CH | Ph-4-F |
| 3,5-Cl$_2$ | CF$_3$ | NHCHO | Ph-4-F |
| 3,5-Cl$_2$ | CF$_3$ | NHC(O)CH$_3$ | Ph-4-F |
| 3,5-Cl$_2$ | CF$_3$ | N(CH$_3$)C(O)CH$_3$ | Ph-4-F |
| 3,5-Cl$_2$ | CF$_3$ | N[C(O)CH$_3$]$_2$ | Ph-4-F |
| 3,5-Cl$_2$ | CF$_3$ | NHC(O)Et | Ph-4-F |
| 3,5-Cl$_2$ | CF$_3$ | NHC(O)CF$_3$ | Ph-4-F |
| 3,5-Cl$_2$ | CF$_3$ | NHC(O)Ph | Ph-4-F |
| 3,5-Cl$_2$ | CF$_3$ | NHC(O)OCH$_3$ | Ph-4-F |
| 3,5-Cl$_2$ | CF$_3$ | NHC(O)OEt | Ph-4-F |
| 3,5-Cl$_2$ | CF$_3$ | NHC(O)OBu-t | Ph-4-F |
| 3,5-Cl$_2$ | CF$_3$ | NHC(O)NHCH$_3$ | Ph-4-F |
| 3,5-Cl$_2$ | CF$_3$ | NHC(O)NHPh | Ph-4-F |
| 3,5-Cl$_2$ | CF$_3$ | NHPh | Ph-4-F |
| 3,5-Cl$_2$ | CF$_3$ | NHSO$_2$CH$_3$ | Ph-4-F |
| 3,5-Cl$_2$ | CF$_3$ | NHSO$_2$NH$_2$ | Ph-4-F |
| 3,5-Cl$_2$ | CF$_3$ | NHSO$_2$NHCH$_3$ | Ph-4-F |
| 3,5-Cl$_2$ | CF$_3$ | NHSO$_2$NHPh | Ph-4-F |
| 3,5-Cl$_2$ | CF$_3$ | NHSO$_2$Ph | Ph-4-F |
| 3,5-Cl$_2$ | CF$_3$ | N=CHCH$_3$ | Ph-4-F |
| 3,5-Cl$_2$ | CF$_3$ | N=C(CH$_3$)$_2$ | Ph-4-F |
| 3,5-Cl$_2$ | CF$_3$ | N=CHPh | Ph-4-F |
| 3,5-Cl$_2$ | CF$_3$ | CH$_3$ | Ph-2-Cl |
| 3,5-Cl$_2$ | CF$_3$ | CH$_2$OCH$_3$ | Ph-3-Cl |
| 3,5-Cl$_2$ | CF$_3$ | CH$_3$ | Ph-4-Cl |
| 3,5-Cl$_2$ | CF$_3$ | CH$_2$OCH$_3$ | Ph-4-Cl |
| 3,5-Cl$_2$ | CF$_3$ | C(O)CH$_3$ | Ph-4-Cl |
| 3,5-Cl$_2$ | CF$_3$ | C(O)OCH$_3$ | Ph-4-Cl |
| 3,5-Cl$_2$ | CF$_3$ | C(O)CH$_3$ | Ph-3-Br |
| 3,5-Cl$_2$ | CF$_3$ | C(O)OCH$_3$ | Ph-4-Br |
| 3,5-Cl$_2$ | CF$_3$ | CH$_3$ | Ph-4-I |
| 3,5-Cl$_2$ | CF$_3$ | CH$_2$OCH$_3$ | Ph-4-CH$_3$ |
| 3,5-Cl$_2$ | CF$_3$ | C(O)CH$_3$ | Ph-3-CF$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | C(O)OCH$_3$ | Ph-4-CF$_3$ |
| 3,5-Cl$_2$ | CF$_3$ | CH$_3$ | Ph-4-CH$_2$SCH$_3$ |
| 3,5-Cl$_2$ | CF$_3$ | CH$_2$OCH$_3$ | Ph-4-CH$_2$S(O)CH$_3$ |
| 3,5-Cl$_2$ | CF$_3$ | C(O)CH$_3$ | Ph-4-CH$_2$SO$_2$CH$_3$ |
| 3,5-Cl$_2$ | CF$_3$ | C(O)OCH$_3$ | Ph-2-OH |
| 3,5-Cl$_2$ | CF$_3$ | CH$_3$ | Ph-3-OCH$_3$ |
| 3,5-Cl$_2$ | CF$_3$ | CH$_2$OCH$_3$ | Ph-4-OCH$_3$ |
| 3,5-Cl$_2$ | CF$_3$ | C(O)CH$_3$ | Ph-2-OEt |
| 3,5-Cl$_2$ | CF$_3$ | C(O)OCH$_3$ | Ph-3-OCHF$_2$ |
| 3,5-Cl$_2$ | CF$_3$ | CH$_3$ | Ph-4-OCHF$_2$ |
| 3,5-Cl$_2$ | CF$_3$ | CH$_2$OCH$_3$ | Ph-3-OCF$_3$ |
| 3,5-Cl$_2$ | CF$_3$ | C(O)CH$_3$ | Ph-4-OCF$_3$ |
| 3,5-Cl$_2$ | CF$_3$ | C(O)OCH$_3$ | Ph-3-OC(O)NHCH$_3$ |
| 3,5-Cl$_2$ | CF$_3$ | CH$_3$ | Ph-4-OC(O)NHCH$_3$ |
| 3,5-Cl$_2$ | CF$_3$ | CH$_3$ | Ph-4-OSO$_2$CH$_3$ |
| 3,5-Cl$_2$ | CF$_3$ | CH$_2$OCH$_3$ | Ph-4-OSO$_2$CH$_3$ |
| 3,5-Cl$_2$ | CF$_3$ | C(O)CH$_3$ | Ph-4-OSO$_2$CH$_3$ |
| 3,5-Cl$_2$ | CF$_3$ | C(O)OCH$_3$ | Ph-4-OSO$_2$CH$_3$ |
| 3,5-Cl$_2$ | CF$_3$ | CH$_2$OCH$_3$ | Ph-4-SCH$_3$ |
| 3,5-Cl$_2$ | CF$_3$ | C(O)CH$_3$ | Ph-4-S(O)CH$_3$ |
| 3,5-Cl$_2$ | CF$_3$ | C(O)OCH$_3$ | Ph-4-SO$_2$CH$_3$ |
| 3,5-Cl$_2$ | CF$_3$ | CH$_3$ | Ph-4-SCHF$_2$ |
| 3,5-Cl$_2$ | CF$_3$ | CH$_2$OCH$_3$ | Ph-4-S(O)CHF$_2$ |
| 3,5-Cl$_2$ | CF$_3$ | C(O)CH$_3$ | Ph-4-SO$_2$CHF$_2$ |
| 3,5-Cl$_2$ | CF$_3$ | C(O)OCH$_3$ | Ph-4-SCF$_3$ |
| 3,5-Cl$_2$ | CF$_3$ | CH$_3$ | Ph-4-S(O)CF$_3$ |
| 3,5-Cl$_2$ | CF$_3$ | CH$_2$OCH$_3$ | Ph-4-SO$_2$CF$_3$ |
| 3,5-Cl$_2$ | CF$_3$ | C(O)CH$_3$ | Ph-4-SO$_2$OCH$_3$ |
| 3,5-Cl$_2$ | CF$_3$ | C(O)OCH$_3$ | Ph-4-SO$_2$NH$_2$ |
| 3,5-Cl$_2$ | CF$_3$ | CH$_3$ | Ph-4-SO$_2$NHCH$_3$ |
| 3,5-Cl$_2$ | CF$_3$ | CH$_2$OCH$_3$ | Ph-4-SO$_2$N(CH$_3$)$_2$ |
| 3,5-Cl$_2$ | CF$_3$ | C(O)CH$_3$ | Ph-3-NO$_2$ |
| 3,5-Cl$_2$ | CF$_3$ | CH$_3$ | Ph-4-NO$_2$ |
| 3,5-Cl$_2$ | CF$_3$ | CH$_2$OCH$_3$ | Ph-4-NO$_2$ |
| 3,5-Cl$_2$ | CF$_3$ | C(O)CH$_3$ | Ph-4-NO$_2$ |
| 3,5-Cl$_2$ | CF$_3$ | C(O)OCH$_3$ | Ph-4-NO$_2$ |
| 3,5-Cl$_2$ | CF$_3$ | C(O)OCH$_3$ | Ph-4-NHC(O)CH$_3$ |
| 3,5-Cl$_2$ | CF$_3$ | CH$_3$ | Ph-4-NHC(O)CF$_3$ |
| 3,5-Cl$_2$ | CF$_3$ | CH$_2$OCH$_3$ | Ph-4-NHC(O)NHCH$_3$ |
| 3,5-Cl$_2$ | CF$_3$ | C(O)CH$_3$ | Ph-4-NHSO$_2$CH$_3$ |
| 3,5-Cl$_2$ | CF$_3$ | C(O)OCH$_3$ | Ph-4-NHSO$_2$CF$_3$ |
| 3,5-Cl$_2$ | CF$_3$ | CH$_3$ | Ph-4-N(CH$_3$)$_2$ |
| 3,5-Cl$_2$ | CF$_3$ | CH$_2$OCH$_3$ | Ph-4-CH=NOCH$_3$ |
| 3,5-Cl$_2$ | CF$_3$ | C(O)CH$_3$ | Ph-4-C(CH$_3$)=NOCH$_3$ |
| 3,5-Cl$_2$ | CF$_3$ | CH$_3$ | Ph-2-CN |
| 3,5-Cl$_2$ | CF$_3$ | CH$_2$OCH$_3$ | Ph-2-CN |
| 3,5-Cl$_2$ | CF$_3$ | C(O)CH3 | Ph-2-CN |
| 3,5-Cl$_2$ | CF$_3$ | C(O)OCH$_3$ | Ph-2-CN |
| 3,5-Cl$_2$ | CF$_3$ | CH$_3$ | Ph-3-CN |
| 3,5-Cl$_2$ | CF$_3$ | CH$_2$OCH$_3$ | Ph-3-CN |
| 3,5-Cl$_2$ | CF$_3$ | C(O)CH$_3$ | Ph-3-CN |
| 3,5-Cl$_2$ | CF$_3$ | C(O)OCH$_3$ | Ph-3-CN |
| 3,5-Cl$_2$ | CF$_3$ | CH$_3$ | Ph-4-CN |
| 3,5-Cl$_2$ | CF$_3$ | CH$_2$OCH$_3$ | Ph-4-CN |
| 3,5-Cl$_2$ | CF$_3$ | C(O)CH$_3$ | Ph-4-CN |
| 3,5-Cl$_2$ | CF$_3$ | C(O)OCH$_3$ | Ph-4-CN |
| 3,5-Cl$_2$ | CF$_3$ | C(O)OCH$_3$ | Ph-4-C(O)OH |
| 3,5-Cl$_2$ | CF$_3$ | CH$_3$ | Ph-4-C(O)OCH$_3$ |
| 3,5-Cl$_2$ | CF$_3$ | CH$_2$OCH$_3$ | Ph-4-C(O)OEt |
| 3,5-Cl$_2$ | CF$_3$ | C(O)CH$_3$ | Ph-4-C(O)NH$_2$ |
| 3,5-Cl$_2$ | CF$_3$ | C(O)OCH$_3$ | Ph-4-C(O)NHCH$_2$CH$_2$Cl |
| 3,5-Cl$_2$ | CF$_3$ | CH$_3$ | Ph-2-C(O)NHPr-i |
| 3,5-Cl$_2$ | CF$_3$ | CH$_2$OCH$_3$ | Ph-4-C(O)NHCH$_2$CF$_3$ |
| 3,5-Cl$_2$ | CF$_3$ | C(O)CH$_3$ | Ph-4-C(S)NH$_2$ |
| 3,5-Cl$_2$ | CF$_3$ | CH$_3$ | Ph-2,4-F$_2$ |
| 3,5-Cl$_2$ | CF$_3$ | Et | Ph-2,4-F$_2$ |
| 3,5-Cl$_2$ | CF$_3$ | CH$_2$OCH$_3$ | Ph-2,4-F$_2$ |
| 3,5-Cl$_2$ | CF$_3$ | C(O)CH$_3$ | Ph-2,4-F$_2$ |
| 3,5-Cl$_2$ | CF$_3$ | C(O)Pr-i | Ph-2,4-F$_2$ |
| 3,5-Cl$_2$ | CF$_3$ | C(O)Bu-t | Ph-2,4-F$_2$ |
| 3,5-Cl$_2$ | CF$_3$ | C(O)OCH$_3$ | Ph-2,4-F$_2$ |
| 3,5-Cl$_2$ | CF$_3$ | C(O)OCH$_3$ | Ph-2,5-F$_2$ |
| 3,5-Cl$_2$ | CF$_3$ | CH$_3$ | Ph-2,6-F$_2$ |
| 3,5-Cl$_2$ | CF$_3$ | CH$_2$OCH$_3$ | Ph-2,6-F$_2$ |
| 3,5-Cl$_2$ | CF$_3$ | C(O)CH$_3$ | Ph-2,6-F$_2$ |
| 3,5-Cl$_2$ | CF$_3$ | C(O)OCH$_3$ | Ph-2,6-F$_2$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | CH$_3$ | Ph-3,4-F$_2$ |
| 3,5-Cl$_2$ | CF$_3$ | CH$_2$OCH$_3$ | Ph-3,4-F$_2$ |
| 3,5-Cl$_2$ | CF$_3$ | C(O)CH$_3$ | Ph-3,4-F$_2$ |
| 3,5-Cl$_2$ | CF$_3$ | C(O)OCH$_3$ | Ph-3,4-F$_2$ |
| 3,5-Cl$_2$ | CF$_3$ | C(O)OCH$_3$ | Ph-3,5-F$_2$ |
| 3,5-Cl$_2$ | CF$_3$ | CH$_3$ | Ph-2-F-4-Cl |
| 3,5-Cl$_2$ | CF$_3$ | CH$_2$OCH$_3$ | Ph-2-F-4-Cl |
| 3,5-Cl$_2$ | CF$_3$ | C(O)CH$_3$ | Ph-2-F-4-Cl |
| 3,5-Cl$_2$ | CF$_3$ | C(O)OCH$_3$ | Ph-2-F-4-Cl |
| 3,5-Cl$_2$ | CF$_3$ | CH$_3$ | Ph-2-Cl-4-F |
| 3,5-Cl$_2$ | CF$_3$ | CH$_2$OCH$_3$ | Ph-2-F-6-Cl |
| 3,5-Cl$_2$ | CF$_3$ | C(O)CH$_3$ | Ph-3-F-4-Cl |
| 3,5-Cl$_2$ | CF$_3$ | C(O)OCH$_3$ | Ph-3-Cl-4-F |
| 3,5-Cl$_2$ | CF$_3$ | CH$_3$ | Ph-2,3-Cl$_2$ |
| 3,5-Cl$_2$ | CF$_3$ | CH$_2$OCH$_3$ | Ph-2,4-Cl$_2$ |
| 3,5-Cl$_2$ | CF$_3$ | C(O)CH$_3$ | Ph-2,5-Cl$_2$ |
| 3,5-Cl$_2$ | CF$_3$ | C(O)OCH$_3$ | Ph-2,6-Cl$_2$ |
| 3,5-Cl$_2$ | CF$_3$ | CH$_3$ | Ph-3,4-Cl$_2$ |
| 3,5-Cl$_2$ | CF$_3$ | CH$_2$OCH$_3$ | Ph-3,5-Cl$_2$ |
| 3,5-Cl$_2$ | CF$_3$ | C(O)CH$_3$ | Ph-2-F-4-Br |
| 3,5-Cl$_2$ | CF$_3$ | C(O)OCH$_3$ | Ph-2-F-5-Br |
| 3,5-Cl$_2$ | CF$_3$ | CH$_3$ | Ph-3-Br-4-F |
| 3,5-Cl$_2$ | CF$_3$ | CH$_2$OCH$_3$ | Ph-2-F-3-CF$_3$ |
| 3,5-Cl$_2$ | CF$_3$ | C(O)CH$_3$ | Ph-2-F-4-CF$_3$ |
| 3,5-Cl$_2$ | CF$_3$ | C(O)OCH$_3$ | Ph-2-CF$_3$-4-F |
| 3,5-Cl$_2$ | CF$_3$ | CH$_3$ | Ph-2-F-5-CF$_3$ |
| 3,5-Cl$_2$ | CF$_3$ | CH$_2$OCH$_3$ | Ph-2-CF$_3$-5-F |
| 3,5-Cl$_2$ | CF$_3$ | C(O)CH$_3$ | Ph-2-F-6-CF$_3$ |
| 3,5-Cl$_2$ | CF$_3$ | C(O)OCH$_3$ | Ph-3-CF$_3$-4-F |
| 3,5-Cl$_2$ | CF$_3$ | CH$_3$ | Ph-3-F-5-CF$_3$ |
| 3,5-Cl$_2$ | CF$_3$ | CH$_2$OCH$_3$ | Ph-3-OCH$_3$-4-OH |
| 3,5-Cl$_2$ | CF$_3$ | C(O)CH$_3$ | Ph-2,3-(OCH$_3$)$_2$ |
| 3,5-Cl$_2$ | CF$_3$ | C(O)OCH$_3$ | Ph-2,4-(OCH$_3$)$_2$ |
| 3,5-Cl$_2$ | CF$_3$ | CH$_3$ | Ph-2,6-(OCH$_3$)$_2$ |
| 3,5-Cl$_2$ | CF$_3$ | CH$_2$OCH$_3$ | Ph-3,4-(OCH$_3$)$_2$ |
| 3,5-Cl$_2$ | CF$_3$ | C(O)CH$_3$ | Ph-3,5-(OCH$_3$)$_2$ |
| 3,5-Cl$_2$ | CF$_3$ | C(O)OCH$_3$ | Ph-3-OCH$_2$O-4 |
| 3,5-Cl$_2$ | CF$_3$ | CH$_3$ | Ph-3-OCF$_2$O-4 |
| 3,5-Cl$_2$ | CF$_3$ | CH$_3$ | Ph-3-NO$_2$-4-F |
| 3,5-Cl$_2$ | CF$_3$ | CH$_2$OCH$_3$ | Ph-3-NO$_2$-4-F |
| 3,5-Cl$_2$ | CF$_3$ | C(O)CH$_3$ | Ph-3-NO$_2$-4-F |
| 3,5-Cl$_2$ | CF$_3$ | C(O)OCH$_3$ | Ph-3-NO$_2$-4-F |
| 3,5-Cl$_2$ | CF$_3$ | CH$_2$OCH$_3$ | Ph-2,3,4-F$_3$ |
| 3,5-Cl$_2$ | CF$_3$ | C(O)CH$_3$ | Ph-2,3,5-F$_3$ |
| 3,5-Cl$_2$ | CF$_3$ | C(O)OCH$_3$ | Ph-2,4,6-F$_3$ |
| 3,5-Cl$_2$ | CF$_3$ | CH$_3$ | Ph-2,4,6-F$_3$ |
| 3,5-Cl$_2$ | CF$_3$ | CH$_3$ | Ph-2,4,6-F$_3$ |
| 3,5-Cl$_2$ | CF$_3$ | CH$_2$OCH$_3$ | Ph-2,4,6-F$_3$ |
| 3,5-Cl$_2$ | CF$_3$ | C(O)CH$_3$ | Ph-2,4,6-F$_3$ |
| 3,5-Cl$_2$ | CF$_3$ | C(O)OCH$_3$ | Ph-2,4,6-F$_3$ |
| 3,5-Cl$_2$ | CF$_3$ | CH$_2$OCH$_3$ | Ph-2,4,5-F$_3$ |
| 3,5-Cl$_2$ | CF$_3$ | C(O)CH$_3$ | Ph-2,6-F$_2$-4-Br |
| 3,5-Cl$_2$ | CF$_3$ | C(O)OCH$_3$ | Ph-2,4,6-(OCH$_3$)$_3$ |
| 3,5-Cl$_2$ | CF$_3$ | CH$_3$ | Ph-3,4,5-(OCH$_3$)$_3$ |
| 3,5-Cl$_2$ | CF$_3$ | CH$_2$OCH$_3$ | 1-Naph |
| 3,5-Cl$_2$ | CF$_3$ | C(O)CH$_3$ | 2-Naph |
| 3,5-Cl$_2$ | CF$_3$ | C(O)OCH$_3$ | D-1a |
| 3,5-Cl$_2$ | CF$_3$ | CH$_3$ | (D-1b)Br |
| 3,5-Cl$_2$ | CF$_3$ | CH$_2$OCH$_3$ | (D-1c)Cl |
| 3,5-Cl$_2$ | CF$_3$ | C(O)CH$_3$ | (D-1c)Br |
| 3,5-Cl$_2$ | CF$_3$ | C(O)OCH$_3$ | (D-1c)CH$_3$ |
| 3,5-Cl$_2$ | CF$_3$ | CH$_3$ | (D-1c)CF$_3$ |
| 3,5-Cl$_2$ | CF$_3$ | CH$_2$OCH$_3$ | (D-1c)SCH$_3$ |
| 3,5-Cl$_2$ | CF$_3$ | C(O)CH$_3$ | (D-1c)SO$_2$CH$_3$ |
| 3,5-Cl$_2$ | CF$_3$ | C(O)OCH$_3$ | (D-1c)NO$_2$ |
| 3,5-Cl$_2$ | CF$_3$ | CH$_3$ | (D-1c)CN |
| 3,5-Cl$_2$ | CF$_3$ | CH$_2$OCH$_3$ | D-2a |
| 3,5-Cl$_2$ | CF$_3$ | C(O)CH$_3$ | (D-2b)Br |
| 3,5-Cl$_2$ | CF$_3$ | C(O)Bu-t | D-3a |
| 3,5-Cl$_2$ | CF$_3$ | C(O)OCH$_3$ | D-3a |
| 3,5-Cl$_2$ | CF$_3$ | CH$_3$ | (D-3b)CH$_3$ |
| 3,5-Cl$_2$ | CF$_3$ | CH$_2$OCH$_3$ | (D-3b)CN |
| 3,5-Cl$_2$ | CF$_3$ | C(O)CH$_3$ | (D-3c)Cl |
| 3,5-Cl$_2$ | CF$_3$ | C(O)OCH$_3$ | (D-3c)Br |
| 3,5-Cl$_2$ | CF$_3$ | CH$_3$ | (D-3c)SCH$_3$ |
| 3,5-Cl$_2$ | CF$_3$ | CH$_2$OCH$_3$ | (D-3c)SO$_2$CH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | C(O)CH$_3$ | (D-3c)NO$_2$ |
| 3,5-Cl$_2$ | CF$_3$ | C(O)OCH$_3$ | (D-3d)F |
| 3,5-Cl$_2$ | CF$_3$ | CH$_3$ | (D-3d)Cl |
| 3,5-Cl$_2$ | CF$_3$ | CH$_2$OCH$_3$ | (D-3d)Br |
| 3,5-Cl$_2$ | CF$_3$ | C(O)CH$_3$ | (D-3d)I |
| 3,5-Cl$_2$ | CF$_3$ | C(O)OCH$_3$ | (D-3d)CH$_3$ |
| 3,5-Cl$_2$ | CF$_3$ | CH$_3$ | (D-3d)CF$_3$ |
| 3,5-Cl$_2$ | CF$_3$ | CH$_2$OCH$_3$ | (D-3d)NO$_2$ |
| 3,5-Cl$_2$ | CF$_3$ | C(O)CH$_3$ | (D-3d)SCH$_3$ |
| 3,5-Cl$_2$ | CF$_3$ | C(O)OCH$_3$ | (D-3d)SO$_2$CH$_3$ |
| 3,5-Cl$_2$ | CF$_3$ | CH$_3$ | (D-3d)CN |
| 3,5-Cl$_2$ | CF$_3$ | CH$_2$OCH$_3$ | D-4a |
| 3,5-Cl$_2$ | CF$_3$ | C(O)CH$_3$ | (D-4b)Cl |
| 3,5-Cl$_2$ | CF$_3$ | C(O)OCH$_3$ | (D-4b)Br |
| 3,5-Cl$_2$ | CF$_3$ | CH$_3$ | (D-4b)CH$_3$ |
| 3,5-Cl$_2$ | CF$_3$ | CH$_2$OCH$_3$ | (D-4b)NO$_2$ |
| 3,5-Cl$_2$ | CF$_3$ | C(O)CH$_3$ | (D-4b)CN |
| 3,5-Cl$_2$ | CF$_3$ | C(O)OCH$_3$ | (D-4b)C(O)OCH$_3$ |
| 3,5-Cl$_2$ | CF$_3$ | CH$_3$ | D-5a |
| 3,5-Cl$_2$ | CF$_3$ | CH$_2$OCH$_3$ | D-6a |
| 3,5-Cl$_2$ | CF$_3$ | C(O)CH$_3$ | (D-6b)Cl |
| 3,5-Cl$_2$ | CF$_3$ | C(O)OCH$_3$ | (D-6b)Br |
| 3,5-Cl$_2$ | CF$_3$ | CH$_3$ | (D-6c)Cl |
| 3,5-Cl$_2$ | CF$_3$ | CH$_2$OCH$_3$ | (D-6c)Br |
| 3,5-Cl$_2$ | CF$_3$ | C(O)CH$_3$ | D-7a |
| 3,5-Cl$_2$ | CF$_3$ | C(O)OCH$_3$ | (D-7b)CH$_3$ |
| 3,5-Cl$_2$ | CF$_3$ | CH$_3$ | D-8a |
| 3,5-Cl$_2$ | CF$_3$ | CH$_2$OCH$_3$ | D-8a |
| 3,5-Cl$_2$ | CF$_3$ | C(O)CH$_3$ | D-8a |
| 3,5-Cl$_2$ | CF$_3$ | C(O)OCH$_3$ | D-8a |
| 3,5-Cl$_2$ | CF$_3$ | CH$_3$ | (D-8b)Cl |
| 3,5-Cl$_2$ | CF$_3$ | CH$_2$OCH$_3$ | (D-8b)Br |
| 3,5-Cl$_2$ | CF$_3$ | CH$_3$ | (D-8b)CH$_3$ |
| 3,5-Cl$_2$ | CF$_3$ | CH$_2$OCH$_3$ | (D-8b)CH$_3$ |
| 3,5-Cl$_2$ | CF$_3$ | C(O)CH$_3$ | (D-8b)CH$_3$ |
| 3,5-Cl$_2$ | CF$_3$ | C(O)OCH$_3$ | (D-8b)CH$_3$ |
| 3,5-Cl$_2$ | CF$_3$ | C(O)CH$_3$ | (D-8b)Pr-i |
| 3,5-Cl$_2$ | CF$_3$ | C(O)OCH$_3$ | (D-8b)Bu-t |
| 3,5-Cl$_2$ | CF$_3$ | CH$_3$ | (D-8b)CH$_2$F |
| 3,5-Cl$_2$ | CF$_3$ | CH$_2$OCH$_3$ | (D-8b)CHF$_2$ |
| 3,5-Cl$_2$ | CF$_3$ | CH$_3$ | (D-8b)CF$_3$ |
| 3,5-Cl$_2$ | CF$_3$ | CH$_2$OCH$_3$ | (D-8b)CF$_3$ |
| 3,5-Cl$_2$ | CF$_3$ | C(O)CH$_3$ | (D-8b)CF$_3$ |
| 3,5-Cl$_2$ | CF$_3$ | C(O)OCH$_3$ | (D-8b)CF$_3$ |
| 3,5-Cl$_2$ | CF$_3$ | C(O)CH$_3$ | (D-8b)CF$_2$CF$_3$ |
| 3,5-Cl$_2$ | CF$_3$ | C(O)OCH$_3$ | (D-8b)CH$_2$OH |
| 3,5-Cl$_2$ | CF$_3$ | CH$_3$ | (D-8b)CH$_2$OCH$_3$ |
| 3,5-Cl$_2$ | CF$_3$ | CH$_2$OCH$_3$ | (D-8b)CH$_2$OCH$_2$Ph |
| 3,5-Cl$_2$ | CF$_3$ | C(O)CH$_3$ | (D-8b)CH$_2$OTMS |
| 3,5-Cl$_2$ | CF$_3$ | C(O)OCH$_3$ | (D-8b)OCH$_3$ |
| 3,5-Cl$_2$ | CF$_3$ | CH$_3$ | (D-8b)OPh |
| 3,5-Cl$_2$ | CF$_3$ | CH$_2$OCH$_3$ | (D-8b)Ph |
| 3,5-Cl$_2$ | CF$_3$ | C(O)CH$_3$ | D-9a |
| 3,5-Cl$_2$ | CF$_3$ | C(O)OCH$_3$ | (D-9b)CH$_3$ |
| 3,5-Cl$_2$ | CF$_3$ | CH$_3$ | (D-9c)CH$_3$ |
| 3,5-Cl$_2$ | CF$_3$ | CH$_2$OCH$_3$ | D-10a |
| 3,5-Cl$_2$ | CF$_3$ | C(O)CH$_3$ | (D-10b)Cl |
| 3,5-Cl$_2$ | CF$_3$ | C(O)OCH$_3$ | (D-10b)Br |
| 3,5-Cl$_2$ | CF$_3$ | CH$_3$ | (D-10b)CH$_3$ |
| 3,5-Cl$_2$ | CF$_3$ | CH$_2$OCH$_3$ | (D-10b)Et |
| 3,5-Cl$_2$ | CF$_3$ | C(O)CH$_3$ | (D-10b)CF$_3$ |
| 3,5-Cl$_2$ | CF$_3$ | C(O)OCH$_3$ | (D-10b)CF$_2$CF$_3$ |
| 3,5-Cl$_2$ | CF$_3$ | CH$_3$ | (D-10b)OCH$_3$ |
| 3,5-Cl$_2$ | CF$_3$ | CH$_2$OCH$_3$ | (D-10b)SCH$_3$ |
| 3,5-Cl$_2$ | CF$_3$ | C(O)CH$_3$ | D-11a |
| 3,5-Cl$_2$ | CF$_3$ | C(O)OCH$_3$ | (D-11b)Cl |
| 3,5-Cl$_2$ | CF$_3$ | CH$_3$ | (D-11b)Br |
| 3,5-Cl$_2$ | CF$_3$ | CH$_3$ | (D-11b)CH$_3$ |
| 3,5-Cl$_2$ | CF$_3$ | CH$_2$OCH$_3$ | (D-11b)CH$_3$ |
| 3,5-Cl$_2$ | CF$_3$ | C(O)CH$_3$ | (D-11b)CH$_3$ |
| 3,5-Cl$_2$ | CF$_3$ | C(O)OCH$_3$ | (D-11b)CH$_3$ |
| 3,5-Cl$_2$ | CF$_3$ | CH$_2$OCH$_3$ | (D-11b)Bu-t |
| 3,5-Cl$_2$ | CF$_3$ | C(O)CH$_3$ | D-12a |
| 3,5-Cl$_2$ | CF$_3$ | C(O)OCH$_3$ | (D-12b)OCH$_3$ |
| 3,5-Cl$_2$ | CF$_3$ | CH$_3$ | (D-12c)Cl |
| 3,5-Cl$_2$ | CF$_3$ | CH$_2$OCH$_3$ | (D-12c)Br |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | C(O)CH$_3$ | D-13a |
| 3,5-Cl$_2$ | CF$_3$ | CH$_3$ | (D-13b)CH$_3$ |
| 3,5-Cl$_2$ | CF$_3$ | CH$_2$OCH$_3$ | (D-13b)CH$_3$ |
| 3,5-Cl$_2$ | CF$_3$ | C(O)CH$_3$ | (D-13b)CH$_3$ |
| 3,5-Cl$_2$ | CF$_3$ | C(O)OCH$_3$ | (D-13b)CH$_3$ |
| 3,5-Cl$_2$ | CF$_3$ | C(O)OCH$_3$ | (D-13b)Et |
| 3,5-Cl$_2$ | CF$_3$ | CH$_3$ | (D-13b)Pr-i |
| 3,5-Cl$_2$ | CF$_3$ | CH$_2$OCH$_3$ | (D-13b)SCH$_3$ |
| 3,5-Cl$_2$ | CF$_3$ | CH$_3$ | D-14a |
| 3,5-Cl$_2$ | CF$_3$ | Et | D-14a |
| 3,5-Cl$_2$ | CF$_3$ | CH$_2$OCH$_3$ | D-14a |
| 3,5-Cl$_2$ | CF$_3$ | CH$_2$OEt | D-14a |
| 3,5-Cl$_2$ | CF$_3$ | CH$_2$OCH$_2$CF$_3$ | D-14a |
| 3,5-Cl$_2$ | CF$_3$ | CH$_2$OC(O)CH$_3$ | D-14a |
| 3,5-Cl$_2$ | CF$_3$ | CH$_2$OC(O)Et | D-14a |
| 3,5-Cl$_2$ | CF$_3$ | CH$_2$OC(O)Pr-i | D-14a |
| 3,5-Cl$_2$ | CF$_3$ | CH$_2$OC(O)Pr-c | D-14a |
| 3,5-Cl$_2$ | CF$_3$ | CH$_2$OC(O)Bu-t | D-14a |
| 3,5-Cl$_2$ | CF$_3$ | CH$_2$OC(O)Ph | D-14a |
| 3,5-Cl$_2$ | CF$_3$ | CH$_2$OC(O)OCH$_3$ | D-14a |
| 3,5-Cl$_2$ | CF$_3$ | CH$_2$CN | D-14a |
| 3,5-Cl$_2$ | CF$_3$ | CH$_2$C≡CH | D-14a |
| 3,5-Cl$_2$ | CF$_3$ | C(O)CH$_3$ | D-14a |
| 3,5-Cl$_2$ | CF$_3$ | C(O)Et | D-14a |
| 3,5-Cl$_2$ | CF$_3$ | C(O)Pr-n | D-14a |
| 3,5-Cl$_2$ | CF$_3$ | C(O)Pr-i | D-14a |
| 3,5-Cl$_2$ | CF$_3$ | C(O)Pr-c | D-14a |
| 3,5-Cl$_2$ | CF$_3$ | C(O)Bu-t | D-14a |
| 3,5-Cl$_2$ | CF$_3$ | C(O)CH$_2$OCH$_3$ | D-14a |
| 3,5-Cl$_2$ | CF$_3$ | C(O)OCH$_3$ | D-14a |
| 3,5-Cl$_2$ | CF$_3$ | C(O)OEt | D-14a |
| 3,5-Cl$_2$ | CF$_3$ | C(O)OPr-n | D-14a |
| 3,5-Cl$_2$ | CF$_3$ | C(O)OPr-i | D-14a |
| 3,5-Cl$_2$ | CF$_3$ | C(O)OPr-c | D-14a |
| 3,5-Cl$_2$ | CF$_3$ | C(O)OCH$_2$Cl | D-14a |
| 3,5-Cl$_2$ | CF$_3$ | C(O)OCH$_2$CH$_2$Cl | D-14a |
| 3,5-Cl$_2$ | CF$_3$ | C(O)OCH$_2$CH$_2$OCH$_3$ | D-14a |
| 3,5-Cl$_2$ | CF$_3$ | C(O)OCH$_2$CH═CH$_2$ | D-14a |
| 3,5-Cl$_2$ | CF$_3$ | C(O)CH$_3$ | (D-14b)Cl |
| 3,5-Cl$_2$ | CF$_3$ | C(O)OCH$_3$ | (D-14b)Br |
| 3,5-Cl$_2$ | CF$_3$ | CH$_3$ | (D-14b)CH$_3$ |
| 3,5-Cl$_2$ | CF$_3$ | CH$_2$OCH$_3$ | (D-14b)Et |
| 3,5-Cl$_2$ | CF$_3$ | C(O)CH$_3$ | (D-14b)CF$_3$ |
| 3,5-Cl$_2$ | CF$_3$ | C(O)OCH$_3$ | (D-14b)NO$_2$ |
| 3,5-Cl$_2$ | CF$_3$ | CH$_3$ | (D-14b)CN |
| 3,5-Cl$_2$ | CF$_3$ | CH$_2$OCH$_3$ | (D-14b)Ph |
| 3,5-Cl$_2$ | CF$_3$ | C(O)CH$_3$ | (D-14c)F |
| 3,5-Cl$_2$ | CF$_3$ | C(O)OCH$_3$ | (D-14c)Cl |
| 3,5-Cl$_2$ | CF$_3$ | CH$_3$ | (D-14c)Br |
| 3,5-Cl$_2$ | CF$_3$ | CH$_2$OCH$_3$ | (D-14c)I |
| 3,5-Cl$_2$ | CF$_3$ | C(O)CH$_3$ | (D-14c)CH$_3$ |
| 3,5-Cl$_2$ | CF$_3$ | C(O)OCH$_3$ | (D-14c)CF$_3$ |
| 3,5-Cl$_2$ | CF$_3$ | CH$_3$ | (D-14c)OCH$_3$ |
| 3,5-Cl$_2$ | CF$_3$ | CH$_2$OCH$_3$ | (D-14c)OCH$_2$CF$_3$ |
| 3,5-Cl$_2$ | CF$_3$ | C(O)CH$_3$ | (D-14c)NO$_2$ |
| 3,5-Cl$_2$ | CF$_3$ | C(O)OCH$_3$ | (D-14c)CN |
| 3,5-Cl$_2$ | CF$_3$ | CH$_3$ | (D-14c)C(O)OCH$_3$ |
| 3,5-Cl$_2$ | CF$_3$ | CH2OCH$_3$ | (D-14c)TMS |
| 3,5-Cl$_2$ | CF$_3$ | CH$_3$ | (D-15a)CH$_3$ |
| 3,5-Cl$_2$ | CF$_3$ | CH$_2$OCH$_3$ | (D-15a)CH$_3$ |
| 3,5-Cl$_2$ | CF$_3$ | CH$_2$OEt | (D-15a)CH$_3$ |
| 3,5-Cl$_2$ | CF$_3$ | CH$_2$OC(O)CH$_3$ | (D-15a)CH$_3$ |
| 3,5-Cl$_2$ | CF$_3$ | C(O)CH$_3$ | (D-15a)Et |
| 3,5-Cl$_2$ | CF$_3$ | C(O)OCH$_3$ | (D-15a)CH$_2$OCH$_2$Ph |
| 3,5-Cl$_2$ | CF$_3$ | CH$_3$ | (D-15a)CH$_2$C(O)NHPh |
| 3,5-Cl$_2$ | CF$_3$ | CH$_2$OCH$_3$ | (D-15a)CH$_2$Ph |
| 3,5-Cl$_2$ | CF$_3$ | C(O)CH$_3$ | (D-15b)Cl |
| 3,5-Cl$_2$ | CF$_3$ | C(O)OCH$_3$ | (D-15c)Cl |
| 3,5-Cl$_2$ | CF$_3$ | CH$_3$ | (D-15c)Br |
| 3,5-Cl$_2$ | CF$_3$ | CH$_2$OCH$_3$ | (D-15c)CH$_3$ |
| 3,5-Cl$_2$ | CF$_3$ | C(O)CH$_3$ | (D-15c)CN |
| 3,5-Cl$_2$ | CF$_3$ | C(O)OCH$_3$ | (D-16a)CH$_3$ |
| 3,5-Cl$_2$ | CF$_3$ | CH$_3$ | (D-16a)CHF$_2$ |
| 3,5-Cl$_2$ | CF$_3$ | CH$_2$OCH$_3$ | (D-16a)CF$_2$Br |
| 3,5-Cl$_2$ | CF$_3$ | C(O)CH$_3$ | (D-16b)Cl |
| 3,5-Cl$_2$ | CF$_3$ | C(O)OCH$_3$ | (D-16b)CH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | CH$_3$ | (D-16c)Cl |
| 3,5-Cl$_2$ | CF$_3$ | CH$_2$OCH$_3$ | (D-16c)CH$_3$ |
| 3,5-Cl$_2$ | CF$_3$ | CH$_3$ | (D-17a)CH$_3$ |
| 3,5-Cl$_2$ | CF$_3$ | CH$_2$OCH$_3$ | (D-17a)CH$_3$ |
| 3,5-Cl$_2$ | CF$_3$ | C(O)CH$_3$ | (D-17a)CH$_3$ |
| 3,5-Cl$_2$ | CF$_3$ | C(O)OCH$_3$ | (D-17a)CH$_3$ |
| 3,5-Cl$_2$ | CF$_3$ | C(O)CH$_3$ | (D-17b)Cl |
| 3,5-Cl$_2$ | CF$_3$ | C(O)OCH$_3$ | (D-17b)Br |
| 3,5-Cl$_2$ | CF$_3$ | CH$_3$ | (D-17b)CH$_3$ |
| 3,5-Cl$_2$ | CF$_3$ | CH$_2$OCH$_3$ | (D-17b)CF$_3$ |
| 3,5-Cl$_2$ | CF$_3$ | C(O)CH$_3$ | (D-17b)C(O)OCH$_3$ |
| 3,5-Cl$_2$ | CF$_3$ | C(O)OCH$_3$ | D-18a |
| 3,5-Cl$_2$ | CF$_3$ | CH$_3$ | (D-18b)CH$_3$ |
| 3,5-Cl$_2$ | CF$_3$ | CH$_2$OCH$_3$ | (D-18b)Et |
| 3,5-Cl$_2$ | CF$_3$ | C(O)CH$_3$ | (D-18b)Bu-t |
| 3,5-Cl$_2$ | CF$_3$ | C(O)OCH$_3$ | (D-18b)Ph |
| 3,5-Cl$_2$ | CF$_3$ | CH$_3$ | (D-18c)CH$_3$ |
| 3,5-Cl$_2$ | CF$_3$ | CH$_2$OCH$_3$ | (D-18c)C(O)CH$_3$ |
| 3,5-Cl$_2$ | CF$_3$ | C(O)CH$_3$ | (D-18c)Ph |
| 3,5-Cl$_2$ | CF$_3$ | C(O)OCH$_3$ | D-19a |
| 3,5-Cl$_2$ | CF$_3$ | CH$_3$ | (D-19b)Cl |
| 3,5-Cl$_2$ | CF$_3$ | CH$_2$OCH$_3$ | (D-19b)Br |
| 3,5-Cl$_2$ | CF$_3$ | C(O)CH$_3$ | (D-19b)CH$_3$ |
| 3,5-Cl$_2$ | CF$_3$ | C(O)OCH$_3$ | (D-19b)CF$_3$ |
| 3,5-Cl$_2$ | CF$_3$ | CH$_3$ | D-20a |
| 3,5-Cl$_2$ | CF$_3$ | CH$_2$OCH$_3$ | (D-20b)Cl |
| 3,5-Cl$_2$ | CF$_3$ | C(O)CH$_3$ | (D-20b)Br |
| 3,5-Cl$_2$ | CF$_3$ | C(O)OCH$_3$ | (D-20b)CH$_3$ |
| 3,5-Cl$_2$ | CF$_3$ | CH$_3$ | (D-20b)CF$_3$ |
| 3,5-Cl$_2$ | CF$_3$ | CH$_3$ | D-21a |
| 3,5-Cl$_2$ | CF$_3$ | CH$_2$OCH$_3$ | D-21a |
| 3,5-Cl$_2$ | CF$_3$ | CH$_3$ | (D-21b)Br |
| 3,5-Cl$_2$ | CF$_3$ | CH$_2$OCH$_3$ | (D-21b)Br |
| 3,5-Cl$_2$ | CF$_3$ | CH$_3$ | (D-21b)CH$_3$ |
| 3,5-Cl$_2$ | CF$_3$ | CH$_2$OCH$_3$ | (D-21b)CH$_3$ |
| 3,5-Cl$_2$ | CF$_3$ | CH$_3$ | (D-21b)CF$_3$ |
| 3,5-Cl$_2$ | CF$_3$ | CH$_2$OCH$_3$ | (D-21b)CF$_3$ |
| 3,5-Cl$_2$ | CF$_3$ | CH$_2$OCH$_3$ | (D-21b)O(E-6a) |
| 3,5-Cl$_2$ | CF$_3$ | CH$_3$ | (D-21c)Cl |
| 3,5-Cl$_2$ | CF$_3$ | CH$_2$OCH$_3$ | (D-21c)Cl |
| 3,5-Cl$_2$ | CF$_3$ | CH$_3$ | (D-21c)Br |
| 3,5-Cl$_2$ | CF$_3$ | CH$_2$OCH$_3$ | (D-21c)Br |
| 3,5-Cl$_2$ | CF$_3$ | C(O)CH$_3$ | (D-21c)CH$_3$ |
| 3,5-Cl$_2$ | CF$_3$ | C(O)OCH$_3$ | (D-21c)CF$_3$ |
| 3,5-Cl$_2$ | CF$_3$ | CH$_3$ | (D-21c)SCH$_3$ |
| 3,5-Cl$_2$ | CF$_3$ | CH$_2$OCH$_3$ | (D-21c)SCN |
| 3,5-Cl$_2$ | CF$_3$ | C(O)CH$_3$ | (D-21c)NO$_2$ |
| 3,5-Cl$_2$ | CF$_3$ | C(O)OCH$_3$ | (D-21c)N(CH$_3$)$_2$ |
| 3,5-Cl$_2$ | CF$_3$ | CH$_3$ | (D-21c)CN |
| 3,5-Cl$_2$ | CF$_3$ | CH$_3$ | D-22a |
| 3,5-Cl$_2$ | CF$_3$ | CH$_2$OCH$_3$ | D-22a |
| 3,5-Cl$_2$ | CF$_3$ | C(O)CH$_3$ | D-22a |
| 3,5-Cl$_2$ | CF$_3$ | C(O)OCH$_3$ | D-22a |
| 3,5-Cl$_2$ | CF$_3$ | CH$_3$ | (D-22b)Cl |
| 3,5-Cl$_2$ | CF$_3$ | CH$_2$OCH$_3$ | (D-22b)Cl |
| 3,5-Cl$_2$ | CF$_3$ | C(O)CH$_3$ | (D-22b)Cl |
| 3,5-Cl$_2$ | CF$_3$ | C(O)OCH$_3$ | (D-22b)Cl |
| 3,5-Cl$_2$ | CF$_3$ | CH$_2$OCH$_3$ | (D-22b)Br |
| 3,5-Cl$_2$ | CF$_3$ | C(O)CH$_3$ | (D-22b)CH$_3$ |
| 3,5-Cl$_2$ | CF$_3$ | C(O)OCH$_3$ | (D-22b)Et |
| 3,5-Cl$_2$ | CF$_3$ | CH$_3$ | (D-22b)Pr-i |
| 3,5-Cl$_2$ | CF$_3$ | CH$_2$OCH$_3$ | (D-22b)CH$_2$l |
| 3,5-Cl$_2$ | CF$_3$ | C(O)CH$_3$ | (D-22b)CF$_3$ |
| 3,5-Cl$_2$ | CF$_3$ | C(O)OCH$_3$ | (D-22b)CF$_2$Cl |
| 3,5-Cl$_2$ | CF$_3$ | CH$_3$ | (D-22b)CF$_2$Br |
| 3,5-Cl$_2$ | CF$_3$ | CH$_2$OCH$_3$ | (D-22b)CH$_2$SCH$_3$ |
| 3,5-Cl$_2$ | CF$_3$ | C(O)CH$_3$ | (D-22b)CH$_2$SO$_2$CH$_3$ |
| 3,5-Cl$_2$ | CF$_3$ | C(O)OCH$_3$ | (D-22b)CH$_2$CN |
| 3,5-Cl$_2$ | CF$_3$ | CH$_3$ | (D-22b)OCH$_3$ |
| 3,5-Cl$_2$ | CF$_3$ | CH$_2$OCH$_3$ | (D-22b)SCH$_3$ |
| 3,5-Cl$_2$ | CF$_3$ | C(O)CH$_3$ | (D-22b)NHCH$_3$ |
| 3,5-Cl$_2$ | CF$_3$ | C(O)OCH$_3$ | (D-22b)N(CH$_3$)$_2$ |
| 3,5-Cl$_2$ | CF$_3$ | CH$_3$ | D-23a |
| 3,5-Cl$_2$ | CF$_3$ | CH$_2$OCH$_3$ | (D-23b)Cl |
| 3,5-Cl$_2$ | CF$_3$ | C(O)CH$_3$ | (D-23b)Br |
| 3,5-Cl$_2$ | CF$_3$ | C(O)OCH$_3$ | (D-23b)CH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | CH$_3$ | (D-23b)SCH$_3$ |
| 3,5-Cl$_2$ | CF$_3$ | CH$_2$OCH$_3$ | (D-23c)CH$_3$ |
| 3,5-Cl$_2$ | CF$_3$ | C(O)CH$_3$ | D-24a |
| 3,5-Cl$_2$ | CF$_3$ | C(O)OCH$_3$ | (D-25a)CH$_3$ |
| 3,5-Cl$_2$ | CF$_3$ | CH$_3$ | (D-25b)Cl |
| 3,5-Cl$_2$ | CF$_3$ | CH$_2$OCH$_3$ | (D-25b)Br |
| 3,5-Cl$_2$ | CF$_3$ | C(O)CH$_3$ | (D-25b)CF$_3$ |
| 3,5-Cl$_2$ | CF$_3$ | C(O)OCH3 | (D-25c)Cl |
| 3,5-Cl$_2$ | CF$_3$ | CH$_3$ | (D-25c)Br |
| 3,5-Cl$_2$ | CF$_3$ | CH$_2$OCH$_3$ | (D-25c)CH$_3$ |
| 3,5-Cl$_2$ | CF$_3$ | C(O)CH$_3$ | (D-25c)Pr-i |
| 3,5-Cl$_2$ | CF$_3$ | C(O)OCH$_3$ | (D-25c)CH$_2$CH$_2$Cl |
| 3,5-Cl$_2$ | CF$_3$ | CH$_3$ | (D-25c)CH$_2$Ph |
| 3,5-Cl$_2$ | CF$_3$ | CH2OCH$_3$ | (D-25c)NO$_2$ |
| 3,5-Cl$_2$ | CF$_3$ | C(O)CH$_3$ | (D-26a)CH$_3$ |
| 3,5-Cl$_2$ | CF$_3$ | C(O)OCH$_3$ | (D-26b)CN |
| 3,5-Cl$_2$ | CF$_3$ | CH$_3$ | (D-27a)CH$_3$ |
| 3,5-Cl$_2$ | CF$_3$ | CH$_2$OCH$_3$ | (D-27b)Cl |
| 3,5-Cl$_2$ | CF$_3$ | C(O)CH$_3$ | (D-27b)Br |
| 3,5-Cl$_2$ | CF$_3$ | C(O)OCH$_3$ | (D-27b)CH$_3$ |
| 3,5-Cl$_2$ | CF$_3$ | CH$_3$ | (D-27b)SCH$_3$ |
| 3,5-Cl$_2$ | CF$_3$ | CH$_2$OCH$_3$ | (D-27b)SO$_2$CH$_3$ |
| 3,5-Cl$_2$ | CF$_3$ | C(O)CH$_3$ | (D-27b)NO2 |
| 3,5-Cl$_2$ | CF$_3$ | C(O)OCH$_3$ | D-28a |
| 3,5-Cl$_2$ | CF$_3$ | CH$_3$ | D-29a |
| 3,5-Cl$_2$ | CF$_3$ | CH$_2$OCH$_3$ | (D-29b)CH$_3$ |
| 3,5-Cl$_2$ | CF$_3$ | C(O)CH$_3$ | (D-29b)CN |
| 3,5-Cl$_2$ | CF$_3$ | C(O)OCH$_3$ | D-30a |
| 3,5-Cl$_2$ | CF$_3$ | CH$_3$ | (D-30b)CH$_3$ |
| 3,5-Cl$_2$ | CF$_3$ | CH$_2$OCH$_3$ | (D-30b)Et |
| 3,5-Cl$_2$ | CF$_3$ | C(O)CH$_3$ | (D-30b)Pr-n |
| 3,5-Cl$_2$ | CF$_3$ | C(O)OCH$_3$ | (D-30b)Bu-t |
| 3,5-Cl$_2$ | CF$_3$ | CH$_3$ | (D-30b)CF$_3$ |
| 3,5-Cl$_2$ | CF$_3$ | CH$_2$OCH$_3$ | (D-30b)CF$_2$CF$_2$CF$_3$ |
| 3,5-Cl$_2$ | CF$_3$ | C(O)CH$_3$ | (D-30b)CH$_2$Ph |
| 3,5-Cl$_2$ | CF$_3$ | C(O)OCH$_3$ | (D-30b)OEt |
| 3,5-Cl$_2$ | CF$_3$ | CH$_3$ | (D-30b)SCH$_3$ |
| 3,5-Cl$_2$ | CF$_3$ | CH2OCH$_3$ | (D-30b)Ph |
| 3,5-Cl$_2$ | CF$_3$ | C(O)CH$_3$ | (D-30b)-(D-1a) |
| 3,5-Cl$_2$ | CF$_3$ | C(O)OCH$_3$ | (D-30b)-(D-3a) |
| 3,5-Cl$_2$ | CF$_3$ | CH$_3$ | (D-30b)-(D-52a) |
| 3,5-Cl$_2$ | CF$_3$ | CH$_2$OCH$_3$ | D-31a |
| 3,5-Cl$_2$ | CF$_3$ | C(O)CH$_3$ | (D-31b)Cl |
| 3,5-Cl$_2$ | CF$_3$ | C(O)OCH$_3$ | (D-31b)Br |
| 3,5-Cl$_2$ | CF$_3$ | CH$_3$ | (D-31b)CH$_3$ |
| 3,5-Cl$_2$ | CF$_3$ | CH$_2$OCH$_3$ | (D-31b)CH$_2$Cl |
| 3,5-Cl$_2$ | CF$_3$ | C(O)CH$_3$ | (D-31b)CF$_3$ |
| 3,5-Cl$_2$ | CF$_3$ | C(O)OCH$_3$ | (D-31b)CH$_2$SCH$_3$ |
| 3,5-Cl$_2$ | CF$_3$ | CH$_3$ | (D-31b)OEt |
| 3,5-Cl$_2$ | CF$_3$ | CH$_2$OCH$_3$ | (D-31b)SCH$_3$ |
| 3,5-Cl$_2$ | CF$_3$ | C(O)CH$_3$ | (D-31b)S(O)CH$_3$ |
| 3,5-Cl$_2$ | CF$_3$ | C(O)OCH$_3$ | (D-31b)SO$_2$CH$_3$ |
| 3,5-Cl$_2$ | CF$_3$ | CH$_3$ | (D-32a)Cl |
| 3,5-Cl$_2$ | CF$_3$ | CH$_2$OCH$_3$ | (D-32a)CH$_3$ |
| 3,5-Cl$_2$ | CF$_3$ | C(O)CH$_3$ | (D-32a)CF3 |
| 3,5-Cl$_2$ | CF$_3$ | C(O)OCH$_3$ | (D-32a)SPr-i |
| 3,5-Cl$_2$ | CF$_3$ | CH$_3$ | (D-32a)NHC(O)OEt |
| 3,5-Cl$_2$ | CF$_3$ | CH$_2$OCH$_3$ | (D-32a)Ph |
| 3,5-Cl$_2$ | CF$_3$ | C(O)CH$_3$ | D-33a |
| 3,5-Cl$_2$ | CF$_3$ | C(O)OCH$_3$ | (D-33b)CH$_3$ |
| 3,5-Cl$_2$ | CF$_3$ | CH$_3$ | (D-33b)CF$_3$ |
| 3,5-Cl$_2$ | CF$_3$ | CH$_2$OCH$_3$ | (D-33b)OCH$_3$ |
| 3,5-Cl$_2$ | CF$_3$ | C(O)CH$_3$ | (D-33b)SCH$_3$ |
| 3,5-Cl$_2$ | CF$_3$ | C(O)OCH$_3$ | (D-33b)SEt |
| 3,5-Cl$_2$ | CF$_3$ | CH$_3$ | (D-33b)SO$_2$Et |
| 3,5-Cl$_2$ | CF$_3$ | CH$_2$OCH$_3$ | D-34a |
| 3,5-Cl$_2$ | CF$_3$ | C(O)CH$_3$ | (D-34b)Cl |
| 3,5-Cl$_2$ | CF$_3$ | C(O)OCH$_3$ | (D-34b)Br |
| 3,5-Cl$_2$ | CF$_3$ | CH$_3$ | (D-34b)CH$_3$ |
| 3,5-Cl$_2$ | CF$_3$ | CH$_2$OCH$_3$ | (D-34b)CF$_3$ |
| 3,5-Cl$_2$ | CF$_3$ | C(O)CH$_3$ | (D-34b)CF$_2$CF$_2$CF$_3$ |
| 3,5-Cl$_2$ | CF$_3$ | C(O)OCH$_3$ | (D-34b)CN |
| 3,5-Cl$_2$ | CF$_3$ | CH$_3$ | (D-34b)C(O)OCH$_3$ |
| 3,5-Cl$_2$ | CF$_3$ | CH$_3$ | D-35a |
| 3,5-Cl$_2$ | CF$_3$ | CH$_2$OCH$_3$ | D-35a |
| 3,5-Cl$_2$ | CF$_3$ | C(O)CH$_3$ | D-35a |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | C(O)OCH$_3$ | D-35a |
| 3,5-Cl$_2$ | CF$_3$ | CH$_2$OCH$_3$ | (D-35b)Cl |
| 3,5-Cl$_2$ | CF$_3$ | C(O)CH$_3$ | (D-35b)Br |
| 3,5-Cl$_2$ | CF$_3$ | C(O)OCH$_3$ | (D-35b)CH$_3$ |
| 3,5-Cl$_2$ | CF$_3$ | CH$_3$ | (D-35b)Et |
| 3,5-Cl$_2$ | CF$_3$ | CH$_2$OCH$_3$ | (D-35b)CF$_3$ |
| 3,5-Cl$_2$ | CF$_3$ | C(O)CH$_3$ | (D-35b)CF$_2$SO$_2$NH$_2$ |
| 3,5-Cl$_2$ | CF$_3$ | C(O)OCH$_3$ | (D-35b)OCH$_3$ |
| 3,5-Cl$_2$ | CF$_3$ | CH$_3$ | (D-35b)SCH$_3$ |
| 3,5-Cl$_2$ | CF$_3$ | CH$_2$OCH$_3$ | (D-35b)SPr-i |
| 3,5-Cl$_2$ | CF$_3$ | C(O)CH$_3$ | (D-35b)N(CH$_3$)$_2$ |
| 3,5-Cl$_2$ | CF$_3$ | C(O)OCH$_3$ | D-36a |
| 3,5-Cl$_2$ | CF$_3$ | CH$_3$ | (D-36b)F |
| 3,5-Cl$_2$ | CF$_3$ | CH$_2$OCH$_3$ | (D-36b)Cl |
| 3,5-Cl$_2$ | CF$_3$ | C(O)CH$_3$ | (D-36b)Br |
| 3,5-Cl$_2$ | CF$_3$ | C(O)OCH$_3$ | (D-36b)I |
| 3,5-Cl$_2$ | CF$_3$ | CH$_3$ | (D-36b)CH$_3$ |
| 3,5-Cl$_2$ | CF$_3$ | CH$_2$OCH$_3$ | (D-36b)CF$_3$ |
| 3,5-Cl$_2$ | CF$_3$ | C(O)CH$_3$ | (D-36b)OCH$_3$ |
| 3,5-Cl$_2$ | CF$_3$ | C(O)OCH$_3$ | (D-36b)NO$_2$ |
| 3,5-Cl$_2$ | CF$_3$ | CH$_3$ | D-37a |
| 3,5-Cl$_2$ | CF$_3$ | CH2OCH3 | (D-37b)CH$_3$ |
| 3,5-Cl$_2$ | CF$_3$ | C(O)CH$_3$ | D-38a |
| 3,5-Cl$_2$ | CF$_3$ | C(O)OCH$_3$ | (D-39a)CH$_3$ |
| 3,5-Cl$_2$ | CF$_3$ | CH$_3$ | (D-39a)Et |
| 3,5-Cl$_2$ | CF$_3$ | CH2OCH3 | (D-40a)CH$_3$ |
| 3,5-Cl$_2$ | CF$_3$ | C(O)CH$_3$ | D-41a |
| 3,5-Cl$_2$ | CF$_3$ | C(O)OCH$_3$ | (D-41b)CF$_3$ |
| 3,5-Cl$_2$ | CF$_3$ | CH$_3$ | (D-42a)CH$_3$ |
| 3,5-Cl$_2$ | CF$_3$ | CH$_2$OCH$_3$ | (D-42a)C(O)CH$_3$ |
| 3,5-Cl$_2$ | CF$_3$ | C(O)CH$_3$ | (D-42a)C(O)OEt |
| 3,5-Cl$_2$ | CF$_3$ | C(O)OCH$_3$ | (D-42a)C(O)NHCH$_2$Ph |
| 3,5-Cl$_2$ | CF$_3$ | CH$_3$ | (D-42a)-(D-52a) |
| 3,5-Cl$_2$ | CF$_3$ | CH$_2$OCH$_3$ | (D-42b)Cl |
| 3,5-Cl$_2$ | CF$_3$ | C(O)CH$_3$ | (D-42b)Br |
| 3,5-Cl$_2$ | CF$_3$ | C(O)OCH$_3$ | (D-42b)CH$_3$ |
| 3,5-Cl$_2$ | CF$_3$ | CH$_3$ | (D-42b)Pr-i |
| 3,5-Cl$_2$ | CF$_3$ | CH$_2$OCH$_3$ | (D-42b)OCH$_3$ |
| 3,5-Cl$_2$ | CF$_3$ | C(O)CH$_3$ | (D-42b)SCH$_3$ |
| 3,5-Cl$_2$ | CF$_3$ | C(O)OCH$_3$ | (D-42b)N(CH$_3$)$_2$ |
| 3,5-Cl$_2$ | CF$_3$ | CH$_3$ | (D-43a)CH$_3$ |
| 3,5-Cl$_2$ | CF$_3$ | CH$_2$OCH$_3$ | (D-43b)Cl |
| 3,5-Cl$_2$ | CF$_3$ | C(O)CH$_3$ | (D-43b)Br |
| 3,5-Cl$_2$ | CF$_3$ | C(O)OCH$_3$ | (D-43b)CH$_3$ |
| 3,5-Cl$_2$ | CF$_3$ | CH$_3$ | (D-43b)OCH$_3$ |
| 3,5-Cl$_2$ | CF$_3$ | CH$_2$OCH$_3$ | (D-43b)SCH$_3$ |
| 3,5-Cl$_2$ | CF$_3$ | C(O)CH$_3$ | (D-43b)NO$_2$ |
| 3,5-Cl$_2$ | CF$_3$ | C(O)OCH$_3$ | (D-43b)N(CH$_3$)$_2$ |
| 3,5-Cl$_2$ | CF$_3$ | CH$_3$ | (D-43b)Ph |
| 3,5-Cl$_2$ | CF$_3$ | CH$_2$OCH$_3$ | D-44a |
| 3,5-Cl$_2$ | CF$_3$ | C(O)CH$_3$ | (D-45a)CH$_3$ |
| 3,5-Cl$_2$ | CF$_3$ | C(O)OCH$_3$ | (D-45b)Cl |
| 3,5-Cl$_2$ | CF$_3$ | CH$_3$ | (D-45b)Br |
| 3,5-Cl$_2$ | CF$_3$ | CH$_2$OCH$_3$ | (D-45b)OCH$_3$ |
| 3,5-Cl$_2$ | CF$_3$ | C(O)CH$_3$ | (D-45b)SCH$_3$ |
| 3,5-Cl$_2$ | CF$_3$ | C(O)OCH$_3$ | (D-45b)Ph |
| 3,5-Cl$_2$ | CF$_3$ | CH$_3$ | (D-47a)CH$_3$ |
| 3,5-Cl$_2$ | CF$_3$ | CH$_2$OCH$_3$ | (D-47a)Et |
| 3,5-Cl$_2$ | CF$_3$ | C(O)CH$_3$ | D-48a |
| 3,5-Cl$_2$ | CF$_3$ | C(O)OCH$_3$ | (D-48b)CH$_3$ |
| 3,5-Cl$_2$ | CF$_3$ | CH$_3$ | (D-48b)SCH$_3$ |
| 3,5-Cl$_2$ | CF$_3$ | CH$_2$OCH$_3$ | D-49a |
| 3,5-Cl$_2$ | CF$_3$ | C(O)CH$_3$ | (D-49b)CH$_3$ |
| 3,5-Cl$_2$ | CF$_3$ | C(O)OCH$_3$ | (D-50a)CH$_3$ |
| 3,5-Cl$_2$ | CF$_3$ | CH$_3$ | (D-51a)CH$_3$ |
| 3,5-Cl$_2$ | CF$_3$ | CH$_2$OCH$_3$ | (D-51a)Et |
| 3,5-Cl$_2$ | CF$_3$ | C(O)CH$_3$ | (D-51a)CH$_2$CN |
| 3,5-Cl$_2$ | CF$_3$ | C(O)OCH$_3$ | (D-51a)CH$_2$CH=CH$_2$ |
| 3,5-Cl$_2$ | CF$_3$ | CH$_3$ | (D-51a)CH2Ph |
| 3,5-Cl$_2$ | CF$_3$ | CH$_3$ | D-52a |
| 3,5-Cl$_2$ | CF$_3$ | CH$_2$OCH$_3$ | D-52a |
| 3,5-Cl$_2$ | CF$_3$ | C(O)CH$_3$ | D-52a |
| 3,5-Cl$_2$ | CF$_3$ | C(O)OCH$_3$ | D-52a |
| 3,5-Cl$_2$ | CF$_3$ | CH$_2$OCH$_3$ | (D-52b)F |
| 3,5-Cl$_2$ | CF$_3$ | CH$_3$ | (D-52b)Cl |
| 3,5-Cl$_2$ | CF$_3$ | CH$_2$OCH$_3$ | (D-52b)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | C(O)CH$_3$ | (D-52b)Cl |
| 3,5-Cl$_2$ | CF$_3$ | C(O)OCH$_3$ | (D-52b)Cl |
| 3,5-Cl$_2$ | CF$_3$ | C(O)CH$_3$ | (D-52b)Br |
| 3,5-Cl$_2$ | CF$_3$ | C(O)OCH$_3$ | (D-52b)CH$_3$ |
| 3,5-Cl$_2$ | CF$_3$ | CH$_3$ | (D-52b)OCH$_3$ |
| 3,5-Cl$_2$ | CF$_3$ | CH$_2$OCH$_3$ | (D-52b)SCH$_3$ |
| 3,5-Cl$_2$ | CF$_3$ | CH$_3$ | (D-52c)Cl |
| 3,5-Cl$_2$ | CF$_3$ | CH$_2$OCH$_3$ | (D-52c)Cl |
| 3,5-Cl$_2$ | CF$_3$ | C(O)CH$_3$ | (D-52c)Cl |
| 3,5-Cl$_2$ | CF$_3$ | C(O)OCH$_3$ | (D-52c)Cl |
| 3,5-Cl$_2$ | CF$_3$ | CH$_3$ | (D-52c)Br |
| 3,5-Cl$_2$ | CF$_3$ | CH$_2$OCH$_3$ | (D-52c)Br |
| 3,5-Cl$_2$ | CF$_3$ | C(O)CH$_3$ | (D-52c)Br |
| 3,5-Cl$_2$ | CF$_3$ | C(O)OCH$_3$ | (D-52c)Br |
| 3,5-Cl$_2$ | CF$_3$ | C(O)CH$_3$ | (D-52c)CH$_3$ |
| 3,5-Cl$_2$ | CF$_3$ | C(O)OCH$_3$ | (D-52c)CF$_3$ |
| 3,5-Cl$_2$ | CF$_3$ | CH$_3$ | (D-52c)OCH$_3$ |
| 3,5-Cl$_2$ | CF$_3$ | CH$_2$OCH$_3$ | (D-52c)CN |
| 3,5-Cl$_2$ | CF$_3$ | C(O)CH$_3$ | (D-52c)C(O)OCH$_3$ |
| 3,5-Cl$_2$ | CF$_3$ | C(O)OCH$_3$ | (D-52c)C(O)NH$_2$ |
| 3,5-Cl$_2$ | CF$_3$ | CH$_3$ | (D-52d)F |
| 3,5-Cl$_2$ | CF$_3$ | Et | (D-52d)F |
| 3,5-Cl$_2$ | CF$_3$ | CH$_2$OCH$_3$ | (D-52d)F |
| 3,5-Cl$_2$ | CF$_3$ | CH$_2$OEt | (D-52d)F |
| 3,5-Cl$_2$ | CF$_3$ | CH$_2$OCH$_2$CF$_3$ | (D-52d)F |
| 3,5-Cl$_2$ | CF$_3$ | CH$_2$OC(O)CH$_3$ | (D-52d)F |
| 3,5-Cl$_2$ | CF$_3$ | CH$_2$OC(O)Et | (D-52d)F |
| 3,5-Cl$_2$ | CF$_3$ | CH$_2$OC(O)Pr-i | (D-52d)F |
| 3,5-Cl$_2$ | CF$_3$ | CH$_2$OC(O)Pr-c | (D-52d)F |
| 3,5-Cl$_2$ | CF$_3$ | CH$_2$OC(O)Bu-t | (D-52d)F |
| 3,5-Cl$_2$ | CF$_3$ | CH$_2$OC(O)Ph | (D-52d)F |
| 3,5-Cl$_2$ | CF$_3$ | CH$_2$OC(O)OCH$_3$ | (D-52d)F |
| 3,5-Cl$_2$ | CF$_3$ | CH$_2$CN | (D-52d)F |
| 3,5-Cl$_2$ | CF$_3$ | CH$_2$C=CH | (D-52d)F |
| 3,5-Cl$_2$ | CF$_3$ | C(O)CH$_3$ | (D-52d)F |
| 3,5-Cl$_2$ | CF$_3$ | C(O)Et | (D-52d)F |
| 3,5-Cl$_2$ | CF$_3$ | C(O)Pr-n | (D-52d)F |
| 3,5-Cl$_2$ | CF$_3$ | C(O)Pr-i | (D-52d)F |
| 3,5-Cl$_2$ | CF$_3$ | C(O)Pr-c | (D-52d)F |
| 3,5-Cl$_2$ | CF$_3$ | C(O)Bu-t | (D-52d)F |
| 3,5-Cl$_2$ | CF$_3$ | C(O)CH$_2$OCH$_3$ | (D-52d)F |
| 3,5-Cl$_2$ | CF$_3$ | C(O)OCH$_3$ | (D-52d)F |
| 3,5-Cl$_2$ | CF$_3$ | C(O)OEt | (D-52d)F |
| 3,5-Cl$_2$ | CF$_3$ | C(O)OPr-n | (D-52d)F |
| 3,5-Cl$_2$ | CF$_3$ | C(O)OPr-i | (D-52d)F |
| 3,5-Cl$_2$ | CF$_3$ | C(O)OPr-c | (D-52d)F |
| 3,5-Cl$_2$ | CF$_3$ | C(O)OCH$_2$Cl | (D-52d)F |
| 3,5-Cl$_2$ | CF$_3$ | C(O)OCH$_2$CH$_2$Cl | (D-52d)F |
| 3,5-Cl$_2$ | CF$_3$ | C(O)OCH$_2$CH$_2$OCH$_3$ | (D-52d)F |
| 3,5-Cl$_2$ | CF$_3$ | C(O)OCH$_2$CH=CH$_2$ | (D-52d)F |
| 3,5-Cl$_2$ | CF$_3$ | CH$_3$ | (D-52d)Cl |
| 3,5-Cl$_2$ | CF$_3$ | Et | (D-52d)Cl |
| 3,5-Cl$_2$ | CF$_3$ | CH$_2$OCH$_3$ | (D-52d)Cl |
| 3,5-Cl$_2$ | CF$_3$ | CH$_2$OEt | (D-52d)Cl |
| 3,5-Cl$_2$ | CF$_3$ | CH$_2$OCH$_2$CF$_3$ | (D-52d)Cl |
| 3,5-Cl$_2$ | CF$_3$ | CH$_2$OCH$_2$CH$_2$OCH$_3$ | (D-52d)Cl |
| 3,5-Cl$_2$ | CF$_3$ | CH$_2$OC(O)CH$_3$ | (D-52d)Cl |
| 3,5-Cl$_2$ | CF$_3$ | CH$_2$OC(O)Et | (D-52d)Cl |
| 3,5-Cl$_2$ | CF$_3$ | CH$_2$OC(O)Pr-n | (D-52d)Cl |
| 3,5-Cl$_2$ | CF$_3$ | CH$_2$OC(O)Pr-i | (D-52d)Cl |
| 3,5-Cl$_2$ | CF$_3$ | CH$_2$OC(O)Pr-c | (D-52d)Cl |
| 3,5-Cl$_2$ | CF$_3$ | CH$_2$OC(O)Bu-t | (D-52d)Cl |
| 3,5-Cl$_2$ | CF$_3$ | CH$_2$OC(O)Ph | (D-52d)Cl |
| 3,5-Cl$_2$ | CF$_3$ | CH$_2$OC(O)OCH$_3$ | (D-52d)Cl |
| 3,5-Cl$_2$ | CF$_3$ | CH$_2$OC(O)OEt | (D-52d)Cl |
| 3,5-Cl$_2$ | CF$_3$ | CH$_2$OC(O)OPh | (D-52d)Cl |
| 3,5-Cl$_2$ | CF$_3$ | CH$_2$SC(O)CH$_3$ | (D-52d)Cl |
| 3,5-Cl$_2$ | CF$_3$ | CH$_2$SC(S)OCH$_3$ | (D-52d)Cl |
| 3,5-Cl$_2$ | CF$_3$ | CH$_2$SC(S)N(CH$_3$)$_2$ | (D-52d)Cl |
| 3,5-Cl$_2$ | CF$_3$ | CH$_2$NHC(O)OCH$_3$ | (D-52d)Cl |
| 3,5-Cl$_2$ | CF$_3$ | CH$_2$CN | (D-52d)Cl |
| 3,5-Cl$_2$ | CF$_3$ | CH$_2$C=CH | (D-52d)Cl |
| 3,5-Cl$_2$ | CF$_3$ | C(O)CH$_3$ | (D-52d)Cl |
| 3,5-Cl$_2$ | CF$_3$ | C(O)Et | (D-52d)Cl |
| 3,5-Cl$_2$ | CF$_3$ | C(O)Pr-n | (D-52d)Cl |
| 3,5-Cl$_2$ | CF$_3$ | C(O)Pr-i | (D-52d)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | C(O)Pr-c | (D-52d)Cl |
| 3,5-Cl$_2$ | CF$_3$ | C(O)Bu-t | (D-52d)Cl |
| 3,5-Cl$_2$ | CF$_3$ | C(O)CH$_2$OCH$_3$ | (D-52d)Cl |
| 3,5-Cl$_2$ | CF$_3$ | C(O)CH$_2$SCH$_3$ | (D-52d)Cl |
| 3,5-Cl$_2$ | CF$_3$ | C(O)OCH$_3$ | (D-52d)Cl |
| 3,5-Cl$_2$ | CF$_3$ | C(O)OEt | (D-52d)Cl |
| 3,5-Cl$_2$ | CF$_3$ | C(O)OPr-n | (D-52d)Cl |
| 3,5-Cl$_2$ | CF$_3$ | C(O)OPr-i | (D-52d)Cl |
| 3,5-Cl$_2$ | CF$_3$ | C(O)OPr-c | (D-52d)Cl |
| 3,5-Cl$_2$ | CF$_3$ | C(O)OCH$_2$Cl | (D-52d)Cl |
| 3,5-Cl$_2$ | CF$_3$ | C(O)OCH$_2$CH$_2$Cl | (D-52d)Cl |
| 3,5-Cl$_2$ | CF$_3$ | C(O)OCH$_2$CH$_2$OCH$_3$ | (D-52d)Cl |
| 3,5-Cl$_2$ | CF$_3$ | C(O)OCH$_2$CH=CH$_2$ | (D-52d)Cl |
| 3,5-Cl$_2$ | CF$_3$ | C(O)OCH$_2$C≡CH | (D-52d)Cl |
| 3,5-Cl$_2$ | CF$_3$ | SCCl$_3$ | (D-52d)Cl |
| 3,5-Cl$_2$ | CF$_3$ | SN(Bu-n)$_2$ | (D-52d)Cl |
| 3,5-Cl$_2$ | CF$_3$ | SN(Pr-i)CH$_2$CH$_2$C(O)OEt | (D-52d)Cl |
| 3,5-Cl$_2$ | CF$_3$ | SN(CH$_2$Ph)CH$_2$CH$_2$C(O)OEt | (D-52d)Cl |
| 3,5-Cl$_2$ | CF$_3$ | SN(CH$_3$)C(O)OBu-n | (D-52d)Cl |
| 3,5-Cl$_2$ | CF$_3$ | CH$_3$ | (D-52d)Br |
| 3,5-Cl$_2$ | CF$_3$ | Et | (D-52d)Br |
| 3,5-Cl$_2$ | CF$_3$ | CH$_2$OCH$_3$ | (D-52d)Br |
| 3,5-Cl$_2$ | CF$_3$ | CH$_2$OEt | (D-52d)Br |
| 3,5-Cl$_2$ | CF$_3$ | CH$_2$OCH$_2$CF$_3$ | (D-52d)Br |
| 3,5-Cl$_2$ | CF$_3$ | CH$_2$OC(O)CH$_3$ | (D-52d)Br |
| 3,5-Cl$_2$ | CF$_3$ | CH$_2$OC(O)Et | (D-52d)Br |
| 3,5-Cl$_2$ | CF$_3$ | CH$_2$OC(O)Pr-i | (D-52d)Br |
| 3,5-Cl$_2$ | CF$_3$ | CH$_2$OC(O)Pr-c | (D-52d)Br |
| 3,5-Cl$_2$ | CF$_3$ | CH$_2$OC(O)Bu-t | (D-52d)Br |
| 3,5-Cl$_2$ | CF$_3$ | CH$_2$OC(O)Ph | (D-52d)Br |
| 3,5-Cl$_2$ | CF$_3$ | CH$_2$OC(O)OCH$_3$ | (D-52d)Br |
| 3,5-Cl$_2$ | CF$_3$ | CH$_2$CN | (D-52d)Br |
| 3,5-Cl$_2$ | CF$_3$ | CH$_2$C≡CH | (D-52d)Br |
| 3,5-Cl$_2$ | CF$_3$ | C(O)CH$_3$ | (D-52d)Br |
| 3,5-Cl$_2$ | CF$_3$ | C(O)Et | (D-52d)Br |
| 3,5-Cl$_2$ | CF$_3$ | C(O)Pr-n | (D-52d)Br |
| 3,5-Cl$_2$ | CF$_3$ | C(O)Pr-i | (D-52d)Br |
| 3,5-Cl$_2$ | CF$_3$ | C(O)Pr-c | (D-52d)Br |
| 3,5-Cl$_2$ | CF$_3$ | C(O)Bu-t | (D-52d)Br |
| 3,5-Cl$_2$ | CF$_3$ | C(O)CH$_2$OCH$_3$ | (D-52d)Br |
| 3,5-Cl$_2$ | CF$_3$ | C(O)OCH$_3$ | (D-52d)Br |
| 3,5-Cl$_2$ | CF$_3$ | C(O)OEt | (D-52d)Br |
| 3,5-Cl$_2$ | CF$_3$ | C(O)OPr-n | (D-52d)Br |
| 3,5-Cl$_2$ | CF$_3$ | C(O)OPr-i | (D-52d)Br |
| 3,5-Cl$_2$ | CF$_3$ | C(O)OPr-c | (D-52d)Br |
| 3,5-Cl$_2$ | CF$_3$ | C(O)OCH$_2$Cl | (D-52d)Br |
| 3,5-Cl$_2$ | CF$_3$ | C(O)OCH$_2$CH$_2$Cl | (D-52d)Br |
| 3,5-Cl$_2$ | CF$_3$ | C(O)OCH$_2$CH$_2$OCH$_3$ | (D-52d)Br |
| 3,5-Cl$_2$ | CF$_3$ | C(O)OCH$_2$CH=CH$_2$ | (D-52d)Br |
| 3,5-Cl$_2$ | CF$_3$ | CH$_3$ | (D-52d)I |
| 3,5-Cl$_2$ | CF$_3$ | CH$_2$OCH$_3$ | (D-52d)CH$_3$ |
| 3,5-Cl$_2$ | CF$_3$ | CH$_3$ | (D-52d)CF$_3$ |
| 3,5-Cl$_2$ | CF$_3$ | CH$_2$OCH$_3$ | (D-52d)CF$_3$ |
| 3,5-Cl$_2$ | CF$_3$ | C(O)CH$_3$ | (D-52d)CF$_3$ |
| 3,5-Cl$_2$ | CF$_3$ | C(O)OCH$_3$ | (D-52d)CF$_3$ |
| 3,5-Cl$_2$ | CF$_3$ | C(O)CH$_3$ | (D-52d)OCH$_3$ |
| 3,5-Cl$_2$ | CF$_3$ | CH$_3$ | (D-52d)OCHF$_2$ |
| 3,5-Cl$_2$ | CF$_3$ | CH$_2$OCH$_3$ | (D-52d)OCHF$_2$ |
| 3,5-Cl$_2$ | CF$_3$ | C(O)CH$_3$ | (D-52d)OCHF$_2$ |
| 3,5-Cl$_2$ | CF$_3$ | C(O)OCH$_3$ | (D-52d)OCHF$_2$ |
| 3,5-Cl$_2$ | CF$_3$ | C(O)OCH$_3$ | (D-52d)OCF$_2$CHF$_2$ |
| 3,5-Cl$_2$ | CF$_3$ | CH$_3$ | (D-52d)SPr-n |
| 3,5-Cl$_2$ | CF$_3$ | CH$_3$ | (D-52d)NO$_2$ |
| 3,5-Cl$_2$ | CF$_3$ | CH$_2$OCH$_3$ | (D-52d)NO$_2$ |
| 3,5-Cl$_2$ | CF$_3$ | C(O)CH$_3$ | (D-52d)NO$_2$ |
| 3,5-Cl$_2$ | CF$_3$ | C(O)OCH$_3$ | (D-52d)NO$_2$ |
| 3,5-Cl$_2$ | CF$_3$ | CH$_3$ | (D-52d)CN |
| 3,5-Cl$_2$ | CF$_3$ | CH$_2$OCH$_3$ | (D-52d)CN |
| 3,5-Cl$_2$ | CF$_3$ | CH$_2$OEt | (D-52d)CN |
| 3,5-Cl$_2$ | CF$_3$ | CH$_2$OC(O)CH$_3$ | (D-52d)CN |
| 3,5-Cl$_2$ | CF$_3$ | CH$_2$OC(O)OCH$_3$ | (D-52d)CN |
| 3,5-Cl$_2$ | CF$_3$ | CH$_2$CN | (D-52d)CN |
| 3,5-Cl$_2$ | CF$_3$ | C(O)CH$_3$ | (D-52d)CN |
| 3,5-Cl$_2$ | CF$_3$ | C(O)Et | (D-52d)CN |
| 3,5-Cl$_2$ | CF$_3$ | C(O)Pr-i | (D-52d)CN |
| 3,5-Cl$_2$ | CF$_3$ | C(O)OCH$_3$ | (D-52d)CN |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | CH$_2$OCH$_3$ | (D-52d)C(O)OCH$_3$ |
| 3,5-Cl$_2$ | CF$_3$ | C(O)CH$_3$ | (D-52d)C(O)NH$_2$ |
| 3,5-Cl$_2$ | CF$_3$ | CH$_3$ | (D-52e)F |
| 3,5-Cl$_2$ | CF$_3$ | CH$_2$OCH$_3$ | (D-52e)F |
| 3,5-Cl$_2$ | CF$_3$ | C(O)CH$_3$ | (D-52e)F |
| 3,5-Cl$_2$ | CF$_3$ | C(O)OCH$_3$ | (D-52e)F |
| 3,5-Cl$_2$ | CF$_3$ | CH$_3$ | (D-52e)Cl |
| 3,5-Cl$_2$ | CF$_3$ | CH$_2$OCH$_3$ | (D-52e)Cl |
| 3,5-Cl$_2$ | CF$_3$ | C(O)CH$_3$ | (D-52e)Cl |
| 3,5-Cl$_2$ | CF$_3$ | C(O)OCH$_3$ | (D-52e)Cl |
| 3,5-Cl$_2$ | CF$_3$ | CH$_3$ | (D-52e)Br |
| 3,5-Cl$_2$ | CF$_3$ | CH$_2$OCH$_3$ | (D-52e)Br |
| 3,5-Cl$_2$ | CF$_3$ | C(O)CH$_3$ | (D-52e)Br |
| 3,5-Cl$_2$ | CF$_3$ | C(O)OCH$_3$ | (D-52e)Br |
| 3,5-Cl$_2$ | CF$_3$ | C(O)OCH$_3$ | (D-52e)CH$_3$ |
| 3,5-Cl$_2$ | CF$_3$ | CH$_3$ | (D-52e)OCH$_3$ |
| 3,5-Cl$_2$ | CF$_3$ | CH$_2$OCH$_3$ | (D-52e)NO$_2$ |
| 3,5-Cl$_2$ | CF$_3$ | C(O)CH$_3$ | (D-52e)C(O)OEt |
| 3,5-Cl$_2$ | CF$_3$ | CH$_3$ | (D-52f)-3-F-5-Cl |
| 3,5-Cl$_2$ | CF$_3$ | CH$_2$OCH$_3$ | (D-52f)-3-F-5-Cl |
| 3,5-Cl$_2$ | CF$_3$ | C(O)CH$_3$ | (D-52f)-3-F-5-Cl |
| 3,5-Cl$_2$ | CF$_3$ | C(O)OCH$_3$ | (D-52f)-3-F-5-Cl |
| 3,5-Cl$_2$ | CF$_3$ | C(O)OCH$_3$ | (D-52f)-3,5-Cl$_2$ |
| 3,5-Cl$_2$ | CF$_3$ | CH$_3$ | (D-52f)-3-Cl-5-CF$_3$ |
| 3,5-Cl$_2$ | CF$_3$ | CH$_2$OCH$_3$ | (D-52g)-5,6-Cl$_2$ |
| 3,5-Cl$_2$ | CF$_3$ | CH$_3$ | D-53a |
| 3,5-Cl$_2$ | CF$_3$ | CH$_2$OCH$_3$ | D-53a |
| 3,5-Cl$_2$ | CF$_3$ | C(O)CH$_3$ | D-53a |
| 3,5-Cl$_2$ | CF$_3$ | C(O)OCH$_3$ | D-53a |
| 3,5-Cl$_2$ | CF$_3$ | C(O)CH$_3$ | (D-53b)F |
| 3,5-Cl$_2$ | CF$_3$ | C(O)OCH$_3$ | (D-53b)Cl |
| 3,5-Cl$_2$ | CF$_3$ | CH$_3$ | (D-53b)Br |
| 3,5-Cl$_2$ | CF$_3$ | CH$_2$OCH$_3$ | (D-53b)CH$_3$ |
| 3,5-Cl$_2$ | CF$_3$ | C(O)CH$_3$ | (D-53b)OCH$_3$ |
| 3,5-Cl$_2$ | CF$_3$ | C(O)OCH$_3$ | (D-53b)SCH$_3$ |
| 3,5-Cl$_2$ | CF$_3$ | CH$_3$ | (D-53b)CN |
| 3,5-Cl$_2$ | CF$_3$ | CH$_2$OCH$_3$ | (D-53c)Cl |
| 3,5-Cl$_2$ | CF$_3$ | C(O)CH$_3$ | (D-53c)CH$_3$ |
| 3,5-Cl$_2$ | CF$_3$ | C(O)OCH$_3$ | (D-53c)CF$_3$ |
| 3,5-Cl$_2$ | CF$_3$ | CH$_3$ | (D-53c)CH$_2$OCH$_3$ |
| 3,5-Cl$_2$ | CF$_3$ | CH$_2$OCH$_3$ | (D-53d)Cl |
| 3,5-Cl$_2$ | CF$_3$ | C(O)CH$_3$ | (D-53d)Br |
| 3,5-Cl$_2$ | CF$_3$ | C(O)OCH$_3$ | (D-53d)CH$_3$ |
| 3,5-Cl$_2$ | CF$_3$ | CH$_3$ | (D-53d)CF$_3$ |
| 3,5-Cl$_2$ | CF$_3$ | CH$_2$OCH$_3$ | (D-53d)OCH$_3$ |
| 3,5-Cl$_2$ | CF$_3$ | C(O)CH$_3$ | (D-53d)CN |
| 3,5-Cl$_2$ | CF$_3$ | C(O)OCH$_3$ | (D-53d)SO$_2$NH$_2$ |
| 3,5-Cl$_2$ | CF$_3$ | CH$_3$ | (D-53e)F |
| 3,5-Cl$_2$ | CF$_3$ | CH$_2$OCH$_3$ | (D-53e)F |
| 3,5-Cl$_2$ | CF$_3$ | C(O)CH$_3$ | (D-53e)F |
| 3,5-Cl$_2$ | CF$_3$ | C(O)OCH$_3$ | (D-53e)Cl |
| 3,5-Cl$_2$ | CF$_3$ | CH$_3$ | (D-53e)Cl |
| 3,5-Cl$_2$ | CF$_3$ | Et | (D-53e)Cl |
| 3,5-Cl$_2$ | CF$_3$ | CH$_2$OCH$_3$ | (D-53e)Cl |
| 3,5-Cl$_2$ | CF$_3$ | CH$_2$OEt | (D-53e)Cl |
| 3,5-Cl$_2$ | CF$_3$ | CH$_2$OC(O)CH$_3$ | (D-53e)Cl |
| 3,5-Cl$_2$ | CF$_3$ | CH$_2$OC(O)Et | (D-53e)Cl |
| 3,5-Cl$_2$ | CF$_3$ | CH$_2$OC(O)OCH$_3$ | (D-53e)Cl |
| 3,5-Cl$_2$ | CF$_3$ | CH$_2$CN | (D-53e)Cl |
| 3,5-Cl$_2$ | CF$_3$ | C(O)CH$_3$ | (D-53e)Cl |
| 3,5-Cl$_2$ | CF$_3$ | C(O)Et | (D-53e)Cl |
| 3,5-Cl$_2$ | CF$_3$ | C(O)Pr-n | (D-53e)Cl |
| 3,5-Cl$_2$ | CF$_3$ | C(O)Pr-i | (D-53e)Cl |
| 3,5-Cl$_2$ | CF$_3$ | C(O)Pr-c | (D-53e)Cl |
| 3,5-Cl$_2$ | CF$_3$ | C(O)OCH$_3$ | (D-53e)Cl |
| 3,5-Cl$_2$ | CF$_3$ | C(O)OEt | (D-53e)Cl |
| 3,5-Cl$_2$ | CF$_3$ | C(O)OPr-n | (D-53e)Cl |
| 3,5-Cl$_2$ | CF$_3$ | C(O)OPr-i | (D-53e)Cl |
| 3,5-Cl$_2$ | CF$_3$ | C(O)OCH$_2$Cl | (D-53e)Cl |
| 3,5-Cl$_2$ | CF$_3$ | C(O)OCH$_2$CH$_2$OCH$_3$ | (D-53e)Cl |
| 3,5-Cl$_2$ | CF$_3$ | C(O)OCH$_2$CH=CH$_2$ | (D-53e)Cl |
| 3,5-Cl$_2$ | CF$_3$ | CH$_3$ | (D-53e)Br |
| 3,5-Cl$_2$ | CF$_3$ | CH$_2$OCH$_3$ | (D-53e)Br |
| 3,5-Cl$_2$ | CF$_3$ | C(O)CH$_3$ | (D-53e)Br |
| 3,5-Cl$_2$ | CF$_3$ | C(O)OCH$_3$ | (D-53e)Br |
| 3,5-Cl$_2$ | CF$_3$ | CH$_3$ | (D-53e)I |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | CH$_2$OCH$_3$ | (D-53e)CH$_3$ |
| 3,5-Cl$_2$ | CF$_3$ | C(O)CH$_3$ | (D-53e)CF$_3$ |
| 3,5-Cl$_2$ | CF$_3$ | C(O)OCH$_3$ | (D-53e)OCH$_3$ |
| 3,5-Cl$_2$ | CF$_3$ | CH$_3$ | (D-53e)NO$_2$ |
| 3,5-Cl$_2$ | CF$_3$ | CH$_3$ | (D-53e)CN |
| 3,5-Cl$_2$ | CF$_3$ | CH$_2$OCH$_3$ | (D-53e)CN |
| 3,5-Cl$_2$ | CF$_3$ | C(O)CH$_3$ | (D-53e)CN |
| 3,5-Cl$_2$ | CF$_3$ | C(O)OCH$_3$ | (D-53e)CN |
| 3,5-Cl$_2$ | CF$_3$ | CH$_2$OCH$_3$ | (D-53e)C(O)OCH$_3$ |
| 3,5-Cl$_2$ | CF$_3$ | C(O)CH$_3$ | (D-53f)-2,6-F$_2$ |
| 3,5-Cl$_2$ | CF$_3$ | C(O)OCH$_3$ | (D-53g)-4-CF$_3$-6-Cl |
| 3,5-Cl$_2$ | CF$_3$ | CH$_3$ | (D-53h)-5,6-Cl$_2$ |
| 3,5-Cl$_2$ | CF$_3$ | CH$_3$ | D-54a |
| 3,5-Cl$_2$ | CF$_3$ | CH$_3$ | (D-54b)Cl |
| 3,5-Cl$_2$ | CF$_3$ | CH$_2$OCH$_3$ | (D-54b)Cl |
| 3,5-Cl$_2$ | CF$_3$ | C(O)CH$_3$ | (D-54b)Cl |
| 3,5-Cl$_2$ | CF$_3$ | C(O)OCH$_3$ | (D-54b)Cl |
| 3,5-Cl$_2$ | CF$_3$ | CH$_2$OCH$_3$ | (D-54b)Br |
| 3,5-Cl$_2$ | CF$_3$ | C(O)CH$_3$ | (D-54b)CH$_3$ |
| 3,5-Cl$_2$ | CF$_3$ | C(O)OCH$_3$ | (D-54b)CF$_3$ |
| 3,5-Cl$_2$ | CF$_3$ | CH$_3$ | (D-54b)OCH3 |
| 3,5-Cl$_2$ | CF$_3$ | CH$_2$OCH$_3$ | (D-54b)NO$_2$ |
| 3,5-Cl$_2$ | CF$_3$ | C(O)CH$_3$ | (D-54b)CN |
| 3,5-Cl$_2$ | CF$_3$ | C(O)OCH$_3$ | (D-54b)C(O)NH$_2$ |
| 3,5-Cl$_2$ | CF$_3$ | CH$_3$ | (D-54c)Cl |
| 3,5-Cl$_2$ | CF$_3$ | CH$_2$OCH$_3$ | (D-54c)OCH$_3$ |
| 3,5-Cl$_2$ | CF$_3$ | C(O)CH$_3$ | (D-54c)NO$_2$ |
| 3,5-Cl$_2$ | CF$_3$ | C(O)OCH$_3$ | (D-54c)CN |
| 3,5-Cl$_2$ | CF$_3$ | CH$_3$ | (D-54d)-2,6-F$_2$ |
| 3,5-Cl$_2$ | CF$_3$ | CH$_2$OCH$_3$ | D-54e |
| 3,5-Cl$_2$ | CF$_3$ | CH$_3$ | D-55a |
| 3,5-Cl$_2$ | CF$_3$ | Et | D-55a |
| 3,5-Cl$_2$ | CF$_3$ | CH$_2$OCH$_3$ | D-55a |
| 3,5-Cl$_2$ | CF$_3$ | CH$_2$OEt | D-55a |
| 3,5-Cl$_2$ | CF$_3$ | CH$_2$OCH$_2$CF$_3$ | D-55a |
| 3,5-Cl$_2$ | CF$_3$ | CH$_2$OCH$_2$CH$_2$OCH$_3$ | D-55a |
| 3,5-Cl$_2$ | CF$_3$ | CH$_2$OC(O)CH$_3$ | D-55a |
| 3,5-Cl$_2$ | CF$_3$ | CH$_2$OC(O)Et | D-55a |
| 3,5-Cl$_2$ | CF$_3$ | CH$_2$OC(O)Pr-n | D-55a |
| 3,5-Cl$_2$ | CF$_3$ | CH$_2$OC(O)Pr-i | D-55a |
| 3,5-Cl$_2$ | CF$_3$ | CH$_2$OC(O)Pr-c | D-55a |
| 3,5-Cl$_2$ | CF$_3$ | CH$_2$OC(O)Bu-t | D-55a |
| 3,5-Cl$_2$ | CF$_3$ | CH$_2$OC(O)Ph | D-55a |
| 3,5-Cl$_2$ | CF$_3$ | CH$_2$OC(O)OCH$_3$ | D-55a |
| 3,5-Cl$_2$ | CF$_3$ | CH$_2$OC(O)OEt | D-55a |
| 3,5-Cl$_2$ | CF$_3$ | CH$_2$OC(O)OPh | D-55a |
| 3,5-Cl$_2$ | CF$_3$ | CH$_2$SC(O)CH$_3$ | D-55a |
| 3,5-Cl$_2$ | CF$_3$ | CH$_2$SC(S)OCH$_3$ | D-55a |
| 3,5-Cl$_2$ | CF$_3$ | CH$_2$SC(S)N(CH$_3$)$_2$ | D-55a |
| 3,5-Cl$_2$ | CF$_3$ | CH$_2$NHC(O)OCH$_3$ | D-55a |
| 3,5-Cl$_2$ | CF$_3$ | CH$_2$CN | D-55a |
| 3,5-Cl$_2$ | CF$_3$ | CH$_2$C≡CH | D-55a |
| 3,5-Cl$_2$ | CF$_3$ | C(O)CH$_3$ | D-55a |
| 3,5-Cl$_2$ | CF$_3$ | C(O)Et | D-55a |
| 3,5-Cl$_2$ | CF$_3$ | C(O)Pr-n | D-55a |
| 3,5-Cl$_2$ | CF$_3$ | C(O)Pr-i | D-55a |
| 3,5-Cl$_2$ | CF$_3$ | C(O)Pr-c | D-55a |
| 3,5-Cl$_2$ | CF$_3$ | C(O)Bu-t | D-55a |
| 3,5-Cl$_2$ | CF$_3$ | C(O)CH$_2$OCH$_3$ | D-55a |
| 3,5-Cl$_2$ | CF$_3$ | C(O)CH2SCH$_3$ | D-55a |
| 3,5-Cl$_2$ | CF$_3$ | C(O)OCH$_3$ | D-55a |
| 3,5-Cl$_2$ | CF$_3$ | C(O)OEt | D-55a |
| 3,5-Cl$_2$ | CF$_3$ | C(O)OPr-n | D-55a |
| 3,5-Cl$_2$ | CF$_3$ | C(O)OPr-i | D-55a |
| 3,5-Cl$_2$ | CF$_3$ | C(O)OPr-c | D-55a |
| 3,5-Cl$_2$ | CF$_3$ | C(O)OCH$_2$Cl | D-55a |
| 3,5-Cl$_2$ | CF$_3$ | C(O)OCH$_2$CH$_2$Cl | D-55a |
| 3,5-Cl$_2$ | CF$_3$ | C(O)OCH$_2$CH$_2$OCH$_3$ | D-55a |
| 3,5-Cl$_2$ | CF$_3$ | C(O)OCH$_2$CH=CH$_2$ | D-55a |
| 3,5-Cl$_2$ | CF$_3$ | C(O)OCH$_2$C≡CH | D-55a |
| 3,5-Cl$_2$ | CF$_3$ | SCCl$_3$ | D-55a |
| 3,5-Cl$_2$ | CF$_3$ | SN(Bu-n)$_2$ | D-55a |
| 3,5-Cl$_2$ | CF$_3$ | SN(Pr-i)CH$_2$CH$_2$C(O)OEt | D-55a |
| 3,5-Cl$_2$ | CF$_3$ | SN(CH$_2$Ph)CH$_2$CH$_2$C(O)OEt | D-55a |
| 3,5-Cl$_2$ | CF$_3$ | SN(CH$_3$)C(O)OBu-n | D-55a |
| 3,5-Cl$_2$ | CF$_3$ | C(O)CH$_3$ | (D-55b)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | CH$_3$ | (D-55b)CH$_3$ |
| 3,5-Cl$_2$ | CF$_3$ | CH$_2$OCH$_3$ | (D-55b)CH$_3$ |
| 3,5-Cl$_2$ | CF$_3$ | C(O)CH$_3$ | (D-55b)CH$_3$ |
| 3,5-Cl$_2$ | CF$_3$ | C(O)OCH$_3$ | (D-55b)CH$_3$ |
| 3,5-Cl$_2$ | CF$_3$ | C(O)OCH$_3$ | (D-55b)CF$_3$ |
| 3,5-Cl$_2$ | CF$_3$ | CH$_3$ | (D-55b)OCH$_3$ |
| 3,5-Cl$_2$ | CF$_3$ | CH$_3$ | (D-55c)F |
| 3,5-Cl$_2$ | CF$_3$ | Et | (D-55c)F |
| 3,5-Cl$_2$ | CF$_3$ | CH$_2$OCH$_3$ | (D-55c)F |
| 3,5-Cl$_2$ | CF$_3$ | CH$_2$OEt | (D-55c)F |
| 3,5-Cl$_2$ | CF$_3$ | CH$_2$OCH$_2$CF$_3$ | (D-55c)F |
| 3,5-Cl$_2$ | CF$_3$ | CH$_2$OC(O)CH$_3$ | (D-55c)F |
| 3,5-Cl$_2$ | CF$_3$ | CH$_2$OC(O)Et | (D-55c)F |
| 3,5-Cl$_2$ | CF$_3$ | CH$_2$OC(O)Pr-i | (D-55c)F |
| 3,5-Cl$_2$ | CF$_3$ | CH$_2$OC(O)Pr-c | (D-55c)F |
| 3,5-Cl$_2$ | CF$_3$ | CH$_2$OC(O)Bu-t | (D-55c)F |
| 3,5-Cl$_2$ | CF$_3$ | CH$_2$OC(O)Ph | (D-55c)F |
| 3,5-Cl$_2$ | CF$_3$ | CH$_2$OC(O)OCH$_3$ | (D-55c)F |
| 3,5-Cl$_2$ | CF$_3$ | CH$_2$CN | (D-55c)F |
| 3,5-Cl$_2$ | CF$_3$ | CH$_2$C≡CH | (D-55c)F |
| 3,5-Cl$_2$ | CF$_3$ | C(O)CH$_3$ | (D-55c)F |
| 3,5-Cl$_2$ | CF$_3$ | C(O)Et | (D-55c)F |
| 3,5-Cl$_2$ | CF$_3$ | C(O)Pr-n | (D-55c)F |
| 3,5-Cl$_2$ | CF$_3$ | C(O)Pr-i | (D-55c)F |
| 3,5-Cl$_2$ | CF$_3$ | C(O)Pr-c | (D-55c)F |
| 3,5-Cl$_2$ | CF$_3$ | C(O)Bu-t | (D-55c)F |
| 3,5-Cl$_2$ | CF$_3$ | C(O)CH$_2$OCH$_3$ | (D-55c)F |
| 3,5-Cl$_2$ | CF$_3$ | C(O)OCH$_3$ | (D-55c)F |
| 3,5-Cl$_2$ | CF$_3$ | C(O)OEt | (D-55c)F |
| 3,5-Cl$_2$ | CF$_3$ | C(O)OPr-n | (D-55c)F |
| 3,5-Cl$_2$ | CF$_3$ | C(O)OPr-i | (D-55c)F |
| 3,5-Cl$_2$ | CF$_3$ | C(O)OPr-c | (D-55c)F |
| 3,5-Cl$_2$ | CF$_3$ | C(O)OCH$_2$Cl | (D-55c)F |
| 3,5-Cl$_2$ | CF$_3$ | C(O)OCH$_2$CH$_2$Cl | (D-55c)F |
| 3,5-Cl$_2$ | CF$_3$ | C(O)OCH$_2$CH$_2$OCH$_3$ | (D-55c)F |
| 3,5-Cl$_2$ | CF$_3$ | C(O)OCH$_2$CH=CH$_2$ | (D-55c)F |
| 3,5-Cl$_2$ | CF$_3$ | CH$_3$ | (D-55c)Cl |
| 3,5-Cl$_2$ | CF$_3$ | Et | (D-55c)Cl |
| 3,5-Cl$_2$ | CF$_3$ | n-Pr | (D-55c)Cl |
| 3,5-Cl$_2$ | CF$_3$ | i-Pr | (D-55c)Cl |
| 3,5-Cl$_2$ | CF$_3$ | c-Pr | (D-55c)Cl |
| 3,5-Cl$_2$ | CF$_3$ | n-Bu | (D-55c)Cl |
| 3,5-Cl$_2$ | CF$_3$ | CH$_2$CF$_3$ | (D-55c)Cl |
| 3,5-Cl$_2$ | CF$_3$ | CH$_2$OCH$_3$ | (D-55c)Cl |
| 3,5-Cl$_2$ | CF$_3$ | CH$_2$OEt | (D-55c)Cl |
| 3,5-Cl$_2$ | CF$_3$ | CH$_2$OCH$_2$CH$_2$Cl | (D-55c)Cl |
| 3,5-Cl$_2$ | CF$_3$ | CH$_2$OCH$_2$CHF$_2$ | (D-55c)Cl |
| 3,5-Cl$_2$ | CF$_3$ | CH$_2$OCH$_2$CHCl$_2$ | (D-55c)Cl |
| 3,5-Cl$_2$ | CF$_3$ | CH$_2$OCH$_2$CF$_3$ | (D-55c)Cl |
| 3,5-Cl$_2$ | CF$_3$ | CH$_2$OCH$_2$CH$_2$OCH$_3$ | (D-55c)Cl |
| 3,5-Cl$_2$ | CF$_3$ | CH$_2$OCH$_2$CH$_2$OC(O)CH$_3$ | (D-55c)Cl |
| 3,5-Cl$_2$ | CF$_3$ | CH$_2$OCH$_2$CH$_2$OC(O)Ph | (D-55c)Cl |
| 3,5-Cl$_2$ | CF$_3$ | CH$_2$OCH$_2$C(O)OEt | (D-55c)Cl |
| 3,5-Cl$_2$ | CF$_3$ | CH$_2$OCH$_2$CH=CH$_2$ | (D-55c)Cl |
| 3,5-Cl$_2$ | CF$_3$ | CH$_2$OCH$_2$C≡CH | (D-55c)Cl |
| 3,5-Cl$_2$ | CF$_3$ | CH$_2$OCH$_2$Ph | (D-55c)Cl |
| 3,5-Cl$_2$ | CF$_3$ | CH$_2$OC(O)CH$_3$ | (D-55c)Cl |
| 3,5-Cl$_2$ | CF$_3$ | CH$_2$OC(O)Et | (D-55c)Cl |
| 3,5-Cl$_2$ | CF$_3$ | CH$_2$OC(O)Pr-n | (D-55c)Cl |
| 3,5-Cl$_2$ | CF$_3$ | CH$_2$OC(O)Pr-i | (D-55c)Cl |
| 3,5-Cl$_2$ | CF$_3$ | CH$_2$OC(O)Pr-c | (D-55c)Cl |
| 3,5-Cl$_2$ | CF$_3$ | CH$_2$OC(O)Bu-n | (D-55c)Cl |
| 3,5-Cl$_2$ | CF$_3$ | CH$_2$OC(O)Bu-i | (D-55c)Cl |
| 3,5-Cl$_2$ | CF$_3$ | CH$_2$OC(O)Bu-s | (D-55c)Cl |
| 3,5-Cl$_2$ | CF$_3$ | CH$_2$OC(O)Bu-t | (D-55c)Cl |
| 3,5-Cl$_2$ | CF$_3$ | CH$_2$OC(O)Pen-n | (D-55c)Cl |
| 3,5-Cl$_2$ | CF$_3$ | CH$_2$OC(O)Pen-c | (D-55c)Cl |
| 3,5-Cl$_2$ | CF$_3$ | CH$_2$OC(O)Hex-n | (D-55c)Cl |
| 3,5-Cl$_2$ | CF$_3$ | CH$_2$OC(O)Hex-c | (D-55c)Cl |
| 3,5-Cl$_2$ | CF$_3$ | CH$_2$OC(O)CH$_2$Cl | (D-55c)Cl |
| 3,5-Cl$_2$ | CF$_3$ | CH$_2$OC(O)CH$_2$OCH$_3$ | (D-55c)Cl |
| 3,5-Cl$_2$ | CF$_3$ | CH$_2$OC(O)CH$_2$OPh | (D-55c)Cl |
| 3,5-Cl$_2$ | CF$_3$ | CH$_2$OC(O)CH$_2$SPh | (D-55c)Cl |
| 3,5-Cl$_2$ | CF$_3$ | CH$_2$OC(O)CH$_2$NH$_2$ | (D-55c)Cl |
| 3,5-Cl$_2$ | CF$_3$ | CH$_2$OC(O)CH$_2$N(Et)$_2$ | (D-55c)Cl |
| 3,5-Cl$_2$ | CF$_3$ | CH$_2$OC(O)CH$_2$NHC(O)OCH$_3$ | (D-55c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | CH$_2$OC(O)CH$_2$NHC(O)OBu-t | (D-55c)Cl |
| 3,5-Cl$_2$ | CF$_3$ | CH$_2$OC(O)CH$_2$NHC(O)Ph | (D-55c)Cl |
| 3,5-Cl$_2$ | CF$_3$ | CH$_2$OC(O)CH$_2$Ph | (D-55c)Cl |
| 3,5-Cl$_2$ | CF$_3$ | CH$_2$OC(O)CH$_2$(D-1a) | (D-55c)Cl |
| 3,5-Cl$_2$ | CF$_3$ | CH$_2$OC(O)CH$_2$(D-3a) | (D-55c)Cl |
| 3,5-Cl$_2$ | CF$_3$ | CH$_2$OC(O)CH$_2$(D-53a) | (D-55c)Cl |
| 3,5-Cl$_2$ | CF$_3$ | CH$_2$OC(O)CH$_2$CH$_2$Ph | (D-55c)Cl |
| 3,5-Cl$_2$ | CF$_3$ | CH$_2$OC(O)Ph | (D-55c)Cl |
| 3,5-Cl$_2$ | CF$_3$ | CH$_2$OC(O)(D-1a) | (D-55c)Cl |
| 3,5-Cl$_2$ | CF$_3$ | CH$_2$OC(O)(D-2a) | (D-55c)Cl |
| 3,5-Cl$_2$ | CF$_3$ | CH$_2$OC(O)(D-3a) | (D-55c)Cl |
| 3,5-Cl$_2$ | CF$_3$ | CH$_2$OC(O)(D-53a) | (D-55c)Cl |
| 3,5-Cl$_2$ | CF$_3$ | CH$_2$OC(O)(D-54a) | (D-55c)Cl |
| 3,5-Cl$_2$ | CF$_3$ | CH$_2$OC(O)OCH$_3$ | (D-55c)Cl |
| 3,5-Cl$_2$ | CF$_3$ | CH$_2$OC(O)OEt | (D-55c)Cl |
| 3,5-Cl$_2$ | CF$_3$ | CH$_2$OC(O)OBu-n | (D-55c)Cl |
| 3,5-Cl$_2$ | CF$_3$ | CH$_2$OC(O)OBu-i | (D-55c)Cl |
| 3,5-Cl$_2$ | CF$_3$ | CH$_2$OC(O)OHex-c | (D-55c)Cl |
| 3,5-Cl$_2$ | CF$_3$ | CH$_2$OC(O)OCH$_2$(E-5a) | (D-55c)Cl |
| 3,5-Cl$_2$ | CF$_3$ | CH$_2$OC(O)OCH$_2$Ph | (D-55c)Cl |
| 3,5-Cl$_2$ | CF$_3$ | CH$_2$OC(O)OPh | (D-55c)Cl |
| 3,5-Cl$_2$ | CF$_3$ | CH$_2$OC(O)NH$_2$ | (D-55c)Cl |
| 3,5-Cl$_2$ | CF$_3$ | CH$_2$OC(O)NHPh | (D-55c)Cl |
| 3,5-Cl$_2$ | CF$_3$ | CH$_2$OPh | (D-55c)Cl |
| 3,5-Cl$_2$ | CF$_3$ | CH$_2$CH$_2$OCH$_3$ | (D-55c)Cl |
| 3,5-Cl$_2$ | CF$_3$ | CH(CH$_3$)CH$_2$OCH$_3$ | (D-55c)Cl |
| 3,5-Cl$_2$ | CF$_3$ | CH$_2$SCH$_3$ | (D-55c)Cl |
| 3,5-Cl$_2$ | CF$_3$ | CH$_2$SO$_2$CH$_3$ | (D-55c)Cl |
| 3,5-Cl$_2$ | CF$_3$ | CH$_2$SEt | (D-55c)Cl |
| 3,5-Cl$_2$ | CF$_3$ | CH$_2$SO$_2$Et | (D-55c)Cl |
| 3,5-Cl$_2$ | CF$_3$ | CH$_2$SCF$_3$ | (D-55c)Cl |
| 3,5-Cl$_2$ | CF$_3$ | CH$_2$SCH$_2$Ph | (D-55c)Cl |
| 3,5-Cl$_2$ | CF$_3$ | CH$_2$SO$_2$CH$_2$Ph | (D-55c)Cl |
| 3,5-Cl$_2$ | CF$_3$ | CH$_2$SC(O)CH$_3$ | (D-55c)Cl |
| 3,5-Cl$_2$ | CF$_3$ | CH$_2$SC(O)Et | (D-55c)Cl |
| 3,5-Cl$_2$ | CF$_3$ | CH$_2$SC(O)Ph | (D-55c)Cl |
| 3,5-Cl$_2$ | CF$_3$ | CH$_2$SC(S)OCH$_3$ | (D-55c)Cl |
| 3,5-Cl$_2$ | CF$_3$ | CH$_2$SC(S)OEt | (D-55c)Cl |
| 3,5-Cl$_2$ | CF$_3$ | CH$_2$SC(S)OPr-n | (D-55c)Cl |
| 3,5-Cl$_2$ | CF$_3$ | CH$_2$SC(S)OPr-i | (D-55c)Cl |
| 3,5-Cl$_2$ | CF$_3$ | CH$_2$SC(S)OBu-n | (D-55c)Cl |
| 3,5-Cl$_2$ | CF$_3$ | CH$_2$SC(S)OBu-i | (D-55c)Cl |
| 3,5-Cl$_2$ | CF$_3$ | CH$_2$SC(S)N(CH$_3$)$_2$ | (D-55c)Cl |
| 3,5-Cl$_2$ | CF$_3$ | CH$_2$SC(S)(T-14) | (D-55c)Cl |
| 3,5-Cl$_2$ | CF$_3$ | CH$_2$SC(S)(T-17) | (D-55c)Cl |
| 3,5-Cl$_2$ | CF$_3$ | CH$_2$SC(S)(T-18) | (D-55c)Cl |
| 3,5-Cl$_2$ | CF$_3$ | CH$_2$SC(S)(D-14a) | (D-55c)Cl |
| 3,5-Cl$_2$ | CF$_3$ | CH$_2$SPh | (D-55c)Cl |
| 3,5-Cl$_2$ | CF$_3$ | CH$_2$S(O)Ph | (D-55c)Cl |
| 3,5-Cl$_2$ | CF$_3$ | CH$_2$SO2Ph | (D-55c)Cl |
| 3,5-Cl$_2$ | CF$_3$ | CH$_2$S(D-34b)Ph | (D-55c)Cl |
| 3,5-Cl$_2$ | CF$_3$ | CH$_2$S(D-35b)SCH$_3$ | (D-55c)Cl |
| 3,5-Cl$_2$ | CF$_3$ | CH$_2$S(D-50a)Et | (D-55c)Cl |
| 3,5-Cl$_2$ | CF$_3$ | CH$_2$S(D-50a)Ph | (D-55c)Cl |
| 3,5-Cl$_2$ | CF$_3$ | CH$_2$NHCH$_3$ | (D-55c)Cl |
| 3,5-Cl$_2$ | CF$_3$ | CH$_2$N(CH$_3$)$_2$ | (D-55c)Cl |
| 3,5-Cl$_2$ | CF$_3$ | CH$_2$N(Et)$_2$ | (D-55c)Cl |
| 3,5-Cl$_2$ | CF$_3$ | CH$_2$NHBu-n | (D-55c)Cl |
| 3,5-Cl$_2$ | CF$_3$ | CH$_2$NHCH$_2$Ph | (D-55c)Cl |
| 3,5-Cl$_2$ | CF$_3$ | CH$_2$(T-14) | (D-55c)Cl |
| 3,5-Cl$_2$ | CF$_3$ | CH$_2$(T-17) | (D-55c)Cl |
| 3,5-Cl$_2$ | CF$_3$ | CH$_2$(T-18) | (D-55c)Cl |
| 3,5-Cl$_2$ | CF$_3$ | CH$_2$(T-19) | (D-55c)Cl |
| 3,5-Cl$_2$ | CF$_3$ | CH$_2$(T-20) | (D-55c)Cl |
| 3,5-Cl$_2$ | CF$_3$ | CH$_2$N(CH$_3$)C(O)CH$_3$ | (D-55c)Cl |
| 3,5-Cl$_2$ | CF$_3$ | CH$_2$N(Ph)C(O)CH$_3$ | (D-55c)Cl |
| 3,5-Cl$_2$ | CF$_3$ | CH$_2$NHC(O)OCH$_3$ | (D-55c)Cl |
| 3,5-Cl$_2$ | CF$_3$ | CH$_2$N(CH$_3$)C(O)OCH$_3$ | (D-55c)Cl |
| 3,5-Cl$_2$ | CF$_3$ | CH$_2$N(CH$_3$)SO$_2$CH$_3$ | (D-55c)Cl |
| 3,5-Cl$_2$ | CF$_3$ | CH$_2$N(Ph)SO$_2$CH$_3$ | (D-55c)Cl |
| 3,5-Cl$_2$ | CF$_3$ | CH$_2$NHPh | (D-55c)Cl |
| 3,5-Cl$_2$ | CF$_3$ | CH$_2$Si(CH$_3$)$_3$ | (D-55c)Cl |
| 3,5-Cl$_2$ | CF$_3$ | CH$_2$CHO | (D-55c)Cl |
| 3,5-Cl$_2$ | CF$_3$ | CH$_2$C(O)CH$_3$ | (D-55c)Cl |
| 3,5-Cl$_2$ | CF$_3$ | CH$_2$CN | (D-55c)Cl |
| 3,5-Cl$_2$ | CF$_3$ | CH$_2$C(O)OH | (D-55c)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | CH$_2$C(O)OCH$_3$ | (D-55c)Cl |
| 3,5-Cl$_2$ | CF$_3$ | CH$_2$C(O)OEt | (D-55c)Cl |
| 3,5-Cl$_2$ | CF$_3$ | CH$_2$C(O)OPr-n | (D-55c)Cl |
| 3,5-Cl$_2$ | CF$_3$ | CH$_2$C(O)OBu-t | (D-55c)Cl |
| 3,5-Cl$_2$ | CF$_3$ | CH$_2$CH=CH$_2$ | (D-55c)Cl |
| 3,5-Cl$_2$ | CF$_3$ | CH$_2$C≡CH? | (D-55c)Cl |
| 3,5-Cl$_2$ | CF$_3$ | CH(CH$_3$)C≡CH | (D-55c)Cl |
| 3,5-Cl$_2$ | CF$_3$ | CH$_2$Ph | (D-55c)Cl |
| 3,5-Cl$_2$ | CF$_3$ | C(O)CH$_3$ | (D-55c)Cl |
| 3,5-Cl$_2$ | CF$_3$ | C(O)Et | (D-55c)Cl |
| 3,5-Cl$_2$ | CF$_3$ | C(O)Pr-n | (D-55c)Cl |
| 3,5-Cl$_2$ | CF$_3$ | C(O)Pr-i | (D-55c)Cl |
| 3,5-Cl$_2$ | CF$_3$ | C(O)Pr-c | (D-55c)Cl |
| 3,5-Cl$_2$ | CF$_3$ | C(O)Bu-n | (D-55c)Cl |
| 3,5-Cl$_2$ | CF$_3$ | C(O)Bu-i | (D-55c)Cl |
| 3,5-Cl$_2$ | CF$_3$ | C(O)CH$_2$Pr-c | (D-55c)Cl |
| 3,5-Cl$_2$ | CF$_3$ | C(O)Bu-s | (D-55c)Cl |
| 3,5-Cl$_2$ | CF$_3$ | C(O)Bu-t | (D-55c)Cl |
| 3,5-Cl$_2$ | CF$_3$ | C(O)Pen-c | (D-55c)Cl |
| 3,5-Cl$_2$ | CF$_3$ | C(O)CH$_2$Cl | (D-55c)Cl |
| 3,5-Cl$_2$ | CF$_3$ | C(O)CH$_2$CF$_3$ | (D-55c)Cl |
| 3,5-Cl$_2$ | CF$_3$ | C(O)CH$_2$OCH$_3$ | (D-55c)Cl |
| 3,5-Cl$_2$ | CF$_3$ | C(O)CH$_2$OEt | (D-55c)Cl |
| 3,5-Cl$_2$ | CF$_3$ | C(O)CH$_2$SCH$_3$ | (D-55c)Cl |
| 3,5-Cl$_2$ | CF$_3$ | C(O)CH$_2$S(O)CH$_3$ | (D-55c)Cl |
| 3,5-Cl$_2$ | CF$_3$ | C(O)CH$_2$SO$_2$CH$_3$ | (D-55c)Cl |
| 3,5-Cl$_2$ | CF$_3$ | C(O)CH=CH$_2$ | (D-55c)Cl |
| 3,5-Cl$_2$ | CF$_3$ | C(O)C≡CH | (D-55c)Cl |
| 3,5-Cl$_2$ | CF$_3$ | C(O)C(O)OCH$_3$ | (D-55c)Cl |
| 3,5-Cl$_2$ | CF$_3$ | C(O)C(O)OEt | (D-55c)Cl |
| 3,5-Cl$_2$ | CF$_3$ | C(O)Ph | (D-55c)Cl |
| 3,5-Cl$_2$ | CF$_3$ | C(O)(Ph-4-OCH$_3$) | (D-55c)Cl |
| 3,5-Cl$_2$ | CF$_3$ | C(O)(Ph-4-NO$_2$) | (D-55c)Cl |
| 3,5-Cl$_2$ | CF$_3$ | C(O)(Ph-4-CN) | (D-55c)Cl |
| 3,5-Cl$_2$ | CF$_3$ | C(O)(1-Naph) | (D-55c)Cl |
| 3,5-Cl$_2$ | CF$_3$ | C(O)(2-Naph) | (D-55c)Cl |
| 3,5-Cl$_2$ | CF$_3$ | C(O)(D-1a) | (D-55c)Cl |
| 3,5-Cl$_2$ | CF$_3$ | C(O)(D-2a) | (D-55c)Cl |
| 3,5-Cl$_2$ | CF$_3$ | C(O)(D-3a) | (D-55c)Cl |
| 3,5-Cl$_2$ | CF$_3$ | C(O)(D-4a) | (D-55c)Cl |
| 3,5-Cl$_2$ | CF$_3$ | C(O)(D-52a) | (D-55c)Cl |
| 3,5-Cl$_2$ | CF$_3$ | C(O)(D-53a) | (D-55c)Cl |
| 3,5-Cl$_2$ | CF$_3$ | C(O)(D-54a) | (D-55c)Cl |
| 3,5-Cl$_2$ | CF$_3$ | C(O)OCH$_3$ | (D-55c)Cl |
| 3,5-Cl$_2$ | CF$_3$ | C(O)OEt | (D-55c)Cl |
| 3,5-Cl$_2$ | CF$_3$ | C(O)OPr-n | (D-55c)Cl |
| 3,5-Cl$_2$ | CF$_3$ | C(O)OPr-i | (D-55c)Cl |
| 3,5-Cl$_2$ | CF$_3$ | C(O)OPr-c | (D-55c)Cl |
| 3,5-Cl$_2$ | CF$_3$ | C(O)OBu-n | (D-55c)Cl |
| 3,5-Cl$_2$ | CF$_3$ | C(O)OBu-i | (D-55c)Cl |
| 3,5-Cl$_2$ | CF$_3$ | C(O)OBu-s | (D-55c)Cl |
| 3,5-Cl$_2$ | CF$_3$ | C(O)OBu-t | (D-55c)Cl |
| 3,5-Cl$_2$ | CF$_3$ | C(O)OPen-n | (D-55c)Cl |
| 3,5-Cl$_2$ | CF$_3$ | C(O)OCH$_2$Bu-t | (D-55c)Cl |
| 3,5-Cl$_2$ | CF$_3$ | C(O)OPen-c | (D-55c)Cl |
| 3,5-Cl$_2$ | CF$_3$ | C(O)OHex-n | (D-55c)Cl |
| 3,5-Cl$_2$ | CF$_3$ | C(O)OHex-c | (D-55c)Cl |
| 3,5-Cl$_2$ | CF$_3$ | C(O)OHep | (D-55c)Cl |
| 3,5-Cl$_2$ | CF$_3$ | C(O)O(Oct) | (D-55c)Cl |
| 3,5-Cl$_2$ | CF$_3$ | C(O)OCH$_2$Cl | (D-55c)Cl |
| 3,5-Cl$_2$ | CF$_3$ | C(O)OCH$_2$CH$_2$F | (D-55c)Cl |
| 3,5-Cl$_2$ | CF$_3$ | C(O)OCH$_2$CH$_2$Cl | (D-55c)Cl |
| 3,5-Cl$_2$ | CF$_3$ | C(O)OCH$_2$CH$_2$Br | (D-55c)Cl |
| 3,5-Cl$_2$ | CF$_3$ | C(O)OCHClCH$_3$ | (D-55c)Cl |
| 3,5-Cl$_2$ | CF$_3$ | C(O)OCH$_2$CHF$_2$ | (D-55c)Cl |
| 3,5-Cl$_2$ | CF$_3$ | C(O)OCH$_2$CF$_3$ | (D-55c)Cl |
| 3,5-Cl$_2$ | CF$_3$ | C(O)OCH$_2$CCl$_3$ | (D-55c)Cl |
| 3,5-Cl$_2$ | CF$_3$ | C(O)OCHClCCl$_3$ | (D-55c)Cl |
| 3,5-Cl$_2$ | CF$_3$ | C(O)OCH$_2$CH$_2$CH$_2$Cl | (D-55c)Cl |
| 3,5-Cl$_2$ | CF$_3$ | C(O)OCH$_2$CH$_2$OCH$_3$ | (D-55c)Cl |
| 3,5-Cl$_2$ | CF$_3$ | C(O)OCH$_2$CH$_2$OCH$_2$Ph | (D-55c)Cl |
| 3,5-Cl$_2$ | CF$_3$ | C(O)OCH$_2$CH$_2$OPh | (D-55c)Cl |
| 3,5-Cl$_2$ | CF$_3$ | C(O)OCH$_2$CH$_2$OCH$_2$CH$_2$OCH$_3$ | (D-55c)Cl |
| 3,5-Cl$_2$ | CF$_3$ | C(O)OCH$_2$CH$_2$SCH$_3$ | (D-55c)Cl |
| 3,5-Cl$_2$ | CF$_3$ | C(O)OCH$_2$CH$_2$SO$_2$CH$_3$ | (D-55c)Cl |
| 3,5-Cl$_2$ | CF$_3$ | C(O)OCH=CH$_2$ | (D-55c)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | C(O)OCH$_2$CH═CH$_2$ | (D-55c)Cl |
| 3,5-Cl$_2$ | CF$_3$ | C(O)OCH$_2$CH$_2$CH═CH$_2$ | (D-55c)Cl |
| 3,5-Cl$_2$ | CF$_3$ | C(O)OCH$_2$C≡CH | (D-55c)Cl |
| 3,5-Cl$_2$ | CF$_3$ | C(O)OCH$_2$Ph | (D-55c)Cl |
| 3,5-Cl$_2$ | CF$_3$ | C(O)OCH$_2$(Ph-4-NO$_2$) | (D-55c)Cl |
| 3,5-Cl$_2$ | CF$_3$ | C(O)OPh | (D-55c)Cl |
| 3,5-Cl$_2$ | CF$_3$ | C(O)SCH$_3$ | (D-55c)Cl |
| 3,5-Cl$_2$ | CF$_3$ | C(O)SEt | (D-55c)Cl |
| 3,5-Cl$_2$ | CF$_3$ | C(O)SPr-n | (D-55c)Cl |
| 3,5-Cl$_2$ | CF$_3$ | C(O)NH$_2$ | (D-55c)Cl |
| 3,5-Cl$_2$ | CF$_3$ | C(O)N(CH$_3$)$_2$ | (D-55c)Cl |
| 3,5-Cl$_2$ | CF$_3$ | C(S)OCH$_3$ | (D-55c)Cl |
| 3,5-Cl$_2$ | CF$_3$ | C(S)OEt | (D-55c)Cl |
| 3,5-Cl$_2$ | CF$_3$ | C(S)SCH$_3$ | (D-55c)Cl |
| 3,5-Cl$_2$ | CF$_3$ | C(S)SEt | (D-55c)Cl |
| 3,5-Cl$_2$ | CF$_3$ | Ph | (D-55c)Cl |
| 3,5-Cl$_2$ | CF$_3$ | Ph-4-F | (D-55c)Cl |
| 3,5-Cl$_2$ | CF$_3$ | SCH$_3$ | (D-55c)Cl |
| 3,5-Cl$_2$ | CF$_3$ | SCCl$_3$ | (D-55c)Cl |
| 3,5-Cl$_2$ | CF$_3$ | SPh | (D-55c)Cl |
| 3,5-Cl$_2$ | CF$_3$ | SN(Et)$_2$ | (D-55c)Cl |
| 3,5-Cl$_2$ | CF$_3$ | SN(Pr-i)$_2$ | (D-55c)Cl |
| 3,5-Cl$_2$ | CF$_3$ | SN(Bu-n)$_2$ | (D-55c)Cl |
| 3,5-Cl$_2$ | CF$_3$ | S(T-18) | (D-55c)Cl |
| 3,5-Cl$_2$ | CF$_3$ | SN(CH$_3$)CH$_2$CH$_2$C(O)OEt | (D-55c)Cl |
| 3,5-Cl$_2$ | CF$_3$ | SN(Et)CH$_2$CH$_2$C(O)OEt | (D-55c)Cl |
| 3,5-Cl$_2$ | CF$_3$ | SN(Pr-i)CH$_2$CH$_2$C(O)OEt | (D-55c)Cl |
| 3,5-Cl$_2$ | CF$_3$ | SN(CH$_2$Ph)CH$_2$CH$_2$C(O)OEt | (D-55c)Cl |
| 3,5-Cl$_2$ | CF$_3$ | SN(CH$_3$)C(O)OEt | (D-55c)Cl |
| 3,5-Cl$_2$ | CF$_3$ | SN(CH$_3$)C(O)OPr-n | (D-55c)Cl |
| 3,5-Cl$_2$ | CF$_3$ | SN(CH$_3$)C(O)OBu-n | (D-55c)Cl |
| 3,5-Cl$_2$ | CF$_3$ | SN(CH$_3$)C(O)OHex-n | (D-55c)Cl |
| 3,5-Cl$_2$ | CF$_3$ | SN(Et)C(O)OEt | (D-55c)Cl |
| 3,5-Cl$_2$ | CF$_3$ | SN(Et)C(O)OPr-n | (D-55c)Cl |
| 3,5-Cl$_2$ | CF$_3$ | SN(Et)C(O)OBu-n | (D-55c)Cl |
| 3,5-Cl$_2$ | CF$_3$ | SN(Pr-i)C(O)OEt | (D-55c)Cl |
| 3,5-Cl$_2$ | CF$_3$ | SN(Pr-i)C(O)OPr-n | (D-55c)Cl |
| 3,5-Cl$_2$ | CF$_3$ | SN(Pr-i)C(O)OBu-n | (D-55c)Cl |
| 3,5-Cl$_2$ | CF$_3$ | SO$_2$CH$_3$ | (D-55c)Cl |
| 3,5-Cl$_2$ | CF$_3$ | SO$_2$Et | (D-55c)Cl |
| 3,5-Cl$_2$ | CF$_3$ | CH$_3$ | (D-55c)Br |
| 3,5-Cl$_2$ | CF$_3$ | Et | (D-55c)Br |
| 3,5-Cl$_2$ | CF$_3$ | c-Pr | (D-55c)Br |
| 3,5-Cl$_2$ | CF$_3$ | CH$_2$OCH$_3$ | (D-55c)Br |
| 3,5-Cl$_2$ | CF$_3$ | CH$_2$OEt | (D-55c)Br |
| 3,5-Cl$_2$ | CF$_3$ | CH$_2$OCH$_2$CH$_2$Cl | (D-55c)Br |
| 3,5-Cl$_2$ | CF$_3$ | CH$_2$OCH$_2$CHF$_2$ | (D-55c)Br |
| 3,5-Cl$_2$ | CF$_3$ | CH$_2$OCH$_2$CF$_3$ | (D-55c)Br |
| 3,5-Cl$_2$ | CF$_3$ | CH$_2$OCH$_2$CH$_2$OCH$_3$ | (D-55c)Br |
| 3,5-Cl$_2$ | CF$_3$ | CH$_2$OCH$_2$Ph | (D-55c)Br |
| 3,5-Cl$_2$ | CF$_3$ | CH$_2$OC(O)CH$_3$ | (D-55c)Br |
| 3,5-Cl$_2$ | CF$_3$ | CH$_2$OC(O)Et | (D-55c)Br |
| 3,5-Cl$_2$ | CF$_3$ | CH$_2$OC(O)Pr-n | (D-55c)Br |
| 3,5-Cl$_2$ | CF$_3$ | CH$_2$OC(O)Pr-i | (D-55c)Br |
| 3,5-Cl$_2$ | CF$_3$ | CH$_2$OC(O)Pr-c | (D-55c)Br |
| 3,5-Cl$_2$ | CF$_3$ | CH$_2$OC(O)Bu-n | (D-55c)Br |
| 3,5-Cl$_2$ | CF$_3$ | CH$_2$OC(O)Bu-i | (D-55c)Br |
| 3,5-Cl$_2$ | CF$_3$ | CH$_2$OC(O)Bu-s | (D-55c)Br |
| 3,5-Cl$_2$ | CF$_3$ | CH$_2$OC(O)Bu-t | (D-55c)Br |
| 3,5-Cl$_2$ | CF$_3$ | CH$_2$OC(O)CH$_2$Ph | (D-55c)Br |
| 3,5-Cl$_2$ | CF$_3$ | CH$_2$OC(O)Ph | (D-55c)Br |
| 3,5-Cl$_2$ | CF$_3$ | CH$_2$OC(O)OCH$_3$ | (D-55c)Br |
| 3,5-Cl$_2$ | CF$_3$ | CH$_2$OC(O)OEt | (D-55c)Br |
| 3,5-Cl$_2$ | CF$_3$ | CH$_2$OC(O)OBu-n | (D-55c)Br |
| 3,5-Cl$_2$ | CF$_3$ | CH$_2$OC(O)OBu-i | (D-55c)Br |
| 3,5-Cl$_2$ | CF$_3$ | CH$_2$OC(O)OCH$_2$Ph | (D-55c)Br |
| 3,5-Cl$_2$ | CF$_3$ | CH$_2$OC(O)OPh | (D-55c)Br |
| 3,5-Cl$_2$ | CF$_3$ | CH$_2$OC(O)NHPh | (D-55c)Br |
| 3,5-Cl$_2$ | CF$_3$ | CH$_2$OPh | (D-55c)Br |
| 3,5-Cl$_2$ | CF$_3$ | CH$_2$SCH$_3$ | (D-55c)Br |
| 3,5-Cl$_2$ | CF$_3$ | CH$_2$SO$_2$CH$_3$ | (D-55c)Br |
| 3,5-Cl$_2$ | CF$_3$ | CH$_2$SC(O)CH3 | (D-55c)Br |
| 3,5-Cl$_2$ | CF$_3$ | CH$_2$SC(O)Et | (D-55c)Br |
| 3,5-Cl$_2$ | CF$_3$ | CH$_2$SC(O)Ph | (D-55c)Br |
| 3,5-Cl$_2$ | CF$_3$ | CH$_2$SC(S)OCH$_3$ | (D-55c)Br |
| 3,5-Cl$_2$ | CF$_3$ | CH$_2$SC(S)OEt | (D-55c)Br |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | CH$_2$SC(S)OPr-n | (D-55c)Br |
| 3,5-Cl$_2$ | CF$_3$ | CH$_2$SC(S)OPr-i | (D-55c)Br |
| 3,5-Cl$_2$ | CF$_3$ | CH$_2$SC(S)N(CH$_3$)$_2$ | (D-55c)Br |
| 3,5-Cl$_2$ | CF$_3$ | CH$_2$SC(S)(T-14) | (D-55c)Br |
| 3,5-Cl$_2$ | CF$_3$ | CH$_2$N(CH$_3$)$_2$ | (D-55c)Br |
| 3,5-Cl$_2$ | CF$_3$ | CH$_2$N(CH$_3$)C(O)CH$_3$ | (D-55c)Br |
| 3,5-Cl$_2$ | CF$_3$ | CH$_2$NHC(O)OCH$_3$ | (D-55c)Br |
| 3,5-Cl$_2$ | CF$_3$ | CH$_2$N(CH$_3$)C(O)OCH$_3$ | (D-55c)Br |
| 3,5-Cl$_2$ | CF$_3$ | CH$_2$N(CH$_3$)SO$_2$CH$_3$ | (D-55c)Br |
| 3,5-Cl$_2$ | CF$_3$ | CH$_2$CN | (D-55c)Br |
| 3,5-Cl$_2$ | CF$_3$ | CH$_2$C(O)OCH$_3$ | (D-55c)Br |
| 3,5-Cl$_2$ | CF$_3$ | CH$_2$CH=CH$_2$ | (D-55c)Br |
| 3,5-Cl$_2$ | CF$_3$ | CH$_2$C≡CH | (D-55c)Br |
| 3,5-Cl$_2$ | CF$_3$ | C(O)CH$_3$ | (D-55c)Br |
| 3,5-Cl$_2$ | CF$_3$ | C(O)Et | (D-55c)Br |
| 3,5-Cl$_2$ | CF$_3$ | C(O)Pr-n | (D-55c)Br |
| 3,5-Cl$_2$ | CF$_3$ | C(O)Pr-i | (D-55c)Br |
| 3,5-Cl$_2$ | CF$_3$ | C(O)Pr-c | (D-55c)Br |
| 3,5-Cl$_2$ | CF$_3$ | C(O)Bu-n | (D-55c)Br |
| 3,5-Cl$_2$ | CF$_3$ | C(O)Bu-i | (D-55c)Br |
| 3,5-Cl$_2$ | CF$_3$ | C(O)Bu-s | (D-55c)Br |
| 3,5-Cl$_2$ | CF$_3$ | C(O)Bu-t | (D-55c)Br |
| 3,5-Cl$_2$ | CF$_3$ | C(O)CH$_2$OCH$_3$ | (D-55c)Br |
| 3,5-Cl$_2$ | CF$_3$ | C(O)CH$_2$SCH$_3$ | (D-55c)Br |
| 3,5-Cl$_2$ | CF$_3$ | C(O)CH$_2$SO$_2$CH$_3$ | (D-55c)Br |
| 3,5-Cl$_2$ | CF$_3$ | C(O)CH=CH$_2$ | (D-55c)Br |
| 3,5-Cl$_2$ | CF$_3$ | C(O)Ph | (D-55c)Br |
| 3,5-Cl$_2$ | CF$_3$ | C(O)OCH$_3$ | (D-55c)Br |
| 3,5-Cl$_2$ | CF$_3$ | C(O)OEt | (D-55c)Br |
| 3,5-Cl$_2$ | CF$_3$ | C(O)OPr-n | (D-55c)Br |
| 3,5-Cl$_2$ | CF$_3$ | C(O)OPr-i | (D-55c)Br |
| 3,5-Cl$_2$ | CF$_3$ | C(O)OPr-c | (D-55c)Br |
| 3,5-Cl$_2$ | CF$_3$ | C(O)OBu-i | (D-55c)Br |
| 3,5-Cl$_2$ | CF$_3$ | C(O)OCH$_2$Cl | (D-55c)Br |
| 3,5-Cl$_2$ | CF$_3$ | C(O)OCH$_2$CH$_2$Cl | (D-55c)Br |
| 3,5-Cl$_2$ | CF$_3$ | C(O)OCH$_2$CH$_2$OCH$_3$ | (D-55c)Br |
| 3,5-Cl$_2$ | CF$_3$ | C(O)OCH$_2$CH$_2$SO$_2$CH$_3$ | (D-55c)Br |
| 3,5-Cl$_2$ | CF$_3$ | C(O)OCH=CH$_2$ | (D-55c)Br |
| 3,5-Cl$_2$ | CF$_3$ | C(O)OCH$_2$CH=CH$_2$ | (D-55c)Br |
| 3,5-Cl$_2$ | CF$_3$ | C(O)OCH$_2$C≡CH | (D-55c)Br |
| 3,5-Cl$_2$ | CF$_3$ | C(O)SCH$_3$ | (D-55c)Br |
| 3,5-Cl$_2$ | CF$_3$ | C(S)OCH$_3$ | (D-55c)Br |
| 3,5-Cl$_2$ | CF$_3$ | C(S)SCH$_3$ | (D-55c)Br |
| 3,5-Cl$_2$ | CF$_3$ | SCCl$_3$ | (D-55c)Br |
| 3,5-Cl$_2$ | CF$_3$ | SN(Bu-n)$_2$ | (D-55c)Br |
| 3,5-Cl$_2$ | CF$_3$ | S(T-18) | (D-55c)Br |
| 3,5-Cl$_2$ | CF$_3$ | SN(Pr-i)CH$_2$CH$_2$C(O)OEt | (D-55c)Br |
| 3,5-Cl$_2$ | CF$_3$ | SN(CH$_2$Ph)CH$_2$CH$_2$C(O)OEt | (D-55c)Br |
| 3,5-Cl$_2$ | CF$_3$ | SN(CH$_3$)C(O)OBu-n | (D-55c)Br |
| 3,5-Cl$_2$ | CF$_3$ | CH$_3$ | (D-55c)I |
| 3,5-Cl$_2$ | CF$_3$ | CH$_2$OCH$_3$ | (D-55c)I |
| 3,5-Cl$_2$ | CF$_3$ | C(O)CH$_3$ | (D-55c)I |
| 3,5-Cl$_2$ | CF$_3$ | C(O)OCH$_3$ | (D-55c)I |
| 3,5-Cl$_2$ | CF$_3$ | CH$_2$OCH$_3$ | (D-55c)CH$_3$ |
| 3,5-Cl$_2$ | CF$_3$ | C(O)CH$_3$ | (D-55c)OCH$_2$CF$_3$ |
| 3,5-Cl$_2$ | CF$_3$ | C(O)OCH$_3$ | (D-55c)SO$_2$CH$_3$ |
| 3,5-Cl$_2$ | CF$_3$ | CH$_3$ | (D-55c)NO$_2$ |
| 3,5-Cl$_2$ | CF$_3$ | CH$_2$OCH$_3$ | (D-55c)NO$_2$ |
| 3,5-Cl$_2$ | CF$_3$ | CH$_2$OEt | (D-55c)NO$_2$ |
| 3,5-Cl$_2$ | CF$_3$ | CH$_2$OC(O)CH$_3$ | (D-55c)NO$_2$ |
| 3,5-Cl$_2$ | CF$_3$ | CH$_2$OC(O)OCH$_3$ | (D-55c)NO$_2$ |
| 3,5-Cl$_2$ | CF$_3$ | CH$_2$CN | (D-55c)NO$_2$ |
| 3,5-Cl$_2$ | CF$_3$ | C(O)CH$_3$ | (D-55c)NO$_2$ |
| 3,5-Cl$_2$ | CF$_3$ | C(O)Et | (D-55c)NO$_2$ |
| 3,5-Cl$_2$ | CF$_3$ | C(O)Pr-i | (D-55c)NO$_2$ |
| 3,5-Cl$_2$ | CF$_3$ | C(O)OCH$_3$ | (D-55c)NO$_2$ |
| 3,5-Cl$_2$ | CF$_3$ | CH$_3$ | (D-55c)CH=NOCH$_3$ |
| 3,5-Cl$_2$ | CF$_3$ | CH$_3$ | (D-55c)CN |
| 3,5-Cl$_2$ | CF$_3$ | CH$_2$OCH$_3$ | (D-55c)CN |
| 3,5-Cl$_2$ | CF$_3$ | CH$_2$OEt | (D-55c)CN |
| 3,5-Cl$_2$ | CF$_3$ | CH$_2$OC(O)CH$_3$ | (D-55c)CN |
| 3,5-Cl$_2$ | CF$_3$ | CH$_2$OC(O)OCH$_3$ | (D-55c)CN |
| 3,5-Cl$_2$ | CF$_3$ | CH$_2$CN | (D-55c)CN |
| 3,5-Cl$_2$ | CF$_3$ | C(O)CH3 | (D-55c)CN |
| 3,5-Cl$_2$ | CF$_3$ | C(O)Et | (D-55c)CN |
| 3,5-Cl$_2$ | CF$_3$ | C(O)Pr-i | (D-55c)CN |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | C(O)OCH$_3$ | (D-55c)CN |
| 3,5-Cl$_2$ | CF$_3$ | CH$_2$OCH$_3$ | (D-55c)C(O)OCH$_3$ |
| 3,5-Cl$_2$ | CF$_3$ | C(O)CH$_3$ | (D-55c)SO$_2$NH$_2$ |
| 3,5-Cl$_2$ | CF$_3$ | CH$_3$ | D-56a |
| 3,5-Cl$_2$ | CF$_3$ | Et | D-56a |
| 3,5-Cl$_2$ | CF$_3$ | CH$_2$OCH$_3$ | D-56a |
| 3,5-Cl$_2$ | CF$_3$ | CH$_2$OEt | D-56a |
| 3,5-Cl$_2$ | CF$_3$ | CH$_2$OCH$_2$CF$_3$ | D-56a |
| 3,5-Cl$_2$ | CF$_3$ | CH$_2$OC(O)CH$_3$ | D-56a |
| 3,5-Cl$_2$ | CF$_3$ | CH$_2$OC(O)Et | D-56a |
| 3,5-Cl$_2$ | CF$_3$ | CH$_2$OC(O)Pr-i | D-56a |
| 3,5-Cl$_2$ | CF$_3$ | CH$_2$OC(O)Pr-c | D-56a |
| 3,5-Cl$_2$ | CF$_3$ | CH$_2$OC(O)Bu-t | D-56a |
| 3,5-Cl$_2$ | CF$_3$ | CH$_2$OC(O)Ph | D-56a |
| 3,5-Cl$_2$ | CF$_3$ | CH$_2$OC(O)OCH$_3$ | D-56a |
| 3,5-Cl$_2$ | CF$_3$ | CH$_2$CN | D-56a |
| 3,5-Cl$_2$ | CF$_3$ | CH2C≡CH | D-56a |
| 3,5-Cl$_2$ | CF$_3$ | C(O)CH$_3$ | D-56a |
| 3,5-Cl$_2$ | CF$_3$ | C(O)Et | D-56a |
| 3,5-Cl$_2$ | CF$_3$ | C(O)Pr-n | D-56a |
| 3,5-Cl$_2$ | CF$_3$ | C(O)Pr-i | D-56a |
| 3,5-Cl$_2$ | CF$_3$ | C(O)Pr-c | D-56a |
| 3,5-Cl$_2$ | CF$_3$ | C(O)Bu-t | D-56a |
| 3,5-Cl$_2$ | CF$_3$ | C(O)CH$_2$OCH$_3$ | D-56a |
| 3,5-Cl$_2$ | CF$_3$ | C(O)OCH$_3$ | D-56a |
| 3,5-Cl$_2$ | CF$_3$ | C(O)OEt | D-56a |
| 3,5-Cl$_2$ | CF$_3$ | C(O)OPr-n | D-56a |
| 3,5-Cl$_2$ | CF$_3$ | C(O)OPr-i | D-56a |
| 3,5-Cl$_2$ | CF$_3$ | C(O)OPr-c | D-56a |
| 3,5-Cl$_2$ | CF$_3$ | C(O)OCH$_2$Cl | D-56a |
| 3,5-Cl$_2$ | CF$_3$ | C(O)OCH$_2$CH2Cl | D-56a |
| 3,5-Cl$_2$ | CF$_3$ | C(O)OCH$_2$CH2OCH$_3$ | D-56a |
| 3,5-Cl$_2$ | CF$_3$ | C(O)OCH$_2$CH═CH$_2$ | D-56a |
| 3,5-Cl$_2$ | CF$_3$ | CH$_3$ | (D-56b)Cl |
| 3,5-Cl$_2$ | CF$_3$ | CH2OCH$_3$ | (D-56b)Cl |
| 3,5-Cl$_2$ | CF$_3$ | C(O)CH$_3$ | (D-56b)Cl |
| 3,5-Cl$_2$ | CF$_3$ | C(O)OCH$_3$ | (D-56b)Cl |
| 3,5-Cl$_2$ | CF$_3$ | C(O)OCH$_3$ | (D-56b)CH$_3$ |
| 3,5-Cl$_2$ | CF$_3$ | CH$_3$ | (D-56b)Et |
| 3,5-Cl$_2$ | CF$_3$ | CH2OCH$_3$ | (D-56b)Bu-t |
| 3,5-Cl$_2$ | CF$_3$ | C(O)CH$_3$ | (D-56b)OCH$_3$ |
| 3,5-Cl$_2$ | CF$_3$ | CH$_3$ | (D-56c)Cl |
| 3,5-Cl$_2$ | CF$_3$ | CH$_2$OCH$_3$ | (D-56c)Cl |
| 3,5-Cl$_2$ | CF$_3$ | C(O)CH$_3$ | (D-56c)Cl |
| 3,5-Cl$_2$ | CF$_3$ | C(O)OCH$_3$ | (D-56c)Cl |
| 3,5-Cl$_2$ | CF$_3$ | C(O)OCH$_3$ | (D-56c)I |
| 3,5-Cl$_2$ | CF$_3$ | CH$_3$ | (D-56c)CH$_3$ |
| 3,5-Cl$_2$ | CF$_3$ | CH$_2$OCH$_3$ | (D-56c)Bu-t |
| 3,5-Cl$_2$ | CF$_3$ | C(O)CH$_3$ | (D-56c)OCH$_3$ |
| 3,5-Cl$_2$ | CF$_3$ | C(O)OCH$_3$ | (D-56c)OCHF$_2$ |
| 3,5-Cl$_2$ | CF$_3$ | CH$_3$ | (D-56c)CN |
| 3,5-Cl$_2$ | CF$_3$ | CH$_2$OCH$_3$ | (D-56c)C(O)NH$_2$ |
| 3,5-Cl$_2$ | CF$_3$ | C(O)CH$_3$ | (D-56d)F |
| 3,5-Cl$_2$ | CF$_3$ | C(O)OCH$_3$ | (D-56d)OCH$_3$ |
| 3,5-Cl$_2$ | CF$_3$ | CH$_3$ | (D-56d)CN |
| 3,5-Cl$_2$ | CF$_3$ | CH$_3$ | D-57a |
| 3,5-Cl$_2$ | CF$_3$ | Et | D-57a |
| 3,5-Cl$_2$ | CF$_3$ | CH$_2$OCH$_3$ | D-57a |
| 3,5-Cl$_2$ | CF$_3$ | CH$_2$OEt | D-57a |
| 3,5-Cl$_2$ | CF$_3$ | CH$_2$OCH$_2$CF$_3$ | D-57a |
| 3,5-Cl$_2$ | CF$_3$ | CH$_2$OCH2CH$_2$OCH$_3$ | D-57a |
| 3,5-Cl$_2$ | CF$_3$ | CH$_2$OC(O)CH$_3$ | D-57a |
| 3,5-Cl$_2$ | CF$_3$ | CH$_2$OC(O)Et | D-57a |
| 3,5-Cl$_2$ | CF$_3$ | CH$_2$OC(O)Pr-n | D-57a |
| 3,5-Cl$_2$ | CF$_3$ | CH$_2$OC(O)Pr-i | D-57a |
| 3,5-Cl$_2$ | CF$_3$ | CH$_2$OC(O)Pr-c | D-57a |
| 3,5-Cl$_2$ | CF$_3$ | CH$_2$OC(O)Bu-t | D-57a |
| 3,5-Cl$_2$ | CF$_3$ | CH$_2$OC(O)Ph | D-57a |
| 3,5-Cl$_2$ | CF$_3$ | CH$_2$OC(O)OCH$_3$ | D-57a |
| 3,5-Cl$_2$ | CF$_3$ | CH$_2$OC(O)OEt | D-57a |
| 3,5-Cl$_2$ | CF$_3$ | CH$_2$OC(O)OPh | D-57a |
| 3,5-Cl$_2$ | CF$_3$ | CH$_2$SC(O)CH$_3$ | D-57a |
| 3,5-Cl$_2$ | CF$_3$ | CH$_2$SC(S)OCH$_3$ | D-57a |
| 3,5-Cl$_2$ | CF$_3$ | CH$_2$SC(S)N(CH$_3$)$_2$ | D-57a |
| 3,5-Cl$_2$ | CF$_3$ | CH$_2$NHC(O)OCH$_3$ | D-57a |
| 3,5-Cl$_2$ | CF$_3$ | CH$_2$CN | D-57a |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | CH$_2$C≡CH | D-57a |
| 3,5-Cl$_2$ | CF$_3$ | C(O)CH$_3$ | D-57a |
| 3,5-Cl$_2$ | CF$_3$ | C(O)Et | D-57a |
| 3,5-Cl$_2$ | CF$_3$ | C(O)Pr-n | D-57a |
| 3,5-Cl$_2$ | CF$_3$ | C(O)Pr-i | D-57a |
| 3,5-Cl$_2$ | CF$_3$ | C(O)Pr-c | D-57a |
| 3,5-Cl$_2$ | CF$_3$ | C(O)Bu-t | D-57a |
| 3,5-Cl$_2$ | CF$_3$ | C(O)CH$_2$OCH$_3$ | D-57a |
| 3,5-Cl$_2$ | CF$_3$ | C(O)CH$_2$SCH$_3$ | D-57a |
| 3,5-Cl$_2$ | CF$_3$ | C(O)OCH$_3$ | D-57a |
| 3,5-Cl$_2$ | CF$_3$ | C(O)OEt | D-57a |
| 3,5-Cl$_2$ | CF$_3$ | C(O)OPr-n | D-57a |
| 3,5-Cl$_2$ | CF$_3$ | C(O)OPr-i | D-57a |
| 3,5-Cl$_2$ | CF$_3$ | C(O)OPr-c | D-57a |
| 3,5-Cl$_2$ | CF$_3$ | C(O)OCH$_2$Cl | D-57a |
| 3,5-Cl$_2$ | CF$_3$ | C(O)OCH$_2$CH$_2$Cl | D-57a |
| 3,5-Cl$_2$ | CF$_3$ | C(O)OCH$_2$CH$_2$OCH$_3$ | D-57a |
| 3,5-Cl$_2$ | CF$_3$ | C(O)OCH$_2$CH=CH$_2$ | D-57a |
| 3,5-Cl$_2$ | CF$_3$ | C(O)OCH$_2$CH≡CH | D-57a |
| 3,5-Cl$_2$ | CF$_3$ | SCCl$_3$ | D-57a |
| 3,5-Cl$_2$ | CF$_3$ | SN(Bu-n)$_2$ | D-57a |
| 3,5-Cl$_2$ | CF$_3$ | SN(Pr-i)CH$_2$CH$_2$C(O)OEt | D-57a |
| 3,5-Cl$_2$ | CF$_3$ | SN(CH$_2$Ph)CH$_2$CH$_2$C(O)OEt | D-57a |
| 3,5-Cl$_2$ | CF$_3$ | SN(CH$_3$)C(O)OBu-n | D-57a |
| 3,5-Cl$_2$ | CF$_3$ | CH$_3$ | (D-57b)F |
| 3,5-Cl$_2$ | CF$_3$ | Et | (D-57b)F |
| 3,5-Cl$_2$ | CF$_3$ | CH$_2$OCH$_3$ | (D-57b)F |
| 3,5-Cl$_2$ | CF$_3$ | CH$_2$OEt | (D-57b)F |
| 3,5-Cl$_2$ | CF$_3$ | CH$_2$OC(O)CH$_3$ | (D-57b)F |
| 3,5-Cl$_2$ | CF$_3$ | CH$_2$OC(O)Et | (D-57b)F |
| 3,5-Cl$_2$ | CF$_3$ | CH$_2$OC(O)OCH$_3$ | (D-57b)F |
| 3,5-Cl$_2$ | CF$_3$ | CH$_2$CN | (D-57b)F |
| 3,5-Cl$_2$ | CF$_3$ | C(O)CH$_3$ | (D-57b)F |
| 3,5-Cl$_2$ | CF$_3$ | C(O)Et | (D-57b)F |
| 3,5-Cl$_2$ | CF$_3$ | C(O)Pr-n | (D-57b)F |
| 3,5-Cl$_2$ | CF$_3$ | C(O)Pr-i | (D-57b)F |
| 3,5-Cl$_2$ | CF$_3$ | C(O)Pr-c | (D-57b)F |
| 3,5-Cl$_2$ | CF$_3$ | C(O)OCH$_3$ | (D-57b)F |
| 3,5-Cl$_2$ | CF$_3$ | C(O)OEt | (D-57b)F |
| 3,5-Cl$_2$ | CF$_3$ | C(O)OPr-n | (D-57b)F |
| 3,5-Cl$_2$ | CF$_3$ | C(O)OPr-i | (D-57b)F |
| 3,5-Cl$_2$ | CF$_3$ | C(O)OCH$_2$Cl | (D-57b)F |
| 3,5-Cl$_2$ | CF$_3$ | C(O)OCH$_2$CH$_2$OCH$_3$ | (D-57b)F |
| 3,5-Cl$_2$ | CF$_3$ | C(O)OCH$_2$CH=CH$_2$ | (D-57b)F |
| 3,5-Cl$_2$ | CF$_3$ | CH$_3$ | (D-57b)Cl |
| 3,5-Cl$_2$ | CF$_3$ | Et | (D-57b)Cl |
| 3,5-Cl$_2$ | CF$_3$ | CH$_2$OCH$_3$ | (D-57b)Cl |
| 3,5-Cl$_2$ | CF$_3$ | CH$_2$OEt | (D-57b)Cl |
| 3,5-Cl$_2$ | CF$_3$ | CH$_2$OCH$_2$CF$_3$ | (D-57b)Cl |
| 3,5-Cl$_2$ | CF$_3$ | CH$_2$OCH$_2$CH$_2$OCH$_3$ | (D-57b)Cl |
| 3,5-Cl$_2$ | CF$_3$ | CH$_2$OC(O)CH$_3$ | (D-57b)Cl |
| 3,5-Cl$_2$ | CF$_3$ | CH$_2$OC(O)Et | (D-57b)Cl |
| 3,5-Cl$_2$ | CF$_3$ | CH$_2$OC(O)Pr-n | (D-57b)Cl |
| 3,5-Cl$_2$ | CF$_3$ | CH$_2$OC(O)Pr-i | (D-57b)Cl |
| 3,5-Cl$_2$ | CF$_3$ | CH$_2$OC(O)Pr-c | (D-57b)Cl |
| 3,5-Cl$_2$ | CF$_3$ | CH$_2$OC(O)Bu-t | (D-57b)Cl |
| 3,5-Cl$_2$ | CF$_3$ | CH$_2$OC(O)Ph | (D-57b)Cl |
| 3,5-Cl$_2$ | CF$_3$ | CH$_2$OC(O)OCH$_3$ | (D-57b)Cl |
| 3,5-Cl$_2$ | CF$_3$ | CH$_2$OC(O)OEt | (D-57b)Cl |
| 3,5-Cl$_2$ | CF$_3$ | CH$_2$OC(O)OPh | (D-57b)Cl |
| 3,5-Cl$_2$ | CF$_3$ | CH$_2$SC(O)CH$_3$ | (D-57b)Cl |
| 3,5-Cl$_2$ | CF$_3$ | CH$_2$SC(S)OCH$_3$ | (D-57b)Cl |
| 3,5-Cl$_2$ | CF$_3$ | CH$_2$SC(S)N(CH$_3$)$_2$ | (D-57b)Cl |
| 3,5-Cl$_2$ | CF$_3$ | CH$_2$NHC(O)OCH$_3$ | (D-57b)Cl |
| 3,5-Cl$_2$ | CF$_3$ | CH$_2$CN | (D-57b)Cl |
| 3,5-Cl$_2$ | CF$_3$ | CH$_2$C≡CH | (D-57b)Cl |
| 3,5-Cl$_2$ | CF$_3$ | C(O)CH$_3$ | (D-57b)Cl |
| 3,5-Cl$_2$ | CF$_3$ | C(O)Et | (D-57b)Cl |
| 3,5-Cl$_2$ | CF$_3$ | C(O)Pr-n | (D-57b)Cl |
| 3,5-Cl$_2$ | CF$_3$ | C(O)Pr-i | (D-57b)Cl |
| 3,5-Cl$_2$ | CF$_3$ | C(O)Pr-c | (D-57b)Cl |
| 3,5-Cl$_2$ | CF$_3$ | C(O)Bu-t | (D-57b)Cl |
| 3,5-Cl$_2$ | CF$_3$ | C(O)CH$_2$OCH$_3$ | (D-57b)Cl |
| 3,5-Cl$_2$ | CF$_3$ | C(O)CH$_2$SCH3 | (D-57b)Cl |
| 3,5-Cl$_2$ | CF$_3$ | C(O)OCH$_3$ | (D-57b)Cl |
| 3,5-Cl$_2$ | CF$_3$ | C(O)OEt | (D-57b)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | C(O)OPr-n | (D-57b)Cl |
| 3,5-Cl$_2$ | CF$_3$ | C(O)OPr-i | (D-57b)Cl |
| 3,5-Cl$_2$ | CF$_3$ | C(O)OPr-c | (D-57b)Cl |
| 3,5-Cl$_2$ | CF$_3$ | C(O)OCH$_2$Cl | (D-57b)Cl |
| 3,5-Cl$_2$ | CF$_3$ | C(O)OCH$_2$CH$_2$Cl | (D-57b)Cl |
| 3,5-Cl$_2$ | CF$_3$ | C(O)OCH$_2$CH$_2$OCH$_3$ | (D-57b)Cl |
| 3,5-Cl$_2$ | CF$_3$ | C(O)OCH$_2$CH=CH$_2$ | (D-57b)Cl |
| 3,5-Cl$_2$ | CF$_3$ | C(O)OCH$_2$C≡CH | (D-57b)Cl |
| 3,5-Cl$_2$ | CF$_3$ | SCCl$_3$ | (D-57b)Cl |
| 3,5-Cl$_2$ | CF$_3$ | SN(Bu-n)$_2$ | (D-57b)Cl |
| 3,5-Cl$_2$ | CF$_3$ | SN(Pr-i)CH$_2$CH$_2$C(O)OEt | (D-57b)Cl |
| 3,5-Cl$_2$ | CF$_3$ | SN(CH$_2$Ph)CH$_2$CH$_2$C(O)OEt | (D-57b)Cl |
| 3,5-Cl$_2$ | CF$_3$ | SN(CH$_3$)C(O)OBu-n | (D-57b)Cl |
| 3,5-Cl$_2$ | CF$_3$ | CH$_3$ | (D-57b)Br |
| 3,5-Cl$_2$ | CF$_3$ | Et | (D-57b)Br |
| 3,5-Cl$_2$ | CF$_3$ | CH$_2$OCH$_3$ | (D-57b)Br |
| 3,5-Cl$_2$ | CF$_3$ | CH$_2$OEt | (D-57b)Br |
| 3,5-Cl$_2$ | CF$_3$ | CH$_2$OCH2CF$_3$ | (D-57b)Br |
| 3,5-Cl$_2$ | CF$_3$ | CH$_2$OC(O)CH$_3$ | (D-57b)Br |
| 3,5-Cl$_2$ | CF$_3$ | CH$_2$OC(O)Et | (D-57b)Br |
| 3,5-Cl$_2$ | CF$_3$ | CH$_2$OC(O)Pr-i | (D-57b)Br |
| 3,5-Cl$_2$ | CF$_3$ | CH$_2$OC(O)Pr-c | (D-57b)Br |
| 3,5-Cl$_2$ | CF$_3$ | CH$_2$OC(O)Bu-t | (D-57b)Br |
| 3,5-Cl$_2$ | CF$_3$ | CH$_2$OC(O)Ph | (D-57b)Br |
| 3,5-Cl$_2$ | CF$_3$ | CH$_2$OC(O)OCH$_3$ | (D-57b)Br |
| 3,5-Cl$_2$ | CF$_3$ | CH$_2$CN | (D-57b)Br |
| 3,5-Cl$_2$ | CF$_3$ | CH$_2$C≡CH | (D-57b)Br |
| 3,5-Cl$_2$ | CF$_3$ | C(O)CH$_3$ | (D-57b)Br |
| 3,5-Cl$_2$ | CF$_3$ | C(O)Et | (D-57b)Br |
| 3,5-Cl$_2$ | CF$_3$ | C(O)Pr-n | (D-57b)Br |
| 3,5-Cl$_2$ | CF$_3$ | C(O)Pr-i | (D-57b)Br |
| 3,5-Cl$_2$ | CF$_3$ | C(O)Pr-c | (D-57b)Br |
| 3,5-Cl$_2$ | CF$_3$ | C(O)Bu-t | (D-57b)Br |
| 3,5-Cl$_2$ | CF$_3$ | C(O)CH$_2$OCH$_3$ | (D-57b)Br |
| 3,5-Cl$_2$ | CF$_3$ | C(O)OCH$_3$ | (D-57b)Br |
| 3,5-Cl$_2$ | CF$_3$ | C(O)OEt | (D-57b)Br |
| 3,5-Cl$_2$ | CF$_3$ | C(O)OPr-n | (D-57b)Br |
| 3,5-Cl$_2$ | CF$_3$ | C(O)OPr-i | (D-57b)Br |
| 3,5-Cl$_2$ | CF$_3$ | C(O)OPr-c | (D-57b)Br |
| 3,5-Cl$_2$ | CF$_3$ | C(O)OCH$_2$Cl | (D-57b)Br |
| 3,5-Cl$_2$ | CF$_3$ | C(O)OCH$_2$CH$_2$Cl | (D-57b)Br |
| 3,5-Cl$_2$ | CF$_3$ | C(O)OCH$_2$CH$_2$OCH$_3$ | (D-57b)Br |
| 3,5-Cl$_2$ | CF$_3$ | C(O)OCH$_2$CH=CH$_2$ | (D-57b)Br |
| 3,5-Cl$_2$ | CF$_3$ | CH$_2$OCH$_3$ | (D-57b)CH$_3$ |
| 3,5-Cl$_2$ | CF$_3$ | C(O)CH$_3$ | (D-57b)CF$_3$ |
| 3,5-Cl$_2$ | CF$_3$ | NH$_2$ | (D-57b)CF$_3$ |
| 3,5-Cl$_2$ | CF$_3$ | C(O)OCH$_3$ | (D-57b)OCH$_3$ |
| 3,5-Cl$_2$ | CF$_3$ | CH$_3$ | (D-57b)SCH$_3$ |
| 3,5-Cl$_2$ | CF$_3$ | CH$_2$OCH | (D-57b)SO$_2$CH$_3$ |
| 3,5-Cl$_2$ | CF$_3$ | C(O)OCH$_3$ | (D-57b)N(CH$_3$)$_2$ |
| 3,5-Cl$_2$ | CF$_3$ | CH$_3$ | (D-57b)CN |
| 3,5-Cl$_2$ | CF$_3$ | CH$_2$OCH$_3$ | (D-57b)CN |
| 3,5-Cl$_2$ | CF$_3$ | CH$_2$OEt | (D-57b)CN |
| 3,5-Cl$_2$ | CF$_3$ | CH$_2$OC(O)CH$_3$ | (D-57b)CN |
| 3,5-Cl$_2$ | CF$_3$ | CH$_2$OC(O)OCH$_3$ | (D-57b)CN |
| 3,5-Cl$_2$ | CF$_3$ | CH$_2$CN | (D-57b)CN |
| 3,5-Cl$_2$ | CF$_3$ | C(O)CH$_3$ | (D-57b)CN |
| 3,5-Cl$_2$ | CF$_3$ | C(O)Et | (D-57b)CN |
| 3,5-Cl$_2$ | CF$_3$ | C(O)Pr-i | (D-57b)CN |
| 3,5-Cl$_2$ | CF$_3$ | C(O)OCH$_3$ | (D-57b)CN |
| 3,5-Cl$_2$ | CF$_3$ | C(O)OCH$_3$ | (D-57b)C(O)OCH$_3$ |
| 3,5-Cl$_2$ | CF$_3$ | CH$_3$ | (D-57c)Cl |
| 3,5-Cl$_2$ | CF$_3$ | CH$_2$OCH$_3$ | (D-57c)OCH$_3$ |
| 3,5-Cl$_2$ | CF$_3$ | CH$_3$ | D-58a |
| 3,5-Cl$_2$ | CF$_3$ | Et | D-58a |
| 3,5-Cl$_2$ | CF$_3$ | CH$_2$OCH$_3$ | D-58a |
| 3,5-Cl$_2$ | CF$_3$ | CH$_2$OEt | D-58a |
| 3,5-Cl$_2$ | CF$_3$ | CH$_2$OCH2CF$_3$ | D-58a |
| 3,5-Cl$_2$ | CF$_3$ | CH$_2$OC(O)CH$_3$ | D-58a |
| 3,5-Cl$_2$ | CF$_3$ | CH$_2$OC(O)Et | D-58a |
| 3,5-Cl$_2$ | CF$_3$ | CH$_2$OC(O)Pr-i | D-58a |
| 3,5-Cl$_2$ | CF$_3$ | CH$_2$OC(O)Pr-c | D-58a |
| 3,5-Cl$_2$ | CF$_3$ | CH$_2$OC(O)Bu-t | D-58a |
| 3,5-Cl$_2$ | CF$_3$ | CH$_2$OC(O)Ph | D-58a |
| 3,5-Cl$_2$ | CF$_3$ | CH$_2$OC(O)OCH$_3$ | D-58a |
| 3,5-Cl$_2$ | CF$_3$ | CH$_2$CN | D-58a |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | CH$_2$C≡CH | D-58a |
| 3,5-Cl$_2$ | CF$_3$ | C(O)CH$_3$ | D-58a |
| 3,5-Cl$_2$ | CF$_3$ | C(O)Et | D-58a |
| 3,5-Cl$_2$ | CF$_3$ | C(O)Pr-n | D-58a |
| 3,5-Cl$_2$ | CF$_3$ | C(O)Pr-i | D-58a |
| 3,5-Cl$_2$ | CF$_3$ | C(O)Pr-c | D-58a |
| 3,5-Cl$_2$ | CF$_3$ | C(O)Bu-t | D-58a |
| 3,5-Cl$_2$ | CF$_3$ | C(O)CH$_2$OCH$_3$ | D-58a |
| 3,5-Cl$_2$ | CF$_3$ | C(O)OCH$_3$ | D-58a |
| 3,5-Cl$_2$ | CF$_3$ | C(O)OEt | D-58a |
| 3,5-Cl$_2$ | CF$_3$ | C(O)OPr-n | D-58a |
| 3,5-Cl$_2$ | CF$_3$ | C(O)OPr-i | D-58a |
| 3,5-Cl$_2$ | CF$_3$ | C(O)OPr-c | D-58a |
| 3,5-Cl$_2$ | CF$_3$ | C(O)OCH$_2$Cl | D-58a |
| 3,5-Cl$_2$ | CF$_3$ | C(O)OCH$_2$CH2Cl | D-58a |
| 3,5-Cl$_2$ | CF$_3$ | C(O)OCH$_2$CH$_2$OCH$_3$ | D-58a |
| 3,5-Cl$_2$ | CF$_3$ | C(O)OCH$_2$CH═CH$_2$ | D-58a |
| 3,5-Cl$_2$ | CF$_3$ | CH$_3$ | (D-58b)Cl |
| 3,5-Cl$_2$ | CF$_3$ | Et | (D-58b)Cl |
| 3,5-Cl$_2$ | CF$_3$ | CH$_2$OCH$_3$ | (D-58b)Cl |
| 3,5-Cl$_2$ | CF$_3$ | CH$_2$OEt | (D-58b)Cl |
| 3,5-Cl$_2$ | CF$_3$ | CH$_2$OCH$_2$CF$_3$ | (D-58b)Cl |
| 3,5-Cl$_2$ | CF$_3$ | CH$_2$OCH$_2$CH$_2$OCH$_3$ | (D-58b)Cl |
| 3,5-Cl$_2$ | CF$_3$ | CH$_2$OC(O)CH$_3$ | (D-58b)Cl |
| 3,5-Cl$_2$ | CF$_3$ | CH$_2$OC(O)Et | (D-58b)Cl |
| 3,5-Cl$_2$ | CF$_3$ | CH$_2$OC(O)Pr-n | (D-58b)Cl |
| 3,5-Cl$_2$ | CF$_3$ | CH$_2$OC(O)Pr-i | (D-58b)Cl |
| 3,5-Cl$_2$ | CF$_3$ | CH$_2$OC(O)Pr-c | (D-58b)Cl |
| 3,5-Cl$_2$ | CF$_3$ | CH$_2$OC(O)Bu-t | (D-58b)Cl |
| 3,5-Cl$_2$ | CF$_3$ | CH$_2$OC(O)Ph | (D-58b)Cl |
| 3,5-Cl$_2$ | CF$_3$ | CH$_2$OC(O)OCH$_3$ | (D-58b)Cl |
| 3,5-Cl$_2$ | CF$_3$ | CH$_2$OC(O)OEt | (D-58b)Cl |
| 3,5-Cl$_2$ | CF$_3$ | CH$_2$OC(O)OPh | (D-58b)Cl |
| 3,5-Cl$_2$ | CF$_3$ | CH$_2$SC(O)CH$_3$ | (D-58b)Cl |
| 3,5-Cl$_2$ | CF$_3$ | CH$_2$SC(S)OCH$_3$ | (D-58b)Cl |
| 3,5-Cl$_2$ | CF$_3$ | CH$_2$SC(S)N(CH3)$_2$ | (D-58b)Cl |
| 3,5-Cl$_2$ | CF$_3$ | CH$_2$NHC(O)OCH$_3$ | (D-58b)Cl |
| 3,5-Cl$_2$ | CF$_3$ | CH$_2$CN | (D-58b)Cl |
| 3,5-Cl$_2$ | CF$_3$ | CH$_2$C≡CH | (D-58b)Cl |
| 3,5-Cl$_2$ | CF$_3$ | C(O)CH$_3$ | (D-58b)Cl |
| 3,5-Cl$_2$ | CF$_3$ | C(O)Et | (D-58b)Cl |
| 3,5-Cl$_2$ | CF$_3$ | C(O)Pr-n | (D-58b)Cl |
| 3,5-Cl$_2$ | CF$_3$ | C(O)Pr-i | (D-58b)Cl |
| 3,5-Cl$_2$ | CF$_3$ | C(O)Pr-c | (D-58b)Cl |
| 3,5-Cl$_2$ | CF$_3$ | C(O)Bu-t | (D-58b)Cl |
| 3,5-Cl$_2$ | CF$_3$ | C(O)CH$_2$OCH$_3$ | (D-58b)Cl |
| 3,5-Cl$_2$ | CF$_3$ | C(O)CH$_2$SCH$_3$ | (D-58b)Cl |
| 3,5-Cl$_2$ | CF$_3$ | C(O)OCH$_3$ | (D-58b)Cl |
| 3,5-Cl$_2$ | CF$_3$ | C(O)OEt | (D-58b)Cl |
| 3,5-Cl$_2$ | CF$_3$ | C(O)OPr-n | (D-58b)Cl |
| 3,5-Cl$_2$ | CF$_3$ | C(O)OPr-i | (D-58b)Cl |
| 3,5-Cl$_2$ | CF$_3$ | C(O)OPr-c | (D-58b)Cl |
| 3,5-Cl$_2$ | CF$_3$ | C(O)OCH$_2$Cl | (D-58b)Cl |
| 3,5-Cl$_2$ | CF$_3$ | C(O)OCH$_2$CH$_2$Cl | (D-58b)Cl |
| 3,5-Cl$_2$ | CF$_3$ | C(O)OCH$_2$CH$_2$OCH$_3$ | (D-58b)Cl |
| 3,5-Cl$_2$ | CF$_3$ | C(O)OCH$_2$CH═CH$_2$ | (D-58b)Cl |
| 3,5-Cl$_2$ | CF$_3$ | C(O)OCH$_2$C≡CH | (D-58b)Cl |
| 3,5-Cl$_2$ | CF$_3$ | SCCl$_3$ | (D-58b)Cl |
| 3,5-Cl$_2$ | CF$_3$ | SN(Bu-n)$_2$ | (D-58b)Cl |
| 3,5-Cl$_2$ | CF$_3$ | SN(Pr-i)CH$_2$CH$_2$C(O)OEt | (D-58b)Cl |
| 3,5-Cl$_2$ | CF$_3$ | SN(CH$_2$Ph)CH$_2$CH$_2$C(O)OEt | (D-58b)Cl |
| 3,5-Cl$_2$ | CF$_3$ | SN(CH$_3$)C(O)OBu-n | (D-58b)Cl |
| 3,5-Cl$_2$ | CF$_3$ | CH$_3$ | (D-58b)Br |
| 3,5-Cl$_2$ | CF$_3$ | Et | (D-58b)Br |
| 3,5-Cl$_2$ | CF$_3$ | CH$_2$OCH$_3$ | (D-58b)Br |
| 3,5-Cl$_2$ | CF$_3$ | CH$_2$OEt | (D-58b)Br |
| 3,5-Cl$_2$ | CF$_3$ | CH$_2$OC(O)CH$_3$ | (D-58b)Br |
| 3,5-Cl$_2$ | CF$_3$ | CH$_2$OC(O)Et | (D-58b)Br |
| 3,5-Cl$_2$ | CF$_3$ | CH$_2$OC(O)OCH$_3$ | (D-58b)Br |
| 3,5-Cl$_2$ | CF$_3$ | CH$_2$CN | (D-58b)Br |
| 3,5-Cl$_2$ | CF$_3$ | C(O)CH$_3$ | (D-58b)Br |
| 3,5-Cl$_2$ | CF$_3$ | C(O)Et | (D-58b)Br |
| 3,5-Cl$_2$ | CF$_3$ | C(O)Pr-n | (D-58b)Br |
| 3,5-Cl$_2$ | CF$_3$ | C(O)Pr-i | (D-58b)Br |
| 3,5-Cl$_2$ | CF$_3$ | C(O)Pr-c | (D-58b)Br |
| 3,5-Cl$_2$ | CF$_3$ | C(O)OCH$_3$ | (D-58b)Br |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_3$ | C(O)OEt | (D-58b)Br |
| 3,5-Cl$_2$ | CF$_3$ | C(O)OPr-n | (D-58b)Br |
| 3,5-Cl$_2$ | CF$_3$ | C(O)OPr-i | (D-58b)Br |
| 3,5-Cl$_2$ | CF$_3$ | C(O)OCH$_2$Cl | (D-58b)Br |
| 3,5-Cl$_2$ | CF$_3$ | C(O)OCH$_2$CH$_2$OCH$_3$ | (D-58b)Br |
| 3,5-Cl$_2$ | CF$_3$ | C(O)OCH$_2$CH=CH$_2$ | (D-58b)Br |
| 3,5-Cl$_2$ | CF$_3$ | C(O)CH$_3$ | (D-58b)CH$_3$ |
| 3,5-Cl$_2$ | CF$_3$ | C(O)OCH$_3$ | (D-58b)CH$_2$OCH$_3$ |
| 3,5-Cl$_2$ | CF$_3$ | CH$_3$ | (D-58b)CH$_2$SCH$_3$ |
| 3,5-Cl$_2$ | CF$_3$ | CH$_2$OCH$_3$ | (D-58b)NO$_2$ |
| 3,5-Cl$_2$ | CF$_3$ | CH$_3$ | (D-58b)CN |
| 3,5-Cl$_2$ | CF$_3$ | CH$_2$OCH$_3$ | (D-58b)CN |
| 3,5-Cl$_2$ | CF$_3$ | CH$_2$OEt | (D-58b)CN |
| 3,5-Cl$_2$ | CF$_3$ | CH$_2$OC(O)CH$_3$ | (D-58b)CN |
| 3,5-Cl$_2$ | CF$_3$ | CH$_2$OC(O)OCH$_3$ | (D-58b)CN |
| 3,5-Cl$_2$ | CF$_3$ | CH$_2$CN | (D-58b)CN |
| 3,5-Cl$_2$ | CF$_3$ | C(O)CH$_3$ | (D-58b)CN |
| 3,5-Cl$_2$ | CF$_3$ | C(O)Et | (D-58b)CN |
| 3,5-Cl$_2$ | CF$_3$ | C(O)Pr-i | (D-58b)CN |
| 3,5-Cl$_2$ | CF$_3$ | C(O)OCH$_3$ | (D-58b)CN |
| 3,5-Cl$_2$ | CF$_3$ | C(O)CH$_3$ | (D-58b)C(O)OCH$_3$ |
| 3,5-Cl$_2$ | CF$_3$ | C(O)OCH$_3$ | (D-58b)C(O)NH$_2$ |
| 3,5-Cl$_2$ | CF$_3$ | CH$_3$ | (D-58c)F |
| 3,5-Cl$_2$ | CF$_3$ | CH$_2$OCH$_3$ | (D-58c)Cl |
| 3,5-Cl$_2$ | CF$_3$ | C(O)CH$_3$ | (D-58c)CH$_3$ |
| 3,5-Cl$_2$ | CF$_3$ | C(O)OCH$_3$ | (D-58c)OCH$_3$ |
| 3,5-Cl$_2$ | CF$_3$ | CH$_3$ | (D-58c)CN |
| 3,5-Cl$_2$ | CF$_3$ | CH$_2$OCH$_3$ | (D-58d)Cl |
| 3,5-Cl$_2$ | CF$_3$ | C(O)CH$_3$ | (D-58d)OCH$_3$ |
| 3,5-Cl$_2$ | CF$_3$ | C(O)OCH$_3$ | (D-58d)SCH$_3$ |
| 3,5-Cl$_2$ | CF$_3$ | CH$_3$ | (D-58d)CN |
| 3,5-Cl$_2$ | CF$_3$ | CH$_3$ | D-59a |
| 3,5-Cl$_2$ | CF$_3$ | CH$_2$OCH$_3$ | D-59a |
| 3,5-Cl$_2$ | CF$_3$ | C(O)CH$_3$ | D-59a |
| 3,5-Cl$_2$ | CF$_3$ | C(O)OCH$_3$ | D-59a |
| 3,5-Cl$_2$ | CF$_3$ | CH$_3$ | (D-59b)F |
| 3,5-Cl$_2$ | CF$_3$ | CH$_2$OCH$_3$ | (D-59b)F |
| 3,5-Cl$_2$ | CF$_3$ | C(O)CH$_3$ | (D-59b)F |
| 3,5-Cl$_2$ | CF$_3$ | C(O)OCH$_3$ | (D-59b)F |
| 3,5-Cl$_2$ | CF$_3$ | CH$_3$ | (D-59b)Cl |
| 3,5-Cl$_2$ | CF$_3$ | CH$_2$OCH$_3$ | (D-59b)Cl |
| 3,5-Cl$_2$ | CF$_3$ | CH$_2$OEt | (D-59b)Cl |
| 3,5-Cl$_2$ | CF$_3$ | CH$_2$OC(O)CH$_3$ | (D-59b)Cl |
| 3,5-Cl$_2$ | CF$_3$ | CH$_2$OC(O)OCH$_3$ | (D-59b)Cl |
| 3,5-Cl$_2$ | CF$_3$ | CH$_2$CN | (D-59b)Cl |
| 3,5-Cl$_2$ | CF$_3$ | C(O)CH$_3$ | (D-59b)Cl |
| 3,5-Cl$_2$ | CF$_3$ | C(O)Et | (D-59b)Cl |
| 3,5-Cl$_2$ | CF$_3$ | C(O)Pr-i | (D-59b)Cl |
| 3,5-Cl$_2$ | CF$_3$ | C(O)OCH$_3$ | (D-59b)Cl |
| 3,5-Cl$_2$ | CF$_3$ | CH$_3$ | (D-59b)Br |
| 3,5-Cl$_2$ | CF$_3$ | CH$_2$OCH$_3$ | (D-59b)Br |
| 3,5-Cl$_2$ | CF$_3$ | C(O)CH$_3$ | (D-59b)Br |
| 3,5-Cl$_2$ | CF$_3$ | C(O)OCH$_3$ | (D-59b)Br |
| 3,5-Cl$_2$ | CF$_3$ | CH$_3$ | (D-59b)I |
| 3,5-Cl$_2$ | CF$_3$ | CH$_2$OCH$_3$ | (D-59b)I |
| 3,5-Cl$_2$ | CF$_3$ | C(O)CH3 | (D-59b)I |
| 3,5-Cl$_2$ | CF$_3$ | C(O)OCH$_3$ | (D-59b)I |
| 3,5-Cl$_2$ | CF$_3$ | CH$_2$OCH$_3$ | (D-59b)CH$_3$ |
| 3,5-Cl$_2$ | CF$_3$ | C(O)CH$_3$ | (D-59b)OCH$_3$ |
| 3,5-Cl$_2$ | CF$_3$ | C(O)OCH$_3$ | (D-59b)SCH$_3$ |
| 3,5-Cl$_2$ | CF$_3$ | CH$_3$ | (D-59b)CN |
| 3,5-Cl$_2$ | CF$_3$ | CH$_2$OCH$_3$ | (D-59b)C(O)OCH$_3$ |
| 3,5-Cl$_2$ | CF$_3$ | C(O)CH$_3$ | (D-59b)C(O)NH$_2$ |
| 3,5-Cl$_2$ | CF$_3$ | C(O)OCH$_3$ | D-60a |
| 3,5-Cl$_2$ | CF$_3$ | CH$_3$ | D-61a |
| 3,5-Cl$_2$ | CF$_3$ | CH$_2$OCH$_3$ | (D-61b)Cl |
| 3,5-Cl$_2$ | CF$_3$ | C(O)CH$_3$ | D-62a |
| 3,5-Cl$_2$ | CF$_3$ | C(O)OCH$_3$ | (D-62b)I |
| 3,5-Cl$_2$ | CF$_3$ | CH$_3$ | (D-62b)CH$_3$ |
| 3,5-Cl$_2$ | CF$_3$ | CH$_2$OCH$_3$ | (D-62b)CF$_3$ |
| 3,5-Cl$_2$ | CF$_3$ | C(O)CH$_3$ | D-63a |
| 3,5-Cl$_2$ | CF$_3$ | C(O)OCH$_3$ | (D-63b)CH$_3$ |
| 3,5-Cl$_2$ | CF$_3$ | CH$_3$ | D-64a |
| 3,5-Cl$_2$ | CF$_3$ | CH$_2$OCH$_3$ | (D-65b)Cl |
| 3,5-Cl$_2$ | CF$_3$ | =CH$_2$ | |
| 3,5-Cl$_2$ | CF$_3$ | =CHOCH$_3$ | |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_3$ | =CHOEt | |
| 3,5-Cl$_2$ | CF$_3$ | =CHOPr-n | |
| 3,5-Cl$_2$ | CF$_3$ | =CHOPr-i | |
| 3,5-Cl$_2$ | CF$_3$ | =CHN(CH$_3$)$_2$ | |
| 3,5-Cl$_2$ | CF$_3$ | =C(CH$_3$)OEt | |
| 3,5-Cl$_2$ | CF$_3$ | =C(CH$_3$)SCH$_3$ | |
| 3,5-Cl$_2$ | CF$_3$ | =C(CH$_3$)N(CH$_3$)$_2$ | |
| 3,5-Cl$_2$ | CF$_3$ | =C(CF$_3$)SPh | |
| 3,5-Cl$_2$ | CF$_3$ | =C(OCH$_3$)SCH$_3$ | |
| 3,5-Cl$_2$ | CF$_3$ | =C(OCH$_3$)SEt | |
| 3,5-Cl$_2$ | CF$_3$ | =C(OCH$_3$)SCH$_2$OCH$_3$ | |
| 3,5-Cl$_2$ | CF$_3$ | =C(OCH$_3$)SCH$_2$OEt | |
| 3,5-Cl$_2$ | CF$_3$ | =C(OCH$_3$)SCH$_2$SCH$_3$ | |
| 3,5-Cl$_2$ | CF$_3$ | =C(OCH$_3$)SCH$_2$C(O)Ph | |
| 3,5-Cl$_2$ | CF$_3$ | =C(OCH$_3$)SCH$_2$CN | |
| 3,5-Cl$_2$ | CF$_3$ | =C(OCH$_3$)SCH$_2$C(O)OCH$_3$ | |
| 3,5-Cl$_2$ | CF$_3$ | =C(OCH$_3$)SCH$_2$CH=CH$_2$ | |
| 3,5-Cl$_2$ | CF$_3$ | =C(OCH$_3$)SCH$_2$Cl=CH | |
| 3,5-Cl$_2$ | CF$_3$ | =C(OCH$_3$)SCH$_2$Ph | |
| 3,5-Cl$_2$ | CF$_3$ | =C(OCH$_3$)SC(O)CH$_3$ | |
| 3,5-Cl$_2$ | CF$_3$ | =C(OCH$_3$)SC(O)OCH$_3$ | |
| 3,5-Cl$_2$ | CF$_3$ | =C(OEt)$_2$ | |
| 3,5-Cl$_2$ | CF$_3$ | =C(OEt)SCH$_3$ | |
| 3,5-Cl$_2$ | CF$_3$ | =C(OEt)SCH$_2$Ph | |
| 3,5-Cl$_2$ | CF$_3$ | =C(OEt)N(CH$_3$)$_2$ | |
| 3,5-Cl$_2$ | CF$_3$ | =C(SCH$_3$)$_2$ | |
| 3,5-Cl$_2$ | CF$_3$ | =C(SCH$_3$)N(CH$_3$)$_2$ | |
| 3,5-Cl$_2$ | CF$_3$ | =C(SEt)$_2$ | |
| 3,5-Cl$_2$ | CF$_3$ | =C(SBu-t)N(CH$_3$)$_2$ | |
| 3,5-Cl$_2$ | CF$_3$ | =C(OPh)$_2$ | |
| 3,5-Cl$_2$ | CF$_3$ | =C(OPh)N(CH$_3$)$_2$ | |
| 3,5-Cl$_2$ | CF$_3$ | =C(OPh)N(Et)$_2$ | |
| 3,5-Cl$_2$ | CF$_3$ | =C(SPh)N(CH$_3$)$_2$ | |
| 3,5-Cl$_2$ | CF$_3$ | =C(Ph)SCH$_3$ | |
| 3,5-Cl$_2$ | CF$_3$ | =C(Ph)SO$_2$CH$_3$ | |
| 3,5-Cl$_2$ | CF$_2$Cl | H | CH=NOCH$_3$ |
| 3,5-Cl$_2$ | CF$_2$Cl | CH$_2$OCH$_3$ | CH=NOCH$_3$ |
| 3,5-Cl$_2$ | CF$_2$Cl | CH$_2$OEt | CH=NOCH$_3$ |
| 3,5-Cl$_2$ | CF$_2$Cl | H | CH=NOEt |
| 3,5-Cl$_2$ | CF$_2$Cl | CH$_2$OCH$_3$ | CH=NOEt |
| 3,5-Cl$_2$ | CF$_2$Cl | H | CH=NOPr-n |
| 3,5-Cl$_2$ | CF$_2$Cl | H | CH=NOCH$_2$CF$_3$ |
| 3,5-Cl$_2$ | CF$_2$Cl | H | CH=NOCH$_2$CH=CH$_2$ |
| 3,5-Cl$_2$ | CF$_2$Cl | H | CH=NOCH$_2$C≡CH |
| 3,5-Cl$_2$ | CF$_2$Cl | H | C(O)OCH$_3$ |
| 3,5-Cl$_2$ | CF$_2$Cl | CH$_3$ | C(O)OCH$_3$ |
| 3,5-Cl$_2$ | CF$_2$Cl | Et | C(O)OCH$_3$ |
| 3,5-Cl$_2$ | CF$_2$Cl | CH$_2$OCH$_3$ | C(O)OCH$_3$ |
| 3,5-Cl$_2$ | CF$_2$Cl | CH$_2$OEt | C(O)OCH$_3$ |
| 3,5-Cl$_2$ | CF$_2$Cl | CH$_2$OCH$_2$CF$_3$ | C(O)OCH$_3$ |
| 3,5-Cl$_2$ | CF$_2$Cl | CH$_2$OC(O)CH$_3$ | C(O)OCH$_3$ |
| 3,5-Cl$_2$ | CF$_2$Cl | CH$_2$OC(O)Et | C(O)OCH$_3$ |
| 3,5-Cl$_2$ | CF$_2$Cl | CH$_2$OC(O)Bu-t | C(O)OCH$_3$ |
| 3,5-Cl$_2$ | CF$_2$Cl | CH$_2$OC(O)OCH$_3$ | C(O)OCH$_3$ |
| 3,5-Cl$_2$ | CF$_2$Cl | E-5a | C(O)OCH$_3$ |
| 3,5-Cl$_2$ | CF$_2$Cl | CH$_2$NHC(O)OCH$_3$ | C(O)OCH$_3$ |
| 3,5-Cl$_2$ | CF$_2$Cl | CH$_2$CN | C(O)OCH$_3$ |
| 3,5-Cl$_2$ | CF$_2$Cl | CH$_2$C≡CH | C(O)OCH$_3$ |
| 3,5-Cl$_2$ | CF$_2$Cl | CH$_2$Ph | C(O)OCH$_3$ |
| 3,5-Cl$_2$ | CF$_2$Cl | C(O)CH$_3$ | C(O)OCH$_3$ |
| 3,5-Cl$_2$ | CF$_2$Cl | C(O)Et | C(O)OCH$_3$ |
| 3,5-Cl$_2$ | CF$_2$Cl | C(O)Pr-n | C(O)OCH$_3$ |
| 3,5-Cl$_2$ | CF$_2$Cl | C(O)Pr-i | C(O)OCH$_3$ |
| 3,5-Cl$_2$ | CF$_2$Cl | C(O)Bu-t | C(O)OCH$_3$ |
| 3,5-Cl$_2$ | CF$_2$Cl | C(O)CH$_2$Cl | C(O)OCH$_3$ |
| 3,5-Cl$_2$ | CF$_2$Cl | C(O)CH$_2$OCH$_3$ | C(O)OCH$_3$ |
| 3,5-Cl$_2$ | CF$_2$Cl | C(O)CH$_2$OEt | C(O)OCH$_3$ |
| 3,5-Cl$_2$ | CF$_2$Cl | C(O)CH$_2$SCH$_3$ | C(O)OCH$_3$ |
| 3,5-Cl$_2$ | CF$_2$Cl | C(O)Ph | C(O)OCH$_3$ |
| 3,5-Cl$_2$ | CF$_2$Cl | C(O)OCH$_3$ | C(O)OCH$_3$ |
| 3,5-Cl$_2$ | CF$_2$Cl | C(O)OCH$_2$Cl | C(O)OCH$_3$ |
| 3,5-Cl$_2$ | CF$_2$Cl | C(O)OCH$_2$CH$_2$Cl | C(O)OCH$_3$ |
| 3,5-Cl$_2$ | CF$_2$Cl | H | C(O)OEt |
| 3,5-Cl$_2$ | CF$_2$Cl | CH$_3$ | C(O)OEt |
| 3,5-Cl$_2$ | CF$_2$Cl | Et | C(O)OEt |
| 3,5-Cl$_2$ | CF$_2$Cl | CH$_2$OCH$_3$ | C(O)OEt |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$ | CF$_2$Cl | C(O)CH$_3$ | C(O)OEt |
| 3,5-Cl$_2$ | CF$_2$Cl | C(O)Et | C(O)OEt |
| 3,5-Cl$_2$ | CF$_2$Cl | C(O)Bu-t | C(O)OEt |
| 3,5-Cl$_2$ | CF$_2$Cl | C(O)CH$_2$OCH$_3$ | C(O)OEt |
| 3,5-Cl$_2$ | CF$_2$Cl | C(O)OCH$_3$ | C(O)OEt |
| 3,5-Cl$_2$ | CF$_2$Cl | H | C(O)OPr-n |
| 3,5-Cl$_2$ | CF$_2$Cl | H | C(O)OPr-i |
| 3,5-Cl$_2$ | CF$_2$Cl | CH$_3$ | C(O)OPr-i |
| 3,5-Cl$_2$ | CF$_2$Cl | CH$_2$OCH$_3$ | C(O)OPr-i |
| 3,5-Cl$_2$ | CF$_2$Cl | CH$_2$CN | C(O)OPr-i |
| 3,5-Cl$_2$ | CF$_2$Cl | CH$_2$C≡CH | C(O)OPr-i |
| 3,5-Cl$_2$ | CF$_2$Cl | C(O)CH$_3$ | C(O)OPr-i |
| 3,5-Cl$_2$ | CF$_2$Cl | C(O)Et | C(O)OPr-i |
| 3,5-Cl$_2$ | CF$_2$Cl | C(O)Bu-t | C(O)OPr-i |
| 3,5-Cl$_2$ | CF$_2$Cl | C(O)CH$_2$OCH$_3$ | C(O)OPr-i |
| 3,5-Cl$_2$ | CF$_2$Cl | C(O)OCH$_3$ | C(O)OPr-i |
| 3,5-Cl$_2$ | CF$_2$Cl | C(O)OEt | C(O)OPr-i |
| 3,5-Cl$_2$ | CF$_2$Cl | H | C(O)OBu-t |
| 3,5-Cl$_2$ | CF$_2$Cl | C(O)CH$_3$ | C(O)OBu-t |
| 3,5-Cl$_2$ | CF$_2$Cl | C(O)Et | C(O)OBu-t |
| 3,5-Cl$_2$ | CF$_2$Cl | C(O)CH$_2$CF$_3$ | C(O)OBu-t |
| 3,5-Cl$_2$ | CF$_2$Cl | C(O)OCH$_3$ | C(O)OBu-t |
| 3,5-Cl$_2$ | CF$_2$Cl | C(O)OCH3 | C(O)OCH$_2$CH$_2$OCH$_3$ |
| 3,5-Cl$_2$ | CF$_2$Cl | H | C(O)NH$_2$ |
| 3,5-Cl$_2$ | CF$_2$Cl | CH$_3$ | C(O)NH$_2$ |
| 3,5-Cl$_2$ | CF$_2$Cl | CH$_3$ | C(O)NHC(O)CH$_3$ |
| 3,5-Cl$_2$ | CF$_2$Cl | CH$_3$ | C(O)NHC(O)OCH$_3$ |
| 3,5-Cl$_2$ | CF$_2$Cl | H | C(S)NH$_2$ |
| 3,5-Cl$_2$ | CF$_2$Cl | CH$_3$ | D-14a |
| 3,5-Cl$_2$ | CF$_2$Cl | C(O)CH$_3$ | D-14a |
| 3,5-Cl$_2$ | CF$_2$Cl | C(O)OCH$_3$ | D-14a |
| 3,5-Cl$_2$ | CF$_2$Cl | CH$_3$ | (D-52d)Cl |
| 3,5-Cl$_2$ | CF$_2$Cl | CH$_2$OCH$_3$ | (D-52d)Cl |
| 3,5-Cl$_2$ | CF$_2$Cl | C(O)CH$_3$ | (D-52d)Cl |
| 3,5-Cl$_2$ | CF$_2$Cl | C(O)Et | (D-52d)Cl |
| 3,5-Cl$_2$ | CF$_2$Cl | C(O)OCH$_3$ | (D-52d)Cl |
| 3,5-Cl$_2$ | CF$_2$Cl | CH$_3$ | (D-52d)Br |
| 3,5-Cl$_2$ | CF$_2$Cl | C(O)OCH$_3$ | (D-52d)Br |
| 3,5-Cl$_2$ | CF$_2$Cl | CH$_3$ | (D-52d)CN |
| 3,5-Cl$_2$ | CF$_2$Cl | CH$_3$ | (D-53e)Cl |
| 3,5-Cl$_2$ | CF$_2$Cl | C(O)OCH$_3$ | (D-53e)Cl |
| 3,5-Cl$_2$ | CF$_2$Cl | CH$_3$ | D-55a |
| 3,5-Cl$_2$ | CF$_2$Cl | C(O)CH$_3$ | D-55a |
| 3,5-Cl$_2$ | CF$_2$Cl | C(O)Pr-i | D-55a |
| 3,5-Cl$_2$ | CF$_2$Cl | C(O)Bu-t | (D-55c)Cl |
| 3,5-Cl$_2$ | CF$_2$Cl | CH$_3$ | (D-55c)Cl |
| 3,5-Cl$_2$ | CF$_2$Cl | Et | (D-55c)Cl |
| 3,5-Cl$_2$ | CF$_2$Cl | CH$_2$OCH$_3$ | (D-55c)Cl |
| 3,5-Cl$_2$ | CF$_2$Cl | CH$_2$OEt | (D-55c)Cl |
| 3,5-Cl$_2$ | CF$_2$Cl | CH$_2$OC(O)CH$_3$ | (D-55c)Cl |
| 3,5-Cl$_2$ | CF$_2$Cl | CH$_2$OC(O)Bu-t | (D-55c)Cl |
| 3,5-Cl$_2$ | CF$_2$Cl | CH$_2$OC(O)OCH$_3$ | (D-55c)Cl |
| 3,5-Cl$_2$ | CF$_2$Cl | CH$_2$CN | (D-55c)Cl |
| 3,5-Cl$_2$ | CF$_2$Cl | CH$_2$C≡CH | (D-55c)Cl |
| 3,5-Cl$_2$ | CF$_2$Cl | C(O)CH$_3$ | (D-55c)Cl |
| 3,5-Cl$_2$ | CF$_2$Cl | C(O)Et | (D-55c)Cl |
| 3,5-Cl$_2$ | CF$_2$Cl | C(O)Pr-n | (D-55c)Cl |
| 3,5-Cl$_2$ | CF$_2$Cl | C(O)Pr-i | (D-55c)Cl |
| 3,5-Cl$_2$ | CF$_2$Cl | C(O)Pr-c | (D-55c)Cl |
| 3,5-Cl$_2$ | CF$_2$Cl | C(O)Bu-t | (D-55c)Cl |
| 3,5-Cl$_2$ | CF$_2$Cl | C(O)CH$_2$Cl | (D-55c)Cl |
| 3,5-Cl$_2$ | CF$_2$Cl | C(O)CH$_2$OCH$_3$ | (D-55c)Cl |
| 3,5-Cl$_2$ | CF$_2$Cl | C(O)CH$_2$OEt | (D-55c)Cl |
| 3,5-Cl$_2$ | CF$_2$Cl | C(O)CH$_2$SCH$_3$ | (D-55c)Cl |
| 3,5-Cl$_2$ | CF$_2$Cl | C(O)CH$_2$S(O)CH$_3$ | (D-55c)Cl |
| 3,5-Cl$_2$ | CF$_2$Cl | C(O)C(O)OEt | (D-55c)Cl |
| 3,5-Cl$_2$ | CF$_2$Cl | C(O)Ph | (D-55c)Cl |
| 3,5-Cl$_2$ | CF$_2$Cl | C(O)(D-52a) | (D-55c)Cl |
| 3,5-Cl$_2$ | CF$_2$Cl | C(O)OCH$_3$ | (D-55c)Cl |
| 3,5-Cl$_2$ | CF$_2$Cl | C(O)OEt | (D-55c)Cl |
| 3,5-Cl$_2$ | CF$_2$Cl | C(O)OPr-n | (D-55c)Cl |
| 3,5-Cl$_2$ | CF$_2$Cl | C(O)OPr-i | (D-55c)Cl |
| 3,5-Cl$_2$ | CF$_2$Cl | C(O)OBu-n | (D-55c)Cl |
| 3,5-Cl$_2$ | CF$_2$Cl | C(O)OBu-i | (D-55c)Cl |
| 3,5-Cl$_2$ | CF$_2$Cl | C(O)OBu-t | (D-55c)Cl |
| 3,5-Cl$_2$ | CF$_2$Cl | C(O)OCH$_2$Cl | (D-55c)Cl |

TABLE 2-continued

In the table, the number showing the substitution position of substituent (X)$_m$
corresponds to the position number indicated in the following
structural formulae. The indication "—" means no-substitution.

| | | | |
|---|---|---|---|
| 3,5-Cl$_2$ | CF$_2$Cl | C(O)OCH$_2$CH$_2$Cl | (D-55c)Cl |
| 3,5-Cl$_2$ | CF$_2$Cl | C(O)OCH$_2$CH$_2$OCH$_3$ | (D-55c)Cl |
| 3,5-Cl$_2$ | CF$_2$Cl | C(O)OCH$_2$CH═CH$_2$ | (D-55c)Cl |
| 3,5-Cl$_2$ | CF$_2$Cl | C(O)OPh | (D-55c)Cl |
| 3,5-Cl$_2$ | CF$_2$Cl | CH$_3$ | (D-55c)Br |
| 3,5-Cl$_2$ | CF$_2$Cl | Et | (D-55c)Br |
| 3,5-Cl$_2$ | CF$_2$Cl | CH$_2$OCH$_3$ | (D-55c)Br |
| 3,5-Cl$_2$ | CF$_2$Cl | CH$_2$OEt | (D-55c)Br |
| 3,5-Cl$_2$ | CF$_2$Cl | CH$_2$OC(O)CH$_3$ | (D-55c)Br |
| 3,5-Cl$_2$ | CF$_2$Cl | C(O)CH$_3$ | (D-55c)Br |
| 3,5-Cl$_2$ | CF$_2$Cl | C(O)Et | (D-55c)Br |
| 3,5-Cl$_2$ | CF$_2$Cl | C(O)Pr-n | (D-55c)Br |
| 3,5-Cl$_2$ | CF$_2$Cl | C(O)Pr-i | (D-55c)Br |
| 3,5-Cl$_2$ | CF$_2$Cl | C(O)Pr-c | (D-55c)Br |
| 3,5-Cl$_2$ | CF$_2$Cl | C(O)Bu-t | (D-55c)Br |
| 3,5-Cl$_2$ | CF$_2$Cl | C(O)CH$_2$OCH$_3$ | (D-55c)Br |
| 3,5-Cl$_2$ | CF$_2$Cl | C(O)Ph | (D-55c)Br |
| 3,5-Cl$_2$ | CF$_2$Cl | C(O)OCH$_3$ | (D-55c)Br |
| 3,5-Cl$_2$ | CF$_2$Cl | C(O)OEt | (D-55c)Br |
| 3,5-Cl$_2$ | CF$_2$Cl | C(O)OPr-n | (D-55c)Br |
| 3,5-Cl$_2$ | CF$_2$Cl | C(O)OBu-i | (D-55c)Br |
| 3,5-Cl$_2$ | CF$_2$Cl | C(O)OCH$_2$Cl | (D-55c)Br |
| 3,5-Cl$_2$ | CF$_2$Cl | C(O)OCH$_2$CH$_2$OCH$_3$ | (D-55c)Br |
| 3,5-Cl$_2$ | CF$_2$Cl | CH$_3$ | D-57a |
| 3,5-Cl$_2$ | CF$_2$Cl | C(O)CH$_3$ | D-57a |
| 3,5-Cl$_2$ | CF$_2$Cl | C(O)Pr-n | D-57a |
| 3,5-Cl$_2$ | CF$_2$Cl | C(O)Pr-i | D-57a |
| 3,5-Cl$_2$ | CF$_2$Cl | C(O)OCH$_3$ | D-57a |
| 3,5-Cl$_2$ | CF$_2$Cl | CH$_3$ | D-58a |
| 3,5-Cl$_2$ | CF$_2$Cl | CH$_3$ | (D-58b)Cl |
| 3,5-Cl$_2$ | CF$_2$Cl | CH$_2$OCH$_3$ | (D-58b)Cl |
| 3,5-Cl$_2$ | CF$_2$Cl | C(O)CH$_3$ | (D-58b)Cl |
| 3,5-Cl$_2$ | CF$_2$Cl | C(O)OCH$_3$ | (D-58b)Cl |
| 3,5-Cl$_2$ | CF$_2$Cl | C(O)OCH$_3$ | (D-58b)Cl |
| 3,5-Cl$_2$ | CCl$_2$ | C(O)CH$_3$ | (D-55c)Br |
| 3,5-Cl$_2$ | CFCl$_2$ | H | CH═NOCH$_3$ |
| 3,5-Cl$_2$ | CF$_2$Br | H | CH═NOEt |
| 3,5-Cl$_2$ | CF$_2$Br | H | C(O)OCH$_3$ |
| 3,5-Cl$_2$ | CF$_2$Br | Et | C(O)OCH$_3$ |
| 3,5-Cl$_2$ | CF$_2$Br | CH$_2$OCH$_3$ | C(O)OCH$_3$ |
| 3,5-Cl$_2$ | CF$_2$Br | CH$_2$OEt | C(O)OCH$_3$ |
| 3,5-Cl$_2$ | CF$_2$Br | CH$_2$OCH$_2$CF$_3$ | C(O)OCH$_3$ |
| 3,5-Cl$_2$ | CF$_2$Br | C(O)Et | C(O)OCH$_3$ |
| 3,5-Cl$_2$ | CF$_2$Br | C(O)OCH$_3$ | C(O)OEt |
| 3,5-Cl$_2$ | CF$_2$Br | H | C(O)NH$_2$ |
| 3,5-Cl$_2$ | CF$_2$Br | CH$_3$ | (D-55c)Cl |
| 3,5-Cl$_2$ | CF$_2$Br | CH$_2$OCH$_3$ | (D-55c)Cl |
| 3,5-Cl$_2$ | CF$_2$Br | C(O)CH$_3$ | (D-55c)Cl |
| 3,5-Cl$_2$ | CF$_2$Br | C(O)Et | (D-55c)Cl |
| 3,5-Cl$_2$ | CF$_2$Br | C(O)Pr-i | (D-55c)Cl |
| 3,5-Cl$_2$ | CF$_2$Br | C(O)CH$_2$OCH$_3$ | (D-55c)Cl |
| 3,5-Cl$_2$ | CF$_2$Br | C(O)OCH$_3$ | (D-55c)Cl |
| 3,5-Cl$_2$ | CF$_2$Br | C(O)CH$_3$ | (D-55c)Br |
| 3,5-Cl$_2$ | CF$_2$Br | C(O)Et | (D-55c)Br |
| 3,5-Cl$_2$ | CF$_2$Br | C(O)Pr-i | (D-55c)Br |
| 3,5-Cl$_2$ | CFClBr | H | CH═NOCH$_3$ |
| 3,5-Cl$_2$ | CFBr$_2$ | H | CH═NOEt |
| 3,5-Cl$_2$ | CF$_2$I | CH$_2$OEt | C(O)OCH$_3$ |
| 3,5-Cl$_2$ | CF$_2$CHF$_2$ | H | CH═NOCH$_3$ |
| 3,5-Cl$_2$ | CF$_2$CHF$_2$ | H | CH═NOEt |
| 3,5-Cl$_2$ | CF$_2$CHF$_2$ | H | C(O)OCH$_3$ |
| 3,5-Cl$_2$ | CF$_2$CHF$_2$ | Et | C(O)OCH$_3$ |
| 3,5-Cl$_2$ | CF$_2$CHF$_2$ | CH$_2$OCH$_3$ | C(O)OCH$_3$ |
| 3,5-Cl$_2$ | CF$_2$CHF$_2$ | CH$_2$OEt | C(O)OCH$_3$ |
| 3,5-Cl$_2$ | CF$_2$CHF$_2$ | CH$_2$OCH$_2$CF$_3$ | C(O)OCH$_3$ |
| 3,5-Cl$_2$ | CF$_2$CHF$_2$ | C(O)Et | C(O)OCH$_3$ |
| 3,5-Cl$_2$ | CF$_2$CHF$_2$ | C(O)OCH$_3$ | C(O)OEt |
| 3,5-Cl$_2$ | CF$_2$CHF$_2$ | H | C(O)NH$_2$ |
| 3,5-Cl$_2$ | CF$_2$CHF$_2$ | CH$_3$ | (D-55c)Cl |
| 3,5-Cl$_2$ | CF$_2$CHF$_2$ | CH$_2$OCH$_3$ | (D-55c)Cl |
| 3,5-Cl$_2$ | CF$_2$CHF$_2$ | C(O)CH$_3$ | (D-55c)Cl |
| 3,5-Cl$_2$ | CF$_2$CHF$_2$ | C(O)Et | (D-55c)Cl |
| 3,5-Cl$_2$ | CF$_2$CHF$_2$ | C(O)Pr-i | (D-55c)Cl |
| 3,5-Cl$_2$ | CF$_2$CHF$_2$ | C(O)CH$_2$OCH$_3$ | (D-55c)Cl |
| 3,5-Cl$_2$ | CF$_2$CHF$_2$ | C(O)OCH$_3$ | (D-55c)Cl |
| 3,5-Cl$_2$ | CF$_2$CHF$_2$ | C(O)CH$_3$ | (D-55c)Br |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Cl$_2$ | CF$_2$CHF$_2$ | C(O)Et | (D-55c)Br |
| 3,5-Cl$_2$ | CF$_2$CHF$_2$ | C(O)Pr-i | (D-55c)Br |
| 3,5-Cl$_2$ | CF$_2$CF$_3$ | H | CH=NOCH$_3$ |
| 3,5-Cl$_2$ | CF$_2$CF$_3$ | H | CH=NOEt |
| 3,5-Cl$_2$ | CF$_2$CF$_3$ | CH$_2$OEt | C(O)OCH$_3$ |
| 3,5-Cl$_2$ | CF$_2$CF$_3$ | CH$_2$OCH$_2$CF$_3$ | C(O)OCH$_3$ |
| 3,5-Cl$_2$ | CF$_2$CF$_3$ | C(O)Et | C(O)OCH$_3$ |
| 3,5-Cl$_2$ | CF$_2$CF$_3$ | C(O)CH$_3$ | (D-55c)Cl |
| 3,5-Cl$_2$ | CF$_2$CF$_3$ | C(O)Pr-i | (D-55c)Cl |
| 3,5-Cl$_2$ | CF$_2$CF$_3$ | C(O)OCH$_3$ | (D-55c)Cl |
| 3,5-Cl$_2$ | CF$_2$CF$_3$ | C(O)CH$_3$ | (D-55c)Br |
| 3,5-Cl$_2$ | CF$_2$CF$_2$Cl | CH$_2$OCH$_2$CF$_3$ | C(O)OCH$_3$ |
| 3,5-Cl$_2$ | CFClCF$_3$ | C(O)Et | C(O)OCH$_3$ |
| 3,5-Cl$_2$ | CFClCF$_2$Cl | C(O)CH$_3$ | (D-55c)Cl |
| 3,5-Cl$_2$ | CF$_2$CF$_2$Br | C(O)Pr-i | (D-55c)Cl |
| 3,5-Cl$_2$ | CFBrCF$_3$ | C(O)OCH$_3$ | (D-55c)Cl |
| 3,5-Cl$_2$ | CF$_2$CHFCF$_3$ | C(O)CH$_3$ | (D-55c)Br |
| 3,5-Cl$_2$ | CF$_2$CF$_2$CF$_3$ | H | CH=NOCH$_3$ |
| 3,5-Cl$_2$ | CF$_2$CF$_2$CF$_3$ | CH$_2$OEt | C(O)OCH$_3$ |
| 3,5-Cl$_2$ | CF$_2$CF$_2$CF$_3$ | C(O)Et | C(O)OCH$_3$ |
| 3,5-Cl$_2$ | CF$_2$CF$_2$CF$_3$ | C(O)CH$_3$ | (D-55c)Cl |
| 3,5-Cl$_2$ | CF$_2$CF$_2$CF$_3$ | C(O)OCH$_3$ | (D-55c)Cl |
| 3,5-Cl$_2$ | CF(CF$_3$)$_2$ | H | CH=NOCH$_3$ |
| 3,5-Cl$_2$ | CF$_2$CFClCF$_2$Cl | H | CH=NOEt |
| 3,5-Cl$_2$ | CF$_2$CFBrCF$_2$Cl | CH$_2$OEt | C(O)OCH$_3$ |
| 3,5-Cl$_2$ | CH$_2$OCH$_2$CF$_3$ | CH$_2$OCH$_2$CF$_3$ | C(O)OCH$_3$ |
| 3,5-Cl$_2$ | CH$_2$OCH(CF$_3$)$_2$ | C(O)Et | C(O)OCH$_3$ |
| 3,5-Cl$_2$ | CF$_2$OCH$_3$ | H | CH=NOCH$_3$ |
| 3,5-Cl$_2$ | CF$_2$OCH$_3$ | H | CH=NOEt |
| 3,5-Cl$_2$ | CF$_2$OCH$_3$ | CH$_2$OEt | C(O)OCH$_3$ |
| 3,5-Cl$_2$ | CF$_2$OCH$_3$ | CH$_2$OCH$_2$CF$_3$ | C(O)OCH$_3$ |
| 3,5-Cl$_2$ | CF$_2$OCH$_3$ | C(O)Et | C(O)OCH$_3$ |
| 3,5-Cl$_2$ | CF$_2$OCH$_3$ | C(O)CH$_3$ | (D-55c)Cl |
| 3,5-Cl$_2$ | CF$_2$OCH$_3$ | C(O)Pr-i | (D-55c)Cl |
| 3,5-Cl$_2$ | CF$_2$OCH$_3$ | C(O)OCH$_3$ | (D-55c)Cl |
| 3,5-Cl$_2$ | CF$_2$OCH$_3$ | C(O)CH$_3$ | (D-55c)Br |
| 3,5-Cl$_2$ | CH$_2$SCF$_3$ | C(O)CH$_3$ | (D-55c)Cl |
| 3,5-Cl$_2$ | CH$_2$CH$_2$SCF$_3$ | C(O)Pr-i | (D-55c)Cl |
| 3,5-Cl$_2$ | CF$_2$SCH$_3$ | H | CH=NOCH$_3$ |
| 3,5-Cl$_2$ | CF$_2$SCH$_3$ | CH$_2$OEt | C(O)OCH$_3$ |
| 3,5-Cl$_2$ | CF$_2$SCH$_3$ | C(O)Et | C(O)OCH$_3$ |
| 3,5-Cl$_2$ | CF$_2$SCH$_3$ | C(O)CH$_3$ | (D-55c)Cl |
| 3,5-Cl$_2$ | CF$_2$SCH$_3$ | C(O)OCH$_3$ | (D-55c)Cl |
| 3,5-Cl$_2$ | CF$_2$SPr-n | C(O)OCH$_3$ | (D-55c)Cl |
| 3,5-Cl$_2$ | CF$_2$SPr-i | C(O)CH$_3$ | (D-55c)Br |
| 3,5-Cl$_2$ | CF$_2$SCH$_2$Ph | H | CH=NOCH$_3$ |
| 3,5-Cl$_2$ | CF$_2$SPh | H | CH=NOEt |
| 3,5-Cl$_2$ | CF$_2$CN | CH$_2$OEt | C(O)OCH$_3$ |
| 3,5-Cl$_2$ | CF$_2$C(O)OCH$_3$ | CH$_2$OCH$_2$CF$_3$ | C(O)OCH$_3$ |
| 3,5-Cl$_2$ | CF$_2$C(O)OEt | C(O)Et | C(O)OCH$_3$ |
| 3,5-Cl$_2$ | CF$_2$C(O)NH$_2$ | C(O)CH$_3$ | (D-55c)Cl |
| 3,5-Cl$_2$ | CF$_2$SO$_2$N(CH$_3$)$_2$ | C(O)Pr-i | (D-55c)Cl |
| 3,5-Cl$_2$ | T-3 | H | CH=NOCH$_3$ |
| 3,5-Cl$_2$ | T-3 | H | CH=NOEt |
| 3,5-Cl$_2$ | T-3 | CH$_2$OEt | C(O)OCH$_3$ |
| 3,5-Cl$_2$ | T-3 | CH$_2$OCH$_2$CF$_3$ | C(O)OCH$_3$ |
| 3,5-Cl$_2$ | T-3 | C(O)Et | C(O)OCH$_3$ |
| 3,5-Cl$_2$ | T-3 | C(O)CH$_3$ | (D-55c)Cl |
| 3,5-Cl$_2$ | T-3 | C(O)Pr-i | (D-55c)Cl |
| 3,5-Cl$_2$ | T-3 | C(O)OCH$_3$ | (D-55c)Cl |
| 3,5-Cl$_2$ | T-3 | C(O)CH$_3$ | (D-55c)Br |
| 3,5-Cl$_2$ | T-4 | H | CH=NOCH$_3$ |
| 3,5-Cl$_2$ | T-4 | CH$_2$OEt | C(O)OCH$_3$ |
| 3,5-Cl$_2$ | T-4 | C(O)Et | C(O)OCH$_3$ |
| 3,5-Cl$_2$ | T-4 | C(O)CH$_3$ | (D-55c)Cl |
| 3,5-Cl$_2$ | T-4 | C(O)OCH$_3$ | (D-55c)Cl |
| 3,5-Cl$_2$ | T-5 | C(O)OCH$_3$ | (D-55c)Cl |
| 3,5-Cl$_2$ | CN | C(O)CH$_3$ | (D-55c)Br |
| 3,5-Cl$_2$ | Ph | H | CH=NOCH$_3$ |
| 3,5-Cl$_2$ | Ph-2-F | H | CH=NOEt |
| 3,5-Cl$_2$ | Ph-3-F | CH$_2$OEt | C(O)OCH$_3$ |
| 3,5-Cl$_2$ | Ph-4-F | CH$_2$OCH$_2$CF$_3$ | C(O)OCH$_3$ |
| 3,5-Cl$_2$ | Ph-2-Cl | C(O)Et | C(O)OCH$_3$ |
| 3,5-Cl$_2$ | Ph-3-Cl | C(O)CH$_3$ | (D-55c)Cl |
| 3,5-Cl$_2$ | Ph-4-Cl | C(O)Pr-i | (D-55c)Cl |
| 3-Br-4-F | CHF$_2$ | C(O)OCH$_3$ | (D-55c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Br-4-F | $CF_3$ | H | $CH=NOCH_3$ |
| 3-Br-4-F | $CF_3$ | $CH_2OCH_3$ | $CH=NOCH_3$ |
| 3-Br-4-F | $CF_3$ | H | $CH=NOEt$ |
| 3-Br-4-F | $CF_3$ | H | $C(O)OCH_3$ |
| 3-Br-4-F | $CF_3$ | Et | $C(O)OCH_3$ |
| 3-Br-4-F | $CF_3$ | $CH_2OCH_3$ | $C(O)OCH_3$ |
| 3-Br-4-F | $CF_3$ | $CH_2OEt$ | $C(O)OCH_3$ |
| 3-Br-4-F | $CF_3$ | $CH_2OCH2CF_3$ | $C(O)OCH_3$ |
| 3-Br-4-F | $CF_3$ | $CH_2OC(O)CH_3$ | $C(O)OCH_3$ |
| 3-Br-4-F | $CF_3$ | $CH_2OC(O)Et$ | $C(O)OCH_3$ |
| 3-Br-4-F | $CF_3$ | $CH_2OC(O)OCH_3$ | $C(O)OCH_3$ |
| 3-Br-4-F | $CF_3$ | E-5a | $C(O)OCH_3$ |
| 3-Br-4-F | $CF_3$ | $C(O)CH_3$ | $C(O)OCH_3$ |
| 3-Br-4-F | $CF_3$ | $C(O)Et$ | $C(O)OCH_3$ |
| 3-Br-4-F | $CF_3$ | $C(O)Pr-n$ | $C(O)OCH_3$ |
| 3-Br-4-F | $CF_3$ | $C(O)Pr-i$ | $C(O)OCH_3$ |
| 3-Br-4-F | $CF_3$ | $C(O)Bu-t$ | $C(O)OCH_3$ |
| 3-Br-4-F | $CF_3$ | $C(O)CH_2OCH_3$ | $C(O)OCH_3$ |
| 3-Br-4-F | $CF_3$ | $C(O)CH_2SCH_3$ | $C(O)OCH_3$ |
| 3-Br-4-F | $CF_3$ | $C(O)OCH_3$ | $C(O)OEt$ |
| 3-Br-4-F | $CF_3$ | H | $C(O)OPr-i$ |
| 3-Br-4-F | $CF_3$ | $C(O)OCH_3$ | $C(O)OPr-i$ |
| 3-Br-4-F | $CF_3$ | H | $C(O)NH_2$ |
| 3-Br-4-F | $CF_3$ | $CH_3$ | (D-52d)Cl |
| 3-Br-4-F | $CF_3$ | $CH_2OCH_3$ | (D-52d)Cl |
| 3-Br-4-F | $CF_3$ | $C(O)OCH_3$ | (D-52d)Cl |
| 3-Br-4-F | $CF_3$ | $CH_3$ | (D-55c)Cl |
| 3-Br-4-F | $CF_3$ | $CH_2OCH_3$ | (D-52d)Cl |
| 3-Br-4-F | $CF_3$ | $CH_2OC(O)CH_3$ | (D-52d)Cl |
| 3-Br-4-F | $CF_3$ | $CH_2OC(O)Bu-t$ | (D-52d)Cl |
| 3-Br-4-F | $CF_3$ | $CH_2OC(O)OCH_3$ | (D-52d)Cl |
| 3-Br-4-F | $CF_3$ | $CH_2CN$ | (D-52d)Cl |
| 3-Br-4-F | $CF_3$ | $C(O)CH_3$ | (D-52d)Cl |
| 3-Br-4-F | $CF_3$ | $C(O)Et$ | (D-52d)Cl |
| 3-Br-4-F | $CF_3$ | $C(O)Pr-n$ | (D-52d)Cl |
| 3-Br-4-F | $CF_3$ | $C(O)Pr-i$ | (D-52d)Cl |
| 3-Br-4-F | $CF_3$ | $C(O)Pr-c$ | (D-52d)Cl |
| 3-Br-4-F | $CF_3$ | $C(O)Bu-t$ | (D-52d)Cl |
| 3-Br-4-F | $CF_3$ | $C(O)CH_2Cl$ | (D-52d)Cl |
| 3-Br-4-F | $CF_3$ | $C(O)CH_2OCH_3$ | (D-52d)Cl |
| 3-Br-4-F | $CF_3$ | $C(O)CH_2OEt$ | (D-52d)Cl |
| 3-Br-4-F | $CF_3$ | $C(O)CH_2SCH_3$ | (D-52d)Cl |
| 3-Br-4-F | $CF_3$ | $C(O)CH_2S(O)CH_3$ | (D-52d)Cl |
| 3-Br-4-F | $CF_3$ | $C(O)C(O)OEt$ | (D-52d)Cl |
| 3-Br-4-F | $CF_3$ | $C(O)OCH_3$ | (D-52d)Cl |
| 3-Br-4-F | $CF_3$ | $C(O)OPr-n$ | (D-52d)Cl |
| 3-Br-4-F | $CF_3$ | $C(O)OCH_2Cl$ | (D-52d)Cl |
| 3-Br-4-F | $CF_3$ | $C(O)OCH_2CH_2Cl$ | (D-52d)Cl |
| 3-Br-4-F | $CF_3$ | $C(O)OCH_2CH_2OCH_3$ | (D-52d)Cl |
| 3-Br-4-F | $CF_3$ | $C(O)OCH_2CH=CH_2$ | (D-52d)Cl |
| 3-Br-4-F | $CF_3$ | CH3 | (D-55c)Br |
| 3-Br-4-F | $CF_3$ | $CH_2OC(O)CH_3$ | (D-55c)Br |
| 3-Br-4-F | $CF_3$ | $C(O)CH_3$ | (D-55c)Br |
| 3-Br-4-F | $CF_3$ | $C(O)Et$ | (D-55c)Br |
| 3-Br-4-F | $CF_3$ | $C(O)Pr-n$ | (D-55c)Br |
| 3-Br-4-F | $CF_3$ | $C(O)Pr-i$ | (D-55c)Br |
| 3-Br-4-F | $CF_3$ | $C(O)OCH_3$ | (D-55c)Br |
| 3-Br-4-F | $CF_3$ | $C(O)OEt$ | (D-55c)Br |
| 3-Br-4-F | $CF_3$ | $C(O)OCH_2CH_2OCH_3$ | (D-55c)Br |
| 3-Br-4-F | $CF_2Cl$ | $C(O)Pr-i$ | D-57a |
| 3-Br-4-F | $CF_2Cl$ | H | $CH=NOCH_3$ |
| 3-Br-4-F | $CF_2Cl$ | H | $CH=NOEt$ |
| 3-Br-4-F | $CF_2Cl$ | H | $C(O)OCH_3$ |
| 3-Br-4-F | $CF_2Cl$ | Et | $C(O)OCH_3$ |
| 3-Br-4-F | $CF_2Cl$ | $CH_2OCH_3$ | $C(O)OCH_3$ |
| 3-Br-4-F | $CF_2Cl$ | $CH_2OEt$ | $C(O)OCH_3$ |
| 3-Br-4-F | $CF_2Cl$ | $CH_2OCH_2CF_3$ | $C(O)OCH_3$ |
| 3-Br-4-F | $CF_2Cl$ | $C(O)Et$ | $C(O)OCH_3$ |
| 3-Br-4-F | $CF_2Cl$ | $C(O)OCH_3$ | $C(O)OEt$ |
| 3-Br-4-F | $CF_2Cl$ | H | $C(O)NH_2$ |
| 3-Br-4-F | $CF_2Cl$ | CH3 | (D-55c)Cl |
| 3-Br-4-F | $CF_2Cl$ | $CH_2OCH_3$ | (D-55c)Cl |
| 3-Br-4-F | $CF_2Cl$ | $C(O)CH_3$ | (D-55c)Cl |
| 3-Br-4-F | $CF_2Cl$ | $C(O)Et$ | (D-55c)Cl |
| 3-Br-4-F | $CF_2Cl$ | $C(O)Pr-i$ | (D-55c)Cl |
| 3-Br-4-F | $CF_2Cl$ | $C(O)CH_2OCH_3$ | (D-55c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Br-4-F | CF$_2$Cl | C(O)OCH$_3$ | (D-55c)Cl |
| 3-Br-4-F | CF$_2$Cl | C(O)CH$_3$ | (D-55c)Br |
| 3-Br-4-F | CF$_2$Cl | C(O)Et | (D-55c)Br |
| 3-Br-4-F | CF$_2$Cl | C(O)Pr-i | (D-55c)Br |
| 3-Br-4-F | CF$_2$Br | C(O)CH$_3$ | (D-55c)Br |
| 3-Br-4-F | CF$_2$CHF$_2$ | H | CH=NOCH$_3$ |
| 2-F-4-Br | CF$_3$ | H | CH=NOEt |
| 2-F-4-Br | CF$_3$ | CH$_2$OEt | C(O)OCH$_3$ |
| 2-F-5-Br | CF$_3$ | CH$_2$OCH$_2$CF$_3$ | C(O)OCH$_3$ |
| 2-F-5-Br | CHF$_2$ | C(O)Et | C(O)OCH$_3$ |
| 2-F-5-Br | CF$_3$ | H | CH=NOCH$_3$ |
| 2-F-5-Br | CF$_3$ | CH$_2$OCH$_3$ | CH=NOCH$_3$ |
| 2-F-5-Br | CF$_3$ | H | CH=NOEt |
| 2-F-5-Br | CF$_3$ | H | C(O)OCH$_3$ |
| 2-F-5-Br | CF$_3$ | Et | C(O)OCH$_3$ |
| 2-F-5-Br | CF$_3$ | CH$_2$OCH$_3$ | C(O)OCH$_3$ |
| 2-F-5-Br | CF$_3$ | CH$_2$OEt | C(O)OCH$_3$ |
| 2-F-5-Br | CF$_3$ | CH$_2$OCH$_2$CF$_3$ | C(O)OCH$_3$ |
| 2-F-5-Br | CF$_3$ | CH$_2$OC(O)CH$_3$ | C(O)OCH$_3$ |
| 2-F-5-Br | CF$_3$ | CH$_2$OC(O)Et | C(O)OCH$_3$ |
| 2-F-5-Br | CF$_3$ | CH$_2$OC(O)OCH$_3$ | C(O)OCH$_3$ |
| 2-F-5-Br | CF$_3$ | E-5a | C(O)OCH$_3$ |
| 2-F-5-Br | CF$_3$ | C(O)CH$_3$ | C(O)OCH$_3$ |
| 2-F-5-Br | CF$_3$ | C(O)Et | C(O)OCH$_3$ |
| 2-F-5-Br | CF$_3$ | C(O)Pr-n | C(O)OCH$_3$ |
| 2-F-5-Br | CF$_3$ | C(O)Pr-i | C(O)OCH$_3$ |
| 2-F-5-Br | CF$_3$ | C(O)Bu-t | C(O)OCH$_3$ |
| 2-F-5-Br | CF$_3$ | C(O)CH$_2$OCH$_3$ | C(O)OCH$_3$ |
| 2-F-5-Br | CF$_3$ | C(O)CH$_2$SCH$_3$ | C(O)OCH$_3$ |
| 2-F-5-Br | CF$_3$ | C(O)OCH$_3$ | C(O)OEt |
| 2-F-5-Br | CF$_3$ | H | C(O)OPr-i |
| 2-F-5-Br | CF$_3$ | C(O)OCH$_3$ | C(O)OPr-i |
| 2-F-5-Br | CF$_3$ | H | C(O)NH$_2$ |
| 2-F-5-Br | CF$_3$ | CH$_3$ | (D-52d)Cl |
| 2-F-5-Br | CF$_3$ | CH$_2$OCH$_3$ | (D-52d)Cl |
| 2-F-5-Br | CF$_3$ | C(O)OCH$_3$ | (D-52d)Cl |
| 2-F-5-Br | CF$_3$ | CH$_3$ | (D-55c)Cl |
| 2-F-5-Br | CF$_3$ | CH$_2$OCH$_3$ | (D-55c)Cl |
| 2-F-5-Br | CF$_3$ | CH$_2$OC(O)CH$_3$ | (D-55c)Cl |
| 2-F-5-Br | CF$_3$ | CH2OC(O)Bu-t | (D-55c)Cl |
| 2-F-5-Br | CF$_3$ | CH$_2$OC(O)OCH$_3$ | (D-55c)Cl |
| 2-F-5-Br | CF$_3$ | CH$_2$CN | (D-55c)Cl |
| 2-F-5-Br | CF$_3$ | C(O)CH$_3$ | (D-55c)Cl |
| 2-F-5-Br | CF$_3$ | C(O)Et | (D-55c)Cl |
| 2-F-5-Br | CF$_3$ | C(O)Pr-n | (D-55c)Cl |
| 2-F-5-Br | CF$_3$ | C(O)Pr-i | (D-55c)Cl |
| 2-F-5-Br | CF$_3$ | C(O)Pr-c | (D-55c)Cl |
| 2-F-5-Br | CF$_3$ | C(O)Bu-t | (D-55c)Cl |
| 2-F-5-Br | CF$_3$ | C(O)CH$_2$Cl | (D-55c)Cl |
| 2-F-5-Br | CF$_3$ | C(O)CH$_2$OCH$_3$ | (D-55c)Cl |
| 2-F-5-Br | CF$_3$ | C(O)CH$_2$OEt | (D-55c)Cl |
| 2-F-5-Br | CF$_3$ | C(O)CH$_2$SCH$_3$ | (D-55c)Cl |
| 2-F-5-Br | CF$_3$ | C(O)CH$_2$S(O)CH$_3$ | (D-55c)Cl |
| 2-F-5-Br | CF$_3$ | C(O)C(O)OEt | (D-55c)Cl |
| 2-F-5-Br | CF$_3$ | C(O)OCH$_3$ | (D-55c)Cl |
| 2-F-5-Br | CF$_3$ | C(O)OPr-n | (D-55c)Cl |
| 2-F-5-Br | CF$_3$ | C(O)OCH$_2$Cl | (D-55c)Cl |
| 2-F-5-Br | CF$_3$ | C(O)OCH$_2$CH$_2$Cl | (D-55c)Cl |
| 2-F-5-Br | CF$_3$ | C(O)OCH$_2$CH$_2$OCH$_3$ | (D-55c)Cl |
| 2-F-5-Br | CF$_3$ | C(O)OCH$_2$CH=CH$_2$ | (D-55c)Cl |
| 2-F-5-Br | CF$_3$ | CH$_3$ | (D-55c)Br |
| 2-F-5-Br | CF$_3$ | CH$_2$OC(O)CH$_3$ | (D-55c)Br |
| 2-F-5-Br | CF$_3$ | C(O)CH$_3$ | (D-55c)Br |
| 2-F-5-Br | CF$_3$ | C(O)Et | (D-55c)Br |
| 2-F-5-Br | CF$_3$ | C(O)Pr-n | (D-55c)Br |
| 2-F-5-Br | CF$_3$ | C(O)Pr-i | (D-55c)Br |
| 2-F-5-Br | CF$_3$ | C(O)OCH$_3$ | (D-55c)Br |
| 2-F-5-Br | CF$_3$ | C(O)OEt | (D-55c)Br |
| 2-F-5-Br | CF$_3$ | C(O)OCH$_2$CH$_2$OCH$_3$ | (D-55c)Br |
| 2-F-5-Br | CF$_3$ | C(O)Pr-i | D-57a |
| 2-F-5-Br | CF$_2$Cl | H | CH=NOCH$_3$ |
| 2-F-5-Br | CF$_2$Cl | H | CH=NOEt |
| 2-F-5-Br | CF$_2$Cl | H | C(O)OCH$_3$ |
| 2-F-5-Br | CF$_2$Cl | Et | C(O)OCH$_3$ |
| 2-F-5-Br | CF$_2$Cl | CH$_2$OCH$_3$ | C(O)OCH$_3$ |
| 2-F-5-Br | CF$_2$Cl | CH$_2$OEt | C(O)OCH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 2-F-5-Br | CF$_2$Cl | CH$_2$OCH$_2$CF$_3$ | C(O)OCH$_3$ |
| 2-F-5-Br | CF$_2$Cl | C(O)Et | C(O)OCH$_3$ |
| 2-F-5-Br | CF$_2$Cl | C(O)OCH$_3$ | C(O)OEt |
| 2-F-5-Br | CF$_2$Cl | H | C(O)NH$_2$ |
| 2-F-5-Br | CF$_2$Cl | CH3 | (D-55c)Cl |
| 2-F-5-Br | CF$_2$Cl | CH$_2$OCH$_3$ | (D-55c)Cl |
| 2-F-5-Br | CF$_2$Cl | C(O)CH$_3$ | (D-55c)Cl |
| 2-F-5-Br | CF$_2$Cl | C(O)Et | (D-55c)Cl |
| 2-F-5-Br | CF$_2$Cl | C(O)Pr-i | (D-55c)Cl |
| 2-F-5-Br | CF$_2$Cl | C(O)CH$_2$OCH$_3$ | (D-55c)Cl |
| 2-F-5-Br | CF$_2$Cl | C(O)OCH$_3$ | (D-55c)Cl |
| 2-F-5-Br | CF$_2$Cl | C(O)CH$_3$ | (D-55c)Br |
| 2-F-5-Br | CF$_2$Cl | C(O)Et | (D-55c)Br |
| 2-F-5-Br | CF$_2$Cl | C(O)Pr-i | (D-55c)Br |
| 2-F-5-Br | CF$_2$Br | C(O)CH$_3$ | (D-55c)Cl |
| 2-F-5-Br | CF$_2$CHF$_2$ | C(O)Pr-i | (D-55c)Cl |
| 2-Cl-5-Br | CHF$_2$ | H | CH=NOCH$_3$ |
| 3-Cl-5-Br | CHF$_2$ | H | CH=NOEt |
| 3-Cl-5-Br | CHF$_2$ | CH$_2$OEt | C(O)OCH$_3$ |
| 3-Cl-5-Br | CHF$_2$ | CH$_2$OCH$_2$CF$_3$ | C(O)OCH$_3$ |
| 3-Cl-5-Br | CHF$_2$ | C(O)Et | C(O)OCH$_3$ |
| 3-Cl-5-Br | CHF$_2$ | C(O)CH$_3$ | (D-55c)Cl |
| 3-Cl-5-Br | CHF$_2$ | C(O)Pr-i | (D-55c)Cl |
| 3-Cl-5-Br | CHF$_2$ | C(O)OCH$_3$ | (D-55c)Cl |
| 3-Cl-5-Br | CHF$_2$ | C(O)CH$_3$ | (D-55c)Br |
| 3-Cl-5-Br | CHFCl | C(O)OCH$_3$ | (D-55c)Cl |
| 3-Cl-5-Br | CHCl$_2$ | C(O)CH$_3$ | (D-55c)Br |
| 3-Cl-5-Br | CHFBr | H | CH=NOCH$_3$ |
| 3-Cl-5-Br | CF$_3$ | H | CH=NOCH$_3$ |
| 3-Cl-5-Br | CF$_3$ | CH$_2$OCH$_3$ | CH=NOCH$_3$ |
| 3-Cl-5-Br | CF$_3$ | CH$_2$OEt | CH=NOCH$_3$ |
| 3-Cl-5-Br | CF$_3$ | H | CH=NOEt |
| 3-Cl-5-Br | CF$_3$ | CH$_2$OCH$_3$ | CH=NOEt |
| 3-Cl-5-Br | CF$_3$ | H | CH=NOPr-n |
| 3-Cl-5-Br | CF$_3$ | H | CH=NOCH$_2$CF$_3$ |
| 3-Cl-5-Br | CF$_3$ | H | CH=NOCH$_2$CH=CH$_2$ |
| 3-Cl-5-Br | CF$_3$ | H | CH=NOCH$_2$C≡CH |
| 3-Cl-5-Br | CF$_3$ | H | C(O)OCH$_3$ |
| 3-Cl-5-Br | CF$_3$ | CH$_3$ | C(O)OCH$_3$ |
| 3-Cl-5-Br | CF$_3$ | Et | C(O)OCH$_3$ |
| 3-Cl-5-Br | CF$_3$ | CH$_2$OCH$_3$ | C(O)OCH$_3$ |
| 3-Cl-5-Br | CF$_3$ | CH$_2$OEt | C(O)OCH$_3$ |
| 3-Cl-5-Br | CF$_3$ | CH$_2$OCH$_2$CF$_3$ | C(O)OCH$_3$ |
| 3-Cl-5-Br | CF$_3$ | CH$_2$OC(O)CH$_3$ | C(O)OCH$_3$ |
| 3-Cl-5-Br | CF$_3$ | CH$_2$OC(O)Et | C(O)OCH$_3$ |
| 3-Cl-5-Br | CF$_3$ | CH$_2$OC(O)Bu-t | C(O)OCH$_3$ |
| 3-Cl-5-Br | CF$_3$ | CH$_2$OC(O)OCH$_3$ | C(O)OCH$_3$ |
| 3-Cl-5-Br | CF$_3$ | E-5a | C(O)OCH$_3$ |
| 3-Cl-5-Br | CF$_3$ | CH$_2$NHC(O)OCH$_3$ | C(O)OCH$_3$ |
| 3-Cl-5-Br | CF$_3$ | CH$_2$CN | C(O)OCH$_3$ |
| 3-Cl-5-Br | CF$_3$ | CH$_2$C≡CH | C(O)OCH$_3$ |
| 3-Cl-5-Br | CF$_3$ | CH$_2$Ph | C(O)OCH$_3$ |
| 3-Cl-5-Br | CF$_3$ | C(O)CH$_3$ | C(O)OCH$_3$ |
| 3-Cl-5-Br | CF$_3$ | C(O)Et | C(O)OCH$_3$ |
| 3-Cl-5-Br | CF$_3$ | C(O)Pr-n | C(O)OCH$_3$ |
| 3-Cl-5-Br | CF$_3$ | C(O)Pr-i | C(O)OCH$_3$ |
| 3-Cl-5-Br | CF$_3$ | C(O)Bu-t | C(O)OCH$_3$ |
| 3-Cl-5-Br | CF$_3$ | C(O)CH$_2$Cl | C(O)OCH$_3$ |
| 3-Cl-5-Br | CF$_3$ | C(O)CH$_2$OCH$_3$ | C(O)OCH$_3$ |
| 3-Cl-5-Br | CF$_3$ | C(O)CH$_2$OEt | C(O)OCH$_3$ |
| 3-Cl-5-Br | CF$_3$ | C(O)CH$_2$SCH$_3$ | C(O)OCH$_3$ |
| 3-Cl-5-Br | CF$_3$ | C(O)Ph | C(O)OCH$_3$ |
| 3-Cl-5-Br | CF$_3$ | C(O)OCH$_3$ | C(O)OCH$_3$ |
| 3-Cl-5-Br | CF$_3$ | C(O)OCH$_2$Cl | C(O)OCH$_3$ |
| 3-Cl-5-Br | CF$_3$ | C(O)OCH$_2$CH$_2$Cl | C(O)OCH$_3$ |
| 3-Cl-5-Br | CF$_3$ | H | C(O)OEt |
| 3-Cl-5-Br | CF$_3$ | CH$_3$ | C(O)OEt |
| 3-Cl-5-Br | CF$_3$ | Et | C(O)OEt |
| 3-Cl-5-Br | CF$_3$ | CH$_2$OCH$_3$ | C(O)OEt |
| 3-Cl-5-Br | CF$_3$ | C(O)CH$_3$ | C(O)OEt |
| 3-Cl-5-Br | CF$_3$ | C(O)Et | C(O)OEt |
| 3-Cl-5-Br | CF$_3$ | C(O)Bu-t | C(O)OEt |
| 3-Cl-5-Br | CF$_3$ | C(O)CH$_2$OCH$_3$ | C(O)OEt |
| 3-Cl-5-Br | CF$_3$ | C(O)OCH$_3$ | C(O)OEt |
| 3-Cl-5-Br | CF$_3$ | H | C(O)OPr-n |
| 3-Cl-5-Br | CF$_3$ | H | C(O)OPr-i |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Cl-5-Br | CF$_3$ | CH$_3$ | C(O)OPr-i |
| 3-Cl-5-Br | CF$_3$ | CH$_2$OCH$_3$ | C(O)OPr-i |
| 3-Cl-5-Br | CF$_3$ | CH$_2$CN | C(O)OPr-i |
| 3-Cl-5-Br | CF$_3$ | CH$_2$C≡CH | C(O)OPr-i |
| 3-Cl-5-Br | CF$_3$ | C(O)CH$_3$ | C(O)OPr-i |
| 3-Cl-5-Br | CF$_3$ | C(O)Et | C(O)OPr-i |
| 3-Cl-5-Br | CF$_3$ | C(O)Bu-t | C(O)OPr-i |
| 3-Cl-5-Br | CF$_3$ | C(O)CH$_2$OCH$_3$ | C(O)OPr-i |
| 3-Cl-5-Br | CF$_3$ | C(O)OCH$_3$ | C(O)OPr-i |
| 3-Cl-5-Br | CF$_3$ | C(O)OEt | C(O)OPr-i |
| 3-Cl-5-Br | CF$_3$ | H | C(O)OBu-t |
| 3-Cl-5-Br | CF$_3$ | C(O)CH$_3$ | C(O)OBu-t |
| 3-Cl-5-Br | CF$_3$ | C(O)Et | C(O)OBu-t |
| 3-Cl-5-Br | CF$_3$ | C(O)CH$_2$CF$_3$ | C(O)OBu-t |
| 3-Cl-5-Br | CF$_3$ | C(O)OCH$_3$ | C(O)OBu-t |
| 3-Cl-5-Br | CF$_3$ | C(O)OCH$_3$ | C(O)OCH$_2$CH$_2$OCH$_3$ |
| 3-Cl-5-Br | CF$_3$ | H | C(O)NH$_2$ |
| 3-Cl-5-Br | CF$_3$ | CH$_3$ | C(O)NH$_2$ |
| 3-Cl-5-Br | CF$_3$ | CH$_3$ | C(O)NHC(O)CH$_3$ |
| 3-Cl-5-Br | CF$_3$ | CH$_3$ | C(O)NHC(O)OCH$_3$ |
| 3-Cl-5-Br | CF$_3$ | H | C(S)NH$_2$ |
| 3-Cl-5-Br | CF$_3$ | CH$_3$ | D-14a |
| 3-Cl-5-Br | CF$_3$ | C(O)CH$_3$ | D-14a |
| 3-Cl-5-Br | CF$_3$ | C(O)OCH$_3$ | D-14a |
| 3-Cl-5-Br | CF$_3$ | CH$_3$ | (D-52d)Cl |
| 3-Cl-5-Br | CF$_3$ | CH$_2$OCH$_3$ | (D-52d)Cl |
| 3-Cl-5-Br | CF$_3$ | C(O)CH$_3$ | (D-52d)Cl |
| 3-Cl-5-Br | CF$_3$ | C(O)Et | (D-52d)Cl |
| 3-Cl-5-Br | CF$_3$ | C(O)OCH$_3$ | (D-52d)Cl |
| 3-Cl-5-Br | CF$_3$ | CH$_3$ | (D-52d)Br |
| 3-Cl-5-Br | CF$_3$ | C(O)OCH$_3$ | (D-52d)Br |
| 3-Cl-5-Br | CF$_3$ | CH$_3$ | (D-52d)CN |
| 3-Cl-5-Br | CF$_3$ | CH$_3$ | (D-53e)Cl |
| 3-Cl-5-Br | CF$_3$ | C(O)OCH$_3$ | (D-53e)Cl |
| 3-Cl-5-Br | CF$_3$ | CH$_3$ | D-55a |
| 3-Cl-5-Br | CF$_3$ | C(O)CH$_3$ | D-55a |
| 3-Cl-5-Br | CF$_3$ | C(O)Pr-i | D-55a |
| 3-Cl-5-Br | CF$_3$ | C(O)Bu-t | D-55a |
| 3-Cl-5-Br | CF$_3$ | CH$_3$ | (D-55c)Cl |
| 3-Cl-5-Br | CF$_3$ | Et | (D-55c)Cl |
| 3-Cl-5-Br | CF$_3$ | CH$_2$OCH$_3$ | (D-55c)Cl |
| 3-Cl-5-Br | CF$_3$ | CH$_2$OEt | (D-55c)Cl |
| 3-Cl-5-Br | CF$_3$ | CH$_2$OC(O)CH$_3$ | (D-55c)Cl |
| 3-Cl-5-Br | CF$_3$ | CH$_2$OC(O)Bu-t | (D-55c)Cl |
| 3-Cl-5-Br | CF$_3$ | CH$_2$OC(O)OCH$_3$ | (D-55c)Cl |
| 3-Cl-5-Br | CF$_3$ | CH$_2$CN | (D-55c)Cl |
| 3-Cl-5-Br | CF$_3$ | CH$_2$C≡CH | (D-55c)Cl |
| 3-Cl-5-Br | CF$_3$ | C(O)CH$_3$ | (D-55c)Cl |
| 3-Cl-5-Br | CF$_3$ | C(O)Et | (D-55c)Cl |
| 3-Cl-5-Br | CF$_3$ | C(O)Pr-n | (D-55c)Cl |
| 3-Cl-5-Br | CF$_3$ | C(O)Pr-i | (D-55c)Cl |
| 3-Cl-5-Br | CF$_3$ | C(O)Pr-c | (D-55c)Cl |
| 3-Cl-5-Br | CF$_3$ | C(O)Bu-t | (D-55c)Cl |
| 3-Cl-5-Br | CF$_3$ | C(O)CH$_2$Cl | (D-55c)Cl |
| 3-Cl-5-Br | CF$_3$ | C(O)CH$_2$OCH$_3$ | (D-55c)Cl |
| 3-Cl-5-Br | CF$_3$ | C(O)CH$_2$OEt | (D-55c)Cl |
| 3-Cl-5-Br | CF$_3$ | C(O)CH$_2$SCH$_3$ | (D-55c)Cl |
| 3-Cl-5-Br | CF$_3$ | C(O)CH$_2$S(O)CH$_3$ | (D-55c)Cl |
| 3-Cl-5-Br | CF$_3$ | C(O)C(O)OEt | (D-55c)Cl |
| 3-Cl-5-Br | CF$_3$ | C(O)Ph | (D-55c)Cl |
| 3-Cl-5-Br | CF$_3$ | C(O)(D-52a) | (D-55c)Cl |
| 3-Cl-5-Br | CF$_3$ | C(O)OCH$_3$ | (D-55c)Cl |
| 3-Cl-5-Br | CF$_3$ | C(O)OEt | (D-55c)Cl |
| 3-Cl-5-Br | CF$_3$ | C(O)OPr-n | (D-55c)Cl |
| 3-Cl-5-Br | CF$_3$ | C(O)OPr-i | (D-55c)Cl |
| 3-Cl-5-Br | CF$_3$ | C(O)OBu-n | (D-55c)Cl |
| 3-Cl-5-Br | CF$_3$ | C(O)OBu-i | (D-55c)Cl |
| 3-Cl-5-Br | CF$_3$ | C(O)OBu-t | (D-55c)Cl |
| 3-Cl-5-Br | CF$_3$ | C(O)OCH$_2$Cl | (D-55c)Cl |
| 3-Cl-5-Br | CF$_3$ | C(O)OCH$_2$CH$_2$Cl | (D-55c)Cl |
| 3-Cl-5-Br | CF$_3$ | C(O)OCH$_2$CH$_2$OCH$_3$ | (D-55c)Cl |
| 3-Cl-5-Br | CF$_3$ | C(O)OCH$_2$CH=CH$_2$ | (D-55c)Cl |
| 3-Cl-5-Br | CF$_3$ | C(O)OPh | (D-55c)Cl |
| 3-Cl-5-Br | CF$_3$ | CH$_3$ | (D-55c)Br |
| 3-Cl-5-Br | CF$_3$ | Et | (D-55c)Br |
| 3-Cl-5-Br | CF$_3$ | CH$_2$OCH$_3$ | (D-55c)Br |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Cl-5-Br | CF$_3$ | CH$_2$OEt | (D-55c)Br |
| 3-Cl-5-Br | CF$_3$ | CH$_2$OC(O)CH$_3$ | (D-55c)Br |
| 3-Cl-5-Br | CF$_3$ | C(O)CH$_3$ | (D-55c)Br |
| 3-Cl-5-Br | CF$_3$ | C(O)Et | (D-55c)Br |
| 3-Cl-5-Br | CF$_3$ | C(O)Pr-n | (D-55c)Br |
| 3-Cl-5-Br | CF$_3$ | C(O)Pr-i | (D-55c)Br |
| 3-Cl-5-Br | CF$_3$ | C(O)Pr-c | (D-55c)Br |
| 3-Cl-5-Br | CF$_3$ | C(O)Bu-t | (D-55c)Br |
| 3-Cl-5-Br | CF$_3$ | C(O)CH$_2$OCH$_3$ | (D-55c)Br |
| 3-Cl-5-Br | CF$_3$ | C(O)Ph | (D-55c)Br |
| 3-Cl-5-Br | CF$_3$ | C(O)OCH$_3$ | (D-55c)Br |
| 3-Cl-5-Br | CF$_3$ | C(O)OEt | (D-55c)Br |
| 3-Cl-5-Br | CF$_3$ | C(O)OPr-n | (D-55c)Br |
| 3-Cl-5-Br | CF$_3$ | C(O)OBu-i | (D-55c)Br |
| 3-Cl-5-Br | CF$_3$ | C(O)OCH$_2$Cl | (D-55c)Br |
| 3-Cl-5-Br | CF$_3$ | C(O)OCH$_2$CH$_2$OCH$_3$ | (D-55c)Br |
| 3-Cl-5-Br | CF$_3$ | CH$_3$ | D-57a |
| 3-Cl-5-Br | CF$_3$ | C(O)CH$_3$ | D-57a |
| 3-Cl-5-Br | CF$_3$ | C(O)Pr-n | D-57a |
| 3-Cl-5-Br | CF$_3$ | C(O)Pr-i | D-57a |
| 3-Cl-5-Br | CF$_3$ | C(O)OCH$_3$ | D-57a |
| 3-Cl-5-Br | CF$_3$ | CH$_3$ | D-58a |
| 3-Cl-5-Br | CF$_3$ | CH$_3$ | (D-58b)Cl |
| 3-Cl-5-Br | CF$_3$ | CH$_2$OCH$_3$ | (D-58b)Cl |
| 3-Cl-5-Br | CF$_3$ | C(O)CH$_3$ | (D-58b)Cl |
| 3-Cl-5-Br | CF$_3$ | C(O)OCH$_3$ | (D-58b)Cl |
| 3-Cl-5-Br | CF$_2$Cl | H | CH=NOCH$_3$ |
| 3-Cl-5-Br | CF$_2$Cl | CH$_2$OCH$_3$ | CH=NOCH$_3$ |
| 3-Cl-5-Br | CF$_2$Cl | H | CH=NOEt |
| 3-Cl-5-Br | CF$_2$Cl | H | C(O)OCH$_3$ |
| 3-Cl-5-Br | CF$_2$Cl | Et | C(O)OCH$_3$ |
| 3-Cl-5-Br | CF$_2$Cl | CH$_2$OCH$_3$ | C(O)OCH$_3$ |
| 3-Cl-5-Br | CF$_2$Cl | CH$_2$OEt | C(O)OCH$_3$ |
| 3-Cl-5-Br | CF$_2$Cl | CH$_2$OCH$_2$CF$_3$ | C(O)OCH$_3$ |
| 3-Cl-5-Br | CF$_2$Cl | CH$_2$OC(O)CH$_3$ | C(O)OCH$_3$ |
| 3-Cl-5-Br | CF$_2$Cl | CH$_2$OC(O)Et | C(O)OCH$_3$ |
| 3-Cl-5-Br | CF$_2$Cl | CH$_2$OC(O)OCH$_3$ | C(O)OCH$_3$ |
| 3-Cl-5-Br | CF$_2$Cl | E-5a | C(O)OCH$_3$ |
| 3-Cl-5-Br | CF$_2$Cl | C(O)CH$_3$ | C(O)OCH$_3$ |
| 3-Cl-5-Br | CF$_2$Cl | C(O)Et | C(O)OCH$_3$ |
| 3-Cl-5-Br | CF$_2$Cl | C(O)Pr-n | C(O)OCH$_3$ |
| 3-Cl-5-Br | CF$_2$Cl | C(O)Pr-i | C(O)OCH$_3$ |
| 3-Cl-5-Br | CF$_2$Cl | C(O)Bu-t | C(O)OCH$_3$ |
| 3-Cl-5-Br | CF$_2$Cl | C(O)CH$_2$OCH$_3$ | C(O)OCH$_3$ |
| 3-Cl-5-Br | CF$_2$Cl | C(O)CH$_2$SCH$_3$ | C(O)OCH$_3$ |
| 3-Cl-5-Br | CF$_2$Cl | C(O)OCH$_3$ | C(O)OEt |
| 3-Cl-5-Br | CF$_2$Cl | H | C(O)OPr-i |
| 3-Cl-5-Br | CF$_2$Cl | C(O)OCH$_3$ | C(O)OPr-i |
| 3-Cl-5-Br | CF$_2$Cl | H | C(O)NH$_2$ |
| 3-Cl-5-Br | CF$_2$Cl | CH$_3$ | (D-52d)Cl |
| 3-Cl-5-Br | CF$_2$Cl | CH$_2$OCH$_3$ | (D-52d)Cl |
| 3-Cl-5-Br | CF$_2$Cl | C(O)OCH$_3$ | (D-52d)Cl |
| 3-Cl-5-Br | CF$_2$Cl | CH$_3$ | (D-55c)Cl |
| 3-Cl-5-Br | CF$_2$Cl | CH$_2$OCH3 | (D-55c)Cl |
| 3-Cl-5-Br | CF$_2$Cl | CH$_2$OC(O)CH$_3$ | (D-55c)Cl |
| 3-Cl-5-Br | CF$_2$Cl | CH$_2$OC(O)Bu-t | (D-55c)Cl |
| 3-Cl-5-Br | CF$_2$Cl | CH$_2$OC(O)OCH$_3$ | (D-55c)Cl |
| 3-Cl-5-Br | CF$_2$Cl | CH$_2$CN | (D-55c)Cl |
| 3-Cl-5-Br | CF$_2$Cl | C(O)CH$_3$ | (D-55c)Cl |
| 3-Cl-5-Br | CF$_2$Cl | C(O)Et | (D-55c)Cl |
| 3-Cl-5-Br | CF$_2$Cl | C(O)Pr-n | (D-55c)Cl |
| 3-Cl-5-Br | CF$_2$Cl | C(O)Pr-i | (D-55c)Cl |
| 3-Cl-5-Br | CF$_2$Cl | C(O)Pr-c | (D-55c)Cl |
| 3-Cl-5-Br | CF$_2$Cl | C(O)Bu-t | (D-55c)Cl |
| 3-Cl-5-Br | CF$_2$Cl | C(O)CH$_2$Cl | (D-55c)Cl |
| 3-Cl-5-Br | CF$_2$Cl | C(O)CH$_2$OCH$_3$ | (D-55c)Cl |
| 3-Cl-5-Br | CF$_2$Cl | C(O)CH$_2$OEt | (D-55c)Cl |
| 3-Cl-5-Br | CF$_2$Cl | C(O)CH$_2$SCH$_3$ | (D-55c)Cl |
| 3-Cl-5-Br | CF$_2$Cl | C(O)CH$_2$S(O)CH$_3$ | (D-55c)Cl |
| 3-Cl-5-Br | CF$_2$Cl | C(O)C(O)OEt | (D-55c)Cl |
| 3-Cl-5-Br | CF$_2$Cl | C(O)OCH$_3$ | (D-55c)Cl |
| 3-Cl-5-Br | CF$_2$Cl | C(O)OPr-n | (D-55c)Cl |
| 3-Cl-5-Br | CF$_2$Cl | C(O)OCH$_2$Cl | (D-55c)Cl |
| 3-Cl-5-Br | CF$_2$Cl | C(O)OCH$_2$CH$_2$Cl | (D-55c)Cl |
| 3-Cl-5-Br | CF$_2$Cl | C(O)OCH$_2$CH$_2$OCH$_3$ | (D-55c)Cl |
| 3-Cl-5-Br | CF$_2$Cl | C(O)OCH$_2$CH=CH$_2$ | (D-55c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-Br | CF$_2$Cl | CH$_3$ | (D-55c)Br |
| 3-Cl-5-Br | CF$_2$Cl | CH$_2$OC(O)CH$_3$ | (D-55c)Br |
| 3-Cl-5-Br | CF$_2$Cl | C(O)CH$_3$ | (D-55c)Br |
| 3-Cl-5-Br | CF$_2$Cl | C(O)Et | (D-55c)Br |
| 3-Cl-5-Br | CF$_2$Cl | C(O)Pr-n | (D-55c)Br |
| 3-Cl-5-Br | CF$_2$Cl | C(O)Pr-i | (D-55c)Br |
| 3-Cl-5-Br | CF$_2$Cl | C(O)OCH$_3$ | (D-55c)Br |
| 3-Cl-5-Br | CF$_2$Cl | C(O)OEt | (D-55c)Br |
| 3-Cl-5-Br | CF$_2$Cl | C(O)OCH$_2$CH$_2$OCH$_3$ | (D-55c)Br |
| 3-Cl-5-Br | CF$_2$Cl | C(O)Pr-i | D-57a |
| 3-Cl-5-Br | CF$_2$Br | H | CH=NOCH$_3$ |
| 3-Cl-5-Br | CF$_2$Br | H | CH=NOEt |
| 3-Cl-5-Br | CF$_2$Br | CH$_2$OEt | C(O)OCH$_3$ |
| 3-Cl-5-Br | CF$_2$Br | CH$_2$OCH$_2$CF$_3$ | C(O)OCH$_3$ |
| 3-Cl-5-Br | CF$_2$Br | C(O)Et | C(O)OCH$_3$ |
| 3-Cl-5-Br | CF$_2$Br | C(O)CH$_3$ | (D-55c)Cl |
| 3-Cl-5-Br | CF$_2$Br | C(O)Pr-i | (D-55c)Cl |
| 3-Cl-5-Br | CF$_2$Br | C(O)OCH$_3$ | (D-55c)Cl |
| 3-Cl-5-Br | CF$_2$Br | C(O)CH$_3$ | (D-55c)Br |
| 3-Cl-5-Br | CF2CHF2 | H | CH=NOCH$_3$ |
| 3-Cl-5-Br | CF2CHF2 | H | CH=NOEt |
| 3-Cl-5-Br | CF2CHF2 | CH$_2$OEt | C(O)OCH$_3$ |
| 3-Cl-5-Br | CF2CHF2 | CH$_2$OCH$_2$CF$_3$ | C(O)OCH$_3$ |
| 3-Cl-5-Br | CF2CHF2 | C(O)Et | C(O)OCH$_3$ |
| 3-Cl-5-Br | CF2CHF2 | C(O)CH$_3$ | (D-55c)Cl |
| 3-Cl-5-Br | CF2CHF2 | C(O)Pr-i | (D-55c)Cl |
| 3-Cl-5-Br | CF$_2$CHF$_2$ | C(O)OCH$_3$ | (D-55c)Cl |
| 3-Cl-5-Br | CF$_2$CHF$_2$ | C(O)CH$_3$ | (D-55c)Br |
| 3-Cl-5-Br | CF$_2$CF$_2$ | H | CH=NOEt |
| 3-Cl-5-Br | CF2OCH3 | CH$_2$OEt | C(O)OCH$_3$ |
| 3-Cl-5-Br | CF2SCH3 | CH$_2$OCH$_2$CF$_3$ | C(O)OCH$_3$ |
| 3-Cl-5-Br | T-3 | C(O)Et | C(O)OCH$_3$ |
| 3,4-Br$_2$ | CF$_3$ | H | CH=NOCH$_3$ |
| 3,4-Br$_2$ | CF$_3$ | CH$_2$OCH$_3$ | CH=NOCH$_3$ |
| 3,4-Br$_2$ | CF$_3$ | H | CH=NOEt |
| 3,4-Br$_2$ | CF$_3$ | H | C(O)OCH$_3$ |
| 3,4-Br$_2$ | CF$_3$ | Et | C(O)OCH$_3$ |
| 3,4-Br$_2$ | CF$_3$ | CH$_2$OCH$_3$ | C(O)OCH$_3$ |
| 3,4-Br$_2$ | CF$_3$ | CH$_2$OEt | C(O)OCH$_3$ |
| 3,4-Br$_2$ | CF$_3$ | CH$_2$OCH$_2$CF$_3$ | C(O)OCH$_3$ |
| 3,4-Br$_2$ | CF$_3$ | CH$_2$OC(O)CH$_3$ | C(O)OCH$_3$ |
| 3,4-Br$_2$ | CF$_3$ | CH$_2$OC(O)Et | C(O)OCH$_3$ |
| 3,4-Br$_2$ | CF$_3$ | CH$_2$OC(O)OCH$_3$ | C(O)OCH$_3$ |
| 3,4-Br$_2$ | CF$_3$ | E-5a | C(O)OCH$_3$ |
| 3,4-Br$_2$ | CF$_3$ | C(O)Et | C(O)OCH$_3$ |
| 3,4-Br$_2$ | CF$_3$ | C(O)Pr-n | C(O)OCH$_3$ |
| 3,4-Br$_2$ | CF$_3$ | C(O)Bu-t | C(O)OCH$_3$ |
| 3,4-Br$_2$ | CF$_3$ | C(O)CH$_2$SCH$_3$ | C(O)OCH$_3$ |
| 3,4-Br$_2$ | CF$_3$ | C(O)OCH$_3$ | C(O)OEt |
| 3,4-Br$_2$ | CF$_3$ | H | C(O)OPr-i |
| 3,4-Br$_2$ | CF$_3$ | H | C(O)NH$_2$ |
| 3,4-Br$_2$ | CF$_3$ | C(O)OCH$_3$ | (D-52d)Cl |
| 3,4-Br$_2$ | CF$_3$ | CH3 | (D-55c)Cl |
| 3,4-Br$_2$ | CF$_3$ | CH$_2$OCH$_3$ | (D-55c)Cl |
| 3,4-Br$_2$ | CF$_3$ | C(O)CH3 | (D-55c)Cl |
| 3,4-Br$_2$ | CF$_3$ | C(O)Et | (D-55c)Cl |
| 3,4-Br$_2$ | CF$_3$ | C(O)Pr-i | (D-55c)Cl |
| 3,4-Br$_2$ | CF$_3$ | C(O)CH$_2$OCH$_3$ | (D-55c)Cl |
| 3,4-Br$_2$ | CF$_3$ | C(O)CH$_2$OEt | (D-55c)Cl |
| 3,4-Br$_2$ | CF$_3$ | C(O)CH$_2$SCH$_3$ | (D-55c)Cl |
| 3,4-Br$_2$ | CF$_3$ | C(O)OCH$_3$ | (D-55c)Cl |
| 3,4-Br$_2$ | CF$_3$ | C(O)OPr-n | (D-55c)Cl |
| 3,4-Br$_2$ | CF$_3$ | C(O)OCH$_2$CH$_2$Cl | (D-55c)Cl |
| 3,4-Br$_2$ | CF$_3$ | C(O)OCH$_2$CH2OCH$_3$ | (D-55c)Cl |
| 3,4-Br$_2$ | CF$_3$ | C(O)OCH$_2$CH=CH$_2$ | (D-55c)Cl |
| 3,4-Br$_2$ | CF$_3$ | CH$_2$OC(O)CH$_3$ | (D-55c)Br |
| 3,4-Br$_2$ | CF$_3$ | C(O)CH$_3$ | (D-55c)Br |
| 3,4-Br$_2$ | CF$_3$ | C(O)Et | (D-55c)Br |
| 3,4-Br$_2$ | CF$_3$ | C(O)Pr-n | (D-55c)Br |
| 3,4-Br$_2$ | CF$_3$ | C(O)Pr-i | (D-55c)Br |
| 3,4-Br$_2$ | CF$_3$ | C(O)OCH$_3$ | (D-55c)Br |
| 3,4-Br$_2$ | CF$_2$Cl | C(O)OEt | (D-55c)Br |
| 3,4-Br$_2$ | CF$_2$Cl | H | CH=NOCH$_3$ |
| 3,4-Br$_2$ | CF$_2$Cl | H | CH=NOEt |
| 3,4-Br$_2$ | CF$_2$Cl | CH$_2$OEt | C(O)OCH$_3$ |
| 3,4-Br$_2$ | CF$_2$Cl | CH$_2$OCH$_2$CF$_3$ | C(O)OCH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,4-Br$_2$ | CF$_2$Cl | C(O)Et | C(O)OCH$_3$ |
| 3,4-Br$_2$ | CF$_2$Cl | C(O)CH$_3$ | (D-55c)Cl |
| 3,4-Br$_2$ | CF$_2$Cl | C(O)Pr-i | (D-55c)Cl |
| 3,4-Br$_2$ | CF$_2$Cl | C(O)OCH$_3$ | (D-55c)Cl |
| 3,4-Br$_2$ | CF$_2$Cl | C(O)CH$_3$ | (D-55c)Br |
| 3,5-Br$_2$ | CHF$_2$ | H | CH=NOCH$_3$ |
| 3,5-Br$_2$ | CHF$_2$ | H | CH=NOEt |
| 3,5-Br$_2$ | CHF$_2$ | CH$_2$OEt | C(O)OCH$_3$ |
| 3,5-Br$_2$ | CHF$_2$ | CH$_2$OCH$_2$CF$_3$ | C(O)OCH$_3$ |
| 3,5-Br$_2$ | CHF$_2$ | C(O)Et | C(O)OCH$_3$ |
| 3,5-Br$_2$ | CHF$_2$ | C(O)CH$_3$ | (D-55c)Cl |
| 3,5-Br$_2$ | CHF$_2$ | C(O)Pr-i | (D-55c)Cl |
| 3,5-Br$_2$ | CHF$_2$ | C(O)OCH$_3$ | (D-55c)Cl |
| 3,5-Br$_2$ | CHF$_2$ | C(O)CH$_3$ | (D-55c)Br |
| 3,5-Br$_2$ | CHFCl | C(O)CH$_3$ | (D-55c)Cl |
| 3,5-Br$_2$ | CHCl$_2$ | C(O)Pr-i | (D-55c)Cl |
| 3,5-Br$_2$ | CHFBr | C(O)OCH$_3$ | (D-55c)Cl |
| 3,5-Br$_2$ | CF$_3$ | H | CH=NOCH$_3$ |
| 3,5-Br$_2$ | CF$_3$ | CH$_2$OCH$_3$ | CH=NOCH$_3$ |
| 3,5-Br$_2$ | CF$_3$ | CH$_2$OEt | CH=NOCH$_3$ |
| 3,5-Br$_2$ | CF$_3$ | H | CH=NOEt |
| 3,5-Br$_2$ | CF$_3$ | CH$_2$OCH$_3$ | CH=NOEt |
| 3,5-Br$_2$ | CF$_3$ | H | CH=NOPr-n |
| 3,5-Br$_2$ | CF$_3$ | H | CH=NOCH$_2$CF$_3$ |
| 3,5-Br$_2$ | CF$_3$ | H | CH=NOCH$_2$CH=CH$_2$ |
| 3,5-Br$_2$ | CF$_3$ | H | CH=NOCH$_2$C=CH |
| 3,5-Br$_2$ | CF$_3$ | H | C(O)OCH$_3$ |
| 3,5-Br$_2$ | CF$_3$ | CH$_3$ | C(O)OCH$_3$ |
| 3,5-Br$_2$ | CF$_3$ | Et | C(O)OCH$_3$ |
| 3,5-Br$_2$ | CF$_3$ | CH$_2$OCH$_3$ | C(O)OCH$_3$ |
| 3,5-Br$_2$ | CF$_3$ | CH$_2$OEt | C(O)OCH$_3$ |
| 3,5-Br$_2$ | CF$_3$ | CH$_2$OCH$_2$CF$_3$ | C(O)OCH$_3$ |
| 3,5-Br$_2$ | CF$_3$ | CH$_2$OC(O)CH$_3$ | C(O)OCH$_3$ |
| 3,5-Br$_2$ | CF$_3$ | CH$_2$OC(O)Et | C(O)OCH$_3$ |
| 3,5-Br$_2$ | CF$_3$ | CH$_2$OC(O)Bu-t | C(O)OCH$_3$ |
| 3,5-Br$_2$ | CF$_3$ | CH$_2$OC(O)OCH$_3$ | C(O)OCH$_3$ |
| 3,5-Br$_2$ | CF$_3$ | E-5a | C(O)OCH$_3$ |
| 3,5-Br$_2$ | CF$_3$ | CH$_2$NHC(O)OCH$_3$ | C(O)OCH$_3$ |
| 3,5-Br$_2$ | CF$_3$ | CH$_2$CN | C(O)OCH$_3$ |
| 3,5-Br$_2$ | CF$_3$ | CH$_2$C=CH | C(O)OCH$_3$ |
| 3,5-Br$_2$ | CF$_3$ | CH$_2$Ph | C(O)OCH$_3$ |
| 3,5-Br$_2$ | CF$_3$ | C(O)CH$_3$ | C(O)OCH$_3$ |
| 3,5-Br$_2$ | CF$_3$ | C(O)Et | C(O)OCH$_3$ |
| 3,5-Br$_2$ | CF$_3$ | C(O)Pr-n | C(O)OCH$_3$ |
| 3,5-Br$_2$ | CF$_3$ | C(O)Pr-i | C(O)OCH$_3$ |
| 3,5-Br$_2$ | CF$_3$ | C(O)Bu-t | C(O)OCH$_3$ |
| 3,5-Br$_2$ | CF$_3$ | C(O)CH$_2$Cl | C(O)OCH$_3$ |
| 3,5-Br$_2$ | CF$_3$ | C(O)CH$_2$OCH$_3$ | C(O)OCH$_3$ |
| 3,5-Br$_2$ | CF$_3$ | C(O)CH$_2$OEt | C(O)OCH$_3$ |
| 3,5-Br$_2$ | CF$_3$ | C(O)CH$_2$SCH$_3$ | C(O)OCH$_3$ |
| 3,5-Br$_2$ | CF$_3$ | C(O)Ph | C(O)OCH$_3$ |
| 3,5-Br$_2$ | CF$_3$ | C(O)OCH$_3$ | C(O)OCH$_3$ |
| 3,5-Br$_2$ | CF$_3$ | C(O)OCH$_2$Cl | C(O)OCH$_3$ |
| 3,5-Br$_2$ | CF$_3$ | C(O)OCH$_2$CH$_2$Cl | C(O)OCH$_3$ |
| 3,5-Br$_2$ | CF$_3$ | H | C(O)OEt |
| 3,5-Br$_2$ | CF$_3$ | CH$_3$ | C(O)OEt |
| 3,5-Br$_2$ | CF$_3$ | Et | C(O)OEt |
| 3,5-Br$_2$ | CF$_3$ | CH$_2$OCH$_3$ | C(O)OEt |
| 3,5-Br$_2$ | CF$_3$ | C(O)CH$_3$ | C(O)OEt |
| 3,5-Br$_2$ | CF$_3$ | C(O)Et | C(O)OEt |
| 3,5-Br$_2$ | CF$_3$ | C(O)Bu-t | C(O)OEt |
| 3,5-Br$_2$ | CF$_3$ | C(O)CH$_2$OCH$_3$ | C(O)OEt |
| 3,5-Br$_2$ | CF$_3$ | C(O)OCH$_3$ | C(O)OEt |
| 3,5-Br$_2$ | CF$_3$ | H | C(O)OPr-n |
| 3,5-Br$_2$ | CF$_3$ | H | C(O)OPr-i |
| 3,5-Br$_2$ | CF$_3$ | CH$_3$ | C(O)OPr-i |
| 3,5-Br$_2$ | CF$_3$ | CH$_2$OCH$_3$ | C(O)OPr-i |
| 3,5-Br$_2$ | CF$_3$ | CH$_2$CN | C(O)OPr-i |
| 3,5-Br$_2$ | CF$_3$ | CH$_2$C=CH | C(O)OPr-i |
| 3,5-Br$_2$ | CF$_3$ | C(O)CH$_3$ | C(O)OPr-i |
| 3,5-Br$_2$ | CF$_3$ | C(O)Et | C(O)OPr-i |
| 3,5-Br$_2$ | CF$_3$ | C(O)Bu-t | C(O)OPr-i |
| 3,5-Br$_2$ | CF$_3$ | C(O)CH$_2$OCH$_3$ | C(O)OPr-i |
| 3,5-Br$_2$ | CF$_3$ | C(O)OCH$_3$ | C(O)OPr-i |
| 3,5-Br$_2$ | CF$_3$ | C(O)OEt | C(O)OPr-i |
| 3,5-Br$_2$ | CF$_3$ | H | C(O)OBu-t |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Br$_2$ | CF$_3$ | C(O)CH$_3$ | C(O)OBu-t |
| 3,5-Br$_2$ | CF$_3$ | C(O)Et | C(O)OBu-t |
| 3,5-Br$_2$ | CF$_3$ | C(O)CH$_2$CF$_3$ | C(O)OBu-t |
| 3,5-Br$_2$ | CF$_3$ | C(O)OCH$_3$ | C(O)OBu-t |
| 3,5-Br$_2$ | CF$_3$ | C(O)OCH$_3$ | C(O)OCH$_2$CH$_2$OCH$_3$ |
| 3,5-Br$_2$ | CF$_3$ | H | C(O)NH$_2$ |
| 3,5-Br$_2$ | CF$_3$ | CH$_3$ | C(O)NH$_2$ |
| 3,5-Br$_2$ | CF$_3$ | CH$_3$ | C(O)NHC(O)CH$_3$ |
| 3,5-Br$_2$ | CF$_3$ | CH$_3$ | C(O)NHC(O)OCH$_3$ |
| 3,5-Br$_2$ | CF$_3$ | H | C(S)NH$_2$ |
| 3,5-Br$_2$ | CF$_3$ | CH$_3$ | D-14a |
| 3,5-Br$_2$ | CF$_3$ | C(O)CH$_3$ | D-14a |
| 3,5-Br$_2$ | CF$_3$ | C(O)OCH$_3$ | D-14a |
| 3,5-Br$_2$ | CF$_3$ | CH$_3$ | (D-52d)Cl |
| 3,5-Br$_2$ | CF$_3$ | CH$_2$OCH$_3$ | (D-52d)Cl |
| 3,5-Br$_2$ | CF$_3$ | C(O)CH$_3$ | (D-52d)Cl |
| 3,5-Br$_2$ | CF$_3$ | C(O)Et | (D-52d)Cl |
| 3,5-Br$_2$ | CF$_3$ | C(O)OCH$_3$ | (D-52d)Cl |
| 3,5-Br$_2$ | CF$_3$ | CH$_3$ | (D-52d)Br |
| 3,5-Br$_2$ | CF$_3$ | C(O)OCH$_3$ | (D-52d)Br |
| 3,5-Br$_2$ | CF$_3$ | CH$_3$ | (D-52d)CN |
| 3,5-Br$_2$ | CF$_3$ | CH$_3$ | (D-53e)Cl |
| 3,5-Br$_2$ | CF$_3$ | C(O)OCH$_3$ | (D-53e)Cl |
| 3,5-Br$_2$ | CF$_3$ | CH$_3$ | D-55a |
| 3,5-Br$_2$ | CF$_3$ | C(O)OCH$_3$ | D-55a |
| 3,5-Br$_2$ | CF$_3$ | C(O)Pr-i | D-55a |
| 3,5-Br$_2$ | CF$_3$ | C(O)Bu-t | D-55a |
| 3,5-Br$_2$ | CF$_3$ | CH$_3$ | (D-55c)Cl |
| 3,5-Br$_2$ | CF$_3$ | Et | (D-55c)Cl |
| 3,5-Br$_2$ | CF$_3$ | CH$_2$OCH$_3$ | (D-55c)Cl |
| 3,5-Br$_2$ | CF$_3$ | CH$_2$OEt | (D-55c)Cl |
| 3,5-Br$_2$ | CF$_3$ | CH$_2$OC(O)CH$_3$ | (D-55c)Cl |
| 3,5-Br$_2$ | CF$_3$ | CH$_2$OC(O)Bu-t | (D-55c)Cl |
| 3,5-Br$_2$ | CF$_3$ | CH$_2$OC(O)OCH$_3$ | (D-55c)Cl |
| 3,5-Br$_2$ | CF$_3$ | CH$_2$CN | (D-55c)Cl |
| 3,5-Br$_2$ | CF$_3$ | CH$_2$C≡CH | (D-55c)Cl |
| 3,5-Br$_2$ | CF$_3$ | C(O)CH$_3$ | (D-55c)Cl |
| 3,5-Br$_2$ | CF$_3$ | C(O)Et | (D-55c)Cl |
| 3,5-Br$_2$ | CF$_3$ | C(O)Pr-n | (D-55c)Cl |
| 3,5-Br$_2$ | CF$_3$ | C(O)Pr-i | (D-55c)Cl |
| 3,5-Br$_2$ | CF$_3$ | C(O)Pr-c | (D-55c)Cl |
| 3,5-Br$_2$ | CF$_3$ | C(O)Bu-t | (D-55c)Cl |
| 3,5-Br$_2$ | CF$_3$ | C(O)CH$_2$Cl | (D-55c)Cl |
| 3,5-Br$_2$ | CF$_3$ | C(O)CH$_2$OCH$_3$ | (D-55c)Cl |
| 3,5-Br$_2$ | CF$_3$ | C(O)CH$_2$OEt | (D-55c)Cl |
| 3,5-Br$_2$ | CF$_3$ | C(O)CH$_2$SCH$_3$ | (D-55c)Cl |
| 3,5-Br$_2$ | CF$_3$ | C(O)CH$_2$S(O)CH$_3$ | (D-55c)Cl |
| 3,5-Br$_2$ | CF$_3$ | C(O)C(O)OEt | (D-55c)Cl |
| 3,5-Br$_2$ | CF$_3$ | C(O)Ph | (D-55c)Cl |
| 3,5-Br$_2$ | CF$_3$ | C(O)(D-52a) | (D-55c)Cl |
| 3,5-Br$_2$ | CF$_3$ | C(O)OCH$_3$ | (D-55c)Cl |
| 3,5-Br$_2$ | CF$_3$ | C(O)OEt | (D-55c)Cl |
| 3,5-Br$_2$ | CF$_3$ | C(O)OPr-n | (D-55c)Cl |
| 3,5-Br$_2$ | CF$_3$ | C(O)OPr-i | (D-55c)Cl |
| 3,5-Br$_2$ | CF$_3$ | C(O)OBu-n | (D-55c)Cl |
| 3,5-Br$_2$ | CF$_3$ | C(O)OBu-i | (D-55c)Cl |
| 3,5-Br$_2$ | CF$_3$ | C(O)OBu-t | (D-55c)Cl |
| 3,5-Br$_2$ | CF$_3$ | C(O)OCH$_2$Cl | (D-55c)Cl |
| 3,5-Br$_2$ | CF$_3$ | C(O)OCH$_2$CH$_2$Cl | (D-55c)Cl |
| 3,5-Br$_2$ | CF$_3$ | C(O)OCH$_2$CH$_2$OCH$_3$ | (D-55c)Cl |
| 3,5-Br$_2$ | CF$_3$ | C(O)OCH$_2$CH=CH$_2$ | (D-55c)Cl |
| 3,5-Br$_2$ | CF$_3$ | C(O)Pr-n | (D-55c)Cl |
| 3,5-Br$_2$ | CF$_3$ | CH$_3$ | (D-55c)Br |
| 3,5-Br$_2$ | CF$_3$ | Et | (D-55c)Br |
| 3,5-Br$_2$ | CF$_3$ | CH$_2$OCH$_3$ | (D-55c)Br |
| 3,5-Br$_2$ | CF$_3$ | CH$_2$OEt | (D-55c)Br |
| 3,5-Br$_2$ | CF$_3$ | CH$_2$OC(O)CH$_3$ | (D-55c)Br |
| 3,5-Br$_2$ | CF$_3$ | C(O)CH$_3$ | (D-55c)Br |
| 3,5-Br$_2$ | CF$_3$ | C(O)Et | (D-55c)Br |
| 3,5-Br$_2$ | CF$_3$ | C(O)Pr-n | (D-55c)Br |
| 3,5-Br$_2$ | CF$_3$ | C(O)Pr-i | (D-55c)Br |
| 3,5-Br$_2$ | CF$_3$ | C(O)Pr-c | (D-55c)Br |
| 3,5-Br$_2$ | CF$_3$ | C(O)Bu-t | (D-55c)Br |
| 3,5-Br$_2$ | CF$_3$ | C(O)CH$_2$OCH$_3$ | (D-55c)Br |
| 3,5-Br$_2$ | CF$_3$ | C(O)Ph | (D-55c)Br |
| 3,5-Br$_2$ | CF$_3$ | C(O)OCH$_3$ | (D-55c)Br |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Br$_2$ | CF$_3$ | C(O)OEt | (D-55c)Br |
| 3,5-Br$_2$ | CF$_3$ | C(O)OPr-n | (D-55c)Br |
| 3,5-Br$_2$ | CF$_3$ | C(O)OBu-i | (D-55c)Br |
| 3,5-Br$_2$ | CF$_3$ | C(O)OCH$_2$Cl | (D-55c)Br |
| 3,5-Br$_2$ | CF$_3$ | C(O)OCH$_2$CH$_2$OCH$_3$ | (D-55c)Br |
| 3,5-Br$_2$ | CF$_3$ | CH$_3$ | D-57a |
| 3,5-Br$_2$ | CF$_3$ | C(O)CH$_3$ | D-57a |
| 3,5-Br$_2$ | CF$_3$ | C(O)Pr-n | D-57a |
| 3,5-Br$_2$ | CF$_3$ | C(O)Pr-i | D-57a |
| 3,5-Br$_2$ | CF$_3$ | C(O)OCH$_3$ | D-57a |
| 3,5-Br$_2$ | CF$_3$ | CH$_3$ | D-58a |
| 3,5-Br$_2$ | CF$_3$ | CH$_3$ | (D-58b)Cl |
| 3,5-Br$_2$ | CF$_3$ | CH$_2$OCH$_3$ | (D-58b)Cl |
| 3,5-Br$_2$ | CF$_3$ | C(O)CH$_3$ | (D-58b)Cl |
| 3,5-Br$_2$ | CF$_3$ | C(O)OCH$_3$ | (D-58b)Cl |
| 3,5-Br$_2$ | CF$_2$Cl | H | CH=NOCH$_3$ |
| 3,5-Br$_2$ | CF$_2$Cl | CH$_2$OCH$_3$ | CH=NOCH$_3$ |
| 3,5-Br$_2$ | CF$_2$Cl | H | CH=NOEt |
| 3,5-Br$_2$ | CF$_2$Cl | H | C(O)OCH$_3$ |
| 3,5-Br$_2$ | CF$_2$Cl | Et | C(O)OCH$_3$ |
| 3,5-Br$_2$ | CF$_2$Cl | CH$_2$OCH$_3$ | C(O)OCH$_3$ |
| 3,5-Br$_2$ | CF$_2$Cl | CH$_2$OEt | C(O)OCH$_3$ |
| 3,5-Br$_2$ | CF$_2$Cl | CH$_2$OCH$_2$CF$_3$ | C(O)OCH$_3$ |
| 3,5-Br$_2$ | CF$_2$Cl | CH$_2$OC(O)CH$_3$ | C(O)OCH$_3$ |
| 3,5-Br$_2$ | CF$_2$Cl | CH$_2$OC(O)Et | C(O)OCH$_3$ |
| 3,5-Br$_2$ | CF$_2$Cl | CH$_2$OC(O)OCH$_3$ | C(O)OCH$_3$ |
| 3,5-Br$_2$ | CF$_2$Cl | E-5a | C(O)OCH3 |
| 3,5-Br$_2$ | CF$_2$Cl | C(O)CH$_3$ | C(O)OCH3 |
| 3,5-Br$_2$ | CF$_2$Cl | C(O)Et | C(O)OCH3 |
| 3,5-Br$_2$ | CF$_2$Cl | C(O)Pr-n | C(O)OCH3 |
| 3,5-Br$_2$ | CF$_2$Cl | C(O)Pr-i | C(O)OCH3 |
| 3,5-Br$_2$ | CF$_2$Cl | C(O)Bu-t | C(O)OCH3 |
| 3,5-Br$_2$ | CF$_2$Cl | C(O)CH$_2$OCH$_3$ | C(O)OCH3 |
| 3,5-Br$_2$ | CF$_2$Cl | C(O)CH$_2$SCH$_3$ | C(O)OCH3 |
| 3,5-Br$_2$ | CF$_2$Cl | C(O)OCH$_3$ | C(O)OEt |
| 3,5-Br$_2$ | CF$_2$Cl | H | C(O)OPr-i |
| 3,5-Br$_2$ | CF$_2$Cl | C(O)OCH$_3$ | C(O)OPr-i |
| 3,5-Br$_2$ | CF$_2$Cl | H | C(O)NH$_2$ |
| 3,5-Br$_2$ | CF$_2$Cl | CH$_3$ | (D-52d)Cl |
| 3,5-Br$_2$ | CF$_2$Cl | CH$_2$OCH$_3$ | (D-52d)Cl |
| 3,5-Br$_2$ | CF$_2$Cl | C(O)OCH$_3$ | (D-52d)Cl |
| 3,5-Br$_2$ | CF$_2$Cl | CH$_3$ | (D-55c)Cl |
| 3,5-Br$_2$ | CF$_2$Cl | CH$_2$OCH$_3$ | (D-55c)Cl |
| 3,5-Br$_2$ | CF$_2$Cl | CH$_2$OC(O)CH$_3$ | (D-55c)Cl |
| 3,5-Br$_2$ | CF$_2$Cl | CH$_2$OC(O)Bu-t | (D-55c)Cl |
| 3,5-Br$_2$ | CF$_2$Cl | CH$_2$OC(O)OCH$_3$ | (D-55c)Cl |
| 3,5-Br$_2$ | CF$_2$Cl | CH$_2$CN | (D-55c)Cl |
| 3,5-Br$_2$ | CF$_2$Cl | C(O)CH$_3$ | (D-55c)Cl |
| 3,5-Br$_2$ | CF$_2$Cl | C(O)Et | (D-55c)Cl |
| 3,5-Br$_2$ | CF$_2$Cl | C(O)Pr-n | (D-55c)Cl |
| 3,5-Br$_2$ | CF$_2$Cl | C(O)Pr-i | (D-55c)Cl |
| 3,5-Br$_2$ | CF$_2$Cl | C(O)Pr-c | (D-55c)Cl |
| 3,5-Br$_2$ | CF$_2$Cl | C(O)Bu-t | (D-55c)Cl |
| 3,5-Br$_2$ | CF$_2$Cl | C(O)CH$_2$Cl | (D-55c)Cl |
| 3,5-Br$_2$ | CF$_2$Cl | C(O)CH$_2$OCH$_3$ | (D-55c)Cl |
| 3,5-Br$_2$ | CF$_2$Cl | C(O)CH$_2$OEt | (D-55c)Cl |
| 3,5-Br$_2$ | CF$_2$Cl | C(O)CH$_2$SCH$_3$ | (D-55c)Cl |
| 3,5-Br$_2$ | CF$_2$Cl | C(O)CH$_2$S(O)CH$_3$ | (D-55c)Cl |
| 3,5-Br$_2$ | CF$_2$Cl | C(O)C(O)OEt | (D-55c)Cl |
| 3,5-Br$_2$ | CF$_2$Cl | C(O)OCH$_3$ | (D-55c)Cl |
| 3,5-Br$_2$ | CF$_2$Cl | C(O)OPr-n | (D-55c)Cl |
| 3,5-Br$_2$ | CF$_2$Cl | C(O)OCH$_2$Cl | (D-55c)Cl |
| 3,5-Br$_2$ | CF$_2$Cl | C(O)OCH$_2$CH$_2$Cl | (D-55c)Cl |
| 3,5-Br$_2$ | CF$_2$Cl | C(O)OCH$_2$CH$_2$OCH$_3$ | (D-55c)Cl |
| 3,5-Br$_2$ | CF$_2$Cl | C(O)OCH$_2$CH=CH$_2$ | (D-55c)Cl |
| 3,5-Br$_2$ | CF$_2$Cl | CH$_3$ | (D-55c)Br |
| 3,5-Br$_2$ | CF$_2$Cl | CH$_2$OC(O)CH$_3$ | (D-55c)Br |
| 3,5-Br$_2$ | CF$_2$Cl | C(O)CH$_3$ | (D-55c)Br |
| 3,5-Br$_2$ | CF$_2$Cl | C(O)Et | (D-55c)Br |
| 3,5-Br$_2$ | CF$_2$Cl | C(O)Pr-n | (D-55c)Br |
| 3,5-Br$_2$ | CF$_2$Cl | C(O)Pr-i | (D-55c)Br |
| 3,5-Br$_2$ | CF$_2$Cl | C(O)OCH$_3$ | (D-55c)Br |
| 3,5-Br$_2$ | CF$_2$Cl | C(O)OEt | (D-55c)Br |
| 3,5-Br$_2$ | CF$_2$Cl | C(O)OCH$_2$CH$_2$OCH$_3$ | (D-55c)Br |
| 3,5-Br$_2$ | CF$_2$Cl | C(O)Pr-i | D-57a |
| 3,5-Br$_2$ | CF$_2$Br | H | CH=NOCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-Br$_2$ | CF$_2$Br | H | CH=NOEt |
| 3,5-Br$_2$ | CF$_2$Br | CH$_2$OEt | C(O)OCH$_3$ |
| 3,5-Br$_2$ | CF$_2$Br | CH$_2$OCH$_2$CF$_3$ | C(O)OCH$_3$ |
| 3,5-Br$_2$ | CF$_2$Br | C(O)Et | C(O)OCH$_3$ |
| 3,5-Br$_2$ | CF$_2$Br | C(O)CH$_3$ | (D-55c)Cl |
| 3,5-Br$_2$ | CF$_2$Br | C(O)Pr-i | (D-55c)Cl |
| 3,5-Br$_2$ | CF$_2$Br | C(O)OCH$_3$ | (D-55c)Cl |
| 3,5-Br$_2$ | CF$_2$Br | C(O)CH$_3$ | (D-55c)Br |
| 3,5-Br$_2$ | CF$_2$CHF$_2$ | H | CH=NOCH$_3$ |
| 3,5-Br$_2$ | CF$_2$CHF$_2$ | H | CH=NOEt |
| 3,5-Br$_2$ | CF$_2$CHF$_2$ | CH$_2$OEt | C(O)OCH$_3$ |
| 3,5-Br$_2$ | CF$_2$CHF$_2$ | CH$_2$OCH$_2$CF$_3$ | C(O)OCH$_3$ |
| 3,5-Br$_2$ | CF$_2$CHF$_2$ | C(O)Et | C(O)OCH$_3$ |
| 3,5-Br$_2$ | CF$_2$CHF$_2$ | C(O)CH$_3$ | (D-55c)Cl |
| 3,5-Br$_2$ | CF$_2$CHF$_2$ | C(O)Pr-i | (D-55c)Cl |
| 3,5-Br$_2$ | CF$_2$CHF$_2$ | C(O)OCH$_3$ | (D-55c)Cl |
| 3,5-Br$_2$ | CF$_2$CHF$_2$ | C(O)CH$_3$ | (D-55c)Br |
| 3,5-Br$_2$ | CF$_2$CF$_3$ | C(O)CH$_3$ | (D-55c)Br |
| 3,5-Br$_2$ | CF$_2$OCH$_3$ | H | CH=NOCH$_3$ |
| 3,5-Br$_2$ | CF$_2$SCH$_3$ | H | CH=NOEt |
| 3,5-Br$_2$ | T-3 | CH$_2$OEt | C(O)OCH$_3$ |
| 3-F-5-I | CF$_3$ | H | CH=NOCH$_3$ |
| 3-F-5-I | CF$_3$ | CH$_2$OCH$_3$ | CH=NOCH$_3$ |
| 3-F-5-I | CF$_3$ | H | CH=NOEt |
| 3-F-5-I | CF$_3$ | H | C(O)OCH$_3$ |
| 3-F-5-I | CF$_3$ | Et | C(O)OCH$_3$ |
| 3-F-5-I | CF$_3$ | CH$_2$OCH$_3$ | C(O)OCH$_3$ |
| 3-F-5-I | CF$_3$ | CH$_2$OEt | C(O)OCH$_3$ |
| 3-F-5-I | CF$_3$ | CH$_2$OCH$_2$CF$_3$ | C(O)OCH$_3$ |
| 3-F-5-I | CF$_3$ | CH$_2$OC(O)CH$_3$ | C(O)OCH$_3$ |
| 3-F-5-I | CF$_3$ | CH$_2$OC(O)Et | C(O)OCH$_3$ |
| 3-F-5-I | CF$_3$ | CH$_2$OC(O)OCH$_3$ | C(O)OCH$_3$ |
| 3-F-5-I | CF$_3$ | E-5a | C(O)OCH$_3$ |
| 3-F-5-I | CF$_3$ | C(O)Et | C(O)OCH$_3$ |
| 3-F-5-I | CF$_3$ | C(O)Pr-n | C(O)OCH$_3$ |
| 3-F-5-I | CF$_3$ | C(O)Bu-t | C(O)OCH$_3$ |
| 3-F-5-I | CF$_3$ | C(O)CH$_2$SCH$_3$ | C(O)OCH$_3$ |
| 3-F-5-I | CF$_3$ | C(O)OCH$_3$ | C(O)OEt |
| 3-F-5-I | CF$_3$ | H | C(O)OPr-i |
| 3-F-5-I | CF$_3$ | H | C(O)NH$_2$ |
| 3-F-5-I | CF$_3$ | C(O)OCH$_3$ | (D-52d)Cl |
| 3-F-5-I | CF$_3$ | CH$_3$ | (D-55c)Cl |
| 3-F-5-I | CF$_3$ | CH$_2$OCH$_3$ | (D-55c)Cl |
| 3-F-5-I | CF$_3$ | C(O)CH$_3$ | (D-55c)Cl |
| 3-F-5-I | CF$_3$ | C(O)Et | (D-55c)Cl |
| 3-F-5-I | CF$_3$ | C(O)Pr-i | (D-55c)Cl |
| 3-F-5-I | CF$_3$ | C(O)CH$_2$OCH$_3$ | (D-55c)Cl |
| 3-F-5-I | CF$_3$ | C(O)CH$_2$OEt | (D-55c)Cl |
| 3-F-5-I | CF$_3$ | C(O)CH$_2$SCH$_3$ | (D-55c)Cl |
| 3-F-5-I | CF$_3$ | C(O)OCH$_3$ | (D-55c)Cl |
| 3-F-5-I | CF$_3$ | C(O)OPr-n | (D-55c)Cl |
| 3-F-5-I | CF$_3$ | C(O)OCH$_2$CH$_2$Cl | (D-55c)Cl |
| 3-F-5-I | CF$_3$ | C(O)OCH$_2$CH$_2$OCH$_3$ | (D-55c)Cl |
| 3-F-5-I | CF$_3$ | C(O)OCH$_2$CH=CH$_2$ | (D-55c)Cl |
| 3-F-5-I | CF$_3$ | CH$_2$OC(O)CH$_3$ | (D-55c)Br |
| 3-F-5-I | CF$_3$ | C(O)CH$_3$ | (D-55c)Br |
| 3-F-5-I | CF$_3$ | C(O)Et | (D-55c)Br |
| 3-F-5-I | CF$_3$ | C(O)Pr-n | (D-55c)Br |
| 3-F-5-I | CF$_3$ | C(O)Pr-i | (D-55c)Br |
| 3-F-5-I | CF$_3$ | C(O)OCH$_3$ | (D-55c)Br |
| 3-F-5-I | CF$_3$ | C(O)OEt | (D-55c)Br |
| 3-F-5-I | CF$_2$Cl | H | CH=NOCH$_3$ |
| 3-F-5-I | CF$_2$Cl | H | CH=NOEt |
| 3-F-5-I | CF$_2$Cl | CH$_2$OEt | C(O)OCH$_3$ |
| 3-F-5-I | CF$_2$Cl | CH$_2$OCH$_2$CF$_3$ | C(O)OCH$_3$ |
| 3-F-5-I | CF$_2$Cl | C(O)Et | C(O)OCH$_3$ |
| 3-F-5-I | CF$_2$Cl | C(O)CH$_3$ | (D-55c)Cl |
| 3-F-5-I | CF$_2$Cl | C(O)Pr-i | (D-55c)Cl |
| 3-F-5-I | CF$_2$Cl | C(O)OCH$_3$ | (D-55c)Cl |
| 3-F-5-I | CF$_2$Cl | C(O)CH$_3$ | (D-55c)Br |
| 3-Cl-5-I | CHF$_2$ | CH$_2$OCH$_2$CF$_3$ | C(O)OCH$_3$ |
| 3-Cl-5-I | CF$_3$ | H | CH=NOCH$_3$ |
| 3-Cl-5-I | CF$_3$ | CH$_2$OCH$_3$ | CH=NOCH$_3$ |
| 3-Cl-5-I | CF$_3$ | H | CH=NOEt |
| 3-Cl-5-I | CF$_3$ | H | C(O)OCH$_3$ |
| 3-Cl-5-I | CF$_3$ | Et | C(O)OCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-I | $CF_3$ | $CH_2OCH_3$ | $C(O)OCH_3$ |
| 3-Cl-5-I | $CF_3$ | $CH_2OEt$ | $C(O)OCH_3$ |
| 3-Cl-5-I | $CF_3$ | $CH_2OCH2CF_3$ | $C(O)OCH_3$ |
| 3-Cl-5-I | $CF_3$ | $CH_2OC(O)CH_3$ | $C(O)OCH_3$ |
| 3-Cl-5-I | $CF_3$ | $CH_2OC(O)Et$ | $C(O)OCH_3$ |
| 3-Cl-5-I | $CF_3$ | $CH_2OC(O)OCH_3$ | $C(O)OCH_3$ |
| 3-Cl-5-I | $CF_3$ | E-5a | $C(O)OCH_3$ |
| 3-Cl-5-I | $CF_3$ | $C(O)CH_3$ | $C(O)OCH_3$ |
| 3-Cl-5-I | $CF_3$ | $C(O)Et$ | $C(O)OCH_3$ |
| 3-Cl-5-I | $CF_3$ | $C(O)Pr-n$ | $C(O)OCH_3$ |
| 3-Cl-5-I | $CF_3$ | $C(O)Pr-i$ | $C(O)OCH_3$ |
| 3-Cl-5-I | $CF_3$ | $C(O)Bu-t$ | $C(O)OCH_3$ |
| 3-Cl-5-I | $CF_3$ | $C(O)CH_2OCH_3$ | $C(O)OCH_3$ |
| 3-Cl-5-I | $CF_3$ | $C(O)CH_2SCH_3$ | $C(O)OCH_3$ |
| 3-Cl-5-I | $CF_3$ | $C(O)OCH_3$ | $C(O)OEt$ |
| 3-Cl-5-I | $CF_3$ | H | $C(O)OPr-i$ |
| 3-Cl-5-I | $CF_3$ | $C(O)OCH_3$ | $C(O)OPr-i$ |
| 3-Cl-5-I | $CF_3$ | H | $C(O)NH_2$ |
| 3-Cl-5-I | $CF_3$ | $CH_3$ | (D-52d)Cl |
| 3-Cl-5-I | $CF_3$ | $CH_2OCH_3$ | (D-52d)Cl |
| 3-Cl-5-I | $CF_3$ | $C(O)OCH_3$ | (D-52d)Cl |
| 3-Cl-5-I | $CF_3$ | $CH_3$ | (D-55c)Cl |
| 3-Cl-5-I | $CF_3$ | $CH_2OCH_3$ | (D-55c)Cl |
| 3-Cl-5-I | $CF_3$ | $CH_2OC(O)CH_3$ | (D-55c)Cl |
| 3-Cl-5-I | $CF_3$ | $CH_2OC(O)Bu-t$ | (D-55c)Cl |
| 3-Cl-5-I | $CF_3$ | $CH_2OC(O)OCH_3$ | (D-55c)Cl |
| 3-Cl-5-I | $CF_3$ | $CH_2CN$ | (D-55c)Cl |
| 3-Cl-5-I | $CF_3$ | $C(O)CH_3$ | (D-55c)Cl |
| 3-Cl-5-I | $CF_3$ | $C(O)Et$ | (D-55c)Cl |
| 3-Cl-5-I | $CF_3$ | $C(O)Pr-n$ | (D-55c)Cl |
| 3-Cl-5-I | $CF_3$ | $C(O)Pr-i$ | (D-55c)Cl |
| 3-Cl-5-I | $CF_3$ | $C(O)Pr-c$ | (D-55c)Cl |
| 3-Cl-5-I | $CF_3$ | $C(O)Bu-t$ | (D-55c)Cl |
| 3-Cl-5-I | $CF_3$ | $C(O)CH_2Cl$ | (D-55c)Cl |
| 3-Cl-5-I | $CF_3$ | $C(O)CH_2OCH_3$ | (D-55c)Cl |
| 3-Cl-5-I | $CF_3$ | $C(O)CH_2OEt$ | (D-55c)Cl |
| 3-Cl-5-I | $CF_3$ | $C(O)CH_2SCH_3$ | (D-55c)Cl |
| 3-Cl-5-I | $CF_3$ | $C(O)CH_2S(O)CH_3$ | (D-55c)Cl |
| 3-Cl-5-I | $CF_3$ | $C(O)C(O)OEt$ | (D-55c)Cl |
| 3-Cl-5-I | $CF_3$ | $C(O)OCH_3$ | (D-55c)Cl |
| 3-Cl-5-I | $CF_3$ | $C(O)OPr-n$ | (D-55c)Cl |
| 3-Cl-5-I | $CF_3$ | $C(O)OCH_2Cl$ | (D-55c)Cl |
| 3-Cl-5-I | $CF_3$ | $C(O)OCH_2CH_2Cl$ | (D-55c)Cl |
| 3-Cl-5-I | $CF_3$ | $C(O)OCH_2CH_2OCH_3$ | (D-55c)Cl |
| 3-Cl-5-I | $CF_3$ | $C(O)OCH_2CH=CH_2$ | (D-55c)Cl |
| 3-Cl-5-I | $CF_3$ | $CH_3$ | (D-55c)Br |
| 3-Cl-5-I | $CF_3$ | $CH_2OC(O)CH_3$ | (D-55c)Br |
| 3-Cl-5-I | $CF_3$ | $C(O)CH_3$ | (D-55c)Br |
| 3-Cl-5-I | $CF_3$ | $C(O)Et$ | (D-55c)Br |
| 3-Cl-5-I | $CF_3$ | $C(O)Pr-n$ | (D-55c)Br |
| 3-Cl-5-I | $CF_3$ | $C(O)Pr-i$ | (D-55c)Br |
| 3-Cl-5-I | $CF_3$ | $C(O)OCH_3$ | (D-55c)Br |
| 3-Cl-5-I | $CF_3$ | $C(O)OEt$ | (D-55c)Br |
| 3-Cl-5-I | $CF_3$ | $C(O)OCH_2CH_2OCH_3$ | (D-55c)Br |
| 3-Cl-5-I | $CF_3$ | $C(O)Pr-i$ | D-57a |
| 3-Cl-5-I | $CF_2Cl$ | H | $CH=NOCH_3$ |
| 3-Cl-5-I | $CF_2Cl$ | H | $CH=NOEt$ |
| 3-Cl-5-I | $CF_2Cl$ | H | $C(O)OCH_3$ |
| 3-Cl-5-I | $CF_2Cl$ | Et | $C(O)OCH_3$ |
| 3-Cl-5-I | $CF_2Cl$ | $CH_2OCH_3$ | $C(O)OCH_3$ |
| 3-Cl-5-I | $CF_2Cl$ | $CH_2OEt$ | $C(O)OCH_3$ |
| 3-Cl-5-I | $CF_2Cl$ | $CH_2OCH_2CF_3$ | $C(O)OCH_3$ |
| 3-Cl-5-I | $CF_2Cl$ | $C(O)Et$ | $C(O)OCH_3$ |
| 3-Cl-5-I | $CF_2Cl$ | $C(O)OCH_3$ | $C(O)OEt$ |
| 3-Cl-5-I | $CF_2Cl$ | H | $C(O)NH_2$ |
| 3-Cl-5-I | $CF_2Cl$ | $CH_3$ | (D-55c)Cl |
| 3-Cl-5-I | $CF_2Cl$ | $CH_2OCH_3$ | (D-55c)Cl |
| 3-Cl-5-I | $CF_2Cl$ | $C(O)CH_3$ | (D-55c)Cl |
| 3-Cl-5-I | $CF_2Cl$ | $C(O)Et$ | (D-55c)Cl |
| 3-Cl-5-I | $CF_2Cl$ | $C(O)Pr-i$ | (D-55c)Cl |
| 3-Cl-5-I | $CF_2Cl$ | $C(O)CH_2OCH_3$ | (D-55c)Cl |
| 3-Cl-5-I | $CF_2Cl$ | $C(O)OCH_3$ | (D-55c)Cl |
| 3-Cl-5-I | $CF_2Cl$ | $C(O)CH_3$ | (D-55c)Br |
| 3-Cl-5-I | $CF_2Cl$ | $C(O)Et$ | (D-55c)Br |
| 3-Cl-5-I | $CF_2Cl$ | $C(O)Pr-i$ | (D-55c)Br |
| 3-Cl-5-I | $CF_2Cl$ | $C(O)Et$ | $C(O)OCH_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-I | CF$_2$Cl | C(O)CH$_3$ | (D-55c)Cl |
| 3,5-I$_2$ | CF$_3$ | H | CH=NOCH$_3$ |
| 3,5-I$_2$ | CF$_3$ | H | CH=NOEt |
| 3,5-I$_2$ | CF$_3$ | CH$_2$OEt | C(O)OCH$_3$ |
| 3,5-I$_2$ | CF$_3$ | CH$_2$OCH$_2$CF$_3$ | C(O)OCH$_3$ |
| 3,5-I$_2$ | CF$_3$ | C(O)Et | C(O)OCH$_3$ |
| 3,5-I$_2$ | CF$_3$ | C(O)CH$_3$ | (D-55c)Cl |
| 3,5-I$_2$ | CF$_3$ | C(O)Pr-i | (D-55c)Cl |
| 3,5-I$_2$ | CF$_3$ | C(O)OCH3 | (D-55c)Cl |
| 3,5-I$_2$ | CF$_3$ | C(O)CH3 | (D-55c)Br |
| 3-F-4-CH$_3$ | CF$_3$ | C(O)Pr-i | (D-55c)Cl |
| 3-F-5-CH$_3$ | CF$_3$ | C(O)OCH$_3$ | (D-55c)Cl |
| 3-Cl-4-CH$_3$ | CF$_3$ | C(O)CH$_3$ | (D-55c)Br |
| 3-Cl-5-CH$_3$ | CF$_3$ | H | CH=NOCH$_3$ |
| 3-Cl-5-CH$_3$ | CF$_3$ | H | CH=NOEt |
| 3-Cl-5-CH$_3$ | CF$_3$ | H | C(O)OCH$_3$ |
| 3-Cl-5-CH$_3$ | CF$_3$ | Et | C(O)OCH$_3$ |
| 3-Cl-5-CH$_3$ | CF$_3$ | CH$_2$OCH$_3$ | C(O)OCH$_3$ |
| 3-Cl-5-CH$_3$ | CF$_3$ | CH$_2$OEt | C(O)OCH$_3$ |
| 3-Cl-5-CH$_3$ | CF$_3$ | CH$_2$OCH$_2$CF$_3$ | C(O)OCH$_3$ |
| 3-Cl-5-CH$_3$ | CF$_3$ | C(O)Et | C(O)OCH$_3$ |
| 3-Cl-5-CH$_3$ | CF$_3$ | C(O)OCH$_3$ | C(O)OEt |
| 3-Cl-5-CH$_3$ | CF$_3$ | H | C(O)NH$_2$ |
| 3-Cl-5-CH$_3$ | CF$_3$ | CH$_3$ | (D-55c)Cl |
| 3-Cl-5-CH$_3$ | CF$_3$ | CH$_2$OCH$_3$ | (D-55c)Cl |
| 3-Cl-5-CH$_3$ | CF$_3$ | C(O)CH$_3$ | (D-55c)Cl |
| 3-Cl-5-CH$_3$ | CF$_3$ | C(O)Et | (D-55c)Cl |
| 3-Cl-5-CH$_3$ | CF$_3$ | C(O)Pr-i | (D-55c)Cl |
| 3-Cl-5-CH$_3$ | CF$_3$ | C(O)CH$_2$OCH$_3$ | (D-55c)Cl |
| 3-Cl-5-CH$_3$ | CF$_3$ | C(O)OCH$_3$ | (D-55c)Cl |
| 3-Cl-5-CH$_3$ | CF$_3$ | C(O)CH$_3$ | (D-55c)Br |
| 3-Cl-5-CH$_3$ | CF$_3$ | C(O)Et | (D-55c)Br |
| 3-Cl-5-CH$_3$ | CF$_3$ | C(O)Pr-i | (D-55c)Br |
| 3-Cl-5-CH$_3$ | CF$_2$Cl | H | CH=NOCH$_3$ |
| 3-Cl-5-CH$_3$ | CF$_2$Cl | CH$_2$OEt | C(O)OCH$_3$ |
| 3-Cl-5-CH$_3$ | CF$_2$Cl | C(O)Et | C(O)OCH$_3$ |
| 3-Cl-5-CH$_3$ | CF$_2$Cl | C(O)CH$_3$ | (D-55c)Cl |
| 3-Cl-5-CH$_3$ | CF$_2$Cl | C(O)OCH$_3$ | (D-55c)Cl |
| 3-Br-5-CH$_3$ | CF$_3$ | H | CH=NOCH$_3$ |
| 3-Br-5-CH$_3$ | CF$_3$ | H | CH=NOEt |
| 3-Br-5-CH$_3$ | CF$_3$ | H | C(O)OCH$_3$ |
| 3-Br-5-CH$_3$ | CF$_3$ | Et | C(O)OCH$_3$ |
| 3-Br-5-CH$_3$ | CF$_3$ | CH$_2$OCH$_3$ | C(O)OCH$_3$ |
| 3-Br-5-CH$_3$ | CF$_3$ | CH$_2$OEt | C(O)OCH$_3$ |
| 3-Br-5-CH$_3$ | CF$_3$ | CH$_2$OCH$_2$CF$_3$ | C(O)OCH$_3$ |
| 3-Br-5-CH$_3$ | CF$_3$ | C(O)Et | C(O)OCH$_3$ |
| 3-Br-5-CH$_3$ | CF$_3$ | C(O)OCH$_3$ | C(O)OEt |
| 3-Br-5-CH$_3$ | CF$_3$ | H | C(O)NH$_2$ |
| 3-Br-5-CH$_3$ | CF$_3$ | CH$_3$ | (D-55c)Cl |
| 3-Br-5-CH$_3$ | CF$_3$ | CH$_2$OCH$_3$ | (D-55c)Cl |
| 3-Br-5-CH$_3$ | CF$_3$ | C(O)CH$_3$ | (D-55c)Cl |
| 3-Br-5-CH$_3$ | CF$_3$ | C(O)Et | (D-55c)Cl |
| 3-Br-5-CH$_3$ | CF$_3$ | C(O)Pr-i | (D-55c)Cl |
| 3-Br-5-CH$_3$ | CF$_3$ | C(O)CH$_2$OCH$_3$ | (D-55c)Cl |
| 3-Br-5-CH$_3$ | CF$_3$ | C(O)OCH$_3$ | (D-55c)Cl |
| 3-Br-5-CH$_3$ | CF$_3$ | C(O)CH$_3$ | (D-55c)Br |
| 3-Br-5-CH$_3$ | CF$_3$ | C(O)Et | (D-55c)Br |
| 3-Br-5-CH$_3$ | CF$_3$ | C(O)Pr-i | (D-55c)Br |
| 3-Br-5-CH$_3$ | CF$_2$Cl | H | CH=NOCH$_3$ |
| 3,5-(CH$_3$)$_2$ | CF$_3$ | H | CH=NOCH$_3$ |
| 3,5-(CH$_3$)$_2$ | CF$_3$ | H | CH=NOEt |
| 3,5-(CH$_3$)$_2$ | CF$_3$ | CH$_2$OEt | C(O)OCH$_3$ |
| 3,5-(CH$_3$)$_2$ | CF$_3$ | CH$_2$OCH$_2$CF$_3$ | C(O)OCH$_3$ |
| 3,5-(CH$_3$)$_2$ | CF$_3$ | C(O)Et | C(O)OCH$_3$ |
| 3,5-(CH$_3$)$_2$ | CF$_3$ | C(O)CH$_3$ | (D-55c)Cl |
| 3,5-(CH$_3$)$_2$ | CF$_3$ | C(O)Pr-i | (D-55c)Cl |
| 3,5-(CH$_3$)$_2$ | CF$_3$ | C(O)OCH$_3$ | (D-55c)Cl |
| 3,5-(CH$_3$)$_2$ | CF$_3$ | C(O)CH$_3$ | (D-55c)Br |
| 3-Br-5-Et | CF$_3$ | H | CH=NOEt |
| 3-Cl-5-Pr-i | CF$_3$ | CH$_2$OEt | C(O)OCH$_3$ |
| 3-Br-5-Pr-i | CF$_3$ | CH$_2$OCH$_2$CF$_3$ | C(O)OCH$_3$ |
| 3-Cl-5-Bu-t | CF$_3$ | C(O)Et | C(O)OCH$_3$ |
| 3-Br-5-Bu-t | CF$_3$ | C(O)CH$_3$ | (D-55c)Cl |
| 2-F-3-CF3 | CF$_3$ | C(O)Pr-i | (D-55c)Cl |
| 3-CF$_3$-4-F | CHF$_2$ | C(O)OCH$_3$ | (D-55c)Cl |
| 3-CF$_3$-4-F | CF$_3$ | H | CH=NOCH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-CF$_3$-4-F | CF$_3$ | CH$_2$OCH$_3$ | CH=NOCH$_3$ |
| 3-CF$_3$-4-F | CF$_3$ | H | CH=NOEt |
| 3-CF$_3$-4-F | CF$_3$ | H | C(O)OCH3 |
| 3-CF$_3$-4-F | CF$_3$ | Et | C(O)OCH3 |
| 3-CF$_3$-4-F | CF$_3$ | CH$_2$OCH$_3$ | C(O)OCH3 |
| 3-CF$_3$-4-F | CF$_3$ | CH$_2$OEt | C(O)OCH3 |
| 3-CF$_3$-4-F | CF$_3$ | CH$_2$OCH$_2$CF$_3$ | C(O)OCH3 |
| 3-CF$_3$-4-F | CF$_3$ | CH$_2$OC(O)CH$_3$ | C(O)OCH3 |
| 3-CF$_3$-4-F | CF$_3$ | CH$_2$OC(O)Et | C(O)OCH3 |
| 3-CF$_3$-4-F | CF$_3$ | CH$_2$OC(O)OCH$_3$ | C(O)OCH3 |
| 3-CF$_3$-4-F | CF$_3$ | E-5a | C(O)OCH3 |
| 3-CF$_3$-4-F | CF$_3$ | C(O)CH$_3$ | C(O)OCH3 |
| 3-CF$_3$-4-F | CF$_3$ | C(O)Et | C(O)OCH3 |
| 3-CF$_3$-4-F | CF$_3$ | C(O)Pr-n | C(O)OCH3 |
| 3-CF$_3$-4-F | CF$_3$ | C(O)Pr-i | C(O)OCH3 |
| 3-CF$_3$-4-F | CF$_3$ | C(O)Bu-t | C(O)OCH3 |
| 3-CF$_3$-4-F | CF$_3$ | C(O)CH$_2$OCH$_3$ | C(O)OCH3 |
| 3-CF$_3$-4-F | CF$_3$ | C(O)CH$_2$SCH$_3$ | C(O)OCH3 |
| 3-CF$_3$-4-F | CF$_3$ | C(O)OCH$_3$ | C(O)OEt |
| 3-CF$_3$-4-F | CF$_3$ | H | C(O)OPr-i |
| 3-CF$_3$-4-F | CF$_3$ | C(O)OCH$_3$ | C(O)OPr-i |
| 3-CF$_3$-4-F | CF$_3$ | H | C(O)NH$_2$ |
| 3-CF$_3$-4-F | CF$_3$ | CH$_3$ | (D-52d)Cl |
| 3-CF$_3$-4-F | CF$_3$ | CH$_2$OCH$_3$ | (D-52d)Cl |
| 3-CF$_3$-4-F | CF$_3$ | C(O)OCH$_3$ | (D-52d)Cl |
| 3-CF$_3$-4-F | CF$_3$ | CH$_3$ | (D-55c)Cl |
| 3-CF$_3$-4-F | CF$_3$ | CH$_2$OCH$_3$ | (D-55c)Cl |
| 3-CF$_3$-4-F | CF$_3$ | CH$_2$OC(O)CH$_3$ | (D-55c)Cl |
| 3-CF$_3$-4-F | CF$_3$ | CH$_2$OC(O)Bu-t | (D-55c)Cl |
| 3-CF$_3$-4-F | CF$_3$ | CH$_2$OC(O)OCH$_3$ | (D-55c)Cl |
| 3-CF$_3$-4-F | CF$_3$ | CH$_2$CN | (D-55c)Cl |
| 3-CF$_3$-4-F | CF$_3$ | C(O)CH$_3$ | (D-55c)Cl |
| 3-CF$_3$-4-F | CF$_3$ | C(O)Et | (D-55c)Cl |
| 3-CF$_3$-4-F | CF$_3$ | C(O)Pr-n | (D-55c)Cl |
| 3-CF$_3$-4-F | CF$_3$ | C(O)Pr-i | (D-55c)Cl |
| 3-CF$_3$-4-F | CF$_3$ | C(O)Pr-c | (D-55c)Cl |
| 3-CF$_3$-4-F | CF$_3$ | C(O)Bu-t | (D-55c)Cl |
| 3-CF$_3$-4-F | CF$_3$ | C(O)CH$_2$Cl | (D-55c)Cl |
| 3-CF$_3$-4-F | CF$_3$ | C(O)CH$_2$OCH$_3$ | (D-55c)Cl |
| 3-CF$_3$-4-F | CF$_3$ | C(O)CH$_2$OEt | (D-55c)Cl |
| 3-CF$_3$-4-F | CF$_3$ | C(O)CH$_2$SCH$_3$ | (D-55c)Cl |
| 3-CF$_3$-4-F | CF$_3$ | C(O)CH$_2$S(O)CH$_3$ | (D-55c)Cl |
| 3-CF$_3$-4-F | CF$_3$ | C(O)C(O)OEt | (D-55c)Cl |
| 3-CF$_3$-4-F | CF$_3$ | C(O)OCH$_3$ | (D-55c)Cl |
| 3-CF$_3$-4-F | CF$_3$ | C(O)OPr-n | (D-55c)Cl |
| 3-CF$_3$-4-F | CF$_3$ | C(O)OCH$_2$Cl | (D-55c)Cl |
| 3-CF$_3$-4-F | CF$_3$ | C(O)OCH$_2$CH$_2$Cl | (D-55c)Cl |
| 3-CF$_3$-4-F | CF$_3$ | C(O)OCH$_2$CH$_2$OCH$_3$ | (D-55c)Cl |
| 3-CF$_3$-4-F | CF$_3$ | C(O)OCH$_2$CH=CH$_2$ | (D-55c)Cl |
| 3-CF$_3$-4-F | CF$_3$ | CH$_3$ | (D-55c)Br |
| 3-CF$_3$-4-F | CF$_3$ | CH$_2$OC(O)CH$_3$ | (D-55c)Br |
| 3-CF$_3$-4-F | CF$_3$ | C(O)CH$_3$ | (D-55c)Br |
| 3-CF$_3$-4-F | CF$_3$ | C(O)Et | (D-55c)Br |
| 3-CF$_3$-4-F | CF$_3$ | C(O)Pr-n | (D-55c)Br |
| 3-CF$_3$-4-F | CF$_3$ | C(O)Pr-i | (D-55c)Br |
| 3-CF$_3$-4-F | CF$_3$ | C(O)OCH$_3$ | (D-55c)Br |
| 3-CF$_3$-4-F | CF$_3$ | C(O)OEt | (D-55c)Br |
| 3-CF$_3$-4-F | CF$_3$ | C(O)OCH$_2$CH$_2$OCH$_3$ | (D-55c)Br |
| 3-CF$_3$-4-F | CF$_3$ | C(O)Pr-i | D-57a |
| 3-CF$_3$-4-F | CF$_2$Cl | H | CH=NOCH$_3$ |
| 3-CF$_3$-4-F | CF$_2$Cl | H | CH=NOEt |
| 3-CF$_3$-4-F | CF$_2$Cl | H | C(O)OCH$_3$ |
| 3-CF$_3$-4-F | CF$_2$Cl | Et | C(O)OCH$_3$ |
| 3-CF$_3$-4-F | CF$_2$Cl | CH$_2$OCH$_3$ | C(O)OCH$_3$ |
| 3-CF$_3$-4-F | CF$_2$Cl | CH$_2$OEt | C(O)OCH$_3$ |
| 3-CF$_3$-4-F | CF$_2$Cl | CH$_2$OCH$_2$CF$_3$ | C(O)OCH$_3$ |
| 3-CF$_3$-4-F | CF$_2$Cl | C(O)Et | C(O)OCH$_3$ |
| 3-CF$_3$-4-F | CF$_2$Cl | C(O)OCH$_3$ | C(O)OEt |
| 3-CF$_3$-4-F | CF$_2$Cl | H | C(O)NH2 |
| 3-CF$_3$-4-F | CF$_2$Cl | CH$_3$ | (D-55c)Cl |
| 3-CF$_3$-4-F | CF$_2$Cl | CH$_2$OCH$_3$ | (D-55c)Cl |
| 3-CF$_3$-4-F | CF$_2$Cl | C(O)CH$_3$ | (D-55c)Cl |
| 3-CF$_3$-4-F | CF$_2$Cl | C(O)Et | (D-55c)Cl |
| 3-CF$_3$-4-F | CF$_2$Cl | C(O)Pr-i | (D-55c)Cl |
| 3-CF$_3$-4-F | CF$_2$Cl | C(O)CH$_2$OCH$_3$ | (D-55c)Cl |
| 3-CF$_3$-4-F | CF$_2$Cl | C(O)OCH$_3$ | (D-55c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-CF$_3$-4-F | CF$_2$Cl | C(O)CH$_3$ | (D-55c)Br |
| 3-CF$_3$-4-F | CF$_2$Cl | C(O)Et | (D-55c)Br |
| 3-CF$_3$-4-F | CF$_2$Cl | C(O)Pr-i | (D-55c)Br |
| 3-CF$_3$-4-F | CF$_2$Br | C(O)CH$_3$ | (D-55c)Br |
| 3-F-5-CF$_3$ | CF$_2$CHF$_2$ | H | CH=NOCH$_3$ |
| 3-F-5-CF$_3$ | CF$_3$ | H | CH=NOEt |
| 3-F-5-CF$_3$ | CHF$_2$ | CH$_2$OEt | C(O)OCH$_3$ |
| 3-F-5-CF$_3$ | CF$_3$ | H | CH=NOCH$_3$ |
| 3-F-5-CF$_3$ | CF$_3$ | CH$_2$OCH$_3$ | CH=NOCH$_3$ |
| 3-F-5-CF$_3$ | CF$_3$ | H | CH=NOEt |
| 3-F-5-CF$_3$ | CF$_3$ | H | C(O)OCH$_3$ |
| 3-F-5-CF$_3$ | CF$_3$ | Et | C(O)OCH$_3$ |
| 3-F-5-CF$_3$ | CF$_3$ | CH$_2$OCH$_3$ | C(O)OCH$_3$ |
| 3-F-5-CF$_3$ | CF$_3$ | CH$_2$OEt | C(O)OCH$_3$ |
| 3-F-5-CF$_3$ | CF$_3$ | CH$_2$OCH$_2$CF$_3$ | C(O)OCH$_3$ |
| 3-F-5-CF$_3$ | CF$_3$ | CH$_2$OC(O)CH$_3$ | C(O)OCH$_3$ |
| 3-F-5-CF$_3$ | CF$_3$ | CH$_2$OC(O)Et | C(O)OCH$_3$ |
| 3-F-5-CF$_3$ | CF$_3$ | CH$_2$OC(O)OCH$_3$ | C(O)OCH$_3$ |
| 3-F-5-CF$_3$ | CF$_3$ | E-5a | C(O)OCH$_3$ |
| 3-F-5-CF$_3$ | CF$_3$ | C(O)CH$_3$ | C(O)OCH$_3$ |
| 3-F-5-CF$_3$ | CF$_3$ | C(O)Et | C(O)OCH$_3$ |
| 3-F-5-CF$_3$ | CF$_3$ | C(O)Pr-n | C(O)OCH$_3$ |
| 3-F-5-CF$_3$ | CF$_3$ | C(O)Pr-i | C(O)OCH$_3$ |
| 3-F-5-CF$_3$ | CF$_3$ | C(O)Bu-t | C(O)OCH$_3$ |
| 3-F-5-CF$_3$ | CF$_3$ | C(O)CH$_2$OCH$_3$ | C(O)OCH$_3$ |
| 3-F-5-CF$_3$ | CF$_3$ | C(O)CH$_2$SCH$_3$ | C(O)OCH$_3$ |
| 3-F-5-CF$_3$ | CF$_3$ | C(O)OCH$_3$ | C(O)OEt |
| 3-F-5-CF$_3$ | CF$_3$ | H | C(O)OPr-i |
| 3-F-5-CF$_3$ | CF$_3$ | C(O)OCH$_3$ | C(O)OPr-i |
| 3-F-5-CF$_3$ | CF$_3$ | H | C(O)NH$_2$ |
| 3-F-5-CF$_3$ | CF$_3$ | CH$_3$ | (D-52d)Cl |
| 3-F-5-CF$_3$ | CF$_3$ | CH$_2$OCH$_3$ | (D-52d)Cl |
| 3-F-5-CF$_3$ | CF$_3$ | C(O)OCH$_3$ | (D-52d)Cl |
| 3-F-5-CF$_3$ | CF$_3$ | CH$_3$ | (D-55c)Cl |
| 3-F-5-CF$_3$ | CF$_3$ | CH2OCH$_3$ | (D-55c)Cl |
| 3-F-5-CF$_3$ | CF$_3$ | CH$_2$OC(O)CH$_3$ | (D-55c)Cl |
| 3-F-5-CF$_3$ | CF$_3$ | CH$_2$OC(O)Bu-t | (D-55c)Cl |
| 3-F-5-CF$_3$ | CF$_3$ | CH$_2$OC(O)OCH$_3$ | (D-55c)Cl |
| 3-F-5-CF$_3$ | CF$_3$ | CH$_2$CN | (D-55c)Cl |
| 3-F-5-CF$_3$ | CF$_3$ | C(O)CH$_3$ | (D-55c)Cl |
| 3-F-5-CF$_3$ | CF$_3$ | C(O)Et | (D-55c)Cl |
| 3-F-5-CF$_3$ | CF$_3$ | C(O)Pr-n | (D-55c)Cl |
| 3-F-5-CF$_3$ | CF$_3$ | C(O)Pr-i | (D-55c)Cl |
| 3-F-5-CF$_3$ | CF$_3$ | C(O)Pr-c | (D-55c)Cl |
| 3-F-5-CF$_3$ | CF$_3$ | C(O)Bu-t | (D-55c)Cl |
| 3-F-5-CF$_3$ | CF$_3$ | C(O)CH$_2$Cl | (D-55c)Cl |
| 3-F-5-CF$_3$ | CF$_3$ | C(O)CH$_2$OCH$_3$ | (D-55c)Cl |
| 3-F-5-CF$_3$ | CF$_3$ | C(O)CH$_2$OEt | (D-55c)Cl |
| 3-F-5-CF$_3$ | CF$_3$ | C(O)CH$_2$SCH$_3$ | (D-55c)Cl |
| 3-F-5-CF$_3$ | CF$_3$ | C(O)CH$_2$S(O)CH$_3$ | (D-55c)Cl |
| 3-F-5-CF$_3$ | CF$_3$ | C(O)C(O)OEt | (D-55c)Cl |
| 3-F-5-CF$_3$ | CF$_3$ | C(O)OCH$_3$ | (D-55c)Cl |
| 3-F-5-CF$_3$ | CF$_3$ | C(O)OPr-n | (D-55c)Cl |
| 3-F-5-CF$_3$ | CF$_3$ | C(O)OCH$_2$Cl | (D-55c)Cl |
| 3-F-5-CF$_3$ | CF$_3$ | C(O)OCH$_2$CH$_2$Cl | (D-55c)Cl |
| 3-F-5-CF$_3$ | CF$_3$ | C(O)OCH$_2$CH$_2$OCH$_3$ | (D-55c)Cl |
| 3-F-5-CF$_3$ | CF$_3$ | C(O)OCH$_2$CH=CH$_2$ | (D-55c)Cl |
| 3-F-5-CF$_3$ | CF$_3$ | CH$_3$ | (D-55c)Br |
| 3-F-5-CF$_3$ | CF$_3$ | CH$_2$OC(O)CH$_3$ | (D-55c)Br |
| 3-F-5-CF$_3$ | CF$_3$ | C(O)CH$_3$ | (D-55c)Br |
| 3-F-5-CF$_3$ | CF$_3$ | C(O)Et | (D-55c)Br |
| 3-F-5-CF$_3$ | CF$_3$ | C(O)Pr-n | (D-55c)Br |
| 3-F-5-CF$_3$ | CF$_3$ | C(O)Pr-i | (D-55c)Br |
| 3-F-5-CF$_3$ | CF$_3$ | C(O)OCH$_3$ | (D-55c)Br |
| 3-F-5-CF$_3$ | CF$_3$ | C(O)OEt | (D-55c)Br |
| 3-F-5-CF$_3$ | CF$_3$ | C(O)OCH$_2$CH$_2$OCH$_3$ | (D-55c)Br |
| 3-F-5-CF$_3$ | CF$_3$ | C(O)Pr-i | D-57a |
| 3-F-5-CF$_3$ | CF$_2$Cl | H | CH=NOCH$_3$ |
| 3-F-5-CF$_3$ | CF$_2$Cl | H | CH=NOEt |
| 3-F-5-CF$_3$ | CF$_2$Cl | H | C(O)OCH$_3$ |
| 3-F-5-CF$_3$ | CF$_2$Cl | Et | C(O)OCH$_3$ |
| 3-F-5-CF$_3$ | CF$_2$Cl | CH$_2$OCH$_3$ | C(O)OCH$_3$ |
| 3-F-5-CF$_3$ | CF$_2$Cl | CH$_2$OEt | C(O)OCH$_3$ |
| 3-F-5-CF$_3$ | CF$_2$Cl | CH$_2$OCH$_2$CF$_3$ | C(O)OCH$_3$ |
| 3-F-5-CF$_3$ | CF$_2$Cl | C(O)Et | C(O)OCH$_3$ |
| 3-F-5-CF$_3$ | CF$_2$Cl | C(O)OCH$_3$ | C(O)OEt |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-F-5-CF$_3$ | CF$_2$Cl | H | C(O)NH$_2$ |
| 3-F-5-CF$_3$ | CF$_2$Cl | CH$_3$ | (D-55c)Cl |
| 3-F-5-CF$_3$ | CF$_2$Cl | CH$_2$OCH$_3$ | (D-55c)Cl |
| 3-F-5-CF$_3$ | CF$_2$Cl | C(O)CH$_3$ | (D-55c)Cl |
| 3-F-5-CF$_3$ | CF$_2$Cl | C(O)Et | (D-55c)Cl |
| 3-F-5-CF$_3$ | CF$_2$Cl | C(O)Pr-i | (D-55c)Cl |
| 3-F-5-CF$_3$ | CF$_2$Cl | C(O)CH$_2$OCH$_3$ | (D-55c)Cl |
| 3-F-5-CF$_3$ | CF$_2$Cl | C(O)OCH$_3$ | (D-55c)Cl |
| 3-F-5-CF$_3$ | CF$_2$Cl | C(O)CH$_3$ | (D-55c)Br |
| 3-F-5-CF$_3$ | CF$_2$Cl | C(O)Et | (D-55c)Br |
| 3-F-5-CF$_3$ | CF$_2$Cl | C(O)Pr-i | (D-55c)Br |
| 3-F-5-CF$_3$ | CF$_2$Br | CH$_2$OCH$_2$CF$_3$ | C(O)OCH$_3$ |
| 3-F-5-CF$_3$ | CF$_2$CHF$_2$ | C(O)Et | C(O)OCH$_3$ |
| 3-CF$_3$-4-Cl | CHF$_2$ | C(O)CH$_3$ | (D-55c)Cl |
| 3-CF$_3$-4-Cl | CF$_3$ | H | CH=NOCH$_3$ |
| 3-CF$_3$-4-Cl | CF$_3$ | CH$_2$OCH$_3$ | CH=NOCH$_3$ |
| 3-CF$_3$-4-Cl | CF$_3$ | H | CH=NOEt |
| 3-CF$_3$-4-Cl | CF$_3$ | H | C(O)OCH$_3$ |
| 3-CF$_3$-4-Cl | CF$_3$ | Et | C(O)OCH$_3$ |
| 3-CF$_3$-4-Cl | CF$_3$ | CH$_2$OCH$_3$ | C(O)OCH$_3$ |
| 3-CF$_3$-4-Cl | CF$_3$ | CH$_2$OEt | C(O)OCH$_3$ |
| 3-CF$_3$-4-Cl | CF$_3$ | CH$_2$OCH$_2$CF$_3$ | C(O)OCH$_3$ |
| 3-CF$_3$-4-Cl | CF$_3$ | CH$_2$OC(O)CH$_3$ | C(O)OCH$_3$ |
| 3-CF$_3$-4-Cl | CF$_3$ | CH$_2$OC(O)Et | C(O)OCH$_3$ |
| 3-CF$_3$-4-Cl | CF$_3$ | CH$_2$OC(O)OCH$_3$ | C(O)OCH$_3$ |
| 3-CF$_3$-4-Cl | CF$_3$ | E-5a | C(O)OCH$_3$ |
| 3-CF$_3$-4-Cl | CF$_3$ | C(O)CH$_3$ | C(O)OCH$_3$ |
| 3-CF$_3$-4-Cl | CF$_3$ | C(O)Et | C(O)OCH$_3$ |
| 3-CF$_3$-4-Cl | CF$_3$ | C(O)Pr-n | C(O)OCH$_3$ |
| 3-CF$_3$-4-Cl | CF$_3$ | C(O)Pr-i | C(O)OCH$_3$ |
| 3-CF$_3$-4-Cl | CF$_3$ | C(O)Bu-t | C(O)OCH$_3$ |
| 3-CF$_3$-4-Cl | CF$_3$ | C(O)CH$_2$OCH$_3$ | C(O)OCH$_3$ |
| 3-CF$_3$-4-Cl | CF$_3$ | C(O)CH$_2$SCH$_3$ | C(O)OCH$_3$ |
| 3-CF$_3$-4-Cl | CF$_3$ | C(O)OCH$_3$ | C(O)OEt |
| 3-CF$_3$-4-Cl | CF$_3$ | H | C(O)OPr-i |
| 3-CF$_3$-4-Cl | CF$_3$ | C(O)OCH$_3$ | C(O)OPr-i |
| 3-CF$_3$-4-Cl | CF$_3$ | H | C(O)NH$_2$ |
| 3-CF$_3$-4-Cl | CF$_3$ | CH$_3$ | (D-52d)Cl |
| 3-CF$_3$-4-Cl | CF$_3$ | CH$_2$OCH$_3$ | (D-52d)Cl |
| 3-CF$_3$-4-Cl | CF$_3$ | C(O)OCH$_3$ | (D-52d)Cl |
| 3-CF$_3$-4-Cl | CF$_3$ | CH$_3$ | (D-55d)Cl |
| 3-CF$_3$-4-Cl | CF$_3$ | CH$_2$OCH$_3$ | (D-55d)Cl |
| 3-CF$_3$-4-Cl | CF$_3$ | CH$_2$OC(O)CH$_3$ | (D-55d)Cl |
| 3-CF$_3$-4-Cl | CF$_3$ | CH$_2$OC(O)Bu-t | (D-55d)Cl |
| 3-CF$_3$-4-Cl | CF$_3$ | CH$_2$OC(O)OCH$_3$ | (D-55d)Cl |
| 3-CF$_3$-4-Cl | CF$_3$ | CH$_2$CN | (D-55d)Cl |
| 3-CF$_3$-4-Cl | CF$_3$ | C(O)CH$_3$ | (D-55d)Cl |
| 3-CF$_3$-4-Cl | CF$_3$ | C(O)Et | (D-55d)Cl |
| 3-CF$_3$-4-Cl | CF$_3$ | C(O)Pr-n | (D-55d)Cl |
| 3-CF$_3$-4-Cl | CF$_3$ | C(O)Pr-i | (D-55d)Cl |
| 3-CF$_3$-4-Cl | CF$_3$ | C(O)Pr-c | (D-55d)Cl |
| 3-CF$_3$-4-Cl | CF$_3$ | C(O)Bu-t | (D-55d)Cl |
| 3-CF$_3$-4-Cl | CF$_3$ | C(O)CH$_2$Cl | (D-55d)Cl |
| 3-CF$_3$-4-Cl | CF$_3$ | C(O)CH$_2$OCH$_3$ | (D-55d)Cl |
| 3-CF$_3$-4-Cl | CF$_3$ | C(O)CH$_2$OEt | (D-55d)Cl |
| 3-CF$_3$-4-Cl | CF$_3$ | C(O)CH$_2$SCH$_3$ | (D-55d)Cl |
| 3-CF$_3$-4-Cl | CF$_3$ | C(O)CH$_2$S(O)CH$_3$ | (D-55d)Cl |
| 3-CF$_3$-4-Cl | CF$_3$ | C(O)C(O)OEt | (D-55d)Cl |
| 3-CF$_3$-4-Cl | CF$_3$ | C(O)OCH$_3$ | (D-55d)Cl |
| 3-CF$_3$-4-Cl | CF$_3$ | C(O)OPr-n | (D-55d)Cl |
| 3-CF$_3$-4-Cl | CF$_3$ | C(O)OCH$_2$Cl | (D-55c)Cl |
| 3-CF$_3$-4-Cl | CF$_3$ | C(O)OCH$_2$CH$_2$Cl | (D-55c)Cl |
| 3-CF$_3$-4-Cl | CF$_3$ | C(O)OCH$_2$CH$_2$OCH$_3$ | (D-55c)Cl |
| 3-CF$_3$-4-Cl | CF$_3$ | C(O)OCH$_2$CH=CH$_2$ | (D-55c)Cl |
| 3-CF$_3$-4-Cl | CF$_3$ | CH$_3$ | (D-55c)Br |
| 3-CF$_3$-4-Cl | CF$_3$ | CH$_2$OC(O)CH$_3$ | (D-55c)Br |
| 3-CF$_3$-4-Cl | CF$_3$ | C(O)CH$_3$ | (D-55c)Br |
| 3-CF$_3$-4-Cl | CF$_3$ | C(O)Et | (D-55c)Br |
| 3-CF$_3$-4-Cl | CF$_3$ | C(O)Pr-n | (D-55c)Br |
| 3-CF$_3$-4-Cl | CF$_3$ | C(O)Pr-i | (D-55c)Br |
| 3-CF$_3$-4-Cl | CF$_3$ | C(O)OCH$_3$ | (D-55c)Br |
| 3-CF$_3$-4-Cl | CF$_3$ | C(O)OEt | (D-55c)Br |
| 3-CF$_3$-4-Cl | CF$_3$ | C(O)OCH$_2$CH$_2$OCH$_3$ | (D-55c)Br |
| 3-CF$_3$-4-Cl | CF$_3$ | C(O)Pr-i | D-57a |
| 3-CF$_3$-4-Cl | CF$_2$Cl | H | CH=NOCH$_3$ |
| 3-CF$_3$-4-Cl | CF$_2$Cl | H | CH=NOEt |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-CF$_3$-4-Cl | CF$_2$Cl | H | C(O)OCH$_3$ |
| 3-CF$_3$-4-Cl | CF$_2$Cl | Et | C(O)OCH$_3$ |
| 3-CF$_3$-4-Cl | CF$_2$Cl | CH$_2$OCH$_3$ | C(O)OCH$_3$ |
| 3-CF$_3$-4-Cl | CF$_2$Cl | CH$_2$OEt | C(O)OCH$_3$ |
| 3-CF$_3$-4-Cl | CF$_2$Cl | CH$_2$OCH$_2$CF$_3$ | C(O)OCH$_3$ |
| 3-CF$_3$-4-Cl | CF$_2$Cl | C(O)Et | C(O)OCH$_3$ |
| 3-CF$_3$-4-Cl | CF$_2$Cl | C(O)OCH$_3$ | C(O)OEt |
| 3-CF$_3$-4-Cl | CF$_2$Cl | H | C(O)NH$_2$ |
| 3-CF$_3$-4-Cl | CF$_2$Cl | CH$_3$ | (D-55c)Cl |
| 3-CF$_3$-4-Cl | CF$_2$Cl | CH$_2$OCH$_3$ | (D-55c)Cl |
| 3-CF$_3$-4-Cl | CF$_2$Cl | C(O)CH$_3$ | (D-55c)Cl |
| 3-CF$_3$-4-Cl | CF$_2$Cl | C(O)Et | (D-55c)Cl |
| 3-CF$_3$-4-Cl | CF$_2$Cl | C(O)Pr-i | (D-55c)Cl |
| 3-CF$_3$-4-Cl | CF$_2$Cl | C(O)CH$_2$OCH$_3$ | (D-55c)Cl |
| 3-CF$_3$-4-Cl | CF$_2$Cl | C(O)OCH$_3$ | (D-55c)Cl |
| 3-CF$_3$-4-Cl | CF$_2$Cl | C(O)CH$_3$ | (D-55c)Cl |
| 3-CF$_3$-4-Cl | CF$_2$Cl | C(O)Et | (D-55c)Cl |
| 3-CF$_3$-4-Cl | CF$_2$Cl | C(O)Pr-i | (D-55c)Cl |
| 3-CF$_3$-4-Cl | CF$_2$Br | C(O)Pr-i | (D-55c)Cl |
| 3-CF$_3$-4-Cl | CF$_2$CHF$_2$ | C(O)OCH$_3$ | (D-55c)Cl |
| 3-Cl-5-CF$_3$ | CHF$_2$ | H | CH=NOCH$_3$ |
| 3-Cl-5-CF$_3$ | CHF$_2$ | CH$_2$OEt | C(O)OCH$_3$ |
| 3-Cl-5-CF$_3$ | CHF$_2$ | C(O)Et | C(O)OCH$_3$ |
| 3-Cl-5-CF$_3$ | CHF$_2$ | C(O)CH$_3$ | (D-55c)Cl |
| 3-Cl-5-CF$_3$ | CHF$_2$ | C(O)OCH3 | (D-55c)Cl |
| 3-Cl-5-CF$_3$ | CF$_3$ | H | CH=NOCH$_3$ |
| 3-Cl-5-CF$_3$ | CF$_3$ | CH$_2$OCH$_3$ | CH=NOCH$_3$ |
| 3-Cl-5-CF$_3$ | CF$_3$ | CH$_2$OEt | CH=NOCH$_3$ |
| 3-Cl-5-CF$_3$ | CF$_3$ | H | CH=NOEt |
| 3-Cl-5-CF$_3$ | CF$_3$ | CH$_2$OCH$_3$ | CH=NOEt |
| 3-Cl-5-CF$_3$ | CF$_3$ | H | C(O)OCH$_3$ |
| 3-Cl-5-CF$_3$ | CF$_3$ | CH$_3$ | C(O)OCH$_3$ |
| 3-Cl-5-CF$_3$ | CF$_3$ | Et | C(O)OCH$_3$ |
| 3-Cl-5-CF$_3$ | CF$_3$ | CH$_2$OCH$_3$ | C(O)OCH$_3$ |
| 3-Cl-5-CF$_3$ | CF$_3$ | CH$_2$OEt | C(O)OCH$_3$ |
| 3-Cl-5-CF$_3$ | CF$_3$ | CH$_2$OCH$_2$CF$_3$ | C(O)OCH$_3$ |
| 3-Cl-5-CF$_3$ | CF$_3$ | CH$_2$OC(O)CH$_3$ | C(O)OCH$_3$ |
| 3-Cl-5-CF$_3$ | CF$_3$ | CH$_2$OC(O)Et | C(O)OCH$_3$ |
| 3-Cl-5-CF$_3$ | CF$_3$ | CH2OC(O)Bu-t | C(O)OCH$_3$ |
| 3-Cl-5-CF$_3$ | CF$_3$ | CH$_2$OC(O)OCH$_3$ | C(O)OCH$_3$ |
| 3-Cl-5-CF$_3$ | CF$_3$ | E-5a | C(O)OCH$_3$ |
| 3-Cl-5-CF$_3$ | CF$_3$ | CH$_2$NHC(O)OCH$_3$ | C(O)OCH$_3$ |
| 3-Cl-5-CF$_3$ | CF$_3$ | CH$_2$CN | C(O)OCH$_3$ |
| 3-Cl-5-CF$_3$ | CF$_3$ | C(O)CH$_3$ | C(O)OCH$_3$ |
| 3-Cl-5-CF$_3$ | CF$_3$ | C(O)Et | C(O)OCH$_3$ |
| 3-Cl-5-CF$_3$ | CF$_3$ | C(O)Pr-n | C(O)OCH$_3$ |
| 3-Cl-5-CF$_3$ | CF$_3$ | C(O)Pr-i | C(O)OCH$_3$ |
| 3-Cl-5-CF$_3$ | CF$_3$ | C(O)Bu-t | C(O)OCH$_3$ |
| 3-Cl-5-CF$_3$ | CF$_3$ | C(O)CH$_2$OCH$_3$ | C(O)OCH$_3$ |
| 3-Cl-5-CF$_3$ | CF$_3$ | C(O)CH$_2$SCH$_3$ | C(O)OCH$_3$ |
| 3-Cl-5-CF$_3$ | CF$_3$ | C(O)Ph | C(O)OCH$_3$ |
| 3-Cl-5-CF$_3$ | CF$_3$ | C(O)OCH$_2$CH$_2$Cl | C(O)OCH$_3$ |
| 3-Cl-5-CF$_3$ | CF$_3$ | H | C(O)OEt |
| 3-Cl-5-CF$_3$ | CF$_3$ | CH$_2$OCH$_3$ | C(O)OEt |
| 3-Cl-5-CF$_3$ | CF$_3$ | C(O)Bu-t | C(O)OEt |
| 3-Cl-5-CF$_3$ | CF$_3$ | C(O)CH$_2$OCH$_3$ | C(O)OEt |
| 3-Cl-5-CF$_3$ | CF$_3$ | C(O)OCH$_3$ | C(O)OEt |
| 3-Cl-5-CF$_3$ | CF$_3$ | H | C(O)OPr-i |
| 3-Cl-5-CF$_3$ | CF$_3$ | C(O)CH$_3$ | C(O)OPr-i |
| 3-Cl-5-CF$_3$ | CF$_3$ | C(O)CH$_2$OCH$_3$ | C(O)OPr-i |
| 3-Cl-5-CF$_3$ | CF$_3$ | C(O)OCH$_3$ | C(O)OPr-i |
| 3-Cl-5-CF$_3$ | CF$_3$ | C(O)OCH$_3$ | C(O)OCH$_2$CH$_2$OCH$_3$ |
| 3-Cl-5-CF$_3$ | CF$_3$ | H | C(O)NH$_2$ |
| 3-Cl-5-CF$_3$ | CF$_3$ | C(O)CH$_3$ | D-14a |
| 3-Cl-5-CF$_3$ | CF$_3$ | CH$_3$ | (D-52d)Cl |
| 3-Cl-5-CF$_3$ | CF$_3$ | CH$_2$OCH$_3$ | (D-52d)Cl |
| 3-Cl-5-CF$_3$ | CF$_3$ | C(O)Et | (D-52d)Cl |
| 3-Cl-5-CF$_3$ | CF$_3$ | C(O)OCH$_3$ | (D-52d)Cl |
| 3-Cl-5-CF$_3$ | CF$_3$ | CH$_3$ | (D-52d)Br |
| 3-Cl-5-CF$_3$ | CF$_3$ | CH$_3$ | (D-52d)CN |
| 3-Cl-5-CF$_3$ | CF$_3$ | CH$_3$ | (D-53e)Cl |
| 3-Cl-5-CF$_3$ | CF$_3$ | CH$_3$ | D-55a |
| 3-Cl-5-CF$_3$ | CF$_3$ | CH$_3$ | (D-55c)Cl |
| 3-Cl-5-CF$_3$ | CF$_3$ | Et | (D-55c)Cl |
| 3-Cl-5-CF$_3$ | CF$_3$ | CH$_2$OCH$_3$ | (D-55c)Cl |
| 3-Cl-5-CF$_3$ | CF$_3$ | CH$_2$OEt | (D-55c)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Cl-5-CF$_3$ | CF$_3$ | CH$_2$OC(O)CH$_3$ | (D-55c)Cl |
| 3-Cl-5-CF$_3$ | CF$_3$ | CH$_2$OC(O)Bu-t | (D-55c)Cl |
| 3-Cl-5-CF$_3$ | CF$_3$ | CH$_2$OC(O)OCH$_3$ | (D-55c)Cl |
| 3-Cl-5-CF$_3$ | CF$_3$ | CH$_2$CN | (D-55c)Cl |
| 3-Cl-5-CF$_3$ | CF$_3$ | C(O)CH$_3$ | (D-55c)Cl |
| 3-Cl-5-CF$_3$ | CF$_3$ | C(O)Et | (D-55c)Cl |
| 3-Cl-5-CF$_3$ | CF$_3$ | C(O)Pr-n | (D-55c)Cl |
| 3-Cl-5-CF$_3$ | CF$_3$ | C(O)Pr-i | (D-55c)Cl |
| 3-Cl-5-CF$_3$ | CF$_3$ | C(O)Pr-c | (D-55c)Cl |
| 3-Cl-5-CF$_3$ | CF$_3$ | C(O)Bu-t | (D-55c)Cl |
| 3-Cl-5-CF$_3$ | CF$_3$ | C(O)CH$_2$Cl | (D-55c)Cl |
| 3-Cl-5-CF$_3$ | CF$_3$ | C(O)CH$_2$OCH$_3$ | (D-55c)Cl |
| 3-Cl-5-CF$_3$ | CF$_3$ | C(O)CH$_2$OEt | (D-55c)Cl |
| 3-Cl-5-CF$_3$ | CF$_3$ | C(O)CH$_2$SCH3 | (D-55c)Cl |
| 3-Cl-5-CF$_3$ | CF$_3$ | C(O)CH$_2$S(O)CH$_3$ | (D-55c)Cl |
| 3-Cl-5-CF$_3$ | CF$_3$ | C(O)C(O)OEt | (D-55c)Cl |
| 3-Cl-5-CF$_3$ | CF$_3$ | C(O)Ph | (D-55c)Cl |
| 3-Cl-5-CF$_3$ | CF$_3$ | C(O)(D-52a) | (D-55c)Cl |
| 3-Cl-5-CF$_3$ | CF$_3$ | C(O)OCH$_3$ | (D-55c)Cl |
| 3-Cl-5-CF$_3$ | CF$_3$ | C(O)OEt | (D-55c)Cl |
| 3-Cl-5-CF$_3$ | CF$_3$ | C(O)OPr-n | (D-55c)Cl |
| 3-Cl-5-CF$_3$ | CF$_3$ | C(O)OPr-i | (D-55c)Cl |
| 3-Cl-5-CF$_3$ | CF$_3$ | C(O)OBu-n | (D-55c)Cl |
| 3-Cl-5-CF$_3$ | CF$_3$ | C(O)OBu-i | (D-55c)Cl |
| 3-Cl-5-CF$_3$ | CF$_3$ | C(O)OCH$_2$Cl | (D-55c)Cl |
| 3-Cl-5-CF$_3$ | CF$_3$ | C(O)OCH2CH$_2$Cl | (D-55c)Cl |
| 3-Cl-5-CF$_3$ | CF$_3$ | C(O)OCH$_2$CH$_2$OCH$_3$ | (D-55c)Cl |
| 3-Cl-5-CF$_3$ | CF$_3$ | C(O)OCH$_2$CH=CH$_2$ | (D-55c)Cl |
| 3-Cl-5-CF$_3$ | CF$_3$ | CH$_3$ | (D-55c)Br |
| 3-Cl-5-CF$_3$ | CF$_3$ | Et | (D-55c)Br |
| 3-Cl-5-CF$_3$ | CF$_3$ | CH$_2$OCH$_3$ | (D-55c)Br |
| 3-Cl-5-CF$_3$ | CF$_3$ | CH$_2$OEt | (D-55c)Br |
| 3-Cl-5-CF$_3$ | CF$_3$ | CH$_2$OC(O)CH$_3$ | (D-55c)Br |
| 3-Cl-5-CF$_3$ | CF$_3$ | C(O)CH$_3$ | (D-55c)Br |
| 3-Cl-5-CF$_3$ | CF$_3$ | C(O)Et | (D-55c)Br |
| 3-Cl-5-CF$_3$ | CF$_3$ | C(O)Pr-n | (D-55c)Br |
| 3-Cl-5-CF$_3$ | CF$_3$ | C(O)Pr-i | (D-55c)Br |
| 3-Cl-5-CF$_3$ | CF$_3$ | C(O)Pr-c | (D-55c)Br |
| 3-Cl-5-CF$_3$ | CF$_3$ | C(O)CH$_2$OCH$_3$ | (D-55c)Br |
| 3-Cl-5-CF$_3$ | CF$_3$ | C(O)OCH$_3$ | (D-55c)Br |
| 3-Cl-5-CF$_3$ | CF$_3$ | C(O)OEt | (D-55c)Br |
| 3-Cl-5-CF$_3$ | CF$_3$ | C(O)OPr-n | (D-55c)Br |
| 3-Cl-5-CF$_3$ | CF$_3$ | C(O)OBu-i | (D-55c)Br |
| 3-Cl-5-CF$_3$ | CF$_3$ | C(O)OCH$_2$Cl | (D-55c)Br |
| 3-Cl-5-CF$_3$ | CF$_3$ | C(O)OCH$_2$CH$_2$OCH$_3$ | (D-55c)Br |
| 3-Cl-5-CF$_3$ | CF$_3$ | CH$_3$ | D-57a |
| 3-Cl-5-CF$_3$ | CF$_3$ | C(O)CH$_3$ | D-57a |
| 3-Cl-5-CF$_3$ | CF$_3$ | C(O)Pr-i | D-57a |
| 3-Cl-5-CF$_3$ | CF$_3$ | CH$_3$ | D-58a |
| 3-Cl-5-CF$_3$ | CF$_2$Cl | H | CH=NOCH$_3$ |
| 3-Cl-5-CF$_3$ | CF$_2$Cl | CH$_2$OCH$_3$ | CH=NOCH$_3$ |
| 3-Cl-5-CF$_3$ | CF$_2$Cl | H | CH=NOEt |
| 3-Cl-5-CF$_3$ | CF$_2$Cl | H | C(O)OCH$_3$ |
| 3-Cl-5-CF$_3$ | CF$_2$Cl | Et | C(O)OCH$_3$ |
| 3-Cl-5-CF$_3$ | CF$_2$Cl | CH$_2$OCH$_3$ | C(O)OCH$_3$ |
| 3-Cl-5-CF$_3$ | CF$_2$Cl | CH$_2$OEt | C(O)OCH$_3$ |
| 3-Cl-5-CF$_3$ | CF$_2$Cl | CH$_2$OCH2CF$_3$ | C(O)OCH$_3$ |
| 3-Cl-5-CF$_3$ | CF$_2$Cl | CH$_2$OC(O)CH$_3$ | C(O)OCH$_3$ |
| 3-Cl-5-CF$_3$ | CF$_2$Cl | CH$_2$OC(O)Et | C(O)OCH$_3$ |
| 3-Cl-5-CF$_3$ | CF$_2$Cl | CH$_2$OC(O)OCH$_3$ | C(O)OCH$_3$ |
| 3-Cl-5-CF$_3$ | CF$_2$Cl | E-5a | C(O)OCH$_3$ |
| 3-Cl-5-CF$_3$ | CF$_2$Cl | C(O)Et | C(O)OCH$_3$ |
| 3-Cl-5-CF$_3$ | CF$_2$Cl | C(O)Pr-n | C(O)OCH$_3$ |
| 3-Cl-5-CF$_3$ | CF$_2$Cl | C(O)Bu-t | C(O)OCH$_3$ |
| 3-Cl-5-CF$_3$ | CF$_2$Cl | C(O)CH$_2$SCH$_3$ | C(O)OCH$_3$ |
| 3-Cl-5-CF$_3$ | CF$_2$Cl | C(O)OCH$_3$ | C(O)OEt |
| 3-Cl-5-CF$_3$ | CF$_2$Cl | H | C(O)OPr-i |
| 3-Cl-5-CF$_3$ | CF$_2$Cl | H | C(O)NH$_2$ |
| 3-Cl-5-CF$_3$ | CF$_2$Cl | C(O)OCH$_3$ | (D-52d)Cl |
| 3-Cl-5-CF$_3$ | CF$_2$Cl | CH$_3$ | (D-55c)Cl |
| 3-Cl-5-CF$_3$ | CF$_2$Cl | CH$_2$OCH$_3$ | (D-55c)Cl |
| 3-Cl-5-CF$_3$ | CF$_2$Cl | C(O)CH$_3$ | (D-55c)Cl |
| 3-Cl-5-CF$_3$ | CF$_2$Cl | C(O)Et | (D-55c)Cl |
| 3-Cl-5-CF$_3$ | CF$_2$Cl | C(O)Pr-i | (D-55c)Cl |
| 3-Cl-5-CF$_3$ | CF$_2$Cl | C(O)CH$_2$OCH$_3$ | (D-55c)Cl |
| 3-Cl-5-CF$_3$ | CF$_2$Cl | C(O)CH$_2$OEt | (D-55c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-CF$_3$ | CF$_2$Cl | C(O)CH$_2$SCH$_3$ | (D-55c)Cl |
| 3-Cl-5-CF$_3$ | CF$_2$Cl | C(O)OCH$_3$ | (D-55c)Cl |
| 3-Cl-5-CF$_3$ | CF$_2$Cl | C(O)OPr-n | (D-55c)Cl |
| 3-Cl-5-CF$_3$ | CF$_2$Cl | C(O)OCH$_2$CH$_2$Cl | (D-55c)Cl |
| 3-Cl-5-CF$_3$ | CF$_2$Cl | C(O)OCH$_2$CH$_2$OCH$_3$ | (D-55c)Cl |
| 3-Cl-5-CF$_3$ | CF$_2$Cl | C(O)OCH$_2$CH=CH$_2$ | (D-55c)Cl |
| 3-Cl-5-CF$_3$ | CF$_2$Cl | CH$_2$OC(O)CH$_3$ | (D-55c)Br |
| 3-Cl-5-CF$_3$ | CF$_2$Cl | C(O)CH$_3$ | (D-55c)Br |
| 3-Cl-5-CF$_3$ | CF$_2$Cl | C(O)Et | (D-55c)Br |
| 3-Cl-5-CF$_3$ | CF$_2$Cl | C(O)Pr-n | (D-55c)Br |
| 3-Cl-5-CF$_3$ | CF$_2$Cl | C(O)Pr-i | (D-55c)Br |
| 3-Cl-5-CF$_3$ | CF$_2$Cl | C(O)OCH$_3$ | (D-55c)Br |
| 3-Cl-5-CF$_3$ | CF$_2$Cl | C(O)OEt | (D-55c)Br |
| 3-Cl-5-CF$_3$ | CF$_2$Br | H | CH=NOCH$_3$ |
| 3-Cl-5-CF$_3$ | CF$_2$Br | CH$_2$OEt | C(O)OCH$_3$ |
| 3-Cl-5-CF$_3$ | CF$_2$Br | C(O)Et | C(O)OCH$_3$ |
| 3-Cl-5-CF$_3$ | CF$_2$Br | C(O)CH$_3$ | (D-55c)Cl |
| 3-Cl-5-CF$_3$ | CF$_2$Br | C(O)OCH$_3$ | (D-55c)Cl |
| 3-Cl-5-CF$_3$ | CF$_2$CHF$_2$ | H | CH=NOCH$_3$ |
| 3-Cl-5-CF$_3$ | CF$_2$CHF$_2$ | CH$_2$OEt | C(O)OCH$_3$ |
| 3-Cl-5-CF$_3$ | CF$_2$CHF$_2$ | C(O)Et | C(O)OCH$_3$ |
| 3-Cl-5-CF$_3$ | CF$_2$CHF$_2$ | C(O)CH$_3$ | (D-55c)Cl |
| 3-Cl-5-CF$_3$ | CF$_2$CHF$_2$ | C(O)OCH$_3$ | (D-55c)Cl |
| 3-Br-5-CF$_3$ | CHF$_2$ | H | CH=NOCH$_3$ |
| 3-Br-5-CF$_3$ | CHF$_2$ | CH$_2$OEt | C(O)OCH$_3$ |
| 3-Br-5-CF$_3$ | CHF$_2$ | C(O)Et | C(O)OCH$_3$ |
| 3-Br-5-CF$_3$ | CHF$_2$ | C(O)CH$_3$ | (D-55c)Cl |
| 3-Br-5-CF$_3$ | CHF$_2$ | C(O)OCH$_3$ | (D-55c)Cl |
| 3-Br-5-CF$_3$ | CF$_3$ | H | CH=NOCH$_3$ |
| 3-Br-5-CF$_3$ | CF$_3$ | CH$_2$OCH$_3$ | CH=NOCH$_3$ |
| 3-Br-5-CF$_3$ | CF$_3$ | CH$_2$OEt | CH=NOCH$_3$ |
| 3-Br-5-CF$_3$ | CF$_3$ | H | CH=NOEt |
| 3-Br-5-CF$_3$ | CF$_3$ | CH$_2$OCH$_3$ | CH=NOEt |
| 3-Br-5-CF$_3$ | CF$_3$ | H | C(O)OCH$_3$ |
| 3-Br-5-CF$_3$ | CF$_3$ | CH$_3$ | C(O)OCH$_3$ |
| 3-Br-5-CF$_3$ | CF$_3$ | Et | C(O)OCH$_3$ |
| 3-Br-5-CF$_3$ | CF$_3$ | CH$_2$OCH$_3$ | C(O)OCH$_3$ |
| 3-Br-5-CF$_3$ | CF$_3$ | CH$_2$OEt | C(O)OCH$_3$ |
| 3-Br-5-CF$_3$ | CF$_3$ | CH$_2$OCH$_2$CF$_3$ | C(O)OCH$_3$ |
| 3-Br-5-CF$_3$ | CF$_3$ | CH$_2$OC(O)CH$_3$ | C(O)OCH$_3$ |
| 3-Br-5-CF$_3$ | CF$_3$ | CH$_2$OC(O)Et | C(O)OCH$_3$ |
| 3-Br-5-CF$_3$ | CF$_3$ | CH$_2$OC(O)Bu-t | C(O)OCH$_3$ |
| 3-Br-5-CF$_3$ | CF$_3$ | CH$_2$OC(O)OCH$_3$ | C(O)OCH$_3$ |
| 3-Br-5-CF$_3$ | CF$_3$ | E-5a | C(O)OCH$_3$ |
| 3-Br-5-CF$_3$ | CF$_3$ | CH$_2$NHC(O)OCH$_3$ | C(O)OCH$_3$ |
| 3-Br-5-CF$_3$ | CF$_3$ | CH$_2$CN | C(O)OCH$_3$ |
| 3-Br-5-CF$_3$ | CF$_3$ | C(O)CH$_3$ | C(O)OCH$_3$ |
| 3-Br-5-CF$_3$ | CF$_3$ | C(O)Et | C(O)OCH$_3$ |
| 3-Br-5-CF$_3$ | CF$_3$ | C(O)Pr-n | C(O)OCH$_3$ |
| 3-Br-5-CF$_3$ | CF$_3$ | C(O)Pr-i | C(O)OCH$_3$ |
| 3-Br-5-CF$_3$ | CF$_3$ | C(O)Bu-t | C(O)OCH$_3$ |
| 3-Br-5-CF$_3$ | CF$_3$ | C(O)CH$_2$OCH$_3$ | C(O)OCH$_3$ |
| 3-Br-5-CF$_3$ | CF$_3$ | C(O)CH$_2$SCH$_3$ | C(O)OCH$_3$ |
| 3-Br-5-CF$_3$ | CF$_3$ | C(O)Ph | C(O)OCH$_3$ |
| 3-Br-5-CF$_3$ | CF$_3$ | C(O)OCH$_2$CH$_2$Cl | C(O)OCH$_3$ |
| 3-Br-5-CF$_3$ | CF$_3$ | H | C(O)OEt |
| 3-Br-5-CF$_3$ | CF$_3$ | CH$_2$OCH$_3$ | C(O)OEt |
| 3-Br-5-CF$_3$ | CF$_3$ | C(O)Bu-t | C(O)OEt |
| 3-Br-5-CF$_3$ | CF$_3$ | C(O)CH$_2$OCH$_3$ | C(O)OEt |
| 3-Br-5-CF$_3$ | CF$_3$ | C(O)OCH$_3$ | C(O)OEt |
| 3-Br-5-CF$_3$ | CF$_3$ | H | C(O)OPr-i |
| 3-Br-5-CF$_3$ | CF$_3$ | C(O)CH$_3$ | C(O)OPr-i |
| 3-Br-5-CF$_3$ | CF$_3$ | C(O)CH$_2$OCH$_3$ | C(O)OPr-i |
| 3-Br-5-CF$_3$ | CF$_3$ | C(O)OCH$_3$ | C(O)OCH$_2$CH$_2$OCH$_3$ |
| 3-Br-5-CF$_3$ | CF$_3$ | H | C(O)NH$_2$ |
| 3-Br-5-CF$_3$ | CF$_3$ | C(O)CH3 | D-14a |
| 3-Br-5-CF$_3$ | CF$_3$ | CH3 | (D-52d)Cl |
| 3-Br-5-CF$_3$ | CF$_3$ | CH$_2$OCH$_3$ | (D-52d)Cl |
| 3-Br-5-CF$_3$ | CF$_3$ | C(O)Et | (D-52d)Cl |
| 3-Br-5-CF$_3$ | CF$_3$ | C(O)OCH$_3$ | (D-52d)Cl |
| 3-Br-5-CF$_3$ | CF$_3$ | CH$_3$ | (D-52d)Br |
| 3-Br-5-CF$_3$ | CF$_3$ | CH$_3$ | (D-52d)CN |
| 3-Br-5-CF$_3$ | CF$_3$ | CH$_3$ | (D-53e)Cl |
| 3-Br-5-CF$_3$ | CF$_3$ | CH$_3$ | D-55a |
| 3-Br-5-CF$_3$ | CF$_3$ | CH$_3$ | (D-55c)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Br-5-CF$_3$ | CF$_3$ | Et | (D-55c)Cl |
| 3-Br-5-CF$_3$ | CF$_3$ | CH$_2$OCH$_3$ | (D-55c)Cl |
| 3-Br-5-CF$_3$ | CF$_3$ | CH$_2$OEt | (D-55c)Cl |
| 3-Br-5-CF$_3$ | CF$_3$ | CH$_2$OC(O)CH$_3$ | (D-55c)Cl |
| 3-Br-5-CF$_3$ | CF$_3$ | CH$_2$OC(O)Bu-t | (D-55c)Cl |
| 3-Br-5-CF$_3$ | CF$_3$ | CH$_2$OC(O)OCH$_3$ | (D-55c)Cl |
| 3-Br-5-CF$_3$ | CF$_3$ | CH$_2$CN | (D-55c)Cl |
| 3-Br-5-CF$_3$ | CF$_3$ | C(O)CH$_3$ | (D-55c)Cl |
| 3-Br-5-CF$_3$ | CF$_3$ | C(O)Et | (D-55c)Cl |
| 3-Br-5-CF$_3$ | CF$_3$ | C(O)Pr-n | (D-55c)Cl |
| 3-Br-5-CF$_3$ | CF$_3$ | C(O)Pr-i | (D-55c)Cl |
| 3-Br-5-CF$_3$ | CF$_3$ | C(O)Pr-c | (D-55c)Cl |
| 3-Br-5-CF$_3$ | CF$_3$ | C(O)Bu-t | (D-55c)Cl |
| 3-Br-5-CF$_3$ | CF$_3$ | C(O)CH$_2$Cl | (D-55c)Cl |
| 3-Br-5-CF$_3$ | CF$_3$ | C(O)CH$_2$OCH$_3$ | (D-55c)Cl |
| 3-Br-5-CF$_3$ | CF$_3$ | C(O)CH$_2$OEt | (D-55c)Cl |
| 3-Br-5-CF$_3$ | CF$_3$ | C(O)CH$_2$SCH$_3$ | (D-55c)Cl |
| 3-Br-5-CF$_3$ | CF$_3$ | C(O)CH$_2$S(O)CH$_3$ | (D-55c)Cl |
| 3-Br-5-CF$_3$ | CF$_3$ | C(O)C(O)OEt | (D-55c)Cl |
| 3-Br-5-CF$_3$ | CF$_3$ | C(O)Ph | (D-55c)Cl |
| 3-Br-5-CF$_3$ | CF$_3$ | C(O)(D-52a) | (D-55c)Cl |
| 3-Br-5-CF$_3$ | CF$_3$ | C(O)OCH$_3$ | (D-55c)Cl |
| 3-Br-5-CF$_3$ | CF$_3$ | C(O)OEt | (D-55c)Cl |
| 3-Br-5-CF$_3$ | CF$_3$ | C(O)OPr-n | (D-55c)Cl |
| 3-Br-5-CF$_3$ | CF$_3$ | C(O)OPr-i | (D-55c)Cl |
| 3-Br-5-CF$_3$ | CF$_3$ | C(O)OBu-n | (D-55c)Cl |
| 3-Br-5-CF$_3$ | CF$_3$ | C(O)OBu-i | (D-55c)Cl |
| 3-Br-5-CF$_3$ | CF$_3$ | C(O)OCH$_2$Cl | (D-55c)Cl |
| 3-Br-5-CF$_3$ | CF$_3$ | C(O)OCH$_2$CH$_2$Cl | (D-55c)Cl |
| 3-Br-5-CF$_3$ | CF$_3$ | C(O)OCH$_2$CH$_2$OCH$_3$ | (D-55c)Cl |
| 3-Br-5-CF$_3$ | CF$_3$ | C(O)OCH$_2$CH=CH$_2$ | (D-55c)Cl |
| 3-Br-5-CF$_3$ | CF$_3$ | CH$_3$ | (D-55c)Br |
| 3-Br-5-CF$_3$ | CF$_3$ | Et | (D-55c)Br |
| 3-Br-5-CF$_3$ | CF$_3$ | CH$_2$OCH$_3$ | (D-55c)Br |
| 3-Br-5-CF$_3$ | CF$_3$ | CH$_2$OEt | (D-55c)Br |
| 3-Br-5-CF$_3$ | CF$_3$ | CH$_2$OC(O)CH$_3$ | (D-55c)Br |
| 3-Br-5-CF$_3$ | CF$_3$ | C(O)CH$_3$ | (D-55c)Br |
| 3-Br-5-CF$_3$ | CF$_3$ | C(O)Et | (D-55c)Br |
| 3-Br-5-CF$_3$ | CF$_3$ | C(O)Pr-n | (D-55c)Br |
| 3-Br-5-CF$_3$ | CF$_3$ | C(O)Pr-i | (D-55c)Br |
| 3-Br-5-CF$_3$ | CF$_3$ | C(O)Pr-c | (D-55c)Br |
| 3-Br-5-CF$_3$ | CF$_3$ | C(O)CH$_2$OCH$_3$ | (D-55c)Br |
| 3-Br-5-CF$_3$ | CF$_3$ | C(O)OCH$_3$ | (D-55c)Br |
| 3-Br-5-CF$_3$ | CF$_3$ | C(O)OEt | (D-55c)Br |
| 3-Br-5-CF$_3$ | CF$_3$ | C(O)OPr-n | (D-55c)Br |
| 3-Br-5-CF$_3$ | CF$_3$ | C(O)OBu-i | (D-55c)Br |
| 3-Br-5-CF$_3$ | CF$_3$ | C(O)OCH$_2$Cl | (D-55c)Br |
| 3-Br-5-CF$_3$ | CF$_3$ | C(O)OCH$_2$CH$_2$OCH$_3$ | (D-55c)Br |
| 3-Br-5-CF$_3$ | CF$_3$ | CH$_3$ | D-57a |
| 3-Br-5-CF$_3$ | CF$_3$ | C(O)CH$_3$ | D-57a |
| 3-Br-5-CF$_3$ | CF$_3$ | C(O)Pr-i | D-57a |
| 3-Br-5-CF$_3$ | CF$_3$ | CH$_3$ | D-58a |
| 3-Br-5-CF$_3$ | CF$_2$Cl | H | CH=NOCH$_3$ |
| 3-Br-5-CF$_3$ | CF$_2$Cl | CH$_2$OCH$_3$ | CH=NOCH$_3$ |
| 3-Br-5-CF$_3$ | CF$_2$Cl | H | CH=NOEt |
| 3-Br-5-CF$_3$ | CF$_2$Cl | H | C(O)OCH$_3$ |
| 3-Br-5-CF$_3$ | CF$_2$Cl | Et | C(O)OCH$_3$ |
| 3-Br-5-CF$_3$ | CF$_2$Cl | CH$_2$OCH$_3$ | C(O)OCH$_3$ |
| 3-Br-5-CF$_3$ | CF$_2$Cl | CH$_2$OEt | C(O)OCH$_3$ |
| 3-Br-5-CF$_3$ | CF$_2$Cl | CH$_2$OCH$_2$CF$_3$ | C(O)OCH$_3$ |
| 3-Br-5-CF$_3$ | CF$_2$Cl | CH$_2$OC(O)CH$_3$ | C(O)OCH$_3$ |
| 3-Br-5-CF$_3$ | CF$_2$Cl | CH$_2$OC(O)Et | C(O)OCH$_3$ |
| 3-Br-5-CF$_3$ | CF$_2$Cl | CH$_2$OC(O)OCH$_3$ | C(O)OCH$_3$ |
| 3-Br-5-CF$_3$ | CF$_2$Cl | E-5a | C(O)OCH$_3$ |
| 3-Br-5-CF$_3$ | CF$_2$Cl | C(O)Et | C(O)OCH$_3$ |
| 3-Br-5-CF$_3$ | CF$_2$Cl | C(O)Pr-n | C(O)OCH$_3$ |
| 3-Br-5-CF$_3$ | CF$_2$Cl | C(O)Bu-t | C(O)OCH$_3$ |
| 3-Br-5-CF$_3$ | CF$_2$Cl | C(O)CH$_2$SCH$_3$ | C(O)OCH$_3$ |
| 3-Br-5-CF$_3$ | CF$_2$Cl | C(O)OCH$_3$ | C(O)OEt |
| 3-Br-5-CF$_3$ | CF$_2$Cl | H | C(O)OPr-i |
| 3-Br-5-CF$_3$ | CF$_2$Cl | H | C(O)NH$_2$ |
| 3-Br-5-CF$_3$ | CF$_2$Cl | C(O)OCH$_3$ | (D-52d)Cl |
| 3-Br-5-CF$_3$ | CF$_2$Cl | CH$_3$ | (D-52d)Cl |
| 3-Br-5-CF$_3$ | CF$_2$Cl | CH$_2$OCH$_3$ | (D-52d)Cl |
| 3-Br-5-CF$_3$ | CF$_2$Cl | C(O)CH$_3$ | (D-52d)Cl |
| 3-Br-5-CF$_3$ | CF$_2$Cl | C(O)Et | (D-52d)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Br-5-CF$_3$ | CF$_2$Cl | C(O)Pr-i | (D-52d)Cl |
| 3-Br-5-CF$_3$ | CF$_2$Cl | C(O)CH$_2$OCH$_3$ | (D-52d)Cl |
| 3-Br-5-CF$_3$ | CF$_2$Cl | C(O)CH$_2$OEt | (D-52d)Cl |
| 3-Br-5-CF$_3$ | CF$_2$Cl | C(O)CH$_2$SCH$_3$ | (D-52d)Cl |
| 3-Br-5-CF$_3$ | CF$_2$Cl | C(O)OCH$_3$ | (D-52d)Cl |
| 3-Br-5-CF$_3$ | CF$_2$Cl | C(O)OPr-n | (D-52d)Cl |
| 3-Br-5-CF$_3$ | CF$_2$Cl | C(O)OCH$_2$CH$_2$Cl | (D-52d)Cl |
| 3-Br-5-CF$_3$ | CF$_2$Cl | C(O)OCH$_2$CH$_2$OCH$_3$ | (D-52d)Cl |
| 3-Br-5-CF$_3$ | CF$_2$Cl | C(O)OCH$_2$CH=CH$_2$ | (D-52d)Cl |
| 3-Br-5-CF$_3$ | CF$_2$Cl | CH$_2$OC(O)CH$_3$ | (D-55c)Br |
| 3-Br-5-CF$_3$ | CF$_2$Cl | C(O)CH$_3$ | (D-55c)Br |
| 3-Br-5-CF$_3$ | CF$_2$Cl | C(O)Et | (D-55c)Br |
| 3-Br-5-CF$_3$ | CF$_2$Cl | C(O)Pr-n | (D-55c)Br |
| 3-Br-5-CF$_3$ | CF$_2$Cl | C(O)Pr-i | (D-55c)Br |
| 3-Br-5-CF$_3$ | CF$_2$Cl | C(O)OCH$_3$ | (D-55c)Br |
| 3-Br-5-CF$_3$ | CF$_2$Cl | C(O)OEt | (D-55c)Br |
| 3-Br-5-CF$_3$ | CF$_2$Br | H | CH=NOCH$_3$ |
| 3-Br-5-CF$_3$ | CF$_2$Br | CH$_2$OEt | C(O)OCH$_3$ |
| 3-Br-5-CF$_3$ | CF$_2$Br | C(O)Et | C(O)OCH$_3$ |
| 3-Br-5-CF$_3$ | CF$_2$Br | C(O)CH$_3$ | (D-55c)Cl |
| 3-Br-5-CF$_3$ | CF$_2$Br | C(O)OCH$_3$ | (D-55c)Cl |
| 3-Br-5-CF$_3$ | CF$_2$CHF$_2$ | H | CH=NOCH$_3$ |
| 3-Br-5-CF$_3$ | CF$_2$CHF$_2$ | CH$_2$OEt | C(O)OCH$_3$ |
| 3-Br-5-CF$_3$ | CF$_2$CHF$_2$ | C(O)Et | C(O)OCH$_3$ |
| 3-Br-5-CF$_3$ | CF$_2$CHF$_2$ | C(O)CH$_3$ | (D-55c)Cl |
| 3-Br-5-CF$_3$ | CF$_2$CHF$_2$ | C(O)OCH$_3$ | (D-55c)Cl |
| 3-CH$_3$-5-CF$_3$ | CF$_3$ | H | CH=NOCH$_3$ |
| 3-CH$_3$-5-CF$_3$ | CF$_3$ | H | CH=NOEt |
| 3-CH$_3$-5-CF$_3$ | CF$_3$ | H | C(O)OCH$_3$ |
| 3-CH$_3$-5-CF$_3$ | CF$_3$ | Et | C(O)OCH$_3$ |
| 3-CH$_3$-5-CF$_3$ | CF$_3$ | CH$_2$OCH$_3$ | C(O)OCH$_3$ |
| 3-CH$_3$-5-CF$_3$ | CF$_3$ | CH$_2$OEt | C(O)OCH$_3$ |
| 3-CH$_3$-5-CF$_3$ | CF$_3$ | CH$_2$OCH$_2$CF$_3$ | C(O)OCH$_3$ |
| 3-CH$_3$-5-CF$_3$ | CF$_3$ | C(O)Et | C(O)OCH$_3$ |
| 3-CH$_3$-5-CF$_3$ | CF$_3$ | C(O)OCH$_3$ | C(O)OEt |
| 3-CH$_3$-5-CF$_3$ | CF$_3$ | H | C(O)NH$_2$ |
| 3-CH$_3$-5-CF$_3$ | CF$_3$ | CH$_3$ | (D-55c)Cl |
| 3-CH$_3$-5-CF$_3$ | CF$_3$ | CH$_2$OCH$_3$ | (D-55c)Cl |
| 3-CH$_3$-5-CF$_3$ | CF$_3$ | C(O)CH$_3$ | (D-55c)Cl |
| 3-CH$_3$-5-CF$_3$ | CF$_3$ | C(O)Et | (D-55c)Cl |
| 3-CH$_3$-5-CF$_3$ | CF$_3$ | C(O)Pr-i | (D-55c)Cl |
| 3-CH$_3$-5-CF$_3$ | CF$_3$ | C(O)CH$_2$OCH$_3$ | (D-55c)Cl |
| 3-CH$_3$-5-CF$_3$ | CF$_3$ | C(O)OCH$_3$ | (D-55c)Cl |
| 3-CH$_3$-5-CF$_3$ | CF$_3$ | C(O)CH$_3$ | (D-55c)Br |
| 3-CH$_3$-5-CF$_3$ | CF$_3$ | C(O)Et | (D-55c)Br |
| 3-CH$_3$-5-CF$_3$ | CF$_3$ | C(O)Pr-i | (D-55c)Br |
| 3-CH$_3$-5-CF$_3$ | CF$_2$Cl | H | CH=NOCH$_3$ |
| 3-CH$_3$-5-CF$_3$ | CF$_2$Cl | CH$_2$OEt | C(O)OCH$_3$ |
| 3-CH$_3$-5-CF$_3$ | CF$_2$Cl | C(O)Et | C(O)OCH$_3$ |
| 3-CH$_3$-5-CF$_3$ | CF$_2$Cl | C(O)CH$_3$ | (D-55c)Cl |
| 3-CH$_3$-5-CF$_3$ | CF$_2$Cl | C(O)OCH$_3$ | (D-55c)Cl |
| 3-Et-5-CF$_3$ | CF$_3$ | C(O)CH$_3$ | (D-55c)Br |
| 3-i-Pr-5-CF$_3$ | CF$_3$ | H | CH=NOCH$_3$ |
| 3-t-Bu-5-CF$_3$ | CF$_3$ | H | CH=NOEt |
| 3,5-(CF$_3$)$_2$ | CHF$_2$ | H | CH=NOCH$_3$ |
| 3,5-(CF$_3$)$_2$ | CHF$_2$ | H | CH=NOEt |
| 3,5-(CF$_3$)$_2$ | CHF$_2$ | CH$_2$OEt | C(O)OCH$_3$ |
| 3,5-(CF$_3$)$_2$ | CHF$_2$ | CH$_2$OCH$_2$CF$_3$ | C(O)OCH$_3$ |
| 3,5-(CF$_3$)$_2$ | CHF$_2$ | C(O)Et | C(O)OCH$_3$ |
| 3,5-(CF$_3$)$_2$ | CHF$_2$ | C(O)CH$_3$ | (D-55c)Cl |
| 3,5-(CF$_3$)$_2$ | CHF$_2$ | C(O)Pr-i | (D-55c)Cl |
| 3,5-(CF$_3$)$_2$ | CHF$_2$ | C(O)OCH$_3$ | (D-55c)Cl |
| 3,5-(CF$_3$)$_2$ | CHF$_2$ | C(O)CH$_3$ | (D-55c)Br |
| 3,5-(CF$_3$)$_2$ | CHFCl | CH$_2$OEt | C(O)OCH$_3$ |
| 3,5-(CF$_3$)$_2$ | CHCl$_2$ | CH$_2$OCH$_2$CF$_3$ | C(O)OCH$_3$ |
| 3,5-(CF$_3$)$_2$ | CHFBr | C(O)Et | C(O)OCH$_3$ |
| 3,5-(CF$_3$)$_2$ | CF$_3$ | H | CH=NOCH$_3$ |
| 3,5-(CF$_3$)$_2$ | CF$_3$ | CH$_2$OCH$_3$ | CH=NOCH$_3$ |
| 3,5-(CF$_3$)$_2$ | CF$_3$ | CH$_2$OEt | CH=NOCH$_3$ |
| 3,5-(CF$_3$)$_2$ | CF$_3$ | H | CH=NOEt |
| 3,5-(CF$_3$)$_2$ | CF$_3$ | CH$_2$OCH$_3$ | CH=NOEt |
| 3,5-(CF$_3$)$_2$ | CF$_3$ | H | CH=NOPr-n |
| 3,5-(CF$_3$)$_2$ | CF$_3$ | H | CH=NOCH$_2$CF$_3$ |
| 3,5-(CF$_3$)$_2$ | CF$_3$ | H | CH=NOCH$_2$CH=CH$_2$ |
| 3,5-(CF$_3$)$_2$ | CF$_3$ | H | CH=NOCH$_2$C=CH |
| 3,5-(CF$_3$)$_2$ | CF$_3$ | H | C(O)OCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-$(CF_3)_2$ | $CF_3$ | $CH_3$ | $C(O)OCH_3$ |
| 3,5-$(CF_3)_2$ | $CF_3$ | Et | $C(O)OCH_3$ |
| 3,5-$(CF_3)_2$ | $CF_3$ | $CH_2OCH_3$ | $C(O)OCH_3$ |
| 3,5-$(CF_3)_2$ | $CF_3$ | $CH_2OEt$ | $C(O)OCH_3$ |
| 3,5-$(CF_3)_2$ | $CF_3$ | $CH_2OCH_2CF_3$ | $C(O)OCH_3$ |
| 3,5-$(CF_3)_2$ | $CF_3$ | $CH_2OC(O)CH_3$ | $C(O)OCH_3$ |
| 3,5-$(CF_3)_2$ | $CF_3$ | $CH_2OC(O)Et$ | $C(O)OCH_3$ |
| 3,5-$(CF_3)_2$ | $CF_3$ | $CH_2OC(O)Bu$-t | $C(O)OCH_3$ |
| 3,5-$(CF_3)_2$ | $CF_3$ | $CH_2OC(O)OCH_3$ | $C(O)OCH_3$ |
| 3,5-$(CF_3)_2$ | $CF_3$ | E-5a | $C(O)OCH_3$ |
| 3,5-$(CF_3)_2$ | $CF_3$ | $CH_2NHC(O)OCH_3$ | $C(O)OCH_3$ |
| 3,5-$(CF_3)_2$ | $CF_3$ | $CH_2CN$ | $C(O)OCH_3$ |
| 3,5-$(CF_3)_2$ | $CF_3$ | $CH_2C\equiv CH$ | $C(O)OCH_3$ |
| 3,5-$(CF_3)_2$ | $CF_3$ | $CH2Ph$ | $C(O)OCH_3$ |
| 3,5-$(CF_3)_2$ | $CF_3$ | $C(O)CH_3$ | $C(O)OCH_3$ |
| 3,5-$(CF_3)_2$ | $CF_3$ | $C(O)Et$ | $C(O)OCH_3$ |
| 3,5-$(CF_3)_2$ | $CF_3$ | $C(O)Pr$-n | $C(O)OCH_3$ |
| 3,5-$(CF_3)_2$ | $CF_3$ | $C(O)Pr$-i | $C(O)OCH_3$ |
| 3,5-$(CF_3)_2$ | $CF_3$ | $C(O)Bu$-t | $C(O)OCH_3$ |
| 3,5-$(CF_3)_2$ | $CF_3$ | $C(O)CH_2Cl$ | $C(O)OCH_3$ |
| 3,5-$(CF_3)_2$ | $CF_3$ | $C(O)CH_2OCH_3$ | $C(O)OCH_3$ |
| 3,5-$(CF_3)_2$ | $CF_3$ | $C(O)CH_2OEt$ | $C(O)OCH_3$ |
| 3,5-$(CF_3)_2$ | $CF_3$ | $C(O)CH_2SCH_3$ | $C(O)OCH_3$ |
| 3,5-$(CF_3)_2$ | $CF_3$ | $C(O)Ph$ | $C(O)OCH_3$ |
| 3,5-$(CF_3)_2$ | $CF_3$ | $C(O)OCH_3$ | $C(O)OCH_3$ |
| 3,5-$(CF_3)_2$ | $CF_3$ | $C(O)OCH_2Cl$ | $C(O)OCH_3$ |
| 3,5-$(CF_3)_2$ | $CF_3$ | $C(O)OCH_2CH_2Cl$ | $C(O)OCH_3$ |
| 3,5-$(CF_3)_2$ | $CF_3$ | H | $C(O)OEt$ |
| 3,5-$(CF_3)_2$ | $CF_3$ | $CH_3$ | $C(O)OEt$ |
| 3,5-$(CF_3)_2$ | $CF_3$ | Et | $C(O)OEt$ |
| 3,5-$(CF_3)_2$ | $CF_3$ | $CH_2OCH_3$ | $C(O)OEt$ |
| 3,5-$(CF_3)_2$ | $CF_3$ | $C(O)CH_3$ | $C(O)OEt$ |
| 3,5-$(CF_3)_2$ | $CF_3$ | $C(O)Et$ | $C(O)OEt$ |
| 3,5-$(CF_3)_2$ | $CF_3$ | $C(O)Bu$-t | $C(O)OEt$ |
| 3,5-$(CF_3)_2$ | $CF_3$ | $C(O)CH_2OCH_3$ | $C(O)OEt$ |
| 3,5-$(CF_3)_2$ | $CF_3$ | $C(O)OCH_3$ | $C(O)OEt$ |
| 3,5-$(CF_3)_2$ | $CF_3$ | H | $C(O)OPr$-n |
| 3,5-$(CF_3)_2$ | $CF_3$ | H | $C(O)OPr$-i |
| 3,5-$(CF_3)_2$ | $CF_3$ | $CH_3$ | $C(O)OPr$-i |
| 3,5-$(CF_3)_2$ | $CF_3$ | $CH_2OCH_3$ | $C(O)OPr$-i |
| 3,5-$(CF_3)_2$ | $CF_3$ | $CH_2CN$ | $C(O)OPr$-i |
| 3,5-$(CF_3)_2$ | $CF_3$ | $CH_2C\equiv CH$ | $C(O)OPr$-i |
| 3,5-$(CF_3)_2$ | $CF_3$ | $C(O)CH_3$ | $C(O)OPr$-i |
| 3,5-$(CF_3)_2$ | $CF_3$ | $C(O)Et$ | $C(O)OPr$-i |
| 3,5-$(CF_3)_2$ | $CF_3$ | $C(O)Bu$-t | $C(O)OPr$-i |
| 3,5-$(CF_3)_2$ | $CF_3$ | $C(O)CH_2OCH_3$ | $C(O)OPr$-i |
| 3,5-$(CF_3)_2$ | $CF_3$ | $C(O)OCH_3$ | $C(O)OPr$-i |
| 3,5-$(CF_3)_2$ | $CF_3$ | $C(O)OEt$ | $C(O)OPr$-i |
| 3,5-$(CF_3)_2$ | $CF_3$ | H | $C(O)OBu$-t |
| 3,5-$(CF_3)_2$ | $CF_3$ | $C(O)CH_3$ | $C(O)OBu$-t |
| 3,5-$(CF_3)_2$ | $CF_3$ | $C(O)Et$ | $C(O)OBu$-t |
| 3,5-$(CF_3)_2$ | $CF_3$ | $C(O)CH_2CF_3$ | $C(O)OBu$-t |
| 3,5-$(CF_3)_2$ | $CF_3$ | $C(O)OCH_3$ | $C(O)OBu$-t |
| 3,5-$(CF_3)_2$ | $CF_3$ | $C(O)OCH_3$ | $C(O)OCH_2CH_2OCH_3$ |
| 3,5-$(CF_3)_2$ | $CF_3$ | H | $C(O)NH_2$ |
| 3,5-$(CF_3)_2$ | $CF_3$ | $CH_3$ | $C(O)NH_2$ |
| 3,5-$(CF_3)_2$ | $CF_3$ | $CH_3$ | $C(O)NHC(O)CH_3$ |
| 3,5-$(CF_3)_2$ | $CF_3$ | $CH_3$ | $C(O)NHC(O)OCH_3$ |
| 3,5-$(CF_3)_2$ | $CF_3$ | H | $C(S)NH_2$ |
| 3,5-$(CF_3)_2$ | $CF_3$ | $CH_3$ | D-14a |
| 3,5-$(CF_3)_2$ | $CF_3$ | $C(O)CH_3$ | D-14a |
| 3,5-$(CF_3)_2$ | $CF_3$ | $C(O)OCH_3$ | D-14a |
| 3,5-$(CF_3)_2$ | $CF_3$ | $CH_3$ | (D-52d)Cl |
| 3,5-$(CF_3)_2$ | $CF_3$ | $CH_2OCH_3$ | (D-52d)Cl |
| 3,5-$(CF_3)_2$ | $CF_3$ | $C(O)CH_3$ | (D-52d)Cl |
| 3,5-$(CF_3)_2$ | $CF_3$ | $C(O)Et$ | (D-52d)Cl |
| 3,5-$(CF_3)_2$ | $CF_3$ | $C(O)OCH_3$ | (D-52d)Cl |
| 3,5-$(CF_3)_2$ | $CF_3$ | $CH_3$ | (D-52d)Br |
| 3,5-$(CF_3)_2$ | $CF_3$ | $C(O)OCH_3$ | (D-52d)Br |
| 3,5-$(CF_3)_2$ | $CF_3$ | $CH_3$ | (D-52d)CN |
| 3,5-$(CF_3)_2$ | $CF_3$ | $CH_3$ | (D-53e)Cl |
| 3,5-$(CF_3)_2$ | $CF_3$ | $C(O)OCH_3$ | (D-53e)Cl |
| 3,5-$(CF_3)_2$ | $CF_3$ | $CH_3$ | D-55a |
| 3,5-$(CF_3)_2$ | $CF_3$ | $C(O)CH_3$ | D-55a |
| 3,5-$(CF_3)_2$ | $CF_3$ | $C(O)Pr$-i | D-55a |
| 3,5-$(CF_3)_2$ | $CF_3$ | $C(O)Bu$-t | D-55a |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-$(CF_3)_2$ | $CF_3$ | $CH_3$ | (D-55c)Cl |
| 3,5-$(CF_3)_2$ | $CF_3$ | Et | (D-55c)Cl |
| 3,5-$(CF_3)_2$ | $CF_3$ | $CH_2OCH_3$ | (D-55c)Cl |
| 3,5-$(CF_3)_2$ | $CF_3$ | $CH_2OEt$ | (D-55c)Cl |
| 3,5-$(CF_3)_2$ | $CF_3$ | $CH_2OC(O)CH_3$ | (D-55c)Cl |
| 3,5-$(CF_3)_2$ | $CF_3$ | $CH_2OC(O)Bu$-t | (D-55c)Cl |
| 3,5-$(CF_3)_2$ | $CF_3$ | $CH_2OC(O)OCH_3$ | (D-55c)Cl |
| 3,5-$(CF_3)_2$ | $CF_3$ | $CH_2CN$ | (D-55c)Cl |
| 3,5-$(CF_3)_2$ | $CF_3$ | $CH_2C\equiv CH$ | (D-55c)Cl |
| 3,5-$(CF_3)_2$ | $CF_3$ | $C(O)CH_3$ | (D-55c)Cl |
| 3,5-$(CF_3)_2$ | $CF_3$ | C(O)Et | (D-55c)Cl |
| 3,5-$(CF_3)_2$ | $CF_3$ | C(O)Pr-n | (D-55c)Cl |
| 3,5-$(CF_3)_2$ | $CF_3$ | C(O)Pr-i | (D-55c)Cl |
| 3,5-$(CF_3)_2$ | $CF_3$ | C(O)Pr-c | (D-55c)Cl |
| 3,5-$(CF_3)_2$ | $CF_3$ | C(O)Bu-t | (D-55c)Cl |
| 3,5-$(CF_3)_2$ | $CF_3$ | $C(O)CH_2Cl$ | (D-55c)Cl |
| 3,5-$(CF_3)_2$ | $CF_3$ | $C(O)CH_2OCH_3$ | (D-55c)Cl |
| 3,5-$(CF_3)_2$ | $CF_3$ | $C(O)CH_2OEt$ | (D-55c)Cl |
| 3,5-$(CF_3)_2$ | $CF_3$ | $C(O)CH_2SCH_3$ | (D-55c)Cl |
| 3,5-$(CF_3)_2$ | $CF_3$ | $C(O)CH_2S(O)CH_3$ | (D-55c)Cl |
| 3,5-$(CF_3)_2$ | $CF_3$ | C(O)C(O)OEt | (D-55c)Cl |
| 3,5-$(CF_3)_2$ | $CF_3$ | C(O)Ph | (D-55c)Cl |
| 3,5-$(CF_3)_2$ | $CF_3$ | C(O)(D-52a) | (D-55c)Cl |
| 3,5-$(CF_3)_2$ | $CF_3$ | $C(O)OCH_3$ | (D-55c)Cl |
| 3,5-$(CF_3)_2$ | $CF_3$ | C(O)OEt | (D-55c)Cl |
| 3,5-$(CF_3)_2$ | $CF_3$ | C(O)OPr-n | (D-55c)Cl |
| 3,5-$(CF_3)_2$ | $CF_3$ | C(O)OPr-i | (D-55c)Cl |
| 3,5-$(CF_3)_2$ | $CF_3$ | C(O)OBu-n | (D-55c)Cl |
| 3,5-$(CF_3)_2$ | $CF_3$ | C(O)OBu-i | (D-55c)Cl |
| 3,5-$(CF_3)_2$ | $CF_3$ | C(O)OBu-t | (D-55c)Cl |
| 3,5-$(CF_3)_2$ | $CF_3$ | $C(O)OCH_2Cl$ | (D-55c)Cl |
| 3,5-$(CF_3)_2$ | $CF_3$ | $C(O)OCH_2CH_2Cl$ | (D-55c)Cl |
| 3,5-$(CF_3)_2$ | $CF_3$ | $C(O)OCH_2CH_2OCH3$ | (D-55c)Cl |
| 3,5-$(CF_3)_2$ | $CF_3$ | $C(O)OCH_2CH=CH_2$ | (D-55c)Cl |
| 3,5-$(CF_3)_2$ | $CF_3$ | C(O)OPh | (D-55c)Cl |
| 3,5-$(CF_3)_2$ | $CF_3$ | $CH_3$ | (D-55c)Br |
| 3,5-$(CF_3)_2$ | $CF_3$ | Et | (D-55c)Br |
| 3,5-$(CF_3)_2$ | $CF_3$ | $CH_2OCH_3$ | (D-55c)Br |
| 3,5-$(CF_3)_2$ | $CF_3$ | $CH_2OEt$ | (D-55c)Br |
| 3,5-$(CF_3)_2$ | $CF_3$ | $CH_2OC(O)CH_3$ | (D-55c)Br |
| 3,5-$(CF_3)_2$ | $CF_3$ | $C(O)CH_3$ | (D-55c)Br |
| 3,5-$(CF_3)_2$ | $CF_3$ | C(O)Et | (D-55c)Br |
| 3,5-$(CF_3)_2$ | $CF_3$ | C(O)Pr-n | (D-55c)Br |
| 3,5-$(CF_3)_2$ | $CF_3$ | C(O)Pr-i | (D-55c)Br |
| 3,5-$(CF_3)_2$ | $CF_3$ | C(O)Pr-c | (D-55c)Br |
| 3,5-$(CF_3)_2$ | $CF_3$ | C(O)Bu-t | (D-55c)Br |
| 3,5-$(CF_3)_2$ | $CF_3$ | $C(O)CH_2OCH_3$ | (D-55c)Br |
| 3,5-$(CF_3)_2$ | $CF_3$ | C(O)Ph | (D-55c)Br |
| 3,5-$(CF_3)_2$ | $CF_3$ | $C(O)OCH_3$ | (D-55c)Br |
| 3,5-$(CF_3)_2$ | $CF_3$ | C(O)OEt | (D-55c)Br |
| 3,5-$(CF_3)_2$ | $CF_3$ | C(O)OPr-n | (D-55c)Br |
| 3,5-$(CF_3)_2$ | $CF_3$ | C(O)OBu-i | (D-55c)Br |
| 3,5-$(CF_3)_2$ | $CF_3$ | $C(O)OCH_2Cl$ | (D-55c)Br |
| 3,5-$(CF_3)_2$ | $CF_3$ | $C(O)OCH_2CH_2OCH_3$ | (D-55c)Br |
| 3,5-$(CF_3)_2$ | $CF_3$ | $CH_3$ | D-57a |
| 3,5-$(CF_3)_2$ | $CF_3$ | C(O)CH3 | D-57a |
| 3,5-$(CF_3)_2$ | $CF_3$ | C(O)Pr-n | D-57a |
| 3,5-$(CF_3)_2$ | $CF_3$ | C(O)Pr-i | D-57a |
| 3,5-$(CF_3)_2$ | $CF_3$ | $C(O)OCH_3$ | D-57a |
| 3,5-$(CF_3)_2$ | $CF_3$ | $CH_3$ | D-58a |
| 3,5-$(CF_3)_2$ | $CF_3$ | $CH_3$ | (D-58b)Cl |
| 3,5-$(CF_3)_2$ | $CF_3$ | CH2OCH$_3$ | (D-58b)Cl |
| 3,5-$(CF_3)_2$ | $CF_3$ | $C(O)CH_3$ | (D-58b)Cl |
| 3,5-$(CF_3)_2$ | $CF_3$ | $C(O)OCH_3$ | (D-58b)Cl |
| 3,5-$(CF_3)_2$ | $CF_2Cl$ | H | $CH=NOCH_3$ |
| 3,5-$(CF_3)_2$ | $CF_2Cl$ | $CH_2OCH_3$ | $CH=NOCH_3$ |
| 3,5-$(CF_3)_2$ | $CF_2Cl$ | H | CH=NOEt |
| 3,5-$(CF_3)_2$ | $CF_2Cl$ | H | $C(O)OCH_3$ |
| 3,5-$(CF_3)_2$ | $CF_2Cl$ | Et | $C(O)OCH_3$ |
| 3,5-$(CF_3)_2$ | $CF_2Cl$ | $CH_2OCH_3$ | $C(O)OCH_3$ |
| 3,5-$(CF_3)_2$ | $CF_2Cl$ | $CH_2OEt$ | $C(O)OCH_3$ |
| 3,5-$(CF_3)_2$ | $CF_2Cl$ | $CH_2OCH2CF_3$ | $C(O)OCH_3$ |
| 3,5-$(CF_3)_2$ | $CF_2Cl$ | $CH_2OC(O)CH_3$ | $C(O)OCH_3$ |
| 3,5-$(CF_3)_2$ | $CF_2Cl$ | $CH_2OC(O)Et$ | $C(O)OCH_3$ |
| 3,5-$(CF_3)_2$ | $CF_2Cl$ | $CH_2OC(O)OCH_3$ | $C(O)OCH_3$ |
| 3,5-$(CF_3)_2$ | $CF_2Cl$ | E-5a | $C(O)OCH_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-(CF$_3$)$_2$ | CF$_2$Cl | C(O)CH$_3$ | C(O)OCH$_3$ |
| 3,5-(CF$_3$)$_2$ | CF$_2$Cl | C(O)Et | C(O)OCH$_3$ |
| 3,5-(CF$_3$)$_2$ | CF$_2$Cl | C(O)Pr-n | C(O)OCH$_3$ |
| 3,5-(CF$_3$)$_2$ | CF$_2$Cl | C(O)Pr-i | C(O)OCH$_3$ |
| 3,5-(CF$_3$)$_2$ | CF$_2$Cl | C(O)Bu-t | C(O)OCH$_3$ |
| 3,5-(CF$_3$)$_2$ | CF$_2$Cl | C(O)CH$_2$OCH$_3$ | C(O)OCH$_3$ |
| 3,5-(CF$_3$)$_2$ | CF$_2$Cl | C(O)CH$_2$SCH$_3$ | C(O)OCH$_3$ |
| 3,5-(CF$_3$)$_2$ | CF$_2$Cl | C(O)OCH$_3$ | C(O)OEt |
| 3,5-(CF$_3$)$_2$ | CF$_2$Cl | H | C(O)OPr-i |
| 3,5-(CF$_3$)$_2$ | CF$_2$Cl | C(O)OCH$_3$ | C(O)OPr-i |
| 3,5-(CF$_3$)$_2$ | CF$_2$Cl | H | C(O)NH$_2$ |
| 3,5-(CF$_3$)$_2$ | CF$_2$Cl | CH$_3$ | (D-52d)Cl |
| 3,5-(CF$_3$)$_2$ | CF$_2$Cl | CH$_2$OCH$_3$ | (D-52d)Cl |
| 3,5-(CF$_3$)$_2$ | CF$_2$Cl | C(O)OCH$_3$ | (D-52d)Cl |
| 3,5-(CF$_3$)$_2$ | CF$_2$Cl | CH$_3$ | (D-55c)Cl |
| 3,5-(CF$_3$)$_2$ | CF$_2$Cl | CH$_2$OCH$_3$ | (D-55c)Cl |
| 3,5-(CF$_3$)$_2$ | CF$_2$Cl | CH$_2$OC(O)CH$_3$ | (D-55c)Cl |
| 3,5-(CF$_3$)$_2$ | CF$_2$Cl | CH$_2$OC(O)Bu-t | (D-55c)Cl |
| 3,5-(CF$_3$)$_2$ | CF$_2$Cl | CH$_2$OC(O)OCH$_3$ | (D-55c)Cl |
| 3,5-(CF$_3$)$_2$ | CF$_2$Cl | CH$_2$CN | (D-55c)Cl |
| 3,5-(CF$_3$)$_2$ | CF$_2$Cl | C(O)CH$_3$ | (D-55c)Cl |
| 3,5-(CF$_3$)$_2$ | CF$_2$Cl | C(O)Et | (D-55c)Cl |
| 3,5-(CF$_3$)$_2$ | CF$_2$Cl | C(O)Pr-n | (D-55c)Cl |
| 3,5-(CF$_3$)$_2$ | CF$_2$Cl | C(O)Pr-i | (D-55c)Cl |
| 3,5-(CF$_3$)$_2$ | CF$_2$Cl | C(O)Pr-c | (D-55c)Cl |
| 3,5-(CF$_3$)$_2$ | CF$_2$Cl | C(O)Bu-t | (D-55c)Cl |
| 3,5-(CF$_3$)$_2$ | CF$_2$Cl | C(O)CH$_2$Cl | (D-55c)Cl |
| 3,5-(CF$_3$)$_2$ | CF$_2$Cl | C(O)CH$_2$OCH$_3$ | (D-55c)Cl |
| 3,5-(CF$_3$)$_2$ | CF$_2$Cl | C(O)CH$_2$OEt | (D-55c)Cl |
| 3,5-(CF$_3$)$_2$ | CF$_2$Cl | C(O)CH$_2$SCH$_3$ | (D-55c)Cl |
| 3,5-(CF$_3$)$_2$ | CF$_2$Cl | C(O)CH$_2$S(O)CH$_3$ | (D-55c)Cl |
| 3,5-(CF$_3$)$_2$ | CF$_2$Cl | C(O)C(O)OEt | (D-55c)Cl |
| 3,5-(CF$_3$)$_2$ | CF$_2$Cl | C(O)OCH$_3$ | (D-55c)Cl |
| 3,5-(CF$_3$)$_2$ | CF$_2$Cl | C(O)OPr-n | (D-55c)Cl |
| 3,5-(CF$_3$)$_2$ | CF$_2$Cl | C(O)OCH$_2$Cl | (D-55c)Cl |
| 3,5-(CF$_3$)$_2$ | CF$_2$Cl | C(O)OCH$_2$CH$_2$Cl | (D-55c)Cl |
| 3,5-(CF$_3$)$_2$ | CF$_2$Cl | C(O)OCH$_2$CH$_2$OCH$_3$ | (D-55c)Cl |
| 3,5-(CF$_3$)$_2$ | CF$_2$Cl | C(O)OCH$_2$CH=CH$_2$ | (D-55c)Cl |
| 3,5-(CF$_3$)$_2$ | CF$_2$Cl | CH$_3$ | (D-55c)Br |
| 3,5-(CF$_3$)$_2$ | CF$_2$Cl | CH$_2$OC(O)CH3 | (D-55c)Br |
| 3,5-(CF$_3$)$_2$ | CF$_2$Cl | C(O)CH$_3$ | (D-55c)Br |
| 3,5-(CF$_3$)$_2$ | CF$_2$Cl | C(O)Et | (D-55c)Br |
| 3,5-(CF$_3$)$_2$ | CF$_2$Cl | C(O)Pr-n | (D-55c)Br |
| 3,5-(CF$_3$)$_2$ | CF$_2$Cl | C(O)Pr-i | (D-55c)Br |
| 3,5-(CF$_3$)$_2$ | CF$_2$Cl | C(O)OCH$_3$ | (D-55c)Br |
| 3,5-(CF$_3$)$_2$ | CF$_2$Cl | C(O)OEt | (D-55c)Br |
| 3,5-(CF$_3$)$_2$ | CF$_2$Cl | C(O)OCH$_2$CH$_2$OCH$_3$ | (D-55c)Br |
| 3,5-(CF$_3$)$_2$ | CF$_2$Cl | C(O)Pr-i | D-57a |
| 3,5-(CF$_3$)$_2$ | CF$_2$Br | H | CH=NOCH$_3$ |
| 3,5-(CF$_3$)$_2$ | CF$_2$Br | H | CH=NOEt |
| 3,5-(CF$_3$)$_2$ | CF$_2$Br | CH$_2$OEt | C(O)OCH$_3$ |
| 3,5-(CF$_3$)$_2$ | CF$_2$Br | CH$_2$OCH$_2$CF$_3$ | C(O)OCH$_3$ |
| 3,5-(CF$_3$)$_2$ | CF$_2$Br | C(O)Et | C(O)OCH$_3$ |
| 3,5-(CF$_3$)$_2$ | CF$_2$Br | C(O)CH$_3$ | (D-55c)Cl |
| 3,5-(CF$_3$)$_2$ | CF$_2$Br | C(O)Pr-i | (D-55c)Cl |
| 3,5-(CF$_3$)$_2$ | CF$_2$Br | C(O)OCH$_3$ | (D-55c)Cl |
| 3,5-(CF$_3$)$_2$ | CF$_2$Br | C(O)CH$_3$ | (D-55c)Br |
| 3,5-(CF$_3$)$_2$ | CF$_2$CHF$_2$ | H | CH=NOCH$_3$ |
| 3,5-(CF$_3$)$_2$ | CF$_2$CHF$_2$ | H | CH=NOEt |
| 3,5-(CF$_3$)$_2$ | CF$_2$CHF$_2$ | CH$_2$OEt | C(O)OCH$_3$ |
| 3,5-(CF$_3$)$_2$ | CF$_2$CHF$_2$ | CH$_2$OCH$_2$CF$_3$ | C(O)OCH$_3$ |
| 3,5-(CF$_3$)$_2$ | CF$_2$CHF$_2$ | C(O)Et | C(O)OCH$_3$ |
| 3,5-(CF$_3$)$_2$ | CF$_2$CHF$_2$ | C(O)CH$_3$ | (D-55c)Cl |
| 3,5-(CF$_3$)$_2$ | CF$_2$CHF$_2$ | C(O)Pr-i | (D-55c)Cl |
| 3,5-(CF$_3$)$_2$ | CF$_2$CHF$_2$ | C(O)OCH$_3$ | (D-55c)Cl |
| 3,5-(CF$_3$)$_2$ | CF$_2$CHF$_2$ | C(O)CH$_3$ | (D-55c)Br |
| 3,5-(CF$_3$)$_2$ | CF$_2$CF$_3$ | C(O)CH$_3$ | (D-55c)Cl |
| 3,5-(CF$_3$)$_2$ | CF$_2$OCH$_3$ | C(O)Pr-i | (D-55c)Cl |
| 3,5-(CF$_3$)$_2$ | CF$_2$SCH$_3$ | C(O)OCH$_3$ | (D-55c)Cl |
| 3,5-(CF$_3$)$_2$ | T-3 | C(O)CH$_3$ | (D-55c)Br |
| 3-Cl-5-CF$_2$CF$_3$ | CF$_3$ | H | CH=NOCH$_3$ |
| 3-Cl-5-CF$_2$CF$_3$ | CF$_3$ | H | CH=NOEt |
| 3-Cl-5-CF$_2$CF$_3$ | CF$_3$ | CH$_2$OEt | C(O)OCH$_3$ |
| 3-Cl-5-CF$_2$CF$_3$ | CF$_3$ | CH$_2$OCH$_2$CF$_3$ | C(O)OCH$_3$ |
| 3-Cl-5-CF$_2$CF$_3$ | CF$_3$ | C(O)Et | C(O)OCH$_3$ |
| 3-Cl-5-CF$_2$CF$_3$ | CF$_3$ | C(O)CH$_3$ | (D-55c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-CF$_2$CF$_3$ | CF$_3$ | C(O)Pr-i | (D-55c)Cl |
| 3-Cl-5-CF$_2$CF$_3$ | CF$_3$ | C(O)OCH$_3$ | (D-55c)Cl |
| 3-Cl-5-CF$_2$CF$_3$ | CF$_3$ | C(O)CH$_3$ | (D-55c)Br |
| 3-Br-5-CF$_2$CF$_3$ | CF$_3$ | H | CH=NOCH$_3$ |
| 3-Br-5-CF$_2$CF$_3$ | CF$_3$ | H | CH=NOEt |
| 3-Br-5-CF$_2$CF$_3$ | CF$_3$ | CH$_2$OEt | C(O)OCH$_3$ |
| 3-Br-5-CF$_2$CF$_3$ | CF$_3$ | CH$_2$OCH$_2$CF$_3$ | C(O)OCH$_3$ |
| 3-Br-5-CF$_2$CF$_3$ | CF$_3$ | C(O)Et | C(O)OCH$_3$ |
| 3-Br-5-CF$_2$CF$_3$ | CF$_3$ | C(O)CH3 | (D-55c)Cl |
| 3-Br-5-CF$_2$CF$_3$ | CF$_3$ | C(O)Pr-i | (D-55c)Cl |
| 3-Br-5-CF$_2$CF$_3$ | CF$_3$ | C(O)OCH$_3$ | (D-55c)Cl |
| 3-Br-5-CF$_2$CF$_3$ | CF$_3$ | C(O)CH$_3$ | (D-55c)Br |
| 3-CH$_3$-5-CF$_2$CF$_3$ | CF$_3$ | H | CH=NOCH$_3$ |
| 3-CH$_3$-5-CF$_2$CF$_3$ | CF$_3$ | CH$_2$OEt | C(O)OCH$_3$ |
| 3-CH$_3$-5-CF$_2$CF$_3$ | CF$_3$ | C(O)Et | C(O)OCH$_3$ |
| 3-CH$_3$-5-CF$_2$CF$_3$ | CF$_3$ | C(O)CH$_3$ | (D-55c)Cl |
| 3-CH$_3$-5-CF$_2$CF$_3$ | CF$_3$ | C(O)OCH$_3$ | (D-55c)Cl |
| 3-Cl-5-CF$_2$CF$_2$CF$_3$ | CF$_3$ | H | CH=NOCH$_3$ |
| 3-Cl-5-CF$_2$CF$_2$CF$_3$ | CF$_3$ | CH$_2$OEt | C(O)OCH$_3$ |
| 3-Cl-5-CF$_2$CF$_2$CF$_3$ | CF$_3$ | C(O)Et | C(O)OCH$_3$ |
| 3-Cl-5-CF$_2$CF$_2$CF$_3$ | CF$_3$ | C(O)CH$_3$ | (D-55c)Cl |
| 3-Cl-5-CF$_2$CF$_2$CF$_3$ | CF$_3$ | C(O)OCH$_3$ | (D-55c)Cl |
| 3-Br-5-CF$_2$CF$_2$CF$_3$ | CF$_3$ | H | CH=NOCH$_3$ |
| 3-Br-5-CF$_2$CF$_2$CF$_3$ | CF$_3$ | CH$_2$OEt | C(O)OCH$_3$ |
| 3-Br-5-CF$_2$CF$_2$CF$_3$ | CF$_3$ | C(O)Et | C(O)OCH$_3$ |
| 3-Br-5-CF$_2$CF$_2$CF$_3$ | CF$_3$ | C(O)CH$_3$ | (D-55c)Cl |
| 3-Br-5-CF$_2$CF$_2$CF$_3$ | CF$_3$ | C(O)OCH$_3$ | (D-55c)Cl |
| 3-CH$_3$-5-CF$_2$CF$_2$CF$_3$ | CF$_3$ | H | CH=NOCH$_3$ |
| 3-CH$_3$-5-CF$_2$CF$_2$CF$_3$ | CF$_3$ | CH$_2$OEt | C(O)OCH$_3$ |
| 3-CH$_3$-5-CF$_2$CF$_2$CF$_3$ | CF$_3$ | C(O)Et | C(O)OCH$_3$ |
| 3-CH$_3$-5-CF$_2$CF$_2$CF$_3$ | CF$_3$ | C(O)CH$_3$ | (D-55c)Cl |
| 3-CH$_3$-5-CF$_2$CF$_2$CF$_3$ | CF$_3$ | C(O)OCH$_3$ | (D-55c)Cl |
| 3-Cl-5-CF(CF$_3$)$_2$ | CF$_3$ | H | CH=NOCH$_3$ |
| 3-Cl-5-CF(CF$_3$)$_2$ | CF$_3$ | CH$_2$OEt | C(O)OCH$_3$ |
| 3-Cl-5-CF(CF$_3$)$_2$ | CF$_3$ | C(O)Et | C(O)OCH$_3$ |
| 3-Cl-5-CF(CF$_3$)$_2$ | CF$_3$ | C(O)CH$_3$ | (D-55c)Cl |
| 3-Cl-5-CF(CF$_3$)$_2$ | CF$_3$ | C(O)OCH$_3$ | (D-55c)Cl |
| 3-Br-5-CF(CF$_3$)$_2$ | CF$_3$ | H | CH=NOCH$_3$ |
| 3-Br-5-CF(CF$_3$)$_2$ | CF$_3$ | CH$_2$OEt | C(O)OCH$_3$ |
| 3-Br-5-CF(CF$_3$)$_2$ | CF$_3$ | C(O)Et | C(O)OCH$_3$ |
| 3-Br-5-CF(CF$_3$)$_2$ | CF$_3$ | C(O)CH$_3$ | (D-55c)Cl |
| 3-Br-5-CF(CF$_3$)$_2$ | CF$_3$ | C(O)OCH$_3$ | (D-55c)Cl |
| 3-CH$_3$-5-CF(CF$_3$)$_2$ | CF$_3$ | H | CH=NOCH$_3$ |
| 3-CH$_3$-5-CF(CF$_3$)$_2$ | CF$_3$ | CH$_2$OEt | C(O)OCH$_3$ |
| 3-CH$_3$-5-CF(CF$_3$)$_2$ | CF$_3$ | C(O)Et | C(O)OCH$_3$ |
| 3-CH$_3$-5-CF(CF$_3$)$_2$ | CF$_3$ | C(O)CH$_3$ | (D-55c)Cl |
| 3-CH$_3$-5-CF(CF$_3$)$_2$ | CF$_3$ | C(O)OCH$_3$ | (D-55c)Cl |
| 3-Cl-5-CH$_2$OCH$_3$ | CF$_3$ | H | CH=NOCH$_3$ |
| 3-Cl-5-CH$_2$OCH$_2$CF$_3$ | CF$_3$ | H | CH=NOEt |
| 3-Cl-5-C(CF$_3$)$_2$OH | CF$_3$ | H | CH=NOCH$_3$ |
| 3-Cl-5-C(CF$_3$)$_2$OH | CF$_3$ | CH$_2$OEt | C(O)OCH$_3$ |
| 3-Cl-5-C(CF$_3$)$_2$OH | CF$_3$ | C(O)Et | C(O)OCH$_3$ |
| 3-Cl-5-C(CF$_3$)$_2$OH | CF$_3$ | C(O)CH$_3$ | (D-55c)Cl |
| 3-Cl-5-C(CF$_3$)$_2$OH | CF$_3$ | C(O)OCH$_3$ | (D-55c)Cl |
| 3-Br-5-C(CF$_3$)$_2$OH | CF$_3$ | H | CH=NOCH$_3$ |
| 3-Br-5-C(CF$_3$)$_2$OH | CF$_3$ | CH$_2$OEt | C(O)OCH$_3$ |
| 3-Br-5-C(CF$_3$)$_2$OH | CF$_3$ | C(O)Et | C(O)OCH$_3$ |
| 3-Br-5-C(CF$_3$)$_2$OH | CF$_3$ | C(O)CH$_3$ | (D-55c)Cl |
| 3-Br-5-C(CF$_3$)$_2$OH | CF$_3$ | C(O)OCH$_3$ | (D-55c)Cl |
| 3-CH$_3$-5-C(CF$_3$)$_2$OH | CF$_3$ | H | CH=NOCH$_3$ |
| 3-CH$_3$-5-C(CF$_3$)$_2$OH | CF$_3$ | CH$_2$OEt | C(O)OCH$_3$ |
| 3-CH$_3$-5-C(CF$_3$)$_2$OH | CF$_3$ | C(O)Et | C(O)OCH$_3$ |
| 3-CH$_3$-5-C(CF$_3$)$_2$OH | CF$_3$ | C(O)CH$_3$ | (D-55c)Cl |
| 3-CH$_3$-5-C(CF$_3$)$_2$OH | CF$_3$ | C(O)OCH$_3$ | (D-55c)Cl |
| 3,5-[C(CF$_3$)$_2$OH]$_2$ | CF$_3$ | CH$_2$OEt | C(O)OCH$_3$ |
| 3-Cl-5-C(CF$_3$)$_2$OCH$_3$ | CF$_3$ | H | CH=NOCH$_3$ |
| 3-Cl-5-C(CF$_3$)$_2$OCH$_3$ | CF$_3$ | CH$_2$OEt | C(O)OCH$_3$ |
| 3-Cl-5-C(CF$_3$)$_2$OCH$_3$ | CF$_3$ | C(O)Et | C(O)OCH$_3$ |
| 3-Cl-5-C(CF$_3$)$_2$OCH$_3$ | CF$_3$ | C(O)CH$_3$ | (D-55c)Cl |
| 3-Cl-5-C(CF$_3$)$_2$OCH$_3$ | CF$_3$ | C(O)OCH$_3$ | (D-55c)Cl |
| 3-Br-5-C(CF$_3$)$_2$OCH$_3$ | CF$_3$ | H | CH=NOCH$_3$ |
| 3-Br-5-C(CF$_3$)$_2$OCH$_3$ | CF$_3$ | CH$_2$OEt | C(O)OCH$_3$ |
| 3-Br-5-C(CF$_3$)$_2$OCH$_3$ | CF$_3$ | C(O)Et | C(O)OCH$_3$ |
| 3-Br-5-C(CF$_3$)$_2$OCH$_3$ | CF$_3$ | C(O)CH$_3$ | (D-55c)Cl |
| 3-Br-5-C(CF$_3$)$_2$OCH$_3$ | CF$_3$ | C(O)OCH$_3$ | (D-55c)Cl |
| 3-CH$_3$-5-C(CF$_3$)$_2$OCH$_3$ | CF$_3$ | H | CH=NOCH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-CH$_3$-5-C(CF$_3$)$_2$OCH$_3$ | CF$_3$ | CH$_2$OEt | C(O)OCH$_3$ |
| 3-CH$_3$-5-C(CF$_3$)$_2$OCH$_3$ | CF$_3$ | C(O)Et | C(O)OCH$_3$ |
| 3-CH$_3$-5-C(CF$_3$)$_2$OCH$_3$ | CF$_3$ | C(O)CH$_3$ | (D-55c)Cl |
| 3-CH$_3$-5-C(CF$_3$)$_2$OCH$_3$ | CF$_3$ | C(O)OCH$_3$ | (D-55c)Cl |
| 3,5-[C(CF$_3$)$_2$OCH$_3$]$_2$ | CF$_3$ | CH$_2$OCH$_2$CF$_3$ | C(O)OCH$_3$ |
| 3-CF$_3$-5-CH$_2$SCH$_3$ | CF$_3$ | C(O)Et | C(O)OCH$_3$ |
| 3-CF$_3$-5-CH$_2$S(O)CH$_3$ | CF$_3$ | C(O)CH$_3$ | (D-55c)Cl |
| 3-CF$_3$-5-CH$_2$SO$_2$CH$_3$ | CF$_3$ | C(O)Pr-i | (D-55c)Cl |
| 3-Cl-4-OCH$_3$ | CF$_3$ | C(O)OCH$_3$ | (D-55c)Cl |
| 3-Cl-5-OCH$_3$ | CF$_3$ | C(O)CH$_3$ | (D-55c)Br |
| 3-Br-5-OCH$_3$ | CF$_3$ | H | CH=NOCH$_3$ |
| 3-Br-5-OCH$_3$ | CF$_3$ | CH$_2$OEt | C(O)OCH$_3$ |
| 3-Br-5-OCH$_3$ | CF$_3$ | C(O)Et | C(O)OCH$_3$ |
| 3-Br-5-OCH$_3$ | CF$_3$ | C(O)CH$_3$ | (D-55c)Cl |
| 3-Br-5-OCH$_3$ | CF$_3$ | C(O)OCH$_3$ | (D-55c)Cl |
| 3-CF$_3$-5-OCH$_3$ | CF$_3$ | H | CH=NOCH$_3$ |
| 3-CF$_3$-5-OCH$_3$ | CF$_3$ | H | CH=NOEt |
| 3-CF$_3$-5-OCH$_3$ | CF$_3$ | H | C(O)OCH$_3$ |
| 3-CF$_3$-5-OCH$_3$ | CF$_3$ | Et | C(O)OCH$_3$ |
| 3-CF$_3$-5-OCH$_3$ | CF$_3$ | CH$_2$OCH$_3$ | C(O)OCH$_3$ |
| 3-CF$_3$-5-OCH$_3$ | CF$_3$ | CH$_2$OEt | C(O)OCH$_3$ |
| 3-CF$_3$-5-OCH$_3$ | CF$_3$ | CH$_2$OCH$_2$CF$_3$ | C(O)OCH$_3$ |
| 3-CF$_3$-5-OCH$_3$ | CF$_3$ | C(O)Et | C(O)OCH$_3$ |
| 3-CF$_3$-5-OCH$_3$ | CF$_3$ | C(O)OCH$_3$ | C(O)OEt |
| 3-CF$_3$-5-OCH$_3$ | CF$_3$ | H | C(O)NH$_2$ |
| 3-CF$_3$-5-OCH$_3$ | CF$_3$ | CH$_3$ | (D-55c)Cl |
| 3-CF$_3$-5-OCH$_3$ | CF$_3$ | CH$_2$OCH$_3$ | (D-55c)Cl |
| 3-CF$_3$-5-OCH$_3$ | CF$_3$ | C(O)CH$_3$ | (D-55c)Cl |
| 3-CF$_3$-5-OCH$_3$ | CF$_3$ | C(O)Et | (D-55c)Cl |
| 3-CF$_3$-5-OCH$_3$ | CF$_3$ | C(O)Pr-i | (D-55c)Cl |
| 3-CF$_3$-5-OCH$_3$ | CF$_3$ | C(O)CH$_2$OCH$_3$ | (D-55c)Cl |
| 3-CF$_3$-5-OCH$_3$ | CF$_3$ | C(O)OCH$_3$ | (D-55c)Cl |
| 3-CF$_3$-5-OCH$_3$ | CF$_3$ | C(O)CH$_3$ | (D-55c)Br |
| 3-CF$_3$-5-OCH$_3$ | CF$_3$ | C(O)Et | (D-55c)Br |
| 3-CF$_3$-5-OCH$_3$ | CF$_3$ | C(O)Pr-i | (D-55c)Br |
| 3-CF$_3$-5-OCH$_3$ | CF$_2$Cl | H | CH=NOCH$_3$ |
| 3-CF$_3$-5-OCH$_3$ | CF$_2$Cl | CH$_2$OEt | C(O)OCH$_3$ |
| 3-CF$_3$-5-OCH$_3$ | CF$_2$Cl | C(O)Et | C(O)OCH$_3$ |
| 3-CF$_3$-5-OCH$_3$ | CF$_2$Cl | C(O)CH$_3$ | (D-55c)Cl |
| 3-CF$_3$-5-OCH$_3$ | CF$_2$Cl | C(O)OCH$_3$ | (D-55c)Cl |
| 3-F-4-OCHF$_2$ | CF$_3$ | H | CH=NOCH$_3$ |
| 3-Cl-4-OCHF$_2$ | CF$_3$ | H | CH=NOEt |
| 3-Cl-5-OCHF$_2$ | CHF$_2$ | CH$_2$OEt | C(O)OCH$_3$ |
| 3-Cl-5-OCHF$_2$ | CF$_3$ | H | CH=NOCH$_3$ |
| 3-Cl-5-OCHF$_2$ | CF$_3$ | CH$_2$OCH$_3$ | CH=NOCH$_3$ |
| 3-Cl-5-OCHF$_2$ | CF$_3$ | H | CH=NOEt |
| 3-Cl-5-OCHF$_2$ | CF$_3$ | H | C(O)OCH$_3$ |
| 3-Cl-5-OCHF$_2$ | CF$_3$ | Et | C(O)OCH$_3$ |
| 3-Cl-5-OCHF$_2$ | CF$_3$ | CH$_2$OCH$_3$ | C(O)OCH$_3$ |
| 3-Cl-5-OCHF$_2$ | CF$_3$ | CH$_2$OEt | C(O)OCH$_3$ |
| 3-Cl-5-OCHF$_2$ | CF$_3$ | CH$_2$OCH$_2$CF$_3$ | C(O)OCH$_3$ |
| 3-Cl-5-OCHF$_2$ | CF$_3$ | CH$_2$OC(O)CH$_3$ | C(O)OCH$_3$ |
| 3-Cl-5-OCHF$_2$ | CF$_3$ | CH$_2$OC(O)Et | C(O)OCH$_3$ |
| 3-Cl-5-OCHF$_2$ | CF$_3$ | CH$_2$OC(O)OCH$_3$ | C(O)OCH$_3$ |
| 3-Cl-5-OCHF$_2$ | CF$_3$ | E-5a | C(O)OCH$_3$ |
| 3-Cl-5-OCHF$_2$ | CF$_3$ | C(O)CH$_3$ | C(O)OCH$_3$ |
| 3-Cl-5-OCHF$_2$ | CF$_3$ | C(O)Et | C(O)OCH$_3$ |
| 3-Cl-5-OCHF$_2$ | CF$_3$ | C(O)Pr-n | C(O)OCH$_3$ |
| 3-Cl-5-OCHF$_2$ | CF$_3$ | C(O)Pr-i | C(O)OCH$_3$ |
| 3-Cl-5-OCHF$_2$ | CF$_3$ | C(O)Bu-t | C(O)OCH$_3$ |
| 3-Cl-5-OCHF$_2$ | CF$_3$ | C(O)CH$_2$OCH$_3$ | C(O)OCH$_3$ |
| 3-Cl-5-OCHF$_2$ | CF$_3$ | C(O)CH$_2$SCH$_3$ | C(O)OCH$_3$ |
| 3-Cl-5-OCHF$_2$ | CF$_3$ | C(O)OCH$_3$ | C(O)OEt |
| 3-Cl-5-OCHF$_2$ | CF$_3$ | H | C(O)OPr-i |
| 3-Cl-5-OCHF$_2$ | CF$_3$ | C(O)OCH$_3$ | C(O)OPr-i |
| 3-Cl-5-OCHF$_2$ | CF$_3$ | H | C(O)NH$_2$ |
| 3-Cl-5-OCHF$_2$ | CF$_3$ | CH$_3$ | (D-52d)Cl |
| 3-Cl-5-OCHF$_2$ | CF$_3$ | CH$_2$OCH$_3$ | (D-52d)Cl |
| 3-Cl-5-OCHF$_2$ | CF$_3$ | C(O)OCH$_3$ | (D-52d)Cl |
| 3-Cl-5-OCHF$_2$ | CF$_3$ | CH$_3$ | (D-52d)Cl |
| 3-Cl-5-OCHF$_2$ | CF$_3$ | CH$_2$OCH$_3$ | (D-52d)Cl |
| 3-Cl-5-OCHF$_2$ | CF$_3$ | CH$_2$OC(O)CH$_3$ | (D-52d)Cl |
| 3-Cl-5-OCHF$_2$ | CF$_3$ | CH$_2$OC(O)Bu-t | (D-52d)Cl |
| 3-Cl-5-OCHF$_2$ | CF$_3$ | CH$_2$OC(O)OCH$_3$ | (D-52d)Cl |
| 3-Cl-5-OCHF$_2$ | CF$_3$ | CH$_2$CN | (D-52d)Cl |
| 3-Cl-5-OCHF$_2$ | CF$_3$ | C(O)CH$_3$ | (D-52d)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Cl-5-OCHF$_2$ | CF$_3$ | C(O)Et | (D-52d)Cl |
| 3-Cl-5-OCHF$_2$ | CF$_3$ | C(O)Pr-n | (D-52d)Cl |
| 3-Cl-5-OCHF$_2$ | CF$_3$ | C(O)Pr-i | (D-52d)Cl |
| 3-Cl-5-OCHF$_2$ | CF$_3$ | C(O)Pr-c | (D-52d)Cl |
| 3-Cl-5-OCHF$_2$ | CF$_3$ | C(O)Bu-t | (D-52d)Cl |
| 3-Cl-5-OCHF$_2$ | CF$_3$ | C(O)CH$_2$Cl | (D-52d)Cl |
| 3-Cl-5-OCHF$_2$ | CF$_3$ | C(O)CH$_2$OCH$_3$ | (D-52d)Cl |
| 3-Cl-5-OCHF$_2$ | CF$_3$ | C(O)CH$_2$OEt | (D-52d)Cl |
| 3-Cl-5-OCHF$_2$ | CF$_3$ | C(O)CH$_2$SCH$_3$ | (D-52d)Cl |
| 3-Cl-5-OCHF$_2$ | CF$_3$ | C(O)CH$_2$S(O)CH$_3$ | (D-52d)Cl |
| 3-Cl-5-OCHF$_2$ | CF$_3$ | C(O)C(O)OEt | (D-52d)Cl |
| 3-Cl-5-OCHF$_2$ | CF$_3$ | C(O)OCH$_3$ | (D-52d)Cl |
| 3-Cl-5-OCHF$_2$ | CF$_3$ | C(O)OPr-n | (D-52d)Cl |
| 3-Cl-5-OCHF$_2$ | CF$_3$ | C(O)OCH$_2$Cl | (D-52d)Cl |
| 3-Cl-5-OCHF$_2$ | CF$_3$ | C(O)OCH$_2$CH$_2$Cl | (D-52d)Cl |
| 3-Cl-5-OCHF$_2$ | CF$_3$ | C(O)OCH$_2$CH$_2$OCH$_3$ | (D-52d)Cl |
| 3-Cl-5-OCHF$_2$ | CF$_3$ | C(O)OCH$_2$CH=CH$_2$ | (D-52d)Cl |
| 3-Cl-5-OCHF$_2$ | CF$_3$ | CH$_3$ | (D-55c)Br |
| 3-Cl-5-OCHF$_2$ | CF$_3$ | CH$_2$OC(O)CH$_3$ | (D-55c)Br |
| 3-Cl-5-OCHF$_2$ | CF$_3$ | C(O)CH$_3$ | (D-55c)Br |
| 3-Cl-5-OCHF$_2$ | CF$_3$ | C(O)Et | (D-55c)Br |
| 3-Cl-5-OCHF$_2$ | CF$_3$ | C(O)Pr-n | (D-55c)Br |
| 3-Cl-5-OCHF$_2$ | CF$_3$ | C(O)Pr-i | (D-55c)Br |
| 3-Cl-5-OCHF$_2$ | CF$_3$ | C(O)OCH$_3$ | (D-55c)Br |
| 3-Cl-5-OCHF$_2$ | CF$_3$ | C(O)OEt | (D-55c)Br |
| 3-Cl-5-OCHF$_2$ | CF$_3$ | C(O)OCH$_2$CH$_2$OCH$_3$ | (D-55c)Br |
| 3-Cl-5-OCHF$_2$ | CF$_3$ | C(O)Pr-i | D-57a |
| 3-Cl-5-OCHF$_2$ | CF$_2$Cl | H | CH=NOCH$_3$ |
| 3-Cl-5-OCHF$_2$ | CF$_2$Cl | H | CH=NOEt |
| 3-Cl-5-OCHF$_2$ | CF$_2$Cl | H | C(O)OCH3 |
| 3-Cl-5-OCHF$_2$ | CF$_2$Cl | Et | C(O)OCH3 |
| 3-Cl-5-OCHF$_2$ | CF$_2$Cl | CH$_2$OCH$_3$ | C(O)OCH3 |
| 3-Cl-5-OCHF$_2$ | CF$_2$Cl | CH$_2$OEt | C(O)OCH3 |
| 3-Cl-5-OCHF$_2$ | CF$_2$Cl | CH$_2$OCH$_2$CF$_3$ | C(O)OCH3 |
| 3-Cl-5-OCHF$_2$ | CF$_2$Cl | C(O)Et | C(O)OCH3 |
| 3-Cl-5-OCHF$_2$ | CF$_2$Cl | C(O)OCH$_3$ | C(O)OEt |
| 3-Cl-5-OCHF$_2$ | CF$_2$Cl | H | C(O)NH$_2$ |
| 3-Cl-5-OCHF$_2$ | CF$_2$Cl | CH$_3$ | (D-55c)Cl |
| 3-Cl-5-OCHF$_2$ | CF$_2$Cl | CH$_2$OCH$_3$ | (D-55c)Cl |
| 3-Cl-5-OCHF$_2$ | CF$_2$Cl | C(O)CH$_3$ | (D-55c)Cl |
| 3-Cl-5-OCHF$_2$ | CF$_2$Cl | C(O)Et | (D-55c)Cl |
| 3-Cl-5-OCHF$_2$ | CF$_2$Cl | C(O)Pr-i | (D-55c)Cl |
| 3-Cl-5-OCHF$_2$ | CF$_2$Cl | C(O)CH$_2$OCH$_3$ | (D-55c)Cl |
| 3-Cl-5-OCHF$_2$ | CF$_2$Cl | C(O)OCH$_3$ | (D-55c)Cl |
| 3-Cl-5-OCHF$_2$ | CF$_2$Cl | C(O)CH$_3$ | (D-55c)Br |
| 3-Cl-5-OCHF$_2$ | CF$_2$Cl | C(O)Et | (D-55c)Br |
| 3-Cl-5-OCHF$_2$ | CF$_2$Cl | C(O)Pr-i | (D-55c)Br |
| 3-Cl-5-OCHF$_2$ | CF$_2$Br | CH$_2$OCH$_2$CF$_3$ | C(O)OCH$_3$ |
| 3-Cl-5-OCHF$_2$ | CF$_2$CHF$_2$ | C(O)Et | C(O)OCH$_3$ |
| 3-Br-4-OCHF$_2$ | CF$_3$ | C(O)CH$_3$ | (D-55c)Cl |
| 3-Br-5-OCHF$_2$ | CF$_3$ | H | CH=NOCH$_3$ |
| 3-Br-5-OCHF$_2$ | CF$_3$ | CH$_2$OCH$_3$ | CH=NOCH$_3$ |
| 3-Br-5-OCHF$_2$ | CF$_3$ | H | CH=NOEt |
| 3-Br-5-OCHF$_2$ | CF$_3$ | H | C(O)OCH$_3$ |
| 3-Br-5-OCHF$_2$ | CF$_3$ | Et | C(O)OCH$_3$ |
| 3-Br-5-OCHF$_2$ | CF$_3$ | CH$_2$OCH$_3$ | C(O)OCH$_3$ |
| 3-Br-5-OCHF$_2$ | CF$_3$ | CH$_2$OEt | C(O)OCH$_3$ |
| 3-Br-5-OCHF$_2$ | CF$_3$ | CH$_2$OCH$_2$CF$_3$ | C(O)OCH$_3$ |
| 3-Br-5-OCHF$_2$ | CF$_3$ | CH$_2$OC(O)CH$_3$ | C(O)OCH$_3$ |
| 3-Br-5-OCHF$_2$ | CF$_3$ | CH$_2$OC(O)Et | C(O)OCH$_3$ |
| 3-Br-5-OCHF$_2$ | CF$_3$ | CH$_2$OC(O)OCH$_3$ | C(O)OCH$_3$ |
| 3-Br-5-OCHF$_2$ | CF$_3$ | E-5a | C(O)OCH$_3$ |
| 3-Br-5-OCHF$_2$ | CF$_3$ | C(O)Et | C(O)OCH$_3$ |
| 3-Br-5-OCHF$_2$ | CF$_3$ | C(O)Pr-n | C(O)OCH$_3$ |
| 3-Br-5-OCHF$_2$ | CF$_3$ | C(O)Bu-t | C(O)OCH$_3$ |
| 3-Br-5-OCHF$_2$ | CF$_3$ | C(O)CH$_2$SCH$_3$ | C(O)OCH$_3$ |
| 3-Br-5-OCHF$_2$ | CF$_3$ | C(O)OCH$_3$ | C(O)OEt |
| 3-Br-5-OCHF$_2$ | CF$_3$ | H | C(O)OPr-i |
| 3-Br-5-OCHF$_2$ | CF$_3$ | H | C(O)NH2 |
| 3-Br-5-OCHF$_2$ | CF$_3$ | C(O)OCH$_3$ | (D-52d)Cl |
| 3-Br-5-OCHF$_2$ | CF$_3$ | CH$_3$ | (D-52d)Cl |
| 3-Br-5-OCHF$_2$ | CF$_3$ | CH$_2$OCH$_3$ | (D-52d)Cl |
| 3-Br-5-OCHF$_2$ | CF$_3$ | C(O)CH$_3$ | (D-52d)Cl |
| 3-Br-5-OCHF$_2$ | CF$_3$ | C(O)Et | (D-52d)Cl |
| 3-Br-5-OCHF$_2$ | CF$_3$ | C(O)Pr-i | (D-52d)Cl |
| 3-Br-5-OCHF$_2$ | CF$_3$ | C(O)CH$_2$OCH$_3$ | (D-52d)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Br-5-OCHF$_2$ | CF$_3$ | C(O)CH$_2$OEt | (D-52d)Cl |
| 3-Br-5-OCHF$_2$ | CF$_3$ | C(O)CH$_2$SCH$_3$ | (D-52d)Cl |
| 3-Br-5-OCHF$_2$ | CF$_3$ | C(O)OCH$_3$ | (D-52d)Cl |
| 3-Br-5-OCHF$_2$ | CF$_3$ | C(O)OPr-n | (D-52d)Cl |
| 3-Br-5-OCHF$_2$ | CF$_3$ | C(O)OCH$_2$CH2Cl | (D-52d)Cl |
| 3-Br-5-OCHF$_2$ | CF$_3$ | C(O)OCH$_2$CH$_2$OCH$_3$ | (D-52d)Cl |
| 3-Br-5-OCHF$_2$ | CF$_3$ | C(O)OCH$_2$CH=CH$_2$ | (D-52d)Cl |
| 3-Br-5-OCHF$_2$ | CF$_3$ | CH$_2$OC(O)CH$_3$ | (D-55c)Br |
| 3-Br-5-OCHF$_2$ | CF$_3$ | C(O)CH$_3$ | (D-55c)Br |
| 3-Br-5-OCHF$_2$ | CF$_3$ | C(O)Et | (D-55c)Br |
| 3-Br-5-OCHF$_2$ | CF$_3$ | C(O)Pr-n | (D-55c)Br |
| 3-Br-5-OCHF$_2$ | CF$_3$ | C(O)Pr-i | (D-55c)Br |
| 3-Br-5-OCHF$_2$ | CF$_3$ | C(O)OCH$_3$ | (D-55c)Br |
| 3-Br-5-OCHF$_2$ | CF$_3$ | C(O)OEt | (D-55c)Br |
| 3-Br-5-OCHF$_2$ | CF$_2$Cl | H | CH=NOCH$_3$ |
| 3-Br-5-OCHF$_2$ | CF$_2$Cl | H | CH=NOEt |
| 3-Br-5-OCHF$_2$ | CF$_2$Cl | CH$_2$OEt | C(O)OCH$_3$ |
| 3-Br-5-OCHF$_2$ | CF$_2$Cl | CH$_2$OCH$_2$CF$_3$ | C(O)OCH$_3$ |
| 3-Br-5-OCHF$_2$ | CF$_2$Cl | C(O)Et | C(O)OCH$_3$ |
| 3-Br-5-OCHF$_2$ | CF$_2$Cl | C(O)CH$_3$ | (D-55c)Cl |
| 3-Br-5-OCHF$_2$ | CF$_2$Cl | C(O)Pr-i | (D-55c)Cl |
| 3-Br-5-OCHF$_2$ | CF$_2$Cl | C(O)OCH$_3$ | (D-55c)Cl |
| 3-Br-5-OCHF$_2$ | CF$_2$Cl | C(O)CH$_3$ | (D-55c)Br |
| 3-CH$_3$-5-OCHF$_2$ | CF$_3$ | C(O)Pr-i | (D-55c)Cl |
| 3-CF$_3$-5-OCHF$_2$ | CF$_3$ | H | CH=NOCH$_3$ |
| 3-CF$_3$-5-OCHF$_2$ | CF$_3$ | CH$_2$OCH$_3$ | CH=NOCH$_3$ |
| 3-CF$_3$-5-OCHF$_2$ | CF$_3$ | H | CH=NOEt |
| 3-CF$_3$-5-OCHF$_2$ | CF$_3$ | H | C(O)OCH$_3$ |
| 3-CF$_3$-5-OCHF$_2$ | CF$_3$ | Et | C(O)OCH$_3$ |
| 3-CF$_3$-5-OCHF$_2$ | CF$_3$ | CH$_2$OCH$_3$ | C(O)OCH$_3$ |
| 3-CF$_3$-5-OCHF$_2$ | CF$_3$ | CH$_2$OEt | C(O)OCH$_3$ |
| 3-CF$_3$-5-OCHF$_2$ | CF$_3$ | CH$_2$OCH$_2$CF$_3$ | C(O)OCH$_3$ |
| 3-CF$_3$-5-OCHF$_2$ | CF$_3$ | CH$_2$OC(O)CH$_3$ | C(O)OCH$_3$ |
| 3-CF$_3$-5-OCHF$_2$ | CF$_3$ | CH$_2$OC(O)Et | C(O)OCH$_3$ |
| 3-CF$_3$-5-OCHF$_2$ | CF$_3$ | CH$_2$OC(O)OCH$_3$ | C(O)OCH$_3$ |
| 3-CF$_3$-5-OCHF$_2$ | CF$_3$ | E-5a | C(O)OCH$_3$ |
| 3-CF$_3$-5-OCHF$_2$ | CF$_3$ | C(O)Et | C(O)OCH$_3$ |
| 3-CF$_3$-5-OCHF$_2$ | CF$_3$ | C(O)Pr-n | C(O)OCH$_3$ |
| 3-CF$_3$-5-OCHF$_2$ | CF$_3$ | C(O)Bu-t | C(O)OCH$_3$ |
| 3-CF$_3$-5-OCHF$_2$ | CF$_3$ | C(O)CH$_2$SCH$_3$ | C(O)OCH$_3$ |
| 3-CF$_3$-5-OCHF$_2$ | CF$_3$ | C(O)OCH$_3$ | C(O)OEt |
| 3-CF$_3$-5-OCHF$_2$ | CF$_3$ | H | C(O)OPr-i |
| 3-CF$_3$-5-OCHF$_2$ | CF$_3$ | H | C(O)NH$_2$ |
| 3-CF$_3$-5-OCHF$_2$ | CF$_3$ | C(O)OCH$_3$ | (D-52d)Cl |
| 3-CF$_3$-5-OCHF$_2$ | CF$_3$ | CH$_3$ | (D-55c)Cl |
| 3-CF$_3$-5-OCHF$_2$ | CF$_3$ | CH$_2$OCH$_3$ | (D-55c)Cl |
| 3-CF$_3$-5-OCHF$_2$ | CF$_3$ | C(O)CH$_3$ | (D-55c)Cl |
| 3-CF$_3$-5-OCHF$_2$ | CF$_3$ | C(O)Et | (D-55c)Cl |
| 3-CF$_3$-5-OCHF$_2$ | CF$_3$ | C(O)Pr-i | (D-55c)Cl |
| 3-CF$_3$-5-OCHF$_2$ | CF$_3$ | C(O)CH$_2$OCH$_3$ | (D-55c)Cl |
| 3-CF$_3$-5-OCHF$_2$ | CF$_3$ | C(O)CH$_2$OEt | (D-55c)Cl |
| 3-CF$_3$-5-OCHF$_2$ | CF$_3$ | C(O)CH$_2$SCH$_3$ | (D-55c)Cl |
| 3-CF$_3$-5-OCHF$_2$ | CF$_3$ | C(O)OCH$_3$ | (D-55c)Cl |
| 3-CF$_3$-5-OCHF$_2$ | CF$_3$ | C(O)OPr-n | (D-55c)Cl |
| 3-CF$_3$-5-OCHF$_2$ | CF$_3$ | C(O)OCH$_2$CH$_2$Cl | (D-55c)Cl |
| 3-CF$_3$-5-OCHF$_2$ | CF$_3$ | C(O)OCH$_2$CH$_2$OCH$_3$ | (D-55c)Cl |
| 3-CF$_3$-5-OCHF$_2$ | CF$_3$ | C(O)OCH$_2$CH=CH$_2$ | (D-55c)Cl |
| 3-CF$_3$-5-OCHF$_2$ | CF$_3$ | CH$_2$OC(O)CH$_3$ | (D-55c)Br |
| 3-CF$_3$-5-OCHF$_2$ | CF$_3$ | C(O)CH3 | (D-55c)Br |
| 3-CF$_3$-5-OCHF$_2$ | CF$_3$ | C(O)Et | (D-55c)Br |
| 3-CF$_3$-5-OCHF$_2$ | CF$_3$ | C(O)Pr-n | (D-55c)Br |
| 3-CF$_3$-5-OCHF$_2$ | CF$_3$ | C(O)Pr-i | (D-55c)Br |
| 3-CF$_3$-5-OCHF$_2$ | CF$_3$ | C(O)OCH$_3$ | (D-55c)Br |
| 3-CF$_3$-5-OCHF$_2$ | CF$_3$ | C(O)OEt | (D-55c)Br |
| 3-CF$_3$-5-OCHF$_2$ | CF$_2$Cl | H | CH=NOCH$_3$ |
| 3-CF$_3$-5-OCHF$_2$ | CF$_2$Cl | H | CH=NOEt |
| 3-CF$_3$-5-OCHF$_2$ | CF$_2$Cl | CH$_2$OEt | C(O)OCH$_3$ |
| 3-CF$_3$-5-OCHF$_2$ | CF$_2$Cl | CH$_2$OCH$_2$CF$_3$ | C(O)OCH$_3$ |
| 3-CF$_3$-5-OCHF$_2$ | CF$_2$Cl | C(O)Et | C(O)OCH$_3$ |
| 3-CF$_3$-5-OCHF$_2$ | CF$_2$Cl | C(O)CH$_3$ | (D-55c)Cl |
| 3-CF$_3$-5-OCHF$_2$ | CF$_2$Cl | C(O)Pr-i | (D-55c)Cl |
| 3-CF$_3$-5-OCHF$_2$ | CF$_2$Cl | C(O)OCH$_3$ | (D-55c)Cl |
| 3-CF$_3$-5-OCHF$_2$ | CF$_2$Cl | C(O)CH$_3$ | (D-55c)Br |
| 3,5-(OCHF$_2$)$_2$ | CF$_3$ | C(O)OCH$_3$ | (D-55c)Cl |
| 3-F-4-OCF$_3$ | CF$_3$ | C(O)CH$_3$ | (D-55c)Br |
| 3-Cl-4-OCF$_3$ | CF$_3$ | H | CH=NOCH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Cl-5-OCF$_3$ | CHF$_2$ | H | CH=NOEt |
| 3-Cl-5-OCF$_3$ | CF$_3$ | H | CH=NOCH$_3$ |
| 3-Cl-5-OCF$_3$ | CF$_3$ | CH$_2$OCH$_3$ | CH=NOCH$_3$ |
| 3-Cl-5-OCF$_3$ | CF$_3$ | H | CH=NOEt |
| 3-Cl-5-OCF$_3$ | CF$_3$ | H | C(O)OCH$_3$ |
| 3-Cl-5-OCF$_3$ | CF$_3$ | Et | C(O)OCH$_3$ |
| 3-Cl-5-OCF$_3$ | CF$_3$ | CH$_2$OCH$_3$ | C(O)OCH$_3$ |
| 3-Cl-5-OCF$_3$ | CF$_3$ | CH$_2$OEt | C(O)OCH$_3$ |
| 3-Cl-5-OCF$_3$ | CF$_3$ | CH$_2$OCH$_2$CF$_3$ | C(O)OCH$_3$ |
| 3-Cl-5-OCF$_3$ | CF$_3$ | CH$_2$OC(O)CH$_3$ | C(O)OCH$_3$ |
| 3-Cl-5-OCF$_3$ | CF$_3$ | CH$_2$OC(O)Et | C(O)OCH$_3$ |
| 3-Cl-5-OCF$_3$ | CF$_3$ | CH$_2$OC(O)OCH$_3$ | C(O)OCH$_3$ |
| 3-Cl-5-OCF$_3$ | CF$_3$ | E-5a | C(O)OCH$_3$ |
| 3-Cl-5-OCF$_3$ | CF$_3$ | C(O)CH$_3$ | C(O)OCH$_3$ |
| 3-Cl-5-OCF$_3$ | CF$_3$ | C(O)Et | C(O)OCH$_3$ |
| 3-Cl-5-OCF$_3$ | CF$_3$ | C(O)Pr-n | C(O)OCH$_3$ |
| 3-Cl-5-OCF$_3$ | CF$_3$ | C(O)Pr-i | C(O)OCH$_3$ |
| 3-Cl-5-OCF$_3$ | CF$_3$ | C(O)Bu-t | C(O)OCH$_3$ |
| 3-Cl-5-OCF$_3$ | CF$_3$ | C(O)CH$_2$OCH$_3$ | C(O)OCH$_3$ |
| 3-Cl-5-OCF$_3$ | CF$_3$ | C(O)CH$_2$SCH$_3$ | C(O)OCH$_3$ |
| 3-Cl-5-OCF$_3$ | CF$_3$ | C(O)OCH$_3$ | C(O)OEt |
| 3-Cl-5-OCF$_3$ | CF$_3$ | H | C(O)OPr-i |
| 3-Cl-5-OCF$_3$ | CF$_3$ | C(O)OCH$_3$ | C(O)OPr-i |
| 3-Cl-5-OCF$_3$ | CF$_3$ | H | C(O)NH$_2$ |
| 3-Cl-5-OCF$_3$ | CF$_3$ | CH$_3$ | (D-52d)Cl |
| 3-Cl-5-OCF$_3$ | CF$_3$ | CH$_2$OCH$_3$ | (D-52d)Cl |
| 3-Cl-5-OCF$_3$ | CF$_3$ | C(O)OCH$_3$ | (D-52d)Cl |
| 3-Cl-5-OCF$_3$ | CF$_3$ | CH$_3$ | (D-55c)Cl |
| 3-Cl-5-OCF$_3$ | CF$_3$ | CH$_2$OCH$_3$ | (D-55c)Cl |
| 3-Cl-5-OCF$_3$ | CF$_3$ | CH$_2$OC(O)CH$_3$ | (D-55c)Cl |
| 3-Cl-5-OCF$_3$ | CF$_3$ | CH$_2$OC(O)Bu-t | (D-55c)Cl |
| 3-Cl-5-OCF$_3$ | CF$_3$ | CH$_2$OC(O)OCH$_3$ | (D-55c)Cl |
| 3-Cl-5-OCF$_3$ | CF$_3$ | CH$_2$CN | (D-55c)Cl |
| 3-Cl-5-OCF$_3$ | CF$_3$ | C(O)CH$_3$ | (D-55c)Cl |
| 3-Cl-5-OCF$_3$ | CF$_3$ | C(O)Et | (D-55c)Cl |
| 3-Cl-5-OCF$_3$ | CF$_3$ | C(O)Pr-n | (D-55c)Cl |
| 3-Cl-5-OCF$_3$ | CF$_3$ | C(O)Pr-i | (D-55c)Cl |
| 3-Cl-5-OCF$_3$ | CF$_3$ | C(O)Pr-c | (D-55c)Cl |
| 3-Cl-5-OCF$_3$ | CF$_3$ | C(O)Bu-t | (D-55c)Cl |
| 3-Cl-5-OCF$_3$ | CF$_3$ | C(O)CH$_2$Cl | (D-55c)Cl |
| 3-Cl-5-OCF$_3$ | CF$_3$ | C(O)CH$_2$OCH$_3$ | (D-55c)Cl |
| 3-Cl-5-OCF$_3$ | CF$_3$ | C(O)CH$_2$OEt | (D-55c)Cl |
| 3-Cl-5-OCF$_3$ | CF$_3$ | C(O)CH$_2$SCH$_3$ | (D-55c)Cl |
| 3-Cl-5-OCF$_3$ | CF$_3$ | C(O)CH$_2$S(O)CH$_3$ | (D-55c)Cl |
| 3-Cl-5-OCF$_3$ | CF$_3$ | C(O)C(O)OEt | (D-55c)Cl |
| 3-Cl-5-OCF$_3$ | CF$_3$ | C(O)OCH$_3$ | (D-55c)Cl |
| 3-Cl-5-OCF$_3$ | CF$_3$ | C(O)OPr-n | (D-55c)Cl |
| 3-Cl-5-OCF$_3$ | CF$_3$ | C(O)OCH$_2$Cl | (D-55c)Cl |
| 3-Cl-5-OCF$_3$ | CF$_3$ | C(O)OCH$_2$CH$_2$Cl | (D-55c)Cl |
| 3-Cl-5-OCF$_3$ | CF$_3$ | C(O)OCH$_2$CH$_2$OCH$_3$ | (D-55c)Cl |
| 3-Cl-5-OCF$_3$ | CF$_3$ | C(O)OCH$_2$CH=CH$_2$ | (D-55c)Cl |
| 3-Cl-5-OCF$_3$ | CF$_3$ | CH$_3$ | (D-55c)Cl |
| 3-Cl-5-OCF$_3$ | CF$_3$ | CH$_2$OC(O)CH$_3$ | (D-55c)Br |
| 3-Cl-5-OCF$_3$ | CF$_3$ | C(O)CH3 | (D-55c)Br |
| 3-Cl-5-OCF$_3$ | CF$_3$ | C(O)Et | (D-55c)Br |
| 3-Cl-5-OCF$_3$ | CF$_3$ | C(O)Pr-n | (D-55c)Br |
| 3-Cl-5-OCF$_3$ | CF$_3$ | C(O)Pr-i | (D-55c)Br |
| 3-Cl-5-OCF$_3$ | CF$_3$ | C(O)OCH$_3$ | (D-55c)Br |
| 3-Cl-5-OCF$_3$ | CF$_3$ | C(O)OEt | (D-55c)Br |
| 3-Cl-5-OCF$_3$ | CF$_3$ | C(O)OCH$_2$CH$_2$OCH$_3$ | (D-55c)Br |
| 3-Cl-5-OCF$_3$ | CF$_3$ | C(O)Pr-i | D-57a |
| 3-Cl-5-OCF$_3$ | CF$_2$Cl | H | CH=NOCH$_3$ |
| 3-Cl-5-OCF$_3$ | CF$_2$Cl | H | CH=NOEt |
| 3-Cl-5-OCF$_3$ | CF$_2$Cl | H | C(O)OCH$_3$ |
| 3-Cl-5-OCF$_3$ | CF$_2$Cl | Et | C(O)OCH$_3$ |
| 3-Cl-5-OCF$_3$ | CF$_2$Cl | CH$_2$OCH$_3$ | C(O)OCH$_3$ |
| 3-Cl-5-OCF$_3$ | CF$_2$Cl | CH$_2$OEt | C(O)OCH$_3$ |
| 3-Cl-5-OCF$_3$ | CF$_2$Cl | CH$_2$OCH$_2$CF$_3$ | C(O)OCH$_3$ |
| 3-Cl-5-OCF$_3$ | CF$_2$Cl | C(O)Et | C(O)OCH$_3$ |
| 3-Cl-5-OCF$_3$ | CF$_2$Cl | C(O)OCH$_3$ | C(O)OEt |
| 3-Cl-5-OCF$_3$ | CF$_2$Cl | H | C(O)NH$_2$ |
| 3-Cl-5-OCF$_3$ | CF$_2$Cl | CH$_3$ | (D-55c)Cl |
| 3-Cl-5-OCF$_3$ | CF$_2$Cl | CH$_2$OCH$_3$ | (D-55c)Cl |
| 3-Cl-5-OCF$_3$ | CF$_2$Cl | C(O)CH$_3$ | (D-55c)Cl |
| 3-Cl-5-OCF$_3$ | CF$_2$Cl | C(O)Et | (D-55c)Cl |
| 3-Cl-5-OCF$_3$ | CF$_2$Cl | C(O)Pr-i | (D-55c)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Cl-5-OCF$_3$ | CF$_2$Cl | C(O)CH$_2$OCH$_3$ | (D-55c)Cl |
| 3-Cl-5-OCF$_3$ | CF$_2$Cl | C(O)OCH$_3$ | (D-55c)Cl |
| 3-Cl-5-OCF$_3$ | CF$_2$Cl | C(O)CH$_3$ | (D-55c)Br |
| 3-Cl-5-OCF$_3$ | CF$_2$Cl | C(O)Et | (D-55c)Br |
| 3-Cl-5-OCF$_3$ | CF$_2$Cl | C(O)Pr-i | (D-55c)Br |
| 3-Cl-5-OCF$_3$ | CF$_2$Cl | CH$_2$OEt | C(O)OCH$_3$ |
| 3-Cl-5-OCF$_3$ | CF$_2$CHF$_2$ | CH$_2$OCH$_2$CF$_3$ | C(O)OCH$_3$ |
| 3-Br-4-OCF$_3$ | CF$_3$ | C(O)Et | C(O)OCH$_3$ |
| 3-Br-5-OCF$_3$ | CF$_3$ | H | CH=NOCH$_3$ |
| 3-Br-5-OCF$_3$ | CF$_3$ | CH$_2$OCH$_3$ | CH=NOCH$_3$ |
| 3-Br-5-OCF$_3$ | CF$_3$ | H | CH=NOEt |
| 3-Br-5-OCF$_3$ | CF$_3$ | H | C(O)OCH$_3$ |
| 3-Br-5-OCF$_3$ | CF$_3$ | Et | C(O)OCH$_3$ |
| 3-Br-5-OCF$_3$ | CF$_3$ | CH$_2$OCH$_3$ | C(O)OCH$_3$ |
| 3-Br-5-OCF$_3$ | CF$_3$ | CH$_2$OEt | C(O)OCH$_3$ |
| 3-Br-5-OCF$_3$ | CF$_3$ | CH$_2$OCH$_2$CF$_3$ | C(O)OCH$_3$ |
| 3-Br-5-OCF$_3$ | CF$_3$ | CH$_2$OC(O)CH$_3$ | C(O)OCH$_3$ |
| 3-Br-5-OCF$_3$ | CF$_3$ | CH$_2$OC(O)Et | C(O)OCH$_3$ |
| 3-Br-5-OCF$_3$ | CF$_3$ | CH$_2$OC(O)OCH$_3$ | C(O)OCH$_3$ |
| 3-Br-5-OCF$_3$ | CF$_3$ | E-5a | C(O)OCH$_3$ |
| 3-Br-5-OCF$_3$ | CF$_3$ | C(O)Et | C(O)OCH$_3$ |
| 3-Br-5-OCF$_3$ | CF$_3$ | C(O)Pr-n | C(O)OCH$_3$ |
| 3-Br-5-OCF$_3$ | CF$_3$ | C(O)Bu-t | C(O)OCH$_3$ |
| 3-Br-5-OCF$_3$ | CF$_3$ | C(O)CH$_2$SCH$_3$ | C(O)OCH$_3$ |
| 3-Br-5-OCF$_3$ | CF$_3$ | C(O)OCH$_3$ | C(O)OCH$_3$ |
| 3-Br-5-OCF$_3$ | CF$_3$ | H | C(O)OPr-i |
| 3-Br-5-OCF$_3$ | CF$_3$ | H | C(O)NH$_2$ |
| 3-Br-5-OCF$_3$ | CF$_3$ | C(O)OCH$_3$ | (D-52d)Cl |
| 3-Br-5-OCF$_3$ | CF$_3$ | CH$_3$ | (D-55c)Cl |
| 3-Br-5-OCF$_3$ | CF$_3$ | CH$_2$OCH$_3$ | (D-55c)Cl |
| 3-Br-5-OCF$_3$ | CF$_3$ | C(O)CH$_3$ | (D-55c)Cl |
| 3-Br-5-OCF$_3$ | CF$_3$ | C(O)Et | (D-55c)Cl |
| 3-Br-5-OCF$_3$ | CF$_3$ | C(O)Pr-i | (D-55c)Cl |
| 3-Br-5-OCF$_3$ | CF$_3$ | C(O)CH$_2$OCH$_3$ | (D-55c)Cl |
| 3-Br-5-OCF$_3$ | CF$_3$ | C(O)CH$_2$OEt | (D-55c)Cl |
| 3-Br-5-OCF$_3$ | CF$_3$ | C(O)CH$_2$SCH$_3$ | (D-55c)Cl |
| 3-Br-5-OCF$_3$ | CF$_3$ | C(O)OCH$_3$ | (D-55c)Cl |
| 3-Br-5-OCF$_3$ | CF$_3$ | C(O)OPr-n | (D-55c)Cl |
| 3-Br-5-OCF$_3$ | CF$_3$ | C(O)OCH$_2$CH$_2$Cl | (D-55c)Cl |
| 3-Br-5-OCF$_3$ | CF$_3$ | C(O)OCH$_2$CH$_2$OCH$_3$ | (D-55c)Cl |
| 3-Br-5-OCF$_3$ | CF$_3$ | C(O)OCH$_2$CH=CH$_2$ | (D-55c)Cl |
| 3-Br-5-OCF$_3$ | CF$_3$ | CH$_2$OC(O)CH$_3$ | (D-55c)Br |
| 3-Br-5-OCF$_3$ | CF$_3$ | C(O)CH$_3$ | (D-55c)Br |
| 3-Br-5-OCF$_3$ | CF$_3$ | C(O)Et | (D-55c)Br |
| 3-Br-5-OCF$_3$ | CF$_3$ | C(O)Pr-n | (D-55c)Br |
| 3-Br-5-OCF$_3$ | CF$_3$ | C(O)Pr-i | (D-55c)Br |
| 3-Br-5-OCF$_3$ | CF$_3$ | C(O)OCH3 | (D-55c)Br |
| 3-Br-5-OCF$_3$ | CF$_3$ | C(O)OEt | (D-55c)Br |
| 3-Br-5-OCF$_3$ | CF$_2$Cl | H | CH=NOCH$_3$ |
| 3-Br-5-OCF$_3$ | CF$_2$Cl | H | CH=NOEt |
| 3-Br-5-OCF$_3$ | CF$_2$Cl | CH$_2$OEt | C(O)OCH$_3$ |
| 3-Br-5-OCF$_3$ | CF$_2$Cl | CH$_2$OCH$_2$CF$_3$ | C(O)OCH$_3$ |
| 3-CF$_3$-5-OCF$_3$ | CF$_3$ | C(O)Et | C(O)OCH$_3$ |
| 3-Br-5-OCF$_3$ | CF$_2$Cl | C(O)CH$_3$ | (D-55c)Cl |
| 3-Br-5-OCF$_3$ | CF$_2$Cl | C(O)Pr-i | (D-55c)Cl |
| 3-Br-5-OCF$_3$ | CF$_2$Cl | C(O)OCH$_3$ | (D-55c)Cl |
| 3-Br-5-OCF$_3$ | CF$_2$Cl | C(O)CH$_3$ | (D-55c)Br |
| 3-CH$_3$-5-OCF$_3$ | CF$_3$ | C(O)CH$_3$ | (D-55c)Cl |
| 3-CF$_3$-5-OCF$_3$ | CF$_3$ | H | CH=NOCH$_3$ |
| 3-CF$_3$-5-OCF$_3$ | CF$_3$ | CH$_2$OCH$_3$ | CH=NOCH$_3$ |
| 3-CF$_3$-5-OCF$_3$ | CF$_3$ | H | CH=NOEt |
| 3-CF$_3$-5-OCF$_3$ | CF$_3$ | H | C(O)OCH$_3$ |
| 3-CF$_3$-5-OCF$_3$ | CF$_3$ | Et | C(O)OCH$_3$ |
| 3-CF$_3$-5-OCF$_3$ | CF$_3$ | CH$_2$OCH$_3$ | C(O)OCH$_3$ |
| 3-CF$_3$-5-OCF$_3$ | CF$_3$ | CH$_2$OEt | C(O)OCH$_3$ |
| 3-CF$_3$-5-OCF$_3$ | CF$_3$ | CH$_2$OCH$_2$CF$_3$ | C(O)OCH$_3$ |
| 3-CF$_3$-5-OCF$_3$ | CF$_3$ | CH$_2$OC(O)CH$_3$ | C(O)OCH$_3$ |
| 3-CF$_3$-5-OCF$_3$ | CF$_3$ | CH$_2$OC(O)Et | C(O)OCH$_3$ |
| 3-CF$_3$-5-OCF$_3$ | CF$_3$ | CH$_2$OC(O)OCH$_3$ | C(O)OCH$_3$ |
| 3-CF$_3$-5-OCF$_3$ | CF$_3$ | E-5a | C(O)OCH$_3$ |
| 3-CF$_3$-5-OCF$_3$ | CF$_3$ | C(O)Et | C(O)OCH$_3$ |
| 3-CF$_3$-5-OCF$_3$ | CF$_3$ | C(O)Pr-n | C(O)OCH$_3$ |
| 3-CF$_3$-5-OCF$_3$ | CF$_3$ | C(O)Bu-t | C(O)OCH$_3$ |
| 3-CF$_3$-5-OCF$_3$ | CF$_3$ | C(O)CH$_2$SCH$_3$ | C(O)OCH$_3$ |
| 3-CF$_3$-5-OCF$_3$ | CF$_3$ | C(O)OCH$_3$ | C(O)OEt |
| 3-CF$_3$-5-OCF$_3$ | CF$_3$ | H | C(O)OPr-i |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-CF$_3$-5-OCF$_3$ | CF$_3$ | H | C(O)NH$_2$ |
| 3-CF$_3$-5-OCF$_3$ | CF$_3$ | C(O)OCH$_3$ | (D-52d)Cl |
| 3-CF$_3$-5-OCF$_3$ | CF$_3$ | CH$_3$ | (D-55c)Cl |
| 3-CF$_3$-5-OCF$_3$ | CF$_3$ | CH$_2$OCH$_3$ | (D-55c)Cl |
| 3-CF$_3$-5-OCF$_3$ | CF$_3$ | C(O)CH$_3$ | (D-55c)Cl |
| 3-CF$_3$-5-OCF$_3$ | CF$_3$ | C(O)Et | (D-55c)Cl |
| 3-CF$_3$-5-OCF$_3$ | CF$_3$ | C(O)Pr-i | (D-55c)Cl |
| 3-CF$_3$-5-OCF$_3$ | CF$_3$ | C(O)CH$_2$OCH$_3$ | (D-55c)Cl |
| 3-CF$_3$-5-OCF$_3$ | CF$_3$ | C(O)CH$_2$OEt | (D-55c)Cl |
| 3-CF$_3$-5-OCF$_3$ | CF$_3$ | C(O)CH$_2$SCH$_3$ | (D-55c)Cl |
| 3-CF$_3$-5-OCF$_3$ | CF$_3$ | C(O)OCH$_3$ | (D-55c)Cl |
| 3-CF$_3$-5-OCF$_3$ | CF$_3$ | C(O)OPr-n | (D-55c)Cl |
| 3-CF$_3$-5-OCF$_3$ | CF$_3$ | C(O)OCH$_2$CH$_2$Cl | (D-55c)Cl |
| 3-CF$_3$-5-OCF$_3$ | CF$_3$ | C(O)OCH$_2$CH$_2$OCH3 | (D-55c)Cl |
| 3-CF$_3$-5-OCF$_3$ | CF$_3$ | C(O)OCH$_2$CH=CH$_2$ | (D-55c)Cl |
| 3-CF$_3$-5-OCF$_3$ | CF$_3$ | CH$_2$OC(O)CH$_3$ | (D-55c)Br |
| 3-CF$_3$-5-OCF$_3$ | CF$_3$ | C(O)CH$_3$ | (D-55c)Br |
| 3-CF$_3$-5-OCF$_3$ | CF$_3$ | C(O)Et | (D-55c)Br |
| 3-CF$_3$-5-OCF$_3$ | CF$_3$ | C(O)Pr-n | (D-55c)Br |
| 3-CF$_3$-5-OCF$_3$ | CF$_3$ | C(O)Pr-i | (D-55c)Br |
| 3-CF$_3$-5-OCF$_3$ | CF$_3$ | C(O)OCH$_3$ | (D-55c)Br |
| 3-CF$_3$-5-OCF$_3$ | CF$_3$ | C(O)OEt | (D-55c)Br |
| 3-CF$_3$-5-OCF$_3$ | CF$_2$Cl | H | CH=NOCH$_3$ |
| 3-CF$_3$-5-OCF$_3$ | CF$_2$Cl | H | CH=NOEt |
| 3-CF$_3$-5-OCF$_3$ | CF$_2$Cl | CH$_2$OEt | C(O)OCH$_3$ |
| 3-CF$_3$-5-OCF$_3$ | CF$_2$Cl | CH$_2$OCH$_2$CF$_3$ | C(O)OCH$_3$ |
| 3-CF$_3$-5-OCF$_3$ | CF$_2$Cl | C(O)Et | C(O)OCH$_3$ |
| 3-CF$_3$-5-OCF$_3$ | CF$_2$Cl | C(O)CH$_3$ | (D-55c)Cl |
| 3-CF$_3$-5-OCF$_3$ | CF$_2$Cl | C(O)Pr-i | (D-55c)Cl |
| 3-CF$_3$-5-OCF$_3$ | CF$_2$Cl | C(O)OCH$_3$ | (D-55c)Cl |
| 3-CF$_3$-5-OCF$_3$ | CF$_2$Cl | C(O)CH$_3$ | (D-55c)Br |
| 3-F-5-OCF$_2$Br | CF$_3$ | C(O)Pr-i | (D-55c)Cl |
| 3-Cl-5-OCF$_2$Br | CF$_3$ | C(O)OCH$_3$ | (D-55c)Cl |
| 3-CH$_3$-5-OCF$_2$Br | CF$_3$ | C(O)CH$_3$ | (D-55c)Br |
| 3-F-5-OCF$_2$CHF$_2$ | CF$_3$ | H | CH=NOCH$_3$ |
| 3-Cl-5-OCF$_2$CHF$_2$ | CF$_3$ | H | CH=NOEt |
| 3-CH$_3$-5-OCF$_2$CHF$_2$ | CF$_3$ | CH$_2$OEt | C(O)OCH$_3$ |
| 3-F-5-OCF$_2$CHFCl | CF$_3$ | CH$_2$OCH$_2$CF$_3$ | C(O)OCH$_3$ |
| 3-Cl-5-OCF$_2$CHFCl | CF$_3$ | C(O)Et | C(O)OCH$_3$ |
| 3-Br-5-OCF$_2$CHFCl | CF$_3$ | C(O)CH$_3$ | (D-55c)Cl |
| 3-F-5-OCF$_2$CHFCF$_3$ | CF$_3$ | C(O)Pr-i | (D-55c)Cl |
| 3-Cl-5-OCF$_2$CHFCF$_3$ | CF$_3$ | C(O)OCH$_3$ | (D-55c)Cl |
| 3-CH$_3$-5-OCF$_2$CHFCF$_3$ | CF$_3$ | C(O)CH$_3$ | (D-55c)Br |
| 3-F-5-OCF$_2$CHFOCF$_3$ | CF$_3$ | H | CH=NOCH$_3$ |
| 3-Cl-5-OCF$_2$CHFOCF$_3$ | CF$_3$ | H | CH=NOEt |
| 3-CH$_3$-5-OCF$_2$CHFOCF$_3$ | CF$_3$ | CH$_2$OEt | C(O)OCH$_3$ |
| 3-CF$_2$OCF$_2$O-4 | CF$_3$ | CH$_2$OCH$_2$CF$_3$ | C(O)OCH$_3$ |
| 3-OCF$_2$O-4 | CF$_3$ | C(O)Et | C(O)OCH$_3$ |
| 3-OCF$_2$CF$_2$O-4 | CF$_3$ | C(O)CH$_3$ | (D-55c)Cl |
| 3-Cl-5-SCH$_3$ | CF$_3$ | C(O)Pr-i | (D-55c)Cl |
| 3-Cl-5-S(O)CH$_3$ | CF$_3$ | C(O)OCH$_3$ | (D-55c)Cl |
| 3-Cl-5-SO$_2$CH$_3$ | CF$_3$ | C(O)CH$_3$ | (D-55c)Br |
| 3-Br-5-SCH$_3$ | CF$_3$ | H | CH=NOCH$_3$ |
| 3-Br-5-S(O)CH$_3$ | CF$_3$ | H | CH=NOEt |
| 3-Br-5-SO$_2$CH$_3$ | CF$_3$ | CH$_2$OEt | C(O)OCH$_3$ |
| 3-Cl-5-SCF$_3$ | CHF$_2$ | CH$_2$OCH$_2$CF$_3$ | C(O)OCH$_3$ |
| 3-Cl-5-SCF$_3$ | CF$_3$ | H | CH=NOCH$_3$ |
| 3-Cl-5-SCF$_3$ | CF$_3$ | CH$_2$OCH$_3$ | CH=NOCH$_3$ |
| 3-Cl-5-SCF$_3$ | CF$_3$ | H | CH=NOEt |
| 3-Cl-5-SCF$_3$ | CF$_3$ | H | C(O)OCH$_3$ |
| 3-Cl-5-SCF$_3$ | CF$_3$ | Et | C(O)OCH$_3$ |
| 3-Cl-5-SCF$_3$ | CF$_3$ | CH$_2$OCH$_3$ | C(O)OCH$_3$ |
| 3-Cl-5-SCF$_3$ | CF$_3$ | CH$_2$OEt | C(O)OCH$_3$ |
| 3-Cl-5-SCF$_3$ | CF$_3$ | CH$_2$OCH$_2$CF$_3$ | C(O)OCH$_3$ |
| 3-Cl-5-SCF$_3$ | CF$_3$ | CH$_2$OC(O)CH$_3$ | C(O)OCH$_3$ |
| 3-Cl-5-SCF$_3$ | CF$_3$ | CH$_2$OC(O)Et | C(O)OCH$_3$ |
| 3-Cl-5-SCF$_3$ | CF$_3$ | CH$_2$OC(O)OCH$_3$ | C(O)OCH$_3$ |
| 3-Cl-5-SCF$_3$ | CF$_3$ | E-5a | C(O)OCH$_3$ |
| 3-Cl-5-SCF$_3$ | CF$_3$ | C(O)CH$_3$ | C(O)OCH$_3$ |
| 3-Cl-5-SCF$_3$ | CF$_3$ | C(O)Et | C(O)OCH$_3$ |
| 3-Cl-5-SCF$_3$ | CF$_3$ | C(O)Pr-n | C(O)OCH$_3$ |
| 3-Cl-5-SCF$_3$ | CF$_3$ | C(O)Pr-i | C(O)OCH$_3$ |
| 3-Cl-5-SCF$_3$ | CF$_3$ | C(O)Bu-t | C(O)OCH$_3$ |
| 3-Cl-5-SCF$_3$ | CF$_3$ | C(O)CH$_2$OCH$_3$ | C(O)OCH$_3$ |
| 3-Cl-5-SCF$_3$ | CF$_3$ | C(O)CH$_2$SCH$_3$ | C(O)OCH$_3$ |
| 3-Cl-5-SCF$_3$ | CF$_3$ | C(O)OCH$_3$ | C(O)OEt |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Cl-5-SCF$_3$ | CF$_3$ | H | C(O)OPr-i |
| 3-Cl-5-SCF$_3$ | CF$_3$ | C(O)OCH$_3$ | C(O)OPr-i |
| 3-Cl-5-SCF$_3$ | CF$_3$ | H | C(O)NH$_2$ |
| 3-Cl-5-SCF$_3$ | CF$_3$ | CH$_3$ | (D-52d)Cl |
| 3-Cl-5-SCF$_3$ | CF$_3$ | CH$_2$OCH$_3$ | (D-52d)Cl |
| 3-Cl-5-SCF$_3$ | CF$_3$ | C(O)OCH$_3$ | (D-52d)Cl |
| 3-Cl-5-SCF$_3$ | CF$_3$ | CH$_3$ | (D-55c)Cl |
| 3-Cl-5-SCF$_3$ | CF$_3$ | CH$_2$OCH$_3$ | (D-55c)Cl |
| 3-Cl-5-SCF$_3$ | CF$_3$ | CH$_2$OC(O)CH$_3$ | (D-55c)Cl |
| 3-Cl-5-SCF$_3$ | CF$_3$ | CH$_2$OC(O)Bu-t | (D-55c)Cl |
| 3-Cl-5-SCF$_3$ | CF$_3$ | CH$_2$OC(O)OCH$_3$ | (D-55c)Cl |
| 3-Cl-5-SCF$_3$ | CF$_3$ | CH$_2$CN | (D-55c)Cl |
| 3-Cl-5-SCF$_3$ | CF$_3$ | C(O)CH$_3$ | (D-55c)Cl |
| 3-Cl-5-SCF$_3$ | CF$_3$ | C(O)Et | (D-55c)Cl |
| 3-Cl-5-SCF$_3$ | CF$_3$ | C(O)Pr-n | (D-55c)Cl |
| 3-Cl-5-SCF$_3$ | CF$_3$ | C(O)Pr-i | (D-55c)Cl |
| 3-Cl-5-SCF$_3$ | CF$_3$ | C(O)Pr-c | (D-55c)Cl |
| 3-Cl-5-SCF$_3$ | CF$_3$ | C(O)Bu-t | (D-55c)Cl |
| 3-Cl-5-SCF$_3$ | CF$_3$ | C(O)CH$_2$Cl | (D-55c)Cl |
| 3-Cl-5-SCF$_3$ | CF$_3$ | C(O)CH$_2$OCH$_3$ | (D-55c)Cl |
| 3-Cl-5-SCF$_3$ | CF$_3$ | C(O)CH$_2$OEt | (D-55c)Cl |
| 3-Cl-5-SCF$_3$ | CF$_3$ | C(O)CH$_2$SCH$_3$ | (D-55c)Cl |
| 3-Cl-5-SCF$_3$ | CF$_3$ | C(O)CH$_2$S(O)CH$_3$ | (D-55c)Cl |
| 3-Cl-5-SCF$_3$ | CF$_3$ | C(O)C(O)OEt | (D-55c)Cl |
| 3-Cl-5-SCF$_3$ | CF$_3$ | C(O)OCH$_3$ | (D-55c)Cl |
| 3-Cl-5-SCF$_3$ | CF$_3$ | C(O)OPr-n | (D-55c)Cl |
| 3-Cl-5-SCF$_3$ | CF$_3$ | C(O)OCH$_2$Cl | (D-55c)Cl |
| 3-Cl-5-SCF$_3$ | CF$_3$ | C(O)OCH$_2$CH$_2$Cl | (D-55c)Cl |
| 3-Cl-5-SCF$_3$ | CF$_3$ | C(O)OCH$_2$CH$_2$OCH$_3$ | (D-55c)Cl |
| 3-Cl-5-SCF$_3$ | CF$_3$ | C(O)OCH$_2$CH=CH$_2$ | (D-55c)Cl |
| 3-Cl-5-SCF$_3$ | CF$_3$ | CH$_3$ | (D-55c)Br |
| 3-Cl-5-SCF$_3$ | CF$_3$ | CH$_2$OC(O)CH$_3$ | (D-55c)Br |
| 3-Cl-5-SCF$_3$ | CF$_3$ | C(O)CH$_3$ | (D-55c)Br |
| 3-Cl-5-SCF$_3$ | CF$_3$ | C(O)Et | (D-55c)Br |
| 3-Cl-5-SCF$_3$ | CF$_3$ | C(O)Pr-n | (D-55c)Br |
| 3-Cl-5-SCF$_3$ | CF$_3$ | C(O)Pr-i | (D-55c)Br |
| 3-Cl-5-SCF$_3$ | CF$_3$ | C(O)OCH$_3$ | (D-55c)Br |
| 3-Cl-5-SCF$_3$ | CF$_3$ | C(O)OEt | (D-55c)Br |
| 3-Cl-5-SCF$_3$ | CF$_3$ | C(O)OCH$_2$CH$_2$OCH$_3$ | (D-55c)Br |
| 3-Cl-5-SCF$_3$ | CF$_3$ | C(O)Pr-i | D-57a |
| 3-Cl-5-SCF$_3$ | CF$_2$Cl | H | CH=NOCH$_3$ |
| 3-Cl-5-SCF$_3$ | CF$_2$Cl | H | CH=NOEt |
| 3-Cl-5-SCF$_3$ | CF$_2$Cl | H | C(O)OCH$_3$ |
| 3-Cl-5-SCF$_3$ | CF$_2$Cl | Et | C(O)OCH$_3$ |
| 3-Cl-5-SCF$_3$ | CF$_2$Cl | CH$_2$OCH$_3$ | C(O)OCH$_3$ |
| 3-Cl-5-SCF$_3$ | CF$_2$Cl | CH$_2$OEt | C(O)OCH$_3$ |
| 3-Cl-5-SCF$_3$ | CF$_2$Cl | CH$_2$OCH$_2$CF$_3$ | C(O)OCH$_3$ |
| 3-Cl-5-SCF$_3$ | CF$_2$Cl | C(O)Et | C(O)OCH$_3$ |
| 3-Cl-5-SCF$_3$ | CF$_2$Cl | C(O)OCH$_3$ | C(O)OEt |
| 3-Cl-5-SCF$_3$ | CF$_2$Cl | H | C(O)NH$_2$ |
| 3-Cl-5-SCF$_3$ | CF$_2$Cl | CH$_3$ | (D-55c)Cl |
| 3-Cl-5-SCF$_3$ | CF$_2$Cl | CH$_2$OCH$_3$ | (D-55c)Cl |
| 3-Cl-5-SCF$_3$ | CF$_2$Cl | C(O)CH$_3$ | (D-55c)Cl |
| 3-Cl-5-SCF$_3$ | CF$_2$Cl | C(O)Et | (D-55c)Cl |
| 3-Cl-5-SCF$_3$ | CF$_2$Cl | C(O)Pr-i | (D-55c)Cl |
| 3-Cl-5-SCF$_3$ | CF$_2$Cl | C(O)CH$_2$OCH$_3$ | (D-55c)Cl |
| 3-Cl-5-SCF$_3$ | CF$_2$Cl | C(O)OCH$_3$ | (D-55c)Cl |
| 3-Cl-5-SCF$_3$ | CF$_2$Cl | C(O)CH$_3$ | (D-55c)Br |
| 3-Cl-5-SCF$_3$ | CF$_2$Cl | C(O)Et | (D-55c)Br |
| 3-Cl-5-SCF$_3$ | CF$_2$Cl | C(O)Pr-i | (D-55c)Br |
| 3-Cl-5-SCF$_3$ | CF$_2$Cl | C(O)Et | C(O)OCH$_3$ |
| 3-Cl-5-SCF$_3$ | CF$_2$Cl | C(O)CH$_3$ | (D-55c)Cl |
| 3-Cl-5-S(O)CF$_3$ | CF$_3$ | H | CH=NOCH$_3$ |
| 3-Cl-5-S(O)CF$_3$ | CF$_3$ | H | CH=NOEt |
| 3-Cl-5-S(O)CF$_3$ | CF$_3$ | CH$_2$OEt | C(O)OCH$_3$ |
| 3-Cl-5-S(O)CF$_3$ | CF$_3$ | CH$_2$OCH$_2$CF$_3$ | C(O)OCH$_3$ |
| 3-Cl-5-S(O)CF$_3$ | CF$_3$ | C(O)Et | C(O)OCH$_3$ |
| 3-Cl-5-S(O)CF$_3$ | CF$_3$ | C(O)CH$_3$ | (D-55c)Cl |
| 3-Cl-5-S(O)CF$_3$ | CF$_3$ | C(O)Pr-i | (D-55c)Cl |
| 3-Cl-5-S(O)CF$_3$ | CF$_3$ | C(O)OCH$_3$ | (D-55c)Cl |
| 3-Cl-5-S(O)CF$_3$ | CF$_3$ | C(O)CH$_3$ | (D-55c)Br |
| 3-Cl-5-SO$_2$CF$_3$ | CF$_3$ | H | CH=NOCH$_3$ |
| 3-Cl-5-SO$_2$CF$_3$ | CF$_3$ | H | CH=NOEt |
| 3-Cl-5-SO$_2$CF$_3$ | CF$_3$ | CH$_2$OEt | C(O)OCH$_3$ |
| 3-Cl-5-SO$_2$CF$_3$ | CF$_3$ | CH$_2$OCH$_2$CF$_3$ | C(O)OCH$_3$ |
| 3-Cl-5-SO$_2$CF$_3$ | CF$_3$ | C(O)Et | C(O)OCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-SO$_2$CF$_3$ | CF$_3$ | C(O)CH$_3$ | (D-55c)Cl |
| 3-Cl-5-SO$_2$CF$_3$ | CF$_3$ | C(O)Pr-i | (D-55c)Cl |
| 3-Cl-5-SO$_2$CF$_3$ | CF$_3$ | C(O)OCH$_3$ | (D-55c)Cl |
| 3-Cl-5-SO$_2$CF$_3$ | CF$_3$ | C(O)CH$_3$ | (D-55c)Br |
| 3-Br-5-SCF$_3$ | CF$_3$ | H | CH=NOCH$_3$ |
| 3-Br-5-SCF$_3$ | CF$_3$ | CH$_2$OCH$_3$ | CH=NOCH$_3$ |
| 3-Br-5-SCF$_3$ | CF$_3$ | H | CH=NOEt |
| 3-Br-5-SCF$_3$ | CF$_3$ | H | C(O)OCH$_3$ |
| 3-Br-5-SCF$_3$ | CF$_3$ | Et | C(O)OCH$_3$ |
| 3-Br-5-SCF$_3$ | CF$_3$ | CH$_2$OCH$_3$ | C(O)OCH$_3$ |
| 3-Br-5-SCF$_3$ | CF$_3$ | CH$_2$OEt | C(O)OCH$_3$ |
| 3-Br-5-SCF$_3$ | CF$_3$ | CH$_2$OCH$_2$CF$_3$ | C(O)OCH$_3$ |
| 3-Br-5-SCF$_3$ | CF$_3$ | CH$_2$OC(O)CH$_3$ | C(O)OCH$_3$ |
| 3-Br-5-SCF$_3$ | CF$_3$ | CH$_2$OC(O)Et | C(O)OCH$_3$ |
| 3-Br-5-SCF$_3$ | CF$_3$ | CH$_2$OC(O)OCH$_3$ | C(O)OCH$_3$ |
| 3-Br-5-SCF$_3$ | CF$_3$ | E-5a | C(O)OCH$_3$ |
| 3-Br-5-SCF$_3$ | CF$_3$ | C(O)Et | C(O)OCH$_3$ |
| 3-Br-5-SCF$_3$ | CF$_3$ | C(O)Pr-n | C(O)OCH$_3$ |
| 3-Br-5-SCF$_3$ | CF$_3$ | C(O)Bu-t | C(O)OCH$_3$ |
| 3-Br-5-SCF$_3$ | CF$_3$ | C(O)CH$_2$SCH$_3$ | C(O)OCH$_3$ |
| 3-Br-5-SCF$_3$ | CF$_3$ | C(O)OCH$_3$ | C(O)OEt |
| 3-Br-5-SCF$_3$ | CF$_3$ | H | C(O)OPr-i |
| 3-Br-5-SCF$_3$ | CF$_3$ | H | C(O)NH$_2$ |
| 3-Br-5-SCF$_3$ | CF$_3$ | C(O)OCH$_3$ | (D-52d)Cl |
| 3-Br-5-SCF$_3$ | CF$_3$ | CH$_3$ | (D-55c)Cl |
| 3-Br-5-SCF$_3$ | CF$_3$ | CH$_2$OCH$_3$ | (D-55c)Cl |
| 3-Br-5-SCF$_3$ | CF$_3$ | C(O)CH$_3$ | (D-55c)Cl |
| 3-Br-5-SCF$_3$ | CF$_3$ | C(O)Et | (D-55c)Cl |
| 3-Br-5-SCF$_3$ | CF$_3$ | C(O)Pr-i | (D-55c)Cl |
| 3-Br-5-SCF$_3$ | CF$_3$ | C(O)CH$_2$OCH$_3$ | (D-55c)Cl |
| 3-Br-5-SCF$_3$ | CF$_3$ | C(O)CH$_2$OEt | (D-55c)Cl |
| 3-Br-5-SCF$_3$ | CF$_3$ | C(O)CH$_2$SCH$_3$ | (D-55c)Cl |
| 3-Br-5-SCF$_3$ | CF$_3$ | C(O)OCH$_3$ | (D-55c)Cl |
| 3-Br-5-SCF$_3$ | CF$_3$ | C(O)OPr-n | (D-55c)Cl |
| 3-Br-5-SCF$_3$ | CF$_3$ | C(O)OCH$_2$CH$_2$Cl | (D-55c)Cl |
| 3-Br-5-SCF$_3$ | CF$_3$ | C(O)OCH$_2$CH$_2$OCH$_3$ | (D-55c)Cl |
| 3-Br-5-SCF$_3$ | CF$_3$ | C(O)OCH$_2$CH=CH$_2$ | (D-55c)Cl |
| 3-Br-5-SCF$_3$ | CF$_3$ | CH$_2$OC(O)CH$_3$ | (D-55c)Br |
| 3-Br-5-SCF$_3$ | CF$_3$ | C(O)CH$_3$ | (D-55c)Br |
| 3-Br-5-SCF$_3$ | CF$_3$ | C(O)Et | (D-55c)Br |
| 3-Br-5-SCF$_3$ | CF$_3$ | C(O)Pr-n | (D-55c)Br |
| 3-Br-5-SCF$_3$ | CF$_3$ | C(O)Pr-i | (D-55c)Br |
| 3-Br-5-SCF$_3$ | CF$_3$ | C(O)OCH$_3$ | (D-55c)Br |
| 3-Br-5-SCF$_3$ | CF$_3$ | C(O)OEt | (D-55c)Br |
| 3-Br-5-SCF$_3$ | CF$_2$Cl | H | CH=NOCH$_3$ |
| 3-Br-5-SCF$_3$ | CF$_2$Cl | H | CH=NOEt |
| 3-Br-5-SCF$_3$ | CF$_2$Cl | CH$_2$OEt | C(O)OCH$_3$ |
| 3-Br-5-SCF$_3$ | CF$_2$Cl | CH$_2$OCH$_2$CF$_3$ | C(O)OCH$_3$ |
| 3-Br-5-SCF$_3$ | CF$_2$Cl | C(O)Et | C(O)OCH$_3$ |
| 3-Br-5-SCF$_3$ | CF$_2$Cl | C(O)CH$_3$ | (D-55c)Cl |
| 3-Br-5-SCF$_3$ | CF$_2$Cl | C(O)Pr-i | (D-55c)Cl |
| 3-Br-5-SCF$_3$ | CF$_2$Cl | C(O)OCH$_3$ | (D-55c)Cl |
| 3-Br-5-SCF$_3$ | CF$_2$Cl | C(O)CH$_3$ | (D-55c)Br |
| 3-Br-5-S(O)CF$_3$ | CF$_3$ | H | CH=NOCH$_3$ |
| 3-Br-5-S(O)CF$_3$ | CF$_3$ | H | CH=NOEt |
| 3-Br-5-S(O)CF$_3$ | CF$_3$ | CH$_2$OEt | C(O)OCH$_3$ |
| 3-Br-5-S(O)CF$_3$ | CF$_3$ | CH$_2$OCH$_2$CF$_3$ | C(O)OCH$_3$ |
| 3-Br-5-S(O)CF$_3$ | CF$_3$ | C(O)Et | C(O)OCH$_3$ |
| 3-Br-5-S(O)CF$_3$ | CF$_3$ | C(O)CH$_3$ | (D-55c)Cl |
| 3-Br-5-S(O)CF$_3$ | CF$_3$ | C(O)Pr-i | (D-55c)Cl |
| 3-Br-5-S(O)CF$_3$ | CF$_3$ | C(O)OCH$_3$ | (D-55c)Cl |
| 3-Br-5-S(O)CF$_3$ | CF$_3$ | C(O)CH$_3$ | (D-55c)Br |
| 3-Br-5-S(O)CF$_3$ | CF$_3$ | H | CH=NOCH$_3$ |
| 3-Br-5-S(O)CF$_3$ | CF$_3$ | CH$_2$OEt | C(O)OCH$_3$ |
| 3-Br-5-S(O)CF$_3$ | CF$_3$ | CH$_2$OCH$_2$CF$_3$ | C(O)OCH$_3$ |
| 3-Br-5-S(O)CF$_3$ | CF$_3$ | C(O)Et | C(O)OCH$_3$ |
| 3-Br-5-S(O)CF$_3$ | CF$_3$ | C(O)CH$_3$ | (D-55c)Cl |
| 3-Br-5-S(O)CF$_3$ | CF$_3$ | C(O)Pr-i | (D-55c)Cl |
| 3-Br-5-S(O)CF$_3$ | CF$_3$ | C(O)OCH$_3$ | (D-55c)Cl |
| 3-Br-5-S(O)CF$_3$ | CF$_3$ | C(O)CH$_3$ | (D-55c)Br |
| 3-Cl-5-SCF$_2$CHFCl | CF$_3$ | H | CH=NOCH$_3$ |
| 3-Cl-5-SCF$_2$CHFCl | CF$_3$ | H | CH=NOEt |
| 3-Cl-5-SCF$_2$CHFCl | CF$_3$ | CH$_2$OEt | C(O)OCH$_3$ |
| 3-Cl-5-SCF$_2$CHFCl | CF$_3$ | CH$_2$OCH$_2$CF$_3$ | C(O)OCH$_3$ |
| 3-Cl-5-SCF$_2$CHFCl | CF$_3$ | C(O)Et | C(O)OCH$_3$ |
| 3-Cl-5-SCF$_2$CHFCl | CF$_3$ | C(O)CH$_3$ | (D-55c)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Cl-5-SCF$_2$CHFCl | CF$_3$ | C(O)Pr-i | (D-55c)Cl |
| 3-Cl-5-SCF$_2$CHFCl | CF$_3$ | C(O)OCH$_3$ | (D-55c)Cl |
| 3-Cl-5-SCF$_2$CHFCl | CF$_3$ | C(O)CH$_3$ | (D-55c)Br |
| 3-Cl-5-S(O)CF$_2$CHFCl | CF$_3$ | C(O)Pr-i | (D-55c)Cl |
| 3-Cl-5-S(O)CF$_2$CHFCl | CF$_3$ | C(O)OCH$_3$ | (D-55c)Cl |
| 3-Br-5-SCF$_2$CHFCl | CF$_3$ | H | CH=NOCH$_3$ |
| 3-Br-5-SCF$_2$CHFCl | CF$_3$ | H | CH=NOEt |
| 3-Br-5-SCF$_2$CHFCl | CF$_3$ | CH$_2$OEt | C(O)OCH$_3$ |
| 3-Br-5-SCF$_2$CHFCl | CF$_3$ | CH$_2$OCH$_2$CF$_3$ | C(O)OCH$_3$ |
| 3-Br-5-SCF$_2$CHFCl | CF$_3$ | C(O)Et | C(O)OCH$_3$ |
| 3-Br-5-SCF$_2$CHFCl | CF$_3$ | C(O)CH$_3$ | (D-55c)Cl |
| 3-Br-5-SCF$_2$CHFCl | CF$_3$ | C(O)Pr-i | (D-55c)Cl |
| 3-Br-5-SCF$_2$CHFCl | CF$_3$ | C(O)OCH$_3$ | (D-55c)Cl |
| 3-Br-5-SCF$_2$CHFCl | CF$_3$ | C(O)CH$_3$ | (D-55c)Br |
| 3-Br-5-S(O)CF$_2$CHFCl | CF$_3$ | C(O)CH$_3$ | (D-55c)Br |
| 3-Br-5-S(O)CF$_2$CHFCl | CF$_3$ | H | CH=NOCH$_3$ |
| 3-Cl-5-SPh | CF$_3$ | H | CH=NOEt |
| 3-Cl-5-S(O)Ph | CF$_3$ | CH$_2$OEt | C(O)OCH$_3$ |
| 3-Cl-5-SO$_2$Ph | CF$_3$ | CH$_2$OCH$_2$CF$_3$ | C(O)OCH$_3$ |
| 3-NO$_2$-4-F | CF$_3$ | C(O)Et | C(O)OCH$_3$ |
| 2-F-5-NO$_2$ | CF$_3$ | C(O)CH$_3$ | (D-55c)Cl |
| 3-F-5-NO$_2$ | CF$_3$ | C(O)Pr-i | (D-55c)Cl |
| 3-NO$_2$-4-Cl | CF$_3$ | C(O)OCH$_3$ | (D-55c)Cl |
| 3-Cl-5-NO$_2$ | CF$_3$ | H | CH=NOCH$_3$ |
| 3-Cl-5-NO$_2$ | CF$_3$ | H | CH=NOEt |
| 3-Cl-5-NO$_2$ | CF$_3$ | CH$_2$OEt | C(O)OCH$_3$ |
| 3-Cl-5-NO$_2$ | CF$_3$ | CH$_2$OCH$_2$CF$_3$ | C(O)OCH$_3$ |
| 3-Cl-5-NO$_2$ | CF$_3$ | C(O)Et | C(O)OCH$_3$ |
| 3-Cl-5-NO$_2$ | CF$_3$ | C(O)CH$_3$ | (D-55c)Cl |
| 3-Cl-5-NO$_2$ | CF$_3$ | C(O)Pr-i | (D-55c)Cl |
| 3-Cl-5-NO$_2$ | CF$_3$ | C(O)OCH$_3$ | (D-55c)Cl |
| 3-Cl-5-NO$_2$ | CF$_3$ | C(O)CH$_3$ | (D-55c)Br |
| 3-Br-5-NO$_2$ | CF$_3$ | H | CH=NOCH$_3$ |
| 3-Br-5-NO$_2$ | CF$_3$ | H | CH=NOEt |
| 3-Br-5-NO$_2$ | CF$_3$ | CH$_2$OEt | C(O)OCH$_3$ |
| 3-Br-5-NO$_2$ | CF$_3$ | CH$_2$OCH$_2$CF$_3$ | C(O)OCH$_3$ |
| 3-Br-5-NO$_2$ | CF$_3$ | C(O)Et | C(O)OCH$_3$ |
| 3-Br-5-NO$_2$ | CF$_3$ | C(O)CH$_3$ | (D-55c)Cl |
| 3-Br-5-NO$_2$ | CF$_3$ | C(O)Pr-i | (D-55c)Cl |
| 3-Br-5-NO$_2$ | CF$_3$ | C(O)OCH$_3$ | (D-55c)Cl |
| 3-Br-5-NO$_2$ | CF$_3$ | C(O)CH$_3$ | (D-55c)Br |
| 3-CH$_3$-5-NO$_2$ | CF$_3$ | C(O)CH$_3$ | (D-55c)Br |
| 3-CF$_3$-4-NO$_2$ | CF$_3$ | H | CH=NOCH$_3$ |
| 3-CF$_3$-5-NO$_2$ | CF$_3$ | H | CH=NOCH$_3$ |
| 3-CF$_3$-5-NO$_2$ | CF$_3$ | H | CH=NOEt |
| 3-CF$_3$-5-NO$_2$ | CF$_3$ | H | C(O)OCH$_3$ |
| 3-CF$_3$-5-NO$_2$ | CF$_3$ | Et | C(O)OCH$_3$ |
| 3-CF$_3$-5-NO$_2$ | CF$_3$ | CH$_2$OCH$_3$ | C(O)OCH$_3$ |
| 3-CF$_3$-5-NO$_2$ | CF$_3$ | CH$_2$OEt | C(O)OCH$_3$ |
| 3-CF$_3$-5-NO$_2$ | CF$_3$ | CH$_2$OCH$_2$CF$_3$ | C(O)OCH$_3$ |
| 3-CF$_3$-5-NO$_2$ | CF$_3$ | C(O)Et | C(O)OCH$_3$ |
| 3-CF$_3$-5-NO$_2$ | CF$_3$ | C(O)OCH$_3$ | C(O)OEt |
| 3-CF$_3$-5-NO$_2$ | CF$_3$ | H | C(O)NH$_2$ |
| 3-CF$_3$-5-NO$_2$ | CF$_3$ | CH$_3$ | (D-55c)Cl |
| 3-CF$_3$-5-NO$_2$ | CF$_3$ | CH$_2$OCH$_3$ | (D-55c)Cl |
| 3-CF$_3$-5-NO$_2$ | CF$_3$ | C(O)CH$_3$ | (D-55c)Cl |
| 3-CF$_3$-5-NO$_2$ | CF$_3$ | C(O)Et | (D-55c)Cl |
| 3-CF$_3$-5-NO$_2$ | CF$_3$ | C(O)Pr-i | (D-55c)Cl |
| 3-CF$_3$-5-NO$_2$ | CF$_3$ | C(O)CH$_2$OCH$_3$ | (D-55c)Cl |
| 3-CF$_3$-5-NO$_2$ | CF$_3$ | C(O)OCH$_3$ | (D-55c)Cl |
| 3-CF$_3$-5-NO$_2$ | CF$_3$ | C(O)CH$_3$ | (D-55c)Br |
| 3-CF$_3$-5-NO$_2$ | CF$_3$ | C(O)Et | (D-55c)Br |
| 3-CF$_3$-5-NO$_2$ | CF$_3$ | C(O)Pr-i | (D-55c)Br |
| 3-CF$_3$-5-NO$_2$ | CF$_2$Cl | H | CH=NOCH$_3$ |
| 3-CF$_3$-5-NO$_2$ | CF$_2$Cl | CH$_2$OEt | C(O)OCH$_3$ |
| 3-CF$_3$-5-NO$_2$ | CF$_2$Cl | C(O)Et | C(O)OCH$_3$ |
| 3-CF$_3$-5-NO$_2$ | CF$_2$Cl | C(O)CH$_3$ | (D-55c)Cl |
| 3-CF$_3$-5-NO$_2$ | CF$_2$Cl | C(O)OCH$_3$ | (D-55c)Cl |
| 3,5-(NO$_2$)$_2$ | CF$_3$ | H | CH=NOEt |
| 3-Cl-5-NHC(O)CF$_3$ | CF$_3$ | CH$_2$OEt | C(O)OCH$_3$ |
| 3-Cl-5-N(CH$_3$)C(O)CF$_3$ | CF$_3$ | CH$_2$OCH$_2$CF$_3$ | C(O)OCH$_3$ |
| 3-Cl-5-N(Et)C(O)CF$_3$ | CF$_3$ | C(O)Et | C(O)OCH$_3$ |
| 3-Cl-5-N(CH$_3$)C(O)CF$_2$Cl | CF$_3$ | C(O)CH$_3$ | (D-55c)Cl |
| 3-Cl-5-N(Et)C(O)CF$_2$Cl | CF$_3$ | C(O)Pr-i | (D-55c)Cl |
| 3-Cl-5-N(CH$_3$)C(O)CF$_2$Br | CF$_3$ | C(O)OCH$_3$ | (D-55c)Cl |
| 3-Cl-5-N(Et)C(O)CF$_2$Br | CF$_3$ | C(O)CH$_3$ | (D-55c)Br |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Cl-5-N(CH$_3$)SO$_2$CF$_3$ | CF$_3$ | H | CH=NOCH$_3$ |
| 3-Cl-5-N(Et)SO$_2$CF$_3$ | CF$_3$ | H | CH=NOEt |
| 3-CF$_3$-5-NHC(O)CH$_3$ | CF$_3$ | CH$_2$OEt | C(O)OCH$_3$ |
| 3-CF$_3$-5-NHC(O)CF$_3$ | CF$_3$ | CH$_2$OCH$_2$CF$_3$ | C(O)OCH$_3$ |
| 3-CF$_3$-5-N(CH$_3$)C(O)CH$_3$ | CF$_3$ | C(O)Et | C(O)OCH$_3$ |
| 3-CF$_3$-5-N(Et)C(O)CH$_3$ | CF$_3$ | C(O)CH$_3$ | (D-55c)Cl |
| 3-CF$_3$-5-N(CH$_3$)C(O)CF$_3$ | CF$_3$ | C(O)Pr-i | (D-55c)Cl |
| 3-CF$_3$-5-N(Et)C(O)CF$_3$ | CF$_3$ | C(O)OCH$_3$ | (D-55c)Cl |
| 3-CF$_3$-5-N(CH$_3$)C(O)CF$_2$Cl | CF$_3$ | C(O)CH$_3$ | (D-55c)Br |
| 3-CF$_3$-5-N(Et)C(O)CF$_2$Cl | CF$_3$ | H | CH=NOCH$_3$ |
| 3-CF$_3$-5-N(CH$_3$)C(O)CF$_2$Br | CF$_3$ | H | CH=NOEt |
| 3-CF$_3$-5-N(Et)C(O)CF$_2$Br | CF$_3$ | CH$_2$OEt | C(O)OCH$_3$ |
| 3-CF$_3$-5-N(CH$_3$)SO$_2$CF$_3$ | CF$_3$ | CH$_2$OCH$_2$CF$_3$ | C(O)OCH$_3$ |
| 3-CF$_3$-5-N(Et)SO$_2$CF$_3$ | CF$_3$ | C(O)Et | C(O)OCH$_3$ |
| 3-NO$_2$-5-NHC(O)CH$_3$ | CF$_3$ | C(O)CH$_3$ | (D-55c)Cl |
| 3-CN-4-F | CF$_3$ | C(O)Pr-i | (D-55c)Cl |
| 3-F-4-CN | CF$_3$ | C(O)OCH$_3$ | (D-55c)Cl |
| 3-F-5-CN | CF$_3$ | C(O)CH$_3$ | (D-55c)Br |
| 3-Cl-4-CN | CF$_3$ | H | CH=NOCH$_3$ |
| 3-Cl-5-CN | CF$_3$ | H | CH=NOCH$_3$ |
| 3-Cl-5-CN | CF$_3$ | H | CH=NOEt |
| 3-Cl-5-CN | CF$_3$ | H | C(O)OCH$_3$ |
| 3-Cl-5-CN | CF$_3$ | Et | C(O)OCH$_3$ |
| 3-Cl-5-CN | CF$_3$ | CH$_2$OCH$_3$ | C(O)OCH$_3$ |
| 3-Cl-5-CN | CF$_3$ | CH$_2$OEt | C(O)OCH$_3$ |
| 3-Cl-5-CN | CF$_3$ | CH$_2$OCH$_2$CF$_3$ | C(O)OCH$_3$ |
| 3-Cl-5-CN | CF$_3$ | C(O)Et | C(O)OCH$_3$ |
| 3-Cl-5-CN | CF$_3$ | C(O)OCH$_3$ | C(O)OEt |
| 3-Cl-5-CN | CF$_3$ | H | C(O)NH$_2$ |
| 3-Cl-5-CN | CF$_3$ | CH$_3$ | (D-55c)Cl |
| 3-Cl-5-CN | CF$_3$ | CH$_2$OCH$_3$ | (D-55c)Cl |
| 3-Cl-5-CN | CF$_3$ | C(O)CH$_3$ | (D-55c)Cl |
| 3-Cl-5-CN | CF$_3$ | C(O)Et | (D-55c)Cl |
| 3-Cl-5-CN | CF$_3$ | C(O)Pr-i | (D-55c)Cl |
| 3-Cl-5-CN | CF$_3$ | C(O)CH$_2$OCH$_3$ | (D-55c)Cl |
| 3-Cl-5-CN | CF$_3$ | C(O)OCH$_3$ | (D-55c)Cl |
| 3-Cl-5-CN | CF$_3$ | C(O)CH$_3$ | (D-55c)Br |
| 3-Cl-5-CN | CF$_3$ | C(O)Et | (D-55c)Br |
| 3-Cl-5-CN | CF$_3$ | C(O)Pr-i | (D-55c)Br |
| 3-Cl-5-CN | CF$_2$Cl | H | CH=NOEt |
| 3-Br-4-CN | CF$_3$ | CH$_2$OEt | C(O)OCH$_3$ |
| 3-Br-5-CN | CF$_3$ | H | CH=NOCH$_3$ |
| 3-Br-5-CN | CF$_3$ | H | CH=NOEt |
| 3-Br-5-CN | CF$_3$ | H | C(O)OCH$_3$ |
| 3-Br-5-CN | CF$_3$ | Et | C(O)OCH$_3$ |
| 3-Br-5-CN | CF$_3$ | CH$_2$OCH$_3$ | C(O)OCH$_3$ |
| 3-Br-5-CN | CF$_3$ | CH$_2$OEt | C(O)OCH$_3$ |
| 3-Br-5-CN | CF$_3$ | CH$_2$OCH$_2$CF$_3$ | C(O)OCH$_3$ |
| 3-Br-5-CN | CF$_3$ | C(O)Et | C(O)OCH$_3$ |
| 3-Br-5-CN | CF$_3$ | C(O)OCH$_3$ | C(O)OEt |
| 3-Br-5-CN | CF$_3$ | H | C(O)NH$_2$ |
| 3-Br-5-CN | CF$_3$ | CH$_3$ | (D-55c)Cl |
| 3-Br-5-CN | CF$_3$ | CH$_2$OCH$_3$ | (D-55c)Cl |
| 3-Br-5-CN | CF$_3$ | C(O)CH$_3$ | (D-55c)Cl |
| 3-Br-5-CN | CF$_3$ | C(O)Et | (D-55c)Cl |
| 3-Br-5-CN | CF$_3$ | C(O)Pr-i | (D-55c)Cl |
| 3-Br-5-CN | CF$_3$ | C(O)CH$_2$OCH$_3$ | (D-55c)Cl |
| 3-Br-5-CN | CF$_3$ | C(O)OCH$_3$ | (D-55c)Cl |
| 3-Br-5-CN | CF$_3$ | C(O)CH$_3$ | (D-55c)Br |
| 3-Br-5-CN | CF$_3$ | C(O)Et | (D-55c)Br |
| 3-Br-5-CN | CF$_3$ | C(O)Pr-i | (D-55c)Br |
| 3-Br-5-CN | CF$_2$Cl | CH$_2$OCH$_2$CF$_3$ | C(O)OCH$_3$ |
| 3-CH$_3$-4-CN | CF$_3$ | C(O)Et | C(O)OCH$_3$ |
| 3-CH$_3$-5-CN | CF$_3$ | C(O)CH$_3$ | (D-55c)Cl |
| 3-CF$_3$-5-CN | CF$_3$ | H | CH=NOCH$_3$ |
| 3-CF$_3$-5-CN | CF$_3$ | CH$_2$OCH$_3$ | CH=NOCH$_3$ |
| 3-CF$_3$-5-CN | CF$_3$ | H | CH=NOEt |
| 3-CF$_3$-5-CN | CF$_3$ | H | C(O)OCH$_3$ |
| 3-CF$_3$-5-CN | CF$_3$ | Et | C(O)OCH$_3$ |
| 3-CF$_3$-5-CN | CF$_3$ | CH$_2$OCH$_3$ | C(O)OCH$_3$ |
| 3-CF$_3$-5-CN | CF$_3$ | CH$_2$OEt | C(O)OCH$_3$ |
| 3-CF$_3$-5-CN | CF$_3$ | CH$_2$OCH$_2$CF$_3$ | C(O)OCH$_3$ |
| 3-CF$_3$-5-CN | CF$_3$ | CH$_2$OC(O)CH$_3$ | C(O)OCH$_3$ |
| 3-CF$_3$-5-CN | CF$_3$ | CH2OC(O)Et | C(O)OCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-$CF_3$-5-CN | $CF_3$ | $CH_2OC(O)OCH_3$ | $C(O)OCH_3$ |
| 3-$CF_3$-5-CN | $CF_3$ | E-5a | $C(O)OCH_3$ |
| 3-$CF_3$-5-CN | $CF_3$ | $C(O)Et$ | $C(O)OCH_3$ |
| 3-$CF_3$-5-CN | $CF_3$ | $C(O)Pr$-n | $C(O)OCH_3$ |
| 3-$CF_3$-5-CN | $CF_3$ | $C(O)Bu$-t | $C(O)OCH_3$ |
| 3-$CF_3$-5-CN | $CF_3$ | $C(O)CH_2SCH_3$ | $C(O)OCH_3$ |
| 3-$CF_3$-5-CN | $CF_3$ | $C(O)OCH_3$ | $C(O)OEt$ |
| 3-$CF_3$-5-CN | $CF_3$ | H | $C(O)OPr$-i |
| 3-$CF_3$-5-CN | $CF_3$ | H | $C(O)NH_2$ |
| 3-$CF_3$-5-CN | $CF_3$ | $C(O)OCH_3$ | (D-52d)Cl |
| 3-$CF_3$-5-CN | $CF_3$ | $CH_3$ | (D-55c)Cl |
| 3-$CF_3$-5-CN | $CF_3$ | $CH_2OCH_3$ | (D-55c)Cl |
| 3-$CF_3$-5-CN | $CF_3$ | $C(O)CH_3$ | (D-55c)Cl |
| 3-$CF_3$-5-CN | $CF_3$ | $C(O)Et$ | (D-55c)Cl |
| 3-$CF_3$-5-CN | $CF_3$ | $C(O)Pr$-i | (D-55c)Cl |
| 3-$CF_3$-5-CN | $CF_3$ | $C(O)CH_2OCH_3$ | (D-55c)Cl |
| 3-$CF_3$-5-CN | $CF_3$ | $C(O)CH_2OEt$ | (D-55c)Cl |
| 3-$CF_3$-5-CN | $CF_3$ | $C(O)CH_2SCH_3$ | (D-55c)Cl |
| 3-$CF_3$-5-CN | $CF_3$ | $C(O)OCH_3$ | (D-55c)Cl |
| 3-$CF_3$-5-CN | $CF_3$ | $C(O)OPr$-n | (D-55c)Cl |
| 3-$CF_3$-5-CN | $CF_3$ | $C(O)OCH_2CH_2Cl$ | (D-55c)Cl |
| 3-$CF_3$-5-CN | $CF_3$ | $C(O)OCH_2CH_2OCH_3$ | (D-55c)Cl |
| 3-$CF_3$-5-CN | $CF_3$ | $C(O)OCH_2CH=CH_2$ | (D-55c)Cl |
| 3-$CF_3$-5-CN | $CF_3$ | $CH_2OC(O)CH_3$ | (D-55c)Br |
| 3-$CF_3$-5-CN | $CF_3$ | $C(O)CH_3$ | (D-55c)Br |
| 3-$CF_3$-5-CN | $CF_3$ | $C(O)Et$ | (D-55c)Br |
| 3-$CF_3$-5-CN | $CF_3$ | $C(O)OPr$-n | (D-55c)Br |
| 3-$CF_3$-5-CN | $CF_3$ | $C(O)Pr$-i | (D-55c)Br |
| 3-$CF_3$-5-CN | $CF_3$ | $C(O)OCH_3$ | (D-55c)Br |
| 3-$CF_3$-5-CN | $CF_3$ | $C(O)Et$ | (D-55c)Br |
| 3-$CF_3$-5-CN | $CF_2Cl$ | H | $CH=NOCH_3$ |
| 3-$CF_3$-5-CN | $CF_2Cl$ | H | $CH=NOEt$ |
| 3-$CF_3$-5-CN | $CF_2Cl$ | $CH_2OEt$ | $C(O)OCH_3$ |
| 3-$CF_3$-5-CN | $CF_2Cl$ | $CH_2OCH_2CF_3$ | $C(O)OCH_3$ |
| 3-$CF_3$-5-CN | $CF_2Cl$ | $C(O)Et$ | $C(O)OCH_3$ |
| 3-$CF_3$-5-CN | $CF_2Cl$ | $C(O)OCH3$ | (D-55c)Cl |
| 3-$CF_3$-5-CN | $CF_2Cl$ | $C(O)Pr$-i | (D-55c)Cl |
| 3-$CF_3$-5-CN | $CF_2Cl$ | $C(O)OCH_3$ | (D-55c)Cl |
| 3-$CF_3$-5-CN | $CF_2Cl$ | $C(O)CH_3$ | (D-55c)Br |
| 3-$NO_2$-5-CN | $CF_3$ | $C(O)Pr$-i | (D-55c)Cl |
| 3,5-$(CN)_2$ | $CF_3$ | $C(O)OCH_3$ | (D-55c)Cl |
| 3-F-5-$C(O)OCH_3$ | $CF_3$ | $C(O)CH_3$ | (D-55c)Br |
| 3-F-5-$C(O)NH_2$ | $CF_3$ | H | $CH=NOCH_3$ |
| 3-F-5-$C(O)NHCH_3$ | $CF_3$ | H | $CH=NOEt$ |
| 3-F-5-$C(O)N(CH_3)_2CF_3$ | $CF_3$ | $CH_2OEt$ | $C(O)OCH_3$ |
| 3-Cl-5-$C(O)OCH_3$ | $CF_3$ | $CH_2OCH_2CF_3$ | $C(O)OCH_3$ |
| 3-Cl-5-$C(O)NH2$ | $CF_3$ | $C(O)Et$ | $C(O)OCH_3$ |
| 3-Cl-5-$C(O)NHCH_3$ | $CF_3$ | $C(O)CH_3$ | (D-55c)Cl |
| 3-Cl-5-$C(O)N(CH_3)_2$ | $CF_3$ | $C(O)Pr$-i | (D-55c)Cl |
| 3-Br-5-$C(O)OCH_3$ | $CF_3$ | $C(O)OCH_3$ | (D-55c)Cl |
| 3-Br-5-$C(O)NH_2$ | $CF_3$ | $C(O)CH_3$ | (D-55c)Br |
| 3-Br-5-$C(O)NHCH_3$ | $CF_3$ | H | $CH=NOCH_3$ |
| 3-Br-5-$C(O)N(CH_3)_2$ | $CF_3$ | H | $CH=NOEt$ |
| 3-$CF_3$-5-$C(O)OCH_3$ | $CF_3$ | $CH_2OEt$ | $C(O)OCH_3$ |
| 3-$CF_3$-5-$C(O)NH_2$ | $CF_3$ | $CH_2OCH_2CF_3$ | $C(O)OCH_3$ |
| 3-$CF_3$-5-$C(O)NHCH_3$ | $CF_3$ | $C(O)Et$ | $C(O)OCH_3$ |
| 3-$CF_3$-5-$C(O)N(CH_3)_2$ | $CF_3$ | $C(O)CH_3$ | (D-55c)Cl |
| 3-$NO_2$-5-$C(O)OCH_3$ | $CF_3$ | $C(O)Pr$-i | (D-55c)Cl |
| 3-$NO_2$-5-$C(O)NH_2$ | $CF_3$ | $C(O)OCH_3$ | (D-55c)Cl |
| 3-$NO_2$-5-$C(O)NHCH_3$ | $CF_3$ | $C(O)CH_3$ | (D-55c)Br |
| 3-$NO_2$-5-$C(O)N(CH_3)_2$ | $CF_3$ | H | $CH=NOCH_3$ |
| 3-Cl-5-$SO_2OCH_3$ | $CF_3$ | H | $CH=NOEt$ |
| 3-$CH_3$-5-$SO_2OCH_3$ | $CF_3$ | $CH_2OEt$ | $C(O)OCH_3$ |
| 3-Cl-5-$SO_2NH_2$ | $CF_3$ | $CH_2OCH_2CF_3$ | $C(O)OCH_3$ |
| 3-$CH_3$-5-$SO_2NH_2$ | $CF_3$ | $C(O)Et$ | $C(O)OCH_3$ |
| 3-Cl-5-$SO_2NHCH_3$ | $CF_3$ | $C(O)CH_3$ | (D-55c)Cl |
| 3-Cl-5-$SO_2N(CH_3)_2$ | $CF_3$ | $C(O)Pr$-i | (D-55c)Cl |
| 3-$CH_3$-5-Ph | $CF_3$ | $C(O)OCH_3$ | (D-55c)Cl |
| 2-CH=CHCH=CH-3 | $CF_3$ | $C(O)CH_3$ | (D-55c)Br |
| 3-CH=CHCH=CH-4 | $CF_3$ | H | $CH=NOCH_3$ |
| 2,3,4-$F_3$ | $CF_3$ | H | $CH=NOEt$ |
| 2,3,5-$F_3$ | $CF_3$ | $CH_2OEt$ | $C(O)OCH_3$ |
| 2,3,6-$F_3$ | $CF_3$ | $CH_2OCH_2CF_3$ | $C(O)OCH_3$ |
| 2,4,5-$F_3$ | $CF_3$ | $C(O)Et$ | $C(O)OCH_3$ |
| 3,4,5-$F_3$ | $CF_3$ | H | $CH=NOCH_3$ |
| 3,4,5-$F_3$ | $CF_3$ | $CH_2OCH_3$ | $CH=NOCH_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4,5-F$_3$ | CF$_3$ | H | CH=NOEt |
| 3,4,5-F$_3$ | CF$_3$ | H | C(O)OCH$_3$ |
| 3,4,5-F$_3$ | CF$_3$ | Et | C(O)OCH$_3$ |
| 3,4,5-F$_3$ | CF$_3$ | CH$_2$OCH$_3$ | C(O)OCH$_3$ |
| 3,4,5-F$_3$ | CF$_3$ | CH$_2$OEt | C(O)OCH$_3$ |
| 3,4,5-F$_3$ | CF$_3$ | CH$_2$OCH$_2$CF$_3$ | C(O)OCH$_3$ |
| 3,4,5-F$_3$ | CF$_3$ | CH$_2$OC(O)CH$_3$ | C(O)OCH$_3$ |
| 3,4,5-F$_3$ | CF$_3$ | CH$_2$OC(O)Et | C(O)OCH$_3$ |
| 3,4,5-F$_3$ | CF$_3$ | CH$_2$OC(O)OCH$_3$ | C(O)OCH$_3$ |
| 3,4,5-F$_3$ | CF$_3$ | E-5a | C(O)OCH$_3$ |
| 3,4,5-F$_3$ | CF$_3$ | C(O)Et | C(O)OCH$_3$ |
| 3,4,5-F$_3$ | CF$_3$ | C(O)Pr-n | C(O)OCH$_3$ |
| 3,4,5-F$_3$ | CF$_3$ | C(O)Bu-t | C(O)OCH$_3$ |
| 3,4,5-F$_3$ | CF$_3$ | C(O)CH$_2$SCH$_3$ | C(O)OCH$_3$ |
| 3,4,5-F$_3$ | CF$_3$ | C(O)OCH$_3$ | C(O)OEt |
| 3,4,5-F$_3$ | CF$_3$ | H | C(O)OPr-i |
| 3,4,5-F$_3$ | CF$_3$ | H | C(O)NH$_2$ |
| 3,4,5-F$_3$ | CF$_3$ | C(O)OCH$_3$ | (D-52d)Cl |
| 3,4,5-F$_3$ | CF$_3$ | CH$_3$ | (D-52d)Cl |
| 3,4,5-F$_3$ | CF$_3$ | CH$_2$OCH$_3$ | (D-52d)Cl |
| 3,4,5-F$_3$ | CF$_3$ | C(O)CH$_3$ | (D-52d)Cl |
| 3,4,5-F$_3$ | CF$_3$ | C(O)Et | (D-52d)Cl |
| 3,4,5-F$_3$ | CF$_3$ | C(O)Pr-i | (D-52d)Cl |
| 3,4,5-F$_3$ | CF$_3$ | C(O)CH$_2$OCH$_3$ | (D-52d)Cl |
| 3,4,5-F$_3$ | CF$_3$ | C(O)CH$_2$OEt | (D-52d)Cl |
| 3,4,5-F$_3$ | CF$_3$ | C(O)CH$_2$SCH$_3$ | (D-52d)Cl |
| 3,4,5-F$_3$ | CF$_3$ | C(O)OCH$_3$ | (D-52d)Cl |
| 3,4,5-F$_3$ | CF$_3$ | C(O)OPr-n | (D-52d)Cl |
| 3,4,5-F$_3$ | CF$_3$ | C(O)OCH$_2$CH$_2$Cl | (D-52d)Cl |
| 3,4,5-F$_3$ | CF$_3$ | C(O)OCH$_2$CH$_2$OCH$_3$ | (D-52d)Cl |
| 3,4,5-F$_3$ | CF$_3$ | C(O)OCH$_2$CH=CH$_2$ | (D-52d)Cl |
| 3,4,5-F$_3$ | CF$_3$ | CH$_2$OC(O)CH$_3$ | (D-55c)Br |
| 3,4,5-F$_3$ | CF$_3$ | C(O)CH$_3$ | (D-55c)Br |
| 3,4,5-F$_3$ | CF$_3$ | C(O)Et | (D-55c)Br |
| 3,4,5-F$_3$ | CF$_3$ | C(O)Pr-n | (D-55c)Br |
| 3,4,5-F$_3$ | CF$_3$ | C(O)Pr-i | (D-55c)Br |
| 3,4,5-F$_3$ | CF$_3$ | C(O)OCH$_3$ | (D-55c)Br |
| 3,4,5-F$_3$ | CF$_3$ | C(O)OEt | (D-55c)Br |
| 3,4,5-F$_3$ | CF$_2$Cl | H | CH=NOCH$_3$ |
| 3,4,5-F$_3$ | CF$_2$Cl | H | CH=NOEt |
| 3,4,5-F$_3$ | CF$_2$Cl | CH$_2$OEt | C(O)OCH$_3$ |
| 3,4,5-F$_3$ | CF$_2$Cl | CH$_2$OCH$_2$CF$_3$ | C(O)OCH$_3$ |
| 3,4,5-F$_3$ | CF$_2$Cl | C(O)Et | C(O)OCH$_3$ |
| 3,4,5-F$_3$ | CF$_2$Cl | C(O)CH3 | (D-55c)Cl |
| 3,4,5-F$_3$ | CF$_2$Cl | C(O)Pr-i | (D-55c)Cl |
| 3,4,5-F$_3$ | CF$_2$Cl | C(O)OCH$_3$ | (D-55c)Cl |
| 3,4,5-F$_3$ | CF$_2$Cl | C(O)CH$_3$ | (D-55c)Br |
| 2,6-F$_2$-3-Cl | CF$_3$ | C(O)CH$_3$ | (D-55c)Cl |
| 3,5-Cl$_2$-4-F | CHF$_2$ | H | CH=NOCH$_3$ |
| 3,5-Cl$_2$-4-F | CHF$_2$ | CH$_2$OEt | C(O)OCH$_3$ |
| 3,5-Cl$_2$-4-F | CHF$_2$ | C(O)Et | C(O)OCH$_3$ |
| 3,5-Cl$_2$-4-F | CHF$_2$ | C(O)CH$_3$ | (D-55c)Cl |
| 3,5-Cl$_2$-4-F | CHF$_2$ | C(O)OCH$_3$ | (D-55c)Cl |
| 3,5-Cl$_2$-4-F | CF$_3$ | H | CH=NOCH$_3$ |
| 3,5-Cl$_2$-4-F | CF$_3$ | CH$_2$OCH$_3$ | CH=NOCH$_3$ |
| 3,5-Cl$_2$-4-F | CF$_3$ | CH$_2$OEt | CH=NOCH$_3$ |
| 3,5-Cl$_2$-4-F | CF$_3$ | H | CH=NOEt |
| 3,5-Cl$_2$-4-F | CF$_3$ | CH$_2$OCH$_3$ | CH=NOEt |
| 3,5-Cl$_2$-4-F | CF$_3$ | H | C(O)OCH$_3$ |
| 3,5-Cl$_2$-4-F | CF$_3$ | CH$_3$ | C(O)OCH$_3$ |
| 3,5-Cl$_2$-4-F | CF$_3$ | Et | C(O)OCH$_3$ |
| 3,5-Cl$_2$-4-F | CF$_3$ | CH$_2$OCH$_3$ | C(O)OCH$_3$ |
| 3,5-Cl$_2$-4-F | CF$_3$ | CH$_2$OEt | C(O)OCH$_3$ |
| 3,5-Cl$_2$-4-F | CF$_3$ | CH$_2$OCH$_2$CF$_3$ | C(O)OCH$_3$ |
| 3,5-Cl$_2$-4-F | CF$_3$ | CH$_2$OC(O)CH$_3$ | C(O)OCH$_3$ |
| 3,5-Cl$_2$-4-F | CF$_3$ | CH$_2$OC(O)Et | C(O)OCH$_3$ |
| 3,5-Cl$_2$-4-F | CF$_3$ | CH$_2$OC(O)Bu-t | C(O)OCH$_3$ |
| 3,5-Cl$_2$-4-F | CF$_3$ | CH$_2$OC(O)OCH$_3$ | C(O)OCH$_3$ |
| 3,5-Cl$_2$-4-F | CF$_3$ | E-5a | C(O)OCH$_3$ |
| 3,5-Cl$_2$-4-F | CF$_3$ | CH$_2$NHC(O)OCH$_3$ | C(O)OCH$_3$ |
| 3,5-Cl$_2$-4-F | CF$_3$ | CH$_2$CN | C(O)OCH$_3$ |
| 3,5-Cl$_2$-4-F | CF$_3$ | C(O)CH$_3$ | C(O)OCH$_3$ |
| 3,5-Cl$_2$-4-F | CF$_3$ | C(O)Et | C(O)OCH$_3$ |
| 3,5-Cl$_2$-4-F | CF$_3$ | C(O)Pr-n | C(O)OCH$_3$ |
| 3,5-Cl$_2$-4-F | CF$_3$ | C(O)Pr-i | C(O)OCH$_3$ |
| 3,5-Cl$_2$-4-F | CF$_3$ | C(O)Bu-t | C(O)OCH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$-4-F | CF$_3$ | C(O)CH$_2$OCH$_3$ | C(O)OCH$_3$ |
| 3,5-Cl$_2$-4-F | CF$_3$ | C(O)CH$_2$SCH$_3$ | C(O)OCH$_3$ |
| 3,5-Cl$_2$-4-F | CF$_3$ | C(O)Ph | C(O)OCH$_3$ |
| 3,5-Cl$_2$-4-F | CF$_3$ | C(O)OCH$_2$CH$_2$Cl | C(O)OCH$_3$ |
| 3,5-Cl$_2$-4-F | CF$_3$ | H | C(O)OEt |
| 3,5-Cl$_2$-4-F | CF$_3$ | CH$_2$OCH$_3$ | C(O)OEt |
| 3,5-Cl$_2$-4-F | CF$_3$ | C(O)Bu-t | C(O)OEt |
| 3,5-Cl$_2$-4-F | CF$_3$ | C(O)CH$_2$OCH$_3$ | C(O)OEt |
| 3,5-Cl$_2$-4-F | CF$_3$ | C(O)OCH$_3$ | C(O)OEt |
| 3,5-Cl$_2$-4-F | CF$_3$ | H | C(O)OPr-i |
| 3,5-Cl$_2$-4-F | CF$_3$ | C(O)CH$_3$ | C(O)OPr-i |
| 3,5-Cl$_2$-4-F | CF$_3$ | C(O)CH$_2$OCH$_3$ | C(O)OPr-i |
| 3,5-Cl$_2$-4-F | CF$_3$ | C(O)OCH$_3$ | C(O)OPr-i |
| 3,5-Cl$_2$-4-F | CF$_3$ | C(O)OCH$_3$ | C(O)OCH$_2$CH$_2$OCH$_3$ |
| 3,5-Cl$_2$-4-F | CF$_3$ | H | C(O)NH$_2$ |
| 3,5-Cl$_2$-4-F | CF$_3$ | C(O)CH$_3$ | D-14a |
| 3,5-Cl$_2$-4-F | CF$_3$ | CH$_3$ | (D-52d)Cl |
| 3,5-Cl$_2$-4-F | CF$_3$ | CH$_2$OCH$_3$ | (D-52d)Cl |
| 3,5-Cl$_2$-4-F | CF$_3$ | C(O)Et | (D-52d)Cl |
| 3,5-Cl$_2$-4-F | CF$_3$ | C(O)OCH$_3$ | (D-52d)Cl |
| 3,5-Cl$_2$-4-F | CF$_3$ | CH$_3$ | (D-52d)Br |
| 3,5-Cl$_2$-4-F | CF$_3$ | CH$_3$ | (D-52d)CN |
| 3,5-Cl$_2$-4-F | CF$_3$ | CH$_3$ | (D-53e)Cl |
| 3,5-Cl$_2$-4-F | CF$_3$ | CH$_3$ | D-55a |
| 3,5-Cl$_2$-4-F | CF$_3$ | CH$_3$ | (D-55c)Cl |
| 3,5-Cl$_2$-4-F | CF$_3$ | Et | (D-55c)Cl |
| 3,5-Cl$_2$-4-F | CF$_3$ | CH$_2$OCH$_3$ | (D-55c)Cl |
| 3,5-Cl$_2$-4-F | CF$_3$ | CH$_2$OEt | (D-55c)Cl |
| 3,5-Cl$_2$-4-F | CF$_3$ | CH$_2$OC(O)CH$_3$ | (D-55c)Cl |
| 3,5-Cl$_2$-4-F | CF$_3$ | CH$_2$OC(O)Bu-t | (D-55c)Cl |
| 3,5-Cl$_2$-4-F | CF$_3$ | CH$_2$OC(O)OCH$_3$ | (D-55c)Cl |
| 3,5-Cl$_2$-4-F | CF$_3$ | CH$_2$CN | (D-55c)Cl |
| 3,5-Cl$_2$-4-F | CF$_3$ | C(O)CH$_3$ | (D-55c)Cl |
| 3,5-Cl$_2$-4-F | CF$_3$ | C(O)Et | (D-55c)Cl |
| 3,5-Cl$_2$-4-F | CF$_3$ | C(O)Pr-n | (D-55c)Cl |
| 3,5-Cl$_2$-4-F | CF$_3$ | C(O)Pr-i | (D-55c)Cl |
| 3,5-Cl$_2$-4-F | CF$_3$ | C(O)Pr-c | (D-55c)Cl |
| 3,5-Cl$_2$-4-F | CF$_3$ | C(O)Bu-t | (D-55c)Cl |
| 3,5-Cl$_2$-4-F | CF$_3$ | C(O)CH$_2$Cl | (D-55c)Cl |
| 3,5-Cl$_2$-4-F | CF$_3$ | C(O)CH$_2$OCH$_3$ | (D-55c)Cl |
| 3,5-Cl$_2$-4-F | CF$_3$ | C(O)CH$_2$OEt | (D-55c)Cl |
| 3,5-Cl$_2$-4-F | CF$_3$ | C(O)CH$_2$SCH$_3$ | (D-55c)Cl |
| 3,5-Cl$_2$-4-F | CF$_3$ | C(O)CH$_2$S(O)CH$_3$ | (D-55c)Cl |
| 3,5-Cl$_2$-4-F | CF$_3$ | C(O)C(O)OEt | (D-55c)Cl |
| 3,5-Cl$_2$-4-F | CF$_3$ | C(O)Ph | (D-55c)Cl |
| 3,5-Cl$_2$-4-F | CF$_3$ | C(O)(D-52a) | (D-55c)Cl |
| 3,5-Cl$_2$-4-F | CF$_3$ | C(O)OCH$_3$ | (D-55c)Cl |
| 3,5-Cl$_2$-4-F | CF$_3$ | C(O)OEt | (D-55c)Cl |
| 3,5-Cl$_2$-4-F | CF$_3$ | C(O)OPr-n | (D-55c)Cl |
| 3,5-Cl$_2$-4-F | CF$_3$ | C(O)OPr-i | (D-55c)Cl |
| 3,5-Cl$_2$-4-F | CF$_3$ | C(O)OBu-n | (D-55c)Cl |
| 3,5-Cl$_2$-4-F | CF$_3$ | C(O)OBu-i | (D-55c)Cl |
| 3,5-Cl$_2$-4-F | CF$_3$ | C(O)OCH$_2$Cl | (D-55c)Cl |
| 3,5-Cl$_2$-4-F | CF$_3$ | C(O)OCH$_2$CH$_2$Cl | (D-55c)Cl |
| 3,5-Cl$_2$-4-F | CF$_3$ | C(O)OCH$_2$CH$_2$OCH$_3$ | (D-55c)Cl |
| 3,5-Cl$_2$-4-F | CF$_3$ | C(O)OCH$_2$CH=CH$_2$ | (D-55c)Cl |
| 3,5-Cl$_2$-4-F | CF$_3$ | CH$_3$ | (D-55c)Br |
| 3,5-Cl$_2$-4-F | CF$_3$ | Et | (D-55c)Br |
| 3,5-Cl$_2$-4-F | CF$_3$ | CH$_2$OCH$_3$ | (D-55c)Br |
| 3,5-Cl$_2$-4-F | CF$_3$ | CH$_2$OEt | (D-55c)Br |
| 3,5-Cl$_2$-4-F | CF$_3$ | CH$_2$OC(O)CH$_3$ | (D-55c)Br |
| 3,5-Cl$_2$-4-F | CF$_3$ | C(O)CH$_3$ | (D-55c)Br |
| 3,5-Cl$_2$-4-F | CF$_3$ | C(O)Et | (D-55c)Br |
| 3,5-Cl$_2$-4-F | CF$_3$ | C(O)Pr-n | (D-55c)Br |
| 3,5-Cl$_2$-4-F | CF$_3$ | C(O)Pr-i | (D-55c)Br |
| 3,5-Cl$_2$-4-F | CF$_3$ | C(O)Pr-c | (D-55c)Br |
| 3,5-Cl$_2$-4-F | CF$_3$ | C(O)CH$_2$OCH$_3$ | (D-55c)Br |
| 3,5-Cl$_2$-4-F | CF$_3$ | C(O)OCH$_3$ | (D-55c)Br |
| 3,5-Cl$_2$-4-F | CF$_3$ | C(O)OEt | (D-55c)Br |
| 3,5-Cl$_2$-4-F | CF$_3$ | C(O)OPr-n | (D-55c)Br |
| 3,5-Cl$_2$-4-F | CF$_3$ | C(O)OBu-i | (D-55c)Br |
| 3,5-Cl$_2$-4-F | CF$_3$ | C(O)OCH$_2$Cl | (D-55c)Br |
| 3,5-Cl$_2$-4-F | CF$_3$ | C(O)OCH$_2$CH$_2$OCH$_3$ | (D-55c)Br |
| 3,5-Cl$_2$-4-F | CF$_3$ | CH$_3$ | D-57a |
| 3,5-Cl$_2$-4-F | CF$_3$ | C(O)CH$_3$ | D-57a |
| 3,5-Cl$_2$-4-F | CF$_3$ | C(O)Pr-i | D-57a |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Cl$_2$-4-F | CF$_3$ | CH$_3$ | D-58a |
| 3,5-Cl$_2$-4-F | CF$_2$Cl | H | CH=NOCH$_3$ |
| 3,5-Cl$_2$-4-F | CF$_2$Cl | CH$_2$OCH$_3$ | CH=NOCH$_3$ |
| 3,5-Cl$_2$-4-F | CF$_2$Cl | H | CH=NOEt |
| 3,5-Cl$_2$-4-F | CF$_2$Cl | H | C(O)OCH$_3$ |
| 3,5-Cl$_2$-4-F | CF$_2$Cl | Et | C(O)OCH$_3$ |
| 3,5-Cl$_2$-4-F | CF$_2$Cl | CH$_2$OCH$_3$ | C(O)OCH$_3$ |
| 3,5-Cl$_2$-4-F | CF$_2$Cl | CH$_2$OEt | C(O)OCH$_3$ |
| 3,5-Cl$_2$-4-F | CF$_2$Cl | CH$_2$OCH$_2$CF$_3$ | C(O)OCH$_3$ |
| 3,5-Cl$_2$-4-F | CF$_2$Cl | CH$_2$OC(O)CH$_3$ | C(O)OCH$_3$ |
| 3,5-Cl$_2$-4-F | CF$_2$Cl | CH$_2$OC(O)Et | C(O)OCH$_3$ |
| 3,5-Cl$_2$-4-F | CF$_2$Cl | CH$_2$OC(O)OCH$_3$ | C(O)OCH$_3$ |
| 3,5-Cl$_2$-4-F | CF$_2$Cl | E-5a | C(O)OCH$_3$ |
| 3,5-Cl$_2$-4-F | CF$_2$Cl | C(O)Et | C(O)OCH$_3$ |
| 3,5-Cl$_2$-4-F | CF$_2$Cl | C(O)Pr-n | C(O)OCH$_3$ |
| 3,5-Cl$_2$-4-F | CF$_2$Cl | C(O)Bu-t | C(O)OCH$_3$ |
| 3,5-Cl$_2$-4-F | CF$_2$Cl | C(O)CH$_2$SCH$_3$ | C(O)OCH$_3$ |
| 3,5-Cl$_2$-4-F | CF$_2$Cl | C(O)OCH$_3$ | C(O)OEt |
| 3,5-Cl$_2$-4-F | CF$_2$Cl | H | C(O)OPr-i |
| 3,5-Cl$_2$-4-F | CF$_2$Cl | H | C(O)NH$_2$ |
| 3,5-Cl$_2$-4-F | CF$_2$Cl | C(O)OCH$_3$ | (D-52d)Cl |
| 3,5-Cl$_2$-4-F | CF$_2$Cl | CH$_3$ | (D-55c)Cl |
| 3,5-Cl$_2$-4-F | CF$_2$Cl | CH$_2$OCH$_3$ | (D-55c)Cl |
| 3,5-Cl$_2$-4-F | CF$_2$Cl | C(O)CH$_3$ | (D-55c)Cl |
| 3,5-Cl$_2$-4-F | CF$_2$Cl | C(O)Et | (D-55c)Cl |
| 3,5-Cl$_2$-4-F | CF$_2$Cl | C(O)Pr-i | (D-55c)Cl |
| 3,5-Cl$_2$-4-F | CF$_2$Cl | C(O)CH$_2$OCH$_3$ | (D-55c)Cl |
| 3,5-Cl$_2$-4-F | CF$_2$Cl | C(O)CH$_2$OEt | (D-55c)Cl |
| 3,5-Cl$_2$-4-F | CF$_2$Cl | C(O)CH$_2$SCH$_3$ | (D-55c)Cl |
| 3,5-Cl$_2$-4-F | CF$_2$Cl | C(O)OCH$_3$ | (D-55c)Cl |
| 3,5-Cl$_2$-4-F | CF$_2$Cl | C(O)OPr-n | (D-55c)Cl |
| 3,5-Cl$_2$-4-F | CF$_2$Cl | C(O)OCH$_2$CH$_2$Cl | (D-55c)Cl |
| 3,5-Cl$_2$-4-F | CF$_2$Cl | C(O)OCH$_2$CH$_2$OCH$_3$ | (D-55c)Cl |
| 3,5-Cl$_2$-4-F | CF$_2$Cl | C(O)OCH$_2$CH=CH$_2$ | (D-55c)Cl |
| 3,5-Cl$_2$-4-F | CF$_2$Cl | CH$_2$OC(O)CH$_3$ | (D-55c)Br |
| 3,5-Cl$_2$-4-F | CF$_2$Cl | C(O)CH$_3$ | (D-55c)Br |
| 3,5-Cl$_2$-4-F | CF$_2$Cl | C(O)Et | (D-55c)Br |
| 3,5-Cl$_2$-4-F | CF$_2$Cl | C(O)Pr-n | (D-55c)Br |
| 3,5-Cl$_2$-4-F | CF$_2$Cl | C(O)Pr-i | (D-55c)Br |
| 3,5-Cl$_2$-4-F | CF$_2$Cl | C(O)OCH$_3$ | (D-55c)Br |
| 3,5-Cl$_2$-4-F | CF$_2$Cl | C(O)OEt | (D-55c)Br |
| 3,5-Cl$_2$-4-F | CF$_2$Br | H | CH=NOCH$_3$ |
| 3,5-Cl$_2$-4-F | CF$_2$Br | CH$_2$OEt | C(O)OCH$_3$ |
| 3,5-Cl$_2$-4-F | CF$_2$Br | C(O)Et | C(O)OCH$_3$ |
| 3,5-Cl$_2$-4-F | CF$_2$Br | C(O)CH$_3$ | (D-55c)Cl |
| 3,5-Cl$_2$-4-F | CF$_2$Br | C(O)OCH$_3$ | (D-55c)Cl |
| 3,5-Cl$_2$-4-F | CF$_2$CHF$_2$ | H | CH=NOCH$_3$ |
| 3,5-Cl$_2$-4-F | CF$_2$CHF$_2$ | CH$_2$OEt | C(O)OCH$_3$ |
| 3,5-Cl$_2$-4-F | CF$_2$CHF$_2$ | C(O)Et | C(O)OCH$_3$ |
| 3,5-Cl$_2$-4-F | CF$_2$CHF$_2$ | C(O)CH$_3$ | (D-55c)Cl |
| 3,5-Cl$_2$-4-F | CF$_2$CHF$_2$ | C(O)OCH$_3$ | (D-55c)Cl |
| 3,4,5-Cl$_3$ | CHF$_2$ | H | CH=NOCH$_3$ |
| 3,4,5-Cl$_3$ | CHF$_2$ | H | CH=NOEt |
| 3,4,5-Cl$_3$ | CHF$_2$ | CH$_2$OEt | C(O)OCH$_3$ |
| 3,4,5-Cl$_3$ | CHF$_2$ | CH$_2$OCH2CF$_3$ | C(O)OCH$_3$ |
| 3,4,5-Cl$_3$ | CHF$_2$ | C(O)Et | C(O)OCH$_3$ |
| 3,4,5-Cl$_3$ | CHF$_2$ | C(O)CH$_3$ | (D-55c)Cl |
| 3,4,5-Cl$_3$ | CHF$_2$ | C(O)Pr-i | (D-55c)Cl |
| 3,4,5-Cl$_3$ | CHF$_2$ | C(O)OCH$_3$ | (D-55c)Cl |
| 3,4,5-Cl$_3$ | CHF$_2$ | C(O)CH$_3$ | (D-55c)Br |
| 3,4,5-Cl$_3$ | CHFCl | C(O)Pr-i | (D-55c)Cl |
| 3,4,5-Cl$_3$ | CHCl$_2$ | C(O)OCH$_3$ | (D-55c)Cl |
| 3,4,5-Cl$_3$ | CHFBr | C(O)CH$_3$ | (D-55c)Br |
| 3,4,5-Cl$_3$ | CF$_3$ | H | CH=NOCH$_3$ |
| 3,4,5-Cl$_3$ | CF$_3$ | CH$_2$OCH$_3$ | CH=NOCH$_3$ |
| 3,4,5-Cl$_3$ | CF$_3$ | CH$_2$OEt | CH=NOCH$_3$ |
| 3,4,5-Cl$_3$ | CF$_3$ | H | CH=NOEt |
| 3,4,5-Cl$_3$ | CF$_3$ | CH$_2$OCH$_3$ | CH=NOEt |
| 3,4,5-Cl$_3$ | CF$_3$ | H | CH=NOPr-n |
| 3,4,5-Cl$_3$ | CF$_3$ | H | CH=NOCH$_2$CF$_3$ |
| 3,4,5-Cl$_3$ | CF$_3$ | H | CH=NOCH$_2$CH=CH$_2$ |
| 3,4,5-Cl$_3$ | CF$_3$ | H | CH=NOCH$_2$C=CH |
| 3,4,5-Cl$_3$ | CF$_3$ | H | C(O)OCH$_3$ |
| 3,4,5-Cl$_3$ | CF$_3$ | CH$_3$ | C(O)OCH$_3$ |
| 3,4,5-Cl$_3$ | CF$_3$ | Et | C(O)OCH$_3$ |
| 3,4,5-Cl$_3$ | CF$_3$ | CH$_2$OCH$_3$ | C(O)OCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4,5-Cl$_3$ | CF$_3$ | CH$_2$OEt | C(O)OCH$_3$ |
| 3,4,5-Cl$_3$ | CF$_3$ | CH$_2$OCH2CF$_3$ | C(O)OCH$_3$ |
| 3,4,5-Cl$_3$ | CF$_3$ | CH$_2$OC(O)CH$_3$ | C(O)OCH$_3$ |
| 3,4,5-Cl$_3$ | CF$_3$ | CH$_2$OC(O)Et | C(O)OCH$_3$ |
| 3,4,5-Cl$_3$ | CF$_3$ | CH$_2$OC(O)Bu-t | C(O)OCH$_3$ |
| 3,4,5-Cl$_3$ | CF$_3$ | CH$_2$OC(O)OCH$_3$ | C(O)OCH$_3$ |
| 3,4,5-Cl$_3$ | CF$_3$ | E-5a | C(O)OCH$_3$ |
| 3,4,5-Cl$_3$ | CF$_3$ | CH$_2$NHC(O)OCH$_3$ | C(O)OCH$_3$ |
| 3,4,5-Cl$_3$ | CF$_3$ | CH$_2$CN | C(O)OCH$_3$ |
| 3,4,5-Cl$_3$ | CF$_3$ | CH$_2$C≡CH | C(O)OCH$_3$ |
| 3,4,5-Cl$_3$ | CF$_3$ | CH$_2$Ph | C(O)OCH$_3$ |
| 3,4,5-Cl$_3$ | CF$_3$ | C(O)CH$_3$ | C(O)OCH$_3$ |
| 3,4,5-Cl$_3$ | CF$_3$ | C(O)Et | C(O)OCH$_3$ |
| 3,4,5-Cl$_3$ | CF$_3$ | C(O)Pr-n | C(O)OCH$_3$ |
| 3,4,5-Cl$_3$ | CF$_3$ | C(O)Pr-i | C(O)OCH$_3$ |
| 3,4,5-Cl$_3$ | CF$_3$ | C(O)Bu-t | C(O)OCH$_3$ |
| 3,4,5-Cl$_3$ | CF$_3$ | C(O)CH$_2$Cl | C(O)OCH$_3$ |
| 3,4,5-Cl$_3$ | CF$_3$ | C(O)CH$_2$OCH$_3$ | C(O)OCH$_3$ |
| 3,4,5-Cl$_3$ | CF$_3$ | C(O)CH$_2$OEt | C(O)OCH$_3$ |
| 3,4,5-Cl$_3$ | CF$_3$ | C(O)CH$_2$SCH$_3$ | C(O)OCH$_3$ |
| 3,4,5-Cl$_3$ | CF$_3$ | C(O)Ph | C(O)OCH$_3$ |
| 3,4,5-Cl$_3$ | CF$_3$ | C(O)OCH$_3$ | C(O)OCH$_3$ |
| 3,4,5-Cl$_3$ | CF$_3$ | C(O)OCH$_2$Cl | C(O)OCH$_3$ |
| 3,4,5-Cl$_3$ | CF$_3$ | C(O)OCH$_2$CH$_2$Cl | C(O)OCH$_3$ |
| 3,4,5-Cl$_3$ | CF$_3$ | H | C(O)OEt |
| 3,4,5-Cl$_3$ | CF$_3$ | CH$_3$ | C(O)OEt |
| 3,4,5-Cl$_3$ | CF$_3$ | Et | C(O)OEt |
| 3,4,5-Cl$_3$ | CF$_3$ | CH$_2$OCH$_3$ | C(O)OEt |
| 3,4,5-Cl$_3$ | CF$_3$ | C(O)CH$_3$ | C(O)OEt |
| 3,4,5-Cl$_3$ | CF$_3$ | C(O)Et | C(O)OEt |
| 3,4,5-Cl$_3$ | CF$_3$ | C(O)Bu-t | C(O)OEt |
| 3,4,5-Cl$_3$ | CF$_3$ | C(O)CH$_2$OCH$_3$ | C(O)OEt |
| 3,4,5-Cl$_3$ | CF$_3$ | C(O)OCH$_3$ | C(O)OEt |
| 3,4,5-Cl$_3$ | CF$_3$ | H | C(O)OPr-n |
| 3,4,5-Cl$_3$ | CF$_3$ | H | C(O)OPr-i |
| 3,4,5-Cl$_3$ | CF$_3$ | CH$_3$ | C(O)OPr-i |
| 3,4,5-Cl$_3$ | CF$_3$ | CH$_2$OCH$_3$ | C(O)OPr-i |
| 3,4,5-Cl$_3$ | CF$_3$ | CH$_2$CN | C(O)OPr-i |
| 3,4,5-Cl$_3$ | CF$_3$ | CH$_2$C≡CH | C(O)OPr-i |
| 3,4,5-Cl$_3$ | CF$_3$ | C(O)CH$_3$ | C(O)OPr-i |
| 3,4,5-Cl$_3$ | CF$_3$ | C(O)Et | C(O)OPr-i |
| 3,4,5-Cl$_3$ | CF$_3$ | C(O)Bu-t | C(O)OPr-i |
| 3,4,5-Cl$_3$ | CF$_3$ | C(O)CH$_2$OCH$_3$ | C(O)OPr-i |
| 3,4,5-Cl$_3$ | CF$_3$ | C(O)OCH$_3$ | C(O)OPr-i |
| 3,4,5-Cl$_3$ | CF$_3$ | C(O)OEt | C(O)OPr-i |
| 3,4,5-Cl$_3$ | CF$_3$ | H | C(O)OBu-t |
| 3,4,5-Cl$_3$ | CF$_3$ | C(O)CH$_3$ | C(O)OBu-t |
| 3,4,5-Cl$_3$ | CF$_3$ | C(O)Et | C(O)OBu-t |
| 3,4,5-Cl$_3$ | CF$_3$ | C(O)CH$_2$CF$_3$ | C(O)OBu-t |
| 3,4,5-Cl$_3$ | CF$_3$ | C(O)OCH$_3$ | C(O)OBu-t |
| 3,4,5-Cl$_3$ | CF$_3$ | C(O)OCH$_3$ | C(O)OCH$_2$CH$_2$OCH$_3$ |
| 3,4,5-Cl$_3$ | CF$_3$ | H | C(O)NH$_2$ |
| 3,4,5-Cl$_3$ | CF$_3$ | CH$_3$ | C(O)NH$_2$ |
| 3,4,5-Cl$_3$ | CF$_3$ | CH$_3$ | C(O)NHC(O)CH$_3$ |
| 3,4,5-Cl$_3$ | CF$_3$ | CH$_3$ | C(O)NHC(O)OCH$_3$ |
| 3,4,5-Cl$_3$ | CF$_3$ | H | C(S)NH$_2$ |
| 3,4,5-Cl$_3$ | CF$_3$ | CH$_3$ | D-14a |
| 3,4,5-Cl$_3$ | CF$_3$ | C(O)CH$_3$ | D-14a |
| 3,4,5-Cl$_3$ | CF$_3$ | C(O)OCH$_3$ | D-14a |
| 3,4,5-Cl$_3$ | CF$_3$ | CH$_3$ | (D-52d)Cl |
| 3,4,5-Cl$_3$ | CF$_3$ | CH$_2$OCH$_3$ | (D-52d)Cl |
| 3,4,5-Cl$_3$ | CF$_3$ | C(O)CH$_3$ | (D-52d)Cl |
| 3,4,5-Cl$_3$ | CF$_3$ | C(O)Et | (D-52d)Cl |
| 3,4,5-Cl$_3$ | CF$_3$ | C(O)OCH$_3$ | (D-52d)Cl |
| 3,4,5-Cl$_3$ | CF$_3$ | CH$_3$ | (D-52d)Br |
| 3,4,5-Cl$_3$ | CF$_3$ | C(O)OCH$_3$ | (D-52d)Br |
| 3,4,5-Cl$_3$ | CF$_3$ | CH$_3$ | (D-52d)CN |
| 3,4,5-Cl$_3$ | CF$_3$ | CH$_3$ | (D-53e)Cl |
| 3,4,5-Cl$_3$ | CF$_3$ | C(O)OCH$_3$ | (D-53e)Cl |
| 3,4,5-Cl$_3$ | CF$_3$ | CH$_3$ | D-55a |
| 3,4,5-Cl$_3$ | CF$_3$ | C(O)CH$_3$ | D-55a |
| 3,4,5-Cl$_3$ | CF$_3$ | C(O)Pr-i | D-55a |
| 3,4,5-Cl$_3$ | CF$_3$ | C(O)Bu-t | D-55a |
| 3,4,5-Cl$_3$ | CF$_3$ | CH$_3$ | (D-55c)Cl |
| 3,4,5-Cl$_3$ | CF$_3$ | Et | (D-55c)Cl |
| 3,4,5-Cl$_3$ | CF$_3$ | CH$_2$OCH$_3$ | (D-55c)Cl |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,4,5-Cl$_3$ | CF$_3$ | CH$_2$OEt | (D-55c)Cl |
| 3,4,5-Cl$_3$ | CF$_3$ | CH$_2$OC(O)CH$_3$ | (D-55c)Cl |
| 3,4,5-Cl$_3$ | CF$_3$ | CH$_2$OC(O)Bu-t | (D-55c)Cl |
| 3,4,5-Cl$_3$ | CF$_3$ | CH$_2$OC(O)OCH$_3$ | (D-55c)Cl |
| 3,4,5-Cl$_3$ | CF$_3$ | CH$_2$CN | (D-55c)Cl |
| 3,4,5-Cl$_3$ | CF$_3$ | CH$_2$C≡CH | (D-55c)Cl |
| 3,4,5-Cl$_3$ | CF$_3$ | C(O)CH$_3$ | (D-55c)Cl |
| 3,4,5-Cl$_3$ | CF$_3$ | C(O)Et | (D-55c)Cl |
| 3,4,5-Cl$_3$ | CF$_3$ | C(O)Pr-n | (D-55c)Cl |
| 3,4,5-Cl$_3$ | CF$_3$ | C(O)Pr-i | (D-55c)Cl |
| 3,4,5-Cl$_3$ | CF$_3$ | C(O)Pr-c | (D-55c)Cl |
| 3,4,5-Cl$_3$ | CF$_3$ | C(O)Bu-t | (D-55c)Cl |
| 3,4,5-Cl$_3$ | CF$_3$ | C(O)CH$_2$Cl | (D-55c)Cl |
| 3,4,5-Cl$_3$ | CF$_3$ | C(O)CH$_2$OCH$_3$ | (D-55c)Cl |
| 3,4,5-Cl$_3$ | CF$_3$ | C(O)CH$_2$OEt | (D-55c)Cl |
| 3,4,5-Cl$_3$ | CF$_3$ | C(O)CH$_2$SCH$_3$ | (D-55c)Cl |
| 3,4,5-Cl$_3$ | CF$_3$ | C(O)CH$_2$S(O)CH$_3$ | (D-55c)Cl |
| 3,4,5-Cl$_3$ | CF$_3$ | C(O)C(O)OEt | (D-55c)Cl |
| 3,4,5-Cl$_3$ | CF$_3$ | C(O)Ph | (D-55c)Cl |
| 3,4,5-Cl$_3$ | CF$_3$ | C(O)(D-52a) | (D-55c)Cl |
| 3,4,5-Cl$_3$ | CF$_3$ | C(O)OCH$_3$ | (D-55c)Cl |
| 3,4,5-Cl$_3$ | CF$_3$ | C(O)OEt | (D-55c)Cl |
| 3,4,5-Cl$_3$ | CF$_3$ | C(O)OPr-n | (D-55c)Cl |
| 3,4,5-Cl$_3$ | CF$_3$ | C(O)OPr-i | (D-55c)Cl |
| 3,4,5-Cl$_3$ | CF$_3$ | C(O)OBu-n | (D-55c)Cl |
| 3,4,5-Cl$_3$ | CF$_3$ | C(O)OBu-i | (D-55c)Cl |
| 3,4,5-Cl$_3$ | CF$_3$ | C(O)OBu-t | (D-55c)Cl |
| 3,4,5-Cl$_3$ | CF$_3$ | C(O)OCH$_2$Cl | (D-55c)Cl |
| 3,4,5-Cl$_3$ | CF$_3$ | C(O)OCH$_2$CH$_2$Cl | (D-55c)Cl |
| 3,4,5-Cl$_3$ | CF$_3$ | C(O)OCH$_2$CH$_2$OCH$_3$ | (D-55c)Cl |
| 3,4,5-Cl$_3$ | CF$_3$ | C(O)OCH$_2$CH=CH$_2$ | (D-55c)Cl |
| 3,4,5-Cl$_3$ | CF$_3$ | C(O)OPh | (D-55c)Cl |
| 3,4,5-Cl$_3$ | CF$_3$ | CH$_3$ | (D-55c)Br |
| 3,4,5-Cl$_3$ | CF$_3$ | Et | (D-55c)Br |
| 3,4,5-Cl$_3$ | CF$_3$ | CH$_2$OCH$_3$ | (D-55c)Br |
| 3,4,5-Cl$_3$ | CF$_3$ | CH$_2$OEt | (D-55c)Br |
| 3,4,5-Cl$_3$ | CF$_3$ | CH$_2$OC(O)CH$_3$ | (D-55c)Br |
| 3,4,5-Cl$_3$ | CF$_3$ | C(O)CH$_3$ | (D-55c)Br |
| 3,4,5-Cl$_3$ | CF$_3$ | C(O)Et | (D-55c)Br |
| 3,4,5-Cl$_3$ | CF$_3$ | C(O)Pr-n | (D-55c)Br |
| 3,4,5-Cl$_3$ | CF$_3$ | C(O)Pr-i | (D-55c)Br |
| 3,4,5-Cl$_3$ | CF$_3$ | C(O)Pr-c | (D-55c)Br |
| 3,4,5-Cl$_3$ | CF$_3$ | C(O)Bu-t | (D-55c)Br |
| 3,4,5-Cl$_3$ | CF$_3$ | C(O)CH$_2$OCH$_3$ | (D-55c)Br |
| 3,4,5-Cl$_3$ | CF$_3$ | C(O)Ph | (D-55c)Br |
| 3,4,5-Cl$_3$ | CF$_3$ | C(O)OCH$_3$ | (D-55c)Br |
| 3,4,5-Cl$_3$ | CF$_3$ | C(O)OEt | (D-55c)Br |
| 3,4,5-Cl$_3$ | CF$_3$ | C(O)OPr-n | (D-55c)Br |
| 3,4,5-Cl$_3$ | CF$_3$ | C(O)OBu-i | (D-55c)Br |
| 3,4,5-Cl$_3$ | CF$_3$ | C(O)OCH$_2$Cl | (D-55c)Br |
| 3,4,5-Cl$_3$ | CF$_3$ | C(O)OCH$_2$CH$_2$OCH$_3$ | (D-55c)Br |
| 3,4,5-Cl$_3$ | CF$_3$ | CH$_3$ | D-57a |
| 3,4,5-Cl$_3$ | CF$_3$ | C(O)CH$_3$ | D-57a |
| 3,4,5-Cl$_3$ | CF$_3$ | C(O)Pr-n | D-57a |
| 3,4,5-Cl$_3$ | CF$_3$ | C(O)Pr-i | D-57a |
| 3,4,5-Cl$_3$ | CF$_3$ | C(O)OCH$_3$ | D-57a |
| 3,4,5-Cl$_3$ | CF$_3$ | CH$_3$ | D-58a |
| 3,4,5-Cl$_3$ | CF$_3$ | CH$_3$ | (D-58b)Cl |
| 3,4,5-Cl$_3$ | CF$_3$ | CH$_2$OCH$_3$ | (D-58b)Cl |
| 3,4,5-Cl$_3$ | CF$_3$ | C(O)CH$_3$ | (D-58b)Cl |
| 3,4,5-Cl$_3$ | CF$_3$ | C(O)OCH$_3$ | (D-58b)Cl |
| 3,4,5-Cl$_3$ | CF$_2$Cl | H | CH=NOCH$_3$ |
| 3,4,5-Cl$_3$ | CF$_2$Cl | CH$_2$OCH$_3$ | CH=NOCH$_3$ |
| 3,4,5-Cl$_3$ | CF$_2$Cl | H | CH=NOEt |
| 3,4,5-Cl$_3$ | CF$_2$Cl | H | C(O)OCH$_3$ |
| 3,4,5-Cl$_3$ | CF$_2$Cl | Et | C(O)OCH$_3$ |
| 3,4,5-Cl$_3$ | CF$_2$Cl | CH$_2$OCH$_3$ | C(O)OCH$_3$ |
| 3,4,5-Cl$_3$ | CF$_2$Cl | CH$_2$OEt | C(O)OCH$_3$ |
| 3,4,5-Cl$_3$ | CF$_2$Cl | CH$_2$OCH$_2$CF$_3$ | C(O)OCH$_3$ |
| 3,4,5-Cl$_3$ | CF$_2$Cl | CH$_2$OC(O)CH$_3$ | C(O)OCH$_3$ |
| 3,4,5-Cl$_3$ | CF$_2$Cl | CH$_2$OC(O)Et | C(O)OCH$_3$ |
| 3,4,5-Cl$_3$ | CF$_2$Cl | CH$_2$OC(O)OCH$_3$ | C(O)OCH$_3$ |
| 3,4,5-Cl$_3$ | CF$_2$Cl | E-5a | C(O)OCH$_3$ |
| 3,4,5-Cl$_3$ | CF$_2$Cl | C(O)CH$_3$ | C(O)OCH$_3$ |
| 3,4,5-Cl$_3$ | CF$_2$Cl | C(O)Et | C(O)OCH$_3$ |
| 3,4,5-Cl$_3$ | CF$_2$Cl | C(O)Pr-n | C(O)OCH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,4,5-Cl$_3$ | CF$_2$Cl | C(O)Pr-i | C(O)OCH$_3$ |
| 3,4,5-Cl$_3$ | CF$_2$Cl | C(O)Bu-t | C(O)OCH$_3$ |
| 3,4,5-Cl$_3$ | CF$_2$Cl | C(O)CH$_2$OCH$_3$ | C(O)OCH$_3$ |
| 3,4,5-Cl$_3$ | CF$_2$Cl | C(O)CH$_2$SCH$_3$ | C(O)OCH$_3$ |
| 3,4,5-Cl$_3$ | CF$_2$Cl | C(O)OCH$_3$ | C(O)OEt |
| 3,4,5-Cl$_3$ | CF$_2$Cl | H | C(O)OPr-i |
| 3,4,5-Cl$_3$ | CF$_2$Cl | C(O)OCH$_3$ | C(O)OPr-i |
| 3,4,5-Cl$_3$ | CF$_2$Cl | H | C(O)NH$_2$ |
| 3,4,5-Cl$_3$ | CF$_2$Cl | CH$_3$ | (D-52d)Cl |
| 3,4,5-Cl$_3$ | CF$_2$Cl | CH$_2$OCH$_3$ | (D-52d)Cl |
| 3,4,5-Cl$_3$ | CF$_2$Cl | C(O)OCH$_3$ | (D-52d)Cl |
| 3,4,5-Cl$_3$ | CF$_2$Cl | CH$_3$ | (D-55c)Cl |
| 3,4,5-Cl$_3$ | CF$_2$Cl | CH$_2$OCH$_3$ | (D-52d)Cl |
| 3,4,5-Cl$_3$ | CF$_2$Cl | CH$_2$OC(O)CH$_3$ | (D-52d)Cl |
| 3,4,5-Cl$_3$ | CF$_2$Cl | CH$_2$OC(O)Bu-t | (D-55c)Cl |
| 3,4,5-Cl$_3$ | CF$_2$Cl | CH$_2$OC(O)OCH$_3$ | (D-52d)Cl |
| 3,4,5-Cl$_3$ | CF$_2$Cl | CH$_2$CN | (D-52d)Cl |
| 3,4,5-Cl$_3$ | CF$_2$Cl | C(O)CH$_3$ | (D-55c)Cl |
| 3,4,5-Cl$_3$ | CF$_2$Cl | C(O)Et | (D-52d)Cl |
| 3,4,5-Cl$_3$ | CF$_2$Cl | C(O)Pr-n | (D-55c)Cl |
| 3,4,5-Cl$_3$ | CF$_2$Cl | C(O)Pr-i | (D-52d)Cl |
| 3,4,5-Cl$_3$ | CF$_2$Cl | C(O)Pr-c | (D-52d)Cl |
| 3,4,5-Cl$_3$ | CF$_2$Cl | C(O)Bu-t | (D-55c)Cl |
| 3,4,5-Cl$_3$ | CF$_2$Cl | C(O)CH$_2$Cl | (D-52d)Cl |
| 3,4,5-Cl$_3$ | CF$_2$Cl | C(O)CH$_2$OCH$_3$ | (D-52d)Cl |
| 3,4,5-Cl$_3$ | CF$_2$Cl | C(O)CH$_2$OEt | (D-55c)Cl |
| 3,4,5-Cl$_3$ | CF$_2$Cl | C(O)CH$_2$SCH$_3$ | (D-55c)Cl |
| 3,4,5-Cl$_3$ | CF$_2$Cl | C(O)CH$_2$S(O)CH$_3$ | (D-52d)Cl |
| 3,4,5-Cl$_3$ | CF$_2$Cl | C(O)C(O)OEt | (D-52d)Cl |
| 3,4,5-Cl$_3$ | CF$_2$Cl | C(O)OCH$_3$ | (D-55c)Cl |
| 3,4,5-Cl$_3$ | CF$_2$Cl | C(O)OPr-n | (D-52d)Cl |
| 3,4,5-Cl$_3$ | CF$_2$Cl | C(O)OCH$_2$Cl | (D-52d)Cl |
| 3,4,5-Cl$_3$ | CF$_2$Cl | C(O)OCH$_2$CH$_2$Cl | (D-55c)Cl |
| 3,4,5-Cl$_3$ | CF$_2$Cl | C(O)OCH$_2$CH$_2$OCH$_3$ | (D-52d)Cl |
| 3,4,5-Cl$_3$ | CF$_2$Cl | C(O)OCH$_2$CH=CH$_2$ | (D-55c)Cl |
| 3,4,5-Cl$_3$ | CF$_2$Cl | CH$_3$ | (D-55c)Br |
| 3,4,5-Cl$_3$ | CF$_2$Cl | CH$_2$OC(O)CH$_3$ | (D-55c)Br |
| 3,4,5-Cl$_3$ | CF$_2$Cl | C(O)CH$_3$ | (D-55c)Br |
| 3,4,5-Cl$_3$ | CF$_2$Cl | C(O)Et | (D-55c)Br |
| 3,4,5-Cl$_3$ | CF$_2$Cl | C(O)Pr-n | (D-55c)Br |
| 3,4,5-Cl$_3$ | CF$_2$Cl | C(O)Pr-i | (D-55c)Br |
| 3,4,5-Cl$_3$ | CF$_2$Cl | C(O)OCH$_3$ | (D-55c)Br |
| 3,4,5-Cl$_3$ | CF$_2$Cl | C(O)OEt | (D-55c)Br |
| 3,4,5-Cl$_3$ | CF$_2$Cl | C(O)OCH$_2$CH$_2$OCH$_3$ | (D-55c)Br |
| 3,4,5-Cl$_3$ | CF$_2$Cl | C(O)Pr-i | D-57a |
| 3,4,5-Cl$_3$ | CF$_2$Br | H | CH=NOCH$_3$ |
| 3,4,5-Cl$_3$ | CF$_2$Br | H | CH=NOEt |
| 3,4,5-Cl$_3$ | CF$_2$Br | CH$_2$OEt | C(O)OCH$_3$ |
| 3,4,5-Cl$_3$ | CF$_2$Br | CH$_2$OCH$_2$CF$_3$ | C(O)OCH$_3$ |
| 3,4,5-Cl$_3$ | CF$_2$Br | C(O)Et | C(O)OCH$_3$ |
| 3,4,5-Cl$_3$ | CF$_2$Br | C(O)CH$_3$ | (D-55c)Cl |
| 3,4,5-Cl$_3$ | CF$_2$Br | C(O)Pr-i | (D-55c)Cl |
| 3,4,5-Cl$_3$ | CF$_2$Br | C(O)OCH$_3$ | (D-55c)Cl |
| 3,4,5-Cl$_3$ | CF$_2$Br | C(O)CH$_3$ | (D-55c)Br |
| 3,4,5-Cl$_3$ | CF$_2$CHF$_2$ | H | CH=NOCH$_3$ |
| 3,4,5-Cl$_3$ | CF$_2$CHF$_2$ | H | CH=NOEt |
| 3,4,5-Cl$_3$ | CF$_2$CHF$_2$ | CH$_2$OEt | C(O)OCH$_3$ |
| 3,4,5-Cl$_3$ | CF$_2$CHF$_2$ | CH$_2$OCH$_2$CF$_3$ | C(O)OCH$_3$ |
| 3,4,5-Cl$_3$ | CF$_2$CHF$_2$ | C(O)Et | C(O)OCH$_3$ |
| 3,4,5-Cl$_3$ | CF$_2$CHF$_2$ | C(O)CH$_3$ | (D-55c)Cl |
| 3,4,5-Cl$_3$ | CF$_2$CHF$_2$ | C(O)Pr-i | (D-55c)Cl |
| 3,4,5-Cl$_3$ | CF$_2$CHF$_2$ | C(O)OCH$_3$ | (D-55c)Cl |
| 3,4,5-Cl$_3$ | CF$_2$CHF$_2$ | C(O)CH$_3$ | (D-55c)Br |
| 3,4,5-Cl$_3$ | CF$_2$CF$_3$ | H | CH=NOCH$_3$ |
| 3,4,5-Cl$_3$ | CF$_2$OCH$_3$ | H | CH=NOEt |
| 3,4,5-Cl$_3$ | CF$_2$SCH$_3$ | CH$_2$OEt | C(O)OCH$_3$ |
| 3,4,5-Cl$_3$ | T-3 | CH$_2$OCH$_2$CF$_3$ | C(O)OCH$_3$ |
| 3,5-Br$_2$-4-F | CHF$_2$ | H | CH=NOCH$_3$ |
| 3,5-Br$_2$-4-F | CHF$_2$ | CH$_2$OEt | C(O)OCH$_3$ |
| 3,5-Br$_2$-4-F | CHF$_2$ | C(O)Et | C(O)OCH$_3$ |
| 3,5-Br$_2$-4-F | CHF$_2$ | C(O)CH$_3$ | (D-55c)Cl |
| 3,5-Br$_2$-4-F | CHF$_2$ | C(O)OCH$_3$ | (D-55c)Cl |
| 3,5-Br$_2$-4-F | CF$_3$ | H | CH=NOCH$_3$ |
| 3,5-Br$_2$-4-F | CF$_3$ | CH$_2$OCH$_3$ | CH=NOCH$_3$ |
| 3,5-Br$_2$-4-F | CF$_3$ | CH$_2$OEt | CH=NOCH$_3$ |
| 3,5-Br$_2$-4-F | CF$_3$ | H | CH=NOEt |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Br$_2$-4-F | CF$_3$ | CH$_2$OCH$_3$ | CH=NOEt |
| 3,5-Br$_2$-4-F | CF$_3$ | H | C(O)OCH$_3$ |
| 3,5-Br$_2$-4-F | CF$_3$ | CH$_3$ | C(O)OCH$_3$ |
| 3,5-Br$_2$-4-F | CF$_3$ | Et | C(O)OCH$_3$ |
| 3,5-Br$_2$-4-F | CF$_3$ | CH$_2$OCH$_3$ | C(O)OCH$_3$ |
| 3,5-Br$_2$-4-F | CF$_3$ | CH$_2$OEt | C(O)OCH$_3$ |
| 3,5-Br$_2$-4-F | CF$_3$ | CH$_2$OCH2CF$_3$ | C(O)OCH$_3$ |
| 3,5-Br$_2$-4-F | CF$_3$ | CH$_2$OC(O)CH$_3$ | C(O)OCH$_3$ |
| 3,5-Br$_2$-4-F | CF$_3$ | CH$_2$OC(O)Et | C(O)OCH$_3$ |
| 3,5-Br$_2$-4-F | CF$_3$ | CH$_2$OC(O)Bu-t | C(O)OCH$_3$ |
| 3,5-Br$_2$-4-F | CF$_3$ | CH$_2$OC(O)OCH$_3$ | C(O)OCH$_3$ |
| 3,5-Br$_2$-4-F | CF$_3$ | E-5a | C(O)OCH$_3$ |
| 3,5-Br$_2$-4-F | CF$_3$ | CH$_2$NHC(O)OCH$_3$ | C(O)OCH$_3$ |
| 3,5-Br$_2$-4-F | CF$_3$ | CH$_2$CN | C(O)OCH$_3$ |
| 3,5-Br$_2$-4-F | CF$_3$ | C(O)CH$_3$ | C(O)OCH$_3$ |
| 3,5-Br$_2$-4-F | CF$_3$ | C(O)Et | C(O)OCH$_3$ |
| 3,5-Br$_2$-4-F | CF$_3$ | C(O)Pr-n | C(O)OCH$_3$ |
| 3,5-Br$_2$-4-F | CF$_3$ | C(O)Pr-i | C(O)OCH$_3$ |
| 3,5-Br$_2$-4-F | CF$_3$ | C(O)Bu-t | C(O)OCH$_3$ |
| 3,5-Br$_2$-4-F | CF$_3$ | C(O)CH$_2$OCH$_3$ | C(O)OCH$_3$ |
| 3,5-Br$_2$-4-F | CF$_3$ | C(O)CH$_2$SCH$_3$ | C(O)OCH$_3$ |
| 3,5-Br$_2$-4-F | CF$_3$ | C(O)Ph | C(O)OCH$_3$ |
| 3,5-Br$_2$-4-F | CF$_3$ | C(O)OCH$_2$CH$_2$Cl | C(O)OCH$_3$ |
| 3,5-Br$_2$-4-F | CF$_3$ | H | C(O)OEt |
| 3,5-Br$_2$-4-F | CF$_3$ | CH$_2$OCH$_3$ | C(O)OEt |
| 3,5-Br$_2$-4-F | CF$_3$ | C(O)Bu-t | C(O)OEt |
| 3,5-Br$_2$-4-F | CF$_3$ | C(O)CH$_2$OCH$_3$ | C(O)OEt |
| 3,5-Br$_2$-4-F | CF$_3$ | C(O)OCH$_3$ | C(O)OEt |
| 3,5-Br$_2$-4-F | CF$_3$ | H | C(O)OPr-i |
| 3,5-Br$_2$-4-F | CF$_3$ | C(O)CH$_3$ | C(O)OPr-i |
| 3,5-Br$_2$-4-F | CF$_3$ | C(O)CH$_2$OCH$_3$ | C(O)OPr-i |
| 3,5-Br$_2$-4-F | CF$_3$ | C(O)OCH3 | C(O)OPr-i |
| 3,5-Br$_2$-4-F | CF$_3$ | C(O)OCH$_3$ | C(O)OCH$_2$CH$_2$OCH$_3$ |
| 3,5-Br$_2$-4-F | CF$_3$ | H | C(O)NH$_2$ |
| 3,5-Br$_2$-4-F | CF$_3$ | C(O)CH$_3$ | D-14a |
| 3,5-Br$_2$-4-F | CF$_3$ | CH$_3$ | (D-52d)Cl |
| 3,5-Br$_2$-4-F | CF$_3$ | CH$_2$OCH$_3$ | (D-52d)Cl |
| 3,5-Br$_2$-4-F | CF$_3$ | C(O)Et | (D-52d)Cl |
| 3,5-Br$_2$-4-F | CF$_3$ | C(O)OCH$_3$ | (D-52d)Cl |
| 3,5-Br$_2$-4-F | CF$_3$ | CH$_3$ | (D-52d)Br |
| 3,5-Br$_2$-4-F | CF$_3$ | CH$_3$ | (D-52d)CN |
| 3,5-Br$_2$-4-F | CF$_3$ | CH$_3$ | (D-53e)Cl |
| 3,5-Br$_2$-4-F | CF$_3$ | CH$_3$ | D-55a |
| 3,5-Br$_2$-4-F | CF$_3$ | CH$_3$ | (D-55c)Cl |
| 3,5-Br$_2$-4-F | CF$_3$ | Et | (D-55c)Cl |
| 3,5-Br$_2$-4-F | CF$_3$ | CH$_2$OCH$_3$ | (D-55c)Cl |
| 3,5-Br$_2$-4-F | CF$_3$ | CH$_2$OEt | (D-55c)Cl |
| 3,5-Br$_2$-4-F | CF$_3$ | CH$_2$OC(O)CH$_3$ | (D-55c)Cl |
| 3,5-Br$_2$-4-F | CF$_3$ | CH$_2$OC(O)Bu-t | (D-55c)Cl |
| 3,5-Br$_2$-4-F | CF$_3$ | CH$_2$OC(O)OCH$_3$ | (D-55c)Cl |
| 3,5-Br$_2$-4-F | CF$_3$ | CH$_2$CN | (D-55c)Cl |
| 3,5-Br$_2$-4-F | CF$_3$ | C(O)CH$_3$ | (D-55c)Cl |
| 3,5-Br$_2$-4-F | CF$_3$ | C(O)Et | (D-55c)Cl |
| 3,5-Br$_2$-4-F | CF$_3$ | C(O)Pr-n | (D-55c)Cl |
| 3,5-Br$_2$-4-F | CF$_3$ | C(O)Pr-i | (D-55c)Cl |
| 3,5-Br$_2$-4-F | CF$_3$ | C(O)Pr-c | (D-55c)Cl |
| 3,5-Br$_2$-4-F | CF$_3$ | C(O)Bu-t | (D-55c)Cl |
| 3,5-Br$_2$-4-F | CF$_3$ | C(O)CH$_2$Cl | (D-55c)Cl |
| 3,5-Br$_2$-4-F | CF$_3$ | C(O)CH$_2$OCH$_3$ | (D-55c)Cl |
| 3,5-Br$_2$-4-F | CF$_3$ | C(O)CH$_2$OEt | (D-55c)Cl |
| 3,5-Br$_2$-4-F | CF$_3$ | C(O)CH$_2$SCH$_3$ | (D-55c)Cl |
| 3,5-Br$_2$-4-F | CF$_3$ | C(O)CH$_2$S(O)CH$_3$ | (D-55c)Cl |
| 3,5-Br$_2$-4-F | CF$_3$ | C(O)C(O)OEt | (D-55c)Cl |
| 3,5-Br$_2$-4-F | CF$_3$ | C(O)Ph | (D-55c)Cl |
| 3,5-Br$_2$-4-F | CF$_3$ | C(O)(D-52a) | (D-55c)Cl |
| 3,5-Br$_2$-4-F | CF$_3$ | C(O)OCH$_3$ | (D-55c)Cl |
| 3,5-Br$_2$-4-F | CF$_3$ | C(O)OEt | (D-55c)Cl |
| 3,5-Br$_2$-4-F | CF$_3$ | C(O)OPr-n | (D-55c)Cl |
| 3,5-Br$_2$-4-F | CF$_3$ | C(O)OPr-i | (D-55c)Cl |
| 3,5-Br$_2$-4-F | CF$_3$ | C(O)OBu-n | (D-55c)Cl |
| 3,5-Br$_2$-4-F | CF$_3$ | C(O)OBu-i | (D-55c)Cl |
| 3,5-Br$_2$-4-F | CF$_3$ | C(O)OCH$_2$Cl | (D-55c)Cl |
| 3,5-Br$_2$-4-F | CF$_3$ | C(O)OCH$_2$CH$_2$Cl | (D-55c)Cl |
| 3,5-Br$_2$-4-F | CF$_3$ | C(O)OCH$_2$CH$_2$OCH$_3$ | (D-55c)Cl |
| 3,5-Br$_2$-4-F | CF$_3$ | C(O)OCH$_2$CH=CH$_2$ | (D-55c)Cl |
| 3,5-Br$_2$-4-F | CF$_3$ | CH$_3$ | (D-55c)Br |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-Br$_2$-4-F | CF$_3$ | Et | (D-55c)Br |
| 3,5-Br$_2$-4-F | CF$_3$ | CH$_2$OCH$_3$ | (D-55c)Br |
| 3,5-Br$_2$-4-F | CF$_3$ | CH$_2$OEt | (D-55c)Br |
| 3,5-Br$_2$-4-F | CF$_3$ | CH$_2$OC(O)CH$_3$ | (D-55c)Br |
| 3,5-Br$_2$-4-F | CF$_3$ | C(O)CH$_3$ | (D-55c)Br |
| 3,5-Br$_2$-4-F | CF$_3$ | C(O)Et | (D-55c)Br |
| 3,5-Br$_2$-4-F | CF$_3$ | C(O)Pr-n | (D-55c)Br |
| 3,5-Br$_2$-4-F | CF$_3$ | C(O)Pr-i | (D-55c)Br |
| 3,5-Br$_2$-4-F | CF$_3$ | C(O)Pr-c | (D-55c)Br |
| 3,5-Br$_2$-4-F | CF$_3$ | C(O)CH$_2$OCH$_3$ | (D-55c)Br |
| 3,5-Br$_2$-4-F | CF$_3$ | C(O)OCH$_3$ | (D-55c)Br |
| 3,5-Br$_2$-4-F | CF$_3$ | C(O)OEt | (D-55c)Br |
| 3,5-Br$_2$-4-F | CF$_3$ | C(O)OPr-n | (D-55c)Br |
| 3,5-Br$_2$-4-F | CF$_3$ | C(O)OBu-i | (D-55c)Br |
| 3,5-Br$_2$-4-F | CF$_3$ | C(O)OCH$_2$Cl | (D-55c)Br |
| 3,5-Br$_2$-4-F | CF$_3$ | C(O)OCH$_2$CH$_2$OCH$_3$ | (D-55c)Br |
| 3,5-Br$_2$-4-F | CF$_3$ | CH$_3$ | D-57a |
| 3,5-Br$_2$-4-F | CF$_3$ | C(O)CH$_3$ | D-57a |
| 3,5-Br$_2$-4-F | CF$_3$ | C(O)Pr-i | D-57a |
| 3,5-Br$_2$-4-F | CF$_3$ | CH$_3$ | D-58a |
| 3,5-Br$_2$-4-F | CF$_2$Cl | H | CH=NOCH$_3$ |
| 3,5-Br$_2$-4-F | CF$_2$Cl | CH$_2$OCH$_3$ | CH=NOCH$_3$ |
| 3,5-Br$_2$-4-F | CF$_2$Cl | H | CH=NOEt |
| 3,5-Br$_2$-4-F | CF$_2$Cl | H | C(O)OCH$_3$ |
| 3,5-Br$_2$-4-F | CF$_2$Cl | Et | C(O)OCH$_3$ |
| 3,5-Br$_2$-4-F | CF$_2$Cl | CH$_2$OCH$_3$ | C(O)OCH$_3$ |
| 3,5-Br$_2$-4-F | CF$_2$Cl | CH$_2$OEt | C(O)OCH$_3$ |
| 3,5-Br$_2$-4-F | CF$_2$Cl | CH$_2$OCH2CF$_3$ | C(O)OCH$_3$ |
| 3,5-Br$_2$-4-F | CF$_2$Cl | CH$_2$OC(O)CH$_3$ | C(O)OCH$_3$ |
| 3,5-Br$_2$-4-F | CF$_2$Cl | CH$_2$OC(O)Et | C(O)OCH$_3$ |
| 3,5-Br$_2$-4-F | CF$_2$Cl | CH$_2$OC(O)OCH$_3$ | C(O)OCH$_3$ |
| 3,5-Br$_2$-4-F | CF$_2$Cl | E-5a | C(O)OCH$_3$ |
| 3,5-Br$_2$-4-F | CF$_2$Cl | C(O)Et | C(O)OCH$_3$ |
| 3,5-Br$_2$-4-F | CF$_2$Cl | C(O)Pr-n | C(O)OCH$_3$ |
| 3,5-Br$_2$-4-F | CF$_2$Cl | C(O)Bu-t | C(O)OCH$_3$ |
| 3,5-Br$_2$-4-F | CF$_2$Cl | C(O)CH$_2$SCH$_3$ | C(O)OCH$_3$ |
| 3,5-Br$_2$-4-F | CF$_2$Cl | C(O)OCH$_3$ | C(O)OEt |
| 3,5-Br$_2$-4-F | CF$_2$Cl | C(O)OCH$_3$ | C(O)OPr-i |
| 3,5-Br$_2$-4-F | CF$_2$Cl | H | C(O)NH$_2$ |
| 3,5-Br$_2$-4-F | CF$_2$Cl | C(O)OCH$_3$ | (D-52d)Cl |
| 3,5-Br$_2$-4-F | CF$_2$Cl | CH$_3$ | (D-55c)Cl |
| 3,5-Br$_2$-4-F | CF$_2$Cl | CH$_2$OCH$_3$ | (D-55c)Cl |
| 3,5-Br$_2$-4-F | CF$_2$Cl | C(O)CH$_3$ | (D-55c)Cl |
| 3,5-Br$_2$-4-F | CF$_2$Cl | C(O)Et | (D-55c)Cl |
| 3,5-Br$_2$-4-F | CF$_2$Cl | C(O)Pr-i | (D-55c)Cl |
| 3,5-Br$_2$-4-F | CF$_2$Cl | C(O)CH$_2$OCH$_3$ | (D-55c)Cl |
| 3,5-Br$_2$-4-F | CF$_2$Cl | C(O)CH$_2$OEt | (D-55c)Cl |
| 3,5-Br$_2$-4-F | CF$_2$Cl | C(O)CH$_2$SCH$_3$ | (D-55c)Cl |
| 3,5-Br$_2$-4-F | CF$_2$Cl | C(O)OCH$_3$ | (D-55c)Cl |
| 3,5-Br$_2$-4-F | CF$_2$Cl | C(O)OPr-n | (D-55c)Cl |
| 3,5-Br$_2$-4-F | CF$_2$Cl | C(O)OCH$_2$CH$_2$Cl | (D-55c)Cl |
| 3,5-Br$_2$-4-F | CF$_2$Cl | C(O)OCH$_2$CH$_2$OCH$_3$ | (D-55c)Cl |
| 3,5-Br$_2$-4-F | CF$_2$Cl | C(O)OCH$_2$CH=CH$_2$ | (D-55c)Cl |
| 3,5-Br$_2$-4-F | CF$_2$Cl | CH$_2$OC(O)CH$_3$ | (D-55c)Br |
| 3,5-Br$_2$-4-F | CF$_2$Cl | C(O)CH$_3$ | (D-55c)Br |
| 3,5-Br$_2$-4-F | CF$_2$Cl | C(O)Et | (D-55c)Br |
| 3,5-Br$_2$-4-F | CF$_2$Cl | C(O)Pr-n | (D-55c)Br |
| 3,5-Br$_2$-4-F | CF$_2$Cl | C(O)Pr-i | (D-55c)Br |
| 3,5-Br$_2$-4-F | CF$_2$Cl | C(O)OCH$_3$ | (D-55c)Br |
| 3,5-Br$_2$-4-F | CF$_2$Cl | C(O)OEt | (D-55c)Br |
| 3,5-Br$_2$-4-F | CF$_2$Br | H | CH=NOCH$_3$ |
| 3,5-Br$_2$-4-F | CF$_2$Br | CH$_2$OEt | C(O)OCH$_3$ |
| 3,5-Br$_2$-4-F | CF$_2$Br | C(O)Et | C(O)OCH$_3$ |
| 3,5-Br$_2$-4-F | CF$_2$Br | C(O)CH$_3$ | (D-55c)Cl |
| 3,5-Br$_2$-4-F | CF$_2$Br | C(O)OCH$_3$ | (D-55c)Cl |
| 3,5-Br$_2$-4-F | CF$_2$CHF$_2$ | H | CH=NOCH$_3$ |
| 3,5-Br$_2$-4-F | CF$_2$CHF$_2$ | CH$_2$OEt | C(O)OCH$_3$ |
| 3,5-Br$_2$-4-F | CF$_2$CHF$_2$ | C(O)Et | C(O)OCH$_3$ |
| 3,5-Br$_2$-4-F | CF$_2$CHF$_2$ | C(O)CH$_3$ | (D-55c)Cl |
| 3,5-Br$_2$-4-F | CF$_2$CHF$_2$ | C(O)OCH$_3$ | (D-55c)Cl |
| 3,4,5-Br$_3$ | CF$_3$ | H | CH=NOCH$_3$ |
| 3,4,5-Br$_3$ | CF$_3$ | CH$_2$OCH$_3$ | CH=NOCH$_3$ |
| 3,4,5-Br$_3$ | CF$_3$ | H | CH=NOEt |
| 3,4,5-Br$_3$ | CF$_3$ | H | C(O)OCH$_3$ |
| 3,4,5-Br$_3$ | CF$_3$ | Et | C(O)OCH$_3$ |
| 3,4,5-Br$_3$ | CF$_3$ | CH$_2$OCH$_3$ | C(O)OCH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,4,5-Br$_3$ | CF$_3$ | CH$_2$OEt | C(O)OCH$_3$ |
| 3,4,5-Br$_3$ | CF$_3$ | CH$_2$OCH$_2$CF$_3$ | C(O)OCH$_3$ |
| 3,4,5-Br$_3$ | CF$_3$ | CH$_2$OC(O)CH$_3$ | C(O)OCH$_3$ |
| 3,4,5-Br$_3$ | CF$_3$ | CH$_2$OC(O)Et | C(O)OCH$_3$ |
| 3,4,5-Br$_3$ | CF$_3$ | CH$_2$OC(O)OCH$_3$ | C(O)OCH$_3$ |
| 3,4,5-Br$_3$ | CF$_3$ | E-5a | C(O)OCH$_3$ |
| 3,4,5-Br$_3$ | CF$_3$ | C(O)Et | C(O)OCH$_3$ |
| 3,4,5-Br$_3$ | CF$_3$ | C(O)Pr-n | C(O)OCH$_3$ |
| 3,4,5-Br$_3$ | CF$_3$ | C(O)Bu-t | C(O)OCH$_3$ |
| 3,4,5-Br$_3$ | CF$_3$ | C(O)CH$_2$SCH$_3$ | C(O)OCH$_3$ |
| 3,4,5-Br$_3$ | CF$_3$ | C(O)OCH$_3$ | C(O)OEt |
| 3,4,5-Br$_3$ | CF$_3$ | H | C(O)OPr-i |
| 3,4,5-Br$_3$ | CF$_3$ | H | C(O)NH$_2$ |
| 3,4,5-Br$_3$ | CF$_3$ | C(O)OCH$_3$ | (D-52d)Cl |
| 3,4,5-Br$_3$ | CF$_3$ | CH$_3$ | (D-55c)Cl |
| 3,4,5-Br$_3$ | CF$_3$ | CH$_2$OCH$_3$ | (D-55c)Cl |
| 3,4,5-Br$_3$ | CF$_3$ | C(O)CH$_3$ | (D-55c)Cl |
| 3,4,5-Br$_3$ | CF$_3$ | C(O)Et | (D-55c)Cl |
| 3,4,5-Br$_3$ | CF$_3$ | C(O)Pr-i | (D-55c)Cl |
| 3,4,5-Br$_3$ | CF$_3$ | C(O)CH$_2$OCH$_3$ | (D-55c)Cl |
| 3,4,5-Br$_3$ | CF$_3$ | C(O)CH$_2$OEt | (D-55c)Cl |
| 3,4,5-Br$_3$ | CF$_3$ | C(O)CH$_2$SCH$_3$ | (D-55c)Cl |
| 3,4,5-Br$_3$ | CF$_3$ | C(O)OCH$_3$ | (D-55c)Cl |
| 3,4,5-Br$_3$ | CF$_3$ | C(O)OPr-n | (D-55c)Cl |
| 3,4,5-Br$_3$ | CF$_3$ | C(O)OCH$_2$CH$_2$Cl | (D-55c)Cl |
| 3,4,5-Br$_3$ | CF$_3$ | C(O)OCH$_2$CH$_2$OCH$_3$ | (D-55c)Cl |
| 3,4,5-Br$_3$ | CF$_3$ | C(O)OCH$_2$CH=CH$_2$ | (D-55c)Cl |
| 3,4,5-Br$_3$ | CF$_3$ | CH$_2$OC(O)CH$_3$ | (D-55c)Br |
| 3,4,5-Br$_3$ | CF$_3$ | C(O)CH$_3$ | (D-55c)Br |
| 3,4,5-Br$_3$ | CF$_3$ | C(O)Et | (D-55c)Br |
| 3,4,5-Br$_3$ | CF$_3$ | C(O)Pr-n | (D-55c)Br |
| 3,4,5-Br$_3$ | CF$_3$ | C(O)Pr-i | (D-55c)Br |
| 3,4,5-Br$_3$ | CF$_3$ | C(O)OCH$_3$ | (D-55c)Br |
| 3,4,5-Br$_3$ | CF$_3$ | C(O)OEt | (D-55c)Br |
| 3,4,5-Br$_3$ | CF$_2$Cl | H | CH=NOCH$_3$ |
| 3,4,5-Br$_3$ | CF$_2$Cl | H | CH=NOEt |
| 3,4,5-Br$_3$ | CF$_2$Cl | CH$_2$OEt | C(O)OCH$_3$ |
| 3,4,5-Br$_3$ | CF$_2$Cl | CH$_2$OCH$_2$CF$_3$ | C(O)OCH$_3$ |
| 3,4,5-Br$_3$ | CF$_2$Cl | C(O)Et | C(O)OCH$_3$ |
| 3,4,5-Br$_3$ | CF$_2$Cl | C(O)CH$_3$ | (D-55c)Cl |
| 3,4,5-Br$_3$ | CF$_2$Cl | C(O)Pr-i | (D-55c)Cl |
| 3,4,5-Br$_3$ | CF$_2$Cl | C(O)OCH$_3$ | (D-55c)Cl |
| 3,4,5-Br$_3$ | CF$_2$Cl | C(O)CH$_3$ | (D-55c)Br |
| 2,3-F$_2$-4-CH$_3$ | CF$_3$ | C(O)Et | C(O)OCH$_3$ |
| 3,5-F$_2$-4-CH$_3$ | CF$_3$ | C(O)CH$_3$ | (D-55c)Cl |
| 2-F-3-CH$_3$-5-Cl | CF$_3$ | C(O)Pr-i | (D-55c)Cl |
| 3,5-Cl$_2$-4-CH$_3$ | CF$_3$ | H | CH=NOCH$_3$ |
| 3,5-Cl$_2$-4-CH$_3$ | CF$_3$ | CH$_2$OEt | C(O)OCH$_3$ |
| 3,5-Cl$_2$-4-CH$_3$ | CF$_3$ | C(O)Et | C(O)OCH$_3$ |
| 3,5-Cl$_2$-4-CH$_3$ | CF$_3$ | C(O)CH$_3$ | (D-55c)Cl |
| 3,5-Cl$_2$-4-CH$_3$ | CF$_3$ | C(O)OCH$_3$ | (D-55c)Cl |
| 3,5-Br$_2$-4-CH$_3$ | CF$_3$ | H | CH=NOCH$_3$ |
| 3,5-Br$_2$-4-CH$_3$ | CF$_3$ | CH$_2$OEt | C(O)OCH$_3$ |
| 3,5-Br$_2$-4-CH$_3$ | CF$_3$ | C(O)Et | C(O)OCH$_3$ |
| 3,5-Br$_2$-4-CH$_3$ | CF$_3$ | C(O)CH$_3$ | (D-55c)Cl |
| 3,5-Br$_2$-4-CH$_3$ | CF$_3$ | C(O)OCH$_3$ | (D-55c)Cl |
| 2,3-F$_2$-4-CF$_3$ | CF$_3$ | C(O)OCH$_3$ | (D-55c)Cl |
| 3,4-F$_2$-5-CF$_3$ | CHF$_2$ | H | CH=NOCH$_3$ |
| 3,4-F$_2$-5-CF$_3$ | CHF$_2$ | CH$_2$OEt | C(O)OCH$_3$ |
| 3,4-F$_2$-5-CF$_3$ | CHF$_2$ | C(O)Et | C(O)OCH$_3$ |
| 3,4-F$_2$-5-CF$_3$ | CHF$_2$ | C(O)CH$_3$ | (D-55c)Cl |
| 3,4-F$_2$-5-CF$_3$ | CHF$_2$ | C(O)OCH$_3$ | (D-55c)Cl |
| 3,4-F$_2$-5-CF$_3$ | CF$_3$ | H | CH=NOCH$_3$ |
| 3,4-F$_2$-5-CF$_3$ | CF$_3$ | CH$_2$OCH$_3$ | CH=NOCH$_3$ |
| 3,4-F$_2$-5-CF$_3$ | CF$_3$ | CH$_2$OEt | CH=NOCH$_3$ |
| 3,4-F$_2$-5-CF$_3$ | CF$_3$ | H | CH=NOEt |
| 3,4-F$_2$-5-CF$_3$ | CF$_3$ | CH$_2$OCH$_3$ | CH=NOEt |
| 3,4-F$_2$-5-CF$_3$ | CF$_3$ | H | C(O)OCH$_3$ |
| 3,4-F$_2$-5-CF$_3$ | CF$_3$ | CH$_3$ | C(O)OCH$_3$ |
| 3,4-F$_2$-5-CF$_3$ | CF$_3$ | Et | C(O)OCH$_3$ |
| 3,4-F$_2$-5-CF$_3$ | CF$_3$ | CH$_2$OCH$_3$ | C(O)OCH$_3$ |
| 3,4-F$_2$-5-CF$_3$ | CF$_3$ | CH$_2$OEt | C(O)OCH$_3$ |
| 3,4-F$_2$-5-CF$_3$ | CF$_3$ | CH$_2$OCH$_2$CF$_3$ | C(O)OCH$_3$ |
| 3,4-F$_2$-5-CF$_3$ | CF$_3$ | CH$_2$OC(O)CH$_3$ | C(O)OCH$_3$ |
| 3,4-F$_2$-5-CF$_3$ | CF$_3$ | CH$_2$OC(O)Et | C(O)OCH$_3$ |
| 3,4-F$_2$-5-CF$_3$ | CF$_3$ | CH$_2$OC(O)Bu-t | C(O)OCH$_3$ |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,4-F$_2$-5-CF$_3$ | CF$_3$ | CH$_2$OC(O)OCH$_3$ | C(O)OCH$_3$ |
| 3,4-F$_2$-5-CF$_3$ | CF$_3$ | E-5a | C(O)OCH$_3$ |
| 3,4-F$_2$-5-CF$_3$ | CF$_3$ | CH$_2$NHC(O)OCH$_3$ | C(O)OCH$_3$ |
| 3,4-F$_2$-5-CF$_3$ | CF$_3$ | CH$_2$CN | C(O)OCH$_3$ |
| 3,4-F$_2$-5-CF$_3$ | CF$_3$ | C(O)CH$_3$ | C(O)OCH$_3$ |
| 3,4-F$_2$-5-CF$_3$ | CF$_3$ | C(O)Et | C(O)OCH$_3$ |
| 3,4-F$_2$-5-CF$_3$ | CF$_3$ | C(O)Pr-n | C(O)OCH$_3$ |
| 3,4-F$_2$-5-CF$_3$ | CF$_3$ | C(O)Pr-i | C(O)OCH$_3$ |
| 3,4-F$_2$-5-CF$_3$ | CF$_3$ | C(O)Bu-t | C(O)OCH$_3$ |
| 3,4-F$_2$-5-CF$_3$ | CF$_3$ | C(O)CH$_2$OCH$_3$ | C(O)OCH$_3$ |
| 3,4-F$_2$-5-CF$_3$ | CF$_3$ | C(O)CH$_2$SCH$_3$ | C(O)OCH$_3$ |
| 3,4-F$_2$-5-CF$_3$ | CF$_3$ | C(O)Ph | C(O)OCH$_3$ |
| 3,4-F$_2$-5-CF$_3$ | CF$_3$ | C(O)OCH$_2$CH$_2$Cl | C(O)OCH$_3$ |
| 3,4-F$_2$-5-CF$_3$ | CF$_3$ | H | C(O)OEt |
| 3,4-F$_2$-5-CF$_3$ | CF$_3$ | CH$_2$OCH$_3$ | C(O)OEt |
| 3,4-F$_2$-5-CF$_3$ | CF$_3$ | C(O)Bu-t | C(O)OEt |
| 3,4-F$_2$-5-CF$_3$ | CF$_3$ | C(O)CH$_2$OCH$_3$ | C(O)OEt |
| 3,4-F$_2$-5-CF$_3$ | CF$_3$ | C(O)OCH$_3$ | C(O)OEt |
| 3,4-F$_2$-5-CF$_3$ | CF$_3$ | H | C(O)OPr-i |
| 3,4-F$_2$-5-CF$_3$ | CF$_3$ | C(O)CH$_3$ | C(O)OPr-i |
| 3,4-F$_2$-5-CF$_3$ | CF$_3$ | C(O)CH$_2$OCH$_3$ | C(O)OPr-i |
| 3,4-F$_2$-5-CF$_3$ | CF$_3$ | C(O)OCH$_3$ | C(O)OPr-i |
| 3,4-F$_2$-5-CF$_3$ | CF$_3$ | C(O)OCH$_3$ | C(O)OCH$_2$CH$_2$OCH$_3$ |
| 3,4-F$_2$-5-CF$_3$ | CF$_3$ | H | C(O)NH$_2$ |
| 3,4-F$_2$-5-CF$_3$ | CF$_3$ | C(O)CH$_3$ | D-14a |
| 3,4-F$_2$-5-CF$_3$ | CF$_3$ | CH$_3$ | (D-52d)Cl |
| 3,4-F$_2$-5-CF$_3$ | CF$_3$ | CH$_2$OCH$_3$ | (D-52d)Cl |
| 3,4-F$_2$-5-CF$_3$ | CF$_3$ | C(O)Et | (D-52d)Cl |
| 3,4-F$_2$-5-CF$_3$ | CF$_3$ | C(O)OCH$_3$ | (D-52d)Cl |
| 3,4-F$_2$-5-CF$_3$ | CF$_3$ | CH$_3$ | (D-52d)Br |
| 3,4-F$_2$-5-CF$_3$ | CF$_3$ | CH$_3$ | (D-52d)CN |
| 3,4-F$_2$-5-CF$_3$ | CF$_3$ | CH$_3$ | (D-53e)Cl |
| 3,4-F$_2$-5-CF$_3$ | CF$_3$ | CH$_3$ | D-55a |
| 3,4-F$_2$-5-CF$_3$ | CF$_3$ | CH$_3$ | (D-55c)Cl |
| 3,4-F$_2$-5-CF$_3$ | CF$_3$ | Et | (D-55c)Cl |
| 3,4-F$_2$-5-CF$_3$ | CF$_3$ | CH$_2$OCH$_3$ | (D-55c)Cl |
| 3,4-F$_2$-5-CF$_3$ | CF$_3$ | CH$_2$OEt | (D-55c)Cl |
| 3,4-F$_2$-5-CF$_3$ | CF$_3$ | CH$_2$OC(O)CH$_3$ | (D-55c)Cl |
| 3,4-F$_2$-5-CF$_3$ | CF$_3$ | CH$_2$OC(O)Bu-t | (D-55c)Cl |
| 3,4-F$_2$-5-CF$_3$ | CF$_3$ | CH$_2$OC(O)OCH$_3$ | (D-55c)Cl |
| 3,4-F$_2$-5-CF$_3$ | CF$_3$ | CH$_2$CN | (D-55c)Cl |
| 3,4-F$_2$-5-CF$_3$ | CF$_3$ | C(O)CH$_3$ | (D-55c)Cl |
| 3,4-F$_2$-5-CF$_3$ | CF$_3$ | C(O)Et | (D-55c)Cl |
| 3,4-F$_2$-5-CF$_3$ | CF$_3$ | C(O)Pr-n | (D-55c)Cl |
| 3,4-F$_2$-5-CF$_3$ | CF$_3$ | C(O)Pr-i | (D-55c)Cl |
| 3,4-F$_2$-5-CF$_3$ | CF$_3$ | C(O)Pr-c | (D-55c)Cl |
| 3,4-F$_2$-5-CF$_3$ | CF$_3$ | C(O)Bu-t | (D-55c)Cl |
| 3,4-F$_2$-5-CF$_3$ | CF$_3$ | C(O)CH$_2$Cl | (D-55c)Cl |
| 3,4-F$_2$-5-CF$_3$ | CF$_3$ | C(O)CH$_2$OCH$_3$ | (D-55c)Cl |
| 3,4-F$_2$-5-CF$_3$ | CF$_3$ | C(O)CH$_2$OEt | (D-55c)Cl |
| 3,4-F$_2$-5-CF$_3$ | CF$_3$ | C(O)CH$_2$SCH$_3$ | (D-55c)Cl |
| 3,4-F$_2$-5-CF$_3$ | CF$_3$ | C(O)CH$_2$S(O)CH$_3$ | (D-55c)Cl |
| 3,4-F$_2$-5-CF$_3$ | CF$_3$ | C(O)C(O)OEt | (D-55c)Cl |
| 3,4-F$_2$-5-CF$_3$ | CF$_3$ | C(O)Ph | (D-55c)Cl |
| 3,4-F$_2$-5-CF$_3$ | CF$_3$ | C(O)(D-52a) | (D-55c)Cl |
| 3,4-F$_2$-5-CF$_3$ | CF$_3$ | C(O)OCH$_3$ | (D-55c)Cl |
| 3,4-F$_2$-5-CF$_3$ | CF$_3$ | C(O)OEt | (D-55c)Cl |
| 3,4-F$_2$-5-CF$_3$ | CF$_3$ | C(O)OPr-n | (D-55c)Cl |
| 3,4-F$_2$-5-CF$_3$ | CF$_3$ | C(O)OPr-i | (D-55c)Cl |
| 3,4-F$_2$-5-CF$_3$ | CF$_3$ | C(O)OBu-n | (D-55c)Cl |
| 3,4-F$_2$-5-CF$_3$ | CF$_3$ | C(O)OBu-i | (D-55c)Cl |
| 3,4-F$_2$-5-CF$_3$ | CF$_3$ | C(O)OCH$_2$Cl | (D-55c)Cl |
| 3,4-F$_2$-5-CF$_3$ | CF$_3$ | C(O)OCH$_2$CH$_2$Cl | (D-55c)Cl |
| 3,4-F$_2$-5-CF$_3$ | CF$_3$ | C(O)OCH$_2$CH$_2$OCH$_3$ | (D-55c)Cl |
| 3,4-F$_2$-5-CF$_3$ | CF$_3$ | C(O)OCH$_2$CH=CH$_2$ | (D-55c)Cl |
| 3,4-F$_2$-5-CF$_3$ | CF$_3$ | CH$_3$ | (D-55c)Br |
| 3,4-F$_2$-5-CF$_3$ | CF$_3$ | Et | (D-55c)Br |
| 3,4-F$_2$-5-CF$_3$ | CF$_3$ | CH$_2$OCH$_3$ | (D-55c)Br |
| 3,4-F$_2$-5-CF$_3$ | CF$_3$ | CH$_2$OEt | (D-55c)Br |
| 3,4-F$_2$-5-CF$_3$ | CF$_3$ | CH$_2$OC(O)CH$_3$ | (D-55c)Br |
| 3,4-F$_2$-5-CF$_3$ | CF$_3$ | C(O)CH$_3$ | (D-55c)Br |
| 3,4-F$_2$-5-CF$_3$ | CF$_3$ | C(O)Et | (D-55c)Br |
| 3,4-F$_2$-5-CF$_3$ | CF$_3$ | C(O)Pr-n | (D-55c)Br |
| 3,4-F$_2$-5-CF$_3$ | CF$_3$ | C(O)Pr-i | (D-55c)Br |
| 3,4-F$_2$-5-CF$_3$ | CF$_3$ | C(O)Pr-c | (D-55c)Br |
| 3,4-F$_2$-5-CF$_3$ | CF$_3$ | C(O)CH$_2$OCH$_3$ | (D-55c)Br |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,4-F$_2$-5-CF$_3$ | CF$_3$ | C(O)OCH$_3$ | (D-55c)Br |
| 3,4-F$_2$-5-CF$_3$ | CF$_3$ | C(O)OEt | (D-55c)Br |
| 3,4-F$_2$-5-CF$_3$ | CF$_3$ | C(O)OPr-n | (D-55c)Br |
| 3,4-F$_2$-5-CF$_3$ | CF$_3$ | C(O)OBu-i | (D-55c)Br |
| 3,4-F$_2$-5-CF$_3$ | CF$_3$ | C(O)OCH$_2$Cl | (D-55c)Br |
| 3,4-F$_2$-5-CF$_3$ | CF$_3$ | C(O)OCH$_2$CH$_2$OCH$_3$ | (D-55c)Br |
| 3,4-F$_2$-5-CF$_3$ | CF$_3$ | CH$_3$ | D-57a |
| 3,4-F$_2$-5-CF$_3$ | CF$_3$ | C(O)CH$_3$ | D-57a |
| 3,4-F$_2$-5-CF$_3$ | CF$_3$ | C(O)Pr-i | D-57a |
| 3,4-F$_2$-5-CF$_3$ | CF$_3$ | CH$_3$ | D-58a |
| 3,4-F$_2$-5-CF$_3$ | CF$_2$Cl | H | CH=NOCH$_3$ |
| 3,4-F$_2$-5-CF$_3$ | CF$_2$Cl | CH$_2$OCH$_3$ | CH=NOCH$_3$ |
| 3,4-F$_2$-5-CF$_3$ | CF$_2$Cl | H | CH=NOEt |
| 3,4-F$_2$-5-CF$_3$ | CF$_2$Cl | H | C(O)OCH$_3$ |
| 3,4-F$_2$-5-CF$_3$ | CF$_2$Cl | Et | C(O)OCH$_3$ |
| 3,4-F$_2$-5-CF$_3$ | CF$_2$Cl | CH$_2$OCH$_3$ | C(O)OCH$_3$ |
| 3,4-F$_2$-5-CF$_3$ | CF$_2$Cl | CH$_2$OEt | C(O)OCH$_3$ |
| 3,4-F$_2$-5-CF$_3$ | CF$_2$Cl | CH$_2$OCH2CF$_3$ | C(O)OCH$_3$ |
| 3,4-F$_2$-5-CF$_3$ | CF$_2$Cl | CH$_2$OC(O)CH$_3$ | C(O)OCH$_3$ |
| 3,4-F$_2$-5-CF$_3$ | CF$_2$Cl | CH$_2$OC(O)Et | C(O)OCH$_3$ |
| 3,4-F$_2$-5-CF$_3$ | CF$_2$Cl | CH$_2$OC(O)OCH$_3$ | C(O)OCH$_3$ |
| 3,4-F$_2$-5-CF$_3$ | CF$_2$Cl | E-5a | C(O)OCH$_3$ |
| 3,4-F$_2$-5-CF$_3$ | CF$_2$Cl | C(O)Et | C(O)OCH$_3$ |
| 3,4-F$_2$-5-CF$_3$ | CF$_2$Cl | C(O)Pr-n | C(O)OCH$_3$ |
| 3,4-F$_2$-5-CF$_3$ | CF$_2$Cl | C(O)Bu-t | C(O)OCH$_3$ |
| 3,4-F$_2$-5-CF$_3$ | CF$_2$Cl | C(O)CH$_2$SCH$_3$ | C(O)OCH$_3$ |
| 3,4-F$_2$-5-CF$_3$ | CF$_2$Cl | C(O)OCH$_3$ | C(O)OEt |
| 3,4-F$_2$-5-CF$_3$ | CF$_2$Cl | H | C(O)OPr-i |
| 3,4-F$_2$-5-CF$_3$ | CF$_2$Cl | H | C(O)NH$_2$ |
| 3,4-F$_2$-5-CF$_3$ | CF$_2$Cl | C(O)OCH$_3$ | (D-52d)Cl |
| 3,4-F$_2$-5-CF$_3$ | CF$_2$Cl | CH$_3$ | (D-55c)Cl |
| 3,4-F$_2$-5-CF$_3$ | CF$_2$Cl | CH$_2$OCH$_3$ | (D-55c)Cl |
| 3,4-F$_2$-5-CF$_3$ | CF$_2$Cl | C(O)CH$_3$ | (D-55c)Cl |
| 3,4-F$_2$-5-CF$_3$ | CF$_2$Cl | C(O)Et | (D-55c)Cl |
| 3,4-F$_2$-5-CF$_3$ | CF$_2$Cl | C(O)Pr-i | (D-52d)Cl |
| 3,4-F$_2$-5-CF$_3$ | CF$_2$Cl | C(O)CH$_2$OCH$_3$ | (D-55c)Cl |
| 3,4-F$_2$-5-CF$_3$ | CF$_2$Cl | C(O)CH$_2$OEt | (D-55c)Cl |
| 3,4-F$_2$-5-CF$_3$ | CF$_2$Cl | C(O)CH$_2$SCH$_3$ | (D-55c)Cl |
| 3,4-F$_2$-5-CF$_3$ | CF$_2$Cl | C(O)OCH$_3$ | (D-55c)Cl |
| 3,4-F$_2$-5-CF$_3$ | CF$_2$Cl | C(O)OPr-n | (D-52d)Cl |
| 3,4-F$_2$-5-CF$_3$ | CF$_2$Cl | C(O)OCH$_2$CH$_2$Cl | (D-55c)Cl |
| 3,4-F$_2$-5-CF$_3$ | CF$_2$Cl | C(O)OCH$_2$CH$_2$OCH$_3$ | (D-55c)Cl |
| 3,4-F$_2$-5-CF$_3$ | CF$_2$Cl | C(O)OCH$_2$CH=CH$_2$ | (D-55c)Cl |
| 3,4-F$_2$-5-CF$_3$ | CF$_2$Cl | CH$_2$OC(O)CH$_3$ | (D-55c)Cl |
| 3,4-F$_2$-5-CF$_3$ | CF$_2$Cl | C(O)CH$_3$ | (D-55c)Cl |
| 3,4-F$_2$-5-CF$_3$ | CF$_2$Cl | C(O)Et | (D-55c)Cl |
| 3,4-F$_2$-5-CF$_3$ | CF$_2$Cl | C(O)Pr-n | (D-55c)Cl |
| 3,4-F$_2$-5-CF$_3$ | CF$_2$Cl | C(O)Pr-i | (D-55c)Cl |
| 3,4-F$_2$-5-CF$_3$ | CF$_2$Cl | C(O)OCH$_3$ | (D-55c)Cl |
| 3,4-F$_2$-5-CF$_3$ | CF$_2$Cl | C(O)OEt | (D-55c)Cl |
| 3,4-F$_2$-5-CF$_3$ | CF$_2$Br | H | CH=NOCH$_3$ |
| 3,4-F$_2$-5-CF$_3$ | CF$_2$Br | CH$_2$OEt | C(O)OCH$_3$ |
| 3,4-F$_2$-5-CF$_3$ | CF$_2$Br | C(O)Et | C(O)OCH$_3$ |
| 3,4-F$_2$-5-CF$_3$ | CF$_2$Br | C(O)CH$_3$ | (D-55c)Cl |
| 3,4-F$_2$-5-CF$_3$ | CF$_2$Br | C(O)OCH$_3$ | (D-55c)Cl |
| 3,4-F$_2$-5-CF$_3$ | CF$_2$CHF$_2$ | H | CH=NOCH$_3$ |
| 3,4-F$_2$-5-CF$_3$ | CF$_2$CHF$_2$ | CH$_2$OEt | C(O)OCH$_3$ |
| 3,4-F$_2$-5-CF$_3$ | CF$_2$CHF$_2$ | C(O)Et | C(O)OCH$_3$ |
| 3,4-F$_2$-5-CF$_3$ | CF$_2$CHF$_2$ | C(O)CH$_3$ | (D-55c)Cl |
| 3,4-F$_2$-5-CF$_3$ | CF$_2$CHF$_2$ | C(O)OCH$_3$ | (D-55c)Cl |
| 2-F-3-Cl-5-CF$_3$ | CF$_3$ | C(O)CH$_3$ | (D-55c)Br |
| 3-Cl-4-F-5-CF$_3$ | CHF$_2$ | H | CH=NOCH$_3$ |
| 3-Cl-4-F-5-CF$_3$ | CHF$_2$ | CH$_2$OEt | C(O)OCH$_3$ |
| 3-Cl-4-F-5-CF$_3$ | CHF$_2$ | C(O)Et | C(O)OCH$_3$ |
| 3-Cl-4-F-5-CF$_3$ | CHF$_2$ | C(O)CH$_3$ | (D-55c)Cl |
| 3-Cl-4-F-5-CF$_3$ | CHF$_2$ | C(O)OCH$_3$ | (D-55c)Cl |
| 3-Cl-4-F-5-CF$_3$ | CF$_3$ | H | CH=NOCH$_3$ |
| 3-Cl-4-F-5-CF$_3$ | CF$_3$ | CH$_2$OCH$_3$ | CH=NOCH$_3$ |
| 3-Cl-4-F-5-CF$_3$ | CF$_3$ | CH$_2$OEt | CH=NOCH$_3$ |
| 3-Cl-4-F-5-CF$_3$ | CF$_3$ | H | CH=NOEt |
| 3-Cl-4-F-5-CF$_3$ | CF$_3$ | CH$_2$OCH$_3$ | CH=NOEt |
| 3-Cl-4-F-5-CF$_3$ | CF$_3$ | H | C(O)OCH$_3$ |
| 3-Cl-4-F-5-CF$_3$ | CF$_3$ | CH$_3$ | C(O)OCH$_3$ |
| 3-Cl-4-F-5-CF$_3$ | CF$_3$ | Et | C(O)OCH$_3$ |
| 3-Cl-4-F-5-CF$_3$ | CF$_3$ | CH$_2$OCH$_3$ | C(O)OCH$_3$ |
| 3-Cl-4-F-5-CF$_3$ | CF$_3$ | CH$_2$OEt | C(O)OCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-4-F-5-CF$_3$ | CF$_3$ | CH$_2$OCH$_2$CF$_3$ | C(O)OCH$_3$ |
| 3-Cl-4-F-5-CF$_3$ | CF$_3$ | CH$_2$OC(O)CH$_3$ | C(O)OCH$_3$ |
| 3-Cl-4-F-5-CF$_3$ | CF$_3$ | CH$_2$OC(O)Et | C(O)OCH$_3$ |
| 3-Cl-4-F-5-CF$_3$ | CF$_3$ | CH$_2$OC(O)Bu-t | C(O)OCH$_3$ |
| 3-Cl-4-F-5-CF$_3$ | CF$_3$ | CH$_2$OC(O)OCH$_3$ | C(O)OCH$_3$ |
| 3-Cl-4-F-5-CF$_3$ | CF$_3$ | E-5a | C(O)OCH$_3$ |
| 3-Cl-4-F-5-CF$_3$ | CF$_3$ | CH$_2$NHC(O)OCH$_3$ | C(O)OCH$_3$ |
| 3-Cl-4-F-5-CF$_3$ | CF$_3$ | CH$_2$CN | C(O)OCH$_3$ |
| 3-Cl-4-F-5-CF$_3$ | CF$_3$ | C(O)CH$_3$ | C(O)OCH$_3$ |
| 3-Cl-4-F-5-CF$_3$ | CF$_3$ | C(O)Et | C(O)OCH$_3$ |
| 3-Cl-4-F-5-CF$_3$ | CF$_3$ | C(O)Pr-n | C(O)OCH$_3$ |
| 3-Cl-4-F-5-CF$_3$ | CF$_3$ | C(O)Pr-i | C(O)OCH$_3$ |
| 3-Cl-4-F-5-CF$_3$ | CF$_3$ | C(O)Bu-t | C(O)OCH$_3$ |
| 3-Cl-4-F-5-CF$_3$ | CF$_3$ | C(O)CH$_2$OCH$_3$ | C(O)OCH$_3$ |
| 3-Cl-4-F-5-CF$_3$ | CF$_3$ | C(O)CH$_2$SCH$_3$ | C(O)OCH$_3$ |
| 3-Cl-4-F-5-CF$_3$ | CF$_3$ | C(O)Ph | C(O)OCH$_3$ |
| 3-Cl-4-F-5-CF$_3$ | CF$_3$ | C(O)OCH$_2$CH$_2$Cl | C(O)OCH$_3$ |
| 3-Cl-4-F-5-CF$_3$ | CF$_3$ | H | C(O)OEt |
| 3-Cl-4-F-5-CF$_3$ | CF$_3$ | CH$_2$OCH$_3$ | C(O)OEt |
| 3-Cl-4-F-5-CF$_3$ | CF$_3$ | C(O)Bu-t | C(O)OEt |
| 3-Cl-4-F-5-CF$_3$ | CF$_3$ | C(O)CH$_2$OCH$_3$ | C(O)OEt |
| 3-Cl-4-F-5-CF$_3$ | CF$_3$ | C(O)OCH$_3$ | C(O)OEt |
| 3-Cl-4-F-5-CF$_3$ | CF$_3$ | H | C(O)OPr-i |
| 3-Cl-4-F-5-CF$_3$ | CF$_3$ | C(O)CH$_3$ | C(O)OPr-i |
| 3-Cl-4-F-5-CF$_3$ | CF$_3$ | C(O)CH$_2$OCH$_3$ | C(O)OPr-i |
| 3-Cl-4-F-5-CF$_3$ | CF$_3$ | C(O)OCH$_3$ | C(O)OPr-i |
| 3-Cl-4-F-5-CF$_3$ | CF$_3$ | C(O)OCH$_3$ | C(O)OCH$_2$CH$_2$OCH$_3$ |
| 3-Cl-4-F-5-CF$_3$ | CF$_3$ | H | C(O)NH$_2$ |
| 3-Cl-4-F-5-CF$_3$ | CF$_3$ | C(O)CH$_3$ | D-14a |
| 3-Cl-4-F-5-CF$_3$ | CF$_3$ | CH$_3$ | (D-52d)Cl |
| 3-Cl-4-F-5-CF$_3$ | CF$_3$ | CH$_2$OCH$_3$ | (D-52d)Cl |
| 3-Cl-4-F-5-CF$_3$ | CF$_3$ | C(O)Et | (D-52d)Cl |
| 3-Cl-4-F-5-CF$_3$ | CF$_3$ | C(O)OCH$_3$ | (D-52d)Cl |
| 3-Cl-4-F-5-CF$_3$ | CF$_3$ | CH$_3$ | (D-52d)Br |
| 3-Cl-4-F-5-CF$_3$ | CF$_3$ | CH$_3$ | (D-52d)CN |
| 3-Cl-4-F-5-CF$_3$ | CF$_3$ | CH$_3$ | (D-53e)Cl |
| 3-Cl-4-F-5-CF$_3$ | CF$_3$ | CH$_3$ | D-55a |
| 3-Cl-4-F-5-CF$_3$ | CF$_3$ | CH$_3$ | (D-55c)Cl |
| 3-Cl-4-F-5-CF$_3$ | CF$_3$ | Et | (D-55c)Cl |
| 3-Cl-4-F-5-CF$_3$ | CF$_3$ | CH$_2$OCH$_3$ | (D-55c)Cl |
| 3-Cl-4-F-5-CF$_3$ | CF$_3$ | CH$_2$OEt | (D-55c)Cl |
| 3-Cl-4-F-5-CF$_3$ | CF$_3$ | CH$_2$OC(O)CH$_3$ | (D-55c)Cl |
| 3-Cl-4-F-5-CF$_3$ | CF$_3$ | CH$_2$OC(O)Bu-t | (D-55c)Cl |
| 3-Cl-4-F-5-CF$_3$ | CF$_3$ | CH$_2$OC(O)OCH$_3$ | (D-55c)Cl |
| 3-Cl-4-F-5-CF$_3$ | CF$_3$ | CH$_2$CN | (D-55c)Cl |
| 3-Cl-4-F-5-CF$_3$ | CF$_3$ | C(O)CH$_3$ | (D-55c)Cl |
| 3-Cl-4-F-5-CF$_3$ | CF$_3$ | C(O)Et | (D-55c)Cl |
| 3-Cl-4-F-5-CF$_3$ | CF$_3$ | C(O)Pr-n | (D-55c)Cl |
| 3-Cl-4-F-5-CF$_3$ | CF$_3$ | C(O)Pr-i | (D-55c)Cl |
| 3-Cl-4-F-5-CF$_3$ | CF$_3$ | C(O)Pr-c | (D-55c)Cl |
| 3-Cl-4-F-5-CF$_3$ | CF$_3$ | C(O)Bu-t | (D-55c)Cl |
| 3-Cl-4-F-5-CF$_3$ | CF$_3$ | C(O)CH$_2$Cl | (D-55c)Cl |
| 3-Cl-4-F-5-CF$_3$ | CF$_3$ | C(O)CH$_2$OCH$_3$ | (D-55c)Cl |
| 3-Cl-4-F-5-CF$_3$ | CF$_3$ | C(O)CH$_2$OEt | (D-55c)Cl |
| 3-Cl-4-F-5-CF$_3$ | CF$_3$ | C(O)CH$_2$SCH$_3$ | (D-55c)Cl |
| 3-Cl-4-F-5-CF$_3$ | CF$_3$ | C(O)CH$_2$S(O)CH$_3$ | (D-55c)Cl |
| 3-Cl-4-F-5-CF$_3$ | CF$_3$ | C(O)C(O)OEt | (D-55c)Cl |
| 3-Cl-4-F-5-CF$_3$ | CF$_3$ | C(O)Ph | (D-55c)Cl |
| 3-Cl-4-F-5-CF$_3$ | CF$_3$ | C(O)(D-52a) | (D-55c)Cl |
| 3-Cl-4-F-5-CF$_3$ | CF$_3$ | C(O)OCH$_3$ | (D-55c)Cl |
| 3-Cl-4-F-5-CF$_3$ | CF$_3$ | C(O)OEt | (D-55c)Cl |
| 3-Cl-4-F-5-CF$_3$ | CF$_3$ | C(O)OPr-n | (D-55c)Cl |
| 3-Cl-4-F-5-CF$_3$ | CF$_3$ | C(O)OPr-i | (D-55c)Cl |
| 3-Cl-4-F-5-CF$_3$ | CF$_3$ | C(O)OBu-n | (D-55c)Cl |
| 3-Cl-4-F-5-CF$_3$ | CF$_3$ | C(O)OBu-i | (D-55c)Cl |
| 3-Cl-4-F-5-CF$_3$ | CF$_3$ | C(O)OCH$_2$Cl | (D-55c)Cl |
| 3-Cl-4-F-5-CF$_3$ | CF$_3$ | C(O)OCH$_2$CH$_2$Cl | (D-55c)Cl |
| 3-Cl-4-F-5-CF$_3$ | CF$_3$ | C(O)OCH$_2$CH$_2$OCH$_3$ | (D-55c)Cl |
| 3-Cl-4-F-5-CF$_3$ | CF$_3$ | C(O)OCH$_2$CH=CH$_2$ | (D-55c)Cl |
| 3-Cl-4-F-5-CF$_3$ | CF$_3$ | CH$_3$ | (D-55c)Br |
| 3-Cl-4-F-5-CF$_3$ | CF$_3$ | Et | (D-55c)Br |
| 3-Cl-4-F-5-CF$_3$ | CF$_3$ | CH$_2$OCH$_3$ | (D-55c)Br |
| 3-Cl-4-F-5-CF$_3$ | CF$_3$ | CH$_2$OEt | (D-55c)Br |
| 3-Cl-4-F-5-CF$_3$ | CF$_3$ | CH$_2$OC(O)CH$_3$ | (D-55c)Br |
| 3-Cl-4-F-5-CF$_3$ | CF$_3$ | C(O)CH$_3$ | (D-55c)Br |
| 3-Cl-4-F-5-CF$_3$ | CF$_3$ | C(O)Et | (D-55c)Br |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3-Cl-4-F-5-CF$_3$ | CF$_3$ | C(O)Pr-n | (D-55c)Br |
| 3-Cl-4-F-5-CF$_3$ | CF$_3$ | C(O)Pr-i | (D-55c)Br |
| 3-Cl-4-F-5-CF$_3$ | CF$_3$ | C(O)Pr-c | (D-55c)Br |
| 3-Cl-4-F-5-CF$_3$ | CF$_3$ | C(O)CH$_2$OCH$_3$ | (D-55c)Br |
| 3-Cl-4-F-5-CF$_3$ | CF$_3$ | C(O)OCH$_3$ | (D-55c)Br |
| 3-Cl-4-F-5-CF$_3$ | CF$_3$ | C(O)OEt | (D-55c)Br |
| 3-Cl-4-F-5-CF$_3$ | CF$_3$ | C(O)OPr-n | (D-55c)Br |
| 3-Cl-4-F-5-CF$_3$ | CF$_3$ | C(O)OBu-i | (D-55c)Br |
| 3-Cl-4-F-5-CF$_3$ | CF$_3$ | C(O)OCH$_2$Cl | (D-55c)Br |
| 3-Cl-4-F-5-CF$_3$ | CF$_3$ | C(O)OCH$_2$CH$_2$OCH$_3$ | (D-55c)Br |
| 3-Cl-4-F-5-CF$_3$ | CF$_3$ | CH$_3$ | D-57a |
| 3-Cl-4-F-5-CF$_3$ | CF$_3$ | C(O)CH$_3$ | D-57a |
| 3-Cl-4-F-5-CF$_3$ | CF$_3$ | C(O)Pr-i | D-57a |
| 3-Cl-4-F-5-CF$_3$ | CF$_3$ | CH$_3$ | D-58a |
| 3-Cl-4-F-5-CF$_3$ | CF$_2$Cl | H | CH=NOCH$_3$ |
| 3-Cl-4-F-5-CF$_3$ | CF$_2$Cl | CH$_2$OCH$_3$ | CH=NOCH$_3$ |
| 3-Cl-4-F-5-CF$_3$ | CF$_2$Cl | H | CH=NOEt |
| 3-Cl-4-F-5-CF$_3$ | CF$_2$Cl | H | C(O)OCH$_3$ |
| 3-Cl-4-F-5-CF$_3$ | CF$_2$Cl | Et | C(O)OCH$_3$ |
| 3-Cl-4-F-5-CF$_3$ | CF$_2$Cl | CH$_2$OCH$_3$ | C(O)OCH$_3$ |
| 3-Cl-4-F-5-CF$_3$ | CF$_2$Cl | CH$_2$OEt | C(O)OCH$_3$ |
| 3-Cl-4-F-5-CF$_3$ | CF$_2$Cl | CH$_2$OCH$_2$CF$_3$ | C(O)OCH$_3$ |
| 3-Cl-4-F-5-CF$_3$ | CF$_2$Cl | CH$_2$OC(O)CH$_3$ | C(O)OCH$_3$ |
| 3-Cl-4-F-5-CF$_3$ | CF$_2$Cl | CH$_2$OC(O)Et | C(O)OCH$_3$ |
| 3-Cl-4-F-5-CF$_3$ | CF$_2$Cl | CH$_2$OC(O)OCH$_3$ | C(O)OCH$_3$ |
| 3-Cl-4-F-5-CF$_3$ | CF$_2$Cl | E-5a | C(O)OCH$_3$ |
| 3-Cl-4-F-5-CF$_3$ | CF$_2$Cl | C(O)Et | C(O)OCH$_3$ |
| 3-Cl-4-F-5-CF$_3$ | CF$_2$Cl | C(O)Pr-n | C(O)OCH$_3$ |
| 3-Cl-4-F-5-CF$_3$ | CF$_2$Cl | C(O)Bu-t | C(O)OCH$_3$ |
| 3-Cl-4-F-5-CF$_3$ | CF$_2$Cl | C(O)CH$_2$SCH$_3$ | C(O)OCH$_3$ |
| 3-Cl-4-F-5-CF$_3$ | CF$_2$Cl | C(O)OCH$_3$ | C(O)OEt |
| 3-Cl-4-F-5-CF$_3$ | CF$_2$Cl | H | C(O)OPr-i |
| 3-Cl-4-F-5-CF$_3$ | CF$_2$Cl | H | C(O)NH$_2$ |
| 3-Cl-4-F-5-CF$_3$ | CF$_2$Cl | C(O)OCH$_3$ | (D-52d)Cl |
| 3-Cl-4-F-5-CF$_3$ | CF$_2$Cl | CH$_3$ | (D-55c)Cl |
| 3-Cl-4-F-5-CF$_3$ | CF$_2$Cl | CH$_2$OCH$_3$ | (D-55c)Cl |
| 3-Cl-4-F-5-CF$_3$ | CF$_2$Cl | C(O)CH$_3$ | (D-55c)Cl |
| 3-Cl-4-F-5-CF$_3$ | CF$_2$Cl | C(O)Et | (D-55c)Cl |
| 3-Cl-4-F-5-CF$_3$ | CF$_2$Cl | C(O)Pr-i | (D-55c)Cl |
| 3-Cl-4-F-5-CF$_3$ | CF$_2$Cl | C(O)CH$_2$OCH$_3$ | (D-55c)Cl |
| 3-Cl-4-F-5-CF$_3$ | CF$_2$Cl | C(O)CH$_2$OEt | (D-55c)Cl |
| 3-Cl-4-F-5-CF$_3$ | CF$_2$Cl | C(O)CH$_2$SCH$_3$ | (D-55c)Cl |
| 3-Cl-4-F-5-CF$_3$ | CF$_2$Cl | C(O)OCH$_3$ | (D-55c)Cl |
| 3-Cl-4-F-5-CF$_3$ | CF$_2$Cl | C(O)OPr-n | (D-55c)Cl |
| 3-Cl-4-F-5-CF$_3$ | CF$_2$Cl | C(O)OCH$_2$CH$_2$Cl | (D-55c)Cl |
| 3-Cl-4-F-5-CF$_3$ | CF$_2$Cl | C(O)OCH$_2$CH$_2$OCH$_3$ | (D-55c)Cl |
| 3-Cl-4-F-5-CF$_3$ | CF$_2$Cl | C(O)OCH$_2$CH=CH$_2$ | (D-55c)Cl |
| 3-Cl-4-F-5-CF$_3$ | CF$_2$Cl | CH$_2$OC(O)CH$_3$ | (D-55c)Br |
| 3-Cl-4-F-5-CF$_3$ | CF$_2$Cl | C(O)CH$_3$ | (D-55c)Br |
| 3-Cl-4-F-5-CF$_3$ | CF$_2$Cl | C(O)Et | (D-55c)Br |
| 3-Cl-4-F-5-CF$_3$ | CF$_2$Cl | C(O)Pr-n | (D-55c)Br |
| 3-Cl-4-F-5-CF$_3$ | CF$_2$Cl | C(O)Pr-i | (D-55c)Br |
| 3-Cl-4-F-5-CF$_3$ | CF$_2$Cl | C(O)OCH$_3$ | (D-55c)Br |
| 3-Cl-4-F-5-CF$_3$ | CF$_2$Cl | C(O)OEt | (D-55c)Br |
| 3-Cl-4-F-5-CF$_3$ | CF$_2$Br | H | CH=NOCH$_3$ |
| 3-Cl-4-F-5-CF$_3$ | CF$_2$Br | CH$_2$OEt | C(O)OCH$_3$ |
| 3-Cl-4-F-5-CF$_3$ | CF$_2$Br | C(O)Et | C(O)OCH$_3$ |
| 3-Cl-4-F-5-CF$_3$ | CF$_2$Br | C(O)CH$_3$ | (D-55c)Cl |
| 3-Cl-4-F-5-CF$_3$ | CF$_2$Br | C(O)OCH$_3$ | (D-55c)Cl |
| 3-Cl-4-F-5-CF$_3$ | CF$_2$CHF$_2$ | H | CH=NOCH$_3$ |
| 3-Cl-4-F-5-CF$_3$ | CF$_2$CHF$_2$ | CH$_2$OEt | C(O)OCH$_3$ |
| 3-Cl-4-F-5-CF$_3$ | CF$_2$CHF$_2$ | C(O)Et | C(O)OCH$_3$ |
| 3-Cl-4-F-5-CF$_3$ | CF$_2$CHF$_2$ | C(O)CH$_3$ | (D-55c)Cl |
| 3-Cl-4-F-5-CF$_3$ | CF$_2$CHF$_2$ | C(O)OCH$_3$ | (D-55c)Cl |
| 3,4-Cl$_2$-5-CF$_3$ | CF$_3$ | H | CH=NOCH$_3$ |
| 3,4-Cl$_2$-5-CF$_3$ | CHF$_2$ | CH$_2$OEt | C(O)OCH$_3$ |
| 3,4-Cl$_2$-5-CF$_3$ | CHF$_2$ | C(O)Et | C(O)OCH$_3$ |
| 3,4-Cl$_2$-5-CF$_3$ | CHF$_2$ | C(O)CH$_3$ | (D-55c)Cl |
| 3,4-Cl$_2$-5-CF$_3$ | CHF$_2$ | C(O)OCH$_3$ | (D-55c)Cl |
| 3,4-Cl$_2$-5-CF$_3$ | CF$_3$ | H | CH=NOCH$_3$ |
| 3,4-Cl$_2$-5-CF$_3$ | CF$_3$ | CH$_2$OCH$_3$ | CH=NOCH$_3$ |
| 3,4-Cl$_2$-5-CF$_3$ | CF$_3$ | CH$_2$OEt | CH=NOCH$_3$ |
| 3,4-Cl$_2$-5-CF$_3$ | CF$_3$ | H | CH=NOEt |
| 3,4-Cl$_2$-5-CF$_3$ | CF$_3$ | CH$_2$OCH$_3$ | CH=NOEt |
| 3,4-Cl$_2$-5-CF$_3$ | CF$_3$ | H | C(O)OCH$_3$ |
| 3,4-Cl$_2$-5-CF$_3$ | CF$_3$ | CH$_3$ | C(O)OCH$_3$ |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4-Cl$_2$-5-CF$_3$ | CF$_3$ | Et | C(O)OCH$_3$ |
| 3,4-Cl$_2$-5-CF$_3$ | CF$_3$ | CH$_2$OCH$_3$ | C(O)OCH$_3$ |
| 3,4-Cl$_2$-5-CF$_3$ | CF$_3$ | CH$_2$OEt | C(O)OCH$_3$ |
| 3,4-Cl$_2$-5-CF$_3$ | CF$_3$ | CH$_2$OCH$_2$CF$_3$ | C(O)OCH$_3$ |
| 3,4-Cl$_2$-5-CF$_3$ | CF$_3$ | CH$_2$OC(O)CH$_3$ | C(O)OCH$_3$ |
| 3,4-Cl$_2$-5-CF$_3$ | CF$_3$ | CH$_2$OC(O)Et | C(O)OCH$_3$ |
| 3,4-Cl$_2$-5-CF$_3$ | CF$_3$ | CH$_2$OC(O)Bu-t | C(O)OCH$_3$ |
| 3,4-Cl$_2$-5-CF$_3$ | CF$_3$ | CH$_2$OC(O)OCH$_3$ | C(O)OCH$_3$ |
| 3,4-Cl$_2$-5-CF$_3$ | CF$_3$ | E-5a | C(O)OCH$_3$ |
| 3,4-Cl$_2$-5-CF$_3$ | CF$_3$ | CH$_2$NHC(O)OCH$_3$ | C(O)OCH$_3$ |
| 3,4-Cl$_2$-5-CF$_3$ | CF$_3$ | CH$_2$CN | C(O)OCH$_3$ |
| 3,4-Cl$_2$-5-CF$_3$ | CF$_3$ | C(O)CH$_3$ | C(O)OCH$_3$ |
| 3,4-Cl$_2$-5-CF$_3$ | CF$_3$ | C(O)Et | C(O)OCH$_3$ |
| 3,4-Cl$_2$-5-CF$_3$ | CF$_3$ | C(O)Pr-n | C(O)OCH$_3$ |
| 3,4-Cl$_2$-5-CF$_3$ | CF$_3$ | C(O)Pr-i | C(O)OCH$_3$ |
| 3,4-Cl$_2$-5-CF$_3$ | CF$_3$ | C(O)Bu-t | C(O)OCH$_3$ |
| 3,4-Cl$_2$-5-CF$_3$ | CF$_3$ | C(O)CH$_2$OCH$_3$ | C(O)OCH$_3$ |
| 3,4-Cl$_2$-5-CF$_3$ | CF$_3$ | C(O)CH$_2$SCH$_3$ | C(O)OCH$_3$ |
| 3,4-Cl$_2$-5-CF$_3$ | CF$_3$ | C(O)Ph | C(O)OCH$_3$ |
| 3,4-Cl$_2$-5-CF$_3$ | CF$_3$ | C(O)OCH$_2$CH$_2$Cl | C(O)OCH$_3$ |
| 3,4-Cl$_2$-5-CF$_3$ | CF$_3$ | H | C(O)OEt |
| 3,4-Cl$_2$-5-CF$_3$ | CF$_3$ | CH$_2$OCH$_3$ | C(O)OEt |
| 3,4-Cl$_2$-5-CF$_3$ | CF$_3$ | C(O)Bu-t | C(O)OEt |
| 3,4-Cl$_2$-5-CF$_3$ | CF$_3$ | C(O)CH$_2$OCH$_3$ | C(O)OEt |
| 3,4-Cl$_2$-5-CF$_3$ | CF$_3$ | C(O)OCH$_3$ | C(O)OEt |
| 3,4-Cl$_2$-5-CF$_3$ | CF$_3$ | H | C(O)OPr-i |
| 3,4-Cl$_2$-5-CF$_3$ | CF$_3$ | C(O)CH$_3$ | C(O)OPr-i |
| 3,4-Cl$_2$-5-CF$_3$ | CF$_3$ | C(O)CH$_2$OCH$_3$ | C(O)OPr-i |
| 3,4-Cl$_2$-5-CF$_3$ | CF$_3$ | C(O)OCH$_3$ | C(O)OPr-i |
| 3,4-Cl$_2$-5-CF$_3$ | CF$_3$ | C(O)OCH$_3$ | C(O)OCH$_2$CH$_2$OCH$_3$ |
| 3,4-Cl$_2$-5-CF$_3$ | CF$_3$ | H | C(O)NH$_2$ |
| 3,4-Cl$_2$-5-CF$_3$ | CF$_3$ | C(O)CH$_3$ | D-14a |
| 3,4-Cl$_2$-5-CF$_3$ | CF$_3$ | CH$_3$ | (D-52d)Cl |
| 3,4-Cl$_2$-5-CF$_3$ | CF$_3$ | CH$_2$OCH$_3$ | (D-52d)Cl |
| 3,4-Cl$_2$-5-CF$_3$ | CF$_3$ | C(O)Et | (D-52d)Cl |
| 3,4-Cl$_2$-5-CF$_3$ | CF$_3$ | C(O)OCH$_3$ | (D-52d)Cl |
| 3,4-Cl$_2$-5-CF$_3$ | CF$_3$ | CH$_3$ | (D-52d)Br |
| 3,4-Cl$_2$-5-CF$_3$ | CF$_3$ | CH$_3$ | (D-52ct)CN |
| 3,4-Cl$_2$-5-CF$_3$ | CF$_3$ | CH$_3$ | (D-53e)Cl |
| 3,4-Cl$_2$-5-CF$_3$ | CF$_3$ | CH$_3$ | D-55a |
| 3,4-Cl$_2$-5-CF$_3$ | CF$_3$ | CH$_3$ | (D-55c)Cl |
| 3,4-Cl$_2$-5-CF$_3$ | CF$_3$ | Et | (D-55c)Cl |
| 3,4-Cl$_2$-5-CF$_3$ | CF$_3$ | CH$_2$OCH$_3$ | (D-55c)Cl |
| 3,4-Cl$_2$-5-CF$_3$ | CF$_3$ | CH$_2$OEt | (D-55c)Cl |
| 3,4-Cl$_2$-5-CF$_3$ | CF$_3$ | CH$_2$OC(O)CH$_3$ | (D-55c)Cl |
| 3,4-Cl$_2$-5-CF$_3$ | CF$_3$ | CH$_2$OC(O)Bu-t | (D-55c)Cl |
| 3,4-Cl$_2$-5-CF$_3$ | CF$_3$ | CH$_2$OC(O)OCH$_3$ | (D-55c)Cl |
| 3,4-Cl$_2$-5-CF$_3$ | CF$_3$ | CH$_2$CN | (D-55c)Cl |
| 3,4-Cl$_2$-5-CF$_3$ | CF$_3$ | C(O)CH$_3$ | (D-55c)Cl |
| 3,4-Cl$_2$-5-CF$_3$ | CF$_3$ | C(O)Et | (D-55c)Cl |
| 3,4-Cl$_2$-5-CF$_3$ | CF$_3$ | C(O)Pr-n | (D-55c)Cl |
| 3,4-Cl$_2$-5-CF$_3$ | CF$_3$ | C(O)Pr-i | (D-55c)Cl |
| 3,4-Cl$_2$-5-CF$_3$ | CF$_3$ | C(O)Pr-c | (D-55c)Cl |
| 3,4-Cl$_2$-5-CF$_3$ | CF$_3$ | C(O)Bu-t | (D-55c)Cl |
| 3,4-Cl$_2$-5-CF$_3$ | CF$_3$ | C(O)CH$_2$Cl | (D-55c)Cl |
| 3,4-Cl$_2$-5-CF$_3$ | CF$_3$ | C(O)CH$_2$OCH$_3$ | (D-55c)Cl |
| 3,4-Cl$_2$-5-CF$_3$ | CF$_3$ | C(O)CH$_2$OEt | (D-55c)Cl |
| 3,4-Cl$_2$-5-CF$_3$ | CF$_3$ | C(O)CH$_2$SCH$_3$ | (D-55c)Cl |
| 3,4-Cl$_2$-5-CF$_3$ | CF$_3$ | C(O)CH$_2$S(O)CH$_3$ | (D-55c)Cl |
| 3,4-Cl$_2$-5-CF$_3$ | CF$_3$ | C(O)C(O)OEt | (D-55c)Cl |
| 3,4-Cl$_2$-5-CF$_3$ | CF$_3$ | C(O)Ph | (D-55c)Cl |
| 3,4-Cl$_2$-5-CF$_3$ | CF$_3$ | C(O)(D-52a) | (D-55c)Cl |
| 3,4-Cl$_2$-5-CF$_3$ | CF$_3$ | C(O)OCH$_3$ | (D-55c)Cl |
| 3,4-Cl$_2$-5-CF$_3$ | CF$_3$ | C(O)OEt | (D-55c)Cl |
| 3,4-Cl$_2$-5-CF$_3$ | CF$_3$ | C(O)OPr-n | (D-55c)Cl |
| 3,4-Cl$_2$-5-CF$_3$ | CF$_3$ | C(O)OPr-i | (D-55c)Cl |
| 3,4-Cl$_2$-5-CF$_3$ | CF$_3$ | C(O)OBu-n | (D-55c)Cl |
| 3,4-Cl$_2$-5-CF$_3$ | CF$_3$ | C(O)OBu-I | (D-55c)Cl |
| 3,4-Cl$_2$-5-CF$_3$ | CF$_3$ | C(O)OCH$_2$Cl | (D-55c)Cl |
| 3,4-Cl$_2$-5-CF$_3$ | CF$_3$ | C(O)OCH$_2$CH$_2$Cl | (D-55c)Cl |
| 3,4-Cl$_2$-5-CF$_3$ | CF$_3$ | C(O)OCH$_2$CH$_2$OCH$_3$ | (D-55c)Cl |
| 3,4-Cl$_2$-5-CF$_3$ | CF$_3$ | C(O)OCH$_2$CH=CH$_2$ | (D-55c)Cl |
| 3,4-Cl$_2$-5-CF$_3$ | CF$_3$ | CH$_3$ | (D-55c)Br |
| 3,4-Cl$_2$-5-CF$_3$ | CF$_3$ | Et | (D-55c)Br |
| 3,4-Cl$_2$-5-CF$_3$ | CF$_3$ | CH$_2$OCH$_3$ | (D-55c)Br |
| 3,4-Cl$_2$-5-CF$_3$ | CF$_3$ | CH$_2$OEt | (D-55c)Br |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4-Cl$_2$-5-CF$_3$ | CF$_3$ | CH$_2$OC(O)CH$_3$ | (D-55c)Br |
| 3,4-Cl$_2$-5-CF$_3$ | CF$_3$ | C(O)CH$_3$ | (D-55c)Br |
| 3,4-Cl$_2$-5-CF$_3$ | CF$_3$ | C(O)Et | (D-55c)Br |
| 3,4-Cl$_2$-5-CF$_3$ | CF$_3$ | C(O)Pr-n | (D-55c)Br |
| 3,4-Cl$_2$-5-CF$_3$ | CF$_3$ | C(O)Pr-i | (D-55c)Br |
| 3,4-Cl$_2$-5-CF$_3$ | CF$_3$ | C(O)Pr-C | (D-55c)Br |
| 3,4-Cl$_2$-5-CF$_3$ | CF$_3$ | C(O)CH$_2$OCH$_3$ | (D-55c)Br |
| 3,4-Cl$_2$-5-CF$_3$ | CF$_3$ | C(O)OCH$_3$ | (D-55c)Br |
| 3,4-Cl$_2$-5-CF$_3$ | CF$_3$ | C(O)OEt | (D-55c)Br |
| 3,4-Cl$_2$-5-CF$_3$ | CF$_3$ | C(O)OPr-n | (D-55c)Br |
| 3,4-Cl$_2$-5-CF$_3$ | CF$_3$ | C(O)OBu-i | (D-55c)Br |
| 3,4-Cl$_2$-5-CF$_3$ | CF$_3$ | C(O)OCH$_2$Cl | (D-55c)Br |
| 3,4-Cl$_2$-5-CF$_3$ | CF$_3$ | C(O)OCH$_2$CH$_2$OCH$_3$ | (D-55c)Br |
| 3,4-Cl$_2$-5-CF$_3$ | CF$_3$ | CH$_3$ | D-57a |
| 3,4-Cl$_2$-5-CF$_3$ | CF$_3$ | C(O)CH$_3$ | D-57a |
| 3,4-Cl$_2$-5-CF$_3$ | CF$_3$ | C(O)Pr-i | D-57a |
| 3,4-Cl$_2$-5-CF$_3$ | CF$_3$ | CH$_3$ | D-58a |
| 3,4-Cl$_2$-5-CF$_3$ | CF$_2$Cl | H | CH=NOCH$_3$ |
| 3,4-Cl$_2$-5-CF$_3$ | CF$_2$Cl | CH$_2$OCH$_3$ | CH=NOCH$_3$ |
| 3,4-Cl$_2$-5-CF$_3$ | CF$_2$Cl | H | CH=NOEt |
| 3,4-Cl$_2$-5-CF$_3$ | CF$_2$Cl | H | C(O)OCH$_3$ |
| 3,4-Cl$_2$-5-CF$_3$ | CF$_2$Cl | Et | C(O)OCH$_3$ |
| 3,4-Cl$_2$-5-CF$_3$ | CF$_2$Cl | CH$_2$OCH$_3$ | C(O)OCH$_3$ |
| 3,4-Cl$_2$-5-CF$_3$ | CF$_2$Cl | CH$_2$OEt | C(O)OCH$_3$ |
| 3,4-Cl$_2$-5-CF$_3$ | CF$_2$Cl | CH$_2$OCH$_2$CF$_3$ | C(O)OCH$_3$ |
| 3,4-Cl$_2$-5-CF$_3$ | CF$_2$Cl | CH$_2$OC(O)CH$_3$ | C(O)OCH$_3$ |
| 3,4-Cl$_2$-5-CF$_3$ | CF$_2$Cl | CH$_2$OC(O)Et | C(O)OCH$_3$ |
| 3,4-Cl$_2$-5-CF$_3$ | CF$_2$Cl | CH$_2$OC(O)OCH$_3$ | C(O)OCH$_3$ |
| 3,4-Cl$_2$-5-CF$_3$ | CF$_2$Cl | E-5a | C(O)OCH$_3$ |
| 3,4-Cl$_2$-5-CF$_3$ | CF$_2$Cl | C(O)Et | C(O)OCH$_3$ |
| 3,4-Cl$_2$-5-CF$_3$ | CF$_2$Cl | C(O)Pr-n | C(O)OCH$_3$ |
| 3,4-Cl$_2$-5-CF$_3$ | CF$_2$Cl | C(O)Bu-t | C(O)OCH$_3$ |
| 3,4-Cl$_2$-5-CF$_3$ | CF$_2$Cl | C(O)CH$_2$SCH$_3$ | C(O)OCH$_3$ |
| 3,4-Cl$_2$-5-CF$_3$ | CF$_2$Cl | C(O)OCH$_3$ | C(O)OEt |
| 3,4-Cl$_2$-5-CF$_3$ | CF$_2$Cl | H | C(O)OPr-i |
| 3,4-Cl$_2$-5-CF$_3$ | CF$_2$Cl | H | C(O)NH$_2$ |
| 3,4-Cl$_2$-5-CF$_3$ | CF$_2$Cl | C(O)OCH$_3$ | (D-52d)Cl |
| 3,4-Cl$_2$-5-CF$_3$ | CF$_2$Cl | CH$_3$ | (D-55c)Cl |
| 3,4-Cl$_2$-5-CF$_3$ | CF$_2$Cl | CH$_2$OCH$_3$ | (D-55c)Cl |
| 3,4-Cl$_2$-5-CF$_3$ | CF$_2$Cl | C(O)CH$_3$ | (D-55c)Cl |
| 3,4-Cl$_2$-5-CF$_3$ | CF$_2$Cl | C(O)Et | (D-55c)Cl |
| 3,4-Cl$_2$-5-CF$_3$ | CF$_2$Cl | C(O)Pr-i | (D-55c)Cl |
| 3,4-Cl$_2$-5-CF$_3$ | CF$_2$Cl | C(O)CH$_2$OCH$_3$ | (D-55c)Cl |
| 3,4-Cl$_2$-5-CF$_3$ | CF$_2$Cl | C(O)CH$_2$OEt | (D-55c)Cl |
| 3,4-Cl$_2$-5-CF$_3$ | CF$_2$Cl | C(O)CH$_2$SCH$_3$ | (D-55c)Cl |
| 3,4-Cl$_2$-5-CF$_3$ | CF$_2$Cl | C(O)OCH$_3$ | (D-55c)Cl |
| 3,4-Cl$_2$-5-CF$_3$ | CF$_2$Cl | C(O)OPr-n | (D-55c)Cl |
| 3,4-Cl$_2$-5-CF$_3$ | CF$_2$Cl | C(O)OCH$_2$CH$_2$Cl | (D-55c)Cl |
| 3,4-Cl$_2$-5-CF$_3$ | CF$_2$Cl | C(O)OCH$_2$CH$_2$OCH$_3$ | (D-55c)Cl |
| 3,4-Cl$_2$-5-CF$_3$ | CF$_2$Cl | C(O)OCH$_2$CH=CH$_2$ | (D-55c)Cl |
| 3,4-Cl$_2$-5-CF$_3$ | CF$_2$Cl | CH$_2$OC(O)CH$_3$ | (D-55c)Br |
| 3,4-Cl$_2$-5-CF$_3$ | CF$_2$Cl | C(O)CH$_3$ | (D-55c)Br |
| 3,4-Cl$_2$-5-CF$_3$ | CF$_2$Cl | C(O)Et | (D-55c)Br |
| 3,4-Cl$_2$-5-CF$_3$ | CF$_2$Cl | C(O)Pr-n | (D-55c)Br |
| 3,4-Cl$_2$-5-CF$_3$ | CF$_2$Cl | C(O)Pr-i | (D-55c)Br |
| 3,4-Cl$_2$-5-CF$_3$ | CF$_2$Cl | C(O)OCH$_3$i | (D-55c)Br |
| 3,4-Cl$_2$-5-CF$_3$ | CF$_2$Cl | C(O)OEt | (D-55c)Br |
| 3,4-Cl$_2$-5-CF$_3$ | CF$_2$Br | H | CH=NOCH$_3$ |
| 3,4-Cl$_2$-5-CF$_3$ | CF$_2$Br | CH$_2$OEt | C(O)OCH$_3$ |
| 3,4-Cl$_2$-5-CF$_3$ | CF$_2$Br | C(O)Et | C(O)OCH$_3$ |
| 3,4-Cl$_2$-5-CF$_3$ | CF$_2$Br | C(O)CH$_3$ | (D-55c)Cl |
| 3,4-Cl$_2$-5-CF$_3$ | CF$_2$Br | C(O)OCH$_3$ | (D-55c)Cl |
| 3,4-Cl$_2$-5-CF$_3$ | CF$_2$CHF$_2$ | H | CH=NOCH$_3$ |
| 3,4-Cl$_2$-5-CF$_3$ | CF$_2$CHF$_2$ | CH$_2$OEt | C(O)OCH$_3$ |
| 3,4-Cl$_2$-5-CF$_3$ | CF$_2$CHF$_2$ | C(O)Et | C(O)OCH$_3$ |
| 3,4-Cl$_2$-5-CF$_3$ | CF$_2$CHF$_2$ | C(O)CH$_3$ | (D-55c)Cl |
| 3,4-Cl$_2$-5-CF$_3$ | CF$_2$CHF$_2$ | C(O)OCH$_3$ | (D-55c)Cl |
| 3,5-(CF$_3$)$_2$-4-Cl | CHF$_2$ | H | CH=NOCH$_3$ |
| 3,5-(CF$_3$)$_2$-4-Cl | CHF$_2$ | CH$_2$OEt | C(O)OCH$_3$ |
| 3,5-(CF$_3$)$_2$-4-Cl | CHF$_2$ | C(O)Et | C(O)OCH$_3$ |
| 3,5-(CF$_3$)$_2$-4-Cl | CHF$_2$ | C(O)CH$_3$ | (D-55c)Cl |
| 3,5-(CF$_3$)$_2$-4-Cl | CHF$_2$ | C(O)OCH$_3$ | (D-55c)Cl |
| 3,5-(CF$_3$)$_2$-4-Cl | CF$_3$ | H | CH=NOCH$_3$ |
| 3,5-(CF$_3$)$_2$-4-Cl | CF$_3$ | CH$_2$OCH$_3$ | CH=NOCH$_3$ |
| 3,5-(CF$_3$)$_2$-4-Cl | CF$_3$ | CH$_2$OEt | CH=NOCH$_3$ |
| 3,5-(CF$_3$)$_2$-4-Cl | CF$_3$ | H | CH=NOEt |

TABLE 2-continued

In the table, the number showing the substitution position of substituent (X)$_m$ corresponds to the position number indicated in the following structural formulae. The indication "—" means no-substitution.

| | | | |
|---|---|---|---|
| 3,5-(CF$_3$)$_2$-4-Cl | CF$_3$ | CH$_2$OCH$_3$ | CH=NOEt |
| 3,5-(CF$_3$)$_2$-4-Cl | CF$_3$ | H | C(O)OCH$_3$ |
| 3,5-(CF$_3$)$_2$-4-Cl | CF$_3$ | CH$_3$ | C(O)OCH$_3$ |
| 3,5-(CF$_3$)$_2$-4-Cl | CF$_3$ | Et | C(O)OCH$_3$ |
| 3,5-(CF$_3$)$_2$-4-Cl | CF$_3$ | CH$_2$OCH$_3$ | C(O)OCH$_3$ |
| 3,5-(CF$_3$)$_2$-4-Cl | CF$_3$ | CH$_2$OEt | C(O)OCH$_3$ |
| 3,5-(CF$_3$)$_2$-4-Cl | CF$_3$ | CH$_2$OCH$_2$CF$_3$ | C(O)OCH$_3$ |
| 3,5-(CF$_3$)$_2$-4-Cl | CF$_3$ | CH$_2$OC(O)CH$_3$ | C(O)OCH$_3$ |
| 3,5-(CF$_3$)$_2$-4-Cl | CF$_3$ | CH$_2$OC(O)Et | C(O)OCH$_3$ |
| 3,5-(CF$_3$)$_2$-4-Cl | CF$_3$ | CH$_2$OC(O)Bu-t | C(O)OCH$_3$ |
| 3,5-(CF$_3$)$_2$-4-Cl | CF$_3$ | CH$_2$OC(O)OCH$_3$ | C(O)OCH$_3$ |
| 3,5-(CF$_3$)$_2$-4-Cl | CF$_3$ | E-5a | C(O)OCH$_3$ |
| 3,5-(CF$_3$)$_2$-4-Cl | CF$_3$ | CH$_2$NHC(O)OCH$_3$ | C(O)OCH$_3$ |
| 3,5-(CF$_3$)$_2$-4-Cl | CF$_3$ | CH$_2$CN | C(O)OCH$_3$ |
| 3,5-(CF$_3$)$_2$-4-Cl | CF$_3$ | C(O)CH$_3$ | C(O)OCH$_3$ |
| 3,5-(CF$_3$)$_2$-4-Cl | CF$_3$ | C(O)Et | C(O)OCH$_3$ |
| 3,5-(CF$_3$)$_2$-4-Cl | CF$_3$ | C(O)Pr-n | C(O)OCH$_3$ |
| 3,5-(CF$_3$)$_2$-4-Cl | CF$_3$ | C(O)Pr-i | C(O)OCH$_3$ |
| 3,5-(CF$_3$)$_2$-4-Cl | CF$_3$ | C(O)Bu-t | C(O)OCH$_3$ |
| 3,5-(CF$_3$)$_2$-4-Cl | CF$_3$ | C(O)CH$_2$OCH$_3$ | C(O)OCH$_3$ |
| 3,5-(CF$_3$)$_2$-4-Cl | CF$_3$ | (O)CH$_2$SCH$_3$ | C(O)OCH$_3$ |
| 3,5-(CF$_3$)$_2$-4-Cl | CF$_3$ | C(O)Ph | C(O)OCH$_3$ |
| 3,5-(CF$_3$)$_2$-4-Cl | CF$_3$ | C(O)OCH$_2$CH$_2$Cl | C(O)OCH$_3$ |
| 3,5-(CF$_3$)$_2$-4-Cl | CF$_3$ | H | C(O)OEt |
| 3,5-(CF$_3$)$_2$-4-Cl | CF$_3$ | CH$_2$OCH$_3$ | C(O)OEt |
| 3,5-(CF$_3$)$_2$-4-Cl | CF$_3$ | C(O)Bu-t | C(O)OEt |
| 3,5-(CF$_3$)$_2$-4-Cl | CF$_3$ | C(O)CH$_2$OCH$_3$ | C(O)OEt |
| 3,5-(CF$_3$)$_2$-4-Cl | CF$_3$ | C(O)OCH$_3$ | C(O)OEt |
| 3,5-(CF$_3$)$_2$-4-Cl | CF$_3$ | H | C(O)OPr-i |
| 3,5-(CF$_3$)$_2$-4-Cl | CF$_3$ | C(O)CH$_3$ | C(O)OPr-i |
| 3,5-(CF$_3$)$_2$-4-Cl | CF$_3$ | C(O)CH$_2$OCH$_3$ | C(O)OPr-i |
| 3,5-(CF$_3$)$_2$-4-Cl | CF$_3$ | C(O)OCH$_3$ | C(O)OPr-i |
| 3,5-(CF$_3$)$_2$-4-Cl | CF$_3$ | C(O)OCH$_3$ | C(O)OCH$_2$CH$_2$OCH$_3$ |
| 3,5-(CF$_3$)$_2$-4-Cl | CF$_3$ | H | C(O)NH$_2$ |
| 3,5-(CF$_3$)$_2$-4-Cl | CF$_3$ | C(O)CH$_3$ | D-14a |
| 3,5-(CF$_3$)$_2$-4-Cl | CF$_3$ | CH$_3$ | (D-52d)Cl |
| 3,5-(CF$_3$)$_2$-4-Cl | CF$_3$ | CH$_2$OCH3 | (D-52d)Cl |
| 3,5-(CF$_3$)$_2$-4-Cl | CF$_3$ | C(O)Et | (D-52d)Cl |
| 3,5-(CF$_3$)$_2$-4-Cl | CF$_3$ | C(O)OCH$_3$ | (D-52d)Cl |
| 3,5-(CF$_3$)$_2$-4-Cl | CF$_3$ | CH$_3$ | (D-52d)Br |
| 3,5-(CF$_3$)$_2$-4-Cl | CF$_3$ | CH$_3$ | (D-52d)CN |
| 3,5-(CF$_3$)$_2$-4-Cl | CF$_3$ | CH$_3$ | (D-53e)Cl |
| 3,5-(CF$_3$)$_2$-4-Cl | CF$_3$ | CH$_3$ | D-55a |
| 3,5-(CF$_3$)$_2$-4-Cl | CF$_3$ | CH$_3$ | (D-55c)Cl |
| 3,5-(CF$_3$)$_2$-4-Cl | CF$_3$ | Et | (D-55c)Cl |
| 3,5-(CF$_3$)$_2$-4-Cl | CF$_3$ | CH$_2$OCH$_3$ | (D-55c)Cl |
| 3,5-(CF$_3$)$_2$-4-Cl | CF$_3$ | CH$_2$OEt | (D-55c)Cl |
| 3,5-(CF$_3$)$_2$-4-Cl | CF$_3$ | CH$_2$OC(O)CH$_3$ | (D-55c)Cl |
| 3,5-(CF$_3$)$_2$-4-Cl | CF$_3$ | CH$_2$OC(O)Bu-t | (D-55c)Cl |
| 3,5-(CF$_3$)$_2$-4-Cl | CF$_3$ | CH$_2$OC(O)OCH$_3$ | (D-55c)Cl |
| 3,5-(CF$_3$)$_2$-4-Cl | CF$_3$ | CH$_2$CN | (D-55c)Cl |
| 3,5-(CF$_3$)$_2$-4-Cl | CF$_3$ | C(O)CH$_3$ | (D-55c)Cl |
| 3,5-(CF$_3$)$_2$-4-Cl | CF$_3$ | C(O)Et | (D-55c)Cl |
| 3,5-(CF$_3$)$_2$-4-Cl | CF$_3$ | C(O)Pr-n | (D-55c)Cl |
| 3,5-(CF$_3$)$_2$-4-Cl | CF$_3$ | C(O)Pr-i | (D-55c)Cl |
| 3,5-(CF$_3$)$_2$-4-Cl | CF$_3$ | C(O)Pr-c | (D-55c)Cl |
| 3,5-(CF$_3$)$_2$-4-Cl | CF$_3$ | C(O)Bu-t | (D-55c)Cl |
| 3,5-(CF$_3$)$_2$-4-Cl | CF$_3$ | C(O)CH$_2$Cl | (D-55c)Cl |
| 3,5-(CF$_3$)$_2$-4-Cl | CF$_3$ | C(O)CH$_2$OCH$_3$ | (D-55c)Cl |
| 3,5-(CF$_3$)$_2$-4-Cl | CF$_3$ | C(O)CH$_2$OEt | (D-55c)Cl |
| 3,5-(CF$_3$)$_2$-4-Cl | CF$_3$ | C(O)CH$_2$SCH$_3$ | (D-55c)Cl |
| 3,5-(CF$_3$)$_2$-4-Cl | CF$_3$ | C(O)CH$_2$S(O)CH$_3$ | (D-55c)Cl |
| 3,5-(CF$_3$)$_2$-4-Cl | CF$_3$ | C(O)C(O)OEt | (D-55c)Cl |
| 3,5-(CF$_3$)$_2$-4-Cl | CF$_3$ | C(O)Ph | (D-55c)Cl |
| 3,5-(CF$_3$)$_2$-4-Cl | CF$_3$ | C(O)(D-52a) | (D-55c)Cl |
| 3,5-(CF$_3$)$_2$-4-Cl | CF$_3$ | C(O)OCH$_3$ | (D-55c)Cl |
| 3,5-(CF$_3$)$_2$-4-Cl | CF$_3$ | C(O)OEt | (D-55c)Cl |
| 3,5-(CF$_3$)$_2$-4-Cl | CF$_3$ | C(O)OPr-n | (D-55c)Cl |
| 3,5-(CF$_3$)$_2$-4-Cl | CF$_3$ | C(O)OPr-i | (D-55c)Cl |
| 3,5-(CF$_3$)$_2$-4-Cl | CF$_3$ | C(O)OBu-n | (D-55c)Cl |
| 3,5-(CF$_3$)$_2$-4-Cl | CF$_3$ | C(O)OBu-i | (D-55c)Cl |
| 3,5-(CF$_3$)$_2$-4-Cl | CF$_3$ | C(O)OCH$_2$Cl | (D-55c)Cl |
| 3,5-(CF$_3$)$_2$-4-Cl | CF$_3$ | C(O)OCH$_2$CH$_2$Cl | (D-55c)Cl |
| 3,5-(CF$_3$)$_2$-4-Cl | CF$_3$ | C(O)OCH$_2$CH$_2$OCH$_3$ | (D-55c)Cl |
| 3,5-(CF$_3$)$_2$-4-Cl | CF$_3$ | C(O)OCH$_2$CH=CH$_2$ | (D-55c)Cl |
| 3,5-(CF$_3$)$_2$-4-Cl | CF$_3$ | CH$_3$ | (D-55c)Br |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,5-(CF$_3$)$_2$-4-Cl | CF$_3$ | Et | (D-55c)Br |
| 3,5-(CF$_3$)$_2$-4-Cl | CF$_3$ | CH$_2$OCH$_3$ | (D-55c)Br |
| 3,5-(CF$_3$)$_2$-4-Cl | CF$_3$ | CH$_2$OEt | (D-55c)Br |
| 3,5-(CF$_3$)$_2$-4-Cl | CF$_3$ | CH$_2$OC(O)CH$_3$ | (D-55c)Br |
| 3,5-(CF$_3$)$_2$-4-Cl | CF$_3$ | C(O)CH$_3$ | (D-55c)Br |
| 3,5-(CF$_3$)$_2$-4-Cl | CF$_3$ | C(O)Et | (D-55c)Br |
| 3,5-(CF$_3$)$_2$-4-Cl | CF$_3$ | C(O)Pr-n | (D-55c)Br |
| 3,5-(CF$_3$)$_2$-4-Cl | CF$_3$ | C(O)Pr-i | (D-55c)Br |
| 3,5-(CF$_3$)$_2$-4-Cl | CF$_3$ | C(O)Pr-c | (D-55c)Br |
| 3,5-(CF$_3$)$_2$-4-Cl | CF$_3$ | C(O)CH$_2$OCH$_3$ | (D-55c)Br |
| 3,5-(CF$_3$)$_2$-4-Cl | CF$_3$ | C(O)OCH$_3$ | (D-55c)Br |
| 3,5-(CF$_3$)$_2$-4-Cl | CF$_3$ | C(O)OEt | (D-55c)Br |
| 3,5-(CF$_3$)$_2$-4-Cl | CF$_3$ | C(O)OPr-n | (D-55c)Br |
| 3,5-(CF$_3$)$_2$-4-Cl | CF$_3$ | C(O)OBu-i | (D-55c)Br |
| 3,5-(CF$_3$)$_2$-4-Cl | CF$_3$ | C(O)OCH$_2$Cl | (D-55c)Br |
| 3,5-(CF$_3$)$_2$-4-Cl | CF$_3$ | C(O)OCH$_2$CH$_2$OCH$_3$ | (D-55c)Br |
| 3,5-(CF$_3$)$_2$-4-Cl | CF$_3$ | CH$_3$ | D-57a |
| 3,5-(CF$_3$)$_2$-4-Cl | CF$_3$ | C(O)CH$_3$ | D-57a |
| 3,5-(CF$_3$)$_2$-4-Cl | CF$_3$ | C(O)Pr-i | D-57a |
| 3,5-(CF$_3$)$_2$-4-Cl | CF$_3$ | CH$_3$ | D-58a |
| 3,5-(CF$_3$)$_2$-4-Cl | CF$_2$Cl | H | CH=NOCH$_3$ |
| 3,5-(CF$_3$)$_2$-4-Cl | CF$_2$Cl | CH$_2$OCH$_3$ | CH=NOCH$_3$ |
| 3,5-(CF$_3$)$_2$-4-Cl | CF$_2$Cl | H | CH=NOEt |
| 3,5-(CF$_3$)$_2$-4-Cl | CF$_2$Cl | H | C(O)OCH$_3$ |
| 3,5-(CF$_3$)$_2$-4-Cl | CF$_2$Cl | Et | C(O)OCH$_3$ |
| 3,5-(CF$_3$)$_2$-4-Cl | CF$_2$Cl | CH$_2$OCH$_3$ | C(O)OCH$_3$ |
| 3,5-(CF$_3$)$_2$-4-Cl | CF$_2$Cl | CH$_2$OEt | C(O)OCH$_3$ |
| 3,5-(CF$_3$)$_2$-4-Cl | CF$_2$Cl | CH$_2$OCH$_2$CF$_3$ | C(O)OCH$_3$ |
| 3,5-(CF$_3$)$_2$-4-Cl | CF$_2$Cl | CH$_2$OC(O)CH$_3$ | C(O)OCH$_3$ |
| 3,5-(CF$_3$)$_2$-4-Cl | CF$_2$Cl | CH$_2$OC(O)Et | C(O)OCH$_3$ |
| 3,5-(CF$_3$)$_2$-4-Cl | CF$_2$Cl | CH$_2$OC(O)OCH$_3$ | C(O)OCH$_3$ |
| 3,5-(CF$_3$)$_2$-4-Cl | CF$_2$Cl | E-5a | C(O)OCH$_3$ |
| 3,5-(CF$_3$)$_2$-4-Cl | CF$_2$Cl | C(O)Et | C(O)OCH$_3$ |
| 3,5-(CF$_3$)$_2$-4-Cl | CF$_2$Cl | C(O)Pr-n | C(O)OCH$_3$ |
| 3,5-(CF$_3$)$_2$-4-Cl | CF$_2$Cl | C(O)Bu-t | C(O)OCH$_3$ |
| 3,5-(CF$_3$)$_2$-4-Cl | CF$_2$Cl | C(O)CH$_2$SCH$_3$ | C(O)OCH$_3$ |
| 3,5-(CF$_3$)$_2$-4-Cl | CF$_2$Cl | C(O)OCH$_3$ | C(O)OEt |
| 3,5-(CF$_3$)$_2$-4-Cl | CF$_2$Cl | H | C(O)OPr-i |
| 3,5-(CF$_3$)$_2$-4-Cl | CF$_2$Cl | H | C(O)NH$_2$ |
| 3,5-(CF$_3$)$_2$-4-Cl | CF$_2$Cl | C(O)OCH$_3$ | (D-52d)Cl |
| 3,5-(CF$_3$)$_2$-4-Cl | CF$_2$Cl | CH$_3$ | (D-52d)Cl |
| 3,5-(CF$_3$)$_2$-4-Cl | CF$_2$Cl | CH$_2$OCH$_3$ | (D-52d)Cl |
| 3,5-(CF$_3$)$_2$-4-Cl | CF$_2$Cl | C(O)CH$_3$ | (D-52d)Cl |
| 3,5-(CF$_3$)$_2$-4-Cl | CF$_2$Cl | C(O)Et | (D-52d)Cl |
| 3,5-(CF$_3$)$_2$-4-Cl | CF$_2$Cl | C(O)Pr-i | (D-52d)Cl |
| 3,5-(CF$_3$)$_2$-4-Cl | CF$_2$Cl | C(O)CH$_2$OCH$_3$ | (D-52d)Cl |
| 3,5-(CF$_3$)$_2$-4-Cl | CF$_2$Cl | C(O)CH$_2$OEt | (D-52d)Cl |
| 3,5-(CF$_3$)$_2$-4-Cl | CF$_2$Cl | C(O)CH$_2$SCH$_3$ | (D-52d)Cl |
| 3,5-(CF$_3$)$_2$-4-Cl | CF$_2$Cl | C(O)OCH$_3$ | (D-52d)Cl |
| 3,5-(CF$_3$)$_2$-4-Cl | CF$_2$Cl | C(O)OPr-n | (D-55c)Cl |
| 3,5-(CF$_3$)$_2$-4-Cl | CF$_2$Cl | C(O)OCH$_2$CH$_2$Cl | (D-52d)Cl |
| 3,5-(CF$_3$)$_2$-4-Cl | CF$_2$Cl | C(O)OCH$_2$CH$_2$OCH$_3$ | (D-52d)Cl |
| 3,5-(CF$_3$)$_2$-4-Cl | CF$_2$Cl | C(O)OCH$_2$CH=CH$_2$ | (D-55c)Cl |
| 3,5-(CF$_3$)$_2$-4-Cl | CF$_2$Cl | CH$_2$OC(O)CH$_3$ | (D-55c)Br |
| 3,5-(CF$_3$)$_2$-4-Cl | CF$_2$Cl | C(O)CH$_3$ | (D-55c)Br |
| 3,5-(CF$_3$)$_2$-4-Cl | CF$_2$Cl | C(O)Et | (D-55c)Br |
| 3,5-(CF$_3$)$_2$-4-Cl | CF$_2$Cl | C(O)Pr-n | (D-55c)Br |
| 3,5-(CF$_3$)$_2$-4-Cl | CF$_2$Cl | C(O)Pr-i | (D-55c)Br |
| 3,5-(CF$_3$)$_2$-4-Cl | CF$_2$Cl | C(O)OCH$_3$ | (D-55c)Br |
| 3,5-(CF$_3$)$_2$-4-Cl | CF$_2$Cl | C(O)OEt | (D-55c)Br |
| 3,5-(CF$_3$)$_2$-4-Cl | CF$_2$Br | H | CH=NOCH$_3$ |
| 3,5-(CF$_3$)$_2$-4-Cl | CF$_2$Br | CH$_2$OEt | C(O)OCH$_3$ |
| 3,5-(CF$_3$)$_2$-4-Cl | CF$_2$Br | C(O)Et | C(O)OCH$_3$ |
| 3,5-(CF$_3$)$_2$-4-Cl | CF$_2$Br | C(O)CH$_3$ | (D-55c)Cl |
| 3,5-(CF$_3$)$_2$-4-Cl | CF$_2$Br | C(O)OCH$_3$ | (D-55c)Cl |
| 3,5-(CF$_3$)$_2$-4-Cl | CF$_2$CHF$_2$ | H | CH=NOCH$_3$ |
| 3,5-(CF$_3$)$_2$-4-Cl | CF$_2$CHF$_2$ | CH$_2$OEt | C(O)OCH$_3$ |
| 3,5-(CF$_3$)$_2$-4-Cl | CF$_2$CHF$_2$ | C(O)Et | C(O)OCH$_3$ |
| 3,5-(CF$_3$)$_2$-4-Cl | CF$_2$CHF$_2$ | C(O)CH$_3$ | (D-55c)Cl |
| 3,5-(CF$_3$)$_2$-4-Cl | CF$_2$CHF$_2$ | C(O)OCH$_3$ | (D-55c)Cl |
| 3,5-Cl$_2$-4-OH | CF$_3$ | H | CH=NOEt |
| 3,5-Br$_2$-4-OH | CF$_3$ | CH$_2$OEt | C(O)OCH$_3$ |
| 3,5-I$_2$-4-OH | CF$_3$ | CH$_2$OCH$_2$CF$_3$ | C(O)OCH$_3$ |
| 3,5-F$_2$-4-OCH$_3$ | CF$_3$ | C(O)Et | C(O)OCH$_3$ |
| 3,5-Cl$_2$-4-OCH$_3$ | CF$_3$ | C(O)CH$_3$ | (D-55c)Cl |
| 3-F-5-Br-4-OCH$_3$ | CF$_3$ | C(O)Pr-i | (D-55c)Cl |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-Br-4-OCH$_3$ | CF$_3$ | C(O)OCH$_3$ | (D-55c)Cl |
| 3,5-Br$_2$-4-OCH$_3$ | CF$_3$ | C(O)CH$_3$ | (D-55c)Br |
| 3,5-Cl$_2$-4-OEt | CF$_3$ | H | CH=NOCH$_3$ |
| 3,5-Br$_2$-4-OEt | CF$_3$ | H | CH=NOEt |
| 3,5-Cl$_2$-4-OPr-n | CF$_3$ | CH$_2$OEt | C(O)OCH$_3$ |
| 3,5-Cl$_2$-4-OCHF$_2$ | CF$_3$ | H | CH=NOCH$_3$ |
| 3,5-Cl$_2$-4-OCHF$_2$ | CF$_3$ | CH$_2$OEt | C(O)OCH$_3$ |
| 3,5-Cl$_2$-4-OCHF$_2$ | CF$_3$ | C(O)Et | C(O)OCH$_3$ |
| 3,5-Cl$_2$-4-OCHF$_2$ | CF$_3$ | C(O)CH$_3$ | (D-55c)Cl |
| 3,5-Cl$_2$-4-OCHF$_2$ | CF$_3$ | C(O)OCH$_3$ | (D-55c)Cl |
| 3,5-Br$_2$-4-OCHF$_2$ | CF$_3$ | H | CH=NOCH$_3$ |
| 3,5-Br$_2$-4-OCHF$_2$ | CF$_3$ | CH$_2$OEt | C(O)OCH$_3$ |
| 3,5-Br$_2$-4-OCHF$_2$ | CF$_3$ | C(O)Et | C(O)OCH$_3$ |
| 3,5-Br$_2$-4-OCHF$_2$ | CF$_3$ | C(O)CH$_3$ | (D-55c)Cl |
| 3,5-Br$_2$-4-OCHF$_2$ | CF$_3$ | C(O)OCH$_3$ | (D-55c)Cl |
| 3,5-F$_2$-4-OCF$_3$ | CF$_3$ | CH$_2$OCH$_2$CF$_3$ | C(O)OCH$_3$ |
| 3,5-Cl$_2$-4-OCH$_2$CH=CH$_2$ | CF$_3$ | C(O)Et | C(O)OCH$_3$ |
| 3,5-Cl$_2$-4-OCH$_2$C≡CH | CF$_3$ | C(O)CH$_3$ | C(O)OCH$_3$ |
| 3,5-Cl$_2$-4-OSi(CH$_3$)$_3$ | CF$_3$ | C(O)Pr-i | (D-55c)Cl |
| 3,5-Cl$_2$-4-OSi(CH$_3$)$_2$Bu-t | CF$_3$ | C(O)OCH$_3$ | (D-55c)Cl |
| 3,5-F$_2$-4-NO$_2$ | CF$_3$ | C(O)CH$_3$ | (D-55c)Cl |
| 3,5-Cl$_2$-4-NO$_2$ | CF$_3$ | H | (D-55c)Br |
| 3,5-Cl$_2$-4-NH$_2$ | CF$_3$ | H | CH=NOCH$_3$ |
| 3,5-Cl$_2$-4-NH$_2$ | CF$_3$ | H | CH=NOEt |
| 3,5-Cl$_2$-4-NH$_2$ | CF$_3$ | CH$_2$OEt | C(O)OCH$_3$ |
| 3,5-Cl$_2$-4-NH$_2$ | CF$_3$ | CH$_2$OCH$_2$CF$_3$ | C(O)OCH$_3$ |
| 3,5-Cl$_2$-4-NH$_2$ | CF$_3$ | C(O)Et | C(O)OCH$_3$ |
| 3,5-Cl$_2$-4-NH$_2$ | CF$_3$ | C(O)CH$_3$ | (D-55c)Cl |
| 3,5-Cl$_2$-4-NH$_2$ | CF$_3$ | C(O)Pr-i | (D-55c)Cl |
| 3,5-Cl$_2$-4-NH$_2$ | CF$_3$ | C(O)OCH$_3$ | (D-55c)Cl |
| 3,5-Cl$_2$-4-NH$_2$ | CF$_3$ | C(O)CH$_3$ | (D-55c)Br |
| 3,5-Br$_2$-4-NH$_2$ | CF$_3$ | H | CH=NOCH$_3$ |
| 3,5-Br$_2$-4-NH$_2$ | CF$_3$ | H | CH=NOEt |
| 3,5-Br$_2$-4-NH$_2$ | CF$_3$ | CH$_2$OEt | C(O)OCH$_3$ |
| 3,5-Br$_2$-4-NH$_2$ | CF$_3$ | CH$_2$OCH$_2$CF$_3$ | C(O)OCH$_3$ |
| 3,5-Br$_2$-4-NH$_2$ | CF$_3$ | C(O)Et | C(O)OCH$_3$ |
| 3,5-Br$_2$-4-NH$_2$ | CF$_3$ | C(O)CH$_3$ | C(O)OCH$_3$ |
| 3,5-Br$_2$-4-NH$_2$ | CF$_3$ | C(O)Pr-i | (D-55c)Cl |
| 3,5-Br$_2$-4-NH$_2$ | CF$_3$ | C(O)OCH$_3$ | (D-55c)Cl |
| 3,5-Br$_2$-4-NH$_2$ | CF$_3$ | C(O)CH$_3$ | (D-55c)Br |
| 3,5-I$_2$-4-NH$_2$ | CF$_3$ | H | CH=NOCH$_3$ |
| 3,5-F$_2$-4-CN | CF$_3$ | H | CH=NOEt |
| 3,5-Cl$_2$-4-CN | CF$_3$ | H | CH=NOCH$_3$ |
| 3,5-Cl$_2$-4-CN | CF$_3$ | CH$_2$OEt | C(O)OCH$_3$ |
| 3,5-Cl$_2$-4-CN | CF$_3$ | C(O)Et | C(O)OCH$_3$ |
| 3,5-Cl$_2$-4-CN | CF$_3$ | C(O)CH$_3$ | (D-55c)Cl |
| 3,5-Cl$_2$-4-CN | CF$_3$ | C(O)OCH$_3$ | (D-55c)Cl |
| 3,5-Br$_2$-4-CN | CF$_3$ | H | CH=NOCH$_3$ |
| 3,5-Br$_2$-4-CN | CF$_3$ | CH$_2$OEt | C(O)OCH$_3$ |
| 3,5-Br$_2$-4-CN | CF$_3$ | C(O)Et | C(O)OCH$_3$ |
| 3,5-Br$_2$-4-CN | CF$_3$ | C(O)CH$_3$ | (D-55c)Cl |
| 3,5-Br$_2$-4-CN | CF$_3$ | C(O)OCH$_3$ | (D-55c)Cl |
| 2,3,5,6-F$_4$ | CF$_3$ | C(O)Et | C(O)OCH$_3$ |
| 2,3,4,5,6-F$_5$ | CF$_3$ | CH$_2$OCH$_2$CF$_3$ | C(O)OCH$_3$ |
| 3-CF$_3$ | CF$_3$ | CH$_3$ | (D-55c)CN |
| 3-CF$_3$ | CF$_3$ | CH$_2$OCH$_3$ | (D-55c)CN |
| 3-CF$_3$ | CF$_3$ | C(O)CH$_3$ | (D-55c)CN |
| 3-CF$_3$ | CF$_3$ | C(O)Et | (D-55c)CN |
| 3-CF$_3$ | CF$_3$ | C(O)Pr-i | (D-55c)CN |
| 3-CF$_3$ | CF$_3$ | C(O)OCH$_3$ | (D-55c)CN |
| 3-CF$_2$CF$_3$ | CF$_3$ | CH$_3$ | (D-55c)CN |
| 3-CF$_2$CF$_3$ | CF$_3$ | CH$_2$OCH$_3$ | (D-55c)CN |
| 3-CF$_2$CF$_3$ | CF$_3$ | C(O)CH$_3$ | (D-55c)CN |
| 3-CF$_2$CF$_3$ | CF$_3$ | C(O)Et | (D-55c)CN |
| 3-CF$_2$CF$_3$ | CF$_3$ | C(O)Pr-i | (D-55c)CN |
| 3-CF$_2$CF$_3$ | CF$_3$ | C(O)OCH$_3$ | (D-55c)CN |
| 3-Cl-4-F | CF$_3$ | CH$_3$ | (D-55c)CN |
| 3-Cl-4-F | CF$_3$ | CH$_2$OCH$_3$ | (D-55c)CN |
| 3-Cl-4-F | CF$_3$ | C(O)CH$_3$ | (D-55c)CN |
| 3-Cl-4-F | CF$_3$ | C(O)Et | (D-55c)CN |
| 3-Cl-4-F | CF$_3$ | C(O)Pr-i | (D-55c)CN |
| 3-Cl-4-F | CF$_3$ | C(O)OCH$_3$ | (D-55c)CN |
| 3-Cl-4-F | CF$_3$ | CH$_3$ | (D-55c)CN |
| 3-Cl-4-F | CF$_3$ | CH$_2$OCH$_3$ | (D-55c)CN |
| 3-Cl-4-F | CF$_3$ | C(O)CH$_3$ | (D-55c)CN |
| 3-Cl-4-F | CF$_3$ | C(O)Et | (D-55c)CN |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-4-F | $CF_3$ | $C(O)Pr$-i | (D-55c)CN |
| 3-Cl-4-F | $CF_3$ | $C(O)OCH_3$ | (D-55c)CN |
| 3,4-$Cl_2$ | $CF_3$ | $CH_3$ | (D-55c)CN |
| 3,4-$Cl_2$ | $CF_3$ | $CH_2OCH_3$ | (D-55c)CN |
| 3,4-$Cl_2$ | $CF_3$ | $C(O)CH_3$ | (D-55c)CN |
| 3,4-$Cl_2$ | $CF_3$ | $C(O)Et$ | (D-55c)CN |
| 3,4-$Cl_2$ | $CF_3$ | $C(O)Pr$-i | (D-55c)CN |
| 3,4-$Cl_2$ | $CF_3$ | $C(O)OCH_3$ | (D-55c)CN |
| 3-Br-4-F | $CF_3$ | $CH_3$ | (D-55c)CN |
| 3-Br-4-F | $CF_3$ | $CH_2OCH_3$ | (D-55c)CN |
| 3-Br-4-F | $CF_3$ | $C(O)CH_3$ | (D-55c)CN |
| 3-Br-4-F | $CF_3$ | $C(O)Et$ | (D-55c)CN |
| 3-Br-4-F | $CF_3$ | $C(O)Pr$-i | (D-55c)CN |
| 3-Br-4-F | $CF_3$ | $C(O)OCH_3$ | (D-55c)CN |
| 3-F-5-Br | $CF_3$ | $CH_3$ | (D-55c)CN |
| 3-F-5-Br | $CF_3$ | $CH_2OCH_3$ | (D-55c)CN |
| 3-F-5-Br | $CF_3$ | $C(O)CH_3$ | (D-55c)CN |
| 3-F-5-Br | $CF_3$ | $C(O)Et$ | (D-55c)CN |
| 3-F-5-Br | $CF_3$ | $C(O)Pr$-i | (D-55c)CN |
| 3-F-5-Br | $CF_3$ | $C(O)OCH_3$ | (D-55c)CN |
| 3-Cl-5-Br | $CF_3$ | $CH_3$ | (D-55c)CN |
| 3-Cl-5-Br | $CF_3$ | $CH_2OCH_3$ | (D-55c)CN |
| 3-Cl-5-Br | $CF_3$ | $CH_2OEt$ | (D-55c)CN |
| 3-Cl-5-Br | $CF_3$ | $CH_2OC(O)CH_3$ | (D-55c)CN |
| 3-Cl-5-Br | $CF_3$ | $CH_2OC(O)OCH_3$ | (D-55c)CN |
| 3-Cl-5-Br | $CF_3$ | $CH_2CN$ | (D-55c)CN |
| 3-Cl-5-Br | $CF_3$ | $C(O)CH_3$ | (D-55c)CN |
| 3-Cl-5-Br | $CF_3$ | $C(O)Et$ | (D-55c)CN |
| 3-Cl-5-Br | $CF_3$ | $C(O)Pr$-i | (D-55c)CN |
| 3-Cl-5-Br | $CF_3$ | $C(O)Pr$-c | (D-55c)CN |
| 3-Cl-5-Br | $CF_3$ | $C(O)OCH_3$ | (D-55c)CN |
| 3,5-$Br_2$ | $CF_3$ | $CH_3$ | (D-55c)CN |
| 3,5-$Br_2$ | $CF_3$ | $CH_2OCH_3$ | (D-55c)CN |
| 3,5-$Br_2$ | $CF_3$ | $CH_2OEt$ | (D-55c)CN |
| 3,5-$Br_2$ | $CF_3$ | $CH_2OC(O)CH_3$ | (D-55c)CN |
| 3,5-$Br_2$ | $CF_3$ | $CH_2OC(O)OCH_3$ | (D-55c)CN |
| 3,5-$Br_2$ | $CF_3$ | $CH_2CN$ | (D-55c)CN |
| 3,5-$Br_2$ | $CF_3$ | $C(O)CH_3$ | (D-55c)CN |
| 3,5-$Br_2$ | $CF_3$ | $C(O)Et$ | (D-55c)CN |
| 3,5-$Br_2$ | $CF_3$ | $C(O)Pr$-i | (D-55c)CN |
| 3,5-$Br_2$ | $CF_3$ | $C(O)Pr$-c | (D-55c)CN |
| 3,5-$Br_2$ | $CF_3$ | $C(O)OCH_3$ | (D-55c)CN |
| 3-Cl-5-I | $CF_3$ | $CH_3$ | (D-55c)CN |
| 3-Cl-5-I | $CF_3$ | $CH_2OCH_3$ | (D-55c)CN |
| 3-Cl-5-I | $CF_3$ | $C(O)CH_3$ | (D-55c)CN |
| 3-Cl-5-I | $CF_3$ | $C(O)Et$ | (D-55c)CN |
| 3-Cl-5-I | $CF_3$ | $C(O)Pr$-i | (D-55c)CN |
| 3-Cl-5-I | $CF_3$ | $C(O)OCH_3$ | (D-55c)CN |
| 3-$CF_3$-4-F | $CF_3$ | $CH_3$ | (D-55c)CN |
| 3-$CF_3$-4-F | $CF_3$ | $CH_2OCH_3$ | (D-55c)CN |
| 3-$CF_3$-4-F | $CF_3$ | $C(O)CH_3$ | (D-55c)CN |
| 3-$CF_3$-4-F | $CF_3$ | $C(O)Et$ | (D-55c)CN |
| 3-$CF_3$-4-F | $CF_3$ | $C(O)Pr$-i | (D-55c)CN |
| 3-$CF_3$-4-F | $CF_3$ | $C(O)OCH_3$ | (D-55c)CN |
| 3-F-5-$CF_3$ | $CF_3$ | $CH_3$ | (D-55c)CN |
| 3-F-5-$CF_3$ | $CF_3$ | $CH_2OCH_3$ | (D-55c)CN |
| 3-F-5-$CF_3$ | $CF_3$ | $C(O)CH_3$ | (D-55c)CN |
| 3-F-5-$CF_3$ | $CF_3$ | $C(O)Et$ | (D-55c)CN |
| 3-F-5-$CF_3$ | $CF_3$ | $C(O)Pr$-i | (D-55c)CN |
| 3-F-5-$CF_3$ | $CF_3$ | $C(O)OCH_3$ | (D-55c)CN |
| 3-$CF_3$-4-Cl | $CF_3$ | $CH_3$ | (D-55c)CN |
| 3-$CF_3$-4-Cl | $CF_3$ | $CH_2OCH_3$ | (D-55c)CN |
| 3-$CF_3$-4-Cl | $CF_3$ | $C(O)CH_3$ | (D-55c)CN |
| 3-$CF_3$-4-Cl | $CF_3$ | $C(O)Et$ | (D-55c)CN |
| 3-$CF_3$-4-Cl | $CF_3$ | $C(O)Pr$-i | (D-55c)CN |
| 3-$CF_3$-4-Cl | $CF_3$ | $C(O)OCH_3$ | (D-55c)CN |
| 3-Cl-5-$CF_3$ | $CF_3$ | $CH_3$ | (D-55c)CN |
| 3-Cl-5-$CF_3$ | $CF_3$ | $CH_2OCH_3$ | (D-55c)CN |
| 3-Cl-5-$CF_3$ | $CF_3$ | $CH_2OEt$ | (D-55c)CN |
| 3-Cl-5-$CF_3$ | $CF_3$ | $CH_2OC(O)CH_3$ | (D-55c)CN |
| 3-Cl-5-$CF_3$ | $CF_3$ | $CH_2OC(O)OCH_3$ | (D-55c)CN |
| 3-Cl-5-$CF_3$ | $CF_3$ | $CH_2CN$ | (D-55c)CN |
| 3-Cl-5-$CF_3$ | $CF_3$ | $C(O)CH_3$ | (D-55c)CN |
| 3-Cl-5-$CF_3$ | $CF_3$ | $C(O)Et$ | (D-55c)CN |
| 3-Cl-5-$CF_3$ | $CF_3$ | $C(O)Pr$-i | (D-55c)CN |
| 3-Cl-5-$CF_3$ | $CF_3$ | $C(O)Pr$-c | (D-55c)CN |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3-Cl-5-CF$_3$ | CF$_3$ | C(O)OCH$_3$ | (D-55c)CN |
| 3-Br-5-CF$_3$ | CF$_3$ | CH$_3$ | (D-55c)CN |
| 3-Br-5-CF$_3$ | CF$_3$ | CH$_2$OCH$_3$ | (D-55c)CN |
| 3-Br-5-CF$_3$ | CF$_3$ | CH$_2$OEt | (D-55c)CN |
| 3-Br-5-CF$_3$ | CF$_3$ | CH$_2$OC(O)CH$_3$ | (D-55c)CN |
| 3-Br-5-CF$_3$ | CF$_3$ | CH$_2$OC(O)OCH$_3$ | (D-55c)CN |
| 3-Br-5-CF$_3$ | CF$_3$ | CH$_2$CN | (D-55c)CN |
| 3-Br-5-CF$_3$ | CF$_3$ | C(O)CH$_3$ | (D-55c)CN |
| 3-Br-5-CF$_3$ | CF$_3$ | C(O)Et | (D-55c)CN |
| 3-Br-5-CF$_3$ | CF$_3$ | C(O)Pr-i | (D-55c)CN |
| 3-Br-5-CF$_3$ | CF$_3$ | C(O)Pr-c | (D-55c)CN |
| 3-Br-5-CF$_3$ | CF$_3$ | C(O)OCH$_3$ | (D-55c)CN |
| 3,5-(CF$_3$)$_2$ | CF$_3$ | CH$_3$ | (D-55c)CN |
| 3,5-(CF$_3$)$_2$ | CF$_3$ | CH$_2$OCH$_3$ | (D-55c)CN |
| 3,5-(CF$_3$)$_2$ | CF$_3$ | CH$_2$OEt | (D-55c)CN |
| 3,5-(CF$_3$)$_2$ | CF$_3$ | CH$_2$OC(O)CH$_3$ | (D-55c)CN |
| 3,5-(CF$_3$)$_2$ | CF$_3$ | CH$_2$OC(O)OCH$_3$ | (D-55c)CN |
| 3,5-(CF$_3$)$_2$ | CF$_3$ | CH$_2$CN | (D-55c)CN |
| 3,5-(CF$_3$)$_2$ | CF$_3$ | C(O)CH$_3$ | (D-55c)CN |
| 3,5-(CF$_3$)$_2$ | CF$_3$ | C(O)Et | (D-55c)CN |
| 3,5-(CF$_3$)$_2$ | CF$_3$ | C(O)Pr-i | (D-55c)CN |
| 3,5-(CF$_3$)$_2$ | CF$_3$ | C(O)Pr-c | (D-55c)CN |
| 3,5-(CF$_3$)$_2$ | CF$_3$ | C(O)OCH$_3$ | (D-55c)CN |
| 3-Cl-5-OCHF$_2$ | CF$_3$ | CH$_3$ | (D-55c)CN |
| 3-Cl-5-OCHF$_2$ | CF$_3$ | CH$_2$OCH$_3$ | (D-55c)CN |
| 3-Cl-5-OCHF$_2$ | CF$_3$ | C(O)CH$_3$ | (D-55c)CN |
| 3-Cl-5-OCHF$_2$ | CF$_3$ | C(O)Et | (D-55c)CN |
| 3-Cl-5-OCHF$_2$ | CF$_3$ | C(O)Pr-i | (D-55c)CN |
| 3-Cl-5-OCHF$_2$ | CF$_3$ | C(O)OCH$_3$ | (D-55c)CN |
| 3-Cl-5-OCHF$_2$ | CF$_3$ | CH$_3$ | (D-55c)CN |
| 3-Cl-5-OCHF$_2$ | CF$_3$ | CH$_2$OCH$_3$ | (D-55c)CN |
| 3-Cl-5-OCF$_3$ | CF$_3$ | C(O)CH$_3$ | (D-55c)CN |
| 3-Cl-5-OCF$_3$ | CF$_3$ | C(O)Et | (D-55c)CN |
| 3-Cl-5-OCF$_3$ | CF$_3$ | C(O)Pr-i | (D-55c)CN |
| 3-Cl-5-OCF$_3$ | CF$_3$ | C(O)OCH$_3$ | (D-55c)CN |
| 3-Cl-5-OCF$_3$ | CF$_3$ | CH$_3$ | (D-55c)CN |
| 3-Cl-5-SCF$_3$ | CF$_3$ | CH$_2$OCH$_3$ | (D-55c)CN |
| 3-Cl-5-SCF$_3$ | CF$_3$ | C(O)CH$_3$ | (D-55c)CN |
| 3-Cl-5-SCF$_3$ | CF$_3$ | C(O)Et | (D-55c)CN |
| 3-Cl-5-SCF$_3$ | CF$_3$ | C(O)Pr-i | (D-55c)CN |
| 3-Cl-5-SCF$_3$ | CF$_3$ | C(O)OCH$_3$ | (D-55c)CN |
| 3,5-Cl$_2$-4-F | CF$_3$ | CH$_3$ | (D-55c)CN |
| 3,5-Cl$_2$-4-F | CF$_3$ | CH$_2$OCH$_3$ | (D-55c)CN |
| 3,5-Cl$_2$-4-F | CF$_3$ | CH$_2$OEt | (D-55c)CN |
| 3,5-Cl$_2$-4-F | CF$_3$ | CH$_2$OC(O)CH$_3$ | (D-55c)CN |
| 3,5-Cl$_2$-4-F | CF$_3$ | CH$_2$OC(O)OCH$_3$ | (D-55c)CN |
| 3,5-Cl$_2$-4-F | CF$_3$ | CH$_2$CN | (D-55c)CN |
| 3,5-Cl$_2$-4-F | CF$_3$ | C(O)CH$_3$ | (D-55c)CN |
| 3,5-Cl$_2$-4-F | CF$_3$ | C(O)Et | (D-55c)CN |
| 3,5-Cl$_2$-4-F | CF$_3$ | C(O)Pr-i | (D-55c)CN |
| 3,5-Cl$_2$-4-F | CF$_3$ | C(O)Pr-c | (D-55c)CN |
| 3,5-Cl$_2$-4-F | CF$_3$ | C(O)OCH$_3$ | (D-55c)CN |
| 3,4,5-Cl$_3$ | CF$_3$ | CH$_3$ | (D-55c)CN |
| 3,4,5-Cl$_3$ | CF$_3$ | CH$_2$OCH$_3$ | (D-55c)CN |
| 3,4,5-Cl$_3$ | CF$_3$ | CH$_2$OEt | (D-55c)CN |
| 3,4,5-Cl$_3$ | CF$_3$ | CH$_2$OC(O)CH$_3$ | (D-55c)CN |
| 3,4,5-Cl$_3$ | CF$_3$ | CH$_2$OC(O)OCH$_3$ | (D-55c)CN |
| 3,4,5-Cl$_3$ | CF$_3$ | CH$_2$CN | (D-55c)CN |
| 3,4,5-Cl$_3$ | CF$_3$ | C(O)CH$_3$ | (D-55c)CN |
| 3,4,5-Cl$_3$ | CF$_3$ | C(O)Et | (D-55c)CN |
| 3,4,5-Cl$_3$ | CF$_3$ | C(O)Pr-i | (D-55c)CN |
| 3,4,5-Cl$_3$ | CF$_3$ | C(O)Pr-c | (D-55c)CN |
| 3,4,5-Cl$_3$ | CF$_3$ | C(O)OCH$_3$ | (D-55c)CN |
| 3,5-Br$_2$-4-F | CF$_3$ | CH$_3$ | (D-55c)CN |
| 3,5-Br$_2$-4-F | CF$_3$ | CH$_2$OCH$_3$ | (D-55c)CN |
| 3,5-Br$_2$-4-F | CF$_3$ | CH$_2$OEt | (D-55c)CN |
| 3,5-Br$_2$-4-F | CF$_3$ | CH$_2$OC(O)CH$_3$ | (D-55c)CN |
| 3,5-Br$_2$-4-F | CF$_3$ | CH$_2$OC(O)OCH$_3$ | (D-55c)CN |
| 3,5-Br$_2$-4-F | CF$_3$ | CH$_2$CN | (D-55c)CN |
| 3,5-Br$_2$-4-F | CF$_3$ | C(O)CH$_3$ | (D-55c)CN |
| 3,5-Br$_2$-4-F | CF$_3$ | C(O)Et | (D-55c)CN |
| 3,5-Br$_2$-4-F | CF$_3$ | C(O)Pr-i | (D-55c)CN |
| 3,5-Br$_2$-4-F | CF$_3$ | C(O)Pr-c | (D-55c)CN |
| 3,5-Br$_2$-4-F | CF$_3$ | C(O)OCH$_3$ | (D-55c)CN |
| 3,4-F$_2$-5-CF$_3$ | CF$_3$ | CH$_3$ | (D-55c)CN |
| 3,4-F$_2$-5-CF$_3$ | CF$_3$ | CH$_2$OCH$_3$ | (D-55c)CN |

TABLE 2-continued

In the table, the number showing the substitution position of substituent $(X)_m$ corresponds to the position number indicated in the following structural formulae. The indication "—" means no-substitution.

| | | | |
|---|---|---|---|
| 3,4-F$_2$-5-CF$_3$ | CF$_3$ | CH$_2$OEt | (D-55c)CN |
| 3,4-F$_2$-5-CF$_3$ | CF$_3$ | CH$_2$OC(O)CH$_3$ | (D-55c)CN |
| 3,4-F$_2$-5-CF$_3$ | CF$_3$ | CH$_2$OC(O)OCH$_3$ | (D-55c)CN |
| 3,4-F$_2$-5-CF$_3$ | CF$_3$ | CH$_2$CN | (D-55c)CN |
| 3,4-F$_2$-5-CF$_3$ | CF$_3$ | C(O)CH$_3$ | (D-55c)CN |
| 3,4-F$_2$-5-CF$_3$ | CF$_3$ | C(O)Et | (D-55c)CN |
| 3,4-F$_2$-5-CF$_3$ | CF$_3$ | C(O)Pr-i | (D-55c)CN |
| 3,4-F$_2$-5-CF$_3$ | CF$_3$ | C(O)Pr-c | (D-55c)CN |
| 3,4-F$_2$-5-CF$_3$ | CF$_3$ | C(O)OCH$_3$ | (D-55c)CN |
| 3-Cl-4-F-5-CF$_3$ | CF$_3$ | CH$_3$ | (D-55c)CN |
| 3-Cl-4-F-5-CF$_3$ | CF$_3$ | CH$_2$OCH$_3$ | (D-55c)CN |
| 3-Cl-4-F-5-CF$_3$ | CF$_3$ | CH$_2$OEt | (D-55c)CN |
| 3-Cl-4-F-5-CF$_3$ | CF$_3$ | CH$_2$OC(O)CH$_3$ | (D-55c)CN |
| 3-Cl-4-F-5-CF$_3$ | CF$_3$ | CH$_2$OC(O)OCH$_3$ | (D-55c)CN |
| 3-Cl-4-F-5-CF$_3$ | CF$_3$ | CH$_2$CN | (D-55c)CN |
| 3-Cl-4-F-5-CF$_3$ | CF$_3$ | C(O)CH3 | (D-55c)CN |
| 3-Cl-4-F-5-CF$_3$ | CF$_3$ | C(O)Et | (D-55c)CN |
| 3-Cl-4-F-5-CF$_3$ | CF$_3$ | C(O)Pr-i | (D-55c)CN |
| 3-Cl-4-F-5-CF$_3$ | CF$_3$ | C(O)Pr-c | (D-55c)CN |
| 3-Cl-4-F-5-CF$_3$ | CF$_3$ | C(O)OCH$_3$ | (D-55c)CN |
| 3,4-Cl$_2$-5-CF$_3$ | CF$_3$ | CH$_3$ | (D-55c)CN |
| 3,4-Cl$_2$-5-CF$_3$ | CF$_3$ | CH$_2$OCH$_3$ | (D-55c)CN |
| 3,4-Cl$_2$-5-CF$_3$ | CF$_3$ | CH$_2$OEt | (D-55c)CN |
| 3,4-Cl$_2$-5-CF$_3$ | CF$_3$ | CH$_2$OC(O)CH$_3$ | (D-55c)CN |
| 3,4-Cl$_2$-5-CF$_3$ | CF$_3$ | CH$_2$OC(O)OCH$_3$ | (D-55c)CN |
| 3,4-Cl$_2$-5-CF$_3$ | CF$_3$ | CH$_2$CN | (D-55c)CN |
| 3,4-Cl$_2$-5-CF$_3$ | CF$_3$ | C(O)CH$_3$ | (D-55c)CN |
| 3,4-Cl$_2$-5-CF$_3$ | CF$_3$ | C(O)Et | (D-55c)CN |
| 3,4-Cl$_2$-5-CF$_3$ | CF$_3$ | C(O)Pr-i | (D-55c)CN |
| 3,4-Cl$_2$-5-CF$_3$ | CF$_3$ | C(O)Pr-c | (D-55c)CN |
| 3,4-Cl$_2$-5-CF$_3$ | CF$_3$ | C(O)OCH$_3$ | (D-55c)CN |
| 3,5-(CF$_3$)$_2$-4-Cl | CF$_3$ | CH$_3$ | (D-55c)CN |
| 3,5-(CF$_3$)$_2$-4-Cl | CF$_3$ | CH$_2$OCH$_3$ | (D-55c)CN |
| 3,5-(CF$_3$)$_2$-4-Cl | CF$_3$ | CH$_2$OEt | (D-55c)CN |
| 3,5-(CF$_3$)$_2$-4-Cl | CF$_3$ | CH$_2$OC(O)CH$_3$ | (D-55c)CN |
| 3,5-(CF$_3$)$_2$-4-Cl | CF$_3$ | CH$_2$OC(O)OCH$_3$ | (D-55c)CN |
| 3,5-(CF$_3$)$_2$-4-Cl | CF$_3$ | CH$_2$CN | (D-55c)CN |
| 3,5-(CF$_3$)$_2$-4-Cl | CF$_3$ | C(O)CH$_3$ | (D-55c)CN |
| 3,5-(CF$_3$)$_2$-4-Cl | CF$_3$ | C(O)Et | (D-55c)CN |
| 3,5-(CF$_3$)$_2$-4-Cl | CF$_3$ | C(O)Pr-i | (D-55c)CN |
| 3,5-(CF$_3$)$_2$-4-Cl | CF$_3$ | C(O)Pr-c | (D-55c)CN |
| 3,5-(CF$_3$)$_2$-4-Cl | CF$_3$ | C(O)OCH$_3$ | (D-55c)CN |

TABLE 3

In the table, the number showing the substitution position of substituents $(X)_m$ and $(Y)_n$ corresponds to the position number indicated in the following structural formulae. The indication "—" means no-substitution.

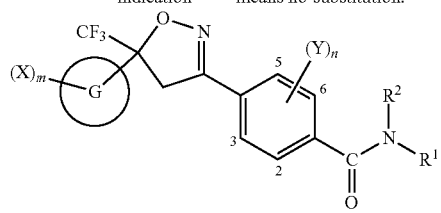

[2]-1

TABLE 3-continued
or
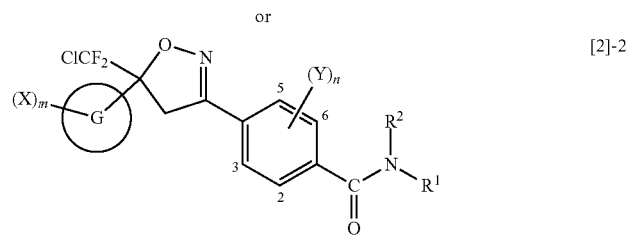
[2]-2
In addition, substituent G in the formulae [2]-1 and [2]-2 is an aromatic 6-membered ring of any of of the following G-1, G-3 or G-4, or an aromatic 5-memberd ring of any one of the following G-13, G-14, G-17a, G-20, G-21 or G-22, respectively.
G-1
G-3
G-4
G-13
G-14
G-17a
G-20
G-21

TABLE 3-continued

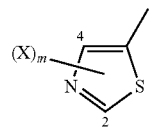

G-22

| G | $(X)_m$ | $(Y)_n$ | $R^2$ | $R^1$ |
|---|---|---|---|---|
| G-1 | 3-CF$_3$ | 2-Pr-i | H | CH=NOCH$_3$ |
| G-1 | 3-CF$_3$ | 2-OEt | H | CH=NOEt |
| G-1 | 3-CF$_3$ | 2-OPr-i | CH$_2$OEt | C(O)OCH$_3$ |
| G-1 | 3-CF$_3$ | 2-OSO$_2$CH$_3$ | CH$_2$OCH$_2$CF$_3$ | C(O)OCH$_3$ |
| G-1 | 3-CF$_3$ | 2-SEt | C(O)Et | C(O)OCH$_3$ |
| G-1 | 3-CF$_3$ | 2-SPr-i | C(O)CH$_3$ | (D-55c)Cl |
| G-1 | 3-CF$_3$ | 2-NHEt | C(O)Pr-i | (D-55c)Cl |
| G-1 | 3-CF$_3$ | 2-NHPr-i | C(O)OCH$_3$ | (D-55c)Cl |
| G-1 | 3-CF$_3$ | 2-N(CH$_3$)$_2$ | C(O)CH$_3$ | (D-55c)Br |
| G-1 | 3-CF$_3$ | 2-NHC(O)CH$_3$ | H | CH=NOCH$_3$ |
| G-1 | 3-CF$_2$CF$_3$ | 2-Pr-i | H | CH=NOEt |
| G-1 | 3-CF$_2$CF$_3$ | 2-OEt | CH$_2$OEt | C(O)OCH$_3$ |
| G-1 | 3-CF$_2$CF$_3$ | 2-OPr-i | CH$_2$OCH$_2$CF$_3$ | C(O)OCH$_3$ |
| G-1 | 3-CF$_2$CF$_3$ | 2-OSO$_2$CH$_3$ | C(O)Et | C(O)OCH$_3$ |
| G-1 | 3-CF$_2$CF$_3$ | 2-SEt | C(O)CH$_3$ | (D-55c)Cl |
| G-1 | 3-CF$_2$CF$_3$ | 2-SPr-i | C(O)Pr-i | (D-55c)Cl |
| G-1 | 3-CF$_2$CF$_3$ | 2-NHEt | C(O)OCH$_3$ | (D-55c)Cl |
| G-1 | 3-CF$_2$CF$_3$ | 2-NHPr-i | C(O)CH$_3$ | (D-55c)Br |
| G-1 | 3-CF$_2$CF$_3$ | 2-N(CH$_3$)$_2$ | H | CH=NOCH$_3$ |
| G-1 | 3-CF$_2$CF$_3$ | 2-NHC(O)CH$_3$ | H | CH=NOEt |
| G-1 | 3-SF$_5$ | 2-Pr-i | CH$_2$OEt | C(O)OCH$_3$ |
| G-1 | 3-SF$_5$ | 2-OEt | CH$_2$OCH$_2$CF$_3$ | C(O)OCH$_3$ |
| G-1 | 3-SF$_5$ | 2-OPr-i | C(O)Et | C(O)OCH$_3$ |
| G-1 | 3-SF$_5$ | 2-OSO$_2$CH$_3$ | C(O)CH$_3$ | (D-55c)Cl |
| G-1 | 3-SF$_5$ | 2-SEt | C(O)Pr-i | (D-55c)Cl |
| G-1 | 3-SF$_5$ | 2-SPr-i | C(O)OCH$_3$ | (D-55c)Cl |
| G-1 | 3-SF$_5$ | 2-NHEt | C(O)CH$_3$ | (D-55c)Br |
| G-1 | 3-SF$_5$ | 2-NHPr-i | H | CH=NOCH$_3$ |
| G-1 | 3-SF$_5$ | 2-N(CH$_3$)$_2$ | H | CH=NOEt |
| G-1 | 3-SF$_5$ | 2-NHC(O)CH$_3$ | CH$_2$OEt | C(O)OCH$_3$ |
| G-1 | 3,5-Cl$_2$ | 3-F | CH$_2$OCH$_2$CF$_3$ | C(O)OCH$_3$ |
| G-1 | 3,5-Cl$_2$ | 3-Cl | C(O)Et | C(O)OCH$_3$ |
| G-1 | 3,5-Cl$_2$ | 3-Br | C(O)CH$_3$ | (D-55c)Cl |
| G-1 | 3,5-Cl$_2$ | 3-CH$_3$ | C(O)Pr-i | (D-55c)Cl |
| G-1 | 3,5-Cl$_2$ | 3-Et | C(O)OCH$_3$ | (D-55c)Cl |
| G-1 | 3,5-Cl$_2$ | 2-Pr-n | C(O)CH$_3$ | (D-55c)Br |
| G-1 | 3,5-Cl$_2$ | 2-Pr-i | H | CH=NOCH$_3$ |
| G-1 | 3,5-Cl$_2$ | 2-Pr-i | H | CH=NOEt |
| G-1 | 3,5-Cl$_2$ | 2-Pr-i | H | C(O)OCH$_3$ |
| G-1 | 3,5-Cl$_2$ | 2-Pr-i | Et | C(O)OCH$_3$ |
| G-1 | 3,5-Cl$_2$ | 2-Pr-i | CH$_2$OCH$_3$ | C(O)OCH$_3$ |
| G-1 | 3,5-Cl$_2$ | 2-Pr-i | CH$_2$OEt | C(O)OCH$_3$ |
| G-1 | 3,5-Cl$_2$ | 2-Pr-i | CH$_2$OCH$_2$CF$_3$ | C(O)OCH$_3$ |
| G-1 | 3,5-Cl$_2$ | 2-Pr-i | C(O)Et | C(O)OCH$_3$ |
| G-1 | 3,5-Cl$_2$ | 2-Pr-i | CH$_2$OCH$_3$ | C(O)OEt |
| G-1 | 3,5-Cl$_2$ | 2-Pr-i | H | C(O)NH$_2$ |
| G-1 | 3,5-Cl$_2$ | 2-Pr-i | CH$_3$ | (D-55c)Cl |
| G-1 | 3,5-Cl$_2$ | 2-Pr-i | CH$_2$OCH$_3$ | (D-55c)Cl |
| G-1 | 3,5-Cl$_2$ | 2-Pr-i | C(O)CH$_3$ | (D-55c)Cl |
| G-1 | 3,5-Cl$_2$ | 2-Pr-i | C(O)Et | (D-55c)Cl |
| G-1 | 3,5-Cl$_2$ | 2-Pr-i | C(O)Pr-i | (D-55c)Cl |
| G-1 | 3,5-Cl$_2$ | 2-Pr-i | C(O)CH$_3$OCH$_3$ | (D-55c)Cl |
| G-1 | 3,5-Cl$_2$ | 2-Pr-i | C(O)OCH$_3$ | (D-55c)Cl |
| G-1 | 3,5-Cl$_2$ | 2-Pr-i | C(O)CH$_3$ | (D-55c)Br |
| G-1 | 3,5-Cl$_2$ | 2-Pr-i | C(O)Et | (D-55c)Br |
| G-1 | 3,5-Cl$_2$ | 2-Pr-i | C(O)Pr-i | (D-55c)Br |
| G-1 | 3,5-Cl$_2$ | 2-Bu-n | H | CH=NOCH$_3$ |
| G-1 | 3,5-Cl$_2$ | 2-Bu-s | H | CH=NOEt |
| G-1 | 3,5-Cl$_2$ | 2-Bu-t | CH$_2$OEt | C(O)OCH$_3$ |
| G-1 | 3,5-Cl$_2$ | 2-CF$_2$CF$_3$ | CH$_2$OCH$_2$CF$_3$ | C(O)OCH$_3$ |
| G-1 | 3,5-Cl$_2$ | 2-CH$_2$OH | C(O)Et | C(O)OCH$_3$ |
| G-1 | 3,5-Cl$_2$ | 2-CH$_2$OCH$_3$ | H | CH=NOCH$_3$ |
| G-1 | 3,5-Cl$_2$ | 2-CH$_2$OCH$_3$ | H | CH=NOEt |
| G-1 | 3,5-Cl$_2$ | 2-CH$_2$OCH$_3$ | CH$_2$OEt | C(O)OCH$_3$ |
| G-1 | 3,5-Cl$_2$ | 2-CH$_2$OCH$_3$ | CH$_2$OCH$_2$CF$_3$ | C(O)OCH$_3$ |
| G-1 | 3,5-Cl$_2$ | 2-CH$_2$OCH$_3$ | C(O)Et | C(O)OCH$_3$ |
| G-1 | 3,5-Cl$_2$ | 2-CH$_2$OCH$_3$ | C(O)CH$_3$ | (D-55c)Cl |
| G-1 | 3,5-Cl$_2$ | 2-CH$_2$OCH$_3$ | C(O)Pr-i | (D-55c)Cl |
| G-1 | 3,5-Cl$_2$ | 2-CH$_2$OCH$_3$ | C(O)OCH$_3$ | (D-55c)Cl |
| G-1 | 3,5-Cl$_2$ | 2-CH$_2$OCH$_3$ | C(O)CH$_3$ | (D-55c)Br |

TABLE 3-continued

| | | | | |
|---|---|---|---|---|
| G-1 | 3,5-Cl$_2$ | 2-CH$_2$OEt | C(O)CH$_3$ | (D-55c)Cl |
| G-1 | 3,5-Cl$_2$ | 2-CH$_2$OPr-n | C(O)Pr-i | (D-55c)Cl |
| G-1 | 3,5-Cl$_2$ | 2-CH$_2$OPr-i | C(O)OCH$_3$ | (D-55c)Cl |
| G-1 | 3,5-Cl$_2$ | 2-CH$_2$OPr-c | C(O)CH$_3$ | (D-55c)Br |
| G-1 | 3,5-Cl$_2$ | 2-CH$_2$OCH$_2$CF$_3$ | H | CH=NOCH$_3$ |
| G-1 | 3,5-Cl$_2$ | 2-CH$_2$CH$_2$OCH$_3$ | H | CH=NOEt |
| G-1 | 3,5-Cl$_2$ | 2-CH$_2$SCH$_3$ | H | CH=NOCH$_3$ |
| G-1 | 3,5-Cl$_2$ | 2-CH$_2$SCH$_3$ | H | CH=NOEt |
| G-1 | 3,5-Cl$_2$ | 2-CH$_2$SCH$_3$ | CH$_2$OEt | C(O)OCH$_3$ |
| G-1 | 3,5-Cl$_2$ | 2-CH$_2$SCH$_3$ | CH$_2$OCH$_2$CF$_3$ | C(O)OCH$_3$ |
| G-1 | 3,5-Cl$_2$ | 2-CH$_2$SCH$_3$ | C(O)Et | C(O)OCH$_3$ |
| G-1 | 3,5-Cl$_2$ | 2-CH$_2$SCH$_3$ | C(O)CH$_3$ | (D-55c)Cl |
| G-1 | 3,5-Cl$_2$ | 2-CH$_2$SCH$_3$ | C(O)Pr-i | (D-55c)Cl |
| G-1 | 3,5-Cl$_2$ | 2-CH$_2$SCH$_3$ | C(O)OCH$_3$ | (D-55c)Cl |
| G-1 | 3,5-Cl$_2$ | 2-CH$_2$SCH$_3$ | C(O)CH$_3$ | (D-55c)Br |
| G-1 | 3,5-Cl$_2$ | 2-CH$_2$S(O)CH$_3$ | CH$_2$OEt | C(O)OCH$_3$ |
| G-1 | 3,5-Cl$_2$ | 2-CH$_2$SO$_2$CH$_3$ | CH$_2$OCH$_2$CF$_3$ | C(O)OCH$_3$ |
| G-1 | 3,5-Cl$_2$ | 2-CH$_2$SCF$_3$ | H | CH=NOCH$_3$ |
| G-1 | 3,5-Cl$_2$ | 2-CH$_2$SCF$_3$ | H | CH=NOEt |
| G-1 | 3,5-Cl$_2$ | 2-CH$_2$SCF$_3$ | CH$_2$OEt | C(O)OCH$_3$ |
| G-1 | 3,5-Cl$_2$ | 2-CH$_2$SCF$_3$ | CH$_2$OCH$_2$CF$_3$ | C(O)OCH$_3$ |
| G-1 | 3,5-Cl$_2$ | 2-CH$_2$SCF$_3$ | C(O)Et | C(O)OCH$_3$ |
| G-1 | 3,5-Cl$_2$ | 2-CH$_2$SCF$_3$ | C(O)CH$_3$ | (D-55c)Cl |
| G-1 | 3,5-Cl$_2$ | 2-CH$_2$SCF$_3$ | C(O)Pr-i | (D-55c)Cl |
| G-1 | 3,5-Cl$_2$ | 2-CH$_2$SCF$_3$ | C(O)OCH$_3$ | (D-55c)Cl |
| G-1 | 3,5-Cl$_2$ | 2-CH$_2$SCF$_3$ | C(O)CH$_3$ | (D-55c)Br |
| G-1 | 3,5-Cl$_2$ | 2-CH$_2$S(O)CF$_3$ | C(O)Et | C(O)OCH$_3$ |
| G-1 | 3,5-Cl$_2$ | 2-CH$_2$SO$_2$CF$_3$ | C(O)CH$_3$ | (D-55c)Cl |
| G-1 | 3,5-Cl$_2$ | 2-CH$_2$Ph | C(O)Pr-i | (D-55c)Cl |
| G-1 | 3,5-Cl$_2$ | 2-CH$_2$(D-14a) | C(O)OCH$_3$ | (D-55c)Cl |
| G-1 | 3,5-Cl$_2$ | 2-CH$_2$(D-24a) | C(O)CH$_3$ | (D-55c)Br |
| G-1 | 3,5-Cl$_2$ | 2-CH$_2$(D-41a) | H | CH=NOCH$_3$ |
| G-1 | 3,5-Cl$_2$ | 3-OCH$_3$ | H | CH=NOEt |
| G-1 | 3,5-Cl$_2$ | 2-OEt | H | CH=NOCH$_3$ |
| G-1 | 3,5-Cl$_2$ | 2-OEt | H | CH=NOEt |
| G-1 | 3,5-Cl$_2$ | 2-OEt | H | C(O)OCH$_3$ |
| G-1 | 3,5-Cl$_2$ | 2-OEt | Et | C(O)OCH$_3$ |
| G-1 | 3,5-Cl$_2$ | 2-OEt | CH$_2$OCH$_3$ | C(O)OCH$_3$ |
| G-1 | 3,5-Cl$_2$ | 2-OEt | CH$_2$OEt | C(O)OCH$_3$ |
| G-1 | 3,5-Cl$_2$ | 2-OEt | CH$_2$OCH$_2$CF$_3$ | C(O)OCH$_3$ |
| G-1 | 3,5-Cl$_2$ | 2-OEt | C(O)Et | C(O)OCH$_3$ |
| G-1 | 3,5-Cl$_2$ | 2-OEt | C(O)OCH$_3$ | C(O)OEt |
| G-1 | 3,5-Cl$_2$ | 2-OEt | H | C(O)NH$_2$ |
| G-1 | 3,5-Cl$_2$ | 2-OEt | CH$_3$ | (D-55c)Cl |
| G-1 | 3,5-Cl$_2$ | 2-OEt | CH$_2$OCH$_3$ | (D-55c)Cl |
| G-1 | 3,5-Cl$_2$ | 2-OEt | C(O)CH$_3$ | (D-55c)Cl |
| G-1 | 3,5-Cl$_2$ | 2-OEt | C(O)Et | (D-55c)Cl |
| G-1 | 3,5-Cl$_2$ | 2-OEt | C(O)Pr-i | (D-55c)Cl |
| G-1 | 3,5-Cl$_2$ | 2-OEt | C(O)CH$_2$OCH$_3$ | (D-55c)Cl |
| G-1 | 3,5-Cl$_2$ | 2-OEt | CH$_2$OCH$_3$ | (D-55c)Cl |
| G-1 | 3,5-Cl$_2$ | 2-OEt | C(O)CH$_3$ | (D-55c)Br |
| G-1 | 3,5-Cl$_2$ | 2-OEt | C(O)Et | (D-55c)Br |
| G-1 | 3,5-Cl$_2$ | 2-OEt | C(O)Pr-i | (D-55c)Br |
| G-1 | 3,5-Cl$_2$ | 2-OPr-n | CH$_2$OEt | C(O)OCH$_3$ |
| G-1 | 3,5-Cl$_2$ | 2-OPr-i | H | CH=NOCH$_3$ |
| G-1 | 3,5-Cl$_2$ | 2-OPr-i | H | CH=NOEt |
| G-1 | 3,5-Cl$_2$ | 2-OPr-i | H | C(O)OCH$_3$ |
| G-1 | 3,5-Cl$_2$ | 2-OPr-i | Et | C(O)OCH$_3$ |
| G-1 | 3,5-Cl$_2$ | 2-OPr-i | CH$_2$OCH$_3$ | C(O)OCH$_3$ |
| G-1 | 3,5-Cl$_2$ | 2-OPr-i | CH$_2$OEt | C(O)OCH$_3$ |
| G-1 | 3,5-Cl$_2$ | 2-OPr-i | CH$_2$OCH$_2$CF$_3$ | C(O)OCH$_3$ |
| G-1 | 3,5-Cl$_2$ | 2-OPr-i | C(O)Et | C(O)OCH$_3$ |
| G-1 | 3,5-Cl$_2$ | 2-OPr-i | C(O)OCH$_3$ | C(O)OEt |
| G-1 | 3,5-Cl$_2$ | 2-OPr-i | H | C(O)NH$_2$ |
| G-1 | 3,5-Cl$_2$ | 2-OPr-i | CH$_3$ | (D-55c)Cl |
| G-1 | 3,5-Cl$_2$ | 2-OPr-i | CH$_2$OCH$_3$ | (D-55c)Cl |
| G-1 | 3,5-Cl$_2$ | 2-OPr-i | C(O)CH$_3$ | (D-55c)Cl |
| G-1 | 3,5-Cl$_2$ | 2-OPr-i | C(O)Et | (D-55c)Cl |
| G-1 | 3,5-Cl$_2$ | 2-OPr-i | C(O)Pr-i | (D-55c)Cl |
| G-1 | 3,5-Cl$_2$ | 2-OPr-i | C(O)CH$_2$OCH$_3$ | (D-55c)Cl |
| G-1 | 3,5-Cl$_2$ | 2-OPr-i | C(O)OCH$_3$ | (D-55c)Cl |
| G-1 | 3,5-Cl$_2$ | 2-OPr-i | C(O)CH$_3$ | (D-55c)Br |
| G-1 | 3,5-Cl$_2$ | 2-OPr-i | C(O)Et | (D-55c)Br |
| G-1 | 3,5-Cl$_2$ | 2-OPr-i | C(O)Pr-i | (D-55c)Br |
| G-1 | 3,5-Cl$_2$ | 2-OBu-n | CH$_2$OCH$_2$CF$_3$ | C(O)OCH$_3$ |
| G-1 | 3,5-Cl$_2$ | 2-OPen-n | C(O)Et | C(O)OCH$_3$ |
| G-1 | 3,5-Cl$_2$ | 2-OHex-n | C(O)CH$_3$ | (D-55c)Cl |
| G-1 | 3,5-Cl$_2$ | 2-OCF$_2$Br | C(O)Pr-i | (D-55c)Cl |
| G-1 | 3,5-Cl$_2$ | 2-OCF$_2$CHF$_2$ | C(O)OCH$_3$ | (D-55c)Cl |
| G-1 | 3,5-Cl$_2$ | 2-OCF$_2$CHFCl | C(O)CH$_3$ | (D-55c)Br |

TABLE 3-continued

| | | | | |
|---|---|---|---|---|
| G-1 | 3,5-Cl$_2$ | 2-OCF$_2$CHFCF$_3$ | H | CH=NOCH$_3$ |
| G-1 | 3,5-Cl$_2$ | 2-OCF$_2$CHFOCF$_3$ | H | CH=NOEt |
| G-1 | 3,5-Cl$_2$ | 2-OSO$_2$CH$_3$ | H | CH=NOCH$_3$ |
| G-1 | 3,5-Cl$_2$ | 2-OSO$_2$CH$_3$ | H | CH=NOEt |
| G-1 | 3,5-Cl$_2$ | 2-OSO$_2$CH$_3$ | H | C(O)OCH$_3$ |
| G-1 | 3,5-Cl$_2$ | 2-OSO$_2$CH$_3$ | Et | C(O)OCH$_3$ |
| G-1 | 3,5-Cl$_2$ | 2-OSO$_2$CH$_3$ | CH$_2$OCH$_3$ | C(O)OCH$_3$ |
| G-1 | 3,5-Cl$_2$ | 2-OSO$_2$CH$_3$ | CH$_2$OEt | C(O)OCH$_3$ |
| G-1 | 3,5-Cl$_2$ | 2-OSO$_2$CH$_3$ | CH$_2$OCH$_2$CF$_3$ | C(O)OCH$_3$ |
| G-1 | 3,5-Cl$_2$ | 2-OSO$_2$CH$_3$ | C(O)Et | C(O)OCH$_3$ |
| G-1 | 3,5-Cl$_2$ | 2-OSO$_2$CH$_3$ | C(O)OCH$_3$ | C(O)OEt |
| G-1 | 3,5-Cl$_2$ | 2-OSO$_2$CH$_3$ | H | C(O)NH$_2$ |
| G-1 | 3,5-Cl$_2$ | 2-OSO$_2$CH$_3$ | CH$_3$ | (D-55c)Cl |
| G-1 | 3,5-Cl$_2$ | 2-OSO$_2$CH$_3$ | CH$_2$OCH$_3$ | (D-55c)Cl |
| G-1 | 3,5-Cl$_2$ | 2-OSO$_2$CH$_3$ | C(O)CH$_3$ | (D-55c)Cl |
| G-1 | 3,5-Cl$_2$ | 2-OSO$_2$CH$_3$ | C(O)Et | (D-55c)Cl |
| G-1 | 3,5-Cl$_2$ | 2-OSO$_2$CH$_3$ | C(O)Pr-i | (D-55c)Cl |
| G-1 | 3,5-Cl$_2$ | 2-OSO$_2$CH$_3$ | C(O)CH$_2$OCH$_3$ | (D-55c)Cl |
| G-1 | 3,5-Cl$_2$ | 2-OSO$_2$CH$_3$ | C(O)CH$_3$ | (D-55c)Cl |
| G-1 | 3,5-Cl$_2$ | 2-OSO$_2$CH$_3$ | C(O)CH$_3$ | (D-55c)Br |
| G-1 | 3,5-Cl$_2$ | 2-OSO$_2$CH$_3$ | C(O)Et | (D-55c)Br |
| G-1 | 3,5-Cl$_2$ | 2-OSO$_2$CH$_3$ | C(O)Pr-i | (D-55c)Br |
| G-1 | 3,5-Cl$_2$ | 2-OSO$_2$Et | CH$_2$OEt | C(O)OCH$_3$ |
| G-1 | 3,5-Cl$_2$ | 2-OSO$_2$Pr-i | CH$_2$OCH$_2$CF$_2$ | C(O)OCH$_3$ |
| G-1 | 3,5-Cl$_2$ | 2-OSO$_2$CF$_3$ | C(O)Et | C(O)OCH$_3$ |
| G-1 | 3,5-Cl$_2$ | 2-OPh | C(O)CH$_3$ | (D-55c)Cl |
| G-1 | 3,5-Cl$_2$ | 2-S(O)CH$_3$ | C(O)Pr-i | (D-55c)Cl |
| G-1 | 3,5-Cl$_2$ | 2-SO$_2$CH$_3$ | C(O)OCH$_3$ | (D-55c)Cl |
| G-1 | 3,5-Cl$_2$ | 2-SEt | H | CH=NOCH$_3$ |
| G-1 | 3,5-Cl$_2$ | 2-SEt | H | CH=NOEt |
| G-1 | 3,5-Cl$_2$ | 2-SEt | H | C(O)OCH$_3$ |
| G-1 | 3,5-Cl$_2$ | 2-SEt | Et | C(O)OCH$_3$ |
| G-1 | 3,5-Cl$_2$ | 2-SEt | CH$_2$OCH$_3$ | C(O)OCH$_3$ |
| G-1 | 3,5-Cl$_2$ | 2-SEt | CH$_2$OEt | C(O)OCH$_3$ |
| G-1 | 3,5-Cl$_2$ | 2-SEt | CH$_2$OCH$_2$CF$_3$ | C(O)OCH$_3$ |
| G-1 | 3,5-Cl$_2$ | 2-SEt | C(O)Et | C(O)OCH$_3$ |
| G-1 | 3,5-Cl$_2$ | 2-SEt | C(O)OCH$_3$ | C(O)OEt |
| G-1 | 3,5-Cl$_2$ | 2-SEt | H | C(O)NH$_2$ |
| G-1 | 3,5-Cl$_2$ | 2-SEt | CH$_3$ | (D-55c)Cl |
| G-1 | 3,5-Cl$_2$ | 2-SEt | C(O)OCH$_3$ | (D-55c)Cl |
| G-1 | 3,5-Cl$_2$ | 2-SEt | C(O)CH$_3$ | (D-55c)Cl |
| G-1 | 3,5-Cl$_2$ | 2-SEt | C(O)Et | (D-55c)Cl |
| G-1 | 3,5-Cl$_2$ | 2-SEt | C(O)Pr-i | (D-55c)Cl |
| G-1 | 3,5-Cl$_2$ | 2-SEt | C(O)CH$_2$OCH$_3$ | (D-55c)Cl |
| G-1 | 3,5-Cl$_2$ | 2-SEt | C(O)OCH$_3$ | (D-55c)Cl |
| G-1 | 3,5-Cl$_2$ | 2-SEt | C(O)CH$_3$ | (D-55c)Cl |
| G-1 | 3,5-Cl$_2$ | 2-SEt | C(O)Et | (D-55c)Br |
| G-1 | 3,5-Cl$_2$ | 2-SEt | C(O)Pr-i | (D-55c)Br |
| G-1 | 3,5-Cl$_2$ | 2-S(O)Et | C(O)CH$_3$ | (D-55c)Br |
| G-1 | 3,5-Cl$_2$ | 2-S(O)Et | H | CH=NOCH$_3$ |
| G-1 | 3,5-Cl$_2$ | 2-SPr-n | H | CH=NOEt |
| G-1 | 3,5-Cl$_2$ | 2-SO$_2$Et | CH$_2$OEt | C(O)OCH$_3$ |
| G-1 | 3,5-Cl$_2$ | 2-SO$_2$Pr-n | CH$_2$OCH$_2$CF$_3$ | C(O)OCH$_3$ |
| G-1 | 3,5-Cl$_2$ | 2-SPr-i | H | CH=NOCH$_3$ |
| G-1 | 3,5-Cl$_2$ | 2-SPr-i | H | CH=NOEt |
| G-1 | 3,5-Cl$_2$ | 2-SPr-i | H | C(O)OCH$_3$ |
| G-1 | 3,5-Cl$_2$ | 2-SPr-i | Et | C(O)OCH$_3$ |
| G-1 | 3,5-Cl$_2$ | 2-SPr-i | CH$_2$OCH$_3$ | C(O)OCH$_3$ |
| G-1 | 3,5-Cl$_2$ | 2-SPr-i | CH$_2$OEt | C(O)OCH$_3$ |
| G-1 | 3,5-Cl$_2$ | 2-SPr-i | CH$_2$OCH$_2$CF$_3$ | C(O)OCH$_3$ |
| G-1 | 3,5-Cl$_2$ | 2-SPr-i | C(O)Et | C(O)OCH$_3$ |
| G-1 | 3,5-Cl$_2$ | 2-SPr-i | C(O)OCH$_3$ | C(O)OEt |
| G-1 | 3,5-Cl$_2$ | 2-SPr-i | H | C(O)NH$_2$ |
| G-1 | 3,5-Cl$_2$ | 2-SPr-i | CH$_3$ | (D-55c)Cl |
| G-1 | 3,5-Cl$_2$ | 2-SPr-i | CH$_2$OCH$_3$ | (D-55c)Cl |
| G-1 | 3,5-Cl$_2$ | 2-SPr-i | C(O)CH$_3$ | (D-55c)Cl |
| G-1 | 3,5-Cl$_2$ | 2-SPr-i | C(O)Et | (D-55c)Cl |
| G-1 | 3,5-Cl$_2$ | 2-SPr-i | C(O)Pr-i | (D-55c)Cl |
| G-1 | 3,5-Cl$_2$ | 2-SPr-i | C(O)CH$_2$OCH$_3$ | (D-55c)Cl |
| G-1 | 3,5-Cl$_2$ | 2-SPr-i | C(O)OCH$_3$ | (D-55c)Cl |
| G-1 | 3,5-Cl$_2$ | 2-SPr-i | C(O)CH$_3$ | (D-55c)Br |
| G-1 | 3,5-Cl$_2$ | 2-SPr-i | C(O)Et | (D-55c)Br |
| G-1 | 3,5-Cl$_2$ | 2-SPr-i | C(O)Pr-i | (D-55c)Br |
| G-1 | 3,5-Cl$_2$ | 2-S(O)Pr-i | C(O)Et | C(O)OCH$_3$ |
| G-1 | 3,5-Cl$_2$ | 2-SO$_2$Pr-i | C(O)CH$_3$ | (D-55c)Cl |
| G-1 | 3,5-Cl$_2$ | 2-S(O)CHF$_2$ | C(O)Pr-i | (D-55c)Cl |
| G-1 | 3,5-Cl$_2$ | 2-SO$_2$CHF$_2$ | C(O)OCH$_3$ | (D-55c)Cl |
| G-1 | 3,5-Cl$_2$ | 2-S(O)CF$_3$ | C(O)CH$_3$ | (D-55c)Br |
| G-1 | 3,5-Cl$_2$ | 2-SO$_2$CF$_3$ | H | CH=NOCH$_3$ |
| G-1 | 3,5-Cl$_2$ | 2-SCF$_2$Br | H | CH=NOEt |

TABLE 3-continued

| | | | | |
|---|---|---|---|---|
| G-1 | 3,5-Cl$_2$ | 2-S(O)CF$_2$Br | CH$_2$OEt | C(O)OCH$_3$ |
| G-1 | 3,5-Cl$_2$ | 2-SO$_2$CF$_2$Br | CH$_2$OCH$_2$CF$_3$ | C(O)OCH$_3$ |
| G-1 | 3,5-Cl$_2$ | 2-SCF$_2$CHFCl | C(O)Et | C(O)OCH$_3$ |
| G-1 | 3,5-Cl$_2$ | 2-S(O)CF$_2$CHFCl | C(O)CH$_3$ | (D-55c)Cl |
| G-1 | 3,5-Cl$_2$ | 2-SO$_2$CF$_2$CHFCl | C(O)Pr-i | (D-55c)Cl |
| G-1 | 3,5-Cl$_2$ | 2-SPh | C(O)OCH$_3$ | (D-55c)Cl |
| G-1 | 3,5-Cl$_2$ | 2-S(O)Ph | C(O)CH$_3$ | (D-55c)Br |
| G-1 | 3,5-Cl$_2$ | 2-SO$_2$Ph | H | CH=NOCH$_3$ |
| G-1 | 3,5-Cl$_2$ | 2-NHEt | H | CH=NOCH$_3$ |
| G-1 | 3,5-Cl$_2$ | 2-NHEt | H | CH=NOEt |
| G-1 | 3,5-Cl$_2$ | 2-NHEt | H | C(O)OCH$_3$ |
| G-1 | 3,5-Cl$_2$ | 2-NHEt | Et | C(O)OCH$_3$ |
| G-1 | 3,5-Cl$_2$ | 2-NHEt | CH$_2$OCH$_3$ | C(O)OCH$_3$ |
| G-1 | 3,5-Cl$_2$ | 2-NHEt | CH$_2$OEt | C(O)OCH$_3$ |
| G-1 | 3,5-Cl$_2$ | 2-NHEt | CH$_2$OCH$_2$CF$_3$ | C(O)OCH$_3$ |
| G-1 | 3,5-Cl$_2$ | 2-NHEt | C(O)Et | C(O)OCH$_3$ |
| G-1 | 3,5-Cl$_2$ | 2-NHEt | CH$_2$OCH$_3$ | C(O)OEt |
| G-1 | 3,5-Cl$_2$ | 2-NHEt | H | C(O)NH$_2$ |
| G-1 | 3,5-Cl$_2$ | 2-NHEt | CH$_3$ | (D-55c)Cl |
| G-1 | 3,5-Cl$_2$ | 2-NHEt | CH$_2$OCH$_3$ | (D-55c)Cl |
| G-1 | 3,5-Cl$_2$ | 2-NHEt | C(O)CH$_3$ | (D-55c)Cl |
| G-1 | 3,5-Cl$_2$ | 2-NHEt | C(O)Et | (D-55c)Cl |
| G-1 | 3,5-Cl$_2$ | 2-NHEt | C(O)Pr-i | (D-55c)Cl |
| G-1 | 3,5-Cl$_2$ | 2-NHEt | C(O)CH$_2$OCH$_3$ | (D-55c)Cl |
| G-1 | 3,5-Cl$_2$ | 2-NHEt | C(O)OCH$_3$ | (D-55c)Cl |
| G-1 | 3,5-Cl$_2$ | 2-NHEt | C(O)CH$_3$ | (D-55c)Br |
| G-1 | 3,5-Cl$_2$ | 2-NHEt | C(O)Et | (D-55c)Br |
| G-1 | 3,5-Cl$_2$ | 2-NHEt | C(O)Pr-i | (D-55c)Br |
| G-1 | 3,5-Cl$_2$ | 2-NHPr-n | H | CH=NOCH$_3$ |
| G-1 | 3,5-Cl$_2$ | 2-NHPr-n | H | CH=NOEt |
| G-1 | 3,5-Cl$_2$ | 2-NHPr-n | CH$_2$OEt | C(O)OCH$_3$ |
| G-1 | 3,5-Cl$_2$ | 2-NHPr-n | CH$_2$OCH$_2$CF$_3$ | C(O)OCH$_3$ |
| G-1 | 3,5-Cl$_2$ | 2-NHPr-n | C(O)Et | C(O)OCH$_3$ |
| G-1 | 3,5-Cl$_2$ | 2-NHPr-n | C(O)CH$_3$ | (D-55c)Cl |
| G-1 | 3,5-Cl$_2$ | 2-NHPr-n | C(O)Pr-i | (D-55c)Cl |
| G-1 | 3,5-Cl$_2$ | 2-NHPr-n | C(O)OCH$_3$ | (D-55c)Cl |
| G-1 | 3,5-Cl$_2$ | 2-NHPr-n | C(O)CH$_3$ | (D-55c)Br |
| G-1 | 3,5-Cl$_2$ | 2-NHPr-i | H | CH=NOCH$_3$ |
| G-1 | 3,5-Cl$_2$ | 2-NHPr-i | H | CH=NOEt |
| G-1 | 3,5-Cl$_2$ | 2-NHPr-i | H | C(O)OCH$_3$ |
| G-1 | 3,5-Cl$_2$ | 2-NHPr-i | Et | C(O)OCH$_3$ |
| G-1 | 3,5-Cl$_2$ | 2-NHPr-i | CH$_2$OCH$_3$ | C(O)OCH$_3$ |
| G-1 | 3,5-Cl$_2$ | 2-NHPr-i | CH$_2$OEt | C(O)OCH$_3$ |
| G-1 | 3,5-Cl$_2$ | 2-NHPr-i | CH$_2$OCH$_2$CF$_3$ | C(O)OCH$_3$ |
| G-1 | 3,5-Cl$_2$ | 2-NHPr-i | C(O)Et | C(O)OCH$_3$ |
| G-1 | 3,5-Cl$_2$ | 2-NHPr-i | C(O)OCH$_3$ | C(O)OEt |
| G-1 | 3,5-Cl$_2$ | 2-NHPr-i | H | C(O)NH$_2$ |
| G-1 | 3,5-Cl$_2$ | 2-NHPr-i | CH$_3$ | (D-55c)Cl |
| G-1 | 3,5-Cl$_2$ | 2-NHPr-i | CH$_2$OCH$_3$ | (D-55c)Cl |
| G-1 | 3,5-Cl$_2$ | 2-NHPr-i | C(O)CH$_3$ | (D-55c)Cl |
| G-1 | 3,5-Cl$_2$ | 2-NHPr-i | C(O)Et | (D-55c)Cl |
| G-1 | 3,5-Cl$_2$ | 2-NHPr-i | C(O)Pr-i | (D-55c)Cl |
| G-1 | 3,5-Cl$_2$ | 2-NHPr-i | C(O)CH$_2$OCH$_3$ | (D-55c)Cl |
| G-1 | 3,5-Cl$_2$ | 2-NHPr-i | C(O)OCH$_3$ | (D-55c)Cl |
| G-1 | 3,5-Cl$_2$ | 2-NHPr-i | C(O)CH$_3$ | (D-55c)Br |
| G-1 | 3,5-Cl$_2$ | 2-NHPr-i | C(O)Et | (D-55c)Br |
| G-1 | 3,5-Cl$_2$ | 2-NHPr-i | C(O)Pr-i | (D-55c)Br |
| G-1 | 3,5-Cl$_2$ | 2-N(CH$_3$)$_2$ | H | CH=NOCH$_3$ |
| G-1 | 3,5-Cl$_2$ | 2-N(CH$_3$)$_2$ | H | CH=NOEt |
| G-1 | 3,5-Cl$_2$ | 2-N(CH$_3$)$_2$ | CH$_2$OEt | C(O)OCH$_3$ |
| G-1 | 3,5-Cl$_2$ | 2-N(CH$_3$)$_2$ | CH$_2$OCH$_2$CF$_3$ | C(O)OCH$_3$ |
| G-1 | 3,5-Cl$_2$ | 2-N(CH$_3$)$_2$ | C(O)Et | C(O)OCH$_3$ |
| G-1 | 3,5-Cl$_2$ | 2-N(CH$_3$)$_2$ | C(O)CH$_3$ | (D-55c)Cl |
| G-1 | 3,5-Cl$_2$ | 2-N(CH$_3$)$_2$ | C(O)Pr-i | (D-55c)Cl |
| G-1 | 3,5-Cl$_2$ | 2-N(CH$_3$)$_2$ | C(O)OCH$_3$ | (D-55c)Cl |
| G-1 | 3,5-Cl$_2$ | 2-N(CH$_3$)$_2$ | C(O)CH$_3$ | (D-55c)Br |
| G-1 | 3,5-Cl$_2$ | 2-N(CH$_3$)Et | H | CH=NOEt |
| G-1 | 3,5-Cl$_2$ | 2-N(Et)$_2$ | CH$_2$OEt | C(O)OCH$_3$ |
| G-1 | 3,5-Cl$_2$ | 2-NHCHO | H | CH=NOCH$_3$ |
| G-1 | 3,5-Cl$_2$ | 2-NHCHO | H | CH=NOEt |
| G-1 | 3,5-Cl$_2$ | 2-NHCHO | CH$_2$OEt | C(O)OCH$_3$ |
| G-1 | 3,5-Cl$_2$ | 2-NHCHO | CH$_2$OCH$_2$CF$_3$ | C(O)OCH$_3$ |
| G-1 | 3,5-Cl$_2$ | 2-NHCHO | C(O)Et | C(O)OCH$_3$ |
| G-1 | 3,5-Cl$_2$ | 2-NHCHO | C(O)CH$_3$ | (D-55c)Cl |
| G-1 | 3,5-Cl$_2$ | 2-NHCHO | C(O)Pr-i | (D-55c)Cl |
| G-1 | 3,5-Cl$_2$ | 2-NHCHO | C(O)OCH$_3$ | (D-55c)Cl |
| G-1 | 3,5-Cl$_2$ | 2-NHCHO | C(O)CH$_3$ | (D-55c)Br |
| G-1 | 3,5-Cl$_2$ | 2-NHC(O)CH$_3$ | H | CH=NOCH$_3$ |
| G-1 | 3,5-Cl$_2$ | 2-NHC(O)CH$_3$ | H | CH=NOEt |
| G-1 | 3,5-Cl$_2$ | 2-NHC(O)CH$_3$ | H | C(O)OCH$_3$ |

TABLE 3-continued

| | | | | |
|---|---|---|---|---|
| G-1 | 3,5-Cl$_2$ | 2-NHC(O)CH$_3$ | Et | C(O)OCH$_3$ |
| G-1 | 3,5-Cl$_2$ | 2-NHC(O)CH$_3$ | CH$_2$OCH$_3$ | C(O)OCH$_3$ |
| G-1 | 3,5-Cl$_2$ | 2-NHC(O)CH$_3$ | CH$_2$OEt | C(O)OCH$_3$ |
| G-1 | 3,5-Cl$_2$ | 2-NHC(O)CH$_3$ | CH$_2$OCH$_2$CF$_3$ | C(O)OCH$_3$ |
| G-1 | 3,5-Cl$_2$ | 2-NHC(O)CH$_3$ | C(O)Et | C(O)OCH$_3$ |
| G-1 | 3,5-Cl$_2$ | 2-NHC(O)CH$_3$ | C(O)OCH$_3$ | C(O)OEt |
| G-1 | 3,5-Cl$_2$ | 2-NHC(O)CH$_3$ | H | C(O)NH$_2$ |
| G-1 | 3,5-Cl$_2$ | 2-NHC(O)CH$_3$ | CH$_3$ | (D-55c)Cl |
| G-1 | 3,5-Cl$_2$ | 2-NHC(O)CH$_3$ | CH$_2$OCH$_3$ | (D-55c)Cl |
| G-1 | 3,5-Cl$_2$ | 2-NHC(O)CH$_3$ | C(O)CH$_3$ | (D-55c)Cl |
| G-1 | 3,5-Cl$_2$ | 2-NHC(O)CH$_3$ | C(O)Et | (D-55c)Cl |
| G-1 | 3,5-Cl$_2$ | 2-NHC(O)CH$_3$ | C(O)Pr-i | (D-55c)Cl |
| G-1 | 3,5-Cl$_2$ | 2-NHC(O)CH$_3$ | C(O)CH$_2$OCH$_3$ | (D-55c)Cl |
| G-1 | 3,5-Cl$_2$ | 2-NHC(O)CH$_3$ | C(O)OCH$_3$ | (D-55c)Cl |
| G-1 | 3,5-Cl$_2$ | 2-NHC(O)CH$_3$ | C(O)CH$_3$ | (D-55c)Br |
| G-1 | 3,5-Cl$_2$ | 2-NHC(O)CH$_3$ | C(O)Et | (D-55c)Br |
| G-1 | 3,5-Cl$_2$ | 2-NHC(O)CH$_3$ | C(O)Pr-i | (D-55c)Br |
| G-1 | 3,5-Cl$_2$ | 2-NHC(O)Et | CH$_2$OCH$_2$CF$_3$ | C(O)OCH$_3$ |
| G-1 | 3,5-Cl$_2$ | 2-NHC(O)Pr-n | C(O)Et | C(O)OCH$_3$ |
| G-1 | 3,5-Cl$_2$ | 2-NHC(O)Pr-i | C(O)CH$_3$ | (D-55c)Cl |
| G-1 | 3,5-Cl$_2$ | 2-NHC(O)Pr-c | C(O)Pr-i | (D-55c)Cl |
| G-1 | 3,5-Cl$_2$ | 2-NHC(O)Bu-t | C(O)OCH$_3$ | (D-55c)Cl |
| G-1 | 3,5-Cl$_2$ | 2-NHC(O)CF$_3$ | H | CH=NOCH$_3$ |
| G-1 | 3,5-Cl$_2$ | 2-NHC(O)CF$_3$ | H | CH=NOEt |
| G-1 | 3,5-Cl$_2$ | 2-NHC(O)CF$_3$ | CH$_2$OEt | C(O)OCH$_3$ |
| G-1 | 3,5-Cl$_2$ | 2-NHC(O)CF$_3$ | CH$_2$OCH$_2$CF$_3$ | C(O)OCH$_3$ |
| G-1 | 3,5-Cl$_2$ | 2-NHC(O)CF$_3$ | C(O)Et | C(O)OCH$_3$ |
| G-1 | 3,5-Cl$_2$ | 2-NHC(O)CF$_3$ | C(O)CH$_3$ | (D-55c)Cl |
| G-1 | 3,5-Cl$_2$ | 2-NHC(O)CF$_3$ | C(O)Pr-i | (D-55c)Cl |
| G-1 | 3,5-Cl$_2$ | 2-NHC(O)CF$_3$ | C(O)OCH$_3$ | (D-55c)Cl |
| G-1 | 3,5-Cl$_2$ | 2-NHC(O)CF$_3$ | C(O)CH$_3$ | (D-55c)Br |
| G-1 | 3,5-Cl$_2$ | 2-NHC(O)OCH$_3$ | H | CH=NOCH$_3$ |
| G-1 | 3,5-Cl$_2$ | 2-NHC(O)OCH$_3$ | H | CH=NOEt |
| G-1 | 3,5-Cl$_2$ | 2-NHC(O)OCH$_3$ | CH$_2$OEt | C(O)OCH$_3$ |
| G-1 | 3,5-Cl$_2$ | 2-NHC(O)OCH$_3$ | CH$_2$OCH$_2$CF$_3$ | C(O)OCH$_3$ |
| G-1 | 3,5-Cl$_2$ | 2-NHC(O)OCH$_3$ | C(O)Et | C(O)OCH$_3$ |
| G-1 | 3,5-Cl$_2$ | 2-NHC(O)OCH$_3$ | C(O)CH$_3$ | (D-55c)Cl |
| G-1 | 3,5-Cl$_2$ | 2-NHC(O)OCH$_3$ | C(O)Pr-i | (D-55c)Cl |
| G-1 | 3,5-Cl$_2$ | 2-NHC(O)OCH$_3$ | C(O)OCH$_3$ | (D-55c)Cl |
| G-1 | 3,5-Cl$_2$ | 2-NHC(O)OCH$_3$ | C(O)CH$_3$ | (D-55c)Br |
| G-1 | 3,5-Cl$_2$ | 2-NHC(O)OEt | C(O)CH$_3$ | (D-55c)Br |
| G-1 | 3,5-Cl$_2$ | 2-NHC(O)SCH$_3$ | H | CH=NOCH$_3$ |
| G-1 | 3,5-Cl$_2$ | 2-NHC(O)SCH$_3$ | H | CH=NOEt |
| G-1 | 3,5-Cl$_2$ | 2-NHC(O)SCH$_3$ | CH$_2$OEt | C(O)OCH$_3$ |
| G-1 | 3,5-Cl$_2$ | 2-NHC(O)SCH$_3$ | CH$_2$OCH$_2$CF$_3$ | C(O)OCH$_3$ |
| G-1 | 3,5-Cl$_2$ | 2-NHC(O)SCH$_3$ | C(O)Et | C(O)OCH$_3$ |
| G-1 | 3,5-Cl$_2$ | 2-NHC(O)SCH$_3$ | C(O)CH$_3$ | (D-55c)Cl |
| G-1 | 3,5-Cl$_2$ | 2-NHC(O)SCH$_3$ | C(O)Pr-i | (D-55c)Cl |
| G-1 | 3,5-Cl$_2$ | 2-NHC(O)SCH$_3$ | C(O)OCH$_3$ | (D-55c)Cl |
| G-1 | 3,5-Cl$_2$ | 2-NHC(O)SCH$_3$ | C(O)CH$_3$ | (D-55c)Br |
| G-1 | 3,5-Cl$_2$ | 2-NHC(O)SEt | H | CH=NOCH$_3$ |
| G-1 | 3,5-Cl$_2$ | 2-NHC(S)OCH$_3$ | H | CH=NOCH$_3$ |
| G-1 | 3,5-Cl$_2$ | 2-NHC(S)OCH$_3$ | H | CH=NOEt |
| G-1 | 3,5-Cl$_2$ | 2-NHC(S)OCH$_3$ | CH$_2$OEt | C(O)OCH$_3$ |
| G-1 | 3,5-Cl$_2$ | 2-NHC(S)OCH$_3$ | CH$_2$OCH$_2$CF$_3$ | C(O)OCH$_3$ |
| G-1 | 3,5-Cl$_2$ | 2-NHC(S)OCH$_3$ | C(O)Et | C(O)OCH$_3$ |
| G-1 | 3,5-Cl$_2$ | 2-NHC(S)OCH$_3$ | C(O)CH$_3$ | (D-55c)Br |
| G-1 | 3,5-Cl$_2$ | 2-NHC(S)OCH$_3$ | C(O)Pr-i | (D-55c)Cl |
| G-1 | 3,5-Cl$_2$ | 2-NHC(S)OCH$_3$ | C(O)OCH$_3$ | (D-55c)Cl |
| G-1 | 3,5-Cl$_2$ | 2-NHC(S)OCH$_3$ | C(O)CH$_3$ | (D-55c)Br |
| G-1 | 3,5-Cl$_2$ | 2-NHC(S)OEt | H | CH=NOEt |
| G-1 | 3,5-Cl$_2$ | 2-NHC(S)SCH$_3$ | H | CH=NOCH$_3$ |
| G-1 | 3,5-Cl$_2$ | 2-NHC(S)SCH$_3$ | H | CH=NOEt |
| G-1 | 3,5-Cl$_2$ | 2-NHC(S)SCH$_3$ | CH$_2$OEt | C(O)OCH$_3$ |
| G-1 | 3,5-Cl$_2$ | 2-NHC(S)SCH$_3$ | CH$_2$OCH$_2$CF$_3$ | C(O)OCH$_3$ |
| G-1 | 3,5-Cl$_2$ | 2-NHC(S)SCH$_3$ | C(O)Et | C(O)OCH$_3$ |
| G-1 | 3,5-Cl$_2$ | 2-NHC(S)SCH$_3$ | C(O)CH$_3$ | (D-55c)Cl |
| G-1 | 3,5-Cl$_2$ | 2-NHC(S)SCH$_3$ | C(O)Pr-i | (D-55c)Cl |
| G-1 | 3,5-Cl$_2$ | 2-NHC(S)SCH$_3$ | C(O)OCH$_3$ | (D-55c)Cl |
| G-1 | 3,5-Cl$_2$ | 2-NHC(S)SCH$_3$ | C(O)CH$_3$ | (D-55c)Br |
| G-1 | 3,5-Cl$_2$ | 2-NHC(S)SEt | CH$_2$OEt | C(O)OCH$_3$ |
| G-1 | 3,5-Cl$_2$ | 2-NHSO$_2$CH$_3$ | H | CH=NOCH$_3$ |
| G-1 | 3,5-Cl$_2$ | 2-NHSO$_2$CH$_3$ | H | CH=NOEt |
| G-1 | 3,5-Cl$_2$ | 2-NHSO$_2$CH$_3$ | CH$_2$OEt | C(O)OCH$_3$ |
| G-1 | 3,5-Cl$_2$ | 2-NHSO$_2$CH$_3$ | CH$_2$OCH$_2$CF$_3$ | C(O)OCH$_3$ |
| G-1 | 3,5-Cl$_2$ | 2-NHSO$_2$CH$_3$ | C(O)Et | C(O)OCH$_3$ |
| G-1 | 3,5-Cl$_2$ | 2-NHSO$_2$CH$_3$ | C(O)CH$_3$ | (D-55c)Cl |
| G-1 | 3,5-Cl$_2$ | 2-NHSO$_2$CH$_3$ | C(O)Pr-i | (D-55c)Cl |
| G-1 | 3,5-Cl$_2$ | 2-NHSO$_2$CH$_3$ | C(O)OCH$_3$ | (D-55c)Cl |
| G-1 | 3,5-Cl$_2$ | 2-NHSO$_2$CH$_3$ | C(O)CH$_3$ | (D-55c)Br |

TABLE 3-continued

| G-1 | 3,5-Cl$_2$ | 2-NHSO$_2$CF$_3$ | H | CH=NOCH$_3$ |
|---|---|---|---|---|
| G-1 | 3,5-Cl$_2$ | 2-NHSO$_2$CF$_3$ | H | CH=NOEt |
| G-1 | 3,5-Cl$_2$ | 2-NHSO$_2$CF$_3$ | CH$_2$OEt | C(O)OCH$_3$ |
| G-1 | 3,5-Cl$_2$ | 2-NHSO$_2$CF$_3$ | CH$_2$OCH$_2$CF$_3$ | C(O)OCH$_3$ |
| G-1 | 3,5-Cl$_2$ | 2-NHSO$_2$CF$_3$ | C(O)Et | C(O)OCH$_3$ |
| G-1 | 3,5-Cl$_2$ | 2-NHSO$_2$CF$_3$ | C(O)CH$_3$ | (D-55c)Cl |
| G-1 | 3,5-Cl$_2$ | 2-NHSO$_2$CF$_3$ | C(O)Pr-i | (D-55c)Cl |
| G-1 | 3,5-Cl$_2$ | 2-NHSO$_2$CF$_3$ | C(O)OCH$_3$ | (D-55c)Cl |
| G-1 | 3,5-Cl$_2$ | 2-NHSO$_2$CF$_3$ | C(O)CH$_3$ | (D-55c)Br |
| G-1 | 3,5-Cl$_2$ | 2-N(CH$_3$)CHO | H | CH=NOCH$_3$ |
| G-1 | 3,5-Cl$_2$ | 2-N(CH$_3$)CHO | H | CH=NOEt |
| G-1 | 3,5-Cl$_2$ | 2-N(CH$_3$)CHO | CH$_2$OEt | C(O)OCH$_3$ |
| G-1 | 3,5-Cl$_2$ | 2-N(CH$_3$)CHO | CH$_2$OCH$_2$CF$_3$ | C(O)OCH$_3$ |
| G-1 | 3,5-Cl$_2$ | 2-N(CH$_3$)CHO | C(O)Et | C(O)OCH$_3$ |
| G-1 | 3,5-Cl$_2$ | 2-N(CH$_3$)CHO | C(O)CH$_3$ | (D-55c)Cl |
| G-1 | 3,5-Cl$_2$ | 2-N(CH$_3$)CHO | C(O)Pr-i | (D-55c)Cl |
| G-1 | 3,5-Cl$_2$ | 2-N(CH$_3$)CHO | C(O)OCH$_3$ | (D-55c)Cl |
| G-1 | 3,5-Cl$_2$ | 2-N(CH$_3$)CHO | C(O)CH$_3$ | (D-55c)Br |
| G-1 | 3,5-Cl$_2$ | 2-N(CH$_3$)C(O)CH$_3$ | CH$_2$OCH$_2$CF$_3$ | C(O)OCH$_3$ |
| G-1 | 3,5-Cl$_2$ | 2-N(CH$_3$)C(O)Et | C(O)Et | C(O)OCH$_3$ |
| G-1 | 3,5-Cl$_2$ | 2-N(CH$_3$)C(O)Pr-n | C(O)CH$_3$ | (D-55c)Cl |
| G-1 | 3,5-Cl$_2$ | 2-N(CH$_3$)C(O)Pr-i | C(O)Pr-i | (D-55c)Cl |
| G-1 | 3,5-Cl$_2$ | 2-N(CH$_3$)C(O)Pr-c | C(O)OCH$_3$ | (D-55c)Cl |
| G-1 | 3,5-Cl$_2$ | 2-N(CH$_3$)C(O)Bu-t | C(O)CH$_3$ | (D-55c)Br |
| G-1 | 3,5-Cl$_2$ | 2-N(CH$_3$)C(O)CF$_3$ | H | CH=NOCH$_3$ |
| G-1 | 3,5-Cl$_2$ | 2-N(CH$_3$)C(O)OCH$_3$ | H | CH=NOEt |
| G-1 | 3,5-Cl$_2$ | 2-N(CH$_3$)C(O)OEt | CH$_2$OEt | C(O)OCH$_3$ |
| G-1 | 3,5-Cl$_2$ | 2-N(CH$_3$)C(O)SCH$_3$ | CH$_2$OCH$_2$CF$_3$ | C(O)OCH$_3$ |
| G-1 | 3,5-Cl$_2$ | 2-N(CH$_3$)C(O)SEt | C(O)Et | C(O)OCH$_3$ |
| G-1 | 3,5-Cl$_2$ | 2-N(CH$_3$)C(S)OCH$_3$ | C(O)CH$_3$ | (D-55c)Cl |
| G-1 | 3,5-Cl$_2$ | 2-N(CH$_3$)C(S)OEt | C(O)Pr-i | (D-55c)Cl |
| G-1 | 3,5-Cl$_2$ | 2-N(CH$_3$)C(S)SCH$_3$ | C(O)OCH$_3$ | (D-55c)Cl |
| G-1 | 3,5-Cl$_2$ | 2-N(CH$_3$)C(S)SEt | C(O)CH$_3$ | (D-55c)Br |
| G-1 | 3,5-Cl$_2$ | 2-N(CH$_3$)SO$_2$CH$_3$ | H | CH=NOCH$_3$ |
| G-1 | 3,5-Cl$_2$ | 2-N(CH$_3$)SO$_2$CF$_3$ | H | CH=NOEt |
| G-1 | 3,5-Cl$_2$ | 2-N(Et)CHO | CH$_2$OEt | C(O)OCH$_3$ |
| G-1 | 3,5-Cl$_2$ | 2-N(Et)C(O)CH$_3$ | CH$_2$OCH$_2$CF$_3$ | C(O)OCH$_3$ |
| G-1 | 3,5-Cl$_2$ | 2-N(Et)C(O)Et | C(O)Et | C(O)OCH$_3$ |
| G-1 | 3,5-Cl$_2$ | 2-N(Et)C(O)Pr-n | C(O)CH$_3$ | (D-55c)Cl |
| G-1 | 3,5-Cl$_2$ | 2-N(Et)C(O)Pr-i | C(O)Pr-i | (D-55c)Cl |
| G-1 | 3,5-Cl$_2$ | 2-N(Et)C(O)Pr-c | C(O)OCH$_3$ | (D-55c)Cl |
| G-1 | 3,5-Cl$_2$ | 2-N(Et)C(O)Bu-t | C(O)CH$_3$ | (D-55c)Br |
| G-1 | 3,5-Cl$_2$ | 2-N(Et)C(O)CF$_3$ | H | CH=NOCH$_3$ |
| G-1 | 3,5-Cl$_2$ | 2-N(Et)C(O)OCH$_3$ | H | CH=NOEt |
| G-1 | 3,5-Cl$_2$ | 2-N(Et)C(O)OEt | CH$_2$OEt | C(O)OCH$_3$ |
| G-1 | 3,5-Cl$_2$ | 2-N(Et)C(O)SCH$_3$ | CH$_2$OCH$_2$CF$_3$ | C(O)OCH$_3$ |
| G-1 | 3,5-Cl$_2$ | 2-N(Et)C(O)SEt | C(O)Et | C(O)OCH$_3$ |
| G-1 | 3,5-Cl$_2$ | 2-N(Et)C(O)OCH$_3$ | C(O)CH$_3$ | (D-55c)Cl |
| G-1 | 3,5-Cl$_2$ | 2-N(Et)C(S)OEt | C(O)Pr-i | (D-55c)Cl |
| G-1 | 3,5-Cl$_2$ | 2-N(Et)C(S)SCH$_3$ | C(O)OCH$_3$ | (D-55c)Cl |
| G-1 | 3,5-Cl$_2$ | 2-N(Et)C(S)SEt | C(O)CH$_3$ | (D-55c)Cl |
| G-1 | 3,5-Cl$_2$ | 2-N(CH$_3$)SO$_2$CH$_3$ | H | CH=NOCH$_3$ |
| G-1 | 3,5-Cl$_2$ | 2-N(CH$_3$)SO$_2$CF$_3$ | H | CH=NOEt |
| G-1 | 3,5-Cl$_2$ | 2-N=CHOCH$_3$ | CH$_2$OEt | C(O)OCH$_3$ |
| G-1 | 3,5-Cl$_2$ | 2-N=C(CH$_3$)OCH$_3$ | H | CH=NOCH$_3$ |
| G-1 | 3,5-Cl$_2$ | 2-N=C(CH$_3$)OCH$_3$ | H | CH=NOEt |
| G-1 | 3,5-Cl$_2$ | 2-N=C(CH$_3$)OCH$_3$ | CH$_2$OEt | C(O)OCH$_3$ |
| G-1 | 3,5-Cl$_2$ | 2-N=C(CH$_3$)OCH$_3$ | CH$_2$OCH$_2$CF$_3$ | C(O)OCH$_3$ |
| G-1 | 3,5-Cl$_2$ | 2-N=C(CH$_3$)OCH$_3$ | C(O)Et | C(O)OCH$_3$ |
| G-1 | 3,5-Cl$_2$ | 2-N=C(CH$_3$)OCH$_3$ | C(O)CH$_3$ | (D-55c)Cl |
| G-1 | 3,5-Cl$_2$ | 2-N=C(CH$_3$)OCH$_3$ | C(O)Pr-i | (D-55c)Cl |
| G-1 | 3,5-Cl$_2$ | 2-N=C(CH$_3$)OCH$_3$ | C(O)OCH$_3$ | (D-55c)Cl |
| G-1 | 3,5-Cl$_2$ | 2-N=C(CH$_3$)OCH$_3$ | C(O)CH$_3$ | (D-55c)Br |
| G-1 | 3,5-Cl$_2$ | 2-(D-5a) | CH$_2$OCH$_2$CF$_3$ | C(O)OCH$_3$ |
| G-1 | 3,5-Cl$_2$ | 2-C(O)OCH$_3$ | C(O)Et | C(O)OCH$_3$ |
| G-1 | 3,5-Cl$_2$ | 2-C(O)NH$_2$ | C(O)CH$_3$ | (D-55c)Cl |
| G-1 | 3,5-Cl$_2$ | 2-(M-11a) | C(O)Pr-i | (D-55c)Cl |
| G-1 | 3,5-Cl$_2$ | 2-C(S)NH$_2$ | H | CH=NOCH$_3$ |
| G-1 | 3,5-Cl$_2$ | 2-C(S)NH$_2$ | H | CH=NOEt |
| G-1 | 3,5-Cl$_2$ | 2-C(S)NH$_2$ | CH$_2$OEt | C(O)OCH$_3$ |
| G-1 | 3,5-Cl$_2$ | 2-C(S)NH$_2$ | CH$_2$OCH$_2$CF$_3$ | C(O)OCH$_3$ |
| G-1 | 3,5-Cl$_2$ | 2-C(S)NH$_2$ | C(O)Et | C(O)OCH$_3$ |
| G-1 | 3,5-Cl$_2$ | 2-C(S)NH$_2$ | C(O)CH$_3$ | (D-55c)Cl |
| G-1 | 3,5-Cl$_2$ | 2-C(S)NH$_2$ | C(O)Pr-i | (D-55c)Cl |
| G-1 | 3,5-Cl$_2$ | 2-C(S)NH$_2$ | C(O)OCH$_3$ | (D-55c)Cl |
| G-1 | 3,5-Cl$_2$ | 2-C(S)NH$_2$ | C(O)CH$_3$ | (D-55c)Br |
| G-1 | 3,5-Cl$_2$ | 2-(M-14a) | C(O)OCH$_3$ | (D-55c)Cl |
| G-1 | 3,5-Cl$_2$ | 2-Ph | C(O)CH$_3$ | (D-55c)Br |
| G-1 | 3,5-Cl$_2$ | 2-(D-14a) | H | CH=NOCH$_3$ |
| G-1 | 3,5-Cl$_2$ | 2-(D-24a) | H | CH=NOEt |

TABLE 3-continued

| | | | | |
|---|---|---|---|---|
| G-1 | 3,5-Cl₂ | 2-(D-41a) | CH₂OEt | C(O)OCH₃ |
| G-1 | 3,5-Cl₂ | 2-(D-48a) | CH₂OCH₂CF₃ | C(O)OCH₃ |
| G-1 | 3,5-Cl₂ | 2-(D-48b)CH₃ | C(O)Et | C(O)OCH₃ |
| G-1 | 3,5-Cl₂ | 2-(D-49a) | C(O)CH₃ | (D-55c)Cl |
| G-1 | 3,5-Cl₂ | 2-(D-50a)H | C(O)Pr-i | (D-55c)Cl |
| G-1 | 3,5-Cl₂ | 2-(D-50a)CH₃ | C(O)OCH₃ | (D-55c)Cl |
| G-1 | 3,5-Cl₂ | 2-(D-51a)H | C(O)CH₃ | (D-55c)Br |
| G-1 | 3,5-Cl₂ | 2-(D-51 a)CH₃ | H | CH=NOCH₃ |
| G-1 | 3,5-Cl₂ | 2,3-F₂ | H | CH=NOEt |
| G-1 | 3,5-Cl₂ | 2,5-F₂ | CH₂OEt | C(O)OCH₃ |
| G-1 | 3,5-Cl₂ | 2,6-F₂ | CH₂OCH₂CF₃ | C(O)OCH₃ |
| G-1 | 3,5-Cl₂ | 2-F-6-Cl | C(O)Et | C(O)OCH₃ |
| G-1 | 3,5-Cl₂ | 2-F-6-Br | C(O)CH₃ | (D-55c)Cl |
| G-1 | 3,5-Cl₂ | 2-F-6-CF₃ | C(O)Pr-i | (D-55c)Cl |
| G-1 | 3,5-Cl₂ | 2-F-6-NO₂ | C(O)OCH₃ | (D-55c)Cl |
| G-1 | 3,5-Cl₂ | 2-Cl-3-F | C(O)CH₃ | (D-55c)Br |
| G-1 | 3,5-Cl₂ | 2-Cl-5-F | H | CH=NOCH₃ |
| G-1 | 3,5-Cl₂ | 2,5-Cl₂ | H | CH=NOEt |
| G-1 | 3,5-Cl₂ | 2,6-Cl₂ | CH₂OEt | C(O)OCH₃ |
| G-1 | 3,5-Cl₂ | 2-Br-3-F | CH₂OCH₂CF₃ | C(O)OCH₃ |
| G-1 | 3,5-Cl₂ | 2-Br-5-F | C(O)Et | C(O)OCH₃ |
| G-1 | 3,5-Cl₂ | 2-CH₃-3-F | H | CH=NOCH₃ |
| G-1 | 3,5-Cl₂ | 2-CH₃-3-F | H | CH=NOEt |
| G-1 | 3,5-Cl₂ | 2-CH₃-3-F | CH₂OEt | C(O)OCH₃ |
| G-1 | 3,5-Cl₂ | 2-CH₃-3-F | CH₂OCH₂CF₃ | C(O)OCH₃ |
| G-1 | 3,5-Cl₂ | 2-CH₃-3-F | C(O)Et | C(O)OCH₃ |
| G-1 | 3,5-Cl₂ | 2-CH₃-3-F | C(O)CH₃ | (D-55c)Cl |
| G-1 | 3,5-Cl₂ | 2-CH₃-3-F | C(O)Pr-i | (D-55c)Cl |
| G-1 | 3,5-Cl₂ | 2-CH₃-3-F | C(O)OCH₃ | (D-55c)Cl |
| G-1 | 3,5-Cl₂ | 2-CH₃-3-F | C(O)CH₃ | (D-55c)Br |
| G-1 | 3,5-Cl₂ | 2-CH₃-3-Cl | C(O)CH₃ | (D-55c)Cl |
| G-1 | 3,5-Cl₂ | 2,3-(CH₃)₂ | C(O)Pr-i | (D-55c)Cl |
| G-1 | 3,5-Cl₂ | 2-CH₃-5-F | C(O)OCH₃ | (D-55c)Cl |
| G-1 | 3,5-Cl₂ | 2-CH₃-5-Cl | C(O)CH₃ | (D-55c)Br |
| G-1 | 3,5-Cl₂ | 2,5-(CH₃)₂ | H | CH=NOCH₃ |
| G-1 | 3,5-Cl₂ | 2-CH₃-6-F | H | CH=NOCH₃ |
| G-1 | 3,5-Cl₂ | 2-CH₃-6-F | H | CH=NOEt |
| G-1 | 3,5-Cl₂ | 2-CH₃-6-F | CH₂OEt | C(O)OCH₃ |
| G-1 | 3,5-Cl₂ | 2-CH₃-6-F | CH₂OCH₂CF₃ | C(O)OCH₃ |
| G-1 | 3,5-Cl₂ | 2-CH₃-6-F | C(O)Et | C(O)OCH₃ |
| G-1 | 3,5-Cl₂ | 2-CH₃-6-F | C(O)CH₃ | (D-55c)Cl |
| G-1 | 3,5-Cl₂ | 2-CH₃-6-F | C(O)Pr-i | (D-55c)Cl |
| G-1 | 3,5-Cl₂ | 2-CH₃-6-F | C(O)OCH₃ | (D-55c)Cl |
| G-1 | 3,5-Cl₂ | 2-CH₃-6-F | C(O)CH₃ | (D-55c)Br |
| G-1 | 3,5-Cl₂ | 2-CH₃-6-F | H | CH=NOEt |
| G-1 | 3,5-Cl₂ | 2,6-(CH₃)₂ | CH₂OEt | C(O)OCH₃ |
| G-1 | 3,5-Cl₂ | 2-CH₃-6-CF₃ | CH₂OCH₂CF₃ | C(O)OCH₃ |
| G-1 | 3,5-Cl₂ | 2-CF₃-5-F | C(O)Et | C(O)OCH₃ |
| G-1 | 3,5-Cl₂ | 2-CF₃-5-Cl | C(O)CH₃ | (D-55c)Cl |
| G-1 | 3,5-Cl₂ | 2-OCH₃-3-F | C(O)Pr-i | (D-55c)Cl |
| G-1 | 3,5-Cl₂ | 2-OCH₃-5-F | C(O)OCH₃ | (D-55c)Cl |
| G-1 | 3,5-Cl₂ | 2-OCH₃-5-Cl | C(O)CH₃ | (D-55c)Br |
| G-1 | 3,5-Cl₂ | 2-CN-3-F | H | CH=NOCH₃ |
| G-1 | 3-Cl-5-Br | 2-Pr-i | H | CH=NOEt |
| G-1 | 3-Cl-5-Br | 2-OEt | CH₂OEt | C(O)OCH₃ |
| G-1 | 3-Cl-5-Br | 2-OPr-i | CH₂OCH₂CF₃ | C(O)OCH₃ |
| G-1 | 3-Cl-5-Br | 2-OSO₂CH₃ | C(O)Et | C(O)OCH₃ |
| G-1 | 3-Cl-5-Br | 2-SEt | C(O)CH₃ | (D-55c)Cl |
| G-1 | 3-Cl-5-Br | 2-SPr-i | C(O)Pr-i | (D-55c)Cl |
| G-1 | 3-Cl-5-Br | 2-NHEt | C(O)OCH₃ | (D-55c)Cl |
| G-1 | 3-Cl-5-Br | 2-NHPr-i | C(O)CH₃ | (D-55c)Br |
| G-1 | 3-Cl-5-Br | 2-N(CH₃)₂ | H | CH=NOCH₃ |
| G-1 | 3-Cl-5-Br | 2-NHC(O)CH₃ | H | CH=NOEt |
| G-1 | 3,5-Br₂ | 2-Pr-i | CH₂OEt | C(O)OCH₃ |
| G-1 | 3,5-Br₂ | 2-OEt | CH₂OCH₂CF₃ | C(O)OCH₃ |
| G-1 | 3,5-Br₂ | 2-OPr-i | C(O)Et | C(O)OCH₃ |
| G-1 | 3,5-Br₂ | 2-OSO₂CH₃ | C(O)CH₃ | (D-55c)Cl |
| G-1 | 3,5-Br₂ | 2-SEt | C(O)Pr-i | (D-55c)Cl |
| G-1 | 3,5-Br₂ | 2-SPr-i | C(O)OCH₃ | (D-55c)Cl |
| G-1 | 3,5-Br₂ | 2-NHEt | C(O)CH₃ | (D-55c)Br |
| G-1 | 3,5-Br₂ | 2-NHPr-i | H | CH=NOCH₃ |
| G-1 | 3,5-Br₂ | 2-N(CH₃)₂ | H | CH=NOEt |
| G-1 | 3,5-Br₂ | 2-NHC(O)CH₃ | CH₂OEt | C(O)OCH₃ |
| G-1 | 3-Cl-5-I | 2-Pr-i | CH₂OCH₂CF₃ | C(O)OCH₃ |
| G-1 | 3-Cl-5-I | 2-OEt | C(O)Et | C(O)OCH₃ |
| G-1 | 3-Cl-5-I | 2-OPr-i | C(O)CH₃ | (D-55c)Cl |
| G-1 | 3-Cl-5-I | 2-OSO₂CH₃ | C(O)Pr-i | (D-55c)Cl |
| G-1 | 3-Cl-5-I | 2-SEt | C(O)OCH₃ | (D-55c)Cl |
| G-1 | 3-Cl-5-I | 2-SPr-i | C(O)CH₃ | (D-55c)Br |
| G-1 | 3-Cl-5-I | 2-NHEt | H | CH=NOCH₃ |

TABLE 3-continued

| | | | | |
|---|---|---|---|---|
| G-1 | 3-Cl-5-I | 2-NHPr-i | H | CH=NOEt |
| G-1 | 3-Cl-5-I | 2-N(CH$_3$)$_2$ | CH$_2$OEt | C(O)OCH$_3$ |
| G-1 | 3-Cl-5-I | 2-NHC(O)CH$_3$ | CH$_2$OCH$_2$CF$_3$ | C(O)OCH$_3$ |
| G-1 | 3-CF$_3$-4-F | 2-Pr-i | C(O)Et | C(O)OCH$_3$ |
| G-1 | 3-CF$_3$-4-F | 2-OEt | C(O)CH$_3$ | (D-55c)Cl |
| G-1 | 3-CF$_3$-4-F | 2-OPr-i | C(O)Pr-i | (D-55c)Cl |
| G-1 | 3-CF$_3$-4-F | 2-OSO$_2$CH$_3$ | C(O)OCH$_3$ | (D-55c)Cl |
| G-1 | 3-CF$_3$-4-F | 2-SEt | C(O)CH$_3$ | (D-55c)Br |
| G-1 | 3-CF$_3$-4-F | 2-SPr-i | H | CH=NOCH$_3$ |
| G-1 | 3-CF$_3$-4-F | 2-NHEt | H | CH=NOEt |
| G-1 | 3-CF$_3$-4-F | 2-NHPr-i | CH$_2$OEt | C(O)OCH$_3$ |
| G-1 | 3-CF$_3$-4-F | 2-N(CH$_3$)$_2$ | CH$_2$OCH$_2$CF$_3$ | C(O)OCH$_3$ |
| G-1 | 3-CF$_3$-4-F | 2-NHC(O)CH$_3$ | C(O)Et | C(O)OCH$_3$ |
| G-1 | 3-F-5-CF$_3$ | 2-Pr-i | C(O)CH$_3$ | (D-55c)Cl |
| G-1 | 3-F-5-CF$_3$ | 2-OEt | C(O)Pr-i | (D-55c)Cl |
| G-1 | 3-F-5-CF$_3$ | 2-OPr-i | C(O)OCH$_3$ | (D-55c)Cl |
| G-1 | 3-F-5-CF$_3$ | 2-OSO$_2$CH$_3$ | C(O)CH$_3$ | (D-55c)Br |
| G-1 | 3-F-5-CF$_3$ | 2-SEt | H | CH=NOCH$_3$ |
| G-1 | 3-F-5-CF$_3$ | 2-SPr-i | H | CH=NOEt |
| G-1 | 3-F-5-CF$_3$ | 2-NHEt | CH$_2$OEt | C(O)OCH$_3$ |
| G-1 | 3-F-5-CF$_3$ | | CH$_2$OCH$_2$CF$_3$ | C(O)OCH$_3$ |
| G-1 | 3-F-5-CF$_3$ | 2-N(CH$_3$)$_2$ | C(O)Et | C(O)OCH$_3$ |
| G-1 | 3-F-5-CF$_3$ | 2-NHC(O)CH$_3$ | C(O)CH$_3$ | (D-55c)Cl |
| G-1 | 3-CF$_3$-4-Cl | 2-Pr-i | C(O)Pr-i | (D-55c)Cl |
| G-1 | 3-CF$_3$-4-Cl | 2-OEt | C(O)OCH$_3$ | (D-55c)Cl |
| G-1 | 3-CF$_3$-4-Cl | 2-OPr-i | C(O)CH$_3$ | (D-55c)Br |
| G-1 | 3-CF$_3$-4-Cl | 2-OSO$_2$CH$_3$ | H | CH=NOCH$_3$ |
| G-1 | 3-CF$_3$-4-Cl | 2-SEt | H | CH=NOEt |
| G-1 | 3-CF$_3$-4-Cl | 2-SPr-i | CH$_2$OEt | C(O)OCH$_3$ |
| G-1 | 3-CF$_3$-4-Cl | 2-NHEt | CH$_2$OCH$_2$CF$_3$ | C(O)OCH$_3$ |
| G-1 | 3-CF$_3$-4-Cl | 2-NHPr-i | C(O)Et | C(O)OCH$_3$ |
| G-1 | 3-CF$_3$-4-Cl | 2-N(CH$_3$)$_2$ | C(O)CH$_3$ | (D-55c)Cl |
| G-1 | 3-CF$_3$-4-Cl | 2-NHC(O)CH$_3$ | C(O)Pr-i | (D-55c)Cl |
| G-1 | 3-Cl-5-CF$_3$ | 2-Pr-i | C(O)OCH$_3$ | (D-55c)Cl |
| G-1 | 3-Cl-5-CF$_3$ | 2-OEt | C(O)CH$_3$ | (D-55c)Br |
| G-1 | 3-Cl-5-CF$_3$ | 2-OPr-i | H | CH=NOCH$_3$ |
| G-1 | 3-Cl-5-CF$_3$ | 2-OSO$_2$CH$_3$ | H | CH=NOEt |
| G-1 | 3-Cl-5-CF$_3$ | 2-SEt | CH$_2$OEt | C(O)OCH$_3$ |
| G-1 | 3-Cl-5-CF$_3$ | 2-SPr-i | CH$_2$OCH$_2$CF$_3$ | C(O)OCH$_3$ |
| G-1 | 3-Cl-5-CF$_3$ | 2-NHEt | C(O)Et | C(O)OCH$_3$ |
| G-1 | 3-Cl-5-CF$_3$ | 2-NHPr-i | C(O)CH$_3$ | (D-55c)Cl |
| G-1 | 3-Cl-5-CF$_3$ | 2-N(CH$_3$)$_2$ | C(O)Pr-i | (D-55c)Cl |
| G-1 | 3-Cl-5-CF$_3$ | 2-NHC(O)CH$_3$ | C(O)OCH$_3$ | (D-55c)Cl |
| G-1 | 3-Br-5-CF$_3$ | 2-Pr-i | C(O)CH$_3$ | (D-55c)Br |
| G-1 | 3-Br-5-CF$_3$ | 2-OEt | H | CH=NOCH$_3$ |
| G-1 | 3-Br-5-CF$_3$ | 2-OPr-i | H | CH=NOEt |
| G-1 | 3-Br-5-CF$_3$ | 2-OSO$_2$CH$_3$ | CH$_2$OEt | C(O)OCH$_3$ |
| G-1 | 3-Br-5-CF$_3$ | 2-SEt | CH$_2$OCH$_2$CF$_3$ | C(O)OCH$_3$ |
| G-1 | 3-Br-5-CF$_3$ | 2-SPr-i | C(O)Et | C(O)OCH$_3$ |
| G-1 | 3-Br-5-CF$_3$ | 2-NHEt | C(O)CH$_3$ | (D-55c)Cl |
| G-1 | 3-Br-5-CF$_3$ | 2-NHPr-i | C(O)Pr-i | (D-55c)Cl |
| G-1 | 3-Br-5-CF$_3$ | 2-N(CH$_3$)$_2$ | C(O)OCH$_3$ | (D-55c)Cl |
| G-1 | 3-Br-5-CF$_3$ | 2-NHC(O)CH$_3$ | C(O)CH$_3$ | (D-55c)Br |
| G-1 | 3,5-(CF$_3$)$_2$ | 2-Pr-i | H | CH=NOCH$_3$ |
| G-1 | 3,5-(CF$_3$)$_2$ | 2-OEt | H | CH=NOEt |
| G-1 | 3,5-(CF$_3$)$_2$ | 2-OPr-i | CH$_2$OEt | C(O)OCH$_3$ |
| G-1 | 3,5-(CF$_3$)$_2$ | 2-OSO$_2$CH$_3$ | CH$_2$OCH$_2$CF$_3$ | C(O)OCH$_3$ |
| G-1 | 3,5-(CF$_3$)$_2$ | 2-SEt | C(O)Et | C(O)OCH$_3$ |
| G-1 | 3,5-(CF$_3$)$_2$ | 2-SPr-i | C(O)CH$_3$ | (D-55c)Cl |
| G-1 | 3,5-(CF$_3$)$_2$ | 2-NHEt | C(O)Pr-i | (D-55c)Cl |
| G-1 | 3,5-(CF$_3$)$_2$ | 2-NHPr-i | C(O)OCH$_3$ | (D-55c)Cl |
| G-1 | 3,5-(CF$_3$)$_2$ | 2-N(CH$_3$)$_2$ | C(O)OCH$_3$ | (D-55c)Br |
| G-1 | 3,5-(CF$_3$)$_2$ | 2-NHC(O)CH3 | H | CH=NOCH$_3$ |
| G-1 | 3,5-Cl$_2$-4-F | 2-Pr-i | H | CH=NOEt |
| G-1 | 3,5-Cl$_2$-4-F | 2-OEt | CH$_2$OEt | C(O)OCH$_3$ |
| G-1 | 3,5-Cl$_2$-4-F | 2-OPr-i | CH$_2$OCH$_2$CF$_3$ | C(O)OCH$_3$ |
| G-1 | 3,5-Cl$_2$-4-F | 2-OSO$_2$CH3 | C(O)Et | C(O)OCH$_3$ |
| G-1 | 3,5-Cl$_2$-4-F | 2-SEt | C(O)CH$_3$ | (D-55c)Cl |
| G-1 | 3,5-Cl$_2$-4-F | 2-SPr-i | C(O)Pr-i | (D-55c)Cl |
| G-1 | 3,5-Cl$_2$-4-F | 2-NHEt | C(O)OCH$_3$ | (D-55c)Cl |
| G-1 | 3,5-Cl$_2$-4-F | 2-NHPr-i | C(O)CH$_3$ | (D-55c)Br |
| G-1 | 3,5-Cl$_2$-4-F | 2-N(CH$_3$)$_2$ | H | CH=NOCH$_3$ |
| G-1 | 3,5-Cl$_2$-4-F | 2-NHC(O)CH$_3$ | H | CH=NOEt |
| G-1 | 3,4,5-Cl$_3$ | 2-Pr-i | CH$_2$OEt | C(O)OCH$_3$ |
| G-1 | 3,4,5-Cl$_3$ | 2-OEt | CH$_2$OCH$_2$CF$_3$ | C(O)OCH$_3$ |
| G-1 | 3,4,5-Cl$_3$ | 2-OPr-i | C(O)Et | C(O)OCH$_3$ |
| G-1 | 3,4,5-Cl$_3$ | 2-OSO$_2$CH$_3$ | C(O)CH$_3$ | (D-55c)Cl |
| G-1 | 3,4,5-Cl$_3$ | 2-SEt | C(O)Pr-i | (D-55c)Cl |
| G-1 | 3,4,5-Cl$_3$ | 2-SPr-i | C(O)OCH$_3$ | (D-55c)Cl |
| G-1 | 3,4,5-Cl$_3$ | 2-NHEt | C(O)CH$_3$ | (D-55c)Br |

TABLE 3-continued

| | | | | |
|---|---|---|---|---|
| G-1 | 3,4,5-Cl$_3$ | 2-NHPr-i | H | CH=NOCH$_3$ |
| G-1 | 3,4,5-Cl$_3$ | 2-N(CH$_3$)$_2$ | H | CH=NOEt |
| G-1 | 3,4,5-Cl$_3$ | 2-NHC(O)CH$_3$ | CH$_2$OEt | C(O)OCH$_3$ |
| G-1 | 3,5-Br$_2$-4-F | 2-Pr-i | CH$_2$OCH$_2$CF$_3$ | C(O)OCH$_3$ |
| G-1 | 3,5-Br$_2$-4-F | 2-OEt | C(O)Et | C(O)OCH$_3$ |
| G-1 | 3,5-Br$_2$-4-F | 2-OPr-i | C(O)CH$_3$ | (D-55c)Cl |
| G-1 | 3,5-Br$_2$-4-F | 2-OSO$_2$CH$_3$ | C(O)Pr-i | (D-55c)Cl |
| G-1 | 3,5-Br$_2$-4-F | 2-SEt | C(O)OCH$_3$ | (D-55c)Cl |
| G-1 | 3,5-Br$_2$-4-F | 2-SPr-i | C(O)CH$_3$ | (D-55c)Br |
| G-1 | 3,5-Br$_2$-4-F | 2-NHEt | H | CH=NOCH$_3$ |
| G-1 | 3,5-Br$_2$-4-F | 2-NHPr-i | H | CH=NOEt |
| G-1 | 3,5-Br$_2$-4-F | 2-N(CH$_3$)$_2$ | CH$_2$OEt | C(O)OCH$_3$ |
| G-1 | 3,5-Br$_2$-4-F | 2-NHC(O)CH$_3$ | CH$_2$OCH$_2$CF$_3$ | C(O)OCH$_3$ |
| G-1 | 3,4-F$_2$-5-CF$_3$ | 2-Pr-i | C(O)Et | C(O)OCH$_3$ |
| G-1 | 3,4-F$_2$-5-CF$_3$ | 2-OEt | C(O)CH$_3$ | (D-55c)Cl |
| G-1 | 3,4-F$_2$-5-CF$_3$ | 2-OPr-i | C(O)Pr-i | (D-55c)Cl |
| G-1 | 3,4-F$_2$-5-CF$_3$ | 2-OSO$_2$CH$_3$ | C(O)OCH$_3$ | (D-55c)Cl |
| G-1 | 3,4-F$_2$-5-CF$_3$ | 2-SEt | C(O)CH$_3$ | (D-55c)Br |
| G-1 | 3,4-F$_2$-5-CF$_3$ | 2-SPr-i | H | CH=NOCH$_3$ |
| G-1 | 3,4-F$_2$-5-CF$_3$ | 2-NHEt | H | CH=NOEt |
| G-1 | 3,4-F$_2$-5-CF$_3$ | 2-NHPr-i | CH$_2$OEt | C(O)OCH$_3$ |
| G-1 | 3,4-F$_2$-5-CF$_3$ | 2-N(CH$_3$)$_2$ | CH$_2$OCH$_2$CF$_3$ | C(O)OCH$_3$ |
| G-1 | 3,4-F$_2$-5-CF$_3$ | 2-NHC(O)CH$_3$ | C(O)Et | C(O)OCH$_3$ |
| G-1 | 3-Cl-4-F-5-CF$_3$ | 2-Pr-i | C(O)CH$_3$ | (D-55c)Cl |
| G-1 | 3-,4-Cl$_2$-5-CF$_3$ | 2-Pr-i | C(O)Pr-i | (D-55c)Cl |
| G-1 | 3,4-Cl$_2$-5-CF$_3$ | 2-Pr-i | C(O)Pr-i | (D-55c)Cl |
| G-1 | 3-,4-Cl$_2$-5-CF$_3$ | 2-OEt | C(O)OCH$_3$ | (D-55c)Cl |
| G-1 | 3-,4-Cl$_2$-5-CF$_3$ | 2-OPr-i | C(O)CH$_3$ | (D-55c)Br |
| G-1 | 3-,4-Cl$_2$-5-CF$_3$ | 2-OSO2CH$_3$ | H | CH=NOCH$_3$ |
| G-1 | 3-,4-Cl$_2$-5-CF$_3$ | 2-SEt | H | CH=NOEt |
| G-1 | 3-,4-Cl$_2$-5-CF$_3$ | 2-SPr-i | CH$_2$OEt | C(O)OCH$_3$ |
| G-1 | 3-,4-Cl$_2$-5-CF$_3$ | 2-NHEt | CH$_2$OCH2CF$_3$ | C(O)OCH$_3$ |
| G-1 | 3-,4-Cl$_2$-5-CF$_3$ | 2-NHPr-i | C(O)Et | C(O)OCH$_3$ |
| G-1 | 3-,4-Cl$_2$-5-CF$_3$ | 2-N(CH$_3$)$_2$ | C(O)CH$_3$ | (D-55c)Cl |
| G-1 | 3-,4-Cl$_2$-5-CF$_3$ | 2-NHC(O)CH$_3$ | C(O)Pr-I | (D-55c)Cl |
| G-1 | 3-Cl-4-F-5-CF$_3$ | 2-OEt | C(O)Pr-i | (D-55c)Cl |
| G-1 | 3-Cl-4-F-5-CF$_3$ | 2-OPr-i | C(O)OCH$_3$ | (D-55c)Cl |
| G-1 | 3-Cl-4-F-5-CF$_3$ | 2-OSO$_2$CH$_3$ | C(O)CH$_3$ | (D-55c)Br |
| G-1 | 3-Cl-4-F-5-CF$_3$ | 2-SEt | H | CH=NOCH$_3$ |
| G-1 | 3-Cl-4-F-5-CF$_3$ | 2-SPr-i | H | CH=NOEt |
| G-1 | 3-Cl-4-F-5-CF$_3$ | 2-NHEt | CH$_2$OEt | C(O)OCH$_3$ |
| G-1 | 3-Cl-4-F-5-CF$_3$ | 2-NHPr-i | CH$_2$OCH$_2$CF$_3$ | C(O)OCH$_3$ |
| G-1 | 3-Cl-4-F-5-CF$_3$ | 2-N(CH$_3$)$_2$ | C(O)Et | C(O)OCH$_3$ |
| G-1 | 3-Cl-4-F-5-CF$_3$ | 2-NHC(O)CH$_3$ | C(O)CH$_3$ | (D-55c)Cl |
| G-1 | 3,5-(CF$_3$)$_2$-4-Cl | 2-Pr-i | C(O)Pr-i | (D-55c)Cl |
| G-1 | 3,5-(CF$_3$)$_2$-4-Cl | 2-OEt | C(O)OCH$_3$ | (D-55c)Cl |
| G-1 | 3,5-(CF$_3$)$_2$-4-Cl | 2-OPr-i | C(O)CH$_3$ | (D-55c)Br |
| G-1 | 3,5-(CF$_3$)$_2$-4-Cl | 2-OSO$_2$CH$_3$ | H | CH=NOCH$_3$ |
| G-1 | 3,5-(CF$_3$)$_2$-4-Cl | 2-SEt | H | CH=NOEt |
| G-1 | 3,5-(CF$_3$)$_2$-4-Cl | 2-SPr-i | CH$_2$OEt | C(O)OCH$_3$ |
| G-1 | 3,5-(CF$_3$)$_2$-4-Cl | 2-NHEt | CH$_2$OCH$_2$CF$_3$ | C(O)OCH$_3$ |
| G-1 | 3,5-(CF$_3$)$_2$-4-Cl | 2-NHPr-i | C(O)Et | C(O)OCH$_3$ |
| G-1 | 3,5-(CF$_3$)$_2$-4-Cl | 2-N(CH$_3$)$_2$ | C(O)CH$_3$ | (D-55c)Cl |
| G-1 | 3,5-(CF$_3$)$_2$-4-Cl | 2-NHC(O)CH$_3$ | C(O)Pr-i | (D-55c)Cl |
| G-3 | 5-Cl | 2-CH$_3$ | C(O)OCH$_3$ | (D-55c)Cl |
| G-3 | 5-CF$_3$ | 2-CH$_3$ | H | CH=NOCH$_3$ |
| G-3 | 5-CF$_3$ | 2-CH$_3$ | H | CH=NOEt |
| G-3 | 5-CF$_3$ | 2-CH$_3$ | CH$_2$OEt | C(O)OCH$_3$ |
| G-3 | 5-CF$_3$ | 2-CH$_3$ | CH$_2$OCH$_2$CF$_3$ | C(O)OCH$_3$ |
| G-3 | 5-CF$_3$ | 2-CH$_3$ | C(O)Et | C(O)OCH$_3$ |
| G-3 | 5-CF$_3$ | 2-CH$_3$ | C(O)CH$_3$ | (D-55c)Cl |
| G-3 | 5-CF$_3$ | 2-CH$_3$ | C(O)Pr-i | (D-55c)Cl |
| G-3 | 5-CF$_3$ | 2-CH$_3$ | C(O)OCH$_3$ | (D-55c)Cl |
| G-3 | 5-CF$_3$ | 2-CH$_3$ | C(O)CH$_3$ | (D-55c)Br |
| G-3 | 5-CF$_3$-6-Cl | 2-CH$_3$ | C(O)CH$_3$ | (D-55c)Br |
| G-3 | 5-NO$_2$-6-Cl | 2-CH$_3$ | H | CH=NOCH$_3$ |
| G-4 | 2-Cl | 2-CH$_3$ | H | CH=NOEt |
| G-4 | 2-Br | 2-CH$_3$ | C(O)Et | C(O)OCH$_3$ |
| G-4 | 2-CF$_3$ | 2-CH$_3$ | H | CH=NOCH$_3$ |
| G-4 | 2-CF$_3$ | 2-CH$_3$ | H | CH=NOEt |
| G-4 | 2-CF$_3$ | 2-CH$_3$ | CH$_2$OEt | C(O)OCH$_3$ |
| G-4 | 2-CF$_3$ | 2-CH$_3$ | CH$_2$OCH$_2$CF$_3$ | C(O)OCH$_3$ |
| G-4 | 2-CF$_3$ | 2-CH$_3$ | C(O)Et | C(O)OCH$_3$ |
| G-4 | 2-CF$_3$ | 2-CH$_3$ | C(O)CH$_3$ | (D-55c)Br |
| G-4 | 2-CF$_3$ | 2-CH$_3$ | C(O)Pr-i | (D-55c)Cl |
| G-4 | 2-CF$_3$ | 2-CH$_3$ | C(O)OCH$_3$ | (D-55c)Cl |
| G-4 | 2-CF$_3$ | 2-CH$_3$ | C(O)CH$_3$ | (D-55c)Br |
| G-4 | 2,6-F$_2$ | 2-CH$_3$ | C(O)Et | C(O)OCH$_3$ |
| G-4 | 2,6-Cl$_2$ | — | C(O)CH$_3$ | (D-55c)Cl |
| G-4 | 2,6-Cl$_2$ | 2-F | C(O)Pr-i | (D-55c)Cl |

TABLE 3-continued

| | | | | |
|---|---|---|---|---|
| G-4 | 2,6-Cl$_2$ | 2-Cl | H | CH=NOCH$_3$ |
| G-4 | 2,6-Cl$_2$ | 2-Cl | H | CH=NOEt |
| G-4 | 2,6-Cl$_2$ | 2-Cl | CH$_2$OEt | C(O)OCH$_3$ |
| G-4 | 2,6-Cl$_2$ | 2-Cl | CH$_2$OCH$_2$CF$_3$ | C(O)OCH$_3$ |
| G-4 | 2,6-Cl$_2$ | 2-Cl | C(O)Et | C(O)OCH$_3$ |
| G-4 | 2,6-Cl$_2$ | 2-Cl | C(O)CH$_3$ | (D-55c)Cl |
| G-4 | 2,6-Cl$_2$ | 2-Cl | C(O)Pr-i | (D-55c)Cl |
| G-4 | 2,6-Cl$_2$ | 2-Cl | C(O)OCH$_3$ | (D-55c)Cl |
| G-4 | 2,6-Cl$_2$ | 2-Cl | C(O)CH$_3$ | (D-55c)Br |
| G-4 | 2,6-Cl$_2$ | 2-Br | H | CH=NOCH$_3$ |
| G-4 | 2,6-Cl$_2$ | 2-Br | H | CH=NOEt |
| G-4 | 2,6-Cl$_2$ | 2-Br | CH$_2$OEt | C(O)OCH$_3$ |
| G-4 | 2,6-Cl$_2$ | 2-Br | CH$_2$OCH$_2$CF$_3$ | C(O)OCH$_3$ |
| G-4 | 2,6-Cl$_2$ | 2-Br | C(O)Et | C(O)OCH$_3$ |
| G-4 | 2,6-Cl$_2$ | 2-Br | C(O)CH$_3$ | (D-55c)Cl |
| G-4 | 2,6-Cl$_2$ | 2-Br | C(O)Pr-i | (D-55c)Cl |
| G-4 | 2,6-Cl$_2$ | 2-Br | C(O)OCH$_3$ | (D-55c)Cl |
| G-4 | 2,6-Cl$_2$ | 2-Br | C(O)CH$_3$ | (D-55c)Br |
| G-4 | 2,6-Cl$_2$ | 2-I | H | CH=NOCH$_3$ |
| G-4 | 2,6-Cl$_2$ | 2-I | H | CH=NOEt |
| G-4 | 2,6-Cl$_2$ | 2-I | CH$_2$OEt | C(O)OCH$_3$ |
| G-4 | 2,6-Cl$_2$ | 2-I | CH$_2$OCH$_2$CF$_3$ | C(O)OCH$_3$ |
| G-4 | 2,6-Cl$_2$ | 2-I | C(O)Et | C(O)OCH$_3$ |
| G-4 | 2,6-Cl$_2$ | 2-I | C(O)CH$_3$ | (D-55c)Cl |
| G-4 | 2,6-Cl$_2$ | 2-I | C(O)Pr-i | (D-55c)Cl |
| G-4 | 2,6-Cl$_2$ | 2-I | C(O)OCH$_3$ | (D-55c)Cl |
| G-4 | 2,6-Cl$_2$ | 2-I | C(O)CH$_3$ | (D-55c)Br |
| G-4 | 2,6-Cl$_2$ | 2-CH$_3$ | H | CH=NOCH$_3$ |
| G-4 | 2,6-Cl$_2$ | 2-CH$_3$ | H | CH=NOEt |
| G-4 | 2,6-Cl$_2$ | 2-CH$_3$ | H | C(O)OCH$_3$ |
| G-4 | 2,6-Cl$_2$ | 2-CH$_3$ | Et | C(O)OCH$_3$ |
| G-4 | 2,6-Cl$_2$ | 2-CH$_3$ | CH$_2$OCH$_3$ | C(O)OCH$_3$ |
| G-4 | 2,6-Cl$_2$ | 2-CH$_3$ | CH$_2$OEt | C(O)OCH$_3$ |
| G-4 | 2,6-Cl$_2$ | 2-CH$_3$ | CH$_2$OCH$_2$CF$_3$ | C(O)OCH$_3$ |
| G-4 | 2,6-Cl$_2$ | 2-CH$_3$ | C(O)Et | C(O)OCH$_3$ |
| G-4 | 2,6-Cl$_2$ | 2-CH$_3$ | CH$_2$OCH$_3$ | C(O)OEt |
| G-4 | 2,6-Cl$_2$ | 2-CH$_3$ | H | C(O)NH$_2$ |
| G-4 | 2,6-Cl$_2$ | 2-CH$_3$ | CH$_3$ | (D-55c)Cl |
| G-4 | 2,6-Cl$_2$ | 2-CH$_3$ | CH$_2$OCH$_3$ | (D-55c)Cl |
| G-4 | 2,6-Cl$_2$ | 2-CH$_3$ | C(O)CH$_3$ | (D-55c)Cl |
| G-4 | 2,6-Cl$_2$ | 2-CH$_3$ | C(O)Et | (D-55c)Cl |
| G-4 | 2,6-Cl$_2$ | 2-CH$_3$ | C(O)Pr-i | (D-55c)Cl |
| G-4 | 2,6-Cl$_2$ | 2-CH$_3$ | C(O)CH$_2$OCH$_2$ | (D-55c)Cl |
| G-4 | 2,6-Cl$_2$ | 2-CH$_3$ | C(O)OCH$_2$ | (D-55c)Cl |
| G-4 | 2,6-Cl$_2$ | 2-CH$_3$ | C(O)CH$_3$ | (D-55c)Br |
| G-4 | 2,6-Cl$_2$ | 2-CH$_3$ | C(O)Et | (D-55c)Br |
| G-4 | 2,6-Cl$_2$ | 2-CH$_3$ | C(O)Pr-i | (D-55c)Br |
| G-4 | 2,6-Cl$_2$ | 2-Et | H | CH=NOCH$_3$ |
| G-4 | 2,6-Cl$_2$ | 2-Et | H | CH=NOEt |
| G-4 | 2,6-Cl$_2$ | 2-Et | CH$_2$OEt | C(O)OCH$_3$ |
| G-4 | 2,6-Cl$_2$ | 2-Et | CH$_2$OCH$_2$CF$_3$ | C(O)OCH$_3$ |
| G-4 | 2,6-Cl$_2$ | 2-Et | C(O)Et | C(O)OCH$_3$ |
| G-4 | 2,6-Cl$_2$ | 2-Et | C(O)CH$_3$ | (D-55c)Cl |
| G-4 | 2,6-Cl$_2$ | 2-Et | C(O)Pr-i | (D-55c)Cl |
| G-4 | 2,6-Cl$_2$ | 2-Et | C(O)OCH$_3$ | (D-55c)Cl |
| G-4 | 2,6-Cl$_2$ | 2-Et | C(O)CH$_3$ | (D-55c)Br |
| G-4 | 2,6-Cl$_2$ | 2-CF$_3$ | H | CH=NOCH$_3$ |
| G-4 | 2,6-Cl$_2$ | 2-CF$_3$ | H | CH=NOEt |
| G-4 | 2,6-Cl$_2$ | 2-CF$_3$ | CH$_2$OEt | C(O)OCH$_3$ |
| G-4 | 2,6-Cl$_2$ | 2-CF$_3$ | CH$_2$OCH$_2$CF$_3$ | C(O)OCH$_3$ |
| G-4 | 2,6-Cl$_2$ | 2-CF$_3$ | C(O)Et | C(O)OCH$_3$ |
| G-4 | 2,6-Cl$_2$ | 2-CF$_3$ | C(O)CH$_3$ | (D-55c)Cl |
| G-4 | 2,6-Cl$_2$ | 2-CF$_3$ | C(O)Pr-i | (D-55c)Cl |
| G-4 | 2,6-Cl$_2$ | 2-CF$_3$ | C(O)OCH$_3$ | (D-55c)Cl |
| G-4 | 2,6-Cl$_2$ | 2-CF$_3$ | C(O)CH$_3$ | (D-55c)Br |
| G-4 | 2,6-Cl$_2$ | 2-OCH$_3$ | C(O)Pr-i | (D-55c)Cl |
| G-4 | 2,6-Cl$_2$ | 2-OCHF$_2$ | C(O)OCH$_3$ | (D-55c)Cl |
| G-4 | 2,6-Cl$_2$ | 2-OCF$_2$ | C(O)CH$_3$ | (D-55c)Br |
| G-4 | 2,6-Cl$_2$ | 2-SCH$_3$ | H | CH=NOCH$_3$ |
| G-4 | 2,6-Cl$_2$ | 2-SCF$_2$ | H | CH=NOEt |
| G-4 | 2,6-Cl$_2$ | 2-NO$_2$ | CH$_2$OEt | C(O)OCH$_3$ |
| G-4 | 2,6-Cl$_2$ | 2-NHCH$_3$ | CH$_2$OCH$_2$CF$_3$ | C(O)OCH$_3$ |
| G-4 | 2,6-Cl$_2$ | 2-NHEt | C(O)Et | C(O)OCH$_3$ |
| G-4 | 2,6-Br$_2$ | 2-CH$_3$ | H | CH=NOCH$_3$ |
| G-4 | 2,6-Br$_2$ | 2-CH$_3$ | H | CH=NOEt |
| G-4 | 2,6-Br$_2$ | 2-CH$_3$ | CH$_2$OEt | C(O)OCH$_3$ |
| G-4 | 2,6-Br$_2$ | 2-CH$_3$ | CH$_2$OCH$_2$CF$_3$ | C(O)OCH$_3$ |
| G-4 | 2,6-Br$_2$ | 2-CH$_3$ | C(O)Et | C(O)OCH$_3$ |
| G-4 | 2,6-Br$_2$ | 2-CH$_3$ | C(O)CH$_3$ | (D-55c)Cl |
| G-4 | 2,6-Br$_2$ | 2-CH$_3$ | C(O)Pr-i | (D-55c)Cl |

TABLE 3-continued

| | | | | |
|---|---|---|---|---|
| G-4 | 2,6-Br$_2$ | 2-CH$_3$ | C(O)OCH$_3$ | (D-55c)Cl |
| G-4 | 2,6-Br$_2$ | 2-CH$_3$ | C(O)CH$_3$ | (D-55c)Br |
| G-4 | 2-Br-6-CF$_3$ | 2-CH$_3$ | H | CH=NOCH$_3$ |
| G-4 | 2-Br-6-CF$_3$ | 2-CH$_3$ | H | CH=NOEt |
| G-4 | 2-Br-6-CF$_3$ | 2-CH$_3$ | CH$_2$OEt | C(O)OCH$_3$ |
| G-4 | 2-Br-6-CF$_3$ | 2-CH$_3$ | CH$_2$OCH$_2$CF$_3$ | C(O)OCH$_3$ |
| G-4 | 2-Br-6-CF$_3$ | 2-CH$_3$ | C(O)Et | C(O)OCH$_3$ |
| G-4 | 2-Br-6-CF$_3$ | 2-CH$_3$ | C(O)CH$_3$ | (D-55c)Cl |
| G-4 | 2-Br-6-CF$_3$ | 2-CH$_3$ | C(O)Pr-i | (D-55c)Cl |
| G-4 | 2-Br-6-CF$_3$ | 2-CH$_3$ | C(O)OCH$_3$ | (D-55c)Cl |
| G-4 | 2-Br-6-CF$_3$ | 2-CH$_3$ | C(O)CH$_3$ | (D-55c)Br |
| G-4 | 2,6-(CF$_3$)$_2$ | 2-CH$_3$ | H | CH=NOCH$_3$ |
| G-4 | 2,6-(CF$_3$)$_2$ | 2-CH$_3$ | H | CH=NOEt |
| G-4 | 2,6-(CF$_3$)$_2$ | 2-CH$_3$ | CH$_2$OEt | C(O)OCH$_3$ |
| G-4 | 2,6-(CF$_3$)$_2$ | 2-CH$_3$ | CH$_2$OCH$_2$CF$_3$ | C(O)OCH$_3$ |
| G-4 | 2,6-(CF$_3$)$_2$ | 2-CH$_3$ | C(O)Et | C(O)OCH$_3$ |
| G-4 | 2,6-(CF$_3$)$_2$ | 2-CH$_3$ | C(O)CH$_3$ | (D-55c)Cl |
| G-4 | 2,6-(CF$_3$)$_2$ | 2-CH$_3$ | C(O)Pr-i | (D-55c)Cl |
| G-4 | 2,6-(CF$_3$)$_2$ | 2-CH$_3$ | C(O)OCH$_3$ | (D-55c)Cl |
| G-4 | 2,6-(CF$_3$)$_2$ | 2-CH$_3$ | C(O)CH$_3$ | (D-55c)Br |
| G-13 | 4-CF$_3$ | 2-CH$_3$ | H | CH=NOCH$_3$ |
| G-13 | 4-CF$_3$ | 2-CH$_3$ | H | CH=NOEt |
| G-13 | 4-CF$_3$ | 2-CH$_3$ | CH$_2$OEt | C(O)OCH$_3$ |
| G-13 | 4-CF$_3$ | 2-CH$_3$ | CH$_2$OCH$_2$CF$_3$ | C(O)OCH$_3$ |
| G-13 | 4-CF$_3$ | 2-CH$_3$ | C(O)Et | C(O)OCH$_3$ |
| G-13 | 4-CF$_3$ | 2-CH$_3$ | C(O)CH$_3$ | (D-55c)Cl |
| G-13 | 4-CF$_3$ | 2-CH$_3$ | C(O)Pr-i | (D-55c)Cl |
| G-13 | 4-CF$_3$ | 2-CH$_3$ | C(O)OCH$_3$ | (D-55c)Cl |
| G-13 | 4-CF$_3$ | 2-CH$_3$ | C(O)CH$_3$ | (D-55c)Br |
| G-13 | 5-CF$_3$ | 2-CH$_3$ | H | CH=NOCH$_3$ |
| G-13 | 5-CF$_3$ | 2-CH$_3$ | H | CH=NOEt |
| G-13 | 5-CF$_3$ | 2-CH$_3$ | CH$_2$OEt | C(O)OCH$_3$ |
| G-13 | 5-CF$_3$ | 2-CH$_3$ | CH$_2$OCH$_2$CF$_3$ | C(O)OCH$_3$ |
| G-13 | 5-CF$_3$ | 2-CH$_3$ | C(O)Et | C(O)OCH$_3$ |
| G-13 | 5-CF$_3$ | 2-CH$_3$ | C(O)CH$_3$ | (D-55c)Cl |
| G-13 | 5-CF$_3$ | 2-CH$_3$ | C(O)Pr-i | (D-55c)Cl |
| G-13 | 5-CF$_3$ | 2-CH$_3$ | C(O)OCH$_3$ | (D-55c)Cl |
| G-13 | 5-CF$_3$ | 2-CH$_3$ | C(O)CH$_3$ | (D-55c)Br |
| G-13 | 4,5-Cl$_2$ | 2-CH$_3$ | H | CH=NOCH$_3$ |
| G-13 | 4,5-Cl$_2$ | 2-CH$_3$ | H | CH=NOEt |
| G-13 | 4,5-Cl$_2$ | 2-CH$_3$ | CH$_2$OEt | C(O)OCH$_3$ |
| G-13 | 4,5-Cl$_2$ | 2-CH$_3$ | CH$_2$OCH$_2$CF$_3$ | C(O)OCH$_3$ |
| G-13 | 4,5-Cl$_2$ | 2-CH$_3$ | C(O)Et | C(O)OCH$_3$ |
| G-13 | 4,5-Cl$_2$ | 2-CH$_3$ | C(O)CH$_3$ | (D-55c)Cl |
| G-13 | 4,5-Cl$_2$ | 2-CH$_3$ | C(O)Pr-i | (D-55c)Cl |
| G-13 | 4,5-Cl$_2$ | 2-CH$_3$ | C(O)OCH$_3$ | (D-55c)Cl |
| G-13 | 4,5-Cl$_2$ | 2-CH$_3$ | C(O)CH$_3$ | (D-55c)Br |
| G-13 | 4-Cl-5-Br | 2-CH$_3$ | H | CH=NOCH$_3$ |
| G-13 | 4-Cl-5-Br | 2-CH$_3$ | CH$_2$OEt | C(O)OCH$_3$ |
| G-13 | 4-Cl-5-Br | 2-CH$_3$ | C(O)Et | C(O)OCH$_3$ |
| G-13 | 4-Cl-5-Br | 2-CH$_3$ | C(O)CH$_3$ | (D-55c)Cl |
| G-13 | 4-Cl-5-Br | 2-CH$_3$ | C(O)OCH$_3$ | (D-55c)Cl |
| G-13 | 4-Br-5-Cl | 2-CH$_3$ | H | CH=NOCH$_3$ |
| G-13 | 4-Br-5-Cl | 2-CH$_3$ | CH$_2$OEt | C(O)OCH$_3$ |
| G-13 | 4-Br-5-Cl | 2-CH$_3$ | C(O)Et | C(O)OCH$_3$ |
| G-13 | 4-Br-5-Cl | 2-CH$_3$ | C(O)CH$_3$ | (D-55c)Cl |
| G-13 | 4-Br-5-Cl | 2-CH$_3$ | C(O)OCH$_3$ | (D-55c)Cl |
| G-13 | 4,5-Br$_2$ | 2-CH$_3$ | H | CH=NOCH$_3$ |
| G-13 | 4,5-Br$_2$ | 2-CH$_3$ | CH$_2$OEt | C(O)OCH$_3$ |
| G-13 | 4,5-Br$_2$ | 2-CH$_3$ | CH$_2$OEt | C(O)OCH$_3$ |
| G-13 | 4,5-Br$_2$ | 2-CH$_3$ | C(O)CH$_3$ | (D-55c)Cl |
| G-13 | 4,5-Br$_2$ | 2-CH$_3$ | C(O)OCH$_3$ | (D-55c)Cl |
| G-14 | 5-CF$_3$ | 2-CH$_3$ | H | CH=NOCH$_3$ |
| G-14 | 5-CF$_3$ | 2-CH$_3$ | H | CH=NOEt |
| G-14 | 5-CF$_3$ | 2-CH$_3$ | CH$_2$OEt | C(O)OCH$_3$ |
| G-14 | 5-CF$_3$ | 2-CH$_3$ | CH$_2$OCH$_2$CF$_3$ | C(O)OCH$_3$ |
| G-14 | 5-CF$_3$ | 2-CH$_3$ | C(O)Et | C(O)OCH$_3$ |
| G-14 | 5-CF$_3$ | 2-CH$_3$ | C(O)CH$_3$ | (D-55c)Cl |
| G-14 | 5-CF$_3$ | 2-CH$_3$ | C(O)Pr-i | (D-55c)Cl |
| G-14 | 5-CF$_3$ | 2-CH$_3$ | C(O)OCH$_3$ | (D-55c)Cl |
| G-14 | 5-CF$_3$ | 2-CH$_3$ | C(O)CH$_3$ | (D-55c)Br |
| G-17a | 5-CF$_3$ | 2-CH$_3$ | H | CH=NOCH$_3$ |
| G-17a | 5-CF$_3$ | 2-CH$_3$ | H | CH=NOEt |
| G-17a | 5-CF$_3$ | 2-CH$_3$ | CH$_2$OEt | C(O)OCH$_3$ |
| G-17a | 5-CF$_3$ | 2-CH$_3$ | CH$_2$OCH$_2$CF$_3$ | C(O)OCH$_3$ |
| G-17a | 5-CF$_3$ | 2-CH$_3$ | C(O)Et | C(O)OCH$_3$ |
| G-17a | 5-CF$_3$ | 2-CH$_3$ | C(O)CH$_3$ | (D-55c)Cl |
| G-17a | 5-CF$_3$ | 2-CH$_3$ | C(O)Pr-i | (D-55c)Cl |
| G-17a | 5-CF$_3$ | 2-CH$_3$ | C(O)OCH$_3$ | (D-55c)Cl |
| G-17a | 5-CF$_3$ | 2-CH$_3$ | C(O)CH$_3$ | (D-55c)Br |

TABLE 3-continued

| G-20 | 4-CF$_3$ | 2-CH$_3$ | H | CH=NOCH$_3$ |
| G-20 | 4-CF$_3$ | 2-CH$_3$ | H | CH=NOEt |
| G-20 | 4-CF$_3$ | 2-CH$_3$ | CH$_2$OEt | C(O)OCH$_3$ |
| G-20 | 4-CF$_3$ | 2-CH$_3$ | CH$_2$OCH$_2$CF$_3$ | C(O)OCH$_3$ |
| G-20 | 4-CF$_3$ | 2-CH$_3$ | C(O)Et | C(O)OCH$_3$ |
| G-20 | 4-CF$_3$ | 2-CH$_3$ | C(O)CH$_3$ | (D-55c)Cl |
| G-20 | 4-CF$_3$ | 2-CH$_3$ | C(O)Pr-i | (D-55c)Cl |
| G-20 | 4-CF$_3$ | 2-CH$_3$ | C(O)OCH$_3$ | (D-55c)Cl |
| G-20 | 4-CF$_3$ | 2-CH$_3$ | C(O)CH$_3$ | (D-55c)Br |
| G-20 | 5-CF$_3$ | 2-CH$_3$ | H | CH=NOCH$_3$ |
| G-20 | 5-CF$_3$ | 2-CH$_3$ | H | CH=NOEt |
| G-20 | 5-CF$_3$ | 2-CH$_3$ | CH$_2$OEt | C(O)OCH$_3$ |
| G-20 | 5-CF$_3$ | 2-CH$_3$ | CH$_2$OCH$_2$CF$_3$ | C(O)OCH$_3$ |
| G-20 | 5-CF$_3$ | 2-CH$_3$ | C(O)Et | C(O)OCH$_3$ |
| G-20 | 5-CF$_3$ | 2-CH$_3$ | C(O)CH$_3$ | (D-55c)Cl |
| G-20 | 5-CF$_3$ | 2-CH$_3$ | C(O)Pr-i | (D-55c)Cl |
| G-20 | 5-CF$_3$ | 2-CH$_3$ | C(O)OCH$_3$ | (D-55c)Cl |
| G-20 | 5-CF$_3$ | 2-CH$_3$ | C(O)CH$_3$ | (D-55c)Br |
| G-21 | 2-CF$_3$ | 2-CH$_3$ | H | CH=NOCH$_3$ |
| G-21 | 2-CF$_3$ | 2-CH$_3$ | H | CH=NOEt |
| G-21 | 2-CF$_3$ | 2-CH$_3$ | CH$_2$OEt | C(O)OCH$_3$ |
| G-21 | 2-CF$_3$ | 2-CH$_3$ | CH$_2$OCH$_2$CF$_3$ | C(O)OCH$_3$ |
| G-21 | 2-CF$_3$ | 2-CH$_3$ | C(O)Et | C(O)OCH$_3$ |
| G-21 | 2-CF$_3$ | 2-CH$_3$ | C(O)CH$_3$ | (D-55c)Cl |
| G-21 | 2-CF$_3$ | 2-CH$_3$ | C(O)Pr-i | (D-55c)Cl |
| G-21 | 2-CF$_3$ | 2-CH$_3$ | C(O)OCH$_3$ | (D-55c)Cl |
| G-21 | 2-CF$_3$ | 2-CH$_3$ | C(O)CH$_3$ | (D-55c)Br |
| G-22 | 2-Cl | 2-CH$_3$ | H | CH=NOCH$_3$ |
| G-22 | 2-Cl | 2-CH$_3$ | CH$_2$OEt | C(O)OCH$_3$ |
| G-22 | 2-Cl | 2-CH$_3$ | C(O)Et | C(O)OCH$_3$ |
| G-22 | 2-Cl | 2-CH$_3$ | C(O)CH$_3$ | (D-55c)Cl |
| G-22 | 2-Cl | 2-CH$_3$ | C(O)OCH$_3$ | (D-55c)Cl |

TABLE 4

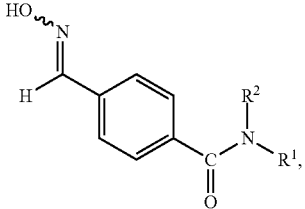

[4]-1

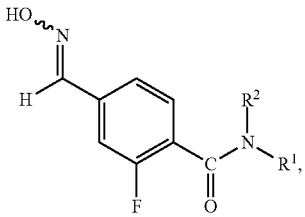

[4]-2

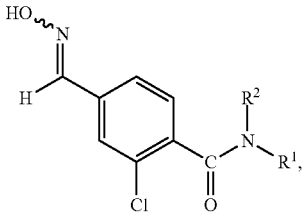

[4]-3

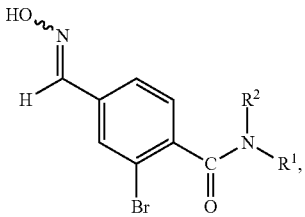

[4]-4

TABLE 4-continued
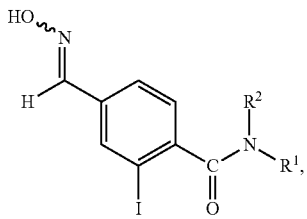  [4]-5
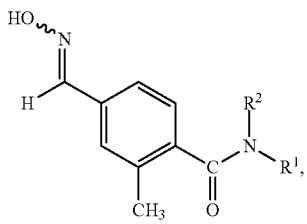  [4]-6
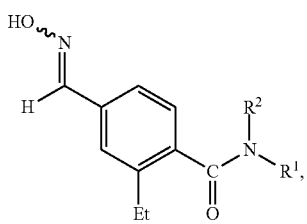  [4]-7
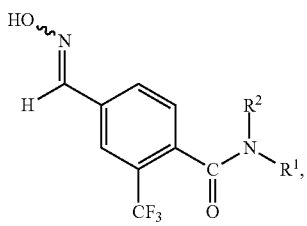  [4]-8
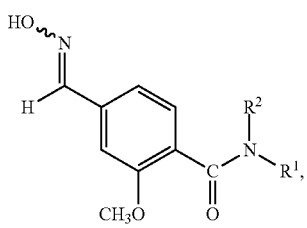  [4]-9
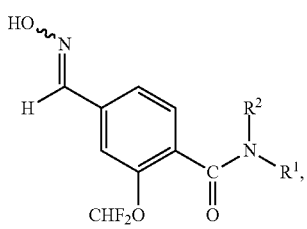  [4]-10
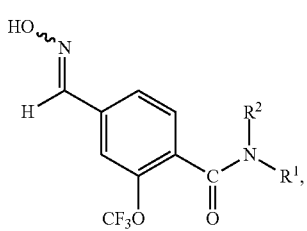  [4]-11

TABLE 4-continued
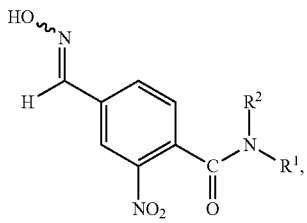 [4]-12
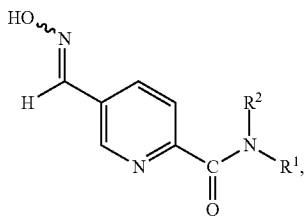 [4]-13
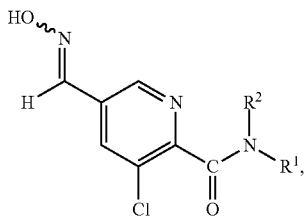 [4]-14
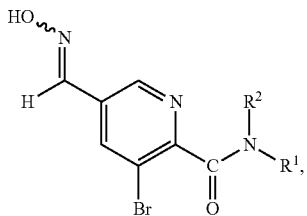 [4]-15
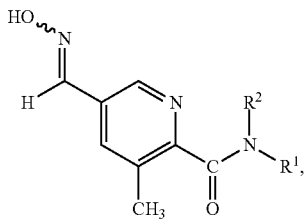 [4]-16
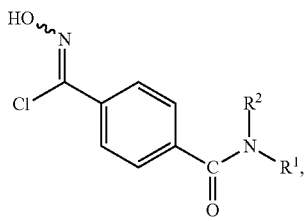 [4]-17
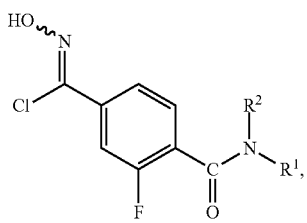 [4]-18

TABLE 4-continued
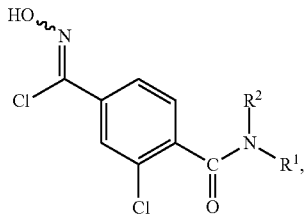  [4]-19
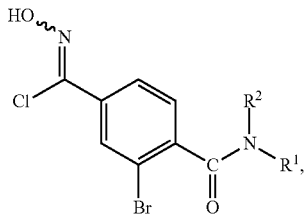  [4]-20
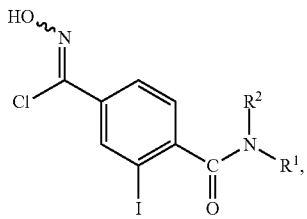  [4]-21
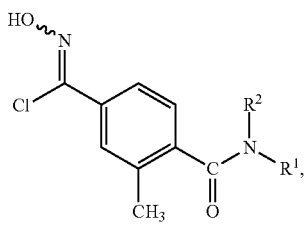  [4]-22
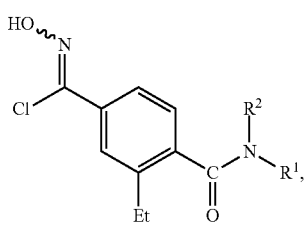  [4]-23
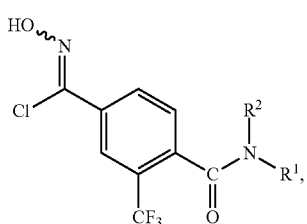  [4]-24
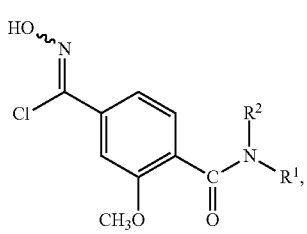  [4]-25

TABLE 4-continued
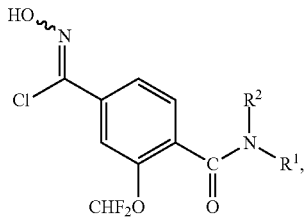   [4]-26
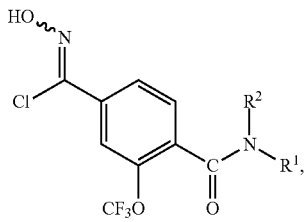   [4]-27
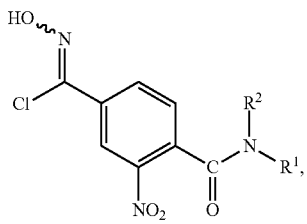   [4]-28
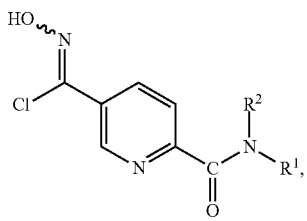   [4]-29
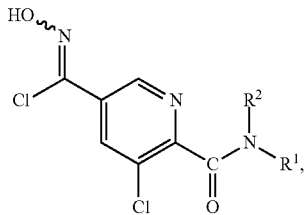   [4]-30
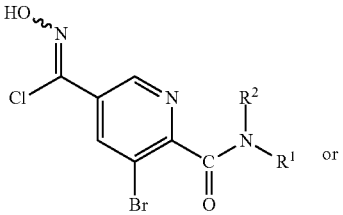   [4]-31
or
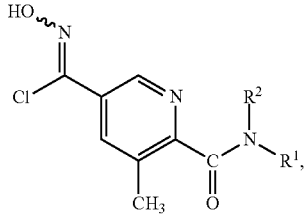   [4]-32

TABLE 4-continued

| R² | R¹ | R² | R¹ |
|---|---|---|---|
| H | CH=NOCH₃ | CH₂OC(O)CH₃ | (D-52d)Br |
| CH₂OCH₃ | CH=NOCH₃ | C(O)CH₃ | (D-52d)Br |
| CH₂OEt | CH=NOCH₃ | C(O)Et | (D-52d)Br |
| CH₂CN | CH=NOCH₃ | C(O)Pr-i | (D-52d)Br |
| CH₂C≡CH | CH=NOCH₃ | C(O)OCH₃ | (D-52d)Br |
| H | CH=NOEt | CH₃ | (D-52d)CN |
| H | C(O)OCH₃ | C(O)OCH₃ | (D-52d)CN |
| CH₃ | C(O)OCH₃ | CH₃ | (D-53e)Cl |
| Et | C(O)OCH₃ | CH₂OCH₃ | (D-53e)Cl |
| n-Pr | C(O)OCH₃ | C(O)CH₃ | (D-53e)Cl |
| i-Pr | C(O)OCH₃ | C(O)OCH₃ | (D-53e)Cl |
| CH₂OCH₃ | C(O)OCH₃ | CH₃ | D-55a |
| CH₂OEt | C(O)OCH₃ | CH₂OCH₃ | D-55a |
| CH₂OCH₂CH₂Cl | C(O)OCH₃ | CH₂OC(O)CH₃ | D-55a |
| CH₂OCH₂CF₃ | C(O)OCH₃ | CH₂CC(O)OCH₃ | D-55a |
| CH₂OCH₂CH₂OCH₃ | C(O)OCH₃ | C(O)CH₃ | D-55a |
| CH₂OCH₂Ph | C(O)OCH₃ | C(O)Et | D-55a |
| CH₂OC(O)CH₃ | C(O)OCH₃ | C(O)Pr-i | D-55a |
| CH₂OC(O)Et | C(O)OCH₃ | C(O)Pr-c | D-55a |
| CH₂OC(O)Pr-n | C(O)OCH₃ | C(O)Bu-t | D-55a |
| CH₂OC(O)Pr-i | C(O)OCH₃ | C(O)OCH₃ | D-55a |
| CH₂OC(O)Pr-c | C(O)OCH₃ | CH₃ | (D-55c)F |
| CH₂OC(O)Bu-t | C(O)OCH₃ | CH₂OCH₃ | (O-55c)F |
| CH₂OC(O)Ph | C(O)OCH₃ | CH₂OC(O)CH₃ | (D-55c)F |
| CH₂OC(O)OCH₃ | C(O)OCH₃ | C(O)CH₃ | (D-55c)F |
| CH₂OC(O)OEt | C(O)OCH₃ | C(O)Et | (D-55c)F |
| CH₂OC(O)OBu-i | C(O)OCH₃ | C(O)Pr-i | (D-55c)F |
| CH₂OC(O)OPh | C(O)OCH₃ | C(O)OCH₃ | (D-55c)F |
| CH₂OPh | C(O)OCH₃ | CH₃ | (D-55c)Cl |
| E-5a | C(O)OCH₃ | Et | (D-55c)Cl |
| CH₂NHC(O)OCH₃ | C(O)OCH₃ | CH₂OCH₃ | (O-55C)Cl |
| CH₂SO₂CH₃ | C(O)OCH₃ | CH₂OEt | (O-55c)Cl |
| CH₂SC(O)CH₃ | C(O)OCH₃ | CH₂OC(O)CH₃ | (O-55c) Cl |
| CH₂CN | C(O)OCH₃ | CH₂OC(O)Et | (D-55c)Cl |
| CH₂C≡CH | C(O)OCH₃ | CH₂OC(O)Pr-n | (D-55c)Cl |
| CH₂Ph | C(O)OCH₃ | CH₂OC(O)Pr-i | (D-55c)Cl |
| C(O)CH₃ | C(O)OCH₃ | CH₂OC(O)Pr-c | (D-55c)Cl |
| C(O)Et | C(O)OCH₃ | CH₂OC(O)Bu-t | (D-55c)Cl |
| C(O)Pr-n | C(O)OCH₃ | CH₂OC(O)OCH₃ | (D-55c)Cl |
| C(O) Pr-i | C(O)OCH₃ | CH₂OC(O)OEt | (D-55c)Cl |
| C(O)Pr-c | C(O)OCH₃ | CH₂OC(O)OBu-i | (D-55c)Cl |
| C(O)Bu-t | C(O)OCH₃ | CH₂OC(O)OPh | (D-55c )Cl |
| C(O)CH₂Cl | C(O)OCH₃ | CH₁OC(O)Ph | (D-55c)Cl |
| C(O)CH₂OCH₃ | C(O)OCH₃ | CH₂CN | (D-55c)Cl |
| C(O)CH₂OEt | C(O)OCH₃ | CH₂C≡CH | (D-55c)Cl |
| C(O)Ph | C(O)OCH₃ | C(O)CH₃ | (D-55c)Cl |
| C(O)OCH₃ | C(O)OCH₃ | C(O)Et | (D-55c)Cl |
| C(O)OCH₂Cl | C(O)OCH₃ | C(O)Pr-n | (D-55c)Cl |
| C(O)OCH₂CH₂Cl | C(O)OCH₃ | C(O)Pr-i | (D-55c)Cl |
| H | C(O)OEt | C(O)Pr-c | (D-55c)Cl |
| CH₃ | C(O)OEt | C(O)Bu-t | (D-55c)Cl |
| Et | C(O)OEt | C(O)CH₂Cl | (D-55c)Cl |
| CH₂OCH₃ | C(O)OEt | C(O)CH₂OCH₃ | (D-55c)Cl |
| CH₂OEt | C(O)OEt | C(O)CH₂OEt | (D-55c)Cl |
| CH₂OCH₂CF₃ | C(O)OEt | C(O)CH₂SO₂CH₃ | (D-55c)Cl |
| CH₂OC(O)CH₃ | C(O)OEt | C(O)C(O)OEt | (D-55c)Cl |
| CH₂OC(O)OCH₃ | C(O)OEt | C(O)Ph | (D-55c) Cl |
| CH₂NHC(O)OEt | C(O)OEt | C(O)(D-52a) | (D-55c)Cl |
| CH₂CN | C(O)OEt | C(O)OCH₃ | (D-55c)Cl |
| CH₂C≡CH | C(O)OEt | C(O)OEt | (D-55c)Cl |
| C(O)CH₃ | C(O)OEt | C(O)OPr-n | (D-55c)Cl |
| C(O)Et | C(O)OEt | C(O)OPr-i | (D-55c)Cl |
| C(O)Pr-n | C(O)OEt | C(O)OPr-c | (D-55c)Cl |
| C(O)Pr-i | C(O)OEt | C(O)OBu-n | (D-55c)Cl |
| C(O)Pr-c | C(O)OEt | C(O)OBu-i | (D-55c)Cl |
| C(O)Bu-t | C(O)OEt | C(O)OBu-t | (D-55c)Cl |
| C(O)CH₂OCH₃ | C(O)OEt | C(O)OCH₂Cl | (D-55c)Cl |
| C(O)OCH₃ | C(O)OEt | C(O)OCH₂CH₂Cl | (D-55c)Cl |
| C(O)OEt | C(O)OEt | C(O)OCH₂CH₂OCH₃ | (D-55c)Cl |
| H | C(O)OPr-n | C(O)OCH₂CH=CH₂ | (D-55c)Cl |
| H | C(O)OPr-i | C(O)OCH₂C≡CH | (D-55c)Cl |
| CH₃ | C(O)OPr-i | C(O)OPh | (D-55c)Cl |
| Et | C(O)OPr-i | CH₃ | (D-55c)Br |
| CH₂OCH₃ | C(O)OPr-i | Et | (D-55c)Br |
| CH₂OEt | C(O)OPr-i | CH₂OCH₃ | (D-55c)Br |
| CH₂OCH₂CF₃ | C(O)OPr-i | CH₂OEt | (D-55c)Br |
| CH₂OC(O)CH₃ | C(O)OPr-i | CH₂OC(O)CH₃ | (D-55c)Br |
| CH₂OC(O)OCH₃ | C(O)OPr-i | CH₃OC(O)OCH₃ | (D-55c)Br |

TABLE 4-continued

| | | | |
|---|---|---|---|
| CH₂NHC(O)OPr-i | C(O)OPr-i | C(O)CH₃ | (D-55c)Br |
| CH₂CN | C(O)OPr-i | C(O)Et | (D-55c)Br |
| CH₂C≡CH | C(O)OPr-i | C(O)Pr-n | (D-55c)Br |
| C(O)CH₃ | C(O)OPr-i | C(O)Pr-i | (D-55c)Br |
| C(O)Et | C(O)OPr-i | C(O)Pr-c | (D-55c)Br |
| C(O)Pr-n | C(O)OPr-i | C(O)Bu-t | (D-55c)Br |
| C(O)Pr-i | C(O)OPr-i | C(O)CH₂OCH₃ | (D-55c)Br |
| C(O)Pr-c | C(O)OPr-i | C(O)Ph | (D-55c)Br |
| C(O)Bu-t | C(O)OPr-i | C(O)OCH₃ | (D-55c)Br |
| C(O)CH₂OCH₃ | C(O)OPr-i | C(O)OEt | (D-55c)Br |
| C(O)OCH₃ | C(O)OPr-i | C(O)OPr-n | (D-55c)Br |
| C(O)OEt | C(O)OPr-i | C(O)OBu-i | (D-55c)Br |
| H | C(O)OPr-c | C(O)OCH₃Cl | (D-55c)Br |
| CH₃ | C(O)OPr-c | C(O)OCH₂CH₂OCH₃ | (D-55c)Br |
| CH₂OCH₃ | C(O)OPr-c | CH₃ | (D-55c)CN |
| CH₂OEt | C(O)OPr-c | C(O)OCH₃ | (D-55c)CN |
| CH₂OCH₂CF₃ | C(O)OPr-c | CH₃ | (D-55c)NO₂ |
| CH₂OC(O)CH₃ | C(O)OPr-c | C(O)OCH₃ | (D-55c)NO₂ |
| CH₂CN | C(O)OPr-c | CH₃ | D-56a |
| CH₂C≡CH | C(O)OPr-c | CH₃OCH₃ | D-56a |
| C(O)CH₃ | C(O)OPr-c | CH₂OC(O)CH₃ | D-56a |
| C(O)Et | C(O)OPr-c | C(O)CH₃ | D-56a |
| C(O)OCH₃ | C(O)OPr-c | C(O)Et | D-56a |
| H | C(O)OBu-t | C(O)Pr-i | D-56a |
| CH₂OCH₃ | C(O)OBu-t | C(O)OCH₃ | D-56a |
| C(O)CH₃ | C(O)OBu-t | CH₃ | D-57a |
| C(O)Et | C(O)OBu-t | CH₂OCH₃ | D-57a |
| C(O)CH₂CF₃ | C(O)OBu-t | CH₂OC(O)CH₃ | D-57a |
| C(O)OCH₃ | C(O)OBu-t | CH₂OC(O)OCH₃ | D-57a |
| H | C(O)OCH₂CH₂OCH₃ | C(O)CH₃ | D-57a |
| CH₂OCH₃ | C(O)OCH₂CH₂OCH₃ | C(O)Et | D-57a |
| C(O)CH₃ | C(O)OCH₂CH₂OCH₃ | C(O)Pr-n | D-57a |
| C(O)OCH₃ | C(O)OCH₂CH₂OCH₃ | C(O)Pr-i | D-57a |
| H | C(O)OCH₂CH=CH₂ | C(O)Pr-c | D-57a |
| CH₂OCH₃ | C(O)OCH₂CH=CH₂ | C(O)Bu-t | D-57a |
| C(O)CH₃ | C(O)OCH₂CH=CH₂ | C(O)OCH₃ | D-57a |
| C(O)OCH₃ | C(O)OCH₂CH=CH₂ | CH₃ | (D-57b)F |
| H | C(O)SCH₃ | CH₂OCH₃ | (D-57b)F |
| CH₂OCH₃ | C(O)SCH₃ | C(O)CH₃ | (D-57b)F |
| CH₂OCH₃CF₃ | C(O)SCH₃ | C(O)OCH₃ | (D-57b) F |
| C(O)Et | C(O)SCH3 | CH₃ | (D-57b)Cl |
| H | C(O)NH₂ | CH₂OCH₃ | (D-57b)Cl |
| CH₃ | C(O)NH₂ | CH₂OC(O)CH₃ | (D-57b)Cl |
| CH₃ | C(O)NHC(O)CH₃ | CH₂OC(O)OCH₃ | (D-57b)Cl |
| CH₃ | C(O)NHC(O)OCH₃ | C(O)CH₃ | (D-57b)Cl |
| H | C(S)NH₂ | C(O)Et | (D-57b)Cl |
| CH₃ | Ph-4-F | C(O)Pr-i | (D-57b)Cl |
| CH₂OCH₃ | Ph-4-F | C(O)Pr-c | (D-57b)Cl |
| C(O)CH₃ | Ph-4-F | C(O)Bu-t | (D-57b)Cl |
| C(O)OCH₃ | Ph-4-F | C(O)OCH₃ | (D-57b)Cl |
| CH₃ | Ph-4-CN | CH₃ | (D-57b)Br |
| CH₂OCH₃ | Ph-4-CN | CH₂OCH₃ | (D-57b)Br |
| C(O)CH₃ | Ph-4-CN | CH₂OC(O)CH₃ | (D-57b)Br |
| C(O)OCH₃ | Ph-4-CN | C(O)CH₃ | (D-57b)Br |
| CH₃ | Ph-2, 4-F₂ | C(O)Et | (D-57b)Br |
| CH₂OCH₃ | Ph-2, 4-F₂ | C(O)Pr-i | (D-57b)Br |
| C(O)CH₃ | Ph-2, 4-F₂ | C(O)OCH₃ | (D-57b)Br |
| C(O)OCH₃ | Ph-2, 4-F₂ | CH₃ | (D-57b)CN |
| CH₃ | D-14a | C(O)OCH₃ | (D-57b)CN |
| CH₂OCH₃ | D-14a | CH₃ | D-58a |
| CH₂OC(O)CH₃ | D-14a | CH₂OCH₃ | D-58a |
| C(O)CH₃ | D-14a | CH₂OC(O)CH₃ | D-58a |
| C(O)Et | D-14a | C(O)CH₃ | D-58a |
| C(O)Pr-i | D-14a | C(O)Et | D-58a |
| C(O)OCH₃ | D-14a | C(O)Pr-i | D-58a |
| CH₃ | (D-52d)F | C(O)OCH₃ | D-58a |
| CH₂OCH₃ | (D-52d)F | CH₃ | (D-58b)Cl |
| CH₂OC(O)CH₃ | (D-52d)F | CH₂OCH₃ | (D-58b)Cl |
| C(O)CH₃ | (D-52d)F | CH₂OC(O)CH₃ | (D-58b)Cl |
| C(O)Et | (D-52d)F | CH₂OC(O)OCH₃ | (D-58b)Cl |
| C(O)Pr-i | (D-52d)F | C(O)CH₃ | (D-58b)Cl |
| C(O)OCH₃ | (D-52d)F | C(O)Et | (D-58b)Cl |
| CH₃ | (D-52d)Cl | C(O)Pr-i | (D-58b)Cl |
| CH₂OCH₃ | (D-52d)Cl | C(O)Pr-c | (D-58b)Cl |
| CH₂OC(O)CH₃ | (D-52d)Cl | C(O)Bu-t | (D-58b)Cl |
| CH₂OC(O)OCH₃ | (D-52d)Cl | C(O)OCH₃ | (D-58b)Cl |
| C(O)CH₃ | (D-52d)Cl | CH₃ | (D-58b)Br |
| C(O)Et | (D-52d)Cl | CH₂OCH₃ | (D-58b)Br |
| C(O)Pr-i | (D-52d)Cl | C(O)CH₃ | (D-58b)Br |
| C(O)Pr-c | (D-52d)Cl | C(O)OCH₃ | (D-58b)Br |

TABLE 4-continued

| | | | |
|---|---|---|---|
| C(O)Bu-t | (D-52d)Cl | CH$_3$ | (D-58b)CN |
| C(O)OCH$_3$ | (D-52d)Cl | C(O)OCH$_3$ | (D-58b)CN |
| CH$_3$ | (D-52d)Br | CH$_3$ | (D-59b)Cl |
| CH$_2$OCH$_3$ | (D-52d)Br | CH$_2$OCH$_3$ | (D-59)Cl |
| CH$_2$OCH$_3$ | (D-55c)CN | C(O)CH$_3$ | (D-55c)CN |
| CH$_2$Oet | (D-55c)CN | C(O)Et | (D-55c)CN |
| CH$_2$OC(O)CH$_3$ | (D-55c)CN | C(O)Pr-n | (D-55c)CN |
| CH$_2$OC(O)OCH$_3$ | (D-55c)CN | C(O)Pr-i | (D-55c)CN |
| CH$_2$CN | (D-55c)CN | C(O)Pr-c | (D-55c)CN |

The compounds of the present invention can effectively control in a low concentration so-called agricultural insects injuring agricultural and horticultural crops and trees, so-called domestic animal pests parasitizing domestic animals and domestic fowls, so-called hygienic pests having an adverse affect on human being's environment such as houses, insects as so-called stored grain insects injuring grains and the like stored in storehouses, and any pests of acarids, crustaceans, mollusks and nematodes generating in the similar scenes.

The insects, acarids, crustaceans, mollusks and nematodos that the compounds of the present invention can control concretely include for example the followings:

Lepidoptera insects, such as *Adoxophyes honmai, Adoxophyes orana faciata, Archips breviplicanus, Archips fuscocupreanus, Grapholita molesta, Homona magnanima, Leguminivora glycinivorella, Matsumuraeses phaseoli, Pandemis heparana, Bucculatrix pyrivorella, Lyonetia clerkella, Lyonetia prunifoliella malinella, Caloptilia theivora, Phyllonorycter ringoniella, Phyllocnistis citrella, Acrolepiopsis sapporensis, Acrolepiopsis suzukiella, Plutella xylostella, Stathmopoda masinissa, Helcystogramma triannulella, Pectinophora gossypiella, Carposina sasakii, Cydla pomonella, Chilo suppressalis, Cnaphalocrocis medinalis, Conogethes punctiferalis, Diaphania indica, Etiella zinckenella, Glyphodes pyloalis, Hellula undalis, Ostrinia furnacalis, Ostrinia scapulalis, Ostrinia nubilalis, Parapediasia teterrella, Parnara guttata, Pieris brassicae, Pieris rapae crucivora, Ascotis selenaria, Pseudoplusia includens, Euproctis pseudoconspersa, Lymantria dispar, Orgyia thyellina, Hyphantria cunea, Lemyra imparilis, Adris tyrannus, Aedia leucomelas, Agrotis ipsilon, Agrotis segetum, Autographa nigrisigna, Ctenoplusia agnata, Helicoverpa armigera, Helicoverpa assulta, Helicoverpa zea, Heliothis virescens, Mamestra brassicae, Mythimna separata, Naranga aenescens, Spodoptera eridania, Spodoptera exigua, Spodoptera frugiperda, Spodoptera littoralis, Spodoptera litura, Spodoptera depravata, Trichoplusia ni, Endopiza viteana, Manduca quinquemaculata, Manduca sexta*, or the like;

Thysanoptera insects, such as *Frankliniella intonsa, Frankliniella occidentalis, Heliothrips haemorrhoidalis, Scirtothrips dorsalis, Thrips palmi, Thrips tabaci, Ponticulothrips diospyrosi*, or the like;

Hemiptera insects, such as *Dolycoris baccarum, Eurydema rugosum, Eysarcoris aeneus, Eysarcoris lewisi, Eysarcoris ventralis, Glaucias subpunctatus, Halyomorpha halys, Nezara antennata, Nezara viridula, Piezodorus hybneri, Plautia crossota, Scotinophora lurida, Cletus punctiger, Leptocorisa chinensis, Riptortus clavatus, Rhopalus msculatus, Cavelerius saccharivorus, Togo hemipteruus, Dysdercus cingulatus, Stephanitis pyrioides, Halticus insularis, Lygus lineolaris, Stenodema sibiricum, Stenotus rubrovittatus, Trigonotylus caelestialium, Arboridia apicalis, Balclutha saltuella, Epiacanthus stramineus, Empoasca fabae, Empoasca nipponica, Empoasca onukii, Empoasca sakaii, Macrosteles striifrons, Nephotettix cinctinceps, Psuedatomoscelis seriatus, Laodelphax striatella, Nilaparvata lugens, Sogatella furcifera, Diaphorina citri, Psylla pyrisuga, Aleurocanthus spiniferus, Bemisia argentifolii, Bemisia tabaci, Dialeurodes citri, Trialeurodes vaporariorum, Viteus vitifolii, Aphis gossypii, Aphis spiraecola, Myzus persicae, Toxoptera aurantii, Drosicha corpulenta, Icerya purchasi, Phenacoccus solani, Planococcus citri, Planococcus kuraunhiae, Pseudococcus comstocki, Ceroplastes ceriferus, Ceroplastes rubens, Aonidiella aurantii, Comstockaspis perniciosa, Fiorinia theae, Pseudaonidia paeoniae, Pseudaulacaspis pentagona, Pseudaulacaspis prunicola, Unaspis euonymi, Unaspis yanonensis, Cimex lectularius*, or the like;

Coleoptera insects, such as *Anomala cuprea, Anomala rufocuprea, Gametis jucunda, Heptophylla picea, Popillia japonica, Lepinotarsa decemlineata, Melanotus fortnumi, Melanotus tamsuyensis, Lasioderma serricorne, Epuraea domina, Epilachna varivestis, Epilachna vigintioctopunctata, Tenebrio molitor, Tribolium castaneum, Anoplophora malasiaca, Monochamus alternatus, Psacothea hilaris, Xylotrechus pyrrhoderus, Callosobruchus chinensis, Aulacophora femoralis, Chaetocnema concinna, Diabrotica undecimpunctata, Diabrotica virgifera, Diabrotica barberi, Oulema oryzae, Phyllotreta striolata, Psylliodes angusticollis, Rhynchites heros, Cylas formicarius, Anthonomus grandis, Echinocnemus squameus, Euscepes postfasciatus, Hypera postica, Lissohoptrus oryzophilus, Otiorhynchus sulcatus, Sitophilus granarius, Sitophilus zeamais, Sphenophorus venatus vestitus, Paederus fuscipes*, or the like;

Diptera insects, such as *Asphondylia yushimai, Sitodiplosis mosellana, Bactrocera cucurbitae, Bactrocera dorsalis, Ceratitis capitata, Hydrellia griseola, Drosophila suzukii, Agromyza oryzae, Chromatomyia horticola, Liriomyza bryoniae, Liriomyza chinensis, Liriomyza sativae, Liriomyza trifolii, Delia platura, Pegomya cunicularia, Rhagoletis pomonella, Mayetiola destructor, Musca domestica, Stomoxys calcitrans, Melophagus ovinus, Hypoderma bovis, Hypoderma lineatum, Oestrus ovis, Glossina palpalis, Glossina morsitans, Prosimulium yezoensis, Tabanus trigonus, Telmatoscopus albipunctatus, Leptoconops nipponensis, Culex pipiens pallens, Aedes aegypti, Aedes albopicutus, Anopheles hyracanus sinesis*, or the like;

Hymenoptera insects, such as *Apethymus kuri, Athalia rosae, Arge pagana, Neodiprion sertifer, Dryocosmus kuriphilus, Eciton burchelli, Eciton schmitti, Camponotus japonicus, Vespa mandarina, Myrmecia* spp., *Solenopsis* spp., *Monomorium pharaonis*, or the like;

Orthoptera insects, such as *Teleogryllus emma, Gryllotalpa orientalis, Locusta migratoria, Oxya yezoensis, Schistocerca gregaria*, or the like;

Collembola insects, such as *Onychiurus folsomi, Onychiurus sibiricus, Bourletiella hortensis*, or the like;

Dictyoptera insect, such as *Periplaneta fuliginosa, Periplaneta japonica, Blattella germanica*, or the like;

Isoptera insects, such as *Coptotermes formosanus, Reticulitermes speratus, Odontotermes formosanus*, or the like;

Siphonaptera insects, such as *Ctenocephalidae felis, Ctenocephalides canis, Echidnophaga gallinacea, Pulex irritans, Xenopsylla cheopis*, or the like;

Mallophaga insects, such as *Menacanthus stramineus, Bovicola bovis*, or the like;

Anoplura insects, such as *Haematopinus eurysternus, Haematopinus suis, Linognathus vituli, Solenopotes capillatus*, or the like;

Tarsonemid mites, such as *Phytonemus pallidus, Polyphagotarsonemus latus, Tarsonemus bilobatus*, or the like;

Eupodid mites, such as *Penthaleus erythrocephalus, Penthaleus major*, or the like;

Spider mites, such as *Oligonychus shinkajii, Panonychus citri, Panonychus mori, Panonychus ulmi, Tetranychus kanzawai, Tetranychus urticae*, or the like;

Eriophyid mites, such as *Acaphylla theavagrans, Aceria tulipae, Aculops lycopersici, Aculops pelekassi, Aculus schlechtendali, Eriophyes chibaensis, Phyllocoptruta oleivora*, or the like;

Acarid mites, such as *Rhizoglyphus robini, Tyrophagus putrescentiae, Tyrophagus similis*, or the like;

Bee brood mites, such as *Varroa jacobsoni*, or the like;

Ixodides, such as *Boophilus microplus, Rhipicephalus sanguineus, Haemaphysalis longicornis, Haemophysalis flava, Haemophysalis campanulata, Ixodes ovatus, Ixodes persulcatus, Amblyomma* spp., *Dermacentor* spp., or the like;

Cheyletidae, such as *Cheyletiella yasguri, Cheyletiella blakei*, or the like;

Demodicidae, such as *Demodex canis, Demodex cati*, or the like;

Psoroptidae, such as *Psoroptes ovis*, or the like;

Scarcoptidae, such as *Sarcoptes scabiei, Notoedres cati, Knemidocoptes* spp., or the like;

Crustacea, such as *Armadillidium vulgare*, or the like;

Gastropoda, such as *Pomacea canaliculata, Achatina fulica, Meghimatium bilineatum, Limax Valentiana, Acusta despecta sieboldiana, Euhadra peliomphala*, or the like;

Nematodes, such as *Prathylenchus coffeae, Prathylenchus penetrans, Prathylenchus vulnus, Globodera rostochiensis, Heterodera glycines, Meloidogyne hapla, Meloidogyne incognita, Aphelenchoides besseyi, Bursaphelenchus xylophilus*, or the like. But the present invention is not limited thereto.

The endo-parasites of domestic animals, domestic fowls, pets and the like that the compounds of the present invention can control concretely include for example the followings:

Nematodes, such as *Haemonchus, Trichostrongylus, Ostertagia, Nematodirus, Cooperia, Ascaris, Bunostomum, Oesophagostomum, Chabertia, Trichuris, Storongylus, Trichonema, Dictyocaulus, Capillaria, Heterakis, Toxocara, Ascaridia, Oxyuris, Ancylostoma, Uncinaria, Toxascaris, Parascaris*, or the like; Filariidae in nematodes, such as *Wuchereria, Brugia, Onchoceca, Dirofilaria, Loa*, or the like;

Dracunculidae in nematodes, such as *Deacunculus*, or the like;

Cestoda, such as *Dipylidium caninum, Taenia taeniaeformis, Taenia solium, Taenia saginata, Hymenolepis diminuta, Moniezia benedeni, Diphyllobothrium latum, Diphyllobothrium erinacei, Echinococcus granulosus, Echinococcus multilocularis*, or the like;

Trematoda, such as *Fasciola hepatica, F. gigantica, Paragonimus westermanii, Fasciolopsic bruski, Eurytrema pancreaticum, E. coelomaticum, Clonorchis sinensis, Schistosoma japonicum, Schistosoma haematobium, Schistosoma mansoni*, or the like;

*Eimeria* spp., such as *Eimeria tenella, Eimeria acervulina, Eimeria brunetti, Eimeria maxima, Eimeria necatrix, Eimeria bovis, Eimeria ovinoidalis*, or the like;

*Trypanosomsa cruzi, Leishmania* spp., *Plasmodium* spp., *Babesis* spp., *Trichomonadidae* spp., *Histomanas* spp., *Giardia* spp., *Toxoplasma* spp., *Entamoeba histolytica, Theileria* spp., or the like. But the present invention is not limited thereto.

Further, the compounds of the present invention are effective for pests acquiring high resistance against existing insecticides such as organic phosphorus compounds, carbamate compounds or pyrethroid compounds, etc.

That is, the compounds of the present invention can effectively control pests that belong to insects such as Collembola, Dictyoptera, Orthoptera, Isoptera, Thysanoptera, Hemiptera, Lepidoptera, Coleoptera, Hymenoptera, Diptera, Isoptera and Anoplura, Acarina, Gastropoda and Nematoda, in a low concentration. On the other hand, the compounds of the present invention have an extremely useful charactristic that they have little adverse affect on mammals, fishes, crustaceans and useful insects (beneficial insect such as honeybee, bumblebee or the like, or, natural enemies such as *Aphytis lingnanensis, Aphidius colemani, Orius strigicollis, Amblyseius californicus*, or the like).

When the compounds of the present invention are used, they can be generally mixed with a suitable solid carrier or liquid carrier, optionally along with surfactant, penetrating agent, spreading agent, thickener, anti-freezing agent, binder, anti-caking agent, disintegrating agent, anti-foaming agent, preservative, stabilizer, and the like, and can be formulated into any desired forms for practical use, such as soluble concentrates, emulsifiable concentrates, wettable powders, water soluble powders, water dispersible granules, water soluble granules, suspension concentrates, concentrated emulsions, suspoemulsions, microemulsions, dustable powders, granules, tablets and emulsifiable gels. From the viewpoint of an elimination or reduction of labor and an improvement of safety, the formulations in any desired forms described above may be included into a water-soluble bag made of water-soluble capsule or water-soluble film.

The solid carrier includes, for example, natural minerals such as quartz, calcite, sepiolite, dolomaite, chalk, kaolinite, pyrofilite, celicite, halocite, methahalocite, kibushi clay, gairome clay, pottery stone, zeaklite, allophane, white sand, mica, talc, bentonite, activeted earth, acid china clay, pumice, attapulgite, zeolite and diatomaceous earth, etc., calcined products of natural minerals such as calcined clay, perlite, white sand balloon (loam balloon), vermiculite, attapulgus clay and calcined diatomaceous earth, etc., inorganic salts such as magnesium carbonate, calcium carbonate, sodium carbonate, sodium hydrogen carbonate, ammonium sulfate, sodium sulfate, magnesium sulfate, diammonium hydrogen phosphate, ammonium dihydrogen phosphate and potassium chloride, etc., saccharides such as glucose, fructose, sucrose and lactose, etc., polysaccharides such as starch, powder cellulose and dextrin, etc., organic materials such as urea, urea derivatives, benzoic acid and a salt of benzoic acid, etc., plants such as wood powder, cork powder, corn head stem, walnut shell and tobacco stem, etc., fly ash, white carbon (e.g., hydrated synthetic silica, anhydrous synthetic silica and hydrated synthetic silicate, etc.) and feritilizers, etc.

As the liquid carrier, there may be mentioned, for example, aromatic hydrocarbons such as xylene, alkyl($C_9$ or $C_{10}$, etc.) benzene, phenylxylylethane and alkyl($C_1$ or $C_3$, etc.)naphthalene, etc., aliphatic hydrocarbons such as machine oil, normal paraffin, isoparaffin and naphthene, etc., a mixture of aromatic hydrocarbons and aliphatic hydrocarbons such as kerosene, etc., alcohols such as ethanol, isopropanol, cyclohexanol, phenoxyethanol and benzylalcohol, etc., polyvalent alcohols such as ethylene glycol, propyleneglycol, diethylene glycol, hexylene glycol, polyethylene glycol and polypropyleneglycol, etc., ethers such as propyl cellosolve, butyl cellosolve, phenyl cellosolve, propyleneglycol monomethyl ether, propyleneglycol monoethyl ether, propyleneglycol monopropyl ether, propyleneglycol monobutyl ether and propyleneglycol monophenyl ether, etc., ketones such as acetophenone, cyclohexanone and γ-butyrolactone, etc., esters such as aliphatic acid methyl ester, dialkyl succinate, dialkyl glutamate, dialkyl adipate and dialkyl phthalate, etc., acid amides such as N-alkyl($C_1$, $C_8$ or $C_{12}$, etc.)pyrrolidone, etc., oil and fats such as soybean oil, linseed oil, rapeseed oil, coconut oil, cottonseed oil and caster oil, etc., dimethylsulfoxide and water.

These solid and liquid carriers may be used alone or in combination of two or more kinds in combination.

As the surfactant, there may be mentioned, for example, nonionic surfactants such as polyoxyethylene alkyl ether, polyoxyethylene alkyl (mono- or di-)phenyl ether, polyoxyethylene (mono-, di- or tri-)styrylphenyl ether, polyoxyethylene polyoxypropylene block copolymer, polyoxyethylene fatty acid (mono- or di-)ester, sorbitan fatty acid ester, polyoxyethylene sorbitan fatty acid ester, caster oil-ethylene oxide adducts, acetylene glycol, acetylene alcohol, ethylene oxide adducts of acetylene glycol, ethylene oxide adducts of acetylene alcohol and alkyl glycoside, etc., anionic surfactants such as alkyl sulfate, alkylbenzenesulfonate, lignine sulfonate, alkylsulfosuccinate, naphthalene sulfonate, alkylnaphthalene sulfonate, formalin condensate salt of naphthalene sulfonic acid, formalin condensate salt of alkylnaphthalene sulfonic acid, polyoxyethylene alkyl ether sulfate or phosphate, polyoxyethylene (mono- or di-)alkylphenyl ether sulfate or phosphate, polyoxyethylene (mono-, di- or tri-) styrylphenyl ether sulfate or phosphate, polycarboxylate (e.g., polyacryaltes, polymaleates and copolymer materials of maleic acid and olefin, etc.) and polystyrenesulfonate, etc., cationic surfactants such as alkylamine salt and alkyl quaternary ammonium salt, etc., amphoteric surfactants such as amino acid type and betaine type, etc., silicone type surfactants and fluorine type surfactants.

A content of these surfactants is not specifically limited, and it is desirably in the range of 0.05 to 20 parts by weight in general based on 100 parts by weight of the preparation according to the present invention. Also, these surfactants may be used alone or in combination of two or more kinds in combination.

A dose of the compound of the present invention to be applied may vary depending on the place to be applied, time to be applied, method to be applied, crops to cultivate, etc., and in general, it is suitable in an amount of about 0.005 to 50 kg or so per a hectare (ha) as an amount of the effective ingredient.

On the other hand, when the compound of the present invention is used for controlling ecto- or endo-parasites of mammals and birds as domestic animals and pets, the effective amount of the compound of the present invention together with additives for formulations can be administered through oral administration, parenteral administration such as injection (intramuscular, subcutaneous, intravenous, intraperitoneal) or the like; transdermal administration such as dipping, spray, bathing, washing, pouring-on and spotting-on, and dusting, or the like; transversal administration. The compound of the present invention can be also administered through a formed product by use of a strip, a plate, a band, a collar, an ear mark, a limb band, a labe apparatus, or the like.

In administration, the compound of the present invention can be formed in an arbitrary dosage form that is suited for the administration route.

The arbitrary dosage form includes solid preparations such as a dustable powder, a granule, wettable powder, a pellete, a tablet, a bolus, a capsule, a formed product containing an active compound; liquid formulations such as an injectable liquid formulation, an oral liquid formulation, a liquid formulation used on skin or in body cavity; solution preparations such as a pour-on agent, a spot-on agent, a flowable agent, an emulsifiable concentrate; semi-solid preparations such as an ointment, gel or the like.

The solid preparations can be mainly used through oral administration or transdermal administration by diluting with water or the like, or by environmental treatment. The solid preparations can be prepared by mixing the active compound with suitable excipients and optionally auxiliary substances and converting to a desired form. The suitable excipients include for example inorganic substances such as carbonates, hydrogen carbonates, phosphates, aluminum oxide, silica, clay or the like, organic substances such as sugar, cellulose, milled cereal, starch or the like.

The injectable liquid formulation can be administered intravenously, intramuscularly and subcutaneously. The injectable liquid formulation can be prepared by dissolving an active compound in a suitable solvent and optionally by adding an additive such as a solubilizing agent, an acid, a base, a buffering salt, an antioxidant, and a protective agent or the like. Suitable solvent is for example water, ethanol, butanol, benzyl alcohol, glycerin, propylene glycol, poethylene glycol, N-methylpyrrolidone, and a mixture thereof, a physiologically permissible vegetable oil, a synthetic oil suitable for injection, or the like. The solubilizing agent includes polyvinyl pyrrolidone, polyoxyethylated castor oil and polyoxyethylated sorbitan ester, or the like. The protective agent includes benzyl alcohol, trichlorobutanol, p-hydroxybenzoic acid ester and n-butanol or the like.

The oral liquid formulation can be administered directly or after dilution. It can be prepared similarly to the injectable liquid formulation.

The flowable agent and the emulsifiable concentrate can be administered directly or after dilution through transdermal administration or environmental treatment.

The liquid formulation used on skin can be administered by pouring on, spreading, rubbing, atomizing, spraying, or dipping (dipping, bathing or washing). These liquid can be prepared similarly to the injectable liquid formulation.

The pour-on agent and the spot-on agent are poured or atomized on the limited spot on the skin, thereby the active compound can be penetrated into the skin and act in the whole body. The pour-on agent and the spot-on agent can be prepared by dissolving, suspending or emulsifying an active ingredient in a suitable skin-fitted solvent or solvent mixture. If required, an auxiliary substance such as a surfactant, a colorant, an absorption promoting agent, an antioxidant, a light stabilizer and an adhesive, etc. may be added.

Suitable solvent includes water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbon, vegetable or synthetic oil, DMF, liquid paraffin, light-duty liquid paraffin, silicone, dimethylacetamide, N-methylpyrrolidone or 2,2-dimethyl-4-oxy-methylene-1,3-dioxolane. The absorption promoting agent includes DMSO, isopropyl myristate, dipropylene glycol pelargonate, silicone oil, aliphatic ester, triglyceride and fatty alcohol. The antioxidant includes sulfite, metabisulfite, ascorbic acid, butylhydroxytoluene, butylhydroxyanisole and tocopherol.

The emulsifiable concentrate can be administrated orally, subcutaneously or injectably. The emulsifiable concentrate can be prepared by dissolving an active ingredient in a hydrophobic phase or a hydrophilic phase, and then homogenating the resulting solution with a suitable emulsifying agent optionally with further an auxiliary substance such as a colorant, an absorption promoting agent, a protective agent, an antioxidant, a light screen and a thickening agent.

The hydrophobic phase (oil) includes paraffin oil, silicone oil, sesame-seed oil, oil of almonds, castor oil, synthetic triglyceride, ethyl stearate, di-n-butyryl adipate, hexyl laurate, dipropylene glycol pelargonate, ester of branched short chain length aliphatic acid with saturated aliphatic acid of chain length C16 to C18, isopropyl myristate, isopropyl palmitate, capryl/caprylic acid ester of saturated fatty alcohol of chain length C12 to C18, isopropyl stearate, oleyl oleate, decyl oleate, ethyl oleate, ethyl lactate, wax-like fatty acid ester, dibutyl phthalate, diisopropyl adipate, isotridecyl alcohol, 2-octyldodecanol, cetylstearyl alcohol, oleyl alcohol.

The hydrophilic phase includes water, propylene glycol, glycerin, sorbitol.

The emulsifying agent includes non-ionic surfactants such as polyoxyethylated castor oil, polyoxyethylated sorbitan mono-olefinate, sorbitan monostearate, glycerin monostearate, polyoxyethyl stearate, alkylphenol polyglycol ether; amphoteric surfactants such as di-sodium N-lauryl (3-iminodipropionate, lecithin or the like; anionic surfactants such as sodium lauryl sulfate, fatty alcohol sulfuric acid ether, monoethanol amine salt of mono/dialkylpolyglycol orthophosphate or the like; cationic surfactants such as cetyl chloride trimethylammonium or the like.

The other auxiliary substance includes carboxymethylcellulose, methylcellulose, polyacrylate, arginate, gelatin, gum arabic, polyvinyl pyrrolidone, polyvinyl alcohol, methylvinyl ether, copolymer of maleic anhydride, polyethylene glycol, wax, colloidal silica.

The semi-solid preparation can be administered by coating or spreading on the skin, or by introducing in body cavity. The gel can be prepared by adding a thickener in an amount enough to provide a clear substance having a viscosity of ointment in a solution prepared for the injectable liquid formulation as mentioned above.

Next, formulation examples of the preparation in case where the compound of the present invention is used are shown below. Provided that formulation examples of the present invention are not limited only thereto. In the interim, in the following Formulation Examples, "part(s)" mean part(s) by weight.

| (Wettable powder) | |
|---|---|
| Compound of the present invention | 0.1 to 80 parts |
| Solid carrier | 5 to 98.9 parts |
| Surfactant | 1 to 10 parts |
| Others | 0 to 5 parts |

As other components, there may be mentioned, for example, a non-caking agent, a decomposition preventing agent, and the like.

| (Emulsifiable concentrate) | |
|---|---|
| Compound of the present invention | 0.1 to 30 parts |
| Liquid carrier | 45 to 95 parts |
| Surfactant | 4.9 to 15 parts |
| Others | 0 to 10 parts |

As other components, there may be mentioned, for example, a spreading agent, a decomposition preventing agent, and the like.

| (Suspension concentrate) | |
|---|---|
| Compound of the present invention | 0.1 to 70 parts |
| Liquid carrier | 15 to 98.89 parts |
| Surfactant | 1 to 12 parts |
| Others | 0.01 to 30 parts |

As other components, there may be mentioned, for example, an antifreezing agent, a thicknening agent, and the like.

| (Water dispersible granule) | |
|---|---|
| Compound of the present invention | 0.1 to 90 parts |
| Solid carrier | 0 to 98.9 parts |
| Surfactant | 1 to 20 parts |
| Others | 0 to 10 parts |

As other components, there may be mentioned, for example, a binder, a decomposition preventing agent, and the like.

| (Soluble concentrate) | |
|---|---|
| Compound of the present invention | 0.01 to 70 parts |
| Liquid carrier | 20 to 99.99 parts |
| Others | 0 to 10 parts |

As other components, there may be mentioned, for example, an antifreezing agent, a spreading agent, and the like.

| (Granule) | |
|---|---|
| Compound of the present invention | 0.01 to 80 parts |
| Solid carrier | 10 to 99.99 parts |
| Others | 0 to 10 parts |

As other components, there may be mentioned, for example, a binder, a decomposition preventing agent, and the like.

| (Dustable powder) | |
|---|---|
| Compound of the present invention | 0.01 to 30 parts |
| Solid carrier | 65 to 99.99 parts |
| Others | 0 to 5 parts |

As other components, there may be mentioned, for example, a drift preventing agent, a decomposition preventing agent, and the like.

Next, formulation examples using the compound of the present invention as an effective ingredient are described in more detail, but the present invention is not limited thereto. In the interim, in the following Formulation Examples, "part(s)" mean part(s) by weight.

(Formulation Example 1) Wettable powder

| | |
|---|---|
| Compound of the present invention No. 5-108 | 20 parts |
| Pyrophylite | 74 parts |
| Solpol 5039 | 4 parts |
| (A mixture of a nonionic surfactant and an anionic surfactant: available from TOHO Chemical Industry Co., LTD, Tradename) | |
| CARPREX #80D | 2 parts |
| (Synthetic hydrated silicic acid: available from Shionogi & Co., Ltd., Tradename) | |

The above materials are uniformly mixed and pulverized to make wettable powder.

(Formulation Example 2) Emulsion

| | |
|---|---|
| Compound of the present invention No. 5-108 | 5 parts |
| Xylene | 75 parts |
| N-methylpyrrolidone | 15 parts |
| Solpol 2680 | 5 parts |
| (A mixture of a nonionic surfactant and an anionic surfactant: available from TOHO Chemical Industry Co., LTD, Tradename) | |

The above materials are uniformly mixed to make emulsifiable concentrate.

(Formulation Example 3) Suspension concentrate

| | |
|---|---|
| Compound of the present invention No. 5-108 | 25 parts |
| Agrisol S-710 | 10 parts |
| (a nonionic surfactant: available from KAO CORPORATION, Tradename) | |
| Lunox 1000C | 0.5 part |
| (an anionic surfactant: available from TOHO Chemical Industry Co., LTD, Tradename) | |
| Xanthan gum | 0.2 part |
| Water | 64.3 parts |

The above materials are uniformly mixed, and then, wet pulverized to make suspension concentrate.

(Formulation Example 4) Water dispersible granule

| | |
|---|---|
| Compound of the present invention No. 5-108 | 75 parts |
| HITENOL NE-15 | 5 parts |
| (an anionic surfactant: available from DAI-ICHI KOGYO SEIYAKU CO., LTD., Tradename) | |
| VANILLEX N | 10 parts |
| (an anionic surfactant: available from Nippon Paper Chemicals Co., Ltd., Tradename) | |
| CARPREX #80D | 10 parts |
| (Synthetic hydrated silicic acid: available from Shionogi & Co., Ltd., Tradename) | |

The above materials are uniformly mixed and pulverized, and then, a small amount of water is added to the mixture and the resulting mixture is mixed under stirring, granulated by an extrusion granulator, and dried to make water dispersible granule.

(Formulation Example 5) Granule

| | |
|---|---|
| Compound of the present invention No. 5-108 | 5 parts |
| Bentonite | 50 parts |
| Talc | 45 parts |

The above materials are uniformly mixed and pulverized, and then, a small amount of water is added to the mixture and the resulting mixture is mixed under stirring, granulated by an extrusion granulator, and dried to make granule.

(Formulation Example 6) Dustable powder

| | |
|---|---|
| Compound of the present invention No. 5-10 | 3 parts |
| CARPREX #80D | 0.5 parts |
| (Synthetic hydrated silicic acid: available from Shionogi & Co., Ltd., Tradename) | |
| Kaolinite | 95 parts |
| Diisopropyl phosphate | 1.5 parts |

The above materials are uniformly mixed and pulverized to make dustable powder. When the formulation is used, it is sprayed by diluting with water in 1- to 10000-fold concentration, or directly without dilution.

(Formulation Example 7) Wettable powder preparation

| | |
|---|---|
| Compound of the present invention No. 5-108 | 25 parts |
| Sodium diisobutylnaphthalenesulfonate | 1 part |
| Calcium n-dodecylbenzenesulfonate | 10 parts |
| Alkylaryl polyglycol ether | 12 parts |
| Sodium salt of naphthalenesulfonic acid formalin condensate | 3 parts |
| Emulsion type silicone | 1 part |
| Silicon dioxide | 3 parts |
| Kaoline | 45 parts |

(Formulation Example 8) Water-soluble concentrate preparation

| | |
|---|---|
| Compound of the present invention No. 5-108 | 20 parts |
| Polyoxyethylene lauryl ether | 3 parts |
| Sodium dioctylsulfosuccinate | 3.5 parts |
| Dimethylsulfoxide | 37 parts |
| 2-Propanol | 36.5 parts |

(Formulation Example 9) Liquid formulation for atomization

| | |
|---|---|
| Compound of the present invention No. 5-108 | 2 parts |
| Dimethylsulfoxide | 10 parts |
| 2-Propanol | 35 parts |
| Acetone | 53 parts |

(Formulation Example 10) Liquid formulation for transdermal administration

| | |
|---|---|
| Compound of the present invention No. 5-108 | 5 parts |
| Hexylene glycol | 50 parts |
| Isopropanol | 45 parts |

| (Formulation Example 11) Liquid formulation for transdermal administration | |
|---|---|
| Compound of the present invention No. 5-108 | 5 parts |
| Propylene glycol monomethyl ether | 50 parts |
| Dipropylene glycol | 45 parts |

| (Formulation Example 12) Liquid formulation for transdermal administration (pouring-on) | |
|---|---|
| Compound of the present invention No. 5-108 | 2 parts |
| Light-duty liquid paraffin | 98 parts |

| (Formulation Example 13) Liquid formulation for transdermal administration (pouring-on) | |
|---|---|
| Compound of the present invention No. 5-108 | 2 parts |
| Light-duty liquid paraffin | 58 parts |
| Olive oil | 30 parts |
| ODO-H | 9 parts |
| Shinetsu silicone | 1 part |

Also, when the compound of the present invention is used as an agricultural chemicals, it may be mixed with other kinds of herbicides, various kinds of insecticides, acaricides, nematocides, fungicides, vegetable growth regulators, synergists, fertilizers, soil improvers, etc., and applied, at the time of preparing the formulation or at the time of spreading, if necessary.

In particular, by mixing with the other agricultural chemicals or plant hormones and applying the mixture, it can be expected that a cost is reduced due to reduction in a dose to be applied, enlargement in insecticidal spectrum or higher prevention and extinction effect of noxious organisms due to synergistic effect by mixing agricultural chemicals. At this time, it is possible to use the compound with a plural number of the conventionally known agricultural chemicals in combination simultaneously. As the kinds of the agricultural chemicals to be used in admixture with the compound of the present invention, there may be mentioned, for example, the compounds described in Farm Chemicals Handbook, 2005 ed. and the like. Specific examples of the general names can be enumerated below, but the invention is not necessarily limited only thereto.

Fungicide: acibenzolar-5-methyl, acylaminobenzamide, acypetacs, aldimorph, amisulbrom, amobam, ampropylos, anilazine, azaconazole, azithiram, azoxystrobin, barium polysulfide, benalaxy, benodanil, benomyl, benquinox, bentaluron, benthiavalicarb, benthiazole, benzamacril, benzamorf, bethoxazine, binapacryl, biphenyl, bitertanol, blasticidin-S, bordeaux mixture, boscalid, bromoconazole, bupirimate, buthiobate, calcium polysulfide, captafol, captan, carpropamid, carbamorph, carbendazim, carboxin, carvone, cheshunt mixture, chinomethionat, chlobenthiazone, chloraniformethane, chloranil, chlorfenazol, chloroneb, chloropicrin, chlorothalonil, chlorquinox, chlozolinate, climbazole, clotrimazole, copper acetate, copper carbonate, basic, copper hydroxide, copper naphthenate, copper oleate, copper oxychloride, copper sulfate, copper sulfate, basic, copper zinc chromate, cufraneb, cuprobam, cyazofamid, cyclafuramid, cycloheximide, cyflufenamid, cymoxanil, cypendazole, cyproconazol, cyprodinil, cyprofuram, dazomet, debacarb, decafentin, dehydroacetic acid, dichlofluanid, dichlone, dichlorophen, dichlozoline, diclobutrazol, diclocymet, diclomedine, dicloran, diethofencarb, difenoconazole, diflumetorim, dimethirimol, dimethomorph, dimoxystrobin, diniconazole, diniconazole-M, dinobuton, dinocap, dinocap-4, dinocap-6, dinocton, dinosulfon, dinoterbon, diphenylamine, dipyrithione, ditalimfos, dithianon, dodemorph, dodine, drazoxolon, edifenphos, epoxiconazole, etaconazole, etem, ethirimol, ethoxyquin, etridiazole, famoxadone, fenarimol, febuconazole, fenamidone, fenaminosulf, fenapanil, fendazosulam, fenfuram, fenhexamid, fenitropan, fenoxanil, fenpiclonil, fenpropidin, fenpropimorph, fentin, ferbam, ferimzone, fluazinam, fludioxonil, flumetover, flumorph, fluoroimide, fluotrimazole, fluoxastrobin, fluquinconazole, flusilazole, flusulfamide, flutolanil, flutriafol, folpet, fosetyl-aluminium, fuberidazole, furalaxyl, furametpyr, furcarbanil, furconazole, furconazole-cis, furmecyclox, furphanate, glyodin, griseofulvin, guazatine, halacrinate, hexachlorobenzene, hexaconazole, hexylthiofos, 8-hydroxyquinoline sulfate, hymexazol, imazalil, imibenconazole, iminoctadine, ipconazole, iprobenfos, iprodione, iprovalicarb, isoprothiolane, isovaledione, kasugamycin, kresoxim-methyl, mancopper, mancozeb, maneb, mebenil, mecarbinzid, mepanipyrim, mepronil, metalaxyl, metalaxyl-M, metam, metazoxolon, metconazole, methasulfocarb, methfuroxam, methyl isothiocyanate, metiram, metominostrobin, metrafenone, metsulfovax, milneb, myclobutanil, myclozolin, nabam, natamycin, nickel bis(dimethyldithiocarbamate), nitrostyrene, nitrothalisopropyl, nuarimol, OCH, octhilinone, ofurace, orysastrobin, oxadixyl, oxine copper, oxycarboxin, oxpoconazole fumarate, pefurzoate, penconazole, pencycuron, penthiopyrad, o-phenylphenol, phosdiphen, phthalide, picoxystrobin, piperalin, polycarbamate, polyoxins, polyoxorim, potassium azide, potassium hydrogen carbonate, proquinazid, probenazole, prochloraz, procymidone, propamocarb hydrochloride, propiconazole, propineb, prothiocarb, prothioconazole, pyracarbolid, pyraclostrobin, pyrazophos, pyridinitril, pyrifenox, pyrimethanil, pyroquilon, pyroxychlor, pyroxyfur, quinomethionate, quinoxyfen, quintozene, quinacetol-sulfate, quinazamid, quinconazole, rabenzazole, sodium azide, sodium hydrogen carbonate, sodium hypochlorite, sulfur, spiroxamine, salycylanilide, silthiofam, simeconazole, tebuconazole, tecnazene, tecoram, tetraconazole, thiabendazole, thiadifluor, thicyofen, thifluzamide, thiochlorfenphim, thiophanate, thiophanate-methyl, thioquinox, thiram, tiadinil, tioxymid, tolclofos-methyl, tolylfluanid, triadimefon, toriadimenol, triamiphos, triarimol, triazoxide, triazbutil, tributyltin oxide, trichlamide, tricyclazole, tridemorph, trifloxystrobin, triflumizole, triforine, triticonazole, validamycin, vinclozolin, zarilamide, zinc sulfate, zineb, ziram, zoxamide, and shiitake mushroom hyphae extract, etc.; Bactericides: benzalkonium chloride, bithionol, bronopol, cresol, formaldehyde, nitrapyrin, oxolinic acid, oxyterracycline, streptomycin and tecloftalam, etc.; Nematocides: aldoxycarb, cadusafos, DBCP, dichlofenthion, DSP, ethoprophos, fenamiphos, fensulfothion, fosthiazate, fosthietan, imicyafos, isamidofos, isazofos, oxamyl and thionazin, etc.;

Acaricides: acequinocyl, acrinathrin, amitraz, BCI-033 (test name), bifenazate, bromopropylate, chinomethionat, chlorobezilate, clofentezine, cyenopyrafen, cyflumetofen, cyhexatine, dicofol, dienochlor, DNOC, etoxazole, fenazaquin, fenbutatin oxide, fenothiocarb, fenpropathrin, fenpyroximate, fluacrypyrim, halfenprox, hexythiazox, milbemectin, propargite, pyridaben, pyrimidifen), S-1870(test name), spirodiclofen, spyromesifen and ebufenpyrad, etc.;

Insecticides: abamectin, acephate, acetamiprid, alanycarb, aldicarb, allethrin, azinphos-methyl, *bacillus thuringiensis*, bendiocarb, benfuracarb, bensultap, bifenthrin, buprofezin, butocarboxim, carbaryl, carbofuran, carbosulfan, cartap, chlorfenapyr, chlorfenvinphos, chlorfluazuron, chlorpyrifos, chlorpyrifos-methyl, chromafenozide, clothianidin, cycloprothrin, cyflumetofen, cyfluthrin, beta-cyfluthrin, cyhalothrin, lambda-cyhalothrin, cypermethrin, cyromazine, deltamethrin, diacloden, diafenthiuron, diazinon, dichlorvos, diflubenzuron, dimethylvinphos, dinotefuran, diofenolan, disulfoton, dimethoate, emamectin-benzoate, EPN, esfenvalerate, ethiofencarb, ethiprole, etofenprox, etrimfos, fenitrothion, fenobucarb, fenoxycarb, fenpropathrin, fenthion, fenvalerate, fipronil, flonicamid, flubendiamide, flucythrinate, flufenerim, flufenoxuron, flufenprox, fluvalinate, tau-fluvalinate, fonophos, formetanate, formothion, furathiocarb, halofenozide, hexaflumuron, hydramethylnon, imidacloprid, isofenphos, indoxacarb, isoprocarb, isoxathion, lepimectin, lufenuron, malathion, metaldehyde, methamidophos, methidathion, methacrifos, metaflumizone, metalcarb, methomyl, methoprene, methoxychlor, methoxyfenozide, methyl bromide, monocrotophos, muscalure, nitenpyram, NNH-0101 (test name), omethoate, oxamyl, oxydemeton-methyl, oxydeprofos, parathion, parathion-methyl, pentachlorophenol (PCP), permethrin, phenthoate, phoxim, phorate, phosalone, phosmet, phosphamidon, pirimicarb, pirimiphos-methyl, profenofos, prothiofos, propaphos, protrifenbute, pymetrozine, pyraclofos, pyridalyl, pyriproxyfen, rotenone, rynaxypyr, SI-0405 (test name), sulprofos, silafluofen, spinosad, sulfotep, SYJ-0159 (test name), tebfenozide, teflubenzuron, tefluthorin, terbufos, tetrachlorvinphos, thiacloprid, thiocyclam, thiodicarb, thiamethoxam, thiofanox, thiometon, tolfenpyrad, tralomethrin, trichlorfon, triazuron, triflumuron and vamidothion, etc.

EXAMPLES

Hereinafter, the present invention will be explained in more detail by specifically referring to Synthetic Examples and Test Examples of the compound of the present invention as working examples to which the present invention is not limited.

Synthetic Examples

Synthetic Example 1

4-[5-(3,5-Dichlorophenyl)-5-trifluoromethyl-4,5-dihydroisoxazole-3-yl]-N-ethyl-4'-fluoro-2-methyl benzoic acid anilide (Compound of the present invention No. 5-005)

Step 1: Production of 3,5-dichloro-1-(1-trifluoromethylethenyl)benzene

In a solution of 25.0 g of 3,5-dichlorophenyl boric acid in 200 mL of tetrahydrofuran and 100 mL of water, 27.5 g of 2-bromo-3,3,3-trifluoropropene, 38.0 g of potassium carbonate and 1.84 g of dichlorobis(triphenylphosphine) palladium (II) were added, and stirred under reflux with heat for 3 hours. After the completion of the reaction, the reaction mixture was left and cooled to room temperature, 500 mL of ice water was added, and extracted with ethyl acetate (500 mL×1). The organic phase was washed with water, dried over anhydrous sodium sulfate, the solvent was distilled off under reduced pressure. The residue was purified with silica gel column chromatography that was eluted with hexane to obtain 25.7 g of the aimed product as colorless oily substance.

$^1$H NMR (CDCl$_3$, Me$_4$Si, 300 MHz) δ7.41 (t, J=2.0 Hz, 1H), 7.3-7.35 (m, 2H), 6.05 (q, J=3.2 Hz, 1H), 5.82 (q, J=3.2 Hz, 1H).

Step 2: Production of 4-bromo-α-chloro-3-methylbenzaldoxime

In a solution of 82.0 g of 4-bromo-3-methylbenzaldoxime in 450 mL of tetrahydrofuran, 120.0 g of concentrated hydrochloric acid was added dropwise under cooling with ice and with stirring over 45 minutes. Then, 220 mL of 8% sodium hypochlorite aqueous solution was added dropwise over 75 minutes carefully so that the temperature of the reaction mixture would not exceed 5° C. After the completion of the addition dropwise, it was continued to stir at a temperature of 10° C. or less for further 90 minutes. After the completion of the reaction, the reaction mixture was blown with nitrogen gas for 45 minutes, then precipitated insoluble material was filtered off, tetrahydrofuran was distilled off under reduced pressure. The residual aqueous solution was extracted with 240.0 g of ethyl acetate, and the organic phase was washed with water (240 mL×2). The insoluble material was filtered off, the solvent was distilled off under reduced pressure to obtain 93.5 g of the aimed product as pale yellow crystal.

Melting point 77.0 to 78.0° C.
$^1$H NMR (CDCl$_3$, Me$_4$Si, 400 MHz) δ8.00 (bs, 1H), 7.71 (d, J=2.2 Hz, 2H), 7.57 (d, J=8.4 Hz, 1H), 7.51 (dd, J=8.4 Hz, 2.2 Hz, 1H), 2.44 (s, 3H).

Step 3: Production of 3-(4-bromo-3-methylphenyl)-5-(3,5-dichlorophenyl)-5-trifluoromethyl-4,5-dihydroisoxazole In a solution of 22.7 g of 3,5-dichloro-1-(1-trifluoromethylethenyl)benzene produced in Step 1 and 26.0 g of 4-bromo-α-chloro-3-methylbenzaldoxime produced in Step 2 in 120 mL of tetrahydrofuran, 15.7 g of potassium hydrogen carbonate was added, and stirred under reflux with heat for 5 hours. After the completion of the reaction, the reaction mixture was left and cooled to room temperature, insoluble material was filtered off, and then the solvent was distilled off under reduced pressure. 150 mL of water was added in the residue, stirred at room temperature for 18 hours, and then precipitated crystal was filtered off, and dried to obtain 38.6 g of the aimed product as white crystal.

Melting point 105.0 to 108.0° C.
$^1$H NMR (CDCl$_3$, Me$_4$Si, 300 MHz) δ7.59 (d, J=8.4 Hz, 1H), 7.45-7.55 (m, 3H), 7.42 (t, J=1.8 Hz, 1H), 7.33 (dd, J=8.4, 2.1 Hz, 1H), 4.07 (d, J=17.1 Hz, 1H), 3.68 (d, J=17.1 Hz, 1H), 2.43 (s, 3H).

Step 4: Production of 4-[5-(3,5-dichlorophenyl)-5-trifluoromethyl-4,5-dihydroisoxazol-3-yl]-2-methyl-benzoyl-chloride In a solution of 18.1 g of 3-(4-bromo-3-methylphenyl)-5-(3,5-dichlorophenyl)-5-trifluoromethyl-4,5-dihydroisoxazole and 3.94 g of sodium acetate in 42 mL of 1,2-dimethoxyethane and 42 mL of water in an autoclave, 0.42 g of triphenyl phosphine and 0.09 of palladium (II) acetate were added, and stirred under atmosphere of 1.5 MPa of carbon monoxide at 110° C. for 7 hours. After the completion of the reaction, the reaction mixture was left and cooled to room temperature, the solid was filtered off, and poured in 100 mL of ethyl acetate. The organic phase was washed with 1% sodium hydrogen carbonate aqueous solution (70 mL×2) and then with 1N hydrochloric acid (55 mL×1), dried over saturated sodium chloride aqueous solution, the solvent was substituted with toluene. In the resulting toluene solution, 2 drops of N,N-dimethylformamide was added, 6.0 g of thionyl chloride was added dropwise at 80° C. with stirring, and continued to stir further for 1.5 hour at the same temperature. After the completion of the reaction, insoluble material was filtered off, and the solvent was distilled off under reduced pressure until the whole amount was reduced by about one-third. Then, 50 mL of hexane was added slowly at 60° C. with stirring. After the completion of the addition dropwise, the reaction mixture was left and cooled to room temperature, and continued to stir at room temperature further for 1 hour. The precipitated crystal was filtered off, and dried to obtain 13.4 g of the aimed product as white crystal.

Melting point 140.5 to 143.0° C.

$^1$H NMR (CDCl$_3$, Me$_4$Si, 300 MHz) δ8.25 (d, J=8.7 Hz, 1H), 7.64 (d, J=8.7 Hz, 1H), 7.59 (s, 1H), 7.51 (s, 2H), 7.43 (s, 1H), 4.11 (d, J=17.4 Hz, 1H), 3.73 (d, J=17.4 Hz, 1H), 2.60 (s, 3H).

Step 5: Production of 4-[5-(3,5-dichloro phenyl)-5-trifluoromethyl-4,5-dihydroisoxazol-3-yl]-4'-fluoro-2-methyl benzoic acid anilide In a solution of 0.40 g of 4-fluoroaniline and 0.35 g of pyridine in 30 mL of dichloromethane, a solution of 1.30 g of 4-[5-(3,5-dichloro phenyl)-5-trifluoromethyl-4,5-dihydroisoxazol-3-yl]-2-methylbenzoyl-chloride in 10 mL of dichloromethane was added dropwise. After the completion of the addition dropwise, it was continued to stir at the same temperature further for 1 hour. After the completion of the reaction, the solvent was distilled under reduced pressure, and the residue was dissolved in 50 mL of ethyl acetate, washed with 20 mL of 2N hydrochloric acid and then with 20 mL of sodium hydrogen carbonate aqueous solution, and dehydrated with and dried over saturated sodium chloride aqueous solution and then anhydrous sodium sulfate, and the solvent was distilled off under reduced pressure. The residue was purified with silica gel column chromatography that was eluated with ethyl acetate-hexane (1:4) to obtain 1.35 g of the aimed product as colorless resinous substance.

$^1$H NMR (CDCl$_3$, Me$_4$Si, 300 MHz) δ7.5-7.65 (m, 7H), 7.4-7.45 (m, 2H), 7.08 (t, J=8.4 Hz, 2H), 4.10 (d, J=17.3 Hz, 1H), 3.72 (d, J=17.3 Hz, 1H), 2.53 (s, 3H).

Step 6: Production of 4-[5-(3,5-dichlorophenyl)-5-trifluoromethyl-4,5-dihydroisoxazol-3-yl]-N-ethyl-4'-fluoro-2-methyl benzoic acid anilide In a solution of 0.26 g of 4-[5-(3,5-dichlorophenyl)-5-trifluoromethyl-4,5-dihydroisoxazol-3-yl]-4'-fluoro-2-methyl benzoic acid anilide in 2 mL of N,N-dimethylformamide, 0.35 g of potassium carbonate and 0.27 g of ethyl bromide was added at room temperature with stirring, and stirred at 80° C. for 5 hours. After the completion of the reaction, the reaction mixture was poured in 10 mL of water, extracted with ethyl acetate (10 mL×1), the organic phase was washed with 10 mL of 2N hydrochloric acid and then dehydrated with and dried over saturated sodium chloride aqueous solution and then anhydrous sodium sulfate, and the solvent was distilled off under reduced pressure. The residue was purified with silica gel column chromatography that was eluated with ethyl acetate-hexane (3:7) to obtain 0.23 g of the aimed product as white crystal.

Melting point 160.0 to 163.0° C.

$^1$H NMR (CDCl$_3$, Me$_4$Si, 300 MHz) δ7.15-7.5 (m, 5H), 6.8-7.1 (m, 5H), 3.99 (d, J=17.1 Hz, 1H), 3.96 (q, J=6.9 Hz, 2H), 3.59 (d, J=17.1 Hz, 1H), 2.36 (s, 3H), 1.24 (t, J=6.9 Hz, 3H).

Synthetic Example 2

4-[5-(3,5-Dichloro phenyl)-5-trifluoromethyl-4,5-dihydroisoxazole-3-yl]-4'-fluoro-N-methoxymethyl-2-methyl benzoic acid anilide (Compound of the present invention No. 5-007)

In a solution of 0.20 g of 4-[5-(3,5-dichlorophenyl)-5-trifluoromethyl-4,5-dihydroisoxazol-3-yl]-4'-fluoro-2-methyl benzoic acid anilide produced in Step 5 of Synthetic Example 1 in 2 mL of tetrahydrofuran, 0.39 mL of tetrahydrofuran solution (1.0 mol/1 L) of lithium bis(trimethylsilyl)amide and then 0.03 g of chloromethyl methyl ether were added dropwise at room temperature with stirring. After the completion of the addition dropwise, it was continued to stir at room temperature further for 20 minutes. After the completion of the reaction, the reaction mixture was poured in 5 m of water, extracted with ethyl acetate (10 mL×1), the organic phase was washed with water and then dehydrated with and dried over saturated sodium chloride aqueous solution and then anhydrous sodium sulfate, and the solvent was distilled off under reduced pressure. The residue was purified with silica gel column chromatography that was eluated with ethyl acetate-hexane (1:1) to obtain 0.07 g of the aimed product as white crystal.

Melting point 140.0 to 143.0° C.

$^1$H NMR (CDCl$_3$, Me$_4$Si, 300 MHz) δ6.75-7.7 (m, 10H), 5.24 (s, 2H), 4.01 (d, J=17.7 Hz, 1H), 3.61 (d, J=17.7 Hz, 1H), 3.55 (s, 3H), 2.40 (s, 3H).

J=17.1 Hz, 1H), 2.43 (s, 3H).

Synthetic Example 3

N-Cyanomethyl-4-[5-(3,5-dichlorophenyl)-5-trifluoromethyl-4,5-dihydroisoxazole-3-yl]-4'-fluoro-2-methyl benzoic acid anilide (Compound of the present invention No. 5-008)

In a solution of 0.30 g of 4-[5-(3,5-dichlorophenyl)-5-trifluoromethyl-4,5-dihydroisoxazol-3-yl]-4'-fluoro-2-methyl benzoic acid anilide produced in Step 5 of Synthetic Example 1 in 2 mL of tetrahydrofuran, 0.14 g bromoacetonitrile and 0.14 g of potassium tert-butoxide were added at room temperature with stirring, and stirred at room temperature for 5 hours. After the completion of the reaction, the reaction mixture was poured in 5 m of water, extracted with ethyl acetate (10 mL×1), the organic phase was washed with 5 mL of 2N hydrochloric acid and then dehydrated with and dried over saturated sodium chloride aqueous solution and then anhydrous sodium sulfate, and the solvent was distilled off under reduced pressure. The residue was purified with silica gel column chromatography that was eluated with ethyl acetate-hexane (3:7) to obtain 0.19 g of the aimed product as pale brown crystal.

Melting point 60.0 to 66.0° C.

$^1$H NMR (CDCl$_3$, Me$_4$Si, 300 MHz) δ7.46 (s, 2H), 7.35 (m, 2H), 7.25-7.35 (m, 1H), 7.0-7.2 (m, 3H), 6.9-7.0 (m, 2H), 4.77 (s, 2H), 4.01 (d, J=17.4 Hz, 1H), 3.62 (d, J=17.4 Hz, 1H), 2.38 (s, 3H).

Synthetic Example 4

Methyl N-[4-[5-(3,5-dichlorophenyl)-5-trifluoromethyl-4,5-dihydroisoxazole-3-yl]-2-methyl benzoyl]-N-(2-pyrimidinyl) carbamate (Compound of the present invention No. 5-014)

In 0.02 g of 55% oily sodium hydride suspended in 3 mL of tetrahydrofuran, a solution of 0.17 g of 4-[5-(3,5-dichlorophenyl)-5-trifluoromethyl-4,5-dihydroisoxazol-3-yl]-2-methyl-N-(2-pyrimidinyl)benzoic acid amide synthesized similarly to Step 5 of Synthetic Example 1 in 3 mL of tetrahydrofuran was added dropwise. After the completion of the addition dropwise, it was continued to stir at the same temperature for 10 minutes, then 0.05 g of methyl chloroformate was added, and continued to stir at the same temperature for 1 hour. After the completion of the reaction, the reaction mixture was poured in 10 mL of ice water, extracted with ethyl acetate (10 mL×2), the organic phase was dehydrated with and dried over saturated sodium chloride aqueous solution and then anhydrous sodium sulfate, and the solvent was distilled off under reduced pressure. The residue was purified with silica gel column chromatography that was eluated with ethyl acetate to obtain 0.11 g of the aimed product as colorless resinous substance.

$^1$H NMR (CDCl$_3$, Me$_4$Si, 300 MHz) δ8.79 (d, J=5.1 Hz, 2H), 7.55 (s, 1H), 7.50 (s, 4H), 7.43 (s, 1H), 7.30 (t, J=4.8 Hz, 1H), 4.08 (d, J=17.4 Hz, 1H), 3.72 (s, 3H), 3.69 (d, J=17.4 Hz, 1H), 2.54 (s, 3H).

Synthetic Example 5

N-Acetyl-4-[5-(3,5-dichlorophenyl)-5-trifluoromethyl-4,5-dihydroisoxazole-3-yl]-2',4'-difluoro-2-methyl benzoic acid anilide (Compound of the present invention No. 5-033)

Step 1: Production of 4-[5-(3,5-dichlorophenyl)-5-trifluoromethyl-4,5-dihydroisoxazole-3-yl]-2',4'-difluoro-2-methyl benzoic acid anilide In a solution of 0.85 g of 2,4-difluoroaniline and 1.42 g of pyridine in 30 mL of dichloromethane, a solution of 2.62 g of 4-[5-(3,5-dichlorophenyl)-5-trifluoromethyl-4,5-dihydroisoxazol-3-yl]-2-methylbenzoyl-chloride synthesized in Step 4 of Synthetic Example 1 in 20 mL of dichloromethane was added dropwise. After the completion of the addition dropwise, it was continued to stir at the same temperature further for 30 minutes. After the completion of the reaction, the solvent was distilled off under reduced pressure, the residue was dissolved in 30 mL of ethyl acetate, washed with 15 mL of 2N hydrochloric acid and then with 15 mL of saturated sodium hydrogen carbonate aqueous solution. The organic phase was dehydrated with and dried over saturated sodium chloride aqueous solution and then anhydrous sodium sulfate, and the solvent was distilled off under reduced pressure. The residue was purified with neutral alumina column chromatography and silica gel chromatography that were eluated with ethyl acetate to obtain 2.92 g of the aimed product as colorless resinous substance.

$^1$H NMR (CDCl$_3$, Me$_4$Si, 300 MHz) δ7.4-7.6 (m, 7H), 6.85-7.0 (m, 2H), 6.65-6.85 (m, 1H), 4.11 (d, J=17.1 Hz, 1H), 3.72 (d, J=17.1 Hz, 1H), 2.55 (s, 3H).

Step 2: Production of

N-acetyl-4-[5-(3,5-dichlorophenyl)-5-trifluoromethyl-4,5-dihydroisoxazole-3-yl]-2',4'-difluoro-2-methyl benzoic acid anilide In 0.04 g of 55% oily sodium hydride suspended in 3 mL of tetrahydrofuran, a solution of 0.30 g of 4-[5-(3,5-dichlorophenyl)-5-trifluoromethyl-4,5-dihydroisoxazol-3-yl]-2',4'-difluoro-2-methyl benzoic acid anilide in 3 mL of tetrahydrofuran was added and continued to stir at the same temperature for 10 minutes. After ceasing the generation of hydrogen gas, 0.07 g of acetyl chloride was added, ice bath was removed and continued to stir for 2 hours, and then 1.2 mL of tetrahydrofuran solution (1.0 mol/1 L) of lithium bis (trimethylsilyl)amide was added and continued to stir at the same temperature further for 16 hours. After the completion of the reaction, the reaction mixture was poured in 10 mL of ice water, extracted with ethyl acetate (10 mL×2), the organic phase was dehydrated with and dried over saturated sodium chloride aqueous solution and then anhydrous sodium sulfate, and the solvent was distilled off under reduced pressure. The residue was purified with silica gel column chromatography that was eluated with ethyl acetate-hexane (1:2) to obtain 0.28 g of the aimed product as colorless resinous substance.

$^1$H NMR (CDCl$_3$, Me$_4$Si, 300 MHz) δ8.3-8.45 (m, 1H), 7.35-7.65 (m, 5H), 6.8-7.0 (m, 3H), 4.11 (d, J=17.1 Hz, 1H), 3.73 (d, J=17.1 Hz, 1H), 2.54 (s, 3H), 2.04 (s, 3H).

Synthetic Example 6

N-Acetyl-4-[5-(3,5-dichlorophenyl)-5-trifluoromethyl-4,5-dihydroisoxazole-3-yl]-2-methyl-N-(1-pyrazolyl)benzoic acid amide (Compound of the present invention No. 5-044)

Step 1: Production of 4-[5-(3,5-dichlorophenyl)-5-trifluoromethyl-4,5-dihydroisoxazole-3-yl]-2-methyl-N-(1-pyrazolyl)benzoic acid amide In 4 mL of N,N-dimethylacetamide, 0.23 g of 50% N,N-dimethylformamide solution of 1-aminopyrazole was added, and 0.30 g of 4-[5-(3,5-dichlorophenyl)-5-trifluoromethyl-4,5-dihydroisoxazol-3-yl]-2-methylbenzoyl-chloride synthesized in Step 4 of Synthetic Example 1 was added at room temperature with stirring, and stirred at the same temperature for 2 hours. After the completion of the reaction, 20 mL of ethyl acetate was added in the reaction mixture, washed with water (20 mL×1), and then the organic phase was dehydrated with and dried over saturated sodium chloride aqueous solution and then anhydrous magnesium sulfate, and the solvent was distilled off under reduced pressure. The residue was purified with neutral alumina column chromatography that was eluated with chloroform to obtain 0.22 g of the aimed product as yellow resinous substance.

$^1$H NMR (CDCl$_3$, Me$_4$Si, 300 MHz) δ7.4-7.75 (m, 9H), 6.38 (bs, 1H), 4.08 (d, J=17.3 Hz, 1H), 3.70 (d, J=17.3 Hz, 1H), 2.53 (s, 3H).

Step 2: Production of N-acetyl-4-[5-(3,5-dichlorophenyl)-5-trifluoromethyl-4,5-dihydroisoxazole-3-yl]-2-methyl-N-(1-pyrazolyl)benzoic acid amide In a solution of 0.20 g of 4-[5-(3,5-dichlorophenyl)-5-trifluoromethyl-4,5-dihydroisoxazol-3-yl]-2-methyl-N-(1-pyrazolyl)benzoic acid amide in 3 mL of tetrahydrofuran, 0.027 g of 60% oily sodium hydride was added and stirred at room temperature for 10 minutes. After ceasing the generation of hydrogen gas, 0.049 g of acetyl chloride was added under cooling with ice and with stirring, and continued to stir at the same temperature further for 10 minutes. After the completion of the reaction, the reaction mixture was poured in 10 mL of ice water, extracted with ethyl acetate (10 mL×1), the organic phase was dehydrated with and dried over saturated sodium chloride aqueous solution and then anhydrous magnesium sulfate, and the solvent was distilled off under reduced pressure. The residue was purified with silica gel column chromatography that was eluted with ethyl acetate-hexane (2:3) to obtain 0.058 g of the aimed product as yellow resinous substance.

$^1$H NMR (CDCl$_3$, Me$_4$Si, 300 MHz) δ7.35-7.7 (m, 8H), 6.33 (t, J=2.4 Hz, 1H), 4.05 (d, J=17.3 Hz, 1H), 3.66 (d, J=17.3 Hz, 1H), 2.48 (s, 3H), 2.38 (s, 3H).

Synthetic Example 7

Methyl N-(5-chloro-2-pyridyl)-N-[4-[5-(3,5-dichlorophenyl)-5-trifluoromethyl-4,5-dihydroisoxazole-3-yl]-2-methylbenzoyl]carbamate (Compound of the present invention No. 5-060)

Step 1: Production of N-(5-chloro-2-pyridyl)-4-[5-(3,5-dichlorophenyl)-5-trifluoromethyl-4,5-dihydroisoxazole-3-yl]-2-methyl benzoic acid amide In a solution of 0.59 g of 2-amino-5-chloropyridine in 10 mL of pyridine, 2.0 g of 4-[5-(3,5-dichlorophenyl)-5-trifluoromethyl-4,5-dihydroisoxazol-3-yl]-2-methylbenzoyl-chloride synthesized in Step 4 of Synthetic Example 1 was added at room temperature with stirring, and stirred at the same temperature for 15 hours. After the completion of the reaction, the solvent was distilled off under reduced pressure, the residue was dissolved in 50 mL of ethyl acetate, then washed with 3N hydrochloric acid (50 mL×1), and then the organic phase was dehydrated with and dried over saturated sodium chloride aqueous solution and then anhydrous magnesium sulfate, and the solvent was distilled off under reduced pressure. The residue was purified with neutral alumina column chromatography that was eluated with chloroform to obtain 1.80 g of the aimed product as white crystal.

Melting point 129.0 to 132.5° C.

$^1$H NMR (CDCl$_3$, Me$_4$Si, 300 MHz) δ8.45 (s, 1H), 8.35 (d, J=8.7 Hz, 1H), 8.09 (d, J=2.4 Hz, 1H), 7.73 (dd, J=8.7, 2.4 Hz, 1H), 7.4-7.65 (m, 6H), 4.11 (d, J=17.4 Hz, 1H), 3.72 (d, J=17.4 Hz, 1H), 2.54 (s, 3H).

Step 2: Production of methyl N-(5-chloro-2-pyridyl)-N-[4-[5-(3,5-dichlorophenyl)-5-trifluoromethyl-4,5-dihydroisoxazole-3-yl]-2-methylbenzoyl]carbamate In a solution of 0.30 g of N-(5-chloro-2-pyridyl)-4-[5-(3,5-dichlorophenyl)-5-trifluoromethyl-4,5-dihydroisoxazol-3-yl]-2-methyl benzoic acid amide in 3 mL of tetrahydrofuran, 0.037 g of 60% oily sodium hydride was added and stirred at room temperature for 10 minutes. After ceasing the generation of hydrogen gas, 0.080 g of methyl chloroformate was added under cooling with ice and with stirring, and continued to stir at the same temperature further for 10 minutes. After the completion of the reaction, the reaction mixture was poured in 10 mL of ice water, extracted with ethyl acetate (10 mL×1), the organic phase was dehydrated with and dried over saturated sodium chloride aqueous solution and then anhydrous magnesium sulfate, and the solvent was distilled off under reduced pressure. The residue was purified with silica gel column chromatography that was eluated with ethyl acetate-hexane (2:3) to obtain 0.29 g of the aimed product as yellow resinous substance.

$^1$H NMR (CDCl$_3$, Me$_4$Si, 300 MHz) δ8.49 (d, J=2.7 Hz, 1H), 7.80 (dd, J=8.7, 2.7 Hz, 1H), 7.4-7.6 (m, 6H), 7.29 (d, J=8.7 Hz, 1H), 4.09 (d, J=17.0 Hz, 1H), 3.70 (d, J=17.0 Hz, 1H), 3.67 (s, 3H), 2.51 (s, 3H).

Synthetic Example 8

Methyl N-(5-cyano-2-pyridyl)-N-[4-[5-(3,5-dichlorophenyl)-5-trifluoromethyl-4,5-dihydroisoxazole-3-yl]-2-methylbenzoyl]carbamate (Compound of the present invention No. 5-071)

Step 1: Production of N-(5-cyano-2-pyridyl)-4-[5-(3,5-dichlorophenyl)-5-trifluoromethyl-4,5-dihydroisoxazole-3-yl]-2-methyl benzoic acid amide In a solution of 0.39 g of 2-amino-5-cyanopyridine and 0.71 g of pyridine in 20 mL of dichloromethane, a solution of 1.31 g of 4-[5-(3,5-dichlorophenyl)-5-trifluoromethyl-4,5-dihydroisoxazol-3-yl]-2-methylbenzoyl-chloride synthesized in Step 4 of Synthetic Example 1 in 20 mL of dichloromethane was added dropwise. After the completion of the addition dropwise, it was continued to stir at the same temperature further for 1 hour. After the completion of the reaction, the solvent was distilled off under reduced pressure, the residue was dissolved in 50 mL of ethyl acetate, precipitated insoluble material was removed through silica gel column, and the solvent was distilled off under reduced pressure. The residual solid was washed with diisopropyl ether to obtain 1.11 g of the aimed product as colorless resinous substance.

$^1$H NMR (CDCl$_3$, Me$_4$Si, 300 MHz) δ8.4-8.6 (m, 3H), 7.95-8.1 (m, 1H), 7.61 (s, 3H), 7.4-7.55 (m, 3H), 4.12 (d, J=17.1 Hz, 1H), 3.73 (d, J=17.1 Hz, 1H), 2.56 (s, 3H).

Step 2: Production of methyl N-(5-cyano-2-pyridyl)-N-[4-[5-(3,5-dichlorophenyl)-5-trifluoromethyl-4,5-dihydroisoxazole-3-yl]-2-methylbenzoyl]carbamate In a suspension of 0.03 g of 55% oily sodium hydride suspended in 3 mL of tetrahydrofuran, a solution of 0.26 g of N-(5-cyano-2-pyridyl)-4-[5-(3,5-dichlorophenyl)-5-trifluoromethyl-4,5-dihydroisoxazole-3-yl]-2-methyl benzoic acid amide in 3 mL of tetrahydrofuran was added under cooling with ice and with stirring and continued to stir at the same temperature for 10 minutes. After ceasing the generation of hydrogen gas, 0.07 g of methyl chloroformate was added, ice bath was removed and continued to stir further for 7 hours. After the completion of the reaction, the reaction mixture was poured in 10 mL of ice water, extracted with ethyl acetate (10 mL×2), the organic phase was dehydrated with and dried over saturated sodium chloride aqueous solution and then anhydrous sodium sulfate, and the solvent was distilled off under reduced pressure. The residue was purified with silica gel column chromatography that was eluated with ethyl acetate-hexane (1:2) to obtain 0.24 g of the aimed product as colorless resinous substance.

$^1$H NMR (CDCl$_3$, Me$_4$Si, 300 MHz) δ8.7-8.75 (m, 1H), 8.05-8.1 (m, 1H), 7.4-7.6 (m, 7H), 4.09 (d, J=17.1 Hz, 1H), 3.72 (s, 3H), 3.70 (d, J=17.1 Hz, 1H), 2.55 (s, 3H).

Synthetic Example 9

N-Acetyl-N-(6-chloro-2-pyridyl)-4-[5-(3,5-dichlorophenyl)-5-trifluoromethyl-4,5-dihydroisoxazole-3-yl]-2-methyl benzoic acid amide (Compound of the present invention No. 5-073)

Step 1: Production of N-(6-chloro-2-pyridyl)-4-[5-(3,5-dichlorophenyl)-5-trifluoromethyl-4,5-dihydroisoxazole-3-yl]-2-methyl benzoic acid amide In a solution of 0.10 g of 2-amino-6-chloropyridine and 0.16 g of pyridine in 5 mL of dichloromethane, a solution of 0.30 g of 4-[5-(3,5-dichlorophenyl)-5-trifluoromethyl-4,5-dihydroisoxazol-3-yl]-2-methylbenzoyl-chloride synthesized in Step 4 of Synthetic Example 1 in 5 mL of dichloromethane was added at room temperature with stirring. After the completion of the addition dropwise, it was stirred at the same temperature further for 2.5 hours. After the completion of the reaction, the solvent was distilled off under reduced pressure, the residue was dissolved in 50 mL of ethyl acetate, and precipitated insoluble material was removed through silica gel column, and the solvent was distilled off under reduced pressure. The residue was purified with silica gel column chromatography that was eluated with ethyl acetate-hexane (1:2) to obtain 0.25 g of the aimed product as colorless resinous substance.

$^1$H NMR (CDCl$_3$, Me$_4$Si, 300 MHz) δ8.29 (d, J=7.8 Hz, 1H), 8.23 (s, 1H), 7.74 (t, J=7.8 Hz, 1H), 7.5-7.6 (m, 6H), 7.13 (d, J=7.2 Hz, 1H), 4.11 (d, J=17.1 Hz, 1H), 3.73 (d, J=17.1 Hz, 1H), 2.55 (s, 3H).

Step 2: Production of N-acetyl-N-(6-chloro-2-pyridyl)-4-[5-(3,5-dichlorophenyl)-5-trifluoromethyl-4,5-dihydroisoxazole-3-yl]-2-methyl benzoic acid amide In a suspension of 0.10 g of 55% oily sodium hydride suspended in 15 mL of N,N-dimethylformamide, a solution of 0.30 g of N-(6-chloro-2-pyridyl)-4-[5-(3,5-dichlorophenyl)-5-trifluoromethyl-4,5-dihydroisoxazole-3-yl]-2-methyl benzoic acid amide in 5 mL of N,N-dimethylformamide was added under cooling with ice and with stirring, and stirred at the same temperature for 10 minutes. After ceasing the generation of hydrogen gas, 0.30 g of acetyl chloride was added, ice bath was removed and continued to stir further for 5 minutes. After the completion of the reaction, the reaction mixture was poured in 20 mL of ice water, extracted with ethyl acetate (50 mL×1), the organic phase was dehydrated with and dried over saturated sodium chloride aqueous solution and then anhydrous sodium sulfate, and the solvent was distilled off under reduced pressure. The residue was purified with silica gel column chromatography that was eluated with ethyl acetate-hexane (1:2) to obtain 0.11 g of the aimed product as colorless resinous substance.

$^1$H NMR (CDCl$_3$, Me$_4$Si, 300 MHz) δ7.64 (t, J=7.8 Hz, 1H), 7.15-7.5 (m, 8H), 4.03 (d, J=17.2 Hz, 1H), 3.64 (d, J=17.2 Hz, 1H), 2.54 (s, 3H), 2.53 (s, 3H).

Synthetic Example 10

N-(6-Bromo-2-pyridyl)-4-[5-(3,5-dichlorophenyl)-5-trifluoromethyl-4,5-dihydroisoxazole-3-yl]-N-methyl-2-methyl benzoic acid amide (Compound of the present invention No. 5-075)

Step 1: Production of N-(6-bromo-2-pyridyl)-4-[5-(3,5-dichlorophenyl)-5-trifluoromethyl-4,5-dihydroisoxazole-3-yl]-2-methyl benzoic acid amide In a solution of 0.13 g of 2-amino-6-bromopyridine and 0.16 g of pyridine in 5 mL of dichloromethane, a solution of 0.30 g of 4-[5-(3,5-dichlorophenyl)-5-trifluoromethyl-4,5-dihydroisoxazol-3-yl]-2-methylbenzoyl-chloride synthesized in Step 4 of Synthetic Example 1 in 5 mL of dichloromethane was added at room temperature with stirring. After the completion of the addition dropwise, it was stirred at the same temperature further for 2 hours. After the completion of the reaction, the solvent was distilled off under reduced pressure, the residue was dissolved in 50 mL of ethyl acetate, and precipitated insoluble material was removed through silica gel column, and the solvent was distilled off under reduced pressure. The residue was purified with silica gel column chromatography that was eluated with ethyl acetate-hexane (1:2) to obtain 0.25 g of the aimed product as colorless resinous substance.

$^1$H NMR (CDCl$_3$, Me$_4$Si, 300 MHz) δ8.32 (d, J=8.1 Hz, 1H), 8.21 (s, 1H), 7.2-7.7 (m, 8H), 4.11 (d, J=17.4 Hz, 1H), 3.73 (d, J=17.4 Hz, 1H), 2.55 (s, 3H).

Step 2: Production of N-(6-bromo-2-pyridyl)-4-[5-(3,5-dichlorophenyl)-5-trifluoromethyl-4,5-dihydroisoxazole-3-yl]-N-methyl-2-methyl benzoic acid amide In a solution of 0.23 g of N-(6-bromo-2-pyridyl)-4-[5-(3,5-dichlorophenyl)-5-trifluoromethyl-4,5-dihydroisoxazole-3-yl]-2-methyl benzoic acid amide in 5 mL of N,N-dimethylformamide, 0.02 g of 55% oily sodium hydride was added at room temperature with stirring, and stirred at the same temperature for 10 minutes. After ceasing the generation of hydrogen gas, 0.30 g of methyl iodide was added, and continued to stir further for 45 minutes. After the completion of the reaction, the reaction mixture was poured in 20 mL of ice water, extracted with ethyl acetate (50 mL×1), the organic phase was dehydrated with and dried over saturated sodium chloride aqueous solution and then anhydrous magnesium sulfate, and the solvent was distilled off under reduced pressure. The residue was purified with silica gel column chromatography that was eluated with ethyl acetate-hexane (1:2) to obtain 0.18 g of the aimed product as colorless resinous substance.

$^1$H NMR (CDCl$_3$, Me$_4$Si, 300 MHz) δ7.45-7.55 (m, 3H), 7.3-7.5 (m, 3H), 7.05-7.3 (m, 3H), 4.06 (d, J=17.4 Hz, 1H), 3.60 (d, J=17.4 Hz, 1H), 3.49 (s, 3H), 2.37 (s, 3H).

Synthetic Example 11

N-Acetyl-N-(5-chloro-2-pyrimidinyl)-4-[5-(3,5-dichlorophenyl)-5-trifluoromethyl-4,5-dihydroisoxazole-3-yl]-2-methyl benzoic acid amide (Compound of the present invention No. 5-100)

Step 1: Production of N-(5-chloro-2-pyrimidinyl)-4-[5-(3,5-dichlorophenyl)-5-trifluoromethyl-4,5-dihydroisoxazole-3-yl]-2-methyl benzoic acid amide In a solution of 3.86 g of 2-amino-5-chloropyrimidine in 100 mL of pyridine, 10.0 g of 4-[5-(3,5-dichlorophenyl)-5-trifluoromethyl-4,5-dihydroisoxazol-3-yl]-2-methylbenzoyl-chloride synthesized in Step 4 of Synthetic Example 1 was added at room temperature with stirring, and stirred at the same temperature for 23 hours. The solvent was distilled off under reduced pressure, the residue was dissolved in 30 mL of 1,4-dioxane, a solution of 3.02 g of potassium hydroxide in 20 mL of water was added and stirred at room temperature for 1.5 hour. After the completion of the reaction, the reaction mixture was diluted with 380 mL of water, precipitated crystal was filtered off, and washed with 150 mL of water. The resulting crude product was dissolved in 50 mL of ethyl acetate with heating, and 50 mL of 2N hydrochloric acid was added and stirred for 1 hour, and then 50 mL of toluene was added, and precipitated crystal was filtered off. Thereafter, the reaction mixture was washed with 50 mL of water, and then with 50 mL of toluene to obtain 7.95 g of the aimed product as white crystal.

Melting point 137.0 to 141.0° C.
$^1$H NMR (CDCl$_3$, Me$_4$Si, 300 MHz) δ8.54 (s, 2H), 8.50 (s, 1H), 7.4-7.65 (m, 6H), 4.10 (d, J=17.3 Hz, 1H), 3.73 (d, J=17.3 Hz, 1H), 2.55 (s, 3H).

Step 2: Production of N-acetyl-N-(5-chloro-2-pyrimidinyl)-4-[5-(3,5-dichlorophenyl)-5-trifluoromethyl-4,5-dihydroisoxazole-3-yl]-2-methyl benzoic acid amide In a solution of 0.20 g of N-(5-chloro-2-pyrimidinyl)-4-[5-(3,5-dichlorophenyl)-5-trifluoromethyl-4,5-dihydroisoxazol-3-yl]-2-methyl benzoic acid amide in 3 mL of tetrahydrofuran, 0.025 g of 55% oily sodium hydride was added under cooling with ice and with stirring and stirred at room temperature for 10 minutes. After ceasing the generation of hydrogen gas, 0.045 g of acetyl chloride was added under cooling with ice and with stirring, and continued to stir at the same temperature further for 1 hour. After the completion of the reaction, the reaction mixture was poured in 10 mL of ice water, extracted with ethyl acetate (10 mL×1), the organic phase was dehydrated with and dried over saturated sodium chloride aqueous solution and then anhydrous magnesium sulfate, and the solvent was distilled off under reduced pressure. The residue was purified with silica gel column chromatography that was eluated with ethyl acetate-hexane (gradient of 1:9 to 3:7) to obtain 0.10 g of the aimed product as white crystal.
Melting point 175.0 to 177.0° C.
$^1$H NMR (CDCl$_3$, Me$_4$Si, 300 MHz) δ8.56 (s, 2H), 7.3-7.55 (m, 6H), 4.03 (d, J=16.8 Hz, 1H), 3.63 (d, J=16.8 Hz, 1H), 2.59 (s, 3H), 2.53 (s, 3H).

Synthetic Example 12

N-(5-Chloro-2-pyrimidinyl)-4-[5-(3,5-dichlorophenyl)-5-trifluoromethyl-4,5-dihydroisoxazole-3-yl]-N-methoxyacetyl-2-methyl benzoic acid amide (Compound of the present invention No. 5-106)

In a solution of 0.27 g of N-(5-chloro-2-pyrimidinyl)-4-[5-(3,5-dichlorophenyl)-5-trifluoromethyl-4,5-dihydroisoxazole-3-yl]-2-methyl benzoic acid amide synthesized in Step 1 of Synthetic Example 11, 0.08 g of triethylamine and a catalytic amount of 4-(dimethylamino)pyridine in 5 mL of tetrahydrofuran, 0.08 g of methoxyacetyl chloride was added at room temperature with stirring, and stirred at the same temperature for 0.5 hour. After the completion of the reaction, the solvent was distilled off under reduced pressure, the residue was passed through short-pass silica gel column that was eluated with ethyl acetate, and thereby insoluble material was removed. The solvent was distilled off under reduced pressure, and purified with silica gel column chromatography that was eluated with ethyl acetate-hexane (3:7) to obtain 0.22 g of the aimed product as colorless resinous substance.
$^1$H NMR (CDCl$_3$, Me$_4$Si, 300 MHz) δ8.55 (s, 2H), 7.3-7.5 (m, 6H), 4.54 (s, 2H), 4.04 (d, J=17.4 Hz, 1H), 3.65 (d, J=17.4 Hz, 1H), 3.44 (s, 3H), 2.55 (s, 3H).

Synthetic Example 13

N-(5-Bromo-2-pyrimidinyl)-4-[5-(3,5-dichlorophenyl)-5-trifluoromethyl-4,5-dihydroisoxazole-3-yl]-N-isobutyryl-2-methyl benzoic acid amide (Compound of the present invention No. 5-122)

Step 1: Production of N-(5-bromo-2-pyrimidinyl)-4-[5-(3,5-dichlorophenyl)-5-trifluoromethyl-4,5-dihydroisoxazole-3-yl]-2-methyl benzoic acid amide In a solution of 2.87 g of 2-amino-5-bromopyrimidine in 40 mL of pyridine, 6.00 g of 4-[5-(3,5-dichlorophenyl)-5-trifluoromethyl-4,5-dihydroisoxazol-3-yl]-2-methylbenzoyl-chloride synthesized in Step 4 of Synthetic Example 1 was added at room temperature with stirring, and stirred at the same temperature for 2 days. The solvent was distilled off under reduced pressure, the residue was dissolved in 30 mL of 1,4-dioxane, a solution of 3.09 g of potassium hydroxide in 30 mL of water was added and stirred at room temperature for 3 hours. After the completion of the reaction, 20 mL of hydrochloric acid was added in the reaction mixture under cooling with ice and with stirring, extracted with ethyl acetate (50 mL×1), the organic phese was washed with 50 mL of 3N hydrochloric acid, and dehydrated with and dried over saturated sodium chloride aqueous solution and then anhydrous magnesium sulfate, and the solvent was distilled off under reduced pressure. The residue was purified with neutral alumina column chromatography that was eluated with chloroform to obtain 5.52 g of the aimed product as white crystal.
Melting point 178.0 to 181.0° C.
$^1$H NMR (CDCl$_3$, Me$_4$Si, 300 MHz) δ9.32 (s, 1H), 8.41 (s, 2H), 7.4-7.65 (m, 6H), 4.12 (d, J=17.4 Hz, 1H), 3.73 (d, J=17.4 Hz, 1H), 2.51 (s, 3H).

Step 2: Production of N-(5-bromo-2-pyrimidinyl)-4-[5-(3,5-dichlorophenyl)-5-trifluoromethyl-4,5-dihydroisoxazole-3-yl]-N-isobutyryl-2-methyl benzoic acid amide In a solution of 1.5 g of N-(5-bromo-2-pyrimidinyl)-4-[5-(3,5-dichlorophenyl)-5-trifluoromethyl-4,5-dihydroisoxazol-3-yl]-2-methyl benzoic acid amide, 0.42 g of triethylamine and 0.03 g of 4-(dimethylamino)pyridine in 50 mL of tetrahydrofuran, 0.42 g of isobutyryl chloride was added at room temperature with stirring and stirred at the same temperature for 18 hours. After the completion of the reaction, 50 mL of water was added in the reaction mixture, extracted with ethyl acetate (80 mL×1), 5 g of silica gel was added in the organic phase, stirred and filtered off, and then the solvent was distilled off under reduced pressure. The residue was subjected to crystallization from diethyl ether and hexane to obtain 0.87 g of the aimed product as white crystal.
Melting point 143.0 to 145.0° C.
$^1$H NMR (CDCl$_3$, Me$_4$Si, 300 MHz) δ8.67 (s, 2H), 7.35-7.55 (m, 6H), 4.05 (d, J=17.1 Hz, 1H), 3.66 (d, J=17.1 Hz, 1H), 3.15-3.3 (m, 1H), 2.54 (s, 3H), 1.28 (d, J=6.8 Hz, 6H).

Synthetic Example 14

4-[5-(3,5-Dichlorophenyl)-5-trifluoromethyl-4,5-dihydroisoxazole-3-yl]-2-methyl-N-methyl-N-(5-pyrimidinyl)benzoic acid amide (Compound of the present invention No. 5-164)

Step 1: Production of 4-[5-(3,5-dichlorophenyl)-5-trifluoromethyl-4,5-dihydroisoxazole-3-yl]-2-methyl-N-(5-pyrimidinyl)benzoic acid amide In a test tube for wicrowave reactor, a solution of 0.20 g of 4-[5-(3,5-dichlorophenyl)-5-trifluoro methyl-4,5-dihydroisoxazol-3-yl]-2-methyl benzoic acid amide synthesized in Step 1 of Synthetic Example 19, 0.10 g of 5-bromopyrimidine, 4.8 mg of copper iodide, 0.21 g of potassium phosphate and 4.4 mg of N,N-dimethyl ethylene diamine in 1 mL of 1,4-dioxane was placed, and reacted by use of a microwave focused chemical synthesizer (Discover manufactured by CEM Corporation) at 120 W and 120° C. for 20 minutes. After the completion of the reaction, insoluble material was removed through silica gel column, and the solvent was distilled off under reduced pressure. The residue was purified with silica gel column chromatography that was eluated with ethyl acetate-hexane (1:1) to obtain 0.13 g of the aimed product as white crystal.

Melting point 207.0 to 211.0° C.

$^1$H NMR (CDCl$_3$, Me$_4$Si, 300 MHz) δ9.09 (s, 2H), 9.04 (s, 1H), 7.4-7.7 (m, 7H), 4.11 (d, J=17.4 Hz, 1H), 3.73 (d, J=17.4 Hz, 1H), 2.56 (s, 3H).

Step 2: Production of 4-[5-(3,5-dichlorophenyl)-5-trifluoromethyl-4,5-dihydroisoxazole-3-yl]-2-methyl-N-methyl-N-(5-pyrimidinyl)benzoic acid amide In a solution of 0.25 g of 4-[5-(3,5-dichlorophenyl)-5-trifluoromethyl-4,5-dihydroisoxazole-3-yl]-2-methyl-N-(5-pyrimidinyl)benzoic acid amide in 4 mL of N,N-dimethylformamide, 0.36 g of methyl iodide and 0.35 g of potassium carbonate were added at room temperature with stirring, and stirred at 80° C. for 1 hour. After the completion of the reaction, 10 mL of water was added in the reaction mixture, and extracted with ethyl acetate (20 mL×1), the organic phase was dehydrated with and dried over saturated sodium chloride aqueous solution and then anhydrous sodium sulfate, and the solvent was distilled off under reduced pressure. The residue was purified with silica gel column chromatography that was eluated with ethyl acetate-hexane (1:2) to obtain 0.09 g of the aimed product as white crystal.

Melting point 197.0 to 200.0° C.

$^1$H NMR (CDCl$_3$, Me$_4$Si, 300 MHz) δ8.96 (s, 1H), 8.51 (s, 2H), 7.3-7.6 (m, 6H), 4.04 (d, J=17.4 Hz, 1H), 3.66 (d, J=17.4 Hz, 1H), 3.50 (s, 3H), 2.36 (s, 3H).

Synthetic Example 15

Methyl N-[4-[5-(3,5-dichlorophenyl)-5-trifluoromethyl-4,5-dihydroisoxazole-3-yl]-2-methylbenzoyl]-N-(5-pyrimidinyl) carbamate (Compound of the present invention No. 5-169)

In a solution of 0.25 g of 4-[5-(3,5-dichlorophenyl)-5-trifluoromethyl-4,5-dihydroisoxazole-3-yl]-2-methyl-N-(5-pyrimidinyl)benzoic acid amide synthesized in Step 1 of Synthetic Example 14, 0.15 g of triethylamine and a catalytic amount of 4-(dimethylamino)pyridine in 4 mL of tetrahydrofuran, 0.15 g of methyl chloroformate was added, and stirred at room temperature for 16 hours. After the completion of the reaction, the solvent was distilled off under reduced pressure, 10 mL of ethyl acetate was added and insoluble material was filtered off. The solvent was distilled off under reduced pressure and the residue was purified with silica gel column chromatography that was eluated with ethyl acetate-hexane (1:1) to obtain 0.14 g of the aimed product as white crystal.

Melting point 72.0 to 76.0° C.

$^1$H NMR (CDCl$_3$, Me$_4$Si, 300 MHz) δ9.24 (s, 2H), 8.72 (s, 1H), 7.4-7.6 (m, 6H), 4.12 (d, J=17.4 Hz, 1H), 3.74 (d, J=17.4 Hz, 1H), 3.66 (s, 3H), 2.49 (s, 3H).

Synthetic Example 16

4-[5-(3,5-Dichlorophenyl)-5-trifluoromethyl-4,5-dihydroisoxazole-3-yl]-2-methyl-N-methyl-N-(2-pyradinyl)benzoic acid amide (Compound of the present invention No. 5-131)

Step 1: Production of 4-[5-(3,5-dichlorophenyl)-5-trifluoromethyl-4,5-dihydroisoxazole-3-yl]-2-methyl-N-(2-pyradinyl)benzoic acid amide In a solution of 0.33 g of 2-aminopyradine in 10 mL of pyridine, 1.50 g of 4-[5-(3,5-dichlorophenyl)-5-trifluoromethyl-4,5-dihydroisoxazol-3-yl]-2-methylbenzoyl-chloride synthesized in Step 4 of Synthetic Example 1 was added at room temperature with stirring, and stirred at room temperature for 20 hours. After the completion of the reaction, the solvent was distilled off under reduced pressure, the residue was dissolved in 30 mL of ethyl acetate, and washed with 30 mL of 3N hydrochloric acid, and then the organic phase was dehydrated with and dried over saturated sodium chloride aqueous solution and then anhydrous magnesium sulfate, and the solvent was distilled off under reduced pressure. The residue was purified with neutral alumina column chromatography that was eluated with chloroform to obtain 1.80 g of the aimed product as white crystal.

Melting point 139.0 to 144.0° C.

$^1$H NMR (CDCl$_3$, Me$_4$Si, 300 MHz) δ8.32 (d, J=8.1 Hz, 1H), 8.21 (s, 1H), 7.2-7.7 (m, 8H), 4.11 (d, J=17.4 Hz, 1H), 3.73 (d, J=17.4 Hz, 1H), 2.55 (s, 3H).

Step 2: Production of 4-[5-(3,5-dichlorophenyl)-5-trifluoromethyl-4,5-dihydroisoxazole-3-yl]-2-methyl-N-methyl-N-(2-pyradinyl)benzoic acid amide In a solution of 0.30 g of 4-[5-(3,5-dichlorophenyl)-5-trifluoromethyl-4,5-dihydroisoxazole-3-yl]-2-methyl-N-(2-pyradinyl)benzoic acid amide in 3 mL of N,N-dimethylformamide, 0.04 g of 55% oily sodium hydride was added and stirred at the same temperature for 10 minutes. After ceasing the generation of hydrogen gas, 0.112 g of methyl iodide was added under cooling with ice and with stirring, and continued to stir at room temperature further for 20 hours. After the completion of the reaction, the reaction mixture was poured in 10 mL of ice water, extracted with ethyl acetate (10 mL×1), the organic phase was dehydrated with and dried over saturated sodium chloride aqueous solution and then anhydrous magnesium sulfate, and the solvent was distilled off under reduced pressure. The residue was purified with silica gel column chromatography that was eluated with ethyl acetate-hexane (1:1) to obtain 0.109 g of the aimed product as yellow resinous substance.

$^1$H NMR (CDCl$_3$, Me$_4$Si, 300 MHz) δ8.5 (bs, 1H), 8.37 (dd, J=2.4, 1.2 Hz, 1H), 8.28 (d, J=2.4 Hz, 1H), 7.35-7.55 (m, 5H), 7.18 (d, J=8.1 Hz, 1H), 4.05 (d, J=17.3 Hz, 1H), 3.66 (d, J=17.3 Hz, 1H), 3.51 (s, 3H), 2.38 (s, 3H).

Synthetic Example 17

4-[5-(3,5-Dichlorophenyl)-5-trifluoromethyl-4,5-dihydroisoxazole-3-yl]-N-ethyl-2-methyl benzoic acid anilide (Compound of the present invention No. 5-002)

In a solution of 0.07 g of N-ethylaniline and 0.06 g of pyridine in 4 mL of dichloromethane, a solution of 0.22 g of 4-[5-(3,5-dichlorophenyl)-5-trifluoromethyl-4,5-dihydroisoxazol-3-yl]-2-methylbenzoyl-chloride synthesized in Step 4 of Synthetic Example 1 in 4 mL of dichloromethane was added dropwise at room temperature with stirring. After the completion of the addition dropwise, it was continued to stir at the same temperature further for 10 minutes. After the completion of the reaction, the reaction mixture was poured in 5 mL of water, and 2N hydrochloric acid was added dropwise, and pH of the aqueous phase was adjusted to 2 to 3, and extracted with chloroform (10 mL×2). The organic phase was dehydrated with and dried over saturated sodium chloride aqueous solution and then anhydrous sodium sulfate, and the solvent was distilled off under reduced pressure. The residue was purified with silica gel column chromatography that was eluted with ethyl acetate-hexane (2:3) to obtain 0.24 g of the aimed product as colorless resinous substance.

¹H NMR (CDCl₃, Me₄Si, 300 MHz) δ6.9-7.5 (m, 11H), 3.9-4.05 (m, 3H), 3.58 (d, J=17.7 Hz, 1H), 2.38 (s, 3H), 1.2-1.3 (m, 3H).

Synthetic Example 18

N-Acetyl-N-(5-chloro-2-pyrimidinyl)-2-methyl-4-[5-(3,4,5-trichlorophenyl)-5-trifluoro-methyl-4,5-dihydroisoxazole-3-yl]benzoic acid amide (Compound of the present invention No. 5-170)

Step 1: Production of 4-bromo-N-(5-chloro-2-pyrimidyl)-2-methyl banzoic acid amide In a suspension of 4.0 g of 4-bromo-2-methyl benzoic acid in 30 mL of toluene, 1.9 mL of thionyl chloride and 3 drops of N,N-dimethylformamide were added, and stirred under reflux with heating for 3 hours. After the completion of the reaction, the solvent was distilled off under reduced pressure to obtain 4.3 g of crude gray crystal of 4-bromo-2-methyl-benzoyl-chloride. In a solution of 2.62 g of 2-amino-5-chloropyrimidine in 170 mL of pyridine, 4.3 g of 4-bromo-2-methylbenzoyl-chloride was added under cooling with ice and with stirring, and stirred under reflux with heating for 1.5 hour. After the completion of the reaction, the solvent was distilled off under reduced pressure, the residue was dissolved in 300 mL of ethyl acetate, and washed with 200 mL of 1N hydrochloric acid and 200 mL of water. The organic phase was dehydrated with and dried over saturated sodium chloride aqueous solution and then anhydrous magnesium sulfate, and the solvent was distilled off under reduced pressure. The residual solid was washed with diisopropyl ether to obtain 2.97 g of the aimed product as white crystal.

Melting point 209.0 to 211.0° C.
¹H NMR (CDCl₃, Me₄Si, 300 MHz) δ8.57 (s, 2H), 8.33 (bs, 1H), 7.35-7.5 (m, 3H), 2.52 (s, 3H).

Step 2: Production of N-(5-chloro-2-pyrimidyl)-4-formyl-2-methyl benzoic acid amide In a solution of 0.37 g of 4-bromo-N-(5-chloro-2-pyrimidyl)-2-methyl banzoic acid amide in 10 mL of N,N-dimethylformamide in an autoclave, 0.12 g of sodium formate and 0.04 g of dichlorobis(triphenyl phosphine) palladium (II) were added, and stirred under atmosphere of 1.05 MPa of carbon monoxide at 120° C. for 3 hours. After the completion of the reaction, the reaction mixture was left and cooled to room temperature, the reaction mixture was poured in 50 mL of water, and extracted with ethyl acetate (25 mL×2). The combined organic phases were washed with water, and dehydrated with and dried over saturated sodium chloride aqueous solution and then anhydrous magnesium sulfate, and then the solvent was distilled off under reduced pressure. The residue was purified with silica gel column chromatography that was eluted with ethyl acetate-hexane (gradient of 1:1 to 1:0) to obtain 0.03 g of the aimed product as white crystal.

Melting point 169.0 to 172.0° C.
¹H NMR (CDCl₃, Me₄Si, 300 MHz) δ10.04 (s, 1H), 9.14 (bs, 1H), 8.44 (s, 2H), 7.78 (s, 1H), 7.77 (d, J=7.5 Hz, 1H), 7.62 (d, J=7.5 Hz, 1H), 2.56 (s, 3H).

Step 3: Production of N-acetyl-N-(5-chloro-2-pyrimidinyl)-4-formyl-2-methyl benzoic acid amide In a solution of 35 mg of N-(5-chloro-2-pyrimidyl)-4-formyl-2-methyl benzoic acid amide, 51 mg of triethylamine and 2 mg of 4-(dimethylamino)pyridine in 5 mL of t-butylmethyl ether, 103 mg of acetic anhydride was added at room temperature and stirred at the same temperature for 4 hours. After the completion of the reaction, 10 mL of water was added in the reaction mixture, and extracted with ethyl acetate (15 mL×2). The combined organic phases were dehydrated with and dried over saturated sodium chloride aqueous solution and then anhydrous magnesium sulfate, and then the solvent was distilled off under reduced pressure. The residue was purified with silica gel column chromatography that was eluted with ethyl acetate-hexane (gradient of 1:1 to 1:0) to obtain 26 mg of the aimed product as colorless resinous substance.

¹H NMR (CDCl₃, Me₄Si, 300 MHz) δ 9.94 (s, 1H), 8.57 (s, 2H), 7.66 (s, 1H), 7.57 (d, J=7.8 Hz, 1H), 7.43 (d, J=7.5 Hz, 1H), 2.61 (s, 3H), 2.58 (s, 3H).

Step 4: Production of N-acetyl-N-(5-chloro-2-pyrimidinyl)-4-hydroxyiminomethyl-2-methyl benzoic acid amide In a solution of 26 mg of N-acetyl-N-(5-chloro-2-pyrimidinyl)-4-formyl-2-methyl benzoic acid amide in 4 mL of methanol and 1 mL of water, 10 mg of hydroxylamine hydrochloride was added at room temperature with stirring and stirred at the same temperature for 4 hours. After the completion of the reaction, 10 mL of water was added in the reaction mixture, and extracted with ethyl acetate (10 mL×2). The combined organic phases were dehydrated with and dried over saturated sodium chloride aqueous solution and then anhydrous magnesium sulfate, and then the solvent was distilled off under reduced pressure. The residue was purified with silica gel column chromatography that was eluted with ethyl acetate-hexane (1:1) to obtain 30 mg of the aimed product as colorless resinous substance.

¹H NMR (CDCl₃-DMSO-d₆, Me₄Si, 300 MHz) δ8.56 (s, 2H), 8.01 (s, 1H), 7.86 (bs, 1H), 7.37 (s, 1H), 7.2-7.35 (m, 2H), 2.61 (s, 3H), 2.53 (s, 3H).

Step 5: Production of N-acetyl-N-(5-chloro-2-pyrimidinyl)-2-methyl-4-[5-(3,4,5-trichlorophenyl)-5-trifluoromethyl-4,5-dihydroisoxazole-3-yl]benzoic acid amide In a solution of 30 mg of N-acetyl-N-(5-chloro-2-pyrimidinyl)-4-hydroxyiminomethyl-2-methyl benzoic acid amide in 5 mL of 1,2-dimethoxyethane, 16 mg of N-chlorosuccinic acid imide was added and stirred at 40° C. for 30 minutes. Then the reaction mixture was left and cooled to room temperature, and 24 mg of 3,4,5-trichloro-1-(1-trifluoromethylethenyl)benzene, 10 mg of potassium hydrogen carbonate and 1 drop of water were added, and continued to stir at room temperature for 1.5 hour. After the completion of the reaction, the reaction mixture was poured in 10 mL of water, and extracted with ethyl acetate (10 mL×2). The combined organic phases were dehydrated with and dried over saturated sodium chloride aqueous solution and then anhydrous magnesium sulfate, and then the solvent was distilled off under reduced pressure. The residue was purified with silica gel column chromatography that was eluated with ethyl acetate-hexane (gradient of 1:3 to 1:1) to obtain 11 mg of the aimed product as colorless resinous substance.

¹H NMR (CDCl₃, Me₄Si, 300 MHz) δ8.57 (s, 2H), 7.61 (s, 2H), 7.46 (s, 1H), 4.35 (s, 2H), 4.03 (d, J=17.4 Hz, 1H), 3.62 (d, J=17.4 Hz, 1H), 2.59 (s, 3H), 2.54 (s, 3H).

Synthetic Example 19

Methyl N-[4-[5-(3,5-dichlorophenyl)-5-trifluoromethyl-4,5-dihydroisoxazole-3-yl]-2-methylbenzoyl] carbamate (Compound of the present invention No. 2-003)

Step 1: Production of N-[4-[5-(3,5-dichlorophenyl)-5-trifluoro methyl-4,5-dihydroisoxazole-3-yl]-2-methyl banzoic acid amide In a mixture of 3.0 g of concentrated ammonia water and 15 mL of tetrahydrofuran, a solution of 3.0 g of 4-[5-(3,5-dichlorophenyl)-5-trifluoromethyl-4,5-dihydroisoxazol-3-yl]-2-methylbenzoyl-chloride synthesized in Step 4 of Synthetic Example 1 in 20 mL of tetrahydrofuran was added dropwise under cooling with ice and with stirring. After the completion of the addition dropwise, it was continued to stir further for 18 hours. After the completion of the reaction, the solvent was distilled off under reduced pressure, the residue was dissolved in 50 mL of ethyl acetate, washed with 50 mL of water, and dehydrated with and dried over saturated sodium chloride aqueous solution and then anhydrous sodium sulfate, and the solvent was distilled off under reduced pressure to obtain 2.9 g of the aimed product as orange crystal.
Melting point 162.0 to 164.0° C.
$^1$H NMR (CDCl$_3$, Me$_4$Si, 400 MHz) δ7.45-7.55 (m, 6H), 6.40 (bs, 1H), 6.00 (bs, 1H), 4.09 (d, J=17.0 Hz, 1H), 3.71 (d, J=17.0 Hz, 1H), 2.49 (s, 3H).

Step 2: Production of methyl N-[4-[5-(3,5-dichlorophenyl)-5-trifluoromethyl-4,5-dihydroisoxazole-3-yl]-2-methylbenzoyl]carbamate In a solution of 0.37 g of 4-[5-(3,5-dichlorophenyl)-5-trifluoromethyl-4,5-dihydroisoxazole-3-yl]-2-methyl banzoic acid amide in 4 mL of dichloromethane, 0.13 g of oxazalyl chloride was added, and stirred under reflux with heating for 6 hours. After the completion of the reaction, the solvent was distilled off under reduced pressure, the residue was dissolved in 2 mL of dichloromethane, and added in a solution of 0.03 g of methanol in 1 mL of dichloromethane, and stirred at room temperature for 15 hours. After the completion of the reaction, the solvent was distilled off under reduced pressure. The residue was purified with silica gel column chromatography that was eluated with ethyl acetate-hexane (gradient of 1:4 to 1:2) to obtain 0.37 g of the aimed product as colorless oily substance.
$^1$H NMR (CDCl$_3$, Me$_4$Si, 400 MHz) δ8.15 (bs, 1H), 7.35-7.6 (m, 6H), 4.08 (d, J=17.2 Hz, 1H), 3.79 (s, 3H), 3.71 (d, J=17.2 Hz, 1H), 2.45 (s, 3H).

Synthetic Example 20

N-[4-[5-(3,5-Dichlorophenyl)-5-trifluoromethyl-4,5-dihydroisoxazole-3-yl]-2-methylbenzoyl]thiocarbamic acid-O-methyl (Compound of the present invention No. 2-011)

In a solution of 0.70 g of 4-[5-(3,5-dichlorophenyl)-5-trifluoromethyl-4,5-dihydroisoxazol-3-yl]-2-methylbenzoyl-chloride synthesized in Step 4 of Synthetic Example 1 in 7 mL of tetrahydrofuran, 0.17 g of potassium thiocyanate was added, and stirred at 40° C. for 1 hour. After the completion of the reaction, the reaction mixture was left and cooled to room temperature, and insoluble material was filtered off, the filtrate was added in a solution of 0.15 g of methanol in 6 mL of tetrahydrofuran, and continued to stir at room temperature further for 18 hours. After the completion of the reaction, the solvent was distilled off under reduced pressure. The residue was purified with silica gel column chromatography that was eluated with ethyl acetate-hexane (gradient of 1:4 to 1:1) to obtain 0.54 g of the aimed product as yellow resinous substance.
$^1$H NMR (CDCl$_3$, Me$_4$Si, 400 MHz) δ8.91 (s, 1H), 7.45-7.6 (m, 5H), 7.44 (t, J=1.8 Hz, 1H), 4.15 (s, 3H), 4.09 (d, J=17.2 Hz, 1H), 3.71 (d, J=17.2 Hz, 1H), 2.50 (s, 3H).

Synthetic Example 21

Methyl N-[4-[5-(3,5-dichlorophenyl)-5-trifluoromethyl-4,5-dihydroisoxazole-3-yl]-2-methylbenzoyl]-N-methyl carbamate (Compound of the present invention No. 3-003)

In a solution of 0.29 g of methyl N-[4-[5-(3,5-dichlorophenyl)-5-trifluoromethyl-4,5-dihydroisoxazole-3-yl]-2-methylbenzoyl]carbamate synthesized in Synthetic Example 19 and 0.10 g of potassium carbonate in 5 mL of N,N-dimethylformamide, 0.11 g of methyl iodide was added, and stirred at room temperature for 16 hours. After the completion of the reaction, the reaction mixture was poured in 50 mL of ice water, and extracted with ethyl acetate (50 mL×1), the organic phase was dehydrated with and dried over saturated sodium chloride aqueous solution and then anhydrous sodium sulfate, and the solvent was distilled off under reduced pressure. The residue was purified with silica gel column chromatography that was eluated with ethyl acetate-hexane (gradient of 1:9 to 1:2) to obtain 0.29 g of the aimed product as white crystal.
Melting point 147.0 to 149.0° C.
$^1$H NMR (CDCl$_3$, Me$_4$Si, 400 MHz) δ7.45-7.55 (m, 4H), 7.43 (t, J=1.8 Hz, 1H), 7.21 (d, J=7.9 Hz, 1H), 4.08 (d, J=17.2 Hz, 1H), 3.69 (d, J=17.2 Hz, 1H), 3.64 (s, 3H), 3.37 (s, 3H), 2.33 (s, 3H).

Synthetic Example 22

Methyl N-[4-[5-(3,5-dichlorophenyl)-5-trifluoromethyl-4,5-dihydroisoxazole-3-yl]-2-methylbenzoyl]-N-(2,2,2-trifluoroethoxymethyl)carbamate (Compound of the present invention No. 3-032)

Step 1: Production of 4-[5-(3,5-dichlorophenyl)-5-trifluoromethyl-4,5-dihydroisoxazole-3-yl]-2-methyl-N-(hydroxymethyl)benzoic acid amide In a solution of 7.00 g of 4-[5-(3,5-dichlorophenyl)-5-trifluoromethyl-4,5-dihydroisoxazol-3-yl]-2-methyl benzoic acid amide synthesized in Step 1 of Synthetic Example 19 in 70 mL of 1,4-dioxane, 1.82 g of 37% formalin, 7.00 g of potassium carbonate and 15 mL of water were added at room temperature with stirring, and stirred at the same temperature for 3 hours. After the completion of the reaction, the reaction mixture was diluted by adding 200 mL of ethyl acetate, washed with water (50 mL×1), and then dehydrated with and dried over saturated sodium chloride aqueous solution and then anhydrous magnesium sulfate, filtered through silica gel, and the solvent was distilled off under reduced pressure to obtain 7.00 g of the crude product as white crystal.
Melting point 69.0 to 73.5° C.

Step 2: Production of N-[4-[5-(3,5-dichlorophenyl)-5-trifluoromethyl-4,5-dihydroisoxazole-3-yl]-2-methyl-N-(2,2,2-trifluoroethoxymethyl)benzoic acid amide In a solution of 1.70 g of 4-[5-(3,5-dichlorophenyl)-5-trifluoromethyl-4,5-dihydroisoxazole-3-yl]-2-methyl-N-(hydroxymethyl)benzoic acid amide in 20 mL of dichloromethane, 0.68 g of thionyl chloride was added at room temperature with stirring, and stirred at the same temperature for 2 hours. Then, the solvent was distilled off under reduced pressure, and the residue was dissolved in 10 mL of tetrahydrofuran. 1.50 g of 2,2,2-trifluoroethanol was added dropwise in a suspension of 0.33 g of 60% oily sodium hydride in 30 mL of tetrahydrofuran under cooling with ice and with stirring, and stirred at the same temperature for 10 minutes. Then, in this reaction mixture, the tetrahydrofuran solution of benzoic acid chloride prepared above was added dropwise under cooling with ice and with stirring. After the completion of the addition dropwise, it was continued to stir at room temperature for 1 hour. After the completion of the reaction, 50 mL of water was added in the reaction mixture, extracted with ethyl acetate (70 mL×1), the organic phase was dehydrated with and dried over saturated sodium chloride aqueous solution and then anhydrous magnesium sulfate, and the solvent was distilled off under reduced pressure. The residue was purified with silica gel column chromatography that was eluated with ethyl acetate-hexane (2:3) to obtain 1.20 g of the aimed product as colorless resinous substance.

$^1$H NMR (CDCl$_3$, Me$_4$Si, 400 MHz) δ7.5-7.55 (m, 4H), 7.4-7.5 (m, 2H), 6.64 (t, J=6.4 Hz, 1H), 5.02 (d, J=7.2 Hz, 2H), 4.05-4.15 (m, 3H), 3.70 (d, J=17.4 Hz, 1H), 2.49 (s, 3H).

Step 3: Production of methyl 4-[5-(3,5-dichlorophenyl)-5-trifluoromethyl-4,5-dihydroisoxazole-3-yl]-2-methylbenzoyl]-N-(2,2,2-trifluoroethoxymethyl)carbamate In a solution of 0.50 g of 4-[5-(3,5-dichlorophenyl)-5-trifluoromethyl-4,5-dihydroisoxazole-3-yl]-2-methyl-N-(2,2,2-trifluoroethoxymethyl)benzoic acid amide in 10 mL of N,N-dimethylformamide, 0.0825 g of 60% oily sodium hydride was added under cooling with ice and with stirring, and stirred at room temperature for 10 minutes. Then, 0.268 g of methyl chloroformate was added, and continued to stir at the same temperature for 30 minutes. After the completion of the reaction, the reaction was poured in 50 mL of water, extracted with ethyl acetate (50 mL×1), the organic phase was dehydrated with and dried over saturated sodium chloride aqueous solution and then anhydrous magnesium sulfate, and the solvent was distilled off under reduced pressure. The residue was purified with silica gel column chromatography that was eluated with ethyl acetate-hexane (1:1) to obtain 0.07 g of the aimed product as colorless resinous substance.

$^1$H NMR (CDCl$_3$, Me$_4$Si, 400 MHz) δ7.5-7.6 (m, 4H), 7.43 (t, J=2.0 Hz, 1H), 7.25 (d, J=8.0 Hz, 1H), 5.43 (s, 2H), 4.15 (q, J=8.6 Hz, 2H), 4.09 (d, J=17.2 Hz, 1H), 3.70 (d, J=17.2 Hz, 1H), 3.67 (s, 3H), 2.39 (s, 3H).

Synthetic Example 23

Methyl N-[4-[5-(3,5-dichlorophenyl)-5-trifluoromethyl-4,5-dihydroisoxazole-3-yl]-2-methylbenzoyl]-N-(2-tetrahydrofuranyl)carbamate (Compound of the present invention No. 3-077)

Step 1: Production of 4-[5-(3,5-dichlorophenyl)-5-trifluoromethyl-4,5-dihydroisoxazole-3-yl]-2-methyl-N-(2-tetrahydrofuranyl)benzoic acid amide In a solution of 1.25 g of 4-[5-(3,5-dichlorophenyl)-5-trifluoromethyl-4,5-dihydroisoxazol-3-yl]-2-methyl benzoic acid amide synthesized in Step 1 of Synthetic Example 19 and 0.32 g of 2,3-dihydrofuran in 30 mL of dichloromethane, 0.01 g of p-toluene sulfonic acid monohydrate was added at room temperature with stirring, and stirred at room temperature for 3 days. After the completion of the reaction, 30 mL of saturated sodium hydrogen carbonate aqueous solution was added in the reaction mixture, extracted with ethyl acetate (30 mL×2), the organic phase was dehydrated with and dried over saturated sodium chloride aqueous solution and then anhydrous sodium sulfate, and the solvent was distilled off under reduced pressure. The residue was purified with silica gel column chromatography that was eluated with ethyl acetate-hexane (1:1) to obtain 1.18 g of the aimed product as colorless resinous substance.

$^1$H NMR (CDCl$_3$, Me$_4$Si, 300 MHz) δ7.3-7.55 (m, 6H), 6.49 (d, J=8.1 Hz, 1H), 5.8-5.9 (m, 1H), 4.09 (d, J=17.1 Hz, 1H), 3.8-4.0 (m, 2H), 3.72 (d, J=17.1 Hz, 1H), 2.42 (s, 3H), 2.2-2.4 (m, 1H), 1.8-2.1 (m, 3H).

Step 2: Production of methyl N-[4-[5-(3,5-dichlorophenyl)-5-trifluoromethyl-4,5-dihydroisoxazole-3-yl]-2-methylbenzoyl]-N-(2-tetrahydrofuranyl)carbamate In a suspension of 0.07 g of 55% oily sodium hydride in 10 mL of tetrahydrofuran, a solution of 0.49 g of 4-[5-(3,5-dichlorophenyl)-5-trifluoromethyl-4,5-dihydroisoxazole-3-yl]-2-methyl-N-(2-tetrahydrofuranyl)benzoic acid amide in 5 mL of tetrahydrofuran was added dropwise under cooling with ice and with stirring. After the completion of the addition dropwise, it was stirred at at room temperature for 10 minutes. Then, 0.15 g of methyl chloroformate was added, and continued to stir at the same temperature further for 15 hours. After the completion of the reaction, the reaction was poured in 10 mL of water, extracted with ethyl acetate (20 mL×2), the organic phase was dehydrated with and dried over saturated sodium chloride aqueous solution and then anhydrous magnesium sulfate, and the solvent was distilled off under reduced pressure. The residue was purified with silica gel column chromatography that was eluated with ethyl acetate-hexane (2:3) to obtain 0.13 g of the aimed product as colorless resinous substance.

$^1$H NMR (CDCl$_3$, Me$_4$Si, 300 MHz) δ7.4-7.6 (m, 5H), 7.30 (d, J=8.1 Hz, 1H), 6.23 (dd, J=7.5, 5.7 Hz, 1H), 4.1-4.25 (m, 1H), 4.09 (d, J=17.4 Hz, 1H), 3.85-3.95 (m, 1H), 3.70 (d, J=17.4 Hz, 1H), 3.50 (s, 3H), 2.52 (s, 3H), 2.15-2.4 (m, 3H), 1.9-2.1 (m, 1H).

Synthetic Example 24

Methyl N-[4-[5-(3,5-dichlorophenyl)-5-trifluoromethyl-4,5-dihydroisoxazole-3-yl]-6-iodo-2-methylbenzoyl]carbamate (Compound of the present invention No. 2-019)

In a solution of 0.24 g of methyl N-[4-[5-(3,5-dichlorophenyl)-5-trifluoromethyl-4,5-dihydroisoxazole-3-yl]-2-methylbenzoyl]carbamate synthesized in Synthetic Example 19 and 0.12 g of N-iodosuccinimide in 3 mL of N,N-dimethylformamide, 0.0112 g of palladium (II) acetate was added, and stirred under nitrogen atmosphere at 100° C. for 4 hours. After the completion of the reaction, the reaction mixture was poured in a solution of 0.03 g of sodium thiosulfate in 30 mL of water, and extracted with ethyl acetate (30 mL×1), the organic phase was dehydrated with and dried over saturated sodium chloride aqueous solution and then anhydrous sodium sulfate, and the solvent was distilled off under reduced pressure. The residue was purified with silica gel column chromatography that was eluated with ethyl acetate-hexane (gradient of 0:1 to 3:2) to obtain 0.11 g of the aimed product as colorless resinous substance.

$^1$H NMR (CDCl$_3$, Me$_4$Si, 400 MHz) δ7.91 (bs, 1H), 7.90 (bs, 1H), 7.54 (bs, 1H), 7.50 (bs, 2H), 7.43 (t, J=1.8 Hz, 1H), 4.04 (d, J=17.2 Hz, 1H), 3.76 (s, 3H), 3.66 (d, J=17.2 Hz, 1H), 2.36 (s, 3H).

Synthetic Example 25

O,S-Diemthyl-4-[5-(3,5-dichlorophenyl)-5-trifluoromethyl-4,5-dihydroisoxazole-3-yl]-2-methylbenzoyl imidothiocarbamate (Compound of the present invention No. 8-001)

In a solution of 0.30 g of N-[4-[5-(3,5-dichlorophenyl)-5-trifluoromethyl-4,5-dihydroisoxazole-3-yl]-2-methylbenzoyl]thiocarbamic acid-O-methyl synthesized in Synthetic Example 20 and 0.12 g of potassium carbonate in 4 mL of N,N-dimethylformamide, 0.13 g of methyl iodide was added, and stirred at room temperature for 14 hours. After the completion of the reaction, the reaction mixture was poured in 50 mL of ice water, and extracted with ethyl acetate (50 mL×1), the organic phase was dehydrated with and dried over saturated sodium chloride aqueous solution and then anhydrous sodium sulfate, and the solvent was distilled off under reduced pressure. The residue was purified with silica gel column chromatography that was eluated with ethyl acetate-hexane (gradient of 1:4 to 1:1) to obtain 0.20 g of the aimed product as yellow resinous substance.

$^1$H NMR (CDCl$_3$, Me$_4$Si, 400 MHz) δ8.09 (d, J=8.2 Hz, 1H), 7.45-7.6 (m, 4H), 7.42 (t, J=1.8 Hz, 1H), 4.10 (d, J=17.2 Hz, 1H), 4.08 (s, 3H), 3.73 (d, J=17.2 Hz, 1H), 2.67 (s, 3H), 2.41 (s, 3H).

Synthetic Example 26

N-Carbamoyl-4-[5-(3,5-dichlorophenyl)-5-trifluoromethyl-4,5-dihydroisoxazole-3-yl]-2-methyl benzoic acid amide (Compound of the present invention No. 4-002)

In a solution of 0.36 g of 4-[5-(3,5-dichlorophenyl)-5-trifluoromethyl-4,5-dihydroisoxazol-3-yl]-2-methyl benzoic acid amide synthesized in Step 1 of Synthetic Example 19 in 4 mL of dichloromethane, 0.13 g of oxalyl chloride was added and stirred under reflux with heating for 6 hours. After the completion of the reaction, the solvent was distilled off under reduced pressure, the residue was dissolved in 5 mL of dichloromethane, and 0.11 g of concentrated ammonia water was added dropwise. After the completion of the addition dropwise, the mixture was stirred at room temperature for 15 hours. After the completion of the reaction, the solvent was distilled off under reduced pressure, and dissolved in 25 mL of ethyl acetate, washed with water, and dehydrated with and dried over saturated sodium chloride aqueous solution and then anhydrous sodium sulfate, and the solvent was distilled off under reduced pressure. The residual solid was washed with chloroform to obtain 0.26 g of the aimed product as pale yellow crystal.

Melting point 201.0 to 205.0° C.

$^1$H NMR (CDCl$_3$, Me$_4$Si, 400 MHz) δ8.30 (bs, 2H), 7.5-7.6 (m, 5H), 7.44 (t, J=1.8 Hz, 1H), 5.38 (bs, 1H), 4.09 (d, J=17.2 Hz, 1H), 3.71 (d, J=17.2 Hz, 1H), 2.52 (s, 3H).

Synthetic Example 27

N-Chloroacetyl-N'-[4-[5-(3,5-dichlorophenyl)-5-trifluoromethyl-4,5-dihydroisoxazole-3-yl]-2-methylbenzoyl]-N'-methyl urea (Compound of the present invention No. 4-006)

Step 1: Production of 4-[5-(3,5-dichlorophenyl)-5-trifluoromethyl-4,5-dihydroisoxazole-3-yl]-2-methyl-N-methyl benzoic acid amide In a mixture of 2.3 g of 40% methylamine aqueous solution and 10 mL of tetrahydrofuran, a solution of 1.0 g of 4-[5-(3,5-dichlorophenyl)-5-trifluoromethyl-4,5-dihydroisoxazol-3-yl]-2-methylbenzoyl-chloride synthesized in Step 4 of Synthetic Example 1 in 10 mL of tetrahydrofuran was added dropwise under cooling with ice and with stirring. After the completion of the addition dropwise, it was continued to stir further for 18 hours. After the completion of the reaction, the solvent was distilled off under reduced pressure, the resiudue was dissolved in 100 mL of ethyl acetate, washed with 50 mL of water, then dehydrated with and dried over saturated sodium chloride aqueous solution and then anhydrous sodium sulfate, and the solvent was distilled off under reduced pressure to obtain 1.0 g of the aimed product as pale yellow crystal.

Melting point 184.0 to 185.0° C.

$^1$H NMR (CDCl$_3$, Me$_4$Si, 300 MHz) δ7.35-7.6 (m, 6H), 5.7-5.9 (m, 1H), 4.08 (d, J=17.1 Hz, 1H), 3.69 (d, J=17.1 Hz, 1H), 3.01 (d, J=4.8 Hz, 3H), 2.47 (s, 3H).

Step 2: Production of N-chloroacetyl-N'-[4-[5-(3,5-dichlorophenyl)-5-trifluoromethyl-4,5-dihydroisoxazole-3-yl]-2-methylbenzoyl]-N'-methyl urea In a solution of 0.86 g of 4-[5-(3,5-dichlorophenyl)-5-trifluoromethyl-4,5-dihydroisoxazole-3-yl]-2-methyl-N-methyl benzoic acid amide in 10 mL of toluene, 0.36 g of chloroacetyl isocyanate was added, and stirred at 50° C. for 24 hours. After the completion of the reaction, the solvent was distilled off under reduced pressure. The residue was purified with silica gel column chromatography that was eluated with ethyl acetate-hexane (gradient of 0:1 to 3:2) to obtain 0.93 g of the aimed product as colorless oily substance.

$^1$H NMR (CDCl$_3$, Me$_4$Si, 400 MHz) δ12.27 (s, 1H), 7.45-7.65 (m, 4H), 7.42 (t, J=1.8 Hz, 1H), 7.27 (d, J=7.9 Hz, 1H), 4.46 (s, 2H), 4.07 (d, J=17.2 Hz, 1H), 3.69 (d, J=17.2 Hz, 1H), 3.07 (s, 3H), 2.36 (s, 3H).

Synthetic Example 28

N-Carbamoyl-4-[5-(3,5-dichlorophenyl)-5-trifluoromethyl-4,5-dihydroisoxazole-3-yl]-2-methyl-N-methyl benzoic acid amide (Compound of the present invention No. 4-003)

A solution of 0.40 g of N-chloroacetyl-N'-[4-[5-(3,5-dichlorophenyl)-5-trifluoromethyl-4,5-dihydroisoxazole-3- yl]-2-methylbenzoyl]-N'-methyl urea synthesized in Synthetic Example 27 and 0.04 g of triethylamine in 4 mL of methanol was stirred at room temperature for 2 hours. After the completion of the reaction, the solvent was distilled off under reduced pressure. The residue was purified with silica gel column chromatography that was eluated with ethyl acetate-hexane (gradient of 1:4 to 4:1) to obtain 0.31 g of the aimed product as white crystal.

Melting point 181.0 to 183.0° C.
$^1$H NMR (CDCl$_3$, Me$_4$Si, 400 MHz) δ8.88 (bs, 1H), 7.5-7.6 (m, 4H), 7.43 (t, J=1.8 Hz, 1H), 7.28 (d, J=7.9 Hz, 1H), 5.76 (bs, 1H), 4.06 (d, J=17.2 Hz, 1H), 3.72 (d, J=17.2 Hz, 1H), 3.04 (s, 3H), 2.36 (s, 3H).

Synthetic Example 29

N-4-[5-(3,5-dichlorophenyl)-5-trifluoromethyl-4,5-dihydroisoxazole-3-yl]-2-methylbenzoyl]-N'-ethyl-N'-methoxycarbonyl urea (Compound of the present invention No. 4-011)

In a solution of 0.50 g of N-[4-[5-(3,5-dichlorophenyl)-5-trifluoromethyl-4,5-dihydroisoxazol-3-yl]-2-methyl benzoyl]-N'-ethyl urea synthesized similarly to Synthetic Example 26 in 4 mL of tetrahydrofuran, 4 mL of 1M tetrahydrofuran solution of lithium hexamethyl disilazane was added at −78° C. with stirring, and stirred at the same temperature for 30 minutes. Then, 0.12 g of methyl chloroformate was added in the reaction mixture at −78° C. with stirring. After the completion of the addition dropwise, it was continued to stir further for 18 hours while the temperature was slowly raised to room temperature. After the completion of the reaction, 30 mL of ice water was added, and extracted with ethyl acetate (30 mL×2). The organic phase was dehydrated with and dried over saturated sodium chloride aqueous solution and anhydrous sodium sulfate, and the solvent was distilled off under reduced pressure. The residue was purified with silica gel column chromatography that was eluated with ethyl acetate-hexane (gradient of 0:1 to 1:2) to obtain 0.29 g of the aimed product as colorless resinous substance.

$^1$H NMR (CDCl$_3$, Me$_4$Si, 400 MHz) δ12.01 (s, 1H), 7.5-7.65 (m, 5H), 7.43 (t, J=1.8 Hz, 1H), 4.11 (d, J=17.2 Hz, 1H), 3.89 (s, 3H), 3.86 (q, J=7.1 Hz, 2H), 3.74 (d, J=17.2 Hz, 1H), 2.53 (s, 3H), 1.21 (t, J=7.1 Hz, 3H).

Synthetic Example 30

4-[5-(3,5-Dichlorophenyl)-5-trifluoromethyl-4,5-dihydroisoxazole-3-yl]-N-(dimethyl-aminomethylidene)-2-methyl benzamide (Compound of the present invention No. 8-006)

A mixture of 6.0 g of 4-[5-(3,5-dichlorophenyl)-5-trifluoromethyl-4,5-dihydroisoxazole-3-yl]-2-methyl benzoic acid amide synthesized in Step 1 of Synthetic Example 19 and 50 mL of N,N-dimethylformamide dimethylacetal were stirred at 120° C. for 1.5 hour. After the completion of the reaction, the solvent was distilled off under reduced pressure. The residual solid was washed with ethyl acetate-hexane mixture (1:20) to obtain 6.2 g of the aimed product as pale yellow crystal.

Melting point 146.0 to 147.0° C.
$^1$H NMR (CDCl$_3$, Me$_4$Si, 400 MHz) δ8.60 (s, 1H), 8.11 (d, J=8.0 Hz, 1H), 7.45-7.55 (m, 4H), 7.4-7.45 (m, 1H), 4.10 (d, J=17.4 Hz, 1H), 3.71 (d, J=17.4 Hz, 1H), 3.21 (s, 3H), 3.19 (s, 3H), 2.64 (s, 3H).

Synthetic Example 31

4-[5-(3,5-Dichlorophenyl)-5-trifluoromethyl-4,5-dihydroisoxazole-3-yl]-N-(ethoxyimino-methyl)-2-methyl benzoic acid amide (Compound of the present invention No. 6-005)

in a solution of 0.25 g of ethoxyamine hydrochloride in 4 mL of water and 8 mL of acetic acid, a solution of 0.20 g of sodium hydroxide in 4 mL of water was added, and then 5 mL of 1,4-dioxane solution of 0.62 g of 4-[5-(3,5-dichlorophenyl)-5-trifluoromethyl-4,5-dihydroisoxazole-3-yl]-N-(dimethylaminomethylidene)-2-methyl benzamide synthesized in Synthetic Example 30 was added dropwise at room temperature with stirring. After the completion of the addition dropwise, it was continued to stir at the same temperature further for 2 hours. After the completion of the reaction, the solvent was distilled off under reduced pressure, 50 mL of ethyl acetate was added in the residue, and washed with water. The organic phase was dehydrated with and dried over saturated sodium chloride and then anhydrous sodium sulfate, the solvent was distilled off under reduced pressure. The residue was purified with silica gel column chromatography that was eluated with ethyl acetate-hexane (2:3) to obtain 0.44 g of the aimed product as white crystal.

Melting point 143.0 to 146.0° C.
$^1$H NMR (CDCl$_3$, Me$_4$Si, 400 MHz) δ8.59 and 8.50 (d, J=9.2 Hz, 1H), 7.78 and 7.70 (d, J=9.2 Hz, 1H), 7.5-7.65 (m, 6H), 4.05-4.2 (m, 3H), 3.71 (d, J=17.4 Hz, 1H), 2.54 (s, 3H), 1.28 (t, J=7.0 Hz, 3H).

Synthetic Example 32

(Z)-4-[5-(3,5-Dichlorophenyl)-5-trifluoromethyl-4,5-dihydroisoxazole-3-yl]-N-(methoxyiminomethyl)-2-methylbenzoic acid amide (Compound of the present invention No. 6-004)

After dissolving 1.8 g of a geometrical isomer of N-[4-[5-(3,5-dichlorophenyl)-5-trifluoromethyl-4,5-dihydroisoxazol-3-yl]-N-(methoxyiminomethyl)-2-methylbenzoic acid amide synthesized similarly to Synthetic Example 31 in 15 mL of acetonirile, the resulting solution was stirred at room temperature. It was continued to stir for 4 days, and then the solvent was distilled off under reduced pressure, the residual solid was re-crystallized from a small amount of acetonitrile to obtain 1.4 g of the aimed product (E/Z=2:98) as white crystal.

Melting point 167.0 to 169.0° C.
$^1$H NMR (CDCl$_3$, Me$_4$Si, 300 MHz) δ8.49 (d, J=9.3 Hz, 1H), 7.77 (d, J=9.3 Hz, 1H), 7.45-7.65 (m, 6H), 4.09 (d, J=17.4 Hz, 1H), 3.90 (s, 3H), 3.71 (d, J=17.4 Hz, 1H), 2.53 (s, 3H).

Synthetic Example 33

4-[5-(3,5-Dichlorophenyl)-5-trifluoromethyl-4,5-dihydroisoxazole-3-yl]-N-(methoxyiminomethyl)-N-methyl-2-methylbenzoic acid amide (Compounds of the present invention Nos. 7-002 and 7-003)

In a solution of 0.20 g of 4-[5-(3,5-dichlorophenyl)-5-trifluoromethyl-4,5-dihydroisoxazol-3-yl]-N-(methoxyiminomethyl)-2-methylbenzoic acid amide synthesized similarly to Synthetic Example 31 and 0.072 g of potassium hydroxide in 10 mL of N,N-dimethylformamide, 0.09 g of methyl iodide was added, and stirred at room temperature for 1 hour. After the completion of the reaction, the reaction mixture was poured in 20 mL of ice water, extracted with ethyl acetate (50 mL×1), the organic phase was dehydrated with and dried over saturated sodium chloride aqueous solution and then anhydrous sodium sulfate, and the solvent was distilled off under reduced pressure. The residue was purified with silica gel column chromatography that was eluated with ethyl acetate-hexane (2:3) to obtain 0.036 g of isomer (1) and 0.086 g of isomer (2) as the aimed products of colorless resinous substance.

$^1$H NMR (CDCl$_3$, Me$_4$Si, 300 MHz)

No. 7-002; δ7.86 (s, 1H), 7.2-7.6 (m, 6H), 4.09 (d, J=18.0 Hz, 1H), 3.75 (s, 3H), 3.70 (d, J=18.0 Hz, 1H), 3.35 (s, 3H), 2.30 (s, 3H).

No. 7-003; δ7.2-7.6 (m, 6H), 6.72 (s, 1H), 4.08 (d, J=18.0 Hz, 1H), 3.86 (s, 3H), 3.70 (d, J=18.0 Hz, 1H), 3.39 (s, 3H), 2.34 (s, 3H).

Synthetic Example 34

Methyl 4-[5-(3,5-dichlorophenyl)-5-trifluoromethyl-4,5-dihydroisoxazole-3-yl]-2-methylbenzoyl]-N-(methoxyiminomethyl) carbamate (Compounds of the present invention Nos. 7-004 and 7-005)

In a solution of 0.2 g of N-[4-[5-(3,5-dichlorophenyl)-5-trifluoromethyl-4,5-dihydroisoxazol-3-yl]-N-(methoxyiminomethyl)-2-methylbenzoic acid amide synthesized similarly to Synthetic Example 31 and 1.0 g of potassium carbonate in 10 mL of N,N-dimethylformamide, 0.5 g of methyl chloroformate was added, and stirred at room temperature for 24 hours. After the completion of the reaction, the reaction mixture was poured in 20 mL of ice water, extracted with ethyl acetate (50 mL×1), the organic phase was dehydrated with and dried over saturated sodium chloride aqueous solution and then anhydrous sodium sulfate, and the solvent was distilled off under reduced pressure. The residue was purified with silica gel column chromatography that was eluated with ethyl acetate-hexane (2:3) to obtain 0.07 g of isomer (1) and 0.12 g of isomer (2) as the aimed products of colorless resinous substance.

$^1$H NMR (CDCl$_3$, Me$_4$Si, 300 MHz)

No. 7-004; δ7.85 (bs, 1H), 7.5-7.6 (m, 4H), 7.4-7.45 (m, 1H), 7.25-7.3 (m, 1H), 4.08 (d, J=17.4 Hz, 1H), 3.65-3.9 (m, 4H), 3.34 (s, 3H), 2.29 (s, 3H).

No. 7-005; δ7.5-7.6 (m, 4H), 7.4-7.5 (m, 1H), 7.25-7.3 (m, 1H), 6.72 (bs, 1H), 4.08 (d, J=17.4 Hz, 1H), 3.84 (s, 3H), 3.70 (d, J=17.4 Hz, 1H), 3.36 (s, 3H), 2.34 (s, 3H).

Synthetic Example 35

(Z)-4-[5-(3,5-Dichlorophenyl)-5-trifluoromethyl-4,5-dihydroisoxazole-3-yl]-2-ethyl-N-(methoxyiminomethyl)benzoic acid amide (Compound of the present invention No. 6-020)

Step 1: Production of methyl 4-[5-(3,5-dichlorophenyl)-5-trifluoromethyl-4,5-dihydroisoxazole-3-yl]-2-ethyl benzoate In a solution of 0.50 g of methyl 2-bromo-4-[5-(3,5-dichlorophenyl)-5-trifluoromethyl-4,5-dihydroisoxazole-3-yl]benzoate and 0.03 g of 1,1'-bis(diphenylphosphino) ferrocene dichloropalladium (11), 2 mL a solution of 1.0M zinc diethyl in hexane was added under an atmosphere of nitrogen, and then stirred under reflux with heating for 1 hour. After the completion of the reaction, 30 mL of 1N hydrochloric acid was added in the reaction mixture, and extracted with ethyl acetate (40 mL×1). The organic phase was dehydrated with and dried over saturated sodium chloride and then anhydrous sodium sulfate, filtered through silica gel, and the solvent was distilled off under reduced pressure. The residue was purified with silica gel column chromatography that was eluated with ethyl acetate-hexane (1:4) to obtain 0.21 g of the aimed product as pale yellow resinous substance.

$^1$H NMR (CDCl$_3$, Me$_4$Si, 300 MHz) δ7.90 (d, J=8.4 Hz, 1H), 7.4-7.7 (m, 5H), 4.11 (d, J=17.4 Hz, 1H), 3.91 (s, 3H), 3.72 (d, J=17.4 Hz, 1H), 3.50 (q, J=7.5 Hz, 2H), 1.25 (t, J=7.5 Hz, 3H).

Step 2: Production of 4-[5-(3,5-dichlorophenyl)-5-trifluoromethyl-4,5-dihydroisoxazole-3-yl]-2-ethyl benzoic acid amide In a solution of 0.21 g of methyl 4-[5-(3,5-dichlorophenyl)-5-trifluoromethyl-4,5-dihydroisoxazole-3-yl]-2-ethyl benzoate in 5 mL of etanol, a solution of 0.10 g of sodium hydroxide in 3 mL of water was added, and stirred under reflux with heating for 3 hours. After the completion of the reaction, the solvent was distilled off under reduced pressure, 10 mL of 1N hydrochloric acid was added, and extracted with ethyl acetate (40 mL×1). The organic phase was dehydrated with and dried over saturated sodium chloride and then anhydrous sodium sulfate, filtered through silica gel, and the solvent was distilled off under reduced pressure. The residue was dissolved in 10 mL of dichloromethane, and 0.10 g of oxalyl chloride and 0.03 g of N,N-dimethylformamide were added, and stirred at room temperature for 30 minutes. After the completion of the reaction, the solvent was distilled off under reduced pressure, the residue was dissolved in 5 mL of tetrahydrofuran, and 10 mL of concentrated ammonia water was added dropwise at room temperature with stirring. The completion of the addition dropwise, it was continued to stir further for 30 minutes. After the completion of the reaction, 30 mL of water was added in the reaction mixture, extracted with ethyl acetate (30 mL×1), the organic phase was dehydrated with and dried over saturated sodium chloride and then anhydrous sodium sulfate, and the solvent was distilled off under reduced pressure to obtain 0.18 g of the crude aimed product as yellow resinous substance.

$^1$H NMR (CDCl$_3$, Me$_4$Si, 300 MHz) δ7.4-7.6 (m, 6H), 5.70 (bs, 2H), 4.09 (d, J=17.4 Hz, 1H), 3.70 (d, J=17.4 Hz, 1H), 2.88 (q, J=7.8 Hz, 2H), 1.26 (t, J=7.8 Hz, 3H).

Step 3: Production of (Z)-4-[5-(3,5-dichlorophenyl)-5-trifluoromethyl-4,5-dihydroisoxazole-3-yl]-2-ethyl-N-(methoxyiminomethyl)benzoic acid amide A mixture of 0.18 g of 4-[5-(3,5-dichlorophenyl)-5-trifluoromethyl-4,5-dihydroisoxazole-3-yl]-2-ethyl benzoic acid amide and 10 mL of N,N-dimethylformamide dimethylacetal was stirred under reflux with heating for 4 hours. After the completion of the reaction, the solvent was distilled off under reduced pressure, the residue was dissolved in 5 mL of 1,4-dioxane, and added dropwise in a solution of 0.10 g of methoxyamine hydrochloride and 0.10 g of sodium hydroxide in 4 mL of water and 4 mL of acetic acid. After the completion of the addition dropwise, it was continued to stir at room temperature further for 30 minutes. After the completion of the reaction, 10 mL of water was added in the reaction mixture, and extracted with ethyl acetate (40 mL×1). The organic phase was dehydrated with and dried over saturated sodium chloride and then anhydrous sodium sulfate, and the solvent was distilled off under reduced pressure. The residue was purified with silica gel column chromatography that was eluated with ethyl acetate-hexane (2:3) to obtain 0.15 g of the aimed product as colorless resinous substance.

$^1$H NMR (CDCl$_3$, Me$_4$Si, 300 MHz) δ8.47 (d, J=9.0 Hz, 1H), 8.02 (s, 1H), 7.77 (d, J=9.0 Hz, 1H), 7.4-7.65 (m, 5H), 4.09 (d, J=17.4 Hz, 1H), 3.90 (s, 3H), 3.71 (d, J=17.4 Hz, 1H), 2.87 (q, J=7.8 Hz, 2H), 1.26 (t, J=7.8 Hz, 3H).

Synthetic Example 36

(Z)-4-[5-(3,5-Dichlorophenyl)-5-trifluoromethyl-4,5-dihydroisoxazole-3-yl]-2-difluoromethoxy-N-(ethoxyiminomethyl)benzoic acid amide (Compound of the present invention No. 6-023)

Step 1: Production of 5-(3,5-dichlorophenyl)-3-(3-difluoromethoxy-4-nitrophenyl)-5-trifluoromethyl-4,5-dihydroisoxazole In a solution of 0.30 g of 5-(3,5-dichlorophenyl)-3-(3-hydroxy-4-nitrophenyl)-5-trifluoromethyl-4,5-dihydroisoxazole in 20 mL of acetonitrile and 3 mL of water, 0.218 g of ethyl bromodifluoroacetate and 0.293 g of potassium carbonate were added, and stirred at 80° C. for 1 hour. After the completion of the reaction, the solvent was distilled off under reduced pressure, 10 mL of water was added in the residue, and extracted with ethyl acetate (20 mL×1). The organic phase was washed with water, and then dehydrated with and dried over saturated sodium chloride and then anhydrous sodium sulfate, and the solvent was distilled off under reduced pressure to obtain the crude aimed product as yellow resinous substance. The resulting product was used as such without purification for the next step.

$^1$H NMR (CDCl$_3$, Me$_4$Si, 300 MHz) δ7.45-8.05 (m, 6H), 6.66 (t, J=72.3 Hz, 1H), 4.08 (d, J=17.4 Hz, 1H), 3.71 (d, J=17.4 Hz, 1H).

Step 2: Production of 3-(4-amino-3-difluoromethoxyphenyl)-5-(3,5-dichlorophenyl)-5-trifluoromethyl-4,5-dihydroisoxazole In a mixture of 5.0 mL of water, 1.0 mL of acetic acid and 1.22 g of reduced iron, a solution of 2.0 g of 5-(3,5-dichlorophenyl)-3-(3-difluoromethoxy-4-nitrophenyl)-5-trifluoromethyl-4,5-dihydroisoxazole in 15 mL of ethyl acetate was added dropwise at 75° C. under stirring with heating. After the completion of the addition dropwise, it was stirred at the same temperature for 2.5 hours. After the completion of the reaction, the reaction mixture was subjected to hot filtration through Celite, 20 ml of water was added in the filtrate, extracted with ethyl acetate (20 ml×2). The combined organic phases were washed with 10 ml of saturated sodium hydrogen carbonate aqueous solution, and then dehydrated with and dried over saturated sodium chloride aqueous solution and then anhydrous sodium sulfate, and then the solvent was distilled off under reduced pressure to obtain 1.7 g of the crude aimed product as yellow resinous substance. The resulting product was used as such without purification for the next step.

$^1$H NMR (CDCl$_3$, Me$_4$Si, 300 MHz) δ6.7-7.5 (m, 6H), 6.50 (t, J=74.1 Hz, 1H), 4.23 (bs, 2H), 4.02 (d, J=17.4 Hz, 1H), 3.63 (d, J=17.4 Hz, 1H).

Step 3: Production of 5-(3,5-dichlorophenyl)-3-(3-difluoromethoxy-4-iodophenyl)-5-trifluoromethyl-4,5-dihydroisoxazole In a solution of 1.00 g of 3-(4-amino-3-difluoromethoxyphenyl)-5-(3,5-dichlorophenyl)-5-trifluoromethyl-4,5-dihydroisoxazole in a mixed solution of 10 mL of acetonitrile and 10 mL of water, 5 mL of concentrated hydrochloric acid was added, and a solution of 0.20 g of sodium nitrite in 2 mL of water was added dropwise slowly under cooling with ice and with stirring. After the completion of the addition dropwise, it was continued to stir at the same temperature further for 20 minutes. Then, a solution of 0.47 g of potassium iodide in 1 mL of water was added dropwise carefully. After the completion of the addition dropwise, it was continued to stir at room temperature further for 30 minutes. After the completion of the reaction, 0.041 g of urea was added in the reaction mixture, stirred at room temperature for 30 minutes, then a solution of 0.10 g of sodium sulfite in 5 mL of water was added, and extracted with ethyl acetate (20 mL×2). The combined organic phases were washed with water, and then dehydrated with and dried over saturated sodium chloride aqueous solution and then anhydrous sodium sulfate, and the solvent was distilled off under reduced pressure. The residue was purified with silica gel column chromatography that were eluated with ethyl acetate-hexane (1:9) to obtain 0.60 g of the aimed product as yellow resinous substance.

$^1$H NMR (CDCl$_3$, Me$_4$Si, 300 MHz) δ7.2-7.95 (m, 6H), 6.57 (t, J=73.2 Hz, 1H), 4.05 (d, J=17.4 Hz, 1H), 3.66 (d, J=17.4 Hz, 1H).

Step 4: Production of 4-[5-(3,5-dichlorophenyl)-5-trifluoromethyl-4,5-dihydroisoxazol-3-yl]-2-difluoromethoxy benzoic acid amide In a solution of 0.30 g of 5-(3,5-dichlorophenyl)-3-(3-difluoromethoxy-4-iodophenyl)-5-trifluoromethyl-4,5-dihydroisoxazole, 0.80 mL of 1,1,1,3,3,3-hexamethyldisilazane and 0.20 mL of diisopropylethylamine in 10 ml of N,N-dimethylformamide, 0.062 g of 1,1'-bis(diphenylphosphino)ferrocene and 0.013 g of palladium (II) acetate were added, and stirred under carbon monoxide atmosphere at 90° C. for 12 hours and then at room temperature for 3 days. After the completion of the reaction, 10 mL of 1N hydrochloric acid was added, and stirred for 10 minutes, extracted with ethyl acetate (10 mL×2). The combined organic phases were washed with water, and then dehydrated with and dried over saturated sodium chloride aqueous solution and then anhydrous sodium sulfate, and the solvent was distilled off under reduced pressure. The residue was purified with silica gel column chromatography that were eluated with ethyl acetate-hexane (2:3) to obtain 0.30 g of the aimed product as yellow resinous substance.

$^1$H NMR (CDCl$_3$, Me$_4$Si, 300 MHz) δ7.35-8.25 (m, 6H), 6.97 (bs, 1H), 6.70 (t, J=72.3 Hz, 1H), 6.27 (bs, 1H), 4.10 (d, J=17.1 Hz, 1H), 3.72 (d, J=17.1 Hz, 1H).

Step 5: Production of (Z)-4-[5-(3,5-dichlorophenyl)-5-trifluoromethyl-4,5-dihydroisoxazole-3-yl]-2-difluoromethoxy-N-(ethoxyiminomethyl)benzoic acid amide A mixture of 0.15 g of 4-[5-(3,5-dichlorophenyl)-5-trifluoromethyl-4,5-dihydroisoxazol-3-yl]-2-difuoro-methoxy benzoic acid amide and 10 mL of N,N-dimethylformamide dimethylacetal was stirred at 120° C. for 1.5 hour. After the completion of the reaction, the residue was dissolved in 3 mL of 1,4-dioxane, a solution of 0.026 g of ethoxyamine hydrochloride in 3 mL of water was added dropwise. After the completion of the addition dropwise, it was continued to stir at room temperature further for 30 minutes. After the completion of the reaction, 10 mL of water was added in the reaction mixture, and extracted with ethyl acetate (10 mL×1). The organic phase was dehydrated with and dried over saturated sodium chloride aqueous solution and then anhydrous sodium sulfate, and the solvent was distilled off under reduced pressure. The residue was purified with silica gel column chromatography that were eluated with ethyl acetate-hexane (1:2) to obtain 0.07 g of the aimed product as colorless resinous substance.

$^1$H NMR (CDCl$_3$, Me$_4$Si, 300 MHz) δ9.95 (d, J=9.0 Hz, 1H), 8.30 (d, J=9.0 Hz, 1H), 7.4-7.85 (m, 6H), 6.74 (t, J=72.0 Hz, 1H), 4.18 (q, J=7.2 Hz, 2H), 4.09 (d, J=17.7 Hz, 1H), 3.71 (d, J=17.7 Hz, 1H), 1.31 (t, J=7.2 Hz, 3H).

Synthetic Example 37

4-[5-(3,5-Dichlorophenyl)-5-trifluoromethyl-4,5-dihydroisoxazole-3-yl]-N-(methoxyiminomethyl)-2-methoxymethyl benzoic acid amide (Compound of the present invention No. 6-031)

Step 1: Production of methyl 2-bromomethyl-4-[5-(3,5-dichlorophenyl)-5-trifluoromethyl-4,5-dihydroisoxazole-3-yl]benzoate In a solution of 3.25 g of methyl 4-[5-(3,5-dichlorophenyl)-5-trifluoromethyl-4,5-dihydroisoxazole-3-yl]-2-methyl benzoate in 15 mL of 1,2-dichloroethane, 1.34 g of N-bromosuccinimide and 0.19 g of 2,2'-azobisisobutyronitrile were added, and stirred under reflux with heating for 1 hour. After the completion of the reaction, the reaction mixture was left and cooled to room temperature, and the solvent was distilled off under reduced pressure. The residue was purified with silica gel column chromatography that was eluated with ethyl acetate-hexane (1:2) to obtain 3.40 g of the aimed product as brown resinous substance.

$^1$H NMR (CDCl$_3$, Me$_4$Si, 300 MHz) δ8.0-8.05 (m, 1H), 7.75 (s, 1H), 7.6-7.7 (m, 1H), 7.51 (s, 2H), 7.4-7.5 (m, 1H), 4.95 (s, 2H), 4.12 (d, J=17.4 Hz, 1H), 3.96 (s, 3H), 3.73 (d, J=17.4 Hz, 1H).

Step 2: Production of methyl 4-[5-(3,5-dichlorophenyl)-5-trifluoromethyl-4,5-dihydroisoxazole-3-yl]-2-methoxymethyl benzoate In a solution of 1.70 g of methyl 2-bromomethyl-4-[5-(3,5-dichlorophenyl)-5-trifluoromethyl-4,5-dihydroisoxazole-3-yl]benzoate in 20 mL of methanol, 0.41 g of potassium tert-butoxide was added, and stirred at room temperature for 23 hours. After the completion of the reaction, the solvent was distilled off under reduced pressure, and 20 mL of water was added in the reaction mixture, and extracted with ethyl acetate (20 mL×2). The combined organic phases were washed with 20 mL of 2N hydrochloric acid and then dehydrated with and dried over saturated sodium chloride aqueous solution and then anhydrous sodium sulfate, and the solvent was distilled off under reduced pressure. The residue was purified with silica gel column chromatography that was eluated with ethyl acetate-hexane (1:4) to obtain 1.12 g of the aimed product as colorless resinous substance.

Step 3: Production of 4-[5-(3,5-dichlorophenyl)-5-trifluoromethyl-4,5-dihydroisoxazole-3-yl]-2-methoxymethyl benzoic acid In a solution of 1.12 g of methyl 4-[5-(3,5-dichlorophenyl)-5-trifluoromethyl-4,5-dihydroisoxazole-3-yl]-2-methoxymethyl benzoate in 30 mL of ethanol, a solution of 0.41 g of potassium hydroxide in 15 mL of water was added, and stirred under reflux with heating for 30 minutes. After the completion of the reaction, the reaction mixture was left and cooled to room temperature, and the solvent was distilled off under reduced pressure, and 10 mL of 2N hydrochloric acid was added in the residue, and extracted with ethyl acetate (20 mL×2). The combined organic phases were washed with water, and then the organic phase was dehydrated with and dried over saturated sodium chloride aqueous solution and then anhydrous magnesium sulfate, and the solvent was distilled off under reduced pressure to obtain 1.04 g of the crude aimed product as white crystal. The resulting product was used as such without purification for the next step.

Step 4: Production of 4-[5-(3,5-dichlorophenyl)-5-trifluoromethyl-4,5-dihydroisoxazol-3-yl]-2-methoxymethyl benzoic acid amide In a solution of 0.80 g of 4-[5-(3,5-dichlorophenyl)-5-trifluoromethyl-4,5-dihydroisoxazole-3-yl]-2-methoxymethyl benzoic acid in 30 mL of dichloromethane, 0.23 g of oxalyl chloride and 0.06 g of N,N-dimethylforamide were added, and stirred at room temperature for 30 minutes. After the completion of the reaction, the solvent was distilled off under reduced pressure, the residue was dissolved in 5 mL of tetrahydrofuran, and a solution of 1.50 g of concentrated ammonia water in 10 mL of tetrahydrofuran was added dropwise at room temperature with stirring. After the completion of the addition dropwise, it was continued to stir further for 1 hour. After the completion of the reaction, the solvent was distilled off under reduced pressure, 10 mL of water was added in the residue, and extracted with ethyl acetate (20 mL×1). The organic phase was washed with 10 mL of 2N hydrochloric acid, and then dehydrated with and dried over saturated sodium chloride aqueous solution and then anhydrous magnesium sulfate, and the solvent was distilled off under reduced pressure. The residue was purified with silica gel column chromatography that were eluated with ethyl acetate-hexane (1:1) to obtain 0.34 g of the aimed product as white crystal.

Melting point 186.0 to 188.0° C.

$^1$H NMR (CDCl$_3$, Me$_4$Si, 300 MHz) δ7.87 (d, J=8.4 Hz, 1H), 7.65-7.75 (m, 2H), 7.50 (s, 2H), 7.4-7.45 (m, 1H), 7.33 (bs, 1H), 5.73 (bs, 1H), 4.61 (s, 2H), 4.11 (d, J=17.4 Hz, 1H), 3.72 (d, J=17.4 Hz, 1H), 3.45 (s, 3H).

Step 5: Production of 4-[5-(3,5-dichlorophenyl)-5-trifluoromethyl-4,5-dihydroisoxazol-3-yl]-N-(methoxyiminomethyl)-2-methoxymethyl benzoic acid amide In a solution of 0.09 g of 4-[5-(3,5-dichlorophenyl)-5-trifluoromethyl-4,5-dihydroisoxazol-3-yl]-2-methoxymethyl benzoic acid amide in 2 mL of tetrahydrofuran, 0.05 g of N,N-dimethylformamide dimethylacetal was added, and stirred at room temperature for 2 hours. After the completion of the reaction, the solvent was distilled off under reduced pressure, and the residue was dissolved in 2 mL of tetrahydrofuran, a solution of 0.02 g of methoxyamine hydrochloride in 2 mL of water was added dropwise. After the completion of the addition dropwise, it was continued to stir at room temperature further for 30 minutes. After the completion of the reaction, the solvent was distilled off under reduced pressure, 5 mL of water was added in the residue, and extracted with ethyl acetate (10 mL×1). The organic phase was dehydrated with and dried over saturated sodium chloride aqueous solution and then anhydrous sulfuric acid, and the solvent was distilled off under reduced pressure. The residue was purified with silica gel column chromatography that were eluated with ethyl acetate-hexane (1:4) to obtain 0.07 g of the aimed product as white crystal.

Melting point 132.0 to 134.0° C.

$^1$H NMR (CDCl$_3$, Me$_4$Si, 300 MHz) δ8.63 and 10.34 (d, J=9.9 and 10.8 Hz, 1H), 7.7-7.95 (m, 4H), 7.51 (s, 2H), 7.4-7.45 (m, 1H), 4.53 and 4.55 (s, 2H), 4.11 (d, J=17.4 Hz, 1H), 3.81 and 3.91 (s, 3H), 3.72 (d, J=17.7 Hz, 1H), 3.51 and 3.53 (s, 3H).

Synthetic Example 38

4-[5-(3,5-Dichlorophenyl)-5-trifluoromethyl-4,5-dihydroisoxazole-3-yl]-2-(dimethyl aminomethyl)-N-(methoxyiminomethyl)benzoic acid amide (Compound of the present invention No. 6-032)

Step 1: Production of methyl 4-[5-(3,5-dichlorophenyl)-5-trifluoromethyl-4,5-dihydroisoxazole-3-yl]-2-(dimethyl-aminomethyl)benzoate In a solution of 1.50 g of methyl 2-bromomethyl-4-[5-(3,5-dichlorophenyl)-5-trifluoromethyl-4,5-dihydroisoxazole-3-yl]benzoate in 20 mL of N,N-dimethylformamide, 0.48 g of dimethylamine hydrochloride and 1.48 g of triethylamine were added, and stirred at room temperature for 2 hours. After the completion of the reaction, 20 mL of water was added in the reaction mixture, and extracted with ethyl acetate (20 mL×2). The combined organic phases were dehydrated with and dried over saturated sodium chloride aqueous solution and then anhydrous sodium sulfate, and the solvent was distilled off under reduced pressure. The residue was purified with silica gel column chromatography that were eluated with ethyl acetate-hexane (1:3) to obtain 1.35 g of the aimed product as colorless resinous substance.

Step 2: Production of 4-[5-(3,5-dichlorophenyl)-5-trifluoromethyl-4,5-dihydroisoxazole-3-yl]-2-(dimethyl-aminomethyl)benzoic acid In a solution of 1.35 g of methyl 4-[5-(3,5-dichlorophenyl)-5-trifluoromethyl-4,5-dihydroisoxazole-3-yl]-2-(dimethyl-aminomethyl)benzoate in 30 mL of ethanol, a solution of 0.48 g of potassium hydroxide in 15 mL of water was added, and stirred under reflux with heating for 30 minutes. After the completion of the reaction, the reaction mixture was left and cooled to room temperature, and 10 mL of 2N hydrochloric acid was added, and the solvent was distilled off under reduced pressure. The residue was dissolved in 20 mL of ethyl acetate, insoluble material was filtered off, and the solvent was distilled off under reduced pressure to obtain 1.05 g of the crude aimed product as white crystal. The resulting product was used as such without purification for the next step.

Step 3: Production of 4-[5-(3,5-dichlorophenyl)-5-trifluoromethyl-4,5-dihydroisoxazol-3-yl]-2-(dimethylaminomethyl)benzoic acid amide In a solution of 1.05 g of 4-[5-(3,5-dichlorophenyl)-5-trifluoromethyl-4,5-dihydroisoxazole-3-yl]-2-(dimethyl-aminomethyl)benzoic acid in 40 mL of dichloromethane, 0.58 g of oxalyl chloride and 0.06 g of N,N-dimethylformamide were added, and stirred at room temperature for 30 minutes. After the completion of the reaction, the solvent was distilled off under reduced pressure, the residue was dissolved in 15 mL of tetrahydrofuran, and a solution of 3.00 g of concentrated ammonia water in 15 mL of tetrahydrofuran was added dropwise under cooling with ice and with stirring. After the completion of the addition dropwise, it was continued to stir at room temperature further for 1 hour. After the completion of the reaction, the solvent was distilled off under reduced pressure, 20 mL of water was added in the residue, and extracted with ethyl acetate (20 mL×2). The organic phases were dehydrated with and dried over saturated sodium chloride aqueous solution and then anhydrous magnesium sulfate, and the solvent was distilled off under reduced pressure to obtain 0.93 g of the aimed product as colorless resinous material. The resulting product was used as such without purification for the next step.

Step 4: Production of 4-[5-(3,5-dichlorophenyl)-5-trifluoromethyl-4,5-dihydroisoxazole-3-yl]-2-(dimethyl-aminomethyl)-N-(methoxyiminomethyl)benzoic acid amide In a solution of 0.30 g of 4-[5-(3,5-dichlorophenyl)-5-trifluoromethyl-4,5-dihydroisoxazol-3-yl]-2-(dimethylaminomethyl)benzoic acid amide in 6 mL of tetrahydrofuran, 0.16 g of N,N-dimethylformamide dimethylacetal was added, and stirred at room temperature for 3 hours. After the completion of the reaction, the solvent was distilled off under reduced pressure, and the residue was dissolved in 6 mL of tetrahydrofuran, a solution of 0.07 g of methoxyamine hydrochloride in 4 mL of water was added dropwise. After the completion of the addition dropwise, it was continued to stir at room temperature further for 30 minutes. After the completion of the reaction, the solvent was distilled off under reduced pressure, 10 mL of water was added in the residue, and extracted with ethyl acetate (20 mL×1). The organic phase was dehydrated with and dried over saturated sodium chloride aqueous solution and then anhydrous magnesium sulfate, and the solvent was distilled off under reduced pressure. The residue was purified with silica gel column chromatography that were eluated with ethyl acetate-hexane (1:2) to obtain 0.02 g of the aimed product as white crystal.

Melting point 144.0 to 146.0° C.

$^1$H NMR (CDCl$_3$, Me$_4$Si, 300 MHz) δ8.09 (d, J=8.1 Hz, 1H), 7.82 (d, J=8.1 Hz, 1H), 7.55-7.65 (m, 2H), 7.52 (s, 2H), 7.4-7.45 (m, 1H), 4.11 (d, J=17.4 Hz, 1H), 3.88 (s, 3H), 3.72 (d, J=17.1 Hz, 1H), 3.54 (s, 2H), 2.28 (s, 6H).

Synthetic Example 39

2-Acetylamino-4-[5-(3,5-dichlorophenyl)-5-trifluoromethyl-4,5-dihydroisoxazole-3-yl]-N-(methoxyiminomethyl)benzoic acid amide (Compound of the present invention No. 6-033)

Step 1: Production of 4-[5-(3,5-dichlorophenyl)-5-trifluoromethyl-4,5-dihydroisoxazole-3-yl]-2-nitro benzoic acid amide In a solution of 0.50 g of 4-[5-(3,5-dichlorophenyl)-5-trifluoromethyl-4,5-dihydroisoxazole-3-yl]-2-nitro benzoic acid in 10 mL of dichloromethane, 0.43 g of oxalyl chloride was added dropwise at room temperature with stirring. After the completion of the addition dropwise, it was continued to stir at the same temperature further for 1.5 hour. After the completion of the reaction, the solvent was distilled off under reduced pressure, and the residue was dissolved in 5 mL of tetrahydrofuran, and 15 mL of concentrated ammonia water was added dropwise under cooling with ice and with stirring. After the completion of the addition dropwise, it was continued to stir at room temperature further for 1 hour. After the completion of the reaction, the solvent was distilled off under reduced pressure, 20 mL of water was added in the residue, and extracted with ethyl acetate (20 mL×2). The organic phases were dehydrated with and dried over saturated sodium chloride aqueous solution and then anhydrous magnesium sulfate, and the solvent was distilled off under reduced pressure to obtain 0.43 g of the crude aimed product as colorless crystal. The resulting product was used as such without purification for the next step.

$^1$H NMR (CDCl$_3$, Me$_4$Si, 300 MHz) δ7.45-8.0 (m, 6H), 6.80 (bs, 2H), 4.10 (d, J=17.4 Hz, 1H), 3.20 (d, J=17.4 Hz, 1H).

Step 2: Production of 2-amino-4-[5-(3,5-dichlorophenyl)-5-trifluoromethyl-4,5-dihydroisoxazole-3-yl]benzoic acid amide In a mixture of 10 mL of water, 2 mL of acetic acid and 0.52 g of reduced iron, a solution of 0.84 g of 4-[5-(3,5-dichlorophenyl)-5-trifluoromethyl-4,5-dihydroisoxazole-3-yl]-2-nitro benzoic acid amide in 10 mL of ethyl acetate was added dropwise at 75° C. with stirring. After the completion of the addition dropwise, it was stirred at the same temperature further for 2.5 hours. After the completion of the reaction, insoluble material was removed by hot filtration, 20 ml of water was added in the filtrate, and the organic phase was collected, and the aqueous phase was extracted with ethyl acetate (10 ml×2). The combined organic phases were washed with 10 ml of saturated sodium hydrogen carbonate aqueous solution, and then dehydrated with and dried over saturated sodium chloride aqueous solution and then anhydrous sodium sulfate, and then the solvent was distilled off under reduced pressure to obtain 0.80 g of the crude aimed product as yellow crystal. The resulting product was used as such without purification for the next step.

Melting point 190.0 to 193.0° C.

$^1$H NMR (CDCl$_3$, Me$_4$Si, 300 MHz) δ7.35-7.5 (m, 6H), 6.9-6.95 (m, 2H), 6.00 (bs, 2H), 4.05 (d, J=17.4 Hz, 1H), 3.56 (d, J=17.4 Hz, 1H).

Step 3: Production of 2-acetylamino-4-[5-(3,5-dichlorophenyl)-5-trifluoromethyl-4,5-dihydroisoxazol-3-yl]benzoic acid amide In a solution of 0.20 g of 2-amino-4-[5-(3,5-dichlorophenyl)-5-trifluoromethyl-4,5-dihydroisoxazole-3-yl]benzoic acid amide and 0.12 g of triethylamine in 5 mL of dichloromethane, 0.05 g of acetyl chloride was added under cooling with ice and with stirring, and stirred at room temperature for 40 minutes. After the completion of the reaction, 10 mL of ethyl acetate was added in the reaction mixture, and washed with 10 mL of water, 10 mL of saturated sodium hydrogen carbonate aqueous solution, and then 10 mL of saturated ammonium chloride aqueous solution in that order. The organic phase was dehydrated with and dried over saturated sodium chloride aqueous solution and then anhydrous magnesium sulfate, and the solvent was distilled off under reduced pressure to obtain 0.21 g of the crude aimed product as yellow crystal. The resulting product was used as such without purification for the next step.

$^1$H NMR (CDCl$_3$, Me$_4$Si, 300 MHz) δ11.30 (s, 1H), 7.4-8.85 (m, 8H), 4.15 (d, J=17.4 Hz, 1H), 3.75 (d, J=17.4 Hz, 1H), 2.05 (s, 3H).

Step 4: Production of 2-acetylamino-4-[5-(3,5-dichlorophenyl)-5-trifluoromethyl-4,5-dihydroisoxazole-3-yl]-N-(methoxyiminomethyl)benzoic acid amide A mixture of 0.21 g of 2-acetylamino-4-[5-(3,5-dichlorophenyl)-5-trifluoromethyl-4,5-dihydroisoxazol-3-yl]benzoic acid amide and 10 mL of N,N-dimethylformamide dimethylacetal was stirred at room temperature for 1.5 hour. After the completion of the reaction, the solvent was distilled off under reduced pressure, and the residue was dissolved in 3 mL of 1,4-dioxane, a solution of 0.025 g of methoxyamine hydrochloride in 3 mL of water was added dropwise. After the completion of the addition dropwise, it was continued to stir at room temperature further for 30 minutes. After the completion of the reaction, the solvent was distilled off under reduced pressure, 5 mL of water was added in the residue, and extracted with ethyl acetate (10 mL×1). The organic phase was dehydrated with and dried over saturated sodium chloride aqueous solution and then anhydrous magnesium sulfate, and the solvent was distilled off under reduced pressure. The residue was purified with silica gel column chromatography that were eluated with ethyl acetate-hexane (1:2) to obtain 0.07 g of the aimed product as colorless resinous substance.

$^1$H NMR (CDCl$_3$, Me$_4$Si, 300 MHz) δ11.00 (bs, 1H), 8.90 (d, J=7.8 Hz, 1H), 8.85 (d, J=1.2 Hz, 1H), 7.45-7.8 (m, 6H), 4.15 (d, J=17.4 Hz, 1H), 3.95 (s, 3H), 3.75 (d, J=17.4 Hz, 1H), 2.25 (s, 3H).

Synthetic Example 40

4-[5-(3-Chloro-5-trifluoromethylphenyl)-5-trifluoromethyl-4,5-dihydroisoxazole-3-yl]-N-(methoxyiminomethyl)-2-methyl benzoic acid amide (Compound of the present invention No. 6-037)

Step 1: Production of 4-bromo-N-(dimethylaminomethylidene)-2-methyl benzoic acid amide A mixture of 0.84 g of 4-bromo-2-methyl benzoic acid amide and 18 mL of N,N-dimethylformamide dimethylacetal was stirred at 70° C. for 30 minutes. After the completion of the reaction, the solvent was distilled off under reduced pressure, and the residue was washed with 5 mL of hexane to obtain 0.67 g of the aimed product as white crystal.

Melting point 87.0 to 89.0° C.

$^1$H NMR (CDCl$_3$, Me$_4$Si, 300 MHz) δ8.57 (s, 1H), 7.97 (d, J=8.1 Hz, 1H), 7.36 (s, 1H), 7.34 (d, J=8.1 Hz, 1H), 3.19 (s, 3H), 3.17 (s, 3H), 2.60 (s, 3H).

Step 2: Production of 4-bromo-N-(methoxyiminomethyl)-2-methyl benzoic acid amide In a solution of 0.67 g of 4-bromo-N-(dimethylaminomethylidene)-2-methyl benzoic acid amide in 10 mL of 1,4-dioxane, a solution of 0.36 g of methoxyamine hydrochloride in 2 mL of water was added, and stirred at room temperature for 1 hour. After the completion of the reaction, the reaction mixture was diluted with 50 mL of ethyl acetate, washed with water, and dehydrated with and dried over saturated sodium chloride aqueous solution and then anhydrous magnesium sulfate, and the solvent was distilled off under reduced pressure to obtain 0.70 g of the aimed product as white crystal.

Melting point 119.0 to 122.0° C.

$^1$H NMR (CDCl$_3$, Me$_4$Si, 300 MHz) δ8.4-8.5 and 8.5-8.6 (m, 1H), 7.65-7.8 (m, 1H), 7.3-7.5 (m, 3H), 3.79 and 3.89 (s, 3H), 2.49 (s, 3H).

Step 3: Production of 4-formyl-N-(methoxyiminomethyl)-2-methyl benzoic acid amide In a solution of 0.20 g of 4-bromo-N-(methoxyiminomethyl)-2-methyl benzoic acid amide in 5 ml of N,N-dimethylformamide, 0.065 g of sodium formate and 0.026 g of dichlorobis(triphenylphosphine) palladium (II) were added, and stirred under carbon monoxide atmosphere at 120° C. for 1.5 hour. After the completion of the reaction, the reaction mixture was left and cooled to room temperature, and poured in 30 mL of water, and extracted with ethyl acetate (20 mL×2). The combined organic phases were washed with water, and dehydrated with and dried over saturated sodium chloride aqueous solution and then anhydrous magnesium sulfate, and the solvent was distilled off under reduced pressure. The residue was purified with silica gel column chromatography that were eluated with ethyl acetate-hexane (gradient of 1:3 to 1:1) to obtain 0.071 g of the aimed product as colorless oily substance.

$^1$H NMR (CDCl$_3$, Me$_4$Si, 300 MHz) δ10.04 (s, 1H), 8.5-8.65 (m, 1H), 7.7-7.85 (m, 3H), 7.63 (d, J=7.8 Hz, 1H), 3.80 and 3.90 (s, 3H), 2.57 (s, 3H).

Step 4: Production of 4-hydroxyiminomethyl-N-(methoxyiminomethyl)-2-methyl benzoic acid amide In a solution of 64 mg of 4-formyl-N-(methoxyiminomethyl)-2-methyl benzoic acid amide in 4 mL of methanol and 1 mL of water, 30 mg of hydroxyamine hydrochloride was added at room temperature with stirring, and continued to stir at the same temperature for 1.5 hour. After the completion of the reaction, 10 mL of water was added in the reaction mixture, and extracted with ethyl acetate (10 mL×2). The combined organic phases were dehydrated with and dried over saturated sodium chloride aqueous solution and then anhydrous magnesium sulfate, and the solvent was distilled off under reduced pressure. The residue was purified with silica gel column chromatography that were eluated with ethyl acetate-hexane (1:1) to obtain 70 mg of the aimed product as white crystal.

Melting point 88.0 to 91.0° C.

$^1$H NMR (CDCl$_3$, Me$_4$Si, 300 MHz) δ8.53 and 9.30 (d, J=10.2 Hz, 1H), 7.79 and 8.69 (d, J=10.2 Hz, 1H), 8.11 (s, 1H), 8.05 (bs, 1H), 7.4-7.55 (m, 3H), 3.85 and 3.90 (s, 3H), 2.51 (s, 3H).

Step 5: Production of 4-[5-(3-chloro-5-trifluoromethylphenyl)-5-trifluoromethyl-4,5-dihydroisoxazole-3-yl]-N-(methoxyiminomethyl)-2-methyl benzoic acid amide In a solution of 81 mg of 4-hydroxyiminomethyl-N-(methoxyiminomethyl)-2-methyl benzoic acid amide in 10 ml of 1,2-dimethoxyethane, 60 mg of N-chlorosuccinimide was added, and stirred at 70° C. for 45 minutes. Then, the reaction mixture was left and cooled to room temperature, and then 60 mg of 3-chloro-5-trifluoromethyl-1-(1-trifluoromethylethenyl)benzene, 40 mg of potassium hydrogen carbonate and 3 drops of water were added, and continued to stir at room temperature further for 15 hours. After the completion of the reaction, the reaction mixture was poured in 10 mL of water, and extracted with ethyl acetate (15 mL×2). The combined organic phases were dehydrated with and dried over saturated sodium chloride aqueous solution and then anhydrous magnesium sulfate, and the solvent was distilled off under reduced pressure. The residue was purified with silica gel column chromatography that were eluated with ethyl acetate-hexane (gradient of 1:5 to 1:3) to obtain 13 mg of the aimed product as colorless resinous substance.

$^1$H NMR (CDCl$_3$, Me$_4$Si, 300 MHz) δ8.49 and 9.25 (d, J=10.2 Hz, 1H), 7.82 (s, 1H), 7.76 (s, 1H), 7.70 (s, 1H), 7.55-7.65 and 7.75-7.8 (m, 1H), 7.5-7.6 (m, 3H), 4.13 (d, J=17.4 Hz, 1H), 3.79 and 3.90 (s, 3H), 3.73 (d, J=17.4 Hz, 1H), 2.53 (s, 3H).

Synthetic Example 41

Methyl N-[2-methyl-4-[5-(3,4,5-trichlorophenyl)-5-trifluoromethyl-4,5-dihydroisoxazole-3-yl]benzoyl] carbamate (Compound of the present invention No. 2-026)

Step 1: Production of 4-formyl-2-methyl benzoic acid amide

In 0.40 g of 4-formyl-2-methylbenzonitrile, 7 mL of concentrated sulfuric acid was added, and stirred at room temperature for 4.5 days. After the completion of the reaction, the reaction mixture was poured in 20 mL of ice water, extracted with ethyl acetate (15 mL×2). The combined organic phases were washed with water, and dehydrated with and dried over saturated sodium chloride aqueous solution and then anhydrous magnesium sulfate, and the solvent was distilled off under reduced pressure. The residue was washed with 5 mL of diisopropyl ether to obtain 0.26 g of the aimed product as white crystal.

Melting point 119.0 to 121.0° C.

$^1$H NMR (CDCl$_3$, Me$_4$Si, 300 MHz) δ10.02 (s, 1H), 7.76 (s, 1H), 7.75 (d, J=7.8 Hz, 1H), 7.60 (d, J=7.8 Hz, 1H), 5.77 (bs, 2H), 2.57 (s, 3H).

Step 2: Production of methyl N-[4-formyl-2-methyl benzoyl]carbamate

In a solution of 80 mg of 4-formyl-2-methyl benzoic acid amide in 6 mL of dichloromethane, 75 mg of oxalyl chloride was added, and stirred under reflux with heating for 3 hours. After the completion of the reaction, the solvent was distilled off under reduced pressure, and the residue was dissolved in 5 mL of dichloromethane, and a mixed solution of 1.5 mL of methanol and 5 mL of dichloromethane was added, and stirred at room temperature for 30 minutes. After the completion of the reaction, the solvent was distilled off under reduced pressure.

The residue was purified with silica gel column chromatography that were eluated with ethyl acetate-hexane (gradient of 1:2 to 2:1) to obtain 41 mg of the aimed product as white crystal.

Melting point 115.0 to 118.0° C.

$^1$H NMR (CDCl$_3$, Me$_4$Si, 300 MHz) δ10.01 (s, 1H), 7.89 (bs, 1H), 7.77 (s, 1H), 7.76 (d, J=7.8 Hz, 1H), 7.50 (d, J=7.8 Hz, 1H), 3.80 (s, 3H), 2.50 (s, 3H).

Step 3: Production of methyl N-[4-hydroxyiminomethyl-2-methylbenzoyl]carbamate

In a solution of 41 mg of methyl N-[4-formyl-2-methyl benzoyl]carbamate in 4 mL of methanol and 1 mL of water, 15 mg of hydroxylamine hydrochloride was added at room temperature with stirring, and continued to stir at the same temperature for 1.5 hour. After the completion of the reaction, 10 mL of water was added in the reaction mixture, and extracted with ethyl acetate (10 mL×2). The combined organic phases were dehydrated with and dried over saturated sodium chloride aqueous solution and then anhydrous magnesium sulfate, and the solvent was distilled off under reduced pressure to obtain 45 mg of the aimed product as white crystal.

Melting point 141.0 to 143.0° C.

$^1$H NMR (CDCl$_3$, Me$_4$Si, 300 MHz) δ8.0-8.15 (m, 3H), 7.3-7.45 (m, 3H), 3.85 (s, 3H), 2.47 (s, 3H).

Step 4: Production of methyl N-[2-methyl-4-[5-(3,4,5-trichlorophenyl)-5-trifluoromethyl-4,5-dihydroisoxazole-3-yl]benzoyl]carbamate In a solution of 45 mg of methyl N-[4-hydroxyiminomethyl-2-methylbenzoyl]carbamate in 10 mL of 1,2-dimethoxyethane, 40 mg of N-chlorosuccinimide was added, and stirred at 60° C. for 45 minutes. Then, the reaction mixture was left and cooled to room temperature, and then 68 mg of 3,4,5-trichloro-1-(1-trifluoromethylethenyl)benzene, 40 mg of potassium hydrogen carbonate and 5 drops of water were added, and continued to stir at room temperature further for 15 hour. After the completion of the reaction, the reaction mixture was poured in 10 mL of water, and extracted with ethyl acetate (15 mL×2). The combined organic phases were dehydrated with and dried over saturated sodium chloride aqueous solution and then anhydrous magnesium sulfate, and then the solvent was distilled off under reduced pressure. The residue was purified with silica gel column chromatography that was eluated with ethyl acetate-hexane (gradient of 1:2 to 1:1) to obtain 23 mg of the aimed product as colorless resinous substance.

$^1$H NMR (CDCl$_3$, Me$_4$Si, 300 MHz) δ7.86 (bs, 1H), 7.64 (s, 2H), 7.5-7.6 (m, 2H), 7.42 (d, J=8.1 Hz, 1H), 4.09 (d, J=17.4 Hz, 1H), 3.80 (s, 3H), 3.68 (d, J=17.4 Hz, 1H), 2.47 (s, 3H).

Synthetic Example 42

N-(5-Chloro-2-pyradinyl)-4-[5-(3,5-dichlorophenyl)-5-trifluoromethyl-4,5-dihydroisoxazole-3-yl]-N-methyl-2-methyl benzoic acid amide (Compound of the present invention No. 5-173)

Step 1: Production of N-(5-chloro-2-pyradinyl)-4-[5-(3,5-dichlorophenyl)-5-trifluoromethyl-4,5-dihydroisoxazole-3-yl]-2-methyl benzoic acid amide In a solution of 0.17 g of 2-amino-5-chloropyradine in 5 mL of pyridine, 0.50 g of 4-[5-(3,5-dichlorophenyl)-5-trifluoromethyl-4,5-dihydroisoxazol-3-yl]-2-methylbenzoylchloride synthesized in Step 4 of Synthetic Example 1 was added dropwise at room temperature with stirring, and stirred at the same temperature for 20 hours. After the completion of the reaction, 30 mL of 3N hydrochloric acid was added in the reaction mixture under cooling with ice and with stirring, and extracted with ethyl acetate (30 mL×1). The organic phase was washed with water, and then dehydrated with and dried over saturated sodium chloride aqueous solution and then anhydrous magnesium sulfate, and the solvent was distilled off under reduced pressure. The residue was purified with silica gel column chromatography that was eluated with ethyl acetate-hexane (3:7) to obtain 0.33 g of the aimed product as white crystal.

Melting point 242.0 to 243.0° C.

$^1$H NMR (CDCl$_3$-DMSO-d$_6$, Me$_4$Si, 300 MHz) δ11.44 (s, 1H), 9.23 (d, J=1.2 Hz, 1H), 8.53 (d, J=1.2 Hz, 1H), 7.55-7.8 (m, 6H), 4.40 (d, J=18.6 Hz, 1H), 4.29 (d, J=18.6 Hz, 1H), 2.42 (s, 3H).

Step 2: Production of N-(5-chloro-2-pyradinyl)-4-[5-(3,5-dichlorophenyl)-5-trifluoromethyl-4,5-dihydroisoxazole-3-yl]-N-methyl-2-methyl benzoic acid amide In a solution of 0.128 g of N-(5-chloro-2-pyradinyl)-4-[5-(3,5-dichlorophenyl)-5-trifluoromethyl-4,5-dihydroisoxazole-3-yl]-2-methyl benzoic acid amide in 3 mL of N,N-dimethylformamide, 0.016 g of 60% oily sodium hydride was added under cooling with ice and with stirring, and stirred at room temperature for 10 minutes. Then, 0.41 g of methyl iodide was added under cooling with ice and with stirring, and continued to stir at room temperature further for 20 hours. After the completion of the reaction, the reaction mixture was poured in 10 mL of ice water, extracted with ethyl acetate (10 mL×2), the organic phase was dehydrated with and dried over saturated sodium chloride aqueous solution and then anhydrous magnesium sulfate, and the solvent was distilled off under reduced pressure. The residue was purified with silica gel column chromatography that was eluated with ethyl acetate-hexane (1:3) to obtain 0.066 g of the aimed product as yellow resinous substance.

$^1$H NMR (CDCl$_3$, Me$_4$Si, 300 MHz) δ8.45 (bs, 1H), 8.36 (d, J=1.5 Hz, 1H), 7.4-7.6 (m, 5H), 7.22 (d, J=8.4 Hz, 1H), 4.07 (d, J=17.5 Hz, 1H), 3.68 (d, J=17.5 Hz, 1H), 3.46 (s, 3H), 2.37 (s, 3H).

Synthetic Example 43

N-(5-Cyano-2-pyrimidinyl)-4-[5-(3,5-dichlorophenyl)-5-trifluoromethyl-4,5-dihydroisoxazole-3-yl]-N-methyl-2-methyl benzoic acid amide (Compound of the present invention No. 5-171)

Step 1: Production of N-(5-cyano-2-pyrimidinyl)-4-[5-(3,5-dichlorophenyl)-5-trifluoromethyl-4,5-dihydroisoxazole-3-yl]-2-methyl benzoic acid amide In a solution of 0.20 g of N-(5-bromo-2-pyrimidinyl)-4-[5-(3,5-dichlorophenyl)-5-trifluoromethyl-4,5-dihydroisoxazole-3-yl]-2-methyl benzoic acid amide synthesized in Step 1 of Synthetic Example 13 in 3 mL of N,N-dimethylacetamide, 0.082 g of zinc cyanide, 0.011 g of zinc, 0.013 g of tris(dibenzylideneacetone)dipalladium and 0.015 g of 1,1'-bis(diphenylphosphino)ferrocene were added, and stirred under nitrogen atmosphere at 100° C. for 2 hours. After the completion of the reaction, the reaction mixture was left and cooled to room temperature, and 20 mL of concentrated ammonia water and 20 mL of water were added, and extracted with ethyl acetate (20 mL×2). The organic phases were washed with water, and dehydrated with and dried over saturated sodium chloride aqueous solution and anhydrous magnesium sulfate, and the solvent was distilled off under reduced pressure. The residue was purified with silica gel column chromatography that was eluated with ethyl acetate-hexane (1:1) to obtain 0.15 g of the aimed product as white crystal.

Melting point 118.0 to 121.0° C.

$^1$H NMR (CDCl$_3$, Me$_4$Si, 300 MHz) δ8.86 (s, 2H), 8.61 (s, 1H), 7.4-7.7 (m, 6H), 4.10 (d, J=17.5 Hz, 1H), 3.72 (d, J=17.5 Hz, 1H), 2.56 (s, 3H).

Step 2: Production of N-(5-cyano-2-pyrimidinyl)-4-[5-(3,5-dichlorophenyl)-5-trifluoromethyl-4,5-dihydroisoxazole-3-yl]-N-methyl-2-methyl benzoic acid amide In a solution of 0.075 g of N-(5-cyano-2-pyradinyl)-4-[5-(3,5-dichlorophenyl)-5-trifluoromethyl-4,5-dihydroisoxazole-3-yl]-2-methyl benzoic acid amide in 2 mL of N,N-dimethylformamide, 0.009 g of 60% oily sodium hydride was added under cooling with ice and with stirring, and stirred at room temperature for 10 minutes. Then, 0.025 g of methyl iodide was added under cooling with ice and with stirring, and continued to stir at room temperature for 2 hours. After the completion of the reaction, the reaction mixture was poured in 10 mL of ice water, extracted with ethyl acetate (10 mL×2), the organic phase was dehydrated with and dried over saturated sodium chloride aqueous solution and then anhydrous magnesium sulfate, and the solvent was distilled off under reduced pressure. The residue was purified with silica gel column chromatography that was eluated with ethyl acetate-hexane (3:7) to obtain 0.039 g of the aimed product as yellow resinous substance.

$^1$H NMR (CDCl$_3$, Me$_4$Si, 300 MHz) δ8.55 (s, 2H), 7.3-7.55 (m, 5H), 7.07 (d, J=8.1 Hz, 1H), 4.07 (d, J=17.0 Hz, 1H), 3.70 (s, 3H), 3.67 (d, J=17.0 Hz, 1H), 2.38 (s, 3H).

Synthetic Example 44

N-(2-Chloro-2-pyrimidinyl)-4-[5-(3,5-dichlorophenyl)-5-trifluoromethyl-4,5-dihydroisoxazole-3-yl]-N-methyl-2-methyl benzoic acid amide (Compound of the present invention No. 5-172)

Step 1: Production of N-(2-chloro-2-pyrimidinyl)-4-[5-(3,5-dichlorophenyl)-5-trifluoromethyl-4,5-dihydroisoxazole-3-yl]-2-methyl benzoic acid amide In a solution of 0.12 g of 5-amino-2-chloropyrimidine in 3 mL of pyridine, 0.36 g of 4-[5-(3,5-dichlorophenyl)-5-trifluoromethyl-4,5-dihydroisoxazol-3-yl]-2-methylbenzoyl-chloride synthesized in Step 4 of Synthetic Example 1 was added at room temperature with stirring, and stirred at the same temperature for 18 hours. After the completion of the reaction, the solvent was distilled off under reduced pressure, 30 mL of 3N hydrochloric acid was added in the residue, and extracted with ethyl acetate (30 mL×1). The organic phase was washed with water, and then dehydrated with and dried over saturated sodium chloride aqueous solution and then anhydrous magnesium sulfate, and the solvent was distilled off under reduced pressure. The residue was purified with silica gel column chromatography that was eluated with ethyl acetate-hexane (2:3) to obtain 0.24 g of the aimed product as white crystal.

Melting point 231.0 to 234.0° C.
$^1$H NMR (CDCl$_3$, Me$_4$Si, 300 MHz) δ8.98 (s, 2H), 7.71 (s, 1H), 7.4-7.65 (m, 6H), 4.10 (d, J=17.5 Hz, 1H), 3.72 (d, J=17.5 Hz, 1H), 2.54 (s, 3H).

Step 2: Production of N-(2-chloro-2-pyrimidinyl)-4-[5-(3,5-dichlorophenyl)-5-trifluoromethyl-4,5-dihydroisoxazole-3-yl]-N-methyl-2-methyl benzoic acid amide In a solution of 0.125 g of N-(2-chloro-5-pyrimidinyl)-4-[5-(3,5-dichlorophenyl)-5-trifluoromethyl-4,5-dihydroisoxazole-3-yl]-2-methyl benzoic acid amide in 3 mL of N,N-dimethylformamide, 0.015 g of 60% oily sodium hydride was added under cooling with ice and with stirring, and stirred at room temperature for 10 minutes. Then, 0.040 g of methyl iodide was added under cooling with ice and with stirring, and continued to stir at room temperature for 2 hours. After the completion of the reaction, the reaction mixture was poured in 10 mL of ice water, extracted with ethyl acetate (10 mL×2), the organic phase was dehydrated with and dried over saturated sodium chloride aqueous solution and then anhydrous magnesium sulfate, and the solvent was distilled off under reduced pressure. The residue was purified with silica gel column chromatography that was eluated with ethyl acetate-hexane (1:1) to obtain 0.030 g of the aimed product as yellow resinous substance.

$^1$H NMR (CDCl$_3$, Me$_4$Si, 300 MHz) δ8.45 (bs, 2H), 7.35-7.6 (m, 5H), 7.18 (bs, 1H), 4.05 (d, J=17.0 Hz, 1H), 3.66 (d, J=17.0 Hz, 1H), 3.45 (bs, 3H), 2.36 (s, 3H).

Synthetic Example 45

Production of the Compound of the Present Invention with Parallel Organic Sythesizer Manufactured by Radleys Discovery Technologies In a solution of 1.78 g of 4-[5-(3,5-dichlorophenyl)-5-trifluoromethyl-4,5-dihydroisoxazol-3-yl]-2-methyl benzoic acid amide synthesized in Step 1 of Synthetic Example 19 in 15 mL of dichloromethane, 0.64 g of oxalyl chloride was added, and stirred under reflux with heating for 6 hours. After the completion of the reaction, the solvent was distilled off under reduced pressure, the resiudual crude benzoylisocyanate was dissolved in 10 mL of dichloromethane.

In 5 reaction tubes for Carousel in which stirrers were placed, each 3.0 mmol of ethanol, 1-propanol, 2-propanol, 2-chloroethanol and 2-methoxyethanol were weighed, 2 mL of dichloromethane was added in each tube. The tubes were covered with lids and placed in a parallel organic synthesizer. In each reaction tube, 2 mL of a solution of the above-mentioned benzoylisocyanate in dichloromethane was added, and continued to stir at the same temperature for 18 hours. After the completion of the reaction, each reaction mixture was purified with medium pressure preparative liquid chromatography (medium pressure collection apparatus: YFLC-Wprep manufacturede by Yamazen Corporation) that was eluated with ethyl acetate-hexane (gradient of 1:9 to 1:1) to obtain the aimed products as colorless resinous substance. The products were confirmed by use of LC-MS (Waters LC-MS system, detector: ZMD, analysis condition: 254 nm, 80% CH$_3$CN-20% H$_2$O-0.1% HCOOH, ionization method: positive electrospray).

Ethyl N-[4-[5-(3,4-dichlorophenyl)-5-trifluoromethyl-4,5-diroisoxazole-3-yl]-2-methyl benzoyl]carbamate; 0.30 g, [M$^+$+H]=488.98.

N-[4-[5-(3,4-Dichlorophenyl)-5-trifluoromethyl-4,5-dihydroisoxazole-3-yl]-2-methyl benzoyl]carbamic acid-n-propyl; 0.30 g, [M$^+$+H]=503.00.

N-[4-[5-(3,4-Dichlorophenyl)-5-trifluoromethyl-4,5-dihydroisoxazole-3-yl]-2-methyl benzoyl]carbamic acid-1-propyl; 0.28 g, [M$^+$+H]=502.97.

N-[4-[5-(3,4-Dichlorophenyl)-5-trifluoromethyl-4,5-dihydroisoxazole-3-yl]-2-methyl benzoyl]carbamic acid-2-chloroethyl; 0.20 g, [M$^+$+H]=522.84.

N-[4-[5-(3,4-Dichlorophenyl)-5-trifluoromethyl-4,5-dihydroisoxazole-3-yl]-2-methyl benzoyl]carbamic acid-2-methoxyethyl; 0.28 g, [M$^+$+H]=519.04.

Synthetic Example 46

Production of the Compound of the Present Invention with Parallel Organic Sythesizer Manufactured by Radleys Discovery Technologies In 5 reaction tubes for Carousel in which stirrers were placed, each 0.15 g of N-[4-[5-(3,4-dichlorophenyl)-5-trifluoromethyl-4,5-dihydroisoxazole-3-yl]-2-methyl benzoyl]

carbamic acid-n-butyl, N-[4-[5-(3,4-dichlorophenyl)-5-trifluoromethyl-4,5-dihydroisoxazole-3-yl]-2-methyl benzoyl] carbamic acid-2-propinyl, N-[4-[5-(3,4-dichlorophenyl)-5-trifluoromethyl-4,5-dihydroisoxazole-3-yl]-2-methyl benzoyl]carbamic acid-2-cyanoethyl, N-[4-[5-(3,4-dichlorophenyl)-5-trifluoromethyl-4,5-dihydroisoxazole-3-yl]-2-methyl benzoyl]carbamic acid-1-methoxycarbonylethyl and N-[4-[5-(3,4-dichlorophenyl)-5-trifluoromethyl-4,5-dihydroisoxazole-3-yl]-2-methyl benzoyl]carbamic acid-2-pyridylmethyl were weighed, 3 mL of N,N-dimethylformamide and 0.08 g of potassium carbonate were added in each tube. The tubes were covered with lids and placed in a parallel organic synthesizer. In each reaction tube, 0.08 g of methyl iodide was added, and continued to stir at the same temperature for 18 hours. After the completion of the reaction, each reaction mixture was purified with medium pressure preparative liquid chromatography (medium pressure collection apparatus: YFLC-Wprep manufacturede by Yamazen Corporation) that was eluated with ethyl acetate-hexane (gradient of 1:9 to 1:2) to obtain the aimed products as colorless resinous substance or white crystal. The products were confirmed by use of LC-MS (Waters LC-MS system, detector: ZMD, analysis condition: 254 nm, 80% $CH_3CN$-20% $H_2O$-0.1% HCOOH, ionization method: positive electrospray).

N-[4-[5-(3,4-Dichlorophenyl)-5-trifluoromethyl-4,5-dihydroisoxazole-3-yl]-2-methyl benzoyl]-N-methyl carbamic acid-n-butyl; 0.15 g, [$M^+$+H]=531.06.

N-[4-[5-(3,4-Dichlorophenyl)-5-trifluoromethyl-4,5-dihydroisoxazole-3-yl]-2-methyl benzoyl]-N-methyl carbamic acid-2-propinyl; 0.15 g, [$M^+$+H]=513.04.

N-[4-[5-(3,4-Dichlorophenyl)-5-trifluoromethyl-4,5-dihydroisoxazole-3-yl]-2-methyl benzoyl]-N-methyl carbamic acid-2-cyanoethyl; 0.04 g, [$M^+$+H]=528.04.

N-[4-[5-(3,4-Dichlorophenyl)-5-trifluoromethyl-4,5-dihydroisoxazole-3-yl]-2-methyl benzoyl]-N-methyl carbamic acid-1-methoxycarbonylethyl; 0.13 g, [$M^+$+H]=561.05.

N-[4-[5-(3,4-Dichlorophenyl)-5-trifluoromethyl-4,5-dihydroisoxazole-3-yl]-2-methyl benzoyl]-N-methyl carbamic acid-2-pyridylmethyl; 0.04 g, [$M^+$+H]=566.04.

Reference Example 1

3,5-Dichloro-4-fluoro-1-(1-trifluoromethylethenyl)benzene

In a solution of 2.00 g of 3,5-dichloro-4-fluoro-iodobenzene and 0.61 g of tert-butylmethyl ether in 18 mL of hexane, 5.3 mL of n-butyl lithium (1.54M hexane solution) was added dropwise at −10° C. with stirring, and stirred at the same temperature for 30 minutes. Then, a solution of 0.57 g of trimethoxyborane in 7 mL of tetrahydrofuran was added dropwise. After the completion of the addition dropwise, it was stirred at the same temperature further for 30 minutes and then the temperature was raised to room temperature. Then, in the reaction mixture, 1.80 g of 2-bromo-3,3,3-trifluoropropene, 1.90 g of potassium carbonate, 10 mL of water and 0.005 g of 1,3-bis(2,6-diisopropylphenyl)imidazole-2-ilidene (1,4-naphthoquinone) palladium (0) dimmer were added, and stirred under nitrogen atmosphere at 60° C. for 15 hours. After the completion of the reaction, the reaction mixture was left and cooled to room temperature, insoluble material was filtered off, and the organic phase was collected and the aqueous phase was extracted with 30 mL of ethyl acetate twice. The combined organic phases were washed with water, and dehydrated with and dried over saturated sodium chloride aqueous solution and then anhydrous sodium sulfate, and the solvent was distilled off under reduced pressure. The residue was purified with silica gel column chromatography that was eluated with hexane to obtain 1.20 g of the aimed product as yellow oily substance.

$^1$H NMR ($CDCl_3$, $Me_4Si$, 300 MHz) δ7.40 (d, J=6.3 Hz, 2H), 6.04 (s, 1H), 5.79 (s, 1H).

Reference Example 2

3-Chloro-5-trifluoromethyl-1-(1-trifluoromethylethenyl)benzene

Step 1: Production of 3-bromo-5-chlorobenzotrifluoride

In a suspension of 3.0 g of 3-chloro-5-trifluoromethylaniline and 2.0 g of copper (II) chloride in 30 mL of acetonitrile, 1.9 g of nitrous acid-tert-butyl was added dropwise at room temperature with stirring. After the completion of the addition dropwise, it was continued to stir at the same temperature for 1 hour and then at 65° C. for 1 hour. After the completion of the reaction, the reaction mixture was left and cooled to room temperature, and insoluble material was filtered off, and 100 mL of 2N hydrochloric acid was added in the filtrate and extracted with diethyl ether (50 mL×2). The combined organic phases were washed with water, and dehydrated with and dried over saturated sodium chloride aqueous solution and then anhydrous sodium sulfate, and the solvent was distilled off under reduced pressure to obtain 2.7 g of the crude aimed product as brown oily substance.

The resulting product was used as such without purification for the next step.

Step 2: Production of 3-chloro-5-trifluoromethyl-1-(1-trifluoromethylethenyl)benzene In a solution of 2.60 g of 3-bromo-5-chlorobenzotrifluoride and 1.2 mL of tert-butylmethyl ether in 25 mL of hexane, 6.38 mL of n-butyl lithium (1.6M hexane solution) was added dropwise at −10° C. with stirring, and stirred at the same temperature for 30 minutes. Then, a solution of 1.09 g of trimethoxyborane in 10 mL of tetrahydrofuran was added dropwise. After the completion of the addition dropwise, it was stirred at the same temperature further for 10 minutes and then the temperature was raised to room temperature. Then, in the reaction mixture, 2.60 g of 2-bromo-3,3,3-trifluoropropene, 2.76 g of potassium carbonate, 15 mL of water and 0.0065 g of 1,3-bis(2,6-diisopropylphenyl)imidazole-2-ilidene (1,4-naphthoquinone) palladium (0) dimmer were added, and stirred under nitrogen atmosphere at 60° C. for 6 hours. After the completion of the reaction, the reaction mixture was left and cooled to room temperature, insoluble material was filtered off, and the organic phase was collected and the aqueous phase was extracted with 30 mL of ethyl acetate twice.

The combined organic phases were washed with water, and dehydrated with and dried over saturated sodium chloride aqueous solution and then anhydrous sodium sulfate, and the solvent was distilled off under reduced pressure. The residue was purified with silica gel column chromatography that was eluated with hexane to obtain 1.50 g of the aimed product as orange oily substance.

$^1$H NMR ($CDCl_3$, $Me_4Si$, 300 MHz) δ7.65 (s, 1H), 7.62 (s, 1H), 7.58 (s, 1H), 6.11 (s, 1H), 5.87 (s, 1H).

Reference Example 3

3-Chloro-4-fluoro-5-trifluoromethyl-1-(1-trifluoromethylethenyl)benzene

Step 1: Production of 5-chloro-6-fluoro-3-nitrobenzotrifluoride

After azeotropically dehydrating 20.0 g of potassium fluoride and 2.0 g of tetramethylammonium chloride in 200 mL of toluene for 2 hours, toluene was distilled off, 100 mL of N,N-dimethylformamide and 8.0 g of 5,6-dichloro-3-nitrobenzotrifluoride were added, and stirred at 100° C. for 15 hours. After the completion of the reaction, the reaction mixture was left and cooled to room temperature, and 500 mL of water was added and extracted with diethyl ether (250 mL×2). The combined organic phases were dehydrated with and dried over saturated sodium chloride aqueous solution and then anhydrous sodium sulfate, and the solvent was distilled off under reduced pressure to obtain 6.1 g of the crude aimed product as red-brown oily substance. The resulting product was used as such without purification for the next step.

Step 2: Production of 3-chloro-4-fluoro-5-trifluoromethylaniline

In a mixture of 7.0 g of reduced iron, 4 mL of acetic acid and 50 mL of water, a solution of 6.0 g of 5-chloro-6-fluoro-3-nitrobenzotrifluoride in 80 mL of acetic acid-ethyl acetate (1:1) was added dropwise at 80° C. with stirring over 30 minutes. After the completion of the addition dropwise, it was continued to stir at the same temperature further for 1 hour. After the completion of the reaction, the reaction mixture was left and cooled to room temperature, insoluble material was filtered off through Celite, the organic phase was collected and washed with 100 mL of water and then 100 mL of saturated sodium hydrogen carbonate aqueous solution. The organic phase was dehydrated with and dried over saturated sodium chloride aqueous solution and then anhydrous sodium sulfate, and the solvent was distilled off under reduced pressure to obtain 6.0 g of the crude aimed product as red-brown oily substance. The resulting product was used as such without purification for the next step.

Step 3: Production of 3-chloro-2-fluoro-5-iodobenzotrifluoride

In 300 mL of 6N hydrochloric acid, 4.00 g of 3-chloro-4-fluoro-5-trifluoromethylaniline was added, and stirred at room temperature for 30 minutes. In the mixture, a solution of 1.42 g of sodium nitrite in 5 mL of water was added dropwise at such a rate that internal temperature would not exceed 5° C. After the completion of the addition dropwise, it was continued to stir at the same temperature further for 1 hour. In the reaction mixture, a solution of 4.70 g of potassium iodide in 15 mL of water was added dropwise at the same temperature with stirring. After the completion of the addition dropwise, it was continued to stir at the same temperature further for 1 hour and then at room temperature for 15 hours. After the completion of the reaction, the reaction mixture was extracted with 50 mL of diethyl ether twice. The combined organic phases were dehydrated with and dried over saturated sodium chloride aqueous solution and then anhydrous sodium sulfate, and the solvent was distilled off under reduced pressure to obtain 2.70 g of the crude aimed product as yellow oily substance. The resulting product was used as such without purification for the next step.

Step 4: Production of 3-chloro-4-fluoro-5-trifluoromethyl-1-(1-trifluoromethylethenyl)benzene In a solution of 2.58 g of 3-chloro-2-fluoro-5-iodobenzotrifluoride and 0.68 g of tert-butylmethyl ether in 20 mL of hexane, 6.0 mL of n-butyl lithium (1.54M hexane solution) was added dropwise at −20° C. with stirring, and stirred at the same temperature for 30 minutes. Then, a solution of 0.88 g of trimethoxyborane in 10 mL of tetrahydrofuran was added dropwise. After the completion of the addition dropwise, it was stirred at the same temperature further for 30 minutes and then the temperature was raised to room temperature. Then, in the reaction mixture, 4.00 g of 2-bromo-3,3,3-trifluoropropene, 2.20 g of potassium carbonate, 15 mL of water and 0.03 g of 1,3-bis(2,6-diisopropylphenyl)imidazole-2-ilidene (1,4-naphthoquinone) palladium (0) dimmer were added, and stirred under nitrogen atmosphere at 60° C. for 6 hours. After the completion of the reaction, the reaction mixture was left and cooled to room temperature, insoluble material was filtered off, and the organic phase was collected and the aqueous phase was extracted with 30 mL of diethyl ether twice.

The combined organic phases were washed with water, and dehydrated with and dried over saturated sodium chloride aqueous solution and then anhydrous sodium sulfate, and the solvent was distilled off under reduced pressure. The residue was purified with silica gel column chromatography that was eluated with hexane to obtain 1.70 g of the aimed product as yellow oily substance.

$^1$H NMR (CDCl$_3$, Me$_4$Si, 300 MHz) δ7.69 (d, J=6.3 Hz, 1H), 7.58 (d, J=5.7 Hz, 1H), 6.10 (s, 1H), 5.83 (s, 1H).

The compounds of the present invention can be produced according to the above-mentioned production methods and working examples. The examples of the compounds produced similarly to Synthetic Examples 1 to 46 are shown in Tables 5 to 15 to which the present invention is not limited. In the meantime, in Tables, the indication "Et" means ethyl, hereinafter similarly thereto, "n-Pr" and "Pr-n" mean normal propyl, "i-Pr" and "Pr-i" mean isopropyl, "c-Pr" and "Pr-c" mean cyclopropyl, "n-Bu" and "Bu-n" mean normal butyl, "s-Bu" and "Bu-s" mean secondary butyl, "i-Bu" and "Bu-i" mean isobutyl, "t-Bu" and "Bu-t" mean tertiary butyl, "c-Bu" and "Bu-c" mean cyclobutyl, "n-Pen" and "Pen-n" mean normal pentyl, "c-Pen" and "Pen-c" mean cyclopentyl, "c-Hex" and "Hex-c" mean cyclohexyl, "Ph" means phenyl, "TMS" means trimethylsilyl, and in Tables, aromatic heterocyclic rings of D-1a to D-59b are the following structures, respectively D-1a:

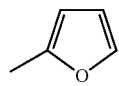

D-2a:

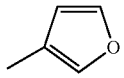

D-3a:

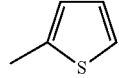

-continued
D-4a: 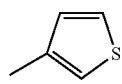
D-8b: 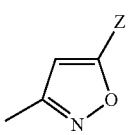
D-13b: 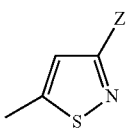
D-14a: 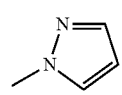
D-15a: 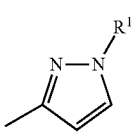
D-21a: 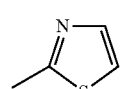
D-35a: 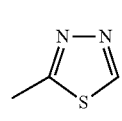
D-41a: 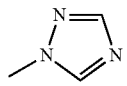
D-52a: 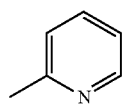
D-52d: 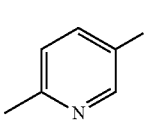
D-52e: 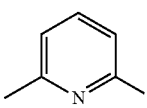
D-53a: 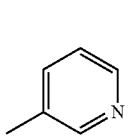
-continued
D-53e: 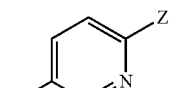
D-54a: 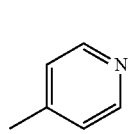
D-55a: 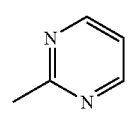
D-55c: 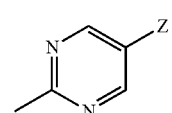
D-57a: 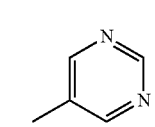
D-57b: 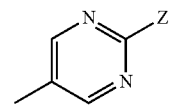
D-57d: 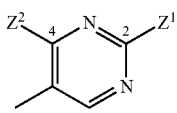
D-58a: 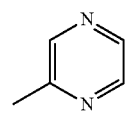
D-58b: 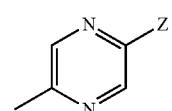
D-59b: 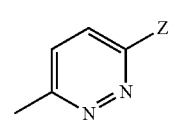
in Tables, saturated heterocyclic rings of E-5a to E-12c are the following structures, respectively,
E-5a: 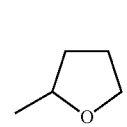

E-6d:

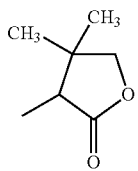

E-12c:

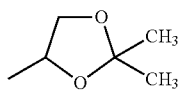

In Tables, partially saturated heterocyclic ring of M-5c is the following structure

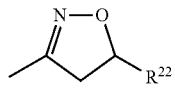 M-5c

In Tables, T-13 to T-22 are the following structures, respectively

T-13:

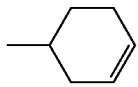

T-14:

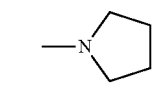

T-18:

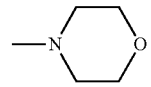

T-22:

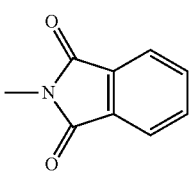

In addition, in Tables, the number showing the substitution position of substituents $(X)_m$ and $(Y)_n$ correspond to the position number indicated in the following strutural formulae. The indication "-" means no-substitution.

Further, in Tables, the indication of "Mw" shows the calculated value of molecular weight, the indication of "$M^+$–H" shows the measured value of molecular ion peak, and "*1" means "resinous" and "*2" means "oily".

TABLE 5

| No. | $(X)_m$ | $(Y)_n$ | $R^2$ | $R^1$ | Mw | $M^+$ + H |
|---|---|---|---|---|---|---|
| 1-001 | 3,5-Cl$_2$ | 2-CH$_3$ | CH$_2$Ph | C(O)OCH$_3$ | 565.37 | 565.00 |
| 1-002 | 3,5-Cl$_2$ | 2-CH$_3$ | H | C(O)OEt | 489.27 | 488.98 |
| 1-003 | 3,5-Cl$_2$ | 2-CH$_3$ | Et | C(O)OEt | 517.32 | 517.07 |
| 1-004 | 3,5-Cl$_2$ | 2-CH$_3$ | H | C(O)OPr-n | 503.30 | 503.00 |
| 1-005 | 3,5-Cl$_2$ | 2-CH$_3$ | H | C(O)OPr-i | 503.30 | 502.97 |
| 1-006 | 3,5-Cl$_2$ | 2-CH$_3$ | CH$_2$C≡CH | C(O)OPr-i | 541.35 | 539.01* |
| 1-007 | 3,5-Cl$_2$ | 2-CH$_3$ | C(O)CH$_3$ | C(O)OPr-i | 545.33 | 543.03* |
| 1-008 | 3,5-Cl$_2$ | 2-CH$_3$ | C(O)OCH$_3$ | C(O)OPr-i | 561.33 | 559.03* |
| 1-009 | 3,5-Cl$_2$ | 2-CH$_3$ | H | C(O)OBu-n | 517.32 | 517.07 |
| 1-010 | 3,5-Cl$_2$ | 2-CH$_3$ | H | C(O)OBu-i | 517.32 | 517.09 |
| 1-011 | 3,5-Cl$_2$ | 2-CH$_3$ | CH$_3$ | C(O)OBu-i | 531.35 | 531.18 |
| 1-012 | 3,5-Cl$_2$ | 2-CH$_3$ | H | C(O)OBu-s(R) | 517.32 | 517.05 |
| 1-013 | 3,5-Cl$_2$ | 2-CH$_3$ | CH$_3$ | C(O)OBu-s(R) | 531.35 | 529.05* |
| 1-014 | 3,5-Cl$_2$ | 2-CH$_3$ | H | C(O)OBu-s(S) | 517.32 | 517.05 |
| 1-015 | 3,5-Cl$_2$ | 2-CH$_3$ | CH$_3$ | C(O)OBu-s(S) | 531.35 | 529.05* |
| 1-016 | 3,5-Cl$_2$ | 2-CH$_3$ | CH$_3$ | C(O)OBu-t | 531.35 | 529.06* |
| 1-017 | 3,5-Cl$_2$ | 2-CH$_3$ | H | C(O)OCH$_2$Pr-c | 515.31 | 515.11 |
| 1-018 | 3,5-Cl$_2$ | 2-CH$_3$ | H | C(O)OBu-c | 515.31 | 513.01* |
| 1-019 | 3,5-Cl$_2$ | 2-CH$_3$ | H | C(O)OPen-n | 531.35 | 531.09 |
| 1-020 | 3,5-Cl$_2$ | 2-CH$_3$ | H | C(O)OCH$_2$Bu-t | 531.35 | 529.04* |
| 1-021 | 3,5-Cl$_2$ | 2-CH$_3$ | H | C(O)OPen-c | 529.34 | 529.03 |
| 1-022 | 3,5-Cl$_2$ | 2-CH$_3$ | CH$_3$ | C(O)OPen-c | 543.36 | 541.05* |
| 1-023 | 3,5-Cl$_2$ | 2-CH$_3$ | H | C(O)OCH$_2$Pen-c | 543.36 | 540.96* |

TABLE 5-continued

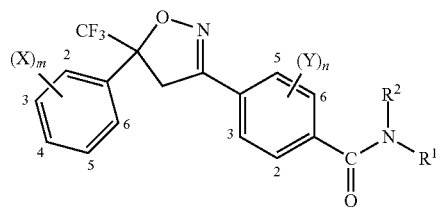

| No. | $(X)_m$ | $(Y)_n$ | $R^2$ | $R^1$ | Mw | $M^+ + H$ |
|---|---|---|---|---|---|---|
| 1-024 | 3,5-Cl$_2$ | 2-CH$_3$ | H | C(O)OHex-c | 543.36 | 541.03* |
| 1-025 | 3,5-Cl$_2$ | 2-CH$_3$ | H | C(O)OCH$_2$Hex-c | 557.39 | 555.03* |
| 1-026 | 3,5-Cl$_2$ | 2-CH$_3$ | H | C(O)OCH$_2$CH$_2$OCH$_3$ | 519.30 | 519.04 |
| 1-027 | 3,5-Cl$_2$ | 2-CH$_3$ | H | C(O)OCH$_2$CH$_2$OPh | 581.37 | 581.07 |
| 1-028 | 3,5-Cl$_2$ | 2-CH$_3$ | H | C(O)O(E-5a) | 531.31 | 529.00* |
| 1-029 | 3,5-Cl$_2$ | 2-CH$_3$ | H | C(O)OCH$_2$(E-5a) | 545.33 | 543.00* |
| 1-030 | 3,5-Cl$_2$ | 2-CH$_3$ | H | C(O)OCH$_2$(E-12c) | 575.36 | 572.99* |
| 1-031 | 3,5-Cl$_2$ | 2-CH$_3$ | H | C(O)OCH$_2$CH$_2$SCH$_3$ | 535.36 | 532.97* |
| 1-032 | 3,5-Cl$_2$ | 2-CH$_3$ | H | C(O)OCH$_2$CH$_2$SO$_2$CH$_3$ | 567.36 | 567.01 |
| 1-033 | 3,5-Cl$_2$ | 2-CH$_3$ | H | C(O)OCH$_2$CH$_2$N(CH$_3$)$_2$ | 532.34 | 532.09 |
| 1-034 | 3,5-Cl$_2$ | 2-CH$_3$ | H | C(O)OCH$_2$CH$_2$(T-14) | 558.38 | 558.13 |
| 1-035 | 3,5-Cl$_2$ | 2-CH$_3$ | H | C(O)OCH$_2$CH$_2$(T-18) | 574.38 | 574.13 |
| 1-036 | 3,5-Cl$_2$ | 2-CH$_3$ | H | C(O)OCH(CH$_3$)C(O)OCH$_3$ | 547.31 | 547.04 |
| 1-037 | 3,5-Cl$_2$ | 2-CH$_3$ | CH$_3$ | C(O)OCH(CH$_3$)C(O)OCH$_3$ | 561.33 | 561.05 |
| 1-038 | 3,5-Cl$_2$ | 2-CH$_3$ | H | C(O)O(E-6d) | 573.34 | 570.99* |
| 1-039 | 3,5-Cl$_2$ | 2-CH$_3$ | H | C(O)OCH$_2$C(CH$_3$)=CH$_2$ | 515.31 | 515.09 |
| 1-040 | 3,5-Cl$_2$ | 2-CH$_3$ | CH$_3$ | C(O)OCH$_2$C(CH$_3$)=CH$_2$ | 529.34 | 529.14 |
| 1-041 | 3,5-Cl$_2$ | 2-CH$_3$ | H | C(O)OCH(Et)CH=CH$_2$ | 529.34 | 527.03* |
| 1-042 | 3,5-Cl$_2$ | 2-CH$_3$ | H | C(O)OC(CH$_3$)$_2$CH=CH$_2$ | 529.34 | 527.01* |
| 1-043 | 3,5-Cl$_2$ | 2-CH$_3$ | H | C(O)OCH$_2$(T-13) | 555.37 | 553.03* |
| 1-044 | 3,5-Cl$_2$ | 2-CH$_3$ | H | C(O)OCH$_2$CCl=CH$_2$ | 535.73 | 532.94* |
| 1-045 | 3,5-Cl$_2$ | 2-CH$_3$ | H | C(O)OCH$_2$C≡CH | 499.27 | 499.03 |
| 1-046 | 3,5-Cl$_2$ | 2-CH$_3$ | H | C(O)OCH$_2$(Ph—4-F) | 569.33 | 569.07 |
| 1-047 | 3,5-Cl$_2$ | 2-CH$_3$ | H | C(O)OCH$_2$(D-1a) | 541.30 | 538.90* |
| 1-048 | 3,5-Cl$_2$ | 2-CH$_3$ | H | C(O)OCH$_2$(D-52a) | 552.33 | 552.05 |
| 1-049 | 3,5-Cl$_2$ | 2-CH$_3$ | CH$_3$ | C(O)OCH$_2$(D-52a) | 566.36 | 566.04 |
| 1-050 | 3,5-Cl$_2$ | 2-CH$_3$ | H | C(O)SCH$_3$ | 491.31 | 490.89 |
| 1-051 | 3,5-Cl$_2$ | 2-CH$_3$ | CH$_3$ | C(O)SPr-n | 533.39 | 533.09 |
| 1-052 | 3,5-Cl$_2$ | 2-CH$_3$ | C(O)CH$_3$ | C(O)OEt | 531.31 | 528.98* |
| 1-053 | 3,5-Cl$_2$ | 2-CH$_3$ | C(O)CH$_2$OCH$_3$ | C(O)OPr-i | 575.36 | 573.02* |
| 1-054 | 3,5-Cl$_2$ | 2-CH$_3$ | H | C(O)OCH$_2$CH$_2$S(D-52a) | 597.05 | 598.09 |
| 1-055 | 3,5-Cl$_2$ | 2-CH$_3$ | H | C(O)OCH$_2$CH(CH$_3$)NO$_2$ | 547.05 | 545.91* |
| 1-056 | 3,5-Cl$_2$ | 2-CH$_3$ | H | C(O)OCH(CH$_3$)C(O)CH$_3$ | 531.31 | 529.04* |
| 1-057 | 3,5-Cl$_2$ | 2-CH$_3$ | H | C(O)OCH$_2$CH$_2$-TMS | 561.45 | 559.04* |
| 1-058 | 3,5-Cl$_2$ | 2-CH$_3$ | H | C(O)OCH$_2$CH$_2$CH$_2$-TMS | 574.11 | 572.97* |

In Table above, the indication of "*" shows the measured value of molecular ion peak of $M^+ - H$ measured with negative mode.

TABLE 6

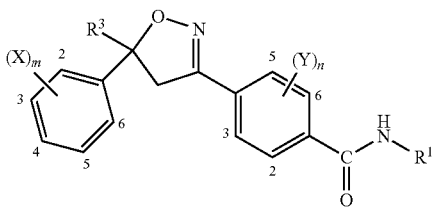

| No. | $(X)_m$ | $R^3$ | $(Y)_n$ | $R^1$ | m.p. (° C.) |
|---|---|---|---|---|---|
| 2-001 | 3,5-Cl$_2$ | CF$_3$ | — | C(O)OEt | *1 |
| 2-002 | 3,5-Cl$_2$ | CF$_3$ | — | C(O)OPr-i | *1 |
| 2-003 | 3,5-Cl$_2$ | CF$_3$ | 2-CH$_3$ | C(O)OCH$_3$ | *2 |
| 2-004 | 3,5-Cl$_2$ | CF$_3$ | 2-CH$_3$ | C(O)OBu-t | *1 |
| 2-005 | 3,5-Cl$_2$ | CF$_3$ | 2-CH$_3$ | C(O)OCH$_2$CH$_2$OCH$_2$CH$_2$OCH$_3$ | *1 |
| 2-006 | 3,5-Cl$_2$ | CF$_3$ | 2-CH$_3$ | C(O)OCH$_2$CH$_2$NHC(O)CH$_3$ | 151.0-153.0 |
| 2-007 | 3,5-Cl$_2$ | CF$_3$ | 2-CH$_3$ | C(O)OCH$_2$CH$_2$(T-22) | *1 |
| 2-008 | 3,5-Cl$_2$ | CF$_3$ | 2-CH$_3$ | C(O)OCH$_2$CH$_2$CN | 170.0-172.0 |
| 2-009 | 3,5-Cl$_2$ | CF$_3$ | 2-CH$_3$ | C(O)OCH$_2$C(O)OCH$_3$ | *1 |
| 2-010 | 3,5-Cl$_2$ | CF$_3$ | 2-CH$_3$ | C(O)SPr-n | 124.0-126.0 |
| 2-011 | 3,5-Cl$_2$ | CF$_3$ | 2-CH$_3$ | C(S)OCH$_3$ | *1 |
| 2-012 | 3,5-Cl$_2$ | CF$_3$ | 2-CH$_3$ | C(S)SCH$_3$ | *1 |
| 2-013 | 3,5-Cl$_2$ | CF$_3$ | 2-Cl | C(O)OCH$_3$ | *1 |

TABLE 6-continued

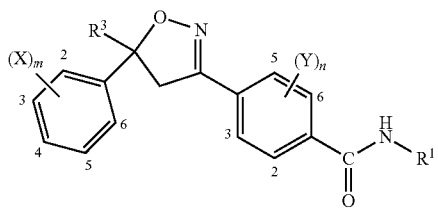

| No. | $(X)_m$ | $R^3$ | $(Y)_n$ | $R^1$ | m.p. (° C.) |
|---|---|---|---|---|---|
| 2-014 | 3,5-Cl$_2$ | CF$_3$ | 2-Br | C(O)OCH$_3$ | *1 |
| 2-015 | 3,5-Cl$_2$ | CF$_3$ | 2-I | C(O)OCH$_3$ | 166.0-168.0 |
| 2-016 | 3,5-Cl$_2$ | CF$_3$ | 2-I | C(O)OPr-i | *1 |
| 2-017 | 3,5-Cl$_2$ | CF$_3$ | 2-NO$_2$ | C(O)OCH$_3$ | 167.0-170.0 |
| 2-018 | 3,5-Cl$_2$ | CF$_3$ | 2-Ph | C(O)OCH$_3$ | *1 |
| 2-019 | 3,5-Cl$_2$ | CF$_3$ | 2-I—6-CH$_3$ | C(O)OCH$_3$ | *1 |
| 2-020 | 3,5-Cl$_2$ | CF$_2$Cl | 2-Cl | C(O)OCH$_3$ | *1 |
| 2-021 | 3-Cl—5-Br | CF$_3$ | 2-CH$_3$ | C(O)OCH$_3$ | *1 |
| 2-022 | 3,5-Br$_2$ | CF$_3$ | 2-CH$_3$ | C(O)OCH$_3$ | *1 |
| 2-023 | 3,5-(CF$_3$)$_2$ | CF$_3$ | 2-CH$_3$ | C(O)OCH$_3$ | *1 |
| 2-024 | 3,5-Cl$_2$ | CF$_3$ | 2-CF$_3$ | C(O)OCH$_3$ | *1 |
| 2-025 | 3,5-Cl$_2$ | CF$_3$ | 2-CH$_2$OCH$_3$ | C(O)OCH$_3$ | *1 |
| 2-026 | 3,4,5-Cl$_2$ | CF$_3$ | 2-CH$_3$ | C(O)OCH$_3$ | *1 |
| 2-027 | 3,5-Cl$_2$ | CF$_3$ | 2-CH$_3$ | C(S)OPr-i | *1 |
| 2-028 | 3,5-Cl$_2$ | CF$_3$ | 2-CH$_3$ | C(S)OBu-n | *1 |
| 2-029 | 3,5-Cl$_2$ | CF$_3$ | 2-CH$_3$ | C(S)OCH$_2$C≡CH | *1 |
| 2-030 | 3,4,5-Cl$_3$ | CF$_3$ | — | C(O)OEt | *1 |

TABLE 7

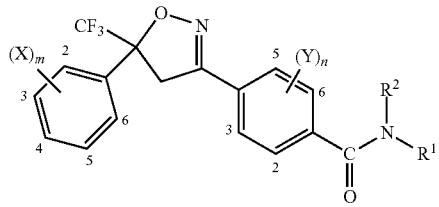

| No. | $(X)_m$ | $(Y)_n$ | $R^2$ | $R^1$ | m.p. (° C.) |
|---|---|---|---|---|---|
| 3-001 | 3,5-Cl$_2$ | — | CH$_3$ | C(O)OEt | *1 |
| 3-002 | 3,5-Cl$_2$ | — | CH$_3$ | C(O)OPr-i | *1 |
| 3-003 | 3,5-Cl$_2$ | 2-CH$_3$ | CH$_3$ | C(O)OCH$_3$ | 147.0-149.0 |
| 3-004 | 3,5-Cl$_2$ | 2-CH$_3$ | Et | C(O)OCH$_3$ | 100.0-102.0 |
| 3-005 | 3,5-Cl$_2$ | 2-CH$_3$ | n-Pr | C(O)OCH$_3$ | *1 |
| 3-006 | 3,5-Cl$_2$ | 2-CH$_3$ | i-Pr | C(O)OCH$_3$ | *1 |
| 3-007 | 3,5-Cl$_2$ | 2-CH$_3$ | CH$_2$OCH$_3$ | C(O)OCH$_3$ | 144.0-146.0 |
| 3-007(+) | | 99% e.e. | $[\alpha]_D^{21.4}$ + 64.25° | (CH$_3$CN, c = 1.250) | *1 |
| 3-007(−) | | 99% e.e. | $[\alpha]_D^{21.4}$ − 63.37° | (CH$_3$CN, c = 1.190) | *1 |
| 3-008 | 3,5-Cl$_2$ | 2-CH$_3$ | CH$_2$CN | C(O)OCH$_3$ | 170.0-171.0 |
| 3-009 | 3,5-Cl$_2$ | 2-CH$_3$ | CH$_2$C(O)OCH$_3$ | C(O)OCH$_3$ | *1 |
| 3-010 | 3,5-Cl$_2$ | 2-CH$_3$ | CH$_2$C≡CH | C(O)OCH$_3$ | 146.0-147.0 |
| 3-011 | 3,5-Cl$_2$ | 2-CH$_3$ | C(O)CH$_3$ | C(O)OCH$_3$ | 116.0-117.0 |
| 3-012 | 3,5-Cl$_2$ | 2-CH$_3$ | C(O)Bu-t | C(O)OCH$_3$ | *1 |
| 3-013 | 3,5-Cl$_2$ | 2-CH$_3$ | C(O)CH$_2$OCH$_3$ | C(O)OCH$_3$ | *1 |
| 3-014 | 3,5-Cl$_2$ | 2-CH$_3$ | C(O)OCH$_3$ | C(O)OCH$_3$ | *1 |
| 3-015 | 3,5-Cl$_2$ | 2-CH$_3$ | CH$_3$ | C(O)OEt | 133.0-135.0 |
| 3-016 | 3,5-Cl$_2$ | 2-CH$_3$ | CH$_3$ | C(O)OPr-i | *1 |
| 3-017 | 3,5-Cl$_2$ | 2-CH$_3$ | Et | C(O)OPr-i | *1 |
| 3-018 | 3,5-Cl$_2$ | 2-CH$_3$ | CH$_2$OCH$_3$ | C(O)OPr-i | *1 |
| 3-019 | 3,5-Cl$_2$ | 2-CH$_3$ | CH$_3$ | C(O)OBu-n | 91.0-93.0 |
| 3-020 | 3,5-Cl$_2$ | 2-CH$_3$ | CH$_3$ | C(O)OCH$_2$CH$_2$OCH$_3$ | *1 |
| 3-021 | 3,5-Cl$_2$ | 2-CH$_3$ | CH$_3$ | C(O)OCH$_2$CH$_2$CN | 171.0-172.0 |
| 3-022 | 3,5-Cl$_2$ | 2-CH$_3$ | CH$_3$ | C(O)OCH$_2$C≡CH | 185.0-187.0 |
| 3-023 | 3,5-Cl$_2$ | 2-CH$_3$ | CH$_3$ | C(O)OCH$_2$(Ph—4-F) | 132.0-133.0 |
| 3-024 | 3,5-Cl$_2$ | 2-Cl | CH$_2$OCH$_3$ | C(O)OCH$_3$ | 103.0-106.0 |
| 3-025 | 3,5-Cl$_2$ | 2-Cl | CH$_2$CN | C(O)OCH$_3$ | 185.0-187.0 |
| 3-026 | 3,5-Cl$_2$ | 2-Br | CH$_2$OCH$_3$ | C(O)OCH$_3$ | *1 |
| 3-027 | 3,5-Cl$_2$ | 2-Br | CH$_2$CN | C(O)OCH$_3$ | *1 |
| 3-028 | 3,5-Cl$_2$ | 2-I | CH$_3$ | C(O)OCH$_3$ | 170.0-172.0 |
| 3-029 | 3,5-Cl$_2$ | 2-I | CH$_2$OCH$_3$ | C(O)OCH$_3$ | 119.5-121.0 |
| 3-030 | 3,5-Cl$_2$ | 2-I | CH$_2$CN | C(O)OCH$_3$ | *1 |

TABLE 7-continued

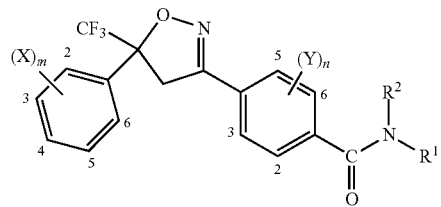

| No. | $(X)_m$ | $(Y)_n$ | $R^2$ | $R^1$ | m.p. (° C.) |
|---|---|---|---|---|---|
| 3-031 | 3,5-Cl$_2$ | 2-CH$_3$ | CH$_2$OEt | C(O)OCH$_3$ | 112.0-114.0 |
| 3-032 | 3,5-Cl$_2$ | 2-CH$_3$ | CH$_2$OCH$_2$CF$_3$ | C(O)OCH$_3$ | *1 |
| 3-033 | 3,5-Cl$_2$ | 2-CH$_3$ | CH$_2$OC(O)CH$_3$ | C(O)OCH$_3$ | *1 |
| 3-034 | 3,5-Cl$_2$ | 2-CH$_3$ | CH$_2$OC(O)Bu-t | C(O)OCH$_3$ | *1 |
| 3-035 | 3,5-Cl$_2$ | 2-CH$_3$ | CH$_2$SCH$_3$ | C(O)OCH$_3$ | *1 |
| 3-036 | 3,5-Cl$_2$ | 2-CH$_3$ | CH$_2$SO$_2$CH$_3$ | C(O)OCH$_3$ | *1 |
| 3-037 | 3,5-Cl$_2$ | 2-CH$_3$ | CH$_2$SC(O)CH$_3$ | C(O)OCH$_3$ | *1 |
| 3-038 | 3,5-Cl$_2$ | 2-CH$_3$ | CH$_2$SC(S)OEt | C(O)OCH$_3$ | *1 |
| 3-039 | 3,5-Cl$_2$ | 2-CH$_3$ | CH$_2$NHC(O)OCH$_3$ | C(O)OCH$_3$ | *1 |
| 3-040 | 3,5-Cl$_2$ | 2-CH$_3$ | CH$_2$C(O)Ph | C(O)OCH$_3$ | *1 |
| 3-041 | 3,5-Cl$_2$ | 2-CH$_3$ | C(O)Et | C(O)OCH$_3$ | 135.0-136.0 |
| 3-042 | 3,5-Cl$_2$ | 2-CH$_3$ | C(O)Pr-n | C(O)OCH$_3$ | 149.0-151.0 |
| 3-043 | 3,5-Cl$_2$ | 2-CH$_3$ | C(O)Pr-i | C(O)OCH$_3$ | *1 |
| 3-044 | 3,5-Cl$_2$ | 2-CH$_3$ | C(O)CH$_2$Cl | C(O)OCH$_3$ | *1 |
| 3-045 | 3,5-Cl$_2$ | 2-CH$_3$ | C(O)CH$_2$SCH$_3$ | C(O)OCH$_3$ | *1 |
| 3-046 | 3,5-Cl$_2$ | 2-CH$_3$ | C(O)Ph | C(O)OCH$_3$ | *1 |
| 3-047 | 3,5-Cl$_2$ | 2-CH$_3$ | C(O)(Ph—4-Cl) | C(O)OCH$_3$ | *1 |
| 3-048 | 3,5-Cl$_2$ | 2-CH$_3$ | C(O)(Ph—4-CH$_3$) | C(O)OCH$_3$ | *1 |
| 3-049 | 3,5-Cl$_2$ | 2-CH$_3$ | C(O)(Ph—4-OCH$_3$) | C(O)OCH$_3$ | *1 |
| 3-050 | 3,5-Cl$_2$ | 2-CH$_3$ | C(O)(Ph—4-NO$_2$) | C(O)OCH$_3$ | *1 |
| 3-051 | 3,5-Cl$_2$ | 2-CH$_3$ | C(O)OCH$_2$Cl | C(O)OCH$_3$ | 112.0-114.0 |
| 3-052 | 3,5-Cl$_2$ | 2-CH$_3$ | C(O)OCH$_2$CH$_2$Cl | C(O)OCH$_3$ | *1 |
| 3-053 | 3,5-Cl$_2$ | 2-CH$_3$ | SCCl$_3$ | C(O)OCH$_3$ | *1 |
| 3-054 | 3,5-Cl$_2$ | 2-CH$_3$ | CH$_2$OCH$_3$ | C(O)OEt | *1 |
| 3-055 | 3,5-Cl$_2$ | 2-CH$_3$ | C(O)Et | C(O)OEt | *1 |
| 3-056 | 3,5-Cl$_2$ | 2-CH$_3$ | C(O)Bu-t | C(O)OEt | *1 |
| 3-057 | 3,5-Cl$_2$ | 2-CH$_3$ | C(O)CH$_2$OCH$_3$ | C(O)OEt | *1 |
| 3-058 | 3,5-Cl$_2$ | 2-CH$_3$ | C(O)OCH$_3$ | C(O)OEt | 121.0-122.0 |
| 3-059 | 3,5-Cl$_2$ | 2-CH$_3$ | CH$_2$CN | C(O)OPr-i | *1 |
| 3-060 | 3,5-Cl$_2$ | 2-CH$_3$ | C(O)Et | C(O)OPr-i | *1 |
| 3-061 | 3,5-Cl$_2$ | 2-CH$_3$ | C(O)Bu-t | C(O)OPr-i | 150.0-152.0 |
| 3-062 | 3,5-Cl$_2$ | 2-CH$_3$ | C(O)OEt | C(O)OPr-i | 121.0-122.0 |
| 3-063 | 3,5-Cl$_2$ | 2-CH$_3$ | Et | C(O)OBu-t | *1 |
| 3-064 | 3,5-Cl$_2$ | 2-CH$_3$ | CH$_2$OCH$_3$ | C(O)OBu-t | *1 |
| 3-065 | 3,5-Cl$_2$ | 2-CH$_3$ | CH$_2$Ph | C(O)OBu-t | *1 |
| 3-066 | 3,5-Cl$_2$ | 2-CH$_3$ | C(O)CH$_3$ | C(O)OBu-t | *1 |
| 3-067 | 3,5-Cl$_2$ | 2-CH$_3$ | C(O)Et | C(O)OBu-t | 150.0-152.0 |
| 3-068 | 3,5-Cl$_2$ | 2-CH$_3$ | C(O)CH$_2$CF$_3$ | C(O)OBu-t | *1 |
| 3-069 | 3,5-Cl$_2$ | 2-CH$_3$ | C(O)OCH$_3$ | C(O)OBu-t | 128.0-130.0 |
| 3-070 | 3,5-Cl$_2$ | 2-CH$_3$ | C(O)OCH$_3$ | C(O)OCH$_2$CH$_2$OCH$_3$ | *1 |
| 3-071 | 3,5-Cl$_2$ | 2-CH$_3$ | —CH$_2$CH$_2$OC(O)— | | *1 |
| 3-072 | 3,5-Cl$_2$ | 2-CH$_3$ | —C(O)C(CH$_3$)$_2$OC(O)— | | *1 |
| 3-073 | 3,5-Cl$_2$ | 2-I | CH$_2$OEt | C(O)OCH$_3$ | *1 |
| 3-074 | 3,5-Cl$_2$ | 2-CH$_3$ | CH$_2$OPr-i | C(O)OCH$_3$ | 110.0-111.0 |
| 3-075 | 3,5-Cl$_2$ | 2-CH$_3$ | CH$_2$OC(O)Et | C(O)OCH$_3$ | *1 |
| 3-076 | 3,5-Cl$_2$ | 2-CH$_3$ | CH$_2$OC(O)OCH$_3$ | C(O)OCH$_3$ | *1 |
| 3-077 | 3,5-Cl$_2$ | 2-CH$_3$ | E-5a | C(O)OCH$_3$ | *1 |
| 3-078 | 3,5-Cl$_2$ | 2-CH$_3$ | C(O)CH$_2$OEt | C(O)OCH$_3$ | *1 |
| 3-079 | 3,5-Cl$_2$ | 2-CH$_3$ | CH$_2$OEt | C(O)OEt | 114.0-115.0 |
| 3-080 | 3-Cl—5-Br | 2-CH$_3$ | CH$_2$OCH$_3$ | C(O)OCH$_3$ | *1 |
| 3-081 | 3,5-(CF$_3$)$_2$ | 2-CH$_3$ | C(O)Et | C(O)OCH$_3$ | 127.0-131.0 |
| 3-082 | 3,5-Cl$_2$ | 2-CH$_2$OCH$_3$ | CH$_3$ | C(O)OEt | 161.0-163.0 |
| 3-083 | 3,5-Cl$_2$ | 2-CH$_2$OCH$_3$ | C(O)CH$_3$ | C(O)OCH$_3$ | 155.0-159.0 |
| 3-084 | 3,5-(CF$_3$)$_2$ | — | CH$_2$OEt | C(O)OCH$_3$ | *1 |
| 3-085 | 3,5-(CF$_3$)$_2$ | — | CH$_2$OCH$_2$CF$_3$ | C(O)OCH$_3$ | *1 |

TABLE 8

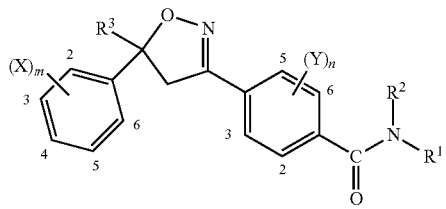

| No. | (X)$_m$ | R$^3$ | (Y)$_n$ | R$^2$ | R$^1$ | m.p. (° C.) |
|---|---|---|---|---|---|---|
| 4-001 | 3,5-Cl$_2$ | CF$_3$ | 2-I | H | C(O)NH$_2$ | 177.0-180.0 |
| 4-002 | 3,5-Cl$_2$ | CF$_3$ | 2-CH$_3$ | H | C(O)NH$_2$ | 201.0-205.0 |
| 4-003 | 3,5-Cl$_2$ | CF$_3$ | 2-CH$_3$ | CH$_3$ | C(O)NH$_2$ | 181.0-183.0 |
| 4-004 | 3,5-Cl$_2$ | CF$_3$ | 2-CH$_3$ | CH$_3$ | C(O)NHC(O)CH$_3$ | *1 |
| 4-005 | 3,5-Cl$_2$ | CF$_3$ | 2-CH$_3$ | H | C(O)NHC(O)CH$_2$Cl | 159.0-161.0 |
| 4-006 | 3,5-Cl$_2$ | CF$_3$ | 2-CH$_3$ | CH$_3$ | C(O)NHC(O)CH$_2$Cl | 184.0-185.0 |
| 4-007 | 3,5-Cl$_2$ | CF$_3$ | 2-CH$_3$ | CH$_3$ | C(O)NHC(O)CCl$_3$ | *1 |
| 4-008 | 3,5-Cl$_2$ | CF$_3$ | 2-CH$_3$ | CH$_3$ | C(O)NHC(O)OCH$_3$ | *1 |
| 4-009 | 3,5-Cl$_2$ | CF$_3$ | 2-CH$_3$ | H | C(S)NH$_2$ | *1 |
| 4-010 | 3,5-Cl$_2$ | CF$_3$ | 2-CH$_3$ | CH$_3$ | C(O)NHC(O)Ph | *1 |
| 4-011 | 3,5-Cl$_2$ | CF$_3$ | 2-CH$_3$ | H | C(O)N(Et)C(O)OCH$_3$ | *1 |
| 4-012 | 3,5-Cl$_2$ | CF$_3$ | 2-CH$_3$ | CH$_2$ | C(O)N(Et)C(O)OCH$_3$ | 169.0-171.0 |
| 4-013 | 3,5-Cl$_2$ | CF$_3$ | 2-CH$_3$ | H | C(O)NHOCH$_3$ | 139.0-142.0 |
| 4-014 | 3,5-Cl$_2$ | CF$_3$ | 2-Cl | H | C(O)NH$_2$ | 87.0-90.0 |
| 4-015 | 3,5-Cl$_2$ | CF$_3$ | 2-Br | H | C(O)NH$_2$ | *1 |

TABLE 9

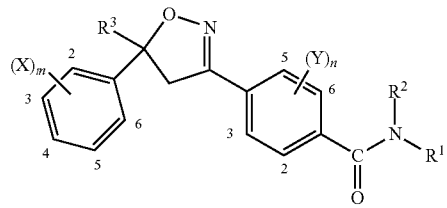

| No. | (X)$_m$ | R$^3$ | (Y)$_n$ | R$^2$ | R$^1$ | m.p. (° C.) |
|---|---|---|---|---|---|---|
| 5-001 | 3,5-Cl$_2$ | CF$_3$ | 2-CH$_3$ | CH$_3$ | Ph | *1 |
| 5-002 | 3,5-Cl$_2$ | CF$_3$ | 2-CH$_3$ | Et | Ph | *1 |
| 5-003 | 3,5-Cl$_2$ | CF$_3$ | 2-CH$_3$ | i-Pr | Ph | *1 |
| 5-004 | 3,5-Cl$_2$ | CF$_3$ | 2-CH$_3$ | CH$_3$ | Ph-4-F | 175.0-178.0 |
| 5-005 | 3,5-Cl$_2$ | CF$_3$ | 2-CH$_3$ | Et | Ph-4-F | 160.0-163.0 |
| 5-006 | 3,5-Cl$_2$ | CF$_3$ | 2-CH$_3$ | CH$_2$CF$_3$ | Ph-4-F | 96.0-101.0 |
| 5-007 | 3,5-Cl$_2$ | CF$_3$ | 2-CH$_3$ | CH$_2$OCH$_3$ | Ph-4-F | 140.0-143.0 |
| 5-008 | 3,5-Cl$_2$ | CF$_3$ | 2-CH$_3$ | CH$_2$CN | Ph-4-F | 60.0-66.0 |
| 5.009 | 3,5-Cl$_2$ | CF$_3$ | 2-CH$_3$ | CH$_2$CH=CH$_2$ | Ph-4-F | *1 |
| 5-010 | 3,5-Cl$_2$ | CF$_3$ | 2-CH$_3$ | C(O)CH$_3$ | Ph-4-F | 61.0-66.0 |
| 5-011 | 3,5-Cl$_2$ | CF$_3$ | 2-CH$_3$ | C(O)OCH$_3$ | Ph-4-F | 89.0-94.0 |
| 5-012 | 3,5-Cl$_2$ | CF$_3$ | 2-CH$_3$ | CH$_3$ | D-52a | *1 |
| 5-013 | 3,5-Cl$_2$ | CF$_3$ | 2-CH$_3$ | C(O)CH$_3$ | D-55a | *1 |
| 5-014 | 3,5-Cl$_2$ | CF$_3$ | 2-CH$_3$ | C(O)OCH$_3$ | D-55a | *1 |
| 5-015 | 3,5-Cl$_2$ | CF$_3$ | 2-Cl | CH$_3$ | (D-55c)Cl | 176.0-178.0 |
| 5-016 | 3,5-Cl$_2$ | CF$_3$ | 2-Cl | C(O)CH$_3$ | (D-55c)Cl | *1 |
| 5-017 | 3,5-Cl$_2$ | CF$_3$ | 2-Cl | C(O)OCH$_3$ | (D-55c)Cl | 114.0-121.0 |
| 5-018 | 3,5-Cl$_2$ | CF$_3$ | 2-CH$_3$ | C(O)Et | Ph-4-F | *1 |
| 5-019 | 3,5-Cl$_2$ | CF$_3$ | 2-CH$_3$ | C(O)Pr-c | Ph-4-F | *1 |
| 5-020 | 3,5-Cl$_2$ | CF$_3$ | 2-CH$_3$ | C(O)Bu-i | Ph-4-F | *1 |
| 5-021 | 3,5-Cl$_2$ | CF$_3$ | 2-CH$_3$ | C(O)CH$_2$OCH$_3$ | Ph-4-F | *1 |
| 5-022 | 3,5-Cl$_2$ | CF$_3$ | 2-CH$_3$ | C(O)NH$_2$ | Ph-4-F | 209.0-211.0 |
| 5-023 | 3,5-Cl$_2$ | CF$_3$ | 2-CH$_3$ | C(O)NHC(O)CH$_2$Cl | Ph-4-F | 141.0-144.0 |
| 5-024 | 3,5-Cl$_2$ | CF$_3$ | 2-CH$_3$ | CH$_3$ | Ph-4-NO$_2$ | *1 |
| 5-025 | 3,5-Cl$_2$ | CF$_3$ | 2-CH$_3$ | C(O)CH$_3$ | Ph-4-NO$_2$ | *1 |
| 5-026 | 3,5-Cl$_2$ | CF$_3$ | 2-CH$_3$ | C(O)OCH$_3$ | Ph-4-NO$_2$ | *1 |
| 5-027 | 3,5-Cl$_2$ | CF$_3$ | 2-CH$_3$ | CH$_3$ | Ph-4-CN | *1 |
| 5-028 | 3,5-Cl$_2$ | CF$_3$ | 2-CH$_3$ | C(O)CH$_3$ | Ph-4-CN | *1 |
| 5-029 | 3,5-Cl$_2$ | CF$_3$ | 2-CH$_3$ | C(O)OCH$_3$ | Ph-4-CN | *1 |
| 5-030 | 3,5-Cl$_2$ | CF$_3$ | 2-CH$_3$ | CH$_3$ | Ph-2,4-F$_2$ | 171.0-173.0 |
| 5-031 | 3,5-Cl$_2$ | CF$_3$ | 2-CH$_3$ | Et | Ph-2,4-F$_2$ | 168.0-169.0 |
| 5-032 | 3,5-Cl$_2$ | CF$_3$ | 2-CH$_3$ | CH$_2$OCH$_3$ | Ph-2,4-F$_2$ | 155.0-158.0 |
| 5-033 | 3,5-Cl$_2$ | CF$_3$ | 2-CH$_3$ | C(O)CH$_3$ | Ph-2,4-F$_2$ | *1 |
| 5-034 | 3,5-Cl$_2$ | CF$_3$ | 2-CH$_3$ | C(O)Pr-i | Ph-2,4-F$_2$ | *1 |
| 5-035 | 3,5-Cl$_2$ | CF$_3$ | 2-CH$_3$ | C(O)Bu-t | Ph-2,4-F$_2$ | *1 |
| 5-036 | 3,5-Cl$_2$ | CF$_3$ | 2-CH$_3$ | C(O)OCH$_3$ | Ph-2,4-F$_2$ | *1 |
| 5-037 | 3,5-Cl$_2$ | CF$_3$ | 2-CH$_3$ | C(O)OCH$_3$ | Ph-2,5-F$_2$ | *1 |
| 5-038 | 3,5-Cl$_2$ | CF$_3$ | 2-CH$_3$ | C(O)Bu-t | D-3a | *1 |
| 5-039 | 3,5-Cl$_2$ | CF$_3$ | 2-CH$_3$ | CH$_3$ | (D-8b)CH$_3$ | *1 |
| 5-040 | 3,5-Cl$_2$ | CF$_3$ | 2-CH$_3$ | C(O)CH$_3$ | (D-8b)CH$_3$ | *1 |
| 5-041 | 3,5-Cl$_2$ | CF$_3$ | 2-CH$_3$ | C(O)OCH$_3$ | (D-8b)CH$_3$ | *1 |

TABLE 9-continued

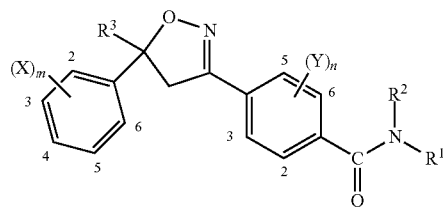

| No. | (X)$_m$ | R$^3$ | (Y)$_n$ | R$^2$ | R$^1$ | m.p. (° C.) |
|---|---|---|---|---|---|---|
| 5-042 | 3,5-Cl$_2$ | CF$_3$ | 2-CH$_3$ | CH$_3$ | (D-13b)CH$_3$ | *1 |
| 5-043 | 3,5-Cl$_2$ | CF$_3$ | 2-CH$_3$ | CH$_3$ | D-14a | *1 |
| 5-044 | 3,5-Cl$_2$ | CF$_3$ | 2-CH$_3$ | C(O)CH$_3$ | D-14a | *1 |
| 5-045 | 3,5-Cl$_2$ | CF$_3$ | 2-CH$_3$ | C(O)OCH$_3$ | D-14a | *1 |
| 5-046 | 3,5-Cl$_2$ | CF$_3$ | 2-CH$_3$ | CH$_3$ | (D-15a)CH$_3$ | *1 |
| 5-047 | 3,5-Cl$_2$ | CF$_3$ | 2-CH$_3$ | CH$_3$ | D-21a | *1 |
| 5-048 | 3,5-Cl$_2$ | CF$_3$ | 2-CH$_3$ | CH$_3$ | D-35a | *1 |
| 5-049 | 3,5-Cl$_2$ | CF$_3$ | 2-CH$_3$ | C(O)OCH$_3$ | D-35a | *1 |
| 5-050 | 3,5-Cl$_2$ | CF$_3$ | 2-CH$_3$ | C(O)CH$_3$ | D-52a | *1 |
| 5-051 | 3,5-Cl$_2$ | CF$_3$ | 2-CH$_3$ | C(O)OCH$_3$ | D-52a | *1 |
| 5-052 | 3,5-Cl$_2$ | CF$_3$ | 2-CH$_3$ | CH$_3$ | (D-52d)Cl | *1 |
| 5-053 | 3,5-Cl$_2$ | CF$_3$ | 2-CH$_3$ | Et | (D-52d)Cl | *1 |
| 5-054 | 3,5-Cl$_2$ | CF$_3$ | 2-CH$_3$ | CH$_2$OCH$_3$ | (D-52d)Cl | *1 |
| 5-055 | 3,5-Cl$_2$ | CF$_3$ | 2-CH$_3$ | CH$_2$CN | (D-52d)Cl | *1 |
| 5-056 | 3,5-Cl$_2$ | CF$_3$ | 2-CH$_3$ | C(O)CH$_3$ | (D-52d)Cl | *1 |
| 5-057 | 3,5-Cl$_2$ | CF$_3$ | 2-CH$_3$ | C(O)Et | (D-52d)Cl | *1 |
| 5-058 | 3,5-Cl$_2$ | CF$_3$ | 2-CH$_3$ | C(O)Pr-n | (D-52d)Cl | *1 |
| 5-059 | 3,5-Cl$_2$ | CF$_3$ | 2-CH$_3$ | C(O)Bu-t | (D-52d)Cl | *1 |
| 5-060 | 3,5-Cl$_2$ | CF$_3$ | 2-CH$_3$ | C(O)OCH$_3$ | (D-52d)Cl | *1 |
| 5-061 | 3,5-Cl$_2$ | CF$_3$ | 2-CH$_3$ | CH$_3$ | (D-52d)Br | *1 |
| 5-062 | 3,5-Cl$_2$ | CF$_3$ | 2-CH$_3$ | C(O)CH$_3$ | (D-52d)Br | *1 |
| 5-063 | 3,5-Cl$_2$ | CF$_3$ | 2-CH$_3$ | C(O)OCH$_3$ | (D-52d)Br | *1 |
| 5-064 | 3,5-Cl$_2$ | CF$_3$ | 2-CH$_3$ | CH$_3$ | (D-52d)CF$_3$ | *1 |
| 5-065 | 3,5-Cl$_2$ | CF$_3$ | 2-CH$_3$ | C(O)CH$_3$ | (D-52d)CF$_3$ | *1 |
| 5-066 | 3,5-Cl$_2$ | CF$_3$ | 2-CH$_3$ | C(O)OCH$_3$ | (D-52d)CF$_3$ | *1 |
| 5-067 | 3,5-Cl$_2$ | CF$_3$ | 2-CH$_3$ | CH$_3$ | (D-52d)NO$_2$ | 103.0-106.0 |
| 5-068 | 3,5-Cl$_2$ | CF$_3$ | 2-CH$_3$ | C(O)CH$_3$ | (D-52d)NO$_2$ | *1 |
| 5-069 | 3,5-Cl$_2$ | CF$_3$ | 2-CH$_3$ | C(O)OCH$_3$ | (D-52d)NO$_2$ | 163.0-165.0 |
| 5-070 | 3,5-Cl$_2$ | CF$_3$ | 2-CH$_3$ | CH$_3$ | (D-52d)CN | *1 |
| 5-071 | 3,5-Cl$_2$ | CF$_3$ | 2-CH$_3$ | C(O)OCH$_3$ | (D-52d)CN | *1 |
| 5-072 | 3,5-Cl$_2$ | CF$_3$ | 2-CH$_3$ | CH$_3$ | (D-52e)Cl | *1 |
| 5-073 | 3,5-Cl$_2$ | CF$_3$ | 2-CH$_3$ | C(O)CH$_3$ | (D-52e)Cl | *1 |
| 5-074 | 3,5-Cl$_2$ | CF$_3$ | 2-CH$_3$ | C(O)OCH$_3$ | (D-52e)Cl | *1 |
| 5-075 | 3,5-Cl$_2$ | CF$_3$ | 2-CH$_3$ | CH$_3$ | (D-52e)Br | *1 |
| 5-076 | 3,5-Cl$_2$ | CF$_3$ | 2-CH$_3$ | C(O)CH$_3$ | (D-52e)Br | *1 |
| 5-077 | 3,5-Cl$_2$ | CF$_3$ | 2-CH$_3$ | C(O)OCH$_3$ | (D-52e)Br | *1 |
| 5-078 | 3,5-Cl$_2$ | CF$_3$ | 2-CH$_3$ | CH$_3$ | D-53a | 227.0-229.0 |
| 5-079 | 3,5-Cl$_2$ | CF$_3$ | 2-CH$_3$ | C(O)CH$_3$ | D-53a | *1 |
| 5-080 | 3,5-Cl$_2$ | CF$_3$ | 2-CH$_3$ | C(O)OCH$_3$ | D-53a | *1 |
| 5-081 | 3,5-Cl$_2$ | CF$_3$ | 2-CH$_3$ | CH$_3$ | (D-53e)Cl | 167.0-169.0 |
| 5-082 | 3,5-Cl$_2$ | CF$_3$ | 2-CH$_3$ | C(O)OCH$_3$ | (D-53e)Cl | *1 |
| 5-083 | 3,5-Cl$_2$ | CF$_3$ | 2-CH$_3$ | CH$_3$ | D-54a | *1 |
| 5-084 | 3,5-Cl$_2$ | CF$_3$ | 2-CH$_3$ | CH$_3$ | D-55a | *1 |
| 5-085 | 3,5-Cl$_2$ | CF$_3$ | 2-CH$_3$ | Et | D-55a | *1 |
| 5-086 | 3,5-Cl$_2$ | CF$_3$ | 2-CH$_3$ | CH$_2$OCH$_3$ | D-55a | *1 |
| 5-087 | 3,5-Cl$_2$ | CF$_3$ | 2-CH$_3$ | CH$_2$CN | D-55a | *1 |
| 5-088 | 3,5-Cl$_2$ | CF$_3$ | 2-CH$_3$ | C(O)Et | D-55a | 133.0-136.5 |
| 5-089 | 3,5-Cl$_2$ | CF$_3$ | 2-CH$_3$ | C(O)Pr-n | D-55a | *1 |
| 5-090 | 3,5-Cl$_2$ | CF$_3$ | 2-CH$_3$ | C(O)Pr-i | D-55a | 168.5-170.0 |
| 5-091 | 3,5-Cl$_2$ | CF$_3$ | 2-CH$_3$ | C(O)Bu-t | D-55a | 180.0-184.0 |
| 5-092 | 3,5-Cl$_2$ | CF$_3$ | 2-CH$_3$ | CH$_3$ | (D-55c)Cl | *1 |
| 5-093 | 3,5-Cl$_2$ | CF$_3$ | 2-CH$_3$ | Et | (D-55c)Cl | *1 |
| 5-094 | 3,5-Cl$_2$ | CF$_3$ | 2-CH$_3$ | CH$_2$OCH$_3$ | (D-55c)Cl | 156.0-158.0 |
| 5-095 | 3,5-Cl$_2$ | CF$_3$ | 2-CH$_3$ | CH$_2$OEt | (D-55c)Cl | *1 |
| 5-096 | 3,5-Cl$_2$ | CF$_3$ | 2-CH$_3$ | CH$_2$OC(O)CH$_3$ | (D-55c)Cl | *1 |
| 5-097 | 3,5-Cl$_2$ | CF$_3$ | 2-CH$_3$ | CH$_2$CN | (D-55c)Cl | *1 |
| 5-098 | 3,5-Cl$_2$ | CF$_3$ | 2-CH$_3$ | CH$_2$CH=CH$_2$ | (D-55c)Cl | *1 |
| 5-099 | 3,5-Cl$_2$ | CF$_3$ | 2-CH$_3$ | CH$_2$C≡CH | (D-55c)Cl | *1 |
| 5-100 | 3,5-Cl$_2$ | CF$_3$ | 2-CH$_3$ | C(O)CH$_3$ | (D-55c)Cl | 175.0-177.0 |
| 5-101 | 3,5-Cl$_2$ | CF$_3$ | 2-CH$_3$ | C(O)Et | (D-55c)Cl | 98.0-100.0 |
| 5-102 | 3,5-Cl$_2$ | CF$_3$ | 2-CH$_3$ | C(O)Pr-n | (D-55c)Cl | *1 |
| 5-103 | 3,5-Cl$_2$ | CF$_3$ | 2-CH$_3$ | C(O)Pr-i | (D-55c)Cl | 131.0-133.0 |
| 5-104 | 3,5-Cl$_2$ | CF$_3$ | 2-CH$_3$ | C(O)Pr-c | (D-55c)Cl | *1 |
| 5-105 | 3,5-Cl$_2$ | CF$_3$ | 2-CH$_3$ | C(O)Bu-t | (D-55c)Cl | *1 |
| 5-106 | 3,5-Cl$_2$ | CF$_3$ | 2-CH$_3$ | C(O)CH$_2$OCH$_3$ | (D-55c)Cl | *1 |
| 5-107 | 3,5-Cl$_2$ | CF$_3$ | 2-CH$_3$ | C(O)Ph | (D-55c)Cl | *1 |
| 5-108 | 3,5-Cl$_2$ | CF$_3$ | 2-CH$_3$ | C(O)OCH$_3$ | (D-55c)Cl | 104.0-107.0 |

TABLE 9-continued

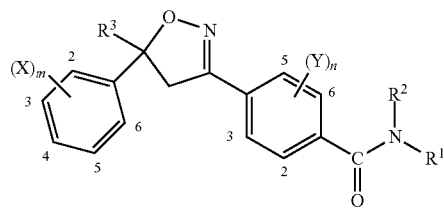

| No. | (X)$_m$ | R$^3$ | (Y)$_n$ | R$^2$ | R$^1$ | m.p. (° C.) |
|---|---|---|---|---|---|---|
| 5-109 | 3,5-Cl$_2$ | CF$_3$ | 2-CH$_3$ | C(O)OEt | (D-55c)Cl | *1 |
| 5-110 | 3,5-Cl$_2$ | CF$_3$ | 2-CH$_3$ | C(O)OPr-n | (D-55c)Cl | *1 |
| 5-111 | 3,5-Cl$_2$ | CF$_3$ | 2-CH$_3$ | C(O)OBu-i | (D-55c)Cl | *1 |
| 5-112 | 3,5-Cl$_2$ | CF$_3$ | 2-CH$_3$ | C(O)OCH$_2$Cl | (D-55c)Cl | *1 |
| 5-113 | 3,5-Cl$_2$ | CF$_3$ | 2-CH$_3$ | C(O)OCH$_2$CH$_2$OCH$_3$ | (D-55c)Cl | *1 |
| 5-114 | 3,5-Cl$_2$ | CF$_3$ | 2-CH$_3$ | CH$_3$ | (D-55c)Br | *1 |
| 5-115 | 3,5-Cl$_2$ | CF$_3$ | 2-CH$_3$ | Et | (D-55c)Br | *1 |
| 5-116 | 3,5-Cl$_2$ | CF$_3$ | 2-CH$_3$ | CH$_2$OCH$_3$ | (D-55c)Br | 137.0-142.0 |
| 5-117 | 3,5-Cl$_2$ | CF$_3$ | 2-CH$_3$ | CH$_2$OC(O)CH$_3$ | (D-55c)Br | *1 |
| 5-118 | 3,5-Cl$_2$ | CF$_3$ | 2-CH$_3$ | CH$_2$CN | (D-55c)Br | *1 |
| 5-119 | 3,5-Cl$_2$ | CF$_3$ | 2-CH$_3$ | C(O)CH$_3$ | (D-55c)Br | 168.0-170.0 |
| 5-120 | 3,5-Cl$_2$ | CF$_3$ | 2-CH$_3$ | C(O)Et | (D-55c)Br | 124.0-127.0 |
| 5-121 | 3,5-Cl$_2$ | CF$_3$ | 2-CH$_3$ | C(O)Pr-n | (D-55c)Br | *1 |
| 5-122 | 3,5-Cl$_2$ | CF$_3$ | 2-CH$_3$ | C(O)Pr-i | (D-55c)Br | 143.0-145.0 |
| 5-123 | 3,5-Cl$_2$ | CF$_3$ | 2-CH$_3$ | C(O)Pr-c | (D-55c)Br | *1 |
| 5-124 | 3,5-Cl$_2$ | CF$_3$ | 2-CH$_3$ | C(O)Bu-t | (D-55c)Br | *1 |
| 5-125 | 3,5-Cl$_2$ | CF$_3$ | 2-CH$_3$ | C(O)CH$_2$OCH$_3$ | (D-55c)Br | *1 |
| 5-126 | 3,5-Cl$_2$ | CF$_3$ | 2-CH$_3$ | C(O)OCH$_3$ | (D-55c)Br | *1 |
| 5-127 | 3,5-Cl$_2$ | CF$_3$ | 2-CH$_3$ | C(O)Et | (D-55c)Br | *1 |
| 5-128 | 3,5-Cl$_2$ | CF$_3$ | 2-CH$_3$ | C(O)OPr-n | (D-55c)Br | *1 |
| 5-129 | 3,5-Cl$_2$ | CF$_3$ | 2-CH$_3$ | C(O)OBu-i | (D-55c)Br | *1 |
| 5-130 | 3,5-Cl$_2$ | CF$_3$ | 2-CH$_3$ | C(O)OCH$_2$Cl | (D-55c)Br | *1 |
| 5-131 | 3,5-Cl$_2$ | CF$_3$ | 2-CH$_3$ | CH$_3$ | D-58a | *1 |
| 5-132 | 3,5-Cl$_2$ | CF$_3$ | 2-CH$_3$ | CH$_3$ | (D-58b)Br | *1 |
| 5-133 | 3,5-Cl$_2$ | CF$_3$ | 2-CH$_3$ | C(O)CH$_3$ | (D-58b)Br | *1 |
| 5-134 | 3,5-Cl$_2$ | CF$_3$ | 2-CH$_3$ | C(O)OCH$_3$ | (D-58b)Br | 87.0-89.0 |
| 5-135 | 3,5-Cl$_2$ | CF$_3$ | 2-CH$_3$ | C(O)CH$_3$ | (D-59b)Cl | 163.0-166.0 |
| 5-136 | 3,5-Cl$_2$ | CF$_3$ | 2-CH$_3$ | C(O)OCH$_3$ | (D-59b)Cl | 169.0-171.0 |
| 5-137 | 3,5-Cl$_2$ | CF$_3$ | 2-I | CH$_3$ | (D-52d)Cl | *1 |
| 5-138 | 3,5-Cl$_2$ | CF$_3$ | 2-I | CH$_3$ | (D-55c)Cl | *1 |
| 5-139 | 3,5-Cl$_2$ | CF$_3$ | 2-I | C(O)CH$_3$ | (D-55c)Cl | 196.0-199.0 |
| 5-140 | 3,5-Cl$_2$ | CF$_3$ | 2-I | C(O)OCH$_3$ | (D-55c)Cl | 177.0-180.0 |
| 5-141 | 3,5-Cl$_2$ | CF$_3$ | 2-CH$_3$ | i-Pr | (D-55c)Cl | 120.0-124.0 |
| 5-142 | 3,5-Cl$_2$ | CF$_3$ | 2-CH$_3$ | CH$_2$C(O)CH$_3$ | (D-55c)Cl | *2 |
| 5-143 | 3,5-Cl$_2$ | CF$_3$ | 2-CH$_3$ | CH$_2$C(O)OCH$_3$ | (D-55c)Cl | *2 |
| 5-144 | 3,5-Cl$_2$ | CF$_3$ | 2-CH$_3$ | CH$_2$SCH$_3$ | (D-55c)Cl | *1 |
| 5-145 | 3,5-Cl$_2$ | CF$_3$ | 2-CH$_3$ | C(O)CH$_2$Cl | (D-55c)Cl | *1 |
| 5-146 | 3,5-Cl$_2$ | CF$_3$ | 2-CH$_3$ | C(O)CH$_2$OEt | (D-55c)Cl | *1 |
| 5-147 | 3,5-Cl$_2$ | CF$_3$ | 2-CH$_3$ | C(O)CH$_2$SCH$_3$ | (D-55c)Cl | *1 |
| 5-148 | 3,5-Cl$_2$ | CF$_3$ | 2-CH$_3$ | C(O)CH$_2$S(O)CH$_3$ | (D-55c)Cl | *1 |
| 5-149 | 3,5-Cl$_2$ | CF$_3$ | 2-CH$_3$ | C(O)C(O)OEt | (D-55c)Cl | *1 |
| 5-150 | 3,5-Cl$_2$ | CF$_3$ | 2-CH$_3$ | C(O)(D-52a) | (D-55c)Cl | *1 |
| 5-151 | 3,5-Cl$_2$ | CF$_3$ | 2-CH$_3$ | C(O)(Ph-4-OCH$_3$) | (D-55c)Cl | 163.0-165.0 |
| 5-152 | 3,5-Cl$_2$ | CF$_3$ | 2-CH$_3$ | C(O)(Ph-4-NO$_2$) | (D-55c)Cl | *1 |
| 5-153 | 3,5-Cl$_2$ | CF$_3$ | 2-CH$_3$ | C(O)OPr-i | (D-55c)Cl | *1 |
| 5-154 | 3,5-Cl$_2$ | CF$_3$ | 2-CH$_3$ | C(O)OBu-n | (D-55c)Cl | *1 |
| 5-155 | 3,5-Cl$_2$ | CF$_3$ | 2-CH$_3$ | C(O)OBu-t | (D-55c)Cl | *1 |
| 5-156 | 3,5-Cl$_2$ | CF$_3$ | 2-CH$_3$ | C(O)OCH$_2$CH$_2$Cl | (D-55c)Cl | 66.0-68.0 |
| 5-157 | 3,5-Cl$_2$ | CF$_3$ | 2-CH$_3$ | C(O)OCH$_2$CH=CH$_2$ | (D-55c)Cl | 73.0-75.0 |
| 5-158 | 3,5-Cl$_2$ | CF$_3$ | 2-CH$_3$ | C(O)OPh | (D-55c)Cl | *1 |
| 5-159 | 3,5-Cl$_2$ | CF$_3$ | 2-CH$_3$ | C(O)N(CH$_3$)$_2$ | (D-55c)Cl | *1 |
| 5-160 | 3,5-Cl$_2$ | CF$_3$ | 2-CH$_3$ | CH$_2$OEt | (D-55c)Br | *1 |
| 5-161 | 3,5-Cl$_2$ | CF$_3$ | 2-CH$_3$ | CH$_2$CH=CH$_2$ | (D-55c)Br | *1 |
| 5-162 | 3,5-Cl$_2$ | CF$_3$ | 2-CH$_3$ | C(O)Ph | (D-55c)Br | *1 |
| 5-163 | 3,5-Cl$_2$ | CF$_3$ | 2-CH$_3$ | C(O)OCH$_2$CH$_2$OCH$_3$ | (D-55c)Br | *1 |
| 5-164 | 3,5-Cl$_2$ | CF$_3$ | 2-CH$_3$ | CH$_3$ | D-57a | 197.0-200.0 |
| 5-165 | 3,5-Cl$_2$ | CF$_3$ | 2-CH$_3$ | C(O)CH$_3$ | D-57a | 68.0-74.0 |
| 5-166 | 3,5-Cl$_2$ | CF$_3$ | 2-CH$_3$ | C(O)Et | D-57a | *1 |
| 5-167 | 3,5-Cl$_2$ | CF$_3$ | 2-CH$_3$ | C(O)Pr-n | D-57a | *1 |
| 5-168 | 3,5-Cl$_2$ | CF$_3$ | 2-CH$_3$ | C(O)Pr-i | D-57a | *1 |
| 5-169 | 3,5-Cl$_2$ | CF$_3$ | 2-CH$_3$ | C(O)OCH$_3$ | D-57a | 72.0-76.0 |
| 5-170 | 3,4,5-Cl$_3$ | CF$_3$ | 2-CH$_3$ | C(O)CH$_3$ | (D-55c)Cl | *1 |
| 5-171 | 3,5-Cl$_2$ | CF$_3$ | 2-CH$_3$ | CH$_3$ | (D-55c)CN | *1 |
| 5-172 | 3,5-Cl$_2$ | CF$_3$ | 2-CH$_3$ | CH$_3$ | (D-57b)Cl | *1 |
| 5-173 | 3,5-Cl$_2$ | CF$_3$ | 2-CH$_3$ | CH$_3$ | (D-58b)Cl | *1 |
| 5-174 | 3,5-Cl$_2$ | CF$_3$ | 2-CH$_3$ | C(O)OCH$_3$ | (D-58b)Cl | 83.0-86.0 |
| 5-175 | 3,5-Cl$_2$ | CF$_3$ | 2-NO$_2$ | C(O)CH$_3$ | (D-55c)Cl | *1 |

TABLE 9-continued

| No. | (X)$_m$ | R$^3$ | (Y)$_n$ | R$^2$ | R$^1$ | m.p. (° C.) |
|---|---|---|---|---|---|---|
| 5-176 | 3,5-Cl$_2$ | CF$_3$ | 2-CH$_3$ | CH$_3$ | D-1a | 108.0-112.0 |
| 5-177 | 3,5-Cl$_2$ | CF$_3$ | 2-CH$_3$ | C(O)OBu-t | D-1a | *1 |
| 5-178 | 3,5-Cl$_2$ | CF$_3$ | 2-CH$_3$ | CH$_2$OC(O)OCH$_3$ | (D-55c)Cl | *1 |
| 5-179 | 3,5-Cl$_2$ | CF$_3$ | 2-CH$_3$ | Et | (D-55c)CN | *1 |
| 5-180 | 3,5-Cl$_2$ | CF$_3$ | 2-CH$_3$ | CH$_2$OCH$_3$ | (D-55c)CN | *1 |
| 5-181 | 3,5-Cl$_2$ | CF$_3$ | 2-CH$_3$ | CH$_2$OC(O)CH$_3$ | (D-55c)CN | *1 |
| 5-182 | 3,5-Cl$_2$ | CF$_3$ | 2-CH$_3$ | C(O)CH$_3$ | (D-55c)CN | *1 |
| 5-183 | 3,5-Cl$_2$ | CF$_3$ | 2-CH$_3$ | C(O)Pr-i | (D-55c)CN | 101.5-103.0 |
| 5-184 | 3,5-Cl$_2$ | CF$_3$ | 2-CH$_3$ | C(O)OCH$_3$ | (D-55c)CN | *1 |
| 5-185 | 3,5-Cl$_2$ | CF$_3$ | 2-CH$_3$ | CH$_2$OCH$_3$ | (D-57b)Cl | *1 |
| 5-186 | 3,5-Cl$_2$ | CF$_3$ | 2-CH$_3$ | C(O)CH$_3$ | (D-57b)Cl | *1 |
| 5-187 | 3,5-Cl$_2$ | CF$_3$ | 2-CH$_3$ | C(O)OCH$_3$ | (D-57b)Cl | *1 |
| 5-188 | 3,5-Cl$_2$ | CF$_3$ | 2-CH$_3$ | CH$_3$ | (D-57d)Cl$_2$ | *1 |
| 5-189 | 3,5-Cl$_2$ | CF$_3$ | 2-CH$_3$ | CH$_2$OCH$_3$ | (D-57d)Cl$_2$ | 189.0-193.0 |
| 5-190 | 3,5-Cl$_2$ | CF$_3$ | 2-CH$_3$ | C(O)CH$_3$ | (D-57d)Cl$_2$ | *1 |
| 5-191 | 3,5-Cl$_2$ | CF$_3$ | 2-CH$_3$ | C(O)OCH$_3$ | (D-57d)Cl$_2$ | *1 |
| 5-192 | 3,5-Cl$_2$ | CF$_3$ | 2-CH$_3$ | C(O)CH$_3$ | D-58a | *1 |
| 5-193 | 3,5-Cl$_2$ | CF$_3$ | 2-CH$_3$ | CH$_2$OCH$_3$ | (D-58b)Cl | *1 |
| 5-194 | 3,5-Cl$_2$ | CF$_3$ | 2-CH$_3$ | C(O)CH$_3$ | (D-58b)Cl | *1 |
| 5-195 | 3,5-Cl$_2$ | CF$_3$ | 2-CH$_3$ | CH$_3$ | (D-58b)CN | *1 |
| 5-196 | 3,5-Cl$_2$ | CF$_3$ | 2-CH$_3$ | CH$_2$OCH$_3$ | (D-58b)CN | *1 |
| 5-197 | 3,5-Cl$_2$ | CF$_3$ | 2-CH$_3$ | C(O)CH$_3$ | (D-58b)CN | *1 |
| 5-198 | 3,5-Cl$_2$ | CF$_3$ | 2-CH$_3$ | CH$_2$OCH$_3$ | D-57a | *1 |
| 5-199 | 3,5-Cl$_2$ | CF$_3$ | 2-CH$_3$ | C(O)OBu-t | Ph | *1 |
| 5-200 | 3,5-(CF$_3$)$_2$ | CF$_3$ | — | CH$_3$ | (D-55c)Cl | 178.0-179.0 |
| 5-201 | 3,5-(CF$_3$)$_2$ | CF$_3$ | — | C(O)CH$_3$ | (D-55c)Cl | 176.0-179.0 |
| 5-202 | 3,5-(CF$_3$)$_2$ | CF$_3$ | — | C(O)Pr-i | (D-55c)Cl | 134.0-136.0 |
| 5-203 | 3,5-(CF$_3$)$_2$ | CF$_3$ | — | C(O)OCH$_3$ | (D-55c)Cl | 167.0-170.0 |
| 5-204 | 3,5-Cl$_2$ | CF$_3$ | 2-CH$_3$ | CH$_2$CN | (D-55c)CN | *1 |
| 5-205 | 3,5-Cl$_2$ | CF$_3$ | 2-CH$_3$ | C(O)Et | (D-55c)CN | *1 |
| 5-206 | 3,5-Cl$_2$ | CF$_3$ | 2-CH$_3$ | CH$_2$CN | D-57a | 80.0-84.0 |

TABLE 10

| No. | (X)$_m$ | R$^3$ | (Y)$_n$ | R$^1$ | m.p. (° C.) |
|---|---|---|---|---|---|
| 6-001 | 3,5-Cl$_2$ | CF$_3$ | — | CH=NOH | 181.0-183.0 |
| 6-002 | 3,5-Cl$_2$ | CF$_3$ | 2-CH$_3$ | CH=NOH | 156.0-160.0 |
| 6-003 | 3,5-Cl$_2$ | CF$_3$ | 2-CH$_3$ | CH=NOCH$_3$(E) | *1 |
| 6-004 | 3,5-Cl$_2$ | CF$_3$ | 2-CH$_3$ | CH=NOCH$_3$(Z) | 167.0-169.0 |
| 6-004(R) | 98% e.e. | | [α]$_D^{21.1}$ − 73.66° (CH$_3$CN, c = 1.250) | | *1 |
| 6-004(S) | 97% e.e. | | [α]$_D^{20.1}$ + 71.70° (CH$_3$CN, c = 1.138) | | 157.0-158.0 |
| 6-005 | 3,5-Cl$_2$ | CF$_3$ | 2-CH$_3$ | CH=NOEt | 143.0-146.0 |
| 6-006 | 3,5-Cl$_2$ | CF$_3$ | 2-CH$_3$ | CH=NOPr-n | 109.0-111.0 |
| 6-007 | 3,5-Cl$_2$ | CF$_3$ | 2-CH$_3$ | CH=NOPr-i | *1 |
| 6-008 | 3,5-Cl$_2$ | CF$_3$ | 2-CH$_3$ | CH=NOCH$_2$CH$_2$Cl | 137.0-139.0 |
| 6-009 | 3,5-Cl$_2$ | CF$_3$ | 2-CH$_3$ | CH=NOCH$_2$CF$_3$ | *1 |
| 6-010 | 3,5-Cl$_2$ | CF$_3$ | 2-CH$_3$ | CH=NOCH$_2$CH=CH$_2$ | 123.0-124.0 |
| 6-011 | 3,5-Cl$_2$ | CF$_3$ | 2-CH$_3$ | C(CH$_3$)=NOCH$_3$ | 159.0-161.0 |
| 6-012 | 3,5-Cl$_2$ | CF$_3$ | 2-Cl | CH=NOCH$_3$ | 140.0-142.0 |
| 6-013 | 3,5-Cl$_2$ | CF$_3$ | 2-Cl | CH=NOEt | 126.0-129.0 |
| 6-014 | 3,5-Cl$_2$ | CF$_3$ | 2-Br | CH=NOCH$_3$(Z) | 146.0-149.0 |
| 6-015 | 3,5-Cl$_2$ | CF$_3$ | 2-Br | CH=NOEt(Z) | 134.0-137.0 |

TABLE 10-continued

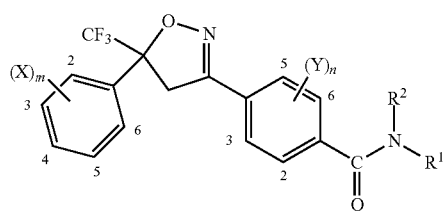

| No. | (X)$_m$ | R$^3$ | (Y)$_n$ | R$^1$ | m.p. (° C.) |
|---|---|---|---|---|---|
| 6-016 | 3,5-Cl$_2$ | CF$_3$ | 2-I | CH=NOCH$_3$(Z) | *1 |
| 6-017 | 3,5-Cl$_2$ | CF$_3$ | 2-I | CH=NOEt | 126.0-129.0 |
| 6-018 | 3,5-Cl$_2$ | CF$_3$ | 2-CH$_3$ | CH=NOEt(Z) | 149.0-150.0 |
| 6-019 | 3,5-Cl$_2$ | CF$_3$ | 2-CH$_3$ | (M-5c)CH$_3$ | 179.0-181.0 |
| 6-020 | 3,5-Cl$_2$ | CF$_3$ | 2-Et | CH=NOCH$_3$(Z) | *1 |
| 6-021 | 3,5-Cl$_2$ | CF$_3$ | 2-CF$_3$ | CH=NOEt(Z) | 164.0-167.0 |
| 6-022 | 3,5-Cl$_2$ | CF$_3$ | 2-OCHF$_2$ | CH=NOCH$_3$(Z) | 137.0-141.0 |
| 6-023 | 3,5-Cl$_2$ | CF$_3$ | 2-OCHF$_2$ | CH=NOEt(Z) | *1 |
| 6-024 | 3,5-Cl$_2$ | CF$_3$ | 2-NO$_2$ | CH=NOCH$_3$(Z) | 229.0-233.0 |
| 6-025 | 3,5-Cl$_2$ | CF$_3$ | 2-CN | CH=NOCH$_3$(Z) | 188.0-190.0 |
| 6-026 | 3,5-Cl$_2$ | CF$_3$ | 2-Ph | CH=NOCH$_3$ | *1 |
| 6-027 | 3,5-Cl$_2$ | CF$_3$ | 2-(D-41a) | CH=NOCH$_3$(Z) | 172.0-174.0 |
| 6-028 | 3,5-Cl$_2$ | CF$_2$Cl | 2-Cl | CH=NOCH$_3$ | *1 |
| 6-029 | 3-Cl-5-Br | CF$_3$ | 2-CH$_3$ | CH=NOCH$_3$ | *1 |
| 6-030 | 3,5-(CF$_3$)$_2$ | CF$_3$ | 2-CH$_3$ | CH=NOCH$_3$ | *1 |
| 6-031 | 3,5-Cl$_2$ | CF$_3$ | 2-CH$_2$OCH$_3$ | CH=NOCH$_3$ | 132.0-134.0 |
| 6-032 | 3,5-Cl$_2$ | CF$_3$ | 2-CH2N(CH$_3$)$_2$ | CH=NOCH$_3$ | 144.0-146.0 |
| 6-033 | 3,5-Cl$_2$ | CF$_3$ | 2-NHC(O)CH$_3$ | CH=NOCH$_3$(Z) | 199.0-201.0 |
| 6-034 | 3,5-Cl$_2$ | CF$_3$ | 2-NHC(O)CH$_3$ | CH=NOEt(Z) | 204.0-205.0 |
| 6-035 | 3,5-Br$_2$ | CF$_3$ | 2-CH$_3$ | CH=NOCH$_3$ | *1 |
| 6-036 | 3,5-Br$_2$ | CF$_3$ | 2-CH$_3$ | CH=NOEt | *1 |
| 6-037 | 3-Cl-5-CF$_3$ | CF$_3$ | 2-CH$_3$ | CH=NOCH$_3$ | *1 |
| 6-038 | 3,5-Cl2-4-F | CF$_3$ | 2-CH$_3$ | CH=NOCH$_3$ | *1 |
| 6-039 | 3,4,5-Cl$_3$ | CF$_3$ | 2-CH$_3$ | CH=NOCH$_3$ | *1 |
| 6-040 | 3,4,5-Cl$_3$ | CF$_3$ | 2-CH$_3$ | CH=NOEt | *1 |
| 6-041 | 3-Cl-4-F-5-CF$_3$ | CF$_3$ | 2-CH$_3$ | CH=NOCH$_3$ | *1 |
| 6-042 | 3,5-Cl$_2$ | CF$_3$ | 2-CH$_3$ | CH=NNHC(O)CH$_3$ | 198.0-203.0 |
| 6-043 | 3,5-Cl$_2$ | CF$_3$ | 2-CH$_3$ | CH=NNHC(O)CH$_3$ | 209.0-211.0 |
| 6-044 | 3,5-Cl$_2$ | CF$_3$ | 2-CH$_3$ | CH=NOCH$_2$C(O)OH | *1 |
| 6-045 | 3,5-Cl$_2$ | CF$_3$ | 2-CH$_3$ | CH=NOCH$_2$(Ph-4-NO$_2$) | *1 |
| 6-046 | 3,5-Cl$_2$ | CF$_3$ | 2-NO$_2$ | CH=NOEt | 204.0-206.0 |
| 6-047 | 3,5-Cl$_2$ | CF$_3$ | 2-(Ph-4-Cl) | CH=NOCH$_3$ | *1 |
| 6-048 | 3,5-Cl$_2$ | CF$_3$ | 2-(D-2a) | CH=NOCH$_3$ | *1 |
| 6-049 | 3,5-Cl$_2$ | CF$_3$ | 2-(D-4a) | CH=NOCH$_3$ | *1 |
| 6-050 | 3,5-(CF$_3$)$_2$ | CF$_3$ | — | CH=NOCH$_3$ | 184.0-186.0 |
| 6-051 | 3,5-(CF$_3$)$_2$ | CF$_3$ | — | CH=NOEt | 86.0-94.0 |
| 6-052 | 3,4,5-Cl$_3$ | CF$_3$ | — | CH=NOCH$_3$ | *1 |
| 6-053 | 3,4,5-Cl$_3$ | CF$_3$ | — | CH=NOEt | 108.0-110.0 |
| 6-054 | 3,4,5-Cl$_3$ | CF$_3$ | — | CH=NOPr-n | 139.0-140.0 |
| 6-055 | 3,4,5-Cl$_3$ | CF$_3$ | — | CH=NOPr-i | *1 |

TABLE 11

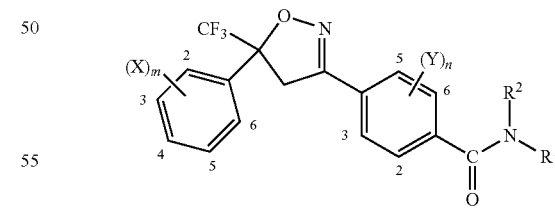

| No. | (X)$_m$ | (Y)$_n$ | R$^2$ | R$^1$ | m.p. (° C.) |
|---|---|---|---|---|---|
| 7-001 | 3,5-Cl$_2$ | 2-CH$_3$ O | CH$_2$OCH$_3$ | CH=NOCH$_3$ | *1 |
| 7-002 | 3,5-Cl$_2$ | 2-CH$_3$ O | CH$_3$ | CH=NOCH$_3$ (isomer1) | *1 |
| 7-003 | 3,5-Cl$_2$ | 2-CH$_3$ O | CH$_3$ | CH=NOCH$_3$ (isomer2) | *1 |
| 7-004 | 3,5-Cl$_2$ | 2-CH$_3$ O | C(O)OCH$_3$ | CH=NOCH$_3$ (isomer1) | *1 |
| 7-005 | 3,5-Cl$_2$ | 2-CH$_3$ O | C(O)OCH$_3$ | CH=NOCH$_3$ (isomer2) | *1 |
| 7-006 | 3,5-Cl$_2$ | 2-CH$_3$ O | CH$_2$OEt | CH=NOCH$_3$ | *1 |
| 7-007 | 3,5-Cl$_2$ | 2-CH$_3$ O | CH$_2$CN | CH=NOCH$_3$ | *1 |
| 7-008 | 3,5-Cl$_2$ | 2-CH$_3$ O | CH$_2$C≡CH | CH=NOCH$_3$ | *1 |
| 7-009 | 3,5-Cl$_2$ | 2-CH$_3$ O | CH$_2$OCH$_3$ | CH=NOEt | *1 |
| 7-010 | 3,5-Cl$_2$ | — | S | H | CH=NOCH$_3$ *1 |
| 7-011 | 3,5-Cl$_2$ | — | S | H | CH=NOEt *1 |

TABLE 11-continued

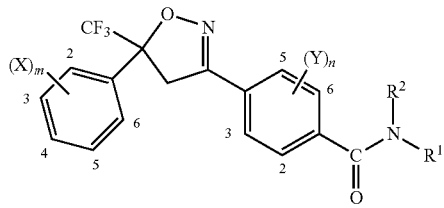

| No. | (X)$_m$ | (Y)$_n$ | R$^2$ | R$^1$ | m.p. (° C.) |
|---|---|---|---|---|---|
| 7-012 | 3,5-Cl$_2$ | 2-CH$_3$ S | H | CH=NOCH$_3$ *1 | |
| 7-013 | 3,5-Cl$_2$ | 2-CH$_3$ O | CH$_2$OCH$_3$ | CH=NOCH$_3$ *1 (isomer1) | |
| 7-014 | 3,5-Cl$_2$ | 2-CH$_3$ O | CH$_2$OC(O)CH$_3$ | CH=NOCH$_3$ *1 (isomer1) | |
| 7-015 | 3,5-Cl$_2$ | 2-CH$_3$ O | CH$_2$OC(O)CH$_3$ | CH=NOCH$_3$ *1 (isomer2) | |
| 7-016 | 3,5-Cl$_2$ | 2-CH$_3$ O | CH$_2$SCH$_3$ | CH=NOCH$_3$ *1 (isomer1) | |
| 7-017 | 3,5-Cl$_2$ | 2-CH$_3$ O | CH$_2$SCH$_3$ | CH=NOCH$_3$ *1 (isomer2) | |
| 7-018 | 3,5-Cl$_2$ | 2-CH$_3$ O | CH$_2$C(O)OCH$_3$ | CH=NOCH$_3$ *1 | |
| 7-019 | 3,5-Cl$_2$ | 2-CH$_3$ O | CH$_2$(D-52a) | CH=NOCH$_3$ *1 | |
| 7-020 | 3,5-Cl$_2$ | 2-CH$_3$ O | CH$_2$CN | CH=NOEt *1 | |
| 7-021 | 3,5-Cl$_2$ | 2-CH$_3$ O | CH$_2$Si(CH$_3$)$_3$ | CH=NOCH$_3$ *1 | |
| 7-022 | 3,4,5-Cl$_3$ | — | S | H | CH=NOCH$_3$ *1 |
| 7-023 | 3,4,5-Cl$_3$ | — | S | H | CH=NOEt *1 |

TABLE 12

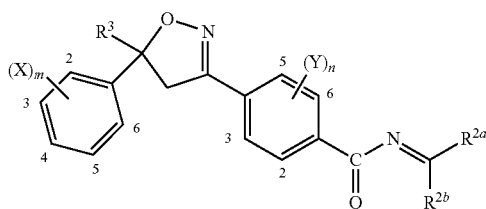

| No. | (X)$_m$ | R$^3$ | (Y)$_n$ | W | R$^{2a}$ | R$^{2b}$ | m.p. (° C.) |
|---|---|---|---|---|---|---|---|
| 8-001 | 3,5-Cl$_2$ | CF$_3$ | 2-CH$_3$ | O | OCH$_3$ | SCH$_3$ | *1 |
| 8-002 | 3,5-Cl$_2$ | CF$_3$ | 2-CH$_3$ | O | OCH$_3$ | SCH$_2$OCH$_3$ | *1 |
| 8-003 | 3,5-Cl$_2$ | CF$_3$ | 2-CH$_3$ | O | OCH$_3$ | SC(O)CH$_3$ | 109.0-111.0 |
| 8-004 | 3,5-Cl$_2$ | CF$_3$ | — | O | N(CH$_3$)$_2$ | H | *1 |
| 8-005 | 3,5-Cl$_2$ | CF$_3$ | — | S | N(CH$_3$)$_2$ | H | 155.0-159.0 |
| 8-006 | 3,5-Cl$_2$ | CF$_3$ | 2-CH$_3$ | O | N(CH$_3$)$_2$ | H | 146.0-147.0 |
| 8-007 | 3,5-Cl$_2$ | CF$_3$ | 2-CH$_3$ | O | N(CH$_3$)$_2$ | CH$_3$ | *1 |
| 8-008 | 3,5-Cl$_2$ | CF$_2$Cl | 2-Cl | O | N(CH$_3$)$_2$ | H | *1 |
| 8-009 | 3,5-Br$_2$ | CF$_3$ | 2-CH$_3$ | O | N(CH$_3$)$_2$ | H | *1 |
| 8-010 | 3,5-(CF$_3$)$_2$ | CF$_3$ | 2-CH$_3$ | O | N(CH$_3$)$_2$ | H | *1 |
| 8-011 | 3,4,5-Cl$_3$ | CF$_3$ | 2-CH$_3$ | O | N(CH$_3$)$_2$ | H | *1 |
| 8-012 | 3,5-Cl$_2$ | CF$_3$ | 2-CH$_3$ | S | N(CH$_3$)$_2$ | H | *1 |
| 8-013 | 3,5-Cl$_2$ | CF$_3$ | 2-CH$_3$ | O | N(CH$_3$)$_2$ | OCH$_3$ | *1 |
| 8-014 | 3,5-Cl$_2$ | CF$_3$ | 2-CH$_3$ | O | N(CH$_3$)$_2$ | SCH$_3$ | *1 |
| 8-015 | 3,5-Cl$_2$ | CF$_3$ | 2-CH$_3$ | O | OEt | SCH$_3$ | 164.0-166.0 |
| 8-016 | 3,5-Cl$_2$ | CF$_3$ | 2-CH$_3$ | O | OBu-n | SCH$_3$ | *1 |
| 8-017 | 3,5-Cl$_2$ | CF$_2$ | 2-CH$_3$ | O | OCH$_2$C≡CH | SCH$_3$ | *1 |

TABLE 13

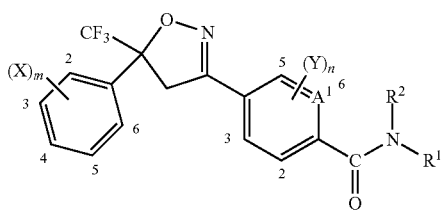

| No. | (X)$_m$ | A$^1$ | (Y)$_n$ | R$^2$ | R$^1$ | m.p. (° C.) |
|---|---|---|---|---|---|---|
| 9-001 | 3,5-Cl$_2$ | N | 2-Cl | H | CH=NOCH$_3$ | 178.0-181.0 |
| 9-002 | 3,5-Cl$_2$ | N | 2-Cl | H | C(O)OCH$_3$ | *1 |

TABLE 14

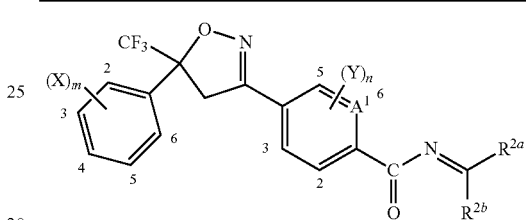

| No. | (X)$_m$ | A$^1$ | (Y)$_n$ | R$^{2a}$ | R$^{2b}$ | m.p. (° C.) |
|---|---|---|---|---|---|---|
| 10-001 | 3,5-Cl$_2$ | N | 2-Cl | N(CH$_3$)$_2$ | H | *1 |

TABLE 15

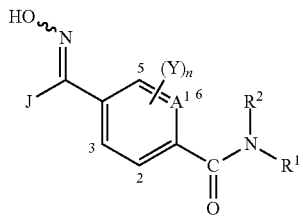

| No. | A$^1$ | (Y)$_n$ | R$^2$ | R$^1$ | J | m.p. (° C.) |
|---|---|---|---|---|---|---|
| 11-001 | C | 2-CH$_3$ | H | C(O)CH$_3$ | H | 141.0-143.0 |
| 11-001 | C | 2-CH$_3$ | H | CH=NOCH$_3$ | H | 88.0-91.0 |
| 11-001 | C | 2-CH$_3$ | C(O)CH$_3$ | (D-55c)Cl | H | *1 |

Among the compounds of the present invention, $^1$H NMR data of the compounds that the measured value of molecular ion peak, melting point or refractive index is not shown are shown in Table 16.

In the meantime, the indication of "(A)" in the table shows a condition in which tetramethylsilane is used as standard substance in chloroform-d solvent and measurement is carried out at 300 MHz (CDCl$_3$, Me$_4$Si, 300 MHz), and the indication "(B)" shows the measurement condition of (CDCl$_3$, Me$_4$Si, 400 MHz), the indication of "(C)" shows the measurement condition of (CDCl$_3$-DMSO-d$_6$, Me$_4$Si, 300 MHz), and the indication of "(D)" shows the measurement condition of (CDCl$_3$-DMSO-d$_6$, Me$_4$Si, 400 MHz).

TABLE 16

| No. | ¹H NMR |
|---|---|
| 2-001 | (A) δ8.57 (bs, 1H), 7.92 (d, J = 8.3 Hz, 2H), 7.77 (d, J = 8.3 Hz, 2H), 7.50 (d, J = 1.7 Hz, 2H), 7.42 (t, J = 1.7 Hz, 1H), 4.27 (q, J = 7.2 Hz, 2H), 4.12 (d, J = 17.1 Hz, 1H), 3.76 (d, J = 17.1 Hz, 1H), 1.31 (t, J = 7.2 Hz, 3H). |
| 2-002 | (A) δ8.54 (bs, 1H), 7.93 (d, J = 8.3 Hz, 2H), 7.77 (d, J = 8.3 Hz, 2H), 7.45-7.55 (m, 2H), 7.42 (t, J = 2.0 Hz, 1H), 4.95-5.15 (m, 1H), 4.13 (d, J = 17.1 Hz, 1H), 3.76 (d, J = 17.1 Hz, 1H), 1.30 (d, J = 6.6 Hz, 6H). |
| 2-004 | (B) δ7.68 (s, 1H), 7.45-7.6 (m, 4H), 7.43 (t, J = 1.8 Hz, 1H), 7.41 (d, J = 7.4 Hz, 1H), 4.08 (d, J = 17.2 Hz, 1H), 3.70 (d, J = 17.2 Hz, 1H), 2.46 (s, 3H), 1.46 (s, 9H). |
| 2-005 | (B) δ8.00 (bs, 1H), 7.45-7.6 (m, 5H), 7.43 (t, J = 1.8 Hz, 1H), 4.3-4.35 (m, 2H), 4.08 (d, J = 17.2 Hz, 1H), 3.71 (d, J = 17.2 Hz, 1H), 3.5-3.7 (m, 6H), 3.38 (s, 3H), 2.46 (s, 3H). |
| 2-007 | (B) δ7.85 (dd, J = 5.5, 3.1 Hz, 2H), 7.84 (bs, 1H), 7.75 (dd, J = 5.5, 3.1 Hz, 2H), 7.45-7.55 (m, 4H), 7.43 (t, J = 1.8 Hz, 1H), 7.42 (d, J = 7.9 Hz, 1H), 4.35-4.45 (m, 2H), 4.07 (d, J = 17.2 Hz, 1H), 3.98 (m, 2H), 3.69 (d, J = 17.2 Hz, 1H), 2.44 (s, 3H). |
| 2-009 | (B) δ8.37 (bs, 1H), 7.45-7.6 (m, 4H), 7.45 (d, J = 8.4 Hz, 1H), 7.43 (t, J = 1.8 Hz, 1H), 4.68 (s, 2H), 4.08 (d, J = 17.2 Hz, 1H), 3.77 (s, 3H), 3.71 (d, J = 17.2 Hz, 1H), 2.45 (s, 3H). |
| 2-012 | (B) δ9.81 (s, 1H), 7.5-7.65 (m, 5H), 7.44 (t, J = 1.8 Hz, 1H), 4.09 (d, J = 17.2 Hz, 1H), 3.72 (d, J = 17.2 Hz, 1H), 2.70 (s, 3H), 2.56 (s, 3H). |
| 2-013 | (B) δ8.45 (s, 1H), 7.71 (d, J = 1.7 Hz, 1H), 7.63 (dd, J = 8.1, 1.7 Hz, 1H), 7.52 (d, J = 8.1 Hz, 1H), 7.45-7.5 (m, 2H), 7.43 (t, J = 1.8 Hz, 1H), 4.07 (d, J = 17.2 Hz, 1H), 3.78 (s, 3H), 3.71 (d, J = 17.2 Hz, 1H). |
| 2-014 | (A) δ7.93 (bs, 1H), 7.89 (d, J = 1.8 Hz, 1H), 7.71 (dd, J = 7.8, 1.2 Hz, 1H), 7.4-7.55 (m, 4H), 4.06 (d, J = 17.4 Hz, 1H), 3.78 (s, 3H), 3.69 (d, J = 17.4 Hz, 1H). |
| 2-016 | (B) δ8.10 (d, J = 1.5 Hz, 1H), 7.79 (s, 1H), 7.74 (dd, J = 8.1, 1.5 Hz, 1H), 7.45-7.5 (m, 2H), 7.43 (t, J = 1.8 Hz, 1H), 7.36 (d, J = 8.1 Hz, 1H), 4.93 (sept, J = 6.2 Hz, 1H), 4.06 (d, J = 17.2 Hz, 1H), 3.68 (d, J = 17.2 Hz, 1H), 1.25 (d, J = 6.2 Hz, 6H). |
| 2-018 | (A) δ7.65-7.75 (m, 3H), 7.3-7.55 (m, 9H), 4.11 (d, J = 17.4 Hz, 1H), 3.73 (d, J = 17.4 Hz, 1H), 3.59 (s, 3H). |
| 2-020 | (A) δ8.28 (s, 1H), 7.71 (d, J = 1.5 Hz, 1H), 7.64 (dd, J = 8.1, 1.5 Hz, 1H), 7.54 (s, 1H), 7.51 (d, J = 1.5 Hz, 2H), 7.42 (t, J = 1.5 Hz, 1H), 4.11 (d, J = 17.4 Hz, 1H), 3.65-3.85 (m, 4H). |
| 2-021 | (A) δ7.83 (s, 1H), 7.65 (s, 1H), 7.5-7.6 (m, 4H), 7.43 (d, J = 8.7 Hz, 1H), 4.08 (d, J = 17.4 Hz, 1H), 3.80 (s, 3H), 3.68 (d, J = 17.4 Hz, 1H), 2.47 (s, 3H). |
| 2-022 | (A) δ8.15 (s, 1H), 7.7-7.75 (m, 1H), 7.70 (bs, 2H), 7.5-7.55 (m, 2H), 7.42 (d, J = 8.4 Hz, 1H), 4.07 (d, J = 17.4 Hz, 1H), 3.80 (s, 3H), 3.71 (d, J = 17.4 Hz, 1H), 2.45 (s, 3H). |
| 2-023 | (A) δ8.08 (s, 2H), 7.97 (s, 1H), 7.91 (s, 1H), 7.55-7.6 (m, 2H), 7.43 (d, J = 8.4 Hz, 1H), 4.20 (d, J = 17.4 Hz, 1H), 3.80 (s, 3H), 3.76 (d, J = 17.4 Hz, 1H), 2.47 (s, 3H). |
| 2-024 | (A) δ7.9-8.0 (m, 3H), 7.4-7.5 (m, 4H), 4.11 (d, J = 17.4 Hz, 1H), 3.73 (s, 3H), 3.72 (d, J = 17.4 Hz, 1H). |
| 2-025 | (A) δ9.73 (s, 1H), 7.65-7.9 (m, 3H), 7.4-7.55 (m, 3H), 4.57 (s, 2H), 4.10 (d, J = 17.4 Hz, 1H), 3.85 (s, 3H), 3.72 (d, J = 17.4 Hz, 1H), 3.51 (s, 3H). |
| 2-027 | (A) δ8.70 (s, 1H), 7.4-7.6 (m, 6H), 5.51 (qui, J = 6.6 Hz, 1H), 4.08 (d, J = 17.4 Hz, 1H), 3.70 (d, J = 17.4 Hz, 1H), 2.48 (s, 3H), 1.26 (d, J = 6.6 Hz, 6H). |
| 2-028 | (A) δ8.80 (s, 1H), 7.4-7.6 (m, 6H), 4.49 (t, J = 6.6 Hz, 2H), 4.08 (d, J = 17.4 Hz, 1H), 3.70 (d, J = 17.4 Hz, 1H), 2.39 (s, 3H), 1.5-1.7 (m, 2H), 1.2-1.45 (m, 2H), 0.90 (t, J = 7.5 Hz, 3H). |
| 2-029 | (A) δ8.90 (s, 1H), 7.4-7.65 (m, 6H), 5.15 (s, 2H), 4.10 (d, J = 17.4 Hz, 1H), 3.71 (d, J = 17.4 Hz, 1H), 2.45-2.6 (m, 4H). |
| 2-030 | (A) δ8.00 (s, 1H), 7.88 (d, J = 8.7 Hz, 2H), 7.77 (d, J = 8.7 Hz, 2H), 7.65 (s, 2H), 4.05-4.2 (m, 3H), 3.73 (d, J = 17.4 Hz, 1H), 1.35 (t, J = 7.2 Hz, 3H). |
| 3-001 | (A) δ7.69 (d, J = 8.7 Hz, 2H), 7.55 (d, J = 8.7 Hz, 2H), 7.45-7.55 (m, 2H), 7.43 (t, J = 2.0 Hz, 1H), 4.09 (d, J = 17.3 Hz, 1H), 4.07 (q, J = 7.1 Hz, 2H), 3.71 (d, J = 17.3 Hz, 1H), 3.36 (s, 3H), 1.06 (t, J = 7.1 Hz, 3H). |
| 3-002 | (A) δ7.69 (d, J = 8.3 Hz, 2H), 7.55 (d, J = 8.3 Hz, 2H), 7.45-7.55 (m, 2H), 7.43 (t, J = 1.8 Hz, 1H), 4.75-4.9 (m, 1H), 4.09 (d, J = 17.3 Hz, 1H), 3.51 (d, J = 17.3 Hz, 1H), 3.34 (s, 3H), 1.06 (d, J = 6.3 Hz, 6H). |
| 3-005 | (B) δ7.4-7.5 (m, 4H), 7.39 (t, J = 1.9 Hz, 1H), 7.14 (d, J = 7.8 Hz, 1H), 4.06 (d, J = 17.2 Hz, 1H), 3.82 (t, J = 9.4 Hz, 2H), 3.68 (d, J = 17.4 Hz, 1H), 3.59 (s, 3H), 2.30 (s, 3H), 1.69 (m, 2H), 0.96 (t, J = 7.4 Hz, 3H). |
| 3-006 | (B) δ7.4-7.6 (m, 5H), 7.2-7.3 (m, 1H), 4.87 (sep, J = 6.7 Hz, 1H), 4.09 (d, J = 17.2 Hz, 1H), 3.70 (d, J = 17.2 Hz, 1H), 3.56 (s, 3H), 2.39 (s, 3H), 1.45 (d, J = 7.0 Hz, 6H). |
| 3-009 | (B) δ7.45-7.55 (m, 5H), 7.43 (t, J = 1.8 Hz, 1H), 4.65 (s, 2H), 4.09 (d, J = 17.2 Hz, 1H), 3.82 (s, 3H), 3.70 (d, J = 17.2 Hz, 1H), 3.63 (s, 3H), 2.39 (s, 3H). |

TABLE 16-continued

| No. | $^1$H NMR |
|---|---|
| 3-012 | (B) δ7.4-7.6 (m, 6H), 4.09 (d, J = 17.2 Hz, 1H), 3.72 (s, 3H), 3.70 (d, J = 17.2 Hz, 1H), 2.45 (s, 3H), 1.37 (s, 9H). |
| 3-013 | (B) δ7.4-7.6 (m, 6H), 4.45 (s, 2H), 4.09 (d, J = 17.2 Hz, 1H), 3.77 (s, 3H), 3.72 (d, J = 17.2 Hz, 1H), 3.42 (s, 3H), 2.59 (s, 3H). |
| 3-014 | (B) δ7.4-7.6 (m, 6H), 4.10 (d, J = 17.2 Hz, 1H), 3.82 (s, 6H), 3.72 (d, J = 17.4 Hz, 1H), 2.53 (s, 3H). |
| 3-016 | (B) δ7.45-7.55 (m, 5H), 7.43 (t, J = 1.8 Hz, 1H), 4.89 (sep, J = 6.2 Hz, 1H), 4.07 (d, J = 17.2 Hz, 1H), 3.69 (d, J = 17.2 Hz, 1H), 3.36 (s, 3H), 2.33 (s, 3H), 1.01 (d, J = 6.2 Hz, 6H). |
| 3-017 | (B) δ7.45-7.55 (m, 5H), 7.43 (t, J = 1.8 Hz, 1H), 4.81 (sep, J = 6.3 Hz, 1H), 4.07 (d, J = 17.2 Hz, 1H), 3.93 (q, J = 7.0 Hz, 2H), 3.69 (d, J = 17.2 Hz, 1H), 2.34 (s, 3H), 1.29 (t, J = 7.0 Hz, 3H), 1.01 (d, J = 6.3 Hz, 6H). |
| 3-018 | (B) δ7.4-7.6 (m, 6H), 5.27 (s, 2H), 4.82 (sep, J = 6.3 Hz, 1H), 4.08 (d, J = 17.2 Hz, 1H), 3.70 (d, J = 17.2 Hz, 1H), 3.50 (s, 3H), 2.40 (s, 3H), 1.00 (d, J = 6.2 Hz, 6H). |
| 3-020 | (B) δ7.45-7.55 (m, 5H), 7.43 (t, J = 1.8 Hz, 1H), 4.1-4.15 (m, 2H), 4.08 (d, J = 17.2 Hz, 1H), 3.69 (d, J = 17.2 Hz, 1H), 3.39 (s, 3H), 3.3-3.35 (m, 2H), 3.26 (s, 3H), 2.33 (s, 3H). |
| 3-026 | (A) δ7.85 (d, J = 1.2 Hz, 1H), 7.68 (dd, J = 7.8, 2.0 Hz, 1H), 7.50 (bs, 2H), 7.44 (t, J = 2.0 Hz, 1H), 7.35 (d, J = 7.8 Hz, 1H), 5.33 (s, 2H), 4.05 (d, J = 17.4 Hz, 1H), 3.73 (s, 3H), 3.68 (d, J = 17.4 Hz, 1H), 3.52 (s, 3H). |
| 3-027 | (A) δ7.87 (d, J = 1.8 Hz, 1H), 7.70 (dd, J = 7.8, 1.8 Hz, 1H), 7.50 (bs, 2H), 7.44 (t, J = 2.0 Hz, 1H), 7.38 (d, J = 7.8 Hz, 1H), 4.81 (s, 2H), 4.07 (d, J = 17.4 Hz, 1H), 3.78 (s, 3H), 3.68 (d, J = 17.4 Hz, 1H). |
| 3-030 | (B) δ8.09 (d, J = 1.7 Hz, 1H), 7.73 (dd, J = 8.1, 1.7 Hz, 1H), 7.45-7.5 (m, 2H), 7.44 (t, J = 1.8 Hz, 1H), 7.29 (d, J = 8.1 Hz, 1H), 4.81 (s, 2H), 4.07 (d, J = 17.2 Hz, 1H), 3.78 (s, 3H), 3.69 (d, J = 17.2 Hz, 1H). |
| 3-033 | (B) δ7.45-7.55 (m, 4H), 7.43 (t, J = 1.8 Hz, 1H), 7.28 (d, J = 8.1 Hz, 1H), 5.86 (s, 2H), 4.09 (d, J = 17.2 Hz, 1H), 3.70 (d, J = 17.2 Hz, 1H), 3.68 (s, 3H), 2.39 (s, 3H), 2.13 (s, 3H). |
| 3-034 | (A) δ7.5-7.55 (m, 4H), 7.43 (t, J = 1.8 Hz, 1H), 7.26 (d, J = 7.8 Hz, 1H), 5.86 (s, 2H), 4.09 (d, J = 17.2 Hz, 1H), 3.70 (d, J = 17.2 Hz, 1H), 3.68 (s, 3H), 2.38 (s, 3H), 1.23 (s, 9H). |
| 3-035 | (B) δ7.5-7.55 (m, 4H), 7.43 (t, J = 1.8 Hz, 1H), 7.23 (d, J = 7.9 Hz, 1H), 5.01 (s, 2H), 4.07 (d, J = 17.2 Hz, 1H), 3.70 (d, J = 17.2 Hz, 1H), 3.65 (s, 3H), 2.38 (s, 3H), 2.33 (s, 3H). |
| 3-036 | (B) δ7.5-7.6 (m, 4H), 7.44 (t, J = 1.8 Hz, 1H), 7.33 (d, J = 8.1 Hz, 1H), 5.22 (s, 2H), 4.09 (d, J = 17.2 Hz, 1H), 3.71 (d, J = 17.2 Hz, 1H), 3.69 (s, 3H), 3.11 (s, 3H), 2.40 (s, 3H). |
| 3-037 | (A) δ7.45-7.55 (m, 4H), 7.43 (t, J = 1.8 Hz, 1H), 7.20 (d, J = 8.1 Hz, 1H), 5.37 (s, 2H), 4.09 (d, J = 17.2 Hz, 1H), 3.70 (d, J = 17.2 Hz, 1H), 3.67 (s, 3H), 2.39 (s, 3H), 2.34 (s, 3H). |
| 3-038 | (B) δ7.45-7.55 (m, 4H), 7.43 (t, J = 1.8 Hz, 1H), 7.23 (d, J = 8.0 Hz, 1H), 5.58 (s, 2H), 4.67 (d, J = 7.1 Hz, 2H), 4.08 (d, J = 17.2 Hz, 1H), 3.69 (d, J = 17.2 Hz, 1H), 3.65 (s, 3H), 2.36 (s, 3H), 1.43 (t, J = 7.1 Hz, 3H). |
| 3-039 | (B) δ7.5-7.55 (m, 4H), 7.43 (t, J = 1.8 Hz, 1H), 7.23 (d, J = 8.1 Hz, 1H), 5.86 (bs, 1H), 5.29 (d, J = 7.0 Hz, 2H), 4.09 (d, J = 17.2 Hz, 1H), 3.72 (s, 3H), 3.69 (d, J = 17.2 Hz, 1H), 3.67 (s, 3H), 2.35 (s, 3H). |
| 3-040 | (B) δ8.0-8.05 (m, 2H), 7.5-7.7 (m, 7H), 7.46 (d, J = 8.0 Hz, 1H), 7.43 (t, J = 1.8 Hz, 1H), 5.18 (s, 2H), 4.10 (d, J = 17.2 Hz, 1H), 3.71 (d, J = 17.2 Hz, 1H), 3.60 (s, 3H), 2.43 (s, 3H). |
| 3-043 | (B) δ7.45-7.6 (m, 5H), 7.43 (t, J = 1.8 Hz, 1H), 4.08 (d, J = 17.2 Hz, 1H), 3.77 (s, 3H), 3.70 (d, J = 17.2 Hz, 1H), 3.40 (sept, J = 6.8 Hz, 1H), 2.58 (s, 3H), 1.24 (d, J = 6.8 Hz, 6H). |
| 3-044 | (B) δ7.45-7.55 (m, 5H), 7.44 (t, J = 1.8 Hz, 1H), 4.63 (s, 2H), 4.08 (d, J = 17.2 Hz, 1H), 3.82 (s, 3H), 3.71 (d, J = 17.2 Hz, 1H), 2.62 (s, 3H). |
| 3-045 | (B) δ7.76 (d, J = 8.6 Hz, 1H), 7.5-7.6 (m, 4H), 7.44 (t, J = 1.8 Hz, 1H), 4.09 (d, J = 17.2 Hz, 1H), 3.78 (s, 3H), 3.77 (s, 2H), 3.71 (d, J = 17.2 Hz, 1H), 2.63 (s, 3H), 2.13 (s, 3H). |
| 3-046 | (B) δ7.8-7.9 (m, 2H), 7.45-7.7 (m, 8H), 7.43 (t, J = 1.8 Hz, 1H), 4.07 (d, J = 17.2 Hz, 1H), 3.72 (s, 3H), 3.69 (d, J = 17.2 Hz, 1H), 2.52 (s, 3H). |
| 3-047 | (A) δ7.81 (d, J = 8.4 Hz, 2H), 7.4-7.55 (m, 7H), 7.43 (t, J = 1.8 Hz, 1H), 4.09 (d, J = 17.2 Hz, 1H), 3.73 (s, 3H), 3.68 (d, J = 17.2 Hz, 1H), 2.52 (s, 3H). |
| 3-048 | (B) δ7.78 (d, J = 8.2 Hz, 2H), 7.5-7.6 (m, 5H), 7.43 (t, J = 1.8 Hz, 1H), 7.29 (d, J = 8.2 Hz, 2H), 4.07 (d, J = 17.2 Hz, 1H), 3.71 (s, 3H), 3.68 (d, J = 17.2 Hz, 1H), 2.52 (s, 3H), 2.43 (s, 3H). |
| 3-049 | (B) δ7.87 (d, J = 9.0 Hz, 2H), 7.45-7.55 (m, 5H), 7.43 (t, J = 1.8 Hz, 1H), 6.97 (d, J = 9.0 Hz, 2H), 4.07 (d, J = 17.2 Hz, 1H), 3.89 (s, 3H), 3.72 (s, 3H), 3.68 (d, J = 17.2 Hz, 1H), 2.52 (s, 3H). |
| 3-050 | (B) δ8.33 (d, J = 8.6 Hz, 2H), 8.00 (d, J = 8.6 Hz, 2H), 7.5-7.65 (m, 5H), 7.43 (t, J = 1.8 Hz, 1H), 4.08 (d, J = 17.2 Hz, 1H), 3.75 (s, 3H), 3.71 (d, J = 17.2 Hz, 1H), 2.55 (s, 3H). |

TABLE 16-continued

| No. | ¹H NMR |
|---|---|
| 3-052 | (B) δ7.5-7.6 (m, 5H), 7.44 (t, J = 1.8 Hz, 1H), 4.43 (t, J = 5.7 Hz, 2H), 4.09 (d, J = 17.2 Hz, 1H), 3.84 (s, 3H), 3.70 (d, J = 17.2 Hz, 1H), 3.60 (t, J = 5.7 Hz, 2H), 2.55 (s, 3H). |
| 3-053 | (B) δ7.5-7.65 (m, 5H), 7.43 (t, J = 1.8 Hz, 1H), 4.10 (d, J = 17.2 Hz, 1H), 3.75 (s, 3H), 3.73 (d, J = 17.2 Hz, 1H), 2.51 (s, 3H). |
| 3-054 | (B) δ7.45-7.55 (m, 4H), 7.43 (t, J = 1.8 Hz, 1H), 7.25 (d, J = 7.9 Hz, 1H), 5.28 (s, 2H), 4.08 (d, J = 17.2 Hz, 1H), 4.06 (q, J = 7.1 Hz, 2H), 3.70 (d, J = 17.2 Hz, 1H), 3.51 (s, 3H), 2.40 (s, 3H), 1.01 (t, J = 7.1 Hz, 3H). |
| 3-055 | (B) δ7.5-7.6 (m, 5H), 7.43 (t, J = 1.8 Hz, 1H), 4.18 (q, J = 7.1 Hz, 2H), 4.08 (d, J = 17.2 Hz, 1H), 3.70 (d, J = 17.2 Hz, 1H), 2.91 (q, J = 7.3 Hz, 2H), 2.59 (s, 3H), 1.19 (t, J = 7.3 Hz, 3H), 1.15 (t, J = 7.1 Hz, 3H). |
| 3-056 | (B) δ7.45-7.6 (m, 4H), 7.43 (t, J = 1.8 Hz, 1H), 7.38 (d, J = 8.4 Hz, 1H), 4.15 (q, J = 7.1 Hz, 2H), 4.08 (d, J = 17.2 Hz, 1H), 3.70 (d, J = 17.2 Hz, 1H), 2.45 (s, 3H), 1.38 (s, 9H), 1.18 (t, J = 7.1 Hz, 3H). |
| 3-057 | (B) δ7.5-7.65 (m, 5H), 7.43 (t, J = 1.8 Hz, 1H), 4.45 (s, 2H), 4.19 (q, J = 7.2 Hz, 2H), 4.08 (d, J = 17.2 Hz, 1H), 3.70 (d, J = 17.2 Hz, 1H), 3.43 (s, 3H), 2.59 (s, 3H), 1.15 (d, J = 7.2 Hz, 3H). |
| 3-059 | (B) δ7.2-7.6 (m, 6H), 4.8-5.0 (m, 1H), 4.77 (s, 2H), 4.09 (d, J = 17.2 Hz, 1H), 3.70 (d, J = 17.2 Hz, 1H), 2.36 (s, 3H), 1.06 (d, J = 6.4 Hz, 6H). |
| 3-060 | (B) δ7.5-7.6 (m, 5H), 7.44 (d, J = 8.1 Hz, 1H), 4.93 (sep, J = 6.2 Hz, 1H), 4.09 (d, J = 17.2 Hz, 1H), 3.71 (d, J = 17.2 Hz, 1H), 2.90 (q, J = 7.3 Hz, 2H), 2.58 (s, 3H), 1.20 (t, J = 7.3 Hz, 3H), 1.11 (d, J = 6.2 Hz, 6H). |
| 3-063 | (A) δ7.4-7.55 (m, 5H), 7.21 (d, J = 7.8 Hz, 1H), 4.08 (d, J = 17.1 Hz, 1H), 3.90 (q, J = 6.9 Hz, 2H), 3.70 (d, J = 17.1 Hz, 1H), 2.35 (s, 3H), 1.28 (t, J = 6.9 Hz, 3H), 1.19 (s, 9H). |
| 3-064 | (B) δ7.45-7.55 (m, 4H), 7.43 (t, J = 1.8 Hz, 1H), 7.29 (d, J = 8.1 Hz, 1H), 5.24 (s, 2H), 4.09 (d, J = 17.2 Hz, 1H), 3.70 (d, J = 17.2 Hz, 1H), 3.50 (s, 3H), 2.41 (s, 3H), 1.19 (s, 9H). |
| 3-065 | (A) δ7.15-7.5 (m, 11H), 5.02 (s, 2H), 4.07 (d, J = 17.1 Hz, 1H), 3.68 (d, J = 17.1 Hz, 1H), 2.33 (s, 3H), 1.14 (s, 9H). |
| 3-066 | (B) δ7.4-7.6 (m, 5H), 7.44 (t, J = 1.8 Hz, 1H), 4.09 (d, J = 17.2 Hz, 1H), 3.71 (d, J = 17.2 Hz, 1H), 2.58 (s, 3H), 2.53 (s, 3H), 1.30 (s, 9H). |
| 3-068 | (B) δ7.4-7.65 (m, 6H), 4.18 (d, J = 17.2 Hz, 1H), 3.75-3.9 (m, 2H), 3.71 (d, J = 17.2 Hz, 1H), 2.60 (s, 3H), 1.33 (s, 9H). |
| 3-070 | (B) δ7.5-7.6 (m, 5H), 7.44 (t, J = 1.8 Hz, 1H), 4.35-4.4 (m, 2H), 4.09 (d, J = 17.2 Hz, 1H), 3.84 (s, 3H), 3.70 (d, J = 17.2 Hz, 1H), 3.45-3.55 (m, 2H), 3.29 (s, 3H), 2.54 (s, 3H). |
| 3-071 | (B) δ7.45-7.6 (m, 4H), 7.43 (t, J = 1.8 Hz, 1H), 7.32 (d, J = 7.9 Hz, 1H), 4.53 (t, J = 8.2 Hz, 2H), 4.21 (t, J = 8.2 Hz, 2H), 4.08 (d, J = 17.2 Hz, 1H), 3.70 (d, J = 17.2 Hz, 1H), 2.37 (s, 3H). |
| 3-072 | (B) δ7.55-7.7 (m, 2H), 7.4-7.55 (m, 4H), 4.10 (d, J = 17.4 Hz, 1H), 3.72 (d, J = 17.4 Hz, 1H), 2.56 (s, 3H), 1.69 (s, 6H). |
| 3-073 | (B) δ8.08 (d, J = 1.7 Hz, 1H), 7.71 (dd, J = 8.1, 1.7 Hz, 1H), 7.50 (bs, 2H), 7.44 (t, J = 1.8 Hz, 1H), 7.26 (d, J = 8.1 Hz, 1H), 5.37 (s, 2H), 4.06 (d, J = 17.2 Hz, 1H), 3.37 (q, J = 7.0 Hz, 2H), 3.72 (s, 3H), 3.68 (d, J = 17.2 Hz, 1H), 1.26 (t, J = 7.0 Hz, 3H). |
| 3-075 | (B) δ7.5-7.55 (m, 4H), 7.43 (t, J = 1.8 Hz, 1H), 7.27 (d, J = 7.9 Hz, 1H), 5.87 (s, 2H), 4.09 (d, J = 17.2 Hz, 1H), 3.70 (d, J = 17.2 Hz, 1H), 3.67 (s, 3H), 2.40 (q, J = 7.5 Hz, 2H), 2.39 (s, 3H), 1.17 (t, J = 7.5 Hz, 3H). |
| 3-076 | (B) δ7.45-7.55 (m, 4H), 7.43 (t, J = 1.8 Hz, 1H), 7.27 (d, J = 8.1 Hz, 1H), 5.91 (s, 2H), 4.09 (d, J = 17.2 Hz, 1H), 3.84 (s, 3H), 3.70 (d, J = 17.2 Hz, 1H), 3.68 (s, 3H), 2.39 (s, 3H). |
| 3-078 | (B) δ7.55-7.65 (m, 5H), 7.43 (t, J = 1.8 Hz, 1H), 4.45 (s, 2H), 4.08 (d, J = 17.2 Hz, 1H), 3.77 (s, 3H), 3.70 (d, J = 17.2 Hz, 1H), 3.56 (q, J = 7.0 Hz, 2H), 2.59 (s, 3H), 1.18 (t, J = 7.0 Hz, 3H). |
| 3-080 | (A) δ7.66 (s, 1H), 7.45-7.6 (m, 4H), 7.2-7.3 (m, 1H), 5.28 (s, 2H), 4.08 (d, J = 17.4 Hz, 1H), 3.68 (d, J = 17.4 Hz, 1H), 3.66 (s, 3H), 3.50 (s, 3H), 2.40 (s, 3H). |
| 3-084 | (A) δ8.08 (s, 2H), 7.97 (s, 1H), 7.74 (d, J = 8.4 Hz, 2H), 7.63 (d, J = 8.4 Hz, 2H), 5.28 (s, 2H), 4.19 (d, J = 17.4 Hz, 1H), 3.65-3.8 (m, 6H), 1.24 (t, J = 7.2 Hz, 3H). |
| 3-085 | (A) δ8.09 (s, 2H), 7.78 (s, 1H), 7.74 (d, J = 8.4 Hz, 2H), 7.63 (d, J = 8.4 Hz, 2H), 5.38 (s, 2H), 4.05-4.3 (m, 3H), 3.76 (d, J = 17.4 Hz, 1H), 3.69 (s, 3H). |
| 4-004 | (B) δ11.65 (s, 1H), 7.5-7.65 (m, 4H), 7.44 (t, J = 1.8 Hz, 1H), 7.28 (d, J = 8.8 Hz, 1H), 4.09 (d, J = 17.2 Hz, 1H), 3.71 (d, J = 17.2 Hz, 1H), 3.07 (s, 3H), 2.49 (s, 3H), 2.37 (s, 3H). |
| 4-007 | (B) δ7.5-7.7 (m, 4H), 7.44 (t, J = 8.1 Hz, 1H), 7.34 (d, J = 7.9 Hz, 1H), 6.65 (bs, 1H), 4.09 (d, J = 17.2 Hz, 1H), 3.72 (d, J = 17.2 Hz, 1H), 3.15 (s, 3H), 2.40 (s, 3H). |
| 4-008 | (B) δ11.55 (s, 1H), 7.5-7.65 (m, 4H), 7.43 (t, J = 1.8 Hz, 1H), 7.28 (d, J = 7.9 Hz, 1H), 4.10 (d, J = 17.2 Hz, 1H), 3.84 (s, 3H), 3.72 (d, J = 17.2 Hz, 1H), 3.06 (s, 3H), 2.37 (s, 3H). |

TABLE 16-continued

| No. | $^1$H NMR |
|---|---|
| 4-009 | (B) δ9.96 (bs, 1H), 9.35 (bs, 1H), 7.45-7.65 (m, 6H), 7.43 (t, J = 1.8 Hz, 1H), 4.10 (d, J = 17.2 Hz, 1H), 3.73 (d, J = 17.2 Hz, 1H), 2.50 (s, 3H). |
| 4-010 | (B) δ12.92 (s, 1H), 7.95-8.05 (m, 2H), 7.45-7.7 (m, 7H), 7.44 (t, J = 1.8 Hz, 1H), 7.34 (d, J = 7.9 Hz, 1H), 4.12 (d, J = 17.2 Hz, 1H), 3.74 (d, J = 17.2 Hz, 1H), 3.17 (s, 3H), 2.41 (s, 3H). |
| 4-015 | (A) δ7.91 (s, 1H), 7.6-7.75 (m, 2H), 7.4-7.55 (m, 3H), 6.14 and 6.00 (s, 1H), 4.07 (d, J = 17.4 Hz, 1H), 3.69 (d, J = 17.4 Hz, 1H). |
| 5-001 | (A) δ6.8-7.7 (m, 11H), 3.99 (d, J = 17.1 Hz, 1H), 3.59 (d, J = 17.1 Hz, 1H), 3.51 (s, 3H), 2.36 (s, 3H). |
| 5-003 | (A) δ6.9-7.6 (m, 11H), 5.05-5.25 (m, 1H), 3.96 (d, J = 17.1 Hz, 1H), 3.56 (d, J = 17.1 Hz, 1H), 2.37 (s, 3H), 1.20 (d, J = 6.9 Hz, 6H). |
| 5-009 | (A) δ6.7-7.65 (m, 10H), 5.85-6.1 (m, 1H), 5.22 (s, 1H), 5.18 (d, J = 6.3 Hz, 1H), 4.50 (d, J = 6.3 Hz, 2H), 4.01 (d, J = 17.1 Hz, 1H), 3.62 (d, J = 17.1 Hz, 1H), 2.36 (s, 3H). |
| 5-012 | (A) δ8.38 (d, J = 4.8 Hz, 1H), 7.3-7.55 (m, 7H), 7.17 (d, J = 8.1 Hz, 1H), 7.04 (dd, J = 7.5, 4.8 Hz, 1H), 4.03 (d, J = 17.3 Hz, 1H), 3.64 (d, J = 17.3 Hz, 1H), 3.53 (s, 3H), 2.36 (s, 3H). |
| 5-013 | (A) δ8.64 (d, J = 5.1 Hz, 2H), 7.2-7.65 (m, 6H), 7.14 (t, J = 5.1 Hz, 1H), 4.01 (d, J = 17.4 Hz, 1H), 3.62 (d, J = 17.4 Hz, 1H), 2.59 (s, 3H), 2.54 (s, 3H). |
| 5-016 | (A) δ8.66 (s, 2H), 7.4-7.65 (m, 6H), 4.04 (d, J = 17.4 Hz, 1H), 3.65 (d, J = 17.4 Hz, 1H), 2.50 (s, 3H). |
| 5-018 | (A) δ7.4-7.65 (m, 5H), 7.0-7.3 (m, 5H), 4.05 (d, J = 17.1 Hz, 1H), 3.65 (d, J = 17.1 Hz, 1H), 2.60 (q, J = 7.5 Hz, 2H), 2.44 (s, 3H), 1.11 (t, J = 7.5 Hz, 3H). |
| 5-019 | (A) δ7.1-7.6 (m, 10H), 4.07 (d, J = 17.4 Hz, 1H), 3.67 (d, J = 17.4 Hz, 1H), 2.47 (s, 3H), 0.8-1.2 (m, 5H). |
| 5-020 | (A) δ7.4-7.5 (m, 5H), 7.2-7.3 (m, 1H), 7.0-7.2 (m, 4H), 4.05 (d, J = 17.4 Hz, 1H), 3.66 (d, J = 17.4 Hz, 1H), 2.45 (s, 3H), 2.45 (d, J = 6.6 Hz, 2H), 2.16 (qui, J = 6.6 Hz, 1H), 0.92 (d, J = 6.6 Hz, 6H). |
| 5-021 | (A) δ7.3-7.5 (m, 5H), 7.19 (d, J = 8.1 Hz, 1H), 6.9-7.1 (m, 4H), 4.52 (s, 2H), 4.02 (d, J = 17.4 Hz, 1H), 3.64 (d, J = 17.4 Hz, 1H), 3.46 (s, 3H), 2.43 (s, 3H). |
| 5-024 | (A) δ8.08 (d, J = 9.1 Hz, 2H), 7.05-7.5 (m, 8H), 4.03 (d, J = 17.3 Hz, 1H), 3.63 (d, J = 17.3 Hz, 1H), 3.51 (s, 3H), 2.37 (s, 3H). |
| 5-025 | (A) δ8.19 (d, J = 9.1 Hz, 2H), 7.2-7.5 (m, 8H), 4.02 (d, J = 17.3 Hz, 1H), 3.63 (d, J = 17.3 Hz, 1H), 2.52 (s, 3H), 2.49 (s, 3H). |
| 5-026 | (B) δ8.34 (d, J = 6.8 Hz, 2H), 7.4-7.6 (m, 8H), 4.10 (d, J = 17.2 Hz, 1H), 3.71 (d, J = 17.2 Hz, 1H), 3.65 (s, 3H), 2.50 (s, 3H). |
| 5-027 | (A) δ7.0-7.6 (m, 10H), 4.04 (d, J = 17.4 Hz, 1H), 3.65 (d, J = 17.4 Hz, 1H), 3.48 (s, 3H), 2.35 (s, 3H). |
| 5-028 | (A) δ7.64 (d, J = 8.1 Hz, 2H), 7.35-7.5 (m, 5H), 7.2-7.3 (m, 3H), 4.03 (d, J = 17.1 Hz, 1H), 3.64 (d, J = 17.1 Hz, 1H), 2.48 (s, 3H), 2.47 (s, 3H). |
| 5-029 | (A) δ7.25-7.8 (m, 10H), 4.10 (d, J = 17.4 Hz, 1H), 3.71 (d, J = 17.4 Hz, 1H), 3.64 (s, 3H), 2.48 (s, 3H). |
| 5-034 | (A) δ7.4-7.55 (m, 5H), 7.3-7.35 (m, 1H), 7.1-7.2 (m, 1H), 6.8-6.95 (m, 2H), 4.05 (d, J = 17.1 Hz, 1H), 3.67 (d, J = 17.1 Hz, 1H), 3.10 (sep, J = 6.6 Hz, 1H), 2.46 (s, 3H), 1.19 (d, J = 6.6 Hz, 6H). |
| 5-035 | (A) δ7.35-7.5 (m, 6H), 7.05-7.15 (m, 1H), 6.8-6.95 (m, 2H), 4.06 (d, J = 17.1 Hz, 1H), 3.67 (d, J = 17.1 Hz, 1H), 2.50 (s, 3H), 1.27 (s, 9H). |
| 5-036 | (A) δ7.25-7.6 (m, 7H), 6.99 (t, J = 8.1 Hz, 2H), 4.10 (d, J = 17.1 Hz, 1H), 3.70 (d, J = 17.1 Hz, 1H), 3.65 (s, 3H), 2.47 (s, 3H). |
| 5-037 | (A) δ7.5-7.6 (m, 4H), 7.4-7.45 (m, 2H), 7.1-7.25 (m, 2H), 7.0-7.1 (m, 1H), 4.10 (d, J = 17.4 Hz, 1H), 3.70 (d, J = 17.4 Hz, 1H), 3.66 (s, 3H), 2.47 (s, 3H). |
| 5-038 | (A) δ7.4-7.6 (m, 6H), 7.25-7.3 (m, 1H), 6.95-7.05 (m, 2H), 4.09 (d, J = 16.8 Hz, 1H), 3.71 (d, J = 16.8 Hz, 1H), 2.49 (s, 3H), 1.23 (s, 9H). |
| 5-039 | (A) δ7.25-7.6 (m, 7H), 4.09 (d, J = 16.8 Hz, 1H), 3.70 (d, J = 16.8 Hz, 1H), 3.36 (s, 3H), 2.35 (s, 6H). |
| 5-040 | (A) δ7.25-7.55 (m, 6H), 6.05 (s, 1H), 4.05 (d, J = 17.4 Hz, 1H), 3.67 (d, J = 17.4 Hz, 1H), 2.51 (s, 3H), 2.48 (s, 3H), 2.37 (s, 3H). |
| 5-041 | (A) δ7.4-7.6 (m, 6H), 6.11 (s, 1H), 4.08 (d, J = 16.8 Hz, 1H), 3.80 (s, 3H), 3.69 (d, J = 16.8 Hz, 1H), 2.49 (s, 3H), 2.47 (s, 3H). |
| 5-042 | (A) δ7.3-7.65 (m, 6H), 6.66 (s, 1H), 4.02 (d, J = 17.4 Hz, 1H), 3.75 (d, J = 17.4 Hz, 1H), 3.36 (s, 3H), 2.47 (s, 3H), 2.33 (s, 3H). |
| 5-043 | (A) δ7.1-7.6 (m, 8H), 6.05 (bs, 1H), 4.01 (d, J = 16.2 Hz, 1H), 3.62 (d, J = 16.2 Hz, 1H), 3.56 (s, 3H), 2.44 (s, 3H). |
| 5-045 | (A) δ7.4-7.65 (m, 8H), 6.40 (t, J = 2.2 Hz, 1H), 4.08 (d, J = 17.0 Hz, 1H), 3.76 (s, 3H), 3.69 (d, J = 17.0 Hz, 1H), 2.50 (s, 3H). |
| 5-046 | (A) δ6.85-7.6 (m, 8H), 4.04 (d, J = 17.4 Hz, 1H), 3.72 (s, 3H), 3.64 (d, J = 17.4 Hz, 1H), 3.50 (s, 3H), 2.31 (s, 3H). |
| 5-047 | (A) δ7.3-7.65 (m, 7H), 7.11 (d, J = 3.6 Hz, 1H), 4.11 (d, J = 17.4 Hz, 1H), 3.73 (d, J = 17.4 Hz, 1H), 3.51 (s, 3H), 2.36 (s, 3H). |

TABLE 16-continued

| No. | $^1$H NMR |
|---|---|
| 5-048 | (A) δ8.38 (s, 1H), 8.27 (d, J = 8.1 Hz, 1H), 7.5-7.6 (m, 4H), 7.27 (s, 1H), 4.13 (d, J = 17.4 Hz, 1H), 4.08 (s, 3H), 3.75 (d, J = 17.4 Hz, 1H), 2.79 (s, 3H). |
| 5-049 | (B) δ8.42 (s, 1H), 7.4-7.7 (m, 6H), 4.18 (s, 3H), 4.12 (d, J = 17.2 Hz, 1H), 3.73 (d, J = 17.2 Hz, 1H), 2.77 (s, 3H). |
| 5-050 | (A) δ8.35-8.45 (m, 1H), 7.15-7.75 (m, 9H), 4.02 (d, J = 17.1 Hz, 1H), 3.63 (d, J = 17.1 Hz, 1H), 2.52 (s, 3H), 2.49 (s, 3H). |
| 5-051 | (A) δ8.5-8.6 (m, 1H), 7.8-7.9 (m, 1H), 7.4-7.6 (m, 6H), 7.25-7.4 (m, 2H), 4.09 (d, J = 17.1 Hz, 1H), 3.69 (d, J = 17.1 Hz, 1H), 3.66 (s, 3H), 2.52 (s, 3H). |
| 5-052 | (A) δ8.33 (d, J = 2.5 Hz, 1H), 7.0-7.55 (m, 8H), 4.06 (d, J = 17.3 Hz, 1H), 3.66 (d, J = 17.3 Hz, 1H), 3.48 (s, 3H), 2.36 (s, 3H). |
| 5-053 | (A) δ8.32 (d, J = 2.4 Hz, 1H), 7.3-7.5 (m, 6H), 7.16 (d, J = 8.1 Hz, 1H), 6.93 (s, 1H), 4.06 (q, J = 7.2 Hz, 2H), 4.06 (d, J = 17.1 Hz, 1H), 3.68 (d, J = 17.1 Hz, 1H), 2.36 (s, 3H), 1.23 (t, J = 7.2 Hz, 3H). |
| 5-054 | (A) δ8.29 (d, J = 2.4 Hz, 1H), 7.3-7.6 (m, 6H), 7.1-7.25 (m, 2H), 5.33 (s, 2H), 4.06 (d, J = 17.1 Hz, 1H), 3.67 (d, J = 17.1 Hz, 1H), 3.40 (s, 3H), 2.42 (s, 3H). |
| 5-055 | (A) δ8.39 (s, 1H), 7.35-7.5 (m, 6H), 7.21 (d, J = 7.8 Hz, 1H), 6.7-6.9 (m, 1H), 4.97 (s, 2H), 4.06 (d, J = 17.1 Hz, 1H), 3.67 (d, J = 17.1 Hz, 1H), 2.35 (s, 3H). |
| 5-056 | (A) δ8.29 (d, J = 2.4 Hz, 1H), 7.6-7.7 (m, 1H), 7.15-7.5 (m, 7H), 4.04 (d, J = 17.4 Hz, 1H), 3.65 (d, J = 17.4 Hz, 1H), 2.52 (s, 3H), 2.51 (s, 3H). |
| 5-057 | (A) δ8.34 (d, J = 2.7 Hz, 1H), 7.65-7.75 (m, 1H), 7.35-7.5 (m, 5H), 7.15-7.5 (m, 2H), 4.04 (d, J = 17.4 Hz, 1H), 3.65 (d, J = 17.4 Hz, 1H), 2.77 (q, J = 7.2 Hz, 2H), 2.50 (s, 3H), 1.91 (t, J = 7.2 Hz, 3H). |
| 5-058 | (A) δ8.33 (d, J = 2.1 Hz, 1H), 7.6-7.7 (m, 1H), 7.35-7.5 (m, 5H), 7.15-7.35 (m, 2H), 4.04 (d, J = 17.4 Hz, 1H), 3.65 (d, J = 17.4 Hz, 1H), 2.71 (t, J = 7.5 Hz, 2H), 2.50 (s, 3H), 1.73 (sxt, J = 7.5 Hz, 2H), 0.97 (t, J = 7.5 Hz, 3H). |
| 5-059 | (A) δ8.36 (d, J = 2.1 Hz, 1H), 7.65-7.75 (m, 1H), 7.35-7.5 (m, 6H), 7.14 (d, J = 8.7 Hz, 1H), 4.07 (d, J = 17.4 Hz, 1H), 3.68 (d, J = 17.4 Hz, 1H), 2.51 (s, 3H), 1.21 (s, 9H). |
| 5-061 | (B) δ8.42 (d, J = 2.6 Hz, 1H), 7.3-7.65 (m, 7H), 7.19 (d, J = 8.0 Hz, 1H), 4.06 (d, J = 17.2 Hz, 1H), 3.66 (d, J = 17.4 Hz, 1H), 3.48 (s, 3H), 2.35 (s, 3H). |
| 5-062 | (B) δ8.4-8.45 (m, 1H), 7.80 (dd, J = 8.4, 2.2 Hz, 1H), 7.35-7.5 (m, 5H), 7.2-7.3 (m, 1H), 7.16 (d, J = 8.4 Hz, 1H), 4.04 (d, J = 17.2 Hz, 1H), 3.64 (d, J = 17.2 Hz, 1H), 2.52 (bs, 6H). |
| 5-063 | (B) δ8.60 (bs, 1H), 7.9-8.0 (m, 1H), 7.4-7.6 (m, 6H), 7.2-7.3 (m, 1H), 4.09 (d, J = 17.2 Hz, 1H), 3.65-3.75 (m, 4H), 2.52 (s, 3H). |
| 5-064 | (A) δ8.65 (bs, 1H), 7.77 (dd, J = 8.4, 2.1 Hz, 1H), 7.4-7.55 (m, 5H), 7.2-7.3 (m, 2H), 4.07 (d, J = 17.2 Hz, 1H), 3.68 (d, J = 17.2 Hz, 1H), 3.50 (s, 3H), 2.37 (s, 3H). |
| 5-065 | (A) δ8.59 (bs, 1H), 7.94 (dd, J = 8.4, 2.4 Hz, 1H), 7.2-7.5 (m, 7H), 4.03 (d, J = 17.2 Hz, 1H), 3.64 (d, J = 17.2 Hz, 1H), 2.55 (s, 3H), 2.53 (s, 3H). |
| 5-066 | (A) δ8.78 (bs, 1H), 8.06 (dd, J = 8.4, 2.1 Hz, 1H), 7.4-7.6 (m, 7H), 4.09 (d, J = 17.2 Hz, 1H), 3.70 (d, J = 17.2 Hz, 1H), 3.69 (s, 3H), 2.54 (s, 3H). |
| 5-068 | (A) δ9.06 (dd, J = 2.7, 0.6 Hz, 1H), 8.46 (dd, J = 9.0, 2.7 Hz, 1H), 7.58 (dd, J = 9.0, 0.6 Hz, 1H), 7.45-7.5 (m, 3H), 7.41 (t, J = 1.8 Hz, 1H), 7.36 (dd, J = 8.1, 1.5 Hz, 1H), 7.28 (d, J = 8.1 Hz, 1H), 4.05 (d, J = 17.2 Hz, 1H), 3.64 (d, J = 17.2 Hz, 1H), 2.58 (bs, 6H). |
| 5-070 | (A) δ8.65 (s, 1H), 7.75-7.85 (m, 1H), 7.4-7.65 (m, 6H), 7.24 (d, J = 7.8 Hz, 1H), 4.08 (d, J = 17.1 Hz, 1H), 3.69 (d, J = 17.1 Hz, 1H), 3.48 (s, 3H), 2.37 (s, 3H). |
| 5-072 | (A) δ7.05-7.55 (m, 9H), 4.06 (d, J = 17.2 Hz, 1H), 3.66 (d, J = 17.2 Hz, 1H), 3.49 (s, 3H), 2.37 (s, 3H). |
| 5-074 | (A) δ7.79 (t, J = 8.1 Hz, 1H), 7.25-7.5 (m, 8H), 4.09 (d, J = 17.2 Hz, 1H), 3.70 (d, J = 17.2 Hz, 1H), 3.68 (s, 3H), 2.51 (s, 3H). |
| 5-076 | (A) δ7.51 (t, J = 7.8 Hz, 1H), 7.25-7.5 (m, 7H), 7.25 (d, J = 7.8 Hz, 1H), 4.03 (d, J = 17.4 Hz, 1H), 3.64 (d, J = 17.4 Hz, 1H), 2.55 (s, 3H), 2.54 (s, 3H). |
| 5-077 | (A) δ7.63 (t, J = 7.8 Hz, 1H), 7.4-7.55 (m, 7H), 7.30 (d, J = 7.8 Hz, 1H), 4.08 (d, J = 17.4 Hz, 1H), 3.70 (d, J = 17.4 Hz, 1H), 3.68 (s, 3H), 2.52 (s, 3H). |
| 5-079 | (A) δ8.45-8.55 (m, 1H), 8.38 (d, J = 2.7 Hz, 1H), 7.2-7.5 (m, 8H), 4.02 (d, J = 17.4 Hz, 1H), 3.63 (d, J = 17.4 Hz, 1H), 2.50 (s, 3H), 2.46 (s, 3H). |
| 5-080 | (A) δ8.6-8.7 (m, 1H), 8.55 (d, J = 2.4 Hz, 1H), 7.35-7.65 (m, 8H), 4.10 (d, J = 17.1 Hz, 1H), 3.71 (d, J = 17.1 Hz, 1H), 3.64 (s, 3H), 2.49 (s, 3H). |
| 5-081 | (A) δ8.1 (bs, 1H), 7.0-7.5 (m, 8H), 4.03 (d, J = 16.8 Hz, 1H), 3.64 (d, J = 16.8 Hz, 1H), 3.48 (bs, 3H), 2.35 (s, 3H). |
| 5-082 | (B) δ8.32 (d, J = 2.8 Hz, 1H), 7.4-7.6 (m, 8H), 4.10 (d, J = 17.6 Hz, 1H), 3.71 (d, J = 17.6 Hz, 1H), 3.65 (s, 3H), 2.47 (s, 3H). |

TABLE 16-continued

| No. | ¹H NMR |
|---|---|
| 5-083 | (A) δ8.46 (d, J = 6.1 Hz, 2H), 7.1-7.5 (m, 6H), 7.04 (d, J = 6.1 Hz, 2H), 4.04 (d, J = 17.3 Hz, 1H), 3.65 (d, J = 17.3 Hz, 1H), 3.48 (s, 3H), 2.36 (s, 3H). |
| 5-084 | (A) δ8.34 (d, J = 4.8 Hz, 2H), 7.45-7.55 (m, 2H), 7.4-7.45 (m, 2H), 7.25-7.3 (m, 1H), 7.06 (d, J = 7.8 Hz, 1H), 6.89 (t, J = 4.8 Hz, 1H), 4.05 (d, J = 17.4 Hz, 1H), 3.67 (s, 3H), 3.65 (d, J = 17.4 Hz, 1H), 2.37 (s, 3H). |
| 5-085 | (A) δ8.36 (d, J = 4.8 Hz, 2H), 7.4-7.55 (m, 4H), 7.2-7.3 (m, 1H), 7.05 (d, J = 7.8 Hz, 1H), 6.89 (t, J = 4.8 Hz, 1H), 4.27 (q, J = 7.1 Hz, 2H), 4.05 (d, J = 17.3 Hz, 1H), 3.65 (d, J = 17.3 Hz, 1H), 2.38 (s, 3H), 1.35 (t, J = 7.1 Hz, 3H). |
| 5-086 | (A) δ8.41 (d, J = 4.8 Hz, 2H), 7.4-7.55 (m, 4H), 7.2-7.3 (m, 1H), 7.07 (d, J = 8.1 Hz, 1H), 6.94 (t, J = 4.8 Hz, 1H), 5.63 (s, 2H), 4.04 (d, J = 17.0 Hz, 1H), 3.64 (d, J = 17.0 Hz, 1H), 3.52 (s, 3H), 2.48 (s, 3H). |
| 5-087 | (A) δ8.41 (d, J = 4.8 Hz, 2H), 7.3-7.55 (m, 5H), 7.11 (d, J = 7.8 Hz, 1H), 6.99 (t, J = 4.8 Hz, 1H), 5.14 (s, 2H), 4.07 (d, J = 17.3 Hz, 1H), 3.67 (d, J = 17.3 Hz, 1H), 2.38 (s, 3H). |
| 5-089 | (A) δ8.66 (d, J = 4.8 Hz, 2H), 7.3-7.5 (m, 6H), 7.16 (t, J = 4.8 Hz, 1H), 4.02 (d, J = 17.1 Hz, 1H), 3.63 (d, J = 17.1 Hz, 1H), 2.83 (t, J = 7.5 Hz, 2H), 2.55 (s, 3H), 1.7-1.85 (m, 2H), 1.00 (t, J = 7.5 Hz, 3H). |
| 5-092 | (A) δ8.3 (s, 2H), 7.35-7.55 (m, 4H), 7.2-7.35 (m, 1H), 7.05 (d, J = 8.1 Hz, 1H), 4.07 (d, J = 17.4 Hz, 1H), 3.67 (d, J = 17.4 Hz, 1H), 3.65 (s, 3H), 2.37 (s, 3H). |
| 5-093 | (A) δ8.29 (s, 2H), 7.4-7.6 (m, 4H), 7.30 (d, J = 8.1 Hz, 1H), 7.04 (d, J = 8.1 Hz, 1H), 4.24 (q, J = 7.2 Hz, 2H), 4.06 (d, J = 16.8 Hz, 1H), 3.66 (d, J = 16.8 Hz, 1H), 2.38 (s, 3H), 1.34 (t, J = 7.2 Hz, 3H). |
| 5-095 | (A) δ8.35 (s, 2H), 7.35-7.55 (m, 4H), 7.2-7.3 (m, 1H), 7.06 (d, J = 8.1 Hz, 1H), 5.65 (s, 2H), 4.06 (d, J = 17.1 Hz, 1H), 3.75 (q, J = 6.9 Hz, 2H), 3.66 (d, J = 17.1 Hz, 1H), 2.46 (s, 3H), 1.20 (t, J = 6.9 Hz, 3H). |
| 5-096 | (A) δ8.35 (s, 2H), 7.2-7.55 (m, 5H), 7.11 (d, J = 8.1 Hz, 1H), 6.12 (s, 2H), 4.07 (d, J = 17.4 Hz, 1H), 3.67 (d, J = 17.4 Hz, 1H), 2.54 (s, 3H), 2.09 (s, 3H). |
| 5-097 | (B) δ8.35 (s, 2H), 7.05-7.6 (m, 6H), 5.11 (s, 2H), 4.07 (d, J = 17.2 Hz, 1H), 3.67 (d, J = 17.2 Hz, 1H), 2.38 (s, 3H). |
| 5-098 | (A) δ8.30 (s, 2H), 7.25-7.55 (m, 5H), 7.05 (d, J = 8.1 Hz, 1H), 5.9-6.1 (m, 1H), 5.26 (dd, J = 17.4, 1.2 Hz, 1H), 5.16 (dd, J = 10.5, 1.2 Hz, 1H), 4.82 (d, J = 5.4 Hz, 2H), 4.06 (d, J = 17.1 Hz, 1H), 3.66 (d, J = 17.1 Hz, 1H), 2.41 (s, 3H). |
| 5-099 | (A) δ8.34 (s, 2H), 7.25-7.55 (m, 5H), 7.09 (d, J = 7.8 Hz, 1H), 4.98 (d, J = 2.4 Hz, 2H), 4.07 (d, J = 17.1 Hz, 1H), 3.67 (d, J = 17.1 Hz, 1H), 2.39 (s, 3H), 2.21 (t, J = 2.4 Hz, 1H). |
| 5-102 | (A) δ8.57 (s, 2H), 7.3-7.5 (m, 6H), 4.03 (d, J = 17.1 Hz, 1H), 3.67 (d, J = 17.1 Hz, 1H), 2.84 (t, J = 7.5 Hz, 2H), 2.53 (s, 3H), 1.75 (sxt, J = 7.5 Hz, 2H), 1.01 (t, J = 6.9 Hz, 3H). |
| 5-104 | (A) δ8.60 (s, 2H), 7.35-7.5 (m, 6H), 4.05 (d, J = 17.1 Hz, 1H), 3.66 (d, J = 17.1 Hz, 1H), 2.57 (s, 3H), 2.05-2.2 (m, 1H), 1.2-1.3 (m, 2H), 1.0-1.1 (m, 2H). |
| 5-105 | (A) δ8.45 (s, 2H), 7.35-7.55 (m, 6H), 4.07 (d, J = 17.1 Hz, 1H), 3.67 (d, J = 17.1 Hz, 1H), 2.54 (s, 3H), 1.36 (s, 9H). |
| 5-107 | (A) δ8.57 (s, 2H), 7.35-7.8 (m, 11H), 4.05 (d, J = 17.1 Hz, 1H), 3.66 (d, J = 17.1 Hz, 1H), 2.57 (s, 3H). |
| 5-109 | (A) δ8.72 (s, 2H), 7.4-7.6 (m, 6H), 4.16 (q, J = 7.2 Hz, 2H), 4.09 (d, J = 16.8 Hz, 1H), 3.71 (d, J = 16.8 Hz, 1H), 2.54 (s, 3H), 1.09 (t, J = 7.2 Hz, 3H). |
| 5-110 | (A)v8.72 (s, 2H), 7.4-7.6 (m, 6H), 4.09 (d, J = 17.4 Hz, 1H), 4.08 (d, J = 6.6 Hz, 2H), 3.70 (d, J = 17.4 Hz, 1H), 2.54 (s, 3H), 1.48 (sxt, J = 6.6 Hz, 2H), 0.77 (t, J = 6.6 Hz, 3H). |
| 5-111 | (A) δ8.72 (s, 2H), 7.4-7.6 (m, 6H), 4.08 (d, J = 17.1 Hz, 1H), 3.90 (d, J = 6.6 Hz, 2H), 3.70 (d, J = 17.1 Hz, 1H), 2.54 (s, 3H), 1.77 (sep, J = 6.6 Hz, 1H), 0.76 (d, J = 6.6 Hz, 6H). |
| 5-112 | (A) δ8.72 (s, 2H), 7.4-7.6 (m, 6H), 5.67 (s, 2H), 4.09 (d, J = 17.4 Hz, 1H), 3.70 (d, J = 17.4 Hz, 1H), 2.56 (s, 3H). |
| 5-113 | (A) δ8.71 (s, 2H), 7.4-7.6 (m, 6H), 4.2-4.3 (m, 2H), 4.09 (d, J = 17.4 Hz, 1H), 3.71 (d, J = 17.4 Hz, 1H), 3.35-3.45 (m, 2H), 3.23 (s, 3H), 2.54 (s, 3H). |
| 5-114 | (B) δ8.38 (s, 2H), 7.05-7.55 (m, 6H), 4.06 (d, J = 17.2 Hz, 1H), 3.66 (d, J = 17.2 Hz, 1H), 3.64 (s, 3H), 2.36 (s, 3H). |
| 5-115 | (A) δ8.37 (s, 2H), 7.25-7.55 (m, 5H), 7.03 (d, J = 8.1 Hz, 1H), 4.24 (q, J = 6.9 Hz, 2H), 4.06 (d, J = 17.1 Hz, 1H), 3.66 (d, J = 17.1 Hz, 1H), 2.37 (s, 3H), 1.34 (t, J = 6.9 Hz, 3H). |
| 5-117 | (A) δ8.44 (s, 2H), 7.3-7.55 (m, 5H), 7.11 (d, J = 8.1 Hz, 1H), 6.12 (s, 2H), 4.07 (d, J = 17.4 Hz, 1H), 3.67 (d, J = 17.4 Hz, 1H), 2.44 (s, 3H), 2.09 (s, 3H). |
| 5-118 | (A) δ8.44 (s, 2H), 7.50 (s, 3H), 7.3-7.45 (m, 2H), 7.10 (d, J = 8.1 Hz, 1H), 5.10 (s, 2H), 4.08 (d, J = 16.8 Hz, 1H), 3.69 (d, J = 16.8 Hz, 1H), 2.37 (s, 3H). |

TABLE 16-continued

| No. | ¹H NMR |
|---|---|
| 5-121 | (A) δ8.67 (s, 2H), 7.3-7.5 (m, 6H), 4.04 (d, J = 17.4 Hz, 1H), 3.65 (d, J = 17.4 Hz, 1H), 2.83 (t, J = 7.5 Hz, 2H), 2.53 (s, 3H), 1.78 (sxt, J = 7.5 Hz, 2H), 1.01 (t, J = 7.5 Hz, 3H). |
| 5-123 | (A) δ8.69 (s, 2H), 7.35-7.5 (m, 6H), 4.05 (d, J = 17.1 Hz, 1H), 3.66 (d, J = 17.1 Hz, 1H), 2.57 (s, 3H), 2.05-2.15 (m, 1H), 0.8-1.1 (m, 4H). |
| 5-124 | (A) δ8.53 (s, 2H), 7.35-7.55 (m, 6H), 4.07 (d, J = 17.4 Hz, 1H), 3.68 (d, J = 17.4 Hz, 1H), 2.54 (s, 3H), 1.36 (s, 9H). |
| 5-125 | (A) δ8.64 (s, 2H), 7.3-7.55 (m, 6H), 4.53 (s, 2H), 4.04 (d, J = 17.1 Hz, 1H), 3.65 (d, J = 17.1 Hz, 1H), 3.44 (s, 3H), 2.55 (s, 3H). |
| 5-126 | (B) δ8.38 (s, 2H), 7.35-7.6 (m, 6H), 4.04 (d, J = 17.2 Hz, 1H), 3.73 (s, 3H), 3.66 (d, J = 17.2 Hz, 1H), 2.54 (s, 3H). |
| 5-127 | (A) δ8.81 (s, 2H), 7.4-7.6 (m, 6H), 4.17 (q, J = 7.2 Hz, 2H), 4.09 (d, J = 17.1 Hz, 1H), 3.71 (d, J = 17.1 Hz, 1H), 2.54 (s, 3H), 1.10 (t, J = 7.2 Hz, 3H). |
| 5-128 | (A) δ8.81 (s, 2H), 7.4-7.6 (m, 6H), 4.0-4.2 (m, 3H), 3.70 (d, J = 16.8 Hz, 1H), 2.54 (s, 3H), 1.49 (sxt, J = 7.5 Hz, 2H), 0.77 (t, J = 7.5 Hz, 3H). |
| 5-129 | (A) δ8.81 (s, 2H), 7.4-7.6 (m, 6H), 4.08 (d, J = 16.8 Hz, 1H), 3.90 (d, J = 6.6 Hz, 2H), 3.70 (d, J = 16.8 Hz, 1H), 2.54 (s, 3H), 1.77 (sep, J = 6.6 Hz, 1H), 0.76 (d, J = 6.6 Hz, 6H). |
| 5-130 | (A) δ8.81 (s, 2H), 7.4-7.6 (m, 6H), 5.67 (s, 2H), 4.09 (d, J = 17.4 Hz, 1H), 3.70 (d, J = 17.4 Hz, 1H), 2.55 (s, 3H). |
| 5-132 | (A) δ8.46 (bs, 1H), 8.45 (d, J = 1.3 Hz, 1H), 7.45-7.55 (m, 4H), 7.43 (t, J = 1.8 Hz, 1H), 7.22 (d, J = 8.1 Hz, 1H), 4.07 (d, J = 17.2 Hz, 1H), 3.68 (d, J = 17.2 Hz, 1H), 3.45 (s, 3H), 2.36 (s, 3H). |
| 5-133 | (A) δ8.40 (d, J = 1.2 Hz, 1H), 8.34 (d, J = 1.8 Hz, 1H), 7.45-7.55 (m, 3H), 7.42 (t, J = 1.8 Hz, 1H), 7.34 (dd, J = 8.4, 1.2 Hz, 1H), 7.25 (d, J = 7.8 Hz, 1H), 4.04 (d, J = 17.2 Hz, 1H), 3.65 (d, J = 17.2 Hz, 1H), 2.60 (s, 3H), 2.51 (s, 3H). |
| 5-137 | (B) δ8.25-8.3 (m, 1H), 8.0-8.1 (m, 1H), 7.5-7.7 (m, 5H), 7.42 (t, J = 1.8 Hz, 1H), 7.2-7.25 (m, 1H), 4.03 (d, J = 17.2 Hz, 1H), 3.65 (d, J = 17.2 Hz, 1H), 3.45 (s, 3H). |
| 5-138 | (A) δ8.63 (s, 2H), 8.03 (s, 1H), 7.35-7.65 (m, 5H), 4.01 (d, J = 17.1 Hz, 1H), 3.62 (d, J = 17.1 Hz, 1H), 2.56 (s, 3H). |
| 5-142 | (A) δ8.22 (s, 2H), 7.51 (bs, 3H), 7.42 (bs, 1H), 7.2-7.35 (m, 2H), 5.02 (bs, 2H), 4.08 (d, J = 17.4 Hz, 1H), 3.68 (d, J = 17.4 Hz, 1H), 2.43 (s, 3H), 2.31 (s, 3H). |
| 5-143 | (A) δ8.26 (s, 2H), 7.51 (bs, 3H), 7.42 (bs, 1H), 7.2-7.35 (m, 2H), 4.95 (bs, 2H), 4.07 (d, J = 17.4 Hz, 1H), 3.82 (s, 3H), 3.68 (d, J = 17.4 Hz, 1H), 2.44 (s, 3H). |
| 5-144 | (A) δ8.33 (s, 2H), 7.25-7.55 (m, 5H), 7.04 (d, J = 8.1 Hz, 1H), 5.36 (s, 2H), 4.06 (d, J = 17.4 Hz, 1H), 3.66 (d, J = 17.4 Hz, 1H), 2.43 (s, 3H), 2.29 (s, 3H). |
| 5-145 | (A) δ8.57 (s, 2H), 7.3-7.5 (m, 6H), 4.73 (s, 2H), 4.03 (d, J = 17.1 Hz, 1H), 3.64 (d, J = 17.1 Hz, 1H), 2.56 (s, 3H). |
| 5-146 | (A) δ8.55 (s, 2H), 7.35-7.5 (m, 6H), 4.53 (s, 2H), 4.04 (d, J = 17.1 Hz, 1H), 3.5-3.7 (m, 3H), 2.56 (s, 3H), 1.13 (t, J = 6.9 Hz, 3H). |
| 5-147 | (A) δ8.54 (s, 2H), 7.35-7.5 (m, 6H), 4.03 (d, J = 17.1 Hz, 1H), 3.88 (s, 2H), 3.64 (d, J = 17.1 Hz, 1H), 2.56 (s, 3H), 2.28 (s, 3H). |
| 5-148 | (A) δ8.55 (s, 2H), 7.35-7.5 (m, 6H), 4.66 (dd, J = 14.1, 3.3 Hz, 1H), 4.20 (dd, J = 14.1, 3.3 Hz, 1H), 4.02 (d, J = 17.1 Hz, 1H), 3.62 (d, J = 17.1 Hz, 1H), 2.87 (s, 3H), 2.55 (s, 3H). |
| 5-149 | (A) δ8.57 (s, 2H), 7.35-7.6 (m, 6H), 4.38 (q, J = 7.2 Hz, 2H), 4.04 (d, J = 17.1 Hz, 1H), 3.65 (d, J = 17.1 Hz, 1H), 2.58 (s, 3H), 1.37 (t, J = 7.2 Hz, 3H). |
| 5-150 | (A) δ8.53 (s, 2H), 8.42 (d, J = 4.1 Hz, 1H), 8.04 (d, J = 8.0 Hz, 1H), 7.8-7.9 (m, 2H), 7.35-7.55 (m, 6H), 4.05 (d, J = 17.0 Hz, 1H), 3.66 (d, J = 17.0 Hz, 1H), 2.62 (s, 3H). |
| 5-152 | (A) δ8.56 (s, 2H), 8.25 (d, J = 8.8 Hz, 2H), 7.92 (d, J = 8.8 Hz, 2H), 7.4-7.65 (m, 6H), 4.05 (d, J = 17.0 Hz, 1H), 3.66 (d, J = 17.0 Hz, 1H), 2.57 (s, 3H). |
| 5-153 | (A) δ8.72 (s, 2H), 7.45-7.6 (m, 5H), 7.43 (t, J = 1.8 Hz, 1H), 4.85-5.0 (m, 1H), 4.09 (d, J = 17.1 Hz, 1H), 3.70 (d, J = 17.1 Hz, 1H), 2.54 (s, 3H), 1.08 (d, J = 6.3 Hz, 6H). |
| 5-154 | (A) δ8.72 (s, 2H), 7.5-7.6 (m, 5H), 7.43 (t, J = 1.8 Hz, 1H), 4.05-4.15 (m, 3H), 3.69 (d, J = 16.5 Hz, 1H), 2.54 (s, 3H), 1.35-1.5 (m, 1H), 1.1-1.2 (m, 3H), 0.80 (t, J = 7.2 Hz, 3H). |
| 5-155 | (A) δ8.73 (s, 2H), 7.5-7.6 (m, 5H), 7.44 (t, J = 1.8 Hz, 1H), 4.09 (d, J = 17.1 Hz, 1H), 3.71 (d, J = 17.1 Hz, 1H), 2.55 (s, 3H), 1.28 (s, 9H). |
| 5-158 | (A) δ8.76 (s, 2H), 7.0-7.65 (m, 11H), 4.07 (d, J = 17.1 Hz, 1H), 3.68 (d, J = 17.1 Hz, 1H), 2.59 (s, 3H). |
| 5-159 | (A) δ8.42 (s, 2H), 7.2-7.5 (m, 6H), 4.07 (d, J = 17.4 Hz, 1H), 3.68 (d, J = 17.4 Hz, 1H), 3.10 (s, 6H), 2.53 (s, 3H). |

TABLE 16-continued

| No. | $^1$H NMR |
|---|---|
| 5-160 | (A) δ8.43 (s, 2H), 7.0-7.55 (m, 6H), 5.65 (s, 2H), 4.06 (d, J = 17.4 Hz, 1H), 3.75 (q, J = 6.6 Hz, 2H), 3.67 (d, J = 17.4 Hz, 1H), 2.45 (s, 3H), 1.20 (t, J = 6.6 Hz, 3H). |
| 5-161 | (A) δ8.38 (s, 2H), 7.0-7.55 (m, 6H), 5.9-6.1 (m, 1H), 5.1-5.35 (m, 2H), 4.82 (d, J = 5.4 Hz, 2H), 4.07 (d, J = 17.1 Hz, 1H), 3.68 (d, J = 17.1 Hz, 1H), 2.41 (s, 3H). |
| 5-162 | (A) δ8.64 (s, 2H), 7.3-7.8 (m, 11H), 4.05 (d, J = 17.4 Hz, 1H), 3.66 (d, J = 17.4 Hz, 1H), 2.56 (s, 3H). |
| 5-163 | (A) δ8.80 (s, 2H), 7.4-7.6 (m, 6H), 4.2-4.3 (m, 2H), 4.09 (d, J = 17.4 Hz, 1H), 3.70 (d, J = 17.4 Hz, 1H), 3.35-3.45 (m, 2H), 3.23 (s, 3H), 2.54 (s, 3H). |
| 5-166 | (A) δ9.08 (s, 1H), 8.53 (s, 2H), 7.2-7.55 (m, 6H), 4.03 (d, J = 17.2 Hz, 1H), 3.40 (d, J = 17.2 Hz, 1H), 2.83 (q, J = 7.2 Hz, 2H), 2.46 (s, 3H), 1.21 (t, J = 7.2 Hz, 3H). |
| 5-167 | (A) δ9.08 (s, 1H), 8.53 (s, 2H), 7.4-7.5 (m, 5H), 7.23 (d, J = 8.1 Hz, 1H), 4.03 (d, J = 17.4 Hz, 1H), 3.64 (d, J = 17.4 Hz, 1H), 2.77 (t, J = 7.2 Hz, 2H), 2.46 (s, 3H), 1.73 (sxt, J = 7.2 Hz, 2H), 0.98 (t, J = 7.2 Hz, 3H). |
| 5-168 | (A) δ9.09 (s, 1H), 8.54 (s, 2H), 7.4-7.6 (m, 5H), 7.26 (d, J = 7.8 Hz, 1H), 4.04 (d, J = 17.4 Hz, 1H), 3.65 (d, J = 17.4 Hz, 1H), 3.22 (sep, J = 6.9 Hz, 1H), 2.48 (s, 3H), 1.25 (d, J = 6.9 Hz, 6H). |
| 5-175 | (A) δ8.79 (s, 2H), 7.4-8.4 (m, 6H), 4.12 (d, J = 17.1 Hz, 1H), 3.75 (d, J = 17.1 Hz, 1H), 2.24 (s, 3H). |
| 5-177 | (A) δ7.3-7.55 (m, 7H), 6.35-6.45 (m, 1H), 6.2-6.3 (m, 1H), 4.08 (d, J = 17.4 Hz, 1H), 3.69 (d, J = 17.4 Hz, 1H), 2.48 (s, 3H), 1.28 (s, 9H). |
| 5-178 | (A) δ8.34 (s, 2H), 7.25-7.55 (m, 5H), 7.10 (d, J = 7.8 Hz, 1H), 6.17 (s, 2H), 4.05 (d, J = 17.4 Hz, 1H), 3.79 (s, 3H), 3.65 (d, J = 17.4 Hz, 1H), 2.44 (s, 3H). |
| 5-179 | (A) δ8.53 (s, 2H), 7.3-7.55 (m, 5H), 7.03 (d, J = 7.8 Hz, 1H), 4.30 (q, J = 7.2 Hz, 2H), 4.08 (d, J = 17.4 Hz, 1H), 3.69 (d, J = 17.4 Hz, 1H), 2.39 (s, 3H), 1.38 (t, J = 7.2 Hz, 3H). |
| 5-180 | (A) δ8.61 (s, 2H), 7.4-7.55 (m, 4H), 7.31 (d, J = 8.0 Hz, 1H), 7.09 (d, J = 8.0 Hz, 1H), 5.63 (s, 2H), 4.06 (d, J = 17.0 Hz, 1H), 3.66 (d, J = 17.0 Hz, 1H), 3.52 (s, 3H), 2.48 (s, 3H). |
| 5-181 | (A) δ8.62 (s, 2H), 7.3-7.55 (m, 5H), 7.12 (d, J = 8.4 Hz, 1H), 6.17 (s, 2H), 4.08 (d, J = 17.4 Hz, 1H), 3.69 (d, J = 17.4 Hz, 1H), 2.45 (s, 3H), 2.10 (s, 3H). |
| 5-182 | (A) δ8.83 (s, 2H), 7.3-7.55 (m, 6H), 4.03 (d, J = 17.2 Hz, 1H), 3.64 (d, J = 17.2 Hz, 1H), 2.62 (s, 3H), 2.58 (s, 3H). |
| 5-184 | (A) δ8.94 (s, 2H), 7.4-7.6 (m, 6H), 4.08 (d, J = 17.2 Hz, 1H), 3.79 (s, 3H), 3.66 (d, J = 17.2 Hz, 1H), 2.57 (s, 3H). |
| 5-185 | (A) δ8.55 (bs, 2H), 7.4-7.55 (m, 6H), 4.95 (bs, 2H), 4.05 (d, J = 17.4 Hz, 1H), 3.70 (d, J = 17.4 Hz, 1H), 3.40 (bs, 3H), 2.40 (s, 3H). |
| 5-186 | (A) δ8.35 (s, 2H), 7.2-7.5 (m, 6H), 4.40 (d, J = 17.4 Hz, 1H), 3.65 (d, J = 17.4 Hz, 1H), 2.60 (s, 3H), 2.45 (s, 3H). |
| 5-187 | (A) δ8.60 (s, 2H), 7.4-7.6 (m, 6H), 4.10 (d, J = 17.4 Hz, 1H), 3.70 (d, J = 17.4 Hz, 1H), 3.65 (s, 3H), 2.45 (s, 3H). |
| 5-188 | (A) δ8.21 and 8.62 (s, 1H), 7.0-7.7 (m, 6H), 3.9-4.15 (m, 1H), 3.64 and 3.73 (d, J = 17.4 Hz, 1H), 3.15 and 3.43 (s, 3H), 2.44 and 2.48 (s, 3H). |
| 5-190 | (A) δ8.36 (s, 1H), 7.3-7.6 (m, 6H), 4.05 (d, J = 17.4 Hz, 1H), 3.67 (d, J = 17.4 Hz, 1H), 2.52 (s, 3H), 2.49 (s, 3H). |
| 5-191 | (A) δ8.55 (s, 1H), 7.35-7.65 (m, 6H), 4.12 (d, J = 17.4 Hz, 1H), 3.73 (d, J = 17.4 Hz, 1H), 3.69 (s, 3H), 2.48 (s, 3H). |
| 5-192 | (A) δ8.3-8.6 (m, 3H), 7.2-7.45 (m, 6H), 4.00 (d, J = 17.4 Hz, 1H), 3.60 (d, J = 17.4 Hz, 1H), 2.60 (s, 3H), 2.50 (s, 3H). |
| 5-193 | (A) δ8.40 (s, 1H), 8.35 (s, 1H), 7.25-7.5 (m, 6H), 5.30 (s, 2H), 4.05 (d, J = 17.4 Hz, 1H), 3.65 (d, J = 17.4 Hz, 1H), 3.40 (s, 3H), 2.40 (s, 3H). |
| 5-194 | (A) δ8.35 (s, 1H), 8.30 (s, 1H), 7.2-7.6 (m, 6H), 4.25 (d, J = 17.4 Hz, 1H), 3.65 (d, J = 17.4 Hz, 1H), 2.60 (s, 3H), 2.50 (s, 3H). |
| 5-195 | (A) δ9.13 (s, 1H), 8.68 (s, 1H), 7.3-7.65 (m, 6H), 4.11 (d, J = 17.4 Hz, 1H), 3.72 (d, J = 17.4 Hz, 1H), 3.44 (s, 3H), 2.39 (s, 3H). |
| 5-197 | (A) δ8.78 (s, 1H), 8.52 (s, 1H), 7.25-7.55 (m, 6H), 4.03 (d, J = 17.4 Hz, 1H), 3.64 (d, J = 17.4 Hz, 1H), 2.60 (s, 3H), 2.56 (s, 3H). |
| 5-198 | (A) δ9.01 (s, 1H), 8.65 (s, 2H), 7.1-7.55 (m, 6H), 5.07 (s, 2H), 4.05 (d, J = 17.4 Hz, 1H), 3.66 (d, J = 17.4 Hz, 1H), 3.43 (s, 3H), 2.40 (s, 3H). |
| 5-199 | (A) δ7.25-7.6 (m, 11H), 4.09 (d, J = 17.4 Hz, 1H), 3.71 (d, J = 17.4 Hz, 1H), 2.51 (s, 3H), 1.20 (s, 9H). |
| 5-204 | (A) δ8.64 (s, 2H), 7.35-7.55 (m, 5H), 7.10 (d, J = 8.0 Hz, 1H), 5.15 (s, 2H), 4.08 (d, J = 17.5 Hz, 1H), 3.68 (d, J = 17.5 Hz, 1H), 2.40 (s, 3H). |

TABLE 16-continued

| No. | ¹H NMR |
|---|---|
| 5-205 | (A) δ8.82 (s, 2H), 7.35-7.55 (m, 6H), 4.04 (d, J = 17.5 Hz, 1H), 3.65 (d, J = 17.5 Hz, 1H), 2.93 (q, J = 7.6 Hz, 2H), 2.58 (s, 3H), 1.27 (t, J = 7.6 Hz, 3H). |
| 6-003 | (B) δ8.58 (d, J = 14.2 Hz, 1H), 7.85 (d, J = 14.2 Hz, 1H), 7.4-7.6 (m, 6H), 4.09 (d, J = 17.4 Hz, 1H), 3.78 (s, 3H), 3.70 (d, J = 17.4 Hz, 1H), 2.51 (s, 3H). |
| 6-007 | (B) δ8.49 (d, J = 9.0 Hz, 1H), 7.77 (d, J = 9.0 Hz, 1H), 7.5-7.65 (m, 5H), 7.44 (t, J = 1.8 Hz, 1H), 4.36 (qui, J = 6.4 Hz, 1H), 4.09 (d, J = 17.4 Hz, 1H), 3.71 (d, J = 17.4 Hz, 1H), 2.54 (s, 3H), 1.26 (d, J = 6.4 Hz, 6H). |
| 6-009 | (A) δ8.45 (d, J = 9.0 Hz, 1H), 7.87 (bs, 1H), 7.5-7.65 (m, 5H), 7.44 (t, J = 1.8 Hz, 1H), 4.31 and 4.45 (q, J = 9.0 Hz, 2H), 4.09 (d, J = 17.4 Hz, 1H), 3.71 (d, J = 17.4 Hz, 1H), 2.54 (s, 3H). |
| 6-016 | (A) δ8.54 (d, J = 9.0 Hz, 1H), 8.18 (s, 1H), 7.7-7.8 (m, 2H), 7.4-7.6 (m, 4H), 4.06 (d, J = 17.4 Hz, 1H), 3.91 (s, 3H), 3.68 (d, J = 17.4 Hz, 1H). |
| 6-026 | (A) δ7.99 (d, J = 9.0 Hz, 1H), 7.77 (d, J = 9.0 Hz, 1H), 7.66 (s, 1H), 7.3-7.6 (m, 10H), 4.11 (d, J = 17.4 Hz, 1H), 3.73 (d, J = 17.4 Hz, 1H), 3.59 (s, 3H). |
| 6-028 | (A) δ8.30 and 9.17 (d, J = 10.2 Hz, 1H), 7.82 and 8.59 (d, J = 10.2 Hz, 1H), 7.85-7.95 (m, 1H), 7.75-7.80 (m, 1H), 7.66 (d, J = 7.8 Hz, 1H), 7.51 (s, 2H), 7.43 (s, 1H), 4.09 (d, J = 17.4 Hz, 1H), 3.80 and 3.92 (s, 3H), 3.73 (d, J = 17.4 Hz, 1H). |
| 6-029 | (A) δ8.50 and 8.59 (d, J = 10.2 Hz, 1H), 7.77 and 7.87 (d, J = 10.2 Hz, 1H), 7.66 (s, 1H), 7.5-7.65 (m, 5H), 4.07 (d, J = 17.4 Hz, 1H), 3.39 and 3.79 (s, 3H), 3.67 (d, J = 17.4 Hz, 1H), 2.52 (s, 3H). |
| 6-030 | (A) δ8.48 and 8.58 (d, J = 10.2 Hz, 1H), 8.08 (s, 2H), 7.97 (s, 1H), 7.76 and 7.87 (d, J = 10.2 Hz, 1H), 7.45-7.65 (m, 3H), 4.20 (d, J = 17.4 Hz, 1H), 3.79 and 3.89 (s, 3H), 3.76 (d, J = 17.4 Hz, 1H), 2.53 (s, 3H). |
| 6-035 | (A) δ8.49 and 8.59 (d, J = 10.2 Hz, 1H), 7.65-7.8 (m, 2H), 7.70 (s, 2H), 7.5-7.65 (m, 3H), 4.07 (d, J = 17.4 Hz, 1H), 3.78 and 3.90 (s, 3H), 3.68 (d, J = 17.4 Hz, 1H), 2.53 (s, 3H). |
| 6-036 | (A) δ8.52 and 8.58 (d, J = 9.9 Hz, 1H), 7.65-7.95 (m, 4H), 7.45-7.65 (m, 3H), 3.95-4.25 (m, 3H), 3.70 (d, J = 17.4 Hz, 1H), 2.54 (s, 3H), 1.28 (t, J = 6.9 Hz, 3H). |
| 6-038 | (A) δ8.48 and 9.23 (d, J = 9.9 Hz, 1H), 7.7-7.85 (m, 1H), 7.5-7.65 (m, 5H), 4.08 (d, J = 17.4 Hz, 1H), 3.79 and 3.89 (s, 3H), 3.68 (d, J = 17.4 Hz, 1H), 2.53 (s, 3H). |
| 6-039 | (A) δ8.48 and 8.58 (d, J = 9.9 Hz, 1H), 7.7-7.85 (m, 1H), 7.64 (s, 2H), 7.5-7.6 (m, 3H), 4.10 (d, J = 17.4 Hz, 1H), 3.79 and 3.89 (s, 3H), 3.69 (d, J = 17.4 Hz, 1H), 2.53 (s, 3H). |
| 6-040 | (A) δ8.51 and 8.59 (d, J = 9.9 Hz, 1H), 7.7-7.85 (m, 1H), 7.64 (s, 2H), 7.5-7.6 (m, 3H), 4.02 and 4.14 (d, J = 7.2 Hz, 2H), 4.08 (d, J = 17.4 Hz, 1H), 3.69 (d, J = 17.4 Hz, 1H), 2.53 (s, 3H), 1.26 and 1.28 (t, J = 7.2 Hz, 3H). |
| 6-041 | (A) δ8.48 and 9.23 (d, J = 9.9 Hz, 1H), 7.7-7.95 (m, 3H), 7.5-7.65 (m, 3H), 4.13 (d, J = 17.4 Hz, 1H), 3.79 and 3.89 (s, 3H), 3.70 (d, J = 17.4 Hz, 1H), 2.53 (s, 3H). |
| 6-044 | (A) δ8.68 (bs, 1H), 7.88 (bs, 1H), 7.35-7.65 (m, 6H), 4.68 (s, 2H), 4.08 (d, J = 17.4 Hz, 1H), 3.70 (d, J = 17.4 Hz, 1H), 2.53 (s, 3H). |
| 6-045 | (A) δ8.50 (d, J = 9.6 Hz, 1H), 8.20 (d, J = 8.4 Hz, 2H), 7.80 (bs, 1H), 7.55 (d, J = 8.4 Hz, 2H), 7.4-7.65 (m, 6H), 5.10 and 5.20 (s, 2H), 4.10 (d, J = 17.4 Hz, 1H), 3.70 (d, J = 17.4 Hz, 1H), 2.55 (s, 3H). |
| 6-047 | (A) δ7.9-8.1 (m, 1H), 7.75-7.8 (m, 1H), 7.67 (s, 1H), 7.4-7.6 (m, 7H), 7.25-7.35 (m, 2H), 4.11 (d, J = 17.4 Hz, 1H), 3.73 (d, J = 17.4 Hz, 1H), 3.67 (s, 3H). |
| 6-048 | (A) δ8.45 (d, J = 9.3 Hz, 1H), 7.87 (d, J = 9.3 Hz, 1H), 7.45-7.75 (m, 7H), 7.44 (bs, 1H), 6.52 (bs, 1H), 4.11 (d, J = 17.4 Hz, 1H), 3.76 (s, 3H), 3.71 (d, J = 17.4 Hz, 1H). |
| 6-049 | (A) δ8.21 (d, J = 9.6 Hz, 1H), 7.95 (d, J = 9.6 Hz, 1H), 7.65-7.8 (m, 2H), 7.60 (d, J = 9.6 Hz, 1H), 7.4-7.55 (m, 5H), 7.10 (d, J = 6.0 Hz, 1H), 4.11 (d, J = 17.4 Hz, 1H), 3.73 (d, J = 17.4 Hz, 1H), 3.69 (s, 3H). |
| 6-052 | (A) δ8.86 (d, J = 9.6 Hz, 1H), 7.75-8.0 (m, 5H), 7.65 (s, 2H), 4.11 (d, J = 17.4 Hz, 1H), 3.94 (s, 3H), 3.70 (d, J = 17.4 Hz, 1H). |
| 6-055 | (A) δ8.87 and 8.60 (d, J = 9.3 Hz, 1H), 7.90 (d, J = 9.0 Hz, 2H), 7.75-7.85 (m, 3H), 7.65 (s, 2H), 4.40 (qui, J = 6.0 Hz, 1H), 4.12 (d, J = 17.4 Hz, 1H), 3.73 (d, J = 17.4 Hz, 1H), 1.2-1.35 (m, 6H). |
| 7-001 | (A) δ7.25-7.55 (m, 6H), 6.89 and 6.91 (s, 1H), 5.22 and 5.25 (s, 2H), 4.09 (d, J = 17.4 Hz, 1H), 3.79 and 3.80 (s, 3H), 3.70 (d, J = 17.4 Hz, 1H), 3.38 and 3.39 (s, 3H), 2.40 and 2.43 (s, 3H). |
| 7-006 | (A) δ7.3-7.6 (m, 6H), 6.90 (s, 1H), 5.25 (s, 2H), 4.09 (d, J = 17.1 Hz, 1H), 3.79 (s, 3H), 3.71 (d, J = 17.1 Hz, 1H), 3.57 (q, J = 7.2 Hz, 2H), 2.40 (s, 3H), 1.20 (t, J = 7.2 Hz, 3H). |
| 7-007 | (A) δ7.25-7.6 (m, 6H), 6.60 (s, 1H), 4.84 (s, 2H), 4.09 (d, J = 17.4 Hz, 1H), 3.95 (s, 3H), 3.71 (d, J = 17.4 Hz, 1H), 2.36 (s, 3H). |
| 7-008 | (A) δ7.25-7.6 (m, 6H), 6.68 (s, 1H), 4.73 (s, 2H), 4.09 (d, J = 17.4 Hz, 1H), 3.87 (s, 3H), 3.70 (d, J = 17.4 Hz, 1H), 2.37 (s, 3H), 2.27 (s, 1H). |

TABLE 16-continued

| No. | ¹H NMR |
|---|---|
| 7-009 | (A) δ7.3-7.6 (m, 6H), 6.88 (s, 1H), 5.24 (s, 2H), 4.08 (d, J = 17.4 Hz, 1H), 4.05 (q, J = 6.9 Hz, 2H), 3.70 (d, J = 17.4 Hz, 1H), 3.88 (s, 3H), 2.40 (s, 3H), 1.22 (t, J = 6.9 Hz, 3H). |
| 7-010 | (A) δ9.15 and 9.80 (d, J = 8.7 Hz, 1H), 8.31 and 9.08 (d, J = 8.7 Hz, 1H), 7.8-7.95 (m, 2H), 7.65-7.8 (m, 2H), 7.51 (s, 2H), 7.44 (bs, 1H), 4.09 (d, J = 17.4 Hz, 1H), 3.86 and 3.97 (s, 3H), 3.71 (d, J = 17.4 Hz, 1H). |
| 7-011 | (A) δ9.15 and 9.81 (d, J = 8.7 Hz, 1H), 8.30 and 9.08 (d, J = 9.5 Hz, 1H), 7.85-7.95 (m, 2H), 7.65-7.8 (m, 2H), 7.51 (s, 2H), 7.43 (bs, 1H), 4.21 (q, J = 7.2 Hz, 2H), 4.09 (d, J = 17.4 Hz, 1H), 3.71 (d, J = 17.4 Hz, 1H), 1.33 (t, J = 7.2 Hz, 3H). |
| 7-012 | (A) δ9.42 (d, J = 9.6 Hz, 1H), 8.26 (d, J = 9.6 Hz, 1H), 7.35-7.6 (m, 6H), 4.07 (d, J = 17.4 Hz, 1H), 3.92 (s, 3H), 3.69 (d, J = 17.4 Hz, 1H), 2.44 (s, 3H). |
| 7-013 | (A) δ7.3-7.6 (m, 6H), 6.90 (s, 1H), 5.20 (s, 2H), 4.10 (d, J = 17.4 Hz, 1H), 3.80 (s, 3H), 3.70 (d, J = 17.4 Hz, 1H), 3.40 (s, 3H), 2.40 (s, 3H). |
| 7-014 | (A) δ7.25-7.65 (m, 7H), 5.69 (bs, 2H), 4.08 (d, J = 17.4 Hz, 1H), 3.78 (s, 3H), 3.70 (d, J = 17.4 Hz, 1H), 2.35 (s, 3H), 2.08 (s, 3H). |
| 7-015 | (A) δ7.25-7.65 (m, 6H), 6.90 (s, 1H), 5.77 (s, 2H), 4.08 (d, J = 17.4 Hz, 1H), 3.81 (s, 3H), 3.70 (d, J = 17.4 Hz, 1H), 2.39 (s, 3H), 2.09 (s, 3H). |
| 7-016 | (A) δ7.25-7.65 (m, 6H), 6.68 (s, 1H), 5.13 (s, 2H), 4.08 (d, J = 17.4 Hz, 1H), 3.82 (s, 3H), 3.69 (d, J = 17.4 Hz, 1H), 2.38 (s, 3H), 2.25 (s, 3H). |
| 7-017 | (A) δ7.79 (bs, 1H), 7.25-7.65 (m, 6H), 5.03 (bs, 2H), 4.08 (d, J = 17.4 Hz, 1H), 3.77 (s, 3H), 3.70 (d, J = 17.4 Hz, 1H), 2.34 (s, 6H). |
| 7-018 | (A) δ7.3-7.6 (m, 6H), 6.68 (bs, 1H), 4.78 (s, 2H), 4.08 (d, J = 17.4 Hz, 1H), 3.80 (s, 3H), 3.79 (s, 3H), 3.69 (d, J = 17.4 Hz, 1H), 2.41 (s, 3H). |
| 7-019 | (A) δ8.56 (bs, 1H), 7.95 (s, 1H), 7.05-7.75 (m, 9H), 5.25 (s, 2H), 4.10 (d, J = 17.4 Hz, 1H), 3.70 (d, J = 17.4 Hz, 1H), 3.65 (s, 3H), 2.40 (s, 3H). |
| 7-020 | (A) δ7.55-7.6 (m, 2H), 7.51 (bs, 2H), 7.44 (t, J = 1.8 Hz, 1H), 7.33 (d, J = 8.0 Hz, 1H), 6.59 (s, 1H), 4.84 (s, 2H), 4.19 (q, J = 7.2 Hz, 2H), 4.08 (d, J = 17.4 Hz, 1H), 3.69 (d, J = 17.4 Hz, 1H), 2.37 (s, 3H), 1.34 (t, J = 7.2 Hz, 3H). |
| 7-021 | (A) δ7.2-7.55 (m, 6H), 6.60 (s, 1H), 4.11 (d, J = 17.4 Hz, 1H), 3.77 (s, 3H), 3.69 (d, J = 17.4 Hz, 1H), 3.52 (s, 2H), 2.36 (s, 3H), 0.15 (s, 9H). |
| 7-022 | (A) δ9.79 (d, J = 9.1 Hz, 1H), 8.29 (d, J = 9.1 Hz, 1H), 7.88 (d, J = 8.7 Hz, 2H), 7.72 (d, J = 8.7 Hz, 2H), 7.64 (s, 2H), 4.10 (d, J = 17.5 Hz, 1H), 3.97 (s, 3H), 3.71 (d, J = 17.5 Hz, 1H). |
| 7-023 | (A) δ9.81 (d, J = 9.3 Hz, 1H), 8.29 (d, J = 9.3 Hz, 1H), 7.89 (d, J = 8.4 Hz, 2H), 7.72 (d, J = 8.4 Hz, 2H), 7.64 (s, 2H), 4.21 (q, J = 7.2 Hz, 2H), 4.10 (d, J = 17.4 Hz, 1H), 3.71 (d, J = 17.4 Hz, 1H), 1.33 (t, J = 7.2 Hz, 3H). |
| 8-002 | (A) δ8.04 (d, J = 8.1 Hz, 1H), 7.5-7.6 (m, 4H), 7.43 (t, J = 1.8 Hz, 1H), 5.07 (s, 2H), 4.10 (d, J = 17.2 Hz, 1H), 4.09 (s, 3H), 3.72 (d, J = 17.2 Hz, 1H), 3.38 (s, 3H), 2.68 (s, 3H). |
| 8-004 | (A) δ8.66 (s, 1H), 8.32 (d, J = 8.7 Hz, 2H), 7.71 (d, J = 8.7 Hz, 2H), 7.52 (s, 2H), 7.43 (s, 1H), 4.12 (d, J = 17.4 Hz, 1H), 3.73 (d, J = 17.4 Hz, 1H), 3.25 (s, 3H), 3.22 (s, 3H). |
| 8-007 | (A) δ7.90 (d, J = 8.6 Hz, 1H), 7.4-7.55 (m, 5H), 4.09 (d, J = 17.4 Hz, 1H), 3.70 (d, J = 17.4 Hz, 1H), 3.16 (s, 3H), 3.13 (s, 3H), 2.62 (s, 3H), 2.35 (s, 3H). |
| 8-008 | (A) δ8.61 (s, 1H), 7.96 (d, J = 7.5 Hz, 1H), 7.66 (s, 1H), 7.62 (d, J = 8.1 Hz, 1H), 7.53 (s, 2H), 7.43 (s, 1H), 4.13 (d, J = 17.4 Hz, 1H), 3.71 (d, J = 17.4 Hz, 1H), 3.22 (s, 3H), 3.18 (s, 3H), 2.35 (s, 3H). |
| 8-009 | (A) δ8.59 (s, 1H), 8.11 (d, J = 8.1 Hz, 1H), 7.7-7.75 (m, 3H), 7.53 (d, J = 8.1 Hz, 1H), 7.51 (s, 1H), 4.09 (d, J = 17.4 Hz, 1H), 3.74 (d, J = 17.4 Hz, 1H), 3.20 (s, 3H), 3.19 (s, 3H), 2.64 (s, 3H). 3.18 (s, 3H), 2.35 (s, 3H). |
| 8-010 | (A) δ8.60 (s, 1H), 8.05-8.15 (m, 3H), 7.96 (s, 1H), 7.53 (d, J = 8.1 Hz, 1H), 7.51 (s, 3H), 4.21 (d, J = 17.4 Hz, 1H), 3.76 (d, J = 17.4 Hz, 1H), 3.20 (s, 3H), 3.18 (s, 3H), 2.65 (s, 3H). |
| 8-011 | (A) δ8.59 (s, 1H), 8.10 (d, J = 8.1 Hz, 1H), 7.65 (s, 2H), 7.50 (d, J = 8.1 Hz, 1H), 7.48 (s, 1H), 4.09 (d, J = 17.4 Hz, 1H), 3.74 (d, J = 17.4 Hz, 1H), 3.20 (s, 3H), 3.18 (s, 3H), 2.64 (s, 3H). |
| 8-012 | (A) δ8.70 (s, 1H), 7.67 (d, J = 7.8 Hz, 1H), 7.51 (bs, 2H), 7.4-7.55 (m, 3H), 4.06 (d, J = 17.4 Hz, 1H), 3.69 (d, J = 17.4 Hz, 1H), 3.31 (s, 3H), 3.20 (s, 3H), 2.48 (s, 3H). |
| 8-013 | (A) δ7.91 (d, J = 8.1 Hz, 1H), 7.4-7.55 (m, 5H), 4.09 (d, J = 17.4 Hz, 1H), 3.92 (s, 3H), 3.70 (d, J = 17.4 Hz, 1H), 3.07 (s, 6H), 2.64 (s, 3H). |
| 8-014 | (A) δ7.97 (d, J = 7.9 Hz, 1H), 7.4-7.6 (m, 5H), 4.10 (d, J = 17.1 Hz, 1H), 3.71 (d, J = 17.1 Hz, 1H), 3.24 (s, 6H), 2.66 (s, 3H), 2.44 (s, 3H). |

TABLE 16-continued

| No. | $^1$H NMR |
|---|---|
| 8-016 | (A) δ8.07 (d, J = 8.1 Hz, 1H), 7.4-7.6 (m, 5H), 4.47 (t, J = 6.6 Hz, 2H), 4.10 (d, J = 17.4 Hz, 1H), 3.69 (d, J = 17.4 Hz, 1H), 2.67 (s, 3H), 2.41 (s, 3H), 1.7-1.9 (m, 2H), 1.4-1.55 (m, 2H), 0.99 (t, J = 7.2 Hz, 3H). |
| 8-017 | (A) δ8.13 (d, J = 8.1 Hz, 1H), 7.4-7.6 (m, 5H), 5.05 (bs, 2H), 4.10 (d, J = 17.4 Hz, 1H), 3.70 (d, J = 17.4 Hz, 1H), 2.68 (s, 3H), 2.60 (bs, 1H), 2.46 (s, 3H). |
| 9-002 | (A) δ9.84 (bs, 1H), 8.80 (d, J = 1.8 Hz, 1H), 8.11 (d, J = 1.8 Hz, 1H), 7.50 (d, J = 1.8 Hz, 2H), 7.46 (t, J = 1.8 Hz, 1H), 4.11 (d, J = 17.4 Hz, 1H), 3.87 (s, 3H), 3.74 (d, J = 17.4 Hz, 1H). |
| 10-001 | (A) δ8.72 (d, J = 1.8 Hz, 1H), 8.69 (s, 1H), 8.09 (d, J = 1.8 Hz, 1H), 7.50 (s, 2H), 7.4-7.45 (m, 1H), 4.08 (d, J = 17.4 Hz, 1H), 3.73 (d, J = 17.4 Hz, 1H), 3.24 (s, 3H), 3.19 (s, 3H). |

Test Examples

Next, usefulness of the compound of the present invention as a pesticide is specifically explained in the following Test Examples to which the present invention is not limited.

Test Example 1

Insecticidal Test Against Cabbage Moth

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leaves of cabbage for about 10 seconds, and after air-drying, they were placed in a laboratory dish, then 5-cabbage moth (*Plutella xylostella*) in the stage of second instar larva per the dish were released therein, and the dish was covered with a lid and contained at a thermostat chamber at 25° C. A number of dead insect(s) after 6 days was counted and a rate of dead insects was calculated by the following calculation equation. Incidentally, the test was carried out with two districts.

Rate of dead insects(%)=(Number of dead insects/Number of released insects)×100

As a result, the following compounds showed an insecticidal rate of 80% or more among the compounds tested.

The compounds of the present invention: No. 1-001*, 1-002*, 1-003*, 1-004*, 1-005*, 1-006*, 1-007*, 1-008*, 1-009, 1-010*, 1-011, 1-012*, 1-013*, 1-014*, 1-015, 1-016*, 1-017*, 1-018*, 1-019 to 1-025, 1-026*, 1-027 to 1-030, 1-031*, 1-032*, 1-033 to 1-035, 1-036*, 1-037*, 1-038, 1-039*, 1-040 to 1-043, 1-044*, 1-045*, 1-046, 1-047*, 1-048*, 1-049*, 1-050*, 1-051, 1-052*, 1-053*, 1-054*, 1-055*, 1-056*, 1-057*, 1-058, 2-001, 2-002, 2-003*, 2-004*, 2-005*, 2-006*, 2-007*, 2-008*, 2-009*, 2-010*, 2-011*, 2-012*, 2-013, 2-014, 2-015*, 2-016*, 2-017*, 2-018, 2-019, 2-020, 2-021, 2-022, 2-023, 2-024, 2-025, 2-026, 2-027**, 2-028, 2-029*, 2-030, 3-001, 3-002, 3-003*, 3-004*, 3-005*, 3-006*, 3-007*, 3-007(+)**, 3-007(-), 3-008*, 3-009*, 3-010*, 3-011*, 3-012*, 3-013*, 3-014*, 3-015*, 3-016*, 3-017*, 3-018*, 3-019, 3-020*, 3-021*, 3-022*, 3-023, 3-024, 3-025, 3-026, 3-027, 3-028*, 3-029, 3-030, 3-031, 3-032, 3-033*, 3-034**, 3-035*, 3-036*, 3-037**, 3-038*, 3-039**, 3-040*, 3-041*, 3-042*, 3-043*, 3-044**, 3-045*, 3-046*, 3-047*, 3-048*, 3-049, 3-050, 3-051**, 3-052*, 3-053*, 3-054**, 3-055*, 3-056*, 3-057*, 3-058*, 3-059*, 3-060*, 3-061*, 3-062*, 3-063*, 3-064*, 3-065, 3-066*, 3-067*, 3-068*, 3-069*, 3-070*, 3-071, 3-072, 3-073, 3-074, 3-075, 3-076, 3-077, 3-078, 3-079, 3-080, 3-081**, 3-082*, 3-083, 3-084, 3-085, 4-001*, 4-002*, 4-003*, 4-004*, 4-005*, 4-006*, 4-007*, 4-008**, 4-009*, 4-010, 4-011, 4-012, 4-013, 4-014, 4-015, 5-001, 5-002*, 5-003*, 5-004*, 5-005*, 5-006*, 5-007*, 5-008*, 5-009*, 5-010*, 5-011*, 5-012*, 5-013*, 5-014*, 5-015, 5-016, 5-017**, 5-018*, 5-019*, 5-020*, 5-021*, 5-022*, 5-023*, 5-024*, 5-025*, 5-026*, 5-027*, 5-028*, 5-029*, 5-030, 5-031, 5-032, 5-033, 5-034, 5-035, 5-036**, 5-038*, 5-039*, 5-040*, 5-041*, 5-042, 5-043*, 5-044*, 5-045*, 5-046*, 5-047, 5-048, 5-049*, 5-050*, 5-051*, 5-052*, 5-053*, 5-054, 5-055, 5-056, 5-057, 5-058, 5-059, 5-060*, 5-061, 5-062, 5-063, 5-064, 5-065, 5-066, 5-067, 5-068, 5-069, 5-070, 5-071, 5-072, 5-073, 5-074, 5-075, 5-076, 5-077**, 5-078*, 5-079*, 5-080*, 5-081*, 5-082*, 5-083*, 5-084*, 5-085*, 5-086*, 5-087**, 5-088*, 5-089, 5-090**, 5-091*, 5-092*, 5-093**, 5-094*, 5-095, 5-096, 5-097, 5-098, 5-099**, 5-100*, 5-101*, 5-102, 5-103, 5-104, 5-105, 5-106, 5-107, 5-108*, 5-109, 5-110, 5-111, 5-112, 5-113, 5-114, 5-115, 5-116, 5-117, 5-118, 5-119, 5-120, 5-121, 5-122, 5-123, 5-124, 5-125, 5-126, 5-127, 5-128, 5-129, 5-130, 5-131, 5-132, 5-133, 5-134, 5-135*, 5-136*, 5-137, 5-138, 5-139, 5-140, 5-141**, 5-142*, 5-143*, 5-144*, 5-145, 5-146, 5-147, 5-148, 5-149, 5-150, 5-151, 5-152, 5-153, 5-154, 5-155, 5-156, 5-157, 5-158, 5-160, 5-161, 5-162, 5-163, 5-164, 5-165, 5-166, 5-167, 5-168, 5-169, 5-170, 5-171, 5-172, 5-173, 5-174, 5-175, 5-176*, 5-177*, 5-178, 5-180, 5-182, 5-183, 5-184**, 5-185*, 5-186*, 5-187*, 5-190, 5-191, 5-192, 5-193, 5-194, 5-195, 5-196, 5-197, 5-198**, 5-199*, 5-200 to 5-203, 5-204, 5-205, 5-206**, 6-001, 6-002*, 6-003, 6-004, 6-004(R), 6-004(S), 6-005, 6-006, 6-007, 6-008, 6-009, 6-010, 6-012, 6-013, 6-014, 6-015, 6-016, 6-017, 6-018**, 6-019*, 6-020, 6-021, 6-022**, 6-023*, 6-024, 6-025, 6-026, 6-027, 6-028, 6-029, 6-030, 6-031, 6-032, 6-033, 6-034, 6-035, 6-036, 6-037, 6-038, 6-039, 6-040, 6-041**, 6-042*, 6-043*, 6-044, 6-045*, 6-046**, 6-047*, 6-048*, 6-050, 6-051, 6-052, 6-053, 6-054, 6-055, 7-001, 7-002, 7-003, 7-004, 7-005, 7-006, 7-007, 7-008, 7-009, 7-010, 7-011, 7-012, 7-013, 7-014, 7-015, 7-016, 7-017, 7-018, 7-019, 7-020, 7-021, 7-022, 7-023**, 8-001*, 8-002, 8-003, 8-004, 8-005, 8-006*, 8-007, 8-012, 8-013, 8-014, 8-016, 8-017*, 9-001**, 9-002.

In the interim, the indication of "*" shows that the insecticidal test was carried out by use of a chemical solution of a concentration of 100 ppm, and the indication "**" shows that the insecticidal test was carried out by use of a chemical solution of a concentration of 10 ppm.

Test Example 2

Insecticidal Test Against Common Cutworm

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leaves of cabbage for about 10 seconds, and after air-drying, they were placed in a laboratory dish, then 5-common cutworm (*Spodoptera litura*) in the stage of second instar larva per the dish were released therein, and the dish was covered with a lid and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-001*, 1-002*, 1-003*, 1-004*, 1-005*, 1-006*, 1-007*, 1-008*, 1-009, 1-010*, 1-011, 1-012*, 1-013*, 1-015, 1-016*, 1-017*, 1-018*, 1-020, 1-021, 1-023, 1-026*, 1-027 to 1-030, 1-033, 1-034, 1-036*, 1-037*, 1-039*, 1-040 to 1-043, 1-044*, 1-045*, 1-046, 1-047*, 1-048*, 1-049*, 1-050*, 1-051, 1-052*, 1-053*, 1-054*, 1-055*, 1-056*, 1-057*, 1-058, 2-003*, 2-004*, 2-005*, 2-006*, 2-009*, 2-010*, 2-011*, 2-012*, 2-013, 2-014, 2-015*, 2-016*, 2-017*, 2-020, 2-021, 2-022, 2-023, 2-024, 2-025, 2-026, 2-027, 2-028, 2-029*, 2-030, 3-002, 3-003*, 3-004*, 3-005*, 3-006*, 3-007*, 3-007(+)**, 3-007(−), 3-008*, 3-009*, 3-010*, 3-011*, 3-012*, 3-013*, 3-014*, 3-015*, 3-016*, 3-017*, 3-018*, 3-019, 3-020*, 3-021*, 3-022*, 3-023, 3-024*, 3-025, 3-026, 3-027**, 3-028*, 3-029, 3-030, 3-031, 3-032, 3-033, 3-034, 3-035*, 3-036*, 3-037**, 3-038*, 3-039**, 3-040*, 3-041*, 3-042*, 3-043*, 3-044**, 3-045*, 3-046*, 3-047, 3-048, 3-049, 3-050, 3-051**, 3-052*, 3-053*, 3-054*, 3-055*, 3-056*, 3-057*, 3-058*, 3-059*, 3-060*, 3-061*, 3-062*, 3-063*, 3-064*, 3-065, 3-066*, 3-067*, 3-068*, 3-069*, 3-070*, 3-071, 3-073, 3-074, 3-075, 3-076, 3-077, 3-078, 3-079, 3-080, 3-081, 3-082, 3-083**, 3-084*, 3-085, 4-001*, 4-002*, 4-003*, 4-004*, 4-005*, 4-006*, 4-007*, 4-008**, 4-009*, 4-010, 4-011, 4-012, 4-013, 4-014, 4-015, 5-001*, 5-002*, 5-003*, 5-004*, 5-005*, 5-006*, 5-007*, 5-008*, 5-009*, 5-010*, 5-011*, 5-012*, 5-013*, 5-014*, 5-015, 5-016, 5-017**, 5-018*, 5-019*, 5-020*, 5-021*, 5-023*, 5-024*, 5-025*, 5-026*, 5-027*, 5-028*, 5-029*, 5-030, 5-031, 5-032, 5-033, 5-034, 5-035, 5-036, 5-037, 5-038*, 5-039*, 5-040*, 5-041*, 5-042, 5-043*, 5-044*, 5-045*, 5-046*, 5-047, 5-048, 5-049*, 5-050*, 5-051*, 5-052*, 5-053, 5-054, 5-055, 5-056, 5-057, 5-058, 5-059**, 5-060*, 5-061, 5-062, 5-063, 5-064, 5-065, 5-066, 5-067, 5-068, 5-069, 5-070, 5-071, 5-072, 5-073, 5-074, 5-075, 5-076, 5-077, 5-078, 5-079**, 5-080*, 5-081*, 5-082, 5-083, 5-084*, 5-085*, 5-086*, 5-087**, 5-088*, 5-089, 5-090**, 5-091*, 5-092*, 5-093**, 5-094*, 5-095*, 5-096, 5-097, 5-098, 5-099, 5-100*, 5-101*, 5-102, 5-103, 5-104, 5-105, 5-106, 5-107, 5-108*, 5-109, 5-110, 5-111, 5-112, 5-113, 5-114, 5-115, 5-116, 5-117, 5-118, 5-119, 5-120, 5-121, 5-122, 5-123, 5-124, 5-125, 5-126, 5-127, 5-128, 5-129, 5-130, 5-131, 5-132, 5-133, 5-134, 5-135**, 5-136*, 5-137, 5-138, 5-139, 5-140, 5-141**, 5-142*, 5-143*, 5-144, 5-145, 5-146, 5-147, 5-148, 5-149, 5-150, 5-151, 5-152, 5-153, 5-154, 5-155, 5-156, 5-157, 5-158, 5-159, 5-160**, 5-161*, 5-162*, 5-163, 5-164, 5-165, 5-166, 5-167, 5-168, 5-169, 5-170, 5-171, 5-172, 5-173, 5-174, 5-175**, 5-177*, 5-178, 5-180, 5-182, 5-183, 5-184**, 5-185*, 5-186*, 5-187*, 5-192, 5-193, 5-194, 5-195, 5-196, 5-197, 5-198**, 5-199*, 5-201, 5-202, 5-204, 5-205, 5-206**, 6-001, 6-002*, 6-003, 6-004, 6-004(R), 6-004(S), 6-005, 6-006, 6-007, 6-008, 6-009, 6-010, 6-011, 6-012, 6-013, 6-014, 6-015, 6-016, 6-017, 6-018, 6-019*, 6-020, 6-021, 6-022**, 6-023*, 6-024, 6-027, 6-028, 6-029, 6-030, 6-031, 6-033, 6-034, 6-035, 6-036, 6-037, 6-038, 6-039, 6-040, 6-041**, 6-042*, 6-043*, 6-045*, 6-046**, 6-047*, 6-048*, 6-049, 6-050, 6-051, 6-052, 6-053, 6-054, 6-055, 7-001, 7-002, 7-003, 7-004, 7-005, 7-006, 7-007, 7-008, 7-009, 7-010, 7-011, 7-012, 7-013, 7-014, 7-015, 7-016, 7-017, 7-018*, 7-019, 7-020, 7-021, 7-022, 7-023**, 8-001*, 8-002, 8-003, 8-004, 8-005, 8-006*, 8-007, 8-012, 8-013, 8-014, 8-015**, 8-016, 8-017*, 9-001**, 9-002.

In the interim, the indication of "*" shows that the insecticidal test was carried out by use of a chemical solution of a concentration of 100 ppm, and the indication "**" shows that the insecticidal test was carried out by use of a chemical solution of a concentration of 10 ppm.

Test Example 3

Insecticidal Test Against Beet Armyworm

A 10% emulsifiable concentrate (depending on the compounds, 10% wettable powder was applied for the test) of the compound of the present invention was diluted with water containing a spreading agent to prepare a chemical solution with a concentration of 100 ppm. To the chemical solution was dipped leaves of cabbage for about 10 seconds, and after air-drying, they were placed in a laboratory dish, then 5-beet armyworm (*Spodoptera exigua*) in the stage of second instar larva per the dish were released therein, and the dish was covered with a lid and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-001, 1-005, 2-003, 2-015, 3-003, 3-007, 3-008, 3-010 to 3-012, 3-026, 3-029 to 3-033, 3-041 to 3-043, 3-045, 3-046, 3-052, 3-058, 3-070, 3-073 to 3-079, 4-001, 5-004, 5-007, 5-010, 5-015 to 5-017, 5-033, 5-045, 5-052, 5-054, 5-057, 5-060, 5-061, 5-070, 5-081, 5-084, 5-092 to 5-094, 5-096, 5-097, 5-100 to 5-108, 5-110, 5-112 to 5-116, 5-119 to 5-122, 5-126, 5-127, 5-130, 5-131, 5-139, 5-140, 5-160, 5-164 to 5-169, 5-173, 5-174, 5-180, 5-182 to 5-184, 5-192, 5-194, 6-004, 6-005, 6-018, 7-001, 7-006, 7-010, 7-012.

Test Example 4

Insecticidal Test Against Oriental Tea Tortix

A 10% emulsifiable concentrate (depending on the compounds, 10% wettable powder was applied for the test) of the compound of the present invention was diluted with water containing a spreading agent to prepare a chemical solution with a concentration of 100 ppm. To the chemical solution was dipped leaves of cabbage for about 10 seconds, and after air-drying, they were placed in a laboratory dish, then 5-oriental tea tortix (*Homona magnanima*) in the stage of second instar larva per the dish were released therein, and the dish was covered with a lid and contained at a thermostat chamber at 25° C. A number of dead insect(s) after 6 days was counted and a rate of dead insects was calculated by the calculation equation similar to that in Test Example 1. Incidentally, the Test was Carried Out with Two Districts. As a result, the following compounds showed an insecticidal rate of 80% or more among the compounds tested.

The compounds of the present invention: No. 1-002, 1-005, 1-007, 1-008, 1-053, 2-004, 2-015, 2-016, 2-020, 2-022, 3-003, 3-007, 3-007(+), 3-015, 3-018, 3-026, 3-028, 3-029, 3-031, 3-032, 3-055, 3-059 to 3-062, 3-066 to 3-069, 3-073, 3-074, 3-076, 3-079, 3-081, 4-001 to 4-005, 4-009, 4-014, 4-015, 5-001, 5-004, 5-007, 5-010, 5-011, 5-013, 5-017 to 5-019, 5-021, 5-028, 5-029, 5-034, 5-044, 5-045, 5-069, 5-079, 5-080, 5-083, 5-096, 5-100, 5-104, 5-106 to 5-110, 5-112, 5-113, 5-117, 5-120, 5-121, 5-123, 5-125, 5-127, 5-130, 5-131, 5-139, 5-140, 5-145, 5-146, 5-148, 5-149, 5-152, 5-164 to 5-169, 5-171, 5-174, 5-178 to 5-184, 5-192, 5-198, 5-204 to 5-206, 6-003, 6-004, 6-004(S), 6-005, 6-009, 6-012, 6-016 to 6-018, 6-020, 6-021, 6-027, 6-051 to 6-055, 7-001, 7-006, 7-007, 7-009 to 7-015, 7-019, 7-022, 7-023, 8-013.

Test Example 5

Insecticidal Test Against Corn Earworm

A 10% emulsifiable concentrate (depending on the compounds, 10% wettable powder was applied for the test) of the compound of the present invention was diluted with water containing a spreading agent to prepare a chemical solution with a concentration of 100 ppm. To the chemical solution was dipped leaves of cabbage for about 10 seconds, and after air-drying, they were placed in a laboratory dish, then 1-corn earworm (*Helicoverpa armigera*) in the stage of second instar larva per the dish were released therein, and the dish was covered with a lid and contained at a thermostat chamber at 25° C. A number of dead insect(s) after 6 days was counted and a rate of dead insects was calculated by the calculation equation similar to that in Test Example 1. Incidentally, the test was carried out with twelve districts.

As a result, the following compounds showed an insecticidal rate of 80% or more among the compounds tested.

The compounds of the present invention: No. 1-001 to 1-008, 1-010, 1-012, 1-014, 1-016, 1-017, 1-026, 1-030, 1-031, 1-036, 1-037, 1-041, 1-045, 1-047, 1-050, 1-052 to 1-054, 2-003 to 2-006, 2-009 to 2-018, 2-020 to 2-027, 2-029, 3-003 to 3-007, 3-007(+), 3-008 to 3-018, 3-022, 3-024 to 3-064, 3-066 to 3-070, 3-073 to 3-081, 3-084, 3-085, 4-001 to 4-015, 5-001 to 5-021, 5-023 to 5-041, 5-043 to 5-046, 5-049 to 5-141, 5-144 to 5-175, 5-177 to 5-187, 5-192 to 5-206, 6-003, 6-004, 6-004(R), 6-004(S), 6-005 to 6-007, 6-009, 6-010, 6-012 to 6-018, 6-020 to 6-029, 6-031, 6-033 to 6-037, 6-039, 6-040, 6-043, 6-046, 6-048 to 6-055, 7-001 to 7-023, 8-001 to 8-003, 8-006, 8-007, 8-013, 8-015, 8-017, 9-001, 9-002.

Test Example 6

Insecticidal Test Against Peach Fruit Moth

A 10% emulsifiable concentrate (depending on the compounds, 10% wettable powder was applied for the test) of the compound of the present invention was diluted with water containing a spreading agent to prepare a chemical solution with a concentration of 100 ppm. To the chemical solution was dipped apple young fruits on which peach fruit moth (*Carpocina sasakii*) laid eggs (20-egg/fruit) for about 10 seconds, and after air-drying, they were placed in a laboratory dish, and the dish was covered with a lid and contained at a thermostat chamber at 25° C. A number of dead insect(s) after 20 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 3-011, 3-033, 3-076, 5-090, 5-164, 6-004, 6-005, 6-018.

Test Example 7

Insecticidal Test Against *Frankliniella occidentalis*

A wet filter paper was laid in a styrol cup having an inner diameter of 7 cm, a leaf of a common bean cut out so as to have the same diameter was laid theron, and 10-*Frankliniella occidentalis* with first instar larva per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 500 ppm. The chemical solution was sprayed with a rotating spray tower in an amount of 2.5 ml per styrol cup, and the styrol cups were covered with lids and contained at a thermostat chamber at 25° C. A number of dead insect(s) after 2 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-001 to 1-037, 1-039 to 1-058, 2-003 to 2-011, 2-013 to 2-029, 3-001 to 3-007, 3-007(+), 3-007(−), 3-008 to 3-083, 4-001, 4-003 to 4-015, 5-001 to 5-021, 5-023 to 5-187, 5-192 to 5-199, 5-204 to 5-206, 6-002 to 6-004, 6-004(S), 6-005 to 6-023, 6-025, 6-027 to 6-033, 6-035 to 6-041, 6-043 to 6-048, 6-050 to 6-055, 7-001 to 7-023, 8-001 to 8-007, 8-012 to 8-017, 9-001, 9-002.

Test Example 8

Insecticidal Test Against *Thrips palmi*

A wet filter paper was laid in a styrol cup having an inner diameter of 7 cm, a leaf of a common bean cut out so as to have the same diameter was laid theron, and 10-Thrips palmi in the stage of adult per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 100 ppm. The chemical solution was sprayed with a rotating spray tower in an amount of 2.5 ml per styrol cup, and the styrol cups were covered with lids and contained at a thermostat chamber at 25° C. A number of dead insect(s) after 2 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-001 to 1-018, 1-020 to 1-022, 1-026, 1-028, 1-031, 1-037, 1-039, 1-040, 1-044, 1-045, 1-049 to 1-053, 1-055, 1-056, 2-002 to 2-005, 2-009 to 2-011, 2-013 to 2-017, 2-019 to 2-027, 2-029, 3-001 to 3-007, 3-007(+), 3-008 to 3-064, 3-066 to 3-071, 3-073 to 3-081, 3-083, 4-001 to 4-005, 4-008, 4-009, 4-011 to 4-015, 5-001 to 5-021, 5-023 to 5-037, 5-039 to 5-083, 5-085 to 5-146, 5-148 to 5-158, 5-160 to 5-172, 5-174 to 5-187, 5-192 to 5-199, 5-204 to 5-206, 6-001 to 6-004, 6-004(S), 6-005 to 6-018, 6-020 to 6-023, 6-025, 6-027 to 6-029, 6-031, 6-035 to 6-037, 6-039, 6-040, 6-045, 6-046, 6-050 to 6-055, 7-001, 7-003 to 7-023, 8-001 to 8-007, 8-013, 8-015, 8-017, 9-001, 9-002.

Test Example 9

Insecticidal Test Against *Eysarcoris lewisi*

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leave sheaths of rice for about 10 seconds, and after air-drying, they were placed in a test tube, then 5-Eysarcoris lewisi in the stage of first instar larva per the test tube were released therein, and the test tube was covered with a sponge and contained at a thermostat chamber at 25° C. A number of dead insect(s) after 2 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-001 to 1-010, 1-012 to 1-014, 1-016 to 1-019, 1-021, 1-026, 1-027, 1-031 to 1-033, 1-036, 1-039, 1-044, 1-045, 1-047 to 1-050, 1-052 to 1-054, 1-056, 2-003 to 2-005, 2-010, 2-011, 2-013 to 2-017, 2-020 to 2-027, 2-029, 3-003 to 3-018, 3-020, 3-021, 3-024 to 3-037, 3-039, 3-041 to 3-064, 3-066 to 3-070, 3-073 to 3-081, 4-001, 4-002, 4-005, 4-007, 4-009, 5-001 to 5-019, 5-021, 5-023, 5-025 to 5-031, 5-033 to 5-035, 5-038, 5-040, 5-043 to 5-046, 5-050 to 5-053, 5-055, 5-056, 5-058, 5-060, 5-061, 5-065, 5-067 to 5-072, 5-078 to 5-088, 5-090 to 5-131, 5-133, 5-134, 5-137 to 5-140, 5-142, 5-145 to 5-160, 5-162 to 5-171, 5-174, 5-175, 5-178, 5-180, 5-182 to 5-184, 5-186, 5-192 to 5-194, 5-198, 5-204 to 5-206, 6-003 to 6-010, 6-012 to 6-018, 6-020, 6-022, 6-027 to 6-029, 6-031, 6-035 to 6-041, 6-052, 7-001, 7-006, 7-007, 7-009, 7-010, 7-012 to 7-017, 7-019, 7-020, 7-022, 8-001, 8-006, 8-007, 8-012, 8-013, 9-002.

Test Example 10

Insecticidal Test Against Brown Rice Planthopper

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leave sheaths of rice for about 10 seconds, and after air-drying, they were placed in a test tube, then 5-brown rice planthopper (*Nilaparvata lugens*) in the second instar larva per the test tube were released therein, and the test tube was covered with a sponge and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-001 to 1-018, 1-021, 1-022, 1-028, 1-033, 1-040, 1-045, 1-049, 1-050, 1-052, 1-053, 2-002 to 2-004, 2-009 to 2-011, 2-013 to 2-016, 2-020 to 2-029, 3-002 to 3-007, 3-007(+), 3-008 to 3-020, 3-024 to 3-036, 3-039, 3-041 to 3-046, 3-048 to 3-064, 3-066 to 3-070, 3-073 to 3-081, 4-001, 4-002, 4-004, 4-005, 4-009, 4-013 to 4-015, 5-001 to 5-006, 5-008, 5-011 to 5-017, 5-027, 5-031, 5-032, 5-035, 5-038, 5-040, 5-043 to 5-045, 5-050, 5-079, 5-080, 5-083 to 5-117, 5-119 to 5-131, 5-138 to 5-142, 5-144 to 5-151, 5-153, 5-154, 5-156 to 5-158, 5-160, 5-162 to 5-171, 5-174, 5-175, 5-177, 5-178, 5-180, 5-182 to 5-184, 5-192 to 5-194, 5-198, 5-199, 5-204 to 5-206, 6-002 to 6-004, 6-004(S), 6-005 to 6-010, 6-012 to 6-020, 6-022, 6-027 to 6-031, 6-035 to 6-041, 6-050*, 6-052, 6-053*, 6-054*, 6-055*, 7-001 to 7-023, 8-001, 8-006, 8-007, 8-012, 8-013, 9-001, 9-002.

"*" means the compound tested at 100 ppm.

Test Example 11

Insecticidal Test Against *Bemisia argentifolii*

A wet filter paper was laid in a styrol cup having an inner diameter of 7 cm, a leaf of a tomato cut out on which *Bemisia argentifolii* laid eggs (10-egg/leaf) was laid thereon. A 10% emulsifiable concentrate (depending on the compounds, 10% wettable powder was applied for the test) of the compound of the present invention was diluted with water containing a spreading agent to prepare a chemical solution with a concentration of 500 ppm. The chemical solution was sprayed with a rotating spray tower in an amount of 2.5 ml per styrol cup, and the styrol cups were covered with lids and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention No. 1-002 to 1-014, 1-016 to 1-026, 1-028, 1-029, 1-036, 1-039, 1-041, 1-042, 1-044 to 1-046, 1-049, 1-050, 1-052, 1-053, 1-056, 1-057, 2-003, 2-004, 2-009 to 2-011, 2-013 to 2-018, 2-020 to 2-028, 3-003 to 3-005, 3-007, 3-011 to 3-020, 3-022, 3-024, 3-026, 3-028 to 3-034, 3-041 to 3-064, 3-066 to 3-070, 3-073 to 3-081, 4-002, 5-001, 5-002, 5-009, 5-010, 5-012 to 5-021, 5-033, 5-035, 5-040, 5-041, 5-044, 5-045, 5-050, 5-051, 5-056 to 5-058, 5-060, 5-062, 5-063, 5-065, 5-066, 5-068, 5-071 to 5-074, 5-076 to 5-080, 5-082 to 5-091, 5-093, 5-096, 5-098, 5-100, 5-102 to 5-113, 5-116, 5-117, 5-119 to 5-131, 5-133, 5-139, 5-140, 5-144 to 5-158, 5-162 to 5-171, 5-174, 5-175, 5-177 to 5-184, 5-192 to 5-194, 5-197, 5-198, 5-204 to 5-206, 6-002 to 6-004, 6-004(S), 6-005 to 6-010, 6-012 to 6-023, 6-025, 6-027 to 6-031, 6-035 to 6-041, 6-043, 6-052, 6-053, 7-001, 7-003 to 7-017, 7-019, 7-020, 7-022, 7-023, 8-003, 8-006, 8-007, 8-012, 9-001, 9-002.

Test Example 12

Insecticidal Test Against Green Peach Aphid

A wet cotton wool was laid in a laboratory dish having an inner diameter of 3 cm, a leaf of a cabbage cut out so as to have the same diameter was laid theron, and 4-green peach aphid (*Myzus persicae*) in the stage of no-wing adult was left. After 1 day, a 10% emulsifiable concentrate (depending on the compounds, 10% wettable powder was applied for the test) of the compound of the present invention was diluted with water containing a spreading agent to prepare a chemical solution with a concentration of 500 ppm, and the chemical solution was sprayed with a rotating spray tower (2.5 mg/cm$^2$), and the laboratory dish was covered with lids and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-002 to 1-014, 1-016 to 1-018, 1-020, 1-021, 1-024, 1-026 to 1-028, 1-031 to 1-033, 1-040, 1-045, 1-046, 1-048, 1-050, 1-052, 1-053, 1-055, 2-003 to 2-005, 2-009 to 2-011, 2-013 to 2-017, 2-020 to 2-028, 2-029*, 2-030, 3-001 to 3-006, 3-007(+), 3-008, 3-010 to 3-020, 3-022 to 3-035, 3-037 to 3-039, 3-041 to 3-048, 3-050 to 3-064, 3-066 to 3-070, 3-073 to 3-081, 4-001, 4-004, 4-006, 4-009, 4-014, 5-002, 5-005, 5-008 to 5-021, 5-026, 5-034, 5-035, 5-039, 5-040, 5-044 to 5-046, 5-053, 5-056, 5-058, 5-063 to 5-066, 5-069, 5-072 to 5-080, 5-082, 5-084 to 5-090, 5-094, 5-096, 5-098 to 5-115, 5-117 to 5-131, 5-133, 5-134, 5-138, 5-139, 5-146 to 5-150, 5-152 to 5-157, 5-163 to 5-174, 5-177, 5-178, 5-180, 5-182 to 5-184, 5-192 to 5-194, 5-198, 5-199, 5-204 to 5-206, 6-002 to 6-010, 6-016 to 6-018, 6-020, 6-026 to 6-029, 6-035 to 6-041, 6-049, 6-052, 6-055, 7-001 to 7-003, 7-005 to 7-010, 7-013 to 7-017, 7-019 to 7-023, 8-001 to 8-004, 8-006, 8-007, 8-013, 8-015, 8-017, 9-002.

"*" means the compound tested at 100 ppm.

Test Example 13

Insecticidal Test Against Japanese Mealybug

A wet filter paper was laid in a styrol cup having an inner diameter of 7 cm, a leaf of a common bean cut out so as to have the same diameter was laid theron, and 10-Japanese mealybug (*Planococcus kraunhiae*) in the first instar larva per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 500 ppm. The chemical solution was sprayed with a rotating spray tower in an amount of 2.5 ml per styrol cup, and the styrol cups were covered with lids and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-002 to 1-014, 1-016 to 1-019, 1-021, 1-022, 1-024, 1-026, 1-027, 1-031, 1-036, 1-037, 1-040, 1-041, 1-045, 1-047, 1-049, 1-050, 1-052, 1-053, 1-057, 2-003 to 2-005, 2-008, 2-010, 2-011, 2-013 to 2-018, 2-020 to 2-028, 3-003 to 3-005, 3-007, 3-008, 3-010 to 3-021, 3-023 to 3-026, 3-028, 3-029, 3-031, 3-032, 3-034, 3-041 to 3-046, 3-049, 3-051, 3-052, 3-054 to 3-062, 3-064, 3-066 to 3-070, 3-073 to 3-081, 3-083, 4-006, 4-009, 4-011, 5-002, 5-004, 5-006, 5-009 to 5-017, 5-019 to 5-021, 5-024, 5-026, 5-032, 5-037, 5-040, 5-044, 5-045, 5-052, 5-054, 5-057, 5-061 to 5-064, 5-067, 5-068, 5-073 to 5-079, 5-081, 5-082, 5-084, 5-086, 5-088 to 5-090, 5-092, 5-094 to 5-097, 5-099 to 5-114, 5-116, 5-117, 5-119 to 5-129, 5-138 to 5-140, 5-142, 5-146 to 5-154, 5-156 to 5-158, 5-160, 5-162 to 5-171, 5-173 to 5-185, 5-192 to 5-194, 5-196 to 5-198, 5-206, 6-002 to 6-010, 6-012 to 6-018, 6-020 to 6-023, 6-025 to 6-031, 6-035 to 6-041, 6-047, 6-048, 6-052, 7-001, 7-003, 7-005 to 7-017, 7-019 to 7-022, 8-003, 8-004, 8-007, 8-012, 8-016, 8-017, 9-001, 9-002.

Test Example 14

Insecticidal Test Against Cucurbit Leaf Beetle

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leaves of cucumber for about 10 seconds, and after air-drying, they were placed in a laboratory dish, then 5-cucurbit leaf beetle (*Aulacophora femoralis*) in the stage of second instar larva per the dish were released therein, and the dish was covered with a lid and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-001 to 1-058, 2-001 to 2-018, 2-020 to 2-029, 3-001 to 3-070, 3-072 to 3-083, 4-001 to 4-015, 5-001 to 5-021, 5-023 to 5-178, 5-180, 5-183 to 5-187, 5-192 to 5-198, 5-204 to 5-206, 6-001 to 6-031, 6-033 to 6-049, 6-052, 7-001 to 7-017, 7-019 to 7-023, 8-001 to 8-007, 8-012 to 8-017, 9-001, 9-002.

Test Example 15

Insecticidal Test Against Serpentine Leaf Miner

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leaves of common bean on which serpentine leaf miner (*Liriomyza trifolii*) laid eggs (10 eggs/leaf) for about 10 seconds, and after air-drying, they were placed on a wet filter paper laid in a styrol cup having an inner diameter of 7 cm, and the styrol cup was covered with a lid and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-002 to 1-010, 1-012, 1-014, 1-016 to 1-019, 1-021, 1-026, 1-028, 1-029, 1-031 to 1-033, 1-036, 1-039, 1-042, 1-044, 1-045, 1-047, 1-050, 1-052, 1-053, 1-055, 1-056, 2-003 to 2-006, 2-008 to 2-011, 2-013 to 2-018, 2-020 to 2-026, 3-003, 3-004, 3-007, 3-008, 3-010 to 3-016, 3-018, 3-020 to 3-022, 3-024 to 3-039, 3-041 to 3-064, 3-066 to 3-070, 3-073 to 3-081, 3-083, 4-001 to 4-009, 4-013, 5-001, 5-004, 5-008, 5-012 to 5-017, 5-019, 5-021, 5-027, 5-040, 5-041, 5-043 to 5-046, 5-049 to 5-053, 5-055, 5-067, 5-068, 5-070 to 5-074, 5-078 to 5-092, 5-094 to 5-097, 5-100 to 5-106, 5-108 to 5-114, 5-117, 5-119 to 5-128, 5-130, 5-131, 5-135, 5-139, 5-140, 5-145 to 5-152, 5-154 to 5-158, 5-163 to 5-171, 5-173 to 5-184, 5-186, 5-192 to 5-194, 5-198, 5-206, 6-002 to 6-004, 6-004(S), 6-005 to 6-018, 6-020 to 6-024, 6-026 to 6-031, 6-035 to 6-041, 6-043, 6-044, 6-052, 7-001 to 7-017, 7-019, 7-020, 7-022, 7-023, 8-001 to 8-003, 8-006, 8-007, 8-012, 8-014, 9-001, 9-002.

Test Example 16

Insecticidal Test Against Two-Spotted Spider Mite

A wet filter paper was laid in a styrol cup having an inner diameter of 7 cm, a leaf of a common bean cut out so as to have the same diameter was laid theron, and 10 larvae of two-spotted spider mite (*Tetranychus urticae*) per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 500 ppm. The chemical solution was sprayed with a rotating spray tower in an amount of 2.5 ml per styrol cup, and the styrol cups were covered with lids and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-001 to 1-010, 1-012 to 1-014, 1-016 to 1-019, 1-021, 1-026, 1-027, 1-031 to 1-033, 1-042, 1-044 to 1-049, 1-052, 1-053, 1-055, 1-056, 2-003 to 2-006, 2-009 to 2-017, 2-020 to 2-027, 3-003 to 3-024, 3-026, 3-028, 3-029, 3-031 to 3-033, 3-035, 3-036, 3-039, 3-041 to 3-046, 3-051 to 3-064, 3-066 to 3-070, 3-073 to 3-081, 4-001 to 4-007, 4-009, 4-014, 4-015, 5-002 to 5-005, 5-009 to 5-011, 5-013, 5-014, 5-018, 5-019, 5-021, 5-039, 5-044 to 5-046, 5-049, 5-052, 5-072, 5-078 to 5-080, 5-084, 5-088, 5-100, 5-102, 5-103, 5-108, 5-115, 5-131, 5-138 to 5-140, 5-145 to 5-148, 5-157, 5-164 to 5-177, 5-192 to 5-194, 5-196, 5-198, 5-203, 5-206, 6-003, 6-004, 6-004(S)\*\*, 6-005 to 6-022, 6-025, 6-027 to 6-031, 6-034 to 6-041, 6-043, 6-050\*, 6-051\*, 6-052, 6-053\*, 6-054\*, 6-055\*, 7-001 to 7-020, 7-022, 7-023, 8-001, 8-003, 8-006, 8-007, 8-012, 8-013, 9-002.

"*" means the compound tested at 100 ppm.

"**" means the compound tested at 10 ppm.

Test Example 17

Insecticidal Test Against Pink Citrus Rust Mite

A wet filter paper was laid in a styrol cup having an inner diameter of 7 cm, a leaf of a mandarin orange cut out so as to have the same diameter was laid theron, and 10 larvae of pink citrus rust mite (*Aculops pelekassi*) per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 100 ppm. The chemical solution was sprayed with a rotating spray tower in an amount of 2.5 ml per styrol cup, and the styrol cups were covered with lids and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-003, 1-005, 1-008, 1-053, 2-003, 2-015, 2-016, 3-004, 3-007, 3-008, 3-010, 3-012, 3-028, 3-031 to 3-033, 3-041 to 3-043, 3-045, 3-046, 3-054, 3-056 to 3-058, 3-074 to 3-079, 4-001, 5-013, 5-081, 5-084, 5-090, 5-092 to 5-097, 5-100 to 5-106, 5-108, 5-115, 5-119, 5-145 to 5-149, 5-156, 5-157, 5-164 to 5-169, 5-171, 6-004, 6-005, 6-009, 6-018, 6-053, 6-054, 7-001.

Test Example 18

Insecticidal Test Against Broad Mite

A wet filter paper was laid in a styrol cup having an inner diameter of 7 cm, a leaf of a common bean cut out so as to have the same diameter was laid theron, and 10 adults of broad mite (*Polyphagotarsonemus latus*) per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 100 ppm. The chemical solution was sprayed with a rotating spray tower in an amount of 2.5 ml per styrol cup, and the styrol cups were covered with lids and contained at a thermostat chamber at 25° C. A number of dead insect(s) after 2 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 2-015, 3-041, 3-043, 3-077 to 3-079, 5-092, 5-165.

Test Example 19

Insecticidal Test Against *Ctenocephalides fells*

After 400 µl of acetone solution in which 4 mg of the compound of the present invention was dissolved in 40 ml of acetone (concentration 100 ppm) was coated on the bottom face and side face of a laboratory dish having an inner diameter of 5.3 cm, acetone was vaporized to prepare a thin film of the compound of the present invention on the inner wall of the laboratory dish. As the surface area of the inner wall is 40 cm$^2$, the treated dosage is 1 µg/cm$^2$. 10 adults of *Ctenocephalides*

*felis* (male and female are mixed) were left in the laboratory dish, covered with lid and contained at a thermostat chamber at 25° C. A number of dead insect(s) after 4 days was counted and a rate of dead insects was calculated by the calculation equation similar to that in Test Example 1. Incidentally, the test was carried out with one district. As a result, the following compounds showed an insecticidal rate of 80% or more among the compounds tested.

The compounds of the present invention: No. 2-003*, 2-015*, 3-004*, 3-007*, 3-008, 3-010 to 3-012, 3-025*, 3-026*, 3-027*, 3-028*, 3-029*, 3-030*, 3-031, 3-033*, 3-041*, 3-042*, 3-043*, 3-058*, 3-074, 3-079, 5-001, 5-002*, 5-012, 5-013, 5-084, 5-092*, 5-093*, 5-094*, 5-095*, 5-096*, 5-097*, 5-100*, 5-101*, 5-102*, 5-103*, 5-104*, 5-105*, 5-106*, 5-108*, 5-109*, 5-113*, 5-114*, 5-115*, 5-116*, 5-118*, 5-119*, 5-120*, 5-122*, 5-126*, 5-131*, 6-002, 6-004 to 6-011, 6-016, 6-018, 7-001, 7-003, 7-005, 7-009.

In the interim, the indication of "*" shows that the insecticidal test was carried out by use of a chemical solution of a concentration of 0.1 µg/cm².

Test Example 20

Insecticidal Test Against American Dog Tick

After 400l of acetone solution in which 4 mg of the compound of the present invention was dissolved in 40 ml of acetone (concentration 100 ppm) was coated on the bottom face and side face of two laboratory dishes having an inner diameter of 5.3 cm, acetone was vaporized to prepare a thin film of the compound of the present invention on the inner wall of the laboratory dish. As the surface area of the inner wall is 40 cm², the treated dosage is 1 µg/cm². 10-American dog tick (*Dermacentor variabilis*) (male and female are mixed) in the stage of protonymph were left in the laboratory dishes, two laboratory dishes together were sealed with a tape so that ticks do not escape, and contained at a thermostat chamber at 25° C. A number of dead insect(s) after 4 days was counted and a rate of dead insects was calculated by the calculation equation similar to that in Test Example 1. Incidentally, the test was carried out with one district.

As a result, the following compounds showed an insecticidal rate of 80% or more among the compounds tested.

The compounds of the present invention: No. 2-003*, 2-015*, 3-004*, 3-007*, 3-008*, 3-010*, 3-011, 3-012*, 3-025*, 3-026*, 3-027*, 3-028*, 3-029*, 3-030*, 3-031*, 3-033*, 3-041*, 3-042*, 3-043*, 3-058*, 3-074*, 3-079*, 5-001, 5-002**, 5-012, 5-013*, 5-052*, 5-061*, 5-063*, 5-084*, 5-092*, 5-093*, 5-094*, 5-095*, 5-096*, 5-097*, 5-100*, 5-101*, 5-102*, 5-103*, 5-104*, 5-105*, 5-106*, 5-108*, 5-109*, 5-113, 5-114*, 5-115*, 5-116*, 5-118*, 5-119*, 5-120*, 5-122*, 5-126*, 5-131*, 6-002*, 6-004*, 6-005*, 6-006*, 6-007*, 6-008*, 6-009*, 6-010*, 6-011*, 6-016*, 6-018*, 6-024*, 6-026*, 7-001*, 7-003*, 7-005*, 7-009*.

In the interim, the indication of "*" shows that the insecticidal test was carried out by use of a chemical solution of a concentration of 0.1 µg/cm².

Test Example 21

Insecticidal Test Against German Cockroach

A chemical solution having a concentration of 1 µg/µl was prepared by diluting the compound of the present invention with acetone. The chemical solution was coated on the abdominal region of male adults of German cockroach (*Blattella germanica*) in an amount of 1l per cockroach, and the treated cockroaches were contained at a thermostat chamber at 25° C. A number of dead insect(s) after 2 days was counted and a rate of dead insects was calculated by the calculation equation similar to that in Test Example 1. Incidentally, the test was carried out with five districts.

As a result, the following compounds showed an insecticidal rate of 80% or more among the compounds tested.

The compounds of the present invention: No. 2-003, 3-007, 3-031, 3-032, 3-041, 3-074, 3-077, 5-094, 5-100 to 5-103, 5-108, 6-004, 6-009, 6-018, 7-001, 7-004.

Test Example 22

Insecticidal Test Against *Musca domestica*

A chemical solution having a concentration of 1 µg/µl was prepared by diluting the compound of the present invention with acetone. The chemical solution was coated on the abdominal region of female adults of *Musca domestica* in an amount of 1l per fly, and the treated flies were contained at a thermostat chamber at 25° C. A number of dead insect(s) after 2 days was counted and a rate of dead insects was calculated by the calculation equation similar to that in Test Example 1. Incidentally, the test was carried out with ten districts.

As a result, the following compounds showed an insecticidal rate of 80% or more among the compounds tested.

The compounds of the present invention: No. 5-234.

Test Example 23

Insecticidal Test Against Corn Earworm
(Comparative Example 1)

A 10% emulsifiable concentrate of the compound of the present invention or comparative compound was diluted with water containing a spreading agent to prepare a chemical solution with a prescribed concentration. To the chemical solution was dipped leaves of cabbage for about 10 seconds, and after air-drying, they were placed in a laboratory dish, then 7-corn earworm (*Helicoverpa armigera*) in the stage of third instar larva per the dish were released therein, and the dish was covered with a perforated lid and contained at a thermostat chamber at 25° C. Artificial feed (1 cm³) was added after 2 days of treatment, and a number of dead insect (s) after 6 days was counted and a rate of dead insects was calculated by the following calculation equation. In the meantime, the test was carried out with two areas.

Rate of dead insects(%)=(Number of dead insects/Number of released insects)×100

The rate of dead insects in each prescribed concentration of the compounds tested is shown in Table 17.

TABLE 17

|  | Concentration (ppm) | | | | |
| --- | --- | --- | --- | --- | --- |
| Tasted Compound | 33 | 10 | 3 | 1 | 0.3 |
| Compound of the present invention No. 3-033 | 100 | 100 | 50.0 | 7.1 | |
| Comparative Compound A | 92.9 | 28.6 | 0 | 0 | |

Comparative Compound A: WO 2005/085216, Compound No. 6-077

Test Example 24

Insecticidal Test Against Oriental Tea Tortix
(Comparative Example 2)

A 10% emulsifiable concentrate of the compound of the present invention or comparative compound was diluted with water containing a spreading agent to prepare a chemical solution with a prescribed concentration. To the chemical solution was dipped leaves of cabbage for about 10 seconds, and after air-drying, they were placed in a laboratory dish, then 7-oriental tea tortix (*Homona magnanima*) in the stage of third instar larva per the dish were released therein, and the dish was covered with a perforated lid and contained at a thermostat chamber at 25° C. A number of dead insect(s) after 6 days was counted and a rate of dead insects was calculated by the following calculation equation. In the meantime, the test was carried out with two areas.

Rate of dead insects(%)=(Number of dead insects/Number of released insects)×100

The rate of dead insects in each prescribed concentration of the compounds tested is shown in Table 18.

TABLE 18

|  | Concentration (ppm) | | | | | |
| --- | --- | --- | --- | --- | --- | --- |
| Tasted Compound | 100 | 33 | 10 | 3 | 1 | 0.3 | 0.1 |
| Compound of the present invention No. 5-165 |  | 100 | 100 | 92.9 | 57.1 | 14.3 |
| Comparative Compound B | 100 | 64.3 | 7.1 | 0 | 0 |  |

Comparative Compound B: WO 2005/085216, Compound No. 5-309

INDUSTRIAL APPLICABILITY

The isoxazoline-substituted benzamide compounds according to the present invention are extremely useful compounds showing an excellent pesticidal activity, particularly an insecticidal and acaricidal activity, and causing little adverse effect against non-targeted beings such as mammals, fishes and useful insects.

The invention claimed is:
1. 4-Hydroxyiminomethyl substituted benzamide compound of formula (2) or a salt thereof:

(2)

wherein
   $A^1$ is carbon atom or nitrogen atom,
   J is hydrogen atom or halogen atom,
   W is oxygen atom or sulfur atom,
   Y is halogen atom, cyano, nitro, $C_1$-$C_6$alkyl, $C_1$-$C_6$haloalkyl, $C_1$-$C_4$alkyl arbitrarily substituted with $R^4$, —$OR^5$, —$N(R^7)R^6$ or —$C(S)NH_2$, when n is 2, each Y may be identical with or different from each other,
   $R^1$ is —$C(R^{1b})$=$NOR^{1a}$, —$C(O)OR^{1c}$, —$C(O)SR^{1c}$, —$C(S)OR^{1c}$, —$C(O)N(R^{1e})R^{1d}$, —$C(S)N(R^{1e})R^{1d}$, phenyl, phenyl substituted with $(Z)_{p1}$, D-3, D-8, D-10, D-11, D-13 to D-15, D-17, D-22, D-35, D-52 to D-58 or D-59,
   $R^{1a}$ is $C_1$-$C_6$alkyl, $C_1$-$C_6$haloalkyl, $C_3$-$C_8$cycloalkyl $C_1$-$C_4$alkyl, $C_3$-$C_6$alkenyl or $C_3$-$C_6$alkynyl,
   $R^{1b}$ is hydrogen atom or $C_1$-$C_6$alkyl,
   $R^{1c}$ is $C_1$-$C_6$alkyl, $C_1$-$C_4$alkyl arbitrarily substituted with $R^{14}$ or $C_3$-$C_6$cycloalkyl,
   $R^{1d}$ is hydrogen atom, —$C(O)R^{15}$, —$C(O)OR^{15}$ or —$C(O)SR^{15}$,
   $R^{1e}$ is hydrogen atom or $C_1$-$C_6$alkyl,
   $R^2$ is $C_1$-$C_6$alkyl, —$CH_2R^{14a}$, E-5, E-24, $C_3$-$C_6$alkynyl, —$C(O)R^{15}$, —$C(O)OR^{15}$, —$C(O)SR^{15}$, —$C(S)OR^{15}$, —$C(S)SR^{15}$, —$C(O)C(O)OR^{15}$, phenyl or phenyl substituted with $(Z)_{p1}$, further when $R^1$ is —$C(R^{1b})$=$NOR^{1a}$, —$C(O)OR^{1c}$, —$C(O)SR^{1c}$, —$C(S)OR^{1c}$, —$C(O)N(R^{1e})R^{1d}$ or —$C(S)N(R^{1e})R^{1d}$, $R^2$ may be hydrogen atom, when $R^1$ is phenyl, phenyl substituted with $(Z)_{p1}$, D-3, D-8, D-10, D-11, D-13 to D-15, D-17, D-22, D-35, D-52 to D-58 or D-59, $R^2$ may be $C_1$-$C_6$haloalkyl or $C_3$-$C_6$alkenyl,
   or $R^2$ together with $R^1$ may form =$C(R^{2b})R^{2a}$,
   $R^{2a}$ is $C_1$-$C_6$alkoxy or di($C_1$-$C_6$alkyl)amino,
   $R^{2b}$ is $C_1$-$C_6$alkyl or $C_1$-$C_6$alkylcarbonylthio,
   D-3, D-8, D-10, D-11, D-13 to D-15, D-17, D-22, D-35, D-52 to D-58 and D-59 are aromatic heterocyclic rings of the following formulae, respectively

D-3

517
-continued

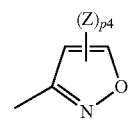
D-8

D-10

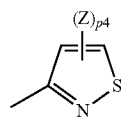
D-11

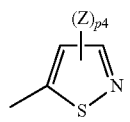
D-13

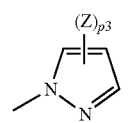
D-14

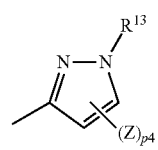
D-15

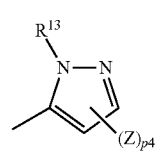
D-17

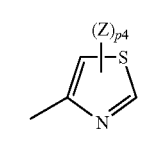
D-22

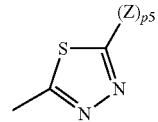
D-35

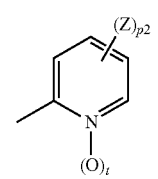
D-52

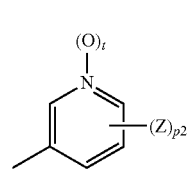
D-53

518
-continued

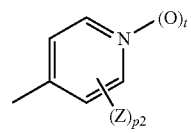
D-54

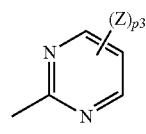
D-55

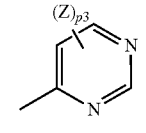
D-56

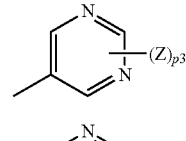
D-57

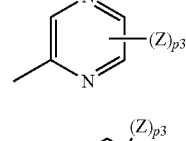
D-58

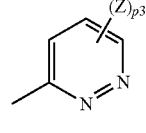
D-59

Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylsulfonyloxy, $C_1$-$C_6$haloalkylsulfonyloxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, $C_1$-$C_6$alkoxycarbonyl, —C(O)NH$_2$ or —C(S)NH$_2$, when p1, p2 or p3 is an integer of 2 or more, each Z may be identical with or different from each other, further, when two Zs are adjacent, the adjacent two Zs may form 5-membered or 6-membered ring together with carbon atoms to which the two Zs are bonded by forming —OCH$_2$O— or —OCH$_2$CH$_2$O—, in this case, hydrogen atoms bonded to each carbon atom forming the ring may be arbitrarily substituted with halogen atom, E-5 and E-24 are saturated heterocyclic rings of the following formulae, respectively,

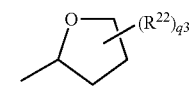
E-5

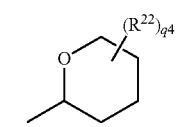
E-24

$R^4$ is $C_1$-$C_6$alkoxy or $C_1$-$C_6$haloalkoxy,
$R^5$ is $C_1$-$C_6$alkyl or $C_1$-$C_6$haloalkyl,
$R^6$ is —CHO, $C_1$-$C_6$alkylcarbonyl, $C_1$-$C_6$haloalkylcarbonyl, $C_1$-$C_6$alkoxycarbonyl, $C_1$-$C_6$alkylthiocarbonyl, $C_1$-$C_6$alkoxythiocarbonyl, $C_1$-$C_6$alkyldithiocarbonyl, $C_1$-$C_6$alkylsulfonyl or $C_1$-$C_6$haloalkylsulfonyl, $R^7$ is hydrogen atom or $C_1$-$C_6$alkyl $R^{13}$ is $C_1$-$C_6$alkyl or $C_1$-$C_6$haloalkyl, $R^{14}$ is cyano, $C_3$-$C_6$cycloalkyl, $C_1$-$C_6$alkoxy, $C_1$-$C_4$alkoxy, $C_1$-$C_6$alkylsulfonyl, —NHC(O)$R^{32}$, —NHC(O)O$R^{32}$, $C_1$-$C_6$alkylcarbonyl or $C_1$-$C_6$alkoxycarbonyl, $R^{14a}$ is cyano, —O$R^{25}$, —NHC(O)O$R^{32}$, —S(O)$_r R^{27}$, $C_1$-$C_6$alkylcarbonyl, $C_1$-$C_6$alkoxycarbonyl or phenyl, $R^{15}$ is $C_1$-$C_6$alkyl, $C_1$-$C_6$haloalkyl, $C_1$-$C_4$alkyl arbitrarily substituted with $R^{31}$, $C_3$-$C_6$cycloalkyl, $C_2$-$C_6$alkenyl, $C_2$-$C_6$alkynyl, phenyl, phenyl substituted with $(Z)_{p1}$, D-52, D-53 or D-54, $R^{25}$ is $C_1$-$C_6$alkyl, $C_1$-$C_6$haloalkyl, $C_1$-$C_4$alkoxy $C_1$-$C_4$alkyl, benzyl, $C_3$-$C_6$alkenyl, $C_3$-$C_6$alkynyl, —C(O)$R^{32}$ or —C(O)O$R^{32}$, $R^{27}$ is $C_1$-$C_6$alkyl, $C_1$-$C_6$haloalkyl, C(O)$R^{32}$ or —C(S)O$R^{32}$, $R^{31}$ is $C_3$-$C_6$cycloalkyl, $C_1$-$C_4$alkoxy, $C_1$-$C_4$haloalkoxy, $C_1$-$C_4$alkylsulfonyl or phenyl, $R^{32}$ is $C_1$-$C_6$alkyl, $C_1$-$C_6$haloalkyl, $C_3$-$C_6$cycloalkyl or phenyl, n is an integer of 0 to 2, p1 is an integer of 1 to 3, p2 and p3 are an integer of 0 to 2, p4 and p5 are an integer of 0 or 1, q3 and q4 are 0, r is an integer of 0 or 2, and t is an integer of 0 or 1.

2. 4-Hydroxyiminomethyl substituted benzamide compound or the salt thereof according to claim 1, wherein $A^1$ is carbon atom, W is oxygen atom, Y is halogen atom, cyano, nitro, $C_1$-$C_6$alkyl, $C_1$-$C_6$haloalkyl, —O$R^5$ or —N($R^7$)$R^6$, $R^1$ is —CH=NO$R^{1a}$, $R^{1a}$ is $C_1$-$C_6$alkyl, $R^2$ is hydrogen atom, —CH$_2 R^{14a}$, $C_3$-$C_6$alkynyl or $C_1$-$C_6$alkoxycarbonyl, $R^5$ is $C_1$-$C_6$alkyl or $C_1$-$C_6$haloalkyl, $R^6$ is —CHO, $C_1$-$C_6$alkylcarbonyl or $C_1$-$C_6$alkoxycarbonyl, $R^{14a}$ is cyano or —O$R^{25}$, $R^{25}$ is $C_1$-$C_4$alkyl, $C_1$-$C_4$haloalkyl or —C(O)O$R^{32}$, and $R^{32}$ is $C_1$-$C_6$alkyl.

3. 4-Hydroxyiminomethyl substituted benzamide compound or the salt thereof according to claim 1, wherein $A^1$ is carbon atom, W is oxygen atom, Y is halogen atom, cyano, nitro, $C_1$-$C_6$alkyl, $C_1$-$C_6$haloalkyl, —O$R^5$ or —N($R^7$)$R^6$, $R^1$ is —C(O)O$R^{1c}$, $R^{1c}$ is $C_1$-$C_6$alkyl or $C_3$-$C_6$cycloalkyl, $R^2$ is hydrogen atom, $C_1$-$C_6$alkyl, —CH$_2 R^{14a}$, E-5, —C(O)$R^{15}$, $C_1$-$C_6$alkoxycarbonyl, $C_1$-$C_6$haloalkoxycarbonyl or $C_1$-$C_6$haloalkylthio, $R^5$ is $C_1$-$C_6$alkyl or $C_1$-$C_6$haloalkyl, $R^6$ is —CHO, $C_1$-$C_6$alkylcarbonyl or $C_1$-$C_6$alkoxycarbonyl, $R^{14a}$ is cyano, —O$R^{25}$, or —NHC(O)O$R^{32}$, $R^{15}$ is $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl or $C_3$-$C_6$cycloalkyl, $R^{25}$ is $C_1$-$C_4$alkyl, $C_1$-$C_4$haloalkyl or —C(O)O$R^{32}$, $R^{32}$ is $C_1$-$C_6$alkyl, n is an integer of 0 or 1, and q3 is 0.

4. 4-Hydroxyiminomethyl substituted benzamide compound or the salt thereof according to claim 1, wherein $A^1$ is carbon atom, W is oxygen atom, Y is halogen atom, cyano, nitro, $C_1$-$C_6$alkyl, $C_1$-$C_6$haloalkyl, —O$R^5$ or —N($R^7$)$R^6$, $R^1$ is —C(O)N($R^{1e}$)$R^{1d}$, $R^{1d}$ is hydrogen atom, —C(O)$R^{15}$ or —C(O)O$R^{15}$, $R^{1e}$ is hydrogen atom or $C_1$-$C_6$alkyl, $R^2$ is hydrogen atom or $C_1$-$C_6$alkyl, $R^5$ is $C_1$-$C_6$alkyl or $C_1$-$C_6$haloalkyl, $R^6$ is —CHO, $C_1$-$C_6$alkylcarbonyl or $C_1$-$C_6$alkoxycarbonyl, $R^{15}$ is $C_1$-$C_6$alkyl or $C_1$-$C_6$haloalkyl, and n is an integer of 0 or 1.

5. 4-Hydroxyiminomethyl substituted benzamide compound or the salt thereof according to claim 1, wherein $A^1$ is carbon atom, W is oxygen atom, Y is halogen atom, cyano, nitro, $C_1$-$C_6$alkyl, $C_1$-$C_6$haloalkyl, —O$R^5$ or —N($R^7$)$R^6$, $R^1$ is phenyl substituted with $(Z)_{p1}$, D-52, D-55, D-56, D-57 or D-58, $R^2$ is $C_1$-$C_6$alkyl, —CH$_2 R^{14a}$, $C_3$-$C_6$alkynyl, —C(O)$R^{15}$, —C(O)O$R^{15}$ or —C(O)C(O)O$R^{15}$, Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl or $C_1$-$C_6$alkylsulfonyl, when p1, p2 or p3 is an integer of 2 or more, each Z may be identical with or different from each other, $R^5$ is $C_1$-$C_6$alkyl or $C_1$-$C_6$haloalkyl, $R^6$ is —CHO, $C_1$-$C_6$alkylcarbonyl or $C_1$-$C_6$alkoxycarbonyl, $R^{14a}$ is cyano or —O$R^{25}$, $R^{15}$ is $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, $C_1$-$C_4$alkylsulfinyl $C_1$-$C_4$alkyl, $C_1$-$C_4$alkylsulfonyl $C_1$-$C_4$alkyl, $C_3$-$C_6$cycloalkyl, $C_2$-$C_6$alkenyl, $C_2$-$C_6$alkynyl, phenyl, phenyl substituted with $(Z)_{p1}$ or D-52, $R^{25}$ is $C_1$-$C_4$alkyl, haloalkyl, —C(O)$R^{32}$ or —C(O)O$R^{32}$, $R^{32}$ is $C_1$-$C_6$alkyl or $C_3$-$C_6$cycloalkyl, n is an integer of 0 or 1, and t is 0.

* * * * *